(12) United States Patent
Hiramatsu et al.

(10) Patent No.: US 7,498,157 B2
(45) Date of Patent: Mar. 3, 2009

(54) THREE-DIMENSIONAL STRUCTURE OF DIPEPTIDYL PEPTIDASE IV

(75) Inventors: Hajime Hiramatsu, Osaka (JP); Kiyoshi Kyono, Osaka (JP); Hideaki Shima, Hyogo (JP); Shigeru Sugiyama, Nara (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 215 days.

(21) Appl. No.: 10/522,789

(22) PCT Filed: Jul. 28, 2003

(86) PCT No.: PCT/JP03/09523

§ 371 (c)(1), (2), (4) Date: Jan. 28, 2005

(87) PCT Pub. No.: WO2004/011640

PCT Pub. Date: Feb. 5, 2004

(65) Prior Publication Data

US 2005/0260732 A1    Nov. 24, 2005

Related U.S. Application Data

(60) Provisional application No. 60/398,761, filed on Jul. 29, 2002.

(51) Int. Cl.
*C12N 9/14* (2006.01)
*G01N 31/00* (2006.01)

(52) U.S. Cl. .......................... 435/195; 436/4
(58) Field of Classification Search ............. 435/195; 436/4
See application file for complete search history.

(56) References Cited

FOREIGN PATENT DOCUMENTS

WO    WO 02/24893 A2    3/2002

OTHER PUBLICATIONS

Wiencek et al. New strategies for protein crystal growth. Ann. Rev. Biomed. Eng. 1999, 1, 505-534.*
Gilliland et al. Crystallization of biological molecules for X-ray diffraction studies. Current Opinion in Structure Biology 1996, 6, 595-603.*
Ke et al. Crystallization of RNA and RNA-protein complexes. Methods 34, 2004, 408-414.*
Certified English translation of U.S. Appl. No. 60/398,761, filed Jul. 29, 2002.
International Search Report mailed Dec. 16, 2003, for PCT application No. PCT/JP2003/009523, filed Jul. 28, 2003.
Abbott et al. "Binding to Human Dipeptidyl Peptidase IV by Adenosine Deaminase and Antibodies that Inhibit Ligand Binding Involves Overlapping, Discontinuous Sites on a Predicted β Propeller Domain" European Journal of Biochemistry (1999) 266:798-810.
Augustyns et al. "The Unique Properties of Dipeptidyl-Peptidase IV (DPP IV/CD26) and the Therapeutic Potential of DPP IV Inhibitors" Current Medicinal Chemistry (1999) 6 (4):311-327.
Darmoul et al. "Dipeptidyl Peptidase IV (CD 26) Gene Expression in Enterocyte-like Colon Cancer Cell Lines HT-29 and Caco-2" The Journal of Biological Chemistry (1992) 267 (7)4824-4833.
Darmoul et al. GenBank Accession No. M80536, H. Sapiens Dipeptidyl Peptidase IV (DPP4) mRNA, Complete CDs (1992).
Engel et al. "The Crystal Structure of Dipeptidyl Peptidase IV (CD26) Reveals its Functional Regulation and Enzymatic Mechanism" Proceedings of the National Academy of Sciences of the United States (2003) 100 (9):5063-5068.
Fulop et al. "Prolyl Oligopeptidase: An Unusualβ-Propeller Domain Regulates Proteolysis" Cell (1998) 94:161-170.
Hiramatsu et al. "The Structure and Function of Human Dipeptidyl Peptidase IV, Possessing a Unique Eight-Bladed βPropeller Fold" Biochemical and Biophysical Research Communications (2003) 302:849-854.
Kabashima et al. "Dipeptidyl Peptidase IV from *Xanthomonas maltophilia*: Sequencing and Expression of the Enzyme Gene and Characterization of the Expressed Enzyme" Journal of Biochemistry (1996) 120 (6):1111-1117.
Lambeir et al. "A Prediction of DPP IV/CD26 Domain Structure from a Physico-Chemical Investigation of Dipeptidyl Peptidase IV (CD26) from Human Seminal Plasma" Biochemica et Biophysica Acta (1997) 1340:215-226.
Medrano et al. "Structure of Proline Iminopeptidase from *Xanthomonas campestis* pv. *Citri*: a Prototype for the Prolyl Oligopeptidase Family" European Molecular Biology Organization Journal (1998) 17 (1):1-9.
Misumi et al. "Molecular Cloning and Sequence Analysis of Human Dipeptidyl Peptidase IV, a Serine Proteinase on the Cell Surface" Biochemica et Biophysica Acta. (1992) 1131:333-336.
Misumi et al. GenBank Accession No. X60708 S40353, Human pcHDP7 mRNA for Liver Dipeptidyl Peptidase IV (1991).
Oefner et al. "High-Resolution Structure of Human Apo Dipeptidyl Peptidase IV/CD26 and its Complex with 1-[({2-[(5-iodopyridin-2-yl)amino]-ethyl}amino)-acetyl]-2-cyano-(S)-pyrrolidine"    Acta Crystallographica (2003) D59:1206-1212.
Ogata et al. "Identification of the Active Site Residues in Dipeptidyl Peptidase IV by Affinity Labeling and Site-Directed Mutagenesis" Biochemistry (1992) 31:2582-2587.
Polgar, L. "The Prolyl Oligopeptidase Family" Cellular and Molecular Life Sciences (2002) 59:349-362.
Rasmussen et al. "Crystal Structure of Human Dipeptidyl Peptidase IV/CD26 in Complex with a Substrate Analog" Nature Structural Biology (2003) 10 (1):19-25.

* cited by examiner

*Primary Examiner*—Suzanne M. Noakes
(74) *Attorney, Agent, or Firm*—Finnegan Henderson Farabow Garrett & Dunner LLP

(57) ABSTRACT

A crystal of a dipeptidyl peptidase IV; a three-dimensional structural coordinate of the dipeptidyl peptidase IV; a method for obtaining a three-dimensional coordinate of a homolog protein of the dipeptidyl peptidase IV; a method for obtaining a three-dimensional structural coordinate of a crystal of a complex of the dipeptidyl peptidase IV and an effector of the dipeptidyl peptidase IV; a method for identifying pharmacophore of the effector of the dipeptidyl peptidase IV; a method for designing, identifying, evaluating or searching; the effector; and a program and a medium therefor for use of the three-dimensional structural coordinate.

5 Claims, 256 Drawing Sheets

F I G. 3
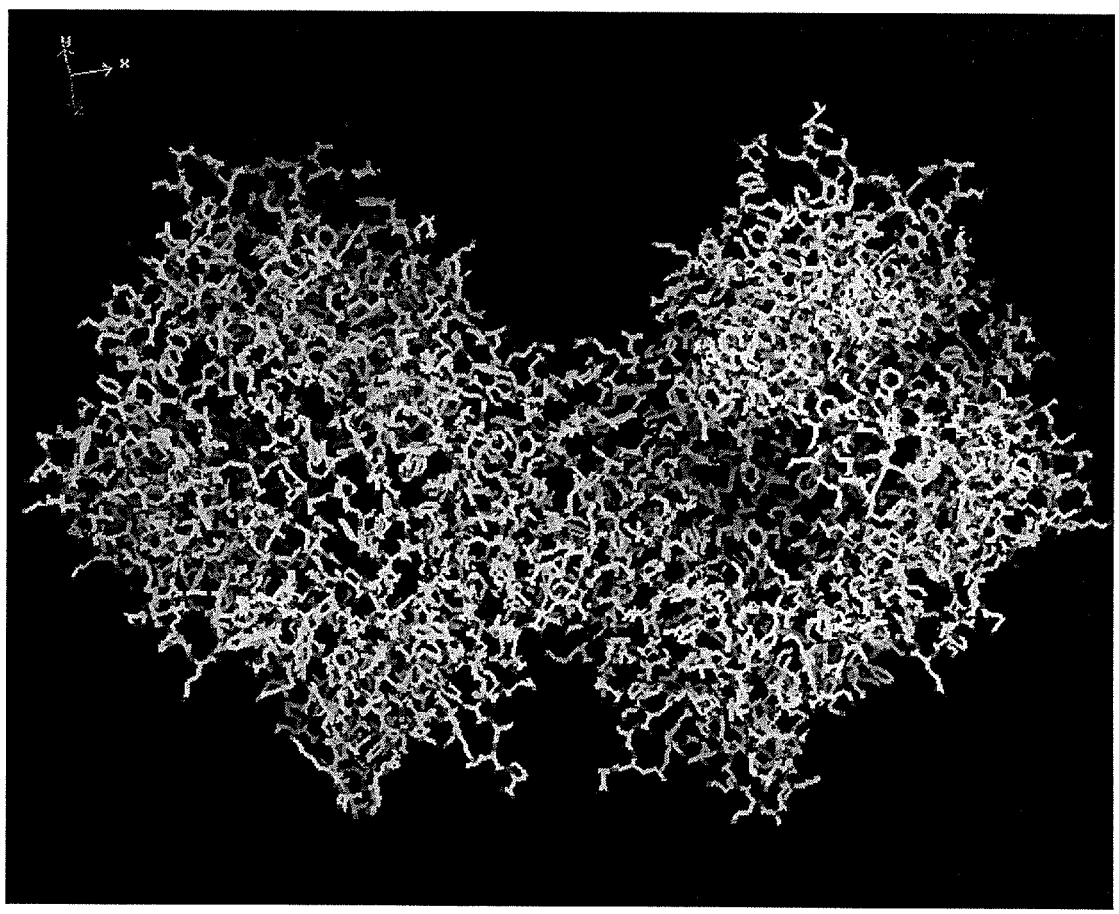

FIG. 4-1

Three-dimensional structural coordinate of dipeptidyl peptidase IV

| | | | | | | | | | | | |
|---|---|---|---|---|---|---|---|---|---|---|---|
| ATOM | 1 | CB | ASP | 38 | 44.493 | 31.885 | 58.927 | 1.00 | 42.46 | A | C |
| ATOM | 2 | CG | ASP | 38 | 44.146 | 32.095 | 57.467 | 1.00 | 42.00 | A | C |
| ATOM | 3 | OD1 | ASP | 38 | 43.664 | 33.198 | 57.133 | 1.00 | 42.55 | A | O |
| ATOM | 4 | OD2 | ASP | 38 | 44.360 | 31.171 | 56.655 | 1.00 | 40.85 | A | O |
| ATOM | 5 | C | ASP | 38 | 45.876 | 29.805 | 58.634 | 1.00 | 41.68 | A | C |
| ATOM | 6 | O | ASP | 38 | 46.980 | 30.327 | 58.778 | 1.00 | 42.02 | A | O |
| ATOM | 7 | N | ASP | 38 | 44.758 | 30.264 | 60.778 | 1.00 | 42.88 | A | N |
| ATOM | 8 | CA | ASP | 38 | 44.639 | 30.404 | 59.296 | 1.00 | 42.51 | A | C |
| ATOM | 9 | N | SER | 39 | 45.679 | 28.711 | 57.905 | 1.00 | 40.69 | A | N |
| ATOM | 10 | CA | SER | 39 | 46.775 | 28.013 | 57.241 | 1.00 | 39.98 | A | C |
| ATOM | 11 | CB | SER | 39 | 46.584 | 26.501 | 57.380 | 1.00 | 40.43 | A | C |
| ATOM | 12 | OG | SER | 39 | 45.410 | 26.079 | 56.703 | 1.00 | 41.11 | A | O |
| ATOM | 13 | C | SER | 39 | 46.960 | 28.343 | 55.763 | 1.00 | 39.60 | A | C |
| ATOM | 14 | O | SER | 39 | 47.870 | 27.813 | 55.123 | 1.00 | 39.66 | A | O |
| ATOM | 15 | N | ARG | 40 | 46.093 | 29.190 | 55.217 | 1.00 | 38.12 | A | N |
| ATOM | 16 | CA | ARG | 40 | 46.194 | 29.575 | 53.810 | 1.00 | 37.02 | A | C |
| ATOM | 17 | CB | ARG | 40 | 45.082 | 30.558 | 53.439 | 1.00 | 36.96 | A | C |
| ATOM | 18 | CG | ARG | 40 | 43.683 | 29.984 | 53.404 | 1.00 | 35.97 | A | C |
| ATOM | 19 | CD | ARG | 40 | 42.688 | 31.098 | 53.137 | 1.00 | 34.97 | A | C |
| ATOM | 20 | NE | ARG | 40 | 42.774 | 32.134 | 54.161 | 1.00 | 35.27 | A | N |
| ATOM | 21 | CZ | ARG | 40 | 42.097 | 33.276 | 54.125 | 1.00 | 35.55 | A | C |
| ATOM | 22 | NH1 | ARG | 40 | 41.280 | 33.528 | 53.111 | 1.00 | 35.54 | A | N |
| ATOM | 23 | NH2 | ARG | 40 | 42.239 | 34.167 | 55.097 | 1.00 | 34.68 | A | N |
| ATOM | 24 | C | ARG | 40 | 47.530 | 30.251 | 53.531 | 1.00 | 35.91 | A | C |
| ATOM | 25 | O | ARG | 40 | 48.100 | 30.901 | 54.407 | 1.00 | 34.18 | A | O |
| ATOM | 26 | N | LYS | 41 | 48.031 | 30.100 | 52.310 | 1.00 | 35.43 | A | N |
| ATOM | 27 | CA | LYS | 41 | 49.286 | 30.749 | 51.937 | 1.00 | 34.97 | A | C |
| ATOM | 28 | CB | LYS | 41 | 49.705 | 30.338 | 50.525 | 1.00 | 35.73 | A | C |
| ATOM | 29 | CG | LYS | 41 | 48.684 | 30.719 | 49.467 | 1.00 | 38.56 | A | C |
| ATOM | 30 | CD | LYS | 41 | 49.026 | 30.151 | 48.096 | 1.00 | 42.36 | A | C |
| ATOM | 31 | CE | LYS | 41 | 47.805 | 30.201 | 47.173 | 1.00 | 45.55 | A | C |
| ATOM | 32 | NZ | LYS | 41 | 48.070 | 29.686 | 45.791 | 1.00 | 47.41 | A | N |
| ATOM | 33 | C | LYS | 41 | 49.038 | 32.257 | 51.957 | 1.00 | 33.41 | A | C |
| ATOM | 34 | O | LYS | 41 | 47.891 | 32.715 | 51.981 | 1.00 | 33.24 | A | O |
| ATOM | 35 | N | THR | 42 | 50.110 | 33.032 | 51.954 | 1.00 | 31.47 | A | N |
| ATOM | 36 | CA | THR | 42 | 49.967 | 34.479 | 51.937 | 1.00 | 30.04 | A | C |
| ATOM | 37 | CB | THR | 42 | 50.860 | 35.139 | 53.000 | 1.00 | 31.23 | A | C |
| ATOM | 38 | OG1 | THR | 42 | 52.234 | 34.843 | 52.725 | 1.00 | 30.79 | A | O |
| ATOM | 39 | CG2 | THR | 42 | 50.501 | 34.622 | 54.386 | 1.00 | 30.12 | A | C |
| ATOM | 40 | C | THR | 42 | 50.389 | 34.971 | 50.558 | 1.00 | 28.34 | A | C |
| ATOM | 41 | O | THR | 42 | 50.977 | 34.220 | 49.782 | 1.00 | 27.76 | A | O |
| ATOM | 42 | N | TYR | 43 | 50.058 | 36.217 | 50.234 | 1.00 | 27.55 | A | N |
| ATOM | 43 | CA | TYR | 43 | 50.465 | 36.782 | 48.954 | 1.00 | 25.72 | A | C |
| ATOM | 44 | CB | TYR | 43 | 49.615 | 38.006 | 48.623 | 1.00 | 26.01 | A | C |
| ATOM | 45 | CG | TYR | 43 | 49.922 | 38.625 | 47.280 | 1.00 | 26.92 | A | C |
| ATOM | 46 | CD1 | TYR | 43 | 50.977 | 39.527 | 47.130 | 1.00 | 26.68 | A | C |
| ATOM | 47 | CE1 | TYR | 43 | 51.253 | 40.113 | 45.895 | 1.00 | 27.02 | A | C |
| ATOM | 48 | CD2 | TYR | 43 | 49.152 | 38.315 | 46.158 | 1.00 | 26.40 | A | C |

FIG. 4-2 (Continued)

| | | | | | | | | | | |
|---|---|---|---|---|---|---|---|---|---|---|
| ATOM | 49 | CE2 | TYR | 43 | 49.424 | 38.891 | 44.919 | 1.00 | 25.89 | A | C |
| ATOM | 50 | CZ | TYR | 43 | 50.473 | 39.790 | 44.796 | 1.00 | 25.91 | A | C |
| ATOM | 51 | OH | TYR | 43 | 50.741 | 40.370 | 43.579 | 1.00 | 25.09 | A | O |
| ATOM | 52 | C | TYR | 43 | 51.933 | 37.165 | 49.160 | 1.00 | 24.97 | A | C |
| ATOM | 53 | O | TYR | 43 | 52.251 | 38.049 | 49.955 | 1.00 | 23.33 | A | O |
| ATOM | 54 | N | THR | 44 | 52.818 | 36.482 | 48.444 | 1.00 | 24.06 | A | N |
| ATOM | 55 | CA | THR | 44 | 54.255 | 36.685 | 48.580 | 1.00 | 25.90 | A | C |
| ATOM | 56 | CB | THR | 44 | 54.960 | 35.336 | 48.547 | 1.00 | 25.86 | A | C |
| ATOM | 57 | OG1 | THR | 44 | 54.696 | 34.709 | 47.285 | 1.00 | 28.12 | A | O |
| ATOM | 58 | CG2 | THR | 44 | 54.439 | 34.436 | 49.655 | 1.00 | 22.61 | A | C |
| ATOM | 59 | C | THR | 44 | 54.917 | 37.576 | 47.530 | 1.00 | 27.35 | A | C |
| ATOM | 60 | O | THR | 44 | 54.296 | 37.956 | 46.535 | 1.00 | 29.11 | A | O |
| ATOM | 61 | N | LEU | 45 | 56.191 | 37.894 | 47.765 | 1.00 | 27.39 | A | N |
| ATOM | 62 | CA | LEU | 45 | 56.978 | 38.722 | 46.853 | 1.00 | 26.43 | A | C |
| ATOM | 63 | CB | LEU | 45 | 58.377 | 38.954 | 47.425 | 1.00 | 26.07 | A | C |
| ATOM | 64 | CG | LEU | 45 | 59.310 | 39.860 | 46.612 | 1.00 | 26.21 | A | C |
| ATOM | 65 | CD1 | LEU | 45 | 58.734 | 41.263 | 46.517 | 1.00 | 25.53 | A | C |
| ATOM | 66 | CD2 | LEU | 45 | 60.672 | 39.896 | 47.266 | 1.00 | 24.37 | A | C |
| ATOM | 67 | C | LEU | 45 | 57.088 | 38.069 | 45.473 | 1.00 | 27.00 | A | C |
| ATOM | 68 | O | LEU | 45 | 56.939 | 38.740 | 44.449 | 1.00 | 27.84 | A | O |
| ATOM | 69 | N | THR | 46 | 57.354 | 36.766 | 45.445 | 1.00 | 26.70 | A | N |
| ATOM | 70 | CA | THR | 46 | 57.448 | 36.038 | 44.182 | 1.00 | 26.95 | A | C |
| ATOM | 71 | CB | THR | 46 | 57.838 | 34.559 | 44.407 | 1.00 | 26.87 | A | C |
| ATOM | 72 | OG1 | THR | 46 | 59.150 | 34.495 | 44.966 | 1.00 | 31.74 | A | O |
| ATOM | 73 | CG2 | THR | 46 | 57.833 | 33.793 | 43.110 | 1.00 | 28.08 | A | C |
| ATOM | 74 | C | THR | 46 | 56.076 | 36.091 | 43.517 | 1.00 | 26.96 | A | C |
| ATOM | 75 | O | THR | 46 | 55.965 | 36.094 | 42.289 | 1.00 | 25.36 | A | O |
| ATOM | 76 | N | ASP | 47 | 55.035 | 36.126 | 44.346 | 1.00 | 27.72 | A | N |
| ATOM | 77 | CA | ASP | 47 | 53.659 | 36.199 | 43.858 | 1.00 | 29.74 | A | C |
| ATOM | 78 | CB | ASP | 47 | 52.670 | 36.173 | 45.026 | 1.00 | 30.90 | A | C |
| ATOM | 79 | CG | ASP | 47 | 52.289 | 34.769 | 45.430 | 1.00 | 30.62 | A | C |
| ATOM | 80 | OD1 | ASP | 47 | 51.778 | 34.595 | 46.553 | 1.00 | 32.28 | A | O |
| ATOM | 81 | OD2 | ASP | 47 | 52.490 | 33.845 | 44.617 | 1.00 | 30.71 | A | O |
| ATOM | 82 | C | ASP | 47 | 53.477 | 37.482 | 43.073 | 1.00 | 28.87 | A | C |
| ATOM | 83 | O | ASP | 47 | 52.918 | 37.478 | 41.979 | 1.00 | 29.50 | A | O |
| ATOM | 84 | N | TYR | 48 | 53.945 | 38.581 | 43.648 | 1.00 | 28.54 | A | N |
| ATOM | 85 | CA | TYR | 48 | 53.859 | 39.878 | 42.994 | 1.00 | 29.04 | A | C |
| ATOM | 86 | CB | TYR | 48 | 54.191 | 40.991 | 43.996 | 1.00 | 27.50 | A | C |
| ATOM | 87 | CG | TYR | 48 | 54.448 | 42.333 | 43.354 | 1.00 | 25.16 | A | C |
| ATOM | 88 | CD1 | TYR | 48 | 53.460 | 42.971 | 42.609 | 1.00 | 23.19 | A | C |
| ATOM | 89 | CE1 | TYR | 48 | 53.703 | 44.184 | 41.982 | 1.00 | 24.84 | A | C |
| ATOM | 90 | CD2 | TYR | 48 | 55.694 | 42.946 | 43.461 | 1.00 | 25.89 | A | C |
| ATOM | 91 | CE2 | TYR | 48 | 55.956 | 44.165 | 42.838 | 1.00 | 26.76 | A | C |
| ATOM | 92 | CZ | TYR | 48 | 54.955 | 44.779 | 42.096 | 1.00 | 27.28 | A | C |
| ATOM | 93 | OH | TYR | 48 | 55.208 | 45.977 | 41.463 | 1.00 | 25.97 | A | O |
| ATOM | 94 | C | TYR | 48 | 54.820 | 39.953 | 41.796 | 1.00 | 28.80 | A | C |
| ATOM | 95 | O | TYR | 48 | 54.445 | 40.401 | 40.714 | 1.00 | 28.24 | A | O |
| ATOM | 96 | N | LEU | 49 | 56.054 | 39.499 | 41.988 | 1.00 | 29.41 | A | N |
| ATOM | 97 | CA | LEU | 49 | 57.046 | 39.552 | 40.918 | 1.00 | 30.39 | A | C |

| ATOM | 98 | CB | LEU | 49 | 58.455 | 39.318 | 41.481 | 1.00 | 27.73 | A | C |
| ATOM | 99 | CG | LEU | 49 | 58.988 | 40.473 | 42.336 | 1.00 | 28.28 | A | C |
| ATOM | 100 | CD1 | LEU | 49 | 60.438 | 40.223 | 42.711 | 1.00 | 26.99 | A | C |
| ATOM | 101 | CD2 | LEU | 49 | 58.860 | 41.773 | 41.555 | 1.00 | 26.02 | A | C |
| ATOM | 102 | C | LEU | 49 | 56.804 | 38.606 | 39.752 | 1.00 | 30.71 | A | C |
| ATOM | 103 | O | LEU | 49 | 57.147 | 38.919 | 38.614 | 1.00 | 30.14 | A | O |
| ATOM | 104 | N | LYS | 50 | 56.198 | 37.459 | 40.024 | 1.00 | 32.51 | A | N |
| ATOM | 105 | CA | LYS | 50 | 55.959 | 36.491 | 38.971 | 1.00 | 33.54 | A | C |
| ATOM | 106 | CB | LYS | 50 | 56.289 | 35.098 | 39.485 | 1.00 | 33.30 | A | C |
| ATOM | 107 | CG | LYS | 50 | 57.763 | 34.940 | 39.790 | 1.00 | 33.89 | A | C |
| ATOM | 108 | CD | LYS | 50 | 58.591 | 35.213 | 38.545 | 1.00 | 35.19 | A | C |
| ATOM | 109 | CE | LYS | 50 | 60.071 | 34.945 | 38.778 | 1.00 | 38.12 | A | C |
| ATOM | 110 | NZ | LYS | 50 | 60.859 | 35.028 | 37.515 | 1.00 | 39.27 | A | N |
| ATOM | 111 | C | LYS | 50 | 54.572 | 36.517 | 38.361 | 1.00 | 34.93 | A | C |
| ATOM | 112 | O | LYS | 50 | 54.272 | 35.719 | 37.478 | 1.00 | 35.13 | A | O |
| ATOM | 113 | N | ASN | 51 | 53.731 | 37.436 | 38.822 | 1.00 | 36.66 | A | N |
| ATOM | 114 | CA | ASN | 51 | 52.379 | 37.569 | 38.294 | 1.00 | 38.39 | A | C |
| ATOM | 115 | CB | ASN | 51 | 52.428 | 37.859 | 36.791 | 1.00 | 41.61 | A | C |
| ATOM | 116 | CG | ASN | 51 | 53.407 | 38.968 | 36.436 | 1.00 | 44.75 | A | C |
| ATOM | 117 | OD1 | ASN | 51 | 53.212 | 40.131 | 36.801 | 1.00 | 46.38 | A | O |
| ATOM | 118 | ND2 | ASN | 51 | 54.470 | 38.609 | 35.717 | 1.00 | 45.80 | A | N |
| ATOM | 119 | C | ASN | 51 | 51.529 | 36.324 | 38.517 | 1.00 | 38.21 | A | C |
| ATOM | 120 | O | ASN | 51 | 50.708 | 35.976 | 37.674 | 1.00 | 40.60 | A | O |
| ATOM | 121 | N | THR | 52 | 51.720 | 35.647 | 39.641 | 1.00 | 36.74 | A | N |
| ATOM | 122 | CA | THR | 52 | 50.942 | 34.451 | 39.926 | 1.00 | 35.44 | A | C |
| ATOM | 123 | CB | THR | 52 | 51.297 | 33.888 | 41.298 | 1.00 | 35.57 | A | C |
| ATOM | 124 | OG1 | THR | 52 | 52.646 | 33.415 | 41.272 | 1.00 | 38.62 | A | O |
| ATOM | 125 | CG2 | THR | 52 | 50.367 | 32.750 | 41.666 | 1.00 | 35.25 | A | C |
| ATOM | 126 | C | THR | 52 | 49.431 | 34.686 | 39.869 | 1.00 | 35.17 | A | C |
| ATOM | 127 | O | THR | 52 | 48.699 | 33.889 | 39.276 | 1.00 | 36.44 | A | O |
| ATOM | 128 | N | TYR | 53 | 48.962 | 35.765 | 40.487 | 1.00 | 33.55 | A | N |
| ATOM | 129 | CA | TYR | 53 | 47.535 | 36.081 | 40.487 | 1.00 | 33.46 | A | C |
| ATOM | 130 | CB | TYR | 53 | 47.084 | 36.407 | 41.903 | 1.00 | 32.64 | A | C |
| ATOM | 131 | CG | TYR | 53 | 47.399 | 35.293 | 42.861 | 1.00 | 33.83 | A | C |
| ATOM | 132 | CD1 | TYR | 53 | 48.341 | 35.462 | 43.872 | 1.00 | 34.11 | A | C |
| ATOM | 133 | CE1 | TYR | 53 | 48.657 | 34.425 | 44.741 | 1.00 | 34.24 | A | C |
| ATOM | 134 | CD2 | TYR | 53 | 46.775 | 34.050 | 42.741 | 1.00 | 36.17 | A | C |
| ATOM | 135 | CE2 | TYR | 53 | 47.084 | 33.001 | 43.605 | 1.00 | 35.64 | A | C |
| ATOM | 136 | CZ | TYR | 53 | 48.026 | 33.199 | 44.601 | 1.00 | 35.74 | A | C |
| ATOM | 137 | OH | TYR | 53 | 48.343 | 32.170 | 45.453 | 1.00 | 35.79 | A | O |
| ATOM | 138 | C | TYR | 53 | 47.266 | 37.248 | 39.548 | 1.00 | 33.40 | A | C |
| ATOM | 139 | O | TYR | 53 | 47.486 | 38.404 | 39.895 | 1.00 | 33.56 | A | O |
| ATOM | 140 | N | ARG | 54 | 46.773 | 36.929 | 38.355 | 1.00 | 34.36 | A | N |
| ATOM | 141 | CA | ARG | 54 | 46.526 | 37.933 | 37.327 | 1.00 | 34.87 | A | C |
| ATOM | 142 | CB | ARG | 54 | 46.993 | 37.387 | 35.972 | 1.00 | 35.72 | A | C |
| ATOM | 143 | CG | ARG | 54 | 46.887 | 38.373 | 34.821 | 1.00 | 39.96 | A | C |
| ATOM | 144 | CD | ARG | 54 | 47.675 | 37.880 | 33.613 | 1.00 | 43.22 | A | C |
| ATOM | 145 | NE | ARG | 54 | 47.651 | 38.831 | 32.506 | 1.00 | 46.70 | A | N |
| ATOM | 146 | CZ | ARG | 54 | 46.587 | 39.068 | 31.744 | 1.00 | 49.10 | A | C |

FIG. 4-4 (Continued)

| | | | | | | | | | | | |
|---|---|---|---|---|---|---|---|---|---|---|---|
| ATOM | 147 | NH1 | ARG | 54 | 45.451 | 38.416 | 31.968 | 1.00 | 49.25 | A | N |
| ATOM | 148 | NH2 | ARG | 54 | 46.657 | 39.957 | 30.757 | 1.00 | 50.00 | A | N |
| ATOM | 149 | C | ARG | 54 | 45.100 | 38.445 | 37.202 | 1.00 | 33.84 | A | C |
| ATOM | 150 | O | ARG | 54 | 44.141 | 37.687 | 37.314 | 1.00 | 34.59 | A | O |
| ATOM | 151 | N | LEU | 55 | 44.982 | 39.748 | 36.966 | 1.00 | 33.05 | A | N |
| ATOM | 152 | CA | LEU | 55 | 43.693 | 40.402 | 36.788 | 1.00 | 32.40 | A | C |
| ATOM | 153 | CB | LEU | 55 | 43.792 | 41.892 | 37.123 | 1.00 | 29.74 | A | C |
| ATOM | 154 | CG | LEU | 55 | 44.042 | 42.344 | 38.557 | 1.00 | 32.26 | A | C |
| ATOM | 155 | CD1 | LEU | 55 | 44.245 | 43.847 | 38.571 | 1.00 | 31.83 | A | C |
| ATOM | 156 | CD2 | LEU | 55 | 42.857 | 41.967 | 39.448 | 1.00 | 33.66 | A | C |
| ATOM | 157 | C | LEU | 55 | 43.298 | 40.271 | 35.322 | 1.00 | 32.61 | A | C |
| ATOM | 158 | O | LEU | 55 | 44.004 | 40.769 | 34.441 | 1.00 | 33.62 | A | O |
| ATOM | 159 | N | LYS | 56 | 42.189 | 39.593 | 35.050 | 1.00 | 31.32 | A | N |
| ATOM | 160 | CA | LYS | 56 | 41.733 | 39.462 | 33.673 | 1.00 | 31.42 | A | C |
| ATOM | 161 | CB | LYS | 56 | 40.584 | 38.453 | 33.564 | 1.00 | 33.54 | A | C |
| ATOM | 162 | CG | LYS | 56 | 40.978 | 36.997 | 33.733 | 1.00 | 34.84 | A | C |
| ATOM | 163 | CD | LYS | 56 | 41.746 | 36.484 | 32.530 | 1.00 | 38.85 | A | C |
| ATOM | 164 | CE | LYS | 56 | 42.120 | 35.009 | 32.698 | 1.00 | 40.95 | A | C |
| ATOM | 165 | NZ | LYS | 56 | 43.117 | 34.537 | 31.685 | 1.00 | 43.33 | A | N |
| ATOM | 166 | C | LYS | 56 | 41.240 | 40.844 | 33.252 | 1.00 | 30.03 | A | C |
| ATOM | 167 | O | LYS | 56 | 40.839 | 41.648 | 34.088 | 1.00 | 28.24 | A | O |
| ATOM | 168 | N | LEU | 57 | 41.286 | 41.120 | 31.956 | 1.00 | 30.20 | A | N |
| ATOM | 169 | CA | LEU | 57 | 40.836 | 42.404 | 31.437 | 1.00 | 29.43 | A | C |
| ATOM | 170 | CB | LEU | 57 | 42.022 | 43.233 | 30.934 | 1.00 | 30.04 | A | C |
| ATOM | 171 | CG | LEU | 57 | 43.230 | 43.474 | 31.844 | 1.00 | 32.13 | A | C |
| ATOM | 172 | CD1 | LEU | 57 | 44.123 | 44.524 | 31.194 | 1.00 | 29.05 | A | C |
| ATOM | 173 | CD2 | LEU | 57 | 42.777 | 43.949 | 33.230 | 1.00 | 34.11 | A | C |
| ATOM | 174 | C | LEU | 57 | 39.911 | 42.132 | 30.271 | 1.00 | 28.16 | A | C |
| ATOM | 175 | O | LEU | 57 | 39.668 | 40.980 | 29.914 | 1.00 | 28.60 | A | O |
| ATOM | 176 | N | TYR | 58 | 39.394 | 43.196 | 29.676 | 1.00 | 26.69 | A | N |
| ATOM | 177 | CA | TYR | 58 | 38.530 | 43.050 | 28.518 | 1.00 | 25.82 | A | C |
| ATOM | 178 | CB | TYR | 58 | 37.071 | 42.890 | 28.934 | 1.00 | 25.51 | A | C |
| ATOM | 179 | CG | TYR | 58 | 36.195 | 42.420 | 27.797 | 1.00 | 26.86 | A | C |
| ATOM | 180 | CD1 | TYR | 58 | 36.051 | 41.062 | 27.514 | 1.00 | 26.92 | A | C |
| ATOM | 181 | CE1 | TYR | 58 | 35.294 | 40.631 | 26.429 | 1.00 | 26.28 | A | C |
| ATOM | 182 | CD2 | TYR | 58 | 35.557 | 43.333 | 26.965 | 1.00 | 25.26 | A | C |
| ATOM | 183 | CE2 | TYR | 58 | 34.803 | 42.911 | 25.882 | 1.00 | 26.13 | A | C |
| ATOM | 184 | CZ | TYR | 58 | 34.675 | 41.564 | 25.619 | 1.00 | 25.74 | A | C |
| ATOM | 185 | OH | TYR | 58 | 33.928 | 41.160 | 24.541 | 1.00 | 27.32 | A | O |
| ATOM | 186 | C | TYR | 58 | 38.681 | 44.288 | 27.647 | 1.00 | 24.95 | A | C |
| ATOM | 187 | O | TYR | 58 | 37.837 | 45.176 | 27.680 | 1.00 | 24.68 | A | O |
| ATOM | 188 | N | SER | 59 | 39.763 | 44.338 | 26.876 | 1.00 | 24.05 | A | N |
| ATOM | 189 | CA | SER | 59 | 40.037 | 45.470 | 25.997 | 1.00 | 24.31 | A | C |
| ATOM | 190 | CB | SER | 59 | 41.547 | 45.657 | 25.817 | 1.00 | 24.38 | A | C |
| ATOM | 191 | OG | SER | 59 | 42.187 | 45.931 | 27.051 | 1.00 | 28.99 | A | O |
| ATOM | 192 | C | SER | 59 | 39.405 | 45.294 | 24.628 | 1.00 | 23.54 | A | C |
| ATOM | 193 | O | SER | 59 | 39.795 | 44.420 | 23.860 | 1.00 | 24.84 | A | O |
| ATOM | 194 | N | LEU | 60 | 38.430 | 46.135 | 24.319 | 1.00 | 23.51 | A | N |
| ATOM | 195 | CA | LEU | 60 | 37.765 | 46.073 | 23.031 | 1.00 | 22.96 | A | C |

FIG. 4-5 (Continued)

| | | | | | | | | | | |
|---|---|---|---|---|---|---|---|---|---|---|
| ATOM | 196 | CB | LEU | 60 | 36.256 | 45.910 | 23.228 | 1.00 | 21.27 | A C |
| ATOM | 197 | CG | LEU | 60 | 35.528 | 46.977 | 24.048 | 1.00 | 20.80 | A C |
| ATOM | 198 | CD1 | LEU | 60 | 35.373 | 48.227 | 23.208 | 1.00 | 19.95 | A C |
| ATOM | 199 | CD2 | LEU | 60 | 34.159 | 46.466 | 24.488 | 1.00 | 18.91 | A C |
| ATOM | 200 | C | LEU | 60 | 38.072 | 47.356 | 22.279 | 1.00 | 23.42 | A C |
| ATOM | 201 | O | LEU | 60 | 38.507 | 48.340 | 22.869 | 1.00 | 23.10 | A O |
| ATOM | 202 | N | ARG | 61 | 37.862 | 47.339 | 20.971 | 1.00 | 25.94 | A N |
| ATOM | 203 | CA | ARG | 61 | 38.102 | 48.522 | 20.153 | 1.00 | 27.08 | A C |
| ATOM | 204 | CB | ARG | 61 | 39.364 | 48.323 | 19.299 | 1.00 | 29.17 | A C |
| ATOM | 205 | CG | ARG | 61 | 40.545 | 47.713 | 20.076 | 1.00 | 34.91 | A C |
| ATOM | 206 | CD | ARG | 61 | 41.790 | 48.612 | 20.088 | 1.00 | 38.62 | A C |
| ATOM | 207 | NE | ARG | 61 | 42.423 | 48.715 | 18.772 | 1.00 | 41.15 | A N |
| ATOM | 208 | CZ | ARG | 61 | 43.337 | 47.871 | 18.299 | 1.00 | 41.78 | A C |
| ATOM | 209 | NH1 | ARG | 61 | 43.754 | 46.848 | 19.033 | 1.00 | 40.61 | A N |
| ATOM | 210 | NH2 | ARG | 61 | 43.821 | 48.042 | 17.076 | 1.00 | 43.39 | A N |
| ATOM | 211 | C | ARG | 61 | 36.869 | 48.724 | 19.270 | 1.00 | 25.92 | A C |
| ATOM | 212 | O | ARG | 61 | 36.616 | 47.939 | 18.358 | 1.00 | 26.31 | A O |
| ATOM | 213 | N | TRP | 62 | 36.087 | 49.758 | 19.568 | 1.00 | 24.63 | A N |
| ATOM | 214 | CA | TRP | 62 | 34.883 | 50.050 | 18.794 | 1.00 | 24.74 | A C |
| ATOM | 215 | CB | TRP | 62 | 34.092 | 51.207 | 19.420 | 1.00 | 23.22 | A C |
| ATOM | 216 | CG | TRP | 62 | 33.472 | 50.900 | 20.741 | 1.00 | 23.78 | A C |
| ATOM | 217 | CD2 | TRP | 62 | 32.302 | 50.110 | 20.972 | 1.00 | 23.80 | A C |
| ATOM | 218 | CE2 | TRP | 62 | 32.082 | 50.085 | 22.368 | 1.00 | 23.69 | A C |
| ATOM | 219 | CE3 | TRP | 62 | 31.416 | 49.419 | 20.133 | 1.00 | 22.71 | A C |
| ATOM | 220 | CD1 | TRP | 62 | 33.906 | 51.310 | 21.972 | 1.00 | 24.25 | A C |
| ATOM | 221 | NE1 | TRP | 62 | 33.075 | 50.824 | 22.955 | 1.00 | 23.12 | A N |
| ATOM | 222 | CZ2 | TRP | 62 | 31.013 | 49.396 | 22.945 | 1.00 | 23.91 | A C |
| ATOM | 223 | CZ3 | TRP | 62 | 30.357 | 48.736 | 20.703 | 1.00 | 24.08 | A C |
| ATOM | 224 | CH2 | TRP | 62 | 30.162 | 48.730 | 22.100 | 1.00 | 25.02 | A C |
| ATOM | 225 | C | TRP | 62 | 35.241 | 50.427 | 17.365 | 1.00 | 25.48 | A C |
| ATOM | 226 | O | TRP | 62 | 35.980 | 51.380 | 17.138 | 1.00 | 27.15 | A O |
| ATOM | 227 | N | ILE | 63 | 34.722 | 49.682 | 16.398 | 1.00 | 26.16 | A N |
| ATOM | 228 | CA | ILE | 63 | 35.000 | 49.991 | 15.003 | 1.00 | 25.88 | A C |
| ATOM | 229 | CB | ILE | 63 | 35.312 | 48.727 | 14.180 | 1.00 | 25.95 | A C |
| ATOM | 230 | CG2 | ILE | 63 | 36.494 | 48.000 | 14.783 | 1.00 | 27.39 | A C |
| ATOM | 231 | CG1 | ILE | 63 | 34.092 | 47.810 | 14.138 | 1.00 | 24.70 | A C |
| ATOM | 232 | CD1 | ILE | 63 | 34.246 | 46.666 | 13.174 | 1.00 | 25.35 | A C |
| ATOM | 233 | C | ILE | 63 | 33.788 | 50.680 | 14.400 | 1.00 | 26.00 | A C |
| ATOM | 234 | O | ILE | 63 | 33.803 | 51.075 | 13.239 | 1.00 | 26.14 | A O |
| ATOM | 235 | N | SER | 64 | 32.738 | 50.812 | 15.202 | 1.00 | 26.48 | A N |
| ATOM | 236 | CA | SER | 64 | 31.510 | 51.470 | 14.768 | 1.00 | 28.43 | A C |
| ATOM | 237 | CB | SER | 64 | 30.764 | 50.603 | 13.754 | 1.00 | 27.24 | A C |
| ATOM | 238 | OG | SER | 64 | 30.181 | 49.481 | 14.392 | 1.00 | 28.00 | A O |
| ATOM | 239 | C | SER | 64 | 30.597 | 51.727 | 15.964 | 1.00 | 29.08 | A C |
| ATOM | 240 | O | SER | 64 | 31.008 | 51.606 | 17.119 | 1.00 | 26.71 | A O |
| ATOM | 241 | N | ASP | 65 | 29.348 | 52.067 | 15.678 | 1.00 | 31.29 | A N |
| ATOM | 242 | CA | ASP | 65 | 28.382 | 52.336 | 16.732 | 1.00 | 34.90 | A C |
| ATOM | 243 | CB | ASP | 65 | 27.384 | 53.397 | 16.269 | 1.00 | 37.81 | A C |
| ATOM | 244 | CG | ASP | 65 | 26.515 | 53.905 | 17.395 | 1.00 | 41.52 | A C |

| | | | | | | | | | | | |
|---|---|---|---|---|---|---|---|---|---|---|---|
| ATOM | 245 | OD1 | ASP | 65 | 27.070 | 54.235 | 18.465 | 1.00 | 43.44 | A | O |
| ATOM | 246 | OD2 | ASP | 65 | 25.281 | 53.986 | 17.211 | 1.00 | 44.76 | A | O |
| ATOM | 247 | C | ASP | 65 | 27.640 | 51.064 | 17.128 | 1.00 | 34.55 | A | C |
| ATOM | 248 | O | ASP | 65 | 26.753 | 51.091 | 17.981 | 1.00 | 33.76 | A | O |
| ATOM | 249 | N | HIS | 66 | 28.023 | 49.946 | 16.520 | 1.00 | 34.31 | A | N |
| ATOM | 250 | CA | HIS | 66 | 27.369 | 48.679 | 16.807 | 1.00 | 35.30 | A | C |
| ATOM | 251 | CB | HIS | 66 | 26.555 | 48.229 | 15.589 | 1.00 | 37.74 | A | C |
| ATOM | 252 | CG | HIS | 66 | 25.648 | 49.288 | 15.052 | 1.00 | 42.72 | A | C |
| ATOM | 253 | CD2 | HIS | 66 | 24.298 | 49.393 | 15.056 | 1.00 | 44.80 | A | C |
| ATOM | 254 | ND1 | HIS | 66 | 26.121 | 50.438 | 14.455 | 1.00 | 45.16 | A | N |
| ATOM | 255 | CE1 | HIS | 66 | 25.101 | 51.206 | 14.114 | 1.00 | 46.24 | A | C |
| ATOM | 256 | NE2 | HIS | 66 | 23.984 | 50.595 | 14.468 | 1.00 | 46.79 | A | N |
| ATOM | 257 | C | HIS | 66 | 28.314 | 47.555 | 17.223 | 1.00 | 33.78 | A | C |
| ATOM | 258 | O | HIS | 66 | 27.966 | 46.736 | 18.068 | 1.00 | 34.67 | A | O |
| ATOM | 259 | N | GLU | 67 | 29.502 | 47.501 | 16.635 | 1.00 | 31.93 | A | N |
| ATOM | 260 | CA | GLU | 67 | 30.432 | 46.434 | 16.979 | 1.00 | 31.45 | A | C |
| ATOM | 261 | CB | GLU | 67 | 30.557 | 45.463 | 15.801 | 1.00 | 31.46 | A | C |
| ATOM | 262 | CG | GLU | 67 | 30.356 | 46.103 | 14.447 | 1.00 | 33.17 | A | C |
| ATOM | 263 | CD | GLU | 67 | 30.357 | 45.092 | 13.311 | 1.00 | 35.48 | A | C |
| ATOM | 264 | OE1 | GLU | 67 | 29.607 | 44.090 | 13.394 | 1.00 | 32.44 | A | O |
| ATOM | 265 | OE2 | GLU | 67 | 31.104 | 45.306 | 12.329 | 1.00 | 36.60 | A | O |
| ATOM | 266 | C | GLU | 67 | 31.818 | 46.866 | 17.442 | 1.00 | 29.97 | A | C |
| ATOM | 267 | O | GLU | 67 | 32.240 | 48.003 | 17.241 | 1.00 | 30.44 | A | O |
| ATOM | 268 | N | TYR | 68 | 32.513 | 45.940 | 18.088 | 1.00 | 29.07 | A | N |
| ATOM | 269 | CA | TYR | 68 | 33.863 | 46.190 | 18.567 | 1.00 | 28.87 | A | C |
| ATOM | 270 | CB | TYR | 68 | 33.866 | 46.447 | 20.073 | 1.00 | 26.31 | A | C |
| ATOM | 271 | CG | TYR | 68 | 33.307 | 45.324 | 20.917 | 1.00 | 23.19 | A | C |
| ATOM | 272 | CD1 | TYR | 68 | 32.000 | 45.376 | 21.400 | 1.00 | 21.93 | A | C |
| ATOM | 273 | CE1 | TYR | 68 | 31.497 | 44.372 | 22.231 | 1.00 | 21.10 | A | C |
| ATOM | 274 | CD2 | TYR | 68 | 34.102 | 44.232 | 21.281 | 1.00 | 23.23 | A | C |
| ATOM | 275 | CE2 | TYR | 68 | 33.610 | 43.225 | 22.110 | 1.00 | 22.67 | A | C |
| ATOM | 276 | CZ | TYR | 68 | 32.304 | 43.305 | 22.582 | 1.00 | 22.02 | A | C |
| ATOM | 277 | OH | TYR | 68 | 31.810 | 42.321 | 23.403 | 1.00 | 22.72 | A | O |
| ATOM | 278 | C | TYR | 68 | 34.747 | 44.987 | 18.256 | 1.00 | 29.51 | A | C |
| ATOM | 279 | O | TYR | 68 | 34.244 | 43.885 | 18.028 | 1.00 | 28.32 | A | O |
| ATOM | 280 | N | LEU | 69 | 36.058 | 45.202 | 18.233 | 1.00 | 29.87 | A | N |
| ATOM | 281 | CA | LEU | 69 | 36.986 | 44.115 | 17.963 | 1.00 | 32.20 | A | C |
| ATOM | 282 | CB | LEU | 69 | 38.154 | 44.602 | 17.106 | 1.00 | 30.73 | A | C |
| ATOM | 283 | CG | LEU | 69 | 37.761 | 45.065 | 15.700 | 1.00 | 30.62 | A | C |
| ATOM | 284 | CD1 | LEU | 69 | 38.978 | 45.629 | 14.963 | 1.00 | 29.98 | A | C |
| ATOM | 285 | CD2 | LEU | 69 | 37.164 | 43.891 | 14.943 | 1.00 | 30.17 | A | C |
| ATOM | 286 | C | LEU | 69 | 37.492 | 43.588 | 19.292 | 1.00 | 34.73 | A | C |
| ATOM | 287 | O | LEU | 69 | 37.474 | 44.305 | 20.294 | 1.00 | 34.80 | A | O |
| ATOM | 288 | N | TYR | 70 | 37.927 | 42.334 | 19.305 | 1.00 | 37.39 | A | N |
| ATOM | 289 | CA | TYR | 70 | 38.423 | 41.726 | 20.528 | 1.00 | 42.16 | A | C |
| ATOM | 290 | CB | TYR | 70 | 37.251 | 41.359 | 21.444 | 1.00 | 42.66 | A | C |
| ATOM | 291 | CG | TYR | 70 | 37.689 | 40.866 | 22.799 | 1.00 | 43.06 | A | C |
| ATOM | 292 | CD1 | TYR | 70 | 38.400 | 41.697 | 23.657 | 1.00 | 43.56 | A | C |
| ATOM | 293 | CE1 | TYR | 70 | 38.837 | 41.253 | 24.892 | 1.00 | 44.69 | A | C |

FIG. 4-7 (Continued)

| | | | | | | | | | | |
|---|---|---|---|---|---|---|---|---|---|---|
| ATOM | 294 | CD2 | TYR | 70 | 37.421 | 39.563 | 23.213 | 1.00 | 43.93 | A C |
| ATOM | 295 | CE2 | TYR | 70 | 37.853 | 39.104 | 24.452 | 1.00 | 44.83 | A C |
| ATOM | 296 | CZ | TYR | 70 | 38.563 | 39.959 | 25.286 | 1.00 | 45.17 | A C |
| ATOM | 297 | OH | TYR | 70 | 39.004 | 39.532 | 26.516 | 1.00 | 47.21 | A O |
| ATOM | 298 | C | TYR | 70 | 39.249 | 40.480 | 20.240 | 1.00 | 45.46 | A C |
| ATOM | 299 | O | TYR | 70 | 38.976 | 39.752 | 19.287 | 1.00 | 46.31 | A O |
| ATOM | 300 | N | LYS | 71 | 40.254 | 40.231 | 21.072 | 1.00 | 49.93 | A N |
| ATOM | 301 | CA | LYS | 71 | 41.113 | 39.064 | 20.895 | 1.00 | 54.71 | A C |
| ATOM | 302 | CB | LYS | 71 | 42.580 | 39.460 | 21.054 | 1.00 | 54.14 | A C |
| ATOM | 303 | CG | LYS | 71 | 43.075 | 40.455 | 20.031 | 1.00 | 56.37 | A C |
| ATOM | 304 | CD | LYS | 71 | 44.559 | 40.712 | 20.226 | 1.00 | 58.61 | A C |
| ATOM | 305 | CE | LYS | 71 | 45.126 | 41.628 | 19.159 | 1.00 | 58.78 | A C |
| ATOM | 306 | NZ | LYS | 71 | 46.590 | 41.830 | 19.361 | 1.00 | 60.82 | A N |
| ATOM | 307 | C | LYS | 71 | 40.790 | 37.952 | 21.889 | 1.00 | 57.38 | A C |
| ATOM | 308 | O | LYS | 71 | 41.109 | 38.062 | 23.075 | 1.00 | 58.38 | A O |
| ATOM | 309 | N | GLN | 72 | 40.158 | 36.884 | 21.406 | 1.00 | 60.30 | A N |
| ATOM | 310 | CA | GLN | 72 | 39.816 | 35.750 | 22.261 | 1.00 | 63.23 | A C |
| ATOM | 311 | CB | GLN | 72 | 38.902 | 34.775 | 21.526 | 1.00 | 64.07 | A C |
| ATOM | 312 | CG | GLN | 72 | 38.313 | 33.695 | 22.417 | 1.00 | 65.84 | A C |
| ATOM | 313 | CD | GLN | 72 | 37.270 | 34.240 | 23.375 | 1.00 | 66.33 | A C |
| ATOM | 314 | OE1 | GLN | 72 | 36.251 | 34.790 | 22.952 | 1.00 | 67.19 | A O |
| ATOM | 315 | NE2 | GLN | 72 | 37.519 | 34.092 | 24.671 | 1.00 | 66.80 | A N |
| ATOM | 316 | C | GLN | 72 | 41.122 | 35.049 | 22.607 | 1.00 | 65.34 | A C |
| ATOM | 317 | O | GLN | 72 | 41.563 | 35.058 | 23.760 | 1.00 | 67.00 | A O |
| ATOM | 318 | N | GLU | 73 | 41.736 | 34.442 | 21.597 | 1.00 | 66.09 | A N |
| ATOM | 319 | CA | GLU | 73 | 43.012 | 33.763 | 21.775 | 1.00 | 67.12 | A C |
| ATOM | 320 | CB | GLU | 73 | 43.008 | 32.420 | 21.046 | 1.00 | 68.53 | A C |
| ATOM | 321 | CG | GLU | 73 | 41.974 | 31.433 | 21.570 | 1.00 | 71.35 | A C |
| ATOM | 322 | CD | GLU | 73 | 42.223 | 31.026 | 23.012 | 1.00 | 72.71 | A C |
| ATOM | 323 | OE1 | GLU | 73 | 41.491 | 30.147 | 23.517 | 1.00 | 73.51 | A O |
| ATOM | 324 | OE2 | GLU | 73 | 43.147 | 31.585 | 23.643 | 1.00 | 74.16 | A O |
| ATOM | 325 | C | GLU | 73 | 44.076 | 34.681 | 21.184 | 1.00 | 66.83 | A C |
| ATOM | 326 | O | GLU | 73 | 44.563 | 35.592 | 21.857 | 1.00 | 67.65 | A O |
| ATOM | 327 | N | ASN | 74 | 44.430 | 34.442 | 19.924 | 1.00 | 65.38 | A N |
| ATOM | 328 | CA | ASN | 74 | 45.411 | 35.273 | 19.236 | 1.00 | 63.38 | A C |
| ATOM | 329 | CB | ASN | 74 | 46.661 | 34.466 | 18.889 | 1.00 | 64.38 | A C |
| ATOM | 330 | CG | ASN | 74 | 47.654 | 34.422 | 20.034 | 1.00 | 66.10 | A C |
| ATOM | 331 | OD1 | ASN | 74 | 48.128 | 35.463 | 20.496 | 1.00 | 65.51 | A O |
| ATOM | 332 | ND2 | ASN | 74 | 47.973 | 33.216 | 20.503 | 1.00 | 66.62 | A N |
| ATOM | 333 | C | ASN | 74 | 44.794 | 35.859 | 17.977 | 1.00 | 61.55 | A C |
| ATOM | 334 | O | ASN | 74 | 45.384 | 36.714 | 17.318 | 1.00 | 62.15 | A O |
| ATOM | 335 | N | ASN | 75 | 43.597 | 35.390 | 17.647 | 1.00 | 58.67 | A N |
| ATOM | 336 | CA | ASN | 75 | 42.888 | 35.886 | 16.481 | 1.00 | 55.82 | A C |
| ATOM | 337 | CB | ASN | 75 | 42.023 | 34.785 | 15.871 | 1.00 | 57.81 | A C |
| ATOM | 338 | CG | ASN | 75 | 41.410 | 33.887 | 16.916 | 1.00 | 58.63 | A C |
| ATOM | 339 | OD1 | ASN | 75 | 40.857 | 34.358 | 17.909 | 1.00 | 59.69 | A O |
| ATOM | 340 | ND2 | ASN | 75 | 41.500 | 32.580 | 16.697 | 1.00 | 58.92 | A N |
| ATOM | 341 | C | ASN | 75 | 42.017 | 37.045 | 16.918 | 1.00 | 52.82 | A C |
| ATOM | 342 | O | ASN | 75 | 41.630 | 37.135 | 18.081 | 1.00 | 53.60 | A O |

FIG. 4-8 (Continued)

| | | | | | | | | | | |
|---|---|---|---|---|---|---|---|---|---|---|
| ATOM | 343 | N | ILE | 76 | 41.715 | 37.937 | 15.985 | 1.00 | 49.11 | A N |
| ATOM | 344 | CA | ILE | 76 | 40.893 | 39.091 | 16.294 | 1.00 | 44.67 | A C |
| ATOM | 345 | CB | ILE | 76 | 41.343 | 40.317 | 15.502 | 1.00 | 44.26 | A C |
| ATOM | 346 | CG2 | ILE | 76 | 40.565 | 41.533 | 15.956 | 1.00 | 43.37 | A C |
| ATOM | 347 | CG1 | ILE | 76 | 42.841 | 40.547 | 15.716 | 1.00 | 45.27 | A C |
| ATOM | 348 | CD1 | ILE | 76 | 43.435 | 41.647 | 14.844 | 1.00 | 45.53 | A C |
| ATOM | 349 | C | ILE | 76 | 39.446 | 38.786 | 15.964 | 1.00 | 42.80 | A C |
| ATOM | 350 | O | ILE | 76 | 39.127 | 38.322 | 14.868 | 1.00 | 41.85 | A O |
| ATOM | 351 | N | LEU | 77 | 38.574 | 39.045 | 16.930 | 1.00 | 40.36 | A N |
| ATOM | 352 | CA | LEU | 77 | 37.151 | 38.801 | 16.772 | 1.00 | 37.65 | A C |
| ATOM | 353 | CB | LEU | 77 | 36.636 | 37.948 | 17.933 | 1.00 | 36.65 | A C |
| ATOM | 354 | CG | LEU | 77 | 37.363 | 36.642 | 18.264 | 1.00 | 35.22 | A C |
| ATOM | 355 | CD1 | LEU | 77 | 36.600 | 35.926 | 19.361 | 1.00 | 34.43 | A C |
| ATOM | 356 | CD2 | LEU | 77 | 37.459 | 35.756 | 17.039 | 1.00 | 34.38 | A C |
| ATOM | 357 | C | LEU | 77 | 36.365 | 40.107 | 16.730 | 1.00 | 35.91 | A C |
| ATOM | 358 | O | LEU | 77 | 36.801 | 41.123 | 17.269 | 1.00 | 35.03 | A O |
| ATOM | 359 | N | VAL | 78 | 35.212 | 40.069 | 16.070 | 1.00 | 34.19 | A N |
| ATOM | 360 | CA | VAL | 78 | 34.330 | 41.226 | 15.981 | 1.00 | 31.96 | A C |
| ATOM | 361 | CB | VAL | 78 | 34.078 | 41.628 | 14.509 | 1.00 | 31.90 | A C |
| ATOM | 362 | CG1 | VAL | 78 | 33.612 | 40.420 | 13.704 | 1.00 | 31.34 | A C |
| ATOM | 363 | CG2 | VAL | 78 | 33.048 | 42.747 | 14.442 | 1.00 | 31.56 | A C |
| ATOM | 364 | C | VAL | 78 | 33.011 | 40.838 | 16.667 | 1.00 | 31.15 | A C |
| ATOM | 365 | O | VAL | 78 | 32.404 | 39.819 | 16.336 | 1.00 | 30.46 | A O |
| ATOM | 366 | N | PHE | 79 | 32.582 | 41.643 | 17.636 | 1.00 | 29.90 | A N |
| ATOM | 367 | CA | PHE | 79 | 31.358 | 41.357 | 18.379 | 1.00 | 28.93 | A C |
| ATOM | 368 | CB | PHE | 79 | 31.618 | 41.420 | 19.888 | 1.00 | 29.14 | A C |
| ATOM | 369 | CG | PHE | 79 | 32.357 | 40.238 | 20.440 | 1.00 | 28.39 | A C |
| ATOM | 370 | CD1 | PHE | 79 | 33.704 | 40.051 | 20.165 | 1.00 | 28.20 | A C |
| ATOM | 371 | CD2 | PHE | 79 | 31.701 | 39.314 | 21.243 | 1.00 | 27.22 | A C |
| ATOM | 372 | CE1 | PHE | 79 | 34.391 | 38.956 | 20.684 | 1.00 | 28.13 | A C |
| ATOM | 373 | CE2 | PHE | 79 | 32.374 | 38.219 | 21.764 | 1.00 | 27.53 | A C |
| ATOM | 374 | CZ | PHE | 79 | 33.725 | 38.040 | 21.483 | 1.00 | 27.59 | A C |
| ATOM | 375 | C | PHE | 79 | 30.186 | 42.281 | 18.091 | 1.00 | 29.06 | A C |
| ATOM | 376 | O | PHE | 79 | 30.354 | 43.487 | 17.912 | 1.00 | 28.29 | A O |
| ATOM | 377 | N | ASN | 80 | 28.990 | 41.704 | 18.058 | 1.00 | 27.80 | A N |
| ATOM | 378 | CA | ASN | 80 | 27.791 | 42.499 | 17.864 | 1.00 | 27.95 | A C |
| ATOM | 379 | CB | ASN | 80 | 26.681 | 41.670 | 17.209 | 1.00 | 27.03 | A C |
| ATOM | 380 | CG | ASN | 80 | 25.354 | 42.412 | 17.160 | 1.00 | 27.26 | A C |
| ATOM | 381 | OD1 | ASN | 80 | 24.679 | 42.587 | 18.182 | 1.00 | 26.87 | A O |
| ATOM | 382 | ND2 | ASN | 80 | 24.980 | 42.866 | 15.974 | 1.00 | 26.94 | A N |
| ATOM | 383 | C | ASN | 80 | 27.405 | 42.874 | 19.289 | 1.00 | 28.06 | A C |
| ATOM | 384 | O | ASN | 80 | 26.991 | 42.024 | 20.066 | 1.00 | 28.61 | A O |
| ATOM | 385 | N | ALA | 81 | 27.566 | 44.140 | 19.642 | 1.00 | 28.12 | A N |
| ATOM | 386 | CA | ALA | 81 | 27.250 | 44.579 | 20.991 | 1.00 | 29.16 | A C |
| ATOM | 387 | CB | ALA | 81 | 27.503 | 46.075 | 21.119 | 1.00 | 27.93 | A C |
| ATOM | 388 | C | ALA | 81 | 25.818 | 44.254 | 21.413 | 1.00 | 31.04 | A C |
| ATOM | 389 | O | ALA | 81 | 25.582 | 43.769 | 22.527 | 1.00 | 30.16 | A O |
| ATOM | 390 | N | GLU | 82 | 24.870 | 44.506 | 20.516 | 1.00 | 32.39 | A N |
| ATOM | 391 | CA | GLU | 82 | 23.461 | 44.282 | 20.809 | 1.00 | 34.46 | A C |

F I G. 4 - 9 (Continued)

| | | | | | | | | | | | |
|---|---|---|---|---|---|---|---|---|---|---|---|
| ATOM | 392 | CB | GLU | 82 | 22.602 | 44.794 | 19.655 | 1.00 | 36.97 | A | C |
| ATOM | 393 | CG | GLU | 82 | 21.115 | 44.827 | 19.968 | 1.00 | 40.49 | A | C |
| ATOM | 394 | CD | GLU | 82 | 20.313 | 45.538 | 18.894 | 1.00 | 44.05 | A | C |
| ATOM | 395 | OE1 | GLU | 82 | 20.343 | 45.087 | 17.726 | 1.00 | 45.13 | A | O |
| ATOM | 396 | OE2 | GLU | 82 | 19.652 | 46.551 | 19.220 | 1.00 | 45.61 | A | O |
| ATOM | 397 | C | GLU | 82 | 23.042 | 42.853 | 21.153 | 1.00 | 33.95 | A | C |
| ATOM | 398 | O | GLU | 82 | 22.055 | 42.662 | 21.864 | 1.00 | 32.29 | A | O |
| ATOM | 399 | N | TYR | 83 | 23.777 | 41.857 | 20.666 | 1.00 | 33.23 | A | N |
| ATOM | 400 | CA | TYR | 83 | 23.423 | 40.468 | 20.947 | 1.00 | 33.39 | A | C |
| ATOM | 401 | CB | TYR | 83 | 22.846 | 39.810 | 19.686 | 1.00 | 34.54 | A | C |
| ATOM | 402 | CG | TYR | 83 | 21.690 | 40.594 | 19.109 | 1.00 | 34.80 | A | C |
| ATOM | 403 | CD1 | TYR | 83 | 20.558 | 40.859 | 19.878 | 1.00 | 35.22 | A | C |
| ATOM | 404 | CE1 | TYR | 83 | 19.527 | 41.657 | 19.396 | 1.00 | 36.27 | A | C |
| ATOM | 405 | CD2 | TYR | 83 | 21.759 | 41.139 | 17.828 | 1.00 | 35.71 | A | C |
| ATOM | 406 | CE2 | TYR | 83 | 20.731 | 41.940 | 17.331 | 1.00 | 37.42 | A | C |
| ATOM | 407 | CZ | TYR | 83 | 19.619 | 42.200 | 18.125 | 1.00 | 37.70 | A | C |
| ATOM | 408 | OH | TYR | 83 | 18.624 | 43.044 | 17.675 | 1.00 | 37.69 | A | O |
| ATOM | 409 | C | TYR | 83 | 24.582 | 39.644 | 21.494 | 1.00 | 33.19 | A | C |
| ATOM | 410 | O | TYR | 83 | 24.396 | 38.511 | 21.934 | 1.00 | 32.91 | A | O |
| ATOM | 411 | N | GLY | 84 | 25.777 | 40.217 | 21.476 | 1.00 | 33.53 | A | N |
| ATOM | 412 | CA | GLY | 84 | 26.933 | 39.513 | 21.995 | 1.00 | 33.40 | A | C |
| ATOM | 413 | C | GLY | 84 | 27.454 | 38.395 | 21.114 | 1.00 | 33.92 | A | C |
| ATOM | 414 | O | GLY | 84 | 28.329 | 37.639 | 21.530 | 1.00 | 33.21 | A | O |
| ATOM | 415 | N | ASN | 85 | 26.918 | 38.269 | 19.904 | 1.00 | 35.26 | A | N |
| ATOM | 416 | CA | ASN | 85 | 27.388 | 37.233 | 18.993 | 1.00 | 37.43 | A | C |
| ATOM | 417 | CB | ASN | 85 | 26.258 | 36.780 | 18.072 | 1.00 | 38.34 | A | C |
| ATOM | 418 | CG | ASN | 85 | 25.764 | 37.878 | 17.166 | 1.00 | 40.02 | A | C |
| ATOM | 419 | OD1 | ASN | 85 | 25.694 | 39.040 | 17.561 | 1.00 | 39.96 | A | O |
| ATOM | 420 | ND2 | ASN | 85 | 25.394 | 37.496 | 15.950 | 1.00 | 41.91 | A | N |
| ATOM | 421 | C | ASN | 85 | 28.556 | 37.794 | 18.188 | 1.00 | 38.80 | A | C |
| ATOM | 422 | O | ASN | 85 | 28.687 | 39.011 | 18.035 | 1.00 | 40.05 | A | O |
| ATOM | 423 | N | SER | 86 | 29.410 | 36.920 | 17.670 | 1.00 | 39.14 | A | N |
| ATOM | 424 | CA | SER | 86 | 30.565 | 37.393 | 16.926 | 1.00 | 39.30 | A | C |
| ATOM | 425 | CB | SER | 86 | 31.723 | 37.587 | 17.895 | 1.00 | 38.90 | A | C |
| ATOM | 426 | OG | SER | 86 | 32.041 | 36.356 | 18.515 | 1.00 | 35.77 | A | O |
| ATOM | 427 | C | SER | 86 | 31.023 | 36.482 | 15.798 | 1.00 | 39.94 | A | C |
| ATOM | 428 | O | SER | 86 | 30.287 | 35.622 | 15.323 | 1.00 | 41.15 | A | O |
| ATOM | 429 | N | SER | 87 | 32.264 | 36.701 | 15.382 | 1.00 | 40.59 | A | N |
| ATOM | 430 | CA | SER | 87 | 32.916 | 35.929 | 14.333 | 1.00 | 40.98 | A | C |
| ATOM | 431 | CB | SER | 87 | 32.152 | 36.053 | 13.010 | 1.00 | 39.16 | A | C |
| ATOM | 432 | OG | SER | 87 | 31.727 | 37.376 | 12.789 | 1.00 | 39.90 | A | O |
| ATOM | 433 | C | SER | 87 | 34.353 | 36.433 | 14.194 | 1.00 | 41.10 | A | C |
| ATOM | 434 | O | SER | 87 | 34.691 | 37.517 | 14.682 | 1.00 | 41.07 | A | O |
| ATOM | 435 | N | VAL | 88 | 35.206 | 35.646 | 13.548 | 1.00 | 41.07 | A | N |
| ATOM | 436 | CA | VAL | 88 | 36.596 | 36.043 | 13.402 | 1.00 | 41.43 | A | C |
| ATOM | 437 | CB | VAL | 88 | 37.502 | 34.836 | 13.114 | 1.00 | 41.29 | A | C |
| ATOM | 438 | CG1 | VAL | 88 | 38.949 | 35.295 | 13.013 | 1.00 | 41.30 | A | C |
| ATOM | 439 | CG2 | VAL | 88 | 37.361 | 33.808 | 14.222 | 1.00 | 40.28 | A | C |
| ATOM | 440 | C | VAL | 88 | 36.827 | 37.096 | 12.331 | 1.00 | 41.63 | A | C |

| | | | | | | | | | | | |
|---|---|---|---|---|---|---|---|---|---|---|---|
| ATOM | 441 | O | VAL | 88 | 36.548 | 36.885 | 11.154 | 1.00 | 41.38 | A | O |
| ATOM | 442 | N | PHE | 89 | 37.343 | 38.238 | 12.767 | 1.00 | 42.23 | A | N |
| ATOM | 443 | CA | PHE | 89 | 37.641 | 39.347 | 11.880 | 1.00 | 42.51 | A | C |
| ATOM | 444 | CB | PHE | 89 | 37.769 | 40.637 | 12.699 | 1.00 | 40.84 | A | C |
| ATOM | 445 | CG | PHE | 89 | 37.990 | 41.865 | 11.870 | 1.00 | 39.96 | A | C |
| ATOM | 446 | CD1 | PHE | 89 | 39.217 | 42.103 | 11.265 | 1.00 | 39.62 | A | C |
| ATOM | 447 | CD2 | PHE | 89 | 36.963 | 42.778 | 11.678 | 1.00 | 40.08 | A | C |
| ATOM | 448 | CE1 | PHE | 89 | 39.415 | 43.231 | 10.480 | 1.00 | 39.60 | A | C |
| ATOM | 449 | CE2 | PHE | 89 | 37.154 | 43.911 | 10.894 | 1.00 | 39.87 | A | C |
| ATOM | 450 | CZ | PHE | 89 | 38.381 | 44.135 | 10.295 | 1.00 | 39.50 | A | C |
| ATOM | 451 | C | PHE | 89 | 38.956 | 39.021 | 11.186 | 1.00 | 43.57 | A | C |
| ATOM | 452 | O | PHE | 89 | 39.156 | 39.335 | 10.019 | 1.00 | 43.51 | A | O |
| ATOM | 453 | N | LEU | 90 | 39.851 | 38.376 | 11.921 | 1.00 | 45.92 | A | N |
| ATOM | 454 | CA | LEU | 90 | 41.143 | 38.001 | 11.380 | 1.00 | 48.60 | A | C |
| ATOM | 455 | CB | LEU | 90 | 42.071 | 39.213 | 11.366 | 1.00 | 48.66 | A | C |
| ATOM | 456 | CG | LEU | 90 | 43.033 | 39.305 | 10.184 | 1.00 | 49.47 | A | C |
| ATOM | 457 | CD1 | LEU | 90 | 42.236 | 39.408 | 8.889 | 1.00 | 50.17 | A | C |
| ATOM | 458 | CD2 | LEU | 90 | 43.933 | 40.515 | 10.346 | 1.00 | 49.94 | A | C |
| ATOM | 459 | C | LEU | 90 | 41.718 | 36.907 | 12.267 | 1.00 | 50.84 | A | C |
| ATOM | 460 | O | LEU | 90 | 42.063 | 37.159 | 13.421 | 1.00 | 50.91 | A | O |
| ATOM | 461 | N | GLU | 91 | 41.815 | 35.694 | 11.726 | 1.00 | 53.65 | A | N |
| ATOM | 462 | CA | GLU | 91 | 42.335 | 34.559 | 12.482 | 1.00 | 56.17 | A | C |
| ATOM | 463 | CB | GLU | 91 | 41.817 | 33.243 | 11.891 | 1.00 | 58.45 | A | C |
| ATOM | 464 | CG | GLU | 91 | 42.048 | 33.070 | 10.403 | 1.00 | 60.92 | A | C |
| ATOM | 465 | CD | GLU | 91 | 41.454 | 31.774 | 9.879 | 1.00 | 62.39 | A | C |
| ATOM | 466 | OE1 | GLU | 91 | 41.875 | 30.694 | 10.350 | 1.00 | 63.50 | A | O |
| ATOM | 467 | OE2 | GLU | 91 | 40.566 | 31.833 | 9.001 | 1.00 | 63.04 | A | O |
| ATOM | 468 | C | GLU | 91 | 43.855 | 34.521 | 12.588 | 1.00 | 56.96 | A | C |
| ATOM | 469 | O | GLU | 91 | 44.572 | 34.841 | 11.641 | 1.00 | 56.93 | A | O |
| ATOM | 470 | N | ASN | 92 | 44.322 | 34.117 | 13.766 | 1.00 | 57.64 | A | N |
| ATOM | 471 | CA | ASN | 92 | 45.738 | 34.028 | 14.100 | 1.00 | 58.91 | A | C |
| ATOM | 472 | CB | ASN | 92 | 45.881 | 33.389 | 15.477 | 1.00 | 59.59 | A | C |
| ATOM | 473 | CG | ASN | 92 | 45.129 | 32.082 | 15.585 | 1.00 | 59.68 | A | C |
| ATOM | 474 | OD1 | ASN | 92 | 45.189 | 31.248 | 14.684 | 1.00 | 59.97 | A | O |
| ATOM | 475 | ND2 | ASN | 92 | 44.420 | 31.894 | 16.691 | 1.00 | 61.11 | A | N |
| ATOM | 476 | C | ASN | 92 | 46.622 | 33.271 | 13.111 | 1.00 | 59.58 | A | C |
| ATOM | 477 | O | ASN | 92 | 47.806 | 33.061 | 13.370 | 1.00 | 59.03 | A | O |
| ATOM | 478 | N | SER | 93 | 46.059 | 32.862 | 11.984 | 1.00 | 60.45 | A | N |
| ATOM | 479 | CA | SER | 93 | 46.828 | 32.127 | 10.991 | 1.00 | 61.76 | A | C |
| ATOM | 480 | CB | SER | 93 | 45.978 | 30.985 | 10.427 | 1.00 | 62.43 | A | C |
| ATOM | 481 | OG | SER | 93 | 46.714 | 30.198 | 9.507 | 1.00 | 64.10 | A | O |
| ATOM | 482 | C | SER | 93 | 47.296 | 33.030 | 9.853 | 1.00 | 62.23 | A | C |
| ATOM | 483 | O | SER | 93 | 48.314 | 32.765 | 9.213 | 1.00 | 62.82 | A | O |
| ATOM | 484 | N | THR | 94 | 46.552 | 34.103 | 9.618 | 1.00 | 62.37 | A | N |
| ATOM | 485 | CA | THR | 94 | 46.852 | 35.036 | 8.541 | 1.00 | 62.69 | A | C |
| ATOM | 486 | CB | THR | 94 | 45.982 | 36.298 | 8.659 | 1.00 | 63.25 | A | C |
| ATOM | 487 | OG1 | THR | 94 | 46.469 | 37.302 | 7.759 | 1.00 | 63.59 | A | O |
| ATOM | 488 | CG2 | THR | 94 | 46.003 | 36.821 | 10.080 | 1.00 | 64.14 | A | C |
| ATOM | 489 | C | THR | 94 | 48.306 | 35.464 | 8.377 | 1.00 | 62.28 | A | C |

| | | | | | | | | | | |
|---|---|---|---|---|---|---|---|---|---|---|
| ATOM | 490 | O | THR | 94 | 48.882 | 35.295 | 7.303 | 1.00 | 61.92 | A | O |
| ATOM | 491 | N | PHE | 95 | 48.908 | 36.013 | 9.426 | 1.00 | 62.57 | A | N |
| ATOM | 492 | CA | PHE | 95 | 50.290 | 36.473 | 9.322 | 1.00 | 63.04 | A | C |
| ATOM | 493 | CB | PHE | 95 | 50.414 | 37.889 | 9.897 | 1.00 | 61.98 | A | C |
| ATOM | 494 | CG | PHE | 95 | 49.456 | 38.869 | 9.289 | 1.00 | 61.01 | A | C |
| ATOM | 495 | CD1 | PHE | 95 | 48.248 | 39.155 | 9.911 | 1.00 | 60.97 | A | C |
| ATOM | 496 | CD2 | PHE | 95 | 49.742 | 39.473 | 8.073 | 1.00 | 60.73 | A | C |
| ATOM | 497 | CE1 | PHE | 95 | 47.337 | 40.026 | 9.330 | 1.00 | 60.46 | A | C |
| ATOM | 498 | CE2 | PHE | 95 | 48.838 | 40.343 | 7.483 | 1.00 | 60.09 | A | C |
| ATOM | 499 | CZ | PHE | 95 | 47.633 | 40.621 | 8.113 | 1.00 | 61.07 | A | C |
| ATOM | 500 | C | PHE | 95 | 51.346 | 35.571 | 9.956 | 1.00 | 63.20 | A | C |
| ATOM | 501 | O | PHE | 95 | 52.178 | 36.035 | 10.736 | 1.00 | 63.66 | A | O |
| ATOM | 502 | N | ASP | 96 | 51.323 | 34.288 | 9.611 | 1.00 | 63.37 | A | N |
| ATOM | 503 | CA | ASP | 96 | 52.298 | 33.347 | 10.149 | 1.00 | 64.05 | A | C |
| ATOM | 504 | CB | ASP | 96 | 51.771 | 31.913 | 10.044 | 1.00 | 65.11 | A | C |
| ATOM | 505 | CG | ASP | 96 | 50.747 | 31.589 | 11.115 | 1.00 | 65.73 | A | C |
| ATOM | 506 | OD1 | ASP | 96 | 49.758 | 32.342 | 11.240 | 1.00 | 66.41 | A | O |
| ATOM | 507 | OD2 | ASP | 96 | 50.929 | 30.580 | 11.829 | 1.00 | 65.32 | A | O |
| ATOM | 508 | C | ASP | 96 | 53.621 | 33.470 | 9.399 | 1.00 | 63.82 | A | C |
| ATOM | 509 | O | ASP | 96 | 54.696 | 33.433 | 10.001 | 1.00 | 64.05 | A | O |
| ATOM | 510 | N | GLU | 97 | 53.540 | 33.619 | 8.083 | 1.00 | 62.95 | A | N |
| ATOM | 511 | CA | GLU | 97 | 54.740 | 33.754 | 7.271 | 1.00 | 62.73 | A | C |
| ATOM | 512 | CB | GLU | 97 | 54.596 | 32.964 | 5.965 | 1.00 | 65.91 | A | C |
| ATOM | 513 | CG | GLU | 97 | 54.954 | 31.478 | 6.064 | 1.00 | 68.84 | A | C |
| ATOM | 514 | CD | GLU | 97 | 53.945 | 30.657 | 6.850 | 1.00 | 70.64 | A | C |
| ATOM | 515 | OE1 | GLU | 97 | 54.160 | 29.432 | 6.988 | 1.00 | 71.38 | A | O |
| ATOM | 516 | OE2 | GLU | 97 | 52.939 | 31.228 | 7.325 | 1.00 | 71.80 | A | O |
| ATOM | 517 | C | GLU | 97 | 55.039 | 35.220 | 6.963 | 1.00 | 60.82 | A | C |
| ATOM | 518 | O | GLU | 97 | 55.462 | 35.557 | 5.857 | 1.00 | 60.31 | A | O |
| ATOM | 519 | N | PHE | 98 | 54.818 | 36.084 | 7.952 | 1.00 | 58.68 | A | N |
| ATOM | 520 | CA | PHE | 98 | 55.067 | 37.513 | 7.797 | 1.00 | 55.93 | A | C |
| ATOM | 521 | CB | PHE | 98 | 54.200 | 38.319 | 8.765 | 1.00 | 55.47 | A | C |
| ATOM | 522 | CG | PHE | 98 | 54.272 | 39.801 | 8.542 | 1.00 | 54.84 | A | C |
| ATOM | 523 | CD1 | PHE | 98 | 53.712 | 40.372 | 7.404 | 1.00 | 53.07 | A | C |
| ATOM | 524 | CD2 | PHE | 98 | 54.931 | 40.624 | 9.450 | 1.00 | 53.89 | A | C |
| ATOM | 525 | CE1 | PHE | 98 | 53.808 | 41.743 | 7.173 | 1.00 | 53.28 | A | C |
| ATOM | 526 | CE2 | PHE | 98 | 55.032 | 41.997 | 9.226 | 1.00 | 53.18 | A | C |
| ATOM | 527 | CZ | PHE | 98 | 54.470 | 42.556 | 8.087 | 1.00 | 52.22 | A | C |
| ATOM | 528 | C | PHE | 98 | 56.536 | 37.820 | 8.060 | 1.00 | 54.61 | A | C |
| ATOM | 529 | O | PHE | 98 | 57.041 | 38.878 | 7.686 | 1.00 | 53.80 | A | O |
| ATOM | 530 | N | GLY | 99 | 57.215 | 36.885 | 8.713 | 1.00 | 53.53 | A | N |
| ATOM | 531 | CA | GLY | 99 | 58.624 | 37.061 | 9.004 | 1.00 | 52.08 | A | C |
| ATOM | 532 | C | GLY | 99 | 58.908 | 38.188 | 9.972 | 1.00 | 51.18 | A | C |
| ATOM | 533 | O | GLY | 99 | 60.037 | 38.673 | 10.051 | 1.00 | 51.30 | A | O |
| ATOM | 534 | N | HIS | 100 | 57.884 | 38.607 | 10.706 | 1.00 | 50.21 | A | N |
| ATOM | 535 | CA | HIS | 100 | 58.026 | 39.681 | 11.686 | 1.00 | 49.15 | A | C |
| ATOM | 536 | CB | HIS | 100 | 57.810 | 41.049 | 11.028 | 1.00 | 48.84 | A | C |
| ATOM | 537 | CG | HIS | 100 | 58.850 | 41.410 | 10.014 | 1.00 | 49.22 | A | C |
| ATOM | 538 | CD2 | HIS | 100 | 58.759 | 41.613 | 8.679 | 1.00 | 49.42 | A | C |

| | | | | | | | | | | |
|---|---|---|---|---|---|---|---|---|---|---|
| ATOM | 539 | ND1 | HIS | 100 | 60.170 | 41.627 | 10.346 | 1.00 49.70 | A | N |
| ATOM | 540 | CE1 | HIS | 100 | 60.848 | 41.951 | 9.259 | 1.00 49.10 | A | C |
| ATOM | 541 | NE2 | HIS | 100 | 60.015 | 41.949 | 8.234 | 1.00 50.14 | A | N |
| ATOM | 542 | C | HIS | 100 | 57.011 | 39.511 | 12.810 | 1.00 48.06 | A | C |
| ATOM | 543 | O | HIS | 100 | 55.920 | 38.977 | 12.602 | 1.00 47.18 | A | O |
| ATOM | 544 | N | SER | 101 | 57.377 | 39.958 | 14.005 | 1.00 46.66 | A | N |
| ATOM | 545 | CA | SER | 101 | 56.467 | 39.878 | 15.136 | 1.00 45.88 | A | C |
| ATOM | 546 | CB | SER | 101 | 57.247 | 39.802 | 16.446 | 1.00 47.41 | A | C |
| ATOM | 547 | OG | SER | 101 | 58.118 | 38.685 | 16.447 | 1.00 51.04 | A | O |
| ATOM | 548 | C | SER | 101 | 55.617 | 41.142 | 15.112 | 1.00 44.53 | A | C |
| ATOM | 549 | O | SER | 101 | 56.133 | 42.248 | 15.282 | 1.00 44.41 | A | O |
| ATOM | 550 | N | ILE | 102 | 54.319 | 40.976 | 14.877 | 1.00 41.90 | A | N |
| ATOM | 551 | CA | ILE | 102 | 53.409 | 42.109 | 14.833 | 1.00 38.95 | A | C |
| ATOM | 552 | CB | ILE | 102 | 52.106 | 41.732 | 14.117 | 1.00 38.54 | A | C |
| ATOM | 553 | CG2 | ILE | 102 | 51.153 | 42.926 | 14.103 | 1.00 38.18 | A | C |
| ATOM | 554 | CG1 | ILE | 102 | 52.424 | 41.288 | 12.686 | 1.00 37.65 | A | C |
| ATOM | 555 | CD1 | ILE | 102 | 51.243 | 40.733 | 11.937 | 1.00 37.11 | A | C |
| ATOM | 556 | C | ILE | 102 | 53.104 | 42.597 | 16.244 | 1.00 38.00 | A | C |
| ATOM | 557 | O | ILE | 102 | 52.441 | 41.919 | 17.024 | 1.00 38.06 | A | O |
| ATOM | 558 | N | ASN | 103 | 53.601 | 43.787 | 16.556 | 1.00 37.54 | A | N |
| ATOM | 559 | CA | ASN | 103 | 53.429 | 44.399 | 17.867 | 1.00 36.65 | A | C |
| ATOM | 560 | CB | ASN | 103 | 54.437 | 45.530 | 18.039 | 1.00 37.69 | A | C |
| ATOM | 561 | CG | ASN | 103 | 54.219 | 46.308 | 19.315 | 1.00 39.56 | A | C |
| ATOM | 562 | OD1 | ASN | 103 | 54.655 | 45.891 | 20.388 | 1.00 43.00 | A | O |
| ATOM | 563 | ND2 | ASN | 103 | 53.528 | 47.439 | 19.211 | 1.00 38.34 | A | N |
| ATOM | 564 | C | ASN | 103 | 52.031 | 44.953 | 18.116 | 1.00 35.79 | A | C |
| ATOM | 565 | O | ASN | 103 | 51.532 | 44.910 | 19.237 | 1.00 35.79 | A | O |
| ATOM | 566 | N | ASP | 104 | 51.405 | 45.490 | 17.078 | 1.00 34.43 | A | N |
| ATOM | 567 | CA | ASP | 104 | 50.079 | 46.067 | 17.236 | 1.00 33.27 | A | C |
| ATOM | 568 | CB | ASP | 104 | 50.200 | 47.388 | 17.998 | 1.00 34.38 | A | C |
| ATOM | 569 | CG | ASP | 104 | 48.896 | 47.823 | 18.618 | 1.00 34.79 | A | C |
| ATOM | 570 | OD1 | ASP | 104 | 48.916 | 48.699 | 19.509 | 1.00 33.92 | A | O |
| ATOM | 571 | OD2 | ASP | 104 | 47.852 | 47.289 | 18.207 | 1.00 36.80 | A | O |
| ATOM | 572 | C | ASP | 104 | 49.436 | 46.281 | 15.865 | 1.00 32.32 | A | C |
| ATOM | 573 | O | ASP | 104 | 50.124 | 46.326 | 14.850 | 1.00 32.03 | A | O |
| ATOM | 574 | N | TYR | 105 | 48.118 | 46.405 | 15.834 | 1.00 31.15 | A | N |
| ATOM | 575 | CA | TYR | 105 | 47.421 | 46.580 | 14.570 | 1.00 32.24 | A | C |
| ATOM | 576 | CB | TYR | 105 | 46.672 | 45.296 | 14.223 | 1.00 34.70 | A | C |
| ATOM | 577 | CG | TYR | 105 | 45.443 | 45.088 | 15.072 | 1.00 37.73 | A | C |
| ATOM | 578 | CD1 | TYR | 105 | 44.220 | 45.636 | 14.698 | 1.00 37.51 | A | C |
| ATOM | 579 | CE1 | TYR | 105 | 43.098 | 45.510 | 15.506 | 1.00 40.43 | A | C |
| ATOM | 580 | CD2 | TYR | 105 | 45.514 | 44.395 | 16.284 | 1.00 39.06 | A | C |
| ATOM | 581 | CE2 | TYR | 105 | 44.393 | 44.263 | 17.103 | 1.00 40.75 | A | C |
| ATOM | 582 | CZ | TYR | 105 | 43.191 | 44.829 | 16.705 | 1.00 41.19 | A | C |
| ATOM | 583 | OH | TYR | 105 | 42.088 | 44.755 | 17.519 | 1.00 44.27 | A | O |
| ATOM | 584 | C | TYR | 105 | 46.441 | 47.743 | 14.638 | 1.00 31.43 | A | C |
| ATOM | 585 | O | TYR | 105 | 46.133 | 48.249 | 15.715 | 1.00 30.78 | A | O |
| ATOM | 586 | N | SER | 106 | 45.940 | 48.152 | 13.479 | 1.00 30.16 | A | N |
| ATOM | 587 | CA | SER | 106 | 45.000 | 49.261 | 13.415 | 1.00 29.23 | A | C |

FIG. 4-13 (Continued)

| | | | | | | | | | | | |
|---|---|---|---|---|---|---|---|---|---|---|---|
| ATOM | 588 | CB | SER | 106 | 45.762 | 50.588 | 13.457 | 1.00 | 29.81 | A | C |
| ATOM | 589 | OG | SER | 106 | 44.924 | 51.668 | 13.090 | 1.00 | 32.32 | A | O |
| ATOM | 590 | C | SER | 106 | 44.146 | 49.187 | 12.157 | 1.00 | 27.65 | A | C |
| ATOM | 591 | O | SER | 106 | 44.657 | 49.085 | 11.051 | 1.00 | 28.57 | A | O |
| ATOM | 592 | N | ILE | 107 | 42.835 | 49.240 | 12.331 | 1.00 | 28.07 | A | N |
| ATOM | 593 | CA | ILE | 107 | 41.922 | 49.171 | 11.198 | 1.00 | 27.70 | A | C |
| ATOM | 594 | CB | ILE | 107 | 40.648 | 48.352 | 11.544 | 1.00 | 25.83 | A | C |
| ATOM | 595 | CG2 | ILE | 107 | 39.557 | 48.620 | 10.522 | 1.00 | 26.35 | A | C |
| ATOM | 596 | CG1 | ILE | 107 | 40.970 | 46.859 | 11.551 | 1.00 | 25.36 | A | C |
| ATOM | 597 | CD1 | ILE | 107 | 41.980 | 46.457 | 12.568 | 1.00 | 23.77 | A | C |
| ATOM | 598 | C | ILE | 107 | 41.502 | 50.556 | 10.743 | 1.00 | 26.85 | A | C |
| ATOM | 599 | O | ILE | 107 | 41.178 | 51.420 | 11.557 | 1.00 | 26.55 | A | O |
| ATOM | 600 | N | SER | 108 | 41.507 | 50.757 | 9.432 | 1.00 | 27.57 | A | N |
| ATOM | 601 | CA | SER | 108 | 41.113 | 52.035 | 8.862 | 1.00 | 26.94 | A | C |
| ATOM | 602 | CB | SER | 108 | 41.331 | 52.033 | 7.346 | 1.00 | 26.30 | A | C |
| ATOM | 603 | OG | SER | 108 | 40.458 | 51.119 | 6.700 | 1.00 | 23.63 | A | O |
| ATOM | 604 | C | SER | 108 | 39.639 | 52.253 | 9.169 | 1.00 | 27.22 | A | C |
| ATOM | 605 | O | SER | 108 | 38.857 | 51.310 | 9.206 | 1.00 | 26.49 | A | O |
| ATOM | 606 | N | PRO | 109 | 39.241 | 53.506 | 9.393 | 1.00 | 28.50 | A | N |
| ATOM | 607 | CD | PRO | 109 | 40.025 | 54.751 | 9.302 | 1.00 | 29.19 | A | C |
| ATOM | 608 | CA | PRO | 109 | 37.839 | 53.794 | 9.693 | 1.00 | 29.39 | A | C |
| ATOM | 609 | CB | PRO | 109 | 37.745 | 55.294 | 9.439 | 1.00 | 30.19 | A | C |
| ATOM | 610 | CG | PRO | 109 | 39.080 | 55.775 | 9.899 | 1.00 | 28.76 | A | C |
| ATOM | 611 | C | PRO | 109 | 36.842 | 52.993 | 8.852 | 1.00 | 29.21 | A | C |
| ATOM | 612 | O | PRO | 109 | 35.901 | 52.425 | 9.391 | 1.00 | 30.65 | A | O |
| ATOM | 613 | N | ASP | 110 | 37.046 | 52.935 | 7.540 | 1.00 | 29.41 | A | N |
| ATOM | 614 | CA | ASP | 110 | 36.120 | 52.202 | 6.676 | 1.00 | 28.98 | A | C |
| ATOM | 615 | CB | ASP | 110 | 36.241 | 52.673 | 5.226 | 1.00 | 27.99 | A | C |
| ATOM | 616 | CG | ASP | 110 | 37.613 | 52.432 | 4.648 | 1.00 | 27.91 | A | C |
| ATOM | 617 | OD1 | ASP | 110 | 38.226 | 51.397 | 4.976 | 1.00 | 28.41 | A | O |
| ATOM | 618 | OD2 | ASP | 110 | 38.075 | 53.274 | 3.852 | 1.00 | 29.14 | A | O |
| ATOM | 619 | C | ASP | 110 | 36.280 | 50.685 | 6.715 | 1.00 | 29.06 | A | C |
| ATOM | 620 | O | ASP | 110 | 35.635 | 49.971 | 5.953 | 1.00 | 30.84 | A | O |
| ATOM | 621 | N | GLY | 111 | 37.148 | 50.196 | 7.589 | 1.00 | 28.25 | A | N |
| ATOM | 622 | CA | GLY | 111 | 37.349 | 48.766 | 7.702 | 1.00 | 28.14 | A | C |
| ATOM | 623 | C | GLY | 111 | 37.890 | 48.064 | 6.470 | 1.00 | 29.53 | A | C |
| ATOM | 624 | O | GLY | 111 | 37.856 | 46.837 | 6.402 | 1.00 | 31.16 | A | O |
| ATOM | 625 | N | GLN | 112 | 38.405 | 48.818 | 5.503 | 1.00 | 29.61 | A | N |
| ATOM | 626 | CA | GLN | 112 | 38.946 | 48.217 | 4.287 | 1.00 | 29.74 | A | C |
| ATOM | 627 | CB | GLN | 112 | 38.777 | 49.171 | 3.109 | 1.00 | 29.94 | A | C |
| ATOM | 628 | CG | GLN | 112 | 37.336 | 49.442 | 2.749 | 1.00 | 31.79 | A | C |
| ATOM | 629 | CD | GLN | 112 | 37.191 | 50.234 | 1.465 | 1.00 | 33.24 | A | C |
| ATOM | 630 | OE1 | GLN | 112 | 36.075 | 50.474 | 1.004 | 1.00 | 36.27 | A | O |
| ATOM | 631 | NE2 | GLN | 112 | 38.314 | 50.644 | 0.880 | 1.00 | 31.73 | A | N |
| ATOM | 632 | C | GLN | 112 | 40.415 | 47.813 | 4.390 | 1.00 | 30.31 | A | C |
| ATOM | 633 | O | GLN | 112 | 40.888 | 46.971 | 3.631 | 1.00 | 31.75 | A | O |
| ATOM | 634 | N | PHE | 113 | 41.141 | 48.418 | 5.320 | 1.00 | 29.82 | A | N |
| ATOM | 635 | CA | PHE | 113 | 42.551 | 48.106 | 5.486 | 1.00 | 28.23 | A | C |
| ATOM | 636 | CB | PHE | 113 | 43.428 | 49.207 | 4.900 | 1.00 | 24.48 | A | C |

FIG. 4-14

| | | | | | | | | | | | |
|---|---|---|---|---|---|---|---|---|---|---|---|
| ATOM | 637 | CG | PHE | 113 | 43.193 | 49.467 | 3.458 | 1.00 | 22.98 | A | C |
| ATOM | 638 | CD1 | PHE | 113 | 42.164 | 50.301 | 3.052 | 1.00 | 20.83 | A | C |
| ATOM | 639 | CD2 | PHE | 113 | 44.010 | 48.880 | 2.496 | 1.00 | 23.28 | A | C |
| ATOM | 640 | CE1 | PHE | 113 | 41.950 | 50.552 | 1.709 | 1.00 | 20.79 | A | C |
| ATOM | 641 | CE2 | PHE | 113 | 43.805 | 49.121 | 1.150 | 1.00 | 22.78 | A | C |
| ATOM | 642 | CZ | PHE | 113 | 42.771 | 49.962 | 0.754 | 1.00 | 22.17 | A | C |
| ATOM | 643 | C | PHE | 113 | 42.919 | 47.974 | 6.947 | 1.00 | 30.31 | A | C |
| ATOM | 644 | O | PHE | 113 | 42.234 | 48.511 | 7.827 | 1.00 | 31.09 | A | O |
| ATOM | 645 | N | ILE | 114 | 44.013 | 47.260 | 7.196 | 1.00 | 29.70 | A | N |
| ATOM | 646 | CA | ILE | 114 | 44.521 | 47.092 | 8.542 | 1.00 | 30.73 | A | C |
| ATOM | 647 | CB | ILE | 114 | 44.342 | 45.642 | 9.075 | 1.00 | 31.72 | A | C |
| ATOM | 648 | CG2 | ILE | 114 | 44.804 | 44.633 | 8.042 | 1.00 | 33.03 | A | C |
| ATOM | 649 | CG1 | ILE | 114 | 45.128 | 45.475 | 10.381 | 1.00 | 32.62 | A | C |
| ATOM | 650 | CD1 | ILE | 114 | 45.028 | 44.092 | 11.007 | 1.00 | 33.60 | A | C |
| ATOM | 651 | C | ILE | 114 | 46.000 | 47.457 | 8.509 | 1.00 | 30.59 | A | C |
| ATOM | 652 | O | ILE | 114 | 46.754 | 46.974 | 7.661 | 1.00 | 28.76 | A | O |
| ATOM | 653 | N | LEU | 115 | 46.388 | 48.343 | 9.423 | 1.00 | 30.68 | A | N |
| ATOM | 654 | CA | LEU | 115 | 47.759 | 48.814 | 9.543 | 1.00 | 29.92 | A | C |
| ATOM | 655 | CB | LEU | 115 | 47.769 | 50.257 | 10.053 | 1.00 | 30.35 | A | C |
| ATOM | 656 | CG | LEU | 115 | 49.135 | 50.941 | 10.131 | 1.00 | 31.72 | A | C |
| ATOM | 657 | CD1 | LEU | 115 | 49.668 | 51.147 | 8.718 | 1.00 | 33.17 | A | C |
| ATOM | 658 | CD2 | LEU | 115 | 49.018 | 52.271 | 10.857 | 1.00 | 30.77 | A | C |
| ATOM | 659 | C | LEU | 115 | 48.481 | 47.911 | 10.530 | 1.00 | 29.61 | A | C |
| ATOM | 660 | O | LEU | 115 | 48.127 | 47.861 | 11.707 | 1.00 | 30.77 | A | O |
| ATOM | 661 | N | LEU | 116 | 49.484 | 47.188 | 10.048 | 1.00 | 28.74 | A | N |
| ATOM | 662 | CA | LEU | 116 | 50.245 | 46.278 | 10.891 | 1.00 | 28.06 | A | C |
| ATOM | 663 | CB | LEU | 116 | 50.624 | 45.023 | 10.103 | 1.00 | 30.07 | A | C |
| ATOM | 664 | CG | LEU | 116 | 49.450 | 44.251 | 9.481 | 1.00 | 30.51 | A | C |
| ATOM | 665 | CD1 | LEU | 116 | 49.978 | 43.171 | 8.570 | 1.00 | 31.10 | A | C |
| ATOM | 666 | CD2 | LEU | 116 | 48.583 | 43.644 | 10.573 | 1.00 | 30.99 | A | C |
| ATOM | 667 | C | LEU | 116 | 51.489 | 46.997 | 11.363 | 1.00 | 28.28 | A | C |
| ATOM | 668 | O | LEU | 116 | 52.145 | 47.690 | 10.591 | 1.00 | 30.37 | A | O |
| ATOM | 669 | N | GLU | 117 | 51.813 | 46.824 | 12.634 | 1.00 | 27.78 | A | N |
| ATOM | 670 | CA | GLU | 117 | 52.962 | 47.484 | 13.227 | 1.00 | 26.58 | A | C |
| ATOM | 671 | CB | GLU | 117 | 52.476 | 48.358 | 14.382 | 1.00 | 25.51 | A | C |
| ATOM | 672 | CG | GLU | 117 | 53.510 | 49.241 | 15.036 | 1.00 | 23.69 | A | C |
| ATOM | 673 | CD | GLU | 117 | 52.897 | 50.076 | 16.138 | 1.00 | 27.72 | A | C |
| ATOM | 674 | OE1 | GLU | 117 | 52.732 | 49.572 | 17.268 | 1.00 | 29.08 | A | O |
| ATOM | 675 | OE2 | GLU | 117 | 52.552 | 51.242 | 15.868 | 1.00 | 30.62 | A | O |
| ATOM | 676 | C | GLU | 117 | 53.997 | 46.491 | 13.738 | 1.00 | 27.81 | A | C |
| ATOM | 677 | O | GLU | 117 | 53.666 | 45.586 | 14.506 | 1.00 | 27.41 | A | O |
| ATOM | 678 | N | TYR | 118 | 55.247 | 46.663 | 13.313 | 1.00 | 27.75 | A | N |
| ATOM | 679 | CA | TYR | 118 | 56.327 | 45.796 | 13.765 | 1.00 | 29.68 | A | C |
| ATOM | 680 | CB | TYR | 118 | 56.473 | 44.586 | 12.837 | 1.00 | 29.52 | A | C |
| ATOM | 681 | CG | TYR | 118 | 56.819 | 44.903 | 11.402 | 1.00 | 28.58 | A | C |
| ATOM | 682 | CD1 | TYR | 118 | 55.922 | 45.572 | 10.573 | 1.00 | 29.31 | A | C |
| ATOM | 683 | CE1 | TYR | 118 | 56.236 | 45.838 | 9.239 | 1.00 | 28.13 | A | C |
| ATOM | 684 | CD2 | TYR | 118 | 58.040 | 44.510 | 10.864 | 1.00 | 28.81 | A | C |
| ATOM | 685 | CE2 | TYR | 118 | 58.362 | 44.769 | 9.541 | 1.00 | 27.91 | A | C |

| | | | | | | | | | | |
|---|---|---|---|---|---|---|---|---|---|---|
| ATOM | 686 | CZ | TYR | 118 | 57.459 | 45.431 | 8.735 | 1.00 | 28.04 | A C |
| ATOM | 687 | OH | TYR | 118 | 57.792 | 45.681 | 7.427 | 1.00 | 29.86 | A O |
| ATOM | 688 | C | TYR | 118 | 57.641 | 46.572 | 13.863 | 1.00 | 31.53 | A C |
| ATOM | 689 | O | TYR | 118 | 57.683 | 47.763 | 13.550 | 1.00 | 32.24 | A O |
| ATOM | 690 | N | ASN | 119 | 58.708 | 45.903 | 14.295 | 1.00 | 32.40 | A N |
| ATOM | 691 | CA | ASN | 119 | 60.008 | 46.557 | 14.459 | 1.00 | 33.64 | A C |
| ATOM | 692 | CB | ASN | 119 | 60.511 | 47.128 | 13.131 | 1.00 | 35.42 | A C |
| ATOM | 693 | CG | ASN | 119 | 61.069 | 46.066 | 12.207 | 1.00 | 36.36 | A C |
| ATOM | 694 | OD1 | ASN | 119 | 61.958 | 45.306 | 12.584 | 1.00 | 37.66 | A O |
| ATOM | 695 | ND2 | ASN | 119 | 60.560 | 46.021 | 10.983 | 1.00 | 37.41 | A N |
| ATOM | 696 | C | ASN | 119 | 59.875 | 47.697 | 15.464 | 1.00 | 34.07 | A C |
| ATOM | 697 | O | ASN | 119 | 60.548 | 48.719 | 15.348 | 1.00 | 34.50 | A O |
| ATOM | 698 | N | TYR | 120 | 58.996 | 47.514 | 16.443 | 1.00 | 33.92 | A N |
| ATOM | 699 | CA | TYR | 120 | 58.741 | 48.517 | 17.472 | 1.00 | 33.38 | A C |
| ATOM | 700 | CB | TYR | 120 | 57.510 | 48.097 | 18.290 | 1.00 | 33.40 | A C |
| ATOM | 701 | CG | TYR | 120 | 57.290 | 48.870 | 19.569 | 1.00 | 33.30 | A C |
| ATOM | 702 | CD1 | TYR | 120 | 58.029 | 48.582 | 20.715 | 1.00 | 33.37 | A C |
| ATOM | 703 | CE1 | TYR | 120 | 57.818 | 49.284 | 21.902 | 1.00 | 34.88 | A C |
| ATOM | 704 | CD2 | TYR | 120 | 56.333 | 49.886 | 19.636 | 1.00 | 33.62 | A C |
| ATOM | 705 | CE2 | TYR | 120 | 56.114 | 50.596 | 20.813 | 1.00 | 32.73 | A C |
| ATOM | 706 | CZ | TYR | 120 | 56.859 | 50.289 | 21.944 | 1.00 | 35.24 | A C |
| ATOM | 707 | OH | TYR | 120 | 56.643 | 50.977 | 23.121 | 1.00 | 37.51 | A O |
| ATOM | 708 | C | TYR | 120 | 59.933 | 48.772 | 18.396 | 1.00 | 33.12 | A C |
| ATOM | 709 | O | TYR | 120 | 60.472 | 47.849 | 19.007 | 1.00 | 33.80 | A O |
| ATOM | 710 | N | VAL | 121 | 60.330 | 50.038 | 18.491 | 1.00 | 31.69 | A N |
| ATOM | 711 | CA | VAL | 121 | 61.441 | 50.446 | 19.343 | 1.00 | 30.32 | A C |
| ATOM | 712 | CB | VAL | 121 | 62.672 | 50.845 | 18.504 | 1.00 | 30.75 | A C |
| ATOM | 713 | CG1 | VAL | 121 | 63.853 | 51.140 | 19.420 | 1.00 | 28.68 | A C |
| ATOM | 714 | CG2 | VAL | 121 | 63.013 | 49.736 | 17.525 | 1.00 | 29.00 | A C |
| ATOM | 715 | C | VAL | 121 | 61.008 | 51.645 | 20.190 | 1.00 | 29.83 | A C |
| ATOM | 716 | O | VAL | 121 | 60.788 | 52.738 | 19.670 | 1.00 | 30.47 | A O |
| ATOM | 717 | N | LYS | 122 | 60.889 | 51.434 | 21.495 | 1.00 | 28.18 | A N |
| ATOM | 718 | CA | LYS | 122 | 60.464 | 52.488 | 22.404 | 1.00 | 27.02 | A C |
| ATOM | 719 | CB | LYS | 122 | 60.214 | 51.910 | 23.799 | 1.00 | 23.73 | A C |
| ATOM | 720 | CG | LYS | 122 | 59.793 | 52.954 | 24.819 | 1.00 | 21.38 | A C |
| ATOM | 721 | CD | LYS | 122 | 59.573 | 52.354 | 26.191 | 1.00 | 20.47 | A C |
| ATOM | 722 | CE | LYS | 122 | 59.078 | 53.406 | 27.174 | 1.00 | 19.23 | A C |
| ATOM | 723 | NZ | LYS | 122 | 60.062 | 54.510 | 27.346 | 1.00 | 18.20 | A N |
| ATOM | 724 | C | LYS | 122 | 61.460 | 53.635 | 22.528 | 1.00 | 27.64 | A C |
| ATOM | 725 | O | LYS | 122 | 62.658 | 53.464 | 22.315 | 1.00 | 28.10 | A O |
| ATOM | 726 | N | GLN | 123 | 60.947 | 54.813 | 22.860 | 1.00 | 27.23 | A N |
| ATOM | 727 | CA | GLN | 123 | 61.791 | 55.979 | 23.071 | 1.00 | 27.82 | A C |
| ATOM | 728 | CB | GLN | 123 | 61.607 | 57.034 | 21.974 | 1.00 | 28.29 | A C |
| ATOM | 729 | CG | GLN | 123 | 62.537 | 58.227 | 22.164 | 1.00 | 28.94 | A C |
| ATOM | 730 | CD | GLN | 123 | 62.339 | 59.308 | 21.131 | 1.00 | 29.91 | A C |
| ATOM | 731 | OE1 | GLN | 123 | 61.218 | 59.744 | 20.889 | 1.00 | 32.37 | A O |
| ATOM | 732 | NE2 | GLN | 123 | 63.431 | 59.761 | 20.524 | 1.00 | 30.94 | A N |
| ATOM | 733 | C | GLN | 123 | 61.385 | 56.545 | 24.428 | 1.00 | 26.89 | A C |
| ATOM | 734 | O | GLN | 123 | 61.837 | 56.036 | 25.453 | 1.00 | 27.03 | A O |

FIG. 4-16 (Continued)

| | | | | | | | | | | | |
|---|---|---|---|---|---|---|---|---|---|---|---|
| ATOM | 735 | N | TRP | 124 | 60.522 | 57.564 | 24.444 | 1.00 | 23.89 | A | N |
| ATOM | 736 | CA | TRP | 124 | 60.081 | 58.149 | 25.713 | 1.00 | 24.21 | A | C |
| ATOM | 737 | CB | TRP | 124 | 59.886 | 59.665 | 25.572 | 1.00 | 23.25 | A | C |
| ATOM | 738 | CG | TRP | 124 | 61.052 | 60.357 | 24.934 | 1.00 | 19.79 | A | C |
| ATOM | 739 | CD2 | TRP | 124 | 62.444 | 60.061 | 25.127 | 1.00 | 19.03 | A | C |
| ATOM | 740 | CE2 | TRP | 124 | 63.175 | 60.913 | 24.270 | 1.00 | 19.13 | A | C |
| ATOM | 741 | CE3 | TRP | 124 | 63.143 | 59.157 | 25.936 | 1.00 | 15.51 | A | C |
| ATOM | 742 | CD1 | TRP | 124 | 60.999 | 61.350 | 24.006 | 1.00 | 18.84 | A | C |
| ATOM | 743 | NE1 | TRP | 124 | 62.270 | 61.690 | 23.597 | 1.00 | 18.74 | A | N |
| ATOM | 744 | CZ2 | TRP | 124 | 64.571 | 60.885 | 24.196 | 1.00 | 17.77 | A | C |
| ATOM | 745 | CZ3 | TRP | 124 | 64.533 | 59.129 | 25.860 | 1.00 | 15.41 | A | C |
| ATOM | 746 | CH2 | TRP | 124 | 65.229 | 59.986 | 24.996 | 1.00 | 17.07 | A | C |
| ATOM | 747 | C | TRP | 124 | 58.787 | 57.494 | 26.209 | 1.00 | 24.57 | A | C |
| ATOM | 748 | O | TRP | 124 | 58.490 | 56.350 | 25.861 | 1.00 | 25.71 | A | O |
| ATOM | 749 | N | ARG | 125 | 58.013 | 58.218 | 27.013 | 1.00 | 24.36 | A | N |
| ATOM | 750 | CA | ARG | 125 | 56.779 | 57.670 | 27.567 | 1.00 | 23.36 | A | C |
| ATOM | 751 | CB | ARG | 125 | 56.189 | 58.621 | 28.609 | 1.00 | 23.81 | A | C |
| ATOM | 752 | CG | ARG | 125 | 54.953 | 58.065 | 29.308 | 1.00 | 23.85 | A | C |
| ATOM | 753 | CD | ARG | 125 | 54.273 | 59.129 | 30.143 | 1.00 | 26.24 | A | C |
| ATOM | 754 | NE | ARG | 125 | 55.090 | 59.579 | 31.269 | 1.00 | 25.99 | A | N |
| ATOM | 755 | CZ | ARG | 125 | 55.293 | 58.867 | 32.372 | 1.00 | 26.04 | A | C |
| ATOM | 756 | NH1 | ARG | 125 | 56.051 | 59.357 | 33.347 | 1.00 | 24.42 | A | N |
| ATOM | 757 | NH2 | ARG | 125 | 54.735 | 57.668 | 32.500 | 1.00 | 25.19 | A | N |
| ATOM | 758 | C | ARG | 125 | 55.706 | 57.324 | 26.541 | 1.00 | 24.00 | A | C |
| ATOM | 759 | O | ARG | 125 | 54.935 | 56.387 | 26.752 | 1.00 | 25.04 | A | O |
| ATOM | 760 | N | HIS | 126 | 55.651 | 58.063 | 25.436 | 1.00 | 23.33 | A | N |
| ATOM | 761 | CA | HIS | 126 | 54.649 | 57.800 | 24.403 | 1.00 | 22.86 | A | C |
| ATOM | 762 | CB | HIS | 126 | 53.649 | 58.943 | 24.353 | 1.00 | 21.14 | A | C |
| ATOM | 763 | CG | HIS | 126 | 52.987 | 59.224 | 25.662 | 1.00 | 22.35 | A | C |
| ATOM | 764 | CD2 | HIS | 126 | 53.027 | 60.316 | 26.463 | 1.00 | 21.51 | A | C |
| ATOM | 765 | ND1 | HIS | 126 | 52.137 | 58.329 | 26.274 | 1.00 | 22.03 | A | N |
| ATOM | 766 | CE1 | HIS | 126 | 51.679 | 58.859 | 27.395 | 1.00 | 23.59 | A | C |
| ATOM | 767 | NE2 | HIS | 126 | 52.202 | 60.064 | 27.532 | 1.00 | 22.48 | A | N |
| ATOM | 768 | C | HIS | 126 | 55.222 | 57.599 | 22.995 | 1.00 | 24.43 | A | C |
| ATOM | 769 | O | HIS | 126 | 54.599 | 56.947 | 22.153 | 1.00 | 23.99 | A | O |
| ATOM | 770 | N | SER | 127 | 56.401 | 58.163 | 22.744 | 1.00 | 23.89 | A | N |
| ATOM | 771 | CA | SER | 127 | 57.039 | 58.072 | 21.434 | 1.00 | 24.38 | A | C |
| ATOM | 772 | CB | SER | 127 | 58.050 | 59.213 | 21.267 | 1.00 | 23.49 | A | C |
| ATOM | 773 | OG | SER | 127 | 58.909 | 59.311 | 22.387 | 1.00 | 23.05 | A | O |
| ATOM | 774 | C | SER | 127 | 57.737 | 56.748 | 21.146 | 1.00 | 24.40 | A | C |
| ATOM | 775 | O | SER | 127 | 58.167 | 56.050 | 22.061 | 1.00 | 26.55 | A | O |
| ATOM | 776 | N | TYR | 128 | 57.841 | 56.420 | 19.861 | 1.00 | 22.67 | A | N |
| ATOM | 777 | CA | TYR | 128 | 58.501 | 55.207 | 19.403 | 1.00 | 22.06 | A | C |
| ATOM | 778 | CB | TYR | 128 | 57.787 | 53.962 | 19.928 | 1.00 | 21.99 | A | C |
| ATOM | 779 | CG | TYR | 128 | 56.413 | 53.712 | 19.331 | 1.00 | 22.49 | A | C |
| ATOM | 780 | CD1 | TYR | 128 | 55.257 | 54.112 | 20.003 | 1.00 | 23.20 | A | C |
| ATOM | 781 | CE1 | TYR | 128 | 53.992 | 53.857 | 19.487 | 1.00 | 19.81 | A | C |
| ATOM | 782 | CD2 | TYR | 128 | 56.267 | 53.049 | 18.109 | 1.00 | 20.70 | A | C |
| ATOM | 783 | CE2 | TYR | 128 | 55.007 | 52.791 | 17.580 | 1.00 | 20.87 | A | C |

| | | | | | | | | | | | |
|---|---|---|---|---|---|---|---|---|---|---|---|
| ATOM | 784 | CZ | TYR | 128 | 53.872 | 53.197 | 18.279 | 1.00 | 22.39 | A | C |
| ATOM | 785 | OH | TYR | 128 | 52.614 | 52.946 | 17.776 | 1.00 | 19.88 | A | O |
| ATOM | 786 | C | TYR | 128 | 58.509 | 55.160 | 17.882 | 1.00 | 22.84 | A | C |
| ATOM | 787 | O | TYR | 128 | 57.800 | 55.922 | 17.224 | 1.00 | 24.63 | A | O |
| ATOM | 788 | N | THR | 129 | 59.328 | 54.281 | 17.320 | 1.00 | 22.88 | A | N |
| ATOM | 789 | CA | THR | 129 | 59.360 | 54.125 | 15.874 | 1.00 | 25.24 | A | C |
| ATOM | 790 | CB | THR | 129 | 60.723 | 54.474 | 15.245 | 1.00 | 27.54 | A | C |
| ATOM | 791 | OG1 | THR | 129 | 61.756 | 53.676 | 15.844 | 1.00 | 33.01 | A | O |
| ATOM | 792 | CG2 | THR | 129 | 61.025 | 55.951 | 15.419 | 1.00 | 28.79 | A | C |
| ATOM | 793 | C | THR | 129 | 59.062 | 52.675 | 15.580 | 1.00 | 24.85 | A | C |
| ATOM | 794 | O | THR | 129 | 59.168 | 51.811 | 16.457 | 1.00 | 22.29 | A | O |
| ATOM | 795 | N | ALA | 130 | 58.692 | 52.411 | 14.337 | 1.00 | 24.54 | A | N |
| ATOM | 796 | CA | ALA | 130 | 58.356 | 51.062 | 13.943 | 1.00 | 25.98 | A | C |
| ATOM | 797 | CB | ALA | 130 | 57.061 | 50.636 | 14.618 | 1.00 | 22.73 | A | C |
| ATOM | 798 | C | ALA | 130 | 58.195 | 50.983 | 12.445 | 1.00 | 26.81 | A | C |
| ATOM | 799 | O | ALA | 130 | 58.277 | 51.988 | 11.740 | 1.00 | 27.92 | A | O |
| ATOM | 800 | N | SER | 131 | 57.978 | 49.767 | 11.965 | 1.00 | 27.15 | A | N |
| ATOM | 801 | CA | SER | 131 | 57.759 | 49.540 | 10.556 | 1.00 | 27.62 | A | C |
| ATOM | 802 | CB | SER | 131 | 58.643 | 48.403 | 10.059 | 1.00 | 28.58 | A | C |
| ATOM | 803 | OG | SER | 131 | 59.995 | 48.822 | 10.022 | 1.00 | 29.90 | A | O |
| ATOM | 804 | C | SER | 131 | 56.290 | 49.187 | 10.426 | 1.00 | 27.17 | A | C |
| ATOM | 805 | O | SER | 131 | 55.651 | 48.779 | 11.397 | 1.00 | 27.00 | A | O |
| ATOM | 806 | N | TYR | 132 | 55.747 | 49.351 | 9.232 | 1.00 | 27.56 | A | N |
| ATOM | 807 | CA | TYR | 132 | 54.341 | 49.061 | 9.029 | 1.00 | 28.28 | A | C |
| ATOM | 808 | CB | TYR | 132 | 53.532 | 50.357 | 9.156 | 1.00 | 27.16 | A | C |
| ATOM | 809 | CG | TYR | 132 | 53.649 | 51.046 | 10.507 | 1.00 | 25.23 | A | C |
| ATOM | 810 | CD1 | TYR | 132 | 52.692 | 50.842 | 11.500 | 1.00 | 24.00 | A | C |
| ATOM | 811 | CE1 | TYR | 132 | 52.790 | 51.483 | 12.735 | 1.00 | 23.00 | A | C |
| ATOM | 812 | CD2 | TYR | 132 | 54.714 | 51.908 | 10.785 | 1.00 | 22.89 | A | C |
| ATOM | 813 | CE2 | TYR | 132 | 54.822 | 52.549 | 12.016 | 1.00 | 21.43 | A | C |
| ATOM | 814 | CZ | TYR | 132 | 53.856 | 52.333 | 12.985 | 1.00 | 22.58 | A | C |
| ATOM | 815 | OH | TYR | 132 | 53.940 | 52.976 | 14.198 | 1.00 | 21.69 | A | O |
| ATOM | 816 | C | TYR | 132 | 54.071 | 48.418 | 7.680 | 1.00 | 28.72 | A | C |
| ATOM | 817 | O | TYR | 132 | 54.794 | 48.639 | 6.712 | 1.00 | 29.54 | A | O |
| ATOM | 818 | N | ASP | 133 | 53.028 | 47.604 | 7.631 | 1.00 | 29.99 | A | N |
| ATOM | 819 | CA | ASP | 133 | 52.629 | 46.956 | 6.392 | 1.00 | 31.05 | A | C |
| ATOM | 820 | CB | ASP | 133 | 53.147 | 45.519 | 6.314 | 1.00 | 31.90 | A | C |
| ATOM | 821 | CG | ASP | 133 | 54.541 | 45.436 | 5.721 | 1.00 | 33.92 | A | C |
| ATOM | 822 | OD1 | ASP | 133 | 54.773 | 46.042 | 4.649 | 1.00 | 33.52 | A | O |
| ATOM | 823 | OD2 | ASP | 133 | 55.400 | 44.756 | 6.321 | 1.00 | 35.83 | A | O |
| ATOM | 824 | C | ASP | 133 | 51.125 | 46.952 | 6.334 | 1.00 | 30.39 | A | C |
| ATOM | 825 | O | ASP | 133 | 50.467 | 46.384 | 7.202 | 1.00 | 33.36 | A | O |
| ATOM | 826 | N | ILE | 134 | 50.579 | 47.598 | 5.315 | 1.00 | 28.05 | A | N |
| ATOM | 827 | CA | ILE | 134 | 49.144 | 47.652 | 5.157 | 1.00 | 25.68 | A | C |
| ATOM | 828 | CB | ILE | 134 | 48.732 | 48.816 | 4.269 | 1.00 | 23.81 | A | C |
| ATOM | 829 | CG2 | ILE | 134 | 47.221 | 48.954 | 4.289 | 1.00 | 22.12 | A | C |
| ATOM | 830 | CG1 | ILE | 134 | 49.421 | 50.095 | 4.752 | 1.00 | 23.64 | A | C |
| ATOM | 831 | CD1 | ILE | 134 | 49.232 | 51.277 | 3.846 | 1.00 | 22.40 | A | C |
| ATOM | 832 | C | ILE | 134 | 48.635 | 46.368 | 4.524 | 1.00 | 27.46 | A | C |

FIG. 4-18 (Continued)

| | | | | | | | | | | |
|---|---|---|---|---|---|---|---|---|---|---|
| ATOM | 833 | O | ILE | 134 | 49.171 | 45.894 | 3.521 | 1.00 27.19 | A | O |
| ATOM | 834 | N | TYR | 135 | 47.599 | 45.805 | 5.127 | 1.00 29.43 | A | N |
| ATOM | 835 | CA | TYR | 135 | 46.985 | 44.588 | 4.628 | 1.00 30.54 | A | C |
| ATOM | 836 | CB | TYR | 135 | 46.800 | 43.588 | 5.772 | 1.00 33.25 | A | C |
| ATOM | 837 | CG | TYR | 135 | 46.276 | 42.242 | 5.343 | 1.00 35.66 | A | C |
| ATOM | 838 | CD1 | TYR | 135 | 47.113 | 41.311 | 4.731 | 1.00 37.89 | A | C |
| ATOM | 839 | CE1 | TYR | 135 | 46.634 | 40.068 | 4.319 | 1.00 40.13 | A | C |
| ATOM | 840 | CD2 | TYR | 135 | 44.939 | 41.903 | 5.535 | 1.00 37.34 | A | C |
| ATOM | 841 | CE2 | TYR | 135 | 44.444 | 40.666 | 5.126 | 1.00 40.17 | A | C |
| ATOM | 842 | CZ | TYR | 135 | 45.296 | 39.751 | 4.518 | 1.00 41.67 | A | C |
| ATOM | 843 | OH | TYR | 135 | 44.811 | 38.526 | 4.105 | 1.00 42.54 | A | O |
| ATOM | 844 | C | TYR | 135 | 45.629 | 44.990 | 4.057 | 1.00 30.05 | A | C |
| ATOM | 845 | O | TYR | 135 | 44.870 | 45.705 | 4.704 | 1.00 28.31 | A | O |
| ATOM | 846 | N | ASP | 136 | 45.341 | 44.536 | 2.841 | 1.00 31.33 | A | N |
| ATOM | 847 | CA | ASP | 136 | 44.083 | 44.837 | 2.168 | 1.00 33.02 | A | C |
| ATOM | 848 | CB | ASP | 136 | 44.323 | 44.857 | 0.655 | 1.00 32.51 | A | C |
| ATOM | 849 | CG | ASP | 136 | 43.057 | 45.095 | -0.146 | 1.00 33.01 | A | C |
| ATOM | 850 | OD1 | ASP | 136 | 43.115 | 45.872 | -1.121 | 1.00 31.21 | A | O |
| ATOM | 851 | OD2 | ASP | 136 | 42.009 | 44.500 | 0.181 | 1.00 34.97 | A | O |
| ATOM | 852 | C | ASP | 136 | 43.019 | 43.797 | 2.549 | 1.00 35.55 | A | C |
| ATOM | 853 | O | ASP | 136 | 42.822 | 42.810 | 1.846 | 1.00 36.12 | A | O |
| ATOM | 854 | N | LEU | 137 | 42.341 | 44.040 | 3.669 | 1.00 38.03 | A | N |
| ATOM | 855 | CA | LEU | 137 | 41.303 | 43.150 | 4.192 | 1.00 40.58 | A | C |
| ATOM | 856 | CB | LEU | 137 | 40.445 | 43.892 | 5.225 | 1.00 40.10 | A | C |
| ATOM | 857 | CG | LEU | 137 | 41.160 | 44.413 | 6.477 | 1.00 39.13 | A | C |
| ATOM | 858 | CD1 | LEU | 137 | 40.206 | 45.257 | 7.307 | 1.00 37.54 | A | C |
| ATOM | 859 | CD2 | LEU | 137 | 41.686 | 43.243 | 7.286 | 1.00 38.91 | A | C |
| ATOM | 860 | C | LEU | 137 | 40.392 | 42.536 | 3.134 | 1.00 42.88 | A | C |
| ATOM | 861 | O | LEU | 137 | 40.038 | 41.362 | 3.225 | 1.00 43.41 | A | O |
| ATOM | 862 | N | ASN | 138 | 39.997 | 43.322 | 2.141 | 1.00 45.42 | A | N |
| ATOM | 863 | CA | ASN | 138 | 39.132 | 42.796 | 1.093 | 1.00 48.50 | A | C |
| ATOM | 864 | CB | ASN | 138 | 38.537 | 43.936 | 0.264 | 1.00 49.71 | A | C |
| ATOM | 865 | CG | ASN | 138 | 37.127 | 44.291 | 0.697 | 1.00 50.83 | A | C |
| ATOM | 866 | OD1 | ASN | 138 | 36.873 | 44.555 | 1.871 | 1.00 51.97 | A | O |
| ATOM | 867 | ND2 | ASN | 138 | 36.202 | 44.296 | -0.254 | 1.00 52.74 | A | N |
| ATOM | 868 | C | ASN | 138 | 39.884 | 41.824 | 0.191 | 1.00 49.47 | A | C |
| ATOM | 869 | O | ASN | 138 | 39.642 | 40.619 | 0.240 | 1.00 50.62 | A | O |
| ATOM | 870 | N | LYS | 139 | 40.794 | 42.346 | -0.626 | 1.00 50.26 | A | N |
| ATOM | 871 | CA | LYS | 139 | 41.581 | 41.507 | -1.526 | 1.00 51.09 | A | C |
| ATOM | 872 | CB | LYS | 139 | 42.510 | 42.374 | -2.382 | 1.00 51.15 | A | C |
| ATOM | 873 | CG | LYS | 139 | 41.785 | 43.427 | -3.212 | 1.00 53.38 | A | C |
| ATOM | 874 | CD | LYS | 139 | 42.753 | 44.331 | -3.974 | 1.00 54.25 | A | C |
| ATOM | 875 | CE | LYS | 139 | 43.550 | 43.564 | -5.021 | 1.00 56.31 | A | C |
| ATOM | 876 | NZ | LYS | 139 | 44.447 | 44.453 | -5.817 | 1.00 56.39 | A | N |
| ATOM | 877 | C | LYS | 139 | 42.413 | 40.528 | -0.703 | 1.00 51.63 | A | C |
| ATOM | 878 | O | LYS | 139 | 43.148 | 39.708 | -1.251 | 1.00 51.80 | A | O |
| ATOM | 879 | N | ARG | 140 | 42.288 | 40.624 | 0.618 | 1.00 51.49 | A | N |
| ATOM | 880 | CA | ARG | 140 | 43.025 | 39.768 | 1.534 | 1.00 51.71 | A | C |
| ATOM | 881 | CB | ARG | 140 | 42.338 | 38.408 | 1.642 | 1.00 53.88 | A | C |

FIG. 4-19

| | | | | | | | | | | | |
|---|---|---|---|---|---|---|---|---|---|---|---|
| ATOM | 882 | CG | ARG | 140 | 40.911 | 38.495 | 2.157 | 1.00 | 57.36 | A | C |
| ATOM | 883 | CD | ARG | 140 | 40.257 | 37.128 | 2.211 | 1.00 | 60.02 | A | C |
| ATOM | 884 | NE | ARG | 140 | 40.936 | 36.235 | 3.142 | 1.00 | 62.76 | A | N |
| ATOM | 885 | CZ | ARG | 140 | 40.633 | 34.950 | 3.294 | 1.00 | 64.87 | A | C |
| ATOM | 886 | NH1 | ARG | 140 | 39.661 | 34.409 | 2.570 | 1.00 | 66.83 | A | N |
| ATOM | 887 | NH2 | ARG | 140 | 41.298 | 34.206 | 4.169 | 1.00 | 65.62 | A | N |
| ATOM | 888 | C | ARG | 140 | 44.464 | 39.603 | 1.066 | 1.00 | 50.29 | A | C |
| ATOM | 889 | O | ARG | 140 | 44.992 | 38.496 | 1.002 | 1.00 | 50.21 | A | O |
| ATOM | 890 | N | GLN | 141 | 45.096 | 40.723 | 0.741 | 1.00 | 49.82 | A | N |
| ATOM | 891 | CA | GLN | 141 | 46.473 | 40.707 | 0.268 | 1.00 | 48.70 | A | C |
| ATOM | 892 | CB | GLN | 141 | 46.487 | 40.815 | -1.260 | 1.00 | 50.32 | A | C |
| ATOM | 893 | CG | GLN | 141 | 47.774 | 40.348 | -1.909 | 1.00 | 55.02 | A | C |
| ATOM | 894 | CD | GLN | 141 | 47.640 | 40.179 | -3.413 | 1.00 | 57.33 | A | C |
| ATOM | 895 | OE1 | GLN | 141 | 48.582 | 39.756 | -4.088 | 1.00 | 57.97 | A | O |
| ATOM | 896 | NE2 | GLN | 141 | 46.465 | 40.509 | -3.947 | 1.00 | 58.85 | A | N |
| ATOM | 897 | C | GLN | 141 | 47.293 | 41.837 | 0.898 | 1.00 | 46.02 | A | C |
| ATOM | 898 | O | GLN | 141 | 46.761 | 42.880 | 1.274 | 1.00 | 45.33 | A | O |
| ATOM | 899 | N | LEU | 142 | 48.594 | 41.610 | 1.013 | 1.00 | 43.34 | A | N |
| ATOM | 900 | CA | LEU | 142 | 49.505 | 42.578 | 1.605 | 1.00 | 41.50 | A | C |
| ATOM | 901 | CB | LEU | 142 | 50.638 | 41.824 | 2.296 | 1.00 | 41.17 | A | C |
| ATOM | 902 | CG | LEU | 142 | 51.489 | 42.501 | 3.359 | 1.00 | 42.33 | A | C |
| ATOM | 903 | CD1 | LEU | 142 | 52.443 | 41.463 | 3.922 | 1.00 | 42.24 | A | C |
| ATOM | 904 | CD2 | LEU | 142 | 52.254 | 43.677 | 2.772 | 1.00 | 42.66 | A | C |
| ATOM | 905 | C | LEU | 142 | 50.062 | 43.498 | 0.520 | 1.00 | 40.87 | A | C |
| ATOM | 906 | O | LEU | 142 | 50.557 | 43.030 | -0.506 | 1.00 | 41.57 | A | O |
| ATOM | 907 | N | ILE | 143 | 49.978 | 44.806 | 0.748 | 1.00 | 39.20 | A | N |
| ATOM | 908 | CA | ILE | 143 | 50.466 | 45.789 | -0.217 | 1.00 | 37.17 | A | C |
| ATOM | 909 | CB | ILE | 143 | 49.921 | 47.202 | 0.104 | 1.00 | 36.58 | A | C |
| ATOM | 910 | CG2 | ILE | 143 | 50.486 | 48.225 | -0.874 | 1.00 | 35.56 | A | C |
| ATOM | 911 | CG1 | ILE | 143 | 48.398 | 47.197 | 0.030 | 1.00 | 34.64 | A | C |
| ATOM | 912 | CD1 | ILE | 143 | 47.777 | 48.494 | 0.468 | 1.00 | 37.28 | A | C |
| ATOM | 913 | C | ILE | 143 | 51.985 | 45.843 | -0.209 | 1.00 | 36.06 | A | C |
| ATOM | 914 | O | ILE | 143 | 52.603 | 45.859 | 0.849 | 1.00 | 36.63 | A | O |
| ATOM | 915 | N | THR | 144 | 52.592 | 45.882 | -1.386 | 1.00 | 35.40 | A | N |
| ATOM | 916 | CA | THR | 144 | 54.046 | 45.933 | -1.459 | 1.00 | 35.79 | A | C |
| ATOM | 917 | CB | THR | 144 | 54.616 | 44.654 | -2.124 | 1.00 | 35.59 | A | C |
| ATOM | 918 | OG1 | THR | 144 | 54.192 | 44.592 | -3.491 | 1.00 | 37.13 | A | O |
| ATOM | 919 | CG2 | THR | 144 | 54.121 | 43.415 | -1.403 | 1.00 | 33.21 | A | C |
| ATOM | 920 | C | THR | 144 | 54.515 | 47.152 | -2.243 | 1.00 | 35.43 | A | C |
| ATOM | 921 | O | THR | 144 | 55.700 | 47.311 | -2.511 | 1.00 | 36.45 | A | O |
| ATOM | 922 | N | GLU | 145 | 53.577 | 48.015 | -2.602 | 1.00 | 36.27 | A | N |
| ATOM | 923 | CA | GLU | 145 | 53.891 | 49.214 | -3.369 | 1.00 | 36.32 | A | C |
| ATOM | 924 | CB | GLU | 145 | 52.962 | 49.297 | -4.586 | 1.00 | 38.36 | A | C |
| ATOM | 925 | CG | GLU | 145 | 53.553 | 48.748 | -5.875 | 1.00 | 42.66 | A | C |
| ATOM | 926 | CD | GLU | 145 | 54.667 | 49.639 | -6.418 | 1.00 | 45.91 | A | C |
| ATOM | 927 | OE1 | GLU | 145 | 55.745 | 49.705 | -5.779 | 1.00 | 45.49 | A | O |
| ATOM | 928 | OE2 | GLU | 145 | 54.456 | 50.283 | -7.476 | 1.00 | 45.56 | A | O |
| ATOM | 929 | C | GLU | 145 | 53.775 | 50.496 | -2.544 | 1.00 | 35.06 | A | C |
| ATOM | 930 | O | GLU | 145 | 52.874 | 50.635 | -1.715 | 1.00 | 34.22 | A | O |

| ATOM | 931 | N | GLU | 146 | 54.692 | 51.428 | -2.782 | 1.00 | 33.82 | A | N |
|---|---|---|---|---|---|---|---|---|---|---|---|
| ATOM | 932 | CA | GLU | 146 | 54.699 | 52.706 | -2.079 | 1.00 | 32.54 | A | C |
| ATOM | 933 | CB | GLU | 146 | 53.594 | 53.608 | -2.630 | 1.00 | 33.84 | A | C |
| ATOM | 934 | CG | GLU | 146 | 53.708 | 53.924 | -4.107 | 1.00 | 33.18 | A | C |
| ATOM | 935 | CD | GLU | 146 | 54.992 | 54.651 | -4.455 | 1.00 | 33.14 | A | C |
| ATOM | 936 | OE1 | GLU | 146 | 55.677 | 55.129 | -3.528 | 1.00 | 32.11 | A | O |
| ATOM | 937 | OE2 | GLU | 146 | 55.309 | 54.754 | -5.660 | 1.00 | 35.19 | A | O |
| ATOM | 938 | C | GLU | 146 | 54.495 | 52.521 | -0.579 | 1.00 | 32.26 | A | C |
| ATOM | 939 | O | GLU | 146 | 53.644 | 53.172 | 0.031 | 1.00 | 32.38 | A | O |
| ATOM | 940 | N | ARG | 147 | 55.287 | 51.638 | 0.013 | 1.00 | 30.84 | A | N |
| ATOM | 941 | CA | ARG | 147 | 55.185 | 51.357 | 1.437 | 1.00 | 29.94 | A | C |
| ATOM | 942 | CB | ARG | 147 | 55.992 | 50.107 | 1.774 | 1.00 | 31.91 | A | C |
| ATOM | 943 | CG | ARG | 147 | 55.376 | 48.821 | 1.262 | 1.00 | 33.35 | A | C |
| ATOM | 944 | CD | ARG | 147 | 55.999 | 47.649 | 1.963 | 1.00 | 34.66 | A | C |
| ATOM | 945 | NE | ARG | 147 | 57.415 | 47.539 | 1.650 | 1.00 | 37.64 | A | N |
| ATOM | 946 | CZ | ARG | 147 | 58.271 | 46.812 | 2.356 | 1.00 | 39.76 | A | C |
| ATOM | 947 | NH1 | ARG | 147 | 57.844 | 46.143 | 3.421 | 1.00 | 40.68 | A | N |
| ATOM | 948 | NH2 | ARG | 147 | 59.546 | 46.737 | 1.987 | 1.00 | 39.79 | A | N |
| ATOM | 949 | C | ARG | 147 | 55.623 | 52.483 | 2.363 | 1.00 | 28.99 | A | C |
| ATOM | 950 | O | ARG | 147 | 56.440 | 53.330 | 2.002 | 1.00 | 29.74 | A | O |
| ATOM | 951 | N | ILE | 148 | 55.066 | 52.486 | 3.568 | 1.00 | 26.79 | A | N |
| ATOM | 952 | CA | ILE | 148 | 55.430 | 53.484 | 4.555 | 1.00 | 25.21 | A | C |
| ATOM | 953 | CB | ILE | 148 | 54.537 | 53.364 | 5.798 | 1.00 | 24.62 | A | C |
| ATOM | 954 | CG2 | ILE | 148 | 55.096 | 54.201 | 6.940 | 1.00 | 25.09 | A | C |
| ATOM | 955 | CG1 | ILE | 148 | 53.116 | 53.794 | 5.427 | 1.00 | 23.14 | A | C |
| ATOM | 956 | CD1 | ILE | 148 | 52.107 | 53.642 | 6.533 | 1.00 | 23.82 | A | C |
| ATOM | 957 | C | ILE | 148 | 56.879 | 53.173 | 4.891 | 1.00 | 24.99 | A | C |
| ATOM | 958 | O | ILE | 148 | 57.240 | 52.014 | 5.068 | 1.00 | 26.06 | A | O |
| ATOM | 959 | N | PRO | 149 | 57.735 | 54.201 | 4.974 | 1.00 | 24.98 | A | N |
| ATOM | 960 | CD | PRO | 149 | 57.443 | 55.645 | 4.930 | 1.00 | 24.87 | A | C |
| ATOM | 961 | CA | PRO | 149 | 59.148 | 53.966 | 5.282 | 1.00 | 26.52 | A | C |
| ATOM | 962 | CB | PRO | 149 | 59.765 | 55.356 | 5.151 | 1.00 | 24.90 | A | C |
| ATOM | 963 | CG | PRO | 149 | 58.659 | 56.244 | 5.614 | 1.00 | 24.49 | A | C |
| ATOM | 964 | C | PRO | 149 | 59.421 | 53.352 | 6.642 | 1.00 | 27.89 | A | C |
| ATOM | 965 | O | PRO | 149 | 58.621 | 53.489 | 7.567 | 1.00 | 27.47 | A | O |
| ATOM | 966 | N | ASN | 150 | 60.551 | 52.657 | 6.748 | 1.00 | 29.59 | A | N |
| ATOM | 967 | CA | ASN | 150 | 60.950 | 52.064 | 8.016 | 1.00 | 30.82 | A | C |
| ATOM | 968 | CB | ASN | 150 | 62.154 | 51.131 | 7.830 | 1.00 | 32.43 | A | C |
| ATOM | 969 | CG | ASN | 150 | 61.775 | 49.805 | 7.189 | 1.00 | 35.16 | A | C |
| ATOM | 970 | OD1 | ASN | 150 | 60.749 | 49.215 | 7.530 | 1.00 | 36.40 | A | O |
| ATOM | 971 | ND2 | ASN | 150 | 62.612 | 49.319 | 6.271 | 1.00 | 36.52 | A | N |
| ATOM | 972 | C | ASN | 150 | 61.336 | 53.245 | 8.900 | 1.00 | 30.50 | A | C |
| ATOM | 973 | O | ASN | 150 | 61.583 | 54.348 | 8.394 | 1.00 | 31.20 | A | O |
| ATOM | 974 | N | ASN | 151 | 61.387 | 53.022 | 10.208 | 1.00 | 28.46 | A | N |
| ATOM | 975 | CA | ASN | 151 | 61.734 | 54.078 | 11.154 | 1.00 | 28.87 | A | C |
| ATOM | 976 | CB | ASN | 151 | 63.137 | 54.622 | 10.877 | 1.00 | 30.74 | A | C |
| ATOM | 977 | CG | ASN | 151 | 64.213 | 53.571 | 11.048 | 1.00 | 34.06 | A | C |
| ATOM | 978 | OD1 | ASN | 151 | 64.360 | 52.678 | 10.219 | 1.00 | 36.24 | A | O |
| ATOM | 979 | ND2 | ASN | 151 | 64.965 | 53.666 | 12.139 | 1.00 | 37.62 | A | N |

| | | | | | | | | | | | |
|---|---|---|---|---|---|---|---|---|---|---|---|
| ATOM | 980 | C | ASN | 151 | 60.734 | 55.230 | 11.111 | 1.00 | 28.16 | A | C |
| ATOM | 981 | O | ASN | 151 | 61.118 | 56.400 | 11.112 | 1.00 | 28.85 | A | O |
| ATOM | 982 | N | THR | 152 | 59.450 | 54.895 | 11.064 | 1.00 | 26.20 | A | N |
| ATOM | 983 | CA | THR | 152 | 58.415 | 55.911 | 11.041 | 1.00 | 24.74 | A | C |
| ATOM | 984 | CB | THR | 152 | 57.119 | 55.389 | 10.399 | 1.00 | 25.27 | A | C |
| ATOM | 985 | OG1 | THR | 152 | 57.351 | 55.125 | 9.009 | 1.00 | 24.18 | A | O |
| ATOM | 986 | CG2 | THR | 152 | 56.004 | 56.426 | 10.538 | 1.00 | 23.99 | A | C |
| ATOM | 987 | C | THR | 152 | 58.139 | 56.319 | 12.474 | 1.00 | 23.46 | A | C |
| ATOM | 988 | O | THR | 152 | 57.933 | 55.476 | 13.340 | 1.00 | 25.16 | A | O |
| ATOM | 989 | N | GLN | 153 | 58.134 | 57.620 | 12.721 | 1.00 | 22.30 | A | N |
| ATOM | 990 | CA | GLN | 153 | 57.916 | 58.129 | 14.063 | 1.00 | 20.67 | A | C |
| ATOM | 991 | CB | GLN | 153 | 58.501 | 59.534 | 14.161 | 1.00 | 19.09 | A | C |
| ATOM | 992 | CG | GLN | 153 | 60.002 | 59.543 | 13.906 | 1.00 | 13.74 | A | C |
| ATOM | 993 | CD | GLN | 153 | 60.495 | 60.853 | 13.331 | 1.00 | 14.57 | A | C |
| ATOM | 994 | OE1 | GLN | 153 | 60.089 | 61.260 | 12.233 | 1.00 | 12.70 | A | O |
| ATOM | 995 | NE2 | GLN | 153 | 61.375 | 61.524 | 14.066 | 1.00 | 10.81 | A | N |
| ATOM | 996 | C | GLN | 153 | 56.460 | 58.112 | 14.495 | 1.00 | 20.53 | A | C |
| ATOM | 997 | O | GLN | 153 | 56.163 | 57.979 | 15.683 | 1.00 | 19.36 | A | O |
| ATOM | 998 | N | TRP | 154 | 55.556 | 58.229 | 13.531 | 1.00 | 20.90 | A | N |
| ATOM | 999 | CA | TRP | 154 | 54.131 | 58.213 | 13.831 | 1.00 | 21.02 | A | C |
| ATOM | 1000 | CB | TRP | 154 | 53.733 | 59.498 | 14.550 | 1.00 | 22.43 | A | C |
| ATOM | 1001 | CG | TRP | 154 | 52.312 | 59.530 | 14.923 | 1.00 | 21.90 | A | C |
| ATOM | 1002 | CD2 | TRP | 154 | 51.695 | 58.791 | 15.976 | 1.00 | 22.22 | A | C |
| ATOM | 1003 | CE2 | TRP | 154 | 50.315 | 59.087 | 15.942 | 1.00 | 23.62 | A | C |
| ATOM | 1004 | CE3 | TRP | 154 | 52.173 | 57.902 | 16.947 | 1.00 | 22.95 | A | C |
| ATOM | 1005 | CD1 | TRP | 154 | 51.321 | 60.228 | 14.308 | 1.00 | 24.44 | A | C |
| ATOM | 1006 | NE1 | TRP | 154 | 50.112 | 59.968 | 14.912 | 1.00 | 24.78 | A | N |
| ATOM | 1007 | CZ2 | TRP | 154 | 49.404 | 58.526 | 16.842 | 1.00 | 22.94 | A | C |
| ATOM | 1008 | CZ3 | TRP | 154 | 51.263 | 57.339 | 17.847 | 1.00 | 22.07 | A | C |
| ATOM | 1009 | CH2 | TRP | 154 | 49.897 | 57.656 | 17.784 | 1.00 | 23.43 | A | C |
| ATOM | 1010 | C | TRP | 154 | 53.291 | 58.054 | 12.576 | 1.00 | 21.43 | A | C |
| ATOM | 1011 | O | TRP | 154 | 53.642 | 58.572 | 11.518 | 1.00 | 22.33 | A | O |
| ATOM | 1012 | N | VAL | 155 | 52.173 | 57.343 | 12.703 | 1.00 | 21.97 | A | N |
| ATOM | 1013 | CA | VAL | 155 | 51.267 | 57.103 | 11.579 | 1.00 | 20.81 | A | C |
| ATOM | 1014 | CB | VAL | 155 | 51.642 | 55.797 | 10.840 | 1.00 | 19.96 | A | C |
| ATOM | 1015 | CG1 | VAL | 155 | 51.835 | 54.687 | 11.842 | 1.00 | 21.34 | A | C |
| ATOM | 1016 | CG2 | VAL | 155 | 50.562 | 55.414 | 9.833 | 1.00 | 20.23 | A | C |
| ATOM | 1017 | C | VAL | 155 | 49.840 | 57.004 | 12.104 | 1.00 | 21.39 | A | C |
| ATOM | 1018 | O | VAL | 155 | 49.601 | 56.425 | 13.162 | 1.00 | 21.74 | A | O |
| ATOM | 1019 | N | THR | 156 | 48.898 | 57.576 | 11.364 | 1.00 | 20.70 | A | N |
| ATOM | 1020 | CA | THR | 156 | 47.504 | 57.557 | 11.768 | 1.00 | 21.67 | A | C |
| ATOM | 1021 | CB | THR | 156 | 47.189 | 58.736 | 12.716 | 1.00 | 22.79 | A | C |
| ATOM | 1022 | OG1 | THR | 156 | 45.771 | 58.848 | 12.890 | 1.00 | 25.50 | A | O |
| ATOM | 1023 | CG2 | THR | 156 | 47.707 | 60.031 | 12.145 | 1.00 | 22.46 | A | C |
| ATOM | 1024 | C | THR | 156 | 46.558 | 57.633 | 10.577 | 1.00 | 22.20 | A | C |
| ATOM | 1025 | O | THR | 156 | 46.861 | 58.276 | 9.577 | 1.00 | 22.72 | A | O |
| ATOM | 1026 | N | TRP | 157 | 45.413 | 56.966 | 10.689 | 1.00 | 21.38 | A | N |
| ATOM | 1027 | CA | TRP | 157 | 44.423 | 56.985 | 9.627 | 1.00 | 21.45 | A | C |
| ATOM | 1028 | CB | TRP | 157 | 43.426 | 55.825 | 9.765 | 1.00 | 21.88 | A | C |

FIG. 4-22 (Continued)

| | | | | | | | | | | |
|---|---|---|---|---|---|---|---|---|---|---|
| ATOM | 1029 | CG  | TRP | 157 | 43.995 | 54.450 | 9.599  | 1.00 | 20.88 | A | C |
| ATOM | 1030 | CD2 | TRP | 157 | 44.315 | 53.800 | 8.364  | 1.00 | 18.96 | A | C |
| ATOM | 1031 | CE2 | TRP | 157 | 44.843 | 52.531 | 8.686  | 1.00 | 19.67 | A | C |
| ATOM | 1032 | CE3 | TRP | 157 | 44.208 | 54.168 | 7.019  | 1.00 | 17.93 | A | C |
| ATOM | 1033 | CD1 | TRP | 157 | 44.328 | 53.571 | 10.592 | 1.00 | 20.82 | A | C |
| ATOM | 1034 | NE1 | TRP | 157 | 44.838 | 52.417 | 10.052 | 1.00 | 21.01 | A | N |
| ATOM | 1035 | CZ2 | TRP | 157 | 45.265 | 51.626 | 7.708  | 1.00 | 19.12 | A | C |
| ATOM | 1036 | CZ3 | TRP | 157 | 44.627 | 53.267 | 6.046  | 1.00 | 19.76 | A | C |
| ATOM | 1037 | CH2 | TRP | 157 | 45.149 | 52.011 | 6.397  | 1.00 | 19.30 | A | C |
| ATOM | 1038 | C   | TRP | 157 | 43.650 | 58.276 | 9.801  | 1.00 | 23.03 | A | C |
| ATOM | 1039 | O   | TRP | 157 | 43.750 | 58.917 | 10.843 | 1.00 | 25.03 | A | O |
| ATOM | 1040 | N   | SER | 158 | 42.889 | 58.663 | 8.784  | 1.00 | 23.17 | A | N |
| ATOM | 1041 | CA  | SER | 158 | 42.064 | 59.855 | 8.889  | 1.00 | 23.44 | A | C |
| ATOM | 1042 | CB  | SER | 158 | 41.667 | 60.362 | 7.502  | 1.00 | 22.82 | A | C |
| ATOM | 1043 | OG  | SER | 158 | 41.208 | 59.311 | 6.679  | 1.00 | 23.84 | A | O |
| ATOM | 1044 | C   | SER | 158 | 40.845 | 59.377 | 9.678  | 1.00 | 23.86 | A | C |
| ATOM | 1045 | O   | SER | 158 | 40.613 | 58.176 | 9.781  | 1.00 | 24.35 | A | O |
| ATOM | 1046 | N   | PRO | 159 | 40.056 | 60.301 | 10.247 | 1.00 | 24.17 | A | N |
| ATOM | 1047 | CD  | PRO | 159 | 40.136 | 61.762 | 10.114 | 1.00 | 24.24 | A | C |
| ATOM | 1048 | CA  | PRO | 159 | 38.876 | 59.922 | 11.029 | 1.00 | 23.40 | A | C |
| ATOM | 1049 | CB  | PRO | 159 | 38.270 | 61.264 | 11.419 | 1.00 | 23.45 | A | C |
| ATOM | 1050 | CG  | PRO | 159 | 39.427 | 62.214 | 11.353 | 1.00 | 24.19 | A | C |
| ATOM | 1051 | C   | PRO | 159 | 37.901 | 59.090 | 10.224 | 1.00 | 25.36 | A | C |
| ATOM | 1052 | O   | PRO | 159 | 37.191 | 58.248 | 10.771 | 1.00 | 27.14 | A | O |
| ATOM | 1053 | N   | VAL | 160 | 37.878 | 59.334 | 8.919  | 1.00 | 25.28 | A | N |
| ATOM | 1054 | CA  | VAL | 160 | 36.977 | 58.640 | 8.014  | 1.00 | 23.99 | A | C |
| ATOM | 1055 | CB  | VAL | 160 | 35.784 | 59.545 | 7.689  | 1.00 | 24.54 | A | C |
| ATOM | 1056 | CG1 | VAL | 160 | 35.066 | 59.064 | 6.449  | 1.00 | 26.50 | A | C |
| ATOM | 1057 | CG2 | VAL | 160 | 34.834 | 59.559 | 8.875  | 1.00 | 26.15 | A | C |
| ATOM | 1058 | C   | VAL | 160 | 37.679 | 58.218 | 6.730  | 1.00 | 23.78 | A | C |
| ATOM | 1059 | O   | VAL | 160 | 38.570 | 58.908 | 6.245  | 1.00 | 24.51 | A | O |
| ATOM | 1060 | N   | GLY | 161 | 37.268 | 57.080 | 6.181  | 1.00 | 24.05 | A | N |
| ATOM | 1061 | CA  | GLY | 161 | 37.876 | 56.579 | 4.962  | 1.00 | 22.93 | A | C |
| ATOM | 1062 | C   | GLY | 161 | 39.121 | 55.786 | 5.286  | 1.00 | 23.87 | A | C |
| ATOM | 1063 | O   | GLY | 161 | 39.144 | 55.045 | 6.269  | 1.00 | 24.24 | A | O |
| ATOM | 1064 | N   | HIS | 162 | 40.164 | 55.950 | 4.476  | 1.00 | 25.01 | A | N |
| ATOM | 1065 | CA  | HIS | 162 | 41.423 | 55.239 | 4.695  | 1.00 | 25.86 | A | C |
| ATOM | 1066 | CB  | HIS | 162 | 41.419 | 53.923 | 3.920  | 1.00 | 26.04 | A | C |
| ATOM | 1067 | CG  | HIS | 162 | 41.075 | 54.087 | 2.475  | 1.00 | 27.52 | A | C |
| ATOM | 1068 | CD2 | HIS | 162 | 41.614 | 54.875 | 1.515  | 1.00 | 27.58 | A | C |
| ATOM | 1069 | ND1 | HIS | 162 | 40.039 | 53.402 | 1.874  | 1.00 | 27.77 | A | N |
| ATOM | 1070 | CE1 | HIS | 162 | 39.956 | 53.764 | 0.606  | 1.00 | 28.51 | A | C |
| ATOM | 1071 | NE2 | HIS | 162 | 40.900 | 54.656 | 0.363  | 1.00 | 28.82 | A | N |
| ATOM | 1072 | C   | HIS | 162 | 42.660 | 56.053 | 4.305  | 1.00 | 25.44 | A | C |
| ATOM | 1073 | O   | HIS | 162 | 43.636 | 55.501 | 3.794  | 1.00 | 24.38 | A | O |
| ATOM | 1074 | N   | LYS | 163 | 42.609 | 57.364 | 4.527  | 1.00 | 24.47 | A | N |
| ATOM | 1075 | CA  | LYS | 163 | 43.751 | 58.221 | 4.224  | 1.00 | 23.45 | A | C |
| ATOM | 1076 | CB  | LYS | 163 | 43.372 | 59.701 | 4.273  | 1.00 | 21.75 | A | C |
| ATOM | 1077 | CG  | LYS | 163 | 42.528 | 60.216 | 3.130  | 1.00 | 21.55 | A | C |

| | | | | | | | | | | |
|---|---|---|---|---|---|---|---|---|---|---|
| ATOM | 1078 | CD | LYS | 163 | 42.281 | 61.706 | 3.335 | 1.00 | 20.23 | A C |
| ATOM | 1079 | CE | LYS | 163 | 41.464 | 62.316 | 2.228 | 1.00 | 18.07 | A C |
| ATOM | 1080 | NZ | LYS | 163 | 41.315 | 63.778 | 2.422 | 1.00 | 20.95 | A N |
| ATOM | 1081 | C | LYS | 163 | 44.781 | 57.961 | 5.309 | 1.00 | 23.44 | A C |
| ATOM | 1082 | O | LYS | 163 | 44.425 | 57.600 | 6.433 | 1.00 | 23.42 | A O |
| ATOM | 1083 | N | LEU | 164 | 46.053 | 58.146 | 4.979 | 1.00 | 23.11 | A N |
| ATOM | 1084 | CA | LEU | 164 | 47.117 | 57.937 | 5.950 | 1.00 | 23.65 | A C |
| ATOM | 1085 | CB | LEU | 164 | 48.014 | 56.773 | 5.524 | 1.00 | 24.35 | A C |
| ATOM | 1086 | CG | LEU | 164 | 47.551 | 55.351 | 5.848 | 1.00 | 25.57 | A C |
| ATOM | 1087 | CD1 | LEU | 164 | 48.519 | 54.349 | 5.219 | 1.00 | 25.59 | A C |
| ATOM | 1088 | CD2 | LEU | 164 | 47.497 | 55.162 | 7.359 | 1.00 | 25.62 | A C |
| ATOM | 1089 | C | LEU | 164 | 47.970 | 59.182 | 6.120 | 1.00 | 23.21 | A C |
| ATOM | 1090 | O | LEU | 164 | 48.175 | 59.943 | 5.177 | 1.00 | 24.34 | A O |
| ATOM | 1091 | N | ALA | 165 | 48.456 | 59.383 | 7.335 | 1.00 | 21.88 | A N |
| ATOM | 1092 | CA | ALA | 165 | 49.319 | 60.508 | 7.649 | 1.00 | 21.58 | A C |
| ATOM | 1093 | CB | ALA | 165 | 48.548 | 61.583 | 8.376 | 1.00 | 21.77 | A C |
| ATOM | 1094 | C | ALA | 165 | 50.406 | 59.953 | 8.545 | 1.00 | 22.07 | A C |
| ATOM | 1095 | O | ALA | 165 | 50.115 | 59.285 | 9.537 | 1.00 | 22.91 | A O |
| ATOM | 1096 | N | TYR | 166 | 51.661 | 60.208 | 8.201 | 1.00 | 22.02 | A N |
| ATOM | 1097 | CA | TYR | 166 | 52.745 | 59.697 | 9.024 | 1.00 | 21.73 | A C |
| ATOM | 1098 | CB | TYR | 166 | 53.185 | 58.319 | 8.520 | 1.00 | 22.38 | A C |
| ATOM | 1099 | CG | TYR | 166 | 53.814 | 58.315 | 7.141 | 1.00 | 22.11 | A C |
| ATOM | 1100 | CD1 | TYR | 166 | 55.148 | 58.661 | 6.964 | 1.00 | 21.28 | A C |
| ATOM | 1101 | CE1 | TYR | 166 | 55.733 | 58.638 | 5.704 | 1.00 | 22.05 | A C |
| ATOM | 1102 | CD2 | TYR | 166 | 53.074 | 57.949 | 6.015 | 1.00 | 20.67 | A C |
| ATOM | 1103 | CE2 | TYR | 166 | 53.648 | 57.923 | 4.753 | 1.00 | 20.02 | A C |
| ATOM | 1104 | CZ | TYR | 166 | 54.981 | 58.268 | 4.603 | 1.00 | 21.75 | A C |
| ATOM | 1105 | OH | TYR | 166 | 55.566 | 58.252 | 3.352 | 1.00 | 20.77 | A O |
| ATOM | 1106 | C | TYR | 166 | 53.927 | 60.643 | 9.057 | 1.00 | 21.64 | A C |
| ATOM | 1107 | O | TYR | 166 | 54.108 | 61.464 | 8.157 | 1.00 | 21.61 | A O |
| ATOM | 1108 | N | VAL | 167 | 54.722 | 60.529 | 10.111 | 1.00 | 20.28 | A N |
| ATOM | 1109 | CA | VAL | 167 | 55.886 | 61.371 | 10.264 | 1.00 | 19.16 | A C |
| ATOM | 1110 | CB | VAL | 167 | 55.924 | 62.011 | 11.644 | 1.00 | 19.56 | A C |
| ATOM | 1111 | CG1 | VAL | 167 | 57.103 | 62.984 | 11.731 | 1.00 | 18.58 | A C |
| ATOM | 1112 | CG2 | VAL | 167 | 54.609 | 62.713 | 11.916 | 1.00 | 18.36 | A C |
| ATOM | 1113 | C | VAL | 167 | 57.135 | 60.537 | 10.078 | 1.00 | 20.06 | A C |
| ATOM | 1114 | O | VAL | 167 | 57.287 | 59.474 | 10.679 | 1.00 | 21.80 | A O |
| ATOM | 1115 | N | TRP | 168 | 58.030 | 61.023 | 9.233 | 1.00 | 19.65 | A N |
| ATOM | 1116 | CA | TRP | 168 | 59.268 | 60.320 | 8.964 | 1.00 | 19.61 | A C |
| ATOM | 1117 | CB | TRP | 168 | 59.164 | 59.558 | 7.646 | 1.00 | 20.07 | A C |
| ATOM | 1118 | CG | TRP | 168 | 60.387 | 58.772 | 7.353 | 1.00 | 23.12 | A C |
| ATOM | 1119 | CD2 | TRP | 168 | 61.319 | 59.011 | 6.300 | 1.00 | 21.38 | A C |
| ATOM | 1120 | CE2 | TRP | 168 | 62.353 | 58.061 | 6.436 | 1.00 | 21.58 | A C |
| ATOM | 1121 | CE3 | TRP | 168 | 61.382 | 59.936 | 5.256 | 1.00 | 21.74 | A C |
| ATOM | 1122 | CD1 | TRP | 168 | 60.873 | 57.712 | 8.066 | 1.00 | 22.86 | A C |
| ATOM | 1123 | NE1 | TRP | 168 | 62.056 | 57.281 | 7.521 | 1.00 | 21.54 | A N |
| ATOM | 1124 | CZ2 | TRP | 168 | 63.445 | 58.012 | 5.563 | 1.00 | 23.71 | A C |
| ATOM | 1125 | CZ3 | TRP | 168 | 62.468 | 59.889 | 4.386 | 1.00 | 23.21 | A C |
| ATOM | 1126 | CH2 | TRP | 168 | 63.484 | 58.934 | 4.546 | 1.00 | 22.74 | A C |

FIG. 4-24 (Continued)

| | | | | | | | | | | | |
|---|---|---|---|---|---|---|---|---|---|---|---|
| ATOM | 1127 | C | TRP | 168 | 60.406 | 61.327 | 8.906 | 1.00 | 19.17 | A | C |
| ATOM | 1128 | O | TRP | 168 | 60.331 | 62.319 | 8.187 | 1.00 | 19.01 | A | O |
| ATOM | 1129 | N | ASN | 169 | 61.452 | 61.072 | 9.682 | 1.00 | 19.26 | A | N |
| ATOM | 1130 | CA | ASN | 169 | 62.589 | 61.969 | 9.732 | 1.00 | 21.05 | A | C |
| ATOM | 1131 | CB | ASN | 169 | 63.374 | 61.902 | 8.417 | 1.00 | 23.39 | A | C |
| ATOM | 1132 | CG | ASN | 169 | 64.056 | 60.565 | 8.217 | 1.00 | 26.24 | A | C |
| ATOM | 1133 | OD1 | ASN | 169 | 64.410 | 60.196 | 7.097 | 1.00 | 29.51 | A | O |
| ATOM | 1134 | ND2 | ASN | 169 | 64.255 | 59.832 | 9.307 | 1.00 | 27.22 | A | N |
| ATOM | 1135 | C | ASN | 169 | 62.122 | 63.394 | 10.007 | 1.00 | 19.72 | A | C |
| ATOM | 1136 | O | ASN | 169 | 62.582 | 64.344 | 9.378 | 1.00 | 19.61 | A | O |
| ATOM | 1137 | N | ASN | 170 | 61.182 | 63.522 | 10.938 | 1.00 | 19.01 | A | N |
| ATOM | 1138 | CA | ASN | 170 | 60.654 | 64.817 | 11.354 | 1.00 | 18.95 | A | C |
| ATOM | 1139 | CB | ASN | 170 | 61.806 | 65.679 | 11.887 | 1.00 | 19.76 | A | C |
| ATOM | 1140 | CG | ASN | 170 | 62.326 | 65.193 | 13.239 | 1.00 | 21.23 | A | C |
| ATOM | 1141 | OD1 | ASN | 170 | 62.690 | 64.025 | 13.404 | 1.00 | 23.29 | A | O |
| ATOM | 1142 | ND2 | ASN | 170 | 62.362 | 66.092 | 14.210 | 1.00 | 21.16 | A | N |
| ATOM | 1143 | C | ASN | 170 | 59.828 | 65.621 | 10.341 | 1.00 | 18.94 | A | C |
| ATOM | 1144 | O | ASN | 170 | 59.594 | 66.815 | 10.541 | 1.00 | 17.99 | A | O |
| ATOM | 1145 | N | ASP | 171 | 59.385 | 64.974 | 9.264 | 1.00 | 18.46 | A | N |
| ATOM | 1146 | CA | ASP | 171 | 58.566 | 65.643 | 8.254 | 1.00 | 18.64 | A | C |
| ATOM | 1147 | CB | ASP | 171 | 59.271 | 65.696 | 6.898 | 1.00 | 18.52 | A | C |
| ATOM | 1148 | CG | ASP | 171 | 60.353 | 66.750 | 6.836 | 1.00 | 17.77 | A | C |
| ATOM | 1149 | OD1 | ASP | 171 | 60.126 | 67.876 | 7.307 | 1.00 | 17.30 | A | O |
| ATOM | 1150 | OD2 | ASP | 171 | 61.436 | 66.454 | 6.294 | 1.00 | 24.17 | A | O |
| ATOM | 1151 | C | ASP | 171 | 57.255 | 64.888 | 8.099 | 1.00 | 20.36 | A | C |
| ATOM | 1152 | O | ASP | 171 | 57.182 | 63.690 | 8.382 | 1.00 | 21.44 | A | O |
| ATOM | 1153 | N | ILE | 172 | 56.225 | 65.585 | 7.632 | 1.00 | 19.52 | A | N |
| ATOM | 1154 | CA | ILE | 172 | 54.908 | 64.983 | 7.466 | 1.00 | 18.52 | A | C |
| ATOM | 1155 | CB | ILE | 172 | 53.813 | 65.966 | 7.899 | 1.00 | 18.99 | A | C |
| ATOM | 1156 | CG2 | ILE | 172 | 52.443 | 65.329 | 7.734 | 1.00 | 17.69 | A | C |
| ATOM | 1157 | CG1 | ILE | 172 | 54.053 | 66.394 | 9.350 | 1.00 | 18.78 | A | C |
| ATOM | 1158 | CD1 | ILE | 172 | 53.167 | 67.538 | 9.795 | 1.00 | 18.44 | A | C |
| ATOM | 1159 | C | ILE | 172 | 54.609 | 64.539 | 6.044 | 1.00 | 18.52 | A | C |
| ATOM | 1160 | O | ILE | 172 | 54.905 | 65.246 | 5.085 | 1.00 | 19.61 | A | O |
| ATOM | 1161 | N | TYR | 173 | 54.017 | 63.358 | 5.921 | 1.00 | 17.61 | A | N |
| ATOM | 1162 | CA | TYR | 173 | 53.645 | 62.808 | 4.625 | 1.00 | 16.59 | A | C |
| ATOM | 1163 | CB | TYR | 173 | 54.519 | 61.612 | 4.256 | 1.00 | 14.94 | A | C |
| ATOM | 1164 | CG | TYR | 173 | 55.983 | 61.921 | 4.121 | 1.00 | 15.66 | A | C |
| ATOM | 1165 | CD1 | TYR | 173 | 56.815 | 61.978 | 5.237 | 1.00 | 16.67 | A | C |
| ATOM | 1166 | CE1 | TYR | 173 | 58.170 | 62.271 | 5.100 | 1.00 | 16.34 | A | C |
| ATOM | 1167 | CD2 | TYR | 173 | 56.541 | 62.165 | 2.870 | 1.00 | 15.99 | A | C |
| ATOM | 1168 | CE2 | TYR | 173 | 57.879 | 62.460 | 2.727 | 1.00 | 13.89 | A | C |
| ATOM | 1169 | CZ | TYR | 173 | 58.685 | 62.512 | 3.838 | 1.00 | 15.53 | A | C |
| ATOM | 1170 | OH | TYR | 173 | 60.004 | 62.837 | 3.678 | 1.00 | 21.66 | A | O |
| ATOM | 1171 | C | TYR | 173 | 52.198 | 62.341 | 4.679 | 1.00 | 17.34 | A | C |
| ATOM | 1172 | O | TYR | 173 | 51.683 | 62.008 | 5.748 | 1.00 | 14.56 | A | O |
| ATOM | 1173 | N | VAL | 174 | 51.552 | 62.306 | 3.518 | 1.00 | 18.18 | A | N |
| ATOM | 1174 | CA | VAL | 174 | 50.174 | 61.865 | 3.444 | 1.00 | 19.46 | A | C |
| ATOM | 1175 | CB | VAL | 174 | 49.212 | 63.060 | 3.319 | 1.00 | 18.88 | A | C |

FIG. 4-25 (Continued)

| | | | | | | | | | | |
|---|---|---|---|---|---|---|---|---|---|---|
| ATOM | 1176 | CG1 | VAL | 174 | 47.775 | 62.564 | 3.207 | 1.00 | 19.37 | A C |
| ATOM | 1177 | CG2 | VAL | 174 | 49.359 | 63.969 | 4.534 | 1.00 | 20.44 | A C |
| ATOM | 1178 | C | VAL | 174 | 49.948 | 60.928 | 2.268 | 1.00 | 21.57 | A C |
| ATOM | 1179 | O | VAL | 174 | 50.485 | 61.129 | 1.185 | 1.00 | 22.86 | A O |
| ATOM | 1180 | N | LYS | 175 | 49.154 | 59.891 | 2.500 | 1.00 | 23.19 | A N |
| ATOM | 1181 | CA | LYS | 175 | 48.824 | 58.934 | 1.461 | 1.00 | 23.86 | A C |
| ATOM | 1182 | CB | LYS | 175 | 49.275 | 57.516 | 1.831 | 1.00 | 24.28 | A C |
| ATOM | 1183 | CG | LYS | 175 | 50.759 | 57.352 | 2.113 | 1.00 | 28.82 | A C |
| ATOM | 1184 | CD | LYS | 175 | 51.100 | 55.895 | 2.422 | 1.00 | 29.18 | A C |
| ATOM | 1185 | CE | LYS | 175 | 51.107 | 55.043 | 1.163 | 1.00 | 29.84 | A C |
| ATOM | 1186 | NZ | LYS | 175 | 52.263 | 55.409 | 0.291 | 1.00 | 31.80 | A N |
| ATOM | 1187 | C | LYS | 175 | 47.314 | 58.935 | 1.338 | 1.00 | 24.49 | A C |
| ATOM | 1188 | O | LYS | 175 | 46.615 | 58.606 | 2.293 | 1.00 | 25.05 | A O |
| ATOM | 1189 | N | ILE | 176 | 46.820 | 59.319 | 0.166 | 1.00 | 24.77 | A N |
| ATOM | 1190 | CA | ILE | 176 | 45.394 | 59.327 | -0.102 | 1.00 | 24.70 | A C |
| ATOM | 1191 | CB | ILE | 176 | 45.095 | 60.028 | -1.437 | 1.00 | 22.88 | A C |
| ATOM | 1192 | CG2 | ILE | 176 | 43.605 | 60.073 | -1.679 | 1.00 | 21.75 | A C |
| ATOM | 1193 | CG1 | ILE | 176 | 45.677 | 61.443 | -1.423 | 1.00 | 21.52 | A C |
| ATOM | 1194 | CD1 | ILE | 176 | 45.016 | 62.379 | -0.424 | 1.00 | 23.58 | A C |
| ATOM | 1195 | C | ILE | 176 | 44.995 | 57.860 | -0.211 | 1.00 | 26.89 | A C |
| ATOM | 1196 | O | ILE | 176 | 43.979 | 57.428 | 0.328 | 1.00 | 26.38 | A O |
| ATOM | 1197 | N | GLU | 177 | 45.829 | 57.097 | -0.906 | 1.00 | 29.47 | A N |
| ATOM | 1198 | CA | GLU | 177 | 45.597 | 55.672 | -1.104 | 1.00 | 31.88 | A C |
| ATOM | 1199 | CB | GLU | 177 | 45.412 | 55.380 | -2.594 | 1.00 | 35.29 | A C |
| ATOM | 1200 | CG | GLU | 177 | 44.308 | 56.190 | -3.248 | 1.00 | 38.36 | A C |
| ATOM | 1201 | CD | GLU | 177 | 42.925 | 55.776 | -2.784 | 1.00 | 41.13 | A C |
| ATOM | 1202 | OE1 | GLU | 177 | 41.951 | 56.495 | -3.105 | 1.00 | 45.06 | A O |
| ATOM | 1203 | OE2 | GLU | 177 | 42.810 | 54.730 | -2.107 | 1.00 | 40.42 | A O |
| ATOM | 1204 | C | GLU | 177 | 46.796 | 54.895 | -0.569 | 1.00 | 31.55 | A C |
| ATOM | 1205 | O | GLU | 177 | 47.940 | 55.223 | -0.872 | 1.00 | 31.59 | A O |
| ATOM | 1206 | N | PRO | 178 | 46.544 | 53.840 | 0.221 | 1.00 | 31.40 | A N |
| ATOM | 1207 | CD | PRO | 178 | 45.218 | 53.240 | 0.438 | 1.00 | 30.50 | A C |
| ATOM | 1208 | CA | PRO | 178 | 47.591 | 53.000 | 0.814 | 1.00 | 29.97 | A C |
| ATOM | 1209 | CB | PRO | 178 | 46.796 | 51.902 | 1.509 | 1.00 | 30.05 | A C |
| ATOM | 1210 | CG | PRO | 178 | 45.567 | 51.805 | 0.684 | 1.00 | 31.07 | A C |
| ATOM | 1211 | C | PRO | 178 | 48.633 | 52.436 | -0.150 | 1.00 | 29.50 | A C |
| ATOM | 1212 | O | PRO | 178 | 49.727 | 52.062 | 0.269 | 1.00 | 31.00 | A O |
| ATOM | 1213 | N | ASN | 179 | 48.308 | 52.379 | -1.436 | 1.00 | 28.20 | A N |
| ATOM | 1214 | CA | ASN | 179 | 49.251 | 51.838 | -2.409 | 1.00 | 27.53 | A C |
| ATOM | 1215 | CB | ASN | 179 | 48.568 | 50.805 | -3.299 | 1.00 | 26.23 | A C |
| ATOM | 1216 | CG | ASN | 179 | 47.474 | 51.409 | -4.144 | 1.00 | 25.74 | A C |
| ATOM | 1217 | OD1 | ASN | 179 | 46.494 | 51.948 | -3.626 | 1.00 | 26.59 | A O |
| ATOM | 1218 | ND2 | ASN | 179 | 47.635 | 51.329 | -5.452 | 1.00 | 26.72 | A N |
| ATOM | 1219 | C | ASN | 179 | 49.854 | 52.916 | -3.285 | 1.00 | 27.48 | A C |
| ATOM | 1220 | O | ASN | 179 | 50.818 | 52.670 | -4.004 | 1.00 | 28.42 | A O |
| ATOM | 1221 | N | LEU | 180 | 49.289 | 54.115 | -3.231 | 1.00 | 26.68 | A N |
| ATOM | 1222 | CA | LEU | 180 | 49.805 | 55.200 | -4.050 | 1.00 | 26.11 | A C |
| ATOM | 1223 | CB | LEU | 180 | 48.658 | 56.125 | -4.456 | 1.00 | 24.86 | A C |
| ATOM | 1224 | CG | LEU | 180 | 47.574 | 55.370 | -5.238 | 1.00 | 25.87 | A C |

| | | | | | | | | | | |
|---|---|---|---|---|---|---|---|---|---|---|
| ATOM | 1225 | CD1 | LEU | 180 | 46.604 | 56.359 | -5.856 | 1.00 | 23.58 | A C |
| ATOM | 1226 | CD2 | LEU | 180 | 48.224 | 54.503 | -6.328 | 1.00 | 22.86 | A C |
| ATOM | 1227 | C | LEU | 180 | 50.938 | 55.996 | -3.391 | 1.00 | 25.78 | A C |
| ATOM | 1228 | O | LEU | 180 | 51.185 | 55.883 | -2.185 | 1.00 | 23.62 | A O |
| ATOM | 1229 | N | PRO | 181 | 51.669 | 56.789 | -4.194 | 1.00 | 24.96 | A N |
| ATOM | 1230 | CD | PRO | 181 | 51.687 | 56.842 | -5.667 | 1.00 | 23.41 | A C |
| ATOM | 1231 | CA | PRO | 181 | 52.766 | 57.580 | -3.634 | 1.00 | 23.35 | A C |
| ATOM | 1232 | CB | PRO | 181 | 53.403 | 58.217 | -4.870 | 1.00 | 22.16 | A C |
| ATOM | 1233 | CG | PRO | 181 | 53.124 | 57.201 | -5.944 | 1.00 | 22.72 | A C |
| ATOM | 1234 | C | PRO | 181 | 52.216 | 58.613 | -2.667 | 1.00 | 22.15 | A C |
| ATOM | 1235 | O | PRO | 181 | 51.144 | 59.173 | -2.880 | 1.00 | 21.88 | A O |
| ATOM | 1236 | N | SER | 182 | 52.954 | 58.864 | -1.601 | 1.00 | 21.65 | A N |
| ATOM | 1237 | CA | SER | 182 | 52.516 | 59.829 | -0.620 | 1.00 | 20.50 | A C |
| ATOM | 1238 | CB | SER | 182 | 52.999 | 59.404 | 0.765 | 1.00 | 22.61 | A C |
| ATOM | 1239 | OG | SER | 182 | 54.408 | 59.345 | 0.806 | 1.00 | 23.55 | A O |
| ATOM | 1240 | C | SER | 182 | 53.034 | 61.222 | -0.947 | 1.00 | 19.05 | A C |
| ATOM | 1241 | O | SER | 182 | 54.003 | 61.380 | -1.687 | 1.00 | 17.74 | A O |
| ATOM | 1242 | N | TYR | 183 | 52.366 | 62.233 | -0.402 | 1.00 | 17.87 | A N |
| ATOM | 1243 | CA | TYR | 183 | 52.786 | 63.606 | -0.611 | 1.00 | 15.17 | A C |
| ATOM | 1244 | CB | TYR | 183 | 51.595 | 64.523 | -0.832 | 1.00 | 12.09 | A C |
| ATOM | 1245 | CG | TYR | 183 | 50.676 | 64.028 | -1.905 | 1.00 | 12.54 | A C |
| ATOM | 1246 | CD1 | TYR | 183 | 49.729 | 63.052 | -1.625 | 1.00 | 8.93 | A C |
| ATOM | 1247 | CE1 | TYR | 183 | 48.916 | 62.554 | -2.610 | 1.00 | 11.95 | A C |
| ATOM | 1248 | CD2 | TYR | 183 | 50.782 | 64.494 | -3.214 | 1.00 | 9.42 | A C |
| ATOM | 1249 | CE2 | TYR | 183 | 49.961 | 63.990 | -4.218 | 1.00 | 10.27 | A C |
| ATOM | 1250 | CZ | TYR | 183 | 49.032 | 63.019 | -3.903 | 1.00 | 10.59 | A C |
| ATOM | 1251 | OH | TYR | 183 | 48.205 | 62.494 | -4.867 | 1.00 | 14.71 | A O |
| ATOM | 1252 | C | TYR | 183 | 53.532 | 64.067 | 0.617 | 1.00 | 15.72 | A C |
| ATOM | 1253 | O | TYR | 183 | 53.208 | 63.679 | 1.740 | 1.00 | 17.69 | A O |
| ATOM | 1254 | N | ARG | 184 | 54.540 | 64.893 | 0.386 | 1.00 | 14.64 | A N |
| ATOM | 1255 | CA | ARG | 184 | 55.342 | 65.436 | 1.452 | 1.00 | 14.10 | A C |
| ATOM | 1256 | CB | ARG | 184 | 56.786 | 65.593 | 0.970 | 1.00 | 16.84 | A C |
| ATOM | 1257 | CG | ARG | 184 | 57.725 | 66.203 | 1.989 | 1.00 | 20.48 | A C |
| ATOM | 1258 | CD | ARG | 184 | 59.170 | 65.912 | 1.629 | 1.00 | 20.61 | A C |
| ATOM | 1259 | NE | ARG | 184 | 60.095 | 66.485 | 2.598 | 1.00 | 20.21 | A N |
| ATOM | 1260 | CZ | ARG | 184 | 61.407 | 66.288 | 2.583 | 1.00 | 19.46 | A C |
| ATOM | 1261 | NH1 | ARG | 184 | 61.954 | 65.529 | 1.650 | 1.00 | 17.13 | A N |
| ATOM | 1262 | NH2 | ARG | 184 | 62.170 | 66.853 | 3.506 | 1.00 | 20.35 | A N |
| ATOM | 1263 | C | ARG | 184 | 54.736 | 66.779 | 1.820 | 1.00 | 14.10 | A C |
| ATOM | 1264 | O | ARG | 184 | 54.569 | 67.650 | 0.972 | 1.00 | 14.71 | A O |
| ATOM | 1265 | N | ILE | 185 | 54.390 | 66.937 | 3.089 | 1.00 | 15.27 | A N |
| ATOM | 1266 | CA | ILE | 185 | 53.804 | 68.175 | 3.572 | 1.00 | 14.44 | A C |
| ATOM | 1267 | CB | ILE | 185 | 52.786 | 67.884 | 4.692 | 1.00 | 16.20 | A C |
| ATOM | 1268 | CG2 | ILE | 185 | 52.091 | 69.175 | 5.115 | 1.00 | 14.78 | A C |
| ATOM | 1269 | CG1 | ILE | 185 | 51.770 | 66.842 | 4.202 | 1.00 | 15.25 | A C |
| ATOM | 1270 | CD1 | ILE | 185 | 51.021 | 67.250 | 2.947 | 1.00 | 12.00 | A C |
| ATOM | 1271 | C | ILE | 185 | 54.847 | 69.172 | 4.091 | 1.00 | 14.33 | A C |
| ATOM | 1272 | O | ILE | 185 | 54.647 | 70.377 | 3.994 | 1.00 | 14.95 | A O |
| ATOM | 1273 | N | THR | 186 | 55.950 | 68.676 | 4.646 | 1.00 | 14.38 | A N |

| | | | | | | | | | | | |
|---|---|---|---|---|---|---|---|---|---|---|---|
| ATOM | 1274 | CA | THR | 186 | 56.995 | 69.555 | 5.169 | 1.00 | 15.05 | A | C |
| ATOM | 1275 | CB | THR | 186 | 57.051 | 69.549 | 6.717 | 1.00 | 15.72 | A | C |
| ATOM | 1276 | OG1 | THR | 186 | 57.308 | 68.218 | 7.181 | 1.00 | 18.48 | A | O |
| ATOM | 1277 | CG2 | THR | 186 | 55.734 | 70.060 | 7.323 | 1.00 | 13.92 | A | C |
| ATOM | 1278 | C | THR | 186 | 58.384 | 69.190 | 4.663 | 1.00 | 17.06 | A | C |
| ATOM | 1279 | O | THR | 186 | 58.643 | 68.055 | 4.262 | 1.00 | 19.33 | A | O |
| ATOM | 1280 | N | TRP | 187 | 59.275 | 70.174 | 4.696 | 1.00 | 18.28 | A | N |
| ATOM | 1281 | CA | TRP | 187 | 60.655 | 70.020 | 4.253 | 1.00 | 16.04 | A | C |
| ATOM | 1282 | CB | TRP | 187 | 60.843 | 70.734 | 2.915 | 1.00 | 13.96 | A | C |
| ATOM | 1283 | CG | TRP | 187 | 60.392 | 69.949 | 1.736 | 1.00 | 14.75 | A | C |
| ATOM | 1284 | CD2 | TRP | 187 | 59.055 | 69.841 | 1.234 | 1.00 | 15.37 | A | C |
| ATOM | 1285 | CE2 | TRP | 187 | 59.093 | 68.954 | 0.135 | 1.00 | 15.22 | A | C |
| ATOM | 1286 | CE3 | TRP | 187 | 57.829 | 70.405 | 1.606 | 1.00 | 12.92 | A | C |
| ATOM | 1287 | CD1 | TRP | 187 | 61.165 | 69.149 | 0.941 | 1.00 | 14.94 | A | C |
| ATOM | 1288 | NE1 | TRP | 187 | 60.392 | 68.549 | -0.020 | 1.00 | 15.60 | A | N |
| ATOM | 1289 | CZ2 | TRP | 187 | 57.949 | 68.616 | -0.597 | 1.00 | 17.91 | A | C |
| ATOM | 1290 | CZ3 | TRP | 187 | 56.692 | 70.074 | 0.881 | 1.00 | 16.75 | A | C |
| ATOM | 1291 | CH2 | TRP | 187 | 56.758 | 69.185 | -0.211 | 1.00 | 17.84 | A | C |
| ATOM | 1292 | C | TRP | 187 | 61.607 | 70.620 | 5.292 | 1.00 | 15.71 | A | C |
| ATOM | 1293 | O | TRP | 187 | 62.804 | 70.725 | 5.053 | 1.00 | 19.54 | A | O |
| ATOM | 1294 | N | THR | 188 | 61.077 | 70.999 | 6.449 | 1.00 | 13.19 | A | N |
| ATOM | 1295 | CA | THR | 188 | 61.892 | 71.605 | 7.493 | 1.00 | 11.35 | A | C |
| ATOM | 1296 | CB | THR | 188 | 61.122 | 72.737 | 8.180 | 1.00 | 11.04 | A | C |
| ATOM | 1297 | OG1 | THR | 188 | 59.835 | 72.253 | 8.587 | 1.00 | 9.11 | A | O |
| ATOM | 1298 | CG2 | THR | 188 | 60.955 | 73.920 | 7.232 | 1.00 | 7.35 | A | C |
| ATOM | 1299 | C | THR | 188 | 62.384 | 70.642 | 8.572 | 1.00 | 12.10 | A | C |
| ATOM | 1300 | O | THR | 188 | 63.198 | 71.016 | 9.415 | 1.00 | 9.49 | A | O |
| ATOM | 1301 | N | GLY | 189 | 61.881 | 69.412 | 8.552 | 1.00 | 14.44 | A | N |
| ATOM | 1302 | CA | GLY | 189 | 62.296 | 68.426 | 9.533 | 1.00 | 16.08 | A | C |
| ATOM | 1303 | C | GLY | 189 | 63.794 | 68.421 | 9.782 | 1.00 | 15.86 | A | C |
| ATOM | 1304 | O | GLY | 189 | 64.584 | 68.685 | 8.881 | 1.00 | 17.65 | A | O |
| ATOM | 1305 | N | LYS | 190 | 64.196 | 68.117 | 11.004 | 1.00 | 17.28 | A | N |
| ATOM | 1306 | CA | LYS | 190 | 65.612 | 68.096 | 11.346 | 1.00 | 18.87 | A | C |
| ATOM | 1307 | CB | LYS | 190 | 66.189 | 69.512 | 11.264 | 1.00 | 20.03 | A | C |
| ATOM | 1308 | CG | LYS | 190 | 67.679 | 69.588 | 11.472 | 1.00 | 22.58 | A | C |
| ATOM | 1309 | CD | LYS | 190 | 68.181 | 70.997 | 11.256 | 1.00 | 27.62 | A | C |
| ATOM | 1310 | CE | LYS | 190 | 69.698 | 71.060 | 11.386 | 1.00 | 31.27 | A | C |
| ATOM | 1311 | NZ | LYS | 190 | 70.207 | 72.451 | 11.273 | 1.00 | 35.57 | A | N |
| ATOM | 1312 | C | LYS | 190 | 65.799 | 67.530 | 12.747 | 1.00 | 18.55 | A | C |
| ATOM | 1313 | O | LYS | 190 | 65.384 | 68.134 | 13.737 | 1.00 | 18.41 | A | O |
| ATOM | 1314 | N | GLU | 191 | 66.426 | 66.362 | 12.811 | 1.00 | 19.79 | A | N |
| ATOM | 1315 | CA | GLU | 191 | 66.674 | 65.661 | 14.062 | 1.00 | 21.70 | A | C |
| ATOM | 1316 | CB | GLU | 191 | 67.796 | 64.653 | 13.851 | 1.00 | 23.41 | A | C |
| ATOM | 1317 | CG | GLU | 191 | 67.894 | 63.598 | 14.937 | 1.00 | 29.95 | A | C |
| ATOM | 1318 | CD | GLU | 191 | 69.018 | 62.605 | 14.689 | 1.00 | 30.89 | A | C |
| ATOM | 1319 | OE1 | GLU | 191 | 68.970 | 61.497 | 15.262 | 1.00 | 33.70 | A | O |
| ATOM | 1320 | OE2 | GLU | 191 | 69.952 | 62.932 | 13.929 | 1.00 | 33.21 | A | O |
| ATOM | 1321 | C | GLU | 191 | 67.015 | 66.583 | 15.236 | 1.00 | 21.53 | A | C |
| ATOM | 1322 | O | GLU | 191 | 67.930 | 67.397 | 15.156 | 1.00 | 22.21 | A | O |

| | | | | | | | | | | | |
|---|---|---|---|---|---|---|---|---|---|---|---|
| ATOM | 1323 | N | ASP | 192 | 66.262 | 66.451 | 16.320 | 1.00 | 21.17 | A | N |
| ATOM | 1324 | CA | ASP | 192 | 66.470 | 67.246 | 17.525 | 1.00 | 22.27 | A | C |
| ATOM | 1325 | CB | ASP | 192 | 67.810 | 66.880 | 18.182 | 1.00 | 23.92 | A | C |
| ATOM | 1326 | CG | ASP | 192 | 67.922 | 65.400 | 18.510 | 1.00 | 25.20 | A | C |
| ATOM | 1327 | OD1 | ASP | 192 | 66.891 | 64.775 | 18.850 | 1.00 | 25.70 | A | O |
| ATOM | 1328 | OD2 | ASP | 192 | 69.049 | 64.866 | 18.438 | 1.00 | 26.25 | A | O |
| ATOM | 1329 | C | ASP | 192 | 66.425 | 68.759 | 17.341 | 1.00 | 21.93 | A | C |
| ATOM | 1330 | O | ASP | 192 | 66.998 | 69.489 | 18.145 | 1.00 | 22.78 | A | O |
| ATOM | 1331 | N | ILE | 193 | 65.748 | 69.242 | 16.304 | 1.00 | 21.66 | A | N |
| ATOM | 1332 | CA | ILE | 193 | 65.685 | 70.684 | 16.071 | 1.00 | 20.08 | A | C |
| ATOM | 1333 | CB | ILE | 193 | 66.747 | 71.113 | 15.039 | 1.00 | 20.73 | A | C |
| ATOM | 1334 | CG2 | ILE | 193 | 66.570 | 72.567 | 14.677 | 1.00 | 18.91 | A | C |
| ATOM | 1335 | CG1 | ILE | 193 | 68.142 | 70.889 | 15.624 | 1.00 | 22.58 | A | C |
| ATOM | 1336 | CD1 | ILE | 193 | 69.263 | 71.198 | 14.671 | 1.00 | 26.43 | A | C |
| ATOM | 1337 | C | ILE | 193 | 64.318 | 71.172 | 15.615 | 1.00 | 19.15 | A | C |
| ATOM | 1338 | O | ILE | 193 | 63.736 | 72.068 | 16.220 | 1.00 | 19.55 | A | O |
| ATOM | 1339 | N | ILE | 194 | 63.814 | 70.594 | 14.534 | 1.00 | 19.04 | A | N |
| ATOM | 1340 | CA | ILE | 194 | 62.506 | 70.967 | 14.021 | 1.00 | 17.41 | A | C |
| ATOM | 1341 | CB | ILE | 194 | 62.596 | 71.547 | 12.587 | 1.00 | 18.89 | A | C |
| ATOM | 1342 | CG2 | ILE | 194 | 61.209 | 71.944 | 12.095 | 1.00 | 16.97 | A | C |
| ATOM | 1343 | CG1 | ILE | 194 | 63.551 | 72.750 | 12.553 | 1.00 | 19.26 | A | C |
| ATOM | 1344 | CD1 | ILE | 194 | 63.118 | 73.936 | 13.395 | 1.00 | 16.78 | A | C |
| ATOM | 1345 | C | ILE | 194 | 61.663 | 69.702 | 13.969 | 1.00 | 18.22 | A | C |
| ATOM | 1346 | O | ILE | 194 | 62.066 | 68.713 | 13.349 | 1.00 | 17.31 | A | O |
| ATOM | 1347 | N | TYR | 195 | 60.511 | 69.726 | 14.642 | 1.00 | 17.31 | A | N |
| ATOM | 1348 | CA | TYR | 195 | 59.592 | 68.593 | 14.639 | 1.00 | 16.19 | A | C |
| ATOM | 1349 | CB | TYR | 195 | 59.338 | 68.071 | 16.053 | 1.00 | 17.03 | A | C |
| ATOM | 1350 | CG | TYR | 195 | 60.560 | 67.776 | 16.893 | 1.00 | 17.58 | A | C |
| ATOM | 1351 | CD1 | TYR | 195 | 61.427 | 68.802 | 17.286 | 1.00 | 18.28 | A | C |
| ATOM | 1352 | CE1 | TYR | 195 | 62.485 | 68.558 | 18.145 | 1.00 | 16.45 | A | C |
| ATOM | 1353 | CD2 | TYR | 195 | 60.799 | 66.490 | 17.377 | 1.00 | 15.00 | A | C |
| ATOM | 1354 | CE2 | TYR | 195 | 61.859 | 66.237 | 18.240 | 1.00 | 15.14 | A | C |
| ATOM | 1355 | CZ | TYR | 195 | 62.694 | 67.275 | 18.624 | 1.00 | 17.41 | A | C |
| ATOM | 1356 | OH | TYR | 195 | 63.725 | 67.041 | 19.515 | 1.00 | 21.26 | A | O |
| ATOM | 1357 | C | TYR | 195 | 58.242 | 69.016 | 14.047 | 1.00 | 16.29 | A | C |
| ATOM | 1358 | O | TYR | 195 | 57.574 | 69.902 | 14.586 | 1.00 | 15.85 | A | O |
| ATOM | 1359 | N | ASN | 196 | 57.851 | 68.380 | 12.942 | 1.00 | 15.27 | A | N |
| ATOM | 1360 | CA | ASN | 196 | 56.578 | 68.656 | 12.286 | 1.00 | 12.88 | A | C |
| ATOM | 1361 | CB | ASN | 196 | 56.772 | 68.894 | 10.790 | 1.00 | 13.47 | A | C |
| ATOM | 1362 | CG | ASN | 196 | 57.591 | 70.133 | 10.489 | 1.00 | 14.66 | A | C |
| ATOM | 1363 | OD1 | ASN | 196 | 57.132 | 71.261 | 10.678 | 1.00 | 10.34 | A | O |
| ATOM | 1364 | ND2 | ASN | 196 | 58.819 | 69.927 | 10.013 | 1.00 | 15.26 | A | N |
| ATOM | 1365 | C | ASN | 196 | 55.686 | 67.438 | 12.457 | 1.00 | 14.12 | A | C |
| ATOM | 1366 | O | ASN | 196 | 56.050 | 66.347 | 12.044 | 1.00 | 16.31 | A | O |
| ATOM | 1367 | N | GLY | 197 | 54.522 | 67.613 | 13.065 | 1.00 | 14.48 | A | N |
| ATOM | 1368 | CA | GLY | 197 | 53.622 | 66.488 | 13.231 | 1.00 | 15.17 | A | C |
| ATOM | 1369 | C | GLY | 197 | 53.880 | 65.638 | 14.458 | 1.00 | 15.48 | A | C |
| ATOM | 1370 | O | GLY | 197 | 53.059 | 64.799 | 14.815 | 1.00 | 15.55 | A | O |
| ATOM | 1371 | N | ILE | 198 | 55.023 | 65.846 | 15.098 | 1.00 | 16.49 | A | N |

| | | | | | | | | | | |
|---|---|---|---|---|---|---|---|---|---|---|
| ATOM | 1372 | CA | ILE | 198 | 55.378 | 65.097 | 16.298 | 1.00 16.59 | A | C |
| ATOM | 1373 | CB | ILE | 198 | 56.425 | 63.991 | 16.011 | 1.00 18.21 | A | C |
| ATOM | 1374 | CG2 | ILE | 198 | 55.874 | 63.013 | 14.987 | 1.00 18.51 | A | C |
| ATOM | 1375 | CG1 | ILE | 198 | 57.724 | 64.602 | 15.494 | 1.00 17.86 | A | C |
| ATOM | 1376 | CD1 | ILE | 198 | 58.798 | 63.565 | 15.214 | 1.00 19.35 | A | C |
| ATOM | 1377 | C | ILE | 198 | 55.946 | 66.057 | 17.318 | 1.00 15.95 | A | C |
| ATOM | 1378 | O | ILE | 198 | 56.507 | 67.091 | 16.966 | 1.00 17.63 | A | O |
| ATOM | 1379 | N | THR | 199 | 55.809 | 65.700 | 18.583 | 1.00 15.42 | A | N |
| ATOM | 1380 | CA | THR | 199 | 56.264 | 66.547 | 19.672 | 1.00 16.68 | A | C |
| ATOM | 1381 | CB | THR | 199 | 55.374 | 66.316 | 20.908 | 1.00 17.40 | A | C |
| ATOM | 1382 | OG1 | THR | 199 | 55.462 | 64.944 | 21.301 | 1.00 18.82 | A | O |
| ATOM | 1383 | CG2 | THR | 199 | 53.924 | 66.619 | 20.583 | 1.00 15.72 | A | C |
| ATOM | 1384 | C | THR | 199 | 57.716 | 66.334 | 20.076 | 1.00 16.00 | A | C |
| ATOM | 1385 | O | THR | 199 | 58.317 | 65.325 | 19.734 | 1.00 16.12 | A | O |
| ATOM | 1386 | N | ASP | 200 | 58.276 | 67.301 | 20.801 | 1.00 16.87 | A | N |
| ATOM | 1387 | CA | ASP | 200 | 59.649 | 67.193 | 21.289 | 1.00 15.49 | A | C |
| ATOM | 1388 | CB | ASP | 200 | 60.315 | 68.576 | 21.418 | 1.00 14.82 | A | C |
| ATOM | 1389 | CG | ASP | 200 | 59.681 | 69.446 | 22.491 | 1.00 17.16 | A | C |
| ATOM | 1390 | OD1 | ASP | 200 | 58.517 | 69.190 | 22.873 | 1.00 16.41 | A | O |
| ATOM | 1391 | OD2 | ASP | 200 | 60.348 | 70.403 | 22.945 | 1.00 15.97 | A | O |
| ATOM | 1392 | C | ASP | 200 | 59.496 | 66.515 | 22.641 | 1.00 15.54 | A | C |
| ATOM | 1393 | O | ASP | 200 | 58.388 | 66.118 | 22.999 | 1.00 17.01 | A | O |
| ATOM | 1394 | N | TRP | 201 | 60.581 | 66.381 | 23.395 | 1.00 15.10 | A | N |
| ATOM | 1395 | CA | TRP | 201 | 60.504 | 65.699 | 24.672 | 1.00 13.14 | A | C |
| ATOM | 1396 | CB | TRP | 201 | 61.885 | 65.619 | 25.326 | 1.00 14.90 | A | C |
| ATOM | 1397 | CG | TRP | 201 | 61.905 | 64.679 | 26.510 | 1.00 15.25 | A | C |
| ATOM | 1398 | CD2 | TRP | 201 | 61.412 | 64.953 | 27.828 | 1.00 13.65 | A | C |
| ATOM | 1399 | CE2 | TRP | 201 | 61.500 | 63.753 | 28.564 | 1.00 13.52 | A | C |
| ATOM | 1400 | CE3 | TRP | 201 | 60.902 | 66.096 | 28.456 | 1.00 11.78 | A | C |
| ATOM | 1401 | CD1 | TRP | 201 | 62.269 | 63.360 | 26.507 | 1.00 13.81 | A | C |
| ATOM | 1402 | NE1 | TRP | 201 | 62.025 | 62.799 | 27.733 | 1.00 13.64 | A | N |
| ATOM | 1403 | CZ2 | TRP | 201 | 61.096 | 63.661 | 29.897 | 1.00 14.03 | A | C |
| ATOM | 1404 | CZ3 | TRP | 201 | 60.502 | 66.009 | 29.778 | 1.00 12.04 | A | C |
| ATOM | 1405 | CH2 | TRP | 201 | 60.601 | 64.797 | 30.486 | 1.00 14.87 | A | C |
| ATOM | 1406 | C | TRP | 201 | 59.529 | 66.327 | 25.662 | 1.00 14.42 | A | C |
| ATOM | 1407 | O | TRP | 201 | 58.635 | 65.656 | 26.175 | 1.00 13.63 | A | O |
| ATOM | 1408 | N | VAL | 202 | 59.691 | 67.615 | 25.931 | 1.00 15.14 | A | N |
| ATOM | 1409 | CA | VAL | 202 | 58.830 | 68.265 | 26.911 | 1.00 14.23 | A | C |
| ATOM | 1410 | CB | VAL | 202 | 59.402 | 69.639 | 27.330 | 1.00 12.99 | A | C |
| ATOM | 1411 | CG1 | VAL | 202 | 59.010 | 70.716 | 26.322 | 1.00 11.02 | A | C |
| ATOM | 1412 | CG2 | VAL | 202 | 58.947 | 69.963 | 28.753 | 1.00 8.71 | A | C |
| ATOM | 1413 | C | VAL | 202 | 57.365 | 68.401 | 26.518 | 1.00 15.76 | A | C |
| ATOM | 1414 | O | VAL | 202 | 56.497 | 68.404 | 27.391 | 1.00 18.74 | A | O |
| ATOM | 1415 | N | TYR | 203 | 57.072 | 68.518 | 25.226 | 1.00 15.58 | A | N |
| ATOM | 1416 | CA | TYR | 203 | 55.676 | 68.606 | 24.805 | 1.00 14.25 | A | C |
| ATOM | 1417 | CB | TYR | 203 | 55.556 | 69.078 | 23.354 | 1.00 14.63 | A | C |
| ATOM | 1418 | CG | TYR | 203 | 55.227 | 70.542 | 23.227 | 1.00 12.35 | A | C |
| ATOM | 1419 | CD1 | TYR | 203 | 56.231 | 71.508 | 23.193 | 1.00 11.91 | A | C |
| ATOM | 1420 | CE1 | TYR | 203 | 55.920 | 72.867 | 23.108 | 1.00 11.20 | A | C |

| | | | | | | | | | | | |
|---|---|---|---|---|---|---|---|---|---|---|---|
| ATOM | 1421 | CD2 | TYR | 203 | 53.902 | 70.966 | 23.177 | 1.00 | 12.17 | A | C |
| ATOM | 1422 | CE2 | TYR | 203 | 53.579 | 72.314 | 23.099 | 1.00 | 10.57 | A | C |
| ATOM | 1423 | CZ | TYR | 203 | 54.588 | 73.259 | 23.061 | 1.00 | 9.67 | A | C |
| ATOM | 1424 | OH | TYR | 203 | 54.259 | 74.586 | 22.970 | 1.00 | 7.05 | A | O |
| ATOM | 1425 | C | TYR | 203 | 55.024 | 67.234 | 24.951 | 1.00 | 14.92 | A | C |
| ATOM | 1426 | O | TYR | 203 | 53.896 | 67.124 | 25.406 | 1.00 | 15.28 | A | O |
| ATOM | 1427 | N | GLU | 204 | 55.744 | 66.185 | 24.570 | 1.00 | 16.35 | A | N |
| ATOM | 1428 | CA | GLU | 204 | 55.222 | 64.826 | 24.684 | 1.00 | 16.96 | A | C |
| ATOM | 1429 | CB | GLU | 204 | 56.238 | 63.812 | 24.130 | 1.00 | 14.28 | A | C |
| ATOM | 1430 | CG | GLU | 204 | 55.928 | 62.380 | 24.540 | 1.00 | 14.97 | A | C |
| ATOM | 1431 | CD | GLU | 204 | 56.872 | 61.345 | 23.947 | 1.00 | 19.54 | A | C |
| ATOM | 1432 | OE1 | GLU | 204 | 56.697 | 60.144 | 24.271 | 1.00 | 18.49 | A | O |
| ATOM | 1433 | OE2 | GLU | 204 | 57.778 | 61.714 | 23.160 | 1.00 | 18.73 | A | O |
| ATOM | 1434 | C | GLU | 204 | 54.868 | 64.431 | 26.128 | 1.00 | 18.02 | A | C |
| ATOM | 1435 | O | GLU | 204 | 53.816 | 63.848 | 26.388 | 1.00 | 17.48 | A | O |
| ATOM | 1436 | N | GLU | 205 | 55.757 | 64.761 | 27.059 | 1.00 | 18.67 | A | N |
| ATOM | 1437 | CA | GLU | 205 | 55.589 | 64.409 | 28.459 | 1.00 | 20.30 | A | C |
| ATOM | 1438 | CB | GLU | 205 | 56.970 | 64.250 | 29.096 | 1.00 | 20.92 | A | C |
| ATOM | 1439 | CG | GLU | 205 | 56.958 | 64.035 | 30.592 | 1.00 | 24.62 | A | C |
| ATOM | 1440 | CD | GLU | 205 | 56.563 | 62.625 | 30.974 | 1.00 | 28.17 | A | C |
| ATOM | 1441 | OE1 | GLU | 205 | 56.398 | 62.355 | 32.182 | 1.00 | 32.15 | A | O |
| ATOM | 1442 | OE2 | GLU | 205 | 56.424 | 61.778 | 30.069 | 1.00 | 31.11 | A | O |
| ATOM | 1443 | C | GLU | 205 | 54.760 | 65.362 | 29.319 | 1.00 | 22.25 | A | C |
| ATOM | 1444 | O | GLU | 205 | 53.996 | 64.915 | 30.164 | 1.00 | 22.34 | A | O |
| ATOM | 1445 | N | GLU | 206 | 54.902 | 66.666 | 29.107 | 1.00 | 22.70 | A | N |
| ATOM | 1446 | CA | GLU | 206 | 54.202 | 67.632 | 29.939 | 1.00 | 23.19 | A | C |
| ATOM | 1447 | CB | GLU | 206 | 55.203 | 68.667 | 30.453 | 1.00 | 25.39 | A | C |
| ATOM | 1448 | CG | GLU | 206 | 56.466 | 68.088 | 31.080 | 1.00 | 27.87 | A | C |
| ATOM | 1449 | CD | GLU | 206 | 56.188 | 67.307 | 32.345 | 1.00 | 29.45 | A | C |
| ATOM | 1450 | OE1 | GLU | 206 | 57.160 | 66.855 | 32.987 | 1.00 | 29.92 | A | O |
| ATOM | 1451 | OE2 | GLU | 206 | 55.000 | 67.144 | 32.696 | 1.00 | 29.12 | A | O |
| ATOM | 1452 | C | GLU | 206 | 53.024 | 68.378 | 29.324 | 1.00 | 24.91 | A | C |
| ATOM | 1453 | O | GLU | 206 | 52.175 | 68.885 | 30.051 | 1.00 | 24.03 | A | O |
| ATOM | 1454 | N | VAL | 207 | 52.957 | 68.452 | 27.999 | 1.00 | 25.41 | A | N |
| ATOM | 1455 | CA | VAL | 207 | 51.880 | 69.199 | 27.375 | 1.00 | 25.29 | A | C |
| ATOM | 1456 | CB | VAL | 207 | 52.444 | 70.235 | 26.398 | 1.00 | 25.95 | A | C |
| ATOM | 1457 | CG1 | VAL | 207 | 51.324 | 71.114 | 25.876 | 1.00 | 28.49 | A | C |
| ATOM | 1458 | CG2 | VAL | 207 | 53.496 | 71.080 | 27.092 | 1.00 | 26.77 | A | C |
| ATOM | 1459 | C | VAL | 207 | 50.801 | 68.409 | 26.653 | 1.00 | 26.09 | A | C |
| ATOM | 1460 | O | VAL | 207 | 49.617 | 68.703 | 26.813 | 1.00 | 27.62 | A | O |
| ATOM | 1461 | N | PHE | 208 | 51.194 | 67.412 | 25.865 | 1.00 | 26.41 | A | N |
| ATOM | 1462 | CA | PHE | 208 | 50.228 | 66.620 | 25.105 | 1.00 | 26.03 | A | C |
| ATOM | 1463 | CB | PHE | 208 | 50.557 | 66.676 | 23.607 | 1.00 | 27.43 | A | C |
| ATOM | 1464 | CG | PHE | 208 | 50.234 | 67.994 | 22.962 | 1.00 | 28.64 | A | C |
| ATOM | 1465 | CD1 | PHE | 208 | 51.234 | 68.911 | 22.679 | 1.00 | 29.07 | A | C |
| ATOM | 1466 | CD2 | PHE | 208 | 48.918 | 68.328 | 22.660 | 1.00 | 30.01 | A | C |
| ATOM | 1467 | CE1 | PHE | 208 | 50.929 | 70.142 | 22.104 | 1.00 | 30.28 | A | C |
| ATOM | 1468 | CE2 | PHE | 208 | 48.604 | 69.556 | 22.086 | 1.00 | 30.23 | A | C |
| ATOM | 1469 | CZ | PHE | 208 | 49.612 | 70.464 | 21.809 | 1.00 | 30.40 | A | C |

| ATOM | 1470 | C   | PHE | 208 | 50.082 | 65.163 | 25.506 | 1.00 | 26.13 | A | C |
| ---- | ---- | --- | --- | --- | ------ | ------ | ------ | ---- | ----- | - | - |
| ATOM | 1471 | O   | PHE | 208 | 49.215 | 64.471 | 24.985 | 1.00 | 27.79 | A | O |
| ATOM | 1472 | N   | SER | 209 | 50.918 | 64.687 | 26.421 | 1.00 | 26.62 | A | N |
| ATOM | 1473 | CA  | SER | 209 | 50.852 | 63.293 | 26.848 | 1.00 | 25.74 | A | C |
| ATOM | 1474 | CB  | SER | 209 | 49.645 | 63.059 | 27.743 | 1.00 | 24.80 | A | C |
| ATOM | 1475 | OG  | SER | 209 | 49.871 | 63.629 | 29.014 | 1.00 | 29.47 | A | O |
| ATOM | 1476 | C   | SER | 209 | 50.773 | 62.377 | 25.642 | 1.00 | 25.50 | A | C |
| ATOM | 1477 | O   | SER | 209 | 50.278 | 61.249 | 25.716 | 1.00 | 25.72 | A | O |
| ATOM | 1478 | N   | ALA | 210 | 51.272 | 62.875 | 24.524 | 1.00 | 23.72 | A | N |
| ATOM | 1479 | CA  | ALA | 210 | 51.263 | 62.112 | 23.299 | 1.00 | 22.80 | A | C |
| ATOM | 1480 | CB  | ALA | 210 | 49.977 | 62.364 | 22.530 | 1.00 | 20.62 | A | C |
| ATOM | 1481 | C   | ALA | 210 | 52.455 | 62.560 | 22.492 | 1.00 | 21.87 | A | C |
| ATOM | 1482 | O   | ALA | 210 | 52.986 | 63.644 | 22.703 | 1.00 | 22.09 | A | O |
| ATOM | 1483 | N   | TYR | 211 | 52.863 | 61.719 | 21.558 | 1.00 | 21.57 | A | N |
| ATOM | 1484 | CA  | TYR | 211 | 54.000 | 62.009 | 20.718 | 1.00 | 21.42 | A | C |
| ATOM | 1485 | CB  | TYR | 211 | 54.725 | 60.711 | 20.405 | 1.00 | 19.58 | A | C |
| ATOM | 1486 | CG  | TYR | 211 | 55.921 | 60.870 | 19.528 | 1.00 | 16.81 | A | C |
| ATOM | 1487 | CD1 | TYR | 211 | 56.853 | 61.870 | 19.770 | 1.00 | 16.07 | A | C |
| ATOM | 1488 | CE1 | TYR | 211 | 58.002 | 61.971 | 19.001 | 1.00 | 18.18 | A | C |
| ATOM | 1489 | CD2 | TYR | 211 | 56.160 | 59.976 | 18.489 | 1.00 | 17.91 | A | C |
| ATOM | 1490 | CE2 | TYR | 211 | 57.306 | 60.065 | 17.716 | 1.00 | 18.80 | A | C |
| ATOM | 1491 | CZ  | TYR | 211 | 58.221 | 61.063 | 17.979 | 1.00 | 18.36 | A | C |
| ATOM | 1492 | OH  | TYR | 211 | 59.360 | 61.149 | 17.224 | 1.00 | 23.65 | A | O |
| ATOM | 1493 | C   | TYR | 211 | 53.588 | 62.689 | 19.428 | 1.00 | 22.96 | A | C |
| ATOM | 1494 | O   | TYR | 211 | 54.365 | 63.443 | 18.837 | 1.00 | 25.79 | A | O |
| ATOM | 1495 | N   | SER | 212 | 52.365 | 62.433 | 18.983 | 1.00 | 20.96 | A | N |
| ATOM | 1496 | CA  | SER | 212 | 51.918 | 63.033 | 17.746 | 1.00 | 19.56 | A | C |
| ATOM | 1497 | CB  | SER | 212 | 50.835 | 62.175 | 17.090 | 1.00 | 20.97 | A | C |
| ATOM | 1498 | OG  | SER | 212 | 49.635 | 62.208 | 17.829 | 1.00 | 21.79 | A | O |
| ATOM | 1499 | C   | SER | 212 | 51.397 | 64.439 | 17.959 | 1.00 | 18.50 | A | C |
| ATOM | 1500 | O   | SER | 212 | 50.933 | 64.789 | 19.040 | 1.00 | 16.31 | A | O |
| ATOM | 1501 | N   | ALA | 213 | 51.493 | 65.236 | 16.901 | 1.00 | 17.84 | A | N |
| ATOM | 1502 | CA  | ALA | 213 | 51.036 | 66.610 | 16.903 | 1.00 | 16.02 | A | C |
| ATOM | 1503 | CB  | ALA | 213 | 52.193 | 67.548 | 17.224 | 1.00 | 14.16 | A | C |
| ATOM | 1504 | C   | ALA | 213 | 50.429 | 66.935 | 15.526 | 1.00 | 15.57 | A | C |
| ATOM | 1505 | O   | ALA | 213 | 50.857 | 67.862 | 14.833 | 1.00 | 13.25 | A | O |
| ATOM | 1506 | N   | LEU | 214 | 49.448 | 66.132 | 15.129 | 1.00 | 14.75 | A | N |
| ATOM | 1507 | CA  | LEU | 214 | 48.734 | 66.339 | 13.874 | 1.00 | 16.09 | A | C |
| ATOM | 1508 | CB  | LEU | 214 | 49.353 | 65.517 | 12.735 | 1.00 | 16.40 | A | C |
| ATOM | 1509 | CG  | LEU | 214 | 49.482 | 63.999 | 12.823 | 1.00 | 17.01 | A | C |
| ATOM | 1510 | CD1 | LEU | 214 | 48.135 | 63.342 | 12.628 | 1.00 | 18.97 | A | C |
| ATOM | 1511 | CD2 | LEU | 214 | 50.434 | 63.535 | 11.742 | 1.00 | 16.98 | A | C |
| ATOM | 1512 | C   | LEU | 214 | 47.273 | 65.963 | 14.124 | 1.00 | 16.65 | A | C |
| ATOM | 1513 | O   | LEU | 214 | 46.966 | 64.933 | 14.728 | 1.00 | 18.12 | A | O |
| ATOM | 1514 | N   | TRP | 215 | 46.366 | 66.811 | 13.666 | 1.00 | 16.16 | A | N |
| ATOM | 1515 | CA  | TRP | 215 | 44.959 | 66.590 | 13.907 | 1.00 | 14.69 | A | C |
| ATOM | 1516 | CB  | TRP | 215 | 44.471 | 67.663 | 14.863 | 1.00 | 15.49 | A | C |
| ATOM | 1517 | CG  | TRP | 215 | 45.230 | 67.669 | 16.145 | 1.00 | 17.52 | A | C |
| ATOM | 1518 | CD2 | TRP | 215 | 46.482 | 68.325 | 16.403 | 1.00 | 17.74 | A | C |

FIG. 4-32 (Continued)

| | | | | | | | | | | | |
|---|---|---|---|---|---|---|---|---|---|---|---|
| ATOM | 1519 | CE2 | TRP | 215 | 46.852 | 68.008 | 17.729 | 1.00 | 17.50 | A | C |
| ATOM | 1520 | CE3 | TRP | 215 | 47.325 | 69.149 | 15.643 | 1.00 | 18.21 | A | C |
| ATOM | 1521 | CD1 | TRP | 215 | 44.904 | 67.004 | 17.289 | 1.00 | 15.79 | A | C |
| ATOM | 1522 | NE1 | TRP | 215 | 45.873 | 67.202 | 18.243 | 1.00 | 17.35 | A | N |
| ATOM | 1523 | CZ2 | TRP | 215 | 48.033 | 68.485 | 18.318 | 1.00 | 18.06 | A | C |
| ATOM | 1524 | CZ3 | TRP | 215 | 48.505 | 69.625 | 16.228 | 1.00 | 18.96 | A | C |
| ATOM | 1525 | CH2 | TRP | 215 | 48.844 | 69.289 | 17.555 | 1.00 | 18.21 | A | C |
| ATOM | 1526 | C | TRP | 215 | 44.110 | 66.605 | 12.661 | 1.00 | 15.55 | A | C |
| ATOM | 1527 | O | TRP | 215 | 43.869 | 67.668 | 12.090 | 1.00 | 16.18 | A | O |
| ATOM | 1528 | N | TRP | 216 | 43.646 | 65.430 | 12.244 | 1.00 | 15.31 | A | N |
| ATOM | 1529 | CA | TRP | 216 | 42.793 | 65.330 | 11.069 | 1.00 | 16.40 | A | C |
| ATOM | 1530 | CB | TRP | 216 | 42.494 | 63.873 | 10.739 | 1.00 | 16.43 | A | C |
| ATOM | 1531 | CG | TRP | 216 | 43.549 | 63.114 | 10.002 | 1.00 | 17.38 | A | C |
| ATOM | 1532 | CD2 | TRP | 216 | 43.823 | 63.169 | 8.599 | 1.00 | 17.01 | A | C |
| ATOM | 1533 | CE2 | TRP | 216 | 44.794 | 62.176 | 8.320 | 1.00 | 17.25 | A | C |
| ATOM | 1534 | CE3 | TRP | 216 | 43.340 | 63.954 | 7.549 | 1.00 | 17.09 | A | C |
| ATOM | 1535 | CD1 | TRP | 216 | 44.352 | 62.125 | 10.508 | 1.00 | 18.55 | A | C |
| ATOM | 1536 | NE1 | TRP | 216 | 45.098 | 61.553 | 9.501 | 1.00 | 18.07 | A | N |
| ATOM | 1537 | CZ2 | TRP | 216 | 45.286 | 61.951 | 7.036 | 1.00 | 15.24 | A | C |
| ATOM | 1538 | CZ3 | TRP | 216 | 43.829 | 63.729 | 6.270 | 1.00 | 17.06 | A | C |
| ATOM | 1539 | CH2 | TRP | 216 | 44.794 | 62.734 | 6.027 | 1.00 | 17.07 | A | C |
| ATOM | 1540 | C | TRP | 216 | 41.461 | 66.016 | 11.355 | 1.00 | 17.17 | A | C |
| ATOM | 1541 | O | TRP | 216 | 40.990 | 66.005 | 12.487 | 1.00 | 18.00 | A | O |
| ATOM | 1542 | N | SER | 217 | 40.847 | 66.605 | 10.334 | 1.00 | 18.39 | A | N |
| ATOM | 1543 | CA | SER | 217 | 39.552 | 67.240 | 10.523 | 1.00 | 19.62 | A | C |
| ATOM | 1544 | CB | SER | 217 | 39.257 | 68.225 | 9.392 | 1.00 | 20.31 | A | C |
| ATOM | 1545 | OG | SER | 217 | 39.234 | 67.589 | 8.133 | 1.00 | 24.00 | A | O |
| ATOM | 1546 | C | SER | 217 | 38.528 | 66.108 | 10.550 | 1.00 | 20.47 | A | C |
| ATOM | 1547 | O | SER | 217 | 38.814 | 64.994 | 10.110 | 1.00 | 20.32 | A | O |
| ATOM | 1548 | N | PRO | 218 | 37.326 | 66.369 | 11.074 | 1.00 | 20.82 | A | N |
| ATOM | 1549 | CD | PRO | 218 | 36.827 | 67.650 | 11.598 | 1.00 | 20.28 | A | C |
| ATOM | 1550 | CA | PRO | 218 | 36.285 | 65.339 | 11.154 | 1.00 | 22.67 | A | C |
| ATOM | 1551 | CB | PRO | 218 | 35.033 | 66.148 | 11.462 | 1.00 | 21.68 | A | C |
| ATOM | 1552 | CG | PRO | 218 | 35.587 | 67.223 | 12.353 | 1.00 | 21.12 | A | C |
| ATOM | 1553 | C | PRO | 218 | 36.123 | 64.404 | 9.950 | 1.00 | 23.46 | A | C |
| ATOM | 1554 | O | PRO | 218 | 36.190 | 63.183 | 10.107 | 1.00 | 25.13 | A | O |
| ATOM | 1555 | N | ASN | 219 | 35.909 | 64.948 | 8.756 | 1.00 | 22.93 | A | N |
| ATOM | 1556 | CA | ASN | 219 | 35.756 | 64.071 | 7.600 | 1.00 | 22.31 | A | C |
| ATOM | 1557 | CB | ASN | 219 | 34.704 | 64.622 | 6.631 | 1.00 | 22.48 | A | C |
| ATOM | 1558 | CG | ASN | 219 | 35.172 | 65.849 | 5.903 | 1.00 | 24.12 | A | C |
| ATOM | 1559 | OD1 | ASN | 219 | 36.373 | 66.076 | 5.760 | 1.00 | 26.01 | A | O |
| ATOM | 1560 | ND2 | ASN | 219 | 34.230 | 66.640 | 5.411 | 1.00 | 26.27 | A | N |
| ATOM | 1561 | C | ASN | 219 | 37.090 | 63.841 | 6.871 | 1.00 | 21.20 | A | C |
| ATOM | 1562 | O | ASN | 219 | 37.115 | 63.307 | 5.760 | 1.00 | 20.94 | A | O |
| ATOM | 1563 | N | GLY | 220 | 38.184 | 64.267 | 7.499 | 1.00 | 18.33 | A | N |
| ATOM | 1564 | CA | GLY | 220 | 39.512 | 64.068 | 6.941 | 1.00 | 17.97 | A | C |
| ATOM | 1565 | C | GLY | 220 | 40.035 | 64.993 | 5.853 | 1.00 | 18.92 | A | C |
| ATOM | 1566 | O | GLY | 220 | 41.157 | 64.801 | 5.375 | 1.00 | 20.28 | A | O |
| ATOM | 1567 | N | THR | 221 | 39.242 | 65.980 | 5.447 | 1.00 | 17.57 | A | N |

| ATOM | 1568 | CA  | THR | 221 | 39.654 | 66.917 | 4.408  | 1.00 | 15.80 | A | C |
|------|------|-----|-----|-----|--------|--------|--------|------|-------|---|---|
| ATOM | 1569 | CB  | THR | 221 | 38.540 | 67.942 | 4.112  | 1.00 | 15.67 | A | C |
| ATOM | 1570 | OG1 | THR | 221 | 37.410 | 67.269 | 3.550  | 1.00 | 16.41 | A | O |
| ATOM | 1571 | CG2 | THR | 221 | 39.019 | 69.004 | 3.147  | 1.00 | 12.96 | A | C |
| ATOM | 1572 | C   | THR | 221 | 40.903 | 67.674 | 4.833  | 1.00 | 16.70 | A | C |
| ATOM | 1573 | O   | THR | 221 | 41.884 | 67.753 | 4.088  | 1.00 | 16.98 | A | O |
| ATOM | 1574 | N   | PHE | 222 | 40.864 | 68.238 | 6.033  | 1.00 | 15.92 | A | N |
| ATOM | 1575 | CA  | PHE | 222 | 41.999 | 69.001 | 6.539  | 1.00 | 15.88 | A | C |
| ATOM | 1576 | CB  | PHE | 222 | 41.508 | 70.253 | 7.262  | 1.00 | 15.20 | A | C |
| ATOM | 1577 | CG  | PHE | 222 | 40.939 | 71.305 | 6.356  | 1.00 | 14.35 | A | C |
| ATOM | 1578 | CD1 | PHE | 222 | 39.569 | 71.542 | 6.323  | 1.00 | 11.89 | A | C |
| ATOM | 1579 | CD2 | PHE | 222 | 41.782 | 72.097 | 5.571  | 1.00 | 14.45 | A | C |
| ATOM | 1580 | CE1 | PHE | 222 | 39.046 | 72.550 | 5.533  | 1.00 | 13.50 | A | C |
| ATOM | 1581 | CE2 | PHE | 222 | 41.269 | 73.112 | 4.771  | 1.00 | 12.61 | A | C |
| ATOM | 1582 | CZ  | PHE | 222 | 39.897 | 73.342 | 4.751  | 1.00 | 15.23 | A | C |
| ATOM | 1583 | C   | PHE | 222 | 42.907 | 68.228 | 7.494  | 1.00 | 16.13 | A | C |
| ATOM | 1584 | O   | PHE | 222 | 42.467 | 67.327 | 8.211  | 1.00 | 16.82 | A | O |
| ATOM | 1585 | N   | LEU | 223 | 44.187 | 68.582 | 7.484  | 1.00 | 15.93 | A | N |
| ATOM | 1586 | CA  | LEU | 223 | 45.159 | 67.983 | 8.385  | 1.00 | 14.81 | A | C |
| ATOM | 1587 | CB  | LEU | 223 | 46.199 | 67.142 | 7.645  | 1.00 | 14.64 | A | C |
| ATOM | 1588 | CG  | LEU | 223 | 47.306 | 66.627 | 8.584  | 1.00 | 14.94 | A | C |
| ATOM | 1589 | CD1 | LEU | 223 | 46.696 | 65.773 | 9.687  | 1.00 | 11.99 | A | C |
| ATOM | 1590 | CD2 | LEU | 223 | 48.338 | 65.830 | 7.808  | 1.00 | 11.50 | A | C |
| ATOM | 1591 | C   | LEU | 223 | 45.848 | 69.162 | 9.031  | 1.00 | 16.80 | A | C |
| ATOM | 1592 | O   | LEU | 223 | 46.398 | 70.028 | 8.341  | 1.00 | 16.53 | A | O |
| ATOM | 1593 | N   | ALA | 224 | 45.790 | 69.219 | 10.353 | 1.00 | 17.34 | A | N |
| ATOM | 1594 | CA  | ALA | 224 | 46.420 | 70.308 | 11.073 | 1.00 | 18.47 | A | C |
| ATOM | 1595 | CB  | ALA | 224 | 45.422 | 70.950 | 12.029 | 1.00 | 17.47 | A | C |
| ATOM | 1596 | C   | ALA | 224 | 47.596 | 69.735 | 11.840 | 1.00 | 18.77 | A | C |
| ATOM | 1597 | O   | ALA | 224 | 47.587 | 68.561 | 12.205 | 1.00 | 19.22 | A | O |
| ATOM | 1598 | N   | TYR | 225 | 48.614 | 70.551 | 12.078 | 1.00 | 17.68 | A | N |
| ATOM | 1599 | CA  | TYR | 225 | 49.764 | 70.068 | 12.819 | 1.00 | 17.56 | A | C |
| ATOM | 1600 | CB  | TYR | 225 | 50.726 | 69.306 | 11.891 | 1.00 | 16.48 | A | C |
| ATOM | 1601 | CG  | TYR | 225 | 51.273 | 70.108 | 10.726 | 1.00 | 15.05 | A | C |
| ATOM | 1602 | CD1 | TYR | 225 | 50.551 | 70.235 | 9.533  | 1.00 | 13.44 | A | C |
| ATOM | 1603 | CE1 | TYR | 225 | 51.050 | 70.968 | 8.456  | 1.00 | 9.19  | A | C |
| ATOM | 1604 | CD2 | TYR | 225 | 52.514 | 70.740 | 10.814 | 1.00 | 14.42 | A | C |
| ATOM | 1605 | CE2 | TYR | 225 | 53.025 | 71.476 | 9.744  | 1.00 | 14.09 | A | C |
| ATOM | 1606 | CZ  | TYR | 225 | 52.286 | 71.583 | 8.567  | 1.00 | 14.11 | A | C |
| ATOM | 1607 | OH  | TYR | 225 | 52.802 | 72.292 | 7.504  | 1.00 | 14.49 | A | O |
| ATOM | 1608 | C   | TYR | 225 | 50.514 | 71.182 | 13.521 | 1.00 | 17.79 | A | C |
| ATOM | 1609 | O   | TYR | 225 | 50.326 | 72.359 | 13.229 | 1.00 | 19.91 | A | O |
| ATOM | 1610 | N   | ALA | 226 | 51.358 | 70.796 | 14.462 | 1.00 | 17.65 | A | N |
| ATOM | 1611 | CA  | ALA | 226 | 52.164 | 71.748 | 15.201 | 1.00 | 17.74 | A | C |
| ATOM | 1612 | CB  | ALA | 226 | 52.060 | 71.472 | 16.687 | 1.00 | 18.89 | A | C |
| ATOM | 1613 | C   | ALA | 226 | 53.601 | 71.575 | 14.740 | 1.00 | 17.39 | A | C |
| ATOM | 1614 | O   | ALA | 226 | 53.966 | 70.527 | 14.204 | 1.00 | 16.05 | A | O |
| ATOM | 1615 | N   | GLN | 227 | 54.412 | 72.606 | 14.941 | 1.00 | 17.45 | A | N |
| ATOM | 1616 | CA  | GLN | 227 | 55.816 | 72.552 | 14.555 | 1.00 | 16.64 | A | C |

FIG. 4-34

| ATOM | 1617 | CB | GLN | 227 | 56.096 | 73.423 | 13.331 | 1.00 | 15.62 | A | C |
| ATOM | 1618 | CG | GLN | 227 | 57.514 | 73.246 | 12.799 | 1.00 | 16.35 | A | C |
| ATOM | 1619 | CD | GLN | 227 | 57.847 | 74.191 | 11.666 | 1.00 | 14.31 | A | C |
| ATOM | 1620 | OE1 | GLN | 227 | 57.877 | 75.408 | 11.851 | 1.00 | 18.11 | A | O |
| ATOM | 1621 | NE2 | GLN | 227 | 58.101 | 73.639 | 10.486 | 1.00 | 12.45 | A | N |
| ATOM | 1622 | C | GLN | 227 | 56.615 | 73.073 | 15.723 | 1.00 | 16.27 | A | C |
| ATOM | 1623 | O | GLN | 227 | 56.346 | 74.159 | 16.225 | 1.00 | 16.33 | A | O |
| ATOM | 1624 | N | PHE | 228 | 57.601 | 72.301 | 16.158 | 1.00 | 17.36 | A | N |
| ATOM | 1625 | CA | PHE | 228 | 58.414 | 72.717 | 17.287 | 1.00 | 16.81 | A | C |
| ATOM | 1626 | CB | PHE | 228 | 58.327 | 71.686 | 18.412 | 1.00 | 14.62 | A | C |
| ATOM | 1627 | CG | PHE | 228 | 56.919 | 71.295 | 18.758 | 1.00 | 14.48 | A | C |
| ATOM | 1628 | CD1 | PHE | 228 | 56.317 | 70.196 | 18.141 | 1.00 | 14.37 | A | C |
| ATOM | 1629 | CD2 | PHE | 228 | 56.183 | 72.036 | 19.674 | 1.00 | 12.73 | A | C |
| ATOM | 1630 | CE1 | PHE | 228 | 55.007 | 69.840 | 18.430 | 1.00 | 13.56 | A | C |
| ATOM | 1631 | CE2 | PHE | 228 | 54.870 | 71.691 | 19.971 | 1.00 | 14.73 | A | C |
| ATOM | 1632 | CZ | PHE | 228 | 54.279 | 70.588 | 19.348 | 1.00 | 15.31 | A | C |
| ATOM | 1633 | C | PHE | 228 | 59.848 | 72.922 | 16.859 | 1.00 | 18.12 | A | C |
| ATOM | 1634 | O | PHE | 228 | 60.410 | 72.121 | 16.112 | 1.00 | 17.47 | A | O |
| ATOM | 1635 | N | ASN | 229 | 60.413 | 74.027 | 17.335 | 1.00 | 20.00 | A | N |
| ATOM | 1636 | CA | ASN | 229 | 61.779 | 74.435 | 17.042 | 1.00 | 20.87 | A | C |
| ATOM | 1637 | CB | ASN | 229 | 61.767 | 75.857 | 16.474 | 1.00 | 21.57 | A | C |
| ATOM | 1638 | CG | ASN | 229 | 63.086 | 76.257 | 15.870 | 1.00 | 24.35 | A | C |
| ATOM | 1639 | OD1 | ASN | 229 | 64.141 | 75.774 | 16.289 | 1.00 | 26.00 | A | O |
| ATOM | 1640 | ND2 | ASN | 229 | 63.025 | 77.153 | 14.887 | 1.00 | 25.62 | A | N |
| ATOM | 1641 | C | ASN | 229 | 62.540 | 74.421 | 18.362 | 1.00 | 21.39 | A | C |
| ATOM | 1642 | O | ASN | 229 | 62.232 | 75.200 | 19.269 | 1.00 | 21.52 | A | O |
| ATOM | 1643 | N | ASP | 230 | 63.516 | 73.530 | 18.481 | 1.00 | 20.96 | A | N |
| ATOM | 1644 | CA | ASP | 230 | 64.300 | 73.444 | 19.706 | 1.00 | 22.78 | A | C |
| ATOM | 1645 | CB | ASP | 230 | 64.275 | 72.026 | 20.268 | 1.00 | 22.69 | A | C |
| ATOM | 1646 | CG | ASP | 230 | 62.880 | 71.551 | 20.580 | 1.00 | 22.37 | A | C |
| ATOM | 1647 | OD1 | ASP | 230 | 62.681 | 71.015 | 21.689 | 1.00 | 21.57 | A | O |
| ATOM | 1648 | OD2 | ASP | 230 | 61.993 | 71.705 | 19.713 | 1.00 | 21.82 | A | O |
| ATOM | 1649 | C | ASP | 230 | 65.734 | 73.825 | 19.412 | 1.00 | 24.50 | A | C |
| ATOM | 1650 | O | ASP | 230 | 66.663 | 73.252 | 19.979 | 1.00 | 24.72 | A | O |
| ATOM | 1651 | N | THR | 231 | 65.904 | 74.803 | 18.527 | 1.00 | 25.87 | A | N |
| ATOM | 1652 | CA | THR | 231 | 67.228 | 75.245 | 18.122 | 1.00 | 26.22 | A | C |
| ATOM | 1653 | CB | THR | 231 | 67.149 | 76.406 | 17.109 | 1.00 | 27.87 | A | C |
| ATOM | 1654 | OG1 | THR | 231 | 66.540 | 75.947 | 15.893 | 1.00 | 28.62 | A | O |
| ATOM | 1655 | CG2 | THR | 231 | 68.545 | 76.947 | 16.813 | 1.00 | 26.63 | A | C |
| ATOM | 1656 | C | THR | 231 | 68.099 | 75.688 | 19.280 | 1.00 | 26.77 | A | C |
| ATOM | 1657 | O | THR | 231 | 69.254 | 75.277 | 19.375 | 1.00 | 27.34 | A | O |
| ATOM | 1658 | N | GLU | 232 | 67.550 | 76.519 | 20.163 | 1.00 | 25.50 | A | N |
| ATOM | 1659 | CA | GLU | 232 | 68.329 | 77.020 | 21.285 | 1.00 | 24.52 | A | C |
| ATOM | 1660 | CB | GLU | 232 | 68.154 | 78.526 | 21.397 | 1.00 | 28.36 | A | C |
| ATOM | 1661 | CG | GLU | 232 | 68.615 | 79.281 | 20.171 | 1.00 | 34.72 | A | C |
| ATOM | 1662 | CD | GLU | 232 | 68.483 | 80.780 | 20.338 | 1.00 | 40.02 | A | C |
| ATOM | 1663 | OE1 | GLU | 232 | 68.767 | 81.509 | 19.363 | 1.00 | 44.21 | A | O |
| ATOM | 1664 | OE2 | GLU | 232 | 68.100 | 81.232 | 21.444 | 1.00 | 42.26 | A | O |
| ATOM | 1665 | C | GLU | 232 | 68.020 | 76.377 | 22.627 | 1.00 | 22.97 | A | C |

| | | | | | | | | | | |
|---|---|---|---|---|---|---|---|---|---|---|
| ATOM | 1666 | O | GLU | 232 | 68.331 | 76.942 | 23.679 | 1.00 | 20.81 | A | O |
| ATOM | 1667 | N | VAL | 233 | 67.416 | 75.194 | 22.596 | 1.00 | 20.32 | A | N |
| ATOM | 1668 | CA | VAL | 233 | 67.091 | 74.499 | 23.832 | 1.00 | 17.88 | A | C |
| ATOM | 1669 | CB | VAL | 233 | 65.853 | 73.618 | 23.648 | 1.00 | 17.88 | A | C |
| ATOM | 1670 | CG1 | VAL | 233 | 65.522 | 72.925 | 24.957 | 1.00 | 14.00 | A | C |
| ATOM | 1671 | CG2 | VAL | 233 | 64.678 | 74.478 | 23.160 | 1.00 | 16.73 | A | C |
| ATOM | 1672 | C | VAL | 233 | 68.261 | 73.642 | 24.304 | 1.00 | 16.00 | A | C |
| ATOM | 1673 | O | VAL | 233 | 68.694 | 72.728 | 23.606 | 1.00 | 15.94 | A | O |
| ATOM | 1674 | N | PRO | 234 | 68.788 | 73.927 | 25.504 | 1.00 | 14.51 | A | N |
| ATOM | 1675 | CD | PRO | 234 | 68.313 | 74.907 | 26.494 | 1.00 | 13.03 | A | C |
| ATOM | 1676 | CA | PRO | 234 | 69.914 | 73.162 | 26.040 | 1.00 | 13.93 | A | C |
| ATOM | 1677 | CB | PRO | 234 | 70.031 | 73.677 | 27.473 | 1.00 | 12.63 | A | C |
| ATOM | 1678 | CG | PRO | 234 | 69.517 | 75.059 | 27.377 | 1.00 | 11.32 | A | C |
| ATOM | 1679 | C | PRO | 234 | 69.643 | 71.663 | 25.987 | 1.00 | 16.20 | A | C |
| ATOM | 1680 | O | PRO | 234 | 68.487 | 71.220 | 26.041 | 1.00 | 15.73 | A | O |
| ATOM | 1681 | N | LEU | 235 | 70.716 | 70.887 | 25.900 | 1.00 | 16.28 | A | N |
| ATOM | 1682 | CA | LEU | 235 | 70.602 | 69.443 | 25.825 | 1.00 | 16.91 | A | C |
| ATOM | 1683 | CB | LEU | 235 | 71.505 | 68.912 | 24.718 | 1.00 | 18.54 | A | C |
| ATOM | 1684 | CG | LEU | 235 | 71.267 | 69.349 | 23.273 | 1.00 | 21.93 | A | C |
| ATOM | 1685 | CD1 | LEU | 235 | 72.434 | 68.856 | 22.412 | 1.00 | 21.90 | A | C |
| ATOM | 1686 | CD2 | LEU | 235 | 69.946 | 68.790 | 22.768 | 1.00 | 19.17 | A | C |
| ATOM | 1687 | C | LEU | 235 | 70.990 | 68.743 | 27.118 | 1.00 | 17.26 | A | C |
| ATOM | 1688 | O | LEU | 235 | 71.939 | 69.157 | 27.793 | 1.00 | 18.36 | A | O |
| ATOM | 1689 | N | ILE | 236 | 70.244 | 67.696 | 27.472 | 1.00 | 14.95 | A | N |
| ATOM | 1690 | CA | ILE | 236 | 70.586 | 66.899 | 28.644 | 1.00 | 12.68 | A | C |
| ATOM | 1691 | CB | ILE | 236 | 69.345 | 66.245 | 29.335 | 1.00 | 10.50 | A | C |
| ATOM | 1692 | CG2 | ILE | 236 | 68.538 | 65.433 | 28.329 | 1.00 | 9.32 | A | C |
| ATOM | 1693 | CG1 | ILE | 236 | 69.806 | 65.298 | 30.448 | 1.00 | 8.74 | A | C |
| ATOM | 1694 | CD1 | ILE | 236 | 70.789 | 65.919 | 31.427 | 1.00 | 7.11 | A | C |
| ATOM | 1695 | C | ILE | 236 | 71.444 | 65.802 | 28.010 | 1.00 | 12.84 | A | C |
| ATOM | 1696 | O | ILE | 236 | 71.105 | 65.276 | 26.942 | 1.00 | 10.11 | A | O |
| ATOM | 1697 | N | GLU | 237 | 72.558 | 65.480 | 28.650 | 1.00 | 12.44 | A | N |
| ATOM | 1698 | CA | GLU | 237 | 73.463 | 64.470 | 28.128 | 1.00 | 14.46 | A | C |
| ATOM | 1699 | CB | GLU | 237 | 74.767 | 65.128 | 27.655 | 1.00 | 13.45 | A | C |
| ATOM | 1700 | CG | GLU | 237 | 74.554 | 66.079 | 26.500 | 1.00 | 18.02 | A | C |
| ATOM | 1701 | CD | GLU | 237 | 75.845 | 66.500 | 25.819 | 1.00 | 23.46 | A | C |
| ATOM | 1702 | OE1 | GLU | 237 | 75.779 | 67.016 | 24.683 | 1.00 | 25.80 | A | O |
| ATOM | 1703 | OE2 | GLU | 237 | 76.928 | 66.324 | 26.408 | 1.00 | 26.23 | A | O |
| ATOM | 1704 | C | GLU | 237 | 73.744 | 63.427 | 29.191 | 1.00 | 13.41 | A | C |
| ATOM | 1705 | O | GLU | 237 | 73.895 | 63.752 | 30.363 | 1.00 | 14.43 | A | O |
| ATOM | 1706 | N | TYR | 238 | 73.801 | 62.169 | 28.781 | 1.00 | 12.83 | A | N |
| ATOM | 1707 | CA | TYR | 238 | 74.052 | 61.093 | 29.721 | 1.00 | 14.06 | A | C |
| ATOM | 1708 | CB | TYR | 238 | 72.810 | 60.840 | 30.595 | 1.00 | 12.42 | A | C |
| ATOM | 1709 | CG | TYR | 238 | 71.566 | 60.419 | 29.856 | 1.00 | 11.79 | A | C |
| ATOM | 1710 | CD1 | TYR | 238 | 71.451 | 59.139 | 29.317 | 1.00 | 16.12 | A | C |
| ATOM | 1711 | CE1 | TYR | 238 | 70.292 | 58.739 | 28.635 | 1.00 | 17.09 | A | C |
| ATOM | 1712 | CD2 | TYR | 238 | 70.496 | 61.295 | 29.701 | 1.00 | 12.13 | A | C |
| ATOM | 1713 | CE2 | TYR | 238 | 69.336 | 60.913 | 29.020 | 1.00 | 12.94 | A | C |
| ATOM | 1714 | CZ | TYR | 238 | 69.243 | 59.634 | 28.487 | 1.00 | 15.48 | A | C |

FIG. 4-36

| ATOM | 1715 | OH | TYR | 238 | 68.127 | 59.257 | 27.775 | 1.00 | 15.96 | A | O |
|---|---|---|---|---|---|---|---|---|---|---|---|
| ATOM | 1716 | C | TYR | 238 | 74.445 | 59.847 | 28.954 | 1.00 | 15.25 | A | C |
| ATOM | 1717 | O | TYR | 238 | 74.059 | 59.667 | 27.798 | 1.00 | 17.74 | A | O |
| ATOM | 1718 | N | SER | 239 | 75.220 | 58.986 | 29.596 | 1.00 | 14.10 | A | N |
| ATOM | 1719 | CA | SER | 239 | 75.689 | 57.779 | 28.943 | 1.00 | 13.87 | A | C |
| ATOM | 1720 | CB | SER | 239 | 76.926 | 57.251 | 29.656 | 1.00 | 11.90 | A | C |
| ATOM | 1721 | OG | SER | 239 | 77.902 | 58.265 | 29.766 | 1.00 | 18.76 | A | O |
| ATOM | 1722 | C | SER | 239 | 74.661 | 56.668 | 28.879 | 1.00 | 13.45 | A | C |
| ATOM | 1723 | O | SER | 239 | 73.755 | 56.587 | 29.700 | 1.00 | 14.39 | A | O |
| ATOM | 1724 | N | PHE | 240 | 74.809 | 55.834 | 27.862 | 1.00 | 12.12 | A | N |
| ATOM | 1725 | CA | PHE | 240 | 73.972 | 54.678 | 27.679 | 1.00 | 12.95 | A | C |
| ATOM | 1726 | CB | PHE | 240 | 73.003 | 54.833 | 26.523 | 1.00 | 12.48 | A | C |
| ATOM | 1727 | CG | PHE | 240 | 71.896 | 53.843 | 26.574 | 1.00 | 11.50 | A | C |
| ATOM | 1728 | CD1 | PHE | 240 | 70.824 | 54.037 | 27.436 | 1.00 | 10.15 | A | C |
| ATOM | 1729 | CD2 | PHE | 240 | 71.980 | 52.655 | 25.858 | 1.00 | 11.95 | A | C |
| ATOM | 1730 | CE1 | PHE | 240 | 69.859 | 53.064 | 27.597 | 1.00 | 10.78 | A | C |
| ATOM | 1731 | CE2 | PHE | 240 | 71.018 | 51.675 | 26.012 | 1.00 | 11.03 | A | C |
| ATOM | 1732 | CZ | PHE | 240 | 69.954 | 51.878 | 26.888 | 1.00 | 10.46 | A | C |
| ATOM | 1733 | C | PHE | 240 | 75.018 | 53.652 | 27.330 | 1.00 | 14.83 | A | C |
| ATOM | 1734 | O | PHE | 240 | 75.722 | 53.805 | 26.335 | 1.00 | 18.18 | A | O |
| ATOM | 1735 | N | TYR | 241 | 75.129 | 52.617 | 28.153 | 1.00 | 13.74 | A | N |
| ATOM | 1736 | CA | TYR | 241 | 76.147 | 51.612 | 27.958 | 1.00 | 13.29 | A | C |
| ATOM | 1737 | CB | TYR | 241 | 76.526 | 51.057 | 29.329 | 1.00 | 13.69 | A | C |
| ATOM | 1738 | CG | TYR | 241 | 76.833 | 52.167 | 30.317 | 1.00 | 10.88 | A | C |
| ATOM | 1739 | CD1 | TYR | 241 | 78.065 | 52.821 | 30.308 | 1.00 | 11.93 | A | C |
| ATOM | 1740 | CE1 | TYR | 241 | 78.326 | 53.894 | 31.168 | 1.00 | 9.47 | A | C |
| ATOM | 1741 | CD2 | TYR | 241 | 75.862 | 52.610 | 31.218 | 1.00 | 12.15 | A | C |
| ATOM | 1742 | CE2 | TYR | 241 | 76.106 | 53.678 | 32.080 | 1.00 | 11.02 | A | C |
| ATOM | 1743 | CZ | TYR | 241 | 77.338 | 54.319 | 32.046 | 1.00 | 12.15 | A | C |
| ATOM | 1744 | OH | TYR | 241 | 77.556 | 55.408 | 32.859 | 1.00 | 10.38 | A | O |
| ATOM | 1745 | C | TYR | 241 | 75.793 | 50.510 | 26.967 | 1.00 | 14.62 | A | C |
| ATOM | 1746 | O | TYR | 241 | 76.686 | 49.948 | 26.322 | 1.00 | 12.20 | A | O |
| ATOM | 1747 | N | SER | 242 | 74.501 | 50.204 | 26.837 | 1.00 | 16.13 | A | N |
| ATOM | 1748 | CA | SER | 242 | 74.053 | 49.180 | 25.888 | 1.00 | 16.13 | A | C |
| ATOM | 1749 | CB | SER | 242 | 74.464 | 49.590 | 24.469 | 1.00 | 16.30 | A | C |
| ATOM | 1750 | OG | SER | 242 | 74.004 | 48.674 | 23.496 | 1.00 | 17.85 | A | O |
| ATOM | 1751 | C | SER | 242 | 74.647 | 47.816 | 26.226 | 1.00 | 17.46 | A | C |
| ATOM | 1752 | O | SER | 242 | 75.219 | 47.625 | 27.303 | 1.00 | 19.13 | A | O |
| ATOM | 1753 | N | ASP | 243 | 74.516 | 46.865 | 25.312 | 1.00 | 19.34 | A | N |
| ATOM | 1754 | CA | ASP | 243 | 75.066 | 45.535 | 25.548 | 1.00 | 23.36 | A | C |
| ATOM | 1755 | CB | ASP | 243 | 74.774 | 44.605 | 24.369 | 1.00 | 27.30 | A | C |
| ATOM | 1756 | CG | ASP | 243 | 73.290 | 44.419 | 24.132 | 1.00 | 33.83 | A | C |
| ATOM | 1757 | OD1 | ASP | 243 | 72.549 | 44.246 | 25.126 | 1.00 | 36.97 | A | O |
| ATOM | 1758 | OD2 | ASP | 243 | 72.862 | 44.438 | 22.955 | 1.00 | 37.15 | A | O |
| ATOM | 1759 | C | ASP | 243 | 76.572 | 45.554 | 25.805 | 1.00 | 23.56 | A | C |
| ATOM | 1760 | O | ASP | 243 | 77.298 | 46.432 | 25.330 | 1.00 | 22.48 | A | O |
| ATOM | 1761 | N | GLU | 244 | 77.016 | 44.559 | 26.567 | 1.00 | 24.45 | A | N |
| ATOM | 1762 | CA | GLU | 244 | 78.412 | 44.363 | 26.944 | 1.00 | 22.80 | A | C |
| ATOM | 1763 | CB | GLU | 244 | 78.534 | 42.984 | 27.605 | 1.00 | 23.73 | A | C |

| | | | | | | | | | | | |
|---|---|---|---|---|---|---|---|---|---|---|---|
| ATOM | 1764 | CG | GLU | 244 | 79.940 | 42.547 | 27.995 | 1.00 | 29.35 | A | C |
| ATOM | 1765 | CD | GLU | 244 | 79.967 | 41.177 | 28.667 | 1.00 | 29.80 | A | C |
| ATOM | 1766 | OE1 | GLU | 244 | 81.079 | 40.680 | 28.958 | 1.00 | 29.53 | A | O |
| ATOM | 1767 | OE2 | GLU | 244 | 78.877 | 40.601 | 28.903 | 1.00 | 29.32 | A | O |
| ATOM | 1768 | C | GLU | 244 | 79.374 | 44.476 | 25.754 | 1.00 | 22.28 | A | C |
| ATOM | 1769 | O | GLU | 244 | 80.533 | 44.854 | 25.913 | 1.00 | 21.94 | A | O |
| ATOM | 1770 | N | SER | 245 | 78.888 | 44.159 | 24.561 | 1.00 | 21.62 | A | N |
| ATOM | 1771 | CA | SER | 245 | 79.724 | 44.205 | 23.370 | 1.00 | 19.92 | A | C |
| ATOM | 1772 | CB | SER | 245 | 79.080 | 43.402 | 22.244 | 1.00 | 19.31 | A | C |
| ATOM | 1773 | OG | SER | 245 | 77.949 | 44.068 | 21.723 | 1.00 | 17.93 | A | O |
| ATOM | 1774 | C | SER | 245 | 80.044 | 45.605 | 22.861 | 1.00 | 19.58 | A | C |
| ATOM | 1775 | O | SER | 245 | 80.874 | 45.762 | 21.971 | 1.00 | 21.35 | A | O |
| ATOM | 1776 | N | LEU | 246 | 79.392 | 46.628 | 23.397 | 1.00 | 18.69 | A | N |
| ATOM | 1777 | CA | LEU | 246 | 79.694 | 47.983 | 22.943 | 1.00 | 18.41 | A | C |
| ATOM | 1778 | CB | LEU | 246 | 78.522 | 48.926 | 23.229 | 1.00 | 18.20 | A | C |
| ATOM | 1779 | CG | LEU | 246 | 78.659 | 50.368 | 22.728 | 1.00 | 17.99 | A | C |
| ATOM | 1780 | CD1 | LEU | 246 | 78.736 | 50.388 | 21.214 | 1.00 | 16.83 | A | C |
| ATOM | 1781 | CD2 | LEU | 246 | 77.458 | 51.181 | 23.192 | 1.00 | 19.98 | A | C |
| ATOM | 1782 | C | LEU | 246 | 80.943 | 48.463 | 23.679 | 1.00 | 18.12 | A | C |
| ATOM | 1783 | O | LEU | 246 | 80.921 | 48.662 | 24.895 | 1.00 | 16.81 | A | O |
| ATOM | 1784 | N | GLN | 247 | 82.034 | 48.635 | 22.940 | 1.00 | 17.84 | A | N |
| ATOM | 1785 | CA | GLN | 247 | 83.295 | 49.073 | 23.532 | 1.00 | 17.30 | A | C |
| ATOM | 1786 | CB | GLN | 247 | 84.400 | 49.038 | 22.480 | 1.00 | 15.11 | A | C |
| ATOM | 1787 | CG | GLN | 247 | 85.791 | 49.234 | 23.045 | 1.00 | 17.62 | A | C |
| ATOM | 1788 | CD | GLN | 247 | 86.875 | 48.770 | 22.090 | 1.00 | 18.47 | A | C |
| ATOM | 1789 | OE1 | GLN | 247 | 86.829 | 49.065 | 20.899 | 1.00 | 20.53 | A | O |
| ATOM | 1790 | NE2 | GLN | 247 | 87.862 | 48.049 | 22.611 | 1.00 | 17.76 | A | N |
| ATOM | 1791 | C | GLN | 247 | 83.224 | 50.461 | 24.170 | 1.00 | 17.66 | A | C |
| ATOM | 1792 | O | GLN | 247 | 83.640 | 50.648 | 25.313 | 1.00 | 17.56 | A | O |
| ATOM | 1793 | N | TYR | 248 | 82.710 | 51.436 | 23.430 | 1.00 | 18.50 | A | N |
| ATOM | 1794 | CA | TYR | 248 | 82.592 | 52.794 | 23.954 | 1.00 | 19.00 | A | C |
| ATOM | 1795 | CB | TYR | 248 | 83.177 | 53.822 | 22.972 | 1.00 | 17.39 | A | C |
| ATOM | 1796 | CG | TYR | 248 | 84.684 | 53.820 | 22.860 | 1.00 | 16.80 | A | C |
| ATOM | 1797 | CD1 | TYR | 248 | 85.353 | 52.812 | 22.172 | 1.00 | 17.20 | A | C |
| ATOM | 1798 | CE1 | TYR | 248 | 86.742 | 52.814 | 22.058 | 1.00 | 17.58 | A | C |
| ATOM | 1799 | CD2 | TYR | 248 | 85.444 | 54.838 | 23.437 | 1.00 | 17.77 | A | C |
| ATOM | 1800 | CE2 | TYR | 248 | 86.839 | 54.851 | 23.333 | 1.00 | 17.22 | A | C |
| ATOM | 1801 | CZ | TYR | 248 | 87.479 | 53.836 | 22.647 | 1.00 | 18.42 | A | C |
| ATOM | 1802 | OH | TYR | 248 | 88.854 | 53.809 | 22.595 | 1.00 | 19.27 | A | O |
| ATOM | 1803 | C | TYR | 248 | 81.130 | 53.134 | 24.212 | 1.00 | 18.87 | A | C |
| ATOM | 1804 | O | TYR | 248 | 80.288 | 53.018 | 23.323 | 1.00 | 19.15 | A | O |
| ATOM | 1805 | N | PRO | 249 | 80.804 | 53.549 | 25.440 | 1.00 | 18.20 | A | N |
| ATOM | 1806 | CD | PRO | 249 | 81.610 | 53.595 | 26.668 | 1.00 | 18.21 | A | C |
| ATOM | 1807 | CA | PRO | 249 | 79.411 | 53.886 | 25.716 | 1.00 | 18.83 | A | C |
| ATOM | 1808 | CB | PRO | 249 | 79.424 | 54.222 | 27.206 | 1.00 | 19.46 | A | C |
| ATOM | 1809 | CG | PRO | 249 | 80.857 | 54.582 | 27.481 | 1.00 | 17.63 | A | C |
| ATOM | 1810 | C | PRO | 249 | 78.937 | 55.042 | 24.852 | 1.00 | 19.66 | A | C |
| ATOM | 1811 | O | PRO | 249 | 79.734 | 55.864 | 24.413 | 1.00 | 20.92 | A | O |
| ATOM | 1812 | N | LYS | 250 | 77.638 | 55.096 | 24.599 | 1.00 | 19.01 | A | N |

FIG. 4-38 (Continued)

| | | | | | | | | | | |
|---|---|---|---|---|---|---|---|---|---|---|
| ATOM | 1813 | CA | LYS | 250 | 77.083 | 56.158 | 23.785 | 1.00 | 19.61 | A C |
| ATOM | 1814 | CB | LYS | 250 | 75.933 | 55.618 | 22.936 | 1.00 | 23.51 | A C |
| ATOM | 1815 | CG | LYS | 250 | 76.320 | 54.428 | 22.089 | 1.00 | 28.40 | A C |
| ATOM | 1816 | CD | LYS | 250 | 75.197 | 54.010 | 21.152 | 1.00 | 30.62 | A C |
| ATOM | 1817 | CE | LYS | 250 | 75.698 | 52.938 | 20.203 | 1.00 | 32.02 | A C |
| ATOM | 1818 | NZ | LYS | 250 | 76.966 | 53.385 | 19.546 | 1.00 | 32.62 | A N |
| ATOM | 1819 | C | LYS | 250 | 76.580 | 57.320 | 24.628 | 1.00 | 17.92 | A C |
| ATOM | 1820 | O | LYS | 250 | 76.130 | 57.130 | 25.758 | 1.00 | 17.90 | A O |
| ATOM | 1821 | N | THR | 251 | 76.663 | 58.524 | 24.077 | 1.00 | 14.61 | A N |
| ATOM | 1822 | CA | THR | 251 | 76.171 | 59.689 | 24.786 | 1.00 | 15.48 | A C |
| ATOM | 1823 | CB | THR | 251 | 77.104 | 60.887 | 24.666 | 1.00 | 13.61 | A C |
| ATOM | 1824 | OG1 | THR | 251 | 78.280 | 60.654 | 25.441 | 1.00 | 15.96 | A O |
| ATOM | 1825 | CG2 | THR | 251 | 76.414 | 62.137 | 25.181 | 1.00 | 13.93 | A C |
| ATOM | 1826 | C | THR | 251 | 74.832 | 60.086 | 24.205 | 1.00 | 16.04 | A C |
| ATOM | 1827 | O | THR | 251 | 74.755 | 60.572 | 23.083 | 1.00 | 17.34 | A O |
| ATOM | 1828 | N | VAL | 252 | 73.779 | 59.860 | 24.977 | 1.00 | 15.27 | A N |
| ATOM | 1829 | CA | VAL | 252 | 72.439 | 60.205 | 24.559 | 1.00 | 16.08 | A C |
| ATOM | 1830 | CB | VAL | 252 | 71.405 | 59.381 | 25.355 | 1.00 | 16.76 | A C |
| ATOM | 1831 | CG1 | VAL | 252 | 69.987 | 59.832 | 25.014 | 1.00 | 16.29 | A C |
| ATOM | 1832 | CG2 | VAL | 252 | 71.595 | 57.895 | 25.050 | 1.00 | 13.65 | A C |
| ATOM | 1833 | C | VAL | 252 | 72.223 | 61.699 | 24.799 | 1.00 | 18.46 | A C |
| ATOM | 1834 | O | VAL | 252 | 72.443 | 62.212 | 25.905 | 1.00 | 19.01 | A O |
| ATOM | 1835 | N | ARG | 253 | 71.799 | 62.398 | 23.754 | 1.00 | 19.18 | A N |
| ATOM | 1836 | CA | ARG | 253 | 71.568 | 63.831 | 23.842 | 1.00 | 18.54 | A C |
| ATOM | 1837 | CB | ARG | 253 | 72.574 | 64.567 | 22.949 | 1.00 | 19.46 | A C |
| ATOM | 1838 | CG | ARG | 253 | 74.014 | 64.439 | 23.457 | 1.00 | 24.49 | A C |
| ATOM | 1839 | CD | ARG | 253 | 75.021 | 65.066 | 22.519 | 1.00 | 29.04 | A C |
| ATOM | 1840 | NE | ARG | 253 | 75.797 | 64.044 | 21.822 | 1.00 | 35.89 | A N |
| ATOM | 1841 | CZ | ARG | 253 | 77.013 | 63.647 | 22.185 | 1.00 | 38.08 | A C |
| ATOM | 1842 | NH1 | ARG | 253 | 77.606 | 64.191 | 23.241 | 1.00 | 39.69 | A N |
| ATOM | 1843 | NH2 | ARG | 253 | 77.633 | 62.699 | 21.497 | 1.00 | 40.12 | A N |
| ATOM | 1844 | C | ARG | 253 | 70.140 | 64.156 | 23.449 | 1.00 | 17.33 | A C |
| ATOM | 1845 | O | ARG | 253 | 69.690 | 63.802 | 22.362 | 1.00 | 18.44 | A O |
| ATOM | 1846 | N | VAL | 254 | 69.432 | 64.836 | 24.344 | 1.00 | 16.85 | A N |
| ATOM | 1847 | CA | VAL | 254 | 68.033 | 65.196 | 24.125 | 1.00 | 15.67 | A C |
| ATOM | 1848 | CB | VAL | 254 | 67.079 | 64.405 | 25.070 | 1.00 | 16.67 | A C |
| ATOM | 1849 | CG1 | VAL | 254 | 65.640 | 64.775 | 24.766 | 1.00 | 16.79 | A C |
| ATOM | 1850 | CG2 | VAL | 254 | 67.308 | 62.899 | 24.951 | 1.00 | 17.24 | A C |
| ATOM | 1851 | C | VAL | 254 | 67.737 | 66.660 | 24.405 | 1.00 | 14.62 | A C |
| ATOM | 1852 | O | VAL | 254 | 68.122 | 67.186 | 25.450 | 1.00 | 15.12 | A O |
| ATOM | 1853 | N | PRO | 255 | 67.048 | 67.340 | 23.475 | 1.00 | 13.71 | A N |
| ATOM | 1854 | CD | PRO | 255 | 66.677 | 66.945 | 22.105 | 1.00 | 10.62 | A C |
| ATOM | 1855 | CA | PRO | 255 | 66.725 | 68.749 | 23.730 | 1.00 | 13.00 | A C |
| ATOM | 1856 | CB | PRO | 255 | 66.064 | 69.193 | 22.431 | 1.00 | 13.28 | A C |
| ATOM | 1857 | CG | PRO | 255 | 66.674 | 68.265 | 21.397 | 1.00 | 13.45 | A C |
| ATOM | 1858 | C | PRO | 255 | 65.735 | 68.674 | 24.899 | 1.00 | 13.86 | A C |
| ATOM | 1859 | O | PRO | 255 | 64.663 | 68.086 | 24.772 | 1.00 | 13.58 | A O |
| ATOM | 1860 | N | TYR | 256 | 66.108 | 69.255 | 26.032 | 1.00 | 13.63 | A N |
| ATOM | 1861 | CA | TYR | 256 | 65.304 | 69.194 | 27.242 | 1.00 | 11.65 | A C |

FIG. 4-39 (Continued)

| | | | | | | | | | | | |
|---|---|---|---|---|---|---|---|---|---|---|---|
| ATOM | 1862 | CB | TYR | 256 | 65.801 | 68.006 | 28.077 | 1.00 | 10.57 | A | C |
| ATOM | 1863 | CG | TYR | 256 | 65.044 | 67.706 | 29.351 | 1.00 | 10.49 | A | C |
| ATOM | 1864 | CD1 | TYR | 256 | 64.949 | 68.646 | 30.378 | 1.00 | 9.61 | A | C |
| ATOM | 1865 | CE1 | TYR | 256 | 64.296 | 68.351 | 31.571 | 1.00 | 7.54 | A | C |
| ATOM | 1866 | CD2 | TYR | 256 | 64.460 | 66.460 | 29.549 | 1.00 | 9.65 | A | C |
| ATOM | 1867 | CE2 | TYR | 256 | 63.799 | 66.156 | 30.735 | 1.00 | 11.05 | A | C |
| ATOM | 1868 | CZ | TYR | 256 | 63.722 | 67.105 | 31.742 | 1.00 | 10.10 | A | C |
| ATOM | 1869 | OH | TYR | 256 | 63.060 | 66.801 | 32.909 | 1.00 | 10.49 | A | O |
| ATOM | 1870 | C | TYR | 256 | 65.488 | 70.492 | 28.012 | 1.00 | 12.70 | A | C |
| ATOM | 1871 | O | TYR | 256 | 66.559 | 70.750 | 28.553 | 1.00 | 15.49 | A | O |
| ATOM | 1872 | N | PRO | 257 | 64.444 | 71.325 | 28.080 | 1.00 | 12.39 | A | N |
| ATOM | 1873 | CD | PRO | 257 | 63.174 | 71.254 | 27.334 | 1.00 | 13.82 | A | C |
| ATOM | 1874 | CA | PRO | 257 | 64.548 | 72.593 | 28.800 | 1.00 | 11.47 | A | C |
| ATOM | 1875 | CB | PRO | 257 | 63.501 | 73.450 | 28.106 | 1.00 | 12.01 | A | C |
| ATOM | 1876 | CG | PRO | 257 | 62.405 | 72.464 | 27.866 | 1.00 | 12.87 | A | C |
| ATOM | 1877 | C | PRO | 257 | 64.296 | 72.489 | 30.298 | 1.00 | 12.85 | A | C |
| ATOM | 1878 | O | PRO | 257 | 63.174 | 72.210 | 30.723 | 1.00 | 15.59 | A | O |
| ATOM | 1879 | N | LYS | 258 | 65.327 | 72.718 | 31.105 | 1.00 | 11.64 | A | N |
| ATOM | 1880 | CA | LYS | 258 | 65.155 | 72.671 | 32.546 | 1.00 | 11.10 | A | C |
| ATOM | 1881 | CB | LYS | 258 | 66.501 | 72.439 | 33.227 | 1.00 | 12.96 | A | C |
| ATOM | 1882 | CG | LYS | 258 | 67.034 | 71.012 | 33.031 | 1.00 | 14.20 | A | C |
| ATOM | 1883 | CD | LYS | 258 | 68.519 | 70.906 | 33.331 | 1.00 | 13.34 | A | C |
| ATOM | 1884 | CE | LYS | 258 | 69.042 | 69.480 | 33.136 | 1.00 | 13.95 | A | C |
| ATOM | 1885 | NZ | LYS | 258 | 68.671 | 68.536 | 34.223 | 1.00 | 10.80 | A | N |
| ATOM | 1886 | C | LYS | 258 | 64.517 | 73.984 | 33.011 | 1.00 | 12.44 | A | C |
| ATOM | 1887 | O | LYS | 258 | 64.368 | 74.921 | 32.224 | 1.00 | 11.13 | A | O |
| ATOM | 1888 | N | ALA | 259 | 64.124 | 74.043 | 34.280 | 1.00 | 13.33 | A | N |
| ATOM | 1889 | CA | ALA | 259 | 63.484 | 75.236 | 34.844 | 1.00 | 14.81 | A | C |
| ATOM | 1890 | CB | ALA | 259 | 63.368 | 75.097 | 36.355 | 1.00 | 16.40 | A | C |
| ATOM | 1891 | C | ALA | 259 | 64.167 | 76.555 | 34.508 | 1.00 | 15.14 | A | C |
| ATOM | 1892 | O | ALA | 259 | 65.317 | 76.787 | 34.881 | 1.00 | 17.32 | A | O |
| ATOM | 1893 | N | GLY | 260 | 63.448 | 77.419 | 33.802 | 1.00 | 16.82 | A | N |
| ATOM | 1894 | CA | GLY | 260 | 63.984 | 78.720 | 33.444 | 1.00 | 15.59 | A | C |
| ATOM | 1895 | C | GLY | 260 | 64.870 | 78.749 | 32.217 | 1.00 | 15.78 | A | C |
| ATOM | 1896 | O | GLY | 260 | 65.379 | 79.812 | 31.852 | 1.00 | 17.65 | A | O |
| ATOM | 1897 | N | ALA | 261 | 65.072 | 77.600 | 31.577 | 1.00 | 13.77 | A | N |
| ATOM | 1898 | CA | ALA | 261 | 65.906 | 77.554 | 30.379 | 1.00 | 11.19 | A | C |
| ATOM | 1899 | CB | ALA | 261 | 66.524 | 76.182 | 30.224 | 1.00 | 10.21 | A | C |
| ATOM | 1900 | C | ALA | 261 | 65.093 | 77.911 | 29.137 | 1.00 | 10.04 | A | C |
| ATOM | 1901 | O | ALA | 261 | 63.896 | 78.160 | 29.212 | 1.00 | 8.71 | A | O |
| ATOM | 1902 | N | VAL | 262 | 65.747 | 77.947 | 27.987 | 1.00 | 11.73 | A | N |
| ATOM | 1903 | CA | VAL | 262 | 65.050 | 78.284 | 26.761 | 1.00 | 12.13 | A | C |
| ATOM | 1904 | CB | VAL | 262 | 66.035 | 78.529 | 25.594 | 1.00 | 11.50 | A | C |
| ATOM | 1905 | CG1 | VAL | 262 | 65.257 | 78.796 | 24.299 | 1.00 | 8.31 | A | C |
| ATOM | 1906 | CG2 | VAL | 262 | 66.939 | 79.732 | 25.920 | 1.00 | 5.79 | A | C |
| ATOM | 1907 | C | VAL | 262 | 64.092 | 77.167 | 26.389 | 1.00 | 13.92 | A | C |
| ATOM | 1908 | O | VAL | 262 | 64.471 | 76.001 | 26.341 | 1.00 | 16.73 | A | O |
| ATOM | 1909 | N | ASN | 263 | 62.844 | 77.536 | 26.139 | 1.00 | 13.49 | A | N |
| ATOM | 1910 | CA | ASN | 263 | 61.816 | 76.585 | 25.773 | 1.00 | 13.67 | A | C |

FIG. 4-40 (Continued)

| | | | | | | | | | | | |
|---|---|---|---|---|---|---|---|---|---|---|---|
| ATOM | 1911 | CB | ASN | 263 | 60.470 | 77.038 | 26.336 | 1.00 | 14.53 | A | C |
| ATOM | 1912 | CG | ASN | 263 | 60.222 | 76.545 | 27.746 | 1.00 | 17.27 | A | C |
| ATOM | 1913 | OD1 | ASN | 263 | 59.342 | 77.058 | 28.444 | 1.00 | 18.62 | A | O |
| ATOM | 1914 | ND2 | ASN | 263 | 60.977 | 75.534 | 28.169 | 1.00 | 16.78 | A | N |
| ATOM | 1915 | C | ASN | 263 | 61.715 | 76.500 | 24.265 | 1.00 | 14.45 | A | C |
| ATOM | 1916 | O | ASN | 263 | 62.170 | 77.395 | 23.561 | 1.00 | 16.33 | A | O |
| ATOM | 1917 | N | PRO | 264 | 61.119 | 75.418 | 23.743 | 1.00 | 14.86 | A | N |
| ATOM | 1918 | CD | PRO | 264 | 60.513 | 74.254 | 24.412 | 1.00 | 15.86 | A | C |
| ATOM | 1919 | CA | PRO | 264 | 60.986 | 75.301 | 22.294 | 1.00 | 15.41 | A | C |
| ATOM | 1920 | CB | PRO | 264 | 60.591 | 73.844 | 22.106 | 1.00 | 14.97 | A | C |
| ATOM | 1921 | CG | PRO | 264 | 59.721 | 73.607 | 23.287 | 1.00 | 14.81 | A | C |
| ATOM | 1922 | C | PRO | 264 | 59.867 | 76.238 | 21.882 | 1.00 | 15.66 | A | C |
| ATOM | 1923 | O | PRO | 264 | 58.954 | 76.496 | 22.663 | 1.00 | 17.42 | A | O |
| ATOM | 1924 | N | THR | 265 | 59.942 | 76.767 | 20.673 | 1.00 | 15.76 | A | N |
| ATOM | 1925 | CA | THR | 265 | 58.895 | 77.648 | 20.199 | 1.00 | 14.67 | A | C |
| ATOM | 1926 | CB | THR | 265 | 59.458 | 78.779 | 19.341 | 1.00 | 15.37 | A | C |
| ATOM | 1927 | OG1 | THR | 265 | 60.162 | 78.228 | 18.223 | 1.00 | 15.98 | A | O |
| ATOM | 1928 | CG2 | THR | 265 | 60.402 | 79.633 | 20.159 | 1.00 | 12.01 | A | C |
| ATOM | 1929 | C | THR | 265 | 58.024 | 76.749 | 19.360 | 1.00 | 15.62 | A | C |
| ATOM | 1930 | O | THR | 265 | 58.465 | 75.683 | 18.932 | 1.00 | 18.75 | A | O |
| ATOM | 1931 | N | VAL | 266 | 56.794 | 77.170 | 19.113 | 1.00 | 15.56 | A | N |
| ATOM | 1932 | CA | VAL | 266 | 55.872 | 76.352 | 18.347 | 1.00 | 12.79 | A | C |
| ATOM | 1933 | CB | VAL | 266 | 54.856 | 75.692 | 19.274 | 1.00 | 12.90 | A | C |
| ATOM | 1934 | CG1 | VAL | 266 | 54.193 | 76.766 | 20.130 | 1.00 | 12.06 | A | C |
| ATOM | 1935 | CG2 | VAL | 266 | 53.821 | 74.920 | 18.466 | 1.00 | 10.69 | A | C |
| ATOM | 1936 | C | VAL | 266 | 55.115 | 77.180 | 17.350 | 1.00 | 12.88 | A | C |
| ATOM | 1937 | O | VAL | 266 | 54.995 | 78.388 | 17.511 | 1.00 | 12.12 | A | O |
| ATOM | 1938 | N | LYS | 267 | 54.601 | 76.501 | 16.327 | 1.00 | 13.52 | A | N |
| ATOM | 1939 | CA | LYS | 267 | 53.817 | 77.107 | 15.262 | 1.00 | 13.08 | A | C |
| ATOM | 1940 | CB | LYS | 267 | 54.692 | 77.389 | 14.050 | 1.00 | 13.64 | A | C |
| ATOM | 1941 | CG | LYS | 267 | 55.642 | 78.570 | 14.165 | 1.00 | 13.17 | A | C |
| ATOM | 1942 | CD | LYS | 267 | 56.348 | 78.713 | 12.833 | 1.00 | 11.33 | A | C |
| ATOM | 1943 | CE | LYS | 267 | 57.313 | 79.864 | 12.788 | 1.00 | 11.66 | A | C |
| ATOM | 1944 | NZ | LYS | 267 | 58.007 | 79.844 | 11.459 | 1.00 | 12.98 | A | N |
| ATOM | 1945 | C | LYS | 267 | 52.713 | 76.136 | 14.851 | 1.00 | 14.81 | A | C |
| ATOM | 1946 | O | LYS | 267 | 52.885 | 74.916 | 14.930 | 1.00 | 14.91 | A | O |
| ATOM | 1947 | N | PHE | 268 | 51.588 | 76.674 | 14.389 | 1.00 | 15.02 | A | N |
| ATOM | 1948 | CA | PHE | 268 | 50.471 | 75.836 | 13.975 | 1.00 | 14.84 | A | C |
| ATOM | 1949 | CB | PHE | 268 | 49.249 | 76.138 | 14.842 | 1.00 | 13.98 | A | C |
| ATOM | 1950 | CG | PHE | 268 | 48.237 | 75.041 | 14.846 | 1.00 | 15.65 | A | C |
| ATOM | 1951 | CD1 | PHE | 268 | 48.467 | 73.872 | 15.562 | 1.00 | 15.51 | A | C |
| ATOM | 1952 | CD2 | PHE | 268 | 47.056 | 75.159 | 14.115 | 1.00 | 18.05 | A | C |
| ATOM | 1953 | CE1 | PHE | 268 | 47.537 | 72.836 | 15.551 | 1.00 | 15.17 | A | C |
| ATOM | 1954 | CE2 | PHE | 268 | 46.120 | 74.120 | 14.101 | 1.00 | 17.28 | A | C |
| ATOM | 1955 | CZ | PHE | 268 | 46.366 | 72.960 | 14.821 | 1.00 | 14.54 | A | C |
| ATOM | 1956 | C | PHE | 268 | 50.117 | 76.029 | 12.497 | 1.00 | 14.63 | A | C |
| ATOM | 1957 | O | PHE | 268 | 50.143 | 77.144 | 11.981 | 1.00 | 16.53 | A | O |
| ATOM | 1958 | N | PHE | 269 | 49.767 | 74.938 | 11.829 | 1.00 | 13.37 | A | N |
| ATOM | 1959 | CA | PHE | 269 | 49.417 | 74.976 | 10.413 | 1.00 | 12.73 | A | C |

| | | | | | | | | | | | |
|---|---|---|---|---|---|---|---|---|---|---|---|
| ATOM | 1960 | CB | PHE | 269 | 50.597 | 74.510 | 9.547 | 1.00 | 12.68 | A | C |
| ATOM | 1961 | CG | PHE | 269 | 51.875 | 75.229 | 9.809 | 1.00 | 10.71 | A | C |
| ATOM | 1962 | CD1 | PHE | 269 | 52.190 | 76.387 | 9.112 | 1.00 | 11.11 | A | C |
| ATOM | 1963 | CD2 | PHE | 269 | 52.758 | 74.759 | 10.770 | 1.00 | 11.04 | A | C |
| ATOM | 1964 | CE1 | PHE | 269 | 53.374 | 77.070 | 9.371 | 1.00 | 12.54 | A | C |
| ATOM | 1965 | CE2 | PHE | 269 | 53.940 | 75.430 | 11.039 | 1.00 | 13.96 | A | C |
| ATOM | 1966 | CZ | PHE | 269 | 54.252 | 76.591 | 10.339 | 1.00 | 13.89 | A | C |
| ATOM | 1967 | C | PHE | 269 | 48.270 | 74.032 | 10.117 | 1.00 | 12.37 | A | C |
| ATOM | 1968 | O | PHE | 269 | 47.937 | 73.157 | 10.910 | 1.00 | 14.50 | A | O |
| ATOM | 1969 | N | VAL | 270 | 47.699 | 74.193 | 8.938 | 1.00 | 13.63 | A | N |
| ATOM | 1970 | CA | VAL | 270 | 46.626 | 73.334 | 8.485 | 1.00 | 15.44 | A | C |
| ATOM | 1971 | CB | VAL | 270 | 45.228 | 73.903 | 8.815 | 1.00 | 14.59 | A | C |
| ATOM | 1972 | CG1 | VAL | 270 | 44.153 | 72.900 | 8.383 | 1.00 | 12.94 | A | C |
| ATOM | 1973 | CG2 | VAL | 270 | 45.110 | 74.183 | 10.304 | 1.00 | 15.69 | A | C |
| ATOM | 1974 | C | VAL | 270 | 46.730 | 73.198 | 6.975 | 1.00 | 16.91 | A | C |
| ATOM | 1975 | O | VAL | 270 | 46.875 | 74.188 | 6.258 | 1.00 | 17.51 | A | O |
| ATOM | 1976 | N | VAL | 271 | 46.681 | 71.966 | 6.494 | 1.00 | 17.37 | A | N |
| ATOM | 1977 | CA | VAL | 271 | 46.726 | 71.746 | 5.067 | 1.00 | 16.54 | A | C |
| ATOM | 1978 | CB | VAL | 271 | 47.928 | 70.879 | 4.646 | 1.00 | 19.07 | A | C |
| ATOM | 1979 | CG1 | VAL | 271 | 47.911 | 69.548 | 5.400 | 1.00 | 20.07 | A | C |
| ATOM | 1980 | CG2 | VAL | 271 | 47.878 | 70.635 | 3.131 | 1.00 | 18.62 | A | C |
| ATOM | 1981 | C | VAL | 271 | 45.456 | 71.041 | 4.641 | 1.00 | 15.09 | A | C |
| ATOM | 1982 | O | VAL | 271 | 44.912 | 70.226 | 5.383 | 1.00 | 13.46 | A | O |
| ATOM | 1983 | N | ASN | 272 | 44.988 | 71.394 | 3.449 | 1.00 | 15.17 | A | N |
| ATOM | 1984 | CA | ASN | 272 | 43.812 | 70.802 | 2.832 | 1.00 | 14.94 | A | C |
| ATOM | 1985 | CB | ASN | 272 | 43.231 | 71.767 | 1.797 | 1.00 | 13.83 | A | C |
| ATOM | 1986 | CG | ASN | 272 | 42.010 | 71.205 | 1.093 | 1.00 | 14.46 | A | C |
| ATOM | 1987 | OD1 | ASN | 272 | 41.822 | 69.989 | 1.007 | 1.00 | 16.67 | A | O |
| ATOM | 1988 | ND2 | ASN | 272 | 41.175 | 72.090 | 0.581 | 1.00 | 15.74 | A | N |
| ATOM | 1989 | C | ASN | 272 | 44.310 | 69.542 | 2.110 | 1.00 | 15.70 | A | C |
| ATOM | 1990 | O | ASN | 272 | 44.755 | 69.617 | 0.967 | 1.00 | 16.88 | A | O |
| ATOM | 1991 | N | THR | 273 | 44.241 | 68.390 | 2.758 | 1.00 | 15.93 | A | N |
| ATOM | 1992 | CA | THR | 273 | 44.717 | 67.169 | 2.124 | 1.00 | 18.97 | A | C |
| ATOM | 1993 | CB | THR | 273 | 44.570 | 65.936 | 3.052 | 1.00 | 19.44 | A | C |
| ATOM | 1994 | OG1 | THR | 273 | 43.201 | 65.794 | 3.471 | 1.00 | 19.69 | A | O |
| ATOM | 1995 | CG2 | THR | 273 | 45.481 | 66.083 | 4.266 | 1.00 | 19.20 | A | C |
| ATOM | 1996 | C | THR | 273 | 44.009 | 66.870 | 0.813 | 1.00 | 19.92 | A | C |
| ATOM | 1997 | O | THR | 273 | 44.550 | 66.154 | -0.028 | 1.00 | 21.20 | A | O |
| ATOM | 1998 | N | ASP | 274 | 42.811 | 67.424 | 0.634 | 1.00 | 20.50 | A | N |
| ATOM | 1999 | CA | ASP | 274 | 42.032 | 67.193 | -0.584 | 1.00 | 20.30 | A | C |
| ATOM | 2000 | CB | ASP | 274 | 40.578 | 67.629 | -0.390 | 1.00 | 21.02 | A | C |
| ATOM | 2001 | CG | ASP | 274 | 39.705 | 66.529 | 0.178 | 1.00 | 23.48 | A | C |
| ATOM | 2002 | OD1 | ASP | 274 | 38.543 | 66.823 | 0.527 | 1.00 | 26.38 | A | O |
| ATOM | 2003 | OD2 | ASP | 274 | 40.168 | 65.375 | 0.275 | 1.00 | 23.88 | A | O |
| ATOM | 2004 | C | ASP | 274 | 42.573 | 67.870 | -1.832 | 1.00 | 19.89 | A | C |
| ATOM | 2005 | O | ASP | 274 | 42.131 | 67.556 | -2.932 | 1.00 | 22.08 | A | O |
| ATOM | 2006 | N | SER | 275 | 43.508 | 68.802 | -1.676 | 1.00 | 18.13 | A | N |
| ATOM | 2007 | CA | SER | 275 | 44.073 | 69.490 | -2.834 | 1.00 | 18.83 | A | C |
| ATOM | 2008 | CB | SER | 275 | 44.284 | 70.969 | -2.518 | 1.00 | 19.37 | A | C |

| | | | | | | | | | | | |
|---|---|---|---|---|---|---|---|---|---|---|---|
| ATOM | 2009 | OG | SER | 275 | 45.197 | 71.121 | -1.444 | 1.00 | 24.82 | A | O |
| ATOM | 2010 | C | SER | 275 | 45.397 | 68.885 | -3.314 | 1.00 | 19.53 | A | C |
| ATOM | 2011 | O | SER | 275 | 45.883 | 69.226 | -4.394 | 1.00 | 19.59 | A | O |
| ATOM | 2012 | N | LEU | 276 | 45.971 | 67.986 | -2.516 | 1.00 | 19.83 | A | N |
| ATOM | 2013 | CA | LEU | 276 | 47.241 | 67.348 | -2.846 | 1.00 | 20.72 | A | C |
| ATOM | 2014 | CB | LEU | 276 | 47.545 | 66.226 | -1.849 | 1.00 | 19.96 | A | C |
| ATOM | 2015 | CG | LEU | 276 | 47.725 | 66.641 | -0.392 | 1.00 | 20.47 | A | C |
| ATOM | 2016 | CD1 | LEU | 276 | 47.991 | 65.410 | 0.456 | 1.00 | 21.68 | A | C |
| ATOM | 2017 | CD2 | LEU | 276 | 48.875 | 67.622 | -0.277 | 1.00 | 18.56 | A | C |
| ATOM | 2018 | C | LEU | 276 | 47.360 | 66.790 | -4.263 | 1.00 | 22.34 | A | C |
| ATOM | 2019 | O | LEU | 276 | 48.290 | 67.137 | -4.994 | 1.00 | 24.63 | A | O |
| ATOM | 2020 | N | SER | 277 | 46.434 | 65.925 | -4.656 | 1.00 | 22.80 | A | N |
| ATOM | 2021 | CA | SER | 277 | 46.501 | 65.325 | -5.983 | 1.00 | 23.82 | A | C |
| ATOM | 2022 | CB | SER | 277 | 45.456 | 64.219 | -6.121 | 1.00 | 22.59 | A | C |
| ATOM | 2023 | OG | SER | 277 | 44.148 | 64.756 | -6.044 | 1.00 | 23.44 | A | O |
| ATOM | 2024 | C | SER | 277 | 46.305 | 66.341 | -7.097 | 1.00 | 24.47 | A | C |
| ATOM | 2025 | O | SER | 277 | 46.699 | 66.104 | -8.231 | 1.00 | 26.86 | A | O |
| ATOM | 2026 | N | SER | 278 | 45.698 | 67.472 | -6.768 | 1.00 | 25.44 | A | N |
| ATOM | 2027 | CA | SER | 278 | 45.431 | 68.522 | -7.745 | 1.00 | 26.20 | A | C |
| ATOM | 2028 | CB | SER | 278 | 44.051 | 69.121 | -7.471 | 1.00 | 25.70 | A | C |
| ATOM | 2029 | OG | SER | 278 | 43.831 | 70.266 | -8.266 | 1.00 | 30.53 | A | O |
| ATOM | 2030 | C | SER | 278 | 46.495 | 69.630 | -7.739 | 1.00 | 25.70 | A | C |
| ATOM | 2031 | O | SER | 278 | 46.603 | 70.414 | -8.683 | 1.00 | 23.48 | A | O |
| ATOM | 2032 | N | VAL | 279 | 47.277 | 69.692 | -6.672 | 1.00 | 26.01 | A | N |
| ATOM | 2033 | CA | VAL | 279 | 48.327 | 70.696 | -6.565 | 1.00 | 28.42 | A | C |
| ATOM | 2034 | CB | VAL | 279 | 48.073 | 71.634 | -5.350 | 1.00 | 29.96 | A | C |
| ATOM | 2035 | CG1 | VAL | 279 | 49.372 | 72.211 | -4.834 | 1.00 | 32.19 | A | C |
| ATOM | 2036 | CG2 | VAL | 279 | 47.148 | 72.768 | -5.776 | 1.00 | 29.00 | A | C |
| ATOM | 2037 | C | VAL | 279 | 49.704 | 70.043 | -6.470 | 1.00 | 28.21 | A | C |
| ATOM | 2038 | O | VAL | 279 | 49.834 | 68.872 | -6.088 | 1.00 | 29.00 | A | O |
| ATOM | 2039 | N | THR | 280 | 50.728 | 70.801 | -6.848 | 1.00 | 26.67 | A | N |
| ATOM | 2040 | CA | THR | 280 | 52.092 | 70.306 | -6.832 | 1.00 | 26.53 | A | C |
| ATOM | 2041 | CB | THR | 280 | 53.023 | 71.217 | -7.645 | 1.00 | 27.22 | A | C |
| ATOM | 2042 | OG1 | THR | 280 | 52.533 | 71.331 | -8.986 | 1.00 | 29.98 | A | O |
| ATOM | 2043 | CG2 | THR | 280 | 54.422 | 70.645 | -7.674 | 1.00 | 26.85 | A | C |
| ATOM | 2044 | C | THR | 280 | 52.618 | 70.254 | -5.418 | 1.00 | 26.01 | A | C |
| ATOM | 2045 | O | THR | 280 | 53.184 | 69.255 | -4.986 | 1.00 | 27.33 | A | O |
| ATOM | 2046 | N | ASN | 281 | 52.402 | 71.341 | -4.696 | 1.00 | 25.17 | A | N |
| ATOM | 2047 | CA | ASN | 281 | 52.876 | 71.474 | -3.334 | 1.00 | 23.78 | A | C |
| ATOM | 2048 | CB | ASN | 281 | 54.190 | 72.250 | -3.388 | 1.00 | 22.28 | A | C |
| ATOM | 2049 | CG | ASN | 281 | 54.925 | 72.287 | -2.071 | 1.00 | 22.87 | A | C |
| ATOM | 2050 | OD1 | ASN | 281 | 54.603 | 71.576 | -1.116 | 1.00 | 20.83 | A | O |
| ATOM | 2051 | ND2 | ASN | 281 | 55.948 | 73.136 | -2.056 | 1.00 | 22.18 | A | N |
| ATOM | 2052 | C | ASN | 281 | 51.818 | 72.211 | -2.506 | 1.00 | 23.12 | A | C |
| ATOM | 2053 | O | ASN | 281 | 51.876 | 73.431 | -2.362 | 1.00 | 22.47 | A | O |
| ATOM | 2054 | N | ALA | 282 | 50.849 | 71.460 | -1.982 | 1.00 | 23.33 | A | N |
| ATOM | 2055 | CA | ALA | 282 | 49.763 | 72.018 | -1.166 | 1.00 | 23.40 | A | C |
| ATOM | 2056 | CB | ALA | 282 | 48.952 | 70.895 | -0.547 | 1.00 | 23.19 | A | C |
| ATOM | 2057 | C | ALA | 282 | 50.320 | 72.912 | -0.071 | 1.00 | 24.45 | A | C |

| | | | | | | | | | | | |
|---|---|---|---|---|---|---|---|---|---|---|---|
| ATOM | 2058 | O | ALA | 282 | 51.180 | 72.487 | 0.694 | 1.00 | 25.49 | A | O |
| ATOM | 2059 | N | THR | 283 | 49.817 | 74.140 | 0.024 | 1.00 | 24.70 | A | N |
| ATOM | 2060 | CA | THR | 283 | 50.326 | 75.074 | 1.021 | 1.00 | 25.33 | A | C |
| ATOM | 2061 | CB | THR | 283 | 50.209 | 76.540 | 0.539 | 1.00 | 27.36 | A | C |
| ATOM | 2062 | OG1 | THR | 283 | 48.834 | 76.874 | 0.353 | 1.00 | 29.84 | A | O |
| ATOM | 2063 | CG2 | THR | 283 | 50.947 | 76.730 | -0.785 | 1.00 | 30.06 | A | C |
| ATOM | 2064 | C | THR | 283 | 49.710 | 74.983 | 2.406 | 1.00 | 24.49 | A | C |
| ATOM | 2065 | O | THR | 283 | 48.487 | 74.960 | 2.578 | 1.00 | 24.13 | A | O |
| ATOM | 2066 | N | SER | 284 | 50.593 | 74.941 | 3.396 | 1.00 | 23.17 | A | N |
| ATOM | 2067 | CA | SER | 284 | 50.200 | 74.872 | 4.791 | 1.00 | 19.88 | A | C |
| ATOM | 2068 | CB | SER | 284 | 51.317 | 74.249 | 5.624 | 1.00 | 15.88 | A | C |
| ATOM | 2069 | OG | SER | 284 | 51.413 | 72.868 | 5.350 | 1.00 | 14.23 | A | O |
| ATOM | 2070 | C | SER | 284 | 49.906 | 76.275 | 5.288 | 1.00 | 19.24 | A | C |
| ATOM | 2071 | O | SER | 284 | 50.774 | 77.148 | 5.253 | 1.00 | 18.08 | A | O |
| ATOM | 2072 | N | ILE | 285 | 48.674 | 76.478 | 5.745 | 1.00 | 17.36 | A | N |
| ATOM | 2073 | CA | ILE | 285 | 48.249 | 77.771 | 6.242 | 1.00 | 16.16 | A | C |
| ATOM | 2074 | CB | ILE | 285 | 46.754 | 78.003 | 5.977 | 1.00 | 16.93 | A | C |
| ATOM | 2075 | CG2 | ILE | 285 | 46.384 | 79.446 | 6.324 | 1.00 | 14.55 | A | C |
| ATOM | 2076 | CG1 | ILE | 285 | 46.434 | 77.691 | 4.513 | 1.00 | 14.89 | A | C |
| ATOM | 2077 | CD1 | ILE | 285 | 47.230 | 78.526 | 3.528 | 1.00 | 15.03 | A | C |
| ATOM | 2078 | C | ILE | 285 | 48.496 | 77.848 | 7.733 | 1.00 | 16.46 | A | C |
| ATOM | 2079 | O | ILE | 285 | 48.116 | 76.963 | 8.489 | 1.00 | 18.69 | A | O |
| ATOM | 2080 | N | GLN | 286 | 49.130 | 78.923 | 8.159 | 1.00 | 16.66 | A | N |
| ATOM | 2081 | CA | GLN | 286 | 49.428 | 79.088 | 9.563 | 1.00 | 16.43 | A | C |
| ATOM | 2082 | CB | GLN | 286 | 50.778 | 79.776 | 9.717 | 1.00 | 16.31 | A | C |
| ATOM | 2083 | CG | GLN | 286 | 51.184 | 80.070 | 11.135 | 1.00 | 17.85 | A | C |
| ATOM | 2084 | CD | GLN | 286 | 52.552 | 80.713 | 11.196 | 1.00 | 21.44 | A | C |
| ATOM | 2085 | OE1 | GLN | 286 | 53.072 | 81.005 | 12.277 | 1.00 | 24.09 | A | O |
| ATOM | 2086 | NE2 | GLN | 286 | 53.149 | 80.939 | 10.028 | 1.00 | 19.13 | A | N |
| ATOM | 2087 | C | GLN | 286 | 48.360 | 79.885 | 10.289 | 1.00 | 16.82 | A | C |
| ATOM | 2088 | O | GLN | 286 | 47.794 | 80.844 | 9.754 | 1.00 | 17.23 | A | O |
| ATOM | 2089 | N | ILE | 287 | 48.070 | 79.453 | 11.507 | 1.00 | 15.99 | A | N |
| ATOM | 2090 | CA | ILE | 287 | 47.116 | 80.137 | 12.355 | 1.00 | 15.11 | A | C |
| ATOM | 2091 | CB | ILE | 287 | 46.036 | 79.182 | 12.894 | 1.00 | 14.14 | A | C |
| ATOM | 2092 | CG2 | ILE | 287 | 45.147 | 79.916 | 13.875 | 1.00 | 14.36 | A | C |
| ATOM | 2093 | CG1 | ILE | 287 | 45.206 | 78.621 | 11.742 | 1.00 | 13.29 | A | C |
| ATOM | 2094 | CD1 | ILE | 287 | 44.111 | 77.675 | 12.202 | 1.00 | 14.31 | A | C |
| ATOM | 2095 | C | ILE | 287 | 47.991 | 80.625 | 13.506 | 1.00 | 15.35 | A | C |
| ATOM | 2096 | O | ILE | 287 | 48.349 | 79.860 | 14.401 | 1.00 | 14.39 | A | O |
| ATOM | 2097 | N | THR | 288 | 48.367 | 81.894 | 13.452 | 1.00 | 15.01 | A | N |
| ATOM | 2098 | CA | THR | 288 | 49.215 | 82.465 | 14.482 | 1.00 | 16.71 | A | C |
| ATOM | 2099 | CB | THR | 288 | 49.688 | 83.874 | 14.093 | 1.00 | 17.36 | A | C |
| ATOM | 2100 | OG1 | THR | 288 | 48.548 | 84.679 | 13.779 | 1.00 | 21.17 | A | O |
| ATOM | 2101 | CG2 | THR | 288 | 50.621 | 83.813 | 12.881 | 1.00 | 17.64 | A | C |
| ATOM | 2102 | C | THR | 288 | 48.510 | 82.553 | 15.818 | 1.00 | 16.02 | A | C |
| ATOM | 2103 | O | THR | 288 | 47.287 | 82.668 | 15.888 | 1.00 | 16.28 | A | O |
| ATOM | 2104 | N | ALA | 289 | 49.301 | 82.488 | 16.881 | 1.00 | 16.31 | A | N |
| ATOM | 2105 | CA | ALA | 289 | 48.787 | 82.582 | 18.232 | 1.00 | 16.67 | A | C |
| ATOM | 2106 | CB | ALA | 289 | 49.887 | 82.262 | 19.207 | 1.00 | 18.89 | A | C |

| ATOM | 2107 | C | ALA | 289 | 48.280 | 84.001 | 18.467 | 1.00 | 18.05 | A | C |
|---|---|---|---|---|---|---|---|---|---|---|---|
| ATOM | 2108 | O | ALA | 289 | 48.629 | 84.927 | 17.733 | 1.00 | 19.12 | A | O |
| ATOM | 2109 | N | PRO | 290 | 47.436 | 84.193 | 19.487 | 1.00 | 18.60 | A | N |
| ATOM | 2110 | CD | PRO | 290 | 46.851 | 83.189 | 20.388 | 1.00 | 18.37 | A | C |
| ATOM | 2111 | CA | PRO | 290 | 46.906 | 85.526 | 19.783 | 1.00 | 19.04 | A | C |
| ATOM | 2112 | CB | PRO | 290 | 45.791 | 85.234 | 20.777 | 1.00 | 17.58 | A | C |
| ATOM | 2113 | CG | PRO | 290 | 46.306 | 84.055 | 21.499 | 1.00 | 19.78 | A | C |
| ATOM | 2114 | C | PRO | 290 | 47.976 | 86.447 | 20.369 | 1.00 | 20.45 | A | C |
| ATOM | 2115 | O | PRO | 290 | 48.866 | 85.995 | 21.092 | 1.00 | 22.14 | A | O |
| ATOM | 2116 | N | ALA | 291 | 47.878 | 87.735 | 20.054 | 1.00 | 19.85 | A | N |
| ATOM | 2117 | CA | ALA | 291 | 48.829 | 88.728 | 20.543 | 1.00 | 19.27 | A | C |
| ATOM | 2118 | CB | ALA | 291 | 48.330 | 90.132 | 20.213 | 1.00 | 17.30 | A | C |
| ATOM | 2119 | C | ALA | 291 | 49.101 | 88.610 | 22.041 | 1.00 | 19.66 | A | C |
| ATOM | 2120 | O | ALA | 291 | 50.238 | 88.791 | 22.489 | 1.00 | 21.52 | A | O |
| ATOM | 2121 | N | SER | 292 | 48.074 | 88.305 | 22.825 | 1.00 | 19.16 | A | N |
| ATOM | 2122 | CA | SER | 292 | 48.275 | 88.185 | 24.264 | 1.00 | 19.97 | A | C |
| ATOM | 2123 | CB | SER | 292 | 46.936 | 87.983 | 24.971 | 1.00 | 19.90 | A | C |
| ATOM | 2124 | OG | SER | 292 | 46.259 | 86.839 | 24.487 | 1.00 | 24.94 | A | O |
| ATOM | 2125 | C | SER | 292 | 49.244 | 87.055 | 24.618 | 1.00 | 20.24 | A | C |
| ATOM | 2126 | O | SER | 292 | 49.686 | 86.948 | 25.760 | 1.00 | 21.86 | A | O |
| ATOM | 2127 | N | MET | 293 | 49.566 | 86.214 | 23.635 | 1.00 | 20.06 | A | N |
| ATOM | 2128 | CA | MET | 293 | 50.504 | 85.104 | 23.818 | 1.00 | 18.78 | A | C |
| ATOM | 2129 | CB | MET | 293 | 49.987 | 83.830 | 23.149 | 1.00 | 17.35 | A | C |
| ATOM | 2130 | CG | MET | 293 | 48.795 | 83.168 | 23.797 | 1.00 | 15.90 | A | C |
| ATOM | 2131 | SD | MET | 293 | 49.139 | 82.503 | 25.424 | 1.00 | 15.89 | A | S |
| ATOM | 2132 | CE | MET | 293 | 47.655 | 82.993 | 26.296 | 1.00 | 16.41 | A | C |
| ATOM | 2133 | C | MET | 293 | 51.831 | 85.487 | 23.161 | 1.00 | 20.24 | A | C |
| ATOM | 2134 | O | MET | 293 | 52.912 | 85.221 | 23.693 | 1.00 | 21.12 | A | O |
| ATOM | 2135 | N | LEU | 294 | 51.738 | 86.116 | 21.995 | 1.00 | 20.44 | A | N |
| ATOM | 2136 | CA | LEU | 294 | 52.918 | 86.532 | 21.255 | 1.00 | 21.31 | A | C |
| ATOM | 2137 | CB | LEU | 294 | 52.498 | 87.104 | 19.900 | 1.00 | 21.19 | A | C |
| ATOM | 2138 | CG | LEU | 294 | 51.850 | 86.092 | 18.944 | 1.00 | 23.63 | A | C |
| ATOM | 2139 | CD1 | LEU | 294 | 51.257 | 86.820 | 17.747 | 1.00 | 22.60 | A | C |
| ATOM | 2140 | CD2 | LEU | 294 | 52.889 | 85.064 | 18.493 | 1.00 | 20.94 | A | C |
| ATOM | 2141 | C | LEU | 294 | 53.818 | 87.533 | 21.981 | 1.00 | 22.05 | A | C |
| ATOM | 2142 | O | LEU | 294 | 54.953 | 87.742 | 21.564 | 1.00 | 23.39 | A | O |
| ATOM | 2143 | N | ILE | 295 | 53.329 | 88.156 | 23.053 | 1.00 | 21.86 | A | N |
| ATOM | 2144 | CA | ILE | 295 | 54.149 | 89.122 | 23.792 | 1.00 | 22.24 | A | C |
| ATOM | 2145 | CB | ILE | 295 | 53.323 | 89.938 | 24.835 | 1.00 | 24.92 | A | C |
| ATOM | 2146 | CG2 | ILE | 295 | 52.084 | 90.536 | 24.196 | 1.00 | 25.08 | A | C |
| ATOM | 2147 | CG1 | ILE | 295 | 52.906 | 89.034 | 25.998 | 1.00 | 25.57 | A | C |
| ATOM | 2148 | CD1 | ILE | 295 | 52.157 | 89.761 | 27.085 | 1.00 | 26.45 | A | C |
| ATOM | 2149 | C | ILE | 295 | 55.271 | 88.426 | 24.565 | 1.00 | 21.97 | A | C |
| ATOM | 2150 | O | ILE | 295 | 56.218 | 89.064 | 25.006 | 1.00 | 23.91 | A | O |
| ATOM | 2151 | N | GLY | 296 | 55.154 | 87.119 | 24.749 | 1.00 | 20.65 | A | N |
| ATOM | 2152 | CA | GLY | 296 | 56.174 | 86.401 | 25.482 | 1.00 | 18.90 | A | C |
| ATOM | 2153 | C | GLY | 296 | 56.165 | 84.922 | 25.167 | 1.00 | 18.45 | A | C |
| ATOM | 2154 | O | GLY | 296 | 55.527 | 84.503 | 24.202 | 1.00 | 18.61 | A | O |
| ATOM | 2155 | N | ASP | 297 | 56.878 | 84.132 | 25.967 | 1.00 | 16.58 | A | N |

FIG. 4-45 (Continued)

| | | | | | | | | | | |
|---|---|---|---|---|---|---|---|---|---|---|
| ATOM | 2156 | CA | ASP | 297 | 56.918 | 82.694 | 25.751 | 1.00 | 16.95 | A | C |
| ATOM | 2157 | CB | ASP | 297 | 57.960 | 82.032 | 26.650 | 1.00 | 18.00 | A | C |
| ATOM | 2158 | CG | ASP | 297 | 59.366 | 82.378 | 26.253 | 1.00 | 18.62 | A | C |
| ATOM | 2159 | OD1 | ASP | 297 | 59.553 | 82.882 | 25.128 | 1.00 | 18.23 | A | O |
| ATOM | 2160 | OD2 | ASP | 297 | 60.284 | 82.134 | 27.063 | 1.00 | 21.29 | A | O |
| ATOM | 2161 | C | ASP | 297 | 55.553 | 82.096 | 26.041 | 1.00 | 16.02 | A | C |
| ATOM | 2162 | O | ASP | 297 | 54.847 | 82.537 | 26.942 | 1.00 | 16.36 | A | O |
| ATOM | 2163 | N | HIS | 298 | 55.190 | 81.079 | 25.279 | 1.00 | 14.79 | A | N |
| ATOM | 2164 | CA | HIS | 298 | 53.901 | 80.449 | 25.460 | 1.00 | 16.82 | A | C |
| ATOM | 2165 | CB | HIS | 298 | 52.846 | 81.207 | 24.661 | 1.00 | 14.81 | A | C |
| ATOM | 2166 | CG | HIS | 298 | 53.245 | 81.448 | 23.241 | 1.00 | 15.31 | A | C |
| ATOM | 2167 | CD2 | HIS | 298 | 52.921 | 80.793 | 22.099 | 1.00 | 14.85 | A | C |
| ATOM | 2168 | ND1 | HIS | 298 | 54.127 | 82.442 | 22.876 | 1.00 | 13.01 | A | N |
| ATOM | 2169 | CE1 | HIS | 298 | 54.327 | 82.392 | 21.572 | 1.00 | 14.39 | A | C |
| ATOM | 2170 | NE2 | HIS | 298 | 53.608 | 81.400 | 21.076 | 1.00 | 14.38 | A | N |
| ATOM | 2171 | C | HIS | 298 | 53.956 | 79.008 | 24.979 | 1.00 | 17.54 | A | C |
| ATOM | 2172 | O | HIS | 298 | 55.008 | 78.519 | 24.560 | 1.00 | 15.53 | A | O |
| ATOM | 2173 | N | TYR | 299 | 52.802 | 78.348 | 25.031 | 1.00 | 17.25 | A | N |
| ATOM | 2174 | CA | TYR | 299 | 52.675 | 76.963 | 24.609 | 1.00 | 16.58 | A | C |
| ATOM | 2175 | CB | TYR | 299 | 52.666 | 76.029 | 25.816 | 1.00 | 15.77 | A | C |
| ATOM | 2176 | CG | TYR | 299 | 53.811 | 76.176 | 26.790 | 1.00 | 17.03 | A | C |
| ATOM | 2177 | CD1 | TYR | 299 | 55.095 | 75.762 | 26.456 | 1.00 | 14.29 | A | C |
| ATOM | 2178 | CE1 | TYR | 299 | 56.119 | 75.807 | 27.380 | 1.00 | 15.79 | A | C |
| ATOM | 2179 | CD2 | TYR | 299 | 53.586 | 76.653 | 28.081 | 1.00 | 15.17 | A | C |
| ATOM | 2180 | CE2 | TYR | 299 | 54.600 | 76.700 | 29.009 | 1.00 | 15.67 | A | C |
| ATOM | 2181 | CZ | TYR | 299 | 55.865 | 76.270 | 28.656 | 1.00 | 15.90 | A | C |
| ATOM | 2182 | OH | TYR | 299 | 56.863 | 76.261 | 29.595 | 1.00 | 16.73 | A | O |
| ATOM | 2183 | C | TYR | 299 | 51.351 | 76.741 | 23.893 | 1.00 | 17.76 | A | C |
| ATOM | 2184 | O | TYR | 299 | 50.349 | 77.411 | 24.178 | 1.00 | 16.87 | A | O |
| ATOM | 2185 | N | LEU | 300 | 51.355 | 75.799 | 22.959 | 1.00 | 16.20 | A | N |
| ATOM | 2186 | CA | LEU | 300 | 50.130 | 75.413 | 22.292 | 1.00 | 16.36 | A | C |
| ATOM | 2187 | CB | LEU | 300 | 50.413 | 74.923 | 20.878 | 1.00 | 16.40 | A | C |
| ATOM | 2188 | CG | LEU | 300 | 49.232 | 74.296 | 20.139 | 1.00 | 14.78 | A | C |
| ATOM | 2189 | CD1 | LEU | 300 | 48.131 | 75.322 | 19.972 | 1.00 | 16.55 | A | C |
| ATOM | 2190 | CD2 | LEU | 300 | 49.692 | 73.789 | 18.785 | 1.00 | 15.08 | A | C |
| ATOM | 2191 | C | LEU | 300 | 49.777 | 74.243 | 23.205 | 1.00 | 17.58 | A | C |
| ATOM | 2192 | O | LEU | 300 | 50.568 | 73.312 | 23.335 | 1.00 | 17.21 | A | O |
| ATOM | 2193 | N | CYS | 301 | 48.629 | 74.290 | 23.873 | 1.00 | 19.46 | A | N |
| ATOM | 2194 | CA | CYS | 301 | 48.288 | 73.202 | 24.782 | 1.00 | 22.20 | A | C |
| ATOM | 2195 | CB | CYS | 301 | 48.208 | 73.722 | 26.220 | 1.00 | 22.63 | A | C |
| ATOM | 2196 | SG | CYS | 301 | 46.943 | 74.962 | 26.503 | 1.00 | 26.56 | A | S |
| ATOM | 2197 | C | CYS | 301 | 47.032 | 72.399 | 24.468 | 1.00 | 23.29 | A | C |
| ATOM | 2198 | O | CYS | 301 | 46.690 | 71.481 | 25.210 | 1.00 | 25.66 | A | O |
| ATOM | 2199 | N | ASP | 302 | 46.341 | 72.731 | 23.386 | 1.00 | 23.55 | A | N |
| ATOM | 2200 | CA | ASP | 302 | 45.148 | 71.976 | 23.015 | 1.00 | 24.19 | A | C |
| ATOM | 2201 | CB | ASP | 302 | 43.999 | 72.223 | 23.991 | 1.00 | 26.49 | A | C |
| ATOM | 2202 | CG | ASP | 302 | 42.789 | 71.355 | 23.680 | 1.00 | 28.68 | A | C |
| ATOM | 2203 | OD1 | ASP | 302 | 42.795 | 70.170 | 24.066 | 1.00 | 30.65 | A | O |
| ATOM | 2204 | OD2 | ASP | 302 | 41.841 | 71.844 | 23.029 | 1.00 | 30.37 | A | O |

| | | | | | | | | | | |
|---|---|---|---|---|---|---|---|---|---|---|
| ATOM | 2205 | C | ASP | 302 | 44.658 | 72.292 | 21.610 | 1.00 23.22 | A | C |
| ATOM | 2206 | O | ASP | 302 | 44.523 | 73.455 | 21.226 | 1.00 24.26 | A | O |
| ATOM | 2207 | N | VAL | 303 | 44.385 | 71.237 | 20.857 | 1.00 21.65 | A | N |
| ATOM | 2208 | CA | VAL | 303 | 43.902 | 71.349 | 19.493 | 1.00 20.79 | A | C |
| ATOM | 2209 | CB | VAL | 303 | 44.926 | 70.803 | 18.480 | 1.00 21.88 | A | C |
| ATOM | 2210 | CG1 | VAL | 303 | 44.420 | 71.028 | 17.051 | 1.00 20.34 | A | C |
| ATOM | 2211 | CG2 | VAL | 303 | 46.273 | 71.465 | 18.702 | 1.00 20.12 | A | C |
| ATOM | 2212 | C | VAL | 303 | 42.657 | 70.494 | 19.417 | 1.00 20.38 | A | C |
| ATOM | 2213 | O | VAL | 303 | 42.687 | 69.306 | 19.744 | 1.00 19.45 | A | O |
| ATOM | 2214 | N | THR | 304 | 41.562 | 71.102 | 18.982 | 1.00 20.04 | A | N |
| ATOM | 2215 | CA | THR | 304 | 40.302 | 70.394 | 18.882 | 1.00 19.30 | A | C |
| ATOM | 2216 | CB | THR | 304 | 39.494 | 70.546 | 20.191 | 1.00 19.73 | A | C |
| ATOM | 2217 | OG1 | THR | 304 | 40.256 | 70.024 | 21.287 | 1.00 20.19 | A | O |
| ATOM | 2218 | CG2 | THR | 304 | 38.168 | 69.812 | 20.090 | 1.00 17.51 | A | C |
| ATOM | 2219 | C | THR | 304 | 39.467 | 70.930 | 17.733 | 1.00 18.56 | A | C |
| ATOM | 2220 | O | THR | 304 | 39.185 | 72.127 | 17.674 | 1.00 19.32 | A | O |
| ATOM | 2221 | N | TRP | 305 | 39.082 | 70.042 | 16.819 | 1.00 18.08 | A | N |
| ATOM | 2222 | CA | TRP | 305 | 38.243 | 70.422 | 15.681 | 1.00 16.88 | A | C |
| ATOM | 2223 | CB | TRP | 305 | 38.332 | 69.394 | 14.546 | 1.00 13.92 | A | C |
| ATOM | 2224 | CG | TRP | 305 | 39.581 | 69.464 | 13.745 | 1.00 13.82 | A | C |
| ATOM | 2225 | CD2 | TRP | 305 | 39.815 | 70.296 | 12.606 | 1.00 13.04 | A | C |
| ATOM | 2226 | CE2 | TRP | 305 | 41.143 | 70.068 | 12.189 | 1.00 13.12 | A | C |
| ATOM | 2227 | CE3 | TRP | 305 | 39.031 | 71.216 | 11.899 | 1.00 13.55 | A | C |
| ATOM | 2228 | CD1 | TRP | 305 | 40.745 | 68.781 | 13.967 | 1.00 13.51 | A | C |
| ATOM | 2229 | NE1 | TRP | 305 | 41.688 | 69.138 | 13.036 | 1.00 11.41 | A | N |
| ATOM | 2230 | CZ2 | TRP | 305 | 41.704 | 70.729 | 11.094 | 1.00 12.03 | A | C |
| ATOM | 2231 | CZ3 | TRP | 305 | 39.591 | 71.873 | 10.809 | 1.00 14.16 | A | C |
| ATOM | 2232 | CH2 | TRP | 305 | 40.914 | 71.625 | 10.419 | 1.00 13.92 | A | C |
| ATOM | 2233 | C | TRP | 305 | 36.803 | 70.477 | 16.155 | 1.00 16.35 | A | C |
| ATOM | 2234 | O | TRP | 305 | 36.368 | 69.613 | 16.917 | 1.00 16.55 | A | O |
| ATOM | 2235 | N | ALA | 306 | 36.064 | 71.484 | 15.704 | 1.00 16.10 | A | N |
| ATOM | 2236 | CA | ALA | 306 | 34.661 | 71.620 | 16.079 | 1.00 17.20 | A | C |
| ATOM | 2237 | CB | ALA | 306 | 34.336 | 73.074 | 16.384 | 1.00 18.47 | A | C |
| ATOM | 2238 | C | ALA | 306 | 33.770 | 71.110 | 14.956 | 1.00 16.79 | A | C |
| ATOM | 2239 | O | ALA | 306 | 32.829 | 70.369 | 15.191 | 1.00 18.46 | A | O |
| ATOM | 2240 | N | THR | 307 | 34.076 | 71.516 | 13.733 | 1.00 18.36 | A | N |
| ATOM | 2241 | CA | THR | 307 | 33.314 | 71.100 | 12.564 | 1.00 18.83 | A | C |
| ATOM | 2242 | CB | THR | 307 | 32.387 | 72.222 | 12.072 | 1.00 18.43 | A | C |
| ATOM | 2243 | OG1 | THR | 307 | 33.178 | 73.254 | 11.473 | 1.00 20.76 | A | O |
| ATOM | 2244 | CG2 | THR | 307 | 31.593 | 72.811 | 13.225 | 1.00 16.72 | A | C |
| ATOM | 2245 | C | THR | 307 | 34.299 | 70.778 | 11.442 | 1.00 20.34 | A | C |
| ATOM | 2246 | O | THR | 307 | 35.494 | 70.626 | 11.689 | 1.00 22.05 | A | O |
| ATOM | 2247 | N | GLN | 308 | 33.798 | 70.688 | 10.213 | 1.00 20.11 | A | N |
| ATOM | 2248 | CA | GLN | 308 | 34.640 | 70.389 | 9.066 | 1.00 19.71 | A | C |
| ATOM | 2249 | CB | GLN | 308 | 33.799 | 69.942 | 7.866 | 1.00 19.44 | A | C |
| ATOM | 2250 | CG | GLN | 308 | 32.845 | 68.791 | 8.118 | 1.00 21.53 | A | C |
| ATOM | 2251 | CD | GLN | 308 | 33.524 | 67.505 | 8.557 | 1.00 23.81 | A | C |
| ATOM | 2252 | OE1 | GLN | 308 | 32.854 | 66.565 | 9.003 | 1.00 25.80 | A | O |
| ATOM | 2253 | NE2 | GLN | 308 | 34.848 | 67.449 | 8.430 | 1.00 21.04 | A | N |

| | | | | | | | | | | | |
|---|---|---|---|---|---|---|---|---|---|---|---|
| ATOM | 2254 | C | GLN | 308 | 35.440 | 71.616 | 8.653 | 1.00 | 19.98 | A | C |
| ATOM | 2255 | O | GLN | 308 | 36.421 | 71.501 | 7.922 | 1.00 | 21.84 | A | O |
| ATOM | 2256 | N | GLU | 309 | 35.022 | 72.789 | 9.114 | 1.00 | 19.41 | A | N |
| ATOM | 2257 | CA | GLU | 309 | 35.710 | 74.019 | 8.751 | 1.00 | 20.93 | A | C |
| ATOM | 2258 | CB | GLU | 309 | 34.920 | 74.764 | 7.685 | 1.00 | 21.98 | A | C |
| ATOM | 2259 | CG | GLU | 309 | 34.709 | 73.971 | 6.419 | 1.00 | 26.38 | A | C |
| ATOM | 2260 | CD | GLU | 309 | 33.890 | 74.731 | 5.413 | 1.00 | 29.11 | A | C |
| ATOM | 2261 | OE1 | GLU | 309 | 33.665 | 74.192 | 4.305 | 1.00 | 31.98 | A | O |
| ATOM | 2262 | OE2 | GLU | 309 | 33.471 | 75.869 | 5.736 | 1.00 | 28.78 | A | O |
| ATOM | 2263 | C | GLU | 309 | 35.924 | 74.939 | 9.932 | 1.00 | 21.37 | A | C |
| ATOM | 2264 | O | GLU | 309 | 36.075 | 76.152 | 9.764 | 1.00 | 21.97 | A | O |
| ATOM | 2265 | N | ARG | 310 | 35.941 | 74.360 | 11.125 | 1.00 | 20.65 | A | N |
| ATOM | 2266 | CA | ARG | 310 | 36.133 | 75.131 | 12.340 | 1.00 | 20.50 | A | C |
| ATOM | 2267 | CB | ARG | 310 | 34.779 | 75.445 | 12.986 | 1.00 | 19.87 | A | C |
| ATOM | 2268 | CG | ARG | 310 | 34.888 | 76.186 | 14.305 | 1.00 | 22.38 | A | C |
| ATOM | 2269 | CD | ARG | 310 | 33.519 | 76.630 | 14.786 | 1.00 | 21.66 | A | C |
| ATOM | 2270 | NE | ARG | 310 | 32.952 | 77.605 | 13.870 | 1.00 | 20.43 | A | N |
| ATOM | 2271 | CZ | ARG | 310 | 31.660 | 77.884 | 13.785 | 1.00 | 19.88 | A | C |
| ATOM | 2272 | NH1 | ARG | 310 | 30.794 | 77.261 | 14.569 | 1.00 | 21.42 | A | N |
| ATOM | 2273 | NH2 | ARG | 310 | 31.235 | 78.776 | 12.902 | 1.00 | 21.69 | A | N |
| ATOM | 2274 | C | ARG | 310 | 37.009 | 74.346 | 13.304 | 1.00 | 19.05 | A | C |
| ATOM | 2275 | O | ARG | 310 | 36.701 | 73.214 | 13.671 | 1.00 | 20.19 | A | O |
| ATOM | 2276 | N | ILE | 311 | 38.108 | 74.959 | 13.710 | 1.00 | 17.88 | A | N |
| ATOM | 2277 | CA | ILE | 311 | 39.044 | 74.320 | 14.619 | 1.00 | 17.41 | A | C |
| ATOM | 2278 | CB | ILE | 311 | 40.371 | 73.991 | 13.859 | 1.00 | 17.28 | A | C |
| ATOM | 2279 | CG2 | ILE | 311 | 40.982 | 75.252 | 13.305 | 1.00 | 14.23 | A | C |
| ATOM | 2280 | CG1 | ILE | 311 | 41.358 | 73.254 | 14.765 | 1.00 | 17.79 | A | C |
| ATOM | 2281 | CD1 | ILE | 311 | 42.589 | 72.763 | 14.011 | 1.00 | 15.43 | A | C |
| ATOM | 2282 | C | ILE | 311 | 39.283 | 75.258 | 15.802 | 1.00 | 17.03 | A | C |
| ATOM | 2283 | O | ILE | 311 | 39.267 | 76.481 | 15.649 | 1.00 | 17.06 | A | O |
| ATOM | 2284 | N | SER | 312 | 39.461 | 74.692 | 16.988 | 1.00 | 16.94 | A | N |
| ATOM | 2285 | CA | SER | 312 | 39.694 | 75.517 | 18.163 | 1.00 | 18.32 | A | C |
| ATOM | 2286 | CB | SER | 312 | 38.631 | 75.244 | 19.235 | 1.00 | 19.09 | A | C |
| ATOM | 2287 | OG | SER | 312 | 39.008 | 74.173 | 20.074 | 1.00 | 18.57 | A | O |
| ATOM | 2288 | C | SER | 312 | 41.084 | 75.269 | 18.736 | 1.00 | 18.45 | A | C |
| ATOM | 2289 | O | SER | 312 | 41.552 | 74.131 | 18.795 | 1.00 | 17.71 | A | O |
| ATOM | 2290 | N | LEU | 313 | 41.738 | 76.349 | 19.148 | 1.00 | 19.07 | A | N |
| ATOM | 2291 | CA | LEU | 313 | 43.080 | 76.271 | 19.708 | 1.00 | 20.08 | A | C |
| ATOM | 2292 | CB | LEU | 313 | 44.093 | 76.931 | 18.768 | 1.00 | 19.12 | A | C |
| ATOM | 2293 | CG | LEU | 313 | 44.239 | 76.409 | 17.341 | 1.00 | 20.02 | A | C |
| ATOM | 2294 | CD1 | LEU | 313 | 45.480 | 77.038 | 16.712 | 1.00 | 19.82 | A | C |
| ATOM | 2295 | CD2 | LEU | 313 | 44.361 | 74.892 | 17.351 | 1.00 | 20.74 | A | C |
| ATOM | 2296 | C | LEU | 313 | 43.172 | 76.957 | 21.062 | 1.00 | 21.08 | A | C |
| ATOM | 2297 | O | LEU | 313 | 42.608 | 78.030 | 21.265 | 1.00 | 21.22 | A | O |
| ATOM | 2298 | N | GLN | 314 | 43.898 | 76.333 | 21.981 | 1.00 | 22.23 | A | N |
| ATOM | 2299 | CA | GLN | 314 | 44.096 | 76.884 | 23.308 | 1.00 | 22.40 | A | C |
| ATOM | 2300 | CB | GLN | 314 | 43.545 | 75.935 | 24.365 | 1.00 | 24.62 | A | C |
| ATOM | 2301 | CG | GLN | 314 | 42.033 | 75.860 | 24.406 | 1.00 | 27.30 | A | C |
| ATOM | 2302 | CD | GLN | 314 | 41.536 | 74.832 | 25.401 | 1.00 | 29.52 | A | C |

| | | | | | | | | | | |
|---|---|---|---|---|---|---|---|---|---|---|
| ATOM | 2303 | OE1 | GLN | 314 | 41.827 | 74.911 | 26.598 | 1.00 | 29.38 | A | O |
| ATOM | 2304 | NE2 | GLN | 314 | 40.786 | 73.854 | 24.911 | 1.00 | 30.52 | A | N |
| ATOM | 2305 | C | GLN | 314 | 45.584 | 77.099 | 23.532 | 1.00 | 22.00 | A | C |
| ATOM | 2306 | O | GLN | 314 | 46.382 | 76.176 | 23.419 | 1.00 | 22.34 | A | O |
| ATOM | 2307 | N | TRP | 315 | 45.954 | 78.333 | 23.833 | 1.00 | 21.50 | A | N |
| ATOM | 2308 | CA | TRP | 315 | 47.343 | 78.667 | 24.070 | 1.00 | 20.70 | A | C |
| ATOM | 2309 | CB | TRP | 315 | 47.748 | 79.873 | 23.226 | 1.00 | 18.74 | A | C |
| ATOM | 2310 | CG | TRP | 315 | 47.480 | 79.711 | 21.746 | 1.00 | 17.87 | A | C |
| ATOM | 2311 | CD2 | TRP | 315 | 48.435 | 79.368 | 20.733 | 1.00 | 14.81 | A | C |
| ATOM | 2312 | CE2 | TRP | 315 | 47.764 | 79.419 | 19.491 | 1.00 | 14.29 | A | C |
| ATOM | 2313 | CE3 | TRP | 315 | 49.793 | 79.029 | 20.753 | 1.00 | 13.32 | A | C |
| ATOM | 2314 | CD1 | TRP | 315 | 46.299 | 79.936 | 21.095 | 1.00 | 15.84 | A | C |
| ATOM | 2315 | NE1 | TRP | 315 | 46.463 | 79.769 | 19.742 | 1.00 | 13.87 | A | N |
| ATOM | 2316 | CZ2 | TRP | 315 | 48.407 | 79.147 | 18.278 | 1.00 | 12.51 | A | C |
| ATOM | 2317 | CZ3 | TRP | 315 | 50.433 | 78.760 | 19.545 | 1.00 | 13.87 | A | C |
| ATOM | 2318 | CH2 | TRP | 315 | 49.736 | 78.822 | 18.325 | 1.00 | 12.57 | A | C |
| ATOM | 2319 | C | TRP | 315 | 47.530 | 78.976 | 25.545 | 1.00 | 21.60 | A | C |
| ATOM | 2320 | O | TRP | 315 | 46.615 | 79.463 | 26.205 | 1.00 | 22.41 | A | O |
| ATOM | 2321 | N | LEU | 316 | 48.721 | 78.689 | 26.056 | 1.00 | 21.81 | A | N |
| ATOM | 2322 | CA | LEU | 316 | 49.033 | 78.915 | 27.458 | 1.00 | 22.64 | A | C |
| ATOM | 2323 | CB | LEU | 316 | 49.034 | 77.573 | 28.192 | 1.00 | 22.20 | A | C |
| ATOM | 2324 | CG | LEU | 316 | 49.655 | 77.484 | 29.584 | 1.00 | 23.04 | A | C |
| ATOM | 2325 | CD1 | LEU | 316 | 48.953 | 78.438 | 30.530 | 1.00 | 24.08 | A | C |
| ATOM | 2326 | CD2 | LEU | 316 | 49.557 | 76.049 | 30.085 | 1.00 | 19.71 | A | C |
| ATOM | 2327 | C | LEU | 316 | 50.383 | 79.617 | 27.618 | 1.00 | 24.44 | A | C |
| ATOM | 2328 | O | LEU | 316 | 51.392 | 79.192 | 27.046 | 1.00 | 26.77 | A | O |
| ATOM | 2329 | N | ARG | 317 | 50.388 | 80.704 | 28.383 | 1.00 | 23.92 | A | N |
| ATOM | 2330 | CA | ARG | 317 | 51.603 | 81.475 | 28.630 | 1.00 | 22.55 | A | C |
| ATOM | 2331 | CB | ARG | 317 | 51.265 | 82.787 | 29.337 | 1.00 | 25.72 | A | C |
| ATOM | 2332 | CG | ARG | 317 | 50.490 | 83.785 | 28.504 | 1.00 | 26.56 | A | C |
| ATOM | 2333 | CD | ARG | 317 | 50.187 | 85.012 | 29.327 | 1.00 | 26.99 | A | C |
| ATOM | 2334 | NE | ARG | 317 | 49.796 | 86.141 | 28.494 | 1.00 | 30.37 | A | N |
| ATOM | 2335 | CZ | ARG | 317 | 49.278 | 87.269 | 28.966 | 1.00 | 30.55 | A | C |
| ATOM | 2336 | NH1 | ARG | 317 | 49.082 | 87.414 | 30.273 | 1.00 | 29.99 | A | N |
| ATOM | 2337 | NH2 | ARG | 317 | 48.972 | 88.256 | 28.132 | 1.00 | 28.53 | A | N |
| ATOM | 2338 | C | ARG | 317 | 52.580 | 80.705 | 29.500 | 1.00 | 21.07 | A | C |
| ATOM | 2339 | O | ARG | 317 | 52.175 | 79.920 | 30.359 | 1.00 | 19.79 | A | O |
| ATOM | 2340 | N | ARG | 318 | 53.871 | 80.941 | 29.290 | 1.00 | 19.43 | A | N |
| ATOM | 2341 | CA | ARG | 318 | 54.876 | 80.259 | 30.084 | 1.00 | 17.08 | A | C |
| ATOM | 2342 | CB | ARG | 318 | 56.263 | 80.850 | 29.845 | 1.00 | 15.15 | A | C |
| ATOM | 2343 | CG | ARG | 318 | 57.345 | 80.075 | 30.564 | 1.00 | 13.58 | A | C |
| ATOM | 2344 | CD | ARG | 318 | 58.671 | 80.165 | 29.853 | 1.00 | 13.59 | A | C |
| ATOM | 2345 | NE | ARG | 318 | 59.687 | 79.341 | 30.504 | 1.00 | 11.13 | A | N |
| ATOM | 2346 | CZ | ARG | 318 | 60.895 | 79.135 | 30.001 | 1.00 | 10.46 | A | C |
| ATOM | 2347 | NH1 | ARG | 318 | 61.220 | 79.694 | 28.850 | 1.00 | 11.29 | A | N |
| ATOM | 2348 | NH2 | ARG | 318 | 61.773 | 78.378 | 30.642 | 1.00 | 10.86 | A | N |
| ATOM | 2349 | C | ARG | 318 | 54.500 | 80.354 | 31.555 | 1.00 | 16.61 | A | C |
| ATOM | 2350 | O | ARG | 318 | 54.794 | 79.448 | 32.318 | 1.00 | 20.33 | A | O |
| ATOM | 2351 | N | ILE | 319 | 53.869 | 81.455 | 31.954 | 1.00 | 16.59 | A | N |

FIG. 4-49

| | | | | | | | | | | |
|---|---|---|---|---|---|---|---|---|---|---|
| ATOM | 2352 | CA | ILE | 319 | 53.396 | 81.607 | 33.330 | 1.00 | 17.40 | A | C |
| ATOM | 2353 | CB | ILE | 319 | 53.389 | 83.078 | 33.776 | 1.00 | 17.03 | A | C |
| ATOM | 2354 | CG2 | ILE | 319 | 52.720 | 83.210 | 35.128 | 1.00 | 17.19 | A | C |
| ATOM | 2355 | CG1 | ILE | 319 | 54.828 | 83.589 | 33.878 | 1.00 | 19.57 | A | C |
| ATOM | 2356 | CD1 | ILE | 319 | 55.712 | 82.743 | 34.787 | 1.00 | 19.56 | A | C |
| ATOM | 2357 | C | ILE | 319 | 51.972 | 81.065 | 33.251 | 1.00 | 17.56 | A | C |
| ATOM | 2358 | O | ILE | 319 | 51.012 | 81.808 | 33.067 | 1.00 | 18.71 | A | O |
| ATOM | 2359 | N | GLN | 320 | 51.870 | 79.747 | 33.381 | 1.00 | 16.94 | A | N |
| ATOM | 2360 | CA | GLN | 320 | 50.623 | 79.001 | 33.246 | 1.00 | 16.12 | A | C |
| ATOM | 2361 | CB | GLN | 320 | 50.939 | 77.516 | 33.420 | 1.00 | 14.59 | A | C |
| ATOM | 2362 | CG | GLN | 320 | 52.000 | 77.044 | 32.444 | 1.00 | 12.17 | A | C |
| ATOM | 2363 | CD | GLN | 320 | 52.304 | 75.577 | 32.570 | 1.00 | 10.79 | A | C |
| ATOM | 2364 | OE1 | GLN | 320 | 51.431 | 74.734 | 32.403 | 1.00 | 12.70 | A | O |
| ATOM | 2365 | NE2 | GLN | 320 | 53.554 | 75.261 | 32.860 | 1.00 | 13.71 | A | N |
| ATOM | 2366 | C | GLN | 320 | 49.368 | 79.351 | 34.038 | 1.00 | 16.32 | A | C |
| ATOM | 2367 | O | GLN | 320 | 48.645 | 78.466 | 34.472 | 1.00 | 14.51 | A | O |
| ATOM | 2368 | N | ASN | 321 | 49.079 | 80.633 | 34.207 | 1.00 | 18.37 | A | N |
| ATOM | 2369 | CA | ASN | 321 | 47.871 | 81.010 | 34.931 | 1.00 | 19.38 | A | C |
| ATOM | 2370 | CB | ASN | 321 | 48.226 | 81.785 | 36.203 | 1.00 | 20.21 | A | C |
| ATOM | 2371 | CG | ASN | 321 | 48.776 | 83.166 | 35.925 | 1.00 | 23.59 | A | C |
| ATOM | 2372 | OD1 | ASN | 321 | 49.166 | 83.491 | 34.804 | 1.00 | 22.35 | A | O |
| ATOM | 2373 | ND2 | ASN | 321 | 48.801 | 83.975 | 36.980 | 1.00 | 27.82 | A | N |
| ATOM | 2374 | C | ASN | 321 | 46.983 | 81.843 | 34.020 | 1.00 | 18.69 | A | C |
| ATOM | 2375 | O | ASN | 321 | 46.095 | 82.555 | 34.479 | 1.00 | 19.10 | A | O |
| ATOM | 2376 | N | TYR | 322 | 47.222 | 81.715 | 32.719 | 1.00 | 17.65 | A | N |
| ATOM | 2377 | CA | TYR | 322 | 46.482 | 82.466 | 31.719 | 1.00 | 18.28 | A | C |
| ATOM | 2378 | CB | TYR | 322 | 47.105 | 83.856 | 31.599 | 1.00 | 18.09 | A | C |
| ATOM | 2379 | CG | TYR | 322 | 46.319 | 84.856 | 30.792 | 1.00 | 20.14 | A | C |
| ATOM | 2380 | CD1 | TYR | 322 | 46.561 | 85.037 | 29.428 | 1.00 | 21.33 | A | C |
| ATOM | 2381 | CE1 | TYR | 322 | 45.843 | 85.987 | 28.694 | 1.00 | 22.14 | A | C |
| ATOM | 2382 | CD2 | TYR | 322 | 45.340 | 85.645 | 31.401 | 1.00 | 20.00 | A | C |
| ATOM | 2383 | CE2 | TYR | 322 | 44.624 | 86.589 | 30.681 | 1.00 | 19.18 | A | C |
| ATOM | 2384 | CZ | TYR | 322 | 44.876 | 86.758 | 29.334 | 1.00 | 21.74 | A | C |
| ATOM | 2385 | OH | TYR | 322 | 44.163 | 87.704 | 28.638 | 1.00 | 24.04 | A | O |
| ATOM | 2386 | C | TYR | 322 | 46.518 | 81.750 | 30.363 | 1.00 | 18.70 | A | C |
| ATOM | 2387 | O | TYR | 322 | 47.583 | 81.587 | 29.764 | 1.00 | 18.36 | A | O |
| ATOM | 2388 | N | SER | 323 | 45.351 | 81.318 | 29.896 | 1.00 | 17.43 | A | N |
| ATOM | 2389 | CA | SER | 323 | 45.237 | 80.638 | 28.612 | 1.00 | 17.45 | A | C |
| ATOM | 2390 | CB | SER | 323 | 44.871 | 79.163 | 28.806 | 1.00 | 16.45 | A | C |
| ATOM | 2391 | OG | SER | 323 | 43.662 | 79.025 | 29.535 | 1.00 | 17.51 | A | O |
| ATOM | 2392 | C | SER | 323 | 44.163 | 81.320 | 27.777 | 1.00 | 17.88 | A | C |
| ATOM | 2393 | O | SER | 323 | 43.250 | 81.943 | 28.314 | 1.00 | 18.20 | A | O |
| ATOM | 2394 | N | VAL | 324 | 44.277 | 81.199 | 26.461 | 1.00 | 18.44 | A | N |
| ATOM | 2395 | CA | VAL | 324 | 43.309 | 81.802 | 25.555 | 1.00 | 18.83 | A | C |
| ATOM | 2396 | CB | VAL | 324 | 43.925 | 82.995 | 24.800 | 1.00 | 19.32 | A | C |
| ATOM | 2397 | CG1 | VAL | 324 | 42.944 | 83.509 | 23.760 | 1.00 | 18.46 | A | C |
| ATOM | 2398 | CG2 | VAL | 324 | 44.290 | 84.105 | 25.785 | 1.00 | 18.78 | A | C |
| ATOM | 2399 | C | VAL | 324 | 42.839 | 80.776 | 24.534 | 1.00 | 18.47 | A | C |
| ATOM | 2400 | O | VAL | 324 | 43.631 | 79.985 | 24.036 | 1.00 | 18.75 | A | O |

| | | | | | | | | | | | |
|---|---|---|---|---|---|---|---|---|---|---|---|
| ATOM | 2401 | N | MET | 325 | 41.549 | 80.772 | 24.231 | 1.00 | 17.55 | A | N |
| ATOM | 2402 | CA | MET | 325 | 41.046 | 79.832 | 23.245 | 1.00 | 17.68 | A | C |
| ATOM | 2403 | CB | MET | 325 | 39.832 | 79.062 | 23.769 | 1.00 | 19.82 | A | C |
| ATOM | 2404 | CG | MET | 325 | 39.272 | 78.043 | 22.774 | 1.00 | 20.18 | A | C |
| ATOM | 2405 | SD | MET | 325 | 37.681 | 77.304 | 23.268 | 1.00 | 23.11 | A | S |
| ATOM | 2406 | CE | MET | 325 | 38.209 | 75.734 | 23.896 | 1.00 | 24.95 | A | C |
| ATOM | 2407 | C | MET | 325 | 40.641 | 80.584 | 21.999 | 1.00 | 18.03 | A | C |
| ATOM | 2408 | O | MET | 325 | 39.932 | 81.583 | 22.076 | 1.00 | 16.88 | A | O |
| ATOM | 2409 | N | ASP | 326 | 41.114 | 80.118 | 20.852 | 1.00 | 18.60 | A | N |
| ATOM | 2410 | CA | ASP | 326 | 40.749 | 80.738 | 19.595 | 1.00 | 20.69 | A | C |
| ATOM | 2411 | CB | ASP | 326 | 41.988 | 81.158 | 18.797 | 1.00 | 22.43 | A | C |
| ATOM | 2412 | CG | ASP | 326 | 42.329 | 82.638 | 18.970 | 1.00 | 26.03 | A | C |
| ATOM | 2413 | OD1 | ASP | 326 | 41.511 | 83.384 | 19.547 | 1.00 | 26.48 | A | O |
| ATOM | 2414 | OD2 | ASP | 326 | 43.415 | 83.063 | 18.518 | 1.00 | 28.75 | A | O |
| ATOM | 2415 | C | ASP | 326 | 39.924 | 79.739 | 18.800 | 1.00 | 19.88 | A | C |
| ATOM | 2416 | O | ASP | 326 | 40.254 | 78.563 | 18.729 | 1.00 | 21.77 | A | O |
| ATOM | 2417 | N | ILE | 327 | 38.832 | 80.208 | 18.223 | 1.00 | 20.27 | A | N |
| ATOM | 2418 | CA | ILE | 327 | 37.980 | 79.355 | 17.419 | 1.00 | 22.22 | A | C |
| ATOM | 2419 | CB | ILE | 327 | 36.529 | 79.393 | 17.941 | 1.00 | 20.50 | A | C |
| ATOM | 2420 | CG2 | ILE | 327 | 35.600 | 78.697 | 16.985 | 1.00 | 19.07 | A | C |
| ATOM | 2421 | CG1 | ILE | 327 | 36.483 | 78.691 | 19.305 | 1.00 | 21.51 | A | C |
| ATOM | 2422 | CD1 | ILE | 327 | 35.164 | 78.766 | 20.006 | 1.00 | 20.97 | A | C |
| ATOM | 2423 | C | ILE | 327 | 38.113 | 79.908 | 16.015 | 1.00 | 23.66 | A | C |
| ATOM | 2424 | O | ILE | 327 | 37.625 | 80.984 | 15.716 | 1.00 | 26.18 | A | O |
| ATOM | 2425 | N | CYS | 328 | 38.804 | 79.162 | 15.161 | 1.00 | 26.09 | A | N |
| ATOM | 2426 | CA | CYS | 328 | 39.069 | 79.608 | 13.805 | 1.00 | 26.75 | A | C |
| ATOM | 2427 | C | CYS | 328 | 38.274 | 78.890 | 12.721 | 1.00 | 27.13 | A | C |
| ATOM | 2428 | O | CYS | 328 | 38.168 | 77.663 | 12.705 | 1.00 | 27.70 | A | O |
| ATOM | 2429 | CB | CYS | 328 | 40.564 | 79.481 | 13.547 | 1.00 | 27.02 | A | C |
| ATOM | 2430 | SG | CYS | 328 | 41.567 | 79.984 | 14.986 | 1.00 | 28.23 | A | S |
| ATOM | 2431 | N | ASP | 329 | 37.729 | 79.686 | 11.807 | 1.00 | 26.60 | A | N |
| ATOM | 2432 | CA | ASP | 329 | 36.913 | 79.198 | 10.710 | 1.00 | 26.21 | A | C |
| ATOM | 2433 | CB | ASP | 329 | 35.595 | 79.969 | 10.690 | 1.00 | 24.92 | A | C |
| ATOM | 2434 | CG | ASP | 329 | 34.684 | 79.595 | 11.842 | 1.00 | 26.75 | A | C |
| ATOM | 2435 | OD1 | ASP | 329 | 35.181 | 79.407 | 12.969 | 1.00 | 27.44 | A | O |
| ATOM | 2436 | OD2 | ASP | 329 | 33.460 | 79.493 | 11.625 | 1.00 | 28.96 | A | O |
| ATOM | 2437 | C | ASP | 329 | 37.613 | 79.349 | 9.367 | 1.00 | 28.54 | A | C |
| ATOM | 2438 | O | ASP | 329 | 38.314 | 80.334 | 9.120 | 1.00 | 29.27 | A | O |
| ATOM | 2439 | N | TYR | 330 | 37.416 | 78.371 | 8.492 | 1.00 | 29.31 | A | N |
| ATOM | 2440 | CA | TYR | 330 | 38.027 | 78.411 | 7.173 | 1.00 | 29.64 | A | C |
| ATOM | 2441 | CB | TYR | 330 | 38.011 | 77.019 | 6.542 | 1.00 | 30.55 | A | C |
| ATOM | 2442 | CG | TYR | 330 | 38.597 | 76.980 | 5.151 | 1.00 | 31.78 | A | C |
| ATOM | 2443 | CD1 | TYR | 330 | 39.919 | 77.367 | 4.919 | 1.00 | 32.26 | A | C |
| ATOM | 2444 | CE1 | TYR | 330 | 40.460 | 77.341 | 3.641 | 1.00 | 32.18 | A | C |
| ATOM | 2445 | CD2 | TYR | 330 | 37.832 | 76.561 | 4.066 | 1.00 | 32.94 | A | C |
| ATOM | 2446 | CE2 | TYR | 330 | 38.364 | 76.526 | 2.779 | 1.00 | 32.62 | A | C |
| ATOM | 2447 | CZ | TYR | 330 | 39.676 | 76.920 | 2.574 | 1.00 | 33.67 | A | C |
| ATOM | 2448 | OH | TYR | 330 | 40.193 | 76.914 | 1.299 | 1.00 | 34.33 | A | O |
| ATOM | 2449 | C | TYR | 330 | 37.314 | 79.387 | 6.243 | 1.00 | 30.14 | A | C |

FIG. 4-51

| | | | | | | | | | | |
|---|---|---|---|---|---|---|---|---|---|---|
| ATOM | 2450 | O | TYR | 330 | 36.098 | 79.313 | 6.058 | 1.00 | 28.65 | A | O |
| ATOM | 2451 | N | ASP | 331 | 38.074 | 80.308 | 5.666 | 1.00 | 31.49 | A | N |
| ATOM | 2452 | CA | ASP | 331 | 37.511 | 81.262 | 4.730 | 1.00 | 33.80 | A | C |
| ATOM | 2453 | CB | ASP | 331 | 38.191 | 82.618 | 4.862 | 1.00 | 36.63 | A | C |
| ATOM | 2454 | CG | ASP | 331 | 37.573 | 83.661 | 3.956 | 1.00 | 39.35 | A | C |
| ATOM | 2455 | OD1 | ASP | 331 | 37.570 | 83.455 | 2.724 | 1.00 | 40.70 | A | O |
| ATOM | 2456 | OD2 | ASP | 331 | 37.084 | 84.684 | 4.479 | 1.00 | 42.41 | A | O |
| ATOM | 2457 | C | ASP | 331 | 37.750 | 80.696 | 3.336 | 1.00 | 35.29 | A | C |
| ATOM | 2458 | O | ASP | 331 | 38.865 | 80.730 | 2.817 | 1.00 | 35.63 | A | O |
| ATOM | 2459 | N | GLU | 332 | 36.690 | 80.170 | 2.743 | 1.00 | 36.11 | A | N |
| ATOM | 2460 | CA | GLU | 332 | 36.755 | 79.562 | 1.426 | 1.00 | 37.77 | A | C |
| ATOM | 2461 | CB | GLU | 332 | 35.388 | 78.970 | 1.080 | 1.00 | 38.87 | A | C |
| ATOM | 2462 | CG | GLU | 332 | 35.234 | 78.510 | -0.354 | 1.00 | 43.60 | A | C |
| ATOM | 2463 | CD | GLU | 332 | 33.869 | 77.897 | -0.620 | 1.00 | 47.15 | A | C |
| ATOM | 2464 | OE1 | GLU | 332 | 33.494 | 77.771 | -1.807 | 1.00 | 48.97 | A | O |
| ATOM | 2465 | OE2 | GLU | 332 | 33.175 | 77.534 | 0.358 | 1.00 | 48.40 | A | O |
| ATOM | 2466 | C | GLU | 332 | 37.231 | 80.465 | 0.293 | 1.00 | 38.19 | A | C |
| ATOM | 2467 | O | GLU | 332 | 37.846 | 79.982 | -0.655 | 1.00 | 39.73 | A | O |
| ATOM | 2468 | N | SER | 333 | 36.968 | 81.764 | 0.375 | 1.00 | 37.67 | A | N |
| ATOM | 2469 | CA | SER | 333 | 37.388 | 82.652 | -0.704 | 1.00 | 38.09 | A | C |
| ATOM | 2470 | CB | SER | 333 | 36.445 | 83.858 | -0.814 | 1.00 | 38.48 | A | C |
| ATOM | 2471 | OG | SER | 333 | 36.669 | 84.795 | 0.223 | 1.00 | 40.60 | A | O |
| ATOM | 2472 | C | SER | 333 | 38.826 | 83.135 | -0.577 | 1.00 | 37.74 | A | C |
| ATOM | 2473 | O | SER | 333 | 39.324 | 83.838 | -1.448 | 1.00 | 38.52 | A | O |
| ATOM | 2474 | N | SER | 334 | 39.496 | 82.761 | 0.506 | 1.00 | 38.49 | A | N |
| ATOM | 2475 | CA | SER | 334 | 40.883 | 83.163 | 0.708 | 1.00 | 37.49 | A | C |
| ATOM | 2476 | CB | SER | 334 | 40.995 | 84.180 | 1.844 | 1.00 | 38.50 | A | C |
| ATOM | 2477 | OG | SER | 334 | 40.954 | 83.536 | 3.108 | 1.00 | 38.48 | A | O |
| ATOM | 2478 | C | SER | 334 | 41.722 | 81.947 | 1.058 | 1.00 | 35.98 | A | C |
| ATOM | 2479 | O | SER | 334 | 42.941 | 82.029 | 1.148 | 1.00 | 36.41 | A | O |
| ATOM | 2480 | N | GLY | 335 | 41.064 | 80.817 | 1.263 | 1.00 | 35.13 | A | N |
| ATOM | 2481 | CA | GLY | 335 | 41.797 | 79.620 | 1.620 | 1.00 | 35.71 | A | C |
| ATOM | 2482 | C | GLY | 335 | 42.579 | 79.872 | 2.894 | 1.00 | 35.19 | A | C |
| ATOM | 2483 | O | GLY | 335 | 43.574 | 79.201 | 3.172 | 1.00 | 35.61 | A | O |
| ATOM | 2484 | N | ARG | 336 | 42.128 | 80.855 | 3.666 | 1.00 | 33.99 | A | N |
| ATOM | 2485 | CA | ARG | 336 | 42.783 | 81.197 | 4.919 | 1.00 | 33.15 | A | C |
| ATOM | 2486 | CB | ARG | 336 | 43.066 | 82.696 | 4.991 | 1.00 | 36.78 | A | C |
| ATOM | 2487 | CG | ARG | 336 | 43.957 | 83.232 | 3.884 | 1.00 | 42.04 | A | C |
| ATOM | 2488 | CD | ARG | 336 | 44.807 | 84.374 | 4.416 | 1.00 | 45.76 | A | C |
| ATOM | 2489 | NE | ARG | 336 | 44.010 | 85.359 | 5.147 | 1.00 | 48.92 | A | N |
| ATOM | 2490 | CZ | ARG | 336 | 44.510 | 86.192 | 6.055 | 1.00 | 50.76 | A | C |
| ATOM | 2491 | NH1 | ARG | 336 | 45.805 | 86.159 | 6.348 | 1.00 | 52.08 | A | N |
| ATOM | 2492 | NH2 | ARG | 336 | 43.718 | 87.057 | 6.675 | 1.00 | 52.33 | A | N |
| ATOM | 2493 | C | ARG | 336 | 41.935 | 80.801 | 6.118 | 1.00 | 30.26 | A | C |
| ATOM | 2494 | O | ARG | 336 | 40.763 | 80.449 | 5.981 | 1.00 | 29.07 | A | O |
| ATOM | 2495 | N | TRP | 337 | 42.544 | 80.869 | 7.294 | 1.00 | 26.94 | A | N |
| ATOM | 2496 | CA | TRP | 337 | 41.869 | 80.531 | 8.533 | 1.00 | 24.29 | A | C |
| ATOM | 2497 | CB | TRP | 337 | 42.616 | 79.403 | 9.248 | 1.00 | 19.88 | A | C |
| ATOM | 2498 | CG | TRP | 337 | 42.460 | 78.074 | 8.561 | 1.00 | 15.10 | A | C |

| | | | | | | | | | | |
|---|---|---|---|---|---|---|---|---|---|---|
| ATOM | 2499 | CD2 | TRP | 337 | 41.481 | 77.077 | 8.861 | 1.00 | 9.80 | A | C |
| ATOM | 2500 | CE2 | TRP | 337 | 41.651 | 76.026 | 7.927 | 1.00 | 9.92 | A | C |
| ATOM | 2501 | CE3 | TRP | 337 | 40.475 | 76.970 | 9.825 | 1.00 | 7.74 | A | C |
| ATOM | 2502 | CD1 | TRP | 337 | 43.173 | 77.601 | 7.485 | 1.00 | 12.90 | A | C |
| ATOM | 2503 | NE1 | TRP | 337 | 42.688 | 76.369 | 7.099 | 1.00 | 9.82 | A | N |
| ATOM | 2504 | CZ2 | TRP | 337 | 40.849 | 74.885 | 7.935 | 1.00 | 9.71 | A | C |
| ATOM | 2505 | CZ3 | TRP | 337 | 39.675 | 75.836 | 9.832 | 1.00 | 7.79 | A | C |
| ATOM | 2506 | CH2 | TRP | 337 | 39.866 | 74.808 | 8.894 | 1.00 | 10.33 | A | C |
| ATOM | 2507 | C | TRP | 337 | 41.783 | 81.758 | 9.425 | 1.00 | 24.55 | A | C |
| ATOM | 2508 | O | TRP | 337 | 42.794 | 82.360 | 9.766 | 1.00 | 26.73 | A | O |
| ATOM | 2509 | N | ASN | 338 | 40.570 | 82.128 | 9.806 | 1.00 | 25.00 | A | N |
| ATOM | 2510 | CA | ASN | 338 | 40.381 | 83.296 | 10.648 | 1.00 | 26.17 | A | C |
| ATOM | 2511 | CB | ASN | 338 | 39.464 | 84.300 | 9.949 | 1.00 | 28.44 | A | C |
| ATOM | 2512 | CG | ASN | 338 | 40.016 | 84.761 | 8.612 | 1.00 | 30.42 | A | C |
| ATOM | 2513 | OD1 | ASN | 338 | 39.320 | 84.711 | 7.596 | 1.00 | 32.04 | A | O |
| ATOM | 2514 | ND2 | ASN | 338 | 41.271 | 85.217 | 8.606 | 1.00 | 28.33 | A | N |
| ATOM | 2515 | C | ASN | 338 | 39.810 | 82.958 | 12.012 | 1.00 | 25.29 | A | C |
| ATOM | 2516 | O | ASN | 338 | 38.957 | 82.084 | 12.148 | 1.00 | 25.29 | A | O |
| ATOM | 2517 | N | CYS | 339 | 40.293 | 83.668 | 13.023 | 1.00 | 25.00 | A | N |
| ATOM | 2518 | CA | CYS | 339 | 39.833 | 83.482 | 14.389 | 1.00 | 24.73 | A | C |
| ATOM | 2519 | C | CYS | 339 | 39.289 | 84.829 | 14.888 | 1.00 | 22.42 | A | C |
| ATOM | 2520 | O | CYS | 339 | 40.051 | 85.717 | 15.249 | 1.00 | 21.56 | A | O |
| ATOM | 2521 | CB | CYS | 339 | 40.992 | 83.014 | 15.285 | 1.00 | 25.93 | A | C |
| ATOM | 2522 | SG | CYS | 339 | 42.199 | 81.865 | 14.526 | 1.00 | 29.61 | A | S |
| ATOM | 2523 | N | LEU | 340 | 37.968 | 84.978 | 14.889 | 1.00 | 22.38 | A | N |
| ATOM | 2524 | CA | LEU | 340 | 37.333 | 86.212 | 15.347 | 1.00 | 20.83 | A | C |
| ATOM | 2525 | CB | LEU | 340 | 35.839 | 86.185 | 15.069 | 1.00 | 19.89 | A | C |
| ATOM | 2526 | CG | LEU | 340 | 35.364 | 86.201 | 13.626 | 1.00 | 19.14 | A | C |
| ATOM | 2527 | CD1 | LEU | 340 | 33.877 | 85.883 | 13.593 | 1.00 | 19.65 | A | C |
| ATOM | 2528 | CD2 | LEU | 340 | 35.647 | 87.551 | 13.012 | 1.00 | 19.21 | A | C |
| ATOM | 2529 | C | LEU | 340 | 37.521 | 86.406 | 16.835 | 1.00 | 20.16 | A | C |
| ATOM | 2530 | O | LEU | 340 | 37.337 | 85.478 | 17.615 | 1.00 | 20.80 | A | O |
| ATOM | 2531 | N | VAL | 341 | 37.866 | 87.625 | 17.225 | 1.00 | 20.46 | A | N |
| ATOM | 2532 | CA | VAL | 341 | 38.066 | 87.949 | 18.627 | 1.00 | 20.11 | A | C |
| ATOM | 2533 | CB | VAL | 341 | 38.536 | 89.399 | 18.786 | 1.00 | 21.45 | A | C |
| ATOM | 2534 | CG1 | VAL | 341 | 38.972 | 89.647 | 20.221 | 1.00 | 22.38 | A | C |
| ATOM | 2535 | CG2 | VAL | 341 | 39.688 | 89.672 | 17.819 | 1.00 | 24.28 | A | C |
| ATOM | 2536 | C | VAL | 341 | 36.770 | 87.749 | 19.403 | 1.00 | 18.51 | A | C |
| ATOM | 2537 | O | VAL | 341 | 36.785 | 87.423 | 20.585 | 1.00 | 17.77 | A | O |
| ATOM | 2538 | N | ALA | 342 | 35.644 | 87.941 | 18.731 | 1.00 | 19.68 | A | N |
| ATOM | 2539 | CA | ALA | 342 | 34.345 | 87.756 | 19.370 | 1.00 | 19.64 | A | C |
| ATOM | 2540 | CB | ALA | 342 | 33.228 | 88.125 | 18.407 | 1.00 | 18.89 | A | C |
| ATOM | 2541 | C | ALA | 342 | 34.177 | 86.302 | 19.829 | 1.00 | 19.19 | A | C |
| ATOM | 2542 | O | ALA | 342 | 33.245 | 85.987 | 20.580 | 1.00 | 18.12 | A | O |
| ATOM | 2543 | N | ARG | 343 | 35.078 | 85.422 | 19.384 | 1.00 | 16.06 | A | N |
| ATOM | 2544 | CA | ARG | 343 | 35.008 | 84.017 | 19.766 | 1.00 | 16.37 | A | C |
| ATOM | 2545 | CB | ARG | 343 | 34.962 | 83.138 | 18.521 | 1.00 | 18.14 | A | C |
| ATOM | 2546 | CG | ARG | 343 | 33.726 | 83.390 | 17.687 | 1.00 | 20.31 | A | C |
| ATOM | 2547 | CD | ARG | 343 | 33.803 | 82.695 | 16.357 | 1.00 | 21.82 | A | C |

FIG. 4-53 (Continued)

```
ATOM   2548  NE   ARG  343      32.615  82.969  15.561  1.00 23.94       A  N
ATOM   2549  CZ   ARG  343      32.373  82.415  14.383  1.00 26.14       A  C
ATOM   2550  NH1  ARG  343      33.242  81.559  13.864  1.00 28.42       A  N
ATOM   2551  NH2  ARG  343      31.256  82.703  13.734  1.00 30.23       A  N
ATOM   2552  C    ARG  343      36.164  83.603  20.650  1.00 17.09       A  C
ATOM   2553  O    ARG  343      36.275  82.452  21.057  1.00 16.76       A  O
ATOM   2554  N    GLN  344      37.030  84.553  20.955  1.00 18.05       A  N
ATOM   2555  CA   GLN  344      38.175  84.267  21.791  1.00 18.90       A  C
ATOM   2556  CB   GLN  344      39.191  85.385  21.645  1.00 18.03       A  C
ATOM   2557  CG   GLN  344      40.585  85.012  22.038  1.00 17.99       A  C
ATOM   2558  CD   GLN  344      41.571  86.088  21.657  1.00 18.02       A  C
ATOM   2559  OE1  GLN  344      41.711  87.089  22.353  1.00 17.71       A  O
ATOM   2560  NE2  GLN  344      42.246  85.897  20.527  1.00 17.42       A  N
ATOM   2561  C    GLN  344      37.708  84.170  23.234  1.00 19.61       A  C
ATOM   2562  O    GLN  344      37.069  85.087  23.730  1.00 21.89       A  O
ATOM   2563  N    HIS  345      38.013  83.057  23.897  1.00 18.47       A  N
ATOM   2564  CA   HIS  345      37.624  82.868  25.287  1.00 17.92       A  C
ATOM   2565  CB   HIS  345      36.786  81.600  25.453  1.00 16.07       A  C
ATOM   2566  CG   HIS  345      35.478  81.641  24.726  1.00 15.01       A  C
ATOM   2567  CD2  HIS  345      34.223  81.895  25.164  1.00 14.43       A  C
ATOM   2568  ND1  HIS  345      35.371  81.420  23.369  1.00 15.56       A  N
ATOM   2569  CE1  HIS  345      34.108  81.535  23.002  1.00 12.57       A  C
ATOM   2570  NE2  HIS  345      33.390  81.823  24.073  1.00 14.20       A  N
ATOM   2571  C    HIS  345      38.854  82.789  26.172  1.00 19.64       A  C
ATOM   2572  O    HIS  345      39.839  82.129  25.825  1.00 22.18       A  O
ATOM   2573  N    ILE  346      38.790  83.460  27.319  1.00 20.11       A  N
ATOM   2574  CA   ILE  346      39.899  83.501  28.264  1.00 21.08       A  C
ATOM   2575  CB   ILE  346      40.135  84.928  28.760  1.00 20.44       A  C
ATOM   2576  CG2  ILE  346      41.357  84.972  29.667  1.00 20.95       A  C
ATOM   2577  CG1  ILE  346      40.338  85.860  27.572  1.00 19.87       A  C
ATOM   2578  CD1  ILE  346      40.466  87.298  27.978  1.00 22.20       A  C
ATOM   2579  C    ILE  346      39.657  82.624  29.482  1.00 23.76       A  C
ATOM   2580  O    ILE  346      38.535  82.537  29.975  1.00 24.67       A  O
ATOM   2581  N    GLU  347      40.714  81.976  29.967  1.00 25.01       A  N
ATOM   2582  CA   GLU  347      40.601  81.123  31.141  1.00 28.30       A  C
ATOM   2583  CB   GLU  347      40.459  79.656  30.733  1.00 26.51       A  C
ATOM   2584  CG   GLU  347      40.089  78.740  31.891  1.00 27.38       A  C
ATOM   2585  CD   GLU  347      40.169  77.268  31.527  1.00 29.51       A  C
ATOM   2586  OE1  GLU  347      39.877  76.936  30.359  1.00 29.48       A  O
ATOM   2587  OE2  GLU  347      40.511  76.439  32.405  1.00 29.57       A  O
ATOM   2588  C    GLU  347      41.836  81.288  32.021  1.00 30.87       A  C
ATOM   2589  O    GLU  347      42.865  80.661  31.777  1.00 33.35       A  O
ATOM   2590  N    MET  348      41.741  82.131  33.044  1.00 32.50       A  N
ATOM   2591  CA   MET  348      42.877  82.347  33.926  1.00 34.46       A  C
ATOM   2592  CB   MET  348      43.215  83.843  34.002  1.00 37.48       A  C
ATOM   2593  CG   MET  348      42.168  84.723  34.661  1.00 41.62       A  C
ATOM   2594  SD   MET  348      42.028  86.340  33.825  1.00 48.03       A  S
ATOM   2595  CE   MET  348      43.541  87.158  34.341  1.00 46.60       A  C
ATOM   2596  C    MET  348      42.628  81.784  35.315  1.00 33.55       A  C
```

FIG. 4-54 (Continued)

| | | | | | | | | | | |
|---|---|---|---|---|---|---|---|---|---|---|
| ATOM | 2597 | O | MET | 348 | 41.656 | 81.070 | 35.541 | 1.00 | 34.35 | A | O |
| ATOM | 2598 | N | SER | 349 | 43.534 | 82.085 | 36.235 | 1.00 | 32.30 | A | N |
| ATOM | 2599 | CA | SER | 349 | 43.428 | 81.623 | 37.612 | 1.00 | 31.26 | A | C |
| ATOM | 2600 | CB | SER | 349 | 43.961 | 80.197 | 37.744 | 1.00 | 31.22 | A | C |
| ATOM | 2601 | OG | SER | 349 | 43.912 | 79.760 | 39.090 | 1.00 | 32.92 | A | O |
| ATOM | 2602 | C | SER | 349 | 44.244 | 82.573 | 38.474 | 1.00 | 31.16 | A | C |
| ATOM | 2603 | O | SER | 349 | 45.355 | 82.950 | 38.113 | 1.00 | 31.25 | A | O |
| ATOM | 2604 | N | THR | 350 | 43.682 | 82.962 | 39.611 | 1.00 | 30.83 | A | N |
| ATOM | 2605 | CA | THR | 350 | 44.340 | 83.896 | 40.516 | 1.00 | 28.43 | A | C |
| ATOM | 2606 | CB | THR | 350 | 43.325 | 84.938 | 41.027 | 1.00 | 28.93 | A | C |
| ATOM | 2607 | OG1 | THR | 350 | 42.251 | 84.268 | 41.703 | 1.00 | 27.68 | A | O |
| ATOM | 2608 | CG2 | THR | 350 | 42.751 | 85.733 | 39.864 | 1.00 | 27.87 | A | C |
| ATOM | 2609 | C | THR | 350 | 44.971 | 83.198 | 41.714 | 1.00 | 27.14 | A | C |
| ATOM | 2610 | O | THR | 350 | 45.781 | 83.786 | 42.431 | 1.00 | 27.62 | A | O |
| ATOM | 2611 | N | THR | 351 | 44.610 | 81.936 | 41.913 | 1.00 | 25.72 | A | N |
| ATOM | 2612 | CA | THR | 351 | 45.109 | 81.161 | 43.035 | 1.00 | 24.77 | A | C |
| ATOM | 2613 | CB | THR | 351 | 43.945 | 80.536 | 43.786 | 1.00 | 25.52 | A | C |
| ATOM | 2614 | OG1 | THR | 351 | 43.166 | 79.746 | 42.877 | 1.00 | 24.95 | A | O |
| ATOM | 2615 | CG2 | THR | 351 | 43.069 | 81.617 | 44.385 | 1.00 | 24.61 | A | C |
| ATOM | 2616 | C | THR | 351 | 46.081 | 80.047 | 42.659 | 1.00 | 25.48 | A | C |
| ATOM | 2617 | O | THR | 351 | 46.648 | 79.392 | 43.535 | 1.00 | 25.57 | A | O |
| ATOM | 2618 | N | GLY | 352 | 46.261 | 79.825 | 41.361 | 1.00 | 25.19 | A | N |
| ATOM | 2619 | CA | GLY | 352 | 47.170 | 78.786 | 40.909 | 1.00 | 24.62 | A | C |
| ATOM | 2620 | C | GLY | 352 | 47.371 | 78.797 | 39.403 | 1.00 | 24.61 | A | C |
| ATOM | 2621 | O | GLY | 352 | 47.417 | 79.853 | 38.774 | 1.00 | 25.15 | A | O |
| ATOM | 2622 | N | TRP | 353 | 47.499 | 77.612 | 38.825 | 1.00 | 23.36 | A | N |
| ATOM | 2623 | CA | TRP | 353 | 47.684 | 77.470 | 37.390 | 1.00 | 21.38 | A | C |
| ATOM | 2624 | CB | TRP | 353 | 48.631 | 76.291 | 37.116 | 1.00 | 17.49 | A | C |
| ATOM | 2625 | CG | TRP | 353 | 48.272 | 75.023 | 37.849 | 1.00 | 16.34 | A | C |
| ATOM | 2626 | CD2 | TRP | 353 | 48.587 | 74.693 | 39.209 | 1.00 | 14.04 | A | C |
| ATOM | 2627 | CE2 | TRP | 353 | 48.053 | 73.409 | 39.462 | 1.00 | 14.33 | A | C |
| ATOM | 2628 | CE3 | TRP | 353 | 49.270 | 75.356 | 40.238 | 1.00 | 14.55 | A | C |
| ATOM | 2629 | CD1 | TRP | 353 | 47.578 | 73.957 | 37.351 | 1.00 | 14.89 | A | C |
| ATOM | 2630 | NE1 | TRP | 353 | 47.445 | 72.985 | 38.311 | 1.00 | 12.84 | A | N |
| ATOM | 2631 | CZ2 | TRP | 353 | 48.180 | 72.768 | 40.709 | 1.00 | 14.93 | A | C |
| ATOM | 2632 | CZ3 | TRP | 353 | 49.398 | 74.719 | 41.480 | 1.00 | 15.27 | A | C |
| ATOM | 2633 | CH2 | TRP | 353 | 48.853 | 73.436 | 41.700 | 1.00 | 15.07 | A | C |
| ATOM | 2634 | C | TRP | 353 | 46.303 | 77.236 | 36.782 | 1.00 | 22.43 | A | C |
| ATOM | 2635 | O | TRP | 353 | 45.307 | 77.292 | 37.495 | 1.00 | 22.69 | A | O |
| ATOM | 2636 | N | VAL | 354 | 46.231 | 76.990 | 35.479 | 1.00 | 22.83 | A | N |
| ATOM | 2637 | CA | VAL | 354 | 44.944 | 76.749 | 34.836 | 1.00 | 24.15 | A | C |
| ATOM | 2638 | CB | VAL | 354 | 44.818 | 77.513 | 33.498 | 1.00 | 25.09 | A | C |
| ATOM | 2639 | CG1 | VAL | 354 | 43.610 | 77.006 | 32.718 | 1.00 | 24.29 | A | C |
| ATOM | 2640 | CG2 | VAL | 354 | 44.673 | 79.007 | 33.762 | 1.00 | 24.71 | A | C |
| ATOM | 2641 | C | VAL | 354 | 44.799 | 75.264 | 34.569 | 1.00 | 24.96 | A | C |
| ATOM | 2642 | O | VAL | 354 | 45.751 | 74.628 | 34.127 | 1.00 | 26.10 | A | O |
| ATOM | 2643 | N | GLY | 355 | 43.609 | 74.722 | 34.841 | 1.00 | 24.28 | A | N |
| ATOM | 2644 | CA | GLY | 355 | 43.354 | 73.303 | 34.640 | 1.00 | 22.67 | A | C |
| ATOM | 2645 | C | GLY | 355 | 44.040 | 72.457 | 35.696 | 1.00 | 22.77 | A | C |

| | | | | | | | | | | | |
|---|---|---|---|---|---|---|---|---|---|---|---|
| ATOM | 2646 | O | GLY | 355 | 44.743 | 72.989 | 36.548 | 1.00 | 22.56 | A | O |
| ATOM | 2647 | N | ARG | 356 | 43.843 | 71.145 | 35.668 | 1.00 | 23.29 | A | N |
| ATOM | 2648 | CA | ARG | 356 | 44.505 | 70.299 | 36.654 | 1.00 | 24.86 | A | C |
| ATOM | 2649 | CB | ARG | 356 | 43.927 | 68.886 | 36.645 | 1.00 | 24.91 | A | C |
| ATOM | 2650 | CG | ARG | 356 | 42.495 | 68.808 | 37.122 | 1.00 | 27.84 | A | C |
| ATOM | 2651 | CD | ARG | 356 | 41.973 | 67.391 | 37.036 | 1.00 | 31.58 | A | C |
| ATOM | 2652 | NE | ARG | 356 | 40.518 | 67.340 | 37.149 | 1.00 | 35.53 | A | N |
| ATOM | 2653 | CZ | ARG | 356 | 39.849 | 67.607 | 38.261 | 1.00 | 37.59 | A | C |
| ATOM | 2654 | NH1 | ARG | 356 | 40.513 | 67.939 | 39.362 | 1.00 | 40.39 | A | N |
| ATOM | 2655 | NH2 | ARG | 356 | 38.520 | 67.547 | 38.272 | 1.00 | 37.65 | A | N |
| ATOM | 2656 | C | ARG | 356 | 45.989 | 70.255 | 36.314 | 1.00 | 25.60 | A | C |
| ATOM | 2657 | O | ARG | 356 | 46.844 | 70.508 | 37.163 | 1.00 | 28.06 | A | O |
| ATOM | 2658 | N | PHE | 357 | 46.285 | 69.940 | 35.060 | 1.00 | 23.61 | A | N |
| ATOM | 2659 | CA | PHE | 357 | 47.659 | 69.876 | 34.587 | 1.00 | 21.95 | A | C |
| ATOM | 2660 | CB | PHE | 357 | 48.029 | 68.442 | 34.205 | 1.00 | 15.99 | A | C |
| ATOM | 2661 | CG | PHE | 357 | 48.173 | 67.524 | 35.380 | 1.00 | 12.89 | A | C |
| ATOM | 2662 | CD1 | PHE | 357 | 49.361 | 67.491 | 36.115 | 1.00 | 11.73 | A | C |
| ATOM | 2663 | CD2 | PHE | 357 | 47.126 | 66.693 | 35.763 | 1.00 | 10.46 | A | C |
| ATOM | 2664 | CE1 | PHE | 357 | 49.507 | 66.638 | 37.216 | 1.00 | 7.55 | A | C |
| ATOM | 2665 | CE2 | PHE | 357 | 47.263 | 65.838 | 36.863 | 1.00 | 11.70 | A | C |
| ATOM | 2666 | CZ | PHE | 357 | 48.459 | 65.811 | 37.591 | 1.00 | 6.24 | A | C |
| ATOM | 2667 | C | PHE | 357 | 47.775 | 70.786 | 33.377 | 1.00 | 23.17 | A | C |
| ATOM | 2668 | O | PHE | 357 | 48.877 | 71.196 | 33.005 | 1.00 | 26.25 | A | O |
| ATOM | 2669 | N | ARG | 358 | 46.626 | 71.100 | 32.782 | 1.00 | 20.84 | A | N |
| ATOM | 2670 | CA | ARG | 358 | 46.541 | 71.972 | 31.615 | 1.00 | 20.05 | A | C |
| ATOM | 2671 | CB | ARG | 358 | 47.156 | 71.297 | 30.396 | 1.00 | 19.30 | A | C |
| ATOM | 2672 | CG | ARG | 358 | 46.496 | 69.991 | 30.011 | 1.00 | 21.15 | A | C |
| ATOM | 2673 | CD | ARG | 358 | 46.866 | 69.613 | 28.598 | 1.00 | 24.58 | A | C |
| ATOM | 2674 | NE | ARG | 358 | 46.293 | 68.333 | 28.205 | 1.00 | 31.68 | A | N |
| ATOM | 2675 | CZ | ARG | 358 | 46.163 | 67.924 | 26.943 | 1.00 | 34.22 | A | C |
| ATOM | 2676 | NH1 | ARG | 358 | 46.564 | 68.701 | 25.939 | 1.00 | 31.56 | A | N |
| ATOM | 2677 | NH2 | ARG | 358 | 45.640 | 66.727 | 26.687 | 1.00 | 33.62 | A | N |
| ATOM | 2678 | C | ARG | 358 | 45.081 | 72.315 | 31.313 | 1.00 | 20.40 | A | C |
| ATOM | 2679 | O | ARG | 358 | 44.168 | 71.608 | 31.734 | 1.00 | 20.47 | A | O |
| ATOM | 2680 | N | PRO | 359 | 44.840 | 73.404 | 30.570 | 1.00 | 21.33 | A | N |
| ATOM | 2681 | CD | PRO | 359 | 45.785 | 74.338 | 29.940 | 1.00 | 20.09 | A | C |
| ATOM | 2682 | CA | PRO | 359 | 43.455 | 73.772 | 30.254 | 1.00 | 21.44 | A | C |
| ATOM | 2683 | CB | PRO | 359 | 43.624 | 74.911 | 29.264 | 1.00 | 20.76 | A | C |
| ATOM | 2684 | CG | PRO | 359 | 44.907 | 75.539 | 29.713 | 1.00 | 21.86 | A | C |
| ATOM | 2685 | C | PRO | 359 | 42.741 | 72.574 | 29.652 | 1.00 | 21.94 | A | C |
| ATOM | 2686 | O | PRO | 359 | 43.314 | 71.866 | 28.827 | 1.00 | 21.94 | A | O |
| ATOM | 2687 | N | SER | 360 | 41.499 | 72.350 | 30.070 | 1.00 | 22.48 | A | N |
| ATOM | 2688 | CA | SER | 360 | 40.723 | 71.208 | 29.596 | 1.00 | 24.26 | A | C |
| ATOM | 2689 | CB | SER | 360 | 39.501 | 70.986 | 30.497 | 1.00 | 25.29 | A | C |
| ATOM | 2690 | OG | SER | 360 | 38.505 | 71.976 | 30.283 | 1.00 | 27.66 | A | O |
| ATOM | 2691 | C | SER | 360 | 40.262 | 71.280 | 28.140 | 1.00 | 25.67 | A | C |
| ATOM | 2692 | O | SER | 360 | 40.117 | 72.359 | 27.555 | 1.00 | 25.66 | A | O |
| ATOM | 2693 | N | GLU | 361 | 40.024 | 70.104 | 27.573 | 1.00 | 25.65 | A | N |
| ATOM | 2694 | CA | GLU | 361 | 39.581 | 69.972 | 26.199 | 1.00 | 27.20 | A | C |

| ATOM | 2695 | CB | GLU | 361 | 39.803 | 68.540 | 25.713 | 1.00 | 30.37 | A | C |
|---|---|---|---|---|---|---|---|---|---|---|---|
| ATOM | 2696 | CG | GLU | 361 | 39.356 | 67.444 | 26.683 | 1.00 | 36.42 | A | C |
| ATOM | 2697 | CD | GLU | 361 | 40.340 | 67.226 | 27.839 | 1.00 | 42.80 | A | C |
| ATOM | 2698 | OE1 | GLU | 361 | 40.317 | 68.002 | 28.822 | 1.00 | 43.77 | A | O |
| ATOM | 2699 | OE2 | GLU | 361 | 41.152 | 66.274 | 27.757 | 1.00 | 46.60 | A | O |
| ATOM | 2700 | C | GLU | 361 | 38.112 | 70.324 | 26.052 | 1.00 | 25.88 | A | C |
| ATOM | 2701 | O | GLU | 361 | 37.295 | 69.955 | 26.888 | 1.00 | 27.12 | A | O |
| ATOM | 2702 | N | PRO | 362 | 37.760 | 71.061 | 24.989 | 1.00 | 23.97 | A | N |
| ATOM | 2703 | CD | PRO | 362 | 38.650 | 71.837 | 24.106 | 1.00 | 23.33 | A | C |
| ATOM | 2704 | CA | PRO | 362 | 36.365 | 71.436 | 24.767 | 1.00 | 22.45 | A | C |
| ATOM | 2705 | CB | PRO | 362 | 36.485 | 72.714 | 23.945 | 1.00 | 23.21 | A | C |
| ATOM | 2706 | CG | PRO | 362 | 37.679 | 72.437 | 23.100 | 1.00 | 21.08 | A | C |
| ATOM | 2707 | C | PRO | 362 | 35.621 | 70.338 | 24.013 | 1.00 | 21.91 | A | C |
| ATOM | 2708 | O | PRO | 362 | 36.216 | 69.582 | 23.249 | 1.00 | 22.96 | A | O |
| ATOM | 2709 | N | HIS | 363 | 34.318 | 70.259 | 24.245 | 1.00 | 21.59 | A | N |
| ATOM | 2710 | CA | HIS | 363 | 33.459 | 69.280 | 23.596 | 1.00 | 19.88 | A | C |
| ATOM | 2711 | CB | HIS | 363 | 32.868 | 68.353 | 24.649 | 1.00 | 18.03 | A | C |
| ATOM | 2712 | CG | HIS | 363 | 33.898 | 67.568 | 25.398 | 1.00 | 16.56 | A | C |
| ATOM | 2713 | CD2 | HIS | 363 | 34.638 | 67.880 | 26.489 | 1.00 | 16.19 | A | C |
| ATOM | 2714 | ND1 | HIS | 363 | 34.292 | 66.303 | 25.019 | 1.00 | 14.56 | A | N |
| ATOM | 2715 | CE1 | HIS | 363 | 35.227 | 65.869 | 25.843 | 1.00 | 14.60 | A | C |
| ATOM | 2716 | NE2 | HIS | 363 | 35.457 | 66.808 | 26.744 | 1.00 | 16.65 | A | N |
| ATOM | 2717 | C | HIS | 363 | 32.364 | 70.081 | 22.903 | 1.00 | 20.84 | A | C |
| ATOM | 2718 | O | HIS | 363 | 31.535 | 70.709 | 23.564 | 1.00 | 20.84 | A | O |
| ATOM | 2719 | N | PHE | 364 | 32.383 | 70.075 | 21.573 | 1.00 | 19.87 | A | N |
| ATOM | 2720 | CA | PHE | 364 | 31.416 | 70.832 | 20.786 | 1.00 | 18.84 | A | C |
| ATOM | 2721 | CB | PHE | 364 | 32.042 | 71.310 | 19.470 | 1.00 | 18.67 | A | C |
| ATOM | 2722 | CG | PHE | 364 | 33.073 | 72.390 | 19.629 | 1.00 | 18.84 | A | C |
| ATOM | 2723 | CD1 | PHE | 364 | 34.341 | 72.096 | 20.117 | 1.00 | 17.51 | A | C |
| ATOM | 2724 | CD2 | PHE | 364 | 32.776 | 73.708 | 19.274 | 1.00 | 16.76 | A | C |
| ATOM | 2725 | CE1 | PHE | 364 | 35.298 | 73.095 | 20.246 | 1.00 | 16.92 | A | C |
| ATOM | 2726 | CE2 | PHE | 364 | 33.727 | 74.711 | 19.401 | 1.00 | 16.24 | A | C |
| ATOM | 2727 | CZ | PHE | 364 | 34.988 | 74.404 | 19.886 | 1.00 | 16.59 | A | C |
| ATOM | 2728 | C | PHE | 364 | 30.172 | 70.046 | 20.432 | 1.00 | 19.35 | A | C |
| ATOM | 2729 | O | PHE | 364 | 30.226 | 68.831 | 20.262 | 1.00 | 20.71 | A | O |
| ATOM | 2730 | N | THR | 365 | 29.050 | 70.750 | 20.313 | 1.00 | 18.81 | A | N |
| ATOM | 2731 | CA | THR | 365 | 27.805 | 70.113 | 19.912 | 1.00 | 18.11 | A | C |
| ATOM | 2732 | CB | THR | 365 | 26.600 | 71.017 | 20.161 | 1.00 | 17.38 | A | C |
| ATOM | 2733 | OG1 | THR | 365 | 26.521 | 71.991 | 19.119 | 1.00 | 22.40 | A | O |
| ATOM | 2734 | CG2 | THR | 365 | 26.741 | 71.734 | 21.487 | 1.00 | 13.72 | A | C |
| ATOM | 2735 | C | THR | 365 | 28.001 | 69.954 | 18.409 | 1.00 | 17.58 | A | C |
| ATOM | 2736 | O | THR | 365 | 28.823 | 70.650 | 17.824 | 1.00 | 16.70 | A | O |
| ATOM | 2737 | N | LEU | 366 | 27.250 | 69.058 | 17.784 | 1.00 | 19.74 | A | N |
| ATOM | 2738 | CA | LEU | 366 | 27.388 | 68.799 | 16.350 | 1.00 | 19.89 | A | C |
| ATOM | 2739 | CB | LEU | 366 | 26.237 | 67.923 | 15.860 | 1.00 | 19.49 | A | C |
| ATOM | 2740 | CG | LEU | 366 | 26.338 | 67.381 | 14.431 | 1.00 | 19.63 | A | C |
| ATOM | 2741 | CD1 | LEU | 366 | 27.606 | 66.542 | 14.282 | 1.00 | 20.45 | A | C |
| ATOM | 2742 | CD2 | LEU | 366 | 25.112 | 66.539 | 14.128 | 1.00 | 17.80 | A | C |
| ATOM | 2743 | C | LEU | 366 | 27.503 | 70.017 | 15.438 | 1.00 | 21.11 | A | C |

FIG. 4-57 (Continued)

| | | | | | | | | | | |
|---|---|---|---|---|---|---|---|---|---|---|
| ATOM | 2744 | O | LEU | 366 | 28.269 | 69.989 | 14.476 | 1.00 | 24.21 | A | O |
| ATOM | 2745 | N | ASP | 367 | 26.764 | 71.084 | 15.722 | 1.00 | 21.26 | A | N |
| ATOM | 2746 | CA | ASP | 367 | 26.830 | 72.261 | 14.867 | 1.00 | 22.95 | A | C |
| ATOM | 2747 | CB | ASP | 367 | 25.567 | 73.114 | 15.005 | 1.00 | 26.09 | A | C |
| ATOM | 2748 | CG | ASP | 367 | 25.458 | 73.796 | 16.355 | 1.00 | 29.82 | A | C |
| ATOM | 2749 | OD1 | ASP | 367 | 26.469 | 73.849 | 17.094 | 1.00 | 28.76 | A | O |
| ATOM | 2750 | OD2 | ASP | 367 | 24.352 | 74.296 | 16.669 | 1.00 | 31.88 | A | O |
| ATOM | 2751 | C | ASP | 367 | 28.047 | 73.130 | 15.139 | 1.00 | 22.76 | A | C |
| ATOM | 2752 | O | ASP | 367 | 28.274 | 74.122 | 14.448 | 1.00 | 25.46 | A | O |
| ATOM | 2753 | N | GLY | 368 | 28.818 | 72.772 | 16.155 | 1.00 | 21.02 | A | N |
| ATOM | 2754 | CA | GLY | 368 | 30.001 | 73.541 | 16.480 | 1.00 | 18.54 | A | C |
| ATOM | 2755 | C | GLY | 368 | 29.740 | 74.946 | 16.987 | 1.00 | 17.42 | A | C |
| ATOM | 2756 | O | GLY | 368 | 30.678 | 75.690 | 17.237 | 1.00 | 17.82 | A | O |
| ATOM | 2757 | N | ASN | 369 | 28.482 | 75.324 | 17.164 | 1.00 | 17.57 | A | N |
| ATOM | 2758 | CA | ASN | 369 | 28.196 | 76.669 | 17.647 | 1.00 | 17.82 | A | C |
| ATOM | 2759 | CB | ASN | 369 | 26.838 | 77.129 | 17.144 | 1.00 | 18.92 | A | C |
| ATOM | 2760 | CG | ASN | 369 | 26.797 | 77.234 | 15.649 | 1.00 | 22.41 | A | C |
| ATOM | 2761 | OD1 | ASN | 369 | 27.657 | 77.871 | 15.038 | 1.00 | 23.56 | A | O |
| ATOM | 2762 | ND2 | ASN | 369 | 25.798 | 76.606 | 15.038 | 1.00 | 26.52 | A | N |
| ATOM | 2763 | C | ASN | 369 | 28.270 | 76.838 | 19.158 | 1.00 | 16.27 | A | C |
| ATOM | 2764 | O | ASN | 369 | 28.185 | 77.949 | 19.665 | 1.00 | 16.44 | A | O |
| ATOM | 2765 | N | SER | 370 | 28.432 | 75.742 | 19.882 | 1.00 | 15.67 | A | N |
| ATOM | 2766 | CA | SER | 370 | 28.533 | 75.824 | 21.330 | 1.00 | 16.34 | A | C |
| ATOM | 2767 | CB | SER | 370 | 27.145 | 75.766 | 21.971 | 1.00 | 14.45 | A | C |
| ATOM | 2768 | OG | SER | 370 | 26.523 | 74.518 | 21.739 | 1.00 | 14.37 | A | O |
| ATOM | 2769 | C | SER | 370 | 29.381 | 74.660 | 21.797 | 1.00 | 16.66 | A | C |
| ATOM | 2770 | O | SER | 370 | 29.565 | 73.701 | 21.058 | 1.00 | 18.15 | A | O |
| ATOM | 2771 | N | PHE | 371 | 29.910 | 74.742 | 23.014 | 1.00 | 17.09 | A | N |
| ATOM | 2772 | CA | PHE | 371 | 30.735 | 73.660 | 23.532 | 1.00 | 16.28 | A | C |
| ATOM | 2773 | CB | PHE | 371 | 32.194 | 73.808 | 23.062 | 1.00 | 14.83 | A | C |
| ATOM | 2774 | CG | PHE | 371 | 32.881 | 75.062 | 23.546 | 1.00 | 11.31 | A | C |
| ATOM | 2775 | CD1 | PHE | 371 | 32.799 | 76.243 | 22.818 | 1.00 | 11.07 | A | C |
| ATOM | 2776 | CD2 | PHE | 371 | 33.635 | 75.050 | 24.726 | 1.00 | 11.89 | A | C |
| ATOM | 2777 | CE1 | PHE | 371 | 33.465 | 77.409 | 23.256 | 1.00 | 12.04 | A | C |
| ATOM | 2778 | CE2 | PHE | 371 | 34.302 | 76.205 | 25.178 | 1.00 | 9.92 | A | C |
| ATOM | 2779 | CZ | PHE | 371 | 34.219 | 77.383 | 24.444 | 1.00 | 9.76 | A | C |
| ATOM | 2780 | C | PHE | 371 | 30.703 | 73.545 | 25.048 | 1.00 | 16.26 | A | C |
| ATOM | 2781 | O | PHE | 371 | 30.362 | 74.495 | 25.752 | 1.00 | 15.15 | A | O |
| ATOM | 2782 | N | TYR | 372 | 31.053 | 72.360 | 25.536 | 1.00 | 16.67 | A | N |
| ATOM | 2783 | CA | TYR | 372 | 31.091 | 72.089 | 26.962 | 1.00 | 16.84 | A | C |
| ATOM | 2784 | CB | TYR | 372 | 30.349 | 70.801 | 27.271 | 1.00 | 16.79 | A | C |
| ATOM | 2785 | CG | TYR | 372 | 28.892 | 70.879 | 26.914 | 1.00 | 18.47 | A | C |
| ATOM | 2786 | CD1 | TYR | 372 | 28.470 | 70.744 | 25.589 | 1.00 | 16.97 | A | C |
| ATOM | 2787 | CE1 | TYR | 372 | 27.129 | 70.850 | 25.255 | 1.00 | 19.91 | A | C |
| ATOM | 2788 | CD2 | TYR | 372 | 27.931 | 71.124 | 27.901 | 1.00 | 18.26 | A | C |
| ATOM | 2789 | CE2 | TYR | 372 | 26.592 | 71.235 | 27.581 | 1.00 | 19.23 | A | C |
| ATOM | 2790 | CZ | TYR | 372 | 26.193 | 71.097 | 26.258 | 1.00 | 21.51 | A | C |
| ATOM | 2791 | OH | TYR | 372 | 24.860 | 71.210 | 25.944 | 1.00 | 23.32 | A | O |
| ATOM | 2792 | C | TYR | 372 | 32.547 | 71.977 | 27.367 | 1.00 | 18.35 | A | C |

| ATOM | 2793 | O   | TYR | 372 | 33.388 | 71.557 | 26.571 | 1.00 | 20.30 | A | O |
|------|------|-----|-----|-----|--------|--------|--------|------|-------|---|---|
| ATOM | 2794 | N   | LYS | 373 | 32.845 | 72.325 | 28.611 | 1.00 | 18.89 | A | N |
| ATOM | 2795 | CA  | LYS | 373 | 34.224 | 72.318 | 29.071 | 1.00 | 19.69 | A | C |
| ATOM | 2796 | CB  | LYS | 373 | 34.907 | 73.541 | 28.459 | 1.00 | 19.69 | A | C |
| ATOM | 2797 | CG  | LYS | 373 | 36.302 | 73.863 | 28.889 | 1.00 | 20.48 | A | C |
| ATOM | 2798 | CD  | LYS | 373 | 36.658 | 75.193 | 28.240 | 1.00 | 23.59 | A | C |
| ATOM | 2799 | CE  | LYS | 373 | 38.048 | 75.703 | 28.601 | 1.00 | 25.15 | A | C |
| ATOM | 2800 | NZ  | LYS | 373 | 38.103 | 77.196 | 28.404 | 1.00 | 24.26 | A | N |
| ATOM | 2801 | C   | LYS | 373 | 34.277 | 72.369 | 30.593 | 1.00 | 20.26 | A | C |
| ATOM | 2802 | O   | LYS | 373 | 33.474 | 73.050 | 31.231 | 1.00 | 21.08 | A | O |
| ATOM | 2803 | N   | ILE | 374 | 35.215 | 71.634 | 31.176 | 1.00 | 20.43 | A | N |
| ATOM | 2804 | CA  | ILE | 374 | 35.358 | 71.624 | 32.621 | 1.00 | 19.63 | A | C |
| ATOM | 2805 | CB  | ILE | 374 | 35.960 | 70.309 | 33.123 | 1.00 | 19.72 | A | C |
| ATOM | 2806 | CG2 | ILE | 374 | 36.100 | 70.361 | 34.650 | 1.00 | 19.46 | A | C |
| ATOM | 2807 | CG1 | ILE | 374 | 35.095 | 69.128 | 32.667 | 1.00 | 19.17 | A | C |
| ATOM | 2808 | CD1 | ILE | 374 | 35.652 | 67.753 | 33.079 | 1.00 | 15.57 | A | C |
| ATOM | 2809 | C   | ILE | 374 | 36.290 | 72.745 | 33.046 | 1.00 | 19.75 | A | C |
| ATOM | 2810 | O   | ILE | 374 | 37.408 | 72.846 | 32.551 | 1.00 | 21.23 | A | O |
| ATOM | 2811 | N   | ILE | 375 | 35.824 | 73.595 | 33.951 | 1.00 | 20.12 | A | N |
| ATOM | 2812 | CA  | ILE | 375 | 36.643 | 74.684 | 34.456 | 1.00 | 20.15 | A | C |
| ATOM | 2813 | CB  | ILE | 375 | 36.396 | 76.014 | 33.700 | 1.00 | 20.38 | A | C |
| ATOM | 2814 | CG2 | ILE | 375 | 36.685 | 75.837 | 32.215 | 1.00 | 20.24 | A | C |
| ATOM | 2815 | CG1 | ILE | 375 | 34.966 | 76.488 | 33.919 | 1.00 | 20.36 | A | C |
| ATOM | 2816 | CD1 | ILE | 375 | 34.645 | 77.772 | 33.186 | 1.00 | 21.00 | A | C |
| ATOM | 2817 | C   | ILE | 375 | 36.346 | 74.893 | 35.929 | 1.00 | 21.63 | A | C |
| ATOM | 2818 | O   | ILE | 375 | 35.283 | 74.512 | 36.426 | 1.00 | 21.72 | A | O |
| ATOM | 2819 | N   | SER | 376 | 37.301 | 75.481 | 36.634 | 1.00 | 22.04 | A | N |
| ATOM | 2820 | CA  | SER | 376 | 37.132 | 75.740 | 38.051 | 1.00 | 23.67 | A | C |
| ATOM | 2821 | CB  | SER | 376 | 38.449 | 76.228 | 38.632 | 1.00 | 21.76 | A | C |
| ATOM | 2822 | OG  | SER | 376 | 38.336 | 76.411 | 40.022 | 1.00 | 26.97 | A | O |
| ATOM | 2823 | C   | SER | 376 | 36.063 | 76.809 | 38.210 | 1.00 | 24.46 | A | C |
| ATOM | 2824 | O   | SER | 376 | 36.042 | 77.768 | 37.445 | 1.00 | 27.59 | A | O |
| ATOM | 2825 | N   | ASN | 377 | 35.164 | 76.659 | 39.177 | 1.00 | 25.41 | A | N |
| ATOM | 2826 | CA  | ASN | 377 | 34.128 | 77.673 | 39.356 | 1.00 | 26.19 | A | C |
| ATOM | 2827 | CB  | ASN | 377 | 32.755 | 77.023 | 39.602 | 1.00 | 25.06 | A | C |
| ATOM | 2828 | CG  | ASN | 377 | 32.682 | 76.222 | 40.894 | 1.00 | 22.15 | A | C |
| ATOM | 2829 | OD1 | ASN | 377 | 33.560 | 76.294 | 41.750 | 1.00 | 23.03 | A | O |
| ATOM | 2830 | ND2 | ASN | 377 | 31.606 | 75.457 | 41.039 | 1.00 | 20.01 | A | N |
| ATOM | 2831 | C   | ASN | 377 | 34.447 | 78.685 | 40.456 | 1.00 | 28.48 | A | C |
| ATOM | 2832 | O   | ASN | 377 | 35.574 | 78.733 | 40.960 | 1.00 | 29.51 | A | O |
| ATOM | 2833 | N   | GLU | 378 | 33.461 | 79.498 | 40.822 | 1.00 | 30.42 | A | N |
| ATOM | 2834 | CA  | GLU | 378 | 33.659 | 80.518 | 41.845 | 1.00 | 33.25 | A | C |
| ATOM | 2835 | CB  | GLU | 378 | 32.401 | 81.390 | 41.988 | 1.00 | 36.97 | A | C |
| ATOM | 2836 | CG  | GLU | 378 | 32.300 | 82.505 | 40.939 | 1.00 | 44.33 | A | C |
| ATOM | 2837 | CD  | GLU | 378 | 31.099 | 83.430 | 41.148 | 1.00 | 49.20 | A | C |
| ATOM | 2838 | OE1 | GLU | 378 | 29.946 | 82.970 | 40.972 | 1.00 | 51.65 | A | O |
| ATOM | 2839 | OE2 | GLU | 378 | 31.312 | 84.619 | 41.489 | 1.00 | 50.97 | A | O |
| ATOM | 2840 | C   | GLU | 378 | 34.065 | 79.975 | 43.208 | 1.00 | 32.75 | A | C |
| ATOM | 2841 | O   | GLU | 378 | 34.582 | 80.718 | 44.040 | 1.00 | 33.80 | A | O |

FIG. 4-59 (Continued)

| | | | | | | | | | | | |
|---|---|---|---|---|---|---|---|---|---|---|---|
| ATOM | 2842 | N | GLU | 379 | 33.842 | 78.687 | 43.436 | 1.00 | 31.75 | A | N |
| ATOM | 2843 | CA | GLU | 379 | 34.192 | 78.070 | 44.709 | 1.00 | 31.73 | A | C |
| ATOM | 2844 | CB | GLU | 379 | 33.083 | 77.141 | 45.182 | 1.00 | 35.37 | A | C |
| ATOM | 2845 | CG | GLU | 379 | 31.752 | 77.788 | 45.416 | 1.00 | 40.59 | A | C |
| ATOM | 2846 | CD | GLU | 379 | 30.678 | 76.751 | 45.677 | 1.00 | 46.30 | A | C |
| ATOM | 2847 | OE1 | GLU | 379 | 30.363 | 75.976 | 44.741 | 1.00 | 48.81 | A | O |
| ATOM | 2848 | OE2 | GLU | 379 | 30.159 | 76.700 | 46.815 | 1.00 | 49.11 | A | O |
| ATOM | 2849 | C | GLU | 379 | 35.466 | 77.252 | 44.589 | 1.00 | 30.70 | A | C |
| ATOM | 2850 | O | GLU | 379 | 35.952 | 76.712 | 45.578 | 1.00 | 30.56 | A | O |
| ATOM | 2851 | N | GLY | 380 | 35.986 | 77.136 | 43.373 | 1.00 | 29.06 | A | N |
| ATOM | 2852 | CA | GLY | 380 | 37.203 | 76.377 | 43.171 | 1.00 | 27.19 | A | C |
| ATOM | 2853 | C | GLY | 380 | 36.979 | 74.931 | 42.781 | 1.00 | 27.69 | A | C |
| ATOM | 2854 | O | GLY | 380 | 37.935 | 74.167 | 42.662 | 1.00 | 27.62 | A | O |
| ATOM | 2855 | N | TYR | 381 | 35.726 | 74.540 | 42.586 | 1.00 | 26.46 | A | N |
| ATOM | 2856 | CA | TYR | 381 | 35.434 | 73.167 | 42.191 | 1.00 | 26.78 | A | C |
| ATOM | 2857 | CB | TYR | 381 | 34.175 | 72.671 | 42.903 | 1.00 | 26.62 | A | C |
| ATOM | 2858 | CG | TYR | 381 | 34.394 | 72.448 | 44.379 | 1.00 | 24.99 | A | C |
| ATOM | 2859 | CD1 | TYR | 381 | 34.864 | 71.225 | 44.853 | 1.00 | 24.93 | A | C |
| ATOM | 2860 | CE1 | TYR | 381 | 35.145 | 71.035 | 46.204 | 1.00 | 26.71 | A | C |
| ATOM | 2861 | CD2 | TYR | 381 | 34.202 | 73.486 | 45.296 | 1.00 | 25.27 | A | C |
| ATOM | 2862 | CE2 | TYR | 381 | 34.480 | 73.312 | 46.647 | 1.00 | 26.88 | A | C |
| ATOM | 2863 | CZ | TYR | 381 | 34.955 | 72.082 | 47.097 | 1.00 | 28.08 | A | C |
| ATOM | 2864 | OH | TYR | 381 | 35.266 | 71.909 | 48.429 | 1.00 | 28.31 | A | O |
| ATOM | 2865 | C | TYR | 381 | 35.261 | 73.100 | 40.678 | 1.00 | 26.94 | A | C |
| ATOM | 2866 | O | TYR | 381 | 34.542 | 73.911 | 40.091 | 1.00 | 28.94 | A | O |
| ATOM | 2867 | N | ARG | 382 | 35.938 | 72.147 | 40.045 | 1.00 | 24.97 | A | N |
| ATOM | 2868 | CA | ARG | 382 | 35.855 | 72.003 | 38.600 | 1.00 | 22.04 | A | C |
| ATOM | 2869 | CB | ARG | 382 | 37.057 | 71.211 | 38.081 | 1.00 | 24.10 | A | C |
| ATOM | 2870 | CG | ARG | 382 | 38.322 | 72.045 | 38.110 | 1.00 | 24.01 | A | C |
| ATOM | 2871 | CD | ARG | 382 | 39.606 | 71.237 | 38.141 | 1.00 | 24.10 | A | C |
| ATOM | 2872 | NE | ARG | 382 | 40.647 | 72.083 | 38.712 | 1.00 | 23.35 | A | N |
| ATOM | 2873 | CZ | ARG | 382 | 41.178 | 73.132 | 38.096 | 1.00 | 23.31 | A | C |
| ATOM | 2874 | NH1 | ARG | 382 | 40.783 | 73.449 | 36.868 | 1.00 | 21.52 | A | N |
| ATOM | 2875 | NH2 | ARG | 382 | 42.052 | 73.907 | 38.738 | 1.00 | 22.46 | A | N |
| ATOM | 2876 | C | ARG | 382 | 34.548 | 71.359 | 38.186 | 1.00 | 20.92 | A | C |
| ATOM | 2877 | O | ARG | 382 | 34.189 | 70.270 | 38.645 | 1.00 | 18.12 | A | O |
| ATOM | 2878 | N | HIS | 383 | 33.840 | 72.068 | 37.313 | 1.00 | 20.45 | A | N |
| ATOM | 2879 | CA | HIS | 383 | 32.545 | 71.647 | 36.813 | 1.00 | 20.33 | A | C |
| ATOM | 2880 | CB | HIS | 383 | 31.440 | 72.370 | 37.581 | 1.00 | 20.76 | A | C |
| ATOM | 2881 | CG | HIS | 383 | 31.177 | 71.797 | 38.939 | 1.00 | 22.34 | A | C |
| ATOM | 2882 | CD2 | HIS | 383 | 31.590 | 72.189 | 40.168 | 1.00 | 21.75 | A | C |
| ATOM | 2883 | ND1 | HIS | 383 | 30.418 | 70.661 | 39.132 | 1.00 | 20.42 | A | N |
| ATOM | 2884 | CE1 | HIS | 383 | 30.374 | 70.380 | 40.422 | 1.00 | 22.91 | A | C |
| ATOM | 2885 | NE2 | HIS | 383 | 31.076 | 71.291 | 41.073 | 1.00 | 22.25 | A | N |
| ATOM | 2886 | C | HIS | 383 | 32.404 | 71.930 | 35.330 | 1.00 | 20.36 | A | C |
| ATOM | 2887 | O | HIS | 383 | 33.240 | 72.608 | 34.728 | 1.00 | 19.84 | A | O |
| ATOM | 2888 | N | ILE | 384 | 31.325 | 71.420 | 34.748 | 1.00 | 19.26 | A | N |
| ATOM | 2889 | CA | ILE | 384 | 31.078 | 71.589 | 33.329 | 1.00 | 17.93 | A | C |
| ATOM | 2890 | CB | ILE | 384 | 30.232 | 70.419 | 32.802 | 1.00 | 17.52 | A | C |

FIG. 4-60 (Continued)

| | | | | | | | | | | |
|---|---|---|---|---|---|---|---|---|---|---|
| ATOM | 2891 | CG2 | ILE | 384 | 30.005 | 70.566 | 31.290 | 1.00 | 15.28 | A C |
| ATOM | 2892 | CG1 | ILE | 384 | 30.928 | 69.097 | 33.155 | 1.00 | 12.97 | A C |
| ATOM | 2893 | CD1 | ILE | 384 | 30.093 | 67.865 | 32.909 | 1.00 | 9.57 | A C |
| ATOM | 2894 | C | ILE | 384 | 30.376 | 72.898 | 33.028 | 1.00 | 19.30 | A C |
| ATOM | 2895 | O | ILE | 384 | 29.333 | 73.198 | 33.605 | 1.00 | 18.50 | A O |
| ATOM | 2896 | N | CYS | 385 | 30.950 | 73.681 | 32.120 | 1.00 | 21.14 | A N |
| ATOM | 2897 | CA | CYS | 385 | 30.349 | 74.953 | 31.745 | 1.00 | 24.26 | A C |
| ATOM | 2898 | C | CYS | 385 | 29.932 | 74.887 | 30.284 | 1.00 | 23.62 | A C |
| ATOM | 2899 | O | CYS | 385 | 30.654 | 74.334 | 29.464 | 1.00 | 23.61 | A O |
| ATOM | 2900 | CB | CYS | 385 | 31.344 | 76.106 | 31.958 | 1.00 | 27.85 | A C |
| ATOM | 2901 | SG | CYS | 385 | 30.561 | 77.640 | 32.569 | 1.00 | 37.75 | A S |
| ATOM | 2902 | N | TYR | 386 | 28.760 | 75.440 | 29.973 | 1.00 | 23.26 | A N |
| ATOM | 2903 | CA | TYR | 386 | 28.237 | 75.470 | 28.609 | 1.00 | 21.88 | A C |
| ATOM | 2904 | CB | TYR | 386 | 26.726 | 75.271 | 28.612 | 1.00 | 21.89 | A C |
| ATOM | 2905 | CG | TYR | 386 | 26.120 | 75.183 | 27.228 | 1.00 | 23.48 | A C |
| ATOM | 2906 | CD1 | TYR | 386 | 24.912 | 75.825 | 26.930 | 1.00 | 23.55 | A C |
| ATOM | 2907 | CE1 | TYR | 386 | 24.323 | 75.712 | 25.665 | 1.00 | 24.11 | A C |
| ATOM | 2908 | CD2 | TYR | 386 | 26.728 | 74.424 | 26.223 | 1.00 | 22.70 | A C |
| ATOM | 2909 | CE2 | TYR | 386 | 26.144 | 74.299 | 24.956 | 1.00 | 23.04 | A C |
| ATOM | 2910 | CZ | TYR | 386 | 24.943 | 74.946 | 24.686 | 1.00 | 24.39 | A C |
| ATOM | 2911 | OH | TYR | 386 | 24.358 | 74.823 | 23.449 | 1.00 | 23.13 | A O |
| ATOM | 2912 | C | TYR | 386 | 28.549 | 76.816 | 27.962 | 1.00 | 22.02 | A C |
| ATOM | 2913 | O | TYR | 386 | 28.187 | 77.868 | 28.493 | 1.00 | 22.52 | A O |
| ATOM | 2914 | N | PHE | 387 | 29.201 | 76.775 | 26.806 | 1.00 | 21.19 | A N |
| ATOM | 2915 | CA | PHE | 387 | 29.582 | 77.988 | 26.080 | 1.00 | 19.95 | A C |
| ATOM | 2916 | CB | PHE | 387 | 31.087 | 77.987 | 25.781 | 1.00 | 17.05 | A C |
| ATOM | 2917 | CG | PHE | 387 | 31.970 | 78.222 | 26.973 | 1.00 | 14.01 | A C |
| ATOM | 2918 | CD1 | PHE | 387 | 32.547 | 79.469 | 27.185 | 1.00 | 9.81 | A C |
| ATOM | 2919 | CD2 | PHE | 387 | 32.293 | 77.178 | 27.835 | 1.00 | 11.20 | A C |
| ATOM | 2920 | CE1 | PHE | 387 | 33.440 | 79.672 | 28.231 | 1.00 | 9.80 | A C |
| ATOM | 2921 | CE2 | PHE | 387 | 33.185 | 77.376 | 28.885 | 1.00 | 10.91 | A C |
| ATOM | 2922 | CZ | PHE | 387 | 33.762 | 78.626 | 29.082 | 1.00 | 9.32 | A C |
| ATOM | 2923 | C | PHE | 387 | 28.888 | 78.153 | 24.727 | 1.00 | 20.94 | A C |
| ATOM | 2924 | O | PHE | 387 | 28.552 | 77.180 | 24.055 | 1.00 | 19.77 | A O |
| ATOM | 2925 | N | GLN | 388 | 28.706 | 79.406 | 24.332 | 1.00 | 21.79 | A N |
| ATOM | 2926 | CA | GLN | 388 | 28.151 | 79.742 | 23.030 | 1.00 | 22.21 | A C |
| ATOM | 2927 | CB | GLN | 388 | 27.024 | 80.760 | 23.177 | 1.00 | 23.86 | A C |
| ATOM | 2928 | CG | GLN | 388 | 25.745 | 80.343 | 22.477 | 1.00 | 29.81 | A C |
| ATOM | 2929 | CD | GLN | 388 | 25.096 | 79.126 | 23.109 | 1.00 | 32.86 | A C |
| ATOM | 2930 | OE1 | GLN | 388 | 24.357 | 78.391 | 22.452 | 1.00 | 34.98 | A O |
| ATOM | 2931 | NE2 | GLN | 388 | 25.356 | 78.913 | 24.395 | 1.00 | 36.34 | A N |
| ATOM | 2932 | C | GLN | 388 | 29.403 | 80.382 | 22.427 | 1.00 | 21.72 | A C |
| ATOM | 2933 | O | GLN | 388 | 29.845 | 81.428 | 22.893 | 1.00 | 22.74 | A O |
| ATOM | 2934 | N | ILE | 389 | 29.982 | 79.745 | 21.415 | 1.00 | 20.66 | A N |
| ATOM | 2935 | CA | ILE | 389 | 31.231 | 80.215 | 20.821 | 1.00 | 21.00 | A C |
| ATOM | 2936 | CB | ILE | 389 | 31.466 | 79.617 | 19.422 | 1.00 | 20.76 | A C |
| ATOM | 2937 | CG2 | ILE | 389 | 31.410 | 78.100 | 19.496 | 1.00 | 19.50 | A C |
| ATOM | 2938 | CG1 | ILE | 389 | 30.448 | 80.165 | 18.429 | 1.00 | 19.48 | A C |
| ATOM | 2939 | CD1 | ILE | 389 | 30.813 | 79.864 | 16.992 | 1.00 | 19.12 | A C |

| ATOM | 2940 | C | ILE | 389 | 31.483 | 81.713 | 20.735 | 1.00 | 23.29 | A | C |
|------|------|---|-----|-----|--------|--------|--------|------|-------|---|---|
| ATOM | 2941 | O | ILE | 389 | 32.640 | 82.146 | 20.776 | 1.00 | 22.48 | A | O |
| ATOM | 2942 | N | ASP | 390 | 30.423 | 82.505 | 20.611 | 1.00 | 24.96 | A | N |
| ATOM | 2943 | CA | ASP | 390 | 30.584 | 83.953 | 20.533 | 1.00 | 26.49 | A | C |
| ATOM | 2944 | CB | ASP | 390 | 29.932 | 84.508 | 19.275 | 1.00 | 29.09 | A | C |
| ATOM | 2945 | CG | ASP | 390 | 28.467 | 84.215 | 19.216 | 1.00 | 30.91 | A | C |
| ATOM | 2946 | OD1 | ASP | 390 | 27.754 | 84.955 | 18.517 | 1.00 | 35.45 | A | O |
| ATOM | 2947 | OD2 | ASP | 390 | 28.029 | 83.236 | 19.858 | 1.00 | 33.49 | A | O |
| ATOM | 2948 | C | ASP | 390 | 30.005 | 84.676 | 21.738 | 1.00 | 26.43 | A | C |
| ATOM | 2949 | O | ASP | 390 | 29.402 | 85.735 | 21.603 | 1.00 | 26.54 | A | O |
| ATOM | 2950 | N | LYS | 391 | 30.163 | 84.078 | 22.910 | 1.00 | 27.05 | A | N |
| ATOM | 2951 | CA | LYS | 391 | 29.707 | 84.679 | 24.150 | 1.00 | 28.81 | A | C |
| ATOM | 2952 | CB | LYS | 391 | 28.348 | 84.128 | 24.566 | 1.00 | 28.62 | A | C |
| ATOM | 2953 | CG | LYS | 391 | 27.203 | 84.790 | 23.824 | 1.00 | 31.00 | A | C |
| ATOM | 2954 | CD | LYS | 391 | 25.867 | 84.228 | 24.256 | 1.00 | 34.06 | A | C |
| ATOM | 2955 | CE | LYS | 391 | 24.733 | 84.772 | 23.413 | 1.00 | 33.69 | A | C |
| ATOM | 2956 | NZ | LYS | 391 | 23.454 | 84.073 | 23.742 | 1.00 | 36.51 | A | N |
| ATOM | 2957 | C | LYS | 391 | 30.772 | 84.369 | 25.183 | 1.00 | 29.11 | A | C |
| ATOM | 2958 | O | LYS | 391 | 31.192 | 83.223 | 25.327 | 1.00 | 29.45 | A | O |
| ATOM | 2959 | N | LYS | 392 | 31.219 | 85.401 | 25.888 | 1.00 | 29.66 | A | N |
| ATOM | 2960 | CA | LYS | 392 | 32.281 | 85.248 | 26.872 | 1.00 | 30.67 | A | C |
| ATOM | 2961 | CB | LYS | 392 | 33.069 | 86.558 | 26.985 | 1.00 | 28.28 | A | C |
| ATOM | 2962 | CG | LYS | 392 | 33.516 | 87.119 | 25.636 | 1.00 | 27.07 | A | C |
| ATOM | 2963 | CD | LYS | 392 | 34.330 | 86.098 | 24.852 | 1.00 | 27.55 | A | C |
| ATOM | 2964 | CE | LYS | 392 | 34.643 | 86.588 | 23.449 | 1.00 | 26.02 | A | C |
| ATOM | 2965 | NZ | LYS | 392 | 35.369 | 87.872 | 23.495 | 1.00 | 25.63 | A | N |
| ATOM | 2966 | C | LYS | 392 | 31.824 | 84.797 | 28.248 | 1.00 | 31.24 | A | C |
| ATOM | 2967 | O | LYS | 392 | 32.637 | 84.679 | 29.162 | 1.00 | 32.17 | A | O |
| ATOM | 2968 | N | ASP | 393 | 30.531 | 84.548 | 28.403 | 1.00 | 31.57 | A | N |
| ATOM | 2969 | CA | ASP | 393 | 30.015 | 84.098 | 29.690 | 1.00 | 33.64 | A | C |
| ATOM | 2970 | CB | ASP | 393 | 29.052 | 85.134 | 30.271 | 1.00 | 36.88 | A | C |
| ATOM | 2971 | CG | ASP | 393 | 29.734 | 86.450 | 30.567 | 1.00 | 41.66 | A | C |
| ATOM | 2972 | OD1 | ASP | 393 | 30.607 | 86.475 | 31.467 | 1.00 | 43.84 | A | O |
| ATOM | 2973 | OD2 | ASP | 393 | 29.409 | 87.455 | 29.895 | 1.00 | 44.39 | A | O |
| ATOM | 2974 | C | ASP | 393 | 29.309 | 82.761 | 29.546 | 1.00 | 32.46 | A | C |
| ATOM | 2975 | O | ASP | 393 | 28.294 | 82.666 | 28.859 | 1.00 | 32.91 | A | O |
| ATOM | 2976 | N | CYS | 394 | 29.841 | 81.731 | 30.198 | 1.00 | 30.05 | A | N |
| ATOM | 2977 | CA | CYS | 394 | 29.243 | 80.410 | 30.115 | 1.00 | 28.94 | A | C |
| ATOM | 2978 | C | CYS | 394 | 28.312 | 80.116 | 31.282 | 1.00 | 27.56 | A | C |
| ATOM | 2979 | O | CYS | 394 | 28.262 | 80.858 | 32.258 | 1.00 | 27.11 | A | O |
| ATOM | 2980 | CB | CYS | 394 | 30.336 | 79.338 | 30.033 | 1.00 | 31.03 | A | C |
| ATOM | 2981 | SG | CYS | 394 | 31.401 | 79.166 | 31.504 | 1.00 | 34.42 | A | S |
| ATOM | 2982 | N | THR | 395 | 27.570 | 79.023 | 31.167 | 1.00 | 25.71 | A | N |
| ATOM | 2983 | CA | THR | 395 | 26.645 | 78.608 | 32.204 | 1.00 | 25.01 | A | C |
| ATOM | 2984 | CB | THR | 395 | 25.208 | 78.512 | 31.647 | 1.00 | 25.50 | A | C |
| ATOM | 2985 | OG1 | THR | 395 | 24.709 | 79.833 | 31.407 | 1.00 | 28.36 | A | O |
| ATOM | 2986 | CG2 | THR | 395 | 24.289 | 77.779 | 32.620 | 1.00 | 21.52 | A | C |
| ATOM | 2987 | C | THR | 395 | 27.048 | 77.251 | 32.772 | 1.00 | 24.22 | A | C |
| ATOM | 2988 | O | THR | 395 | 27.196 | 76.280 | 32.036 | 1.00 | 24.44 | A | O |

FIG. 4-62 (Continued)

| | | | | | | | | | | |
|---|---|---|---|---|---|---|---|---|---|---|
| ATOM | 2989 | N | PHE | 396 | 27.231 | 77.185 | 34.084 | 1.00 23.09 | A | N |
| ATOM | 2990 | CA | PHE | 396 | 27.594 | 75.924 | 34.715 | 1.00 23.03 | A | C |
| ATOM | 2991 | CB | PHE | 396 | 28.138 | 76.182 | 36.116 | 1.00 22.19 | A | C |
| ATOM | 2992 | CG | PHE | 396 | 29.581 | 76.617 | 36.131 | 1.00 23.20 | A | C |
| ATOM | 2993 | CD1 | PHE | 396 | 30.604 | 75.697 | 35.876 | 1.00 22.48 | A | C |
| ATOM | 2994 | CD2 | PHE | 396 | 29.924 | 77.935 | 36.415 | 1.00 20.97 | A | C |
| ATOM | 2995 | CE1 | PHE | 396 | 31.949 | 76.086 | 35.908 | 1.00 20.26 | A | C |
| ATOM | 2996 | CE2 | PHE | 396 | 31.267 | 78.331 | 36.447 | 1.00 21.70 | A | C |
| ATOM | 2997 | CZ | PHE | 396 | 32.279 | 77.400 | 36.194 | 1.00 20.27 | A | C |
| ATOM | 2998 | C | PHE | 396 | 26.373 | 75.008 | 34.764 | 1.00 20.96 | A | C |
| ATOM | 2999 | O | PHE | 396 | 25.311 | 75.412 | 35.218 | 1.00 20.96 | A | O |
| ATOM | 3000 | N | ILE | 397 | 26.523 | 73.779 | 34.279 | 1.00 18.88 | A | N |
| ATOM | 3001 | CA | ILE | 397 | 25.412 | 72.842 | 34.262 | 1.00 18.00 | A | C |
| ATOM | 3002 | CB | ILE | 397 | 25.266 | 72.165 | 32.879 | 1.00 16.55 | A | C |
| ATOM | 3003 | CG2 | ILE | 397 | 25.350 | 73.209 | 31.787 | 1.00 13.63 | A | C |
| ATOM | 3004 | CG1 | ILE | 397 | 26.366 | 71.130 | 32.669 | 1.00 16.02 | A | C |
| ATOM | 3005 | CD1 | ILE | 397 | 26.180 | 70.327 | 31.402 | 1.00 17.85 | A | C |
| ATOM | 3006 | C | ILE | 397 | 25.527 | 71.770 | 35.338 | 1.00 19.16 | A | C |
| ATOM | 3007 | O | ILE | 397 | 24.787 | 70.787 | 35.330 | 1.00 20.44 | A | O |
| ATOM | 3008 | N | THR | 398 | 26.480 | 71.956 | 36.244 | 1.00 18.55 | A | N |
| ATOM | 3009 | CA | THR | 398 | 26.681 | 71.051 | 37.367 | 1.00 19.41 | A | C |
| ATOM | 3010 | CB | THR | 398 | 27.624 | 69.858 | 37.051 | 1.00 19.56 | A | C |
| ATOM | 3011 | OG1 | THR | 398 | 28.978 | 70.321 | 36.960 | 1.00 22.60 | A | O |
| ATOM | 3012 | CG2 | THR | 398 | 27.221 | 69.178 | 35.759 | 1.00 18.50 | A | C |
| ATOM | 3013 | C | THR | 398 | 27.343 | 71.899 | 38.424 | 1.00 20.24 | A | C |
| ATOM | 3014 | O | THR | 398 | 27.979 | 72.903 | 38.104 | 1.00 20.11 | A | O |
| ATOM | 3015 | N | LYS | 399 | 27.185 | 71.511 | 39.681 | 1.00 22.48 | A | N |
| ATOM | 3016 | CA | LYS | 399 | 27.795 | 72.258 | 40.772 | 1.00 23.72 | A | C |
| ATOM | 3017 | CB | LYS | 399 | 27.111 | 73.618 | 40.941 | 1.00 24.42 | A | C |
| ATOM | 3018 | CG | LYS | 399 | 25.689 | 73.583 | 41.462 | 1.00 27.65 | A | C |
| ATOM | 3019 | CD | LYS | 399 | 25.269 | 74.996 | 41.856 | 1.00 30.77 | A | C |
| ATOM | 3020 | CE | LYS | 399 | 23.861 | 75.054 | 42.414 | 1.00 31.89 | A | C |
| ATOM | 3021 | NZ | LYS | 399 | 22.841 | 74.747 | 41.377 | 1.00 35.03 | A | N |
| ATOM | 3022 | C | LYS | 399 | 27.751 | 71.476 | 42.077 | 1.00 22.46 | A | C |
| ATOM | 3023 | O | LYS | 399 | 27.125 | 70.425 | 42.154 | 1.00 21.96 | A | O |
| ATOM | 3024 | N | GLY | 400 | 28.435 | 71.989 | 43.093 | 1.00 21.98 | A | N |
| ATOM | 3025 | CA | GLY | 400 | 28.463 | 71.319 | 44.378 | 1.00 22.66 | A | C |
| ATOM | 3026 | C | GLY | 400 | 29.891 | 71.115 | 44.839 | 1.00 24.94 | A | C |
| ATOM | 3027 | O | GLY | 400 | 30.831 | 71.449 | 44.118 | 1.00 26.10 | A | O |
| ATOM | 3028 | N | THR | 401 | 30.064 | 70.566 | 46.036 | 1.00 25.34 | A | N |
| ATOM | 3029 | CA | THR | 401 | 31.400 | 70.335 | 46.560 | 1.00 26.41 | A | C |
| ATOM | 3030 | CB | THR | 401 | 31.443 | 70.541 | 48.095 | 1.00 27.75 | A | C |
| ATOM | 3031 | OG1 | THR | 401 | 30.615 | 69.567 | 48.741 | 1.00 31.37 | A | O |
| ATOM | 3032 | CG2 | THR | 401 | 30.924 | 71.927 | 48.448 | 1.00 27.06 | A | C |
| ATOM | 3033 | C | THR | 401 | 31.923 | 68.945 | 46.197 | 1.00 24.83 | A | C |
| ATOM | 3034 | O | THR | 401 | 32.027 | 68.049 | 47.036 | 1.00 26.74 | A | O |
| ATOM | 3035 | N | TRP | 402 | 32.229 | 68.790 | 44.915 | 1.00 22.03 | A | N |
| ATOM | 3036 | CA | TRP | 402 | 32.781 | 67.569 | 44.340 | 1.00 18.83 | A | C |
| ATOM | 3037 | CB | TRP | 402 | 31.741 | 66.460 | 44.268 | 1.00 16.39 | A | C |

| ATOM | 3038 | CG | TRP | 402 | 30.434 | 66.886 | 43.709 | 1.00 | 17.90 | A | C |
|------|------|------|-----|-----|--------|--------|--------|------|-------|---|---|
| ATOM | 3039 | CD2 | TRP | 402 | 30.037 | 66.865 | 42.332 | 1.00 | 19.16 | A | C |
| ATOM | 3040 | CE2 | TRP | 402 | 28.701 | 67.320 | 42.278 | 1.00 | 20.21 | A | C |
| ATOM | 3041 | CE3 | TRP | 402 | 30.679 | 66.505 | 41.137 | 1.00 | 18.78 | A | C |
| ATOM | 3042 | CD1 | TRP | 402 | 29.364 | 67.345 | 44.409 | 1.00 | 17.97 | A | C |
| ATOM | 3043 | NE1 | TRP | 402 | 28.318 | 67.605 | 43.562 | 1.00 | 20.57 | A | N |
| ATOM | 3044 | CZ2 | TRP | 402 | 27.989 | 67.425 | 41.078 | 1.00 | 18.32 | A | C |
| ATOM | 3045 | CZ3 | TRP | 402 | 29.972 | 66.608 | 39.943 | 1.00 | 19.71 | A | C |
| ATOM | 3046 | CH2 | TRP | 402 | 28.637 | 67.064 | 39.924 | 1.00 | 18.98 | A | C |
| ATOM | 3047 | C | TRP | 402 | 33.208 | 67.983 | 42.944 | 1.00 | 18.09 | A | C |
| ATOM | 3048 | O | TRP | 402 | 32.956 | 69.117 | 42.540 | 1.00 | 18.12 | A | O |
| ATOM | 3049 | N | GLU | 403 | 33.831 | 67.089 | 42.191 | 1.00 | 17.78 | A | N |
| ATOM | 3050 | CA | GLU | 403 | 34.284 | 67.484 | 40.866 | 1.00 | 19.48 | A | C |
| ATOM | 3051 | CB | GLU | 403 | 35.776 | 67.805 | 40.926 | 1.00 | 20.26 | A | C |
| ATOM | 3052 | CG | GLU | 403 | 36.122 | 68.824 | 41.983 | 1.00 | 21.69 | A | C |
| ATOM | 3053 | CD | GLU | 403 | 37.433 | 69.522 | 41.721 | 1.00 | 23.95 | A | C |
| ATOM | 3054 | OE1 | GLU | 403 | 37.506 | 70.728 | 42.020 | 1.00 | 25.27 | A | O |
| ATOM | 3055 | OE2 | GLU | 403 | 38.384 | 68.880 | 41.223 | 1.00 | 24.57 | A | O |
| ATOM | 3056 | C | GLU | 403 | 34.028 | 66.516 | 39.716 | 1.00 | 19.74 | A | C |
| ATOM | 3057 | O | GLU | 403 | 33.891 | 65.305 | 39.916 | 1.00 | 20.05 | A | O |
| ATOM | 3058 | N | VAL | 404 | 33.957 | 67.073 | 38.508 | 1.00 | 18.47 | A | N |
| ATOM | 3059 | CA | VAL | 404 | 33.760 | 66.273 | 37.305 | 1.00 | 17.63 | A | C |
| ATOM | 3060 | CB | VAL | 404 | 33.070 | 67.073 | 36.165 | 1.00 | 14.78 | A | C |
| ATOM | 3061 | CG1 | VAL | 404 | 32.974 | 66.210 | 34.914 | 1.00 | 11.14 | A | C |
| ATOM | 3062 | CG2 | VAL | 404 | 31.683 | 67.515 | 36.595 | 1.00 | 12.13 | A | C |
| ATOM | 3063 | C | VAL | 404 | 35.153 | 65.875 | 36.836 | 1.00 | 18.38 | A | C |
| ATOM | 3064 | O | VAL | 404 | 35.986 | 66.732 | 36.567 | 1.00 | 20.01 | A | O |
| ATOM | 3065 | N | ILE | 405 | 35.410 | 64.579 | 36.764 | 1.00 | 18.83 | A | N |
| ATOM | 3066 | CA | ILE | 405 | 36.707 | 64.088 | 36.323 | 1.00 | 20.05 | A | C |
| ATOM | 3067 | CB | ILE | 405 | 36.868 | 62.593 | 36.653 | 1.00 | 21.78 | A | C |
| ATOM | 3068 | CG2 | ILE | 405 | 38.254 | 62.123 | 36.283 | 1.00 | 16.28 | A | C |
| ATOM | 3069 | CG1 | ILE | 405 | 36.591 | 62.364 | 38.146 | 1.00 | 24.51 | A | C |
| ATOM | 3070 | CD1 | ILE | 405 | 37.438 | 63.218 | 39.079 | 1.00 | 26.24 | A | C |
| ATOM | 3071 | C | ILE | 405 | 36.858 | 64.290 | 34.817 | 1.00 | 19.94 | A | C |
| ATOM | 3072 | O | ILE | 405 | 37.912 | 64.710 | 34.345 | 1.00 | 20.67 | A | O |
| ATOM | 3073 | N | GLY | 406 | 35.803 | 63.990 | 34.064 | 1.00 | 19.40 | A | N |
| ATOM | 3074 | CA | GLY | 406 | 35.869 | 64.171 | 32.627 | 1.00 | 16.85 | A | C |
| ATOM | 3075 | C | GLY | 406 | 34.566 | 63.983 | 31.881 | 1.00 | 16.78 | A | C |
| ATOM | 3076 | O | GLY | 406 | 33.679 | 63.268 | 32.330 | 1.00 | 17.43 | A | O |
| ATOM | 3077 | N | ILE | 407 | 34.459 | 64.652 | 30.736 | 1.00 | 17.49 | A | N |
| ATOM | 3078 | CA | ILE | 407 | 33.303 | 64.569 | 29.852 | 1.00 | 16.98 | A | C |
| ATOM | 3079 | CB | ILE | 407 | 33.173 | 65.861 | 28.998 | 1.00 | 16.67 | A | C |
| ATOM | 3080 | CG2 | ILE | 407 | 32.157 | 65.671 | 27.874 | 1.00 | 16.93 | A | C |
| ATOM | 3081 | CG1 | ILE | 407 | 32.779 | 67.036 | 29.895 | 1.00 | 16.45 | A | C |
| ATOM | 3082 | CD1 | ILE | 407 | 32.646 | 68.357 | 29.157 | 1.00 | 11.65 | A | C |
| ATOM | 3083 | C | ILE | 407 | 33.611 | 63.392 | 28.934 | 1.00 | 18.17 | A | C |
| ATOM | 3084 | O | ILE | 407 | 34.599 | 63.421 | 28.212 | 1.00 | 18.89 | A | O |
| ATOM | 3085 | N | GLU | 408 | 32.766 | 62.367 | 28.945 | 1.00 | 20.84 | A | N |
| ATOM | 3086 | CA | GLU | 408 | 33.000 | 61.176 | 28.122 | 1.00 | 22.31 | A | C |

FIG. 4-64 (Continued)

| ATOM | 3087 | CB | GLU | 408 | 32.691 | 59.922 | 28.944 | 1.00 | 21.64 | A | C |
|---|---|---|---|---|---|---|---|---|---|---|---|
| ATOM | 3088 | CG | GLU | 408 | 33.457 | 59.860 | 30.254 | 1.00 | 23.48 | A | C |
| ATOM | 3089 | CD | GLU | 408 | 34.963 | 59.947 | 30.048 | 1.00 | 26.15 | A | C |
| ATOM | 3090 | OE1 | GLU | 408 | 35.519 | 59.081 | 29.337 | 1.00 | 28.40 | A | O |
| ATOM | 3091 | OE2 | GLU | 408 | 35.594 | 60.877 | 30.596 | 1.00 | 25.87 | A | O |
| ATOM | 3092 | C | GLU | 408 | 32.262 | 61.097 | 26.780 | 1.00 | 22.35 | A | C |
| ATOM | 3093 | O | GLU | 408 | 32.743 | 60.455 | 25.846 | 1.00 | 23.83 | A | O |
| ATOM | 3094 | N | ALA | 409 | 31.100 | 61.729 | 26.671 | 1.00 | 22.21 | A | N |
| ATOM | 3095 | CA | ALA | 409 | 30.356 | 61.685 | 25.414 | 1.00 | 20.74 | A | C |
| ATOM | 3096 | CB | ALA | 409 | 29.797 | 60.294 | 25.180 | 1.00 | 21.17 | A | C |
| ATOM | 3097 | C | ALA | 409 | 29.235 | 62.708 | 25.386 | 1.00 | 20.05 | A | C |
| ATOM | 3098 | O | ALA | 409 | 28.651 | 63.041 | 26.413 | 1.00 | 19.39 | A | O |
| ATOM | 3099 | N | LEU | 410 | 28.937 | 63.201 | 24.195 | 1.00 | 19.25 | A | N |
| ATOM | 3100 | CA | LEU | 410 | 27.911 | 64.207 | 24.038 | 1.00 | 19.28 | A | C |
| ATOM | 3101 | CB | LEU | 410 | 28.559 | 65.571 | 23.796 | 1.00 | 19.29 | A | C |
| ATOM | 3102 | CG | LEU | 410 | 27.634 | 66.778 | 23.617 | 1.00 | 20.83 | A | C |
| ATOM | 3103 | CD1 | LEU | 410 | 26.959 | 67.089 | 24.935 | 1.00 | 20.92 | A | C |
| ATOM | 3104 | CD2 | LEU | 410 | 28.434 | 67.987 | 23.134 | 1.00 | 20.28 | A | C |
| ATOM | 3105 | C | LEU | 410 | 26.998 | 63.874 | 22.879 | 1.00 | 20.25 | A | C |
| ATOM | 3106 | O | LEU | 410 | 27.453 | 63.649 | 21.758 | 1.00 | 20.84 | A | O |
| ATOM | 3107 | N | THR | 411 | 25.701 | 63.834 | 23.150 | 1.00 | 19.86 | A | N |
| ATOM | 3108 | CA | THR | 411 | 24.741 | 63.561 | 22.100 | 1.00 | 18.40 | A | C |
| ATOM | 3109 | CB | THR | 411 | 23.902 | 62.339 | 22.418 | 1.00 | 15.82 | A | C |
| ATOM | 3110 | OG1 | THR | 411 | 23.017 | 62.649 | 23.498 | 1.00 | 15.79 | A | O |
| ATOM | 3111 | CG2 | THR | 411 | 24.797 | 61.177 | 22.811 | 1.00 | 14.12 | A | C |
| ATOM | 3112 | C | THR | 411 | 23.846 | 64.787 | 22.050 | 1.00 | 20.16 | A | C |
| ATOM | 3113 | O | THR | 411 | 23.971 | 65.684 | 22.882 | 1.00 | 21.79 | A | O |
| ATOM | 3114 | N | SER | 412 | 22.952 | 64.836 | 21.074 | 1.00 | 20.25 | A | N |
| ATOM | 3115 | CA | SER | 412 | 22.061 | 65.972 | 20.945 | 1.00 | 21.09 | A | C |
| ATOM | 3116 | CB | SER | 412 | 21.206 | 65.827 | 19.687 | 1.00 | 22.27 | A | C |
| ATOM | 3117 | OG | SER | 412 | 20.474 | 64.618 | 19.721 | 1.00 | 25.03 | A | O |
| ATOM | 3118 | C | SER | 412 | 21.158 | 66.118 | 22.153 | 1.00 | 21.84 | A | C |
| ATOM | 3119 | O | SER | 412 | 20.598 | 67.185 | 22.379 | 1.00 | 22.97 | A | O |
| ATOM | 3120 | N | ASP | 413 | 21.015 | 65.054 | 22.934 | 1.00 | 22.56 | A | N |
| ATOM | 3121 | CA | ASP | 413 | 20.138 | 65.104 | 24.097 | 1.00 | 24.36 | A | C |
| ATOM | 3122 | CB | ASP | 413 | 19.036 | 64.047 | 23.975 | 1.00 | 26.84 | A | C |
| ATOM | 3123 | CG | ASP | 413 | 18.161 | 64.243 | 22.751 | 1.00 | 30.28 | A | C |
| ATOM | 3124 | OD1 | ASP | 413 | 17.153 | 63.515 | 22.635 | 1.00 | 32.47 | A | O |
| ATOM | 3125 | OD2 | ASP | 413 | 18.474 | 65.111 | 21.904 | 1.00 | 31.81 | A | O |
| ATOM | 3126 | C | ASP | 413 | 20.822 | 64.918 | 25.442 | 1.00 | 24.37 | A | C |
| ATOM | 3127 | O | ASP | 413 | 20.306 | 65.363 | 26.470 | 1.00 | 25.08 | A | O |
| ATOM | 3128 | N | TYR | 414 | 21.974 | 64.259 | 25.444 | 1.00 | 24.23 | A | N |
| ATOM | 3129 | CA | TYR | 414 | 22.672 | 63.998 | 26.694 | 1.00 | 23.03 | A | C |
| ATOM | 3130 | CB | TYR | 414 | 22.369 | 62.572 | 27.155 | 1.00 | 23.61 | A | C |
| ATOM | 3131 | CG | TYR | 414 | 20.925 | 62.332 | 27.520 | 1.00 | 25.79 | A | C |
| ATOM | 3132 | CD1 | TYR | 414 | 20.402 | 62.822 | 28.714 | 1.00 | 26.31 | A | C |
| ATOM | 3133 | CE1 | TYR | 414 | 19.071 | 62.621 | 29.052 | 1.00 | 26.99 | A | C |
| ATOM | 3134 | CD2 | TYR | 414 | 20.074 | 61.629 | 26.666 | 1.00 | 24.67 | A | C |
| ATOM | 3135 | CE2 | TYR | 414 | 18.740 | 61.424 | 26.993 | 1.00 | 25.53 | A | C |

| | | | | | | | | | | |
|---|---|---|---|---|---|---|---|---|---|---|
| ATOM | 3136 | CZ | TYR | 414 | 18.246 | 61.923 | 28.188 | 1.00 | 28.30 | A C |
| ATOM | 3137 | OH | TYR | 414 | 16.925 | 61.731 | 28.531 | 1.00 | 31.69 | A O |
| ATOM | 3138 | C | TYR | 414 | 24.180 | 64.174 | 26.639 | 1.00 | 22.81 | A C |
| ATOM | 3139 | O | TYR | 414 | 24.811 | 64.040 | 25.582 | 1.00 | 22.74 | A O |
| ATOM | 3140 | N | LEU | 415 | 24.741 | 64.469 | 27.809 | 1.00 | 20.51 | A N |
| ATOM | 3141 | CA | LEU | 415 | 26.174 | 64.630 | 27.996 | 1.00 | 18.28 | A C |
| ATOM | 3142 | CB | LEU | 415 | 26.502 | 66.079 | 28.358 | 1.00 | 16.58 | A C |
| ATOM | 3143 | CG | LEU | 415 | 27.945 | 66.406 | 28.745 | 1.00 | 14.79 | A C |
| ATOM | 3144 | CD1 | LEU | 415 | 28.184 | 67.892 | 28.606 | 1.00 | 13.01 | A C |
| ATOM | 3145 | CD2 | LEU | 415 | 28.208 | 65.943 | 30.163 | 1.00 | 14.04 | A C |
| ATOM | 3146 | C | LEU | 415 | 26.518 | 63.684 | 29.149 | 1.00 | 18.57 | A C |
| ATOM | 3147 | O | LEU | 415 | 25.926 | 63.763 | 30.230 | 1.00 | 18.31 | A O |
| ATOM | 3148 | N | TYR | 416 | 27.449 | 62.769 | 28.909 | 1.00 | 19.11 | A N |
| ATOM | 3149 | CA | TYR | 416 | 27.843 | 61.796 | 29.924 | 1.00 | 19.69 | A C |
| ATOM | 3150 | CB | TYR | 416 | 27.963 | 60.407 | 29.309 | 1.00 | 18.66 | A C |
| ATOM | 3151 | CG | TYR | 416 | 26.698 | 59.926 | 28.645 | 1.00 | 17.78 | A C |
| ATOM | 3152 | CD1 | TYR | 416 | 26.297 | 60.438 | 27.410 | 1.00 | 16.67 | A C |
| ATOM | 3153 | CE1 | TYR | 416 | 25.137 | 59.971 | 26.786 | 1.00 | 18.58 | A C |
| ATOM | 3154 | CD2 | TYR | 416 | 25.908 | 58.944 | 29.245 | 1.00 | 16.22 | A C |
| ATOM | 3155 | CE2 | TYR | 416 | 24.754 | 58.475 | 28.636 | 1.00 | 16.35 | A C |
| ATOM | 3156 | CZ | TYR | 416 | 24.374 | 58.986 | 27.406 | 1.00 | 18.54 | A C |
| ATOM | 3157 | OH | TYR | 416 | 23.252 | 58.489 | 26.784 | 1.00 | 19.53 | A O |
| ATOM | 3158 | C | TYR | 416 | 29.167 | 62.178 | 30.540 | 1.00 | 20.71 | A C |
| ATOM | 3159 | O | TYR | 416 | 30.117 | 62.499 | 29.822 | 1.00 | 22.92 | A O |
| ATOM | 3160 | N | TYR | 417 | 29.238 | 62.138 | 31.866 | 1.00 | 19.27 | A N |
| ATOM | 3161 | CA | TYR | 417 | 30.472 | 62.506 | 32.544 | 1.00 | 19.08 | A C |
| ATOM | 3162 | CB | TYR | 417 | 30.408 | 63.981 | 32.970 | 1.00 | 18.38 | A C |
| ATOM | 3163 | CG | TYR | 417 | 29.383 | 64.282 | 34.049 | 1.00 | 17.93 | A C |
| ATOM | 3164 | CD1 | TYR | 417 | 29.721 | 64.213 | 35.399 | 1.00 | 15.25 | A C |
| ATOM | 3165 | CE1 | TYR | 417 | 28.784 | 64.476 | 36.391 | 1.00 | 13.14 | A C |
| ATOM | 3166 | CD2 | TYR | 417 | 28.071 | 64.622 | 33.718 | 1.00 | 17.72 | A C |
| ATOM | 3167 | CE2 | TYR | 417 | 27.120 | 64.885 | 34.710 | 1.00 | 15.27 | A C |
| ATOM | 3168 | CZ | TYR | 417 | 27.488 | 64.808 | 36.040 | 1.00 | 14.25 | A C |
| ATOM | 3169 | OH | TYR | 417 | 26.556 | 65.046 | 37.020 | 1.00 | 14.06 | A O |
| ATOM | 3170 | C | TYR | 417 | 30.768 | 61.615 | 33.747 | 1.00 | 18.77 | A C |
| ATOM | 3171 | O | TYR | 417 | 29.918 | 60.853 | 34.207 | 1.00 | 18.74 | A O |
| ATOM | 3172 | N | ILE | 418 | 31.996 | 61.706 | 34.236 | 1.00 | 17.63 | A N |
| ATOM | 3173 | CA | ILE | 418 | 32.429 | 60.926 | 35.379 | 1.00 | 16.60 | A C |
| ATOM | 3174 | CB | ILE | 418 | 33.626 | 60.019 | 35.015 | 1.00 | 15.54 | A C |
| ATOM | 3175 | CG2 | ILE | 418 | 34.482 | 59.737 | 36.241 | 1.00 | 14.33 | A C |
| ATOM | 3176 | CG1 | ILE | 418 | 33.107 | 58.729 | 34.378 | 1.00 | 15.75 | A C |
| ATOM | 3177 | CD1 | ILE | 418 | 34.183 | 57.767 | 33.964 | 1.00 | 15.48 | A C |
| ATOM | 3178 | C | ILE | 418 | 32.827 | 61.909 | 36.453 | 1.00 | 18.54 | A C |
| ATOM | 3179 | O | ILE | 418 | 33.535 | 62.875 | 36.190 | 1.00 | 20.83 | A O |
| ATOM | 3180 | N | SER | 419 | 32.356 | 61.671 | 37.664 | 1.00 | 19.59 | A N |
| ATOM | 3181 | CA | SER | 419 | 32.670 | 62.556 | 38.764 | 1.00 | 20.34 | A C |
| ATOM | 3182 | CB | SER | 419 | 31.523 | 63.526 | 38.996 | 1.00 | 21.79 | A C |
| ATOM | 3183 | OG | SER | 419 | 30.415 | 62.843 | 39.562 | 1.00 | 24.33 | A O |
| ATOM | 3184 | C | SER | 419 | 32.875 | 61.732 | 40.013 | 1.00 | 20.37 | A C |

FIG. 4-66

| ATOM | 3185 | O | SER | 419 | 32.783 | 60.503 | 39.988 | 1.00 | 20.32 | A | O |
|---|---|---|---|---|---|---|---|---|---|---|---|
| ATOM | 3186 | N | ASN | 420 | 33.152 | 62.427 | 41.107 | 1.00 | 19.64 | A | N |
| ATOM | 3187 | CA | ASN | 420 | 33.357 | 61.786 | 42.387 | 1.00 | 20.07 | A | C |
| ATOM | 3188 | CB | ASN | 420 | 34.773 | 62.053 | 42.863 | 1.00 | 18.49 | A | C |
| ATOM | 3189 | CG | ASN | 420 | 35.099 | 63.518 | 42.872 | 1.00 | 20.69 | A | C |
| ATOM | 3190 | OD1 | ASN | 420 | 34.210 | 64.358 | 42.741 | 1.00 | 21.49 | A | O |
| ATOM | 3191 | ND2 | ASN | 420 | 36.376 | 63.844 | 43.034 | 1.00 | 21.39 | A | N |
| ATOM | 3192 | C | ASN | 420 | 32.350 | 62.368 | 43.379 | 1.00 | 20.90 | A | C |
| ATOM | 3193 | O | ASN | 420 | 32.677 | 62.610 | 44.535 | 1.00 | 21.17 | A | O |
| ATOM | 3194 | N | GLU | 421 | 31.127 | 62.600 | 42.914 | 1.00 | 21.68 | A | N |
| ATOM | 3195 | CA | GLU | 421 | 30.081 | 63.160 | 43.761 | 1.00 | 24.26 | A | C |
| ATOM | 3196 | CB | GLU | 421 | 28.935 | 63.722 | 42.901 | 1.00 | 26.18 | A | C |
| ATOM | 3197 | CG | GLU | 421 | 27.714 | 64.214 | 43.701 | 1.00 | 25.32 | A | C |
| ATOM | 3198 | CD | GLU | 421 | 26.604 | 64.817 | 42.824 | 1.00 | 26.09 | A | C |
| ATOM | 3199 | OE1 | GLU | 421 | 25.563 | 65.237 | 43.373 | 1.00 | 24.11 | A | O |
| ATOM | 3200 | OE2 | GLU | 421 | 26.762 | 64.873 | 41.588 | 1.00 | 27.22 | A | O |
| ATOM | 3201 | C | GLU | 421 | 29.512 | 62.133 | 44.729 | 1.00 | 24.93 | A | C |
| ATOM | 3202 | O | GLU | 421 | 29.185 | 62.457 | 45.868 | 1.00 | 27.30 | A | O |
| ATOM | 3203 | N | TYR | 422 | 29.409 | 60.892 | 44.272 | 1.00 | 23.63 | A | N |
| ATOM | 3204 | CA | TYR | 422 | 28.837 | 59.826 | 45.075 | 1.00 | 23.67 | A | C |
| ATOM | 3205 | CB | TYR | 422 | 28.942 | 58.503 | 44.311 | 1.00 | 23.61 | A | C |
| ATOM | 3206 | CG | TYR | 422 | 28.015 | 57.415 | 44.813 | 1.00 | 24.39 | A | C |
| ATOM | 3207 | CD1 | TYR | 422 | 26.642 | 57.637 | 44.936 | 1.00 | 23.87 | A | C |
| ATOM | 3208 | CE1 | TYR | 422 | 25.781 | 56.618 | 45.347 | 1.00 | 22.11 | A | C |
| ATOM | 3209 | CD2 | TYR | 422 | 28.505 | 56.147 | 45.120 | 1.00 | 24.53 | A | C |
| ATOM | 3210 | CE2 | TYR | 422 | 27.654 | 55.124 | 45.533 | 1.00 | 23.32 | A | C |
| ATOM | 3211 | CZ | TYR | 422 | 26.300 | 55.367 | 45.641 | 1.00 | 23.52 | A | C |
| ATOM | 3212 | OH | TYR | 422 | 25.471 | 54.349 | 46.031 | 1.00 | 24.33 | A | O |
| ATOM | 3213 | C | TYR | 422 | 29.399 | 59.679 | 46.493 | 1.00 | 23.57 | A | C |
| ATOM | 3214 | O | TYR | 422 | 30.599 | 59.478 | 46.704 | 1.00 | 23.17 | A | O |
| ATOM | 3215 | N | LYS | 423 | 28.492 | 59.784 | 47.461 | 1.00 | 23.07 | A | N |
| ATOM | 3216 | CA | LYS | 423 | 28.813 | 59.661 | 48.878 | 1.00 | 22.04 | A | C |
| ATOM | 3217 | CB | LYS | 423 | 29.156 | 58.205 | 49.205 | 1.00 | 24.22 | A | C |
| ATOM | 3218 | CG | LYS | 423 | 27.967 | 57.266 | 49.009 | 1.00 | 25.11 | A | C |
| ATOM | 3219 | CD | LYS | 423 | 28.303 | 55.809 | 49.276 | 1.00 | 26.55 | A | C |
| ATOM | 3220 | CE | LYS | 423 | 27.079 | 54.930 | 49.002 | 1.00 | 28.11 | A | C |
| ATOM | 3221 | NZ | LYS | 423 | 27.302 | 53.498 | 49.336 | 1.00 | 27.79 | A | N |
| ATOM | 3222 | C | LYS | 423 | 29.923 | 60.583 | 49.347 | 1.00 | 21.46 | A | C |
| ATOM | 3223 | O | LYS | 423 | 30.533 | 60.340 | 50.385 | 1.00 | 20.97 | A | O |
| ATOM | 3224 | N | GLY | 424 | 30.167 | 61.647 | 48.583 | 1.00 | 21.39 | A | N |
| ATOM | 3225 | CA | GLY | 424 | 31.201 | 62.608 | 48.930 | 1.00 | 21.20 | A | C |
| ATOM | 3226 | C | GLY | 424 | 32.606 | 62.034 | 48.961 | 1.00 | 21.98 | A | C |
| ATOM | 3227 | O | GLY | 424 | 33.463 | 62.534 | 49.687 | 1.00 | 22.19 | A | O |
| ATOM | 3228 | N | MET | 425 | 32.848 | 60.991 | 48.173 | 1.00 | 22.44 | A | N |
| ATOM | 3229 | CA | MET | 425 | 34.161 | 60.350 | 48.134 | 1.00 | 23.29 | A | C |
| ATOM | 3230 | CB | MET | 425 | 34.003 | 58.826 | 48.056 | 1.00 | 24.14 | A | C |
| ATOM | 3231 | CG | MET | 425 | 33.548 | 58.187 | 49.360 | 1.00 | 25.32 | A | C |
| ATOM | 3232 | SD | MET | 425 | 33.092 | 56.451 | 49.179 | 1.00 | 29.39 | A | S |
| ATOM | 3233 | CE | MET | 425 | 34.663 | 55.611 | 49.406 | 1.00 | 27.92 | A | C |

| | | | | | | | | | | |
|---|---|---|---|---|---|---|---|---|---|---|
| ATOM | 3234 | C | MET | 425 | 35.042 | 60.827 | 46.986 | 1.00 | 22.06 | A | C |
| ATOM | 3235 | O | MET | 425 | 34.836 | 60.457 | 45.835 | 1.00 | 22.61 | A | O |
| ATOM | 3236 | N | PRO | 426 | 36.045 | 61.661 | 47.292 | 1.00 | 21.75 | A | N |
| ATOM | 3237 | CD | PRO | 426 | 36.386 | 62.215 | 48.615 | 1.00 | 21.34 | A | C |
| ATOM | 3238 | CA | PRO | 426 | 36.951 | 62.172 | 46.262 | 1.00 | 20.07 | A | C |
| ATOM | 3239 | CB | PRO | 426 | 37.943 | 63.007 | 47.062 | 1.00 | 20.22 | A | C |
| ATOM | 3240 | CG | PRO | 426 | 37.138 | 63.461 | 48.245 | 1.00 | 19.61 | A | C |
| ATOM | 3241 | C | PRO | 426 | 37.636 | 61.019 | 45.532 | 1.00 | 20.63 | A | C |
| ATOM | 3242 | O | PRO | 426 | 37.920 | 61.107 | 44.343 | 1.00 | 23.99 | A | O |
| ATOM | 3243 | N | GLY | 427 | 37.905 | 59.936 | 46.252 | 1.00 | 19.08 | A | N |
| ATOM | 3244 | CA | GLY | 427 | 38.552 | 58.789 | 45.646 | 1.00 | 18.03 | A | C |
| ATOM | 3245 | C | GLY | 427 | 37.601 | 57.838 | 44.941 | 1.00 | 18.93 | A | C |
| ATOM | 3246 | O | GLY | 427 | 37.965 | 56.706 | 44.642 | 1.00 | 21.55 | A | O |
| ATOM | 3247 | N | GLY | 428 | 36.378 | 58.285 | 44.684 | 1.00 | 18.22 | A | N |
| ATOM | 3248 | CA | GLY | 428 | 35.417 | 57.446 | 43.991 | 1.00 | 17.96 | A | C |
| ATOM | 3249 | C | GLY | 428 | 35.208 | 57.970 | 42.583 | 1.00 | 18.15 | A | C |
| ATOM | 3250 | O | GLY | 428 | 35.577 | 59.108 | 42.289 | 1.00 | 19.00 | A | O |
| ATOM | 3251 | N | ARG | 429 | 34.619 | 57.158 | 41.712 | 1.00 | 16.78 | A | N |
| ATOM | 3252 | CA | ARG | 429 | 34.389 | 57.559 | 40.320 | 1.00 | 17.38 | A | C |
| ATOM | 3253 | CB | ARG | 429 | 35.595 | 57.167 | 39.444 | 1.00 | 19.09 | A | C |
| ATOM | 3254 | CG | ARG | 429 | 36.577 | 58.292 | 39.108 | 1.00 | 20.57 | A | C |
| ATOM | 3255 | CD | ARG | 429 | 37.385 | 58.737 | 40.302 | 1.00 | 22.65 | A | C |
| ATOM | 3256 | NE | ARG | 429 | 38.359 | 59.769 | 39.956 | 1.00 | 25.75 | A | N |
| ATOM | 3257 | CZ | ARG | 429 | 39.078 | 60.445 | 40.852 | 1.00 | 26.83 | A | C |
| ATOM | 3258 | NH1 | ARG | 429 | 38.927 | 60.204 | 42.146 | 1.00 | 26.78 | A | N |
| ATOM | 3259 | NH2 | ARG | 429 | 39.957 | 61.356 | 40.456 | 1.00 | 26.24 | A | N |
| ATOM | 3260 | C | ARG | 429 | 33.134 | 56.889 | 39.756 | 1.00 | 15.74 | A | C |
| ATOM | 3261 | O | ARG | 429 | 32.976 | 55.675 | 39.857 | 1.00 | 12.14 | A | O |
| ATOM | 3262 | N | ASN | 430 | 32.256 | 57.679 | 39.146 | 1.00 | 14.98 | A | N |
| ATOM | 3263 | CA | ASN | 430 | 31.027 | 57.136 | 38.586 | 1.00 | 17.41 | A | C |
| ATOM | 3264 | CB | ASN | 430 | 29.901 | 57.216 | 39.622 | 1.00 | 17.29 | A | C |
| ATOM | 3265 | CG | ASN | 430 | 29.947 | 56.081 | 40.620 | 1.00 | 18.53 | A | C |
| ATOM | 3266 | OD1 | ASN | 430 | 29.607 | 54.938 | 40.297 | 1.00 | 16.68 | A | O |
| ATOM | 3267 | ND2 | ASN | 430 | 30.381 | 56.386 | 41.840 | 1.00 | 15.65 | A | N |
| ATOM | 3268 | C | ASN | 430 | 30.564 | 57.808 | 37.297 | 1.00 | 17.98 | A | C |
| ATOM | 3269 | O | ASN | 430 | 30.849 | 58.976 | 37.043 | 1.00 | 19.64 | A | O |
| ATOM | 3270 | N | LEU | 431 | 29.840 | 57.053 | 36.485 | 1.00 | 17.00 | A | N |
| ATOM | 3271 | CA | LEU | 431 | 29.314 | 57.576 | 35.241 | 1.00 | 17.70 | A | C |
| ATOM | 3272 | CB | LEU | 431 | 29.122 | 56.442 | 34.231 | 1.00 | 15.35 | A | C |
| ATOM | 3273 | CG | LEU | 431 | 28.478 | 56.867 | 32.913 | 1.00 | 15.33 | A | C |
| ATOM | 3274 | CD1 | LEU | 431 | 29.340 | 57.917 | 32.230 | 1.00 | 13.77 | A | C |
| ATOM | 3275 | CD2 | LEU | 431 | 28.296 | 55.645 | 32.018 | 1.00 | 17.37 | A | C |
| ATOM | 3276 | C | LEU | 431 | 27.978 | 58.279 | 35.491 | 1.00 | 19.03 | A | C |
| ATOM | 3277 | O | LEU | 431 | 27.095 | 57.750 | 36.172 | 1.00 | 17.62 | A | O |
| ATOM | 3278 | N | TYR | 432 | 27.840 | 59.475 | 34.933 | 1.00 | 20.33 | A | N |
| ATOM | 3279 | CA | TYR | 432 | 26.620 | 60.248 | 35.083 | 1.00 | 21.23 | A | C |
| ATOM | 3280 | CB | TYR | 432 | 26.848 | 61.442 | 36.014 | 1.00 | 22.85 | A | C |
| ATOM | 3281 | CG | TYR | 432 | 27.068 | 61.070 | 37.464 | 1.00 | 25.34 | A | C |
| ATOM | 3282 | CD1 | TYR | 432 | 28.320 | 60.646 | 37.921 | 1.00 | 24.87 | A | C |

FIG. 4-68

| ATOM | 3283 | CE1 | TYR | 432 | 28.519 | 60.305 | 39.267 | 1.00 | 24.97 | A | C |
|---|---|---|---|---|---|---|---|---|---|---|---|
| ATOM | 3284 | CD2 | TYR | 432 | 26.019 | 61.142 | 38.384 | 1.00 | 24.85 | A | C |
| ATOM | 3285 | CE2 | TYR | 432 | 26.205 | 60.805 | 39.723 | 1.00 | 25.31 | A | C |
| ATOM | 3286 | CZ | TYR | 432 | 27.454 | 60.388 | 40.161 | 1.00 | 25.88 | A | C |
| ATOM | 3287 | OH | TYR | 432 | 27.625 | 60.054 | 41.487 | 1.00 | 25.59 | A | O |
| ATOM | 3288 | C | TYR | 432 | 26.102 | 60.743 | 33.737 | 1.00 | 21.26 | A | C |
| ATOM | 3289 | O | TYR | 432 | 26.860 | 60.870 | 32.770 | 1.00 | 21.07 | A | O |
| ATOM | 3290 | N | LYS | 433 | 24.802 | 61.022 | 33.695 | 1.00 | 20.78 | A | N |
| ATOM | 3291 | CA | LYS | 433 | 24.133 | 61.505 | 32.496 | 1.00 | 20.98 | A | C |
| ATOM | 3292 | CB | LYS | 433 | 23.290 | 60.386 | 31.876 | 1.00 | 21.14 | A | C |
| ATOM | 3293 | CG | LYS | 433 | 22.564 | 60.827 | 30.618 | 1.00 | 25.64 | A | C |
| ATOM | 3294 | CD | LYS | 433 | 21.843 | 59.701 | 29.907 | 1.00 | 25.30 | A | C |
| ATOM | 3295 | CE | LYS | 433 | 20.643 | 59.235 | 30.682 | 1.00 | 25.25 | A | C |
| ATOM | 3296 | NZ | LYS | 433 | 19.801 | 58.370 | 29.817 | 1.00 | 27.99 | A | N |
| ATOM | 3297 | C | LYS | 433 | 23.228 | 62.687 | 32.835 | 1.00 | 20.46 | A | C |
| ATOM | 3298 | O | LYS | 433 | 22.367 | 62.587 | 33.707 | 1.00 | 21.41 | A | O |
| ATOM | 3299 | N | ILE | 434 | 23.427 | 63.812 | 32.162 | 1.00 | 20.15 | A | N |
| ATOM | 3300 | CA | ILE | 434 | 22.591 | 64.980 | 32.417 | 1.00 | 21.18 | A | C |
| ATOM | 3301 | CB | ILE | 434 | 23.427 | 66.225 | 32.815 | 1.00 | 21.51 | A | C |
| ATOM | 3302 | CG2 | ILE | 434 | 24.412 | 66.582 | 31.715 | 1.00 | 22.39 | A | C |
| ATOM | 3303 | CG1 | ILE | 434 | 22.491 | 67.404 | 33.083 | 1.00 | 22.04 | A | C |
| ATOM | 3304 | CD1 | ILE | 434 | 23.171 | 68.591 | 33.699 | 1.00 | 23.38 | A | C |
| ATOM | 3305 | C | ILE | 434 | 21.782 | 65.297 | 31.174 | 1.00 | 20.81 | A | C |
| ATOM | 3306 | O | ILE | 434 | 22.274 | 65.154 | 30.056 | 1.00 | 21.15 | A | O |
| ATOM | 3307 | N | GLN | 435 | 20.538 | 65.716 | 31.372 | 1.00 | 21.40 | A | N |
| ATOM | 3308 | CA | GLN | 435 | 19.666 | 66.034 | 30.248 | 1.00 | 23.73 | A | C |
| ATOM | 3309 | CB | GLN | 435 | 18.202 | 65.851 | 30.646 | 1.00 | 26.08 | A | C |
| ATOM | 3310 | CG | GLN | 435 | 17.227 | 66.030 | 29.496 | 1.00 | 29.99 | A | C |
| ATOM | 3311 | CD | GLN | 435 | 15.802 | 65.806 | 29.929 | 1.00 | 32.10 | A | C |
| ATOM | 3312 | OE1 | GLN | 435 | 15.446 | 64.720 | 30.372 | 1.00 | 34.41 | A | O |
| ATOM | 3313 | NE2 | GLN | 435 | 14.978 | 66.839 | 29.819 | 1.00 | 34.05 | A | N |
| ATOM | 3314 | C | GLN | 435 | 19.891 | 67.450 | 29.743 | 1.00 | 22.81 | A | C |
| ATOM | 3315 | O | GLN | 435 | 19.600 | 68.419 | 30.434 | 1.00 | 22.20 | A | O |
| ATOM | 3316 | N | LEU | 436 | 20.401 | 67.564 | 28.524 | 1.00 | 23.57 | A | N |
| ATOM | 3317 | CA | LEU | 436 | 20.679 | 68.865 | 27.951 | 1.00 | 24.55 | A | C |
| ATOM | 3318 | CB | LEU | 436 | 21.152 | 68.714 | 26.508 | 1.00 | 21.18 | A | C |
| ATOM | 3319 | CG | LEU | 436 | 22.456 | 67.939 | 26.332 | 1.00 | 21.36 | A | C |
| ATOM | 3320 | CD1 | LEU | 436 | 22.938 | 68.116 | 24.910 | 1.00 | 20.02 | A | C |
| ATOM | 3321 | CD2 | LEU | 436 | 23.510 | 68.437 | 27.317 | 1.00 | 19.70 | A | C |
| ATOM | 3322 | C | LEU | 436 | 19.491 | 69.812 | 28.020 | 1.00 | 26.85 | A | C |
| ATOM | 3323 | O | LEU | 436 | 19.672 | 71.016 | 28.168 | 1.00 | 28.66 | A | O |
| ATOM | 3324 | N | SER | 437 | 18.280 | 69.268 | 27.927 | 1.00 | 30.22 | A | N |
| ATOM | 3325 | CA | SER | 437 | 17.059 | 70.075 | 27.977 | 1.00 | 32.38 | A | C |
| ATOM | 3326 | CB | SER | 437 | 15.925 | 69.340 | 27.268 | 1.00 | 32.98 | A | C |
| ATOM | 3327 | OG | SER | 437 | 16.241 | 69.151 | 25.901 | 1.00 | 39.22 | A | O |
| ATOM | 3328 | C | SER | 437 | 16.610 | 70.437 | 29.394 | 1.00 | 33.81 | A | C |
| ATOM | 3329 | O | SER | 437 | 15.805 | 71.352 | 29.577 | 1.00 | 32.20 | A | O |
| ATOM | 3330 | N | ASP | 438 | 17.124 | 69.714 | 30.387 | 1.00 | 35.36 | A | N |
| ATOM | 3331 | CA | ASP | 438 | 16.772 | 69.955 | 31.784 | 1.00 | 36.00 | A | C |

| | | | | | | | | | | |
|---|---|---|---|---|---|---|---|---|---|---|
| ATOM | 3332 | CB | ASP | 438 | 15.468 | 69.226 | 32.123 | 1.00 | 38.49 | A | C |
| ATOM | 3333 | CG | ASP | 438 | 14.996 | 69.498 | 33.543 | 1.00 | 41.58 | A | C |
| ATOM | 3334 | OD1 | ASP | 438 | 15.820 | 69.415 | 34.480 | 1.00 | 43.35 | A | O |
| ATOM | 3335 | OD2 | ASP | 438 | 13.796 | 69.785 | 33.725 | 1.00 | 43.71 | A | O |
| ATOM | 3336 | C | ASP | 438 | 17.904 | 69.470 | 32.700 | 1.00 | 35.28 | A | C |
| ATOM | 3337 | O | ASP | 438 | 18.019 | 68.274 | 32.993 | 1.00 | 33.70 | A | O |
| ATOM | 3338 | N | TYR | 439 | 18.723 | 70.412 | 33.158 | 1.00 | 34.27 | A | N |
| ATOM | 3339 | CA | TYR | 439 | 19.862 | 70.105 | 34.013 | 1.00 | 33.69 | A | C |
| ATOM | 3340 | CB | TYR | 439 | 20.740 | 71.343 | 34.175 | 1.00 | 32.29 | A | C |
| ATOM | 3341 | CG | TYR | 439 | 21.262 | 71.886 | 32.867 | 1.00 | 30.75 | A | C |
| ATOM | 3342 | CD1 | TYR | 439 | 21.565 | 71.028 | 31.810 | 1.00 | 30.00 | A | C |
| ATOM | 3343 | CE1 | TYR | 439 | 22.071 | 71.516 | 30.611 | 1.00 | 28.65 | A | C |
| ATOM | 3344 | CD2 | TYR | 439 | 21.480 | 73.253 | 32.691 | 1.00 | 28.95 | A | C |
| ATOM | 3345 | CE2 | TYR | 439 | 21.987 | 73.749 | 31.496 | 1.00 | 27.97 | A | C |
| ATOM | 3346 | CZ | TYR | 439 | 22.281 | 72.875 | 30.462 | 1.00 | 27.72 | A | C |
| ATOM | 3347 | OH | TYR | 439 | 22.803 | 73.350 | 29.284 | 1.00 | 28.72 | A | O |
| ATOM | 3348 | C | TYR | 439 | 19.543 | 69.538 | 35.390 | 1.00 | 33.65 | A | C |
| ATOM | 3349 | O | TYR | 439 | 20.435 | 69.045 | 36.076 | 1.00 | 33.49 | A | O |
| ATOM | 3350 | N | THR | 440 | 18.285 | 69.612 | 35.806 | 1.00 | 34.13 | A | N |
| ATOM | 3351 | CA | THR | 440 | 17.917 | 69.076 | 37.115 | 1.00 | 34.14 | A | C |
| ATOM | 3352 | CB | THR | 440 | 16.561 | 69.624 | 37.609 | 1.00 | 33.49 | A | C |
| ATOM | 3353 | OG1 | THR | 440 | 15.507 | 69.114 | 36.780 | 1.00 | 32.29 | A | O |
| ATOM | 3354 | CG2 | THR | 440 | 16.559 | 71.144 | 37.571 | 1.00 | 30.29 | A | C |
| ATOM | 3355 | C | THR | 440 | 17.794 | 67.572 | 36.953 | 1.00 | 33.89 | A | C |
| ATOM | 3356 | O | THR | 440 | 17.684 | 66.829 | 37.929 | 1.00 | 35.16 | A | O |
| ATOM | 3357 | N | LYS | 441 | 17.808 | 67.141 | 35.697 | 1.00 | 32.21 | A | N |
| ATOM | 3358 | CA | LYS | 441 | 17.703 | 65.735 | 35.362 | 1.00 | 30.32 | A | C |
| ATOM | 3359 | CB | LYS | 441 | 16.871 | 65.573 | 34.088 | 1.00 | 33.16 | A | C |
| ATOM | 3360 | CG | LYS | 441 | 15.369 | 65.490 | 34.331 | 1.00 | 36.13 | A | C |
| ATOM | 3361 | CD | LYS | 441 | 14.848 | 66.671 | 35.122 | 1.00 | 39.11 | A | C |
| ATOM | 3362 | CE | LYS | 441 | 13.447 | 66.392 | 35.649 | 1.00 | 41.94 | A | C |
| ATOM | 3363 | NZ | LYS | 441 | 12.953 | 67.501 | 36.517 | 1.00 | 44.46 | A | N |
| ATOM | 3364 | C | LYS | 441 | 19.089 | 65.119 | 35.179 | 1.00 | 28.77 | A | C |
| ATOM | 3365 | O | LYS | 441 | 19.668 | 65.159 | 34.088 | 1.00 | 28.32 | A | O |
| ATOM | 3366 | N | VAL | 442 | 19.618 | 64.564 | 36.263 | 1.00 | 25.14 | A | N |
| ATOM | 3367 | CA | VAL | 442 | 20.922 | 63.929 | 36.243 | 1.00 | 24.37 | A | C |
| ATOM | 3368 | CB | VAL | 442 | 21.960 | 64.717 | 37.091 | 1.00 | 24.82 | A | C |
| ATOM | 3369 | CG1 | VAL | 442 | 23.266 | 63.936 | 37.178 | 1.00 | 22.99 | A | C |
| ATOM | 3370 | CG2 | VAL | 442 | 22.216 | 66.084 | 36.469 | 1.00 | 23.65 | A | C |
| ATOM | 3371 | C | VAL | 442 | 20.786 | 62.525 | 36.807 | 1.00 | 24.10 | A | C |
| ATOM | 3372 | O | VAL | 442 | 20.327 | 62.341 | 37.931 | 1.00 | 22.60 | A | O |
| ATOM | 3373 | N | THR | 443 | 21.189 | 61.539 | 36.014 | 1.00 | 23.16 | A | N |
| ATOM | 3374 | CA | THR | 443 | 21.109 | 60.149 | 36.419 | 1.00 | 22.78 | A | C |
| ATOM | 3375 | CB | THR | 443 | 20.352 | 59.306 | 35.375 | 1.00 | 23.02 | A | C |
| ATOM | 3376 | OG1 | THR | 443 | 19.017 | 59.802 | 35.222 | 1.00 | 27.68 | A | O |
| ATOM | 3377 | CG2 | THR | 443 | 20.301 | 57.862 | 35.800 | 1.00 | 22.12 | A | C |
| ATOM | 3378 | C | THR | 443 | 22.493 | 59.548 | 36.551 | 1.00 | 23.54 | A | C |
| ATOM | 3379 | O | THR | 443 | 23.367 | 59.792 | 35.721 | 1.00 | 23.36 | A | O |
| ATOM | 3380 | N | CYS | 444 | 22.701 | 58.761 | 37.596 | 1.00 | 23.18 | A | N |

| ATOM | 3381 | CA  | CYS | 444 | 23.981 | 58.104 | 37.747 | 1.00 | 24.13 | A | C |
|------|------|-----|-----|-----|--------|--------|--------|------|-------|---|---|
| ATOM | 3382 | C   | CYS | 444 | 23.758 | 56.712 | 37.157 | 1.00 | 22.91 | A | C |
| ATOM | 3383 | O   | CYS | 444 | 22.855 | 55.990 | 37.573 | 1.00 | 21.72 | A | O |
| ATOM | 3384 | CB  | CYS | 444 | 24.396 | 58.018 | 39.219 | 1.00 | 25.50 | A | C |
| ATOM | 3385 | SG  | CYS | 444 | 26.053 | 57.282 | 39.443 | 1.00 | 30.81 | A | S |
| ATOM | 3386 | N   | LEU | 445 | 24.573 | 56.348 | 36.175 | 1.00 | 22.64 | A | N |
| ATOM | 3387 | CA  | LEU | 445 | 24.446 | 55.053 | 35.513 | 1.00 | 22.51 | A | C |
| ATOM | 3388 | CB  | LEU | 445 | 24.799 | 55.211 | 34.035 | 1.00 | 19.29 | A | C |
| ATOM | 3389 | CG  | LEU | 445 | 24.049 | 56.349 | 33.341 | 1.00 | 19.36 | A | C |
| ATOM | 3390 | CD1 | LEU | 445 | 24.588 | 56.552 | 31.934 | 1.00 | 16.01 | A | C |
| ATOM | 3391 | CD2 | LEU | 445 | 22.559 | 56.034 | 33.319 | 1.00 | 15.72 | A | C |
| ATOM | 3392 | C   | LEU | 445 | 25.308 | 53.940 | 36.118 | 1.00 | 23.32 | A | C |
| ATOM | 3393 | O   | LEU | 445 | 25.203 | 52.783 | 35.718 | 1.00 | 24.58 | A | O |
| ATOM | 3394 | N   | SER | 446 | 26.148 | 54.274 | 37.087 | 1.00 | 23.95 | A | N |
| ATOM | 3395 | CA  | SER | 446 | 27.028 | 53.269 | 37.660 | 1.00 | 23.89 | A | C |
| ATOM | 3396 | CB  | SER | 446 | 28.469 | 53.555 | 37.222 | 1.00 | 21.87 | A | C |
| ATOM | 3397 | OG  | SER | 446 | 28.882 | 54.847 | 37.648 | 1.00 | 20.09 | A | O |
| ATOM | 3398 | C   | SER | 446 | 26.969 | 53.145 | 39.175 | 1.00 | 23.77 | A | C |
| ATOM | 3399 | O   | SER | 446 | 27.361 | 52.119 | 39.720 | 1.00 | 24.69 | A | O |
| ATOM | 3400 | N   | CYS | 447 | 26.480 | 54.184 | 39.845 | 1.00 | 24.32 | A | N |
| ATOM | 3401 | CA  | CYS | 447 | 26.382 | 54.207 | 41.309 | 1.00 | 26.45 | A | C |
| ATOM | 3402 | C   | CYS | 447 | 25.836 | 52.946 | 41.997 | 1.00 | 25.99 | A | C |
| ATOM | 3403 | O   | CYS | 447 | 26.441 | 52.425 | 42.937 | 1.00 | 24.44 | A | O |
| ATOM | 3404 | CB  | CYS | 447 | 25.518 | 55.396 | 41.763 | 1.00 | 27.33 | A | C |
| ATOM | 3405 | SG  | CYS | 447 | 26.225 | 57.049 | 41.461 | 1.00 | 34.75 | A | S |
| ATOM | 3406 | N   | GLU | 448 | 24.696 | 52.456 | 41.528 | 1.00 | 25.90 | A | N |
| ATOM | 3407 | CA  | GLU | 448 | 24.056 | 51.317 | 42.167 | 1.00 | 24.38 | A | C |
| ATOM | 3408 | CB  | GLU | 448 | 22.581 | 51.637 | 42.334 | 1.00 | 23.47 | A | C |
| ATOM | 3409 | CG  | GLU | 448 | 22.332 | 53.075 | 42.721 | 1.00 | 24.60 | A | C |
| ATOM | 3410 | CD  | GLU | 448 | 22.848 | 53.416 | 44.108 | 1.00 | 27.44 | A | C |
| ATOM | 3411 | OE1 | GLU | 448 | 22.617 | 54.562 | 44.559 | 1.00 | 29.17 | A | O |
| ATOM | 3412 | OE2 | GLU | 448 | 23.478 | 52.548 | 44.751 | 1.00 | 28.81 | A | O |
| ATOM | 3413 | C   | GLU | 448 | 24.201 | 49.941 | 41.537 | 1.00 | 23.54 | A | C |
| ATOM | 3414 | O   | GLU | 448 | 23.722 | 48.970 | 42.104 | 1.00 | 22.25 | A | O |
| ATOM | 3415 | N   | LEU | 449 | 24.844 | 49.844 | 40.377 | 1.00 | 23.78 | A | N |
| ATOM | 3416 | CA  | LEU | 449 | 25.024 | 48.547 | 39.717 | 1.00 | 23.34 | A | C |
| ATOM | 3417 | CB  | LEU | 449 | 25.988 | 48.678 | 38.548 | 1.00 | 20.76 | A | C |
| ATOM | 3418 | CG  | LEU | 449 | 25.680 | 49.712 | 37.472 | 1.00 | 21.20 | A | C |
| ATOM | 3419 | CD1 | LEU | 449 | 26.872 | 49.807 | 36.543 | 1.00 | 20.05 | A | C |
| ATOM | 3420 | CD2 | LEU | 449 | 24.424 | 49.335 | 36.711 | 1.00 | 17.29 | A | C |
| ATOM | 3421 | C   | LEU | 449 | 25.551 | 47.456 | 40.654 | 1.00 | 24.61 | A | C |
| ATOM | 3422 | O   | LEU | 449 | 25.157 | 46.298 | 40.549 | 1.00 | 26.01 | A | O |
| ATOM | 3423 | N   | ASN | 450 | 26.445 | 47.830 | 41.562 | 1.00 | 25.89 | A | N |
| ATOM | 3424 | CA  | ASN | 450 | 27.040 | 46.889 | 42.512 | 1.00 | 27.02 | A | C |
| ATOM | 3425 | CB  | ASN | 450 | 27.939 | 45.913 | 41.754 | 1.00 | 27.92 | A | C |
| ATOM | 3426 | CG  | ASN | 450 | 28.296 | 44.695 | 42.572 | 1.00 | 31.61 | A | C |
| ATOM | 3427 | OD1 | ASN | 450 | 28.521 | 44.786 | 43.783 | 1.00 | 34.65 | A | O |
| ATOM | 3428 | ND2 | ASN | 450 | 28.363 | 43.541 | 41.912 | 1.00 | 31.27 | A | N |
| ATOM | 3429 | C   | ASN | 450 | 27.877 | 47.731 | 43.488 | 1.00 | 26.54 | A | C |

| | | | | | | | | | | | |
|---|---|---|---|---|---|---|---|---|---|---|---|
| ATOM | 3430 | O | ASN | 450 | 29.099 | 47.637 | 43.523 | 1.00 | 26.25 | A | O |
| ATOM | 3431 | N | PRO | 451 | 27.210 | 48.558 | 44.303 | 1.00 | 27.04 | A | N |
| ATOM | 3432 | CD | PRO | 451 | 25.762 | 48.411 | 44.535 | 1.00 | 27.72 | A | C |
| ATOM | 3433 | CA | PRO | 451 | 27.796 | 49.465 | 45.296 | 1.00 | 27.49 | A | C |
| ATOM | 3434 | CB | PRO | 451 | 26.579 | 49.924 | 46.103 | 1.00 | 27.21 | A | C |
| ATOM | 3435 | CG | PRO | 451 | 25.638 | 48.765 | 45.989 | 1.00 | 25.73 | A | C |
| ATOM | 3436 | C | PRO | 451 | 28.938 | 48.983 | 46.187 | 1.00 | 28.75 | A | C |
| ATOM | 3437 | O | PRO | 451 | 29.877 | 49.737 | 46.433 | 1.00 | 30.69 | A | O |
| ATOM | 3438 | N | GLU | 452 | 28.873 | 47.746 | 46.666 | 1.00 | 29.54 | A | N |
| ATOM | 3439 | CA | GLU | 452 | 29.918 | 47.228 | 47.545 | 1.00 | 30.30 | A | C |
| ATOM | 3440 | CB | GLU | 452 | 29.453 | 45.937 | 48.232 | 1.00 | 33.99 | A | C |
| ATOM | 3441 | CG | GLU | 452 | 28.085 | 46.024 | 48.890 | 1.00 | 39.92 | A | C |
| ATOM | 3442 | CD | GLU | 452 | 27.817 | 44.848 | 49.813 | 1.00 | 45.87 | A | C |
| ATOM | 3443 | OE1 | GLU | 452 | 28.084 | 43.693 | 49.402 | 1.00 | 47.97 | A | O |
| ATOM | 3444 | OE2 | GLU | 452 | 27.336 | 45.076 | 50.948 | 1.00 | 47.68 | A | O |
| ATOM | 3445 | C | GLU | 452 | 31.221 | 46.946 | 46.816 | 1.00 | 29.63 | A | C |
| ATOM | 3446 | O | GLU | 452 | 32.308 | 47.199 | 47.344 | 1.00 | 30.27 | A | O |
| ATOM | 3447 | N | ARG | 453 | 31.099 | 46.425 | 45.600 | 1.00 | 27.01 | A | N |
| ATOM | 3448 | CA | ARG | 453 | 32.244 | 46.057 | 44.783 | 1.00 | 24.90 | A | C |
| ATOM | 3449 | CB | ARG | 453 | 31.950 | 44.728 | 44.085 | 1.00 | 23.08 | A | C |
| ATOM | 3450 | CG | ARG | 453 | 32.952 | 44.337 | 43.018 | 1.00 | 22.92 | A | C |
| ATOM | 3451 | CD | ARG | 453 | 32.602 | 42.995 | 42.381 | 1.00 | 20.49 | A | C |
| ATOM | 3452 | NE | ARG | 453 | 33.504 | 42.688 | 41.278 | 1.00 | 18.31 | A | N |
| ATOM | 3453 | CZ | ARG | 453 | 33.439 | 41.595 | 40.531 | 1.00 | 18.93 | A | C |
| ATOM | 3454 | NH1 | ARG | 453 | 32.510 | 40.679 | 40.763 | 1.00 | 19.77 | A | N |
| ATOM | 3455 | NH2 | ARG | 453 | 34.302 | 41.425 | 39.539 | 1.00 | 18.87 | A | N |
| ATOM | 3456 | C | ARG | 453 | 32.695 | 47.071 | 43.738 | 1.00 | 25.72 | A | C |
| ATOM | 3457 | O | ARG | 453 | 33.809 | 46.962 | 43.222 | 1.00 | 24.32 | A | O |
| ATOM | 3458 | N | CYS | 454 | 31.857 | 48.054 | 43.420 | 1.00 | 25.94 | A | N |
| ATOM | 3459 | CA | CYS | 454 | 32.233 | 49.012 | 42.385 | 1.00 | 25.49 | A | C |
| ATOM | 3460 | C | CYS | 454 | 32.038 | 50.473 | 42.699 | 1.00 | 24.24 | A | C |
| ATOM | 3461 | O | CYS | 454 | 30.922 | 50.970 | 42.688 | 1.00 | 26.79 | A | O |
| ATOM | 3462 | CB | CYS | 454 | 31.503 | 48.664 | 41.096 | 1.00 | 26.13 | A | C |
| ATOM | 3463 | SG | CYS | 454 | 32.156 | 47.128 | 40.401 | 1.00 | 30.12 | A | S |
| ATOM | 3464 | N | GLN | 455 | 33.143 | 51.165 | 42.942 | 1.00 | 22.97 | A | N |
| ATOM | 3465 | CA | GLN | 455 | 33.105 | 52.576 | 43.276 | 1.00 | 23.69 | A | C |
| ATOM | 3466 | CB | GLN | 455 | 33.536 | 52.761 | 44.736 | 1.00 | 23.41 | A | C |
| ATOM | 3467 | CG | GLN | 455 | 32.564 | 52.187 | 45.761 | 1.00 | 24.96 | A | C |
| ATOM | 3468 | CD | GLN | 455 | 33.177 | 52.065 | 47.150 | 1.00 | 29.34 | A | C |
| ATOM | 3469 | OE1 | GLN | 455 | 33.981 | 52.907 | 47.574 | 1.00 | 30.98 | A | O |
| ATOM | 3470 | NE2 | GLN | 455 | 32.790 | 51.022 | 47.872 | 1.00 | 28.59 | A | N |
| ATOM | 3471 | C | GLN | 455 | 33.992 | 53.425 | 42.360 | 1.00 | 24.57 | A | C |
| ATOM | 3472 | O | GLN | 455 | 33.837 | 54.645 | 42.294 | 1.00 | 27.40 | A | O |
| ATOM | 3473 | N | TYR | 456 | 34.919 | 52.787 | 41.654 | 1.00 | 22.57 | A | N |
| ATOM | 3474 | CA | TYR | 456 | 35.821 | 53.510 | 40.763 | 1.00 | 21.75 | A | C |
| ATOM | 3475 | CB | TYR | 456 | 37.270 | 53.187 | 41.124 | 1.00 | 20.47 | A | C |
| ATOM | 3476 | CG | TYR | 456 | 38.267 | 54.282 | 40.817 | 1.00 | 21.27 | A | C |
| ATOM | 3477 | CD1 | TYR | 456 | 38.659 | 55.193 | 41.808 | 1.00 | 20.27 | A | C |
| ATOM | 3478 | CE1 | TYR | 456 | 39.618 | 56.165 | 41.548 | 1.00 | 18.67 | A | C |

FIG. 4-72 (Continued)

| | | | | | | | | | | |
|---|---|---|---|---|---|---|---|---|---|---|
| ATOM | 3479 | CD2 | TYR | 456 | 38.858 | 54.385 | 39.552 | 1.00 | 19.29 | A | C |
| ATOM | 3480 | CE2 | TYR | 456 | 39.812 | 55.353 | 39.284 | 1.00 | 16.18 | A | C |
| ATOM | 3481 | CZ | TYR | 456 | 40.190 | 56.236 | 40.283 | 1.00 | 18.92 | A | C |
| ATOM | 3482 | OH | TYR | 456 | 41.151 | 57.183 | 40.023 | 1.00 | 19.64 | A | O |
| ATOM | 3483 | C | TYR | 456 | 35.536 | 53.061 | 39.335 | 1.00 | 21.96 | A | C |
| ATOM | 3484 | O | TYR | 456 | 35.944 | 51.972 | 38.931 | 1.00 | 22.39 | A | O |
| ATOM | 3485 | N | TYR | 457 | 34.846 | 53.899 | 38.567 | 1.00 | 22.09 | A | N |
| ATOM | 3486 | CA | TYR | 457 | 34.499 | 53.540 | 37.196 | 1.00 | 20.82 | A | C |
| ATOM | 3487 | CB | TYR | 457 | 33.001 | 53.717 | 36.956 | 1.00 | 17.91 | A | C |
| ATOM | 3488 | CG | TYR | 457 | 32.147 | 52.613 | 37.512 | 1.00 | 15.58 | A | C |
| ATOM | 3489 | CD1 | TYR | 457 | 31.644 | 52.674 | 38.811 | 1.00 | 13.21 | A | C |
| ATOM | 3490 | CE1 | TYR | 457 | 30.830 | 51.668 | 39.311 | 1.00 | 12.43 | A | C |
| ATOM | 3491 | CD2 | TYR | 457 | 31.819 | 51.512 | 36.727 | 1.00 | 16.86 | A | C |
| ATOM | 3492 | CE2 | TYR | 457 | 31.008 | 50.497 | 37.219 | 1.00 | 15.29 | A | C |
| ATOM | 3493 | CZ | TYR | 457 | 30.518 | 50.582 | 38.507 | 1.00 | 14.49 | A | C |
| ATOM | 3494 | OH | TYR | 457 | 29.728 | 49.568 | 38.985 | 1.00 | 15.62 | A | O |
| ATOM | 3495 | C | TYR | 457 | 35.232 | 54.240 | 36.066 | 1.00 | 21.27 | A | C |
| ATOM | 3496 | O | TYR | 457 | 35.842 | 55.293 | 36.227 | 1.00 | 23.18 | A | O |
| ATOM | 3497 | N | SER | 458 | 35.132 | 53.622 | 34.901 | 1.00 | 21.68 | A | N |
| ATOM | 3498 | CA | SER | 458 | 35.739 | 54.108 | 33.683 | 1.00 | 21.74 | A | C |
| ATOM | 3499 | CB | SER | 458 | 37.083 | 53.429 | 33.474 | 1.00 | 23.93 | A | C |
| ATOM | 3500 | OG | SER | 458 | 37.510 | 53.569 | 32.141 | 1.00 | 29.63 | A | O |
| ATOM | 3501 | C | SER | 458 | 34.751 | 53.664 | 32.621 | 1.00 | 21.73 | A | C |
| ATOM | 3502 | O | SER | 458 | 34.072 | 52.652 | 32.804 | 1.00 | 20.08 | A | O |
| ATOM | 3503 | N | VAL | 459 | 34.665 | 54.405 | 31.520 | 1.00 | 20.58 | A | N |
| ATOM | 3504 | CA | VAL | 459 | 33.722 | 54.061 | 30.468 | 1.00 | 19.99 | A | C |
| ATOM | 3505 | CB | VAL | 459 | 32.457 | 54.949 | 30.568 | 1.00 | 19.45 | A | C |
| ATOM | 3506 | CG1 | VAL | 459 | 32.816 | 56.392 | 30.308 | 1.00 | 19.10 | A | C |
| ATOM | 3507 | CG2 | VAL | 459 | 31.397 | 54.475 | 29.595 | 1.00 | 20.30 | A | C |
| ATOM | 3508 | C | VAL | 459 | 34.309 | 54.161 | 29.059 | 1.00 | 19.99 | A | C |
| ATOM | 3509 | O | VAL | 459 | 35.314 | 54.835 | 28.831 | 1.00 | 21.13 | A | O |
| ATOM | 3510 | N | SER | 460 | 33.667 | 53.472 | 28.122 | 1.00 | 18.73 | A | N |
| ATOM | 3511 | CA | SER | 460 | 34.083 | 53.456 | 26.728 | 1.00 | 16.25 | A | C |
| ATOM | 3512 | CB | SER | 460 | 34.970 | 52.230 | 26.476 | 1.00 | 16.33 | A | C |
| ATOM | 3513 | OG | SER | 460 | 35.476 | 52.194 | 25.151 | 1.00 | 15.85 | A | O |
| ATOM | 3514 | C | SER | 460 | 32.809 | 53.377 | 25.883 | 1.00 | 15.70 | A | C |
| ATOM | 3515 | O | SER | 460 | 32.156 | 52.342 | 25.841 | 1.00 | 14.81 | A | O |
| ATOM | 3516 | N | PHE | 461 | 32.450 | 54.475 | 25.226 | 1.00 | 16.00 | A | N |
| ATOM | 3517 | CA | PHE | 461 | 31.245 | 54.512 | 24.398 | 1.00 | 16.27 | A | C |
| ATOM | 3518 | CB | PHE | 461 | 30.636 | 55.921 | 24.367 | 1.00 | 15.50 | A | C |
| ATOM | 3519 | CG | PHE | 461 | 30.001 | 56.351 | 25.660 | 1.00 | 15.11 | A | C |
| ATOM | 3520 | CD1 | PHE | 461 | 30.779 | 56.764 | 26.735 | 1.00 | 14.16 | A | C |
| ATOM | 3521 | CD2 | PHE | 461 | 28.617 | 56.340 | 25.804 | 1.00 | 14.86 | A | C |
| ATOM | 3522 | CE1 | PHE | 461 | 30.190 | 57.158 | 27.931 | 1.00 | 12.94 | A | C |
| ATOM | 3523 | CE2 | PHE | 461 | 28.021 | 56.733 | 26.996 | 1.00 | 12.76 | A | C |
| ATOM | 3524 | CZ | PHE | 461 | 28.811 | 57.142 | 28.061 | 1.00 | 11.01 | A | C |
| ATOM | 3525 | C | PHE | 461 | 31.551 | 54.102 | 22.971 | 1.00 | 17.94 | A | C |
| ATOM | 3526 | O | PHE | 461 | 32.686 | 54.234 | 22.514 | 1.00 | 17.07 | A | O |
| ATOM | 3527 | N | SER | 462 | 30.532 | 53.612 | 22.269 | 1.00 | 19.22 | A | N |

FIG. 4-73 (Continued)

| | | | | | | | | | | | |
|---|---|---|---|---|---|---|---|---|---|---|---|
| ATOM | 3528 | CA | SER | 462 | 30.694 | 53.212 | 20.877 | 1.00 | 23.70 | A | C |
| ATOM | 3529 | CB | SER | 462 | 29.494 | 52.381 | 20.399 | 1.00 | 23.50 | A | C |
| ATOM | 3530 | OG | SER | 462 | 28.308 | 53.145 | 20.397 | 1.00 | 24.06 | A | O |
| ATOM | 3531 | C | SER | 462 | 30.804 | 54.496 | 20.058 | 1.00 | 24.95 | A | C |
| ATOM | 3532 | O | SER | 462 | 30.572 | 55.581 | 20.577 | 1.00 | 25.95 | A | O |
| ATOM | 3533 | N | LYS | 463 | 31.153 | 54.373 | 18.784 | 1.00 | 27.50 | A | N |
| ATOM | 3534 | CA | LYS | 463 | 31.323 | 55.536 | 17.920 | 1.00 | 31.80 | A | C |
| ATOM | 3535 | CB | LYS | 463 | 31.587 | 55.084 | 16.484 | 1.00 | 33.43 | A | C |
| ATOM | 3536 | CG | LYS | 463 | 33.047 | 55.199 | 16.075 | 1.00 | 35.54 | A | C |
| ATOM | 3537 | CD | LYS | 463 | 33.972 | 54.435 | 17.007 | 1.00 | 36.78 | A | C |
| ATOM | 3538 | CE | LYS | 463 | 35.433 | 54.724 | 16.673 | 1.00 | 39.20 | A | C |
| ATOM | 3539 | NZ | LYS | 463 | 36.384 | 54.098 | 17.641 | 1.00 | 40.26 | A | N |
| ATOM | 3540 | C | LYS | 463 | 30.226 | 56.602 | 17.934 | 1.00 | 33.39 | A | C |
| ATOM | 3541 | O | LYS | 463 | 30.484 | 57.745 | 17.561 | 1.00 | 36.36 | A | O |
| ATOM | 3542 | N | GLU | 464 | 29.015 | 56.254 | 18.354 | 1.00 | 33.23 | A | N |
| ATOM | 3543 | CA | GLU | 464 | 27.945 | 57.247 | 18.410 | 1.00 | 34.54 | A | C |
| ATOM | 3544 | CB | GLU | 464 | 26.960 | 57.058 | 17.256 | 1.00 | 39.82 | A | C |
| ATOM | 3545 | CG | GLU | 464 | 27.528 | 57.366 | 15.882 | 1.00 | 44.96 | A | C |
| ATOM | 3546 | CD | GLU | 464 | 26.578 | 56.961 | 14.772 | 1.00 | 48.72 | A | C |
| ATOM | 3547 | OE1 | GLU | 464 | 25.439 | 57.480 | 14.752 | 1.00 | 50.39 | A | O |
| ATOM | 3548 | OE2 | GLU | 464 | 26.967 | 56.120 | 13.926 | 1.00 | 50.59 | A | O |
| ATOM | 3549 | C | GLU | 464 | 27.186 | 57.202 | 19.729 | 1.00 | 32.77 | A | C |
| ATOM | 3550 | O | GLU | 464 | 26.047 | 57.659 | 19.814 | 1.00 | 32.03 | A | O |
| ATOM | 3551 | N | ALA | 465 | 27.823 | 56.636 | 20.748 | 1.00 | 31.17 | A | N |
| ATOM | 3552 | CA | ALA | 465 | 27.241 | 56.546 | 22.081 | 1.00 | 29.63 | A | C |
| ATOM | 3553 | CB | ALA | 465 | 26.889 | 57.935 | 22.577 | 1.00 | 28.36 | A | C |
| ATOM | 3554 | C | ALA | 465 | 26.015 | 55.645 | 22.164 | 1.00 | 29.47 | A | C |
| ATOM | 3555 | O | ALA | 465 | 25.176 | 55.824 | 23.042 | 1.00 | 28.66 | A | O |
| ATOM | 3556 | N | LYS | 466 | 25.905 | 54.678 | 21.259 | 1.00 | 28.89 | A | N |
| ATOM | 3557 | CA | LYS | 466 | 24.763 | 53.772 | 21.274 | 1.00 | 28.97 | A | C |
| ATOM | 3558 | CB | LYS | 466 | 24.585 | 53.122 | 19.899 | 1.00 | 30.98 | A | C |
| ATOM | 3559 | CG | LYS | 466 | 23.208 | 52.509 | 19.649 | 1.00 | 31.77 | A | C |
| ATOM | 3560 | CD | LYS | 466 | 23.045 | 52.179 | 18.171 | 1.00 | 34.52 | A | C |
| ATOM | 3561 | CE | LYS | 466 | 21.632 | 51.757 | 17.814 | 1.00 | 35.82 | A | C |
| ATOM | 3562 | NZ | LYS | 466 | 21.273 | 50.441 | 18.404 | 1.00 | 38.42 | A | N |
| ATOM | 3563 | C | LYS | 466 | 24.987 | 52.704 | 22.339 | 1.00 | 28.20 | A | C |
| ATOM | 3564 | O | LYS | 466 | 24.040 | 52.126 | 22.869 | 1.00 | 27.93 | A | O |
| ATOM | 3565 | N | TYR | 467 | 26.252 | 52.446 | 22.646 | 1.00 | 26.93 | A | N |
| ATOM | 3566 | CA | TYR | 467 | 26.599 | 51.458 | 23.654 | 1.00 | 26.21 | A | C |
| ATOM | 3567 | CB | TYR | 467 | 26.955 | 50.119 | 23.003 | 1.00 | 27.94 | A | C |
| ATOM | 3568 | CG | TYR | 467 | 25.823 | 49.502 | 22.207 | 1.00 | 30.39 | A | C |
| ATOM | 3569 | CD1 | TYR | 467 | 25.550 | 49.917 | 20.903 | 1.00 | 29.93 | A | C |
| ATOM | 3570 | CE1 | TYR | 467 | 24.494 | 49.373 | 20.184 | 1.00 | 31.13 | A | C |
| ATOM | 3571 | CD2 | TYR | 467 | 25.009 | 48.522 | 22.768 | 1.00 | 29.73 | A | C |
| ATOM | 3572 | CE2 | TYR | 467 | 23.953 | 47.975 | 22.060 | 1.00 | 30.29 | A | C |
| ATOM | 3573 | CZ | TYR | 467 | 23.698 | 48.405 | 20.770 | 1.00 | 30.97 | A | C |
| ATOM | 3574 | OH | TYR | 467 | 22.625 | 47.890 | 20.079 | 1.00 | 32.01 | A | O |
| ATOM | 3575 | C | TYR | 467 | 27.777 | 51.949 | 24.470 | 1.00 | 24.00 | A | C |
| ATOM | 3576 | O | TYR | 467 | 28.491 | 52.852 | 24.064 | 1.00 | 24.63 | A | O |

FIG. 4-74 (Continued)

| ATOM | 3577 | N   | TYR | 468 | 27.969 | 51.370 | 25.641 | 1.00 | 23.06 | A | N |
|------|------|-----|-----|-----|--------|--------|--------|------|-------|---|---|
| ATOM | 3578 | CA  | TYR | 468 | 29.091 | 51.765 | 26.462 | 1.00 | 22.80 | A | C |
| ATOM | 3579 | CB  | TYR | 468 | 28.801 | 53.043 | 27.249 | 1.00 | 23.88 | A | C |
| ATOM | 3580 | CG  | TYR | 468 | 27.588 | 53.011 | 28.155 | 1.00 | 24.49 | A | C |
| ATOM | 3581 | CD1 | TYR | 468 | 26.308 | 53.214 | 27.646 | 1.00 | 23.81 | A | C |
| ATOM | 3582 | CE1 | TYR | 468 | 25.206 | 53.308 | 28.486 | 1.00 | 25.51 | A | C |
| ATOM | 3583 | CD2 | TYR | 468 | 27.734 | 52.883 | 29.537 | 1.00 | 26.39 | A | C |
| ATOM | 3584 | CE2 | TYR | 468 | 26.638 | 52.971 | 30.390 | 1.00 | 25.67 | A | C |
| ATOM | 3585 | CZ  | TYR | 468 | 25.380 | 53.191 | 29.857 | 1.00 | 25.81 | A | C |
| ATOM | 3586 | OH  | TYR | 468 | 24.304 | 53.334 | 30.695 | 1.00 | 25.95 | A | O |
| ATOM | 3587 | C   | TYR | 468 | 29.501 | 50.675 | 27.411 | 1.00 | 21.32 | A | C |
| ATOM | 3588 | O   | TYR | 468 | 28.672 | 50.059 | 28.070 | 1.00 | 22.73 | A | O |
| ATOM | 3589 | N   | GLN | 469 | 30.800 | 50.431 | 27.449 | 1.00 | 20.26 | A | N |
| ATOM | 3590 | CA  | GLN | 469 | 31.368 | 49.429 | 28.315 | 1.00 | 19.27 | A | C |
| ATOM | 3591 | CB  | GLN | 469 | 32.643 | 48.864 | 27.695 | 1.00 | 20.12 | A | C |
| ATOM | 3592 | CG  | GLN | 469 | 33.460 | 47.993 | 28.632 | 1.00 | 21.72 | A | C |
| ATOM | 3593 | CD  | GLN | 469 | 34.891 | 47.845 | 28.169 | 1.00 | 23.85 | A | C |
| ATOM | 3594 | OE1 | GLN | 469 | 35.605 | 48.837 | 28.011 | 1.00 | 25.81 | A | O |
| ATOM | 3595 | NE2 | GLN | 469 | 35.322 | 46.609 | 27.948 | 1.00 | 23.84 | A | N |
| ATOM | 3596 | C   | GLN | 469 | 31.712 | 50.158 | 29.589 | 1.00 | 19.50 | A | C |
| ATOM | 3597 | O   | GLN | 469 | 32.331 | 51.226 | 29.549 | 1.00 | 19.63 | A | O |
| ATOM | 3598 | N   | LEU | 470 | 31.277 | 49.611 | 30.716 | 1.00 | 19.27 | A | N |
| ATOM | 3599 | CA  | LEU | 470 | 31.602 | 50.203 | 32.002 | 1.00 | 20.27 | A | C |
| ATOM | 3600 | CB  | LEU | 470 | 30.410 | 50.136 | 32.961 | 1.00 | 20.14 | A | C |
| ATOM | 3601 | CG  | LEU | 470 | 29.442 | 51.323 | 32.929 | 1.00 | 21.50 | A | C |
| ATOM | 3602 | CD1 | LEU | 470 | 28.373 | 51.132 | 33.996 | 1.00 | 19.33 | A | C |
| ATOM | 3603 | CD2 | LEU | 470 | 30.200 | 52.620 | 33.184 | 1.00 | 19.44 | A | C |
| ATOM | 3604 | C   | LEU | 470 | 32.768 | 49.380 | 32.531 | 1.00 | 20.91 | A | C |
| ATOM | 3605 | O   | LEU | 470 | 32.785 | 48.152 | 32.409 | 1.00 | 19.97 | A | O |
| ATOM | 3606 | N   | ARG | 471 | 33.753 | 50.050 | 33.102 | 1.00 | 22.57 | A | N |
| ATOM | 3607 | CA  | ARG | 471 | 34.917 | 49.344 | 33.610 | 1.00 | 25.83 | A | C |
| ATOM | 3608 | CB  | ARG | 471 | 36.137 | 49.690 | 32.748 | 1.00 | 29.78 | A | C |
| ATOM | 3609 | CG  | ARG | 471 | 35.927 | 49.386 | 31.261 | 1.00 | 31.73 | A | C |
| ATOM | 3610 | CD  | ARG | 471 | 37.091 | 49.871 | 30.426 | 1.00 | 35.14 | A | C |
| ATOM | 3611 | NE  | ARG | 471 | 36.939 | 51.261 | 30.005 | 1.00 | 35.86 | A | N |
| ATOM | 3612 | CZ  | ARG | 471 | 37.961 | 52.061 | 29.723 | 1.00 | 35.39 | A | C |
| ATOM | 3613 | NH1 | ARG | 471 | 39.202 | 51.606 | 29.830 | 1.00 | 37.87 | A | N |
| ATOM | 3614 | NH2 | ARG | 471 | 37.747 | 53.304 | 29.321 | 1.00 | 36.33 | A | N |
| ATOM | 3615 | C   | ARG | 471 | 35.171 | 49.686 | 35.064 | 1.00 | 24.89 | A | C |
| ATOM | 3616 | O   | ARG | 471 | 35.685 | 50.750 | 35.388 | 1.00 | 27.07 | A | O |
| ATOM | 3617 | N   | CYS | 472 | 34.794 | 48.766 | 35.935 | 1.00 | 24.59 | A | N |
| ATOM | 3618 | CA  | CYS | 472 | 34.948 | 48.925 | 37.373 | 1.00 | 25.55 | A | C |
| ATOM | 3619 | C   | CYS | 472 | 36.328 | 48.418 | 37.806 | 1.00 | 23.33 | A | C |
| ATOM | 3620 | O   | CYS | 472 | 36.738 | 47.319 | 37.433 | 1.00 | 22.34 | A | O |
| ATOM | 3621 | CB  | CYS | 472 | 33.812 | 48.150 | 38.059 | 1.00 | 26.66 | A | C |
| ATOM | 3622 | SG  | CYS | 472 | 34.037 | 47.670 | 39.797 | 1.00 | 33.06 | A | S |
| ATOM | 3623 | N   | SER | 473 | 37.049 | 49.219 | 38.583 | 1.00 | 22.51 | A | N |
| ATOM | 3624 | CA  | SER | 473 | 38.377 | 48.809 | 39.022 | 1.00 | 23.17 | A | C |
| ATOM | 3625 | CB  | SER | 473 | 39.446 | 49.724 | 38.414 | 1.00 | 21.92 | A | C |

| ATOM | 3626 | OG | SER | 473 | 39.500 | 50.976 | 39.071 | 1.00 | 23.39 | A | O |
| --- | --- | --- | --- | --- | --- | --- | --- | --- | --- | --- | --- |
| ATOM | 3627 | C | SER | 473 | 38.557 | 48.754 | 40.536 | 1.00 | 23.29 | A | C |
| ATOM | 3628 | O | SER | 473 | 39.685 | 48.758 | 41.028 | 1.00 | 24.44 | A | O |
| ATOM | 3629 | N | GLY | 474 | 37.457 | 48.697 | 41.279 | 1.00 | 23.29 | A | N |
| ATOM | 3630 | CA | GLY | 474 | 37.573 | 48.627 | 42.724 | 1.00 | 23.91 | A | C |
| ATOM | 3631 | C | GLY | 474 | 36.330 | 49.075 | 43.459 | 1.00 | 24.41 | A | C |
| ATOM | 3632 | O | GLY | 474 | 35.434 | 49.658 | 42.849 | 1.00 | 25.28 | A | O |
| ATOM | 3633 | N | PRO | 475 | 36.257 | 48.850 | 44.780 | 1.00 | 24.58 | A | N |
| ATOM | 3634 | CD | PRO | 475 | 35.174 | 49.389 | 45.623 | 1.00 | 25.74 | A | C |
| ATOM | 3635 | CA | PRO | 475 | 37.280 | 48.206 | 45.609 | 1.00 | 24.00 | A | C |
| ATOM | 3636 | CB | PRO | 475 | 36.887 | 48.620 | 47.022 | 1.00 | 22.53 | A | C |
| ATOM | 3637 | CG | PRO | 475 | 35.419 | 48.692 | 46.945 | 1.00 | 25.59 | A | C |
| ATOM | 3638 | C | PRO | 475 | 37.397 | 46.692 | 45.462 | 1.00 | 24.86 | A | C |
| ATOM | 3639 | O | PRO | 475 | 38.294 | 46.081 | 46.044 | 1.00 | 26.60 | A | O |
| ATOM | 3640 | N | GLY | 476 | 36.502 | 46.085 | 44.691 | 1.00 | 24.35 | A | N |
| ATOM | 3641 | CA | GLY | 476 | 36.564 | 44.646 | 44.498 | 1.00 | 23.50 | A | C |
| ATOM | 3642 | C | GLY | 476 | 37.324 | 44.316 | 43.227 | 1.00 | 24.87 | A | C |
| ATOM | 3643 | O | GLY | 476 | 37.925 | 45.198 | 42.613 | 1.00 | 24.65 | A | O |
| ATOM | 3644 | N | LEU | 477 | 37.308 | 43.054 | 42.818 | 1.00 | 24.78 | A | N |
| ATOM | 3645 | CA | LEU | 477 | 38.003 | 42.681 | 41.601 | 1.00 | 25.85 | A | C |
| ATOM | 3646 | CB | LEU | 477 | 37.927 | 41.171 | 41.383 | 1.00 | 26.86 | A | C |
| ATOM | 3647 | CG | LEU | 477 | 38.661 | 40.296 | 42.404 | 1.00 | 27.45 | A | C |
| ATOM | 3648 | CD1 | LEU | 477 | 38.626 | 38.851 | 41.943 | 1.00 | 27.65 | A | C |
| ATOM | 3649 | CD2 | LEU | 477 | 40.102 | 40.759 | 42.556 | 1.00 | 27.87 | A | C |
| ATOM | 3650 | C | LEU | 477 | 37.369 | 43.417 | 40.424 | 1.00 | 27.45 | A | C |
| ATOM | 3651 | O | LEU | 477 | 36.160 | 43.663 | 40.405 | 1.00 | 27.68 | A | O |
| ATOM | 3652 | N | PRO | 478 | 38.183 | 43.792 | 39.428 | 1.00 | 27.18 | A | N |
| ATOM | 3653 | CD | PRO | 478 | 39.645 | 43.637 | 39.362 | 1.00 | 27.65 | A | C |
| ATOM | 3654 | CA | PRO | 478 | 37.684 | 44.505 | 38.253 | 1.00 | 25.83 | A | C |
| ATOM | 3655 | CB | PRO | 478 | 38.908 | 44.569 | 37.351 | 1.00 | 27.68 | A | C |
| ATOM | 3656 | CG | PRO | 478 | 40.023 | 44.676 | 38.335 | 1.00 | 27.43 | A | C |
| ATOM | 3657 | C | PRO | 478 | 36.509 | 43.806 | 37.591 | 1.00 | 24.68 | A | C |
| ATOM | 3658 | O | PRO | 478 | 36.464 | 42.583 | 37.506 | 1.00 | 23.74 | A | O |
| ATOM | 3659 | N | LEU | 479 | 35.561 | 44.600 | 37.116 | 1.00 | 24.02 | A | N |
| ATOM | 3660 | CA | LEU | 479 | 34.376 | 44.068 | 36.465 | 1.00 | 23.10 | A | C |
| ATOM | 3661 | CB | LEU | 479 | 33.186 | 44.151 | 37.420 | 1.00 | 21.62 | A | C |
| ATOM | 3662 | CG | LEU | 479 | 31.845 | 43.702 | 36.854 | 1.00 | 21.11 | A | C |
| ATOM | 3663 | CD1 | LEU | 479 | 31.915 | 42.245 | 36.430 | 1.00 | 21.98 | A | C |
| ATOM | 3664 | CD2 | LEU | 479 | 30.778 | 43.901 | 37.912 | 1.00 | 24.17 | A | C |
| ATOM | 3665 | C | LEU | 479 | 34.077 | 44.857 | 35.199 | 1.00 | 22.18 | A | C |
| ATOM | 3666 | O | LEU | 479 | 33.942 | 46.073 | 35.244 | 1.00 | 22.27 | A | O |
| ATOM | 3667 | N | TYR | 480 | 33.978 | 44.160 | 34.073 | 1.00 | 22.51 | A | N |
| ATOM | 3668 | CA | TYR | 480 | 33.690 | 44.801 | 32.790 | 1.00 | 22.76 | A | C |
| ATOM | 3669 | CB | TYR | 480 | 34.709 | 44.353 | 31.749 | 1.00 | 22.59 | A | C |
| ATOM | 3670 | CG | TYR | 480 | 36.123 | 44.657 | 32.147 | 1.00 | 21.95 | A | C |
| ATOM | 3671 | CD1 | TYR | 480 | 36.702 | 45.885 | 31.843 | 1.00 | 22.81 | A | C |
| ATOM | 3672 | CE1 | TYR | 480 | 37.999 | 46.190 | 32.249 | 1.00 | 23.84 | A | C |
| ATOM | 3673 | CD2 | TYR | 480 | 36.872 | 43.733 | 32.870 | 1.00 | 22.05 | A | C |
| ATOM | 3674 | CE2 | TYR | 480 | 38.165 | 44.027 | 33.286 | 1.00 | 23.52 | A | C |

| ATOM | 3675 | CZ | TYR | 480 | 38.722 | 45.257 | 32.971 | 1.00 | 24.29 | A | C |
|---|---|---|---|---|---|---|---|---|---|---|---|
| ATOM | 3676 | OH | TYR | 480 | 39.998 | 45.556 | 33.379 | 1.00 | 26.37 | A | O |
| ATOM | 3677 | C | TYR | 480 | 32.291 | 44.422 | 32.326 | 1.00 | 23.22 | A | C |
| ATOM | 3678 | O | TYR | 480 | 31.964 | 43.239 | 32.243 | 1.00 | 23.21 | A | O |
| ATOM | 3679 | N | THR | 481 | 31.472 | 45.425 | 32.017 | 1.00 | 23.50 | A | N |
| ATOM | 3680 | CA | THR | 481 | 30.101 | 45.181 | 31.577 | 1.00 | 22.82 | A | C |
| ATOM | 3681 | CB | THR | 481 | 29.097 | 45.513 | 32.702 | 1.00 | 22.81 | A | C |
| ATOM | 3682 | OG1 | THR | 481 | 29.190 | 46.905 | 33.024 | 1.00 | 23.28 | A | O |
| ATOM | 3683 | CG2 | THR | 481 | 29.398 | 44.699 | 33.951 | 1.00 | 21.29 | A | C |
| ATOM | 3684 | C | THR | 481 | 29.740 | 46.015 | 30.351 | 1.00 | 23.25 | A | C |
| ATOM | 3685 | O | THR | 481 | 30.298 | 47.091 | 30.136 | 1.00 | 24.47 | A | O |
| ATOM | 3686 | N | LEU | 482 | 28.809 | 45.512 | 29.547 | 1.00 | 23.21 | A | N |
| ATOM | 3687 | CA | LEU | 482 | 28.363 | 46.219 | 28.350 | 1.00 | 23.54 | A | C |
| ATOM | 3688 | CB | LEU | 482 | 28.310 | 45.268 | 27.155 | 1.00 | 22.93 | A | C |
| ATOM | 3689 | CG | LEU | 482 | 28.216 | 45.922 | 25.773 | 1.00 | 23.14 | A | C |
| ATOM | 3690 | CD1 | LEU | 482 | 29.483 | 46.721 | 25.507 | 1.00 | 23.20 | A | C |
| ATOM | 3691 | CD2 | LEU | 482 | 28.043 | 44.861 | 24.699 | 1.00 | 22.53 | A | C |
| ATOM | 3692 | C | LEU | 482 | 26.981 | 46.767 | 28.643 | 1.00 | 23.83 | A | C |
| ATOM | 3693 | O | LEU | 482 | 26.254 | 46.207 | 29.458 | 1.00 | 25.57 | A | O |
| ATOM | 3694 | N | HIS | 483 | 26.610 | 47.861 | 27.994 | 1.00 | 22.84 | A | N |
| ATOM | 3695 | CA | HIS | 483 | 25.301 | 48.459 | 28.231 | 1.00 | 22.49 | A | C |
| ATOM | 3696 | CB | HIS | 483 | 25.420 | 49.528 | 29.321 | 1.00 | 22.16 | A | C |
| ATOM | 3697 | CG | HIS | 483 | 26.003 | 49.025 | 30.604 | 1.00 | 24.44 | A | C |
| ATOM | 3698 | CD2 | HIS | 483 | 27.289 | 48.904 | 31.012 | 1.00 | 25.98 | A | C |
| ATOM | 3699 | ND1 | HIS | 483 | 25.228 | 48.567 | 31.648 | 1.00 | 25.15 | A | N |
| ATOM | 3700 | CE1 | HIS | 483 | 26.011 | 48.189 | 32.644 | 1.00 | 23.97 | A | C |
| ATOM | 3701 | NE2 | HIS | 483 | 27.266 | 48.382 | 32.283 | 1.00 | 22.74 | A | N |
| ATOM | 3702 | C | HIS | 483 | 24.764 | 49.097 | 26.950 | 1.00 | 22.46 | A | C |
| ATOM | 3703 | O | HIS | 483 | 25.507 | 49.281 | 25.987 | 1.00 | 24.72 | A | O |
| ATOM | 3704 | N | SER | 484 | 23.475 | 49.427 | 26.932 | 1.00 | 20.23 | A | N |
| ATOM | 3705 | CA | SER | 484 | 22.890 | 50.078 | 25.768 | 1.00 | 19.27 | A | C |
| ATOM | 3706 | CB | SER | 484 | 21.789 | 49.216 | 25.164 | 1.00 | 19.99 | A | C |
| ATOM | 3707 | OG | SER | 484 | 20.721 | 49.057 | 26.068 | 1.00 | 26.06 | A | O |
| ATOM | 3708 | C | SER | 484 | 22.335 | 51.427 | 26.213 | 1.00 | 19.12 | A | C |
| ATOM | 3709 | O | SER | 484 | 21.656 | 51.521 | 27.232 | 1.00 | 19.17 | A | O |
| ATOM | 3710 | N | SER | 485 | 22.628 | 52.470 | 25.445 | 1.00 | 19.29 | A | N |
| ATOM | 3711 | CA | SER | 485 | 22.198 | 53.823 | 25.783 | 1.00 | 20.52 | A | C |
| ATOM | 3712 | CB | SER | 485 | 23.025 | 54.841 | 25.000 | 1.00 | 20.72 | A | C |
| ATOM | 3713 | OG | SER | 485 | 24.386 | 54.769 | 25.379 | 1.00 | 23.68 | A | O |
| ATOM | 3714 | C | SER | 485 | 20.727 | 54.160 | 25.604 | 1.00 | 20.05 | A | C |
| ATOM | 3715 | O | SER | 485 | 20.208 | 55.040 | 26.287 | 1.00 | 18.92 | A | O |
| ATOM | 3716 | N | VAL | 486 | 20.055 | 53.477 | 24.688 | 1.00 | 20.23 | A | N |
| ATOM | 3717 | CA | VAL | 486 | 18.653 | 53.764 | 24.444 | 1.00 | 19.23 | A | C |
| ATOM | 3718 | CB | VAL | 486 | 18.058 | 52.816 | 23.380 | 1.00 | 19.24 | A | C |
| ATOM | 3719 | CG1 | VAL | 486 | 18.099 | 51.383 | 23.869 | 1.00 | 19.40 | A | C |
| ATOM | 3720 | CG2 | VAL | 486 | 16.635 | 53.223 | 23.070 | 1.00 | 20.10 | A | C |
| ATOM | 3721 | C | VAL | 486 | 17.817 | 53.655 | 25.705 | 1.00 | 19.72 | A | C |
| ATOM | 3722 | O | VAL | 486 | 16.869 | 54.415 | 25.887 | 1.00 | 20.98 | A | O |
| ATOM | 3723 | N | ASN | 487 | 18.190 | 52.727 | 26.581 | 1.00 | 20.80 | A | N |

FIG. 4-77

| ATOM | 3724 | CA | ASN | 487 | 17.458 | 52.464 | 27.824 | 1.00 | 20.70 | A | C |
|---|---|---|---|---|---|---|---|---|---|---|---|
| ATOM | 3725 | CB | ASN | 487 | 16.587 | 51.229 | 27.620 | 1.00 | 18.89 | A | C |
| ATOM | 3726 | CG | ASN | 487 | 17.403 | 50.007 | 27.171 | 1.00 | 22.56 | A | C |
| ATOM | 3727 | OD1 | ASN | 487 | 16.853 | 48.948 | 26.864 | 1.00 | 24.29 | A | O |
| ATOM | 3728 | ND2 | ASN | 487 | 18.722 | 50.158 | 27.132 | 1.00 | 20.73 | A | N |
| ATOM | 3729 | C | ASN | 487 | 18.354 | 52.220 | 29.047 | 1.00 | 22.59 | A | C |
| ATOM | 3730 | O | ASN | 487 | 17.865 | 51.758 | 30.079 | 1.00 | 22.43 | A | O |
| ATOM | 3731 | N | ASP | 488 | 19.650 | 52.514 | 28.929 | 1.00 | 23.24 | A | N |
| ATOM | 3732 | CA | ASP | 488 | 20.606 | 52.290 | 30.015 | 1.00 | 23.32 | A | C |
| ATOM | 3733 | CB | ASP | 488 | 20.415 | 53.304 | 31.148 | 1.00 | 24.08 | A | C |
| ATOM | 3734 | CG | ASP | 488 | 20.780 | 54.718 | 30.750 | 1.00 | 24.71 | A | C |
| ATOM | 3735 | OD1 | ASP | 488 | 21.933 | 54.956 | 30.345 | 1.00 | 25.68 | A | O |
| ATOM | 3736 | OD2 | ASP | 488 | 19.907 | 55.601 | 30.862 | 1.00 | 26.77 | A | O |
| ATOM | 3737 | C | ASP | 488 | 20.488 | 50.883 | 30.608 | 1.00 | 24.38 | A | C |
| ATOM | 3738 | O | ASP | 488 | 20.709 | 50.689 | 31.803 | 1.00 | 24.38 | A | O |
| ATOM | 3739 | N | LYS | 489 | 20.127 | 49.902 | 29.791 | 1.00 | 24.63 | A | N |
| ATOM | 3740 | CA | LYS | 489 | 20.009 | 48.541 | 30.300 | 1.00 | 25.48 | A | C |
| ATOM | 3741 | CB | LYS | 489 | 18.837 | 47.817 | 29.630 | 1.00 | 25.85 | A | C |
| ATOM | 3742 | CG | LYS | 489 | 17.651 | 47.594 | 30.579 | 1.00 | 28.57 | A | C |
| ATOM | 3743 | CD | LYS | 489 | 17.247 | 48.906 | 31.251 | 1.00 | 30.67 | A | C |
| ATOM | 3744 | CE | LYS | 489 | 16.346 | 48.695 | 32.453 | 1.00 | 29.68 | A | C |
| ATOM | 3745 | NZ | LYS | 489 | 16.283 | 49.944 | 33.278 | 1.00 | 30.13 | A | N |
| ATOM | 3746 | C | LYS | 489 | 21.297 | 47.749 | 30.110 | 1.00 | 26.05 | A | C |
| ATOM | 3747 | O | LYS | 489 | 21.997 | 47.914 | 29.106 | 1.00 | 26.23 | A | O |
| ATOM | 3748 | N | GLY | 490 | 21.605 | 46.894 | 31.084 | 1.00 | 25.12 | A | N |
| ATOM | 3749 | CA | GLY | 490 | 22.812 | 46.094 | 31.019 | 1.00 | 23.91 | A | C |
| ATOM | 3750 | C | GLY | 490 | 22.694 | 44.966 | 30.017 | 1.00 | 25.29 | A | C |
| ATOM | 3751 | O | GLY | 490 | 21.855 | 44.082 | 30.172 | 1.00 | 27.16 | A | O |
| ATOM | 3752 | N | LEU | 491 | 23.531 | 44.991 | 28.986 | 1.00 | 24.58 | A | N |
| ATOM | 3753 | CA | LEU | 491 | 23.503 | 43.953 | 27.969 | 1.00 | 24.98 | A | C |
| ATOM | 3754 | CB | LEU | 491 | 24.298 | 44.385 | 26.737 | 1.00 | 25.21 | A | C |
| ATOM | 3755 | CG | LEU | 491 | 23.809 | 45.621 | 25.980 | 1.00 | 25.03 | A | C |
| ATOM | 3756 | CD1 | LEU | 491 | 24.796 | 45.968 | 24.881 | 1.00 | 22.44 | A | C |
| ATOM | 3757 | CD2 | LEU | 491 | 22.430 | 45.356 | 25.403 | 1.00 | 25.37 | A | C |
| ATOM | 3758 | C | LEU | 491 | 24.081 | 42.649 | 28.505 | 1.00 | 25.59 | A | C |
| ATOM | 3759 | O | LEU | 491 | 23.541 | 41.579 | 28.250 | 1.00 | 27.45 | A | O |
| ATOM | 3760 | N | ARG | 492 | 25.179 | 42.732 | 29.246 | 1.00 | 24.68 | A | N |
| ATOM | 3761 | CA | ARG | 492 | 25.798 | 41.529 | 29.780 | 1.00 | 24.07 | A | C |
| ATOM | 3762 | CB | ARG | 492 | 26.045 | 40.524 | 28.648 | 1.00 | 24.82 | A | C |
| ATOM | 3763 | CG | ARG | 492 | 27.159 | 40.919 | 27.666 | 1.00 | 26.62 | A | C |
| ATOM | 3764 | CD | ARG | 492 | 27.105 | 40.081 | 26.387 | 1.00 | 26.76 | A | C |
| ATOM | 3765 | NE | ARG | 492 | 25.884 | 40.357 | 25.641 | 1.00 | 29.45 | A | N |
| ATOM | 3766 | CZ | ARG | 492 | 25.708 | 41.414 | 24.855 | 1.00 | 30.52 | A | C |
| ATOM | 3767 | NH1 | ARG | 492 | 26.684 | 42.297 | 24.692 | 1.00 | 31.57 | A | N |
| ATOM | 3768 | NH2 | ARG | 492 | 24.540 | 41.610 | 24.261 | 1.00 | 29.62 | A | N |
| ATOM | 3769 | C | ARG | 492 | 27.117 | 41.831 | 30.473 | 1.00 | 23.83 | A | C |
| ATOM | 3770 | O | ARG | 492 | 27.602 | 42.958 | 30.438 | 1.00 | 22.78 | A | O |
| ATOM | 3771 | N | VAL | 493 | 27.680 | 40.807 | 31.109 | 1.00 | 24.93 | A | N |
| ATOM | 3772 | CA | VAL | 493 | 28.966 | 40.911 | 31.791 | 1.00 | 25.89 | A | C |

| | | | | | | | | | | |
|---|---|---|---|---|---|---|---|---|---|---|
| ATOM | 3773 | CB | VAL | 493 | 29.018 | 40.034 | 33.052 | 1.00 | 25.39 | A | C |
| ATOM | 3774 | CG1 | VAL | 493 | 30.401 | 40.104 | 33.667 | 1.00 | 25.63 | A | C |
| ATOM | 3775 | CG2 | VAL | 493 | 27.977 | 40.482 | 34.044 | 1.00 | 25.35 | A | C |
| ATOM | 3776 | C | VAL | 493 | 30.022 | 40.382 | 30.823 | 1.00 | 26.55 | A | C |
| ATOM | 3777 | O | VAL | 493 | 29.858 | 39.307 | 30.250 | 1.00 | 29.06 | A | O |
| ATOM | 3778 | N | LEU | 494 | 31.103 | 41.125 | 30.644 | 1.00 | 26.28 | A | N |
| ATOM | 3779 | CA | LEU | 494 | 32.154 | 40.705 | 29.731 | 1.00 | 25.35 | A | C |
| ATOM | 3780 | CB | LEU | 494 | 32.657 | 41.913 | 28.944 | 1.00 | 23.74 | A | C |
| ATOM | 3781 | CG | LEU | 494 | 31.611 | 42.554 | 28.031 | 1.00 | 22.82 | A | C |
| ATOM | 3782 | CD1 | LEU | 494 | 32.017 | 43.989 | 27.697 | 1.00 | 22.34 | A | C |
| ATOM | 3783 | CD2 | LEU | 494 | 31.453 | 41.706 | 26.769 | 1.00 | 19.11 | A | C |
| ATOM | 3784 | C | LEU | 494 | 33.315 | 40.034 | 30.453 | 1.00 | 26.29 | A | C |
| ATOM | 3785 | O | LEU | 494 | 34.001 | 39.182 | 29.885 | 1.00 | 29.20 | A | O |
| ATOM | 3786 | N | GLU | 495 | 33.536 | 40.420 | 31.703 | 1.00 | 24.94 | A | N |
| ATOM | 3787 | CA | GLU | 495 | 34.623 | 39.859 | 32.498 | 1.00 | 24.93 | A | C |
| ATOM | 3788 | CB | GLU | 495 | 35.969 | 40.445 | 32.060 | 1.00 | 24.61 | A | C |
| ATOM | 3789 | CG | GLU | 495 | 37.153 | 39.938 | 32.862 | 1.00 | 27.02 | A | C |
| ATOM | 3790 | CD | GLU | 495 | 37.332 | 38.435 | 32.733 | 1.00 | 29.02 | A | C |
| ATOM | 3791 | OE1 | GLU | 495 | 37.263 | 37.724 | 33.760 | 1.00 | 29.22 | A | O |
| ATOM | 3792 | OE2 | GLU | 495 | 37.539 | 37.962 | 31.596 | 1.00 | 30.56 | A | O |
| ATOM | 3793 | C | GLU | 495 | 34.357 | 40.210 | 33.951 | 1.00 | 25.32 | A | C |
| ATOM | 3794 | O | GLU | 495 | 34.146 | 41.380 | 34.285 | 1.00 | 24.97 | A | O |
| ATOM | 3795 | N | ASP | 496 | 34.358 | 39.197 | 34.809 | 1.00 | 25.38 | A | N |
| ATOM | 3796 | CA | ASP | 496 | 34.093 | 39.409 | 36.224 | 1.00 | 27.01 | A | C |
| ATOM | 3797 | CB | ASP | 496 | 32.761 | 38.757 | 36.602 | 1.00 | 27.17 | A | C |
| ATOM | 3798 | CG | ASP | 496 | 32.814 | 37.236 | 36.567 | 1.00 | 27.71 | A | C |
| ATOM | 3799 | OD1 | ASP | 496 | 31.755 | 36.611 | 36.759 | 1.00 | 30.85 | A | O |
| ATOM | 3800 | OD2 | ASP | 496 | 33.898 | 36.657 | 36.360 | 1.00 | 29.23 | A | O |
| ATOM | 3801 | C | ASP | 496 | 35.213 | 38.889 | 37.127 | 1.00 | 27.65 | A | C |
| ATOM | 3802 | O | ASP | 496 | 35.177 | 39.071 | 38.345 | 1.00 | 27.02 | A | O |
| ATOM | 3803 | N | ASN | 497 | 36.201 | 38.234 | 36.528 | 1.00 | 27.52 | A | N |
| ATOM | 3804 | CA | ASN | 497 | 37.329 | 37.717 | 37.287 | 1.00 | 29.40 | A | C |
| ATOM | 3805 | CB | ASN | 497 | 38.047 | 38.863 | 37.998 | 1.00 | 28.73 | A | C |
| ATOM | 3806 | CG | ASN | 497 | 38.973 | 39.622 | 37.080 | 1.00 | 29.26 | A | C |
| ATOM | 3807 | OD1 | ASN | 497 | 39.988 | 39.093 | 36.630 | 1.00 | 27.48 | A | O |
| ATOM | 3808 | ND2 | ASN | 497 | 38.628 | 40.870 | 36.792 | 1.00 | 31.42 | A | N |
| ATOM | 3809 | C | ASN | 497 | 36.946 | 36.652 | 38.301 | 1.00 | 30.77 | A | C |
| ATOM | 3810 | O | ASN | 497 | 37.407 | 36.669 | 39.444 | 1.00 | 31.70 | A | O |
| ATOM | 3811 | N | SER | 498 | 36.108 | 35.721 | 37.869 | 1.00 | 31.77 | A | N |
| ATOM | 3812 | CA | SER | 498 | 35.666 | 34.629 | 38.716 | 1.00 | 31.32 | A | C |
| ATOM | 3813 | CB | SER | 498 | 34.644 | 33.778 | 37.974 | 1.00 | 32.01 | A | C |
| ATOM | 3814 | OG | SER | 498 | 33.520 | 34.561 | 37.629 | 1.00 | 35.01 | A | O |
| ATOM | 3815 | C | SER | 498 | 36.854 | 33.772 | 39.093 | 1.00 | 30.55 | A | C |
| ATOM | 3816 | O | SER | 498 | 37.056 | 33.456 | 40.266 | 1.00 | 31.44 | A | O |
| ATOM | 3817 | N | ALA | 499 | 37.638 | 33.398 | 38.087 | 1.00 | 29.46 | A | N |
| ATOM | 3818 | CA | ALA | 499 | 38.814 | 32.566 | 38.304 | 1.00 | 29.07 | A | C |
| ATOM | 3819 | CB | ALA | 499 | 39.626 | 32.477 | 37.033 | 1.00 | 27.47 | A | C |
| ATOM | 3820 | C | ALA | 499 | 39.657 | 33.156 | 39.421 | 1.00 | 30.28 | A | C |
| ATOM | 3821 | O | ALA | 499 | 39.885 | 32.515 | 40.447 | 1.00 | 30.98 | A | O |

| | | | | | | | | | | |
|---|---|---|---|---|---|---|---|---|---|---|
| ATOM | 3822 | N | LEU | 500 | 40.098 | 34.393 | 39.223 | 1.00 | 30.98 | A N |
| ATOM | 3823 | CA | LEU | 500 | 40.919 | 35.073 | 40.208 | 1.00 | 31.89 | A C |
| ATOM | 3824 | CB | LEU | 500 | 41.218 | 36.502 | 39.755 | 1.00 | 31.32 | A C |
| ATOM | 3825 | CG | LEU | 500 | 42.106 | 37.312 | 40.703 | 1.00 | 31.18 | A C |
| ATOM | 3826 | CD1 | LEU | 500 | 43.459 | 36.635 | 40.871 | 1.00 | 29.43 | A C |
| ATOM | 3827 | CD2 | LEU | 500 | 42.269 | 38.711 | 40.155 | 1.00 | 31.85 | A C |
| ATOM | 3828 | C | LEU | 500 | 40.251 | 35.096 | 41.574 | 1.00 | 33.26 | A C |
| ATOM | 3829 | O | LEU | 500 | 40.878 | 34.772 | 42.578 | 1.00 | 33.38 | A O |
| ATOM | 3830 | N | ASP | 501 | 38.984 | 35.484 | 41.624 | 1.00 | 35.48 | A N |
| ATOM | 3831 | CA | ASP | 501 | 38.294 | 35.522 | 42.905 | 1.00 | 38.46 | A C |
| ATOM | 3832 | CB | ASP | 501 | 36.815 | 35.859 | 42.720 | 1.00 | 40.04 | A C |
| ATOM | 3833 | CG | ASP | 501 | 36.068 | 35.942 | 44.043 | 1.00 | 42.67 | A C |
| ATOM | 3834 | OD1 | ASP | 501 | 36.349 | 36.870 | 44.831 | 1.00 | 44.51 | A O |
| ATOM | 3835 | OD2 | ASP | 501 | 35.202 | 35.076 | 44.300 | 1.00 | 44.58 | A O |
| ATOM | 3836 | C | ASP | 501 | 38.432 | 34.149 | 43.557 | 1.00 | 39.76 | A C |
| ATOM | 3837 | O | ASP | 501 | 38.622 | 34.039 | 44.765 | 1.00 | 39.03 | A O |
| ATOM | 3838 | N | LYS | 502 | 38.352 | 33.103 | 42.740 | 1.00 | 41.28 | A N |
| ATOM | 3839 | CA | LYS | 502 | 38.470 | 31.741 | 43.237 | 1.00 | 42.62 | A C |
| ATOM | 3840 | CB | LYS | 502 | 38.206 | 30.746 | 42.100 | 1.00 | 44.22 | A C |
| ATOM | 3841 | CG | LYS | 502 | 37.853 | 29.323 | 42.548 | 1.00 | 45.49 | A C |
| ATOM | 3842 | CD | LYS | 502 | 39.071 | 28.557 | 43.050 | 1.00 | 47.22 | A C |
| ATOM | 3843 | CE | LYS | 502 | 38.700 | 27.147 | 43.516 | 1.00 | 47.98 | A C |
| ATOM | 3844 | NZ | LYS | 502 | 37.783 | 27.155 | 44.696 | 1.00 | 47.33 | A N |
| ATOM | 3845 | C | LYS | 502 | 39.866 | 31.534 | 43.828 | 1.00 | 43.11 | A C |
| ATOM | 3846 | O | LYS | 502 | 40.001 | 31.079 | 44.963 | 1.00 | 43.40 | A O |
| ATOM | 3847 | N | MET | 503 | 40.900 | 31.881 | 43.064 | 1.00 | 42.72 | A N |
| ATOM | 3848 | CA | MET | 503 | 42.280 | 31.735 | 43.528 | 1.00 | 43.17 | A C |
| ATOM | 3849 | CB | MET | 503 | 43.256 | 32.193 | 42.444 | 1.00 | 45.35 | A C |
| ATOM | 3850 | CG | MET | 503 | 43.267 | 31.332 | 41.200 | 1.00 | 48.35 | A C |
| ATOM | 3851 | SD | MET | 503 | 44.396 | 32.004 | 39.952 | 1.00 | 54.36 | A S |
| ATOM | 3852 | CE | MET | 503 | 45.957 | 31.226 | 40.438 | 1.00 | 52.89 | A C |
| ATOM | 3853 | C | MET | 503 | 42.551 | 32.530 | 44.807 | 1.00 | 41.81 | A C |
| ATOM | 3854 | O | MET | 503 | 43.059 | 31.990 | 45.790 | 1.00 | 40.44 | A O |
| ATOM | 3855 | N | LEU | 504 | 42.215 | 33.815 | 44.779 | 1.00 | 41.12 | A N |
| ATOM | 3856 | CA | LEU | 504 | 42.412 | 34.700 | 45.919 | 1.00 | 42.37 | A C |
| ATOM | 3857 | CB | LEU | 504 | 41.914 | 36.103 | 45.566 | 1.00 | 41.90 | A C |
| ATOM | 3858 | CG | LEU | 504 | 42.960 | 37.197 | 45.314 | 1.00 | 42.42 | A C |
| ATOM | 3859 | CD1 | LEU | 504 | 44.111 | 36.668 | 44.472 | 1.00 | 41.70 | A C |
| ATOM | 3860 | CD2 | LEU | 504 | 42.277 | 38.376 | 44.635 | 1.00 | 40.64 | A C |
| ATOM | 3861 | C | LEU | 504 | 41.727 | 34.211 | 47.199 | 1.00 | 43.78 | A C |
| ATOM | 3862 | O | LEU | 504 | 42.056 | 34.664 | 48.298 | 1.00 | 43.47 | A O |
| ATOM | 3863 | N | GLN | 505 | 40.774 | 33.292 | 47.054 | 1.00 | 44.74 | A N |
| ATOM | 3864 | CA | GLN | 505 | 40.053 | 32.737 | 48.198 | 1.00 | 45.12 | A C |
| ATOM | 3865 | CB | GLN | 505 | 38.911 | 31.834 | 47.721 | 1.00 | 47.10 | A C |
| ATOM | 3866 | CG | GLN | 505 | 37.767 | 32.574 | 47.059 | 1.00 | 50.85 | A C |
| ATOM | 3867 | CD | GLN | 505 | 37.091 | 33.544 | 48.005 | 1.00 | 52.28 | A C |
| ATOM | 3868 | OE1 | GLN | 505 | 36.320 | 33.143 | 48.878 | 1.00 | 53.91 | A O |
| ATOM | 3869 | NE2 | GLN | 505 | 37.390 | 34.829 | 47.848 | 1.00 | 53.20 | A N |
| ATOM | 3870 | C | GLN | 505 | 40.981 | 31.920 | 49.090 | 1.00 | 44.28 | A C |

FIG. 4-80 (Continued)

| ATOM | 3871 | O | GLN | 505 | 40.806 | 31.863 | 50.309 | 1.00 | 44.07 | A | O |
|---|---|---|---|---|---|---|---|---|---|---|---|
| ATOM | 3872 | N | ASN | 506 | 41.970 | 31.288 | 48.473 | 1.00 | 43.04 | A | N |
| ATOM | 3873 | CA | ASN | 506 | 42.907 | 30.452 | 49.205 | 1.00 | 43.10 | A | C |
| ATOM | 3874 | CB | ASN | 506 | 43.301 | 29.254 | 48.344 | 1.00 | 47.04 | A | C |
| ATOM | 3875 | CG | ASN | 506 | 43.962 | 28.157 | 49.141 | 1.00 | 50.97 | A | C |
| ATOM | 3876 | OD1 | ASN | 506 | 44.478 | 27.187 | 48.575 | 1.00 | 53.71 | A | O |
| ATOM | 3877 | ND2 | ASN | 506 | 43.945 | 28.293 | 50.467 | 1.00 | 52.33 | A | N |
| ATOM | 3878 | C | ASN | 506 | 44.156 | 31.211 | 49.635 | 1.00 | 41.53 | A | C |
| ATOM | 3879 | O | ASN | 506 | 45.191 | 30.605 | 49.903 | 1.00 | 41.33 | A | O |
| ATOM | 3880 | N | VAL | 507 | 44.060 | 32.538 | 49.696 | 1.00 | 39.25 | A | N |
| ATOM | 3881 | CA | VAL | 507 | 45.186 | 33.367 | 50.110 | 1.00 | 35.74 | A | C |
| ATOM | 3882 | CB | VAL | 507 | 45.801 | 34.155 | 48.927 | 1.00 | 35.80 | A | C |
| ATOM | 3883 | CG1 | VAL | 507 | 46.989 | 34.974 | 49.416 | 1.00 | 34.07 | A | C |
| ATOM | 3884 | CG2 | VAL | 507 | 46.234 | 33.204 | 47.823 | 1.00 | 34.58 | A | C |
| ATOM | 3885 | C | VAL | 507 | 44.726 | 34.369 | 51.154 | 1.00 | 34.07 | A | C |
| ATOM | 3886 | O | VAL | 507 | 43.617 | 34.887 | 51.080 | 1.00 | 33.19 | A | O |
| ATOM | 3887 | N | GLN | 508 | 45.586 | 34.634 | 52.129 | 1.00 | 33.03 | A | N |
| ATOM | 3888 | CA | GLN | 508 | 45.272 | 35.578 | 53.191 | 1.00 | 31.62 | A | C |
| ATOM | 3889 | CB | GLN | 508 | 46.146 | 35.307 | 54.418 | 1.00 | 31.47 | A | C |
| ATOM | 3890 | CG | GLN | 508 | 46.034 | 33.894 | 54.970 | 1.00 | 31.59 | A | C |
| ATOM | 3891 | CD | GLN | 508 | 46.955 | 33.667 | 56.155 | 1.00 | 30.69 | A | C |
| ATOM | 3892 | OE1 | GLN | 508 | 46.994 | 34.471 | 57.083 | 1.00 | 31.83 | A | O |
| ATOM | 3893 | NE2 | GLN | 508 | 47.696 | 32.568 | 56.130 | 1.00 | 28.80 | A | N |
| ATOM | 3894 | C | GLN | 508 | 45.521 | 36.996 | 52.689 | 1.00 | 30.18 | A | C |
| ATOM | 3895 | O | GLN | 508 | 46.480 | 37.648 | 53.097 | 1.00 | 29.60 | A | O |
| ATOM | 3896 | N | MET | 509 | 44.652 | 37.463 | 51.801 | 1.00 | 28.77 | A | N |
| ATOM | 3897 | CA | MET | 509 | 44.775 | 38.797 | 51.236 | 1.00 | 28.64 | A | C |
| ATOM | 3898 | CB | MET | 509 | 43.744 | 38.993 | 50.124 | 1.00 | 30.06 | A | C |
| ATOM | 3899 | CG | MET | 509 | 44.004 | 38.143 | 48.896 | 1.00 | 31.71 | A | C |
| ATOM | 3900 | SD | MET | 509 | 45.605 | 38.540 | 48.171 | 1.00 | 34.08 | A | S |
| ATOM | 3901 | CE | MET | 509 | 45.130 | 39.727 | 46.922 | 1.00 | 30.89 | A | C |
| ATOM | 3902 | C | MET | 509 | 44.602 | 39.890 | 52.280 | 1.00 | 27.67 | A | C |
| ATOM | 3903 | O | MET | 509 | 43.875 | 39.724 | 53.255 | 1.00 | 28.41 | A | O |
| ATOM | 3904 | N | PRO | 510 | 45.279 | 41.032 | 52.085 | 1.00 | 26.51 | A | N |
| ATOM | 3905 | CD | PRO | 510 | 46.198 | 41.361 | 50.978 | 1.00 | 25.01 | A | C |
| ATOM | 3906 | CA | PRO | 510 | 45.180 | 42.150 | 53.023 | 1.00 | 24.17 | A | C |
| ATOM | 3907 | CB | PRO | 510 | 46.401 | 42.985 | 52.672 | 1.00 | 24.51 | A | C |
| ATOM | 3908 | CG | PRO | 510 | 46.442 | 42.847 | 51.185 | 1.00 | 23.21 | A | C |
| ATOM | 3909 | C | PRO | 510 | 43.881 | 42.896 | 52.741 | 1.00 | 23.17 | A | C |
| ATOM | 3910 | O | PRO | 510 | 43.209 | 42.632 | 51.751 | 1.00 | 24.30 | A | O |
| ATOM | 3911 | N | SER | 511 | 43.527 | 43.826 | 53.607 | 1.00 | 22.25 | A | N |
| ATOM | 3912 | CA | SER | 511 | 42.315 | 44.592 | 53.409 | 1.00 | 23.52 | A | C |
| ATOM | 3913 | CB | SER | 511 | 41.375 | 44.441 | 54.606 | 1.00 | 21.47 | A | C |
| ATOM | 3914 | OG | SER | 511 | 42.000 | 44.897 | 55.796 | 1.00 | 22.50 | A | O |
| ATOM | 3915 | C | SER | 511 | 42.734 | 46.043 | 53.258 | 1.00 | 25.81 | A | C |
| ATOM | 3916 | O | SER | 511 | 43.823 | 46.433 | 53.687 | 1.00 | 27.50 | A | O |
| ATOM | 3917 | N | LYS | 512 | 41.869 | 46.838 | 52.642 | 1.00 | 25.44 | A | N |
| ATOM | 3918 | CA | LYS | 512 | 42.148 | 48.242 | 52.437 | 1.00 | 24.17 | A | C |
| ATOM | 3919 | CB | LYS | 512 | 42.178 | 48.555 | 50.943 | 1.00 | 23.04 | A | C |

FIG. 4-81 (Continued)

| | | | | | | | | | | |
|---|---|---|---|---|---|---|---|---|---|---|
| ATOM | 3920 | CG  | LYS | 512 | 42.252 | 50.043 | 50.621 | 1.00 | 21.12 | A C |
| ATOM | 3921 | CD  | LYS | 512 | 42.368 | 50.249 | 49.125 | 1.00 | 21.07 | A C |
| ATOM | 3922 | CE  | LYS | 512 | 42.639 | 51.688 | 48.792 | 1.00 | 19.46 | A C |
| ATOM | 3923 | NZ  | LYS | 512 | 42.779 | 51.870 | 47.343 | 1.00 | 15.68 | A N |
| ATOM | 3924 | C   | LYS | 512 | 41.095 | 49.109 | 53.105 | 1.00 | 24.25 | A C |
| ATOM | 3925 | O   | LYS | 512 | 39.905 | 48.958 | 52.846 | 1.00 | 23.45 | A O |
| ATOM | 3926 | N   | LYS | 513 | 41.546 | 50.017 | 53.960 | 1.00 | 24.50 | A N |
| ATOM | 3927 | CA  | LYS | 513 | 40.661 | 50.941 | 54.647 | 1.00 | 25.28 | A C |
| ATOM | 3928 | CB  | LYS | 513 | 41.040 | 51.041 | 56.124 | 1.00 | 26.65 | A C |
| ATOM | 3929 | CG  | LYS | 513 | 40.202 | 52.025 | 56.914 | 1.00 | 27.55 | A C |
| ATOM | 3930 | CD  | LYS | 513 | 38.754 | 51.577 | 56.954 | 1.00 | 33.11 | A C |
| ATOM | 3931 | CE  | LYS | 513 | 37.901 | 52.476 | 57.844 | 1.00 | 35.12 | A C |
| ATOM | 3932 | NZ  | LYS | 513 | 36.503 | 51.943 | 57.960 | 1.00 | 38.12 | A N |
| ATOM | 3933 | C   | LYS | 513 | 40.806 | 52.312 | 53.999 | 1.00 | 26.42 | A C |
| ATOM | 3934 | O   | LYS | 513 | 41.918 | 52.829 | 53.877 | 1.00 | 28.66 | A O |
| ATOM | 3935 | N   | LEU | 514 | 39.688 | 52.891 | 53.575 | 1.00 | 25.40 | A N |
| ATOM | 3936 | CA  | LEU | 514 | 39.688 | 54.213 | 52.958 | 1.00 | 22.53 | A C |
| ATOM | 3937 | CB  | LEU | 514 | 39.147 | 54.119 | 51.536 | 1.00 | 20.88 | A C |
| ATOM | 3938 | CG  | LEU | 514 | 38.866 | 55.443 | 50.825 | 1.00 | 21.52 | A C |
| ATOM | 3939 | CD1 | LEU | 514 | 40.149 | 56.242 | 50.662 | 1.00 | 20.94 | A C |
| ATOM | 3940 | CD2 | LEU | 514 | 38.244 | 55.153 | 49.476 | 1.00 | 22.59 | A C |
| ATOM | 3941 | C   | LEU | 514 | 38.812 | 55.151 | 53.788 | 1.00 | 22.73 | A C |
| ATOM | 3942 | O   | LEU | 514 | 37.591 | 54.981 | 53.844 | 1.00 | 20.65 | A O |
| ATOM | 3943 | N   | ASP | 515 | 39.435 | 56.132 | 54.437 | 1.00 | 23.05 | A N |
| ATOM | 3944 | CA  | ASP | 515 | 38.693 | 57.076 | 55.268 | 1.00 | 25.43 | A C |
| ATOM | 3945 | CB  | ASP | 515 | 38.581 | 56.535 | 56.693 | 1.00 | 27.35 | A C |
| ATOM | 3946 | CG  | ASP | 515 | 37.419 | 57.142 | 57.458 | 1.00 | 30.82 | A C |
| ATOM | 3947 | OD1 | ASP | 515 | 37.278 | 56.851 | 58.668 | 1.00 | 32.73 | A O |
| ATOM | 3948 | OD2 | ASP | 515 | 36.639 | 57.905 | 56.851 | 1.00 | 32.89 | A O |
| ATOM | 3949 | C   | ASP | 515 | 39.346 | 58.462 | 55.287 | 1.00 | 26.80 | A C |
| ATOM | 3950 | O   | ASP | 515 | 40.054 | 58.835 | 54.357 | 1.00 | 27.23 | A O |
| ATOM | 3951 | N   | PHE | 516 | 39.107 | 59.230 | 56.345 | 1.00 | 27.53 | A N |
| ATOM | 3952 | CA  | PHE | 516 | 39.688 | 60.566 | 56.431 | 1.00 | 28.71 | A C |
| ATOM | 3953 | CB  | PHE | 516 | 38.780 | 61.590 | 55.729 | 1.00 | 28.60 | A C |
| ATOM | 3954 | CG  | PHE | 516 | 37.387 | 61.658 | 56.291 | 1.00 | 28.84 | A C |
| ATOM | 3955 | CD1 | PHE | 516 | 37.160 | 62.115 | 57.583 | 1.00 | 29.59 | A C |
| ATOM | 3956 | CD2 | PHE | 516 | 36.297 | 61.242 | 55.532 | 1.00 | 30.94 | A C |
| ATOM | 3957 | CE1 | PHE | 516 | 35.875 | 62.157 | 58.116 | 1.00 | 28.99 | A C |
| ATOM | 3958 | CE2 | PHE | 516 | 35.002 | 61.279 | 56.058 | 1.00 | 29.88 | A C |
| ATOM | 3959 | CZ  | PHE | 516 | 34.795 | 61.737 | 57.352 | 1.00 | 29.33 | A C |
| ATOM | 3960 | C   | PHE | 516 | 39.943 | 61.024 | 57.861 | 1.00 | 28.58 | A C |
| ATOM | 3961 | O   | PHE | 516 | 39.414 | 60.450 | 58.811 | 1.00 | 29.42 | A O |
| ATOM | 3962 | N   | ILE | 517 | 40.773 | 62.053 | 57.990 | 1.00 | 26.80 | A N |
| ATOM | 3963 | CA  | ILE | 517 | 41.094 | 62.651 | 59.272 | 1.00 | 28.68 | A C |
| ATOM | 3964 | CB  | ILE | 517 | 42.580 | 62.410 | 59.686 | 1.00 | 27.66 | A C |
| ATOM | 3965 | CG2 | ILE | 517 | 42.799 | 60.937 | 59.989 | 1.00 | 23.78 | A C |
| ATOM | 3966 | CG1 | ILE | 517 | 43.538 | 62.861 | 58.581 | 1.00 | 29.30 | A C |
| ATOM | 3967 | CD1 | ILE | 517 | 43.676 | 64.361 | 58.431 | 1.00 | 31.79 | A C |
| ATOM | 3968 | C   | ILE | 517 | 40.829 | 64.132 | 59.041 | 1.00 | 30.84 | A C |

| ATOM | 3969 | O | ILE | 517 | 40.813 | 64.577 | 57.898 | 1.00 | 31.70 | A | O |
|---|---|---|---|---|---|---|---|---|---|---|---|
| ATOM | 3970 | N | ILE | 518 | 40.616 | 64.899 | 60.102 | 1.00 | 32.28 | A | N |
| ATOM | 3971 | CA | ILE | 518 | 40.323 | 66.313 | 59.924 | 1.00 | 33.51 | A | C |
| ATOM | 3972 | CB | ILE | 518 | 38.977 | 66.683 | 60.595 | 1.00 | 33.41 | A | C |
| ATOM | 3973 | CG2 | ILE | 518 | 38.603 | 68.125 | 60.283 | 1.00 | 33.29 | A | C |
| ATOM | 3974 | CG1 | ILE | 518 | 37.871 | 65.765 | 60.072 | 1.00 | 33.38 | A | C |
| ATOM | 3975 | CD1 | ILE | 518 | 36.535 | 65.972 | 60.749 | 1.00 | 33.46 | A | C |
| ATOM | 3976 | C | ILE | 518 | 41.415 | 67.222 | 60.455 | 1.00 | 35.00 | A | C |
| ATOM | 3977 | O | ILE | 518 | 41.883 | 67.069 | 61.580 | 1.00 | 35.82 | A | O |
| ATOM | 3978 | N | LEU | 519 | 41.824 | 68.169 | 59.622 | 1.00 | 36.74 | A | N |
| ATOM | 3979 | CA | LEU | 519 | 42.850 | 69.126 | 59.997 | 1.00 | 39.19 | A | C |
| ATOM | 3980 | CB | LEU | 519 | 44.169 | 68.828 | 59.276 | 1.00 | 38.52 | A | C |
| ATOM | 3981 | CG | LEU | 519 | 44.746 | 67.413 | 59.364 | 1.00 | 39.20 | A | C |
| ATOM | 3982 | CD1 | LEU | 519 | 45.996 | 67.326 | 58.493 | 1.00 | 39.31 | A | C |
| ATOM | 3983 | CD2 | LEU | 519 | 45.068 | 67.059 | 60.806 | 1.00 | 39.59 | A | C |
| ATOM | 3984 | C | LEU | 519 | 42.351 | 70.501 | 59.591 | 1.00 | 40.26 | A | C |
| ATOM | 3985 | O | LEU | 519 | 42.102 | 70.754 | 58.414 | 1.00 | 40.93 | A | O |
| ATOM | 3986 | N | ASN | 520 | 42.198 | 71.382 | 60.574 | 1.00 | 41.70 | A | N |
| ATOM | 3987 | CA | ASN | 520 | 41.736 | 72.735 | 60.321 | 1.00 | 42.46 | A | C |
| ATOM | 3988 | CB | ASN | 520 | 42.760 | 73.474 | 59.467 | 1.00 | 44.27 | A | C |
| ATOM | 3989 | CG | ASN | 520 | 44.078 | 73.635 | 60.177 | 1.00 | 46.04 | A | C |
| ATOM | 3990 | OD1 | ASN | 520 | 44.540 | 72.723 | 60.859 | 1.00 | 47.21 | A | O |
| ATOM | 3991 | ND2 | ASN | 520 | 44.697 | 74.796 | 60.020 | 1.00 | 50.39 | A | N |
| ATOM | 3992 | C | ASN | 520 | 40.384 | 72.728 | 59.638 | 1.00 | 42.18 | A | C |
| ATOM | 3993 | O | ASN | 520 | 40.183 | 73.388 | 58.620 | 1.00 | 42.15 | A | O |
| ATOM | 3994 | N | GLU | 521 | 39.461 | 71.963 | 60.210 | 1.00 | 41.73 | A | N |
| ATOM | 3995 | CA | GLU | 521 | 38.105 | 71.861 | 59.691 | 1.00 | 42.64 | A | C |
| ATOM | 3996 | CB | GLU | 521 | 37.445 | 73.245 | 59.660 | 1.00 | 44.72 | A | C |
| ATOM | 3997 | CG | GLU | 521 | 37.967 | 74.204 | 60.715 | 1.00 | 48.09 | A | C |
| ATOM | 3998 | CD | GLU | 521 | 38.057 | 73.564 | 62.081 | 1.00 | 50.91 | A | C |
| ATOM | 3999 | OE1 | GLU | 521 | 36.994 | 73.245 | 62.661 | 1.00 | 52.95 | A | O |
| ATOM | 4000 | OE2 | GLU | 521 | 39.194 | 73.374 | 62.568 | 1.00 | 51.94 | A | O |
| ATOM | 4001 | C | GLU | 521 | 38.041 | 71.248 | 58.296 | 1.00 | 40.90 | A | C |
| ATOM | 4002 | O | GLU | 521 | 36.967 | 71.171 | 57.701 | 1.00 | 40.88 | A | O |
| ATOM | 4003 | N | THR | 522 | 39.182 | 70.814 | 57.772 | 1.00 | 39.01 | A | N |
| ATOM | 4004 | CA | THR | 522 | 39.206 | 70.221 | 56.442 | 1.00 | 36.94 | A | C |
| ATOM | 4005 | CB | THR | 522 | 40.339 | 70.816 | 55.584 | 1.00 | 38.55 | A | C |
| ATOM | 4006 | OG1 | THR | 522 | 40.127 | 72.223 | 55.431 | 1.00 | 40.51 | A | O |
| ATOM | 4007 | CG2 | THR | 522 | 40.364 | 70.171 | 54.202 | 1.00 | 39.39 | A | C |
| ATOM | 4008 | C | THR | 522 | 39.357 | 68.706 | 56.482 | 1.00 | 34.94 | A | C |
| ATOM | 4009 | O | THR | 522 | 40.086 | 68.152 | 57.305 | 1.00 | 33.48 | A | O |
| ATOM | 4010 | N | LYS | 523 | 38.653 | 68.045 | 55.573 | 1.00 | 33.07 | A | N |
| ATOM | 4011 | CA | LYS | 523 | 38.685 | 66.597 | 55.479 | 1.00 | 30.63 | A | C |
| ATOM | 4012 | CB | LYS | 523 | 37.357 | 66.105 | 54.901 | 1.00 | 31.78 | A | C |
| ATOM | 4013 | CG | LYS | 523 | 36.882 | 64.770 | 55.440 | 1.00 | 34.92 | A | C |
| ATOM | 4014 | CD | LYS | 523 | 35.473 | 64.458 | 54.956 | 1.00 | 37.12 | A | C |
| ATOM | 4015 | CE | LYS | 523 | 34.473 | 65.488 | 55.455 | 1.00 | 40.20 | A | C |
| ATOM | 4016 | NZ | LYS | 523 | 33.111 | 65.296 | 54.873 | 1.00 | 43.74 | A | N |
| ATOM | 4017 | C | LYS | 523 | 39.845 | 66.191 | 54.576 | 1.00 | 28.84 | A | C |

| ATOM | 4018 | O | LYS | 523 | 39.962 | 66.661 | 53.448 | 1.00 | 29.90 | A | O |
| --- | --- | --- | --- | --- | --- | --- | --- | --- | --- | --- | --- |
| ATOM | 4019 | N | PHE | 524 | 40.711 | 65.329 | 55.086 | 1.00 | 26.11 | A | N |
| ATOM | 4020 | CA | PHE | 524 | 41.857 | 64.858 | 54.334 | 1.00 | 23.17 | A | C |
| ATOM | 4021 | CB | PHE | 524 | 43.139 | 65.407 | 54.953 | 1.00 | 22.95 | A | C |
| ATOM | 4022 | CG | PHE | 524 | 43.394 | 66.854 | 54.636 | 1.00 | 21.35 | A | C |
| ATOM | 4023 | CD1 | PHE | 524 | 43.773 | 67.242 | 53.346 | 1.00 | 21.14 | A | C |
| ATOM | 4024 | CD2 | PHE | 524 | 43.265 | 67.830 | 55.620 | 1.00 | 18.86 | A | C |
| ATOM | 4025 | CE1 | PHE | 524 | 44.026 | 68.587 | 53.040 | 1.00 | 19.22 | A | C |
| ATOM | 4026 | CE2 | PHE | 524 | 43.512 | 69.171 | 55.329 | 1.00 | 19.37 | A | C |
| ATOM | 4027 | CZ | PHE | 524 | 43.895 | 69.552 | 54.034 | 1.00 | 19.34 | A | C |
| ATOM | 4028 | C | PHE | 524 | 41.872 | 63.337 | 54.328 | 1.00 | 23.15 | A | C |
| ATOM | 4029 | O | PHE | 524 | 42.084 | 62.703 | 55.356 | 1.00 | 22.01 | A | O |
| ATOM | 4030 | N | TRP | 525 | 41.640 | 62.758 | 53.156 | 1.00 | 24.00 | A | N |
| ATOM | 4031 | CA | TRP | 525 | 41.593 | 61.309 | 53.000 | 1.00 | 23.65 | A | C |
| ATOM | 4032 | CB | TRP | 525 | 40.875 | 60.958 | 51.696 | 1.00 | 23.74 | A | C |
| ATOM | 4033 | CG | TRP | 525 | 39.476 | 61.452 | 51.647 | 1.00 | 24.69 | A | C |
| ATOM | 4034 | CD2 | TRP | 525 | 38.291 | 60.687 | 51.893 | 1.00 | 25.25 | A | C |
| ATOM | 4035 | CE2 | TRP | 525 | 37.195 | 61.572 | 51.800 | 1.00 | 26.02 | A | C |
| ATOM | 4036 | CE3 | TRP | 525 | 38.049 | 59.339 | 52.186 | 1.00 | 25.53 | A | C |
| ATOM | 4037 | CD1 | TRP | 525 | 39.065 | 62.732 | 51.418 | 1.00 | 25.58 | A | C |
| ATOM | 4038 | NE1 | TRP | 525 | 37.693 | 62.815 | 51.508 | 1.00 | 25.32 | A | N |
| ATOM | 4039 | CZ2 | TRP | 525 | 35.874 | 61.151 | 51.990 | 1.00 | 25.72 | A | C |
| ATOM | 4040 | CZ3 | TRP | 525 | 36.735 | 58.919 | 52.374 | 1.00 | 24.54 | A | C |
| ATOM | 4041 | CH2 | TRP | 525 | 35.666 | 59.824 | 52.276 | 1.00 | 24.86 | A | C |
| ATOM | 4042 | C | TRP | 525 | 42.927 | 60.566 | 53.042 | 1.00 | 23.39 | A | C |
| ATOM | 4043 | O | TRP | 525 | 43.994 | 61.127 | 52.803 | 1.00 | 24.19 | A | O |
| ATOM | 4044 | N | TYR | 526 | 42.840 | 59.280 | 53.347 | 1.00 | 22.63 | A | N |
| ATOM | 4045 | CA | TYR | 526 | 44.002 | 58.412 | 53.410 | 1.00 | 22.38 | A | C |
| ATOM | 4046 | CB | TYR | 526 | 44.715 | 58.546 | 54.763 | 1.00 | 22.15 | A | C |
| ATOM | 4047 | CG | TYR | 526 | 43.946 | 57.946 | 55.929 | 1.00 | 24.08 | A | C |
| ATOM | 4048 | CD1 | TYR | 526 | 43.968 | 56.574 | 56.178 | 1.00 | 23.01 | A | C |
| ATOM | 4049 | CE1 | TYR | 526 | 43.215 | 56.017 | 57.204 | 1.00 | 25.01 | A | C |
| ATOM | 4050 | CD2 | TYR | 526 | 43.150 | 58.748 | 56.747 | 1.00 | 24.62 | A | C |
| ATOM | 4051 | CE2 | TYR | 526 | 42.395 | 58.205 | 57.772 | 1.00 | 24.74 | A | C |
| ATOM | 4052 | CZ | TYR | 526 | 42.426 | 56.840 | 57.997 | 1.00 | 25.67 | A | C |
| ATOM | 4053 | OH | TYR | 526 | 41.650 | 56.303 | 59.003 | 1.00 | 25.43 | A | O |
| ATOM | 4054 | C | TYR | 526 | 43.478 | 56.990 | 53.251 | 1.00 | 22.00 | A | C |
| ATOM | 4055 | O | TYR | 526 | 42.294 | 56.724 | 53.482 | 1.00 | 21.71 | A | O |
| ATOM | 4056 | N | GLN | 527 | 44.353 | 56.084 | 52.843 | 1.00 | 19.68 | A | N |
| ATOM | 4057 | CA | GLN | 527 | 43.964 | 54.697 | 52.707 | 1.00 | 20.14 | A | C |
| ATOM | 4058 | CB | GLN | 527 | 43.842 | 54.301 | 51.238 | 1.00 | 19.56 | A | C |
| ATOM | 4059 | CG | GLN | 527 | 45.123 | 54.422 | 50.465 | 1.00 | 23.06 | A | C |
| ATOM | 4060 | CD | GLN | 527 | 44.986 | 53.890 | 49.065 | 1.00 | 23.49 | A | C |
| ATOM | 4061 | OE1 | GLN | 527 | 44.034 | 54.222 | 48.359 | 1.00 | 25.79 | A | O |
| ATOM | 4062 | NE2 | GLN | 527 | 45.937 | 53.066 | 48.648 | 1.00 | 22.35 | A | N |
| ATOM | 4063 | C | GLN | 527 | 45.038 | 53.871 | 53.389 | 1.00 | 20.67 | A | C |
| ATOM | 4064 | O | GLN | 527 | 46.172 | 54.334 | 53.563 | 1.00 | 19.72 | A | O |
| ATOM | 4065 | N | MET | 528 | 44.674 | 52.659 | 53.792 | 1.00 | 21.11 | A | N |
| ATOM | 4066 | CA | MET | 528 | 45.610 | 51.771 | 54.460 | 1.00 | 22.32 | A | C |

| ATOM | 4067 | CB | MET | 528 | 45.372 | 51.753 | 55.967 | 1.00 | 23.57 | A | C |
| --- | --- | --- | --- | --- | --- | --- | --- | --- | --- | --- | --- |
| ATOM | 4068 | CG | MET | 528 | 45.830 | 52.971 | 56.727 | 1.00 | 23.53 | A | C |
| ATOM | 4069 | SD | MET | 528 | 45.605 | 52.683 | 58.492 | 1.00 | 23.56 | A | S |
| ATOM | 4070 | CE | MET | 528 | 46.400 | 54.107 | 59.158 | 1.00 | 21.91 | A | C |
| ATOM | 4071 | C | MET | 528 | 45.482 | 50.347 | 53.974 | 1.00 | 23.25 | A | C |
| ATOM | 4072 | O | MET | 528 | 44.383 | 49.790 | 53.935 | 1.00 | 24.82 | A | O |
| ATOM | 4073 | N | ILE | 529 | 46.605 | 49.751 | 53.600 | 1.00 | 22.51 | A | N |
| ATOM | 4074 | CA | ILE | 529 | 46.587 | 48.363 | 53.183 | 1.00 | 21.97 | A | C |
| ATOM | 4075 | CB | ILE | 529 | 47.644 | 48.078 | 52.116 | 1.00 | 19.54 | A | C |
| ATOM | 4076 | CG2 | ILE | 529 | 47.557 | 46.635 | 51.681 | 1.00 | 18.75 | A | C |
| ATOM | 4077 | CG1 | ILE | 529 | 47.454 | 49.029 | 50.927 | 1.00 | 21.01 | A | C |
| ATOM | 4078 | CD1 | ILE | 529 | 46.045 | 49.038 | 50.335 | 1.00 | 19.28 | A | C |
| ATOM | 4079 | C | ILE | 529 | 46.937 | 47.620 | 54.465 | 1.00 | 24.02 | A | C |
| ATOM | 4080 | O | ILE | 529 | 48.114 | 47.505 | 54.820 | 1.00 | 25.51 | A | O |
| ATOM | 4081 | N | LEU | 530 | 45.911 | 47.153 | 55.175 | 1.00 | 24.47 | A | N |
| ATOM | 4082 | CA | LEU | 530 | 46.114 | 46.443 | 56.438 | 1.00 | 24.76 | A | C |
| ATOM | 4083 | CB | LEU | 530 | 44.915 | 46.640 | 57.370 | 1.00 | 24.08 | A | C |
| ATOM | 4084 | CG | LEU | 530 | 44.451 | 48.052 | 57.726 | 1.00 | 24.92 | A | C |
| ATOM | 4085 | CD1 | LEU | 530 | 43.365 | 47.928 | 58.763 | 1.00 | 26.76 | A | C |
| ATOM | 4086 | CD2 | LEU | 530 | 45.589 | 48.896 | 58.272 | 1.00 | 25.50 | A | C |
| ATOM | 4087 | C | LEU | 530 | 46.337 | 44.953 | 56.241 | 1.00 | 24.39 | A | C |
| ATOM | 4088 | O | LEU | 530 | 45.686 | 44.319 | 55.411 | 1.00 | 24.58 | A | O |
| ATOM | 4089 | N | PRO | 531 | 47.272 | 44.374 | 57.003 | 1.00 | 24.58 | A | N |
| ATOM | 4090 | CD | PRO | 531 | 48.174 | 45.045 | 57.950 | 1.00 | 24.42 | A | C |
| ATOM | 4091 | CA | PRO | 531 | 47.578 | 42.943 | 56.913 | 1.00 | 26.79 | A | C |
| ATOM | 4092 | CB | PRO | 531 | 48.763 | 42.784 | 57.862 | 1.00 | 26.36 | A | C |
| ATOM | 4093 | CG | PRO | 531 | 48.580 | 43.913 | 58.838 | 1.00 | 26.79 | A | C |
| ATOM | 4094 | C | PRO | 531 | 46.388 | 42.078 | 57.312 | 1.00 | 28.05 | A | C |
| ATOM | 4095 | O | PRO | 531 | 45.443 | 42.562 | 57.931 | 1.00 | 31.01 | A | O |
| ATOM | 4096 | N | PRO | 532 | 46.417 | 40.782 | 56.964 | 1.00 | 28.42 | A | N |
| ATOM | 4097 | CD | PRO | 532 | 47.484 | 40.062 | 56.253 | 1.00 | 28.00 | A | C |
| ATOM | 4098 | CA | PRO | 532 | 45.316 | 39.874 | 57.306 | 1.00 | 28.68 | A | C |
| ATOM | 4099 | CB | PRO | 532 | 45.783 | 38.534 | 56.745 | 1.00 | 28.68 | A | C |
| ATOM | 4100 | CG | PRO | 532 | 46.726 | 38.912 | 55.659 | 1.00 | 28.50 | A | C |
| ATOM | 4101 | C | PRO | 532 | 45.113 | 39.799 | 58.814 | 1.00 | 29.80 | A | C |
| ATOM | 4102 | O | PRO | 532 | 46.051 | 40.006 | 59.579 | 1.00 | 31.52 | A | O |
| ATOM | 4103 | N | HIS | 533 | 43.894 | 39.501 | 59.242 | 1.00 | 31.29 | A | N |
| ATOM | 4104 | CA | HIS | 533 | 43.605 | 39.382 | 60.670 | 1.00 | 31.80 | A | C |
| ATOM | 4105 | CB | HIS | 533 | 44.278 | 38.127 | 61.225 | 1.00 | 29.82 | A | C |
| ATOM | 4106 | CG | HIS | 533 | 44.170 | 36.936 | 60.324 | 1.00 | 29.23 | A | C |
| ATOM | 4107 | CD2 | HIS | 533 | 45.114 | 36.247 | 59.641 | 1.00 | 28.40 | A | C |
| ATOM | 4108 | ND1 | HIS | 533 | 42.966 | 36.335 | 60.024 | 1.00 | 28.40 | A | N |
| ATOM | 4109 | CE1 | HIS | 533 | 43.174 | 35.326 | 59.197 | 1.00 | 28.67 | A | C |
| ATOM | 4110 | NE2 | HIS | 533 | 44.469 | 35.251 | 58.949 | 1.00 | 28.85 | A | N |
| ATOM | 4111 | C | HIS | 533 | 44.101 | 40.601 | 61.445 | 1.00 | 33.77 | A | C |
| ATOM | 4112 | O | HIS | 533 | 44.469 | 40.489 | 62.617 | 1.00 | 33.99 | A | O |
| ATOM | 4113 | N | PHE | 534 | 44.121 | 41.758 | 60.787 | 1.00 | 35.52 | A | N |
| ATOM | 4114 | CA | PHE | 534 | 44.578 | 42.987 | 61.427 | 1.00 | 37.29 | A | C |
| ATOM | 4115 | CB | PHE | 534 | 44.249 | 44.203 | 60.555 | 1.00 | 36.11 | A | C |

FIG. 4-85 (Continued)

| | | | | | | | | | | | |
|---|---|---|---|---|---|---|---|---|---|---|---|
| ATOM | 4116 | CG | PHE | 534 | 44.510 | 45.523 | 61.235 | 1.00 | 35.46 | A | C |
| ATOM | 4117 | CD1 | PHE | 534 | 45.811 | 45.956 | 61.475 | 1.00 | 35.65 | A | C |
| ATOM | 4118 | CD2 | PHE | 534 | 43.455 | 46.320 | 61.654 | 1.00 | 33.35 | A | C |
| ATOM | 4119 | CE1 | PHE | 534 | 46.056 | 47.167 | 62.124 | 1.00 | 36.55 | A | C |
| ATOM | 4120 | CE2 | PHE | 534 | 43.688 | 47.530 | 62.304 | 1.00 | 35.26 | A | C |
| ATOM | 4121 | CZ | PHE | 534 | 44.990 | 47.957 | 62.541 | 1.00 | 35.35 | A | C |
| ATOM | 4122 | C | PHE | 534 | 43.920 | 43.158 | 62.790 | 1.00 | 38.07 | A | C |
| ATOM | 4123 | O | PHE | 534 | 42.705 | 43.046 | 62.911 | 1.00 | 38.83 | A | O |
| ATOM | 4124 | N | ASP | 535 | 44.725 | 43.435 | 63.810 | 1.00 | 39.27 | A | N |
| ATOM | 4125 | CA | ASP | 535 | 44.206 | 43.621 | 65.160 | 1.00 | 40.72 | A | C |
| ATOM | 4126 | CB | ASP | 535 | 44.751 | 42.541 | 66.089 | 1.00 | 43.14 | A | C |
| ATOM | 4127 | CG | ASP | 535 | 44.102 | 42.571 | 67.460 | 1.00 | 46.19 | A | C |
| ATOM | 4128 | OD1 | ASP | 535 | 43.704 | 43.668 | 67.912 | 1.00 | 46.58 | A | O |
| ATOM | 4129 | OD2 | ASP | 535 | 43.999 | 41.499 | 68.092 | 1.00 | 48.00 | A | O |
| ATOM | 4130 | C | ASP | 535 | 44.614 | 44.985 | 65.699 | 1.00 | 40.91 | A | C |
| ATOM | 4131 | O | ASP | 535 | 45.799 | 45.270 | 65.837 | 1.00 | 40.57 | A | O |
| ATOM | 4132 | N | LYS | 536 | 43.635 | 45.822 | 66.022 | 1.00 | 41.40 | A | N |
| ATOM | 4133 | CA | LYS | 536 | 43.936 | 47.148 | 66.539 | 1.00 | 42.56 | A | C |
| ATOM | 4134 | CB | LYS | 536 | 42.675 | 48.018 | 66.572 | 1.00 | 44.69 | A | C |
| ATOM | 4135 | CG | LYS | 536 | 42.146 | 48.406 | 65.200 | 1.00 | 47.06 | A | C |
| ATOM | 4136 | CD | LYS | 536 | 41.156 | 49.566 | 65.289 | 1.00 | 49.52 | A | C |
| ATOM | 4137 | CE | LYS | 536 | 40.721 | 50.020 | 63.897 | 1.00 | 50.85 | A | C |
| ATOM | 4138 | NZ | LYS | 536 | 39.965 | 51.303 | 63.921 | 1.00 | 51.05 | A | N |
| ATOM | 4139 | C | LYS | 536 | 44.553 | 47.105 | 67.928 | 1.00 | 42.57 | A | C |
| ATOM | 4140 | O | LYS | 536 | 44.896 | 48.147 | 68.486 | 1.00 | 42.20 | A | O |
| ATOM | 4141 | N | SER | 537 | 44.697 | 45.907 | 68.486 | 1.00 | 42.80 | A | N |
| ATOM | 4142 | CA | SER | 537 | 45.277 | 45.762 | 69.820 | 1.00 | 43.70 | A | C |
| ATOM | 4143 | CB | SER | 537 | 44.744 | 44.499 | 70.513 | 1.00 | 44.09 | A | C |
| ATOM | 4144 | OG | SER | 537 | 45.222 | 43.319 | 69.888 | 1.00 | 43.50 | A | O |
| ATOM | 4145 | C | SER | 537 | 46.796 | 45.696 | 69.737 | 1.00 | 43.27 | A | C |
| ATOM | 4146 | O | SER | 537 | 47.498 | 46.061 | 70.682 | 1.00 | 44.98 | A | O |
| ATOM | 4147 | N | LYS | 538 | 47.295 | 45.230 | 68.598 | 1.00 | 41.93 | A | N |
| ATOM | 4148 | CA | LYS | 538 | 48.729 | 45.110 | 68.380 | 1.00 | 40.13 | A | C |
| ATOM | 4149 | CB | LYS | 538 | 49.024 | 43.917 | 67.470 | 1.00 | 41.29 | A | C |
| ATOM | 4150 | CG | LYS | 538 | 48.521 | 42.590 | 68.013 | 1.00 | 42.24 | A | C |
| ATOM | 4151 | CD | LYS | 538 | 48.834 | 41.446 | 67.073 | 1.00 | 41.97 | A | C |
| ATOM | 4152 | CE | LYS | 538 | 48.317 | 40.140 | 67.638 | 1.00 | 42.57 | A | C |
| ATOM | 4153 | NZ | LYS | 538 | 46.864 | 40.231 | 67.960 | 1.00 | 44.10 | A | N |
| ATOM | 4154 | C | LYS | 538 | 49.280 | 46.372 | 67.741 | 1.00 | 38.59 | A | C |
| ATOM | 4155 | O | LYS | 538 | 48.526 | 47.229 | 67.283 | 1.00 | 38.17 | A | O |
| ATOM | 4156 | N | LYS | 539 | 50.601 | 46.485 | 67.725 | 1.00 | 36.92 | A | N |
| ATOM | 4157 | CA | LYS | 539 | 51.263 | 47.629 | 67.116 | 1.00 | 36.43 | A | C |
| ATOM | 4158 | CB | LYS | 539 | 52.293 | 48.225 | 68.079 | 1.00 | 37.32 | A | C |
| ATOM | 4159 | CG | LYS | 539 | 51.693 | 48.838 | 69.341 | 1.00 | 37.42 | A | C |
| ATOM | 4160 | CD | LYS | 539 | 50.925 | 50.117 | 69.028 | 1.00 | 40.01 | A | C |
| ATOM | 4161 | CE | LYS | 539 | 50.209 | 50.674 | 70.258 | 1.00 | 41.64 | A | C |
| ATOM | 4162 | NZ | LYS | 539 | 51.121 | 51.014 | 71.389 | 1.00 | 43.98 | A | N |
| ATOM | 4163 | C | LYS | 539 | 51.943 | 47.110 | 65.849 | 1.00 | 35.38 | A | C |
| ATOM | 4164 | O | LYS | 539 | 52.699 | 46.137 | 65.893 | 1.00 | 35.49 | A | O |

FIG. 4-86 (Continued)

| | | | | | | | | | | | |
|---|---|---|---|---|---|---|---|---|---|---|---|
| ATOM | 4165 | N | TYR | 540 | 51.658 | 47.747 | 64.719 | 1.00 | 33.00 | A | N |
| ATOM | 4166 | CA | TYR | 540 | 52.229 | 47.316 | 63.452 | 1.00 | 30.12 | A | C |
| ATOM | 4167 | CB | TYR | 540 | 51.131 | 47.135 | 62.397 | 1.00 | 28.99 | A | C |
| ATOM | 4168 | CG | TYR | 540 | 50.204 | 45.968 | 62.630 | 1.00 | 29.13 | A | C |
| ATOM | 4169 | CD1 | TYR | 540 | 49.109 | 46.078 | 63.488 | 1.00 | 28.32 | A | C |
| ATOM | 4170 | CE1 | TYR | 540 | 48.254 | 45.000 | 63.699 | 1.00 | 27.13 | A | C |
| ATOM | 4171 | CD2 | TYR | 540 | 50.421 | 44.748 | 61.990 | 1.00 | 27.62 | A | C |
| ATOM | 4172 | CE2 | TYR | 540 | 49.576 | 43.669 | 62.196 | 1.00 | 26.32 | A | C |
| ATOM | 4173 | CZ | TYR | 540 | 48.495 | 43.800 | 63.051 | 1.00 | 27.64 | A | C |
| ATOM | 4174 | OH | TYR | 540 | 47.661 | 42.724 | 63.260 | 1.00 | 29.67 | A | O |
| ATOM | 4175 | C | TYR | 540 | 53.242 | 48.287 | 62.890 | 1.00 | 29.33 | A | C |
| ATOM | 4176 | O | TYR | 540 | 53.130 | 49.492 | 63.091 | 1.00 | 31.23 | A | O |
| ATOM | 4177 | N | PRO | 541 | 54.270 | 47.772 | 62.199 | 1.00 | 27.71 | A | N |
| ATOM | 4178 | CD | PRO | 541 | 54.717 | 46.383 | 62.020 | 1.00 | 25.95 | A | C |
| ATOM | 4179 | CA | PRO | 541 | 55.238 | 48.708 | 61.634 | 1.00 | 27.56 | A | C |
| ATOM | 4180 | CB | PRO | 541 | 56.361 | 47.794 | 61.148 | 1.00 | 26.81 | A | C |
| ATOM | 4181 | CG | PRO | 541 | 55.662 | 46.512 | 60.867 | 1.00 | 25.92 | A | C |
| ATOM | 4182 | C | PRO | 541 | 54.463 | 49.358 | 60.500 | 1.00 | 27.83 | A | C |
| ATOM | 4183 | O | PRO | 541 | 53.579 | 48.727 | 59.912 | 1.00 | 28.03 | A | O |
| ATOM | 4184 | N | LEU | 542 | 54.763 | 50.613 | 60.200 | 1.00 | 27.70 | A | N |
| ATOM | 4185 | CA | LEU | 542 | 54.032 | 51.307 | 59.154 | 1.00 | 26.55 | A | C |
| ATOM | 4186 | CB | LEU | 542 | 53.220 | 52.440 | 59.791 | 1.00 | 26.11 | A | C |
| ATOM | 4187 | CG | LEU | 542 | 52.252 | 53.292 | 58.959 | 1.00 | 28.68 | A | C |
| ATOM | 4188 | CD1 | LEU | 542 | 51.422 | 54.170 | 59.898 | 1.00 | 29.38 | A | C |
| ATOM | 4189 | CD2 | LEU | 542 | 53.017 | 54.165 | 57.979 | 1.00 | 29.52 | A | C |
| ATOM | 4190 | C | LEU | 542 | 54.924 | 51.855 | 58.042 | 1.00 | 26.16 | A | C |
| ATOM | 4191 | O | LEU | 542 | 55.943 | 52.492 | 58.303 | 1.00 | 28.00 | A | O |
| ATOM | 4192 | N | LEU | 543 | 54.536 | 51.589 | 56.801 | 1.00 | 23.70 | A | N |
| ATOM | 4193 | CA | LEU | 543 | 55.263 | 52.097 | 55.651 | 1.00 | 24.11 | A | C |
| ATOM | 4194 | CB | LEU | 543 | 55.595 | 50.978 | 54.660 | 1.00 | 24.05 | A | C |
| ATOM | 4195 | CG | LEU | 543 | 56.080 | 51.474 | 53.289 | 1.00 | 22.45 | A | C |
| ATOM | 4196 | CD1 | LEU | 543 | 57.209 | 52.487 | 53.475 | 1.00 | 24.00 | A | C |
| ATOM | 4197 | CD2 | LEU | 543 | 56.537 | 50.303 | 52.441 | 1.00 | 20.16 | A | C |
| ATOM | 4198 | C | LEU | 543 | 54.378 | 53.131 | 54.966 | 1.00 | 24.37 | A | C |
| ATOM | 4199 | O | LEU | 543 | 53.283 | 52.819 | 54.511 | 1.00 | 25.72 | A | O |
| ATOM | 4200 | N | LEU | 544 | 54.857 | 54.362 | 54.896 | 1.00 | 24.80 | A | N |
| ATOM | 4201 | CA | LEU | 544 | 54.098 | 55.436 | 54.278 | 1.00 | 23.74 | A | C |
| ATOM | 4202 | CB | LEU | 544 | 54.424 | 56.757 | 54.979 | 1.00 | 23.92 | A | C |
| ATOM | 4203 | CG | LEU | 544 | 53.640 | 58.003 | 54.581 | 1.00 | 22.62 | A | C |
| ATOM | 4204 | CD1 | LEU | 544 | 52.157 | 57.743 | 54.729 | 1.00 | 24.91 | A | C |
| ATOM | 4205 | CD2 | LEU | 544 | 54.069 | 59.166 | 55.460 | 1.00 | 24.25 | A | C |
| ATOM | 4206 | C | LEU | 544 | 54.403 | 55.543 | 52.785 | 1.00 | 23.24 | A | C |
| ATOM | 4207 | O | LEU | 544 | 55.451 | 56.053 | 52.400 | 1.00 | 23.44 | A | O |
| ATOM | 4208 | N | ASP | 545 | 53.477 | 55.049 | 51.962 | 1.00 | 21.43 | A | N |
| ATOM | 4209 | CA | ASP | 545 | 53.595 | 55.075 | 50.508 | 1.00 | 20.10 | A | C |
| ATOM | 4210 | CB | ASP | 545 | 52.570 | 54.132 | 49.902 | 1.00 | 20.20 | A | C |
| ATOM | 4211 | CG | ASP | 545 | 52.826 | 53.848 | 48.444 | 1.00 | 20.73 | A | C |
| ATOM | 4212 | OD1 | ASP | 545 | 53.175 | 54.790 | 47.699 | 1.00 | 22.69 | A | O |
| ATOM | 4213 | OD2 | ASP | 545 | 52.660 | 52.675 | 48.044 | 1.00 | 19.91 | A | O |

FIG. 4-87 (Continued)

| ATOM | 4214 | C | ASP | 545 | 53.281 | 56.499 | 50.078 | 1.00 | 20.41 | A | C |
|---|---|---|---|---|---|---|---|---|---|---|---|
| ATOM | 4215 | O | ASP | 545 | 52.149 | 56.949 | 50.219 | 1.00 | 21.14 | A | O |
| ATOM | 4216 | N | VAL | 546 | 54.263 | 57.201 | 49.524 | 1.00 | 19.56 | A | N |
| ATOM | 4217 | CA | VAL | 546 | 54.043 | 58.591 | 49.157 | 1.00 | 20.20 | A | C |
| ATOM | 4218 | CB | VAL | 546 | 54.867 | 59.511 | 50.090 | 1.00 | 20.60 | A | C |
| ATOM | 4219 | CG1 | VAL | 546 | 54.626 | 60.966 | 49.753 | 1.00 | 20.01 | A | C |
| ATOM | 4220 | CG2 | VAL | 546 | 54.499 | 59.239 | 51.533 | 1.00 | 21.16 | A | C |
| ATOM | 4221 | C | VAL | 546 | 54.320 | 59.032 | 47.723 | 1.00 | 20.28 | A | C |
| ATOM | 4222 | O | VAL | 546 | 55.212 | 58.513 | 47.048 | 1.00 | 22.79 | A | O |
| ATOM | 4223 | N | TYR | 547 | 53.524 | 59.994 | 47.267 | 1.00 | 17.64 | A | N |
| ATOM | 4224 | CA | TYR | 547 | 53.702 | 60.604 | 45.957 | 1.00 | 15.73 | A | C |
| ATOM | 4225 | CB | TYR | 547 | 52.653 | 60.155 | 44.952 | 1.00 | 13.49 | A | C |
| ATOM | 4226 | CG | TYR | 547 | 52.969 | 60.718 | 43.589 | 1.00 | 13.89 | A | C |
| ATOM | 4227 | CD1 | TYR | 547 | 52.160 | 61.688 | 43.006 | 1.00 | 14.20 | A | C |
| ATOM | 4228 | CE1 | TYR | 547 | 52.513 | 62.274 | 41.801 | 1.00 | 13.67 | A | C |
| ATOM | 4229 | CD2 | TYR | 547 | 54.136 | 60.347 | 42.921 | 1.00 | 9.92 | A | C |
| ATOM | 4230 | CE2 | TYR | 547 | 54.492 | 60.926 | 41.726 | 1.00 | 10.35 | A | C |
| ATOM | 4231 | CZ | TYR | 547 | 53.680 | 61.890 | 41.167 | 1.00 | 12.20 | A | C |
| ATOM | 4232 | OH | TYR | 547 | 54.036 | 62.474 | 39.973 | 1.00 | 14.66 | A | O |
| ATOM | 4233 | C | TYR | 547 | 53.522 | 62.076 | 46.266 | 1.00 | 14.99 | A | C |
| ATOM | 4234 | O | TYR | 547 | 54.490 | 62.834 | 46.325 | 1.00 | 14.47 | A | O |
| ATOM | 4235 | N | ALA | 548 | 52.265 | 62.456 | 46.479 | 1.00 | 14.77 | A | N |
| ATOM | 4236 | CA | ALA | 548 | 51.879 | 63.806 | 46.878 | 1.00 | 12.10 | A | C |
| ATOM | 4237 | CB | ALA | 548 | 52.493 | 64.109 | 48.247 | 1.00 | 9.78 | A | C |
| ATOM | 4238 | C | ALA | 548 | 52.163 | 64.950 | 45.923 | 1.00 | 11.87 | A | C |
| ATOM | 4239 | O | ALA | 548 | 52.250 | 66.094 | 46.346 | 1.00 | 12.24 | A | O |
| ATOM | 4240 | N | GLY | 549 | 52.308 | 64.660 | 44.639 | 1.00 | 13.59 | A | N |
| ATOM | 4241 | CA | GLY | 549 | 52.556 | 65.734 | 43.696 | 1.00 | 13.20 | A | C |
| ATOM | 4242 | C | GLY | 549 | 51.306 | 66.578 | 43.573 | 1.00 | 13.15 | A | C |
| ATOM | 4243 | O | GLY | 549 | 50.266 | 66.182 | 44.074 | 1.00 | 12.86 | A | O |
| ATOM | 4244 | N | PRO | 550 | 51.365 | 67.745 | 42.915 | 1.00 | 15.91 | A | N |
| ATOM | 4245 | CD | PRO | 550 | 52.533 | 68.380 | 42.280 | 1.00 | 16.15 | A | C |
| ATOM | 4246 | CA | PRO | 550 | 50.174 | 68.592 | 42.776 | 1.00 | 15.03 | A | C |
| ATOM | 4247 | CB | PRO | 550 | 50.693 | 69.794 | 41.989 | 1.00 | 15.29 | A | C |
| ATOM | 4248 | CG | PRO | 550 | 52.145 | 69.838 | 42.325 | 1.00 | 15.06 | A | C |
| ATOM | 4249 | C | PRO | 550 | 49.074 | 67.848 | 42.026 | 1.00 | 15.37 | A | C |
| ATOM | 4250 | O | PRO | 550 | 49.336 | 67.204 | 41.012 | 1.00 | 16.91 | A | O |
| ATOM | 4251 | N | CYS | 551 | 47.849 | 67.946 | 42.532 | 1.00 | 15.67 | A | N |
| ATOM | 4252 | CA | CYS | 551 | 46.684 | 67.287 | 41.944 | 1.00 | 16.54 | A | C |
| ATOM | 4253 | CB | CYS | 551 | 46.424 | 67.796 | 40.525 | 1.00 | 16.53 | A | C |
| ATOM | 4254 | SG | CYS | 551 | 44.792 | 67.314 | 39.844 | 1.00 | 18.29 | A | S |
| ATOM | 4255 | C | CYS | 551 | 46.811 | 65.766 | 41.925 | 1.00 | 16.83 | A | C |
| ATOM | 4256 | O | CYS | 551 | 46.228 | 65.096 | 41.087 | 1.00 | 20.00 | A | O |
| ATOM | 4257 | N | SER | 552 | 47.574 | 65.219 | 42.856 | 1.00 | 16.56 | A | N |
| ATOM | 4258 | CA | SER | 552 | 47.742 | 63.785 | 42.933 | 1.00 | 16.35 | A | C |
| ATOM | 4259 | CB | SER | 552 | 49.063 | 63.450 | 43.613 | 1.00 | 19.76 | A | C |
| ATOM | 4260 | OG | SER | 552 | 49.023 | 63.805 | 44.987 | 1.00 | 20.36 | A | O |
| ATOM | 4261 | C | SER | 552 | 46.602 | 63.202 | 43.760 | 1.00 | 17.72 | A | C |
| ATOM | 4262 | O | SER | 552 | 45.723 | 63.929 | 44.243 | 1.00 | 17.55 | A | O |

FIG. 4-88 (Continued)

| ATOM | 4263 | N | GLN | 553 | 46.632 | 61.885 | 43.926 | 1.00 | 17.07 | A | N |
|---|---|---|---|---|---|---|---|---|---|---|---|
| ATOM | 4264 | CA | GLN | 553 | 45.628 | 61.179 | 44.699 | 1.00 | 16.87 | A | C |
| ATOM | 4265 | CB | GLN | 553 | 44.301 | 61.090 | 43.937 | 1.00 | 16.43 | A | C |
| ATOM | 4266 | CG | GLN | 553 | 43.249 | 60.292 | 44.695 | 1.00 | 19.53 | A | C |
| ATOM | 4267 | CD | GLN | 553 | 41.844 | 60.468 | 44.163 | 1.00 | 18.87 | A | C |
| ATOM | 4268 | OE1 | GLN | 553 | 41.520 | 60.019 | 43.066 | 1.00 | 20.67 | A | O |
| ATOM | 4269 | NE2 | GLN | 553 | 40.999 | 61.126 | 44.944 | 1.00 | 18.67 | A | N |
| ATOM | 4270 | C | GLN | 553 | 46.123 | 59.781 | 44.996 | 1.00 | 18.09 | A | C |
| ATOM | 4271 | O | GLN | 553 | 46.088 | 58.915 | 44.129 | 1.00 | 18.25 | A | O |
| ATOM | 4272 | N | LYS | 554 | 46.589 | 59.562 | 46.221 | 1.00 | 19.53 | A | N |
| ATOM | 4273 | CA | LYS | 554 | 47.075 | 58.248 | 46.620 | 1.00 | 20.69 | A | C |
| ATOM | 4274 | CB | LYS | 554 | 48.319 | 58.387 | 47.490 | 1.00 | 22.65 | A | C |
| ATOM | 4275 | CG | LYS | 554 | 49.538 | 58.887 | 46.733 | 1.00 | 24.15 | A | C |
| ATOM | 4276 | CD | LYS | 554 | 50.064 | 57.840 | 45.765 | 1.00 | 25.21 | A | C |
| ATOM | 4277 | CE | LYS | 554 | 50.777 | 56.711 | 46.503 | 1.00 | 24.75 | A | C |
| ATOM | 4278 | NZ | LYS | 554 | 51.472 | 55.796 | 45.560 | 1.00 | 23.89 | A | N |
| ATOM | 4279 | C | LYS | 554 | 45.996 | 57.472 | 47.374 | 1.00 | 21.48 | A | C |
| ATOM | 4280 | O | LYS | 554 | 46.108 | 56.258 | 47.549 | 1.00 | 22.39 | A | O |
| ATOM | 4281 | N | ALA | 555 | 44.952 | 58.176 | 47.807 | 1.00 | 20.77 | A | N |
| ATOM | 4282 | CA | ALA | 555 | 43.849 | 57.555 | 48.538 | 1.00 | 20.46 | A | C |
| ATOM | 4283 | CB | ALA | 555 | 43.525 | 58.376 | 49.768 | 1.00 | 18.05 | A | C |
| ATOM | 4284 | C | ALA | 555 | 42.611 | 57.436 | 47.643 | 1.00 | 21.32 | A | C |
| ATOM | 4285 | O | ALA | 555 | 41.996 | 58.442 | 47.285 | 1.00 | 21.75 | A | O |
| ATOM | 4286 | N | ASP | 556 | 42.249 | 56.208 | 47.283 | 1.00 | 21.00 | A | N |
| ATOM | 4287 | CA | ASP | 556 | 41.096 | 55.981 | 46.419 | 1.00 | 20.04 | A | C |
| ATOM | 4288 | CB | ASP | 556 | 41.500 | 56.151 | 44.960 | 1.00 | 20.02 | A | C |
| ATOM | 4289 | CG | ASP | 556 | 42.649 | 55.255 | 44.574 | 1.00 | 19.76 | A | C |
| ATOM | 4290 | OD1 | ASP | 556 | 42.723 | 54.132 | 45.115 | 1.00 | 19.65 | A | O |
| ATOM | 4291 | OD2 | ASP | 556 | 43.470 | 55.666 | 43.723 | 1.00 | 21.90 | A | O |
| ATOM | 4292 | C | ASP | 556 | 40.478 | 54.603 | 46.614 | 1.00 | 20.18 | A | C |
| ATOM | 4293 | O | ASP | 556 | 40.856 | 53.874 | 47.523 | 1.00 | 19.93 | A | O |
| ATOM | 4294 | N | THR | 557 | 39.542 | 54.246 | 45.736 | 1.00 | 20.55 | A | N |
| ATOM | 4295 | CA | THR | 557 | 38.835 | 52.965 | 45.820 | 1.00 | 22.31 | A | C |
| ATOM | 4296 | CB | THR | 557 | 37.331 | 53.154 | 45.578 | 1.00 | 21.37 | A | C |
| ATOM | 4297 | OG1 | THR | 557 | 37.130 | 53.580 | 44.224 | 1.00 | 21.50 | A | O |
| ATOM | 4298 | CG2 | THR | 557 | 36.754 | 54.201 | 46.523 | 1.00 | 21.28 | A | C |
| ATOM | 4299 | C | THR | 557 | 39.294 | 51.898 | 44.826 | 1.00 | 23.72 | A | C |
| ATOM | 4300 | O | THR | 557 | 38.606 | 50.891 | 44.633 | 1.00 | 25.32 | A | O |
| ATOM | 4301 | N | VAL | 558 | 40.441 | 52.105 | 44.194 | 1.00 | 22.84 | A | N |
| ATOM | 4302 | CA | VAL | 558 | 40.931 | 51.143 | 43.219 | 1.00 | 22.53 | A | C |
| ATOM | 4303 | CB | VAL | 558 | 41.970 | 51.802 | 42.294 | 1.00 | 22.67 | A | C |
| ATOM | 4304 | CG1 | VAL | 558 | 42.540 | 50.783 | 41.323 | 1.00 | 19.20 | A | C |
| ATOM | 4305 | CG2 | VAL | 558 | 41.323 | 52.964 | 41.547 | 1.00 | 21.12 | A | C |
| ATOM | 4306 | C | VAL | 558 | 41.544 | 49.906 | 43.871 | 1.00 | 23.92 | A | C |
| ATOM | 4307 | O | VAL | 558 | 42.246 | 50.005 | 44.871 | 1.00 | 23.71 | A | O |
| ATOM | 4308 | N | PHE | 559 | 41.261 | 48.734 | 43.312 | 1.00 | 25.05 | A | N |
| ATOM | 4309 | CA | PHE | 559 | 41.815 | 47.492 | 43.841 | 1.00 | 25.45 | A | C |
| ATOM | 4310 | CB | PHE | 559 | 40.855 | 46.326 | 43.584 | 1.00 | 24.60 | A | C |
| ATOM | 4311 | CG | PHE | 559 | 41.476 | 44.977 | 43.808 | 1.00 | 24.75 | A | C |

FIG. 4-89 (Continued)

| | | | | | | | | | | |
|---|---|---|---|---|---|---|---|---|---|---|
| ATOM | 4312 | CD1 | PHE | 559 | 42.192 | 44.352 | 42.799 | 1.00 | 25.70 | A C |
| ATOM | 4313 | CD2 | PHE | 559 | 41.382 | 44.352 | 45.044 | 1.00 | 25.27 | A C |
| ATOM | 4314 | CE1 | PHE | 559 | 42.810 | 43.118 | 43.021 | 1.00 | 28.04 | A C |
| ATOM | 4315 | CE2 | PHE | 559 | 41.995 | 43.125 | 45.276 | 1.00 | 24.71 | A C |
| ATOM | 4316 | CZ | PHE | 559 | 42.709 | 42.507 | 44.266 | 1.00 | 26.38 | A C |
| ATOM | 4317 | C | PHE | 559 | 43.158 | 47.210 | 43.170 | 1.00 | 26.14 | A C |
| ATOM | 4318 | O | PHE | 559 | 43.250 | 47.246 | 41.943 | 1.00 | 27.21 | A O |
| ATOM | 4319 | N | ARG | 560 | 44.188 | 46.912 | 43.962 | 1.00 | 24.72 | A N |
| ATOM | 4320 | CA | ARG | 560 | 45.508 | 46.644 | 43.397 | 1.00 | 23.52 | A C |
| ATOM | 4321 | CB | ARG | 560 | 46.398 | 47.892 | 43.510 | 1.00 | 20.68 | A C |
| ATOM | 4322 | CG | ARG | 560 | 45.869 | 49.140 | 42.802 | 1.00 | 19.21 | A C |
| ATOM | 4323 | CD | ARG | 560 | 46.885 | 50.285 | 42.869 | 1.00 | 17.64 | A C |
| ATOM | 4324 | NE | ARG | 560 | 46.269 | 51.536 | 43.310 | 1.00 | 20.38 | A N |
| ATOM | 4325 | CZ | ARG | 560 | 45.637 | 52.391 | 42.515 | 1.00 | 20.51 | A C |
| ATOM | 4326 | NH1 | ARG | 560 | 45.543 | 52.149 | 41.218 | 1.00 | 26.51 | A N |
| ATOM | 4327 | NH2 | ARG | 560 | 45.061 | 53.468 | 43.022 | 1.00 | 20.25 | A N |
| ATOM | 4328 | C | ARG | 560 | 46.274 | 45.451 | 43.980 | 1.00 | 24.37 | A C |
| ATOM | 4329 | O | ARG | 560 | 46.112 | 45.081 | 45.145 | 1.00 | 24.84 | A O |
| ATOM | 4330 | N | LEU | 561 | 47.111 | 44.856 | 43.136 | 1.00 | 23.62 | A N |
| ATOM | 4331 | CA | LEU | 561 | 47.968 | 43.740 | 43.511 | 1.00 | 20.95 | A C |
| ATOM | 4332 | CB | LEU | 561 | 47.680 | 42.523 | 42.635 | 1.00 | 18.87 | A C |
| ATOM | 4333 | CG | LEU | 561 | 46.283 | 41.916 | 42.773 | 1.00 | 20.60 | A C |
| ATOM | 4334 | CD1 | LEU | 561 | 46.139 | 40.749 | 41.803 | 1.00 | 19.75 | A C |
| ATOM | 4335 | CD2 | LEU | 561 | 46.045 | 41.460 | 44.203 | 1.00 | 17.53 | A C |
| ATOM | 4336 | C | LEU | 561 | 49.380 | 44.255 | 43.246 | 1.00 | 20.00 | A C |
| ATOM | 4337 | O | LEU | 561 | 49.894 | 44.152 | 42.133 | 1.00 | 20.19 | A O |
| ATOM | 4338 | N | ASN | 562 | 49.999 | 44.822 | 44.274 | 1.00 | 18.97 | A N |
| ATOM | 4339 | CA | ASN | 562 | 51.335 | 45.392 | 44.142 | 1.00 | 18.20 | A C |
| ATOM | 4340 | CB | ASN | 562 | 51.197 | 46.907 | 44.028 | 1.00 | 16.72 | A C |
| ATOM | 4341 | CG | ASN | 562 | 50.364 | 47.491 | 45.148 | 1.00 | 17.45 | A C |
| ATOM | 4342 | OD1 | ASN | 562 | 49.881 | 48.610 | 45.054 | 1.00 | 19.63 | A O |
| ATOM | 4343 | ND2 | ASN | 562 | 50.195 | 46.729 | 46.223 | 1.00 | 18.39 | A N |
| ATOM | 4344 | C | ASN | 562 | 52.291 | 45.035 | 45.289 | 1.00 | 18.48 | A C |
| ATOM | 4345 | O | ASN | 562 | 52.055 | 44.098 | 46.056 | 1.00 | 19.79 | A O |
| ATOM | 4346 | N | TRP | 563 | 53.375 | 45.793 | 45.400 | 1.00 | 17.98 | A N |
| ATOM | 4347 | CA | TRP | 563 | 54.366 | 45.548 | 46.434 | 1.00 | 17.62 | A C |
| ATOM | 4348 | CB | TRP | 563 | 55.538 | 46.537 | 46.290 | 1.00 | 16.04 | A C |
| ATOM | 4349 | CG | TRP | 563 | 56.741 | 46.249 | 47.178 | 1.00 | 15.76 | A C |
| ATOM | 4350 | CD2 | TRP | 563 | 57.474 | 47.200 | 47.968 | 1.00 | 13.80 | A C |
| ATOM | 4351 | CE2 | TRP | 563 | 58.526 | 46.500 | 48.602 | 1.00 | 11.13 | A C |
| ATOM | 4352 | CE3 | TRP | 563 | 57.341 | 48.575 | 48.198 | 1.00 | 13.46 | A C |
| ATOM | 4353 | CD1 | TRP | 563 | 57.367 | 45.041 | 47.361 | 1.00 | 12.65 | A C |
| ATOM | 4354 | NE1 | TRP | 563 | 58.440 | 45.189 | 48.217 | 1.00 | 11.34 | A N |
| ATOM | 4355 | CZ2 | TRP | 563 | 59.439 | 47.128 | 49.453 | 1.00 | 14.40 | A C |
| ATOM | 4356 | CZ3 | TRP | 563 | 58.252 | 49.204 | 49.046 | 1.00 | 16.29 | A C |
| ATOM | 4357 | CH2 | TRP | 563 | 59.291 | 48.476 | 49.664 | 1.00 | 14.18 | A C |
| ATOM | 4358 | C | TRP | 563 | 53.728 | 45.672 | 47.809 | 1.00 | 17.48 | A C |
| ATOM | 4359 | O | TRP | 563 | 54.048 | 44.910 | 48.720 | 1.00 | 18.93 | A O |
| ATOM | 4360 | N | ALA | 564 | 52.813 | 46.620 | 47.953 | 1.00 | 16.80 | A N |

| ATOM | 4361 | CA  | ALA | 564 | 52.151 | 46.838 | 49.232 | 1.00 | 17.11 | A | C |
| --- | --- | --- | --- | --- | --- | --- | --- | --- | --- | --- | --- |
| ATOM | 4362 | CB  | ALA | 564 | 51.248 | 48.068 | 49.153 | 1.00 | 16.72 | A | C |
| ATOM | 4363 | C   | ALA | 564 | 51.341 | 45.616 | 49.655 | 1.00 | 17.89 | A | C |
| ATOM | 4364 | O   | ALA | 564 | 51.322 | 45.256 | 50.834 | 1.00 | 15.94 | A | O |
| ATOM | 4365 | N   | THR | 565 | 50.676 | 44.983 | 48.691 | 1.00 | 18.77 | A | N |
| ATOM | 4366 | CA  | THR | 565 | 49.870 | 43.801 | 48.977 | 1.00 | 19.59 | A | C |
| ATOM | 4367 | CB  | THR | 565 | 49.368 | 43.131 | 47.689 | 1.00 | 20.01 | A | C |
| ATOM | 4368 | OG1 | THR | 565 | 48.606 | 44.069 | 46.922 | 1.00 | 19.76 | A | O |
| ATOM | 4369 | CG2 | THR | 565 | 48.496 | 41.922 | 48.027 | 1.00 | 19.34 | A | C |
| ATOM | 4370 | C   | THR | 565 | 50.718 | 42.793 | 49.739 | 1.00 | 21.27 | A | C |
| ATOM | 4371 | O   | THR | 565 | 50.290 | 42.252 | 50.760 | 1.00 | 22.29 | A | O |
| ATOM | 4372 | N   | TYR | 566 | 51.924 | 42.548 | 49.234 | 1.00 | 22.25 | A | N |
| ATOM | 4373 | CA  | TYR | 566 | 52.848 | 41.615 | 49.864 | 1.00 | 23.40 | A | C |
| ATOM | 4374 | CB  | TYR | 566 | 54.029 | 41.324 | 48.923 | 1.00 | 25.18 | A | C |
| ATOM | 4375 | CG  | TYR | 566 | 55.369 | 41.218 | 49.616 | 1.00 | 25.40 | A | C |
| ATOM | 4376 | CD1 | TYR | 566 | 56.297 | 42.262 | 49.547 | 1.00 | 25.62 | A | C |
| ATOM | 4377 | CE1 | TYR | 566 | 57.513 | 42.196 | 50.226 | 1.00 | 26.85 | A | C |
| ATOM | 4378 | CD2 | TYR | 566 | 55.690 | 40.101 | 50.382 | 1.00 | 26.99 | A | C |
| ATOM | 4379 | CE2 | TYR | 566 | 56.903 | 40.023 | 51.073 | 1.00 | 29.74 | A | C |
| ATOM | 4380 | CZ  | TYR | 566 | 57.809 | 41.074 | 50.991 | 1.00 | 30.16 | A | C |
| ATOM | 4381 | OH  | TYR | 566 | 58.997 | 40.998 | 51.688 | 1.00 | 32.61 | A | O |
| ATOM | 4382 | C   | TYR | 566 | 53.369 | 42.116 | 51.212 | 1.00 | 23.06 | A | C |
| ATOM | 4383 | O   | TYR | 566 | 53.458 | 41.350 | 52.170 | 1.00 | 21.96 | A | O |
| ATOM | 4384 | N   | LEU | 567 | 53.716 | 43.396 | 51.288 | 1.00 | 23.28 | A | N |
| ATOM | 4385 | CA  | LEU | 567 | 54.237 | 43.949 | 52.532 | 1.00 | 24.50 | A | C |
| ATOM | 4386 | CB  | LEU | 567 | 54.588 | 45.429 | 52.359 | 1.00 | 22.74 | A | C |
| ATOM | 4387 | CG  | LEU | 567 | 55.717 | 45.769 | 51.378 | 1.00 | 23.15 | A | C |
| ATOM | 4388 | CD1 | LEU | 567 | 55.833 | 47.279 | 51.263 | 1.00 | 20.37 | A | C |
| ATOM | 4389 | CD2 | LEU | 567 | 57.038 | 45.158 | 51.850 | 1.00 | 21.42 | A | C |
| ATOM | 4390 | C   | LEU | 567 | 53.243 | 43.786 | 53.675 | 1.00 | 26.32 | A | C |
| ATOM | 4391 | O   | LEU | 567 | 53.635 | 43.595 | 54.824 | 1.00 | 27.44 | A | O |
| ATOM | 4392 | N   | ALA | 568 | 51.955 | 43.857 | 53.361 | 1.00 | 26.96 | A | N |
| ATOM | 4393 | CA  | ALA | 568 | 50.930 | 43.712 | 54.383 | 1.00 | 27.44 | A | C |
| ATOM | 4394 | CB  | ALA | 568 | 49.684 | 44.481 | 53.984 | 1.00 | 26.54 | A | C |
| ATOM | 4395 | C   | ALA | 568 | 50.584 | 42.242 | 54.606 | 1.00 | 29.12 | A | C |
| ATOM | 4396 | O   | ALA | 568 | 50.483 | 41.782 | 55.748 | 1.00 | 28.80 | A | O |
| ATOM | 4397 | N   | SER | 569 | 50.417 | 41.506 | 53.509 | 1.00 | 28.58 | A | N |
| ATOM | 4398 | CA  | SER | 569 | 50.062 | 40.094 | 53.586 | 1.00 | 28.31 | A | C |
| ATOM | 4399 | CB  | SER | 569 | 49.750 | 39.553 | 52.191 | 1.00 | 28.85 | A | C |
| ATOM | 4400 | OG  | SER | 569 | 49.420 | 38.174 | 52.247 | 1.00 | 30.69 | A | O |
| ATOM | 4401 | C   | SER | 569 | 51.110 | 39.204 | 54.236 | 1.00 | 27.43 | A | C |
| ATOM | 4402 | O   | SER | 569 | 50.800 | 38.427 | 55.133 | 1.00 | 28.44 | A | O |
| ATOM | 4403 | N   | THR | 570 | 52.350 | 39.311 | 53.781 | 1.00 | 27.24 | A | N |
| ATOM | 4404 | CA  | THR | 570 | 53.420 | 38.483 | 54.314 | 1.00 | 27.02 | A | C |
| ATOM | 4405 | CB  | THR | 570 | 54.410 | 38.094 | 53.199 | 1.00 | 26.90 | A | C |
| ATOM | 4406 | OG1 | THR | 570 | 53.749 | 37.250 | 52.248 | 1.00 | 27.63 | A | O |
| ATOM | 4407 | CG2 | THR | 570 | 55.611 | 37.369 | 53.774 | 1.00 | 23.88 | A | C |
| ATOM | 4408 | C   | THR | 570 | 54.203 | 39.110 | 55.459 | 1.00 | 27.34 | A | C |
| ATOM | 4409 | O   | THR | 570 | 54.362 | 38.496 | 56.512 | 1.00 | 30.01 | A | O |

FIG. 4-91

| ATOM | 4410 | N | GLU | 571 | 54.686 | 40.329 | 55.253 | 1.00 | 26.71 | A | N |
|---|---|---|---|---|---|---|---|---|---|---|---|
| ATOM | 4411 | CA | GLU | 571 | 55.480 | 41.020 | 56.259 | 1.00 | 25.23 | A | C |
| ATOM | 4412 | CB | GLU | 571 | 56.402 | 42.040 | 55.583 | 1.00 | 24.64 | A | C |
| ATOM | 4413 | CG | GLU | 571 | 57.287 | 41.472 | 54.473 | 1.00 | 25.43 | A | C |
| ATOM | 4414 | CD | GLU | 571 | 58.238 | 40.392 | 54.966 | 1.00 | 27.45 | A | C |
| ATOM | 4415 | OE1 | GLU | 571 | 58.582 | 40.421 | 56.164 | 1.00 | 28.11 | A | O |
| ATOM | 4416 | OE2 | GLU | 571 | 58.656 | 39.527 | 54.158 | 1.00 | 27.18 | A | O |
| ATOM | 4417 | C | GLU | 571 | 54.643 | 41.715 | 57.329 | 1.00 | 24.50 | A | C |
| ATOM | 4418 | O | GLU | 571 | 55.188 | 42.368 | 58.213 | 1.00 | 24.29 | A | O |
| ATOM | 4419 | N | ASN | 572 | 53.324 | 41.576 | 57.247 | 1.00 | 24.39 | A | N |
| ATOM | 4420 | CA | ASN | 572 | 52.425 | 42.191 | 58.223 | 1.00 | 24.96 | A | C |
| ATOM | 4421 | CB | ASN | 572 | 52.557 | 41.486 | 59.569 | 1.00 | 25.44 | A | C |
| ATOM | 4422 | CG | ASN | 572 | 52.139 | 40.033 | 59.507 | 1.00 | 29.03 | A | C |
| ATOM | 4423 | OD1 | ASN | 572 | 52.711 | 39.187 | 60.192 | 1.00 | 30.88 | A | O |
| ATOM | 4424 | ND2 | ASN | 572 | 51.128 | 39.734 | 58.694 | 1.00 | 29.67 | A | N |
| ATOM | 4425 | C | ASN | 572 | 52.683 | 43.681 | 58.419 | 1.00 | 25.32 | A | C |
| ATOM | 4426 | O | ASN | 572 | 52.642 | 44.178 | 59.545 | 1.00 | 25.55 | A | O |
| ATOM | 4427 | N | ILE | 573 | 52.944 | 44.387 | 57.321 | 1.00 | 25.48 | A | N |
| ATOM | 4428 | CA | ILE | 573 | 53.208 | 45.824 | 57.360 | 1.00 | 24.87 | A | C |
| ATOM | 4429 | CB | ILE | 573 | 54.396 | 46.198 | 56.446 | 1.00 | 24.59 | A | C |
| ATOM | 4430 | CG2 | ILE | 573 | 54.715 | 47.669 | 56.584 | 1.00 | 22.90 | A | C |
| ATOM | 4431 | CG1 | ILE | 573 | 55.622 | 45.365 | 56.800 | 1.00 | 25.08 | A | C |
| ATOM | 4432 | CD1 | ILE | 573 | 56.805 | 45.636 | 55.900 | 1.00 | 25.36 | A | C |
| ATOM | 4433 | C | ILE | 573 | 51.992 | 46.621 | 56.875 | 1.00 | 25.22 | A | C |
| ATOM | 4434 | O | ILE | 573 | 51.353 | 46.249 | 55.891 | 1.00 | 24.86 | A | O |
| ATOM | 4435 | N | ILE | 574 | 51.681 | 47.718 | 57.557 | 1.00 | 24.59 | A | N |
| ATOM | 4436 | CA | ILE | 574 | 50.557 | 48.555 | 57.159 | 1.00 | 26.14 | A | C |
| ATOM | 4437 | CB | ILE | 574 | 49.926 | 49.297 | 58.359 | 1.00 | 25.88 | A | C |
| ATOM | 4438 | CG2 | ILE | 574 | 48.798 | 50.190 | 57.874 | 1.00 | 26.06 | A | C |
| ATOM | 4439 | CG1 | ILE | 574 | 49.399 | 48.304 | 59.386 | 1.00 | 27.36 | A | C |
| ATOM | 4440 | CD1 | ILE | 574 | 48.794 | 48.968 | 60.607 | 1.00 | 29.19 | A | C |
| ATOM | 4441 | C | ILE | 574 | 51.064 | 49.619 | 56.191 | 1.00 | 27.12 | A | C |
| ATOM | 4442 | O | ILE | 574 | 51.799 | 50.524 | 56.591 | 1.00 | 28.97 | A | O |
| ATOM | 4443 | N | VAL | 575 | 50.683 | 49.521 | 54.924 | 1.00 | 25.92 | A | N |
| ATOM | 4444 | CA | VAL | 575 | 51.128 | 50.517 | 53.962 | 1.00 | 24.87 | A | C |
| ATOM | 4445 | CB | VAL | 575 | 51.387 | 49.904 | 52.569 | 1.00 | 24.76 | A | C |
| ATOM | 4446 | CG1 | VAL | 575 | 51.973 | 50.966 | 51.644 | 1.00 | 20.17 | A | C |
| ATOM | 4447 | CG2 | VAL | 575 | 52.320 | 48.707 | 52.690 | 1.00 | 22.12 | A | C |
| ATOM | 4448 | C | VAL | 575 | 50.054 | 51.585 | 53.837 | 1.00 | 25.21 | A | C |
| ATOM | 4449 | O | VAL | 575 | 48.929 | 51.312 | 53.405 | 1.00 | 25.63 | A | O |
| ATOM | 4450 | N | ALA | 576 | 50.403 | 52.804 | 54.216 | 1.00 | 23.75 | A | N |
| ATOM | 4451 | CA | ALA | 576 | 49.456 | 53.893 | 54.152 | 1.00 | 23.56 | A | C |
| ATOM | 4452 | CB | ALA | 576 | 49.255 | 54.477 | 55.540 | 1.00 | 23.43 | A | C |
| ATOM | 4453 | C | ALA | 576 | 49.879 | 54.988 | 53.180 | 1.00 | 24.06 | A | C |
| ATOM | 4454 | O | ALA | 576 | 51.056 | 55.139 | 52.860 | 1.00 | 22.16 | A | O |
| ATOM | 4455 | N | SER | 577 | 48.888 | 55.740 | 52.710 | 1.00 | 24.49 | A | N |
| ATOM | 4456 | CA | SER | 577 | 49.095 | 56.852 | 51.796 | 1.00 | 23.11 | A | C |
| ATOM | 4457 | CB | SER | 577 | 48.793 | 56.428 | 50.362 | 1.00 | 23.06 | A | C |
| ATOM | 4458 | OG | SER | 577 | 49.750 | 55.475 | 49.921 | 1.00 | 22.88 | A | O |

| | | | | | | | | | | |
|---|---|---|---|---|---|---|---|---|---|---|
| ATOM | 4459 | C | SER | 577 | 48.149 | 57.947 | 52.248 | 1.00 | 22.90 | A C |
| ATOM | 4460 | O | SER | 577 | 47.075 | 57.662 | 52.768 | 1.00 | 24.22 | A O |
| ATOM | 4461 | N | PHE | 578 | 48.546 | 59.196 | 52.046 | 1.00 | 23.49 | A N |
| ATOM | 4462 | CA | PHE | 578 | 47.748 | 60.337 | 52.479 | 1.00 | 21.77 | A C |
| ATOM | 4463 | CB | PHE | 578 | 48.313 | 60.829 | 53.804 | 1.00 | 21.41 | A C |
| ATOM | 4464 | CG | PHE | 578 | 47.585 | 62.005 | 54.383 | 1.00 | 22.79 | A C |
| ATOM | 4465 | CD1 | PHE | 578 | 46.429 | 61.820 | 55.144 | 1.00 | 20.60 | A C |
| ATOM | 4466 | CD2 | PHE | 578 | 48.080 | 63.291 | 54.209 | 1.00 | 19.79 | A C |
| ATOM | 4467 | CE1 | PHE | 578 | 45.783 | 62.901 | 55.730 | 1.00 | 21.26 | A C |
| ATOM | 4468 | CE2 | PHE | 578 | 47.441 | 64.381 | 54.790 | 1.00 | 20.94 | A C |
| ATOM | 4469 | CZ | PHE | 578 | 46.288 | 64.186 | 55.556 | 1.00 | 20.70 | A C |
| ATOM | 4470 | C | PHE | 578 | 47.723 | 61.502 | 51.480 | 1.00 | 21.14 | A C |
| ATOM | 4471 | O | PHE | 578 | 48.766 | 61.909 | 50.973 | 1.00 | 21.08 | A O |
| ATOM | 4472 | N | ASP | 579 | 46.533 | 62.041 | 51.212 | 1.00 | 19.89 | A N |
| ATOM | 4473 | CA | ASP | 579 | 46.389 | 63.173 | 50.302 | 1.00 | 18.01 | A C |
| ATOM | 4474 | CB | ASP | 579 | 45.191 | 62.985 | 49.371 | 1.00 | 17.01 | A C |
| ATOM | 4475 | CG | ASP | 579 | 45.334 | 61.777 | 48.455 | 1.00 | 21.86 | A C |
| ATOM | 4476 | OD1 | ASP | 579 | 46.424 | 61.583 | 47.873 | 1.00 | 22.87 | A O |
| ATOM | 4477 | OD2 | ASP | 579 | 44.342 | 61.024 | 48.299 | 1.00 | 23.17 | A O |
| ATOM | 4478 | C | ASP | 579 | 46.211 | 64.474 | 51.092 | 1.00 | 18.10 | A C |
| ATOM | 4479 | O | ASP | 579 | 45.103 | 64.823 | 51.493 | 1.00 | 20.42 | A O |
| ATOM | 4480 | N | GLY | 580 | 47.306 | 65.189 | 51.313 | 1.00 | 17.22 | A N |
| ATOM | 4481 | CA | GLY | 580 | 47.238 | 66.439 | 52.044 | 1.00 | 15.14 | A C |
| ATOM | 4482 | C | GLY | 580 | 47.065 | 67.610 | 51.098 | 1.00 | 16.53 | A C |
| ATOM | 4483 | O | GLY | 580 | 46.544 | 67.462 | 49.993 | 1.00 | 17.18 | A O |
| ATOM | 4484 | N | ARG | 581 | 47.495 | 68.786 | 51.528 | 1.00 | 15.90 | A N |
| ATOM | 4485 | CA | ARG | 581 | 47.377 | 69.970 | 50.701 | 1.00 | 15.52 | A C |
| ATOM | 4486 | CB | ARG | 581 | 47.956 | 71.172 | 51.444 | 1.00 | 16.17 | A C |
| ATOM | 4487 | CG | ARG | 581 | 47.072 | 71.645 | 52.585 | 1.00 | 16.05 | A C |
| ATOM | 4488 | CD | ARG | 581 | 47.756 | 72.653 | 53.467 | 1.00 | 14.87 | A C |
| ATOM | 4489 | NE | ARG | 581 | 48.617 | 71.990 | 54.441 | 1.00 | 18.25 | A N |
| ATOM | 4490 | CZ | ARG | 581 | 49.321 | 72.624 | 55.375 | 1.00 | 19.44 | A C |
| ATOM | 4491 | NH1 | ARG | 581 | 49.268 | 73.952 | 55.463 | 1.00 | 20.41 | A N |
| ATOM | 4492 | NH2 | ARG | 581 | 50.075 | 71.933 | 56.224 | 1.00 | 15.76 | A N |
| ATOM | 4493 | C | ARG | 581 | 48.107 | 69.742 | 49.386 | 1.00 | 17.75 | A C |
| ATOM | 4494 | O | ARG | 581 | 49.193 | 69.158 | 49.357 | 1.00 | 17.49 | A O |
| ATOM | 4495 | N | GLY | 582 | 47.495 | 70.192 | 48.295 | 1.00 | 18.96 | A N |
| ATOM | 4496 | CA | GLY | 582 | 48.094 | 70.022 | 46.987 | 1.00 | 17.63 | A C |
| ATOM | 4497 | C | GLY | 582 | 47.511 | 68.842 | 46.231 | 1.00 | 18.54 | A C |
| ATOM | 4498 | O | GLY | 582 | 47.673 | 68.757 | 45.017 | 1.00 | 18.99 | A O |
| ATOM | 4499 | N | SER | 583 | 46.842 | 67.923 | 46.925 | 1.00 | 18.00 | A N |
| ATOM | 4500 | CA | SER | 583 | 46.258 | 66.765 | 46.247 | 1.00 | 18.46 | A C |
| ATOM | 4501 | CB | SER | 583 | 45.842 | 65.700 | 47.269 | 1.00 | 18.34 | A C |
| ATOM | 4502 | OG | SER | 583 | 45.058 | 66.253 | 48.303 | 1.00 | 19.12 | A O |
| ATOM | 4503 | C | SER | 583 | 45.068 | 67.218 | 45.392 | 1.00 | 18.03 | A C |
| ATOM | 4504 | O | SER | 583 | 44.601 | 68.344 | 45.536 | 1.00 | 17.42 | A O |
| ATOM | 4505 | N | GLY | 584 | 44.570 | 66.355 | 44.510 | 1.00 | 17.84 | A N |
| ATOM | 4506 | CA | GLY | 584 | 43.481 | 66.779 | 43.637 | 1.00 | 19.22 | A C |
| ATOM | 4507 | C | GLY | 584 | 42.052 | 66.293 | 43.827 | 1.00 | 19.49 | A C |

| | | | | | | | | | | |
|---|---|---|---|---|---|---|---|---|---|---|
| ATOM | 4508 | O | GLY | 584 | 41.724 | 65.570 | 44.767 | 1.00 | 21.57 | A | O |
| ATOM | 4509 | N | TYR | 585 | 41.191 | 66.735 | 42.917 | 1.00 | 19.76 | A | N |
| ATOM | 4510 | CA | TYR | 585 | 39.782 | 66.362 | 42.906 | 1.00 | 18.53 | A | C |
| ATOM | 4511 | CB | TYR | 585 | 39.673 | 64.859 | 42.663 | 1.00 | 18.57 | A | C |
| ATOM | 4512 | CG | TYR | 585 | 40.578 | 64.401 | 41.550 | 1.00 | 18.83 | A | C |
| ATOM | 4513 | CD1 | TYR | 585 | 40.439 | 64.914 | 40.260 | 1.00 | 19.48 | A | C |
| ATOM | 4514 | CE1 | TYR | 585 | 41.300 | 64.533 | 39.235 | 1.00 | 18.11 | A | C |
| ATOM | 4515 | CD2 | TYR | 585 | 41.606 | 63.490 | 41.789 | 1.00 | 19.81 | A | C |
| ATOM | 4516 | CE2 | TYR | 585 | 42.476 | 63.100 | 40.769 | 1.00 | 17.71 | A | C |
| ATOM | 4517 | CZ | TYR | 585 | 42.313 | 63.626 | 39.497 | 1.00 | 18.76 | A | C |
| ATOM | 4518 | OH | TYR | 585 | 43.150 | 63.232 | 38.481 | 1.00 | 20.70 | A | O |
| ATOM | 4519 | C | TYR | 585 | 38.997 | 66.751 | 44.152 | 1.00 | 18.81 | A | C |
| ATOM | 4520 | O | TYR | 585 | 38.046 | 66.067 | 44.521 | 1.00 | 17.85 | A | O |
| ATOM | 4521 | N | GLN | 586 | 39.382 | 67.861 | 44.783 | 1.00 | 20.25 | A | N |
| ATOM | 4522 | CA | GLN | 586 | 38.708 | 68.345 | 45.986 | 1.00 | 20.04 | A | C |
| ATOM | 4523 | CB | GLN | 586 | 39.455 | 67.886 | 47.233 | 1.00 | 20.09 | A | C |
| ATOM | 4524 | CG | GLN | 586 | 39.770 | 66.412 | 47.279 | 1.00 | 20.60 | A | C |
| ATOM | 4525 | CD | GLN | 586 | 40.781 | 66.095 | 48.363 | 1.00 | 24.77 | A | C |
| ATOM | 4526 | OE1 | GLN | 586 | 40.441 | 66.029 | 49.548 | 1.00 | 23.60 | A | O |
| ATOM | 4527 | NE2 | GLN | 586 | 42.044 | 65.919 | 47.962 | 1.00 | 25.12 | A | N |
| ATOM | 4528 | C | GLN | 586 | 38.619 | 69.869 | 46.024 | 1.00 | 22.06 | A | C |
| ATOM | 4529 | O | GLN | 586 | 38.424 | 70.455 | 47.092 | 1.00 | 23.83 | A | O |
| ATOM | 4530 | N | GLY | 587 | 38.783 | 70.518 | 44.877 | 1.00 | 21.79 | A | N |
| ATOM | 4531 | CA | GLY | 587 | 38.707 | 71.969 | 44.853 | 1.00 | 21.24 | A | C |
| ATOM | 4532 | C | GLY | 587 | 40.073 | 72.623 | 44.883 | 1.00 | 21.56 | A | C |
| ATOM | 4533 | O | GLY | 587 | 41.033 | 72.035 | 45.364 | 1.00 | 23.11 | A | O |
| ATOM | 4534 | N | ASP | 588 | 40.154 | 73.856 | 44.397 | 1.00 | 21.25 | A | N |
| ATOM | 4535 | CA | ASP | 588 | 41.415 | 74.580 | 44.339 | 1.00 | 22.09 | A | C |
| ATOM | 4536 | CB | ASP | 588 | 41.287 | 75.763 | 43.382 | 1.00 | 22.35 | A | C |
| ATOM | 4537 | CG | ASP | 588 | 40.944 | 75.340 | 41.965 | 1.00 | 25.14 | A | C |
| ATOM | 4538 | OD1 | ASP | 588 | 40.465 | 76.213 | 41.211 | 1.00 | 25.77 | A | O |
| ATOM | 4539 | OD2 | ASP | 588 | 41.157 | 74.155 | 41.599 | 1.00 | 24.41 | A | O |
| ATOM | 4540 | C | ASP | 588 | 41.955 | 75.079 | 45.675 | 1.00 | 23.08 | A | C |
| ATOM | 4541 | O | ASP | 588 | 43.121 | 75.471 | 45.762 | 1.00 | 22.71 | A | O |
| ATOM | 4542 | N | LYS | 589 | 41.130 | 75.086 | 46.716 | 1.00 | 23.77 | A | N |
| ATOM | 4543 | CA | LYS | 589 | 41.620 | 75.562 | 47.998 | 1.00 | 22.97 | A | C |
| ATOM | 4544 | CB | LYS | 589 | 40.509 | 75.616 | 49.037 | 1.00 | 24.26 | A | C |
| ATOM | 4545 | CG | LYS | 589 | 40.994 | 76.173 | 50.365 | 1.00 | 29.68 | A | C |
| ATOM | 4546 | CD | LYS | 589 | 39.916 | 76.141 | 51.439 | 1.00 | 35.08 | A | C |
| ATOM | 4547 | CE | LYS | 589 | 40.457 | 76.638 | 52.784 | 1.00 | 36.09 | A | C |
| ATOM | 4548 | NZ | LYS | 589 | 39.461 | 76.464 | 53.881 | 1.00 | 36.83 | A | N |
| ATOM | 4549 | C | LYS | 589 | 42.705 | 74.611 | 48.468 | 1.00 | 22.93 | A | C |
| ATOM | 4550 | O | LYS | 589 | 43.711 | 75.032 | 49.033 | 1.00 | 23.71 | A | O |
| ATOM | 4551 | N | ILE | 590 | 42.494 | 73.326 | 48.217 | 1.00 | 21.82 | A | N |
| ATOM | 4552 | CA | ILE | 590 | 43.444 | 72.302 | 48.607 | 1.00 | 21.76 | A | C |
| ATOM | 4553 | CB | ILE | 590 | 42.737 | 70.956 | 48.846 | 1.00 | 20.55 | A | C |
| ATOM | 4554 | CG2 | ILE | 590 | 43.756 | 69.841 | 48.934 | 1.00 | 19.40 | A | C |
| ATOM | 4555 | CG1 | ILE | 590 | 41.901 | 71.025 | 50.126 | 1.00 | 21.94 | A | C |
| ATOM | 4556 | CD1 | ILE | 590 | 41.200 | 69.720 | 50.478 | 1.00 | 22.22 | A | C |

| ATOM | 4557 | C | ILE | 590 | 44.537 | 72.093 | 47.562 | 1.00 | 22.32 | A | C |
|---|---|---|---|---|---|---|---|---|---|---|---|
| ATOM | 4558 | O | ILE | 590 | 45.711 | 71.960 | 47.901 | 1.00 | 23.51 | A | O |
| ATOM | 4559 | N | MET | 591 | 44.157 | 72.071 | 46.291 | 1.00 | 21.59 | A | N |
| ATOM | 4560 | CA | MET | 591 | 45.127 | 71.846 | 45.232 | 1.00 | 21.59 | A | C |
| ATOM | 4561 | CB | MET | 591 | 44.406 | 71.567 | 43.917 | 1.00 | 21.80 | A | C |
| ATOM | 4562 | CG | MET | 591 | 45.309 | 71.000 | 42.838 | 1.00 | 21.85 | A | C |
| ATOM | 4563 | SD | MET | 591 | 44.403 | 70.746 | 41.309 | 1.00 | 22.76 | A | S |
| ATOM | 4564 | CE | MET | 591 | 44.237 | 72.436 | 40.732 | 1.00 | 22.84 | A | C |
| ATOM | 4565 | C | MET | 591 | 46.112 | 72.997 | 45.051 | 1.00 | 21.43 | A | C |
| ATOM | 4566 | O | MET | 591 | 47.289 | 72.771 | 44.791 | 1.00 | 19.25 | A | O |
| ATOM | 4567 | N | HIS | 592 | 45.636 | 74.228 | 45.200 | 1.00 | 21.21 | A | N |
| ATOM | 4568 | CA | HIS | 592 | 46.502 | 75.386 | 45.035 | 1.00 | 21.43 | A | C |
| ATOM | 4569 | CB | HIS | 592 | 45.713 | 76.560 | 44.455 | 1.00 | 22.32 | A | C |
| ATOM | 4570 | CG | HIS | 592 | 45.296 | 76.361 | 43.032 | 1.00 | 24.65 | A | C |
| ATOM | 4571 | CD2 | HIS | 592 | 45.604 | 75.390 | 42.139 | 1.00 | 26.25 | A | C |
| ATOM | 4572 | ND1 | HIS | 592 | 44.471 | 77.243 | 42.368 | 1.00 | 25.75 | A | N |
| ATOM | 4573 | CE1 | HIS | 592 | 44.289 | 76.825 | 41.128 | 1.00 | 25.99 | A | C |
| ATOM | 4574 | NE2 | HIS | 592 | 44.965 | 75.703 | 40.962 | 1.00 | 25.78 | A | N |
| ATOM | 4575 | C | HIS | 592 | 47.197 | 75.817 | 46.319 | 1.00 | 21.38 | A | C |
| ATOM | 4576 | O | HIS | 592 | 47.842 | 76.865 | 46.362 | 1.00 | 20.84 | A | O |
| ATOM | 4577 | N | ALA | 593 | 47.076 | 75.012 | 47.367 | 1.00 | 21.76 | A | N |
| ATOM | 4578 | CA | ALA | 593 | 47.732 | 75.349 | 48.628 | 1.00 | 20.43 | A | C |
| ATOM | 4579 | CB | ALA | 593 | 47.360 | 74.349 | 49.710 | 1.00 | 18.24 | A | C |
| ATOM | 4580 | C | ALA | 593 | 49.241 | 75.361 | 48.427 | 1.00 | 19.92 | A | C |
| ATOM | 4581 | O | ALA | 593 | 49.940 | 76.126 | 49.081 | 1.00 | 21.91 | A | O |
| ATOM | 4582 | N | ILE | 594 | 49.736 | 74.522 | 47.518 | 1.00 | 19.47 | A | N |
| ATOM | 4583 | CA | ILE | 594 | 51.176 | 74.446 | 47.248 | 1.00 | 20.49 | A | C |
| ATOM | 4584 | CB | ILE | 594 | 51.617 | 73.021 | 46.816 | 1.00 | 19.36 | A | C |
| ATOM | 4585 | CG2 | ILE | 594 | 51.467 | 72.051 | 47.966 | 1.00 | 19.38 | A | C |
| ATOM | 4586 | CG1 | ILE | 594 | 50.814 | 72.581 | 45.590 | 1.00 | 21.33 | A | C |
| ATOM | 4587 | CD1 | ILE | 594 | 50.951 | 71.106 | 45.243 | 1.00 | 22.55 | A | C |
| ATOM | 4588 | C | ILE | 594 | 51.658 | 75.410 | 46.169 | 1.00 | 19.88 | A | C |
| ATOM | 4589 | O | ILE | 594 | 52.849 | 75.434 | 45.854 | 1.00 | 17.79 | A | O |
| ATOM | 4590 | N | ASN | 595 | 50.746 | 76.200 | 45.606 | 1.00 | 20.03 | A | N |
| ATOM | 4591 | CA | ASN | 595 | 51.119 | 77.137 | 44.547 | 1.00 | 21.76 | A | C |
| ATOM | 4592 | CB | ASN | 595 | 49.977 | 78.114 | 44.265 | 1.00 | 20.68 | A | C |
| ATOM | 4593 | CG | ASN | 595 | 50.300 | 79.072 | 43.128 | 1.00 | 21.80 | A | C |
| ATOM | 4594 | OD1 | ASN | 595 | 50.640 | 78.652 | 42.024 | 1.00 | 22.78 | A | O |
| ATOM | 4595 | ND2 | ASN | 595 | 50.191 | 80.364 | 43.394 | 1.00 | 22.74 | A | N |
| ATOM | 4596 | C | ASN | 595 | 52.395 | 77.921 | 44.860 | 1.00 | 22.25 | A | C |
| ATOM | 4597 | O | ASN | 595 | 52.442 | 78.688 | 45.824 | 1.00 | 22.44 | A | O |
| ATOM | 4598 | N | ARG | 596 | 53.421 | 77.715 | 44.031 | 1.00 | 22.52 | A | N |
| ATOM | 4599 | CA | ARG | 596 | 54.726 | 78.378 | 44.171 | 1.00 | 22.41 | A | C |
| ATOM | 4600 | CB | ARG | 596 | 54.550 | 79.898 | 44.141 | 1.00 | 21.28 | A | C |
| ATOM | 4601 | CG | ARG | 596 | 53.894 | 80.426 | 42.880 | 1.00 | 21.31 | A | C |
| ATOM | 4602 | CD | ARG | 596 | 53.398 | 81.856 | 43.096 | 1.00 | 22.01 | A | C |
| ATOM | 4603 | NE | ARG | 596 | 54.479 | 82.760 | 43.482 | 1.00 | 20.88 | A | N |
| ATOM | 4604 | CZ | ARG | 596 | 55.467 | 83.112 | 42.671 | 1.00 | 21.35 | A | C |
| ATOM | 4605 | NH1 | ARG | 596 | 55.498 | 82.635 | 41.431 | 1.00 | 22.62 | A | N |

FIG. 4-95

| | | | | | | | | | | |
|---|---|---|---|---|---|---|---|---|---|---|
| ATOM | 4606 | NH2 | ARG | 596 | 56.427 | 83.924 | 43.096 | 1.00 | 19.92 | A | N |
| ATOM | 4607 | C | ARG | 596 | 55.492 | 77.982 | 45.440 | 1.00 | 21.53 | A | C |
| ATOM | 4608 | O | ARG | 596 | 56.482 | 78.611 | 45.804 | 1.00 | 20.59 | A | O |
| ATOM | 4609 | N | ARG | 597 | 55.046 | 76.930 | 46.107 | 1.00 | 21.66 | A | N |
| ATOM | 4610 | CA | ARG | 597 | 55.705 | 76.512 | 47.331 | 1.00 | 21.98 | A | C |
| ATOM | 4611 | CB | ARG | 597 | 54.943 | 77.061 | 48.539 | 1.00 | 23.55 | A | C |
| ATOM | 4612 | CG | ARG | 597 | 55.184 | 78.547 | 48.776 | 1.00 | 28.20 | A | C |
| ATOM | 4613 | CD | ARG | 597 | 56.611 | 78.813 | 49.264 | 1.00 | 30.86 | A | C |
| ATOM | 4614 | NE | ARG | 597 | 56.891 | 80.239 | 49.414 | 1.00 | 34.81 | A | N |
| ATOM | 4615 | CZ | ARG | 597 | 57.074 | 81.088 | 48.401 | 1.00 | 36.01 | A | C |
| ATOM | 4616 | NH1 | ARG | 597 | 57.011 | 80.670 | 47.142 | 1.00 | 33.57 | A | N |
| ATOM | 4617 | NH2 | ARG | 597 | 57.326 | 82.365 | 48.650 | 1.00 | 37.36 | A | N |
| ATOM | 4618 | C | ARG | 597 | 55.869 | 75.011 | 47.458 | 1.00 | 20.79 | A | C |
| ATOM | 4619 | O | ARG | 597 | 55.523 | 74.423 | 48.487 | 1.00 | 20.19 | A | O |
| ATOM | 4620 | N | LEU | 598 | 56.400 | 74.398 | 46.404 | 1.00 | 19.44 | A | N |
| ATOM | 4621 | CA | LEU | 598 | 56.649 | 72.963 | 46.387 | 1.00 | 18.48 | A | C |
| ATOM | 4622 | CB | LEU | 598 | 57.142 | 72.545 | 45.003 | 1.00 | 18.20 | A | C |
| ATOM | 4623 | CG | LEU | 598 | 56.119 | 72.007 | 43.994 | 1.00 | 19.27 | A | C |
| ATOM | 4624 | CD1 | LEU | 598 | 54.800 | 72.731 | 44.107 | 1.00 | 19.49 | A | C |
| ATOM | 4625 | CD2 | LEU | 598 | 56.691 | 72.135 | 42.595 | 1.00 | 18.24 | A | C |
| ATOM | 4626 | C | LEU | 598 | 57.692 | 72.617 | 47.450 | 1.00 | 19.10 | A | C |
| ATOM | 4627 | O | LEU | 598 | 58.644 | 73.363 | 47.679 | 1.00 | 19.27 | A | O |
| ATOM | 4628 | N | GLY | 599 | 57.506 | 71.485 | 48.108 | 1.00 | 19.24 | A | N |
| ATOM | 4629 | CA | GLY | 599 | 58.440 | 71.090 | 49.138 | 1.00 | 20.34 | A | C |
| ATOM | 4630 | C | GLY | 599 | 58.055 | 71.622 | 50.508 | 1.00 | 21.76 | A | C |
| ATOM | 4631 | O | GLY | 599 | 58.882 | 71.640 | 51.422 | 1.00 | 23.58 | A | O |
| ATOM | 4632 | N | THR | 600 | 56.811 | 72.061 | 50.666 | 1.00 | 21.02 | A | N |
| ATOM | 4633 | CA | THR | 600 | 56.381 | 72.578 | 51.958 | 1.00 | 21.20 | A | C |
| ATOM | 4634 | CB | THR | 600 | 56.039 | 74.082 | 51.874 | 1.00 | 21.28 | A | C |
| ATOM | 4635 | OG1 | THR | 600 | 54.887 | 74.271 | 51.052 | 1.00 | 25.68 | A | O |
| ATOM | 4636 | CG2 | THR | 600 | 57.192 | 74.856 | 51.264 | 1.00 | 21.23 | A | C |
| ATOM | 4637 | C | THR | 600 | 55.201 | 71.810 | 52.557 | 1.00 | 21.38 | A | C |
| ATOM | 4638 | O | THR | 600 | 55.386 | 70.724 | 53.100 | 1.00 | 22.42 | A | O |
| ATOM | 4639 | N | PHE | 601 | 53.993 | 72.356 | 52.446 | 1.00 | 21.18 | A | N |
| ATOM | 4640 | CA | PHE | 601 | 52.809 | 71.721 | 53.022 | 1.00 | 22.09 | A | C |
| ATOM | 4641 | CB | PHE | 601 | 51.540 | 72.498 | 52.649 | 1.00 | 24.93 | A | C |
| ATOM | 4642 | CG | PHE | 601 | 51.556 | 73.935 | 53.077 | 1.00 | 26.21 | A | C |
| ATOM | 4643 | CD1 | PHE | 601 | 51.052 | 74.923 | 52.236 | 1.00 | 28.07 | A | C |
| ATOM | 4644 | CD2 | PHE | 601 | 52.105 | 74.308 | 54.299 | 1.00 | 26.83 | A | C |
| ATOM | 4645 | CE1 | PHE | 601 | 51.100 | 76.271 | 52.603 | 1.00 | 29.10 | A | C |
| ATOM | 4646 | CE2 | PHE | 601 | 52.160 | 75.650 | 54.680 | 1.00 | 28.02 | A | C |
| ATOM | 4647 | CZ | PHE | 601 | 51.658 | 76.636 | 53.830 | 1.00 | 28.61 | A | C |
| ATOM | 4648 | C | PHE | 601 | 52.623 | 70.265 | 52.635 | 1.00 | 22.45 | A | C |
| ATOM | 4649 | O | PHE | 601 | 52.235 | 69.451 | 53.470 | 1.00 | 22.89 | A | O |
| ATOM | 4650 | N | GLU | 602 | 52.884 | 69.931 | 51.374 | 1.00 | 22.76 | A | N |
| ATOM | 4651 | CA | GLU | 602 | 52.712 | 68.556 | 50.931 | 1.00 | 21.82 | A | C |
| ATOM | 4652 | CB | GLU | 602 | 52.956 | 68.418 | 49.422 | 1.00 | 22.43 | A | C |
| ATOM | 4653 | CG | GLU | 602 | 54.396 | 68.559 | 48.974 | 1.00 | 27.44 | A | C |
| ATOM | 4654 | CD | GLU | 602 | 54.872 | 70.002 | 48.893 | 1.00 | 29.71 | A | C |

| | | | | | | | | | | |
|---|---|---|---|---|---|---|---|---|---|---|
| ATOM | 4655 | OE1 | GLU | 602 | 54.751 | 70.743 | 49.891 | 1.00 31.66 | A | O |
| ATOM | 4656 | OE2 | GLU | 602 | 55.379 | 70.392 | 47.822 | 1.00 31.46 | A | O |
| ATOM | 4657 | C | GLU | 602 | 53.663 | 67.657 | 51.698 | 1.00 21.67 | A | C |
| ATOM | 4658 | O | GLU | 602 | 53.386 | 66.473 | 51.899 | 1.00 22.33 | A | O |
| ATOM | 4659 | N | VAL | 603 | 54.777 | 68.229 | 52.146 | 1.00 20.78 | A | N |
| ATOM | 4660 | CA | VAL | 603 | 55.772 | 67.468 | 52.897 | 1.00 20.76 | A | C |
| ATOM | 4661 | CB | VAL | 603 | 57.159 | 68.133 | 52.800 | 1.00 18.99 | A | C |
| ATOM | 4662 | CG1 | VAL | 603 | 58.165 | 67.365 | 53.649 | 1.00 15.00 | A | C |
| ATOM | 4663 | CG2 | VAL | 603 | 57.603 | 68.193 | 51.335 | 1.00 15.21 | A | C |
| ATOM | 4664 | C | VAL | 603 | 55.368 | 67.350 | 54.364 | 1.00 21.85 | A | C |
| ATOM | 4665 | O | VAL | 603 | 55.373 | 66.265 | 54.946 | 1.00 20.44 | A | O |
| ATOM | 4666 | N | GLU | 604 | 55.009 | 68.481 | 54.951 | 1.00 24.70 | A | N |
| ATOM | 4667 | CA | GLU | 604 | 54.594 | 68.518 | 56.341 | 1.00 27.84 | A | C |
| ATOM | 4668 | CB | GLU | 604 | 54.322 | 69.964 | 56.770 | 1.00 30.83 | A | C |
| ATOM | 4669 | CG | GLU | 604 | 55.572 | 70.808 | 56.924 | 1.00 37.92 | A | C |
| ATOM | 4670 | CD | GLU | 604 | 56.449 | 70.355 | 58.091 | 1.00 43.63 | A | C |
| ATOM | 4671 | OE1 | GLU | 604 | 57.505 | 70.989 | 58.328 | 1.00 46.30 | A | O |
| ATOM | 4672 | OE2 | GLU | 604 | 56.083 | 69.368 | 58.773 | 1.00 45.85 | A | O |
| ATOM | 4673 | C | GLU | 604 | 53.349 | 67.669 | 56.553 | 1.00 27.28 | A | C |
| ATOM | 4674 | O | GLU | 604 | 53.270 | 66.909 | 57.517 | 1.00 28.68 | A | O |
| ATOM | 4675 | N | ASP | 605 | 52.381 | 67.786 | 55.650 | 1.00 25.92 | A | N |
| ATOM | 4676 | CA | ASP | 605 | 51.151 | 67.021 | 55.785 | 1.00 25.72 | A | C |
| ATOM | 4677 | CB | ASP | 605 | 50.144 | 67.436 | 54.713 | 1.00 24.61 | A | C |
| ATOM | 4678 | CG | ASP | 605 | 49.576 | 68.832 | 54.963 | 1.00 23.36 | A | C |
| ATOM | 4679 | OD1 | ASP | 605 | 48.677 | 69.267 | 54.215 | 1.00 23.15 | A | O |
| ATOM | 4680 | OD2 | ASP | 605 | 50.036 | 69.499 | 55.914 | 1.00 21.27 | A | O |
| ATOM | 4681 | C | ASP | 605 | 51.379 | 65.515 | 55.783 | 1.00 26.18 | A | C |
| ATOM | 4682 | O | ASP | 605 | 50.646 | 64.779 | 56.439 | 1.00 28.35 | A | O |
| ATOM | 4683 | N | GLN | 606 | 52.394 | 65.051 | 55.063 | 1.00 26.16 | A | N |
| ATOM | 4684 | CA | GLN | 606 | 52.704 | 63.627 | 55.056 | 1.00 25.29 | A | C |
| ATOM | 4685 | CB | GLN | 606 | 53.788 | 63.302 | 54.026 | 1.00 24.18 | A | C |
| ATOM | 4686 | CG | GLN | 606 | 53.305 | 63.332 | 52.596 | 1.00 24.92 | A | C |
| ATOM | 4687 | CD | GLN | 606 | 52.206 | 62.321 | 52.330 | 1.00 24.81 | A | C |
| ATOM | 4688 | OE1 | GLN | 606 | 52.373 | 61.122 | 52.560 | 1.00 25.31 | A | O |
| ATOM | 4689 | NE2 | GLN | 606 | 51.075 | 62.801 | 51.840 | 1.00 25.44 | A | N |
| ATOM | 4690 | C | GLN | 606 | 53.207 | 63.268 | 56.447 | 1.00 25.47 | A | C |
| ATOM | 4691 | O | GLN | 606 | 52.838 | 62.238 | 57.002 | 1.00 25.15 | A | O |
| ATOM | 4692 | N | ILE | 607 | 54.059 | 64.129 | 57.001 | 1.00 26.84 | A | N |
| ATOM | 4693 | CA | ILE | 607 | 54.607 | 63.915 | 58.337 | 1.00 28.30 | A | C |
| ATOM | 4694 | CB | ILE | 607 | 55.639 | 65.002 | 58.702 | 1.00 28.21 | A | C |
| ATOM | 4695 | CG2 | ILE | 607 | 56.165 | 64.778 | 60.116 | 1.00 26.82 | A | C |
| ATOM | 4696 | CG1 | ILE | 607 | 56.789 | 64.977 | 57.694 | 1.00 29.86 | A | C |
| ATOM | 4697 | CD1 | ILE | 607 | 57.796 | 66.086 | 57.881 | 1.00 28.34 | A | C |
| ATOM | 4698 | C | ILE | 607 | 53.470 | 63.963 | 59.355 | 1.00 29.50 | A | C |
| ATOM | 4699 | O | ILE | 607 | 53.359 | 63.093 | 60.226 | 1.00 27.80 | A | O |
| ATOM | 4700 | N | GLU | 608 | 52.619 | 64.978 | 59.239 | 1.00 30.32 | A | N |
| ATOM | 4701 | CA | GLU | 608 | 51.508 | 65.099 | 60.164 | 1.00 32.21 | A | C |
| ATOM | 4702 | CB | GLU | 608 | 50.705 | 66.379 | 59.919 | 1.00 33.05 | A | C |
| ATOM | 4703 | CG | GLU | 608 | 49.578 | 66.581 | 60.936 | 1.00 34.99 | A | C |

FIG. 4-97 (Continued)

| ATOM | 4704 | CD | GLU | 608 | 50.054 | 66.482 | 62.389 | 1.00 | 38.42 | A | C |
| --- | --- | --- | --- | --- | --- | --- | --- | --- | --- | --- | --- |
| ATOM | 4705 | OE1 | GLU | 608 | 49.197 | 66.454 | 63.302 | 1.00 | 37.67 | A | O |
| ATOM | 4706 | OE2 | GLU | 608 | 51.285 | 66.435 | 62.625 | 1.00 | 40.64 | A | O |
| ATOM | 4707 | C | GLU | 608 | 50.606 | 63.891 | 60.012 | 1.00 | 32.76 | A | C |
| ATOM | 4708 | O | GLU | 608 | 49.889 | 63.527 | 60.947 | 1.00 | 33.47 | A | O |
| ATOM | 4709 | N | ALA | 609 | 50.643 | 63.270 | 58.836 | 1.00 | 31.32 | A | N |
| ATOM | 4710 | CA | ALA | 609 | 49.827 | 62.090 | 58.595 | 1.00 | 30.73 | A | C |
| ATOM | 4711 | CB | ALA | 609 | 49.883 | 61.682 | 57.123 | 1.00 | 28.50 | A | C |
| ATOM | 4712 | C | ALA | 609 | 50.355 | 60.968 | 59.472 | 1.00 | 30.16 | A | C |
| ATOM | 4713 | O | ALA | 609 | 49.583 | 60.274 | 60.139 | 1.00 | 31.03 | A | O |
| ATOM | 4714 | N | ALA | 610 | 51.674 | 60.803 | 59.479 | 1.00 | 29.26 | A | N |
| ATOM | 4715 | CA | ALA | 610 | 52.310 | 59.758 | 60.274 | 1.00 | 28.48 | A | C |
| ATOM | 4716 | CB | ALA | 610 | 53.826 | 59.818 | 60.114 | 1.00 | 27.67 | A | C |
| ATOM | 4717 | C | ALA | 610 | 51.930 | 59.886 | 61.743 | 1.00 | 27.62 | A | C |
| ATOM | 4718 | O | ALA | 610 | 51.556 | 58.904 | 62.379 | 1.00 | 28.43 | A | O |
| ATOM | 4719 | N | ARG | 611 | 52.025 | 61.094 | 62.282 | 1.00 | 26.94 | A | N |
| ATOM | 4720 | CA | ARG | 611 | 51.674 | 61.309 | 63.678 | 1.00 | 28.98 | A | C |
| ATOM | 4721 | CB | ARG | 611 | 51.812 | 62.787 | 64.042 | 1.00 | 28.96 | A | C |
| ATOM | 4722 | CG | ARG | 611 | 53.239 | 63.291 | 64.032 | 1.00 | 29.26 | A | C |
| ATOM | 4723 | CD | ARG | 611 | 53.281 | 64.799 | 64.187 | 1.00 | 29.92 | A | C |
| ATOM | 4724 | NE | ARG | 611 | 54.641 | 65.322 | 64.102 | 1.00 | 28.90 | A | N |
| ATOM | 4725 | CZ | ARG | 611 | 54.980 | 66.384 | 63.378 | 1.00 | 29.97 | A | C |
| ATOM | 4726 | NH1 | ARG | 611 | 54.055 | 67.028 | 62.680 | 1.00 | 31.41 | A | N |
| ATOM | 4727 | NH2 | ARG | 611 | 56.237 | 66.802 | 63.347 | 1.00 | 29.57 | A | N |
| ATOM | 4728 | C | ARG | 611 | 50.242 | 60.846 | 63.923 | 1.00 | 29.90 | A | C |
| ATOM | 4729 | O | ARG | 611 | 49.983 | 60.084 | 64.856 | 1.00 | 31.08 | A | O |
| ATOM | 4730 | N | GLN | 612 | 49.319 | 61.298 | 63.076 | 1.00 | 30.18 | A | N |
| ATOM | 4731 | CA | GLN | 612 | 47.916 | 60.922 | 63.195 | 1.00 | 30.42 | A | C |
| ATOM | 4732 | CB | GLN | 612 | 47.108 | 61.497 | 62.035 | 1.00 | 30.55 | A | C |
| ATOM | 4733 | CG | GLN | 612 | 47.112 | 63.001 | 61.964 | 1.00 | 33.70 | A | C |
| ATOM | 4734 | CD | GLN | 612 | 46.446 | 63.637 | 63.162 | 1.00 | 34.91 | A | C |
| ATOM | 4735 | OE1 | GLN | 612 | 45.276 | 63.379 | 63.444 | 1.00 | 35.03 | A | O |
| ATOM | 4736 | NE2 | GLN | 612 | 47.188 | 64.475 | 63.875 | 1.00 | 35.30 | A | N |
| ATOM | 4737 | C | GLN | 612 | 47.740 | 59.405 | 63.223 | 1.00 | 30.70 | A | C |
| ATOM | 4738 | O | GLN | 612 | 46.993 | 58.878 | 64.049 | 1.00 | 31.56 | A | O |
| ATOM | 4739 | N | PHE | 613 | 48.415 | 58.698 | 62.324 | 1.00 | 30.50 | A | N |
| ATOM | 4740 | CA | PHE | 613 | 48.291 | 57.248 | 62.301 | 1.00 | 32.33 | A | C |
| ATOM | 4741 | CB | PHE | 613 | 49.043 | 56.653 | 61.114 | 1.00 | 31.37 | A | C |
| ATOM | 4742 | CG | PHE | 613 | 48.537 | 57.126 | 59.787 | 1.00 | 30.49 | A | C |
| ATOM | 4743 | CD1 | PHE | 613 | 47.167 | 57.171 | 59.529 | 1.00 | 30.03 | A | C |
| ATOM | 4744 | CD2 | PHE | 613 | 49.423 | 57.523 | 58.793 | 1.00 | 28.11 | A | C |
| ATOM | 4745 | CE1 | PHE | 613 | 46.687 | 57.604 | 58.300 | 1.00 | 29.96 | A | C |
| ATOM | 4746 | CE2 | PHE | 613 | 48.954 | 57.959 | 57.559 | 1.00 | 28.75 | A | C |
| ATOM | 4747 | CZ | PHE | 613 | 47.585 | 58.001 | 57.309 | 1.00 | 28.70 | A | C |
| ATOM | 4748 | C | PHE | 613 | 48.835 | 56.679 | 63.597 | 1.00 | 34.28 | A | C |
| ATOM | 4749 | O | PHE | 613 | 48.327 | 55.677 | 64.107 | 1.00 | 34.47 | A | O |
| ATOM | 4750 | N | SER | 614 | 49.865 | 57.326 | 64.134 | 1.00 | 35.61 | A | N |
| ATOM | 4751 | CA | SER | 614 | 50.454 | 56.884 | 65.388 | 1.00 | 37.88 | A | C |
| ATOM | 4752 | CB | SER | 614 | 51.723 | 57.677 | 65.683 | 1.00 | 38.32 | A | C |

FIG. 4-98 (Continued)

| ATOM | 4753 | OG | SER | 614 | 52.686 | 57.477 | 64.663 | 1.00 | 38.53 | A | O |
| --- | --- | --- | --- | --- | --- | --- | --- | --- | --- | --- | --- |
| ATOM | 4754 | C | SER | 614 | 49.424 | 57.098 | 66.494 | 1.00 | 39.76 | A | C |
| ATOM | 4755 | O | SER | 614 | 49.283 | 56.276 | 67.398 | 1.00 | 41.47 | A | O |
| ATOM | 4756 | N | LYS | 615 | 48.694 | 58.204 | 66.413 | 1.00 | 40.51 | A | N |
| ATOM | 4757 | CA | LYS | 615 | 47.663 | 58.490 | 67.400 | 1.00 | 41.32 | A | C |
| ATOM | 4758 | CB | LYS | 615 | 47.047 | 59.870 | 67.155 | 1.00 | 42.73 | A | C |
| ATOM | 4759 | CG | LYS | 615 | 47.884 | 61.040 | 67.642 | 1.00 | 44.59 | A | C |
| ATOM | 4760 | CD | LYS | 615 | 47.064 | 62.330 | 67.631 | 1.00 | 46.18 | A | C |
| ATOM | 4761 | CE | LYS | 615 | 47.864 | 63.511 | 68.168 | 1.00 | 46.73 | A | C |
| ATOM | 4762 | NZ | LYS | 615 | 48.314 | 63.301 | 69.577 | 1.00 | 48.03 | A | N |
| ATOM | 4763 | C | LYS | 615 | 46.552 | 57.441 | 67.347 | 1.00 | 40.86 | A | C |
| ATOM | 4764 | O | LYS | 615 | 45.794 | 57.285 | 68.303 | 1.00 | 41.94 | A | O |
| ATOM | 4765 | N | MET | 616 | 46.456 | 56.724 | 66.230 | 1.00 | 39.78 | A | N |
| ATOM | 4766 | CA | MET | 616 | 45.418 | 55.712 | 66.065 | 1.00 | 37.88 | A | C |
| ATOM | 4767 | CB | MET | 616 | 45.246 | 55.374 | 64.578 | 1.00 | 37.42 | A | C |
| ATOM | 4768 | CG | MET | 616 | 44.673 | 56.532 | 63.768 | 1.00 | 35.95 | A | C |
| ATOM | 4769 | SD | MET | 616 | 44.195 | 56.101 | 62.079 | 1.00 | 35.73 | A | S |
| ATOM | 4770 | CE | MET | 616 | 43.946 | 57.730 | 61.385 | 1.00 | 34.06 | A | C |
| ATOM | 4771 | C | MET | 616 | 45.654 | 54.447 | 66.885 | 1.00 | 36.90 | A | C |
| ATOM | 4772 | O | MET | 616 | 44.908 | 53.473 | 66.772 | 1.00 | 37.22 | A | O |
| ATOM | 4773 | N | GLY | 617 | 46.706 | 54.469 | 67.698 | 1.00 | 35.15 | A | N |
| ATOM | 4774 | CA | GLY | 617 | 47.013 | 53.355 | 68.578 | 1.00 | 32.74 | A | C |
| ATOM | 4775 | C | GLY | 617 | 47.445 | 51.995 | 68.065 | 1.00 | 32.72 | A | C |
| ATOM | 4776 | O | GLY | 617 | 47.806 | 51.143 | 68.872 | 1.00 | 33.71 | A | O |
| ATOM | 4777 | N | PHE | 618 | 47.409 | 51.751 | 66.761 | 1.00 | 32.52 | A | N |
| ATOM | 4778 | CA | PHE | 618 | 47.841 | 50.447 | 66.262 | 1.00 | 31.36 | A | C |
| ATOM | 4779 | CB | PHE | 618 | 46.701 | 49.759 | 65.496 | 1.00 | 31.10 | A | C |
| ATOM | 4780 | CG | PHE | 618 | 46.047 | 50.624 | 64.457 | 1.00 | 31.61 | A | C |
| ATOM | 4781 | CD1 | PHE | 618 | 46.743 | 51.025 | 63.322 | 1.00 | 31.30 | A | C |
| ATOM | 4782 | CD2 | PHE | 618 | 44.724 | 51.027 | 64.607 | 1.00 | 30.93 | A | C |
| ATOM | 4783 | CE1 | PHE | 618 | 46.129 | 51.815 | 62.349 | 1.00 | 31.53 | A | C |
| ATOM | 4784 | CE2 | PHE | 618 | 44.104 | 51.814 | 63.642 | 1.00 | 30.94 | A | C |
| ATOM | 4785 | CZ | PHE | 618 | 44.808 | 52.209 | 62.509 | 1.00 | 29.86 | A | C |
| ATOM | 4786 | C | PHE | 618 | 49.109 | 50.521 | 65.404 | 1.00 | 30.95 | A | C |
| ATOM | 4787 | O | PHE | 618 | 49.303 | 49.735 | 64.477 | 1.00 | 30.95 | A | O |
| ATOM | 4788 | N | VAL | 619 | 49.982 | 51.465 | 65.732 | 1.00 | 30.23 | A | N |
| ATOM | 4789 | CA | VAL | 619 | 51.226 | 51.627 | 64.996 | 1.00 | 29.99 | A | C |
| ATOM | 4790 | CB | VAL | 619 | 51.226 | 52.928 | 64.147 | 1.00 | 29.39 | A | C |
| ATOM | 4791 | CG1 | VAL | 619 | 52.632 | 53.200 | 63.617 | 1.00 | 28.74 | A | C |
| ATOM | 4792 | CG2 | VAL | 619 | 50.248 | 52.804 | 62.994 | 1.00 | 26.48 | A | C |
| ATOM | 4793 | C | VAL | 619 | 52.425 | 51.673 | 65.931 | 1.00 | 29.66 | A | C |
| ATOM | 4794 | O | VAL | 619 | 52.400 | 52.342 | 66.962 | 1.00 | 30.05 | A | O |
| ATOM | 4795 | N | ASP | 620 | 53.475 | 50.954 | 65.561 | 1.00 | 29.84 | A | N |
| ATOM | 4796 | CA | ASP | 620 | 54.695 | 50.932 | 66.347 | 1.00 | 29.07 | A | C |
| ATOM | 4797 | CB | ASP | 620 | 55.563 | 49.748 | 65.924 | 1.00 | 27.94 | A | C |
| ATOM | 4798 | CG | ASP | 620 | 56.789 | 49.587 | 66.794 | 1.00 | 27.02 | A | C |
| ATOM | 4799 | OD1 | ASP | 620 | 57.191 | 50.580 | 67.439 | 1.00 | 26.38 | A | O |
| ATOM | 4800 | OD2 | ASP | 620 | 57.358 | 48.473 | 66.818 | 1.00 | 25.22 | A | O |
| ATOM | 4801 | C | ASP | 620 | 55.408 | 52.243 | 66.039 | 1.00 | 30.30 | A | C |

| | | | | | | | | | | |
|---|---|---|---|---|---|---|---|---|---|---|
| ATOM | 4802 | O | ASP | 620 | 56.009 | 52.398 | 64.979 | 1.00 | 29.95 | A | O |
| ATOM | 4803 | N | ASN | 621 | 55.330 | 53.196 | 66.958 | 1.00 | 33.01 | A | N |
| ATOM | 4804 | CA | ASN | 621 | 55.962 | 54.492 | 66.746 | 1.00 | 35.15 | A | C |
| ATOM | 4805 | CB | ASN | 621 | 55.761 | 55.376 | 67.975 | 1.00 | 38.29 | A | C |
| ATOM | 4806 | CG | ASN | 621 | 56.420 | 54.804 | 69.214 | 1.00 | 43.03 | A | C |
| ATOM | 4807 | OD1 | ASN | 621 | 57.648 | 54.821 | 69.346 | 1.00 | 44.79 | A | O |
| ATOM | 4808 | ND2 | ASN | 621 | 55.606 | 54.280 | 70.130 | 1.00 | 45.61 | A | N |
| ATOM | 4809 | C | ASN | 621 | 57.453 | 54.370 | 66.441 | 1.00 | 35.20 | A | C |
| ATOM | 4810 | O | ASN | 621 | 58.083 | 55.330 | 66.004 | 1.00 | 34.67 | A | O |
| ATOM | 4811 | N | LYS | 622 | 58.016 | 53.186 | 66.660 | 1.00 | 36.30 | A | N |
| ATOM | 4812 | CA | LYS | 622 | 59.439 | 52.977 | 66.418 | 1.00 | 35.70 | A | C |
| ATOM | 4813 | CB | LYS | 622 | 60.030 | 52.027 | 67.464 | 1.00 | 37.42 | A | C |
| ATOM | 4814 | CG | LYS | 622 | 60.148 | 52.611 | 68.866 | 1.00 | 39.14 | A | C |
| ATOM | 4815 | CD | LYS | 622 | 60.763 | 51.584 | 69.804 | 1.00 | 43.05 | A | C |
| ATOM | 4816 | CE | LYS | 622 | 60.839 | 52.077 | 71.240 | 1.00 | 45.27 | A | C |
| ATOM | 4817 | NZ | LYS | 622 | 61.516 | 51.077 | 72.123 | 1.00 | 45.73 | A | N |
| ATOM | 4818 | C | LYS | 622 | 59.762 | 52.445 | 65.036 | 1.00 | 34.38 | A | C |
| ATOM | 4819 | O | LYS | 622 | 60.896 | 52.572 | 64.571 | 1.00 | 35.67 | A | O |
| ATOM | 4820 | N | ARG | 623 | 58.783 | 51.846 | 64.374 | 1.00 | 31.86 | A | N |
| ATOM | 4821 | CA | ARG | 623 | 59.030 | 51.308 | 63.046 | 1.00 | 29.60 | A | C |
| ATOM | 4822 | CB | ARG | 623 | 58.821 | 49.791 | 63.058 | 1.00 | 29.94 | A | C |
| ATOM | 4823 | CG | ARG | 623 | 59.767 | 49.071 | 64.009 | 1.00 | 32.12 | A | C |
| ATOM | 4824 | CD | ARG | 623 | 59.117 | 47.832 | 64.614 | 1.00 | 33.42 | A | C |
| ATOM | 4825 | NE | ARG | 623 | 59.247 | 46.663 | 63.758 | 1.00 | 34.25 | A | N |
| ATOM | 4826 | CZ | ARG | 623 | 58.457 | 45.601 | 63.833 | 1.00 | 34.36 | A | C |
| ATOM | 4827 | NH1 | ARG | 623 | 57.476 | 45.572 | 64.725 | 1.00 | 35.41 | A | N |
| ATOM | 4828 | NH2 | ARG | 623 | 58.655 | 44.571 | 63.021 | 1.00 | 33.15 | A | N |
| ATOM | 4829 | C | ARG | 623 | 58.179 | 51.957 | 61.962 | 1.00 | 27.66 | A | C |
| ATOM | 4830 | O | ARG | 623 | 57.315 | 51.313 | 61.363 | 1.00 | 27.44 | A | O |
| ATOM | 4831 | N | ILE | 624 | 58.425 | 53.241 | 61.720 | 1.00 | 25.16 | A | N |
| ATOM | 4832 | CA | ILE | 624 | 57.708 | 53.977 | 60.685 | 1.00 | 24.70 | A | C |
| ATOM | 4833 | CB | ILE | 624 | 57.114 | 55.298 | 61.224 | 1.00 | 24.52 | A | C |
| ATOM | 4834 | CG2 | ILE | 624 | 56.391 | 56.025 | 60.107 | 1.00 | 23.47 | A | C |
| ATOM | 4835 | CG1 | ILE | 624 | 56.136 | 55.021 | 62.371 | 1.00 | 24.01 | A | C |
| ATOM | 4836 | CD1 | ILE | 624 | 55.473 | 56.277 | 62.936 | 1.00 | 19.15 | A | C |
| ATOM | 4837 | C | ILE | 624 | 58.667 | 54.311 | 59.532 | 1.00 | 24.37 | A | C |
| ATOM | 4838 | O | ILE | 624 | 59.651 | 55.034 | 59.709 | 1.00 | 23.38 | A | O |
| ATOM | 4839 | N | ALA | 625 | 58.384 | 53.768 | 58.356 | 1.00 | 22.58 | A | N |
| ATOM | 4840 | CA | ALA | 625 | 59.213 | 54.014 | 57.189 | 1.00 | 21.00 | A | C |
| ATOM | 4841 | CB | ALA | 625 | 59.650 | 52.693 | 56.579 | 1.00 | 20.21 | A | C |
| ATOM | 4842 | C | ALA | 625 | 58.430 | 54.833 | 56.168 | 1.00 | 21.28 | A | C |
| ATOM | 4843 | O | ALA | 625 | 57.209 | 54.966 | 56.275 | 1.00 | 21.90 | A | O |
| ATOM | 4844 | N | ILE | 626 | 59.135 | 55.385 | 55.185 | 1.00 | 19.63 | A | N |
| ATOM | 4845 | CA | ILE | 626 | 58.502 | 56.178 | 54.137 | 1.00 | 18.63 | A | C |
| ATOM | 4846 | CB | ILE | 626 | 58.589 | 57.699 | 54.446 | 1.00 | 18.98 | A | C |
| ATOM | 4847 | CG2 | ILE | 626 | 60.032 | 58.103 | 54.694 | 1.00 | 18.36 | A | C |
| ATOM | 4848 | CG1 | ILE | 626 | 57.973 | 58.501 | 53.296 | 1.00 | 19.11 | A | C |
| ATOM | 4849 | CD1 | ILE | 626 | 57.872 | 59.991 | 53.562 | 1.00 | 18.34 | A | C |
| ATOM | 4850 | C | ILE | 626 | 59.185 | 55.882 | 52.809 | 1.00 | 17.48 | A | C |

FIG. 4-100 (Continued)

| | | | | | | | | | | |
|---|---|---|---|---|---|---|---|---|---|---|
| ATOM | 4851 | O | ILE | 626 | 60.380 | 55.619 | 52.776 | 1.00 | 17.10 | A | O |
| ATOM | 4852 | N | TRP | 627 | 58.425 | 55.893 | 51.719 | 1.00 | 17.62 | A | N |
| ATOM | 4853 | CA | TRP | 627 | 58.998 | 55.622 | 50.409 | 1.00 | 17.62 | A | C |
| ATOM | 4854 | CB | TRP | 627 | 59.190 | 54.118 | 50.206 | 1.00 | 16.80 | A | C |
| ATOM | 4855 | CG | TRP | 627 | 58.096 | 53.441 | 49.427 | 1.00 | 18.70 | A | C |
| ATOM | 4856 | CD2 | TRP | 627 | 58.139 | 53.055 | 48.044 | 1.00 | 17.58 | A | C |
| ATOM | 4857 | CE2 | TRP | 627 | 56.912 | 52.425 | 47.749 | 1.00 | 17.70 | A | C |
| ATOM | 4858 | CE3 | TRP | 627 | 59.095 | 53.179 | 47.028 | 1.00 | 15.10 | A | C |
| ATOM | 4859 | CD1 | TRP | 627 | 56.879 | 53.047 | 49.895 | 1.00 | 18.68 | A | C |
| ATOM | 4860 | NE1 | TRP | 627 | 56.163 | 52.435 | 48.896 | 1.00 | 18.72 | A | N |
| ATOM | 4861 | CZ2 | TRP | 627 | 56.617 | 51.916 | 46.480 | 1.00 | 16.42 | A | C |
| ATOM | 4862 | CZ3 | TRP | 627 | 58.801 | 52.673 | 45.769 | 1.00 | 14.48 | A | C |
| ATOM | 4863 | CH2 | TRP | 627 | 57.575 | 52.048 | 45.507 | 1.00 | 14.63 | A | C |
| ATOM | 4864 | C | TRP | 627 | 58.157 | 56.191 | 49.275 | 1.00 | 18.48 | A | C |
| ATOM | 4865 | O | TRP | 627 | 56.934 | 56.280 | 49.381 | 1.00 | 18.15 | A | O |
| ATOM | 4866 | N | GLY | 628 | 58.829 | 56.579 | 48.193 | 1.00 | 18.70 | A | N |
| ATOM | 4867 | CA | GLY | 628 | 58.140 | 57.146 | 47.049 | 1.00 | 18.30 | A | C |
| ATOM | 4868 | C | GLY | 628 | 58.986 | 57.163 | 45.787 | 1.00 | 18.36 | A | C |
| ATOM | 4869 | O | GLY | 628 | 60.212 | 57.065 | 45.833 | 1.00 | 19.07 | A | O |
| ATOM | 4870 | N | TRP | 629 | 58.312 | 57.300 | 44.654 | 1.00 | 17.25 | A | N |
| ATOM | 4871 | CA | TRP | 629 | 58.945 | 57.322 | 43.343 | 1.00 | 15.27 | A | C |
| ATOM | 4872 | CB | TRP | 629 | 58.306 | 56.214 | 42.494 | 1.00 | 10.48 | A | C |
| ATOM | 4873 | CG | TRP | 629 | 59.131 | 55.698 | 41.357 | 1.00 | 10.84 | A | C |
| ATOM | 4874 | CD2 | TRP | 629 | 59.512 | 54.335 | 41.122 | 1.00 | 9.02 | A | C |
| ATOM | 4875 | CE2 | TRP | 629 | 60.243 | 54.310 | 39.914 | 1.00 | 10.87 | A | C |
| ATOM | 4876 | CE3 | TRP | 629 | 59.312 | 53.135 | 41.818 | 1.00 | 9.31 | A | C |
| ATOM | 4877 | CD1 | TRP | 629 | 59.635 | 56.422 | 40.313 | 1.00 | 10.72 | A | C |
| ATOM | 4878 | NE1 | TRP | 629 | 60.299 | 55.595 | 39.443 | 1.00 | 10.74 | A | N |
| ATOM | 4879 | CZ2 | TRP | 629 | 60.779 | 53.126 | 39.379 | 1.00 | 12.40 | A | C |
| ATOM | 4880 | CZ3 | TRP | 629 | 59.842 | 51.959 | 41.295 | 1.00 | 11.95 | A | C |
| ATOM | 4881 | CH2 | TRP | 629 | 60.571 | 51.965 | 40.080 | 1.00 | 13.29 | A | C |
| ATOM | 4882 | C | TRP | 629 | 58.671 | 58.722 | 42.753 | 1.00 | 15.91 | A | C |
| ATOM | 4883 | O | TRP | 629 | 57.622 | 59.300 | 43.012 | 1.00 | 15.58 | A | O |
| ATOM | 4884 | N | SER | 630 | 59.612 | 59.269 | 41.983 | 1.00 | 16.99 | A | N |
| ATOM | 4885 | CA | SER | 630 | 59.453 | 60.603 | 41.383 | 1.00 | 16.78 | A | C |
| ATOM | 4886 | CB | SER | 630 | 58.258 | 60.644 | 40.421 | 1.00 | 18.65 | A | C |
| ATOM | 4887 | OG | SER | 630 | 58.531 | 59.987 | 39.198 | 1.00 | 22.38 | A | O |
| ATOM | 4888 | C | SER | 630 | 59.234 | 61.656 | 42.450 | 1.00 | 16.69 | A | C |
| ATOM | 4889 | O | SER | 630 | 60.076 | 61.856 | 43.321 | 1.00 | 17.90 | A | O |
| ATOM | 4890 | N | TYR | 631 | 58.093 | 62.335 | 42.368 | 1.00 | 17.21 | A | N |
| ATOM | 4891 | CA | TYR | 631 | 57.737 | 63.362 | 43.335 | 1.00 | 15.51 | A | C |
| ATOM | 4892 | CB | TYR | 631 | 56.380 | 63.969 | 42.981 | 1.00 | 17.16 | A | C |
| ATOM | 4893 | CG | TYR | 631 | 56.161 | 65.353 | 43.545 | 1.00 | 18.38 | A | C |
| ATOM | 4894 | CD1 | TYR | 631 | 55.947 | 65.550 | 44.909 | 1.00 | 18.79 | A | C |
| ATOM | 4895 | CE1 | TYR | 631 | 55.741 | 66.826 | 45.429 | 1.00 | 19.48 | A | C |
| ATOM | 4896 | CD2 | TYR | 631 | 56.168 | 66.470 | 42.714 | 1.00 | 18.85 | A | C |
| ATOM | 4897 | CE2 | TYR | 631 | 55.963 | 67.751 | 43.226 | 1.00 | 19.30 | A | C |
| ATOM | 4898 | CZ | TYR | 631 | 55.748 | 67.918 | 44.580 | 1.00 | 19.21 | A | C |
| ATOM | 4899 | OH | TYR | 631 | 55.520 | 69.173 | 45.084 | 1.00 | 20.71 | A | O |

FIG. 4-101 (Continued)

| ATOM | 4900 | C | TYR | 631 | 57.672 | 62.632 | 44.668 | 1.00 | 15.27 | A | C |
|---|---|---|---|---|---|---|---|---|---|---|---|
| ATOM | 4901 | O | TYR | 631 | 57.946 | 63.201 | 45.731 | 1.00 | 13.23 | A | O |
| ATOM | 4902 | N | GLY | 632 | 57.324 | 61.350 | 44.592 | 1.00 | 14.83 | A | N |
| ATOM | 4903 | CA | GLY | 632 | 57.266 | 60.529 | 45.783 | 1.00 | 15.04 | A | C |
| ATOM | 4904 | C | GLY | 632 | 58.653 | 60.477 | 46.394 | 1.00 | 14.53 | A | C |
| ATOM | 4905 | O | GLY | 632 | 58.816 | 60.652 | 47.596 | 1.00 | 13.85 | A | O |
| ATOM | 4906 | N | GLY | 633 | 59.655 | 60.246 | 45.551 | 1.00 | 15.63 | A | N |
| ATOM | 4907 | CA | GLY | 633 | 61.030 | 60.185 | 46.014 | 1.00 | 14.69 | A | C |
| ATOM | 4908 | C | GLY | 633 | 61.500 | 61.513 | 46.576 | 1.00 | 15.25 | A | C |
| ATOM | 4909 | O | GLY | 633 | 62.251 | 61.561 | 47.555 | 1.00 | 16.82 | A | O |
| ATOM | 4910 | N | TYR | 634 | 61.058 | 62.598 | 45.954 | 1.00 | 13.67 | A | N |
| ATOM | 4911 | CA | TYR | 634 | 61.418 | 63.940 | 46.398 | 1.00 | 13.29 | A | C |
| ATOM | 4912 | CB | TYR | 634 | 60.901 | 64.964 | 45.397 | 1.00 | 11.67 | A | C |
| ATOM | 4913 | CG | TYR | 634 | 60.914 | 66.382 | 45.904 | 1.00 | 12.54 | A | C |
| ATOM | 4914 | CD1 | TYR | 634 | 62.112 | 67.069 | 46.072 | 1.00 | 13.46 | A | C |
| ATOM | 4915 | CE1 | TYR | 634 | 62.125 | 68.398 | 46.484 | 1.00 | 13.37 | A | C |
| ATOM | 4916 | CD2 | TYR | 634 | 59.723 | 67.057 | 46.173 | 1.00 | 11.38 | A | C |
| ATOM | 4917 | CE2 | TYR | 634 | 59.727 | 68.383 | 46.586 | 1.00 | 11.86 | A | C |
| ATOM | 4918 | CZ | TYR | 634 | 60.933 | 69.049 | 46.734 | 1.00 | 12.83 | A | C |
| ATOM | 4919 | OH | TYR | 634 | 60.957 | 70.375 | 47.091 | 1.00 | 12.97 | A | O |
| ATOM | 4920 | C | TYR | 634 | 60.829 | 64.240 | 47.778 | 1.00 | 14.36 | A | C |
| ATOM | 4921 | O | TYR | 634 | 61.524 | 64.721 | 48.672 | 1.00 | 16.28 | A | O |
| ATOM | 4922 | N | VAL | 635 | 59.542 | 63.968 | 47.949 | 1.00 | 14.99 | A | N |
| ATOM | 4923 | CA | VAL | 635 | 58.899 | 64.218 | 49.231 | 1.00 | 15.44 | A | C |
| ATOM | 4924 | CB | VAL | 635 | 57.364 | 64.025 | 49.135 | 1.00 | 15.15 | A | C |
| ATOM | 4925 | CG1 | VAL | 635 | 56.743 | 63.988 | 50.524 | 1.00 | 14.56 | A | C |
| ATOM | 4926 | CG2 | VAL | 635 | 56.758 | 65.167 | 48.326 | 1.00 | 12.62 | A | C |
| ATOM | 4927 | C | VAL | 635 | 59.486 | 63.296 | 50.294 | 1.00 | 16.48 | A | C |
| ATOM | 4928 | O | VAL | 635 | 59.681 | 63.711 | 51.439 | 1.00 | 16.89 | A | O |
| ATOM | 4929 | N | THR | 636 | 59.779 | 62.054 | 49.917 | 1.00 | 16.16 | A | N |
| ATOM | 4930 | CA | THR | 636 | 60.368 | 61.098 | 50.855 | 1.00 | 18.40 | A | C |
| ATOM | 4931 | CB | THR | 636 | 60.701 | 59.746 | 50.175 | 1.00 | 18.30 | A | C |
| ATOM | 4932 | OG1 | THR | 636 | 59.504 | 59.130 | 49.696 | 1.00 | 20.57 | A | O |
| ATOM | 4933 | CG2 | THR | 636 | 61.362 | 58.807 | 51.157 | 1.00 | 20.48 | A | C |
| ATOM | 4934 | C | THR | 636 | 61.676 | 61.676 | 51.396 | 1.00 | 19.91 | A | C |
| ATOM | 4935 | O | THR | 636 | 61.914 | 61.696 | 52.609 | 1.00 | 19.58 | A | O |
| ATOM | 4936 | N | SER | 637 | 62.524 | 62.141 | 50.483 | 1.00 | 19.89 | A | N |
| ATOM | 4937 | CA | SER | 637 | 63.804 | 62.711 | 50.862 | 1.00 | 20.30 | A | C |
| ATOM | 4938 | CB | SER | 637 | 64.599 | 63.086 | 49.614 | 1.00 | 19.17 | A | C |
| ATOM | 4939 | OG | SER | 637 | 64.823 | 61.952 | 48.800 | 1.00 | 19.07 | A | O |
| ATOM | 4940 | C | SER | 637 | 63.615 | 63.938 | 51.749 | 1.00 | 21.61 | A | C |
| ATOM | 4941 | O | SER | 637 | 64.235 | 64.049 | 52.812 | 1.00 | 22.54 | A | O |
| ATOM | 4942 | N | MET | 638 | 62.760 | 64.855 | 51.309 | 1.00 | 21.06 | A | N |
| ATOM | 4943 | CA | MET | 638 | 62.490 | 66.074 | 52.066 | 1.00 | 21.87 | A | C |
| ATOM | 4944 | CB | MET | 638 | 61.417 | 66.895 | 51.354 | 1.00 | 20.36 | A | C |
| ATOM | 4945 | CG | MET | 638 | 61.876 | 67.465 | 50.032 | 1.00 | 21.23 | A | C |
| ATOM | 4946 | SD | MET | 638 | 63.069 | 68.787 | 50.261 | 1.00 | 21.33 | A | S |
| ATOM | 4947 | CE | MET | 638 | 62.006 | 70.229 | 50.125 | 1.00 | 19.31 | A | C |
| ATOM | 4948 | C | MET | 638 | 62.039 | 65.748 | 53.494 | 1.00 | 21.51 | A | C |

F I G. 4 - 1 0 2

| ATOM | 4949 | O | MET | 638 | 62.511 | 66.351 | 54.472 | 1.00 | 19.64 | A | O |
|---|---|---|---|---|---|---|---|---|---|---|---|
| ATOM | 4950 | N | VAL | 639 | 61.116 | 64.798 | 53.600 | 1.00 | 19.63 | A | N |
| ATOM | 4951 | CA | VAL | 639 | 60.611 | 64.372 | 54.891 | 1.00 | 20.04 | A | C |
| ATOM | 4952 | CB | VAL | 639 | 59.524 | 63.287 | 54.746 | 1.00 | 20.08 | A | C |
| ATOM | 4953 | CG1 | VAL | 639 | 59.201 | 62.688 | 56.112 | 1.00 | 20.55 | A | C |
| ATOM | 4954 | CG2 | VAL | 639 | 58.275 | 63.879 | 54.108 | 1.00 | 17.95 | A | C |
| ATOM | 4955 | C | VAL | 639 | 61.758 | 63.793 | 55.692 | 1.00 | 20.25 | A | C |
| ATOM | 4956 | O | VAL | 639 | 61.986 | 64.185 | 56.831 | 1.00 | 23.11 | A | O |
| ATOM | 4957 | N | LEU | 640 | 62.489 | 62.864 | 55.088 | 1.00 | 20.83 | A | N |
| ATOM | 4958 | CA | LEU | 640 | 63.608 | 62.225 | 55.765 | 1.00 | 22.08 | A | C |
| ATOM | 4959 | CB | LEU | 640 | 64.245 | 61.179 | 54.855 | 1.00 | 22.31 | A | C |
| ATOM | 4960 | CG | LEU | 640 | 63.400 | 59.939 | 54.570 | 1.00 | 21.31 | A | C |
| ATOM | 4961 | CD1 | LEU | 640 | 64.143 | 59.041 | 53.611 | 1.00 | 22.16 | A | C |
| ATOM | 4962 | CD2 | LEU | 640 | 63.105 | 59.205 | 55.863 | 1.00 | 22.25 | A | C |
| ATOM | 4963 | C | LEU | 640 | 64.675 | 63.212 | 56.239 | 1.00 | 23.38 | A | C |
| ATOM | 4964 | O | LEU | 640 | 65.416 | 62.922 | 57.182 | 1.00 | 22.99 | A | O |
| ATOM | 4965 | N | GLY | 641 | 64.745 | 64.374 | 55.592 | 1.00 | 23.16 | A | N |
| ATOM | 4966 | CA | GLY | 641 | 65.731 | 65.368 | 55.972 | 1.00 | 23.10 | A | C |
| ATOM | 4967 | C | GLY | 641 | 65.153 | 66.555 | 56.721 | 1.00 | 23.73 | A | C |
| ATOM | 4968 | O | GLY | 641 | 65.782 | 67.609 | 56.802 | 1.00 | 23.94 | A | O |
| ATOM | 4969 | N | SER | 642 | 63.958 | 66.393 | 57.278 | 1.00 | 22.74 | A | N |
| ATOM | 4970 | CA | SER | 642 | 63.318 | 67.484 | 58.002 | 1.00 | 20.76 | A | C |
| ATOM | 4971 | CB | SER | 642 | 61.798 | 67.370 | 57.883 | 1.00 | 19.77 | A | C |
| ATOM | 4972 | OG | SER | 642 | 61.319 | 66.213 | 58.546 | 1.00 | 17.97 | A | O |
| ATOM | 4973 | C | SER | 642 | 63.723 | 67.488 | 59.471 | 1.00 | 21.73 | A | C |
| ATOM | 4974 | O | SER | 642 | 63.656 | 68.519 | 60.140 | 1.00 | 21.40 | A | O |
| ATOM | 4975 | N | GLY | 643 | 64.136 | 66.327 | 59.967 | 1.00 | 22.24 | A | N |
| ATOM | 4976 | CA | GLY | 643 | 64.548 | 66.213 | 61.350 | 1.00 | 22.64 | A | C |
| ATOM | 4977 | C | GLY | 643 | 63.407 | 65.944 | 62.314 | 1.00 | 23.74 | A | C |
| ATOM | 4978 | O | GLY | 643 | 63.585 | 66.064 | 63.528 | 1.00 | 25.32 | A | O |
| ATOM | 4979 | N | SER | 644 | 62.244 | 65.573 | 61.786 | 1.00 | 23.53 | A | N |
| ATOM | 4980 | CA | SER | 644 | 61.067 | 65.301 | 62.616 | 1.00 | 23.38 | A | C |
| ATOM | 4981 | CB | SER | 644 | 59.850 | 64.995 | 61.742 | 1.00 | 24.79 | A | C |
| ATOM | 4982 | OG | SER | 644 | 59.898 | 63.666 | 61.247 | 1.00 | 24.45 | A | O |
| ATOM | 4983 | C | SER | 644 | 61.287 | 64.129 | 63.559 | 1.00 | 23.18 | A | C |
| ATOM | 4984 | O | SER | 644 | 60.565 | 63.961 | 64.536 | 1.00 | 24.28 | A | O |
| ATOM | 4985 | N | GLY | 645 | 62.278 | 63.307 | 63.258 | 1.00 | 23.27 | A | N |
| ATOM | 4986 | CA | GLY | 645 | 62.543 | 62.166 | 64.107 | 1.00 | 24.80 | A | C |
| ATOM | 4987 | C | GLY | 645 | 61.398 | 61.175 | 64.114 | 1.00 | 24.80 | A | C |
| ATOM | 4988 | O | GLY | 645 | 61.379 | 60.248 | 64.920 | 1.00 | 27.93 | A | O |
| ATOM | 4989 | N | VAL | 646 | 60.446 | 61.357 | 63.207 | 1.00 | 23.98 | A | N |
| ATOM | 4990 | CA | VAL | 646 | 59.289 | 60.474 | 63.121 | 1.00 | 22.32 | A | C |
| ATOM | 4991 | CB | VAL | 646 | 58.092 | 61.207 | 62.473 | 1.00 | 24.36 | A | C |
| ATOM | 4992 | CG1 | VAL | 646 | 56.945 | 60.230 | 62.215 | 1.00 | 22.37 | A | C |
| ATOM | 4993 | CG2 | VAL | 646 | 57.636 | 62.351 | 63.381 | 1.00 | 24.11 | A | C |
| ATOM | 4994 | C | VAL | 646 | 59.552 | 59.202 | 62.327 | 1.00 | 21.28 | A | C |
| ATOM | 4995 | O | VAL | 646 | 59.079 | 58.128 | 62.690 | 1.00 | 21.25 | A | O |
| ATOM | 4996 | N | PHE | 647 | 60.303 | 59.326 | 61.239 | 1.00 | 21.00 | A | N |
| ATOM | 4997 | CA | PHE | 647 | 60.593 | 58.182 | 60.380 | 1.00 | 18.33 | A | C |

| ATOM | 4998 | CB  | PHE | 647 | 60.497 | 58.615 | 58.924 | 1.00 | 15.79 | A | C |
|------|------|-----|-----|-----|--------|--------|--------|------|-------|---|---|
| ATOM | 4999 | CG  | PHE | 647 | 59.142 | 59.131 | 58.551 | 1.00 | 16.11 | A | C |
| ATOM | 5000 | CD1 | PHE | 647 | 58.138 | 58.258 | 58.152 | 1.00 | 15.39 | A | C |
| ATOM | 5001 | CD2 | PHE | 647 | 58.841 | 60.479 | 58.680 | 1.00 | 14.43 | A | C |
| ATOM | 5002 | CE1 | PHE | 647 | 56.855 | 58.722 | 57.894 | 1.00 | 13.82 | A | C |
| ATOM | 5003 | CE2 | PHE | 647 | 57.562 | 60.943 | 58.423 | 1.00 | 15.28 | A | C |
| ATOM | 5004 | CZ  | PHE | 647 | 56.568 | 60.061 | 58.031 | 1.00 | 13.75 | A | C |
| ATOM | 5005 | C   | PHE | 647 | 61.944 | 57.555 | 60.663 | 1.00 | 18.46 | A | C |
| ATOM | 5006 | O   | PHE | 647 | 62.943 | 58.250 | 60.825 | 1.00 | 20.84 | A | O |
| ATOM | 5007 | N   | LYS | 648 | 61.958 | 56.232 | 60.722 | 1.00 | 17.11 | A | N |
| ATOM | 5008 | CA  | LYS | 648 | 63.165 | 55.480 | 60.996 | 1.00 | 19.06 | A | C |
| ATOM | 5009 | CB  | LYS | 648 | 62.789 | 54.105 | 61.545 | 1.00 | 17.86 | A | C |
| ATOM | 5010 | CG  | LYS | 648 | 63.961 | 53.242 | 61.955 | 1.00 | 17.94 | A | C |
| ATOM | 5011 | CD  | LYS | 648 | 63.484 | 51.869 | 62.405 | 1.00 | 19.57 | A | C |
| ATOM | 5012 | CE  | LYS | 648 | 64.594 | 51.083 | 63.095 | 1.00 | 19.22 | A | C |
| ATOM | 5013 | NZ  | LYS | 648 | 65.757 | 50.894 | 62.204 | 1.00 | 20.59 | A | N |
| ATOM | 5014 | C   | LYS | 648 | 64.025 | 55.314 | 59.747 | 1.00 | 21.47 | A | C |
| ATOM | 5015 | O   | LYS | 648 | 65.251 | 55.379 | 59.815 | 1.00 | 23.13 | A | O |
| ATOM | 5016 | N   | CYS | 649 | 63.376 | 55.094 | 58.610 | 1.00 | 22.38 | A | N |
| ATOM | 5017 | CA  | CYS | 649 | 64.077 | 54.898 | 57.353 | 1.00 | 24.23 | A | C |
| ATOM | 5018 | C   | CYS | 649 | 63.156 | 55.237 | 56.181 | 1.00 | 24.09 | A | C |
| ATOM | 5019 | O   | CYS | 649 | 61.939 | 55.319 | 56.342 | 1.00 | 23.94 | A | O |
| ATOM | 5020 | CB  | CYS | 649 | 64.527 | 53.447 | 57.237 | 1.00 | 27.68 | A | C |
| ATOM | 5021 | SG  | CYS | 649 | 63.130 | 52.287 | 57.313 | 1.00 | 32.05 | A | S |
| ATOM | 5022 | N   | GLY | 650 | 63.746 | 55.426 | 55.004 | 1.00 | 21.50 | A | N |
| ATOM | 5023 | CA  | GLY | 650 | 62.961 | 55.757 | 53.834 | 1.00 | 21.04 | A | C |
| ATOM | 5024 | C   | GLY | 650 | 63.649 | 55.384 | 52.535 | 1.00 | 21.13 | A | C |
| ATOM | 5025 | O   | GLY | 650 | 64.874 | 55.333 | 52.474 | 1.00 | 21.62 | A | O |
| ATOM | 5026 | N   | ILE | 651 | 62.857 | 55.124 | 51.499 | 1.00 | 19.35 | A | N |
| ATOM | 5027 | CA  | ILE | 651 | 63.388 | 54.753 | 50.195 | 1.00 | 19.18 | A | C |
| ATOM | 5028 | CB  | ILE | 651 | 62.896 | 53.352 | 49.758 | 1.00 | 19.03 | A | C |
| ATOM | 5029 | CG2 | ILE | 651 | 63.601 | 52.933 | 48.481 | 1.00 | 17.31 | A | C |
| ATOM | 5030 | CG1 | ILE | 651 | 63.173 | 52.326 | 50.853 | 1.00 | 19.60 | A | C |
| ATOM | 5031 | CD1 | ILE | 651 | 62.827 | 50.901 | 50.456 | 1.00 | 18.48 | A | C |
| ATOM | 5032 | C   | ILE | 651 | 62.953 | 55.749 | 49.120 | 1.00 | 19.53 | A | C |
| ATOM | 5033 | O   | ILE | 651 | 61.758 | 56.015 | 48.949 | 1.00 | 19.77 | A | O |
| ATOM | 5034 | N   | ALA | 652 | 63.925 | 56.292 | 48.393 | 1.00 | 18.34 | A | N |
| ATOM | 5035 | CA  | ALA | 652 | 63.633 | 57.240 | 47.324 | 1.00 | 15.69 | A | C |
| ATOM | 5036 | CB  | ALA | 652 | 64.323 | 58.574 | 47.594 | 1.00 | 14.05 | A | C |
| ATOM | 5037 | C   | ALA | 652 | 64.107 | 56.662 | 45.996 | 1.00 | 14.98 | A | C |
| ATOM | 5038 | O   | ALA | 652 | 65.288 | 56.367 | 45.827 | 1.00 | 14.12 | A | O |
| ATOM | 5039 | N   | VAL | 653 | 63.175 | 56.487 | 45.064 | 1.00 | 14.68 | A | N |
| ATOM | 5040 | CA  | VAL | 653 | 63.492 | 55.963 | 43.738 | 1.00 | 14.84 | A | C |
| ATOM | 5041 | CB  | VAL | 653 | 62.582 | 54.754 | 43.366 | 1.00 | 17.41 | A | C |
| ATOM | 5042 | CG1 | VAL | 653 | 62.865 | 54.291 | 41.932 | 1.00 | 14.95 | A | C |
| ATOM | 5043 | CG2 | VAL | 653 | 62.806 | 53.607 | 44.352 | 1.00 | 18.10 | A | C |
| ATOM | 5044 | C   | VAL | 653 | 63.292 | 57.063 | 42.694 | 1.00 | 13.22 | A | C |
| ATOM | 5045 | O   | VAL | 653 | 62.224 | 57.669 | 42.620 | 1.00 | 11.12 | A | O |
| ATOM | 5046 | N   | ALA | 654 | 64.331 | 57.317 | 41.901 | 1.00 | 12.68 | A | N |

FIG. 4-104 (Continued)

| | | | | | | | | | | |
|---|---|---|---|---|---|---|---|---|---|---|
| ATOM | 5047 | CA | ALA | 654 | 64.289 | 58.327 | 40.845 | 1.00 | 10.68 | A C |
| ATOM | 5048 | CB | ALA | 654 | 63.513 | 57.790 | 39.650 | 1.00 | 7.27 | A C |
| ATOM | 5049 | C | ALA | 654 | 63.653 | 59.607 | 41.352 | 1.00 | 10.02 | A C |
| ATOM | 5050 | O | ALA | 654 | 62.687 | 60.103 | 40.787 | 1.00 | 13.18 | A O |
| ATOM | 5051 | N | PRO | 655 | 64.208 | 60.179 | 42.420 | 1.00 | 10.68 | A N |
| ATOM | 5052 | CD | PRO | 655 | 65.319 | 59.696 | 43.262 | 1.00 | 8.01 | A C |
| ATOM | 5053 | CA | PRO | 655 | 63.643 | 61.408 | 42.971 | 1.00 | 10.40 | A C |
| ATOM | 5054 | CB | PRO | 655 | 64.092 | 61.344 | 44.422 | 1.00 | 8.50 | A C |
| ATOM | 5055 | CG | PRO | 655 | 65.476 | 60.822 | 44.277 | 1.00 | 6.23 | A C |
| ATOM | 5056 | C | PRO | 655 | 64.090 | 62.714 | 42.327 | 1.00 | 12.92 | A C |
| ATOM | 5057 | O | PRO | 655 | 65.166 | 62.793 | 41.717 | 1.00 | 13.38 | A O |
| ATOM | 5058 | N | VAL | 656 | 63.245 | 63.735 | 42.454 | 1.00 | 12.39 | A N |
| ATOM | 5059 | CA | VAL | 656 | 63.612 | 65.065 | 41.999 | 1.00 | 12.85 | A C |
| ATOM | 5060 | CB | VAL | 656 | 62.373 | 65.946 | 41.769 | 1.00 | 11.42 | A C |
| ATOM | 5061 | CG1 | VAL | 656 | 62.781 | 67.416 | 41.645 | 1.00 | 10.52 | A C |
| ATOM | 5062 | CG2 | VAL | 656 | 61.661 | 65.500 | 40.510 | 1.00 | 10.18 | A C |
| ATOM | 5063 | C | VAL | 656 | 64.382 | 65.560 | 43.236 | 1.00 | 13.79 | A C |
| ATOM | 5064 | O | VAL | 656 | 64.038 | 65.188 | 44.355 | 1.00 | 14.63 | A O |
| ATOM | 5065 | N | SER | 657 | 65.419 | 66.372 | 43.066 | 1.00 | 14.27 | A N |
| ATOM | 5066 | CA | SER | 657 | 66.174 | 66.831 | 44.238 | 1.00 | 14.99 | A C |
| ATOM | 5067 | CB | SER | 657 | 67.589 | 66.231 | 44.231 | 1.00 | 15.67 | A C |
| ATOM | 5068 | OG | SER | 657 | 68.385 | 66.819 | 43.213 | 1.00 | 15.19 | A O |
| ATOM | 5069 | C | SER | 657 | 66.286 | 68.343 | 44.320 | 1.00 | 14.77 | A C |
| ATOM | 5070 | O | SER | 657 | 66.387 | 68.912 | 45.406 | 1.00 | 14.39 | A O |
| ATOM | 5071 | N | ARG | 658 | 66.269 | 68.978 | 43.158 | 1.00 | 15.05 | A N |
| ATOM | 5072 | CA | ARG | 658 | 66.388 | 70.423 | 43.038 | 1.00 | 16.33 | A C |
| ATOM | 5073 | CB | ARG | 658 | 67.845 | 70.787 | 42.747 | 1.00 | 20.44 | A C |
| ATOM | 5074 | CG | ARG | 658 | 68.142 | 72.274 | 42.582 | 1.00 | 24.34 | A C |
| ATOM | 5075 | CD | ARG | 658 | 69.543 | 72.450 | 42.025 | 1.00 | 25.38 | A C |
| ATOM | 5076 | NE | ARG | 658 | 69.905 | 73.838 | 41.757 | 1.00 | 25.70 | A N |
| ATOM | 5077 | CZ | ARG | 658 | 70.353 | 74.683 | 42.676 | 1.00 | 28.34 | A C |
| ATOM | 5078 | NH1 | ARG | 658 | 70.491 | 74.288 | 43.935 | 1.00 | 28.23 | A N |
| ATOM | 5079 | NH2 | ARG | 658 | 70.690 | 75.916 | 42.329 | 1.00 | 29.55 | A N |
| ATOM | 5080 | C | ARG | 658 | 65.515 | 70.775 | 41.850 | 1.00 | 15.87 | A C |
| ATOM | 5081 | O | ARG | 658 | 65.752 | 70.288 | 40.735 | 1.00 | 16.75 | A O |
| ATOM | 5082 | N | TRP | 659 | 64.514 | 71.616 | 42.073 | 1.00 | 13.52 | A N |
| ATOM | 5083 | CA | TRP | 659 | 63.603 | 71.967 | 40.999 | 1.00 | 13.69 | A C |
| ATOM | 5084 | CB | TRP | 659 | 62.465 | 72.823 | 41.550 | 1.00 | 13.63 | A C |
| ATOM | 5085 | CG | TRP | 659 | 61.504 | 71.963 | 42.341 | 1.00 | 17.48 | A C |
| ATOM | 5086 | CD2 | TRP | 659 | 60.690 | 70.898 | 41.829 | 1.00 | 16.63 | A C |
| ATOM | 5087 | CE2 | TRP | 659 | 60.027 | 70.313 | 42.927 | 1.00 | 18.08 | A C |
| ATOM | 5088 | CE3 | TRP | 659 | 60.460 | 70.382 | 40.547 | 1.00 | 16.21 | A C |
| ATOM | 5089 | CD1 | TRP | 659 | 61.300 | 71.980 | 43.692 | 1.00 | 17.21 | A C |
| ATOM | 5090 | NE1 | TRP | 659 | 60.418 | 70.993 | 44.050 | 1.00 | 17.37 | A N |
| ATOM | 5091 | CZ2 | TRP | 659 | 59.145 | 69.233 | 42.785 | 1.00 | 21.55 | A C |
| ATOM | 5092 | CZ3 | TRP | 659 | 59.584 | 69.311 | 40.403 | 1.00 | 18.00 | A C |
| ATOM | 5093 | CH2 | TRP | 659 | 58.937 | 68.746 | 41.516 | 1.00 | 20.15 | A C |
| ATOM | 5094 | C | TRP | 659 | 64.219 | 72.580 | 39.748 | 1.00 | 13.15 | A C |
| ATOM | 5095 | O | TRP | 659 | 63.643 | 72.503 | 38.670 | 1.00 | 11.17 | A O |

FIG. 4-105 (Continued)

| | | | | | | | | | | | |
|---|---|---|---|---|---|---|---|---|---|---|---|
| ATOM | 5096 | N | GLU | 660 | 65.400 | 73.163 | 39.871 | 1.00 | 14.12 | A | N |
| ATOM | 5097 | CA | GLU | 660 | 66.042 | 73.725 | 38.697 | 1.00 | 15.96 | A | C |
| ATOM | 5098 | CB | GLU | 660 | 67.147 | 74.704 | 39.108 | 1.00 | 16.83 | A | C |
| ATOM | 5099 | CG | GLU | 660 | 66.548 | 76.001 | 39.626 | 1.00 | 19.65 | A | C |
| ATOM | 5100 | CD | GLU | 660 | 67.535 | 76.901 | 40.313 | 1.00 | 22.71 | A | C |
| ATOM | 5101 | OE1 | GLU | 660 | 68.310 | 77.600 | 39.617 | 1.00 | 25.18 | A | O |
| ATOM | 5102 | OE2 | GLU | 660 | 67.527 | 76.907 | 41.561 | 1.00 | 23.59 | A | O |
| ATOM | 5103 | C | GLU | 660 | 66.577 | 72.635 | 37.777 | 1.00 | 15.29 | A | C |
| ATOM | 5104 | O | GLU | 660 | 67.001 | 72.922 | 36.659 | 1.00 | 16.67 | A | O |
| ATOM | 5105 | N | TYR | 661 | 66.539 | 71.383 | 38.233 | 1.00 | 14.54 | A | N |
| ATOM | 5106 | CA | TYR | 661 | 67.003 | 70.269 | 37.399 | 1.00 | 14.57 | A | C |
| ATOM | 5107 | CB | TYR | 661 | 67.642 | 69.154 | 38.230 | 1.00 | 13.59 | A | C |
| ATOM | 5108 | CG | TYR | 661 | 68.878 | 69.504 | 39.035 | 1.00 | 15.73 | A | C |
| ATOM | 5109 | CD1 | TYR | 661 | 69.743 | 70.531 | 38.655 | 1.00 | 13.37 | A | C |
| ATOM | 5110 | CE1 | TYR | 661 | 70.889 | 70.805 | 39.390 | 1.00 | 12.74 | A | C |
| ATOM | 5111 | CD2 | TYR | 661 | 69.199 | 68.765 | 40.166 | 1.00 | 16.63 | A | C |
| ATOM | 5112 | CE2 | TYR | 661 | 70.338 | 69.027 | 40.898 | 1.00 | 16.03 | A | C |
| ATOM | 5113 | CZ | TYR | 661 | 71.183 | 70.041 | 40.515 | 1.00 | 13.47 | A | C |
| ATOM | 5114 | OH | TYR | 661 | 72.322 | 70.252 | 41.267 | 1.00 | 8.43 | A | O |
| ATOM | 5115 | C | TYR | 661 | 65.842 | 69.637 | 36.608 | 1.00 | 15.74 | A | C |
| ATOM | 5116 | O | TYR | 661 | 66.077 | 68.854 | 35.675 | 1.00 | 13.97 | A | O |
| ATOM | 5117 | N | TYR | 662 | 64.602 | 69.963 | 36.984 | 1.00 | 13.28 | A | N |
| ATOM | 5118 | CA | TYR | 662 | 63.445 | 69.390 | 36.308 | 1.00 | 13.00 | A | C |
| ATOM | 5119 | CB | TYR | 662 | 62.305 | 69.143 | 37.308 | 1.00 | 14.01 | A | C |
| ATOM | 5120 | CG | TYR | 662 | 61.395 | 68.026 | 36.862 | 1.00 | 14.50 | A | C |
| ATOM | 5121 | CD1 | TYR | 662 | 60.010 | 68.199 | 36.802 | 1.00 | 15.74 | A | C |
| ATOM | 5122 | CE1 | TYR | 662 | 59.184 | 67.201 | 36.273 | 1.00 | 14.99 | A | C |
| ATOM | 5123 | CD2 | TYR | 662 | 61.930 | 66.825 | 36.400 | 1.00 | 14.83 | A | C |
| ATOM | 5124 | CE2 | TYR | 662 | 61.122 | 65.830 | 35.873 | 1.00 | 15.13 | A | C |
| ATOM | 5125 | CZ | TYR | 662 | 59.756 | 66.024 | 35.804 | 1.00 | 15.11 | A | C |
| ATOM | 5126 | OH | TYR | 662 | 58.983 | 65.060 | 35.214 | 1.00 | 17.05 | A | O |
| ATOM | 5127 | C | TYR | 662 | 62.964 | 70.251 | 35.135 | 1.00 | 12.46 | A | C |
| ATOM | 5128 | O | TYR | 662 | 63.320 | 71.423 | 35.030 | 1.00 | 12.22 | A | O |
| ATOM | 5129 | N | ASP | 663 | 62.147 | 69.673 | 34.260 | 1.00 | 12.09 | A | N |
| ATOM | 5130 | CA | ASP | 663 | 61.686 | 70.394 | 33.076 | 1.00 | 13.20 | A | C |
| ATOM | 5131 | CB | ASP | 663 | 60.998 | 69.427 | 32.099 | 1.00 | 11.88 | A | C |
| ATOM | 5132 | CG | ASP | 663 | 59.668 | 68.925 | 32.606 | 1.00 | 13.51 | A | C |
| ATOM | 5133 | OD1 | ASP | 663 | 59.476 | 67.692 | 32.633 | 1.00 | 14.06 | A | O |
| ATOM | 5134 | OD2 | ASP | 663 | 58.809 | 69.758 | 32.962 | 1.00 | 11.87 | A | O |
| ATOM | 5135 | C | ASP | 663 | 60.807 | 71.625 | 33.300 | 1.00 | 13.03 | A | C |
| ATOM | 5136 | O | ASP | 663 | 60.036 | 71.713 | 34.260 | 1.00 | 12.71 | A | O |
| ATOM | 5137 | N | SER | 664 | 60.945 | 72.576 | 32.383 | 1.00 | 12.83 | A | N |
| ATOM | 5138 | CA | SER | 664 | 60.210 | 73.829 | 32.425 | 1.00 | 13.80 | A | C |
| ATOM | 5139 | CB | SER | 664 | 60.433 | 74.600 | 31.120 | 1.00 | 14.92 | A | C |
| ATOM | 5140 | OG | SER | 664 | 59.996 | 73.851 | 30.000 | 1.00 | 14.78 | A | O |
| ATOM | 5141 | C | SER | 664 | 58.715 | 73.688 | 32.674 | 1.00 | 13.35 | A | C |
| ATOM | 5142 | O | SER | 664 | 58.234 | 73.974 | 33.762 | 1.00 | 15.82 | A | O |
| ATOM | 5143 | N | VAL | 665 | 57.987 | 73.247 | 31.658 | 1.00 | 13.43 | A | N |
| ATOM | 5144 | CA | VAL | 665 | 56.540 | 73.101 | 31.733 | 1.00 | 14.34 | A | C |

| | | | | | | | | | | |
|---|---|---|---|---|---|---|---|---|---|---|
| ATOM | 5145 | CB | VAL | 665 | 56.027 | 72.182 | 30.602 | 1.00 14.98 | A | C |
| ATOM | 5146 | CG1 | VAL | 665 | 54.496 | 72.131 | 30.615 | 1.00 15.10 | A | C |
| ATOM | 5147 | CG2 | VAL | 665 | 56.537 | 72.690 | 29.263 | 1.00 13.19 | A | C |
| ATOM | 5148 | C | VAL | 665 | 55.972 | 72.620 | 33.070 | 1.00 14.50 | A | C |
| ATOM | 5149 | O | VAL | 665 | 55.153 | 73.302 | 33.677 | 1.00 14.33 | A | O |
| ATOM | 5150 | N | TYR | 666 | 56.392 | 71.452 | 33.534 | 1.00 15.45 | A | N |
| ATOM | 5151 | CA | TYR | 666 | 55.876 | 70.948 | 34.801 | 1.00 17.06 | A | C |
| ATOM | 5152 | CB | TYR | 666 | 56.323 | 69.501 | 35.038 | 1.00 15.58 | A | C |
| ATOM | 5153 | CG | TYR | 666 | 55.839 | 68.903 | 36.349 | 1.00 13.94 | A | C |
| ATOM | 5154 | CD1 | TYR | 666 | 54.692 | 68.119 | 36.395 | 1.00 14.70 | A | C |
| ATOM | 5155 | CE1 | TYR | 666 | 54.276 | 67.517 | 37.577 | 1.00 13.28 | A | C |
| ATOM | 5156 | CD2 | TYR | 666 | 56.560 | 69.080 | 37.534 | 1.00 13.77 | A | C |
| ATOM | 5157 | CE2 | TYR | 666 | 56.154 | 68.482 | 38.727 | 1.00 12.27 | A | C |
| ATOM | 5158 | CZ | TYR | 666 | 55.012 | 67.700 | 38.737 | 1.00 15.52 | A | C |
| ATOM | 5159 | OH | TYR | 666 | 54.609 | 67.072 | 39.896 | 1.00 18.37 | A | O |
| ATOM | 5160 | C | TYR | 666 | 56.297 | 71.796 | 35.998 | 1.00 17.89 | A | C |
| ATOM | 5161 | O | TYR | 666 | 55.451 | 72.200 | 36.795 | 1.00 19.29 | A | O |
| ATOM | 5162 | N | THR | 667 | 57.592 | 72.066 | 36.125 | 1.00 17.90 | A | N |
| ATOM | 5163 | CA | THR | 667 | 58.092 | 72.833 | 37.265 | 1.00 19.74 | A | C |
| ATOM | 5164 | CB | THR | 667 | 59.621 | 72.953 | 37.251 | 1.00 18.84 | A | C |
| ATOM | 5165 | OG1 | THR | 667 | 60.206 | 71.675 | 36.968 | 1.00 20.18 | A | O |
| ATOM | 5166 | CG2 | THR | 667 | 60.108 | 73.441 | 38.604 | 1.00 17.74 | A | C |
| ATOM | 5167 | C | THR | 667 | 57.537 | 74.246 | 37.339 | 1.00 21.44 | A | C |
| ATOM | 5168 | O | THR | 667 | 56.916 | 74.635 | 38.333 | 1.00 21.51 | A | O |
| ATOM | 5169 | N | GLU | 668 | 57.778 | 75.011 | 36.280 | 1.00 21.85 | A | N |
| ATOM | 5170 | CA | GLU | 668 | 57.330 | 76.389 | 36.200 | 1.00 21.18 | A | C |
| ATOM | 5171 | CB | GLU | 668 | 57.746 | 76.976 | 34.859 | 1.00 20.69 | A | C |
| ATOM | 5172 | CG | GLU | 668 | 59.251 | 77.096 | 34.703 | 1.00 20.20 | A | C |
| ATOM | 5173 | CD | GLU | 668 | 59.657 | 77.559 | 33.322 | 1.00 19.55 | A | C |
| ATOM | 5174 | OE1 | GLU | 668 | 58.783 | 78.068 | 32.588 | 1.00 19.49 | A | O |
| ATOM | 5175 | OE2 | GLU | 668 | 60.851 | 77.422 | 32.977 | 1.00 18.34 | A | O |
| ATOM | 5176 | C | GLU | 668 | 55.828 | 76.517 | 36.394 | 1.00 21.50 | A | C |
| ATOM | 5177 | O | GLU | 668 | 55.339 | 77.559 | 36.814 | 1.00 22.31 | A | O |
| ATOM | 5178 | N | ARG | 669 | 55.098 | 75.449 | 36.101 | 1.00 21.90 | A | N |
| ATOM | 5179 | CA | ARG | 669 | 53.648 | 75.458 | 36.249 | 1.00 21.18 | A | C |
| ATOM | 5180 | CB | ARG | 669 | 53.060 | 74.121 | 35.786 | 1.00 22.06 | A | C |
| ATOM | 5181 | CG | ARG | 669 | 51.546 | 74.026 | 35.922 | 1.00 21.37 | A | C |
| ATOM | 5182 | CD | ARG | 669 | 51.085 | 72.625 | 35.653 | 1.00 20.85 | A | C |
| ATOM | 5183 | NE | ARG | 669 | 51.467 | 72.187 | 34.319 | 1.00 21.84 | A | N |
| ATOM | 5184 | CZ | ARG | 669 | 51.667 | 70.918 | 33.981 | 1.00 21.10 | A | C |
| ATOM | 5185 | NH1 | ARG | 669 | 51.522 | 69.962 | 34.888 | 1.00 19.62 | A | N |
| ATOM | 5186 | NH2 | ARG | 669 | 52.018 | 70.610 | 32.741 | 1.00 20.23 | A | N |
| ATOM | 5187 | C | ARG | 669 | 53.246 | 75.706 | 37.695 | 1.00 21.23 | A | C |
| ATOM | 5188 | O | ARG | 669 | 52.209 | 76.306 | 37.957 | 1.00 20.45 | A | O |
| ATOM | 5189 | N | TYR | 670 | 54.067 | 75.239 | 38.631 | 1.00 21.65 | A | N |
| ATOM | 5190 | CA | TYR | 670 | 53.771 | 75.409 | 40.047 | 1.00 22.27 | A | C |
| ATOM | 5191 | CB | TYR | 670 | 53.752 | 74.048 | 40.764 | 1.00 21.10 | A | C |
| ATOM | 5192 | CG | TYR | 670 | 53.113 | 72.930 | 39.972 | 1.00 20.47 | A | C |
| ATOM | 5193 | CD1 | TYR | 670 | 53.896 | 71.995 | 39.310 | 1.00 20.74 | A | C |

FIG. 4-107 (Continued)

| | | | | | | | | | | |
|---|---|---|---|---|---|---|---|---|---|---|
| ATOM | 5194 | CE1 | TYR | 670 | 53.321 | 70.985 | 38.537 | 1.00 | 22.18 | A C |
| ATOM | 5195 | CD2 | TYR | 670 | 51.726 | 72.831 | 39.850 | 1.00 | 19.78 | A C |
| ATOM | 5196 | CE2 | TYR | 670 | 51.139 | 71.831 | 39.079 | 1.00 | 19.87 | A C |
| ATOM | 5197 | CZ | TYR | 670 | 51.944 | 70.911 | 38.422 | 1.00 | 22.17 | A C |
| ATOM | 5198 | OH | TYR | 670 | 51.388 | 69.931 | 37.623 | 1.00 | 23.11 | A O |
| ATOM | 5199 | C | TYR | 670 | 54.769 | 76.317 | 40.757 | 1.00 | 23.32 | A C |
| ATOM | 5200 | O | TYR | 670 | 54.442 | 76.937 | 41.763 | 1.00 | 24.86 | A O |
| ATOM | 5201 | N | MET | 671 | 55.983 | 76.404 | 40.228 | 1.00 | 24.66 | A N |
| ATOM | 5202 | CA | MET | 671 | 57.029 | 77.207 | 40.851 | 1.00 | 23.96 | A C |
| ATOM | 5203 | CB | MET | 671 | 58.327 | 76.400 | 40.905 | 1.00 | 24.00 | A C |
| ATOM | 5204 | CG | MET | 671 | 58.288 | 75.215 | 41.852 | 1.00 | 23.55 | A C |
| ATOM | 5205 | SD | MET | 671 | 58.383 | 75.732 | 43.565 | 1.00 | 24.97 | A S |
| ATOM | 5206 | CE | MET | 671 | 60.159 | 75.998 | 43.721 | 1.00 | 21.94 | A C |
| ATOM | 5207 | C | MET | 671 | 57.330 | 78.547 | 40.203 | 1.00 | 24.00 | A C |
| ATOM | 5208 | O | MET | 671 | 58.101 | 79.331 | 40.756 | 1.00 | 25.98 | A O |
| ATOM | 5209 | N | GLY | 672 | 56.741 | 78.822 | 39.045 | 1.00 | 22.07 | A N |
| ATOM | 5210 | CA | GLY | 672 | 57.044 | 80.076 | 38.379 | 1.00 | 22.40 | A C |
| ATOM | 5211 | C | GLY | 672 | 58.472 | 80.028 | 37.857 | 1.00 | 22.69 | A C |
| ATOM | 5212 | O | GLY | 672 | 59.005 | 78.947 | 37.641 | 1.00 | 23.27 | A O |
| ATOM | 5213 | N | LEU | 673 | 59.108 | 81.180 | 37.667 | 1.00 | 22.65 | A N |
| ATOM | 5214 | CA | LEU | 673 | 60.477 | 81.209 | 37.151 | 1.00 | 20.90 | A C |
| ATOM | 5215 | CB | LEU | 673 | 60.626 | 82.356 | 36.164 | 1.00 | 19.50 | A C |
| ATOM | 5216 | CG | LEU | 673 | 59.639 | 82.282 | 35.010 | 1.00 | 19.96 | A C |
| ATOM | 5217 | CD1 | LEU | 673 | 59.779 | 83.513 | 34.147 | 1.00 | 20.87 | A C |
| ATOM | 5218 | CD2 | LEU | 673 | 59.892 | 81.027 | 34.203 | 1.00 | 21.63 | A C |
| ATOM | 5219 | C | LEU | 673 | 61.528 | 81.344 | 38.248 | 1.00 | 21.08 | A C |
| ATOM | 5220 | O | LEU | 673 | 61.313 | 82.028 | 39.239 | 1.00 | 21.87 | A O |
| ATOM | 5221 | N | PRO | 674 | 62.692 | 80.700 | 38.072 | 1.00 | 21.90 | A N |
| ATOM | 5222 | CD | PRO | 674 | 63.050 | 79.803 | 36.968 | 1.00 | 21.16 | A C |
| ATOM | 5223 | CA | PRO | 674 | 63.780 | 80.747 | 39.050 | 1.00 | 23.23 | A C |
| ATOM | 5224 | CB | PRO | 674 | 64.618 | 79.510 | 38.709 | 1.00 | 21.90 | A C |
| ATOM | 5225 | CG | PRO | 674 | 63.803 | 78.755 | 37.695 | 1.00 | 22.34 | A C |
| ATOM | 5226 | C | PRO | 674 | 64.617 | 82.023 | 38.943 | 1.00 | 24.90 | A C |
| ATOM | 5227 | O | PRO | 674 | 65.841 | 81.977 | 39.028 | 1.00 | 26.10 | A O |
| ATOM | 5228 | N | THR | 675 | 63.966 | 83.158 | 38.743 | 1.00 | 25.88 | A N |
| ATOM | 5229 | CA | THR | 675 | 64.695 | 84.411 | 38.640 | 1.00 | 27.60 | A C |
| ATOM | 5230 | CB | THR | 675 | 64.208 | 85.237 | 37.447 | 1.00 | 27.12 | A C |
| ATOM | 5231 | OG1 | THR | 675 | 62.811 | 85.524 | 37.599 | 1.00 | 29.30 | A O |
| ATOM | 5232 | CG2 | THR | 675 | 64.431 | 84.471 | 36.156 | 1.00 | 25.59 | A C |
| ATOM | 5233 | C | THR | 675 | 64.496 | 85.211 | 39.918 | 1.00 | 28.74 | A C |
| ATOM | 5234 | O | THR | 675 | 63.543 | 84.982 | 40.660 | 1.00 | 29.47 | A O |
| ATOM | 5235 | N | PRO | 676 | 65.404 | 86.156 | 40.200 | 1.00 | 29.41 | A N |
| ATOM | 5236 | CD | PRO | 676 | 66.625 | 86.508 | 39.457 | 1.00 | 28.96 | A C |
| ATOM | 5237 | CA | PRO | 676 | 65.284 | 86.969 | 41.411 | 1.00 | 29.70 | A C |
| ATOM | 5238 | CB | PRO | 676 | 66.465 | 87.929 | 41.299 | 1.00 | 28.87 | A C |
| ATOM | 5239 | CG | PRO | 676 | 67.467 | 87.142 | 40.533 | 1.00 | 28.27 | A C |
| ATOM | 5240 | C | PRO | 676 | 63.948 | 87.707 | 41.484 | 1.00 | 30.03 | A C |
| ATOM | 5241 | O | PRO | 676 | 63.359 | 87.829 | 42.558 | 1.00 | 29.93 | A O |
| ATOM | 5242 | N | GLU | 677 | 63.463 | 88.190 | 40.343 | 1.00 | 30.62 | A N |

FIG. 4-108 (Continued)

| | | | | | | | | | | |
|---|---|---|---|---|---|---|---|---|---|---|
| ATOM | 5243 | CA | GLU | 677 | 62.203 | 88.923 | 40.348 | 1.00 30.92 | A | C |
| ATOM | 5244 | CB | GLU | 677 | 62.192 | 90.013 | 39.264 | 1.00 32.38 | A | C |
| ATOM | 5245 | CG | GLU | 677 | 62.103 | 89.536 | 37.821 | 1.00 34.78 | A | C |
| ATOM | 5246 | CD | GLU | 677 | 63.380 | 88.877 | 37.331 | 1.00 37.04 | A | C |
| ATOM | 5247 | OE1 | GLU | 677 | 64.480 | 89.356 | 37.697 | 1.00 35.11 | A | O |
| ATOM | 5248 | OE2 | GLU | 677 | 63.276 | 87.891 | 36.566 | 1.00 37.80 | A | O |
| ATOM | 5249 | C | GLU | 677 | 60.952 | 88.065 | 40.231 | 1.00 30.10 | A | C |
| ATOM | 5250 | O | GLU | 677 | 59.893 | 88.564 | 39.849 | 1.00 31.67 | A | O |
| ATOM | 5251 | N | ASP | 678 | 61.067 | 86.777 | 40.546 | 1.00 28.40 | A | N |
| ATOM | 5252 | CA | ASP | 678 | 59.906 | 85.897 | 40.523 | 1.00 26.09 | A | C |
| ATOM | 5253 | CB | ASP | 678 | 59.833 | 85.048 | 39.253 | 1.00 25.88 | A | C |
| ATOM | 5254 | CG | ASP | 678 | 58.472 | 84.359 | 39.097 | 1.00 28.22 | A | C |
| ATOM | 5255 | OD1 | ASP | 678 | 57.885 | 83.980 | 40.128 | 1.00 28.64 | A | O |
| ATOM | 5256 | OD2 | ASP | 678 | 57.980 | 84.189 | 37.956 | 1.00 28.80 | A | O |
| ATOM | 5257 | C | ASP | 678 | 59.920 | 84.982 | 41.737 | 1.00 25.86 | A | C |
| ATOM | 5258 | O | ASP | 678 | 59.481 | 85.382 | 42.810 | 1.00 28.55 | A | O |
| ATOM | 5259 | N | ASN | 679 | 60.442 | 83.768 | 41.591 | 1.00 23.97 | A | N |
| ATOM | 5260 | CA | ASN | 679 | 60.443 | 82.835 | 42.708 | 1.00 21.47 | A | C |
| ATOM | 5261 | CB | ASN | 679 | 59.326 | 81.818 | 42.496 | 1.00 19.41 | A | C |
| ATOM | 5262 | CG | ASN | 679 | 58.894 | 81.146 | 43.778 | 1.00 19.58 | A | C |
| ATOM | 5263 | OD1 | ASN | 679 | 58.491 | 79.981 | 43.775 | 1.00 20.44 | A | O |
| ATOM | 5264 | ND2 | ASN | 679 | 58.957 | 81.879 | 44.882 | 1.00 18.70 | A | N |
| ATOM | 5265 | C | ASN | 679 | 61.760 | 82.099 | 42.957 | 1.00 21.79 | A | C |
| ATOM | 5266 | O | ASN | 679 | 61.770 | 81.055 | 43.601 | 1.00 21.89 | A | O |
| ATOM | 5267 | N | LEU | 680 | 62.873 | 82.636 | 42.472 | 1.00 24.38 | A | N |
| ATOM | 5268 | CA | LEU | 680 | 64.164 | 81.967 | 42.665 | 1.00 26.33 | A | C |
| ATOM | 5269 | CB | LEU | 680 | 65.316 | 82.842 | 42.157 | 1.00 26.74 | A | C |
| ATOM | 5270 | CG | LEU | 680 | 66.726 | 82.275 | 42.385 | 1.00 28.22 | A | C |
| ATOM | 5271 | CD1 | LEU | 680 | 66.844 | 80.903 | 41.747 | 1.00 30.03 | A | C |
| ATOM | 5272 | CD2 | LEU | 680 | 67.772 | 83.211 | 41.801 | 1.00 29.33 | A | C |
| ATOM | 5273 | C | LEU | 680 | 64.449 | 81.556 | 44.109 | 1.00 27.18 | A | C |
| ATOM | 5274 | O | LEU | 680 | 64.977 | 80.471 | 44.347 | 1.00 28.31 | A | O |
| ATOM | 5275 | N | ASP | 681 | 64.111 | 82.411 | 45.072 | 1.00 27.79 | A | N |
| ATOM | 5276 | CA | ASP | 681 | 64.360 | 82.091 | 46.475 | 1.00 28.03 | A | C |
| ATOM | 5277 | CB | ASP | 681 | 63.836 | 83.196 | 47.394 | 1.00 30.36 | A | C |
| ATOM | 5278 | CG | ASP | 681 | 64.774 | 84.386 | 47.473 | 1.00 34.23 | A | C |
| ATOM | 5279 | OD1 | ASP | 681 | 65.908 | 84.289 | 46.952 | 1.00 35.59 | A | O |
| ATOM | 5280 | OD2 | ASP | 681 | 64.380 | 85.417 | 48.067 | 1.00 36.71 | A | O |
| ATOM | 5281 | C | ASP | 681 | 63.773 | 80.753 | 46.920 | 1.00 27.55 | A | C |
| ATOM | 5282 | O | ASP | 681 | 64.428 | 80.005 | 47.647 | 1.00 28.05 | A | O |
| ATOM | 5283 | N | HIS | 682 | 62.551 | 80.438 | 46.502 | 1.00 25.37 | A | N |
| ATOM | 5284 | CA | HIS | 682 | 61.981 | 79.164 | 46.913 | 1.00 25.07 | A | C |
| ATOM | 5285 | CB | HIS | 682 | 60.456 | 79.161 | 46.801 | 1.00 25.14 | A | C |
| ATOM | 5286 | CG | HIS | 682 | 59.832 | 77.914 | 47.349 | 1.00 27.18 | A | C |
| ATOM | 5287 | CD2 | HIS | 682 | 59.091 | 76.948 | 46.754 | 1.00 27.87 | A | C |
| ATOM | 5288 | ND1 | HIS | 682 | 60.021 | 77.503 | 48.650 | 1.00 26.29 | A | N |
| ATOM | 5289 | CE1 | HIS | 682 | 59.428 | 76.336 | 48.832 | 1.00 26.61 | A | C |
| ATOM | 5290 | NE2 | HIS | 682 | 58.857 | 75.977 | 47.697 | 1.00 25.03 | A | N |
| ATOM | 5291 | C | HIS | 682 | 62.559 | 77.983 | 46.130 | 1.00 24.30 | A | C |

FIG. 4-109 (Continued)

| ATOM | 5292 | O | HIS | 682 | 62.463 | 76.837 | 46.572 | 1.00 | 23.47 | A | O |
|------|------|------|-----|-----|--------|--------|--------|------|-------|---|---|
| ATOM | 5293 | N | TYR | 683 | 63.144 | 78.258 | 44.966 | 1.00 | 23.49 | A | N |
| ATOM | 5294 | CA | TYR | 683 | 63.768 | 77.208 | 44.157 | 1.00 | 22.64 | A | C |
| ATOM | 5295 | CB | TYR | 683 | 64.249 | 77.758 | 42.812 | 1.00 | 20.68 | A | C |
| ATOM | 5296 | CG | TYR | 683 | 63.291 | 77.594 | 41.655 | 1.00 | 19.28 | A | C |
| ATOM | 5297 | CD1 | TYR | 683 | 63.325 | 76.461 | 40.857 | 1.00 | 16.29 | A | C |
| ATOM | 5298 | CE1 | TYR | 683 | 62.464 | 76.317 | 39.783 | 1.00 | 16.83 | A | C |
| ATOM | 5299 | CD2 | TYR | 683 | 62.361 | 78.589 | 41.347 | 1.00 | 20.47 | A | C |
| ATOM | 5300 | CE2 | TYR | 683 | 61.495 | 78.453 | 40.276 | 1.00 | 20.17 | A | C |
| ATOM | 5301 | CZ | TYR | 683 | 61.554 | 77.314 | 39.500 | 1.00 | 19.09 | A | C |
| ATOM | 5302 | OH | TYR | 683 | 60.695 | 77.176 | 38.441 | 1.00 | 21.54 | A | O |
| ATOM | 5303 | C | TYR | 683 | 64.989 | 76.727 | 44.924 | 1.00 | 22.32 | A | C |
| ATOM | 5304 | O | TYR | 683 | 65.189 | 75.533 | 45.125 | 1.00 | 22.65 | A | O |
| ATOM | 5305 | N | ARG | 684 | 65.799 | 77.685 | 45.355 | 1.00 | 22.44 | A | N |
| ATOM | 5306 | CA | ARG | 684 | 67.025 | 77.392 | 46.076 | 1.00 | 22.97 | A | C |
| ATOM | 5307 | CB | ARG | 684 | 67.928 | 78.624 | 46.071 | 1.00 | 22.89 | A | C |
| ATOM | 5308 | CG | ARG | 684 | 68.349 | 79.064 | 44.672 | 1.00 | 24.57 | A | C |
| ATOM | 5309 | CD | ARG | 684 | 69.238 | 78.020 | 44.004 | 1.00 | 23.11 | A | C |
| ATOM | 5310 | NE | ARG | 684 | 69.328 | 78.223 | 42.562 | 1.00 | 25.47 | A | N |
| ATOM | 5311 | CZ | ARG | 684 | 69.844 | 79.299 | 41.974 | 1.00 | 27.89 | A | C |
| ATOM | 5312 | NH1 | ARG | 684 | 70.337 | 80.294 | 42.703 | 1.00 | 29.09 | A | N |
| ATOM | 5313 | NH2 | ARG | 684 | 69.846 | 79.388 | 40.648 | 1.00 | 27.04 | A | N |
| ATOM | 5314 | C | ARG | 684 | 66.807 | 76.922 | 47.501 | 1.00 | 22.90 | A | C |
| ATOM | 5315 | O | ARG | 684 | 67.711 | 76.368 | 48.111 | 1.00 | 24.16 | A | O |
| ATOM | 5316 | N | ASN | 685 | 65.608 | 77.121 | 48.030 | 1.00 | 24.64 | A | N |
| ATOM | 5317 | CA | ASN | 685 | 65.331 | 76.715 | 49.399 | 1.00 | 24.41 | A | C |
| ATOM | 5318 | CB | ASN | 685 | 64.599 | 77.831 | 50.134 | 1.00 | 28.42 | A | C |
| ATOM | 5319 | CG | ASN | 685 | 64.455 | 77.547 | 51.610 | 1.00 | 34.24 | A | C |
| ATOM | 5320 | OD1 | ASN | 685 | 65.410 | 77.117 | 52.266 | 1.00 | 38.25 | A | O |
| ATOM | 5321 | ND2 | ASN | 685 | 63.264 | 77.791 | 52.150 | 1.00 | 37.49 | A | N |
| ATOM | 5322 | C | ASN | 685 | 64.545 | 75.419 | 49.537 | 1.00 | 23.72 | A | C |
| ATOM | 5323 | O | ASN | 685 | 64.356 | 74.929 | 50.649 | 1.00 | 23.86 | A | O |
| ATOM | 5324 | N | SER | 686 | 64.101 | 74.852 | 48.417 | 1.00 | 21.55 | A | N |
| ATOM | 5325 | CA | SER | 686 | 63.336 | 73.613 | 48.457 | 1.00 | 19.71 | A | C |
| ATOM | 5326 | CB | SER | 686 | 61.976 | 73.811 | 47.774 | 1.00 | 19.20 | A | C |
| ATOM | 5327 | OG | SER | 686 | 62.114 | 74.112 | 46.397 | 1.00 | 15.00 | A | O |
| ATOM | 5328 | C | SER | 686 | 64.060 | 72.421 | 47.823 | 1.00 | 20.13 | A | C |
| ATOM | 5329 | O | SER | 686 | 63.447 | 71.611 | 47.128 | 1.00 | 21.27 | A | O |
| ATOM | 5330 | N | THR | 687 | 65.362 | 72.307 | 48.060 | 1.00 | 19.02 | A | N |
| ATOM | 5331 | CA | THR | 687 | 66.122 | 71.189 | 47.509 | 1.00 | 17.15 | A | C |
| ATOM | 5332 | CB | THR | 687 | 67.441 | 71.665 | 46.906 | 1.00 | 16.10 | A | C |
| ATOM | 5333 | OG1 | THR | 687 | 68.362 | 71.959 | 47.960 | 1.00 | 17.42 | A | O |
| ATOM | 5334 | CG2 | THR | 687 | 67.214 | 72.920 | 46.058 | 1.00 | 14.71 | A | C |
| ATOM | 5335 | C | THR | 687 | 66.433 | 70.153 | 48.585 | 1.00 | 15.79 | A | C |
| ATOM | 5336 | O | THR | 687 | 66.496 | 70.466 | 49.763 | 1.00 | 15.82 | A | O |
| ATOM | 5337 | N | VAL | 688 | 66.627 | 68.908 | 48.182 | 1.00 | 18.43 | A | N |
| ATOM | 5338 | CA | VAL | 688 | 66.935 | 67.854 | 49.147 | 1.00 | 17.92 | A | C |
| ATOM | 5339 | CB | VAL | 688 | 66.840 | 66.453 | 48.480 | 1.00 | 17.13 | A | C |
| ATOM | 5340 | CG1 | VAL | 688 | 67.092 | 65.352 | 49.503 | 1.00 | 15.01 | A | C |

FIG. 4-110 (Continued)

| | | | | | | | | | | |
|---|---|---|---|---|---|---|---|---|---|---|
| ATOM | 5341 | CG2 | VAL | 688 | 65.459 | 66.279 | 47.845 | 1.00 | 18.49 | A C |
| ATOM | 5342 | C | VAL | 688 | 68.341 | 68.059 | 49.720 | 1.00 | 17.50 | A C |
| ATOM | 5343 | O | VAL | 688 | 68.559 | 67.905 | 50.923 | 1.00 | 15.69 | A O |
| ATOM | 5344 | N | MET | 689 | 69.280 | 68.428 | 48.851 | 1.00 | 16.92 | A N |
| ATOM | 5345 | CA | MET | 689 | 70.672 | 68.647 | 49.246 | 1.00 | 17.40 | A C |
| ATOM | 5346 | CB | MET | 689 | 71.475 | 69.213 | 48.065 | 1.00 | 13.91 | A C |
| ATOM | 5347 | CG | MET | 689 | 71.829 | 68.210 | 46.984 | 1.00 | 10.55 | A C |
| ATOM | 5348 | SD | MET | 689 | 70.465 | 67.740 | 45.909 | 1.00 | 11.73 | A S |
| ATOM | 5349 | CE | MET | 689 | 70.338 | 69.210 | 44.871 | 1.00 | 9.36 | A C |
| ATOM | 5350 | C | MET | 689 | 70.897 | 69.539 | 50.479 | 1.00 | 17.90 | A C |
| ATOM | 5351 | O | MET | 689 | 71.721 | 69.220 | 51.341 | 1.00 | 16.90 | A O |
| ATOM | 5352 | N | SER | 690 | 70.179 | 70.653 | 50.569 | 1.00 | 18.32 | A N |
| ATOM | 5353 | CA | SER | 690 | 70.358 | 71.544 | 51.712 | 1.00 | 21.65 | A C |
| ATOM | 5354 | CB | SER | 690 | 69.621 | 72.866 | 51.501 | 1.00 | 20.29 | A C |
| ATOM | 5355 | OG | SER | 690 | 68.234 | 72.702 | 51.711 | 1.00 | 24.78 | A O |
| ATOM | 5356 | C | SER | 690 | 69.898 | 70.933 | 53.038 | 1.00 | 22.31 | A C |
| ATOM | 5357 | O | SER | 690 | 69.930 | 71.606 | 54.063 | 1.00 | 23.43 | A O |
| ATOM | 5358 | N | ARG | 691 | 69.480 | 69.672 | 53.023 | 1.00 | 21.70 | A N |
| ATOM | 5359 | CA | ARG | 691 | 69.041 | 69.012 | 54.249 | 1.00 | 23.07 | A C |
| ATOM | 5360 | CB | ARG | 691 | 67.591 | 68.546 | 54.113 | 1.00 | 22.90 | A C |
| ATOM | 5361 | CG | ARG | 691 | 66.623 | 69.652 | 53.770 | 1.00 | 22.81 | A C |
| ATOM | 5362 | CD | ARG | 691 | 65.201 | 69.152 | 53.813 | 1.00 | 22.97 | A C |
| ATOM | 5363 | NE | ARG | 691 | 64.236 | 70.240 | 53.694 | 1.00 | 24.03 | A N |
| ATOM | 5364 | CZ | ARG | 691 | 62.963 | 70.134 | 54.061 | 1.00 | 26.18 | A C |
| ATOM | 5365 | NH1 | ARG | 691 | 62.509 | 68.989 | 54.566 | 1.00 | 25.20 | A N |
| ATOM | 5366 | NH2 | ARG | 691 | 62.149 | 71.172 | 53.946 | 1.00 | 26.01 | A N |
| ATOM | 5367 | C | ARG | 691 | 69.922 | 67.811 | 54.593 | 1.00 | 24.24 | A C |
| ATOM | 5368 | O | ARG | 691 | 69.595 | 67.031 | 55.488 | 1.00 | 25.28 | A O |
| ATOM | 5369 | N | ALA | 692 | 71.041 | 67.675 | 53.889 | 1.00 | 24.03 | A N |
| ATOM | 5370 | CA | ALA | 692 | 71.960 | 66.561 | 54.100 | 1.00 | 24.84 | A C |
| ATOM | 5371 | CB | ALA | 692 | 73.270 | 66.826 | 53.360 | 1.00 | 24.20 | A C |
| ATOM | 5372 | C | ALA | 692 | 72.251 | 66.210 | 55.562 | 1.00 | 24.60 | A C |
| ATOM | 5373 | O | ALA | 692 | 72.066 | 65.068 | 55.967 | 1.00 | 24.83 | A O |
| ATOM | 5374 | N | GLU | 693 | 72.707 | 67.181 | 56.347 | 1.00 | 25.74 | A N |
| ATOM | 5375 | CA | GLU | 693 | 73.033 | 66.944 | 57.757 | 1.00 | 27.13 | A C |
| ATOM | 5376 | CB | GLU | 693 | 73.351 | 68.266 | 58.463 | 1.00 | 29.38 | A C |
| ATOM | 5377 | CG | GLU | 693 | 74.829 | 68.606 | 58.583 | 1.00 | 35.02 | A C |
| ATOM | 5378 | CD | GLU | 693 | 75.604 | 67.627 | 59.463 | 1.00 | 39.06 | A C |
| ATOM | 5379 | OE1 | GLU | 693 | 74.984 | 66.948 | 60.316 | 1.00 | 38.42 | A O |
| ATOM | 5380 | OE2 | GLU | 693 | 76.845 | 67.554 | 59.307 | 1.00 | 41.03 | A O |
| ATOM | 5381 | C | GLU | 693 | 71.947 | 66.215 | 58.549 | 1.00 | 26.16 | A C |
| ATOM | 5382 | O | GLU | 693 | 72.250 | 65.505 | 59.506 | 1.00 | 26.78 | A O |
| ATOM | 5383 | N | ASN | 694 | 70.688 | 66.387 | 58.160 | 1.00 | 24.46 | A N |
| ATOM | 5384 | CA | ASN | 694 | 69.594 | 65.734 | 58.873 | 1.00 | 24.35 | A C |
| ATOM | 5385 | CB | ASN | 694 | 68.274 | 66.473 | 58.619 | 1.00 | 26.79 | A C |
| ATOM | 5386 | CG | ASN | 694 | 68.191 | 67.796 | 59.370 | 1.00 | 28.23 | A C |
| ATOM | 5387 | OD1 | ASN | 694 | 67.291 | 68.607 | 59.132 | 1.00 | 29.60 | A O |
| ATOM | 5388 | ND2 | ASN | 694 | 69.127 | 68.015 | 60.287 | 1.00 | 27.09 | A N |
| ATOM | 5389 | C | ASN | 694 | 69.412 | 64.252 | 58.567 | 1.00 | 22.78 | A C |

| ATOM | 5390 | O | ASN | 694 | 68.736 | 63.555 | 59.318 | 1.00 | 22.09 | A | O |
|---|---|---|---|---|---|---|---|---|---|---|---|
| ATOM | 5391 | N | PHE | 695 | 70.008 | 63.764 | 57.481 | 1.00 | 21.23 | A | N |
| ATOM | 5392 | CA | PHE | 695 | 69.876 | 62.351 | 57.135 | 1.00 | 20.87 | A | C |
| ATOM | 5393 | CB | PHE | 695 | 70.297 | 62.085 | 55.686 | 1.00 | 18.97 | A | C |
| ATOM | 5394 | CG | PHE | 695 | 69.262 | 62.465 | 54.663 | 1.00 | 15.41 | A | C |
| ATOM | 5395 | CD1 | PHE | 695 | 68.980 | 63.804 | 54.394 | 1.00 | 16.20 | A | C |
| ATOM | 5396 | CD2 | PHE | 695 | 68.582 | 61.480 | 53.948 | 1.00 | 13.85 | A | C |
| ATOM | 5397 | CE1 | PHE | 695 | 68.033 | 64.160 | 53.419 | 1.00 | 15.80 | A | C |
| ATOM | 5398 | CE2 | PHE | 695 | 67.636 | 61.819 | 52.976 | 1.00 | 14.69 | A | C |
| ATOM | 5399 | CZ | PHE | 695 | 67.360 | 63.165 | 52.710 | 1.00 | 14.36 | A | C |
| ATOM | 5400 | C | PHE | 695 | 70.704 | 61.478 | 58.068 | 1.00 | 22.60 | A | C |
| ATOM | 5401 | O | PHE | 695 | 70.734 | 60.253 | 57.932 | 1.00 | 22.75 | A | O |
| ATOM | 5402 | N | LYS | 696 | 71.388 | 62.111 | 59.014 | 1.00 | 23.86 | A | N |
| ATOM | 5403 | CA | LYS | 696 | 72.189 | 61.369 | 59.980 | 1.00 | 24.30 | A | C |
| ATOM | 5404 | CB | LYS | 696 | 73.119 | 62.315 | 60.744 | 1.00 | 23.88 | A | C |
| ATOM | 5405 | CG | LYS | 696 | 74.230 | 62.883 | 59.891 | 1.00 | 27.19 | A | C |
| ATOM | 5406 | CD | LYS | 696 | 75.160 | 63.793 | 60.672 | 1.00 | 26.74 | A | C |
| ATOM | 5407 | CE | LYS | 696 | 76.354 | 64.211 | 59.816 | 1.00 | 26.44 | A | C |
| ATOM | 5408 | NZ | LYS | 696 | 77.248 | 65.163 | 60.534 | 1.00 | 28.88 | A | N |
| ATOM | 5409 | C | LYS | 696 | 71.256 | 60.670 | 60.962 | 1.00 | 24.58 | A | C |
| ATOM | 5410 | O | LYS | 696 | 71.673 | 59.790 | 61.710 | 1.00 | 24.47 | A | O |
| ATOM | 5411 | N | GLN | 697 | 69.986 | 61.060 | 60.949 | 1.00 | 24.66 | A | N |
| ATOM | 5412 | CA | GLN | 697 | 69.013 | 60.476 | 61.865 | 1.00 | 26.18 | A | C |
| ATOM | 5413 | CB | GLN | 697 | 68.072 | 61.571 | 62.385 | 1.00 | 28.53 | A | C |
| ATOM | 5414 | CG | GLN | 697 | 68.766 | 62.865 | 62.792 | 1.00 | 31.73 | A | C |
| ATOM | 5415 | CD | GLN | 697 | 67.790 | 63.938 | 63.262 | 1.00 | 34.90 | A | C |
| ATOM | 5416 | OE1 | GLN | 697 | 68.086 | 65.133 | 63.195 | 1.00 | 37.16 | A | O |
| ATOM | 5417 | NE2 | GLN | 697 | 66.627 | 63.516 | 63.753 | 1.00 | 36.42 | A | N |
| ATOM | 5418 | C | GLN | 697 | 68.176 | 59.346 | 61.259 | 1.00 | 24.79 | A | C |
| ATOM | 5419 | O | GLN | 697 | 67.294 | 58.808 | 61.923 | 1.00 | 27.00 | A | O |
| ATOM | 5420 | N | VAL | 698 | 68.439 | 58.979 | 60.011 | 1.00 | 21.46 | A | N |
| ATOM | 5421 | CA | VAL | 698 | 67.659 | 57.922 | 59.383 | 1.00 | 18.56 | A | C |
| ATOM | 5422 | CB | VAL | 698 | 66.510 | 58.517 | 58.524 | 1.00 | 19.77 | A | C |
| ATOM | 5423 | CG1 | VAL | 698 | 65.674 | 59.467 | 59.355 | 1.00 | 19.11 | A | C |
| ATOM | 5424 | CG2 | VAL | 698 | 67.077 | 59.233 | 57.296 | 1.00 | 15.74 | A | C |
| ATOM | 5425 | C | VAL | 698 | 68.469 | 56.987 | 58.484 | 1.00 | 18.57 | A | C |
| ATOM | 5426 | O | VAL | 698 | 69.614 | 57.265 | 58.135 | 1.00 | 17.50 | A | O |
| ATOM | 5427 | N | GLU | 699 | 67.850 | 55.868 | 58.121 | 1.00 | 18.32 | A | N |
| ATOM | 5428 | CA | GLU | 699 | 68.456 | 54.885 | 57.236 | 1.00 | 18.24 | A | C |
| ATOM | 5429 | CB | GLU | 699 | 68.007 | 53.488 | 57.636 | 1.00 | 19.38 | A | C |
| ATOM | 5430 | CG | GLU | 699 | 67.600 | 53.411 | 59.097 | 1.00 | 26.18 | A | C |
| ATOM | 5431 | CD | GLU | 699 | 68.384 | 52.377 | 59.891 | 1.00 | 29.91 | A | C |
| ATOM | 5432 | OE1 | GLU | 699 | 69.620 | 52.305 | 59.712 | 1.00 | 31.51 | A | O |
| ATOM | 5433 | OE2 | GLU | 699 | 67.765 | 51.651 | 60.703 | 1.00 | 30.28 | A | O |
| ATOM | 5434 | C | GLU | 699 | 67.857 | 55.286 | 55.891 | 1.00 | 17.20 | A | C |
| ATOM | 5435 | O | GLU | 699 | 66.638 | 55.397 | 55.765 | 1.00 | 16.35 | A | O |
| ATOM | 5436 | N | TYR | 700 | 68.714 | 55.516 | 54.899 | 1.00 | 15.53 | A | N |
| ATOM | 5437 | CA | TYR | 700 | 68.275 | 55.968 | 53.584 | 1.00 | 12.51 | A | C |
| ATOM | 5438 | CB | TYR | 700 | 68.810 | 57.383 | 53.365 | 1.00 | 12.28 | A | C |

| ATOM | 5439 | CG | TYR | 700 | 68.374 | 58.105 | 52.114 | 1.00 | 13.03 | A | C |
| ATOM | 5440 | CD1 | TYR | 700 | 67.027 | 58.171 | 51.746 | 1.00 | 12.78 | A | C |
| ATOM | 5441 | CE1 | TYR | 700 | 66.611 | 58.961 | 50.666 | 1.00 | 7.94 | A | C |
| ATOM | 5442 | CD2 | TYR | 700 | 69.301 | 58.840 | 51.359 | 1.00 | 12.91 | A | C |
| ATOM | 5443 | CE2 | TYR | 700 | 68.895 | 59.629 | 50.282 | 1.00 | 10.45 | A | C |
| ATOM | 5444 | CZ | TYR | 700 | 67.550 | 59.688 | 49.948 | 1.00 | 10.05 | A | C |
| ATOM | 5445 | OH | TYR | 700 | 67.150 | 60.495 | 48.913 | 1.00 | 8.37 | A | O |
| ATOM | 5446 | C | TYR | 700 | 68.743 | 55.056 | 52.468 | 1.00 | 11.71 | A | C |
| ATOM | 5447 | O | TYR | 700 | 69.881 | 54.594 | 52.463 | 1.00 | 10.84 | A | O |
| ATOM | 5448 | N | LEU | 701 | 67.836 | 54.775 | 51.540 | 1.00 | 11.32 | A | N |
| ATOM | 5449 | CA | LEU | 701 | 68.142 | 53.950 | 50.383 | 1.00 | 11.03 | A | C |
| ATOM | 5450 | CB | LEU | 701 | 67.313 | 52.667 | 50.378 | 1.00 | 8.96 | A | C |
| ATOM | 5451 | CG | LEU | 701 | 67.439 | 51.794 | 49.123 | 1.00 | 10.04 | A | C |
| ATOM | 5452 | CD1 | LEU | 701 | 68.841 | 51.873 | 48.511 | 1.00 | 7.25 | A | C |
| ATOM | 5453 | CD2 | LEU | 701 | 67.089 | 50.376 | 49.490 | 1.00 | 5.44 | A | C |
| ATOM | 5454 | C | LEU | 701 | 67.811 | 54.799 | 49.170 | 1.00 | 13.03 | A | C |
| ATOM | 5455 | O | LEU | 701 | 66.660 | 55.219 | 48.986 | 1.00 | 13.35 | A | O |
| ATOM | 5456 | N | LEU | 702 | 68.840 | 55.068 | 48.367 | 1.00 | 12.91 | A | N |
| ATOM | 5457 | CA | LEU | 702 | 68.724 | 55.888 | 47.169 | 1.00 | 11.74 | A | C |
| ATOM | 5458 | CB | LEU | 702 | 69.806 | 56.968 | 47.196 | 1.00 | 11.17 | A | C |
| ATOM | 5459 | CG | LEU | 702 | 69.916 | 57.965 | 46.044 | 1.00 | 12.13 | A | C |
| ATOM | 5460 | CD1 | LEU | 702 | 68.569 | 58.656 | 45.803 | 1.00 | 10.71 | A | C |
| ATOM | 5461 | CD2 | LEU | 702 | 71.006 | 58.981 | 46.368 | 1.00 | 10.37 | A | C |
| ATOM | 5462 | C | LEU | 702 | 68.883 | 55.003 | 45.942 | 1.00 | 13.49 | A | C |
| ATOM | 5463 | O | LEU | 702 | 69.854 | 54.251 | 45.832 | 1.00 | 14.04 | A | O |
| ATOM | 5464 | N | ILE | 703 | 67.935 | 55.111 | 45.016 | 1.00 | 13.82 | A | N |
| ATOM | 5465 | CA | ILE | 703 | 67.934 | 54.297 | 43.806 | 1.00 | 12.92 | A | C |
| ATOM | 5466 | CB | ILE | 703 | 66.931 | 53.152 | 43.964 | 1.00 | 12.98 | A | C |
| ATOM | 5467 | CG2 | ILE | 703 | 66.897 | 52.305 | 42.706 | 1.00 | 15.12 | A | C |
| ATOM | 5468 | CG1 | ILE | 703 | 67.299 | 52.322 | 45.196 | 1.00 | 13.52 | A | C |
| ATOM | 5469 | CD1 | ILE | 703 | 66.202 | 51.383 | 45.663 | 1.00 | 13.28 | A | C |
| ATOM | 5470 | C | ILE | 703 | 67.561 | 55.125 | 42.582 | 1.00 | 14.12 | A | C |
| ATOM | 5471 | O | ILE | 703 | 66.635 | 55.938 | 42.629 | 1.00 | 15.85 | A | O |
| ATOM | 5472 | N | HIS | 704 | 68.265 | 54.909 | 41.473 | 1.00 | 13.28 | A | N |
| ATOM | 5473 | CA | HIS | 704 | 67.987 | 55.678 | 40.265 | 1.00 | 11.81 | A | C |
| ATOM | 5474 | CB | HIS | 704 | 68.670 | 57.048 | 40.391 | 1.00 | 11.13 | A | C |
| ATOM | 5475 | CG | HIS | 704 | 67.968 | 58.156 | 39.667 | 1.00 | 11.66 | A | C |
| ATOM | 5476 | CD2 | HIS | 704 | 67.446 | 58.221 | 38.418 | 1.00 | 10.83 | A | C |
| ATOM | 5477 | ND1 | HIS | 704 | 67.736 | 59.387 | 40.244 | 1.00 | 10.07 | A | N |
| ATOM | 5478 | CE1 | HIS | 704 | 67.098 | 60.162 | 39.385 | 1.00 | 9.04 | A | C |
| ATOM | 5479 | NE2 | HIS | 704 | 66.910 | 59.479 | 38.270 | 1.00 | 11.23 | A | N |
| ATOM | 5480 | C | HIS | 704 | 68.464 | 54.965 | 38.992 | 1.00 | 11.87 | A | C |
| ATOM | 5481 | O | HIS | 704 | 69.503 | 54.306 | 38.980 | 1.00 | 11.87 | A | O |
| ATOM | 5482 | N | GLY | 705 | 67.684 | 55.082 | 37.926 | 1.00 | 11.49 | A | N |
| ATOM | 5483 | CA | GLY | 705 | 68.075 | 54.486 | 36.663 | 1.00 | 11.90 | A | C |
| ATOM | 5484 | C | GLY | 705 | 69.066 | 55.449 | 36.036 | 1.00 | 12.16 | A | C |
| ATOM | 5485 | O | GLY | 705 | 68.911 | 56.660 | 36.153 | 1.00 | 13.94 | A | O |
| ATOM | 5486 | N | THR | 706 | 70.086 | 54.928 | 35.372 | 1.00 | 13.29 | A | N |
| ATOM | 5487 | CA | THR | 706 | 71.101 | 55.782 | 34.770 | 1.00 | 12.51 | A | C |

FIG. 4-113 (Continued)

| ATOM | 5488 | CB | THR | 706 | 72.417 | 55.001 | 34.557 | 1.00 | 11.94 | A | C |
| --- | --- | --- | --- | --- | --- | --- | --- | --- | --- | --- | --- |
| ATOM | 5489 | OG1 | THR | 706 | 72.230 | 53.983 | 33.565 | 1.00 | 12.79 | A | O |
| ATOM | 5490 | CG2 | THR | 706 | 72.840 | 54.344 | 35.861 | 1.00 | 12.66 | A | C |
| ATOM | 5491 | C | THR | 706 | 70.678 | 56.409 | 33.455 | 1.00 | 13.02 | A | C |
| ATOM | 5492 | O | THR | 706 | 71.183 | 57.461 | 33.084 | 1.00 | 14.35 | A | O |
| ATOM | 5493 | N | ALA | 707 | 69.754 | 55.770 | 32.748 | 1.00 | 13.82 | A | N |
| ATOM | 5494 | CA | ALA | 707 | 69.289 | 56.302 | 31.469 | 1.00 | 15.26 | A | C |
| ATOM | 5495 | CB | ALA | 707 | 69.126 | 55.176 | 30.442 | 1.00 | 13.60 | A | C |
| ATOM | 5496 | C | ALA | 707 | 67.970 | 57.030 | 31.644 | 1.00 | 16.56 | A | C |
| ATOM | 5497 | O | ALA | 707 | 67.154 | 57.075 | 30.720 | 1.00 | 17.71 | A | O |
| ATOM | 5498 | N | ASP | 708 | 67.764 | 57.600 | 32.828 | 1.00 | 16.33 | A | N |
| ATOM | 5499 | CA | ASP | 708 | 66.534 | 58.314 | 33.113 | 1.00 | 16.71 | A | C |
| ATOM | 5500 | CB | ASP | 708 | 66.376 | 58.508 | 34.614 | 1.00 | 18.25 | A | C |
| ATOM | 5501 | CG | ASP | 708 | 64.957 | 58.834 | 35.000 | 1.00 | 19.59 | A | C |
| ATOM | 5502 | OD1 | ASP | 708 | 64.304 | 59.612 | 34.266 | 1.00 | 18.82 | A | O |
| ATOM | 5503 | OD2 | ASP | 708 | 64.498 | 58.317 | 36.038 | 1.00 | 19.68 | A | O |
| ATOM | 5504 | C | ASP | 708 | 66.490 | 59.673 | 32.408 | 1.00 | 17.30 | A | C |
| ATOM | 5505 | O | ASP | 708 | 67.131 | 60.647 | 32.843 | 1.00 | 18.75 | A | O |
| ATOM | 5506 | N | ASP | 709 | 65.715 | 59.722 | 31.327 | 1.00 | 13.98 | A | N |
| ATOM | 5507 | CA | ASP | 709 | 65.553 | 60.913 | 30.509 | 1.00 | 13.26 | A | C |
| ATOM | 5508 | CB | ASP | 709 | 65.028 | 60.503 | 29.137 | 1.00 | 11.83 | A | C |
| ATOM | 5509 | CG | ASP | 709 | 63.700 | 59.778 | 29.228 | 1.00 | 13.61 | A | C |
| ATOM | 5510 | OD1 | ASP | 709 | 62.648 | 60.402 | 28.958 | 1.00 | 12.39 | A | O |
| ATOM | 5511 | OD2 | ASP | 709 | 63.706 | 58.584 | 29.593 | 1.00 | 10.85 | A | O |
| ATOM | 5512 | C | ASP | 709 | 64.603 | 61.934 | 31.129 | 1.00 | 13.44 | A | C |
| ATOM | 5513 | O | ASP | 709 | 64.649 | 63.112 | 30.786 | 1.00 | 14.33 | A | O |
| ATOM | 5514 | N | ASN | 710 | 63.743 | 61.473 | 32.034 | 1.00 | 12.40 | A | N |
| ATOM | 5515 | CA | ASN | 710 | 62.761 | 62.331 | 32.702 | 1.00 | 11.63 | A | C |
| ATOM | 5516 | CB | ASN | 710 | 61.566 | 61.469 | 33.094 | 1.00 | 10.91 | A | C |
| ATOM | 5517 | CG | ASN | 710 | 60.388 | 62.276 | 33.572 | 1.00 | 12.77 | A | C |
| ATOM | 5518 | OD1 | ASN | 710 | 59.271 | 61.760 | 33.651 | 1.00 | 14.18 | A | O |
| ATOM | 5519 | ND2 | ASN | 710 | 60.621 | 63.539 | 33.903 | 1.00 | 12.05 | A | N |
| ATOM | 5520 | C | ASN | 710 | 63.395 | 63.010 | 33.938 | 1.00 | 13.10 | A | C |
| ATOM | 5521 | O | ASN | 710 | 63.691 | 64.211 | 33.912 | 1.00 | 12.53 | A | O |
| ATOM | 5522 | N | VAL | 711 | 63.570 | 62.246 | 35.017 | 1.00 | 11.10 | A | N |
| ATOM | 5523 | CA | VAL | 711 | 64.221 | 62.741 | 36.225 | 1.00 | 9.96 | A | C |
| ATOM | 5524 | CB | VAL | 711 | 63.620 | 62.128 | 37.512 | 1.00 | 9.85 | A | C |
| ATOM | 5525 | CG1 | VAL | 711 | 64.415 | 62.570 | 38.719 | 1.00 | 7.61 | A | C |
| ATOM | 5526 | CG2 | VAL | 711 | 62.176 | 62.567 | 37.675 | 1.00 | 11.26 | A | C |
| ATOM | 5527 | C | VAL | 711 | 65.645 | 62.237 | 36.038 | 1.00 | 10.48 | A | C |
| ATOM | 5528 | O | VAL | 711 | 65.949 | 61.068 | 36.280 | 1.00 | 10.00 | A | O |
| ATOM | 5529 | N | HIS | 712 | 66.518 | 63.126 | 35.591 | 1.00 | 10.94 | A | N |
| ATOM | 5530 | CA | HIS | 712 | 67.899 | 62.758 | 35.302 | 1.00 | 11.74 | A | C |
| ATOM | 5531 | CB | HIS | 712 | 68.577 | 63.961 | 34.646 | 1.00 | 10.79 | A | C |
| ATOM | 5532 | CG | HIS | 712 | 67.782 | 64.529 | 33.514 | 1.00 | 11.58 | A | C |
| ATOM | 5533 | CD2 | HIS | 712 | 66.855 | 63.955 | 32.705 | 1.00 | 12.39 | A | C |
| ATOM | 5534 | ND1 | HIS | 712 | 67.833 | 65.858 | 33.154 | 1.00 | 11.87 | A | N |
| ATOM | 5535 | CE1 | HIS | 712 | 66.966 | 66.082 | 32.181 | 1.00 | 12.19 | A | C |
| ATOM | 5536 | NE2 | HIS | 712 | 66.359 | 64.944 | 31.891 | 1.00 | 11.62 | A | N |

| ATOM | 5537 | C | HIS | 712 | 68.698 | 62.222 | 36.491 | 1.00 | 10.63 | A | C |
|---|---|---|---|---|---|---|---|---|---|---|---|
| ATOM | 5538 | O | HIS | 712 | 68.461 | 62.598 | 37.633 | 1.00 | 11.98 | A | O |
| ATOM | 5539 | N | PHE | 713 | 69.631 | 61.319 | 36.210 | 1.00 | 10.82 | A | N |
| ATOM | 5540 | CA | PHE | 713 | 70.458 | 60.720 | 37.251 | 1.00 | 11.00 | A | C |
| ATOM | 5541 | CB | PHE | 713 | 71.533 | 59.823 | 36.634 | 1.00 | 11.14 | A | C |
| ATOM | 5542 | CG | PHE | 713 | 72.270 | 58.989 | 37.639 | 1.00 | 11.47 | A | C |
| ATOM | 5543 | CD1 | PHE | 713 | 71.714 | 57.813 | 38.126 | 1.00 | 11.22 | A | C |
| ATOM | 5544 | CD2 | PHE | 713 | 73.496 | 59.407 | 38.144 | 1.00 | 11.84 | A | C |
| ATOM | 5545 | CE1 | PHE | 713 | 72.367 | 57.066 | 39.109 | 1.00 | 11.98 | A | C |
| ATOM | 5546 | CE2 | PHE | 713 | 74.153 | 58.667 | 39.126 | 1.00 | 13.82 | A | C |
| ATOM | 5547 | CZ | PHE | 713 | 73.586 | 57.495 | 39.610 | 1.00 | 11.04 | A | C |
| ATOM | 5548 | C | PHE | 713 | 71.122 | 61.818 | 38.061 | 1.00 | 11.85 | A | C |
| ATOM | 5549 | O | PHE | 713 | 71.404 | 61.640 | 39.243 | 1.00 | 13.14 | A | O |
| ATOM | 5550 | N | GLN | 714 | 71.377 | 62.948 | 37.403 | 1.00 | 12.47 | A | N |
| ATOM | 5551 | CA | GLN | 714 | 72.001 | 64.113 | 38.022 | 1.00 | 10.55 | A | C |
| ATOM | 5552 | CB | GLN | 714 | 71.851 | 65.321 | 37.082 | 1.00 | 11.91 | A | C |
| ATOM | 5553 | CG | GLN | 714 | 72.055 | 66.695 | 37.740 | 1.00 | 10.69 | A | C |
| ATOM | 5554 | CD | GLN | 714 | 71.501 | 67.827 | 36.891 | 1.00 | 9.77 | A | C |
| ATOM | 5555 | OE1 | GLN | 714 | 70.447 | 67.693 | 36.268 | 1.00 | 10.50 | A | O |
| ATOM | 5556 | NE2 | GLN | 714 | 72.201 | 68.948 | 36.870 | 1.00 | 9.43 | A | N |
| ATOM | 5557 | C | GLN | 714 | 71.355 | 64.417 | 39.368 | 1.00 | 9.91 | A | C |
| ATOM | 5558 | O | GLN | 714 | 72.037 | 64.700 | 40.356 | 1.00 | 8.86 | A | O |
| ATOM | 5559 | N | GLN | 715 | 70.029 | 64.340 | 39.395 | 1.00 | 10.27 | A | N |
| ATOM | 5560 | CA | GLN | 715 | 69.255 | 64.616 | 40.599 | 1.00 | 10.62 | A | C |
| ATOM | 5561 | CB | GLN | 715 | 67.771 | 64.393 | 40.315 | 1.00 | 10.98 | A | C |
| ATOM | 5562 | CG | GLN | 715 | 67.267 | 65.219 | 39.144 | 1.00 | 11.10 | A | C |
| ATOM | 5563 | CD | GLN | 715 | 66.285 | 66.288 | 39.567 | 1.00 | 14.59 | A | C |
| ATOM | 5564 | OE1 | GLN | 715 | 66.381 | 66.828 | 40.671 | 1.00 | 16.72 | A | O |
| ATOM | 5565 | NE2 | GLN | 715 | 65.336 | 66.613 | 38.685 | 1.00 | 12.90 | A | N |
| ATOM | 5566 | C | GLN | 715 | 69.716 | 63.781 | 41.780 | 1.00 | 10.65 | A | C |
| ATOM | 5567 | O | GLN | 715 | 69.976 | 64.322 | 42.853 | 1.00 | 12.32 | A | O |
| ATOM | 5568 | N | SER | 716 | 69.828 | 62.472 | 41.600 | 1.00 | 9.91 | A | N |
| ATOM | 5569 | CA | SER | 716 | 70.299 | 61.630 | 42.700 | 1.00 | 12.35 | A | C |
| ATOM | 5570 | CB | SER | 716 | 69.937 | 60.163 | 42.461 | 1.00 | 10.77 | A | C |
| ATOM | 5571 | OG | SER | 716 | 68.541 | 59.994 | 42.492 | 1.00 | 14.60 | A | O |
| ATOM | 5572 | C | SER | 716 | 71.818 | 61.761 | 42.876 | 1.00 | 13.46 | A | C |
| ATOM | 5573 | O | SER | 716 | 72.341 | 61.556 | 43.976 | 1.00 | 14.90 | A | O |
| ATOM | 5574 | N | ALA | 717 | 72.522 | 62.094 | 41.797 | 1.00 | 12.22 | A | N |
| ATOM | 5575 | CA | ALA | 717 | 73.969 | 62.252 | 41.870 | 1.00 | 13.92 | A | C |
| ATOM | 5576 | CB | ALA | 717 | 74.555 | 62.487 | 40.479 | 1.00 | 12.46 | A | C |
| ATOM | 5577 | C | ALA | 717 | 74.299 | 63.423 | 42.790 | 1.00 | 13.73 | A | C |
| ATOM | 5578 | O | ALA | 717 | 75.257 | 63.375 | 43.560 | 1.00 | 15.24 | A | O |
| ATOM | 5579 | N | GLN | 718 | 73.504 | 64.482 | 42.710 | 1.00 | 13.27 | A | N |
| ATOM | 5580 | CA | GLN | 718 | 73.738 | 65.631 | 43.565 | 1.00 | 13.07 | A | C |
| ATOM | 5581 | CB | GLN | 718 | 72.976 | 66.841 | 43.035 | 1.00 | 13.93 | A | C |
| ATOM | 5582 | CG | GLN | 718 | 73.548 | 67.422 | 41.734 | 1.00 | 15.44 | A | C |
| ATOM | 5583 | CD | GLN | 718 | 74.996 | 67.865 | 41.867 | 1.00 | 13.84 | A | C |
| ATOM | 5584 | OE1 | GLN | 718 | 75.467 | 68.172 | 42.950 | 1.00 | 16.85 | A | O |
| ATOM | 5585 | NE2 | GLN | 718 | 75.699 | 67.915 | 40.755 | 1.00 | 17.86 | A | N |

FIG. 4-115 (Continued)

| | | | | | | | | | | |
|---|---|---|---|---|---|---|---|---|---|---|
| ATOM | 5586 | C | GLN | 718 | 73.350 | 65.343 | 45.026 | 1.00 | 13.24 | A C |
| ATOM | 5587 | O | GLN | 718 | 73.941 | 65.910 | 45.949 | 1.00 | 11.74 | A O |
| ATOM | 5588 | N | ILE | 719 | 72.370 | 64.460 | 45.237 | 1.00 | 12.01 | A N |
| ATOM | 5589 | CA | ILE | 719 | 71.956 | 64.110 | 46.594 | 1.00 | 11.94 | A C |
| ATOM | 5590 | CB | ILE | 719 | 70.691 | 63.201 | 46.616 | 1.00 | 12.50 | A C |
| ATOM | 5591 | CG2 | ILE | 719 | 70.464 | 62.673 | 48.021 | 1.00 | 11.09 | A C |
| ATOM | 5592 | CG1 | ILE | 719 | 69.447 | 63.979 | 46.174 | 1.00 | 14.37 | A C |
| ATOM | 5593 | CD1 | ILE | 719 | 68.170 | 63.143 | 46.154 | 1.00 | 8.64 | A C |
| ATOM | 5594 | C | ILE | 719 | 73.081 | 63.338 | 47.282 | 1.00 | 11.72 | A C |
| ATOM | 5595 | O | ILE | 719 | 73.543 | 63.703 | 48.367 | 1.00 | 10.69 | A O |
| ATOM | 5596 | N | SER | 720 | 73.508 | 62.262 | 46.632 | 1.00 | 11.35 | A N |
| ATOM | 5597 | CA | SER | 720 | 74.557 | 61.405 | 47.155 | 1.00 | 11.02 | A C |
| ATOM | 5598 | CB | SER | 720 | 74.901 | 60.325 | 46.135 | 1.00 | 10.89 | A C |
| ATOM | 5599 | OG | SER | 720 | 75.471 | 60.894 | 44.970 | 1.00 | 13.75 | A O |
| ATOM | 5600 | C | SER | 720 | 75.804 | 62.207 | 47.488 | 1.00 | 12.63 | A C |
| ATOM | 5601 | O | SER | 720 | 76.429 | 61.995 | 48.537 | 1.00 | 11.68 | A O |
| ATOM | 5602 | N | LYS | 721 | 76.159 | 63.129 | 46.594 | 1.00 | 12.18 | A N |
| ATOM | 5603 | CA | LYS | 721 | 77.336 | 63.951 | 46.800 | 1.00 | 12.15 | A C |
| ATOM | 5604 | CB | LYS | 721 | 77.613 | 64.823 | 45.571 | 1.00 | 11.24 | A C |
| ATOM | 5605 | CG | LYS | 721 | 78.764 | 65.796 | 45.756 | 1.00 | 7.41 | A C |
| ATOM | 5606 | CD | LYS | 721 | 79.517 | 66.064 | 44.451 | 1.00 | 9.30 | A C |
| ATOM | 5607 | CE | LYS | 721 | 78.674 | 66.765 | 43.392 | 1.00 | 8.74 | A C |
| ATOM | 5608 | NZ | LYS | 721 | 78.341 | 68.165 | 43.739 | 1.00 | 9.54 | A N |
| ATOM | 5609 | C | LYS | 721 | 77.190 | 64.816 | 48.038 | 1.00 | 13.24 | A C |
| ATOM | 5610 | O | LYS | 721 | 78.150 | 64.982 | 48.791 | 1.00 | 14.49 | A O |
| ATOM | 5611 | N | ALA | 722 | 75.992 | 65.351 | 48.262 | 1.00 | 13.05 | A N |
| ATOM | 5612 | CA | ALA | 722 | 75.760 | 66.198 | 49.432 | 1.00 | 13.21 | A C |
| ATOM | 5613 | CB | ALA | 722 | 74.389 | 66.870 | 49.353 | 1.00 | 9.37 | A C |
| ATOM | 5614 | C | ALA | 722 | 75.874 | 65.369 | 50.702 | 1.00 | 14.04 | A C |
| ATOM | 5615 | O | ALA | 722 | 76.430 | 65.826 | 51.694 | 1.00 | 15.43 | A O |
| ATOM | 5616 | N | LEU | 723 | 75.360 | 64.145 | 50.665 | 1.00 | 14.96 | A N |
| ATOM | 5617 | CA | LEU | 723 | 75.429 | 63.266 | 51.826 | 1.00 | 17.23 | A C |
| ATOM | 5618 | CB | LEU | 723 | 74.626 | 61.984 | 51.570 | 1.00 | 16.86 | A C |
| ATOM | 5619 | CG | LEU | 723 | 73.116 | 62.205 | 51.463 | 1.00 | 18.78 | A C |
| ATOM | 5620 | CD1 | LEU | 723 | 72.428 | 60.932 | 50.991 | 1.00 | 18.74 | A C |
| ATOM | 5621 | CD2 | LEU | 723 | 72.576 | 62.663 | 52.817 | 1.00 | 16.86 | A C |
| ATOM | 5622 | C | LEU | 723 | 76.889 | 62.926 | 52.134 | 1.00 | 17.26 | A C |
| ATOM | 5623 | O | LEU | 723 | 77.320 | 62.990 | 53.280 | 1.00 | 18.48 | A O |
| ATOM | 5624 | N | VAL | 724 | 77.641 | 62.559 | 51.103 | 1.00 | 17.41 | A N |
| ATOM | 5625 | CA | VAL | 724 | 79.050 | 62.234 | 51.257 | 1.00 | 16.64 | A C |
| ATOM | 5626 | CB | VAL | 724 | 79.671 | 61.824 | 49.902 | 1.00 | 14.31 | A C |
| ATOM | 5627 | CG1 | VAL | 724 | 81.187 | 61.819 | 49.987 | 1.00 | 13.56 | A C |
| ATOM | 5628 | CG2 | VAL | 724 | 79.178 | 60.449 | 49.519 | 1.00 | 14.78 | A C |
| ATOM | 5629 | C | VAL | 724 | 79.785 | 63.455 | 51.803 | 1.00 | 18.83 | A C |
| ATOM | 5630 | O | VAL | 724 | 80.665 | 63.337 | 52.662 | 1.00 | 19.09 | A O |
| ATOM | 5631 | N | ASP | 725 | 79.411 | 64.632 | 51.318 | 1.00 | 19.19 | A N |
| ATOM | 5632 | CA | ASP | 725 | 80.051 | 65.848 | 51.776 | 1.00 | 20.26 | A C |
| ATOM | 5633 | CB | ASP | 725 | 79.627 | 67.032 | 50.919 | 1.00 | 22.40 | A C |
| ATOM | 5634 | CG | ASP | 725 | 80.259 | 67.004 | 49.549 | 1.00 | 26.44 | A C |

| | | | | | | | | | | |
|---|---|---|---|---|---|---|---|---|---|---|
| ATOM | 5635 | OD1 | ASP | 725 | 81.149 | 66.151 | 49.319 | 1.00 | 26.28 | A | O |
| ATOM | 5636 | OD2 | ASP | 725 | 79.867 | 67.839 | 48.704 | 1.00 | 30.70 | A | O |
| ATOM | 5637 | C | ASP | 725 | 79.805 | 66.171 | 53.238 | 1.00 | 19.86 | A | C |
| ATOM | 5638 | O | ASP | 725 | 80.486 | 67.024 | 53.792 | 1.00 | 23.33 | A | O |
| ATOM | 5639 | N | VAL | 726 | 78.841 | 65.516 | 53.873 | 1.00 | 17.95 | A | N |
| ATOM | 5640 | CA | VAL | 726 | 78.603 | 65.790 | 55.285 | 1.00 | 17.97 | A | C |
| ATOM | 5641 | CB | VAL | 726 | 77.178 | 66.341 | 55.567 | 1.00 | 18.54 | A | C |
| ATOM | 5642 | CG1 | VAL | 726 | 76.992 | 67.680 | 54.875 | 1.00 | 16.64 | A | C |
| ATOM | 5643 | CG2 | VAL | 726 | 76.121 | 65.339 | 55.120 | 1.00 | 18.24 | A | C |
| ATOM | 5644 | C | VAL | 726 | 78.812 | 64.549 | 56.124 | 1.00 | 17.82 | A | C |
| ATOM | 5645 | O | VAL | 726 | 78.412 | 64.504 | 57.283 | 1.00 | 19.86 | A | O |
| ATOM | 5646 | N | GLY | 727 | 79.439 | 63.541 | 55.535 | 1.00 | 17.13 | A | N |
| ATOM | 5647 | CA | GLY | 727 | 79.711 | 62.317 | 56.263 | 1.00 | 16.84 | A | C |
| ATOM | 5648 | C | GLY | 727 | 78.509 | 61.489 | 56.681 | 1.00 | 17.94 | A | C |
| ATOM | 5649 | O | GLY | 727 | 78.483 | 60.961 | 57.794 | 1.00 | 19.74 | A | O |
| ATOM | 5650 | N | VAL | 728 | 77.517 | 61.371 | 55.802 | 1.00 | 16.62 | A | N |
| ATOM | 5651 | CA | VAL | 728 | 76.331 | 60.571 | 56.085 | 1.00 | 17.26 | A | C |
| ATOM | 5652 | CB | VAL | 728 | 75.030 | 61.302 | 55.643 | 1.00 | 18.46 | A | C |
| ATOM | 5653 | CG1 | VAL | 728 | 73.838 | 60.338 | 55.668 | 1.00 | 16.22 | A | C |
| ATOM | 5654 | CG2 | VAL | 728 | 74.753 | 62.476 | 56.579 | 1.00 | 18.70 | A | C |
| ATOM | 5655 | C | VAL | 728 | 76.411 | 59.230 | 55.347 | 1.00 | 18.03 | A | C |
| ATOM | 5656 | O | VAL | 728 | 76.667 | 59.186 | 54.143 | 1.00 | 18.40 | A | O |
| ATOM | 5657 | N | ASP | 729 | 76.211 | 58.135 | 56.069 | 1.00 | 18.22 | A | N |
| ATOM | 5658 | CA | ASP | 729 | 76.246 | 56.822 | 55.441 | 1.00 | 19.90 | A | C |
| ATOM | 5659 | CB | ASP | 729 | 76.734 | 55.752 | 56.420 | 1.00 | 22.57 | A | C |
| ATOM | 5660 | CG | ASP | 729 | 76.819 | 54.376 | 55.778 | 1.00 | 25.97 | A | C |
| ATOM | 5661 | OD1 | ASP | 729 | 77.340 | 54.278 | 54.649 | 1.00 | 27.13 | A | O |
| ATOM | 5662 | OD2 | ASP | 729 | 76.372 | 53.388 | 56.398 | 1.00 | 30.03 | A | O |
| ATOM | 5663 | C | ASP | 729 | 74.839 | 56.504 | 54.984 | 1.00 | 19.16 | A | C |
| ATOM | 5664 | O | ASP | 729 | 73.868 | 56.863 | 55.649 | 1.00 | 21.91 | A | O |
| ATOM | 5665 | N | PHE | 730 | 74.723 | 55.838 | 53.846 | 1.00 | 18.27 | A | N |
| ATOM | 5666 | CA | PHE | 730 | 73.416 | 55.499 | 53.299 | 1.00 | 16.06 | A | C |
| ATOM | 5667 | CB | PHE | 730 | 72.796 | 56.734 | 52.639 | 1.00 | 14.49 | A | C |
| ATOM | 5668 | CG | PHE | 730 | 73.590 | 57.265 | 51.480 | 1.00 | 12.02 | A | C |
| ATOM | 5669 | CD1 | PHE | 730 | 73.262 | 56.913 | 50.177 | 1.00 | 10.26 | A | C |
| ATOM | 5670 | CD2 | PHE | 730 | 74.691 | 58.082 | 51.694 | 1.00 | 11.55 | A | C |
| ATOM | 5671 | CE1 | PHE | 730 | 74.020 | 57.364 | 49.098 | 1.00 | 10.41 | A | C |
| ATOM | 5672 | CE2 | PHE | 730 | 75.459 | 58.537 | 50.621 | 1.00 | 13.40 | A | C |
| ATOM | 5673 | CZ | PHE | 730 | 75.120 | 58.175 | 49.317 | 1.00 | 9.85 | A | C |
| ATOM | 5674 | C | PHE | 730 | 73.565 | 54.388 | 52.281 | 1.00 | 16.20 | A | C |
| ATOM | 5675 | O | PHE | 730 | 74.675 | 53.990 | 51.945 | 1.00 | 18.49 | A | O |
| ATOM | 5676 | N | GLN | 731 | 72.447 | 53.883 | 51.791 | 1.00 | 17.40 | A | N |
| ATOM | 5677 | CA | GLN | 731 | 72.484 | 52.813 | 50.813 | 1.00 | 17.82 | A | C |
| ATOM | 5678 | CB | GLN | 731 | 71.514 | 51.708 | 51.208 | 1.00 | 20.04 | A | C |
| ATOM | 5679 | CG | GLN | 731 | 71.641 | 51.257 | 52.644 | 1.00 | 25.37 | A | C |
| ATOM | 5680 | CD | GLN | 731 | 73.019 | 50.737 | 52.968 | 1.00 | 28.25 | A | C |
| ATOM | 5681 | OE1 | GLN | 731 | 73.554 | 49.883 | 52.256 | 1.00 | 32.85 | A | O |
| ATOM | 5682 | NE2 | GLN | 731 | 73.603 | 51.238 | 54.055 | 1.00 | 30.12 | A | N |
| ATOM | 5683 | C | GLN | 731 | 72.091 | 53.382 | 49.458 | 1.00 | 17.65 | A | C |

FIG. 4-117 (Continued)

| | | | | | | | | | | |
|---|---|---|---|---|---|---|---|---|---|---|
| ATOM | 5684 | O | GLN | 731 | 71.160 | 54.191 | 49.355 | 1.00 | 17.02 | A O |
| ATOM | 5685 | N | ALA | 732 | 72.802 | 52.962 | 48.421 | 1.00 | 14.78 | A N |
| ATOM | 5686 | CA | ALA | 732 | 72.510 | 53.444 | 47.088 | 1.00 | 15.21 | A C |
| ATOM | 5687 | CB | ALA | 732 | 73.588 | 54.409 | 46.626 | 1.00 | 15.17 | A C |
| ATOM | 5688 | C | ALA | 732 | 72.419 | 52.282 | 46.131 | 1.00 | 15.21 | A C |
| ATOM | 5689 | O | ALA | 732 | 72.940 | 51.207 | 46.396 | 1.00 | 16.17 | A O |
| ATOM | 5690 | N | MET | 733 | 71.737 | 52.504 | 45.019 | 1.00 | 14.57 | A N |
| ATOM | 5691 | CA | MET | 733 | 71.599 | 51.483 | 44.008 | 1.00 | 14.86 | A C |
| ATOM | 5692 | CB | MET | 733 | 70.490 | 50.499 | 44.383 | 1.00 | 15.14 | A C |
| ATOM | 5693 | CG | MET | 733 | 70.288 | 49.386 | 43.353 | 1.00 | 18.04 | A C |
| ATOM | 5694 | SD | MET | 733 | 71.814 | 48.476 | 42.961 | 1.00 | 22.04 | A S |
| ATOM | 5695 | CE | MET | 733 | 71.892 | 47.307 | 44.310 | 1.00 | 17.75 | A C |
| ATOM | 5696 | C | MET | 733 | 71.283 | 52.153 | 42.683 | 1.00 | 14.93 | A C |
| ATOM | 5697 | O | MET | 733 | 70.317 | 52.915 | 42.574 | 1.00 | 13.98 | A O |
| ATOM | 5698 | N | TRP | 734 | 72.113 | 51.884 | 41.680 | 1.00 | 13.82 | A N |
| ATOM | 5699 | CA | TRP | 734 | 71.890 | 52.447 | 40.356 | 1.00 | 13.13 | A C |
| ATOM | 5700 | CB | TRP | 734 | 73.173 | 53.117 | 39.827 | 1.00 | 10.39 | A C |
| ATOM | 5701 | CG | TRP | 734 | 74.187 | 52.159 | 39.267 | 1.00 | 8.77 | A C |
| ATOM | 5702 | CD2 | TRP | 734 | 75.398 | 51.726 | 39.894 | 1.00 | 7.74 | A C |
| ATOM | 5703 | CE2 | TRP | 734 | 75.984 | 50.757 | 39.053 | 1.00 | 9.97 | A C |
| ATOM | 5704 | CE3 | TRP | 734 | 76.045 | 52.062 | 41.087 | 1.00 | 8.70 | A C |
| ATOM | 5705 | CD1 | TRP | 734 | 74.095 | 51.463 | 38.095 | 1.00 | 10.56 | A C |
| ATOM | 5706 | NE1 | TRP | 734 | 75.170 | 50.613 | 37.961 | 1.00 | 12.87 | A N |
| ATOM | 5707 | CZ2 | TRP | 734 | 77.183 | 50.119 | 39.369 | 1.00 | 9.94 | A C |
| ATOM | 5708 | CZ3 | TRP | 734 | 77.238 | 51.428 | 41.400 | 1.00 | 9.32 | A C |
| ATOM | 5709 | CH2 | TRP | 734 | 77.793 | 50.468 | 40.545 | 1.00 | 9.49 | A C |
| ATOM | 5710 | C | TRP | 734 | 71.480 | 51.291 | 39.445 | 1.00 | 14.06 | A C |
| ATOM | 5711 | O | TRP | 734 | 71.903 | 50.155 | 39.653 | 1.00 | 13.91 | A O |
| ATOM | 5712 | N | TYR | 735 | 70.635 | 51.570 | 38.461 | 1.00 | 15.15 | A N |
| ATOM | 5713 | CA | TYR | 735 | 70.223 | 50.544 | 37.504 | 1.00 | 15.51 | A C |
| ATOM | 5714 | CB | TYR | 735 | 68.705 | 50.326 | 37.556 | 1.00 | 14.10 | A C |
| ATOM | 5715 | CG | TYR | 735 | 68.300 | 49.439 | 38.709 | 1.00 | 14.76 | A C |
| ATOM | 5716 | CD1 | TYR | 735 | 68.619 | 48.081 | 38.708 | 1.00 | 14.45 | A C |
| ATOM | 5717 | CE1 | TYR | 735 | 68.360 | 47.278 | 39.816 | 1.00 | 14.33 | A C |
| ATOM | 5718 | CD2 | TYR | 735 | 67.696 | 49.971 | 39.848 | 1.00 | 15.84 | A C |
| ATOM | 5719 | CE2 | TYR | 735 | 67.432 | 49.180 | 40.960 | 1.00 | 14.52 | A C |
| ATOM | 5720 | CZ | TYR | 735 | 67.772 | 47.835 | 40.938 | 1.00 | 16.33 | A C |
| ATOM | 5721 | OH | TYR | 735 | 67.547 | 47.056 | 42.048 | 1.00 | 17.53 | A O |
| ATOM | 5722 | C | TYR | 735 | 70.685 | 50.966 | 36.104 | 1.00 | 16.31 | A C |
| ATOM | 5723 | O | TYR | 735 | 70.103 | 51.858 | 35.466 | 1.00 | 15.82 | A O |
| ATOM | 5724 | N | THR | 736 | 71.763 | 50.330 | 35.654 | 1.00 | 15.44 | A N |
| ATOM | 5725 | CA | THR | 736 | 72.361 | 50.608 | 34.353 | 1.00 | 15.13 | A C |
| ATOM | 5726 | CB | THR | 736 | 73.491 | 49.602 | 34.030 | 1.00 | 14.68 | A C |
| ATOM | 5727 | OG1 | THR | 736 | 74.470 | 49.614 | 35.076 | 1.00 | 15.48 | A O |
| ATOM | 5728 | CG2 | THR | 736 | 74.156 | 49.961 | 32.713 | 1.00 | 14.72 | A C |
| ATOM | 5729 | C | THR | 736 | 71.365 | 50.549 | 33.206 | 1.00 | 15.41 | A C |
| ATOM | 5730 | O | THR | 736 | 70.650 | 49.560 | 33.044 | 1.00 | 16.44 | A O |
| ATOM | 5731 | N | ASP | 737 | 71.335 | 51.614 | 32.414 | 1.00 | 15.92 | A N |
| ATOM | 5732 | CA | ASP | 737 | 70.475 | 51.719 | 31.238 | 1.00 | 16.48 | A C |

FIG. 4-118

| | | | | | | | | | | |
|---|---|---|---|---|---|---|---|---|---|---|
| ATOM | 5733 | CB | ASP | 737 | 70.884 | 50.677 | 30.200 | 1.00 | 15.90 | A C |
| ATOM | 5734 | CG | ASP | 737 | 72.232 | 50.972 | 29.574 | 1.00 | 20.37 | A C |
| ATOM | 5735 | OD1 | ASP | 737 | 72.679 | 50.147 | 28.747 | 1.00 | 24.29 | A O |
| ATOM | 5736 | OD2 | ASP | 737 | 72.847 | 52.020 | 29.895 | 1.00 | 18.74 | A O |
| ATOM | 5737 | C | ASP | 737 | 68.974 | 51.632 | 31.467 | 1.00 | 17.71 | A C |
| ATOM | 5738 | O | ASP | 737 | 68.205 | 51.507 | 30.515 | 1.00 | 18.86 | A O |
| ATOM | 5739 | N | GLU | 738 | 68.553 | 51.692 | 32.722 | 1.00 | 18.39 | A N |
| ATOM | 5740 | CA | GLU | 738 | 67.135 | 51.644 | 33.033 | 1.00 | 19.00 | A C |
| ATOM | 5741 | CB | GLU | 738 | 66.909 | 50.999 | 34.407 | 1.00 | 20.24 | A C |
| ATOM | 5742 | CG | GLU | 738 | 66.904 | 49.485 | 34.380 | 1.00 | 20.93 | A C |
| ATOM | 5743 | CD | GLU | 738 | 65.741 | 48.937 | 33.565 | 1.00 | 24.58 | A C |
| ATOM | 5744 | OE1 | GLU | 738 | 64.588 | 49.289 | 33.878 | 1.00 | 27.21 | A O |
| ATOM | 5745 | OE2 | GLU | 738 | 65.970 | 48.163 | 32.611 | 1.00 | 26.16 | A O |
| ATOM | 5746 | C | GLU | 738 | 66.624 | 53.076 | 33.025 | 1.00 | 19.38 | A C |
| ATOM | 5747 | O | GLU | 738 | 67.327 | 53.991 | 33.461 | 1.00 | 20.83 | A O |
| ATOM | 5748 | N | ASP | 739 | 65.414 | 53.288 | 32.525 | 1.00 | 18.55 | A N |
| ATOM | 5749 | CA | ASP | 739 | 64.892 | 54.642 | 32.493 | 1.00 | 17.49 | A C |
| ATOM | 5750 | CB | ASP | 739 | 64.074 | 54.863 | 31.222 | 1.00 | 18.32 | A C |
| ATOM | 5751 | CG | ASP | 739 | 62.689 | 54.271 | 31.293 | 1.00 | 21.44 | A C |
| ATOM | 5752 | OD1 | ASP | 739 | 61.995 | 54.340 | 30.257 | 1.00 | 24.73 | A O |
| ATOM | 5753 | OD2 | ASP | 739 | 62.285 | 53.752 | 32.358 | 1.00 | 21.35 | A O |
| ATOM | 5754 | C | ASP | 739 | 64.088 | 54.976 | 33.750 | 1.00 | 17.35 | A C |
| ATOM | 5755 | O | ASP | 739 | 64.191 | 54.282 | 34.762 | 1.00 | 15.74 | A O |
| ATOM | 5756 | N | HIS | 740 | 63.291 | 56.034 | 33.687 | 1.00 | 16.96 | A N |
| ATOM | 5757 | CA | HIS | 740 | 62.521 | 56.469 | 34.842 | 1.00 | 18.24 | A C |
| ATOM | 5758 | CB | HIS | 740 | 61.746 | 57.736 | 34.511 | 1.00 | 16.88 | A C |
| ATOM | 5759 | CG | HIS | 740 | 61.145 | 58.392 | 35.710 | 1.00 | 17.57 | A C |
| ATOM | 5760 | CD2 | HIS | 740 | 59.883 | 58.812 | 35.961 | 1.00 | 16.26 | A C |
| ATOM | 5761 | ND1 | HIS | 740 | 61.881 | 58.687 | 36.837 | 1.00 | 17.31 | A N |
| ATOM | 5762 | CE1 | HIS | 740 | 61.097 | 59.262 | 37.732 | 1.00 | 18.51 | A C |
| ATOM | 5763 | NE2 | HIS | 740 | 59.880 | 59.349 | 37.224 | 1.00 | 17.94 | A N |
| ATOM | 5764 | C | HIS | 740 | 61.557 | 55.449 | 35.426 | 1.00 | 19.90 | A C |
| ATOM | 5765 | O | HIS | 740 | 61.191 | 55.539 | 36.599 | 1.00 | 20.00 | A O |
| ATOM | 5766 | N | GLY | 741 | 61.151 | 54.481 | 34.614 | 1.00 | 19.40 | A N |
| ATOM | 5767 | CA | GLY | 741 | 60.216 | 53.484 | 35.084 | 1.00 | 18.82 | A C |
| ATOM | 5768 | C | GLY | 741 | 60.849 | 52.218 | 35.609 | 1.00 | 20.36 | A C |
| ATOM | 5769 | O | GLY | 741 | 60.165 | 51.404 | 36.237 | 1.00 | 22.79 | A O |
| ATOM | 5770 | N | ILE | 742 | 62.145 | 52.045 | 35.368 | 1.00 | 19.61 | A N |
| ATOM | 5771 | CA | ILE | 742 | 62.854 | 50.849 | 35.821 | 1.00 | 17.74 | A C |
| ATOM | 5772 | CB | ILE | 742 | 63.273 | 50.981 | 37.294 | 1.00 | 14.46 | A C |
| ATOM | 5773 | CG2 | ILE | 742 | 64.279 | 49.917 | 37.638 | 1.00 | 14.37 | A C |
| ATOM | 5774 | CG1 | ILE | 742 | 63.865 | 52.370 | 37.540 | 1.00 | 13.43 | A C |
| ATOM | 5775 | CD1 | ILE | 742 | 64.540 | 52.552 | 38.887 | 1.00 | 9.55 | A C |
| ATOM | 5776 | C | ILE | 742 | 61.907 | 49.658 | 35.676 | 1.00 | 19.11 | A C |
| ATOM | 5777 | O | ILE | 742 | 61.805 | 48.825 | 36.571 | 1.00 | 18.97 | A O |
| ATOM | 5778 | N | ALA | 743 | 61.217 | 49.594 | 34.534 | 1.00 | 20.16 | A N |
| ATOM | 5779 | CA | ALA | 743 | 60.246 | 48.538 | 34.268 | 1.00 | 19.71 | A C |
| ATOM | 5780 | CB | ALA | 743 | 59.004 | 49.141 | 33.630 | 1.00 | 19.65 | A C |
| ATOM | 5781 | C | ALA | 743 | 60.717 | 47.350 | 33.430 | 1.00 | 20.08 | A C |

| ATOM | 5782 | O | ALA | 743 | 59.898 | 46.536 | 33.006 | 1.00 | 20.99 | A | O |
|---|---|---|---|---|---|---|---|---|---|---|---|
| ATOM | 5783 | N | SER | 744 | 62.009 | 47.230 | 33.163 | 1.00 | 19.12 | A | N |
| ATOM | 5784 | CA | SER | 744 | 62.438 | 46.074 | 32.389 | 1.00 | 17.34 | A | C |
| ATOM | 5785 | CB | SER | 744 | 63.931 | 46.132 | 32.068 | 1.00 | 14.62 | A | C |
| ATOM | 5786 | OG | SER | 744 | 64.699 | 45.597 | 33.125 | 1.00 | 18.04 | A | O |
| ATOM | 5787 | C | SER | 744 | 62.132 | 44.896 | 33.300 | 1.00 | 16.58 | A | C |
| ATOM | 5788 | O | SER | 744 | 62.137 | 45.032 | 34.519 | 1.00 | 15.47 | A | O |
| ATOM | 5789 | N | SER | 745 | 61.853 | 43.742 | 32.715 | 1.00 | 19.10 | A | N |
| ATOM | 5790 | CA | SER | 745 | 61.524 | 42.558 | 33.503 | 1.00 | 20.03 | A | C |
| ATOM | 5791 | CB | SER | 745 | 61.417 | 41.343 | 32.598 | 1.00 | 20.12 | A | C |
| ATOM | 5792 | OG | SER | 745 | 61.110 | 40.209 | 33.377 | 1.00 | 27.90 | A | O |
| ATOM | 5793 | C | SER | 745 | 62.510 | 42.245 | 34.624 | 1.00 | 19.80 | A | C |
| ATOM | 5794 | O | SER | 745 | 62.130 | 42.078 | 35.781 | 1.00 | 19.78 | A | O |
| ATOM | 5795 | N | THR | 746 | 63.783 | 42.158 | 34.277 | 1.00 | 19.56 | A | N |
| ATOM | 5796 | CA | THR | 746 | 64.796 | 41.849 | 35.265 | 1.00 | 19.48 | A | C |
| ATOM | 5797 | CB | THR | 746 | 66.125 | 41.538 | 34.575 | 1.00 | 20.06 | A | C |
| ATOM | 5798 | OG1 | THR | 746 | 66.463 | 42.615 | 33.691 | 1.00 | 23.41 | A | O |
| ATOM | 5799 | CG2 | THR | 746 | 66.009 | 40.259 | 33.772 | 1.00 | 16.20 | A | C |
| ATOM | 5800 | C | THR | 746 | 64.996 | 42.966 | 36.288 | 1.00 | 19.59 | A | C |
| ATOM | 5801 | O | THR | 746 | 65.066 | 42.706 | 37.488 | 1.00 | 20.63 | A | O |
| ATOM | 5802 | N | ALA | 747 | 65.070 | 44.208 | 35.821 | 1.00 | 18.73 | A | N |
| ATOM | 5803 | CA | ALA | 747 | 65.286 | 45.334 | 36.723 | 1.00 | 18.03 | A | C |
| ATOM | 5804 | CB | ALA | 747 | 65.554 | 46.609 | 35.919 | 1.00 | 15.38 | A | C |
| ATOM | 5805 | C | ALA | 747 | 64.113 | 45.540 | 37.681 | 1.00 | 17.35 | A | C |
| ATOM | 5806 | O | ALA | 747 | 64.291 | 45.989 | 38.814 | 1.00 | 18.52 | A | O |
| ATOM | 5807 | N | HIS | 748 | 62.915 | 45.206 | 37.224 | 1.00 | 16.75 | A | N |
| ATOM | 5808 | CA | HIS | 748 | 61.718 | 45.342 | 38.046 | 1.00 | 16.92 | A | C |
| ATOM | 5809 | CB | HIS | 748 | 60.477 | 45.005 | 37.220 | 1.00 | 13.48 | A | C |
| ATOM | 5810 | CG | HIS | 748 | 59.214 | 44.968 | 38.020 | 1.00 | 14.10 | A | C |
| ATOM | 5811 | CD2 | HIS | 748 | 58.397 | 43.941 | 38.348 | 1.00 | 12.63 | A | C |
| ATOM | 5812 | ND1 | HIS | 748 | 58.663 | 46.094 | 38.595 | 1.00 | 14.71 | A | N |
| ATOM | 5813 | CE1 | HIS | 748 | 57.561 | 45.762 | 39.241 | 1.00 | 13.05 | A | C |
| ATOM | 5814 | NE2 | HIS | 748 | 57.377 | 44.461 | 39.107 | 1.00 | 14.46 | A | N |
| ATOM | 5815 | C | HIS | 748 | 61.790 | 44.415 | 39.263 | 1.00 | 18.16 | A | C |
| ATOM | 5816 | O | HIS | 748 | 61.525 | 44.816 | 40.394 | 1.00 | 20.72 | A | O |
| ATOM | 5817 | N | GLN | 749 | 62.148 | 43.165 | 39.025 | 1.00 | 18.81 | A | N |
| ATOM | 5818 | CA | GLN | 749 | 62.241 | 42.201 | 40.105 | 1.00 | 19.53 | A | C |
| ATOM | 5819 | CB | GLN | 749 | 62.408 | 40.801 | 39.519 | 1.00 | 20.05 | A | C |
| ATOM | 5820 | CG | GLN | 749 | 61.291 | 40.428 | 38.550 | 1.00 | 21.82 | A | C |
| ATOM | 5821 | CD | GLN | 749 | 61.618 | 39.190 | 37.757 | 1.00 | 20.87 | A | C |
| ATOM | 5822 | OE1 | GLN | 749 | 62.047 | 38.187 | 38.316 | 1.00 | 22.37 | A | O |
| ATOM | 5823 | NE2 | GLN | 749 | 61.415 | 39.249 | 36.447 | 1.00 | 20.00 | A | N |
| ATOM | 5824 | C | GLN | 749 | 63.416 | 42.524 | 41.008 | 1.00 | 19.07 | A | C |
| ATOM | 5825 | O | GLN | 749 | 63.335 | 42.388 | 42.231 | 1.00 | 17.88 | A | O |
| ATOM | 5826 | N | HIS | 750 | 64.508 | 42.972 | 40.399 | 1.00 | 18.97 | A | N |
| ATOM | 5827 | CA | HIS | 750 | 65.707 | 43.275 | 41.160 | 1.00 | 16.68 | A | C |
| ATOM | 5828 | CB | HIS | 750 | 66.871 | 43.597 | 40.226 | 1.00 | 14.65 | A | C |
| ATOM | 5829 | CG | HIS | 750 | 68.208 | 43.496 | 40.889 | 1.00 | 13.97 | A | C |
| ATOM | 5830 | CD2 | HIS | 750 | 69.207 | 42.593 | 40.749 | 1.00 | 12.94 | A | C |

| | | | | | | | | | | |
|---|---|---|---|---|---|---|---|---|---|---|
| ATOM | 5831 | ND1 | HIS | 750 | 68.615 | 44.365 | 41.877 | 1.00 | 13.54 | A | N |
| ATOM | 5832 | CE1 | HIS | 750 | 69.804 | 44.000 | 42.320 | 1.00 | 12.57 | A | C |
| ATOM | 5833 | NE2 | HIS | 750 | 70.185 | 42.927 | 41.653 | 1.00 | 12.04 | A | N |
| ATOM | 5834 | C | HIS | 750 | 65.529 | 44.400 | 42.157 | 1.00 | 17.33 | A | C |
| ATOM | 5835 | O | HIS | 750 | 65.945 | 44.277 | 43.309 | 1.00 | 18.09 | A | O |
| ATOM | 5836 | N | ILE | 751 | 64.899 | 45.490 | 41.726 | 1.00 | 17.03 | A | N |
| ATOM | 5837 | CA | ILE | 751 | 64.704 | 46.632 | 42.604 | 1.00 | 15.90 | A | C |
| ATOM | 5838 | CB | ILE | 751 | 64.206 | 47.849 | 41.805 | 1.00 | 17.60 | A | C |
| ATOM | 5839 | CG2 | ILE | 751 | 62.893 | 47.504 | 41.088 | 1.00 | 16.17 | A | C |
| ATOM | 5840 | CG1 | ILE | 751 | 64.065 | 49.058 | 42.736 | 1.00 | 15.94 | A | C |
| ATOM | 5841 | CD1 | ILE | 751 | 63.684 | 50.332 | 42.017 | 1.00 | 12.51 | A | C |
| ATOM | 5842 | C | ILE | 751 | 63.751 | 46.341 | 43.767 | 1.00 | 16.09 | A | C |
| ATOM | 5843 | O | ILE | 751 | 64.062 | 46.632 | 44.919 | 1.00 | 16.37 | A | O |
| ATOM | 5844 | N | TYR | 752 | 62.596 | 45.759 | 43.480 | 1.00 | 16.32 | A | N |
| ATOM | 5845 | CA | TYR | 752 | 61.651 | 45.449 | 44.551 | 1.00 | 16.16 | A | C |
| ATOM | 5846 | CB | TYR | 752 | 60.323 | 44.967 | 43.968 | 1.00 | 13.79 | A | C |
| ATOM | 5847 | CG | TYR | 752 | 59.443 | 46.126 | 43.593 | 1.00 | 12.59 | A | C |
| ATOM | 5848 | CD1 | TYR | 752 | 58.840 | 46.899 | 44.580 | 1.00 | 11.61 | A | C |
| ATOM | 5849 | CE1 | TYR | 752 | 58.102 | 48.026 | 44.258 | 1.00 | 9.67 | A | C |
| ATOM | 5850 | CD2 | TYR | 752 | 59.279 | 46.510 | 42.260 | 1.00 | 12.75 | A | C |
| ATOM | 5851 | CE2 | TYR | 752 | 58.543 | 47.644 | 41.930 | 1.00 | 10.28 | A | C |
| ATOM | 5852 | CZ | TYR | 752 | 57.964 | 48.395 | 42.940 | 1.00 | 9.02 | A | C |
| ATOM | 5853 | OH | TYR | 752 | 57.278 | 49.542 | 42.642 | 1.00 | 12.10 | A | O |
| ATOM | 5854 | C | TYR | 752 | 62.226 | 44.429 | 45.522 | 1.00 | 16.42 | A | C |
| ATOM | 5855 | O | TYR | 752 | 61.927 | 44.467 | 46.719 | 1.00 | 16.42 | A | O |
| ATOM | 5856 | N | THR | 753 | 63.056 | 43.526 | 45.004 | 1.00 | 15.74 | A | N |
| ATOM | 5857 | CA | THR | 753 | 63.700 | 42.521 | 45.835 | 1.00 | 16.30 | A | C |
| ATOM | 5858 | CB | THR | 753 | 64.502 | 41.510 | 44.985 | 1.00 | 15.57 | A | C |
| ATOM | 5859 | OG1 | THR | 753 | 63.601 | 40.677 | 44.253 | 1.00 | 15.74 | A | O |
| ATOM | 5860 | CG2 | THR | 753 | 65.385 | 40.641 | 45.870 | 1.00 | 10.01 | A | C |
| ATOM | 5861 | C | THR | 753 | 64.678 | 43.240 | 46.758 | 1.00 | 18.17 | A | C |
| ATOM | 5862 | O | THR | 753 | 64.788 | 42.923 | 47.941 | 1.00 | 19.02 | A | O |
| ATOM | 5863 | N | HIS | 754 | 65.388 | 44.215 | 46.199 | 1.00 | 18.78 | A | N |
| ATOM | 5864 | CA | HIS | 754 | 66.363 | 44.972 | 46.959 | 1.00 | 18.90 | A | C |
| ATOM | 5865 | CB | HIS | 754 | 67.189 | 45.857 | 46.023 | 1.00 | 19.13 | A | C |
| ATOM | 5866 | CG | HIS | 754 | 68.449 | 46.379 | 46.644 | 1.00 | 19.62 | A | C |
| ATOM | 5867 | CD2 | HIS | 754 | 68.786 | 47.619 | 47.070 | 1.00 | 18.70 | A | C |
| ATOM | 5868 | ND1 | HIS | 754 | 69.539 | 45.576 | 46.904 | 1.00 | 18.44 | A | N |
| ATOM | 5869 | CE1 | HIS | 754 | 70.493 | 46.298 | 47.462 | 1.00 | 17.52 | A | C |
| ATOM | 5870 | NE2 | HIS | 754 | 70.062 | 47.541 | 47.574 | 1.00 | 19.51 | A | N |
| ATOM | 5871 | C | HIS | 754 | 65.663 | 45.828 | 48.007 | 1.00 | 19.38 | A | C |
| ATOM | 5872 | O | HIS | 754 | 66.088 | 45.876 | 49.158 | 1.00 | 19.63 | A | O |
| ATOM | 5873 | N | MET | 755 | 64.589 | 46.502 | 47.615 | 1.00 | 18.83 | A | N |
| ATOM | 5874 | CA | MET | 755 | 63.854 | 47.342 | 48.558 | 1.00 | 19.68 | A | C |
| ATOM | 5875 | CB | MET | 755 | 62.758 | 48.136 | 47.839 | 1.00 | 16.86 | A | C |
| ATOM | 5876 | CG | MET | 755 | 63.283 | 49.173 | 46.876 | 1.00 | 16.00 | A | C |
| ATOM | 5877 | SD | MET | 755 | 62.016 | 50.314 | 46.309 | 1.00 | 20.78 | A | S |
| ATOM | 5878 | CE | MET | 755 | 61.100 | 49.270 | 45.200 | 1.00 | 15.61 | A | C |
| ATOM | 5879 | C | MET | 755 | 63.232 | 46.506 | 49.676 | 1.00 | 20.27 | A | C |

FIG. 4-121 (Continued)

| | | | | | | | | | | |
|---|---|---|---|---|---|---|---|---|---|---|
| ATOM | 5880 | O | MET | 755 | 63.112 | 46.969 | 50.811 | 1.00 | 20.56 | A | O |
| ATOM | 5881 | N | SER | 756 | 62.842 | 45.276 | 49.352 | 1.00 | 20.59 | A | N |
| ATOM | 5882 | CA | SER | 756 | 62.240 | 44.380 | 50.332 | 1.00 | 21.43 | A | C |
| ATOM | 5883 | CB | SER | 756 | 61.740 | 43.106 | 49.646 | 1.00 | 21.74 | A | C |
| ATOM | 5884 | OG | SER | 756 | 60.598 | 43.373 | 48.850 | 1.00 | 21.68 | A | O |
| ATOM | 5885 | C | SER | 756 | 63.224 | 44.023 | 51.444 | 1.00 | 22.50 | A | C |
| ATOM | 5886 | O | SER | 756 | 62.858 | 44.022 | 52.623 | 1.00 | 22.47 | A | O |
| ATOM | 5887 | N | HIS | 757 | 64.466 | 43.716 | 51.073 | 1.00 | 22.47 | A | N |
| ATOM | 5888 | CA | HIS | 757 | 65.483 | 43.384 | 52.065 | 1.00 | 23.01 | A | C |
| ATOM | 5889 | CB | HIS | 757 | 66.828 | 43.032 | 51.407 | 1.00 | 21.90 | A | C |
| ATOM | 5890 | CG | HIS | 757 | 66.837 | 41.721 | 50.682 | 1.00 | 24.99 | A | C |
| ATOM | 5891 | CD2 | HIS | 757 | 67.344 | 41.375 | 49.473 | 1.00 | 26.07 | A | C |
| ATOM | 5892 | ND1 | HIS | 757 | 66.314 | 40.563 | 51.220 | 1.00 | 26.51 | A | N |
| ATOM | 5893 | CE1 | HIS | 757 | 66.497 | 39.564 | 50.375 | 1.00 | 25.15 | A | C |
| ATOM | 5894 | NE2 | HIS | 757 | 67.120 | 40.029 | 49.307 | 1.00 | 25.93 | A | N |
| ATOM | 5895 | C | HIS | 757 | 65.689 | 44.596 | 52.966 | 1.00 | 23.03 | A | C |
| ATOM | 5896 | O | HIS | 757 | 65.823 | 44.474 | 54.186 | 1.00 | 24.03 | A | O |
| ATOM | 5897 | N | PHE | 758 | 65.704 | 45.771 | 52.356 | 1.00 | 22.28 | A | N |
| ATOM | 5898 | CA | PHE | 758 | 65.920 | 46.995 | 53.106 | 1.00 | 24.10 | A | C |
| ATOM | 5899 | CB | PHE | 758 | 66.005 | 48.190 | 52.161 | 1.00 | 20.12 | A | C |
| ATOM | 5900 | CG | PHE | 758 | 66.455 | 49.448 | 52.828 | 1.00 | 17.08 | A | C |
| ATOM | 5901 | CD1 | PHE | 758 | 67.803 | 49.657 | 53.106 | 1.00 | 15.49 | A | C |
| ATOM | 5902 | CD2 | PHE | 758 | 65.537 | 50.429 | 53.176 | 1.00 | 15.44 | A | C |
| ATOM | 5903 | CE1 | PHE | 758 | 68.233 | 50.825 | 53.717 | 1.00 | 14.07 | A | C |
| ATOM | 5904 | CE2 | PHE | 758 | 65.955 | 51.607 | 53.789 | 1.00 | 17.18 | A | C |
| ATOM | 5905 | CZ | PHE | 758 | 67.308 | 51.806 | 54.060 | 1.00 | 15.05 | A | C |
| ATOM | 5906 | C | PHE | 758 | 64.832 | 47.254 | 54.135 | 1.00 | 26.28 | A | C |
| ATOM | 5907 | O | PHE | 758 | 65.120 | 47.546 | 55.295 | 1.00 | 28.09 | A | O |
| ATOM | 5908 | N | ILE | 759 | 63.580 | 47.162 | 53.706 | 1.00 | 27.69 | A | N |
| ATOM | 5909 | CA | ILE | 759 | 62.461 | 47.394 | 54.605 | 1.00 | 29.02 | A | C |
| ATOM | 5910 | CB | ILE | 759 | 61.129 | 47.271 | 53.853 | 1.00 | 28.24 | A | C |
| ATOM | 5911 | CG2 | ILE | 759 | 59.967 | 47.207 | 54.836 | 1.00 | 29.09 | A | C |
| ATOM | 5912 | CG1 | ILE | 759 | 60.990 | 48.446 | 52.884 | 1.00 | 28.85 | A | C |
| ATOM | 5913 | CD1 | ILE | 759 | 61.173 | 49.809 | 53.535 | 1.00 | 27.28 | A | C |
| ATOM | 5914 | C | ILE | 759 | 62.467 | 46.420 | 55.774 | 1.00 | 31.10 | A | C |
| ATOM | 5915 | O | ILE | 759 | 62.292 | 46.822 | 56.925 | 1.00 | 30.20 | A | O |
| ATOM | 5916 | N | LYS | 760 | 62.669 | 45.140 | 55.464 | 1.00 | 32.71 | A | N |
| ATOM | 5917 | CA | LYS | 760 | 62.697 | 44.079 | 56.465 | 1.00 | 33.04 | A | C |
| ATOM | 5918 | CB | LYS | 760 | 62.732 | 42.715 | 55.780 | 1.00 | 34.00 | A | C |
| ATOM | 5919 | CG | LYS | 760 | 61.405 | 42.300 | 55.164 | 1.00 | 37.68 | A | C |
| ATOM | 5920 | CD | LYS | 760 | 61.620 | 41.455 | 53.916 | 1.00 | 40.82 | A | C |
| ATOM | 5921 | CE | LYS | 760 | 62.473 | 40.229 | 54.199 | 1.00 | 42.70 | A | C |
| ATOM | 5922 | NZ | LYS | 760 | 62.952 | 39.600 | 52.933 | 1.00 | 44.73 | A | N |
| ATOM | 5923 | C | LYS | 760 | 63.885 | 44.205 | 57.396 | 1.00 | 33.20 | A | C |
| ATOM | 5924 | O | LYS | 760 | 63.874 | 43.676 | 58.504 | 1.00 | 34.38 | A | O |
| ATOM | 5925 | N | GLN | 761 | 64.914 | 44.902 | 56.939 | 1.00 | 33.26 | A | N |
| ATOM | 5926 | CA | GLN | 761 | 66.106 | 45.100 | 57.744 | 1.00 | 33.22 | A | C |
| ATOM | 5927 | CB | GLN | 761 | 67.295 | 45.422 | 56.830 | 1.00 | 35.03 | A | C |
| ATOM | 5928 | CG | GLN | 761 | 68.638 | 45.584 | 57.525 | 1.00 | 38.28 | A | C |

FIG. 4-122 (Continued)

| | | | | | | | | | | |
|---|---|---|---|---|---|---|---|---|---|---|
| ATOM | 5929 | CD | GLN | 761 | 68.759 | 46.893 | 58.283 | 1.00 | 42.12 | A C |
| ATOM | 5930 | OE1 | GLN | 761 | 68.487 | 47.969 | 57.739 | 1.00 | 43.62 | A O |
| ATOM | 5931 | NE2 | GLN | 761 | 69.177 | 46.811 | 59.544 | 1.00 | 44.19 | A N |
| ATOM | 5932 | C | GLN | 761 | 65.819 | 46.251 | 58.701 | 1.00 | 32.55 | A C |
| ATOM | 5933 | O | GLN | 761 | 66.064 | 46.149 | 59.898 | 1.00 | 32.49 | A O |
| ATOM | 5934 | N | CYS | 762 | 65.276 | 47.337 | 58.161 | 1.00 | 32.03 | A N |
| ATOM | 5935 | CA | CYS | 762 | 64.945 | 48.513 | 58.953 | 1.00 | 33.26 | A C |
| ATOM | 5936 | C | CYS | 762 | 63.888 | 48.216 | 60.023 | 1.00 | 32.69 | A C |
| ATOM | 5937 | O | CYS | 762 | 63.892 | 48.830 | 61.087 | 1.00 | 32.22 | A O |
| ATOM | 5938 | CB | CYS | 762 | 64.470 | 49.643 | 58.025 | 1.00 | 33.90 | A C |
| ATOM | 5939 | SG | CYS | 762 | 63.606 | 51.029 | 58.843 | 1.00 | 40.21 | A S |
| ATOM | 5940 | N | PHE | 763 | 62.993 | 47.271 | 59.742 | 1.00 | 32.59 | A N |
| ATOM | 5941 | CA | PHE | 763 | 61.948 | 46.907 | 60.694 | 1.00 | 34.25 | A C |
| ATOM | 5942 | CB | PHE | 763 | 60.618 | 46.647 | 59.981 | 1.00 | 31.61 | A C |
| ATOM | 5943 | CG | PHE | 763 | 59.919 | 47.892 | 59.525 | 1.00 | 30.04 | A C |
| ATOM | 5944 | CD1 | PHE | 763 | 60.371 | 49.148 | 59.923 | 1.00 | 29.45 | A C |
| ATOM | 5945 | CD2 | PHE | 763 | 58.800 | 47.808 | 58.703 | 1.00 | 28.65 | A C |
| ATOM | 5946 | CE1 | PHE | 763 | 59.718 | 50.300 | 59.510 | 1.00 | 29.27 | A C |
| ATOM | 5947 | CE2 | PHE | 763 | 58.139 | 48.951 | 58.284 | 1.00 | 28.76 | A C |
| ATOM | 5948 | CZ | PHE | 763 | 58.598 | 50.202 | 58.688 | 1.00 | 30.54 | A C |
| ATOM | 5949 | C | PHE | 763 | 62.293 | 45.688 | 61.535 | 1.00 | 36.77 | A C |
| ATOM | 5950 | O | PHE | 763 | 61.499 | 45.276 | 62.381 | 1.00 | 36.29 | A O |
| ATOM | 5951 | N | SER | 764 | 63.463 | 45.102 | 61.290 | 1.00 | 39.62 | A N |
| ATOM | 5952 | CA | SER | 764 | 63.907 | 43.941 | 62.052 | 1.00 | 43.05 | A C |
| ATOM | 5953 | CB | SER | 764 | 65.356 | 43.598 | 61.701 | 1.00 | 44.44 | A C |
| ATOM | 5954 | OG | SER | 764 | 66.215 | 44.709 | 61.913 | 1.00 | 48.06 | A O |
| ATOM | 5955 | C | SER | 764 | 63.799 | 44.314 | 63.522 | 1.00 | 45.02 | A C |
| ATOM | 5956 | O | SER | 764 | 64.195 | 45.412 | 63.916 | 1.00 | 44.75 | A O |
| ATOM | 5957 | N | LEU | 765 | 63.264 | 43.412 | 64.335 | 1.00 | 48.04 | A N |
| ATOM | 5958 | CA | LEU | 765 | 63.092 | 43.716 | 65.747 | 1.00 | 51.59 | A C |
| ATOM | 5959 | CB | LEU | 765 | 61.624 | 44.067 | 66.017 | 1.00 | 50.97 | A C |
| ATOM | 5960 | CG | LEU | 765 | 61.332 | 44.846 | 67.299 | 1.00 | 50.79 | A C |
| ATOM | 5961 | CD1 | LEU | 765 | 61.996 | 46.215 | 67.221 | 1.00 | 50.85 | A C |
| ATOM | 5962 | CD2 | LEU | 765 | 59.834 | 44.996 | 67.481 | 1.00 | 50.72 | A C |
| ATOM | 5963 | C | LEU | 765 | 63.533 | 42.588 | 66.676 | 1.00 | 54.72 | A C |
| ATOM | 5964 | O | LEU | 765 | 62.866 | 41.557 | 66.779 | 1.00 | 55.73 | A O |
| ATOM | 5965 | N | PRO | 766 | 64.667 | 42.776 | 67.372 | 1.00 | 57.13 | A N |
| ATOM | 5966 | CD | PRO | 766 | 65.545 | 43.960 | 67.317 | 1.00 | 57.88 | A C |
| ATOM | 5967 | CA | PRO | 766 | 65.204 | 41.775 | 68.301 | 1.00 | 58.61 | A C |
| ATOM | 5968 | CB | PRO | 766 | 66.600 | 42.309 | 68.604 | 1.00 | 58.49 | A C |
| ATOM | 5969 | CG | PRO | 766 | 66.386 | 43.797 | 68.568 | 1.00 | 58.47 | A C |
| ATOM | 5970 | C | PRO | 766 | 64.352 | 41.639 | 69.565 | 1.00 | 60.07 | A C |
| ATOM | 5971 | O | PRO | 766 | 63.341 | 42.370 | 69.681 | 1.00 | 60.04 | A O |
| ATOM | 5972 | OXT | PRO | 766 | 64.711 | 40.805 | 70.427 | 1.00 | 61.88 | A O |
| TER | 5973 | | PRO | 766 | | | | | | A |
| ATOM | 5974 | CB | ASP | 38 | 95.909 | 45.132 | 76.302 | 1.00 | 32.66 | B C |
| ATOM | 5975 | CG | ASP | 38 | 96.954 | 46.047 | 75.698 | 1.00 | 32.61 | B C |
| ATOM | 5976 | OD1 | ASP | 38 | 96.905 | 47.269 | 75.977 | 1.00 | 30.88 | B O |
| ATOM | 5977 | OD2 | ASP | 38 | 97.816 | 45.544 | 74.942 | 1.00 | 31.65 | B O |

| ATOM | 5978 | C | ASP | 38 | 94.533 | 46.724 | 77.638 | 1.00 | 31.81 | B | C |
|---|---|---|---|---|---|---|---|---|---|---|---|
| ATOM | 5979 | O | ASP | 38 | 93.521 | 46.648 | 76.938 | 1.00 | 32.54 | B | O |
| ATOM | 5980 | N | ASP | 38 | 94.842 | 44.428 | 78.423 | 1.00 | 32.95 | B | N |
| ATOM | 5981 | CA | ASP | 38 | 95.507 | 45.557 | 77.717 | 1.00 | 32.06 | B | C |
| ATOM | 5982 | N | SER | 39 | 94.844 | 47.807 | 78.344 | 1.00 | 31.40 | B | N |
| ATOM | 5983 | CA | SER | 39 | 93.974 | 48.982 | 78.372 | 1.00 | 30.28 | B | C |
| ATOM | 5984 | CB | SER | 39 | 94.048 | 49.652 | 79.741 | 1.00 | 31.88 | B | C |
| ATOM | 5985 | OG | SER | 39 | 95.362 | 50.119 | 80.003 | 1.00 | 34.53 | B | O |
| ATOM | 5986 | C | SER | 39 | 94.289 | 50.017 | 77.305 | 1.00 | 29.15 | B | C |
| ATOM | 5987 | O | SER | 39 | 93.615 | 51.049 | 77.220 | 1.00 | 30.29 | B | O |
| ATOM | 5988 | N | ARG | 40 | 95.312 | 49.755 | 76.499 | 1.00 | 26.40 | B | N |
| ATOM | 5989 | CA | ARG | 40 | 95.685 | 50.686 | 75.442 | 1.00 | 24.29 | B | C |
| ATOM | 5990 | CB | ARG | 40 | 97.004 | 50.257 | 74.788 | 1.00 | 23.19 | B | C |
| ATOM | 5991 | CG | ARG | 40 | 98.228 | 50.429 | 75.670 | 1.00 | 20.84 | B | C |
| ATOM | 5992 | CD | ARG | 40 | 99.470 | 49.917 | 74.969 | 1.00 | 21.38 | B | C |
| ATOM | 5993 | NE | ARG | 40 | 99.404 | 48.479 | 74.728 | 1.00 | 21.28 | B | N |
| ATOM | 5994 | CZ | ARG | 40 | 100.260 | 47.812 | 73.963 | 1.00 | 22.73 | B | C |
| ATOM | 5995 | NH1 | ARG | 40 | 101.247 | 48.461 | 73.361 | 1.00 | 22.52 | B | N |
| ATOM | 5996 | NH2 | ARG | 40 | 100.134 | 46.497 | 73.806 | 1.00 | 22.23 | B | N |
| ATOM | 5997 | C | ARG | 40 | 94.604 | 50.757 | 74.376 | 1.00 | 23.29 | B | C |
| ATOM | 5998 | O | ARG | 40 | 93.881 | 49.793 | 74.150 | 1.00 | 23.24 | B | O |
| ATOM | 5999 | N | LYS | 41 | 94.494 | 51.907 | 73.725 | 1.00 | 23.55 | B | N |
| ATOM | 6000 | CA | LYS | 41 | 93.518 | 52.076 | 72.658 | 1.00 | 24.31 | B | C |
| ATOM | 6001 | CB | LYS | 41 | 93.386 | 53.556 | 72.274 | 1.00 | 25.29 | B | C |
| ATOM | 6002 | CG | LYS | 41 | 94.699 | 54.209 | 71.827 | 1.00 | 29.38 | B | C |
| ATOM | 6003 | CD | LYS | 41 | 94.505 | 55.663 | 71.365 | 1.00 | 28.84 | B | C |
| ATOM | 6004 | CE | LYS | 41 | 94.374 | 55.779 | 69.840 | 1.00 | 28.95 | B | C |
| ATOM | 6005 | NZ | LYS | 41 | 93.307 | 54.922 | 69.251 | 1.00 | 27.49 | B | N |
| ATOM | 6006 | C | LYS | 41 | 94.028 | 51.294 | 71.458 | 1.00 | 24.04 | B | C |
| ATOM | 6007 | O | LYS | 41 | 95.231 | 51.072 | 71.324 | 1.00 | 24.69 | B | O |
| ATOM | 6008 | N | THR | 42 | 93.118 | 50.859 | 70.595 | 1.00 | 23.54 | B | N |
| ATOM | 6009 | CA | THR | 42 | 93.518 | 50.130 | 69.399 | 1.00 | 22.29 | B | C |
| ATOM | 6010 | CB | THR | 42 | 92.454 | 49.083 | 68.959 | 1.00 | 22.69 | B | C |
| ATOM | 6011 | OG1 | THR | 42 | 91.257 | 49.753 | 68.540 | 1.00 | 21.91 | B | O |
| ATOM | 6012 | CG2 | THR | 42 | 92.128 | 48.129 | 70.101 | 1.00 | 20.28 | B | C |
| ATOM | 6013 | C | THR | 42 | 93.641 | 51.178 | 68.304 | 1.00 | 22.33 | B | C |
| ATOM | 6014 | O | THR | 42 | 93.386 | 52.363 | 68.541 | 1.00 | 23.36 | B | O |
| ATOM | 6015 | N | TYR | 43 | 94.045 | 50.750 | 67.116 | 1.00 | 20.55 | B | N |
| ATOM | 6016 | CA | TYR | 43 | 94.158 | 51.662 | 65.986 | 1.00 | 19.19 | B | C |
| ATOM | 6017 | CB | TYR | 43 | 95.233 | 51.153 | 65.020 | 1.00 | 20.32 | B | C |
| ATOM | 6018 | CG | TYR | 43 | 95.516 | 52.062 | 63.853 | 1.00 | 19.92 | B | C |
| ATOM | 6019 | CD1 | TYR | 43 | 94.888 | 51.863 | 62.629 | 1.00 | 22.19 | B | C |
| ATOM | 6020 | CE1 | TYR | 43 | 95.133 | 52.694 | 61.546 | 1.00 | 21.23 | B | C |
| ATOM | 6021 | CD2 | TYR | 43 | 96.403 | 53.126 | 63.970 | 1.00 | 21.09 | B | C |
| ATOM | 6022 | CE2 | TYR | 43 | 96.655 | 53.972 | 62.891 | 1.00 | 21.69 | B | C |
| ATOM | 6023 | CZ | TYR | 43 | 96.013 | 53.742 | 61.682 | 1.00 | 22.25 | B | C |
| ATOM | 6024 | OH | TYR | 43 | 96.247 | 54.553 | 60.600 | 1.00 | 25.44 | B | O |
| ATOM | 6025 | C | TYR | 43 | 92.770 | 51.631 | 65.349 | 1.00 | 18.52 | B | C |
| ATOM | 6026 | O | TYR | 43 | 92.396 | 50.640 | 64.725 | 1.00 | 17.41 | B | O |

| | | | | | | | | | | | |
|---|---|---|---|---|---|---|---|---|---|---|---|
| ATOM | 6027 | N | THR | 44 | 92.007 | 52.709 | 65.532 | 1.00 | 17.70 | B | N |
| ATOM | 6028 | CA | THR | 44 | 90.633 | 52.802 | 65.019 | 1.00 | 18.55 | B | C |
| ATOM | 6029 | CB | THR | 44 | 89.762 | 53.748 | 65.877 | 1.00 | 16.45 | B | C |
| ATOM | 6030 | OG1 | THR | 44 | 90.195 | 55.096 | 65.676 | 1.00 | 16.93 | B | O |
| ATOM | 6031 | CG2 | THR | 44 | 89.875 | 53.409 | 67.346 | 1.00 | 14.45 | B | C |
| ATOM | 6032 | C | THR | 44 | 90.521 | 53.310 | 63.593 | 1.00 | 19.62 | B | C |
| ATOM | 6033 | O | THR | 44 | 91.511 | 53.741 | 62.992 | 1.00 | 21.89 | B | O |
| ATOM | 6034 | N | LEU | 45 | 89.296 | 53.277 | 63.067 | 1.00 | 19.06 | B | N |
| ATOM | 6035 | CA | LEU | 45 | 89.026 | 53.749 | 61.713 | 1.00 | 18.74 | B | C |
| ATOM | 6036 | CB | LEU | 45 | 87.570 | 53.489 | 61.327 | 1.00 | 17.33 | B | C |
| ATOM | 6037 | CG | LEU | 45 | 87.163 | 54.032 | 59.952 | 1.00 | 17.35 | B | C |
| ATOM | 6038 | CD1 | LEU | 45 | 88.050 | 53.417 | 58.873 | 1.00 | 15.87 | B | C |
| ATOM | 6039 | CD2 | LEU | 45 | 85.698 | 53.720 | 59.681 | 1.00 | 16.27 | B | C |
| ATOM | 6040 | C | LEU | 45 | 89.300 | 55.240 | 61.638 | 1.00 | 19.82 | B | C |
| ATOM | 6041 | O | LEU | 45 | 89.827 | 55.743 | 60.638 | 1.00 | 21.32 | B | O |
| ATOM | 6042 | N | THR | 46 | 88.948 | 55.945 | 62.707 | 1.00 | 19.07 | B | N |
| ATOM | 6043 | CA | THR | 46 | 89.156 | 57.382 | 62.760 | 1.00 | 20.55 | B | C |
| ATOM | 6044 | CB | THR | 46 | 88.550 | 57.988 | 64.038 | 1.00 | 21.32 | B | C |
| ATOM | 6045 | OG1 | THR | 46 | 87.148 | 57.700 | 64.083 | 1.00 | 21.56 | B | O |
| ATOM | 6046 | CG2 | THR | 46 | 88.745 | 59.497 | 64.053 | 1.00 | 20.61 | B | C |
| ATOM | 6047 | C | THR | 46 | 90.634 | 57.749 | 62.694 | 1.00 | 21.16 | B | C |
| ATOM | 6048 | O | THR | 46 | 90.999 | 58.759 | 62.092 | 1.00 | 21.06 | B | O |
| ATOM | 6049 | N | ASP | 47 | 91.491 | 56.945 | 63.313 | 1.00 | 21.00 | B | N |
| ATOM | 6050 | CA | ASP | 47 | 92.910 | 57.253 | 63.262 | 1.00 | 22.97 | B | C |
| ATOM | 6051 | CB | ASP | 47 | 93.731 | 56.273 | 64.110 | 1.00 | 25.34 | B | C |
| ATOM | 6052 | CG | ASP | 47 | 93.365 | 56.322 | 65.578 | 1.00 | 27.23 | B | C |
| ATOM | 6053 | OD1 | ASP | 47 | 93.116 | 57.430 | 66.105 | 1.00 | 26.32 | B | O |
| ATOM | 6054 | OD2 | ASP | 47 | 93.339 | 55.244 | 66.208 | 1.00 | 31.41 | B | O |
| ATOM | 6055 | C | ASP | 47 | 93.357 | 57.178 | 61.810 | 1.00 | 22.85 | B | C |
| ATOM | 6056 | O | ASP | 47 | 94.057 | 58.065 | 61.320 | 1.00 | 24.15 | B | O |
| ATOM | 6057 | N | TYR | 48 | 92.951 | 56.124 | 61.114 | 1.00 | 20.92 | B | N |
| ATOM | 6058 | CA | TYR | 48 | 93.332 | 55.998 | 59.720 | 1.00 | 21.40 | B | C |
| ATOM | 6059 | CB | TYR | 48 | 92.823 | 54.676 | 59.136 | 1.00 | 19.45 | B | C |
| ATOM | 6060 | CG | TYR | 48 | 92.867 | 54.612 | 57.624 | 1.00 | 18.60 | B | C |
| ATOM | 6061 | CD1 | TYR | 48 | 94.062 | 54.787 | 56.927 | 1.00 | 18.00 | B | C |
| ATOM | 6062 | CE1 | TYR | 48 | 94.098 | 54.734 | 55.531 | 1.00 | 16.57 | B | C |
| ATOM | 6063 | CD2 | TYR | 48 | 91.702 | 54.383 | 56.885 | 1.00 | 21.30 | B | C |
| ATOM | 6064 | CE2 | TYR | 48 | 91.726 | 54.329 | 55.489 | 1.00 | 19.50 | B | C |
| ATOM | 6065 | CZ | TYR | 48 | 92.925 | 54.503 | 54.822 | 1.00 | 18.43 | B | C |
| ATOM | 6066 | OH | TYR | 48 | 92.942 | 54.434 | 53.452 | 1.00 | 18.40 | B | O |
| ATOM | 6067 | C | TYR | 48 | 92.795 | 57.170 | 58.899 | 1.00 | 21.85 | B | C |
| ATOM | 6068 | O | TYR | 48 | 93.547 | 57.853 | 58.207 | 1.00 | 21.92 | B | O |
| ATOM | 6069 | N | LEU | 49 | 91.497 | 57.416 | 58.996 | 1.00 | 23.08 | B | N |
| ATOM | 6070 | CA | LEU | 49 | 90.885 | 58.485 | 58.223 | 1.00 | 26.78 | B | C |
| ATOM | 6071 | CB | LEU | 49 | 89.359 | 58.437 | 58.381 | 1.00 | 28.14 | B | C |
| ATOM | 6072 | CG | LEU | 49 | 88.688 | 57.157 | 57.872 | 1.00 | 28.75 | B | C |
| ATOM | 6073 | CD1 | LEU | 49 | 87.188 | 57.305 | 57.980 | 1.00 | 28.04 | B | C |
| ATOM | 6074 | CD2 | LEU | 49 | 89.094 | 56.889 | 56.420 | 1.00 | 28.45 | B | C |
| ATOM | 6075 | C | LEU | 49 | 91.391 | 59.886 | 58.544 | 1.00 | 28.33 | B | C |

| | | | | | | | | | | | |
|---|---|---|---|---|---|---|---|---|---|---|---|
| ATOM | 6076 | O | LEU | 49 | 91.404 | 60.758 | 57.673 | 1.00 | 28.77 | B | O |
| ATOM | 6077 | N | LYS | 50 | 91.818 | 60.098 | 59.784 | 1.00 | 30.17 | B | N |
| ATOM | 6078 | CA | LYS | 50 | 92.299 | 61.407 | 60.204 | 1.00 | 30.95 | B | C |
| ATOM | 6079 | CB | LYS | 50 | 91.668 | 61.769 | 61.543 | 1.00 | 31.36 | B | C |
| ATOM | 6080 | CG | LYS | 50 | 90.159 | 61.743 | 61.478 | 1.00 | 33.25 | B | C |
| ATOM | 6081 | CD | LYS | 50 | 89.649 | 62.710 | 60.420 | 1.00 | 34.69 | B | C |
| ATOM | 6082 | CE | LYS | 50 | 88.239 | 62.353 | 59.970 | 1.00 | 36.08 | B | C |
| ATOM | 6083 | NZ | LYS | 50 | 87.310 | 62.113 | 61.113 | 1.00 | 37.00 | B | N |
| ATOM | 6084 | C | LYS | 50 | 93.811 | 61.543 | 60.288 | 1.00 | 31.05 | B | C |
| ATOM | 6085 | O | LYS | 50 | 94.325 | 62.622 | 60.577 | 1.00 | 32.05 | B | O |
| ATOM | 6086 | N | ASN | 51 | 94.525 | 60.456 | 60.033 | 1.00 | 30.75 | B | N |
| ATOM | 6087 | CA | ASN | 51 | 95.978 | 60.493 | 60.074 | 1.00 | 31.14 | B | C |
| ATOM | 6088 | CB | ASN | 51 | 96.502 | 61.541 | 59.090 | 1.00 | 33.97 | B | C |
| ATOM | 6089 | CG | ASN | 51 | 95.964 | 61.344 | 57.689 | 1.00 | 37.06 | B | C |
| ATOM | 6090 | OD1 | ASN | 51 | 96.358 | 60.416 | 56.986 | 1.00 | 39.83 | B | O |
| ATOM | 6091 | ND2 | ASN | 51 | 95.047 | 62.215 | 57.277 | 1.00 | 40.54 | B | N |
| ATOM | 6092 | C | ASN | 51 | 96.472 | 60.828 | 61.471 | 1.00 | 29.86 | B | C |
| ATOM | 6093 | O | ASN | 51 | 97.474 | 61.524 | 61.624 | 1.00 | 31.03 | B | O |
| ATOM | 6094 | N | THR | 52 | 95.770 | 60.335 | 62.486 | 1.00 | 27.96 | B | N |
| ATOM | 6095 | CA | THR | 52 | 96.152 | 60.587 | 63.870 | 1.00 | 26.81 | B | C |
| ATOM | 6096 | CB | THR | 52 | 95.315 | 59.742 | 64.854 | 1.00 | 27.15 | B | C |
| ATOM | 6097 | OG1 | THR | 52 | 93.930 | 60.058 | 64.698 | 1.00 | 27.72 | B | O |
| ATOM | 6098 | CG2 | THR | 52 | 95.724 | 60.030 | 66.291 | 1.00 | 25.06 | B | C |
| ATOM | 6099 | C | THR | 52 | 97.622 | 60.259 | 64.090 | 1.00 | 26.88 | B | C |
| ATOM | 6100 | O | THR | 52 | 98.274 | 60.867 | 64.934 | 1.00 | 27.07 | B | O |
| ATOM | 6101 | N | TYR | 53 | 98.141 | 59.298 | 63.328 | 1.00 | 26.35 | B | N |
| ATOM | 6102 | CA | TYR | 53 | 99.541 | 58.900 | 63.450 | 1.00 | 27.48 | B | C |
| ATOM | 6103 | CB | TYR | 53 | 99.632 | 57.446 | 63.899 | 1.00 | 24.69 | B | C |
| ATOM | 6104 | CG | TYR | 53 | 98.937 | 57.209 | 65.207 | 1.00 | 24.64 | B | C |
| ATOM | 6105 | CD1 | TYR | 53 | 99.433 | 57.761 | 66.389 | 1.00 | 24.67 | B | C |
| ATOM | 6106 | CE1 | TYR | 53 | 98.782 | 57.566 | 67.600 | 1.00 | 24.44 | B | C |
| ATOM | 6107 | CD2 | TYR | 53 | 97.768 | 56.454 | 65.268 | 1.00 | 22.60 | B | C |
| ATOM | 6108 | CE2 | TYR | 53 | 97.107 | 56.255 | 66.474 | 1.00 | 24.81 | B | C |
| ATOM | 6109 | CZ | TYR | 53 | 97.622 | 56.813 | 67.634 | 1.00 | 25.33 | B | C |
| ATOM | 6110 | OH | TYR | 53 | 96.981 | 56.609 | 68.826 | 1.00 | 25.74 | B | O |
| ATOM | 6111 | C | TYR | 53 | 100.279 | 59.076 | 62.131 | 1.00 | 29.01 | B | C |
| ATOM | 6112 | O | TYR | 53 | 100.187 | 58.234 | 61.239 | 1.00 | 30.80 | B | O |
| ATOM | 6113 | N | ARG | 54 | 101.024 | 60.168 | 62.019 | 1.00 | 30.00 | B | N |
| ATOM | 6114 | CA | ARG | 54 | 101.760 | 60.456 | 60.801 | 1.00 | 29.57 | B | C |
| ATOM | 6115 | CB | ARG | 54 | 101.718 | 61.955 | 60.498 | 1.00 | 32.42 | B | C |
| ATOM | 6116 | CG | ARG | 54 | 100.360 | 62.449 | 60.020 | 1.00 | 38.51 | B | C |
| ATOM | 6117 | CD | ARG | 54 | 100.364 | 63.945 | 59.724 | 1.00 | 42.89 | B | C |
| ATOM | 6118 | NE | ARG | 54 | 99.157 | 64.354 | 59.008 | 1.00 | 46.94 | B | N |
| ATOM | 6119 | CZ | ARG | 54 | 98.812 | 63.893 | 57.808 | 1.00 | 48.52 | B | C |
| ATOM | 6120 | NH1 | ARG | 54 | 99.585 | 63.008 | 57.190 | 1.00 | 50.08 | B | N |
| ATOM | 6121 | NH2 | ARG | 54 | 97.697 | 64.314 | 57.224 | 1.00 | 47.87 | B | N |
| ATOM | 6122 | C | ARG | 54 | 103.202 | 59.992 | 60.803 | 1.00 | 27.73 | B | C |
| ATOM | 6123 | O | ARG | 54 | 103.934 | 60.168 | 61.776 | 1.00 | 26.62 | B | O |
| ATOM | 6124 | N | LEU | 55 | 103.596 | 59.384 | 59.693 | 1.00 | 25.96 | B | N |

FIG. 4-126 (Continued)

| | | | | | | | | | | |
|---|---|---|---|---|---|---|---|---|---|---|
| ATOM | 6125 | CA | LEU | 55 | 104.959 | 58.926 | 59.515 | 1.00 | 24.45 | B | C |
| ATOM | 6126 | CB | LEU | 55 | 105.025 | 57.911 | 58.382 | 1.00 | 22.51 | B | C |
| ATOM | 6127 | CG | LEU | 55 | 104.335 | 56.575 | 58.631 | 1.00 | 23.77 | B | C |
| ATOM | 6128 | CD1 | LEU | 55 | 104.287 | 55.792 | 57.336 | 1.00 | 23.51 | B | C |
| ATOM | 6129 | CD2 | LEU | 55 | 105.083 | 55.796 | 59.703 | 1.00 | 22.83 | B | C |
| ATOM | 6130 | C | LEU | 55 | 105.773 | 60.161 | 59.135 | 1.00 | 24.19 | B | C |
| ATOM | 6131 | O | LEU | 55 | 105.428 | 60.867 | 58.187 | 1.00 | 23.47 | B | O |
| ATOM | 6132 | N | LYS | 56 | 106.824 | 60.456 | 59.886 | 1.00 | 23.25 | B | N |
| ATOM | 6133 | CA | LYS | 56 | 107.631 | 61.603 | 59.532 | 1.00 | 23.81 | B | C |
| ATOM | 6134 | CB | LYS | 56 | 108.536 | 62.028 | 60.680 | 1.00 | 25.76 | B | C |
| ATOM | 6135 | CG | LYS | 56 | 107.850 | 62.922 | 61.697 | 1.00 | 29.15 | B | C |
| ATOM | 6136 | CD | LYS | 56 | 108.868 | 63.560 | 62.638 | 1.00 | 31.22 | B | C |
| ATOM | 6137 | CE | LYS | 56 | 108.225 | 64.593 | 63.548 | 1.00 | 32.59 | B | C |
| ATOM | 6138 | NZ | LYS | 56 | 109.235 | 65.233 | 64.439 | 1.00 | 34.54 | B | N |
| ATOM | 6139 | C | LYS | 56 | 108.458 | 61.196 | 58.330 | 1.00 | 23.35 | B | C |
| ATOM | 6140 | O | LYS | 56 | 108.833 | 60.035 | 58.186 | 1.00 | 23.24 | B | O |
| ATOM | 6141 | N | LEU | 57 | 108.717 | 62.162 | 57.462 | 1.00 | 22.99 | B | N |
| ATOM | 6142 | CA | LEU | 57 | 109.477 | 61.945 | 56.247 | 1.00 | 22.29 | B | C |
| ATOM | 6143 | CB | LEU | 57 | 108.612 | 62.292 | 55.040 | 1.00 | 23.21 | B | C |
| ATOM | 6144 | CG | LEU | 57 | 107.169 | 61.794 | 55.037 | 1.00 | 23.82 | B | C |
| ATOM | 6145 | CD1 | LEU | 57 | 106.440 | 62.380 | 53.841 | 1.00 | 24.84 | B | C |
| ATOM | 6146 | CD2 | LEU | 57 | 107.145 | 60.278 | 54.992 | 1.00 | 25.36 | B | C |
| ATOM | 6147 | C | LEU | 57 | 110.681 | 62.870 | 56.256 | 1.00 | 22.04 | B | C |
| ATOM | 6148 | O | LEU | 57 | 110.888 | 63.628 | 57.202 | 1.00 | 22.65 | B | O |
| ATOM | 6149 | N | TYR | 58 | 111.468 | 62.809 | 55.191 | 1.00 | 20.44 | B | N |
| ATOM | 6150 | CA | TYR | 58 | 112.624 | 63.674 | 55.065 | 1.00 | 20.14 | B | C |
| ATOM | 6151 | CB | TYR | 58 | 113.834 | 63.089 | 55.795 | 1.00 | 19.94 | B | C |
| ATOM | 6152 | CG | TYR | 58 | 114.933 | 64.099 | 56.008 | 1.00 | 18.95 | B | C |
| ATOM | 6153 | CD1 | TYR | 58 | 115.845 | 64.392 | 54.998 | 1.00 | 19.13 | B | C |
| ATOM | 6154 | CE1 | TYR | 58 | 116.816 | 65.380 | 55.165 | 1.00 | 18.92 | B | C |
| ATOM | 6155 | CD2 | TYR | 58 | 115.022 | 64.816 | 57.201 | 1.00 | 19.88 | B | C |
| ATOM | 6156 | CE2 | TYR | 58 | 115.987 | 65.807 | 57.378 | 1.00 | 19.69 | B | C |
| ATOM | 6157 | CZ | TYR | 58 | 116.877 | 66.086 | 56.355 | 1.00 | 19.43 | B | C |
| ATOM | 6158 | OH | TYR | 58 | 117.804 | 67.092 | 56.508 | 1.00 | 19.58 | B | O |
| ATOM | 6159 | C | TYR | 58 | 112.917 | 63.819 | 53.590 | 1.00 | 20.38 | B | C |
| ATOM | 6160 | O | TYR | 58 | 113.861 | 63.223 | 53.079 | 1.00 | 20.32 | B | O |
| ATOM | 6161 | N | SER | 59 | 112.085 | 64.604 | 52.909 | 1.00 | 21.33 | B | N |
| ATOM | 6162 | CA | SER | 59 | 112.245 | 64.839 | 51.479 | 1.00 | 22.11 | B | C |
| ATOM | 6163 | CB | SER | 59 | 110.920 | 65.275 | 50.852 | 1.00 | 21.08 | B | C |
| ATOM | 6164 | OG | SER | 59 | 109.985 | 64.212 | 50.843 | 1.00 | 24.94 | B | O |
| ATOM | 6165 | C | SER | 59 | 113.293 | 65.895 | 51.191 | 1.00 | 21.64 | B | C |
| ATOM | 6166 | O | SER | 59 | 113.099 | 67.064 | 51.491 | 1.00 | 23.87 | B | O |
| ATOM | 6167 | N | LEU | 60 | 114.404 | 65.485 | 50.602 | 1.00 | 21.76 | B | N |
| ATOM | 6168 | CA | LEU | 60 | 115.449 | 66.436 | 50.273 | 1.00 | 23.50 | B | C |
| ATOM | 6169 | CB | LEU | 60 | 116.752 | 66.062 | 50.986 | 1.00 | 22.27 | B | C |
| ATOM | 6170 | CG | LEU | 60 | 117.406 | 64.737 | 50.612 | 1.00 | 18.62 | B | C |
| ATOM | 6171 | CD1 | LEU | 60 | 118.176 | 64.900 | 49.320 | 1.00 | 17.05 | B | C |
| ATOM | 6172 | CD2 | LEU | 60 | 118.338 | 64.313 | 51.724 | 1.00 | 19.95 | B | C |
| ATOM | 6173 | C | LEU | 60 | 115.656 | 66.478 | 48.762 | 1.00 | 24.93 | B | C |

| | | | | | | | | | | |
|---|---|---|---|---|---|---|---|---|---|---|
| ATOM | 6174 | O | LEU | 60 | 115.176 | 65.604 | 48.029 | 1.00 | 23.79 | B | O |
| ATOM | 6175 | N | ARG | 61 | 116.375 | 67.495 | 48.302 | 1.00 | 26.02 | B | N |
| ATOM | 6176 | CA | ARG | 61 | 116.634 | 67.659 | 46.881 | 1.00 | 27.11 | B | C |
| ATOM | 6177 | CB | ARG | 61 | 115.693 | 68.728 | 46.329 | 1.00 | 32.13 | B | C |
| ATOM | 6178 | CG | ARG | 61 | 115.779 | 68.979 | 44.833 | 1.00 | 38.27 | B | C |
| ATOM | 6179 | CD | ARG | 61 | 115.002 | 70.243 | 44.495 | 1.00 | 41.78 | B | C |
| ATOM | 6180 | NE | ARG | 61 | 114.937 | 70.506 | 43.063 | 1.00 | 46.51 | B | N |
| ATOM | 6181 | CZ | ARG | 61 | 114.298 | 71.543 | 42.525 | 1.00 | 49.47 | B | C |
| ATOM | 6182 | NH1 | ARG | 61 | 113.671 | 72.420 | 43.307 | 1.00 | 48.74 | B | N |
| ATOM | 6183 | NH2 | ARG | 61 | 114.266 | 71.693 | 41.205 | 1.00 | 50.07 | B | N |
| ATOM | 6184 | C | ARG | 61 | 118.080 | 68.075 | 46.676 | 1.00 | 26.01 | B | C |
| ATOM | 6185 | O | ARG | 61 | 118.475 | 69.180 | 47.052 | 1.00 | 26.36 | B | O |
| ATOM | 6186 | N | TRP | 62 | 118.877 | 67.186 | 46.095 | 1.00 | 25.15 | B | N |
| ATOM | 6187 | CA | TRP | 62 | 120.282 | 67.488 | 45.846 | 1.00 | 24.48 | B | C |
| ATOM | 6188 | CB | TRP | 62 | 121.024 | 66.244 | 45.355 | 1.00 | 20.04 | B | C |
| ATOM | 6189 | CG | TRP | 62 | 121.095 | 65.145 | 46.365 | 1.00 | 18.16 | B | C |
| ATOM | 6190 | CD2 | TRP | 62 | 121.954 | 65.092 | 47.508 | 1.00 | 14.54 | B | C |
| ATOM | 6191 | CE2 | TRP | 62 | 121.639 | 63.910 | 48.215 | 1.00 | 15.18 | B | C |
| ATOM | 6192 | CE3 | TRP | 62 | 122.956 | 65.932 | 48.007 | 1.00 | 12.41 | B | C |
| ATOM | 6193 | CD1 | TRP | 62 | 120.315 | 64.017 | 46.419 | 1.00 | 17.39 | B | C |
| ATOM | 6194 | NE1 | TRP | 62 | 120.639 | 63.272 | 47.528 | 1.00 | 15.77 | B | N |
| ATOM | 6195 | CZ2 | TRP | 62 | 122.292 | 63.546 | 49.397 | 1.00 | 16.35 | B | C |
| ATOM | 6196 | CZ3 | TRP | 62 | 123.606 | 65.575 | 49.183 | 1.00 | 14.94 | B | C |
| ATOM | 6197 | CH2 | TRP | 62 | 123.271 | 64.389 | 49.866 | 1.00 | 16.25 | B | C |
| ATOM | 6198 | C | TRP | 62 | 120.401 | 68.588 | 44.798 | 1.00 | 26.73 | B | C |
| ATOM | 6199 | O | TRP | 62 | 119.863 | 68.457 | 43.698 | 1.00 | 27.86 | B | O |
| ATOM | 6200 | N | ILE | 63 | 121.088 | 69.675 | 45.135 | 1.00 | 27.97 | B | N |
| ATOM | 6201 | CA | ILE | 63 | 121.265 | 70.763 | 44.180 | 1.00 | 29.02 | B | C |
| ATOM | 6202 | CB | ILE | 63 | 120.947 | 72.130 | 44.803 | 1.00 | 29.64 | B | C |
| ATOM | 6203 | CG2 | ILE | 63 | 119.476 | 72.193 | 45.169 | 1.00 | 30.36 | B | C |
| ATOM | 6204 | CG1 | ILE | 63 | 121.830 | 72.372 | 46.027 | 1.00 | 30.01 | B | C |
| ATOM | 6205 | CD1 | ILE | 63 | 121.542 | 73.682 | 46.736 | 1.00 | 27.88 | B | C |
| ATOM | 6206 | C | ILE | 63 | 122.693 | 70.771 | 43.657 | 1.00 | 30.19 | B | C |
| ATOM | 6207 | O | ILE | 63 | 123.062 | 71.609 | 42.835 | 1.00 | 31.12 | B | O |
| ATOM | 6208 | N | SER | 64 | 123.485 | 69.816 | 44.132 | 1.00 | 30.03 | B | N |
| ATOM | 6209 | CA | SER | 64 | 124.876 | 69.668 | 43.718 | 1.00 | 30.53 | B | C |
| ATOM | 6210 | CB | SER | 64 | 125.734 | 70.808 | 44.269 | 1.00 | 29.46 | B | C |
| ATOM | 6211 | OG | SER | 64 | 125.848 | 70.724 | 45.679 | 1.00 | 27.92 | B | O |
| ATOM | 6212 | C | SER | 64 | 125.399 | 68.343 | 44.255 | 1.00 | 31.08 | B | C |
| ATOM | 6213 | O | SER | 64 | 124.630 | 67.488 | 44.691 | 1.00 | 31.36 | B | O |
| ATOM | 6214 | N | ASP | 65 | 126.712 | 68.176 | 44.236 | 1.00 | 31.42 | B | N |
| ATOM | 6215 | CA | ASP | 65 | 127.306 | 66.947 | 44.728 | 1.00 | 32.55 | B | C |
| ATOM | 6216 | CB | ASP | 65 | 128.576 | 66.633 | 43.945 | 1.00 | 33.28 | B | C |
| ATOM | 6217 | CG | ASP | 65 | 129.158 | 65.286 | 44.302 | 1.00 | 35.12 | B | C |
| ATOM | 6218 | OD1 | ASP | 65 | 128.446 | 64.261 | 44.158 | 1.00 | 33.02 | B | O |
| ATOM | 6219 | OD2 | ASP | 65 | 130.331 | 65.259 | 44.728 | 1.00 | 37.02 | B | O |
| ATOM | 6220 | C | ASP | 65 | 127.636 | 67.045 | 46.211 | 1.00 | 32.66 | B | C |
| ATOM | 6221 | O | ASP | 65 | 128.076 | 66.069 | 46.818 | 1.00 | 31.78 | B | O |
| ATOM | 6222 | N | HIS | 66 | 127.399 | 68.217 | 46.796 | 1.00 | 33.06 | B | N |

FIG. 4-128 (Continued)

| | | | | | | | | | | |
|---|---|---|---|---|---|---|---|---|---|---|
| ATOM | 6223 | CA | HIS | 66 | 127.704 | 68.440 | 48.203 | 1.00 | 32.64 | B | C |
| ATOM | 6224 | CB | HIS | 66 | 128.892 | 69.402 | 48.329 | 1.00 | 35.63 | B | C |
| ATOM | 6225 | CG | HIS | 66 | 130.032 | 69.076 | 47.416 | 1.00 | 39.09 | B | C |
| ATOM | 6226 | CD2 | HIS | 66 | 131.260 | 68.562 | 47.669 | 1.00 | 40.29 | B | C |
| ATOM | 6227 | ND1 | HIS | 66 | 129.959 | 69.238 | 46.047 | 1.00 | 41.80 | B | N |
| ATOM | 6228 | CE1 | HIS | 66 | 131.092 | 68.835 | 45.498 | 1.00 | 42.37 | B | C |
| ATOM | 6229 | NE2 | HIS | 66 | 131.897 | 68.420 | 46.459 | 1.00 | 42.11 | B | N |
| ATOM | 6230 | C | HIS | 66 | 126.547 | 69.001 | 49.016 | 1.00 | 31.01 | B | C |
| ATOM | 6231 | O | HIS | 66 | 126.602 | 69.008 | 50.245 | 1.00 | 30.92 | B | O |
| ATOM | 6232 | N | GLU | 67 | 125.505 | 69.479 | 48.345 | 1.00 | 30.05 | B | N |
| ATOM | 6233 | CA | GLU | 67 | 124.379 | 70.067 | 49.062 | 1.00 | 28.07 | B | C |
| ATOM | 6234 | CB | GLU | 67 | 124.457 | 71.591 | 48.984 | 1.00 | 27.21 | B | C |
| ATOM | 6235 | CG | GLU | 67 | 125.601 | 72.179 | 49.781 | 1.00 | 29.99 | B | C |
| ATOM | 6236 | CD | GLU | 67 | 125.745 | 73.675 | 49.593 | 1.00 | 32.09 | B | C |
| ATOM | 6237 | OE1 | GLU | 67 | 126.408 | 74.315 | 50.438 | 1.00 | 33.25 | B | O |
| ATOM | 6238 | OE2 | GLU | 67 | 125.207 | 74.209 | 48.599 | 1.00 | 34.83 | B | O |
| ATOM | 6239 | C | GLU | 67 | 123.015 | 69.619 | 48.583 | 1.00 | 27.52 | B | C |
| ATOM | 6240 | O | GLU | 67 | 122.872 | 69.085 | 47.482 | 1.00 | 27.10 | B | O |
| ATOM | 6241 | N | TYR | 68 | 122.012 | 69.855 | 49.425 | 1.00 | 26.72 | B | N |
| ATOM | 6242 | CA | TYR | 68 | 120.634 | 69.498 | 49.116 | 1.00 | 25.74 | B | C |
| ATOM | 6243 | CB | TYR | 68 | 120.347 | 68.069 | 49.592 | 1.00 | 23.47 | B | C |
| ATOM | 6244 | CG | TYR | 68 | 120.373 | 67.847 | 51.094 | 1.00 | 22.93 | B | C |
| ATOM | 6245 | CD1 | TYR | 68 | 119.339 | 68.319 | 51.914 | 1.00 | 22.75 | B | C |
| ATOM | 6246 | CE1 | TYR | 68 | 119.312 | 68.040 | 53.282 | 1.00 | 21.24 | B | C |
| ATOM | 6247 | CD2 | TYR | 68 | 121.391 | 67.097 | 51.685 | 1.00 | 22.05 | B | C |
| ATOM | 6248 | CE2 | TYR | 68 | 121.379 | 66.812 | 53.053 | 1.00 | 22.38 | B | C |
| ATOM | 6249 | CZ | TYR | 68 | 120.333 | 67.283 | 53.847 | 1.00 | 23.05 | B | C |
| ATOM | 6250 | OH | TYR | 68 | 120.300 | 66.973 | 55.191 | 1.00 | 18.34 | B | O |
| ATOM | 6251 | C | TYR | 68 | 119.657 | 70.481 | 49.759 | 1.00 | 26.00 | B | C |
| ATOM | 6252 | O | TYR | 68 | 119.961 | 71.077 | 50.789 | 1.00 | 26.50 | B | O |
| ATOM | 6253 | N | LEU | 69 | 118.497 | 70.674 | 49.139 | 1.00 | 26.72 | B | N |
| ATOM | 6254 | CA | LEU | 69 | 117.492 | 71.580 | 49.694 | 1.00 | 27.89 | B | C |
| ATOM | 6255 | CB | LEU | 69 | 116.729 | 72.316 | 48.586 | 1.00 | 24.29 | B | C |
| ATOM | 6256 | CG | LEU | 69 | 117.545 | 73.257 | 47.695 | 1.00 | 23.81 | B | C |
| ATOM | 6257 | CD1 | LEU | 69 | 116.656 | 73.891 | 46.633 | 1.00 | 19.95 | B | C |
| ATOM | 6258 | CD2 | LEU | 69 | 118.187 | 74.324 | 48.552 | 1.00 | 24.79 | B | C |
| ATOM | 6259 | C | LEU | 69 | 116.508 | 70.777 | 50.543 | 1.00 | 29.18 | B | C |
| ATOM | 6260 | O | LEU | 69 | 116.226 | 69.609 | 50.260 | 1.00 | 28.86 | B | O |
| ATOM | 6261 | N | TYR | 70 | 115.998 | 71.411 | 51.590 | 1.00 | 29.78 | B | N |
| ATOM | 6262 | CA | TYR | 70 | 115.057 | 70.765 | 52.482 | 1.00 | 31.48 | B | C |
| ATOM | 6263 | CB | TYR | 70 | 115.799 | 70.142 | 53.667 | 1.00 | 28.76 | B | C |
| ATOM | 6264 | CG | TYR | 70 | 114.910 | 69.348 | 54.592 | 1.00 | 26.47 | B | C |
| ATOM | 6265 | CD1 | TYR | 70 | 114.396 | 68.114 | 54.206 | 1.00 | 25.75 | B | C |
| ATOM | 6266 | CE1 | TYR | 70 | 113.544 | 67.398 | 55.038 | 1.00 | 26.40 | B | C |
| ATOM | 6267 | CD2 | TYR | 70 | 114.553 | 69.847 | 55.842 | 1.00 | 28.33 | B | C |
| ATOM | 6268 | CE2 | TYR | 70 | 113.701 | 69.141 | 56.686 | 1.00 | 28.03 | B | C |
| ATOM | 6269 | CZ | TYR | 70 | 113.199 | 67.918 | 56.276 | 1.00 | 28.21 | B | C |
| ATOM | 6270 | OH | TYR | 70 | 112.346 | 67.221 | 57.103 | 1.00 | 30.20 | B | O |
| ATOM | 6271 | C | TYR | 70 | 114.056 | 71.796 | 52.983 | 1.00 | 34.45 | B | C |

FIG. 4-129 (Continued)

| | | | | | | | | | | | |
|---|---|---|---|---|---|---|---|---|---|---|---|
| ATOM | 6272 | O | TYR | 70 | 114.425 | 72.914 | 53.336 | 1.00 | 33.43 | B | O |
| ATOM | 6273 | N | LYS | 71 | 112.787 | 71.410 | 53.002 | 1.00 | 39.59 | B | N |
| ATOM | 6274 | CA | LYS | 71 | 111.714 | 72.284 | 53.461 | 1.00 | 44.28 | B | C |
| ATOM | 6275 | CB | LYS | 71 | 110.408 | 71.904 | 52.763 | 1.00 | 45.57 | B | C |
| ATOM | 6276 | CG | LYS | 71 | 109.994 | 72.828 | 51.640 | 1.00 | 48.26 | B | C |
| ATOM | 6277 | CD | LYS | 71 | 109.416 | 74.116 | 52.192 | 1.00 | 51.24 | B | C |
| ATOM | 6278 | CE | LYS | 71 | 108.213 | 73.827 | 53.075 | 1.00 | 53.11 | B | C |
| ATOM | 6279 | NZ | LYS | 71 | 107.193 | 73.012 | 52.354 | 1.00 | 54.56 | B | N |
| ATOM | 6280 | C | LYS | 71 | 111.523 | 72.186 | 54.973 | 1.00 | 46.60 | B | C |
| ATOM | 6281 | O | LYS | 71 | 110.789 | 71.323 | 55.457 | 1.00 | 46.95 | B | O |
| ATOM | 6282 | N | GLN | 72 | 112.192 | 73.055 | 55.723 | 1.00 | 49.39 | B | N |
| ATOM | 6283 | CA | GLN | 72 | 112.040 | 73.042 | 57.172 | 1.00 | 52.01 | B | C |
| ATOM | 6284 | CB | GLN | 72 | 113.145 | 73.853 | 57.851 | 1.00 | 51.69 | B | C |
| ATOM | 6285 | CG | GLN | 72 | 113.126 | 73.763 | 59.373 | 1.00 | 52.37 | B | C |
| ATOM | 6286 | CD | GLN | 72 | 113.582 | 72.412 | 59.895 | 1.00 | 51.86 | B | C |
| ATOM | 6287 | OE1 | GLN | 72 | 114.778 | 72.161 | 60.048 | 1.00 | 50.84 | B | O |
| ATOM | 6288 | NE2 | GLN | 72 | 112.629 | 71.530 | 60.161 | 1.00 | 52.39 | B | N |
| ATOM | 6289 | C | GLN | 72 | 110.690 | 73.691 | 57.427 | 1.00 | 54.22 | B | C |
| ATOM | 6290 | O | GLN | 72 | 109.890 | 73.814 | 56.498 | 1.00 | 54.44 | B | O |
| ATOM | 6291 | N | GLU | 73 | 110.447 | 74.100 | 58.672 | 1.00 | 56.57 | B | N |
| ATOM | 6292 | CA | GLU | 73 | 109.197 | 74.745 | 59.075 | 1.00 | 58.47 | B | C |
| ATOM | 6293 | CB | GLU | 73 | 109.498 | 76.089 | 59.738 | 1.00 | 60.20 | B | C |
| ATOM | 6294 | CG | GLU | 73 | 110.530 | 76.022 | 60.861 | 1.00 | 62.04 | B | C |
| ATOM | 6295 | CD | GLU | 73 | 110.065 | 75.206 | 62.055 | 1.00 | 62.79 | B | C |
| ATOM | 6296 | OE1 | GLU | 73 | 110.815 | 75.145 | 63.053 | 1.00 | 64.53 | B | O |
| ATOM | 6297 | OE2 | GLU | 73 | 108.957 | 74.628 | 62.001 | 1.00 | 62.71 | B | O |
| ATOM | 6298 | C | GLU | 73 | 108.293 | 74.962 | 57.867 | 1.00 | 59.40 | B | C |
| ATOM | 6299 | O | GLU | 73 | 107.242 | 74.329 | 57.733 | 1.00 | 61.08 | B | O |
| ATOM | 6300 | N | ASN | 74 | 108.717 | 75.863 | 56.989 | 1.00 | 58.30 | B | N |
| ATOM | 6301 | CA | ASN | 74 | 107.987 | 76.156 | 55.768 | 1.00 | 57.33 | B | C |
| ATOM | 6302 | CB | ASN | 74 | 106.771 | 77.035 | 56.054 | 1.00 | 59.07 | B | C |
| ATOM | 6303 | CG | ASN | 74 | 105.474 | 76.399 | 55.581 | 1.00 | 60.80 | B | C |
| ATOM | 6304 | OD1 | ASN | 74 | 105.350 | 76.006 | 54.418 | 1.00 | 61.62 | B | O |
| ATOM | 6305 | ND2 | ASN | 74 | 104.501 | 76.293 | 56.482 | 1.00 | 60.69 | B | N |
| ATOM | 6306 | C | ASN | 74 | 108.938 | 76.858 | 54.815 | 1.00 | 56.35 | B | C |
| ATOM | 6307 | O | ASN | 74 | 108.666 | 76.979 | 53.620 | 1.00 | 56.72 | B | O |
| ATOM | 6308 | N | ASN | 75 | 110.059 | 77.321 | 55.355 | 1.00 | 54.35 | B | N |
| ATOM | 6309 | CA | ASN | 75 | 111.064 | 77.984 | 54.544 | 1.00 | 52.33 | B | C |
| ATOM | 6310 | CB | ASN | 75 | 111.793 | 79.055 | 55.355 | 1.00 | 55.77 | B | C |
| ATOM | 6311 | CG | ASN | 75 | 111.992 | 78.659 | 56.793 | 1.00 | 57.61 | B | C |
| ATOM | 6312 | OD1 | ASN | 75 | 112.467 | 77.563 | 57.088 | 1.00 | 60.07 | B | O |
| ATOM | 6313 | ND2 | ASN | 75 | 111.635 | 79.556 | 57.705 | 1.00 | 59.51 | B | N |
| ATOM | 6314 | C | ASN | 75 | 112.048 | 76.943 | 54.026 | 1.00 | 49.25 | B | C |
| ATOM | 6315 | O | ASN | 75 | 112.052 | 75.798 | 54.477 | 1.00 | 49.19 | B | O |
| ATOM | 6316 | N | ILE | 76 | 112.883 | 77.343 | 53.077 | 1.00 | 45.23 | B | N |
| ATOM | 6317 | CA | ILE | 76 | 113.837 | 76.424 | 52.483 | 1.00 | 41.55 | B | C |
| ATOM | 6318 | CB | ILE | 76 | 113.871 | 76.616 | 50.962 | 1.00 | 41.68 | B | C |
| ATOM | 6319 | CG2 | ILE | 76 | 114.705 | 75.524 | 50.310 | 1.00 | 41.39 | B | C |
| ATOM | 6320 | CG1 | ILE | 76 | 112.445 | 76.583 | 50.415 | 1.00 | 40.24 | B | C |

FIG. 4-130 (Continued)

| | | | | | | | | | | | |
|---|---|---|---|---|---|---|---|---|---|---|---|
| ATOM | 6321 | CD1 | ILE | 76 | 112.341 | 77.009 | 48.967 | 1.00 | 42.01 | B | C |
| ATOM | 6322 | C | ILE | 76 | 115.243 | 76.589 | 53.043 | 1.00 | 39.85 | B | C |
| ATOM | 6323 | O | ILE | 76 | 115.758 | 77.701 | 53.150 | 1.00 | 41.15 | B | O |
| ATOM | 6324 | N | LEU | 77 | 115.862 | 75.472 | 53.400 | 1.00 | 36.42 | B | N |
| ATOM | 6325 | CA | LEU | 77 | 117.208 | 75.498 | 53.941 | 1.00 | 34.22 | B | C |
| ATOM | 6326 | CB | LEU | 77 | 117.227 | 74.901 | 55.351 | 1.00 | 34.28 | B | C |
| ATOM | 6327 | CG | LEU | 77 | 116.155 | 75.359 | 56.346 | 1.00 | 34.54 | B | C |
| ATOM | 6328 | CD1 | LEU | 77 | 116.435 | 74.728 | 57.701 | 1.00 | 33.23 | B | C |
| ATOM | 6329 | CD2 | LEU | 77 | 116.149 | 76.874 | 56.460 | 1.00 | 34.45 | B | C |
| ATOM | 6330 | C | LEU | 77 | 118.121 | 74.683 | 53.036 | 1.00 | 32.91 | B | C |
| ATOM | 6331 | O | LEU | 77 | 117.657 | 73.821 | 52.289 | 1.00 | 32.49 | B | O |
| ATOM | 6332 | N | VAL | 78 | 119.417 | 74.967 | 53.103 | 1.00 | 30.72 | B | N |
| ATOM | 6333 | CA | VAL | 78 | 120.409 | 74.253 | 52.308 | 1.00 | 29.87 | B | C |
| ATOM | 6334 | CB | VAL | 78 | 121.227 | 75.227 | 51.431 | 1.00 | 30.20 | B | C |
| ATOM | 6335 | CG1 | VAL | 78 | 122.327 | 74.480 | 50.691 | 1.00 | 29.01 | B | C |
| ATOM | 6336 | CG2 | VAL | 78 | 120.311 | 75.906 | 50.448 | 1.00 | 31.37 | B | C |
| ATOM | 6337 | C | VAL | 78 | 121.346 | 73.523 | 53.263 | 1.00 | 28.37 | B | C |
| ATOM | 6338 | O | VAL | 78 | 121.781 | 74.087 | 54.261 | 1.00 | 28.38 | B | O |
| ATOM | 6339 | N | PHE | 79 | 121.660 | 72.272 | 52.956 | 1.00 | 26.51 | B | N |
| ATOM | 6340 | CA | PHE | 79 | 122.530 | 71.496 | 53.821 | 1.00 | 24.85 | B | C |
| ATOM | 6341 | CB | PHE | 79 | 121.807 | 70.247 | 54.338 | 1.00 | 24.45 | B | C |
| ATOM | 6342 | CG | PHE | 79 | 120.680 | 70.531 | 55.296 | 1.00 | 22.62 | B | C |
| ATOM | 6343 | CD1 | PHE | 79 | 119.499 | 71.120 | 54.857 | 1.00 | 20.15 | B | C |
| ATOM | 6344 | CD2 | PHE | 79 | 120.789 | 70.168 | 56.636 | 1.00 | 19.84 | B | C |
| ATOM | 6345 | CE1 | PHE | 79 | 118.448 | 71.338 | 55.733 | 1.00 | 20.35 | B | C |
| ATOM | 6346 | CE2 | PHE | 79 | 119.749 | 70.382 | 57.513 | 1.00 | 16.96 | B | C |
| ATOM | 6347 | CZ | PHE | 79 | 118.573 | 70.967 | 57.065 | 1.00 | 18.97 | B | C |
| ATOM | 6348 | C | PHE | 79 | 123.815 | 71.036 | 53.151 | 1.00 | 24.95 | B | C |
| ATOM | 6349 | O | PHE | 79 | 123.841 | 70.729 | 51.960 | 1.00 | 24.94 | B | O |
| ATOM | 6350 | N | ASN | 80 | 124.876 | 70.992 | 53.948 | 1.00 | 23.66 | B | N |
| ATOM | 6351 | CA | ASN | 80 | 126.174 | 70.518 | 53.517 | 1.00 | 23.32 | B | C |
| ATOM | 6352 | CB | ASN | 80 | 127.276 | 71.307 | 54.220 | 1.00 | 22.91 | B | C |
| ATOM | 6353 | CG | ASN | 80 | 128.653 | 70.689 | 54.032 | 1.00 | 22.91 | B | C |
| ATOM | 6354 | OD1 | ASN | 80 | 128.916 | 69.567 | 54.486 | 1.00 | 23.26 | B | O |
| ATOM | 6355 | ND2 | ASN | 80 | 129.542 | 71.421 | 53.364 | 1.00 | 21.99 | B | N |
| ATOM | 6356 | C | ASN | 80 | 126.156 | 69.077 | 54.018 | 1.00 | 24.17 | B | C |
| ATOM | 6357 | O | ASN | 80 | 126.168 | 68.842 | 55.222 | 1.00 | 25.80 | B | O |
| ATOM | 6358 | N | ALA | 81 | 126.116 | 68.116 | 53.105 | 1.00 | 23.17 | B | N |
| ATOM | 6359 | CA | ALA | 81 | 126.054 | 66.713 | 53.496 | 1.00 | 24.07 | B | C |
| ATOM | 6360 | CB | ALA | 81 | 126.025 | 65.819 | 52.246 | 1.00 | 20.69 | B | C |
| ATOM | 6361 | C | ALA | 81 | 127.167 | 66.256 | 54.434 | 1.00 | 25.23 | B | C |
| ATOM | 6362 | O | ALA | 81 | 126.925 | 65.462 | 55.347 | 1.00 | 25.26 | B | O |
| ATOM | 6363 | N | GLU | 82 | 128.377 | 66.764 | 54.222 | 1.00 | 26.73 | B | N |
| ATOM | 6364 | CA | GLU | 82 | 129.525 | 66.351 | 55.024 | 1.00 | 29.51 | B | C |
| ATOM | 6365 | CB | GLU | 82 | 130.820 | 66.835 | 54.361 | 1.00 | 32.02 | B | C |
| ATOM | 6366 | CG | GLU | 82 | 132.124 | 66.326 | 55.005 | 1.00 | 35.72 | B | C |
| ATOM | 6367 | CD | GLU | 82 | 132.287 | 64.800 | 54.955 | 1.00 | 38.90 | B | C |
| ATOM | 6368 | OE1 | GLU | 82 | 132.064 | 64.191 | 53.884 | 1.00 | 38.71 | B | O |
| ATOM | 6369 | OE2 | GLU | 82 | 132.659 | 64.209 | 55.995 | 1.00 | 40.81 | B | O |

FIG. 4-131 (Continued)

| | | | | | | | | | | | |
|---|---|---|---|---|---|---|---|---|---|---|---|
| ATOM | 6370 | C | GLU | 82 | 129.528 | 66.757 | 56.497 | 1.00 | 29.17 | B | C |
| ATOM | 6371 | O | GLU | 82 | 130.102 | 66.051 | 57.324 | 1.00 | 28.55 | B | O |
| ATOM | 6372 | N | TYR | 83 | 128.888 | 67.872 | 56.834 | 1.00 | 29.07 | B | N |
| ATOM | 6373 | CA | TYR | 83 | 128.877 | 68.329 | 58.223 | 1.00 | 28.95 | B | C |
| ATOM | 6374 | CB | TYR | 83 | 129.504 | 69.722 | 58.320 | 1.00 | 30.17 | B | C |
| ATOM | 6375 | CG | TYR | 83 | 130.821 | 69.834 | 57.596 | 1.00 | 33.40 | B | C |
| ATOM | 6376 | CD1 | TYR | 83 | 131.914 | 69.049 | 57.963 | 1.00 | 33.79 | B | C |
| ATOM | 6377 | CE1 | TYR | 83 | 133.120 | 69.129 | 57.271 | 1.00 | 36.07 | B | C |
| ATOM | 6378 | CD2 | TYR | 83 | 130.966 | 70.704 | 56.517 | 1.00 | 35.97 | B | C |
| ATOM | 6379 | CE2 | TYR | 83 | 132.162 | 70.791 | 55.815 | 1.00 | 36.91 | B | C |
| ATOM | 6380 | CZ | TYR | 83 | 133.234 | 70.003 | 56.195 | 1.00 | 38.12 | B | C |
| ATOM | 6381 | OH | TYR | 83 | 134.413 | 70.091 | 55.486 | 1.00 | 42.42 | B | O |
| ATOM | 6382 | C | TYR | 83 | 127.490 | 68.355 | 58.853 | 1.00 | 28.16 | B | C |
| ATOM | 6383 | O | TYR | 83 | 127.340 | 68.093 | 60.044 | 1.00 | 29.04 | B | O |
| ATOM | 6384 | N | GLY | 84 | 126.478 | 68.684 | 58.063 | 1.00 | 25.68 | B | N |
| ATOM | 6385 | CA | GLY | 84 | 125.136 | 68.726 | 58.601 | 1.00 | 24.77 | B | C |
| ATOM | 6386 | C | GLY | 84 | 124.668 | 70.137 | 58.880 | 1.00 | 24.95 | B | C |
| ATOM | 6387 | O | GLY | 84 | 123.511 | 70.345 | 59.222 | 1.00 | 23.68 | B | O |
| ATOM | 6388 | N | ASN | 85 | 125.565 | 71.109 | 58.745 | 1.00 | 26.40 | B | N |
| ATOM | 6389 | CA | ASN | 85 | 125.201 | 72.501 | 58.984 | 1.00 | 27.79 | B | C |
| ATOM | 6390 | CB | ASN | 85 | 126.446 | 73.366 | 59.181 | 1.00 | 28.01 | B | C |
| ATOM | 6391 | CG | ASN | 85 | 127.356 | 73.363 | 57.975 | 1.00 | 31.32 | B | C |
| ATOM | 6392 | OD1 | ASN | 85 | 128.051 | 72.384 | 57.697 | 1.00 | 31.73 | B | O |
| ATOM | 6393 | ND2 | ASN | 85 | 127.338 | 74.472 | 57.250 | 1.00 | 33.71 | B | N |
| ATOM | 6394 | C | ASN | 85 | 124.381 | 73.023 | 57.813 | 1.00 | 28.62 | B | C |
| ATOM | 6395 | O | ASN | 85 | 124.432 | 72.472 | 56.720 | 1.00 | 28.74 | B | O |
| ATOM | 6396 | N | SER | 86 | 123.622 | 74.085 | 58.043 | 1.00 | 30.17 | B | N |
| ATOM | 6397 | CA | SER | 86 | 122.787 | 74.633 | 56.991 | 1.00 | 32.38 | B | C |
| ATOM | 6398 | CB | SER | 86 | 121.392 | 74.005 | 57.061 | 1.00 | 31.71 | B | C |
| ATOM | 6399 | OG | SER | 86 | 120.734 | 74.380 | 58.256 | 1.00 | 32.32 | B | O |
| ATOM | 6400 | C | SER | 86 | 122.658 | 76.145 | 57.063 | 1.00 | 33.63 | B | C |
| ATOM | 6401 | O | SER | 86 | 123.307 | 76.800 | 57.874 | 1.00 | 34.72 | B | O |
| ATOM | 6402 | N | SER | 87 | 121.806 | 76.682 | 56.195 | 1.00 | 35.45 | B | N |
| ATOM | 6403 | CA | SER | 87 | 121.530 | 78.111 | 56.115 | 1.00 | 35.95 | B | C |
| ATOM | 6404 | CB | SER | 87 | 122.588 | 78.825 | 55.280 | 1.00 | 35.50 | B | C |
| ATOM | 6405 | OG | SER | 87 | 123.887 | 78.635 | 55.810 | 1.00 | 39.27 | B | O |
| ATOM | 6406 | C | SER | 87 | 120.191 | 78.233 | 55.418 | 1.00 | 36.74 | B | C |
| ATOM | 6407 | O | SER | 87 | 119.832 | 77.369 | 54.625 | 1.00 | 38.47 | B | O |
| ATOM | 6408 | N | VAL | 88 | 119.444 | 79.288 | 55.723 | 1.00 | 37.17 | B | N |
| ATOM | 6409 | CA | VAL | 88 | 118.154 | 79.498 | 55.084 | 1.00 | 36.32 | B | C |
| ATOM | 6410 | CB | VAL | 88 | 117.357 | 80.636 | 55.750 | 1.00 | 37.21 | B | C |
| ATOM | 6411 | CG1 | VAL | 88 | 116.094 | 80.916 | 54.954 | 1.00 | 36.84 | B | C |
| ATOM | 6412 | CG2 | VAL | 88 | 117.006 | 80.260 | 57.186 | 1.00 | 38.04 | B | C |
| ATOM | 6413 | C | VAL | 88 | 118.422 | 79.897 | 53.647 | 1.00 | 36.83 | B | C |
| ATOM | 6414 | O | VAL | 88 | 119.235 | 80.782 | 53.379 | 1.00 | 36.34 | B | O |
| ATOM | 6415 | N | PHE | 89 | 117.745 | 79.240 | 52.719 | 1.00 | 36.53 | B | N |
| ATOM | 6416 | CA | PHE | 89 | 117.925 | 79.552 | 51.314 | 1.00 | 37.05 | B | C |
| ATOM | 6417 | CB | PHE | 89 | 117.901 | 78.262 | 50.491 | 1.00 | 34.62 | B | C |
| ATOM | 6418 | CG | PHE | 89 | 118.060 | 78.474 | 49.014 | 1.00 | 31.67 | B | C |

| ATOM | 6419 | CD1 | PHE | 89 | 116.963 | 78.790 | 48.223 | 1.00 | 29.04 | B | C |
|---|---|---|---|---|---|---|---|---|---|---|---|
| ATOM | 6420 | CD2 | PHE | 89 | 119.303 | 78.333 | 48.412 | 1.00 | 31.62 | B | C |
| ATOM | 6421 | CE1 | PHE | 89 | 117.095 | 78.958 | 46.857 | 1.00 | 28.72 | B | C |
| ATOM | 6422 | CE2 | PHE | 89 | 119.450 | 78.500 | 47.038 | 1.00 | 32.27 | B | C |
| ATOM | 6423 | CZ | PHE | 89 | 118.342 | 78.813 | 46.258 | 1.00 | 30.91 | B | C |
| ATOM | 6424 | C | PHE | 89 | 116.801 | 80.483 | 50.896 | 1.00 | 39.38 | B | C |
| ATOM | 6425 | O | PHE | 89 | 116.901 | 81.188 | 49.892 | 1.00 | 39.89 | B | O |
| ATOM | 6426 | N | LEU | 90 | 115.733 | 80.493 | 51.688 | 1.00 | 41.53 | B | N |
| ATOM | 6427 | CA | LEU | 90 | 114.581 | 81.332 | 51.403 | 1.00 | 43.78 | B | C |
| ATOM | 6428 | CB | LEU | 90 | 113.849 | 80.788 | 50.173 | 1.00 | 44.69 | B | C |
| ATOM | 6429 | CG | LEU | 90 | 112.818 | 81.664 | 49.462 | 1.00 | 44.94 | B | C |
| ATOM | 6430 | CD1 | LEU | 90 | 113.439 | 83.000 | 49.088 | 1.00 | 44.39 | B | C |
| ATOM | 6431 | CD2 | LEU | 90 | 112.328 | 80.944 | 48.217 | 1.00 | 44.54 | B | C |
| ATOM | 6432 | C | LEU | 90 | 113.653 | 81.348 | 52.613 | 1.00 | 45.79 | B | C |
| ATOM | 6433 | O | LEU | 90 | 113.192 | 80.302 | 53.062 | 1.00 | 44.77 | B | O |
| ATOM | 6434 | N | GLU | 91 | 113.395 | 82.542 | 53.140 | 1.00 | 49.59 | B | N |
| ATOM | 6435 | CA | GLU | 91 | 112.524 | 82.715 | 54.302 | 1.00 | 51.78 | B | C |
| ATOM | 6436 | CB | GLU | 91 | 112.571 | 84.166 | 54.790 | 1.00 | 53.90 | B | C |
| ATOM | 6437 | CG | GLU | 91 | 113.950 | 84.663 | 55.199 | 1.00 | 58.64 | B | C |
| ATOM | 6438 | CD | GLU | 91 | 114.432 | 84.070 | 56.511 | 1.00 | 61.93 | B | C |
| ATOM | 6439 | OE1 | GLU | 91 | 114.607 | 82.835 | 56.585 | 1.00 | 64.17 | B | O |
| ATOM | 6440 | OE2 | GLU | 91 | 114.639 | 84.843 | 57.472 | 1.00 | 63.53 | B | O |
| ATOM | 6441 | C | GLU | 91 | 111.083 | 82.352 | 53.961 | 1.00 | 52.17 | B | C |
| ATOM | 6442 | O | GLU | 91 | 110.549 | 82.777 | 52.939 | 1.00 | 50.91 | B | O |
| ATOM | 6443 | N | ASN | 92 | 110.452 | 81.576 | 54.835 | 1.00 | 53.63 | B | N |
| ATOM | 6444 | CA | ASN | 92 | 109.073 | 81.146 | 54.631 | 1.00 | 54.46 | B | C |
| ATOM | 6445 | CB | ASN | 92 | 108.654 | 80.205 | 55.761 | 1.00 | 55.64 | B | C |
| ATOM | 6446 | CG | ASN | 92 | 108.451 | 80.934 | 57.074 | 1.00 | 57.59 | B | C |
| ATOM | 6447 | OD1 | ASN | 92 | 109.140 | 81.914 | 57.362 | 1.00 | 59.33 | B | O |
| ATOM | 6448 | ND2 | ASN | 92 | 107.512 | 80.451 | 57.885 | 1.00 | 57.67 | B | N |
| ATOM | 6449 | C | ASN | 92 | 108.116 | 82.336 | 54.581 | 1.00 | 53.80 | B | C |
| ATOM | 6450 | O | ASN | 92 | 106.924 | 82.171 | 54.328 | 1.00 | 53.09 | B | O |
| ATOM | 6451 | N | SER | 93 | 108.646 | 83.532 | 54.818 | 1.00 | 53.62 | B | N |
| ATOM | 6452 | CA | SER | 93 | 107.833 | 84.744 | 54.813 | 1.00 | 53.91 | B | C |
| ATOM | 6453 | CB | SER | 93 | 108.078 | 85.527 | 56.100 | 1.00 | 53.85 | B | C |
| ATOM | 6454 | OG | SER | 93 | 109.438 | 85.905 | 56.196 | 1.00 | 54.56 | B | O |
| ATOM | 6455 | C | SER | 93 | 108.097 | 85.658 | 53.618 | 1.00 | 53.82 | B | C |
| ATOM | 6456 | O | SER | 93 | 107.391 | 86.646 | 53.421 | 1.00 | 52.94 | B | O |
| ATOM | 6457 | N | THR | 94 | 109.107 | 85.322 | 52.819 | 1.00 | 54.56 | B | N |
| ATOM | 6458 | CA | THR | 94 | 109.473 | 86.127 | 51.656 | 1.00 | 54.56 | B | C |
| ATOM | 6459 | CB | THR | 94 | 110.616 | 85.473 | 50.858 | 1.00 | 54.40 | B | C |
| ATOM | 6460 | OG1 | THR | 94 | 110.837 | 86.210 | 49.648 | 1.00 | 53.65 | B | O |
| ATOM | 6461 | CG2 | THR | 94 | 110.268 | 84.040 | 50.515 | 1.00 | 55.54 | B | C |
| ATOM | 6462 | C | THR | 94 | 108.330 | 86.418 | 50.689 | 1.00 | 54.94 | B | C |
| ATOM | 6463 | O | THR | 94 | 108.424 | 87.339 | 49.878 | 1.00 | 55.42 | B | O |
| ATOM | 6464 | N | PHE | 95 | 107.256 | 85.640 | 50.762 | 1.00 | 54.35 | B | N |
| ATOM | 6465 | CA | PHE | 95 | 106.125 | 85.865 | 49.873 | 1.00 | 54.57 | B | C |
| ATOM | 6466 | CB | PHE | 95 | 105.956 | 84.681 | 48.914 | 1.00 | 53.35 | B | C |
| ATOM | 6467 | CG | PHE | 95 | 107.158 | 84.426 | 48.043 | 1.00 | 52.21 | B | C |

FIG. 4-133 (Continued)

```
ATOM   6468  CD1  PHE   95    107.978  83.326  48.268  1.00  51.86   B  C
ATOM   6469  CD2  PHE   95    107.476  85.290  47.005  1.00  51.89   B  C
ATOM   6470  CE1  PHE   95    109.095  83.091  47.473  1.00  50.37   B  C
ATOM   6471  CE2  PHE   95    108.594  85.061  46.205  1.00  51.43   B  C
ATOM   6472  CZ   PHE   95    109.403  83.960  46.441  1.00  50.62   B  C
ATOM   6473  C    PHE   95    104.825  86.105  50.639  1.00  55.66   B  C
ATOM   6474  O    PHE   95    103.740  85.784  50.149  1.00  55.16   B  O
ATOM   6475  N    ASP   96    104.941  86.681  51.835  1.00  56.69   B  N
ATOM   6476  CA   ASP   96    103.775  86.964  52.668  1.00  57.24   B  C
ATOM   6477  CB   ASP   96    104.167  87.785  53.900  1.00  58.96   B  C
ATOM   6478  CG   ASP   96    104.793  86.945  54.993  1.00  60.91   B  C
ATOM   6479  OD1  ASP   96    104.234  85.875  55.321  1.00  60.82   B  O
ATOM   6480  OD2  ASP   96    105.835  87.366  55.538  1.00  62.59   B  O
ATOM   6481  C    ASP   96    102.674  87.712  51.933  1.00  57.24   B  C
ATOM   6482  O    ASP   96    101.498  87.401  52.100  1.00  58.26   B  O
ATOM   6483  N    GLU   97    103.050  88.703  51.130  1.00  57.07   B  N
ATOM   6484  CA   GLU   97    102.068  89.496  50.395  1.00  57.68   B  C
ATOM   6485  CB   GLU   97    102.389  90.994  50.512  1.00  59.15   B  C
ATOM   6486  CG   GLU   97    102.397  91.553  51.935  1.00  61.76   B  C
ATOM   6487  CD   GLU   97    103.629  91.140  52.729  1.00  63.57   B  C
ATOM   6488  OE1  GLU   97    103.714  91.490  53.927  1.00  63.88   B  O
ATOM   6489  OE2  GLU   97    104.514  90.467  52.155  1.00  64.73   B  O
ATOM   6490  C    GLU   97    101.970  89.123  48.917  1.00  56.86   B  C
ATOM   6491  O    GLU   97    101.652  89.972  48.080  1.00  58.05   B  O
ATOM   6492  N    PHE   98    102.234  87.859  48.598  1.00  54.75   B  N
ATOM   6493  CA   PHE   98    102.181  87.393  47.214  1.00  52.58   B  C
ATOM   6494  CB   PHE   98    102.730  85.965  47.117  1.00  52.53   B  C
ATOM   6495  CG   PHE   98    102.792  85.434  45.713  1.00  51.74   B  C
ATOM   6496  CD1  PHE   98    103.564  86.073  44.749  1.00  50.75   B  C
ATOM   6497  CD2  PHE   98    102.064  84.305  45.348  1.00  51.54   B  C
ATOM   6498  CE1  PHE   98    103.609  85.597  43.445  1.00  50.51   B  C
ATOM   6499  CE2  PHE   98    102.103  83.822  44.044  1.00  50.40   B  C
ATOM   6500  CZ   PHE   98    102.876  84.469  43.092  1.00  49.83   B  C
ATOM   6501  C    PHE   98    100.764  87.448  46.641  1.00  51.24   B  C
ATOM   6502  O    PHE   98    100.578  87.544  45.427  1.00  50.42   B  O
ATOM   6503  N    GLY   99     99.770  87.383  47.523  1.00  50.67   B  N
ATOM   6504  CA   GLY   99     98.383  87.441  47.094  1.00  48.74   B  C
ATOM   6505  C    GLY   99     97.918  86.192  46.376  1.00  47.41   B  C
ATOM   6506  O    GLY   99     97.020  86.246  45.540  1.00  48.42   B  O
ATOM   6507  N    HIS  100     98.530  85.065  46.712  1.00  45.49   B  N
ATOM   6508  CA   HIS  100     98.200  83.780  46.104  1.00  43.24   B  C
ATOM   6509  CB   HIS  100     98.787  83.686  44.694  1.00  41.93   B  C
ATOM   6510  CG   HIS  100     98.004  84.414  43.651  1.00  39.37   B  C
ATOM   6511  CD2  HIS  100     98.345  85.437  42.833  1.00  38.83   B  C
ATOM   6512  ND1  HIS  100     96.711  84.075  43.321  1.00  39.65   B  N
ATOM   6513  CE1  HIS  100     96.288  84.857  42.344  1.00  38.90   B  C
ATOM   6514  NE2  HIS  100     97.262  85.691  42.029  1.00  38.71   B  N
ATOM   6515  C    HIS  100     98.822  82.677  46.940  1.00  42.56   B  C
ATOM   6516  O    HIS  100     99.916  82.846  47.473  1.00  43.12   B  O
```

| ATOM | 6517 | N | SER | 101 | 98.139 | 81.547 | 47.063 | 1.00 | 41.90 | B | N |
| --- | --- | --- | --- | --- | --- | --- | --- | --- | --- | --- | --- |
| ATOM | 6518 | CA | SER | 101 | 98.716 | 80.442 | 47.817 | 1.00 | 43.20 | B | C |
| ATOM | 6519 | CB | SER | 101 | 97.623 | 79.527 | 48.382 | 1.00 | 43.41 | B | C |
| ATOM | 6520 | OG | SER | 101 | 96.852 | 78.931 | 47.354 | 1.00 | 44.00 | B | O |
| ATOM | 6521 | C | SER | 101 | 99.582 | 79.680 | 46.820 | 1.00 | 42.92 | B | C |
| ATOM | 6522 | O | SER | 101 | 99.083 | 79.213 | 45.794 | 1.00 | 43.33 | B | O |
| ATOM | 6523 | N | ILE | 102 | 100.880 | 79.584 | 47.095 | 1.00 | 41.90 | B | N |
| ATOM | 6524 | CA | ILE | 102 | 101.762 | 78.874 | 46.183 | 1.00 | 42.10 | B | C |
| ATOM | 6525 | CB | ILE | 102 | 103.255 | 79.286 | 46.369 | 1.00 | 43.10 | B | C |
| ATOM | 6526 | CG2 | ILE | 102 | 103.370 | 80.811 | 46.404 | 1.00 | 43.52 | B | C |
| ATOM | 6527 | CG1 | ILE | 102 | 103.824 | 78.700 | 47.660 | 1.00 | 45.01 | B | C |
| ATOM | 6528 | CD1 | ILE | 102 | 105.294 | 79.038 | 47.895 | 1.00 | 46.96 | B | C |
| ATOM | 6529 | C | ILE | 102 | 101.598 | 77.380 | 46.415 | 1.00 | 41.08 | B | C |
| ATOM | 6530 | O | ILE | 102 | 101.677 | 76.901 | 47.544 | 1.00 | 41.27 | B | O |
| ATOM | 6531 | N | ASN | 103 | 101.342 | 76.648 | 45.339 | 1.00 | 40.05 | B | N |
| ATOM | 6532 | CA | ASN | 103 | 101.157 | 75.211 | 45.434 | 1.00 | 39.20 | B | C |
| ATOM | 6533 | CB | ASN | 103 | 100.502 | 74.674 | 44.163 | 1.00 | 39.98 | B | C |
| ATOM | 6534 | CG | ASN | 103 | 100.190 | 73.199 | 44.257 | 1.00 | 39.82 | B | C |
| ATOM | 6535 | OD1 | ASN | 103 | 99.355 | 72.784 | 45.056 | 1.00 | 40.83 | B | O |
| ATOM | 6536 | ND2 | ASN | 103 | 100.866 | 72.396 | 43.448 | 1.00 | 40.75 | B | N |
| ATOM | 6537 | C | ASN | 103 | 102.486 | 74.508 | 45.645 | 1.00 | 37.42 | B | C |
| ATOM | 6538 | O | ASN | 103 | 102.601 | 73.614 | 46.475 | 1.00 | 38.46 | B | O |
| ATOM | 6539 | N | ASP | 104 | 103.491 | 74.912 | 44.880 | 1.00 | 35.77 | B | N |
| ATOM | 6540 | CA | ASP | 104 | 104.808 | 74.303 | 44.982 | 1.00 | 34.14 | B | C |
| ATOM | 6541 | CB | ASP | 104 | 104.819 | 72.955 | 44.248 | 1.00 | 33.54 | B | C |
| ATOM | 6542 | CG | ASP | 104 | 105.987 | 72.072 | 44.655 | 1.00 | 34.77 | B | C |
| ATOM | 6543 | OD1 | ASP | 104 | 106.061 | 70.919 | 44.178 | 1.00 | 33.72 | B | O |
| ATOM | 6544 | OD2 | ASP | 104 | 106.835 | 72.525 | 45.453 | 1.00 | 35.84 | B | O |
| ATOM | 6545 | C | ASP | 104 | 105.827 | 75.253 | 44.367 | 1.00 | 33.07 | B | C |
| ATOM | 6546 | O | ASP | 104 | 105.461 | 76.218 | 43.695 | 1.00 | 33.54 | B | O |
| ATOM | 6547 | N | TYR | 105 | 107.103 | 74.985 | 44.607 | 1.00 | 32.32 | B | N |
| ATOM | 6548 | CA | TYR | 105 | 108.167 | 75.824 | 44.082 | 1.00 | 31.45 | B | C |
| ATOM | 6549 | CB | TYR | 105 | 108.854 | 76.573 | 45.220 | 1.00 | 32.58 | B | C |
| ATOM | 6550 | CG | TYR | 105 | 109.515 | 75.662 | 46.218 | 1.00 | 35.82 | B | C |
| ATOM | 6551 | CD1 | TYR | 105 | 110.859 | 75.306 | 46.091 | 1.00 | 36.01 | B | C |
| ATOM | 6552 | CE1 | TYR | 105 | 111.465 | 74.453 | 47.009 | 1.00 | 36.30 | B | C |
| ATOM | 6553 | CD2 | TYR | 105 | 108.791 | 75.138 | 47.287 | 1.00 | 37.55 | B | C |
| ATOM | 6554 | CE2 | TYR | 105 | 109.387 | 74.282 | 48.208 | 1.00 | 38.47 | B | C |
| ATOM | 6555 | CZ | TYR | 105 | 110.719 | 73.947 | 48.065 | 1.00 | 37.17 | B | C |
| ATOM | 6556 | OH | TYR | 105 | 111.293 | 73.106 | 48.984 | 1.00 | 38.67 | B | O |
| ATOM | 6557 | C | TYR | 105 | 109.180 | 74.972 | 43.347 | 1.00 | 30.07 | B | C |
| ATOM | 6558 | O | TYR | 105 | 109.048 | 73.754 | 43.276 | 1.00 | 29.32 | B | O |
| ATOM | 6559 | N | SER | 106 | 110.203 | 75.623 | 42.815 | 1.00 | 28.45 | B | N |
| ATOM | 6560 | CA | SER | 106 | 111.236 | 74.938 | 42.059 | 1.00 | 26.63 | B | C |
| ATOM | 6561 | CB | SER | 106 | 110.648 | 74.391 | 40.758 | 1.00 | 24.49 | B | C |
| ATOM | 6562 | OG | SER | 106 | 111.662 | 74.145 | 39.806 | 1.00 | 24.16 | B | O |
| ATOM | 6563 | C | SER | 106 | 112.341 | 75.926 | 41.745 | 1.00 | 26.32 | B | C |
| ATOM | 6564 | O | SER | 106 | 112.168 | 76.821 | 40.919 | 1.00 | 28.04 | B | O |
| ATOM | 6565 | N | ILE | 107 | 113.475 | 75.770 | 42.413 | 1.00 | 25.01 | B | N |

FIG. 4-135 (Continued)

| | | | | | | | | | | |
|---|---|---|---|---|---|---|---|---|---|---|
| ATOM | 6566 | CA | ILE | 107 | 114.602 | 76.662 | 42.196 | 1.00 | 24.30 | B | C |
| ATOM | 6567 | CB | ILE | 107 | 115.634 | 76.576 | 43.354 | 1.00 | 21.79 | B | C |
| ATOM | 6568 | CG2 | ILE | 107 | 116.885 | 77.328 | 42.987 | 1.00 | 21.05 | B | C |
| ATOM | 6569 | CG1 | ILE | 107 | 115.050 | 77.161 | 44.639 | 1.00 | 21.30 | B | C |
| ATOM | 6570 | CD1 | ILE | 107 | 114.056 | 76.271 | 45.321 | 1.00 | 23.96 | B | C |
| ATOM | 6571 | C | ILE | 107 | 115.315 | 76.305 | 40.901 | 1.00 | 25.00 | B | C |
| ATOM | 6572 | O | ILE | 107 | 115.418 | 75.132 | 40.548 | 1.00 | 27.32 | B | O |
| ATOM | 6573 | N | SER | 108 | 115.788 | 77.320 | 40.187 | 1.00 | 24.67 | B | N |
| ATOM | 6574 | CA | SER | 108 | 116.534 | 77.102 | 38.959 | 1.00 | 24.23 | B | C |
| ATOM | 6575 | CB | SER | 108 | 116.936 | 78.439 | 38.350 | 1.00 | 23.85 | B | C |
| ATOM | 6576 | OG | SER | 108 | 117.786 | 79.144 | 39.245 | 1.00 | 23.56 | B | O |
| ATOM | 6577 | C | SER | 108 | 117.789 | 76.347 | 39.403 | 1.00 | 25.01 | B | C |
| ATOM | 6578 | O | SER | 108 | 118.223 | 76.484 | 40.546 | 1.00 | 25.28 | B | O |
| ATOM | 6579 | N | PRO | 109 | 118.394 | 75.554 | 38.508 | 1.00 | 25.25 | B | N |
| ATOM | 6580 | CD | PRO | 109 | 118.003 | 75.282 | 37.115 | 1.00 | 25.10 | B | C |
| ATOM | 6581 | CA | PRO | 109 | 119.600 | 74.798 | 38.869 | 1.00 | 26.01 | B | C |
| ATOM | 6582 | CB | PRO | 109 | 120.023 | 74.172 | 37.547 | 1.00 | 24.74 | B | C |
| ATOM | 6583 | CG | PRO | 109 | 118.722 | 73.983 | 36.836 | 1.00 | 25.99 | B | C |
| ATOM | 6584 | C | PRO | 109 | 120.726 | 75.619 | 39.499 | 1.00 | 27.62 | B | C |
| ATOM | 6585 | O | PRO | 109 | 121.413 | 75.139 | 40.403 | 1.00 | 28.26 | B | O |
| ATOM | 6586 | N | ASP | 110 | 120.923 | 76.847 | 39.026 | 1.00 | 28.44 | B | N |
| ATOM | 6587 | CA | ASP | 110 | 121.988 | 77.691 | 39.562 | 1.00 | 29.86 | B | C |
| ATOM | 6588 | CB | ASP | 110 | 122.465 | 78.689 | 38.504 | 1.00 | 30.74 | B | C |
| ATOM | 6589 | CG | ASP | 110 | 121.342 | 79.543 | 37.960 | 1.00 | 32.54 | B | C |
| ATOM | 6590 | OD1 | ASP | 110 | 120.415 | 79.856 | 38.730 | 1.00 | 33.07 | B | O |
| ATOM | 6591 | OD2 | ASP | 110 | 121.391 | 79.912 | 36.767 | 1.00 | 33.02 | B | O |
| ATOM | 6592 | C | ASP | 110 | 121.599 | 78.449 | 40.828 | 1.00 | 30.83 | B | C |
| ATOM | 6593 | O | ASP | 110 | 122.379 | 79.248 | 41.337 | 1.00 | 32.09 | B | O |
| ATOM | 6594 | N | GLY | 111 | 120.397 | 78.197 | 41.335 | 1.00 | 31.58 | B | N |
| ATOM | 6595 | CA | GLY | 111 | 119.945 | 78.863 | 42.545 | 1.00 | 32.15 | B | C |
| ATOM | 6596 | C | GLY | 111 | 119.673 | 80.343 | 42.357 | 1.00 | 32.90 | B | C |
| ATOM | 6597 | O | GLY | 111 | 119.462 | 81.074 | 43.323 | 1.00 | 31.87 | B | O |
| ATOM | 6598 | N | GLN | 112 | 119.666 | 80.783 | 41.105 | 1.00 | 33.93 | B | N |
| ATOM | 6599 | CA | GLN | 112 | 119.440 | 82.184 | 40.783 | 1.00 | 35.14 | B | C |
| ATOM | 6600 | CB | GLN | 112 | 120.005 | 82.486 | 39.396 | 1.00 | 36.07 | B | C |
| ATOM | 6601 | CG | GLN | 112 | 120.885 | 83.717 | 39.329 | 1.00 | 39.16 | B | C |
| ATOM | 6602 | CD | GLN | 112 | 122.019 | 83.551 | 38.337 | 1.00 | 39.62 | B | C |
| ATOM | 6603 | OE1 | GLN | 112 | 122.890 | 82.697 | 38.515 | 1.00 | 38.31 | B | O |
| ATOM | 6604 | NE2 | GLN | 112 | 122.013 | 84.363 | 37.281 | 1.00 | 41.28 | B | N |
| ATOM | 6605 | C | GLN | 112 | 117.970 | 82.577 | 40.826 | 1.00 | 34.39 | B | C |
| ATOM | 6606 | O | GLN | 112 | 117.627 | 83.692 | 41.225 | 1.00 | 35.13 | B | O |
| ATOM | 6607 | N | PHE | 113 | 117.099 | 81.667 | 40.410 | 1.00 | 32.82 | B | N |
| ATOM | 6608 | CA | PHE | 113 | 115.678 | 81.965 | 40.401 | 1.00 | 31.84 | B | C |
| ATOM | 6609 | CB | PHE | 113 | 115.185 | 82.165 | 38.969 | 1.00 | 31.95 | B | C |
| ATOM | 6610 | CG | PHE | 113 | 115.948 | 83.204 | 38.208 | 1.00 | 34.16 | B | C |
| ATOM | 6611 | CD1 | PHE | 113 | 117.150 | 82.886 | 37.587 | 1.00 | 35.65 | B | C |
| ATOM | 6612 | CD2 | PHE | 113 | 115.475 | 84.508 | 38.124 | 1.00 | 35.41 | B | C |
| ATOM | 6613 | CE1 | PHE | 113 | 117.872 | 83.853 | 36.893 | 1.00 | 36.00 | B | C |
| ATOM | 6614 | CE2 | PHE | 113 | 116.185 | 85.479 | 37.436 | 1.00 | 35.02 | B | C |

FIG. 4-136 (Continued)

| | | | | | | | | | | |
|---|---|---|---|---|---|---|---|---|---|---|
| ATOM | 6615 | CZ | PHE | 113 | 117.386 | 85.152 | 36.819 | 1.00 | 35.71 | B C |
| ATOM | 6616 | C | PHE | 113 | 114.831 | 80.896 | 41.058 | 1.00 | 30.65 | B C |
| ATOM | 6617 | O | PHE | 113 | 115.308 | 79.829 | 41.425 | 1.00 | 30.90 | B O |
| ATOM | 6618 | N | ILE | 114 | 113.557 | 81.205 | 41.219 | 1.00 | 30.09 | B N |
| ATOM | 6619 | CA | ILE | 114 | 112.630 | 80.258 | 41.791 | 1.00 | 29.81 | B C |
| ATOM | 6620 | CB | ILE | 114 | 112.394 | 80.504 | 43.293 | 1.00 | 28.60 | B C |
| ATOM | 6621 | CG2 | ILE | 114 | 111.911 | 81.915 | 43.529 | 1.00 | 29.81 | B C |
| ATOM | 6622 | CG1 | ILE | 114 | 111.378 | 79.490 | 43.813 | 1.00 | 30.57 | B C |
| ATOM | 6623 | CD1 | ILE | 114 | 111.336 | 79.367 | 45.325 | 1.00 | 33.23 | B C |
| ATOM | 6624 | C | ILE | 114 | 111.336 | 80.403 | 41.019 | 1.00 | 29.79 | B C |
| ATOM | 6625 | O | ILE | 114 | 110.895 | 81.508 | 40.715 | 1.00 | 28.83 | B O |
| ATOM | 6626 | N | LEU | 115 | 110.756 | 79.265 | 40.671 | 1.00 | 30.43 | B N |
| ATOM | 6627 | CA | LEU | 115 | 109.516 | 79.223 | 39.925 | 1.00 | 29.05 | B C |
| ATOM | 6628 | CB | LEU | 115 | 109.596 | 78.108 | 38.890 | 1.00 | 28.31 | B C |
| ATOM | 6629 | CG | LEU | 115 | 108.449 | 77.898 | 37.912 | 1.00 | 28.22 | B C |
| ATOM | 6630 | CD1 | LEU | 115 | 108.425 | 79.001 | 36.872 | 1.00 | 28.47 | B C |
| ATOM | 6631 | CD2 | LEU | 115 | 108.645 | 76.553 | 37.245 | 1.00 | 29.52 | B C |
| ATOM | 6632 | C | LEU | 115 | 108.424 | 78.923 | 40.932 | 1.00 | 29.59 | B C |
| ATOM | 6633 | O | LEU | 115 | 108.370 | 77.824 | 41.483 | 1.00 | 30.72 | B O |
| ATOM | 6634 | N | LEU | 116 | 107.568 | 79.901 | 41.196 | 1.00 | 30.29 | B N |
| ATOM | 6635 | CA | LEU | 116 | 106.479 | 79.699 | 42.142 | 1.00 | 30.17 | B C |
| ATOM | 6636 | CB | LEU | 116 | 106.129 | 81.001 | 42.861 | 1.00 | 31.28 | B C |
| ATOM | 6637 | CG | LEU | 116 | 107.277 | 81.741 | 43.544 | 1.00 | 33.66 | B C |
| ATOM | 6638 | CD1 | LEU | 116 | 106.732 | 82.988 | 44.229 | 1.00 | 33.41 | B C |
| ATOM | 6639 | CD2 | LEU | 116 | 107.957 | 80.821 | 44.552 | 1.00 | 34.07 | B C |
| ATOM | 6640 | C | LEU | 116 | 105.270 | 79.215 | 41.369 | 1.00 | 30.44 | B C |
| ATOM | 6641 | O | LEU | 116 | 104.835 | 79.845 | 40.401 | 1.00 | 30.69 | B O |
| ATOM | 6642 | N | GLU | 117 | 104.724 | 78.091 | 41.804 | 1.00 | 30.37 | B N |
| ATOM | 6643 | CA | GLU | 117 | 103.563 | 77.513 | 41.159 | 1.00 | 29.50 | B C |
| ATOM | 6644 | CB | GLU | 117 | 103.813 | 76.017 | 40.963 | 1.00 | 30.63 | B C |
| ATOM | 6645 | CG | GLU | 117 | 102.671 | 75.210 | 40.368 | 1.00 | 32.07 | B C |
| ATOM | 6646 | CD | GLU | 117 | 103.023 | 73.728 | 40.270 | 1.00 | 33.58 | B C |
| ATOM | 6647 | OE1 | GLU | 117 | 103.772 | 73.341 | 39.340 | 1.00 | 32.53 | B O |
| ATOM | 6648 | OE2 | GLU | 117 | 102.566 | 72.956 | 41.140 | 1.00 | 32.35 | B O |
| ATOM | 6649 | C | GLU | 117 | 102.312 | 77.756 | 42.009 | 1.00 | 29.67 | B C |
| ATOM | 6650 | O | GLU | 117 | 102.333 | 77.583 | 43.228 | 1.00 | 27.89 | B O |
| ATOM | 6651 | N | TYR | 118 | 101.235 | 78.184 | 41.355 | 1.00 | 29.27 | B N |
| ATOM | 6652 | CA | TYR | 118 | 99.966 | 78.423 | 42.026 | 1.00 | 28.00 | B C |
| ATOM | 6653 | CB | TYR | 118 | 99.928 | 79.818 | 42.643 | 1.00 | 29.37 | B C |
| ATOM | 6654 | CG | TYR | 118 | 100.036 | 80.955 | 41.659 | 1.00 | 29.69 | B C |
| ATOM | 6655 | CD1 | TYR | 118 | 101.256 | 81.301 | 41.092 | 1.00 | 30.04 | B C |
| ATOM | 6656 | CE1 | TYR | 118 | 101.355 | 82.373 | 40.210 | 1.00 | 31.36 | B C |
| ATOM | 6657 | CD2 | TYR | 118 | 98.915 | 81.703 | 41.316 | 1.00 | 30.41 | B C |
| ATOM | 6658 | CE2 | TYR | 118 | 99.003 | 82.768 | 40.439 | 1.00 | 31.17 | B C |
| ATOM | 6659 | CZ | TYR | 118 | 100.222 | 83.101 | 39.891 | 1.00 | 31.56 | B C |
| ATOM | 6660 | OH | TYR | 118 | 100.298 | 84.179 | 39.039 | 1.00 | 33.43 | B O |
| ATOM | 6661 | C | TYR | 118 | 98.814 | 78.240 | 41.038 | 1.00 | 27.66 | B C |
| ATOM | 6662 | O | TYR | 118 | 99.046 | 77.917 | 39.874 | 1.00 | 26.73 | B O |
| ATOM | 6663 | N | ASN | 119 | 97.582 | 78.450 | 41.499 | 1.00 | 27.22 | B N |

FIG. 4-137 (Continued)

| ATOM | 6664 | CA | ASN | 119 | 96.397 | 78.261 | 40.659 | 1.00 | 27.10 | B | C |
|---|---|---|---|---|---|---|---|---|---|---|---|
| ATOM | 6665 | CB | ASN | 119 | 96.422 | 79.203 | 39.449 | 1.00 | 27.22 | B | C |
| ATOM | 6666 | CG | ASN | 119 | 95.918 | 80.599 | 39.777 | 1.00 | 27.62 | B | C |
| ATOM | 6667 | OD1 | ASN | 119 | 94.905 | 80.761 | 40.456 | 1.00 | 26.76 | B | O |
| ATOM | 6668 | ND2 | ASN | 119 | 96.613 | 81.612 | 39.277 | 1.00 | 25.87 | B | N |
| ATOM | 6669 | C | ASN | 119 | 96.342 | 76.810 | 40.171 | 1.00 | 27.88 | B | C |
| ATOM | 6670 | O | ASN | 119 | 95.923 | 76.534 | 39.045 | 1.00 | 27.93 | B | O |
| ATOM | 6671 | N | TYR | 120 | 96.771 | 75.888 | 41.028 | 1.00 | 27.57 | B | N |
| ATOM | 6672 | CA | TYR | 120 | 96.795 | 74.466 | 40.702 | 1.00 | 29.01 | B | C |
| ATOM | 6673 | CB | TYR | 120 | 97.396 | 73.669 | 41.866 | 1.00 | 30.85 | B | C |
| ATOM | 6674 | CG | TYR | 120 | 97.421 | 72.171 | 41.635 | 1.00 | 32.83 | B | C |
| ATOM | 6675 | CD1 | TYR | 120 | 98.466 | 71.568 | 40.940 | 1.00 | 33.76 | B | C |
| ATOM | 6676 | CE1 | TYR | 120 | 98.484 | 70.190 | 40.717 | 1.00 | 35.03 | B | C |
| ATOM | 6677 | CD2 | TYR | 120 | 96.389 | 71.358 | 42.100 | 1.00 | 34.41 | B | C |
| ATOM | 6678 | CE2 | TYR | 120 | 96.394 | 69.981 | 41.880 | 1.00 | 34.35 | B | C |
| ATOM | 6679 | CZ | TYR | 120 | 97.444 | 69.403 | 41.191 | 1.00 | 35.47 | B | C |
| ATOM | 6680 | OH | TYR | 120 | 97.462 | 68.039 | 40.987 | 1.00 | 35.56 | B | O |
| ATOM | 6681 | C | TYR | 120 | 95.431 | 73.863 | 40.364 | 1.00 | 29.17 | B | C |
| ATOM | 6682 | O | TYR | 120 | 94.458 | 74.034 | 41.099 | 1.00 | 31.09 | B | O |
| ATOM | 6683 | N | VAL | 121 | 95.368 | 73.148 | 39.248 | 1.00 | 27.53 | B | N |
| ATOM | 6684 | CA | VAL | 121 | 94.136 | 72.487 | 38.842 | 1.00 | 25.45 | B | C |
| ATOM | 6685 | CB | VAL | 121 | 93.358 | 73.296 | 37.785 | 1.00 | 25.23 | B | C |
| ATOM | 6686 | CG1 | VAL | 121 | 92.105 | 72.534 | 37.376 | 1.00 | 22.18 | B | C |
| ATOM | 6687 | CG2 | VAL | 121 | 92.974 | 74.666 | 38.354 | 1.00 | 21.81 | B | C |
| ATOM | 6688 | C | VAL | 121 | 94.527 | 71.130 | 38.275 | 1.00 | 24.99 | B | C |
| ATOM | 6689 | O | VAL | 121 | 95.188 | 71.031 | 37.242 | 1.00 | 24.18 | B | O |
| ATOM | 6690 | N | LYS | 122 | 94.124 | 70.082 | 38.977 | 1.00 | 24.16 | B | N |
| ATOM | 6691 | CA | LYS | 122 | 94.464 | 68.735 | 38.570 | 1.00 | 24.24 | B | C |
| ATOM | 6692 | CB | LYS | 122 | 94.295 | 67.780 | 39.754 | 1.00 | 23.05 | B | C |
| ATOM | 6693 | CG | LYS | 122 | 94.510 | 66.327 | 39.390 | 1.00 | 20.04 | B | C |
| ATOM | 6694 | CD | LYS | 122 | 94.356 | 65.416 | 40.589 | 1.00 | 20.19 | B | C |
| ATOM | 6695 | CE | LYS | 122 | 94.402 | 63.950 | 40.161 | 1.00 | 20.85 | B | C |
| ATOM | 6696 | NZ | LYS | 122 | 93.363 | 63.632 | 39.136 | 1.00 | 18.96 | B | N |
| ATOM | 6697 | C | LYS | 122 | 93.692 | 68.180 | 37.387 | 1.00 | 24.10 | B | C |
| ATOM | 6698 | O | LYS | 122 | 92.516 | 68.488 | 37.189 | 1.00 | 23.23 | B | O |
| ATOM | 6699 | N | GLN | 123 | 94.384 | 67.368 | 36.592 | 1.00 | 23.36 | B | N |
| ATOM | 6700 | CA | GLN | 123 | 93.758 | 66.691 | 35.472 | 1.00 | 21.22 | B | C |
| ATOM | 6701 | CB | GLN | 123 | 94.455 | 67.007 | 34.145 | 1.00 | 20.62 | B | C |
| ATOM | 6702 | CG | GLN | 123 | 93.689 | 66.433 | 32.948 | 1.00 | 23.42 | B | C |
| ATOM | 6703 | CD | GLN | 123 | 94.242 | 66.857 | 31.591 | 1.00 | 24.37 | B | C |
| ATOM | 6704 | OE1 | GLN | 123 | 95.399 | 66.606 | 31.275 | 1.00 | 26.71 | B | O |
| ATOM | 6705 | NE2 | GLN | 123 | 93.402 | 67.493 | 30.779 | 1.00 | 23.80 | B | N |
| ATOM | 6706 | C | GLN | 123 | 93.856 | 65.194 | 35.805 | 1.00 | 20.06 | B | C |
| ATOM | 6707 | O | GLN | 123 | 93.258 | 64.741 | 36.786 | 1.00 | 17.04 | B | O |
| ATOM | 6708 | N | TRP | 124 | 94.630 | 64.438 | 35.030 | 1.00 | 17.49 | B | N |
| ATOM | 6709 | CA | TRP | 124 | 94.753 | 63.009 | 35.276 | 1.00 | 16.75 | B | C |
| ATOM | 6710 | CB | TRP | 124 | 95.165 | 62.298 | 33.984 | 1.00 | 16.19 | B | C |
| ATOM | 6711 | CG | TRP | 124 | 94.351 | 62.735 | 32.797 | 1.00 | 18.11 | B | C |
| ATOM | 6712 | CD2 | TRP | 124 | 92.939 | 63.014 | 32.764 | 1.00 | 17.55 | B | C |

FIG. 4-138

| ATOM | 6713 | CE2 | TRP | 124 | 92.630 | 63.449 | 31.455 | 1.00 | 16.84 | B | C |
|---|---|---|---|---|---|---|---|---|---|---|---|
| ATOM | 6714 | CE3 | TRP | 124 | 91.909 | 62.942 | 33.713 | 1.00 | 17.02 | B | C |
| ATOM | 6715 | CD1 | TRP | 124 | 94.819 | 62.999 | 31.539 | 1.00 | 19.00 | B | C |
| ATOM | 6716 | NE1 | TRP | 124 | 93.794 | 63.429 | 30.731 | 1.00 | 18.26 | B | N |
| ATOM | 6717 | CZ2 | TRP | 124 | 91.331 | 63.815 | 31.067 | 1.00 | 15.16 | B | C |
| ATOM | 6718 | CZ3 | TRP | 124 | 90.615 | 63.305 | 33.326 | 1.00 | 16.85 | B | C |
| ATOM | 6719 | CH2 | TRP | 124 | 90.342 | 63.737 | 32.011 | 1.00 | 16.12 | B | C |
| ATOM | 6720 | C | TRP | 124 | 95.718 | 62.679 | 36.427 | 1.00 | 17.28 | B | C |
| ATOM | 6721 | O | TRP | 124 | 95.816 | 63.437 | 37.397 | 1.00 | 17.74 | B | O |
| ATOM | 6722 | N | ARG | 125 | 96.430 | 61.560 | 36.339 | 1.00 | 15.31 | B | N |
| ATOM | 6723 | CA | ARG | 125 | 97.317 | 61.185 | 37.429 | 1.00 | 16.66 | B | C |
| ATOM | 6724 | CB | ARG | 125 | 97.666 | 59.702 | 37.323 | 1.00 | 16.96 | B | C |
| ATOM | 6725 | CG | ARG | 125 | 98.908 | 59.288 | 38.076 | 1.00 | 18.35 | B | C |
| ATOM | 6726 | CD | ARG | 125 | 98.689 | 57.987 | 38.794 | 1.00 | 18.85 | B | C |
| ATOM | 6727 | NE | ARG | 125 | 98.049 | 56.965 | 37.972 | 1.00 | 18.57 | B | N |
| ATOM | 6728 | CZ | ARG | 125 | 97.547 | 55.842 | 38.475 | 1.00 | 17.58 | B | C |
| ATOM | 6729 | NH1 | ARG | 125 | 96.972 | 54.944 | 37.693 | 1.00 | 16.96 | B | N |
| ATOM | 6730 | NH2 | ARG | 125 | 97.626 | 55.621 | 39.776 | 1.00 | 17.03 | B | N |
| ATOM | 6731 | C | ARG | 125 | 98.582 | 62.027 | 37.568 | 1.00 | 18.54 | B | C |
| ATOM | 6732 | O | ARG | 125 | 99.075 | 62.227 | 38.674 | 1.00 | 18.06 | B | O |
| ATOM | 6733 | N | HIS | 126 | 99.099 | 62.533 | 36.454 | 1.00 | 20.06 | B | N |
| ATOM | 6734 | CA | HIS | 126 | 100.300 | 63.353 | 36.487 | 1.00 | 18.20 | B | C |
| ATOM | 6735 | CB | HIS | 126 | 101.391 | 62.673 | 35.673 | 1.00 | 18.72 | B | C |
| ATOM | 6736 | CG | HIS | 126 | 101.721 | 61.295 | 36.151 | 1.00 | 19.88 | B | C |
| ATOM | 6737 | CD2 | HIS | 126 | 101.519 | 60.084 | 35.581 | 1.00 | 20.06 | B | C |
| ATOM | 6738 | ND1 | HIS | 126 | 102.341 | 61.054 | 37.360 | 1.00 | 17.75 | B | N |
| ATOM | 6739 | CE1 | HIS | 126 | 102.510 | 59.753 | 37.512 | 1.00 | 19.55 | B | C |
| ATOM | 6740 | NE2 | HIS | 126 | 102.019 | 59.142 | 36.447 | 1.00 | 22.65 | B | N |
| ATOM | 6741 | C | HIS | 126 | 100.079 | 64.772 | 35.966 | 1.00 | 18.28 | B | C |
| ATOM | 6742 | O | HIS | 126 | 100.692 | 65.716 | 36.462 | 1.00 | 18.27 | B | O |
| ATOM | 6743 | N | SER | 127 | 99.204 | 64.921 | 34.974 | 1.00 | 16.08 | B | N |
| ATOM | 6744 | CA | SER | 127 | 98.936 | 66.230 | 34.382 | 1.00 | 16.78 | B | C |
| ATOM | 6745 | CB | SER | 127 | 98.209 | 66.070 | 33.037 | 1.00 | 15.96 | B | C |
| ATOM | 6746 | OG | SER | 127 | 96.999 | 65.349 | 33.179 | 1.00 | 17.80 | B | O |
| ATOM | 6747 | C | SER | 127 | 98.151 | 67.203 | 35.261 | 1.00 | 16.75 | B | C |
| ATOM | 6748 | O | SER | 127 | 97.523 | 66.816 | 36.247 | 1.00 | 17.88 | B | O |
| ATOM | 6749 | N | TYR | 128 | 98.205 | 68.473 | 34.873 | 1.00 | 15.65 | B | N |
| ATOM | 6750 | CA | TYR | 128 | 97.520 | 69.556 | 35.559 | 1.00 | 17.91 | B | C |
| ATOM | 6751 | CB | TYR | 128 | 97.815 | 69.506 | 37.060 | 1.00 | 17.70 | B | C |
| ATOM | 6752 | CG | TYR | 128 | 99.253 | 69.796 | 37.444 | 1.00 | 17.20 | B | C |
| ATOM | 6753 | CD1 | TYR | 128 | 99.725 | 71.107 | 37.540 | 1.00 | 16.17 | B | C |
| ATOM | 6754 | CE1 | TYR | 128 | 101.036 | 71.375 | 37.927 | 1.00 | 16.04 | B | C |
| ATOM | 6755 | CD2 | TYR | 128 | 100.135 | 68.759 | 37.739 | 1.00 | 17.12 | B | C |
| ATOM | 6756 | CE2 | TYR | 128 | 101.449 | 69.016 | 38.123 | 1.00 | 15.90 | B | C |
| ATOM | 6757 | CZ | TYR | 128 | 101.891 | 70.322 | 38.216 | 1.00 | 17.19 | B | C |
| ATOM | 6758 | OH | TYR | 128 | 103.190 | 70.572 | 38.603 | 1.00 | 20.16 | B | O |
| ATOM | 6759 | C | TYR | 128 | 97.977 | 70.897 | 34.992 | 1.00 | 19.77 | B | C |
| ATOM | 6760 | O | TYR | 128 | 98.970 | 70.972 | 34.268 | 1.00 | 21.70 | B | O |
| ATOM | 6761 | N | THR | 129 | 97.239 | 71.955 | 35.291 | 1.00 | 20.48 | B | N |

| | | | | | | | | | | | |
|---|---|---|---|---|---|---|---|---|---|---|---|
| ATOM | 6762 | CA | THR | 129 | 97.647 | 73.276 | 34.840 | 1.00 | 22.26 | B | C |
| ATOM | 6763 | CB | THR | 129 | 96.599 | 73.968 | 33.950 | 1.00 | 23.04 | B | C |
| ATOM | 6764 | OG1 | THR | 129 | 95.353 | 74.045 | 34.652 | 1.00 | 24.93 | B | O |
| ATOM | 6765 | CG2 | THR | 129 | 96.428 | 73.213 | 32.634 | 1.00 | 22.70 | B | C |
| ATOM | 6766 | C | THR | 129 | 97.856 | 74.136 | 36.069 | 1.00 | 22.23 | B | C |
| ATOM | 6767 | O | THR | 129 | 97.462 | 73.765 | 37.182 | 1.00 | 20.98 | B | O |
| ATOM | 6768 | N | ALA | 130 | 98.474 | 75.289 | 35.854 | 1.00 | 22.77 | B | N |
| ATOM | 6769 | CA | ALA | 130 | 98.754 | 76.222 | 36.926 | 1.00 | 23.41 | B | C |
| ATOM | 6770 | CB | ALA | 130 | 99.789 | 75.631 | 37.859 | 1.00 | 19.73 | B | C |
| ATOM | 6771 | C | ALA | 130 | 99.269 | 77.525 | 36.338 | 1.00 | 26.66 | B | C |
| ATOM | 6772 | O | ALA | 130 | 99.514 | 77.632 | 35.133 | 1.00 | 27.20 | B | O |
| ATOM | 6773 | N | SER | 131 | 99.414 | 78.523 | 37.199 | 1.00 | 29.67 | B | N |
| ATOM | 6774 | CA | SER | 131 | 99.934 | 79.818 | 36.796 | 1.00 | 30.14 | B | C |
| ATOM | 6775 | CB | SER | 131 | 99.056 | 80.948 | 37.333 | 1.00 | 30.56 | B | C |
| ATOM | 6776 | OG | SER | 131 | 97.713 | 80.775 | 36.913 | 1.00 | 32.67 | B | O |
| ATOM | 6777 | C | SER | 131 | 101.290 | 79.851 | 37.463 | 1.00 | 31.00 | B | C |
| ATOM | 6778 | O | SER | 131 | 101.448 | 79.334 | 38.569 | 1.00 | 30.79 | B | O |
| ATOM | 6779 | N | TYR | 132 | 102.272 | 80.438 | 36.792 | 1.00 | 32.02 | B | N |
| ATOM | 6780 | CA | TYR | 132 | 103.611 | 80.506 | 37.347 | 1.00 | 31.40 | B | C |
| ATOM | 6781 | CB | TYR | 132 | 104.558 | 79.634 | 36.519 | 1.00 | 28.72 | B | C |
| ATOM | 6782 | CG | TYR | 132 | 104.179 | 78.174 | 36.516 | 1.00 | 26.74 | B | C |
| ATOM | 6783 | CD1 | TYR | 132 | 103.082 | 77.721 | 35.791 | 1.00 | 26.31 | B | C |
| ATOM | 6784 | CE1 | TYR | 132 | 102.696 | 76.383 | 35.834 | 1.00 | 26.45 | B | C |
| ATOM | 6785 | CD2 | TYR | 132 | 104.887 | 77.250 | 37.283 | 1.00 | 26.58 | B | C |
| ATOM | 6786 | CE2 | TYR | 132 | 104.510 | 75.911 | 37.332 | 1.00 | 24.63 | B | C |
| ATOM | 6787 | CZ | TYR | 132 | 103.415 | 75.486 | 36.609 | 1.00 | 25.59 | B | C |
| ATOM | 6788 | OH | TYR | 132 | 103.023 | 74.171 | 36.677 | 1.00 | 25.63 | B | O |
| ATOM | 6789 | C | TYR | 132 | 104.143 | 81.929 | 37.411 | 1.00 | 32.91 | B | C |
| ATOM | 6790 | O | TYR | 132 | 103.743 | 82.790 | 36.636 | 1.00 | 34.01 | B | O |
| ATOM | 6791 | N | ASP | 133 | 105.041 | 82.165 | 38.358 | 1.00 | 35.11 | B | N |
| ATOM | 6792 | CA | ASP | 133 | 105.674 | 83.465 | 38.539 | 1.00 | 36.35 | B | C |
| ATOM | 6793 | CB | ASP | 133 | 104.954 | 84.287 | 39.614 | 1.00 | 38.51 | B | C |
| ATOM | 6794 | CG | ASP | 133 | 103.732 | 85.008 | 39.074 | 1.00 | 41.22 | B | C |
| ATOM | 6795 | OD1 | ASP | 133 | 102.805 | 84.332 | 38.580 | 1.00 | 42.20 | B | O |
| ATOM | 6796 | OD2 | ASP | 133 | 103.702 | 86.253 | 39.139 | 1.00 | 42.84 | B | O |
| ATOM | 6797 | C | ASP | 133 | 107.112 | 83.228 | 38.954 | 1.00 | 35.61 | B | C |
| ATOM | 6798 | O | ASP | 133 | 107.385 | 82.438 | 39.855 | 1.00 | 35.76 | B | O |
| ATOM | 6799 | N | ILE | 134 | 108.031 | 83.908 | 38.285 | 1.00 | 35.21 | B | N |
| ATOM | 6800 | CA | ILE | 134 | 109.444 | 83.764 | 38.585 | 1.00 | 34.01 | B | C |
| ATOM | 6801 | CB | ILE | 134 | 110.267 | 83.750 | 37.287 | 1.00 | 33.62 | B | C |
| ATOM | 6802 | CG2 | ILE | 134 | 111.718 | 83.392 | 37.593 | 1.00 | 31.90 | B | C |
| ATOM | 6803 | CG1 | ILE | 134 | 109.649 | 82.737 | 36.312 | 1.00 | 32.72 | B | C |
| ATOM | 6804 | CD1 | ILE | 134 | 110.204 | 82.794 | 34.909 | 1.00 | 31.29 | B | C |
| ATOM | 6805 | C | ILE | 134 | 109.887 | 84.911 | 39.483 | 1.00 | 34.02 | B | C |
| ATOM | 6806 | O | ILE | 134 | 109.521 | 86.065 | 39.261 | 1.00 | 33.25 | B | O |
| ATOM | 6807 | N | TYR | 135 | 110.662 | 84.573 | 40.507 | 1.00 | 35.09 | B | N |
| ATOM | 6808 | CA | TYR | 135 | 111.167 | 85.539 | 41.475 | 1.00 | 36.09 | B | C |
| ATOM | 6809 | CB | TYR | 135 | 110.657 | 85.174 | 42.868 | 1.00 | 36.02 | B | C |
| ATOM | 6810 | CG | TYR | 135 | 111.222 | 86.011 | 44.000 | 1.00 | 36.66 | B | C |

FIG. 4-140 (Continued)

| | | | | | | | | | | | |
|---|---|---|---|---|---|---|---|---|---|---|---|
| ATOM | 6811 | CD1 | TYR | 135 | 110.635 | 87.222 | 44.363 | 1.00 | 34.73 | B | C |
| ATOM | 6812 | CE1 | TYR | 135 | 111.134 | 87.971 | 45.424 | 1.00 | 34.55 | B | C |
| ATOM | 6813 | CD2 | TYR | 135 | 112.332 | 85.573 | 44.729 | 1.00 | 35.12 | B | C |
| ATOM | 6814 | CE2 | TYR | 135 | 112.839 | 86.316 | 45.786 | 1.00 | 35.07 | B | C |
| ATOM | 6815 | CZ | TYR | 135 | 112.235 | 87.515 | 46.131 | 1.00 | 35.31 | B | C |
| ATOM | 6816 | OH | TYR | 135 | 112.740 | 88.258 | 47.179 | 1.00 | 35.05 | B | O |
| ATOM | 6817 | C | TYR | 135 | 112.688 | 85.511 | 41.470 | 1.00 | 38.19 | B | C |
| ATOM | 6818 | O | TYR | 135 | 113.293 | 84.517 | 41.873 | 1.00 | 37.81 | B | O |
| ATOM | 6819 | N | ASP | 136 | 113.304 | 86.600 | 41.014 | 1.00 | 40.56 | B | N |
| ATOM | 6820 | CA | ASP | 136 | 114.759 | 86.692 | 40.965 | 1.00 | 42.09 | B | C |
| ATOM | 6821 | CB | ASP | 136 | 115.187 | 87.969 | 40.237 | 1.00 | 42.45 | B | C |
| ATOM | 6822 | CG | ASP | 136 | 116.690 | 88.051 | 40.030 | 1.00 | 43.61 | B | C |
| ATOM | 6823 | OD1 | ASP | 136 | 117.107 | 88.577 | 38.978 | 1.00 | 45.53 | B | O |
| ATOM | 6824 | OD2 | ASP | 136 | 117.456 | 87.602 | 40.911 | 1.00 | 41.77 | B | O |
| ATOM | 6825 | C | ASP | 136 | 115.316 | 86.679 | 42.382 | 1.00 | 43.14 | B | C |
| ATOM | 6826 | O | ASP | 136 | 114.972 | 87.522 | 43.209 | 1.00 | 42.49 | B | O |
| ATOM | 6827 | N | LEU | 137 | 116.181 | 85.713 | 42.656 | 1.00 | 44.92 | B | N |
| ATOM | 6828 | CA | LEU | 137 | 116.761 | 85.577 | 43.978 | 1.00 | 48.26 | B | C |
| ATOM | 6829 | CB | LEU | 137 | 117.219 | 84.135 | 44.182 | 1.00 | 48.88 | B | C |
| ATOM | 6830 | CG | LEU | 137 | 116.058 | 83.136 | 44.117 | 1.00 | 49.07 | B | C |
| ATOM | 6831 | CD1 | LEU | 137 | 116.582 | 81.716 | 43.991 | 1.00 | 50.17 | B | C |
| ATOM | 6832 | CD2 | LEU | 137 | 115.199 | 83.291 | 45.361 | 1.00 | 48.91 | B | C |
| ATOM | 6833 | C | LEU | 137 | 117.908 | 86.544 | 44.228 | 1.00 | 50.19 | B | C |
| ATOM | 6834 | O | LEU | 137 | 118.309 | 86.750 | 45.370 | 1.00 | 51.45 | B | O |
| ATOM | 6835 | N | ASN | 138 | 118.429 | 87.139 | 43.160 | 1.00 | 52.26 | B | N |
| ATOM | 6836 | CA | ASN | 138 | 119.522 | 88.096 | 43.280 | 1.00 | 53.21 | B | C |
| ATOM | 6837 | CB | ASN | 138 | 120.330 | 88.151 | 41.983 | 1.00 | 54.36 | B | C |
| ATOM | 6838 | CG | ASN | 138 | 120.728 | 86.775 | 41.484 | 1.00 | 56.39 | B | C |
| ATOM | 6839 | OD1 | ASN | 138 | 121.232 | 85.945 | 42.244 | 1.00 | 57.23 | B | O |
| ATOM | 6840 | ND2 | ASN | 138 | 120.512 | 86.530 | 40.194 | 1.00 | 56.67 | B | N |
| ATOM | 6841 | C | ASN | 138 | 118.935 | 89.472 | 43.567 | 1.00 | 54.11 | B | C |
| ATOM | 6842 | O | ASN | 138 | 119.259 | 90.101 | 44.571 | 1.00 | 54.39 | B | O |
| ATOM | 6843 | N | LYS | 139 | 118.064 | 89.929 | 42.675 | 1.00 | 55.06 | B | N |
| ATOM | 6844 | CA | LYS | 139 | 117.417 | 91.228 | 42.814 | 1.00 | 56.16 | B | C |
| ATOM | 6845 | CB | LYS | 139 | 116.807 | 91.657 | 41.480 | 1.00 | 56.75 | B | C |
| ATOM | 6846 | CG | LYS | 139 | 117.726 | 91.520 | 40.290 | 1.00 | 58.34 | B | C |
| ATOM | 6847 | CD | LYS | 139 | 116.996 | 91.874 | 39.006 | 1.00 | 59.63 | B | C |
| ATOM | 6848 | CE | LYS | 139 | 117.887 | 91.650 | 37.793 | 1.00 | 61.32 | B | C |
| ATOM | 6849 | NZ | LYS | 139 | 117.196 | 91.995 | 36.518 | 1.00 | 62.59 | B | N |
| ATOM | 6850 | C | LYS | 139 | 116.302 | 91.183 | 43.857 | 1.00 | 56.78 | B | C |
| ATOM | 6851 | O | LYS | 139 | 115.669 | 92.202 | 44.139 | 1.00 | 57.22 | B | O |
| ATOM | 6852 | N | ARG | 140 | 116.061 | 90.006 | 44.425 | 1.00 | 57.14 | B | N |
| ATOM | 6853 | CA | ARG | 140 | 114.994 | 89.838 | 45.409 | 1.00 | 57.44 | B | C |
| ATOM | 6854 | CB | ARG | 140 | 115.433 | 90.341 | 46.787 | 1.00 | 58.40 | B | C |
| ATOM | 6855 | CG | ARG | 140 | 116.063 | 89.260 | 47.649 | 1.00 | 61.65 | B | C |
| ATOM | 6856 | CD | ARG | 140 | 116.091 | 89.658 | 49.116 | 1.00 | 64.17 | B | C |
| ATOM | 6857 | NE | ARG | 140 | 116.578 | 88.575 | 49.972 | 1.00 | 67.20 | B | N |
| ATOM | 6858 | CZ | ARG | 140 | 115.979 | 87.394 | 50.112 | 1.00 | 68.02 | B | C |
| ATOM | 6859 | NH1 | ARG | 140 | 114.857 | 87.124 | 49.453 | 1.00 | 68.21 | B | N |

| | | | | | | | | | | |
|---|---|---|---|---|---|---|---|---|---|---|
| ATOM | 6860 | NH2 | ARG | 140 | 116.507 | 86.478 | 50.911 | 1.00 | 68.11 | B | N |
| ATOM | 6861 | C | ARG | 140 | 113.697 | 90.537 | 44.994 | 1.00 | 56.16 | B | C |
| ATOM | 6862 | O | ARG | 140 | 113.067 | 91.225 | 45.795 | 1.00 | 56.03 | B | O |
| ATOM | 6863 | N | GLN | 141 | 113.315 | 90.363 | 43.733 | 1.00 | 54.56 | B | N |
| ATOM | 6864 | CA | GLN | 141 | 112.088 | 90.947 | 43.205 | 1.00 | 53.90 | B | C |
| ATOM | 6865 | CB | GLN | 141 | 112.367 | 92.292 | 42.522 | 1.00 | 55.16 | B | C |
| ATOM | 6866 | CG | GLN | 141 | 113.166 | 92.203 | 41.227 | 1.00 | 57.86 | B | C |
| ATOM | 6867 | CD | GLN | 141 | 113.078 | 93.477 | 40.400 | 1.00 | 59.30 | B | C |
| ATOM | 6868 | OE1 | GLN | 141 | 113.414 | 94.562 | 40.875 | 1.00 | 60.96 | B | O |
| ATOM | 6869 | NE2 | GLN | 141 | 112.620 | 93.350 | 39.158 | 1.00 | 58.33 | B | N |
| ATOM | 6870 | C | GLN | 141 | 111.500 | 89.965 | 42.198 | 1.00 | 52.05 | B | C |
| ATOM | 6871 | O | GLN | 141 | 112.230 | 89.362 | 41.418 | 1.00 | 52.50 | B | O |
| ATOM | 6872 | N | LEU | 142 | 110.186 | 89.794 | 42.213 | 1.00 | 50.43 | B | N |
| ATOM | 6873 | CA | LEU | 142 | 109.564 | 88.861 | 41.284 | 1.00 | 48.86 | B | C |
| ATOM | 6874 | CB | LEU | 142 | 108.196 | 88.415 | 41.815 | 1.00 | 48.84 | B | C |
| ATOM | 6875 | CG | LEU | 142 | 107.024 | 89.395 | 41.857 | 1.00 | 48.67 | B | C |
| ATOM | 6876 | CD1 | LEU | 142 | 106.354 | 89.442 | 40.489 | 1.00 | 49.83 | B | C |
| ATOM | 6877 | CD2 | LEU | 142 | 106.014 | 88.940 | 42.905 | 1.00 | 47.77 | B | C |
| ATOM | 6878 | C | LEU | 142 | 109.423 | 89.467 | 39.896 | 1.00 | 47.71 | B | C |
| ATOM | 6879 | O | LEU | 142 | 108.890 | 90.564 | 39.736 | 1.00 | 48.46 | B | O |
| ATOM | 6880 | N | ILE | 143 | 109.917 | 88.752 | 38.891 | 1.00 | 45.67 | B | N |
| ATOM | 6881 | CA | ILE | 143 | 109.835 | 89.226 | 37.520 | 1.00 | 42.98 | B | C |
| ATOM | 6882 | CB | ILE | 143 | 110.442 | 88.208 | 36.535 | 1.00 | 42.34 | B | C |
| ATOM | 6883 | CG2 | ILE | 143 | 110.204 | 88.659 | 35.099 | 1.00 | 41.35 | B | C |
| ATOM | 6884 | CG1 | ILE | 143 | 111.937 | 88.055 | 36.810 | 1.00 | 41.52 | B | C |
| ATOM | 6885 | CD1 | ILE | 143 | 112.675 | 87.257 | 35.755 | 1.00 | 42.12 | B | C |
| ATOM | 6886 | C | ILE | 143 | 108.385 | 89.481 | 37.131 | 1.00 | 42.92 | B | C |
| ATOM | 6887 | O | ILE | 143 | 107.522 | 88.617 | 37.292 | 1.00 | 41.84 | B | O |
| ATOM | 6888 | N | THR | 144 | 108.128 | 90.680 | 36.620 | 1.00 | 43.57 | B | N |
| ATOM | 6889 | CA | THR | 144 | 106.789 | 91.065 | 36.202 | 1.00 | 44.05 | B | C |
| ATOM | 6890 | CB | THR | 144 | 106.332 | 92.344 | 36.915 | 1.00 | 42.77 | B | C |
| ATOM | 6891 | OG1 | THR | 144 | 107.329 | 93.358 | 36.760 | 1.00 | 45.33 | B | O |
| ATOM | 6892 | CG2 | THR | 144 | 106.124 | 92.080 | 38.388 | 1.00 | 43.31 | B | C |
| ATOM | 6893 | C | THR | 144 | 106.716 | 91.294 | 34.701 | 1.00 | 44.53 | B | C |
| ATOM | 6894 | O | THR | 144 | 105.689 | 91.729 | 34.186 | 1.00 | 46.08 | B | O |
| ATOM | 6895 | N | GLU | 145 | 107.802 | 90.988 | 34.001 | 1.00 | 45.05 | B | N |
| ATOM | 6896 | CA | GLU | 145 | 107.857 | 91.168 | 32.557 | 1.00 | 46.88 | B | C |
| ATOM | 6897 | CB | GLU | 145 | 109.069 | 92.031 | 32.202 | 1.00 | 50.14 | B | C |
| ATOM | 6898 | CG | GLU | 145 | 109.148 | 93.319 | 33.007 | 1.00 | 55.05 | B | C |
| ATOM | 6899 | CD | GLU | 145 | 110.429 | 94.094 | 32.760 | 1.00 | 57.57 | B | C |
| ATOM | 6900 | OE1 | GLU | 145 | 110.696 | 94.443 | 31.591 | 1.00 | 60.26 | B | O |
| ATOM | 6901 | OE2 | GLU | 145 | 111.167 | 94.357 | 33.737 | 1.00 | 59.47 | B | O |
| ATOM | 6902 | C | GLU | 145 | 107.946 | 89.822 | 31.834 | 1.00 | 46.87 | B | C |
| ATOM | 6903 | O | GLU | 145 | 108.648 | 88.916 | 32.286 | 1.00 | 46.76 | B | O |
| ATOM | 6904 | N | GLU | 146 | 107.236 | 89.695 | 30.714 | 1.00 | 46.37 | B | N |
| ATOM | 6905 | CA | GLU | 146 | 107.241 | 88.458 | 29.932 | 1.00 | 45.82 | B | C |
| ATOM | 6906 | CB | GLU | 146 | 108.592 | 88.284 | 29.232 | 1.00 | 46.20 | B | C |
| ATOM | 6907 | CG | GLU | 146 | 108.916 | 89.321 | 28.163 | 1.00 | 45.55 | B | C |
| ATOM | 6908 | CD | GLU | 146 | 108.011 | 89.217 | 26.948 | 1.00 | 45.65 | B | C |

FIG. 4-142 (Continued)

| | | | | | | | | | | |
|---|---|---|---|---|---|---|---|---|---|---|
| ATOM | 6909 | OE1 | GLU | 146 | 107.685 | 88.081 | 26.543 | 1.00 | 45.03 | B | O |
| ATOM | 6910 | OE2 | GLU | 146 | 107.641 | 90.269 | 26.387 | 1.00 | 45.44 | B | O |
| ATOM | 6911 | C | GLU | 146 | 106.978 | 87.241 | 30.821 | 1.00 | 46.25 | B | C |
| ATOM | 6912 | O | GLU | 146 | 107.805 | 86.334 | 30.912 | 1.00 | 47.62 | B | O |
| ATOM | 6913 | N | ARG | 147 | 105.823 | 87.221 | 31.474 | 1.00 | 44.79 | B | N |
| ATOM | 6914 | CA | ARG | 147 | 105.475 | 86.119 | 32.360 | 1.00 | 43.34 | B | C |
| ATOM | 6915 | CB | ARG | 147 | 104.469 | 86.595 | 33.410 | 1.00 | 44.21 | B | C |
| ATOM | 6916 | CG | ARG | 147 | 104.998 | 87.678 | 34.320 | 1.00 | 46.85 | B | C |
| ATOM | 6917 | CD | ARG | 147 | 103.995 | 88.007 | 35.410 | 1.00 | 49.84 | B | C |
| ATOM | 6918 | NE | ARG | 147 | 102.805 | 88.651 | 34.866 | 1.00 | 53.22 | B | N |
| ATOM | 6919 | CZ | ARG | 147 | 101.733 | 88.970 | 35.584 | 1.00 | 54.21 | B | C |
| ATOM | 6920 | NH1 | ARG | 147 | 101.696 | 88.699 | 36.884 | 1.00 | 53.97 | B | N |
| ATOM | 6921 | NH2 | ARG | 147 | 100.701 | 89.569 | 34.999 | 1.00 | 54.56 | B | N |
| ATOM | 6922 | C | ARG | 147 | 104.905 | 84.894 | 31.648 | 1.00 | 41.06 | B | C |
| ATOM | 6923 | O | ARG | 147 | 104.304 | 84.996 | 30.580 | 1.00 | 41.00 | B | O |
| ATOM | 6924 | N | ILE | 148 | 105.103 | 83.732 | 32.259 | 1.00 | 38.31 | B | N |
| ATOM | 6925 | CA | ILE | 148 | 104.590 | 82.485 | 31.721 | 1.00 | 35.74 | B | C |
| ATOM | 6926 | CB | ILE | 148 | 105.019 | 81.305 | 32.616 | 1.00 | 35.07 | B | C |
| ATOM | 6927 | CG2 | ILE | 148 | 104.458 | 79.996 | 32.073 | 1.00 | 34.22 | B | C |
| ATOM | 6928 | CG1 | ILE | 148 | 106.549 | 81.255 | 32.679 | 1.00 | 33.62 | B | C |
| ATOM | 6929 | CD1 | ILE | 148 | 107.104 | 80.131 | 33.517 | 1.00 | 34.57 | B | C |
| ATOM | 6930 | C | ILE | 148 | 103.069 | 82.641 | 31.709 | 1.00 | 34.54 | B | C |
| ATOM | 6931 | O | ILE | 148 | 102.492 | 83.155 | 32.664 | 1.00 | 35.51 | B | O |
| ATOM | 6932 | N | PRO | 149 | 102.401 | 82.199 | 30.631 | 1.00 | 32.42 | B | N |
| ATOM | 6933 | CD | PRO | 149 | 102.929 | 81.387 | 29.525 | 1.00 | 30.91 | B | C |
| ATOM | 6934 | CA | PRO | 149 | 100.942 | 82.321 | 30.526 | 1.00 | 31.27 | B | C |
| ATOM | 6935 | CB | PRO | 149 | 100.632 | 81.762 | 29.134 | 1.00 | 31.04 | B | C |
| ATOM | 6936 | CG | PRO | 149 | 101.963 | 81.707 | 28.437 | 1.00 | 31.84 | B | C |
| ATOM | 6937 | C | PRO | 149 | 100.187 | 81.549 | 31.592 | 1.00 | 31.48 | B | C |
| ATOM | 6938 | O | PRO | 149 | 100.733 | 80.643 | 32.221 | 1.00 | 30.85 | B | O |
| ATOM | 6939 | N | ASN | 150 | 98.927 | 81.919 | 31.794 | 1.00 | 31.40 | B | N |
| ATOM | 6940 | CA | ASN | 150 | 98.085 | 81.206 | 32.744 | 1.00 | 31.30 | B | C |
| ATOM | 6941 | CB | ASN | 150 | 96.832 | 82.019 | 33.108 | 1.00 | 31.58 | B | C |
| ATOM | 6942 | CG | ASN | 150 | 97.086 | 83.037 | 34.211 | 1.00 | 32.97 | B | C |
| ATOM | 6943 | OD1 | ASN | 150 | 97.676 | 82.715 | 35.244 | 1.00 | 31.95 | B | O |
| ATOM | 6944 | ND2 | ASN | 150 | 96.624 | 84.271 | 34.004 | 1.00 | 33.51 | B | N |
| ATOM | 6945 | C | ASN | 150 | 97.673 | 79.929 | 32.013 | 1.00 | 30.52 | B | C |
| ATOM | 6946 | O | ASN | 150 | 97.722 | 79.864 | 30.777 | 1.00 | 29.37 | B | O |
| ATOM | 6947 | N | ASN | 151 | 97.269 | 78.917 | 32.768 | 1.00 | 30.16 | B | N |
| ATOM | 6948 | CA | ASN | 151 | 96.859 | 77.657 | 32.170 | 1.00 | 29.53 | B | C |
| ATOM | 6949 | CB | ASN | 151 | 95.715 | 77.881 | 31.186 | 1.00 | 33.04 | B | C |
| ATOM | 6950 | CG | ASN | 151 | 94.489 | 78.474 | 31.850 | 1.00 | 36.73 | B | C |
| ATOM | 6951 | OD1 | ASN | 151 | 94.530 | 79.586 | 32.376 | 1.00 | 38.47 | B | O |
| ATOM | 6952 | ND2 | ASN | 151 | 93.389 | 77.729 | 31.831 | 1.00 | 40.28 | B | N |
| ATOM | 6953 | C | ASN | 151 | 98.023 | 76.997 | 31.452 | 1.00 | 28.44 | B | C |
| ATOM | 6954 | O | ASN | 151 | 97.856 | 76.412 | 30.382 | 1.00 | 27.56 | B | O |
| ATOM | 6955 | N | THR | 152 | 99.212 | 77.111 | 32.035 | 1.00 | 26.08 | B | N |
| ATOM | 6956 | CA | THR | 152 | 100.384 | 76.489 | 31.452 | 1.00 | 24.37 | B | C |
| ATOM | 6957 | CB | THR | 152 | 101.682 | 77.069 | 32.046 | 1.00 | 25.30 | B | C |

FIG. 4-143

| ATOM | 6958 | OG1 | THR | 152 | 101.862 | 78.407 | 31.566 | 1.00 | 25.07 | B | O |
| --- | --- | --- | --- | --- | --- | --- | --- | --- | --- | --- | --- |
| ATOM | 6959 | CG2 | THR | 152 | 102.882 | 76.231 | 31.643 | 1.00 | 24.98 | B | C |
| ATOM | 6960 | C | THR | 152 | 100.257 | 75.012 | 31.791 | 1.00 | 22.65 | B | C |
| ATOM | 6961 | O | THR | 152 | 99.908 | 74.652 | 32.912 | 1.00 | 21.72 | B | O |
| ATOM | 6962 | N | GLN | 153 | 100.531 | 74.160 | 30.815 | 1.00 | 21.08 | B | N |
| ATOM | 6963 | CA | GLN | 153 | 100.407 | 72.730 | 31.010 | 1.00 | 20.14 | B | C |
| ATOM | 6964 | CB | GLN | 153 | 100.023 | 72.081 | 29.691 | 1.00 | 20.22 | B | C |
| ATOM | 6965 | CG | GLN | 153 | 98.688 | 72.573 | 29.166 | 1.00 | 20.23 | B | C |
| ATOM | 6966 | CD | GLN | 153 | 98.577 | 72.461 | 27.669 | 1.00 | 21.29 | B | C |
| ATOM | 6967 | OE1 | GLN | 153 | 99.365 | 73.054 | 26.939 | 1.00 | 24.47 | B | O |
| ATOM | 6968 | NE2 | GLN | 153 | 97.600 | 71.703 | 27.200 | 1.00 | 20.51 | B | N |
| ATOM | 6969 | C | GLN | 153 | 101.650 | 72.076 | 31.578 | 1.00 | 20.86 | B | C |
| ATOM | 6970 | O | GLN | 153 | 101.574 | 70.996 | 32.154 | 1.00 | 22.44 | B | O |
| ATOM | 6971 | N | TRP | 154 | 102.794 | 72.729 | 31.422 | 1.00 | 20.43 | B | N |
| ATOM | 6972 | CA | TRP | 154 | 104.043 | 72.189 | 31.934 | 1.00 | 18.53 | B | C |
| ATOM | 6973 | CB | TRP | 154 | 104.387 | 70.868 | 31.234 | 1.00 | 18.88 | B | C |
| ATOM | 6974 | CG | TRP | 154 | 105.678 | 70.257 | 31.719 | 1.00 | 19.59 | B | C |
| ATOM | 6975 | CD2 | TRP | 154 | 105.891 | 69.559 | 32.955 | 1.00 | 17.98 | B | C |
| ATOM | 6976 | CE2 | TRP | 154 | 107.261 | 69.232 | 33.019 | 1.00 | 19.74 | B | C |
| ATOM | 6977 | CE3 | TRP | 154 | 105.058 | 69.184 | 34.015 | 1.00 | 16.08 | B | C |
| ATOM | 6978 | CD1 | TRP | 154 | 106.893 | 70.316 | 31.101 | 1.00 | 20.53 | B | C |
| ATOM | 6979 | NE1 | TRP | 154 | 107.849 | 69.705 | 31.877 | 1.00 | 22.41 | B | N |
| ATOM | 6980 | CZ2 | TRP | 154 | 107.819 | 68.545 | 34.104 | 1.00 | 18.81 | B | C |
| ATOM | 6981 | CZ3 | TRP | 154 | 105.614 | 68.502 | 35.097 | 1.00 | 14.46 | B | C |
| ATOM | 6982 | CH2 | TRP | 154 | 106.981 | 68.191 | 35.130 | 1.00 | 14.70 | B | C |
| ATOM | 6983 | C | TRP | 154 | 105.172 | 73.186 | 31.757 | 1.00 | 18.38 | B | C |
| ATOM | 6984 | O | TRP | 154 | 105.159 | 74.005 | 30.840 | 1.00 | 17.07 | B | O |
| ATOM | 6985 | N | VAL | 155 | 106.139 | 73.118 | 32.658 | 1.00 | 18.34 | B | N |
| ATOM | 6986 | CA | VAL | 155 | 107.280 | 74.010 | 32.627 | 1.00 | 20.45 | B | C |
| ATOM | 6987 | CB | VAL | 155 | 107.030 | 75.298 | 33.457 | 1.00 | 21.97 | B | C |
| ATOM | 6988 | CG1 | VAL | 155 | 106.881 | 74.954 | 34.937 | 1.00 | 21.60 | B | C |
| ATOM | 6989 | CG2 | VAL | 155 | 108.180 | 76.281 | 33.260 | 1.00 | 20.89 | B | C |
| ATOM | 6990 | C | VAL | 155 | 108.439 | 73.255 | 33.236 | 1.00 | 21.60 | B | C |
| ATOM | 6991 | O | VAL | 155 | 108.241 | 72.379 | 34.075 | 1.00 | 21.26 | B | O |
| ATOM | 6992 | N | THR | 156 | 109.647 | 73.590 | 32.806 | 1.00 | 22.32 | B | N |
| ATOM | 6993 | CA | THR | 156 | 110.826 | 72.929 | 33.325 | 1.00 | 23.44 | B | C |
| ATOM | 6994 | CB | THR | 156 | 111.028 | 71.569 | 32.677 | 1.00 | 24.53 | B | C |
| ATOM | 6995 | OG1 | THR | 156 | 112.350 | 71.113 | 32.972 | 1.00 | 25.64 | B | O |
| ATOM | 6996 | CG2 | THR | 156 | 110.856 | 71.662 | 31.166 | 1.00 | 25.95 | B | C |
| ATOM | 6997 | C | THR | 156 | 112.092 | 73.727 | 33.094 | 1.00 | 24.37 | B | C |
| ATOM | 6998 | O | THR | 156 | 112.305 | 74.274 | 32.010 | 1.00 | 25.56 | B | O |
| ATOM | 6999 | N | TRP | 157 | 112.929 | 73.795 | 34.123 | 1.00 | 23.78 | B | N |
| ATOM | 7000 | CA | TRP | 157 | 114.192 | 74.500 | 34.021 | 1.00 | 22.95 | B | C |
| ATOM | 7001 | CB | TRP | 157 | 114.848 | 74.650 | 35.399 | 1.00 | 22.02 | B | C |
| ATOM | 7002 | CG | TRP | 157 | 114.239 | 75.678 | 36.293 | 1.00 | 21.39 | B | C |
| ATOM | 7003 | CD2 | TRP | 157 | 114.197 | 77.091 | 36.070 | 1.00 | 22.25 | B | C |
| ATOM | 7004 | CE2 | TRP | 157 | 113.533 | 77.668 | 37.177 | 1.00 | 23.29 | B | C |
| ATOM | 7005 | CE3 | TRP | 157 | 114.658 | 77.928 | 35.046 | 1.00 | 21.12 | B | C |
| ATOM | 7006 | CD1 | TRP | 157 | 113.621 | 75.460 | 37.492 | 1.00 | 22.04 | B | C |

| | | | | | | | | | | |
|---|---|---|---|---|---|---|---|---|---|---|
| ATOM | 7007 | NE1 | TRP | 157 | 113.193 | 76.650 | 38.030 | 1.00 | 22.01 | B | N |
| ATOM | 7008 | CZ2 | TRP | 157 | 113.317 | 79.051 | 37.286 | 1.00 | 22.77 | B | C |
| ATOM | 7009 | CZ3 | TRP | 157 | 114.445 | 79.299 | 35.156 | 1.00 | 22.58 | B | C |
| ATOM | 7010 | CH2 | TRP | 157 | 113.779 | 79.846 | 36.270 | 1.00 | 21.74 | B | C |
| ATOM | 7011 | C | TRP | 157 | 115.096 | 73.640 | 33.153 | 1.00 | 22.79 | B | C |
| ATOM | 7012 | O | TRP | 157 | 114.789 | 72.483 | 32.882 | 1.00 | 23.16 | B | O |
| ATOM | 7013 | N | SER | 158 | 116.198 | 74.211 | 32.697 | 1.00 | 21.93 | B | N |
| ATOM | 7014 | CA | SER | 158 | 117.154 | 73.441 | 31.928 | 1.00 | 22.68 | B | C |
| ATOM | 7015 | CB | SER | 158 | 118.104 | 74.377 | 31.172 | 1.00 | 23.20 | B | C |
| ATOM | 7016 | OG | SER | 158 | 118.550 | 75.444 | 31.996 | 1.00 | 22.94 | B | O |
| ATOM | 7017 | C | SER | 158 | 117.898 | 72.667 | 33.017 | 1.00 | 23.12 | B | C |
| ATOM | 7018 | O | SER | 158 | 117.800 | 73.006 | 34.198 | 1.00 | 23.58 | B | O |
| ATOM | 7019 | N | PRO | 159 | 118.641 | 71.619 | 32.650 | 1.00 | 23.10 | B | N |
| ATOM | 7020 | CD | PRO | 159 | 118.927 | 71.096 | 31.307 | 1.00 | 23.69 | B | C |
| ATOM | 7021 | CA | PRO | 159 | 119.362 | 70.860 | 33.679 | 1.00 | 24.10 | B | C |
| ATOM | 7022 | CB | PRO | 159 | 120.041 | 69.744 | 32.886 | 1.00 | 24.45 | B | C |
| ATOM | 7023 | CG | PRO | 159 | 119.230 | 69.660 | 31.599 | 1.00 | 23.97 | B | C |
| ATOM | 7024 | C | PRO | 159 | 120.384 | 71.738 | 34.391 | 1.00 | 25.41 | B | C |
| ATOM | 7025 | O | PRO | 159 | 120.598 | 71.619 | 35.589 | 1.00 | 26.39 | B | O |
| ATOM | 7026 | N | VAL | 160 | 121.014 | 72.619 | 33.627 | 1.00 | 27.71 | B | N |
| ATOM | 7027 | CA | VAL | 160 | 122.031 | 73.517 | 34.146 | 1.00 | 29.28 | B | C |
| ATOM | 7028 | CB | VAL | 160 | 123.383 | 73.272 | 33.438 | 1.00 | 30.65 | B | C |
| ATOM | 7029 | CG1 | VAL | 160 | 124.421 | 74.249 | 33.939 | 1.00 | 33.70 | B | C |
| ATOM | 7030 | CG2 | VAL | 160 | 123.844 | 71.840 | 33.670 | 1.00 | 31.96 | B | C |
| ATOM | 7031 | C | VAL | 160 | 121.606 | 74.952 | 33.885 | 1.00 | 29.74 | B | C |
| ATOM | 7032 | O | VAL | 160 | 120.889 | 75.224 | 32.923 | 1.00 | 30.93 | B | O |
| ATOM | 7033 | N | GLY | 161 | 122.043 | 75.866 | 34.745 | 1.00 | 29.32 | B | N |
| ATOM | 7034 | CA | GLY | 161 | 121.706 | 77.266 | 34.562 | 1.00 | 28.43 | B | C |
| ATOM | 7035 | C | GLY | 161 | 120.289 | 77.645 | 34.944 | 1.00 | 28.19 | B | C |
| ATOM | 7036 | O | GLY | 161 | 119.839 | 77.359 | 36.053 | 1.00 | 30.02 | B | O |
| ATOM | 7037 | N | HIS | 162 | 119.584 | 78.296 | 34.025 | 1.00 | 26.53 | B | N |
| ATOM | 7038 | CA | HIS | 162 | 118.222 | 78.721 | 34.290 | 1.00 | 25.12 | B | C |
| ATOM | 7039 | CB | HIS | 162 | 118.214 | 79.959 | 35.177 | 1.00 | 26.70 | B | C |
| ATOM | 7040 | CG | HIS | 162 | 119.019 | 81.094 | 34.629 | 1.00 | 29.24 | B | C |
| ATOM | 7041 | CD2 | HIS | 162 | 118.664 | 82.148 | 33.857 | 1.00 | 30.20 | B | C |
| ATOM | 7042 | ND1 | HIS | 162 | 120.378 | 81.208 | 34.830 | 1.00 | 29.95 | B | N |
| ATOM | 7043 | CE1 | HIS | 162 | 120.824 | 82.283 | 34.207 | 1.00 | 30.75 | B | C |
| ATOM | 7044 | NE2 | HIS | 162 | 119.804 | 82.871 | 33.608 | 1.00 | 30.77 | B | N |
| ATOM | 7045 | C | HIS | 162 | 117.384 | 79.021 | 33.059 | 1.00 | 24.68 | B | C |
| ATOM | 7046 | O | HIS | 162 | 116.730 | 80.061 | 33.007 | 1.00 | 24.17 | B | O |
| ATOM | 7047 | N | LYS | 163 | 117.406 | 78.135 | 32.067 | 1.00 | 22.79 | B | N |
| ATOM | 7048 | CA | LYS | 163 | 116.575 | 78.340 | 30.889 | 1.00 | 23.10 | B | C |
| ATOM | 7049 | CB | LYS | 163 | 117.113 | 77.578 | 29.675 | 1.00 | 22.90 | B | C |
| ATOM | 7050 | CG | LYS | 163 | 118.367 | 78.184 | 29.063 | 1.00 | 23.40 | B | C |
| ATOM | 7051 | CD | LYS | 163 | 118.797 | 77.407 | 27.841 | 1.00 | 22.69 | B | C |
| ATOM | 7052 | CE | LYS | 163 | 120.103 | 77.930 | 27.282 | 1.00 | 23.67 | B | C |
| ATOM | 7053 | NZ | LYS | 163 | 120.616 | 77.045 | 26.195 | 1.00 | 24.56 | B | N |
| ATOM | 7054 | C | LYS | 163 | 115.215 | 77.779 | 31.266 | 1.00 | 24.15 | B | C |
| ATOM | 7055 | O | LYS | 163 | 115.079 | 77.104 | 32.282 | 1.00 | 24.69 | B | O |

F I G. 4 - 1 4 5 (Continued)

| | | | | | | | | | | | |
|---|---|---|---|---|---|---|---|---|---|---|---|
| ATOM | 7056 | N | LEU | 164 | 114.210 | 78.062 | 30.450 | 1.00 | 24.82 | B | N |
| ATOM | 7057 | CA | LEU | 164 | 112.870 | 77.572 | 30.704 | 1.00 | 24.27 | B | C |
| ATOM | 7058 | CB | LEU | 164 | 111.991 | 78.672 | 31.293 | 1.00 | 25.27 | B | C |
| ATOM | 7059 | CG | LEU | 164 | 112.216 | 78.969 | 32.769 | 1.00 | 25.61 | B | C |
| ATOM | 7060 | CD1 | LEU | 164 | 111.420 | 80.181 | 33.178 | 1.00 | 25.08 | B | C |
| ATOM | 7061 | CD2 | LEU | 164 | 111.802 | 77.756 | 33.582 | 1.00 | 28.15 | B | C |
| ATOM | 7062 | C | LEU | 164 | 112.231 | 77.068 | 29.435 | 1.00 | 25.20 | B | C |
| ATOM | 7063 | O | LEU | 164 | 112.438 | 77.616 | 28.353 | 1.00 | 26.77 | B | O |
| ATOM | 7064 | N | ALA | 165 | 111.461 | 76.003 | 29.581 | 1.00 | 24.98 | B | N |
| ATOM | 7065 | CA | ALA | 165 | 110.736 | 75.408 | 28.479 | 1.00 | 23.92 | B | C |
| ATOM | 7066 | CB | ALA | 165 | 111.408 | 74.127 | 28.021 | 1.00 | 23.20 | B | C |
| ATOM | 7067 | C | ALA | 165 | 109.394 | 75.106 | 29.114 | 1.00 | 25.13 | B | C |
| ATOM | 7068 | O | ALA | 165 | 109.326 | 74.494 | 30.188 | 1.00 | 24.88 | B | O |
| ATOM | 7069 | N | TYR | 166 | 108.326 | 75.565 | 28.481 | 1.00 | 24.06 | B | N |
| ATOM | 7070 | CA | TYR | 166 | 107.016 | 75.317 | 29.027 | 1.00 | 24.24 | B | C |
| ATOM | 7071 | CB | TYR | 166 | 106.556 | 76.522 | 29.866 | 1.00 | 27.58 | B | C |
| ATOM | 7072 | CG | TYR | 166 | 106.370 | 77.826 | 29.115 | 1.00 | 30.69 | B | C |
| ATOM | 7073 | CD1 | TYR | 166 | 105.171 | 78.115 | 28.465 | 1.00 | 31.46 | B | C |
| ATOM | 7074 | CE1 | TYR | 166 | 104.981 | 79.329 | 27.800 | 1.00 | 32.97 | B | C |
| ATOM | 7075 | CD2 | TYR | 166 | 107.386 | 78.787 | 29.077 | 1.00 | 33.05 | B | C |
| ATOM | 7076 | CE2 | TYR | 166 | 107.210 | 80.005 | 28.412 | 1.00 | 34.06 | B | C |
| ATOM | 7077 | CZ | TYR | 166 | 105.999 | 80.270 | 27.779 | 1.00 | 34.75 | B | C |
| ATOM | 7078 | OH | TYR | 166 | 105.789 | 81.485 | 27.162 | 1.00 | 34.83 | B | O |
| ATOM | 7079 | C | TYR | 166 | 106.039 | 75.003 | 27.917 | 1.00 | 23.86 | B | C |
| ATOM | 7080 | O | TYR | 166 | 106.276 | 75.333 | 26.754 | 1.00 | 22.73 | B | O |
| ATOM | 7081 | N | VAL | 167 | 104.955 | 74.321 | 28.266 | 1.00 | 22.73 | B | N |
| ATOM | 7082 | CA | VAL | 167 | 103.960 | 73.994 | 27.269 | 1.00 | 22.82 | B | C |
| ATOM | 7083 | CB | VAL | 167 | 103.687 | 72.487 | 27.215 | 1.00 | 21.03 | B | C |
| ATOM | 7084 | CG1 | VAL | 167 | 102.528 | 72.200 | 26.274 | 1.00 | 17.71 | B | C |
| ATOM | 7085 | CG2 | VAL | 167 | 104.933 | 71.770 | 26.725 | 1.00 | 20.37 | B | C |
| ATOM | 7086 | C | VAL | 167 | 102.683 | 74.754 | 27.564 | 1.00 | 23.41 | B | C |
| ATOM | 7087 | O | VAL | 167 | 102.196 | 74.779 | 28.692 | 1.00 | 24.72 | B | O |
| ATOM | 7088 | N | TRP | 168 | 102.162 | 75.394 | 26.531 | 1.00 | 23.89 | B | N |
| ATOM | 7089 | CA | TRP | 168 | 100.948 | 76.179 | 26.647 | 1.00 | 24.11 | B | C |
| ATOM | 7090 | CB | TRP | 168 | 101.314 | 77.664 | 26.655 | 1.00 | 24.80 | B | C |
| ATOM | 7091 | CG | TRP | 168 | 100.171 | 78.550 | 26.958 | 1.00 | 27.20 | B | C |
| ATOM | 7092 | CD2 | TRP | 168 | 99.572 | 79.499 | 26.075 | 1.00 | 26.49 | B | C |
| ATOM | 7093 | CE2 | TRP | 168 | 98.496 | 80.091 | 26.769 | 1.00 | 27.49 | B | C |
| ATOM | 7094 | CE3 | TRP | 168 | 99.839 | 79.907 | 24.763 | 1.00 | 27.63 | B | C |
| ATOM | 7095 | CD1 | TRP | 168 | 99.461 | 78.602 | 28.122 | 1.00 | 27.14 | B | C |
| ATOM | 7096 | NE1 | TRP | 168 | 98.452 | 79.526 | 28.017 | 1.00 | 27.81 | B | N |
| ATOM | 7097 | CZ2 | TRP | 168 | 97.682 | 81.074 | 26.194 | 1.00 | 26.74 | B | C |
| ATOM | 7098 | CZ3 | TRP | 168 | 99.029 | 80.886 | 24.189 | 1.00 | 29.25 | B | C |
| ATOM | 7099 | CH2 | TRP | 168 | 97.962 | 81.456 | 24.910 | 1.00 | 28.86 | B | C |
| ATOM | 7100 | C | TRP | 168 | 100.072 | 75.838 | 25.444 | 1.00 | 22.93 | B | C |
| ATOM | 7101 | O | TRP | 168 | 100.577 | 75.692 | 24.328 | 1.00 | 21.98 | B | O |
| ATOM | 7102 | N | ASN | 169 | 98.768 | 75.705 | 25.675 | 1.00 | 21.44 | B | N |
| ATOM | 7103 | CA | ASN | 169 | 97.830 | 75.350 | 24.610 | 1.00 | 22.01 | B | C |
| ATOM | 7104 | CB | ASN | 169 | 97.394 | 76.580 | 23.813 | 1.00 | 23.30 | B | C |

| ATOM | 7105 | CG | ASN | 169 | 96.682 | 77.615 | 24.662 | 1.00 | 27.95 | B | C |
| ATOM | 7106 | OD1 | ASN | 169 | 96.240 | 78.640 | 24.150 | 1.00 | 32.66 | B | O |
| ATOM | 7107 | ND2 | ASN | 169 | 96.570 | 77.361 | 25.961 | 1.00 | 30.33 | B | N |
| ATOM | 7108 | C | ASN | 169 | 98.463 | 74.345 | 23.655 | 1.00 | 21.23 | B | C |
| ATOM | 7109 | O | ASN | 169 | 98.455 | 74.541 | 22.441 | 1.00 | 22.01 | B | O |
| ATOM | 7110 | N | ASN | 170 | 99.031 | 73.283 | 24.221 | 1.00 | 20.60 | B | N |
| ATOM | 7111 | CA | ASN | 170 | 99.661 | 72.208 | 23.459 | 1.00 | 20.97 | B | C |
| ATOM | 7112 | CB | ASN | 170 | 98.615 | 71.515 | 22.592 | 1.00 | 18.68 | B | C |
| ATOM | 7113 | CG | ASN | 170 | 97.629 | 70.741 | 23.412 | 1.00 | 18.15 | B | C |
| ATOM | 7114 | OD1 | ASN | 170 | 97.158 | 71.224 | 24.440 | 1.00 | 16.27 | B | O |
| ATOM | 7115 | ND2 | ASN | 170 | 97.300 | 69.529 | 22.966 | 1.00 | 18.92 | B | N |
| ATOM | 7116 | C | ASN | 170 | 100.859 | 72.581 | 22.598 | 1.00 | 21.31 | B | C |
| ATOM | 7117 | O | ASN | 170 | 101.194 | 71.861 | 21.659 | 1.00 | 20.36 | B | O |
| ATOM | 7118 | N | ASP | 171 | 101.504 | 73.697 | 22.916 | 1.00 | 22.16 | B | N |
| ATOM | 7119 | CA | ASP | 171 | 102.671 | 74.122 | 22.160 | 1.00 | 23.35 | B | C |
| ATOM | 7120 | CB | ASP | 171 | 102.354 | 75.364 | 21.334 | 1.00 | 23.05 | B | C |
| ATOM | 7121 | CG | ASP | 171 | 101.794 | 75.017 | 19.978 | 1.00 | 23.72 | B | C |
| ATOM | 7122 | OD1 | ASP | 171 | 102.505 | 74.338 | 19.210 | 1.00 | 23.33 | B | O |
| ATOM | 7123 | OD2 | ASP | 171 | 100.650 | 75.415 | 19.679 | 1.00 | 26.97 | B | O |
| ATOM | 7124 | C | ASP | 171 | 103.850 | 74.380 | 23.073 | 1.00 | 23.59 | B | C |
| ATOM | 7125 | O | ASP | 171 | 103.672 | 74.647 | 24.264 | 1.00 | 24.18 | B | O |
| ATOM | 7126 | N | ILE | 172 | 105.051 | 74.301 | 22.508 | 1.00 | 23.60 | B | N |
| ATOM | 7127 | CA | ILE | 172 | 106.273 | 74.497 | 23.281 | 1.00 | 25.23 | B | C |
| ATOM | 7128 | CB | ILE | 172 | 107.353 | 73.456 | 22.885 | 1.00 | 23.64 | B | C |
| ATOM | 7129 | CG2 | ILE | 172 | 108.480 | 73.466 | 23.896 | 1.00 | 23.11 | B | C |
| ATOM | 7130 | CG1 | ILE | 172 | 106.743 | 72.056 | 22.846 | 1.00 | 23.95 | B | C |
| ATOM | 7131 | CD1 | ILE | 172 | 107.707 | 70.986 | 22.374 | 1.00 | 23.66 | B | C |
| ATOM | 7132 | C | ILE | 172 | 106.878 | 75.892 | 23.129 | 1.00 | 25.59 | B | C |
| ATOM | 7133 | O | ILE | 172 | 106.881 | 76.474 | 22.048 | 1.00 | 25.83 | B | O |
| ATOM | 7134 | N | TYR | 173 | 107.389 | 76.414 | 24.236 | 1.00 | 26.85 | B | N |
| ATOM | 7135 | CA | TYR | 173 | 108.025 | 77.720 | 24.272 | 1.00 | 27.95 | B | C |
| ATOM | 7136 | CB | TYR | 173 | 107.111 | 78.760 | 24.933 | 1.00 | 27.81 | B | C |
| ATOM | 7137 | CG | TYR | 173 | 105.822 | 79.002 | 24.190 | 1.00 | 29.53 | B | C |
| ATOM | 7138 | CD1 | TYR | 173 | 104.788 | 78.063 | 24.226 | 1.00 | 29.72 | B | C |
| ATOM | 7139 | CE1 | TYR | 173 | 103.599 | 78.271 | 23.535 | 1.00 | 29.08 | B | C |
| ATOM | 7140 | CD2 | TYR | 173 | 105.634 | 80.162 | 23.439 | 1.00 | 28.71 | B | C |
| ATOM | 7141 | CE2 | TYR | 173 | 104.444 | 80.381 | 22.740 | 1.00 | 30.14 | B | C |
| ATOM | 7142 | CZ | TYR | 173 | 103.432 | 79.429 | 22.794 | 1.00 | 30.82 | B | C |
| ATOM | 7143 | OH | TYR | 173 | 102.258 | 79.625 | 22.103 | 1.00 | 31.14 | B | O |
| ATOM | 7144 | C | TYR | 173 | 109.308 | 77.592 | 25.080 | 1.00 | 28.66 | B | C |
| ATOM | 7145 | O | TYR | 173 | 109.412 | 76.735 | 25.960 | 1.00 | 28.10 | B | O |
| ATOM | 7146 | N | VAL | 174 | 110.276 | 78.451 | 24.782 | 1.00 | 29.35 | B | N |
| ATOM | 7147 | CA | VAL | 174 | 111.551 | 78.443 | 25.480 | 1.00 | 29.22 | B | C |
| ATOM | 7148 | CB | VAL | 174 | 112.669 | 77.855 | 24.587 | 1.00 | 29.66 | B | C |
| ATOM | 7149 | CG1 | VAL | 174 | 114.006 | 77.936 | 25.303 | 1.00 | 30.07 | B | C |
| ATOM | 7150 | CG2 | VAL | 174 | 112.351 | 76.403 | 24.231 | 1.00 | 30.25 | B | C |
| ATOM | 7151 | C | VAL | 174 | 111.953 | 79.857 | 25.887 | 1.00 | 30.16 | B | C |
| ATOM | 7152 | O | VAL | 174 | 111.787 | 80.804 | 25.125 | 1.00 | 31.81 | B | O |
| ATOM | 7153 | N | LYS | 175 | 112.474 | 79.990 | 27.099 | 1.00 | 29.78 | B | N |

| | | | | | | | | | | | |
|---|---|---|---|---|---|---|---|---|---|---|---|
| ATOM | 7154 | CA | LYS | 175 | 112.940 | 81.269 | 27.608 | 1.00 | 28.47 | B | C |
| ATOM | 7155 | CB | LYS | 175 | 112.090 | 81.725 | 28.794 | 1.00 | 28.38 | B | C |
| ATOM | 7156 | CG | LYS | 175 | 110.809 | 82.428 | 28.413 | 1.00 | 29.46 | B | C |
| ATOM | 7157 | CD | LYS | 175 | 109.876 | 82.551 | 29.611 | 1.00 | 32.27 | B | C |
| ATOM | 7158 | CE | LYS | 175 | 110.479 | 83.384 | 30.725 | 1.00 | 31.57 | B | C |
| ATOM | 7159 | NZ | LYS | 175 | 110.664 | 84.791 | 30.307 | 1.00 | 33.57 | B | N |
| ATOM | 7160 | C | LYS | 175 | 114.382 | 81.107 | 28.064 | 1.00 | 28.80 | B | C |
| ATOM | 7161 | O | LYS | 175 | 114.662 | 80.355 | 28.999 | 1.00 | 28.36 | B | O |
| ATOM | 7162 | N | ILE | 176 | 115.294 | 81.813 | 27.401 | 1.00 | 28.58 | B | N |
| ATOM | 7163 | CA | ILE | 176 | 116.710 | 81.764 | 27.749 | 1.00 | 28.19 | B | C |
| ATOM | 7164 | CB | ILE | 176 | 117.572 | 82.363 | 26.624 | 1.00 | 27.21 | B | C |
| ATOM | 7165 | CG2 | ILE | 176 | 118.942 | 82.730 | 27.146 | 1.00 | 25.54 | B | C |
| ATOM | 7166 | CG1 | ILE | 176 | 117.697 | 81.354 | 25.483 | 1.00 | 28.29 | B | C |
| ATOM | 7167 | CD1 | ILE | 176 | 116.377 | 80.941 | 24.861 | 1.00 | 27.38 | B | C |
| ATOM | 7168 | C | ILE | 176 | 116.956 | 82.528 | 29.044 | 1.00 | 29.36 | B | C |
| ATOM | 7169 | O | ILE | 176 | 117.910 | 82.251 | 29.768 | 1.00 | 29.16 | B | O |
| ATOM | 7170 | N | GLU | 177 | 116.085 | 83.489 | 29.330 | 1.00 | 31.44 | B | N |
| ATOM | 7171 | CA | GLU | 177 | 116.182 | 84.296 | 30.543 | 1.00 | 33.96 | B | C |
| ATOM | 7172 | CB | GLU | 177 | 116.901 | 85.611 | 30.241 | 1.00 | 35.87 | B | C |
| ATOM | 7173 | CG | GLU | 177 | 118.342 | 85.440 | 29.770 | 1.00 | 37.59 | B | C |
| ATOM | 7174 | CD | GLU | 177 | 119.324 | 85.272 | 30.916 | 1.00 | 39.82 | B | C |
| ATOM | 7175 | OE1 | GLU | 177 | 120.511 | 84.988 | 30.642 | 1.00 | 40.62 | B | O |
| ATOM | 7176 | OE2 | GLU | 177 | 118.914 | 85.433 | 32.088 | 1.00 | 40.43 | B | O |
| ATOM | 7177 | C | GLU | 177 | 114.762 | 84.569 | 31.034 | 1.00 | 34.61 | B | C |
| ATOM | 7178 | O | GLU | 177 | 113.905 | 85.007 | 30.268 | 1.00 | 35.24 | B | O |
| ATOM | 7179 | N | PRO | 178 | 114.495 | 84.312 | 32.323 | 1.00 | 35.55 | B | N |
| ATOM | 7180 | CD | PRO | 178 | 115.451 | 83.907 | 33.367 | 1.00 | 36.07 | B | C |
| ATOM | 7181 | CA | PRO | 178 | 113.160 | 84.530 | 32.894 | 1.00 | 35.46 | B | C |
| ATOM | 7182 | CB | PRO | 178 | 113.383 | 84.357 | 34.402 | 1.00 | 35.40 | B | C |
| ATOM | 7183 | CG | PRO | 178 | 114.862 | 84.563 | 34.587 | 1.00 | 37.12 | B | C |
| ATOM | 7184 | C | PRO | 178 | 112.451 | 85.834 | 32.547 | 1.00 | 35.74 | B | C |
| ATOM | 7185 | O | PRO | 178 | 111.225 | 85.859 | 32.446 | 1.00 | 35.44 | B | O |
| ATOM | 7186 | N | ASN | 179 | 113.198 | 86.912 | 32.346 | 1.00 | 36.89 | B | N |
| ATOM | 7187 | CA | ASN | 179 | 112.560 | 88.188 | 32.021 | 1.00 | 37.31 | B | C |
| ATOM | 7188 | CB | ASN | 179 | 113.211 | 89.329 | 32.807 | 1.00 | 37.54 | B | C |
| ATOM | 7189 | CG | ASN | 179 | 114.454 | 89.860 | 32.137 | 1.00 | 37.86 | B | C |
| ATOM | 7190 | OD1 | ASN | 179 | 115.419 | 89.131 | 31.915 | 1.00 | 39.14 | B | O |
| ATOM | 7191 | ND2 | ASN | 179 | 114.437 | 91.142 | 31.806 | 1.00 | 40.48 | B | N |
| ATOM | 7192 | C | ASN | 179 | 112.573 | 88.540 | 30.535 | 1.00 | 36.88 | B | C |
| ATOM | 7193 | O | ASN | 179 | 112.205 | 89.650 | 30.159 | 1.00 | 38.11 | B | O |
| ATOM | 7194 | N | LEU | 180 | 112.995 | 87.608 | 29.689 | 1.00 | 35.31 | B | N |
| ATOM | 7195 | CA | LEU | 180 | 113.030 | 87.875 | 28.260 | 1.00 | 34.44 | B | C |
| ATOM | 7196 | CB | LEU | 180 | 114.357 | 87.417 | 27.662 | 1.00 | 35.92 | B | C |
| ATOM | 7197 | CG | LEU | 180 | 115.621 | 88.014 | 28.279 | 1.00 | 36.91 | B | C |
| ATOM | 7198 | CD1 | LEU | 180 | 116.828 | 87.572 | 27.470 | 1.00 | 37.09 | B | C |
| ATOM | 7199 | CD2 | LEU | 180 | 115.522 | 89.536 | 28.303 | 1.00 | 37.24 | B | C |
| ATOM | 7200 | C | LEU | 180 | 111.898 | 87.166 | 27.547 | 1.00 | 33.52 | B | C |
| ATOM | 7201 | O | LEU | 180 | 111.406 | 86.149 | 28.015 | 1.00 | 32.50 | B | O |
| ATOM | 7202 | N | PRO | 181 | 111.462 | 87.704 | 26.400 | 1.00 | 34.20 | B | N |

| | | | | | | | | | | |
|---|---|---|---|---|---|---|---|---|---|---|
| ATOM | 7203 | CD | PRO | 181 | 111.853 | 88.984 | 25.784 | 1.00 | 33.21 | B C |
| ATOM | 7204 | CA | PRO | 181 | 110.373 | 87.075 | 25.645 | 1.00 | 33.57 | B C |
| ATOM | 7205 | CB | PRO | 181 | 110.337 | 87.890 | 24.357 | 1.00 | 33.27 | B C |
| ATOM | 7206 | CG | PRO | 181 | 110.691 | 89.259 | 24.846 | 1.00 | 33.21 | B C |
| ATOM | 7207 | C | PRO | 181 | 110.681 | 85.608 | 25.397 | 1.00 | 33.03 | B C |
| ATOM | 7208 | O | PRO | 181 | 111.829 | 85.180 | 25.497 | 1.00 | 33.18 | B O |
| ATOM | 7209 | N | SER | 182 | 109.654 | 84.838 | 25.070 | 1.00 | 33.87 | B N |
| ATOM | 7210 | CA | SER | 182 | 109.835 | 83.415 | 24.829 | 1.00 | 32.06 | B C |
| ATOM | 7211 | CB | SER | 182 | 108.752 | 82.622 | 25.547 | 1.00 | 31.33 | B C |
| ATOM | 7212 | OG | SER | 182 | 107.505 | 82.817 | 24.909 | 1.00 | 30.50 | B O |
| ATOM | 7213 | C | SER | 182 | 109.759 | 83.117 | 23.350 | 1.00 | 31.89 | B C |
| ATOM | 7214 | O | SER | 182 | 109.077 | 83.812 | 22.606 | 1.00 | 33.14 | B O |
| ATOM | 7215 | N | TYR | 183 | 110.463 | 82.077 | 22.927 | 1.00 | 31.53 | B N |
| ATOM | 7216 | CA | TYR | 183 | 110.453 | 81.677 | 21.532 | 1.00 | 30.47 | B C |
| ATOM | 7217 | CB | TYR | 183 | 111.832 | 81.159 | 21.118 | 1.00 | 30.68 | B C |
| ATOM | 7218 | CG | TYR | 183 | 112.962 | 82.117 | 21.408 | 1.00 | 32.75 | B C |
| ATOM | 7219 | CD1 | TYR | 183 | 113.490 | 82.235 | 22.696 | 1.00 | 32.39 | B C |
| ATOM | 7220 | CE1 | TYR | 183 | 114.517 | 83.134 | 22.977 | 1.00 | 33.30 | B C |
| ATOM | 7221 | CD2 | TYR | 183 | 113.492 | 82.926 | 20.398 | 1.00 | 33.06 | B C |
| ATOM | 7222 | CE2 | TYR | 183 | 114.520 | 83.832 | 20.667 | 1.00 | 34.20 | B C |
| ATOM | 7223 | CZ | TYR | 183 | 115.028 | 83.932 | 21.959 | 1.00 | 34.92 | B C |
| ATOM | 7224 | OH | TYR | 183 | 116.036 | 84.832 | 22.233 | 1.00 | 34.60 | B O |
| ATOM | 7225 | C | TYR | 183 | 109.423 | 80.568 | 21.384 | 1.00 | 29.28 | B C |
| ATOM | 7226 | O | TYR | 183 | 109.387 | 79.645 | 22.196 | 1.00 | 29.66 | B O |
| ATOM | 7227 | N | ARG | 184 | 108.579 | 80.659 | 20.364 | 1.00 | 27.67 | B N |
| ATOM | 7228 | CA | ARG | 184 | 107.573 | 79.631 | 20.148 | 1.00 | 26.57 | B C |
| ATOM | 7229 | CB | ARG | 184 | 106.327 | 80.217 | 19.476 | 1.00 | 26.06 | B C |
| ATOM | 7230 | CG | ARG | 184 | 105.215 | 79.191 | 19.285 | 1.00 | 28.64 | B C |
| ATOM | 7231 | CD | ARG | 184 | 103.860 | 79.825 | 19.004 | 1.00 | 30.29 | B C |
| ATOM | 7232 | NE | ARG | 184 | 102.827 | 78.805 | 18.831 | 1.00 | 31.47 | B N |
| ATOM | 7233 | CZ | ARG | 184 | 101.526 | 79.052 | 18.706 | 1.00 | 29.99 | B C |
| ATOM | 7234 | NH1 | ARG | 184 | 100.678 | 78.048 | 18.552 | 1.00 | 30.76 | B N |
| ATOM | 7235 | NH2 | ARG | 184 | 101.068 | 80.294 | 18.740 | 1.00 | 30.05 | B N |
| ATOM | 7236 | C | ARG | 184 | 108.185 | 78.553 | 19.272 | 1.00 | 26.51 | B C |
| ATOM | 7237 | O | ARG | 184 | 108.375 | 78.754 | 18.072 | 1.00 | 28.42 | B O |
| ATOM | 7238 | N | ILE | 185 | 108.493 | 77.411 | 19.876 | 1.00 | 24.50 | B N |
| ATOM | 7239 | CA | ILE | 185 | 109.112 | 76.303 | 19.165 | 1.00 | 22.88 | B C |
| ATOM | 7240 | CB | ILE | 185 | 109.773 | 75.319 | 20.159 | 1.00 | 23.12 | B C |
| ATOM | 7241 | CG2 | ILE | 185 | 110.492 | 74.216 | 19.405 | 1.00 | 22.56 | B C |
| ATOM | 7242 | CG1 | ILE | 185 | 110.753 | 76.067 | 21.064 | 1.00 | 22.32 | B C |
| ATOM | 7243 | CD1 | ILE | 185 | 111.869 | 76.770 | 20.324 | 1.00 | 21.93 | B C |
| ATOM | 7244 | C | ILE | 185 | 108.148 | 75.516 | 18.275 | 1.00 | 24.00 | B C |
| ATOM | 7245 | O | ILE | 185 | 108.569 | 74.930 | 17.275 | 1.00 | 25.07 | B O |
| ATOM | 7246 | N | THR | 186 | 106.866 | 75.489 | 18.632 | 1.00 | 22.70 | B N |
| ATOM | 7247 | CA | THR | 186 | 105.886 | 74.750 | 17.840 | 1.00 | 23.30 | B C |
| ATOM | 7248 | CB | THR | 186 | 105.490 | 73.440 | 18.541 | 1.00 | 22.83 | B C |
| ATOM | 7249 | OG1 | THR | 186 | 105.058 | 73.727 | 19.877 | 1.00 | 27.42 | B O |
| ATOM | 7250 | CG2 | THR | 186 | 106.665 | 72.491 | 18.595 | 1.00 | 19.86 | B C |
| ATOM | 7251 | C | THR | 186 | 104.620 | 75.548 | 17.537 | 1.00 | 23.45 | B C |

| | | | | | | | | | | | |
|---|---|---|---|---|---|---|---|---|---|---|---|
| ATOM | 7252 | O | THR | 186 | 104.266 | 76.469 | 18.265 | 1.00 | 22.05 | B | O |
| ATOM | 7253 | N | TRP | 187 | 103.935 | 75.179 | 16.457 | 1.00 | 24.88 | B | N |
| ATOM | 7254 | CA | TRP | 187 | 102.717 | 75.876 | 16.049 | 1.00 | 25.32 | B | C |
| ATOM | 7255 | CB | TRP | 187 | 103.007 | 76.767 | 14.832 | 1.00 | 25.43 | B | C |
| ATOM | 7256 | CG | TRP | 187 | 104.159 | 77.694 | 15.025 | 1.00 | 25.95 | B | C |
| ATOM | 7257 | CD2 | TRP | 187 | 104.093 | 79.092 | 15.321 | 1.00 | 26.73 | B | C |
| ATOM | 7258 | CE2 | TRP | 187 | 105.420 | 79.548 | 15.487 | 1.00 | 26.07 | B | C |
| ATOM | 7259 | CE3 | TRP | 187 | 103.041 | 80.007 | 15.464 | 1.00 | 27.09 | B | C |
| ATOM | 7260 | CD1 | TRP | 187 | 105.485 | 77.367 | 15.019 | 1.00 | 26.93 | B | C |
| ATOM | 7261 | NE1 | TRP | 187 | 106.249 | 78.474 | 15.298 | 1.00 | 26.08 | B | N |
| ATOM | 7262 | CZ2 | TRP | 187 | 105.723 | 80.878 | 15.789 | 1.00 | 24.50 | B | C |
| ATOM | 7263 | CZ3 | TRP | 187 | 103.346 | 81.332 | 15.764 | 1.00 | 26.71 | B | C |
| ATOM | 7264 | CH2 | TRP | 187 | 104.679 | 81.751 | 15.922 | 1.00 | 25.13 | B | C |
| ATOM | 7265 | C | TRP | 187 | 101.555 | 74.941 | 15.709 | 1.00 | 26.00 | B | C |
| ATOM | 7266 | O | TRP | 187 | 100.481 | 75.402 | 15.339 | 1.00 | 27.74 | B | O |
| ATOM | 7267 | N | THR | 188 | 101.759 | 73.636 | 15.839 | 1.00 | 26.58 | B | N |
| ATOM | 7268 | CA | THR | 188 | 100.708 | 72.672 | 15.516 | 1.00 | 26.89 | B | C |
| ATOM | 7269 | CB | THR | 188 | 101.304 | 71.388 | 14.895 | 1.00 | 26.63 | B | C |
| ATOM | 7270 | OG1 | THR | 188 | 102.291 | 70.836 | 15.781 | 1.00 | 27.13 | B | O |
| ATOM | 7271 | CG2 | THR | 188 | 101.940 | 71.697 | 13.552 | 1.00 | 25.34 | B | C |
| ATOM | 7272 | C | THR | 188 | 99.817 | 72.259 | 16.687 | 1.00 | 27.17 | B | C |
| ATOM | 7273 | O | THR | 188 | 98.916 | 71.437 | 16.512 | 1.00 | 26.92 | B | O |
| ATOM | 7274 | N | GLY | 189 | 100.064 | 72.827 | 17.866 | 1.00 | 26.58 | B | N |
| ATOM | 7275 | CA | GLY | 189 | 99.278 | 72.491 | 19.045 | 1.00 | 27.32 | B | C |
| ATOM | 7276 | C | GLY | 189 | 97.783 | 72.645 | 18.847 | 1.00 | 28.44 | B | C |
| ATOM | 7277 | O | GLY | 189 | 97.333 | 73.673 | 18.345 | 1.00 | 30.95 | B | O |
| ATOM | 7278 | N | LYS | 190 | 97.007 | 71.636 | 19.242 | 1.00 | 27.83 | B | N |
| ATOM | 7279 | CA | LYS | 190 | 95.554 | 71.686 | 19.085 | 1.00 | 27.15 | B | C |
| ATOM | 7280 | CB | LYS | 190 | 95.187 | 71.381 | 17.628 | 1.00 | 29.55 | B | C |
| ATOM | 7281 | CG | LYS | 190 | 93.695 | 71.294 | 17.317 | 1.00 | 31.55 | B | C |
| ATOM | 7282 | CD | LYS | 190 | 93.498 | 71.031 | 15.821 | 1.00 | 36.65 | B | C |
| ATOM | 7283 | CE | LYS | 190 | 92.043 | 70.731 | 15.458 | 1.00 | 39.17 | B | C |
| ATOM | 7284 | NZ | LYS | 190 | 91.127 | 71.870 | 15.744 | 1.00 | 41.50 | B | N |
| ATOM | 7285 | C | LYS | 190 | 94.815 | 70.731 | 20.028 | 1.00 | 26.61 | B | C |
| ATOM | 7286 | O | LYS | 190 | 94.738 | 69.523 | 19.786 | 1.00 | 25.87 | B | O |
| ATOM | 7287 | N | GLU | 191 | 94.262 | 71.299 | 21.096 | 1.00 | 25.05 | B | N |
| ATOM | 7288 | CA | GLU | 191 | 93.516 | 70.558 | 22.110 | 1.00 | 25.10 | B | C |
| ATOM | 7289 | CB | GLU | 191 | 92.461 | 71.475 | 22.728 | 1.00 | 26.71 | B | C |
| ATOM | 7290 | CG | GLU | 191 | 91.821 | 70.933 | 23.987 | 1.00 | 29.36 | B | C |
| ATOM | 7291 | CD | GLU | 191 | 90.752 | 71.859 | 24.514 | 1.00 | 34.15 | B | C |
| ATOM | 7292 | OE1 | GLU | 191 | 90.111 | 71.522 | 25.536 | 1.00 | 36.46 | B | O |
| ATOM | 7293 | OE2 | GLU | 191 | 90.551 | 72.932 | 23.899 | 1.00 | 35.96 | B | O |
| ATOM | 7294 | C | GLU | 191 | 92.849 | 69.263 | 21.631 | 1.00 | 23.31 | B | C |
| ATOM | 7295 | O | GLU | 191 | 92.031 | 69.280 | 20.713 | 1.00 | 20.17 | B | O |
| ATOM | 7296 | N | ASP | 192 | 93.208 | 68.157 | 22.287 | 1.00 | 23.70 | B | N |
| ATOM | 7297 | CA | ASP | 192 | 92.707 | 66.811 | 21.996 | 1.00 | 24.98 | B | C |
| ATOM | 7298 | CB | ASP | 192 | 91.183 | 66.733 | 22.149 | 1.00 | 27.27 | B | C |
| ATOM | 7299 | CG | ASP | 192 | 90.700 | 67.200 | 23.508 | 1.00 | 30.85 | B | C |
| ATOM | 7300 | OD1 | ASP | 192 | 91.335 | 66.855 | 24.533 | 1.00 | 32.45 | B | O |

FIG. 4-150 (Continued)

| | | | | | | | | | | |
|---|---|---|---|---|---|---|---|---|---|---|
| ATOM | 7301 | OD2 | ASP | 192 | 89.671 | 67.908 | 23.548 | 1.00 | 32.44 | B | O |
| ATOM | 7302 | C | ASP | 192 | 93.072 | 66.329 | 20.602 | 1.00 | 25.95 | B | C |
| ATOM | 7303 | O | ASP | 192 | 92.431 | 65.426 | 20.065 | 1.00 | 27.81 | B | O |
| ATOM | 7304 | N | ILE | 193 | 94.091 | 66.926 | 20.000 | 1.00 | 25.46 | B | N |
| ATOM | 7305 | CA | ILE | 193 | 94.485 | 66.512 | 18.665 | 1.00 | 25.50 | B | C |
| ATOM | 7306 | CB | ILE | 193 | 93.970 | 67.502 | 17.595 | 1.00 | 26.97 | B | C |
| ATOM | 7307 | CG2 | ILE | 193 | 94.426 | 67.057 | 16.212 | 1.00 | 26.11 | B | C |
| ATOM | 7308 | CG1 | ILE | 193 | 92.441 | 67.552 | 17.621 | 1.00 | 27.90 | B | C |
| ATOM | 7309 | CD1 | ILE | 193 | 91.784 | 66.246 | 17.210 | 1.00 | 29.23 | B | C |
| ATOM | 7310 | C | ILE | 193 | 95.994 | 66.390 | 18.546 | 1.00 | 25.04 | B | C |
| ATOM | 7311 | O | ILE | 193 | 96.519 | 65.297 | 18.334 | 1.00 | 26.34 | B | O |
| ATOM | 7312 | N | ILE | 194 | 96.691 | 67.510 | 18.682 | 1.00 | 22.43 | B | N |
| ATOM | 7313 | CA | ILE | 194 | 98.139 | 67.505 | 18.589 | 1.00 | 21.47 | B | C |
| ATOM | 7314 | CB | ILE | 194 | 98.618 | 68.429 | 17.456 | 1.00 | 21.58 | B | C |
| ATOM | 7315 | CG2 | ILE | 194 | 100.146 | 68.414 | 17.377 | 1.00 | 18.60 | B | C |
| ATOM | 7316 | CG1 | ILE | 194 | 97.972 | 68.001 | 16.133 | 1.00 | 19.45 | B | C |
| ATOM | 7317 | CD1 | ILE | 194 | 98.331 | 66.613 | 15.678 | 1.00 | 15.81 | B | C |
| ATOM | 7318 | C | ILE | 194 | 98.779 | 67.968 | 19.895 | 1.00 | 21.61 | B | C |
| ATOM | 7319 | O | ILE | 194 | 98.544 | 69.095 | 20.337 | 1.00 | 22.13 | B | O |
| ATOM | 7320 | N | TYR | 195 | 99.580 | 67.095 | 20.508 | 1.00 | 19.09 | B | N |
| ATOM | 7321 | CA | TYR | 195 | 100.272 | 67.429 | 21.750 | 1.00 | 18.17 | B | C |
| ATOM | 7322 | CB | TYR | 195 | 100.079 | 66.331 | 22.798 | 1.00 | 20.45 | B | C |
| ATOM | 7323 | CG | TYR | 195 | 98.647 | 65.941 | 23.094 | 1.00 | 21.37 | B | C |
| ATOM | 7324 | CD1 | TYR | 195 | 97.873 | 65.269 | 22.146 | 1.00 | 20.38 | B | C |
| ATOM | 7325 | CE1 | TYR | 195 | 96.584 | 64.846 | 22.445 | 1.00 | 20.38 | B | C |
| ATOM | 7326 | CD2 | TYR | 195 | 98.087 | 66.187 | 24.349 | 1.00 | 21.55 | B | C |
| ATOM | 7327 | CE2 | TYR | 195 | 96.797 | 65.768 | 24.659 | 1.00 | 20.75 | B | C |
| ATOM | 7328 | CZ | TYR | 195 | 96.052 | 65.094 | 23.705 | 1.00 | 20.48 | B | C |
| ATOM | 7329 | OH | TYR | 195 | 94.785 | 64.650 | 24.020 | 1.00 | 19.77 | B | O |
| ATOM | 7330 | C | TYR | 195 | 101.771 | 67.579 | 21.503 | 1.00 | 18.27 | B | C |
| ATOM | 7331 | O | TYR | 195 | 102.412 | 66.677 | 20.967 | 1.00 | 19.50 | B | O |
| ATOM | 7332 | N | ASN | 196 | 102.334 | 68.710 | 21.897 | 1.00 | 17.52 | B | N |
| ATOM | 7333 | CA | ASN | 196 | 103.762 | 68.941 | 21.725 | 1.00 | 17.79 | B | C |
| ATOM | 7334 | CB | ASN | 196 | 104.011 | 70.187 | 20.867 | 1.00 | 17.21 | B | C |
| ATOM | 7335 | CG | ASN | 196 | 103.366 | 70.106 | 19.489 | 1.00 | 17.04 | B | C |
| ATOM | 7336 | OD1 | ASN | 196 | 103.769 | 69.311 | 18.632 | 1.00 | 16.41 | B | O |
| ATOM | 7337 | ND2 | ASN | 196 | 102.362 | 70.943 | 19.267 | 1.00 | 17.01 | B | N |
| ATOM | 7338 | C | ASN | 196 | 104.380 | 69.160 | 23.104 | 1.00 | 18.89 | B | C |
| ATOM | 7339 | O | ASN | 196 | 103.976 | 70.066 | 23.828 | 1.00 | 21.80 | B | O |
| ATOM | 7340 | N | GLY | 197 | 105.355 | 68.344 | 23.479 | 1.00 | 18.21 | B | N |
| ATOM | 7341 | CA | GLY | 197 | 105.976 | 68.533 | 24.778 | 1.00 | 18.42 | B | C |
| ATOM | 7342 | C | GLY | 197 | 105.185 | 67.948 | 25.941 | 1.00 | 18.43 | B | C |
| ATOM | 7343 | O | GLY | 197 | 105.660 | 67.954 | 27.088 | 1.00 | 17.86 | B | O |
| ATOM | 7344 | N | ILE | 198 | 103.976 | 67.469 | 25.654 | 1.00 | 15.16 | B | N |
| ATOM | 7345 | CA | ILE | 198 | 103.129 | 66.842 | 26.667 | 1.00 | 14.58 | B | C |
| ATOM | 7346 | CB | ILE | 198 | 101.956 | 67.740 | 27.160 | 1.00 | 12.66 | B | C |
| ATOM | 7347 | CG2 | ILE | 198 | 102.477 | 68.784 | 28.109 | 1.00 | 10.73 | B | C |
| ATOM | 7348 | CG1 | ILE | 198 | 101.189 | 68.334 | 25.970 | 1.00 | 14.13 | B | C |
| ATOM | 7349 | CD1 | ILE | 198 | 99.936 | 69.129 | 26.368 | 1.00 | 13.46 | B | C |

FIG. 4-151

| ATOM | 7350 | C | ILE | 198 | 102.523 | 65.585 | 26.101 | 1.00 | 14.46 | B | C |
|---|---|---|---|---|---|---|---|---|---|---|---|
| ATOM | 7351 | O | ILE | 198 | 102.354 | 65.447 | 24.895 | 1.00 | 16.78 | B | O |
| ATOM | 7352 | N | THR | 199 | 102.182 | 64.671 | 26.990 | 1.00 | 15.77 | B | N |
| ATOM | 7353 | CA | THR | 199 | 101.600 | 63.396 | 26.608 | 1.00 | 15.94 | B | C |
| ATOM | 7354 | CB | THR | 199 | 101.982 | 62.350 | 27.630 | 1.00 | 15.69 | B | C |
| ATOM | 7355 | OG1 | THR | 199 | 101.683 | 62.861 | 28.937 | 1.00 | 12.99 | B | O |
| ATOM | 7356 | CG2 | THR | 199 | 103.473 | 62.043 | 27.534 | 1.00 | 15.54 | B | C |
| ATOM | 7357 | C | THR | 199 | 100.085 | 63.448 | 26.522 | 1.00 | 15.87 | B | C |
| ATOM | 7358 | O | THR | 199 | 99.452 | 64.311 | 27.133 | 1.00 | 16.77 | B | O |
| ATOM | 7359 | N | ASP | 200 | 99.510 | 62.534 | 25.745 | 1.00 | 16.29 | B | N |
| ATOM | 7360 | CA | ASP | 200 | 98.058 | 62.450 | 25.619 | 1.00 | 16.42 | B | C |
| ATOM | 7361 | CB | ASP | 200 | 97.654 | 61.812 | 24.279 | 1.00 | 17.56 | B | C |
| ATOM | 7362 | CG | ASP | 200 | 97.960 | 60.321 | 24.207 | 1.00 | 19.40 | B | C |
| ATOM | 7363 | OD1 | ASP | 200 | 98.894 | 59.847 | 24.892 | 1.00 | 20.07 | B | O |
| ATOM | 7364 | OD2 | ASP | 200 | 97.267 | 59.624 | 23.438 | 1.00 | 19.79 | B | O |
| ATOM | 7365 | C | ASP | 200 | 97.657 | 61.578 | 26.806 | 1.00 | 15.56 | B | C |
| ATOM | 7366 | O | ASP | 200 | 98.502 | 61.278 | 27.648 | 1.00 | 16.67 | B | O |
| ATOM | 7367 | N | TRP | 201 | 96.404 | 61.151 | 26.889 | 1.00 | 14.09 | B | N |
| ATOM | 7368 | CA | TRP | 201 | 96.003 | 60.368 | 28.049 | 1.00 | 13.08 | B | C |
| ATOM | 7369 | CB | TRP | 201 | 94.503 | 60.106 | 28.037 | 1.00 | 13.25 | B | C |
| ATOM | 7370 | CG | TRP | 201 | 94.023 | 59.554 | 29.348 | 1.00 | 12.63 | B | C |
| ATOM | 7371 | CD2 | TRP | 201 | 94.135 | 58.198 | 29.801 | 1.00 | 10.35 | B | C |
| ATOM | 7372 | CE2 | TRP | 201 | 93.610 | 58.150 | 31.110 | 1.00 | 11.08 | B | C |
| ATOM | 7373 | CE3 | TRP | 201 | 94.634 | 57.020 | 29.228 | 1.00 | 8.52 | B | C |
| ATOM | 7374 | CD1 | TRP | 201 | 93.449 | 60.253 | 30.370 | 1.00 | 12.43 | B | C |
| ATOM | 7375 | NE1 | TRP | 201 | 93.198 | 59.416 | 31.434 | 1.00 | 12.21 | B | N |
| ATOM | 7376 | CZ2 | TRP | 201 | 93.567 | 56.967 | 31.858 | 1.00 | 11.85 | B | C |
| ATOM | 7377 | CZ3 | TRP | 201 | 94.596 | 55.847 | 29.968 | 1.00 | 8.91 | B | C |
| ATOM | 7378 | CH2 | TRP | 201 | 94.065 | 55.829 | 31.271 | 1.00 | 10.19 | B | C |
| ATOM | 7379 | C | TRP | 201 | 96.719 | 59.040 | 28.264 | 1.00 | 14.63 | B | C |
| ATOM | 7380 | O | TRP | 201 | 97.197 | 58.766 | 29.366 | 1.00 | 14.84 | B | O |
| ATOM | 7381 | N | VAL | 202 | 96.795 | 58.213 | 27.224 | 1.00 | 14.84 | B | N |
| ATOM | 7382 | CA | VAL | 202 | 97.413 | 56.902 | 27.369 | 1.00 | 13.74 | B | C |
| ATOM | 7383 | CB | VAL | 202 | 97.028 | 55.966 | 26.190 | 1.00 | 11.30 | B | C |
| ATOM | 7384 | CG1 | VAL | 202 | 97.960 | 56.155 | 25.010 | 1.00 | 8.57 | B | C |
| ATOM | 7385 | CG2 | VAL | 202 | 97.028 | 54.541 | 26.667 | 1.00 | 8.82 | B | C |
| ATOM | 7386 | C | VAL | 202 | 98.929 | 56.920 | 27.556 | 1.00 | 15.45 | B | C |
| ATOM | 7387 | O | VAL | 202 | 99.471 | 56.095 | 28.292 | 1.00 | 16.05 | B | O |
| ATOM | 7388 | N | TYR | 203 | 99.616 | 57.857 | 26.906 | 1.00 | 15.45 | B | N |
| ATOM | 7389 | CA | TYR | 203 | 101.060 | 57.941 | 27.053 | 1.00 | 13.39 | B | C |
| ATOM | 7390 | CB | TYR | 203 | 101.656 | 58.918 | 26.035 | 1.00 | 12.37 | B | C |
| ATOM | 7391 | CG | TYR | 203 | 102.248 | 58.238 | 24.823 | 1.00 | 8.90 | B | C |
| ATOM | 7392 | CD1 | TYR | 203 | 101.461 | 57.938 | 23.709 | 1.00 | 8.82 | B | C |
| ATOM | 7393 | CE1 | TYR | 203 | 101.989 | 57.260 | 22.619 | 1.00 | 7.48 | B | C |
| ATOM | 7394 | CD2 | TYR | 203 | 103.587 | 57.844 | 24.812 | 1.00 | 5.53 | B | C |
| ATOM | 7395 | CE2 | TYR | 203 | 104.128 | 57.167 | 23.727 | 1.00 | 6.51 | B | C |
| ATOM | 7396 | CZ | TYR | 203 | 103.325 | 56.874 | 22.634 | 1.00 | 8.49 | B | C |
| ATOM | 7397 | OH | TYR | 203 | 103.849 | 56.175 | 21.572 | 1.00 | 8.01 | B | O |
| ATOM | 7398 | C | TYR | 203 | 101.438 | 58.371 | 28.471 | 1.00 | 13.68 | B | C |

| ATOM | 7399 | O | TYR | 203 | 102.369 | 57.832 | 29.056 | 1.00 | 12.65 | B | O |
| --- | --- | --- | --- | --- | --- | --- | --- | --- | --- | --- | --- |
| ATOM | 7400 | N | GLU | 204 | 100.706 | 59.335 | 29.020 | 1.00 | 15.26 | B | N |
| ATOM | 7401 | CA | GLU | 204 | 100.963 | 59.827 | 30.376 | 1.00 | 16.69 | B | C |
| ATOM | 7402 | CB | GLU | 204 | 99.975 | 60.936 | 30.743 | 1.00 | 16.67 | B | C |
| ATOM | 7403 | CG | GLU | 204 | 100.174 | 61.457 | 32.161 | 1.00 | 17.47 | B | C |
| ATOM | 7404 | CD | GLU | 204 | 98.950 | 62.154 | 32.731 | 1.00 | 17.71 | B | C |
| ATOM | 7405 | OE1 | GLU | 204 | 98.197 | 62.785 | 31.964 | 1.00 | 19.00 | B | O |
| ATOM | 7406 | OE2 | GLU | 204 | 98.753 | 62.085 | 33.962 | 1.00 | 18.59 | B | O |
| ATOM | 7407 | C | GLU | 204 | 100.831 | 58.740 | 31.437 | 1.00 | 17.37 | B | C |
| ATOM | 7408 | O | GLU | 204 | 101.681 | 58.597 | 32.305 | 1.00 | 18.22 | B | O |
| ATOM | 7409 | N | GLU | 205 | 99.745 | 57.980 | 31.353 | 1.00 | 18.89 | B | N |
| ATOM | 7410 | CA | GLU | 205 | 99.442 | 56.932 | 32.315 | 1.00 | 19.55 | B | C |
| ATOM | 7411 | CB | GLU | 205 | 97.925 | 56.727 | 32.344 | 1.00 | 20.80 | B | C |
| ATOM | 7412 | CG | GLU | 205 | 97.453 | 55.436 | 32.995 | 1.00 | 23.74 | B | C |
| ATOM | 7413 | CD | GLU | 205 | 97.414 | 55.494 | 34.515 | 1.00 | 26.68 | B | C |
| ATOM | 7414 | OE1 | GLU | 205 | 97.038 | 54.466 | 35.118 | 1.00 | 28.71 | B | O |
| ATOM | 7415 | OE2 | GLU | 205 | 97.744 | 56.547 | 35.106 | 1.00 | 26.12 | B | O |
| ATOM | 7416 | C | GLU | 205 | 100.132 | 55.578 | 32.131 | 1.00 | 19.27 | B | C |
| ATOM | 7417 | O | GLU | 205 | 100.525 | 54.957 | 33.107 | 1.00 | 19.31 | B | O |
| ATOM | 7418 | N | GLU | 206 | 100.291 | 55.124 | 30.893 | 1.00 | 18.93 | B | N |
| ATOM | 7419 | CA | GLU | 206 | 100.876 | 53.808 | 30.660 | 1.00 | 18.63 | B | C |
| ATOM | 7420 | CB | GLU | 206 | 99.989 | 53.016 | 29.705 | 1.00 | 18.05 | B | C |
| ATOM | 7421 | CG | GLU | 206 | 98.535 | 52.921 | 30.139 | 1.00 | 20.39 | B | C |
| ATOM | 7422 | CD | GLU | 206 | 98.359 | 52.143 | 31.422 | 1.00 | 20.74 | B | C |
| ATOM | 7423 | OE1 | GLU | 206 | 97.205 | 51.905 | 31.821 | 1.00 | 21.45 | B | O |
| ATOM | 7424 | OE2 | GLU | 206 | 99.375 | 51.768 | 32.037 | 1.00 | 22.90 | B | O |
| ATOM | 7425 | C | GLU | 206 | 102.293 | 53.766 | 30.136 | 1.00 | 19.32 | B | C |
| ATOM | 7426 | O | GLU | 206 | 102.976 | 52.761 | 30.292 | 1.00 | 20.01 | B | O |
| ATOM | 7427 | N | VAL | 207 | 102.744 | 54.844 | 29.509 | 1.00 | 20.90 | B | N |
| ATOM | 7428 | CA | VAL | 207 | 104.092 | 54.855 | 28.968 | 1.00 | 20.95 | B | C |
| ATOM | 7429 | CB | VAL | 207 | 104.101 | 55.347 | 27.509 | 1.00 | 21.52 | B | C |
| ATOM | 7430 | CG1 | VAL | 207 | 105.486 | 55.151 | 26.918 | 1.00 | 22.17 | B | C |
| ATOM | 7431 | CG2 | VAL | 207 | 103.048 | 54.592 | 26.684 | 1.00 | 19.10 | B | C |
| ATOM | 7432 | C | VAL | 207 | 105.080 | 55.691 | 29.775 | 1.00 | 21.67 | B | C |
| ATOM | 7433 | O | VAL | 207 | 106.052 | 55.160 | 30.301 | 1.00 | 25.32 | B | O |
| ATOM | 7434 | N | PHE | 208 | 104.833 | 56.989 | 29.888 | 1.00 | 21.55 | B | N |
| ATOM | 7435 | CA | PHE | 208 | 105.743 | 57.870 | 30.611 | 1.00 | 21.33 | B | C |
| ATOM | 7436 | CB | PHE | 208 | 105.877 | 59.201 | 29.863 | 1.00 | 21.28 | B | C |
| ATOM | 7437 | CG | PHE | 208 | 106.571 | 59.083 | 28.536 | 1.00 | 21.92 | B | C |
| ATOM | 7438 | CD1 | PHE | 208 | 107.890 | 58.649 | 28.464 | 1.00 | 20.63 | B | C |
| ATOM | 7439 | CD2 | PHE | 208 | 105.893 | 59.373 | 27.353 | 1.00 | 22.58 | B | C |
| ATOM | 7440 | CE1 | PHE | 208 | 108.525 | 58.499 | 27.230 | 1.00 | 22.52 | B | C |
| ATOM | 7441 | CE2 | PHE | 208 | 106.521 | 59.225 | 26.109 | 1.00 | 22.24 | B | C |
| ATOM | 7442 | CZ | PHE | 208 | 107.837 | 58.787 | 26.048 | 1.00 | 22.76 | B | C |
| ATOM | 7443 | C | PHE | 208 | 105.444 | 58.168 | 32.082 | 1.00 | 21.89 | B | C |
| ATOM | 7444 | O | PHE | 208 | 106.298 | 58.727 | 32.768 | 1.00 | 23.07 | B | O |
| ATOM | 7445 | N | SER | 209 | 104.261 | 57.811 | 32.577 | 1.00 | 20.48 | B | N |
| ATOM | 7446 | CA | SER | 209 | 103.922 | 58.094 | 33.976 | 1.00 | 19.86 | B | C |
| ATOM | 7447 | CB | SER | 209 | 104.689 | 57.165 | 34.905 | 1.00 | 18.09 | B | C |

| | | | | | | | | | | |
|---|---|---|---|---|---|---|---|---|---|---|
| ATOM | 7448 | OG | SER | 209 | 104.383 | 55.820 | 34.601 | 1.00 | 21.42 | B | O |
| ATOM | 7449 | C | SER | 209 | 104.285 | 59.543 | 34.286 | 1.00 | 20.55 | B | C |
| ATOM | 7450 | O | SER | 209 | 104.780 | 59.877 | 35.367 | 1.00 | 19.53 | B | O |
| ATOM | 7451 | N | ALA | 210 | 104.031 | 60.394 | 33.302 | 1.00 | 20.69 | B | N |
| ATOM | 7452 | CA | ALA | 210 | 104.319 | 61.809 | 33.393 | 1.00 | 20.47 | B | C |
| ATOM | 7453 | CB | ALA | 210 | 105.809 | 62.044 | 33.228 | 1.00 | 20.63 | B | C |
| ATOM | 7454 | C | ALA | 210 | 103.545 | 62.492 | 32.275 | 1.00 | 20.53 | B | C |
| ATOM | 7455 | O | ALA | 210 | 103.042 | 61.835 | 31.367 | 1.00 | 19.81 | B | O |
| ATOM | 7456 | N | TYR | 211 | 103.461 | 63.813 | 32.354 | 1.00 | 21.78 | B | N |
| ATOM | 7457 | CA | TYR | 211 | 102.733 | 64.634 | 31.390 | 1.00 | 20.95 | B | C |
| ATOM | 7458 | CB | TYR | 211 | 101.944 | 65.681 | 32.175 | 1.00 | 18.35 | B | C |
| ATOM | 7459 | CG | TYR | 211 | 100.984 | 66.566 | 31.411 | 1.00 | 15.38 | B | C |
| ATOM | 7460 | CD1 | TYR | 211 | 100.257 | 66.086 | 30.324 | 1.00 | 14.13 | B | C |
| ATOM | 7461 | CE1 | TYR | 211 | 99.310 | 66.879 | 29.694 | 1.00 | 12.47 | B | C |
| ATOM | 7462 | CD2 | TYR | 211 | 100.738 | 67.863 | 31.846 | 1.00 | 11.95 | B | C |
| ATOM | 7463 | CE2 | TYR | 211 | 99.799 | 68.657 | 31.231 | 1.00 | 12.21 | B | C |
| ATOM | 7464 | CZ | TYR | 211 | 99.087 | 68.165 | 30.156 | 1.00 | 13.68 | B | C |
| ATOM | 7465 | OH | TYR | 211 | 98.158 | 68.977 | 29.550 | 1.00 | 12.73 | B | O |
| ATOM | 7466 | C | TYR | 211 | 103.781 | 65.283 | 30.508 | 1.00 | 22.11 | B | C |
| ATOM | 7467 | O | TYR | 211 | 103.512 | 65.742 | 29.406 | 1.00 | 23.55 | B | O |
| ATOM | 7468 | N | SER | 212 | 105.000 | 65.294 | 31.017 | 1.00 | 23.17 | B | N |
| ATOM | 7469 | CA | SER | 212 | 106.112 | 65.877 | 30.310 | 1.00 | 22.03 | B | C |
| ATOM | 7470 | CB | SER | 212 | 107.286 | 66.055 | 31.265 | 1.00 | 22.38 | B | C |
| ATOM | 7471 | OG | SER | 212 | 108.441 | 66.477 | 30.567 | 1.00 | 24.83 | B | O |
| ATOM | 7472 | C | SER | 212 | 106.547 | 65.017 | 29.141 | 1.00 | 22.20 | B | C |
| ATOM | 7473 | O | SER | 212 | 106.651 | 63.802 | 29.256 | 1.00 | 22.93 | B | O |
| ATOM | 7474 | N | ALA | 213 | 106.791 | 65.668 | 28.013 | 1.00 | 22.14 | B | N |
| ATOM | 7475 | CA | ALA | 213 | 107.267 | 65.011 | 26.812 | 1.00 | 19.72 | B | C |
| ATOM | 7476 | CB | ALA | 213 | 106.157 | 64.882 | 25.803 | 1.00 | 19.85 | B | C |
| ATOM | 7477 | C | ALA | 213 | 108.360 | 65.942 | 26.301 | 1.00 | 21.17 | B | C |
| ATOM | 7478 | O | ALA | 213 | 108.443 | 66.254 | 25.109 | 1.00 | 20.14 | B | O |
| ATOM | 7479 | N | LEU | 214 | 109.175 | 66.409 | 27.243 | 1.00 | 21.21 | B | N |
| ATOM | 7480 | CA | LEU | 214 | 110.298 | 67.295 | 26.961 | 1.00 | 22.06 | B | C |
| ATOM | 7481 | CB | LEU | 214 | 110.049 | 68.697 | 27.534 | 1.00 | 21.02 | B | C |
| ATOM | 7482 | CG | LEU | 214 | 108.958 | 69.546 | 26.878 | 1.00 | 20.19 | B | C |
| ATOM | 7483 | CD1 | LEU | 214 | 108.840 | 70.872 | 27.603 | 1.00 | 21.72 | B | C |
| ATOM | 7484 | CD2 | LEU | 214 | 109.292 | 69.779 | 25.426 | 1.00 | 22.01 | B | C |
| ATOM | 7485 | C | LEU | 214 | 111.528 | 66.688 | 27.615 | 1.00 | 22.30 | B | C |
| ATOM | 7486 | O | LEU | 214 | 111.442 | 66.131 | 28.703 | 1.00 | 25.61 | B | O |
| ATOM | 7487 | N | TRP | 215 | 112.674 | 66.795 | 26.957 | 1.00 | 21.71 | B | N |
| ATOM | 7488 | CA | TRP | 215 | 113.904 | 66.237 | 27.497 | 1.00 | 19.34 | B | C |
| ATOM | 7489 | CB | TRP | 215 | 114.112 | 64.833 | 26.942 | 1.00 | 18.71 | B | C |
| ATOM | 7490 | CG | TRP | 215 | 113.018 | 63.863 | 27.294 | 1.00 | 18.43 | B | C |
| ATOM | 7491 | CD2 | TRP | 215 | 111.910 | 63.481 | 26.468 | 1.00 | 16.56 | B | C |
| ATOM | 7492 | CE2 | TRP | 215 | 111.157 | 62.536 | 27.194 | 1.00 | 14.85 | B | C |
| ATOM | 7493 | CE3 | TRP | 215 | 111.482 | 63.845 | 25.186 | 1.00 | 17.01 | B | C |
| ATOM | 7494 | CD1 | TRP | 215 | 112.890 | 63.155 | 28.456 | 1.00 | 15.04 | B | C |
| ATOM | 7495 | NE1 | TRP | 215 | 111.781 | 62.356 | 28.400 | 1.00 | 13.49 | B | N |
| ATOM | 7496 | CZ2 | TRP | 215 | 109.996 | 61.949 | 26.682 | 1.00 | 14.75 | B | C |

| ATOM | 7497 | CZ3 | TRP | 215 | 110.326 | 63.257 | 24.675 | 1.00 | 15.48 | B | C |
|------|------|-----|-----|-----|---------|--------|--------|------|-------|---|---|
| ATOM | 7498 | CH2 | TRP | 215 | 109.599 | 62.320 | 25.425 | 1.00 | 15.57 | B | C |
| ATOM | 7499 | C | TRP | 215 | 115.110 | 67.096 | 27.149 | 1.00 | 20.78 | B | C |
| ATOM | 7500 | O | TRP | 215 | 115.625 | 67.034 | 26.028 | 1.00 | 20.20 | B | O |
| ATOM | 7501 | N | TRP | 216 | 115.566 | 67.897 | 28.108 | 1.00 | 20.97 | B | N |
| ATOM | 7502 | CA | TRP | 216 | 116.727 | 68.743 | 27.880 | 1.00 | 21.49 | B | C |
| ATOM | 7503 | CB | TRP | 216 | 116.958 | 69.705 | 29.048 | 1.00 | 22.15 | B | C |
| ATOM | 7504 | CG | TRP | 216 | 116.020 | 70.863 | 29.156 | 1.00 | 24.63 | B | C |
| ATOM | 7505 | CD2 | TRP | 216 | 116.097 | 72.099 | 28.437 | 1.00 | 25.56 | B | C |
| ATOM | 7506 | CE2 | TRP | 216 | 115.036 | 72.916 | 28.896 | 1.00 | 26.21 | B | C |
| ATOM | 7507 | CE3 | TRP | 216 | 116.959 | 72.598 | 27.452 | 1.00 | 25.00 | B | C |
| ATOM | 7508 | CD1 | TRP | 216 | 114.945 | 70.974 | 29.994 | 1.00 | 25.92 | B | C |
| ATOM | 7509 | NE1 | TRP | 216 | 114.351 | 72.204 | 29.844 | 1.00 | 26.55 | B | N |
| ATOM | 7510 | CZ2 | TRP | 216 | 114.815 | 74.209 | 28.401 | 1.00 | 24.93 | B | C |
| ATOM | 7511 | CZ3 | TRP | 216 | 116.738 | 73.887 | 26.958 | 1.00 | 25.52 | B | C |
| ATOM | 7512 | CH2 | TRP | 216 | 115.673 | 74.674 | 27.435 | 1.00 | 24.95 | B | C |
| ATOM | 7513 | C | TRP | 216 | 117.982 | 67.896 | 27.747 | 1.00 | 23.03 | B | C |
| ATOM | 7514 | O | TRP | 216 | 118.083 | 66.816 | 28.334 | 1.00 | 21.32 | B | O |
| ATOM | 7515 | N | SER | 217 | 118.941 | 68.398 | 26.975 | 1.00 | 25.91 | B | N |
| ATOM | 7516 | CA | SER | 217 | 120.222 | 67.723 | 26.819 | 1.00 | 26.96 | B | C |
| ATOM | 7517 | CB | SER | 217 | 120.954 | 68.223 | 25.575 | 1.00 | 28.77 | B | C |
| ATOM | 7518 | OG | SER | 217 | 121.212 | 69.612 | 25.676 | 1.00 | 31.27 | B | O |
| ATOM | 7519 | C | SER | 217 | 120.976 | 68.145 | 28.080 | 1.00 | 27.00 | B | C |
| ATOM | 7520 | O | SER | 217 | 120.694 | 69.198 | 28.656 | 1.00 | 26.90 | B | O |
| ATOM | 7521 | N | PRO | 218 | 121.942 | 67.336 | 28.523 | 1.00 | 26.67 | B | N |
| ATOM | 7522 | CD | PRO | 218 | 122.469 | 66.127 | 27.867 | 1.00 | 26.71 | B | C |
| ATOM | 7523 | CA | PRO | 218 | 122.712 | 67.646 | 29.727 | 1.00 | 26.69 | B | C |
| ATOM | 7524 | CB | PRO | 218 | 123.961 | 66.801 | 29.547 | 1.00 | 27.32 | B | C |
| ATOM | 7525 | CG | PRO | 218 | 123.385 | 65.555 | 28.937 | 1.00 | 26.93 | B | C |
| ATOM | 7526 | C | PRO | 218 | 123.005 | 69.116 | 30.010 | 1.00 | 27.70 | B | C |
| ATOM | 7527 | O | PRO | 218 | 122.487 | 69.661 | 30.985 | 1.00 | 30.37 | B | O |
| ATOM | 7528 | N | ASN | 219 | 123.818 | 69.770 | 29.184 | 1.00 | 27.72 | B | N |
| ATOM | 7529 | CA | ASN | 219 | 124.129 | 71.176 | 29.435 | 1.00 | 26.82 | B | C |
| ATOM | 7530 | CB | ASN | 219 | 125.485 | 71.562 | 28.816 | 1.00 | 26.61 | B | C |
| ATOM | 7531 | CG | ASN | 219 | 125.447 | 71.640 | 27.308 | 1.00 | 27.23 | B | C |
| ATOM | 7532 | OD1 | ASN | 219 | 124.376 | 71.725 | 26.706 | 1.00 | 25.21 | B | O |
| ATOM | 7533 | ND2 | ASN | 219 | 126.626 | 71.632 | 26.690 | 1.00 | 30.87 | B | N |
| ATOM | 7534 | C | ASN | 219 | 123.029 | 72.133 | 28.958 | 1.00 | 27.38 | B | C |
| ATOM | 7535 | O | ASN | 219 | 123.212 | 73.351 | 28.943 | 1.00 | 29.12 | B | O |
| ATOM | 7536 | N | GLY | 220 | 121.888 | 71.575 | 28.565 | 1.00 | 26.98 | B | N |
| ATOM | 7537 | CA | GLY | 220 | 120.765 | 72.391 | 28.137 | 1.00 | 26.30 | B | C |
| ATOM | 7538 | C | GLY | 220 | 120.823 | 73.030 | 26.765 | 1.00 | 26.91 | B | C |
| ATOM | 7539 | O | GLY | 220 | 120.097 | 73.986 | 26.500 | 1.00 | 27.55 | B | O |
| ATOM | 7540 | N | THR | 221 | 121.669 | 72.512 | 25.884 | 1.00 | 27.00 | B | N |
| ATOM | 7541 | CA | THR | 221 | 121.775 | 73.073 | 24.547 | 1.00 | 26.99 | B | C |
| ATOM | 7542 | CB | THR | 221 | 123.052 | 72.584 | 23.808 | 1.00 | 27.74 | B | C |
| ATOM | 7543 | OG1 | THR | 221 | 124.213 | 73.084 | 24.481 | 1.00 | 29.49 | B | O |
| ATOM | 7544 | CG2 | THR | 221 | 123.068 | 73.089 | 22.367 | 1.00 | 26.25 | B | C |
| ATOM | 7545 | C | THR | 221 | 120.559 | 72.685 | 23.730 | 1.00 | 26.42 | B | C |

FIG. 4-155

| | | | | | | | | | | |
|---|---|---|---|---|---|---|---|---|---|---|
| ATOM | 7546 | O | THR | 221 | 119.862 | 73.551 | 23.201 | 1.00 | 28.29 | B | O |
| ATOM | 7547 | N | PHE | 222 | 120.305 | 71.386 | 23.619 | 1.00 | 25.34 | B | N |
| ATOM | 7548 | CA | PHE | 222 | 119.158 | 70.921 | 22.850 | 1.00 | 25.13 | B | C |
| ATOM | 7549 | CB | PHE | 222 | 119.480 | 69.645 | 22.069 | 1.00 | 25.65 | B | C |
| ATOM | 7550 | CG | PHE | 222 | 120.722 | 69.723 | 21.246 | 1.00 | 26.36 | B | C |
| ATOM | 7551 | CD1 | PHE | 222 | 121.955 | 69.384 | 21.797 | 1.00 | 26.35 | B | C |
| ATOM | 7552 | CD2 | PHE | 222 | 120.661 | 70.111 | 19.912 | 1.00 | 25.81 | B | C |
| ATOM | 7553 | CE1 | PHE | 222 | 123.115 | 69.425 | 21.031 | 1.00 | 26.12 | B | C |
| ATOM | 7554 | CE2 | PHE | 222 | 121.815 | 70.158 | 19.132 | 1.00 | 28.19 | B | C |
| ATOM | 7555 | CZ | PHE | 222 | 123.046 | 69.814 | 19.693 | 1.00 | 28.46 | B | C |
| ATOM | 7556 | C | PHE | 222 | 117.949 | 70.618 | 23.723 | 1.00 | 24.55 | B | C |
| ATOM | 7557 | O | PHE | 222 | 118.066 | 70.282 | 24.901 | 1.00 | 24.38 | B | O |
| ATOM | 7558 | N | LEU | 223 | 116.780 | 70.746 | 23.119 | 1.00 | 24.19 | B | N |
| ATOM | 7559 | CA | LEU | 223 | 115.540 | 70.442 | 23.789 | 1.00 | 22.85 | B | C |
| ATOM | 7560 | CB | LEU | 223 | 114.618 | 71.667 | 23.878 | 1.00 | 21.81 | B | C |
| ATOM | 7561 | CG | LEU | 223 | 113.248 | 71.340 | 24.503 | 1.00 | 20.49 | B | C |
| ATOM | 7562 | CD1 | LEU | 223 | 113.469 | 70.684 | 25.860 | 1.00 | 21.10 | B | C |
| ATOM | 7563 | CD2 | LEU | 223 | 112.389 | 72.587 | 24.644 | 1.00 | 18.49 | B | C |
| ATOM | 7564 | C | LEU | 223 | 114.885 | 69.380 | 22.934 | 1.00 | 23.23 | B | C |
| ATOM | 7565 | O | LEU | 223 | 114.462 | 69.650 | 21.808 | 1.00 | 22.62 | B | O |
| ATOM | 7566 | N | ALA | 224 | 114.834 | 68.162 | 23.459 | 1.00 | 23.47 | B | N |
| ATOM | 7567 | CA | ALA | 224 | 114.201 | 67.062 | 22.753 | 1.00 | 23.08 | B | C |
| ATOM | 7568 | CB | ALA | 224 | 114.935 | 65.776 | 23.038 | 1.00 | 24.27 | B | C |
| ATOM | 7569 | C | ALA | 224 | 112.761 | 66.968 | 23.248 | 1.00 | 23.38 | B | C |
| ATOM | 7570 | O | ALA | 224 | 112.498 | 67.111 | 24.444 | 1.00 | 23.37 | B | O |
| ATOM | 7571 | N | TYR | 225 | 111.825 | 66.755 | 22.328 | 1.00 | 23.10 | B | N |
| ATOM | 7572 | CA | TYR | 225 | 110.423 | 66.635 | 22.703 | 1.00 | 21.31 | B | C |
| ATOM | 7573 | CB | TYR | 225 | 109.733 | 67.997 | 22.701 | 1.00 | 18.23 | B | C |
| ATOM | 7574 | CG | TYR | 225 | 109.648 | 68.624 | 21.332 | 1.00 | 18.56 | B | C |
| ATOM | 7575 | CD1 | TYR | 225 | 110.680 | 69.443 | 20.849 | 1.00 | 16.52 | B | C |
| ATOM | 7576 | CE1 | TYR | 225 | 110.607 | 70.017 | 19.589 | 1.00 | 13.07 | B | C |
| ATOM | 7577 | CD2 | TYR | 225 | 108.543 | 68.399 | 20.509 | 1.00 | 16.18 | B | C |
| ATOM | 7578 | CE2 | TYR | 225 | 108.466 | 68.970 | 19.244 | 1.00 | 14.89 | B | C |
| ATOM | 7579 | CZ | TYR | 225 | 109.502 | 69.777 | 18.796 | 1.00 | 12.68 | B | C |
| ATOM | 7580 | OH | TYR | 225 | 109.431 | 70.342 | 17.553 | 1.00 | 14.06 | B | O |
| ATOM | 7581 | C | TYR | 225 | 109.705 | 65.712 | 21.737 | 1.00 | 21.55 | B | C |
| ATOM | 7582 | O | TYR | 225 | 110.143 | 65.523 | 20.607 | 1.00 | 22.86 | B | O |
| ATOM | 7583 | N | ALA | 226 | 108.596 | 65.141 | 22.195 | 1.00 | 20.96 | B | N |
| ATOM | 7584 | CA | ALA | 226 | 107.811 | 64.235 | 21.381 | 1.00 | 19.66 | B | C |
| ATOM | 7585 | CB | ALA | 226 | 107.485 | 62.980 | 22.173 | 1.00 | 19.19 | B | C |
| ATOM | 7586 | C | ALA | 226 | 106.528 | 64.921 | 20.962 | 1.00 | 19.73 | B | C |
| ATOM | 7587 | O | ALA | 226 | 106.107 | 65.908 | 21.576 | 1.00 | 21.22 | B | O |
| ATOM | 7588 | N | GLN | 227 | 105.912 | 64.410 | 19.909 | 1.00 | 16.70 | B | N |
| ATOM | 7589 | CA | GLN | 227 | 104.659 | 64.968 | 19.457 | 1.00 | 17.01 | B | C |
| ATOM | 7590 | CB | GLN | 227 | 104.823 | 65.709 | 18.139 | 1.00 | 17.47 | B | C |
| ATOM | 7591 | CG | GLN | 227 | 103.512 | 66.300 | 17.670 | 1.00 | 18.65 | B | C |
| ATOM | 7592 | CD | GLN | 227 | 103.554 | 66.788 | 16.249 | 1.00 | 18.45 | B | C |
| ATOM | 7593 | OE1 | GLN | 227 | 103.724 | 66.007 | 15.320 | 1.00 | 18.91 | B | O |
| ATOM | 7594 | NE2 | GLN | 227 | 103.394 | 68.090 | 16.070 | 1.00 | 19.57 | B | N |

| ATOM | 7595 | C | GLN | 227 | 103.651 | 63.841 | 19.274 | 1.00 | 17.21 | B | C |
|------|------|---|-----|-----|---------|--------|--------|------|-------|---|---|
| ATOM | 7596 | O | GLN | 227 | 103.931 | 62.850 | 18.594 | 1.00 | 17.76 | B | O |
| ATOM | 7597 | N | PHE | 228 | 102.483 | 63.990 | 19.888 | 1.00 | 16.03 | B | N |
| ATOM | 7598 | CA | PHE | 228 | 101.447 | 62.980 | 19.768 | 1.00 | 17.64 | B | C |
| ATOM | 7599 | CB | PHE | 228 | 100.985 | 62.524 | 21.158 | 1.00 | 14.78 | B | C |
| ATOM | 7600 | CG | PHE | 228 | 102.111 | 62.105 | 22.065 | 1.00 | 13.03 | B | C |
| ATOM | 7601 | CD1 | PHE | 228 | 102.659 | 63.003 | 22.982 | 1.00 | 12.33 | B | C |
| ATOM | 7602 | CD2 | PHE | 228 | 102.653 | 60.826 | 21.978 | 1.00 | 12.01 | B | C |
| ATOM | 7603 | CE1 | PHE | 228 | 103.732 | 62.636 | 23.796 | 1.00 | 9.77 | B | C |
| ATOM | 7604 | CE2 | PHE | 228 | 103.725 | 60.450 | 22.786 | 1.00 | 11.27 | B | C |
| ATOM | 7605 | CZ | PHE | 228 | 104.267 | 61.360 | 23.698 | 1.00 | 9.50 | B | C |
| ATOM | 7606 | C | PHE | 228 | 100.263 | 63.523 | 18.955 | 1.00 | 18.96 | B | C |
| ATOM | 7607 | O | PHE | 228 | 99.894 | 64.697 | 19.064 | 1.00 | 19.98 | B | O |
| ATOM | 7608 | N | ASN | 229 | 99.685 | 62.657 | 18.133 | 1.00 | 20.11 | B | N |
| ATOM | 7609 | CA | ASN | 229 | 98.548 | 63.002 | 17.285 | 1.00 | 20.74 | B | C |
| ATOM | 7610 | CB | ASN | 229 | 98.965 | 62.867 | 15.819 | 1.00 | 22.98 | B | C |
| ATOM | 7611 | CG | ASN | 229 | 97.980 | 63.488 | 14.867 | 1.00 | 27.56 | B | C |
| ATOM | 7612 | OD1 | ASN | 229 | 96.795 | 63.610 | 15.174 | 1.00 | 31.63 | B | O |
| ATOM | 7613 | ND2 | ASN | 229 | 98.467 | 63.871 | 13.692 | 1.00 | 30.76 | B | N |
| ATOM | 7614 | C | ASN | 229 | 97.435 | 61.995 | 17.609 | 1.00 | 21.10 | B | C |
| ATOM | 7615 | O | ASN | 229 | 97.550 | 60.816 | 17.283 | 1.00 | 20.02 | B | O |
| ATOM | 7616 | N | ASP | 230 | 96.369 | 62.444 | 18.260 | 1.00 | 22.16 | B | N |
| ATOM | 7617 | CA | ASP | 230 | 95.277 | 61.534 | 18.608 | 1.00 | 24.31 | B | C |
| ATOM | 7618 | CB | ASP | 230 | 94.877 | 61.683 | 20.079 | 1.00 | 23.86 | B | C |
| ATOM | 7619 | CG | ASP | 230 | 95.999 | 61.332 | 21.027 | 1.00 | 25.25 | B | C |
| ATOM | 7620 | OD1 | ASP | 230 | 95.701 | 60.914 | 22.159 | 1.00 | 27.89 | B | O |
| ATOM | 7621 | OD2 | ASP | 230 | 97.180 | 61.485 | 20.656 | 1.00 | 27.78 | B | O |
| ATOM | 7622 | C | ASP | 230 | 94.056 | 61.776 | 17.740 | 1.00 | 24.83 | B | C |
| ATOM | 7623 | O | ASP | 230 | 92.927 | 61.496 | 18.148 | 1.00 | 24.00 | B | O |
| ATOM | 7624 | N | THR | 231 | 94.297 | 62.284 | 16.536 | 1.00 | 25.37 | B | N |
| ATOM | 7625 | CA | THR | 231 | 93.229 | 62.582 | 15.593 | 1.00 | 26.24 | B | C |
| ATOM | 7626 | CB | THR | 231 | 93.802 | 62.868 | 14.193 | 1.00 | 25.71 | B | C |
| ATOM | 7627 | OG1 | THR | 231 | 94.439 | 64.151 | 14.194 | 1.00 | 26.78 | B | O |
| ATOM | 7628 | CG2 | THR | 231 | 92.702 | 62.851 | 13.150 | 1.00 | 23.72 | B | C |
| ATOM | 7629 | C | THR | 231 | 92.148 | 61.510 | 15.467 | 1.00 | 27.04 | B | C |
| ATOM | 7630 | O | THR | 231 | 90.964 | 61.815 | 15.604 | 1.00 | 29.05 | B | O |
| ATOM | 7631 | N | GLU | 232 | 92.545 | 60.265 | 15.211 | 1.00 | 27.00 | B | N |
| ATOM | 7632 | CA | GLU | 232 | 91.574 | 59.183 | 15.038 | 1.00 | 26.30 | B | C |
| ATOM | 7633 | CB | GLU | 232 | 92.017 | 58.286 | 13.877 | 1.00 | 29.71 | B | C |
| ATOM | 7634 | CG | GLU | 232 | 92.177 | 59.036 | 12.563 | 1.00 | 36.71 | B | C |
| ATOM | 7635 | CD | GLU | 232 | 92.971 | 58.253 | 11.519 | 1.00 | 39.94 | B | C |
| ATOM | 7636 | OE1 | GLU | 232 | 92.434 | 57.273 | 10.943 | 1.00 | 41.61 | B | O |
| ATOM | 7637 | OE2 | GLU | 232 | 94.142 | 58.623 | 11.286 | 1.00 | 39.28 | B | O |
| ATOM | 7638 | C | GLU | 232 | 91.320 | 58.328 | 16.282 | 1.00 | 23.78 | B | C |
| ATOM | 7639 | O | GLU | 232 | 90.683 | 57.280 | 16.208 | 1.00 | 23.18 | B | O |
| ATOM | 7640 | N | VAL | 233 | 91.823 | 58.763 | 17.427 | 1.00 | 21.91 | B | N |
| ATOM | 7641 | CA | VAL | 233 | 91.608 | 58.010 | 18.652 | 1.00 | 20.18 | B | C |
| ATOM | 7642 | CB | VAL | 233 | 92.651 | 58.375 | 19.727 | 1.00 | 20.26 | B | C |
| ATOM | 7643 | CG1 | VAL | 233 | 92.352 | 57.627 | 21.016 | 1.00 | 18.23 | B | C |

FIG. 4-157 (Continued)

| | | | | | | | | | | | |
|---|---|---|---|---|---|---|---|---|---|---|---|
| ATOM | 7644 | CG2 | VAL | 233 | 94.050 | 58.032 | 19.223 | 1.00 | 18.80 | B | C |
| ATOM | 7645 | C | VAL | 233 | 90.218 | 58.339 | 19.175 | 1.00 | 18.04 | B | C |
| ATOM | 7646 | O | VAL | 233 | 89.886 | 59.507 | 19.378 | 1.00 | 19.49 | B | O |
| ATOM | 7647 | N | PRO | 234 | 89.383 | 57.315 | 19.394 | 1.00 | 16.04 | B | N |
| ATOM | 7648 | CD | PRO | 234 | 89.633 | 55.876 | 19.231 | 1.00 | 14.37 | B | C |
| ATOM | 7649 | CA | PRO | 234 | 88.025 | 57.544 | 19.896 | 1.00 | 15.33 | B | C |
| ATOM | 7650 | CB | PRO | 234 | 87.461 | 56.133 | 20.030 | 1.00 | 13.91 | B | C |
| ATOM | 7651 | CG | PRO | 234 | 88.247 | 55.363 | 19.013 | 1.00 | 12.89 | B | C |
| ATOM | 7652 | C | PRO | 234 | 88.048 | 58.275 | 21.227 | 1.00 | 14.45 | B | C |
| ATOM | 7653 | O | PRO | 234 | 89.043 | 58.242 | 21.950 | 1.00 | 13.13 | B | O |
| ATOM | 7654 | N | LEU | 235 | 86.941 | 58.927 | 21.547 | 1.00 | 14.92 | B | N |
| ATOM | 7655 | CA | LEU | 235 | 86.831 | 59.676 | 22.791 | 1.00 | 13.91 | B | C |
| ATOM | 7656 | CB | LEU | 235 | 86.131 | 61.005 | 22.536 | 1.00 | 14.93 | B | C |
| ATOM | 7657 | CG | LEU | 235 | 86.627 | 61.937 | 21.434 | 1.00 | 16.83 | B | C |
| ATOM | 7658 | CD1 | LEU | 235 | 85.581 | 63.030 | 21.198 | 1.00 | 17.90 | B | C |
| ATOM | 7659 | CD2 | LEU | 235 | 87.963 | 62.534 | 21.833 | 1.00 | 14.85 | B | C |
| ATOM | 7660 | C | LEU | 235 | 85.998 | 58.911 | 23.803 | 1.00 | 12.70 | B | C |
| ATOM | 7661 | O | LEU | 235 | 84.941 | 58.385 | 23.456 | 1.00 | 13.27 | B | O |
| ATOM | 7662 | N | ILE | 236 | 86.468 | 58.801 | 25.039 | 1.00 | 10.71 | B | N |
| ATOM | 7663 | CA | ILE | 236 | 85.618 | 58.165 | 26.037 | 1.00 | 10.96 | B | C |
| ATOM | 7664 | CB | ILE | 236 | 86.385 | 57.630 | 27.283 | 1.00 | 9.70 | B | C |
| ATOM | 7665 | CG2 | ILE | 236 | 87.316 | 58.692 | 27.859 | 1.00 | 10.05 | B | C |
| ATOM | 7666 | CG1 | ILE | 236 | 85.386 | 57.246 | 28.371 | 1.00 | 7.51 | B | C |
| ATOM | 7667 | CD1 | ILE | 236 | 84.465 | 56.100 | 28.002 | 1.00 | 9.77 | B | C |
| ATOM | 7668 | C | ILE | 236 | 84.774 | 59.369 | 26.456 | 1.00 | 12.91 | B | C |
| ATOM | 7669 | O | ILE | 236 | 85.277 | 60.500 | 26.486 | 1.00 | 13.64 | B | O |
| ATOM | 7670 | N | GLU | 237 | 83.497 | 59.156 | 26.741 | 1.00 | 13.69 | B | N |
| ATOM | 7671 | CA | GLU | 237 | 82.651 | 60.267 | 27.150 | 1.00 | 14.30 | B | C |
| ATOM | 7672 | CB | GLU | 237 | 81.657 | 60.643 | 26.041 | 1.00 | 15.93 | B | C |
| ATOM | 7673 | CG | GLU | 237 | 82.307 | 60.993 | 24.708 | 1.00 | 20.06 | B | C |
| ATOM | 7674 | CD | GLU | 237 | 81.311 | 61.541 | 23.682 | 1.00 | 24.67 | B | C |
| ATOM | 7675 | OE1 | GLU | 237 | 80.133 | 61.125 | 23.713 | 1.00 | 27.11 | B | O |
| ATOM | 7676 | OE2 | GLU | 237 | 81.706 | 62.377 | 22.832 | 1.00 | 25.71 | B | O |
| ATOM | 7677 | C | GLU | 237 | 81.902 | 59.898 | 28.407 | 1.00 | 12.26 | B | C |
| ATOM | 7678 | O | GLU | 237 | 81.473 | 58.759 | 28.569 | 1.00 | 12.02 | B | O |
| ATOM | 7679 | N | TYR | 238 | 81.768 | 60.860 | 29.310 | 1.00 | 12.67 | B | N |
| ATOM | 7680 | CA | TYR | 238 | 81.044 | 60.630 | 30.550 | 1.00 | 13.08 | B | C |
| ATOM | 7681 | CB | TYR | 238 | 81.903 | 59.816 | 31.534 | 1.00 | 11.88 | B | C |
| ATOM | 7682 | CG | TYR | 238 | 83.201 | 60.458 | 31.954 | 1.00 | 15.20 | B | C |
| ATOM | 7683 | CD1 | TYR | 238 | 83.250 | 61.347 | 33.026 | 1.00 | 15.46 | B | C |
| ATOM | 7684 | CE1 | TYR | 238 | 84.458 | 61.920 | 33.430 | 1.00 | 15.78 | B | C |
| ATOM | 7685 | CD2 | TYR | 238 | 84.390 | 60.160 | 31.291 | 1.00 | 14.07 | B | C |
| ATOM | 7686 | CE2 | TYR | 238 | 85.592 | 60.727 | 31.683 | 1.00 | 14.24 | B | C |
| ATOM | 7687 | CZ | TYR | 238 | 85.623 | 61.606 | 32.751 | 1.00 | 13.94 | B | C |
| ATOM | 7688 | OH | TYR | 238 | 86.818 | 62.173 | 33.129 | 1.00 | 12.45 | B | O |
| ATOM | 7689 | C | TYR | 238 | 80.583 | 61.944 | 31.163 | 1.00 | 13.53 | B | C |
| ATOM | 7690 | O | TYR | 238 | 81.095 | 63.008 | 30.832 | 1.00 | 14.88 | B | O |
| ATOM | 7691 | N | SER | 239 | 79.592 | 61.865 | 32.042 | 1.00 | 14.64 | B | N |
| ATOM | 7692 | CA | SER | 239 | 79.040 | 63.047 | 32.684 | 1.00 | 13.89 | B | C |

| | | | | | | | | | | |
|---|---|---|---|---|---|---|---|---|---|---|
| ATOM | 7693 | CB | SER | 239 | 77.597 | 62.783 | 33.085 | 1.00 | 13.29 | B C |
| ATOM | 7694 | OG | SER | 239 | 76.800 | 62.496 | 31.961 | 1.00 | 19.37 | B O |
| ATOM | 7695 | C | SER | 239 | 79.775 | 63.547 | 33.915 | 1.00 | 14.65 | B C |
| ATOM | 7696 | O | SER | 239 | 80.361 | 62.775 | 34.673 | 1.00 | 15.52 | B O |
| ATOM | 7697 | N | PHE | 240 | 79.737 | 64.860 | 34.100 | 1.00 | 14.89 | B N |
| ATOM | 7698 | CA | PHE | 240 | 80.313 | 65.493 | 35.276 | 1.00 | 15.60 | B C |
| ATOM | 7699 | CB | PHE | 240 | 81.543 | 66.325 | 34.932 | 1.00 | 17.00 | B C |
| ATOM | 7700 | CG | PHE | 240 | 82.422 | 66.591 | 36.112 | 1.00 | 14.96 | B C |
| ATOM | 7701 | CD1 | PHE | 240 | 83.325 | 65.629 | 36.547 | 1.00 | 15.66 | B C |
| ATOM | 7702 | CD2 | PHE | 240 | 82.312 | 67.781 | 36.822 | 1.00 | 14.41 | B C |
| ATOM | 7703 | CE1 | PHE | 240 | 84.108 | 65.846 | 37.675 | 1.00 | 13.32 | B C |
| ATOM | 7704 | CE2 | PHE | 240 | 83.087 | 68.009 | 37.950 | 1.00 | 12.45 | B C |
| ATOM | 7705 | CZ | PHE | 240 | 83.988 | 67.039 | 38.379 | 1.00 | 11.23 | B C |
| ATOM | 7706 | C | PHE | 240 | 79.184 | 66.403 | 35.758 | 1.00 | 15.75 | B C |
| ATOM | 7707 | O | PHE | 240 | 78.671 | 67.232 | 34.995 | 1.00 | 14.05 | B O |
| ATOM | 7708 | N | TYR | 241 | 78.785 | 66.231 | 37.013 | 1.00 | 15.13 | B N |
| ATOM | 7709 | CA | TYR | 241 | 77.683 | 67.002 | 37.567 | 1.00 | 14.92 | B C |
| ATOM | 7710 | CB | TYR | 241 | 76.912 | 66.125 | 38.545 | 1.00 | 13.15 | B C |
| ATOM | 7711 | CG | TYR | 241 | 76.480 | 64.848 | 37.880 | 1.00 | 12.77 | B C |
| ATOM | 7712 | CD1 | TYR | 241 | 75.393 | 64.832 | 37.007 | 1.00 | 11.36 | B C |
| ATOM | 7713 | CE1 | TYR | 241 | 75.051 | 63.678 | 36.304 | 1.00 | 12.47 | B C |
| ATOM | 7714 | CD2 | TYR | 241 | 77.215 | 63.674 | 38.041 | 1.00 | 12.85 | B C |
| ATOM | 7715 | CE2 | TYR | 241 | 76.883 | 62.512 | 37.342 | 1.00 | 12.55 | B C |
| ATOM | 7716 | CZ | TYR | 241 | 75.801 | 62.523 | 36.472 | 1.00 | 12.41 | B C |
| ATOM | 7717 | OH | TYR | 241 | 75.489 | 61.395 | 35.748 | 1.00 | 12.90 | B O |
| ATOM | 7718 | C | TYR | 241 | 78.100 | 68.299 | 38.208 | 1.00 | 15.24 | B C |
| ATOM | 7719 | O | TYR | 241 | 77.311 | 69.239 | 38.263 | 1.00 | 17.04 | B O |
| ATOM | 7720 | N | SER | 242 | 79.337 | 68.353 | 38.694 | 1.00 | 16.92 | B N |
| ATOM | 7721 | CA | SER | 242 | 79.864 | 69.570 | 39.305 | 1.00 | 16.89 | B C |
| ATOM | 7722 | CB | SER | 242 | 79.816 | 70.707 | 38.280 | 1.00 | 15.48 | B C |
| ATOM | 7723 | OG | SER | 242 | 80.439 | 71.870 | 38.782 | 1.00 | 18.12 | B O |
| ATOM | 7724 | C | SER | 242 | 79.078 | 69.963 | 40.548 | 1.00 | 16.70 | B C |
| ATOM | 7725 | O | SER | 242 | 78.438 | 69.121 | 41.171 | 1.00 | 18.07 | B O |
| ATOM | 7726 | N | ASP | 243 | 79.136 | 71.241 | 40.912 | 1.00 | 17.57 | B N |
| ATOM | 7727 | CA | ASP | 243 | 78.405 | 71.728 | 42.075 | 1.00 | 19.72 | B C |
| ATOM | 7728 | CB | ASP | 243 | 78.846 | 73.142 | 42.442 | 1.00 | 23.43 | B C |
| ATOM | 7729 | CG | ASP | 243 | 80.275 | 73.188 | 42.950 | 1.00 | 28.70 | B C |
| ATOM | 7730 | OD1 | ASP | 243 | 80.646 | 72.307 | 43.765 | 1.00 | 29.62 | B O |
| ATOM | 7731 | OD2 | ASP | 243 | 81.021 | 74.106 | 42.542 | 1.00 | 29.69 | B O |
| ATOM | 7732 | C | ASP | 243 | 76.917 | 71.708 | 41.772 | 1.00 | 20.24 | B C |
| ATOM | 7733 | O | ASP | 243 | 76.508 | 71.777 | 40.609 | 1.00 | 20.38 | B O |
| ATOM | 7734 | N | GLU | 244 | 76.104 | 71.624 | 42.818 | 1.00 | 19.25 | B N |
| ATOM | 7735 | CA | GLU | 244 | 74.668 | 71.545 | 42.630 | 1.00 | 19.29 | B C |
| ATOM | 7736 | CB | GLU | 244 | 73.966 | 71.376 | 43.988 | 1.00 | 19.46 | B C |
| ATOM | 7737 | CG | GLU | 244 | 73.283 | 72.609 | 44.533 | 1.00 | 23.65 | B C |
| ATOM | 7738 | CD | GLU | 244 | 72.567 | 72.334 | 45.847 | 1.00 | 26.30 | B C |
| ATOM | 7739 | OE1 | GLU | 244 | 73.225 | 71.856 | 46.797 | 1.00 | 28.64 | B O |
| ATOM | 7740 | OE2 | GLU | 244 | 71.349 | 72.595 | 45.934 | 1.00 | 27.72 | B O |
| ATOM | 7741 | C | GLU | 244 | 74.086 | 72.720 | 41.850 | 1.00 | 18.30 | B C |

| | | | | | | | | | | |
|---|---|---|---|---|---|---|---|---|---|---|
| ATOM | 7742 | O | GLU | 244 | 72.958 | 72.647 | 41.355 | 1.00 | 19.81 | B | O |
| ATOM | 7743 | N | SER | 245 | 74.861 | 73.785 | 41.702 | 1.00 | 15.52 | B | N |
| ATOM | 7744 | CA | SER | 245 | 74.381 | 74.958 | 40.986 | 1.00 | 11.95 | B | C |
| ATOM | 7745 | CB | SER | 245 | 75.157 | 76.196 | 41.425 | 1.00 | 11.90 | B | C |
| ATOM | 7746 | OG | SER | 245 | 76.473 | 76.162 | 40.915 | 1.00 | 17.74 | B | O |
| ATOM | 7747 | C | SER | 245 | 74.459 | 74.821 | 39.470 | 1.00 | 9.32 | B | C |
| ATOM | 7748 | O | SER | 245 | 73.883 | 75.625 | 38.752 | 1.00 | 10.56 | B | O |
| ATOM | 7749 | N | LEU | 246 | 75.167 | 73.819 | 38.968 | 1.00 | 8.50 | B | N |
| ATOM | 7750 | CA | LEU | 246 | 75.252 | 73.647 | 37.518 | 1.00 | 8.56 | B | C |
| ATOM | 7751 | CB | LEU | 246 | 76.481 | 72.812 | 37.145 | 1.00 | 8.57 | B | C |
| ATOM | 7752 | CG | LEU | 246 | 76.770 | 72.639 | 35.644 | 1.00 | 11.81 | B | C |
| ATOM | 7753 | CD1 | LEU | 246 | 77.074 | 73.984 | 35.008 | 1.00 | 5.99 | B | C |
| ATOM | 7754 | CD2 | LEU | 246 | 77.949 | 71.694 | 35.449 | 1.00 | 10.70 | B | C |
| ATOM | 7755 | C | LEU | 246 | 73.971 | 72.944 | 37.070 | 1.00 | 10.18 | B | C |
| ATOM | 7756 | O | LEU | 246 | 73.772 | 71.758 | 37.349 | 1.00 | 9.30 | B | O |
| ATOM | 7757 | N | GLN | 247 | 73.094 | 73.685 | 36.393 | 1.00 | 12.01 | B | N |
| ATOM | 7758 | CA | GLN | 247 | 71.815 | 73.144 | 35.938 | 1.00 | 12.00 | B | C |
| ATOM | 7759 | CB | GLN | 247 | 70.995 | 74.230 | 35.245 | 1.00 | 12.36 | B | C |
| ATOM | 7760 | CG | GLN | 247 | 69.584 | 73.806 | 34.884 | 1.00 | 14.88 | B | C |
| ATOM | 7761 | CD | GLN | 247 | 68.727 | 74.978 | 34.446 | 1.00 | 16.57 | B | C |
| ATOM | 7762 | OE1 | GLN | 247 | 69.152 | 75.790 | 33.627 | 1.00 | 18.02 | B | O |
| ATOM | 7763 | NE2 | GLN | 247 | 67.512 | 75.069 | 34.986 | 1.00 | 13.91 | B | N |
| ATOM | 7764 | C | GLN | 247 | 71.974 | 71.942 | 35.022 | 1.00 | 12.63 | B | C |
| ATOM | 7765 | O | GLN | 247 | 71.358 | 70.903 | 35.249 | 1.00 | 13.50 | B | O |
| ATOM | 7766 | N | TYR | 248 | 72.793 | 72.074 | 33.987 | 1.00 | 13.12 | B | N |
| ATOM | 7767 | CA | TYR | 248 | 73.022 | 70.949 | 33.089 | 1.00 | 13.90 | B | C |
| ATOM | 7768 | CB | TYR | 248 | 72.954 | 71.379 | 31.628 | 1.00 | 11.81 | B | C |
| ATOM | 7769 | CG | TYR | 248 | 71.562 | 71.727 | 31.155 | 1.00 | 11.76 | B | C |
| ATOM | 7770 | CD1 | TYR | 248 | 70.967 | 72.942 | 31.498 | 1.00 | 10.54 | B | C |
| ATOM | 7771 | CE1 | TYR | 248 | 69.689 | 73.265 | 31.055 | 1.00 | 11.01 | B | C |
| ATOM | 7772 | CD2 | TYR | 248 | 70.842 | 70.843 | 30.360 | 1.00 | 9.97 | B | C |
| ATOM | 7773 | CE2 | TYR | 248 | 69.562 | 71.155 | 29.911 | 1.00 | 11.67 | B | C |
| ATOM | 7774 | CZ | TYR | 248 | 68.989 | 72.366 | 30.259 | 1.00 | 11.89 | B | C |
| ATOM | 7775 | OH | TYR | 248 | 67.722 | 72.674 | 29.801 | 1.00 | 10.14 | B | O |
| ATOM | 7776 | C | TYR | 248 | 74.385 | 70.340 | 33.353 | 1.00 | 14.77 | B | C |
| ATOM | 7777 | O | TYR | 248 | 75.384 | 71.049 | 33.419 | 1.00 | 15.30 | B | O |
| ATOM | 7778 | N | PRO | 249 | 74.441 | 69.014 | 33.544 | 1.00 | 15.88 | B | N |
| ATOM | 7779 | CD | PRO | 249 | 73.350 | 68.031 | 33.636 | 1.00 | 15.23 | B | C |
| ATOM | 7780 | CA | PRO | 249 | 75.739 | 68.381 | 33.793 | 1.00 | 16.47 | B | C |
| ATOM | 7781 | CB | PRO | 249 | 75.360 | 66.947 | 34.161 | 1.00 | 16.57 | B | C |
| ATOM | 7782 | CG | PRO | 249 | 74.086 | 66.732 | 33.417 | 1.00 | 15.37 | B | C |
| ATOM | 7783 | C | PRO | 249 | 76.568 | 68.468 | 32.515 | 1.00 | 16.66 | B | C |
| ATOM | 7784 | O | PRO | 249 | 76.016 | 68.446 | 31.419 | 1.00 | 15.91 | B | O |
| ATOM | 7785 | N | LYS | 250 | 77.884 | 68.586 | 32.647 | 1.00 | 16.70 | B | N |
| ATOM | 7786 | CA | LYS | 250 | 78.721 | 68.683 | 31.463 | 1.00 | 18.05 | B | C |
| ATOM | 7787 | CB | LYS | 250 | 79.920 | 69.591 | 31.719 | 1.00 | 17.36 | B | C |
| ATOM | 7788 | CG | LYS | 250 | 80.912 | 69.015 | 32.681 | 1.00 | 22.33 | B | C |
| ATOM | 7789 | CD | LYS | 250 | 82.204 | 69.826 | 32.691 | 1.00 | 28.25 | B | C |
| ATOM | 7790 | CE | LYS | 250 | 82.952 | 69.757 | 31.355 | 1.00 | 26.52 | B | C |

| | | | | | | | | | | | |
|---|---|---|---|---|---|---|---|---|---|---|---|
| ATOM | 7791 | NZ | LYS | 250 | 84.262 | 70.465 | 31.442 | 1.00 | 26.19 | B | N |
| ATOM | 7792 | C | LYS | 250 | 79.215 | 67.313 | 31.040 | 1.00 | 17.64 | B | C |
| ATOM | 7793 | O | LYS | 250 | 79.348 | 66.409 | 31.867 | 1.00 | 20.20 | B | O |
| ATOM | 7794 | N | THR | 251 | 79.478 | 67.160 | 29.750 | 1.00 | 15.06 | B | N |
| ATOM | 7795 | CA | THR | 251 | 79.978 | 65.905 | 29.234 | 1.00 | 14.91 | B | C |
| ATOM | 7796 | CB | THR | 251 | 79.317 | 65.537 | 27.896 | 1.00 | 13.86 | B | C |
| ATOM | 7797 | OG1 | THR | 251 | 77.965 | 65.144 | 28.128 | 1.00 | 14.97 | B | O |
| ATOM | 7798 | CG2 | THR | 251 | 80.058 | 64.389 | 27.227 | 1.00 | 13.23 | B | C |
| ATOM | 7799 | C | THR | 251 | 81.473 | 66.016 | 29.015 | 1.00 | 15.66 | B | C |
| ATOM | 7800 | O | THR | 251 | 81.934 | 66.831 | 28.227 | 1.00 | 18.88 | B | O |
| ATOM | 7801 | N | VAL | 252 | 82.231 | 65.194 | 29.720 | 1.00 | 15.28 | B | N |
| ATOM | 7802 | CA | VAL | 252 | 83.675 | 65.195 | 29.578 | 1.00 | 15.13 | B | C |
| ATOM | 7803 | CB | VAL | 252 | 84.335 | 64.717 | 30.882 | 1.00 | 13.64 | B | C |
| ATOM | 7804 | CG1 | VAL | 252 | 85.827 | 64.580 | 30.706 | 1.00 | 10.22 | B | C |
| ATOM | 7805 | CG2 | VAL | 252 | 84.012 | 65.701 | 31.991 | 1.00 | 11.83 | B | C |
| ATOM | 7806 | C | VAL | 252 | 84.027 | 64.264 | 28.422 | 1.00 | 17.21 | B | C |
| ATOM | 7807 | O | VAL | 252 | 83.472 | 63.173 | 28.304 | 1.00 | 17.34 | B | O |
| ATOM | 7808 | N | ARG | 253 | 84.929 | 64.710 | 27.557 | 1.00 | 18.91 | B | N |
| ATOM | 7809 | CA | ARG | 253 | 85.349 | 63.922 | 26.403 | 1.00 | 20.46 | B | C |
| ATOM | 7810 | CB | ARG | 253 | 84.822 | 64.560 | 25.113 | 1.00 | 22.21 | B | C |
| ATOM | 7811 | CG | ARG | 253 | 83.399 | 64.137 | 24.755 | 1.00 | 26.72 | B | C |
| ATOM | 7812 | CD | ARG | 253 | 82.847 | 64.920 | 23.578 | 1.00 | 28.87 | B | C |
| ATOM | 7813 | NE | ARG | 253 | 82.176 | 66.132 | 24.033 | 1.00 | 36.20 | B | N |
| ATOM | 7814 | CZ | ARG | 253 | 80.870 | 66.221 | 24.278 | 1.00 | 38.47 | B | C |
| ATOM | 7815 | NH1 | ARG | 253 | 80.084 | 65.164 | 24.099 | 1.00 | 39.84 | B | N |
| ATOM | 7816 | NH2 | ARG | 253 | 80.352 | 67.360 | 24.727 | 1.00 | 37.97 | B | N |
| ATOM | 7817 | C | ARG | 253 | 86.863 | 63.863 | 26.389 | 1.00 | 19.71 | B | C |
| ATOM | 7818 | O | ARG | 253 | 87.520 | 64.886 | 26.246 | 1.00 | 21.87 | B | O |
| ATOM | 7819 | N | VAL | 254 | 87.404 | 62.656 | 26.538 | 1.00 | 18.34 | B | N |
| ATOM | 7820 | CA | VAL | 254 | 88.847 | 62.434 | 26.594 | 1.00 | 15.15 | B | C |
| ATOM | 7821 | CB | VAL | 254 | 89.257 | 61.924 | 27.994 | 1.00 | 16.16 | B | C |
| ATOM | 7822 | CG1 | VAL | 254 | 90.771 | 61.759 | 28.081 | 1.00 | 15.18 | B | C |
| ATOM | 7823 | CG2 | VAL | 254 | 88.736 | 62.868 | 29.065 | 1.00 | 16.46 | B | C |
| ATOM | 7824 | C | VAL | 254 | 89.313 | 61.397 | 25.585 | 1.00 | 14.67 | B | C |
| ATOM | 7825 | O | VAL | 254 | 88.806 | 60.272 | 25.566 | 1.00 | 14.87 | B | O |
| ATOM | 7826 | N | PRO | 255 | 90.281 | 61.757 | 24.726 | 1.00 | 13.62 | B | N |
| ATOM | 7827 | CD | PRO | 255 | 90.872 | 63.081 | 24.472 | 1.00 | 12.90 | B | C |
| ATOM | 7828 | CA | PRO | 255 | 90.760 | 60.777 | 23.746 | 1.00 | 12.62 | B | C |
| ATOM | 7829 | CB | PRO | 255 | 91.786 | 61.566 | 22.933 | 1.00 | 11.40 | B | C |
| ATOM | 7830 | CG | PRO | 255 | 91.263 | 62.969 | 23.013 | 1.00 | 11.65 | B | C |
| ATOM | 7831 | C | PRO | 255 | 91.379 | 59.645 | 24.553 | 1.00 | 12.46 | B | C |
| ATOM | 7832 | O | PRO | 255 | 92.355 | 59.831 | 25.282 | 1.00 | 13.25 | B | O |
| ATOM | 7833 | N | TYR | 256 | 90.796 | 58.469 | 24.414 | 1.00 | 12.53 | B | N |
| ATOM | 7834 | CA | TYR | 256 | 91.217 | 57.306 | 25.161 | 1.00 | 12.05 | B | C |
| ATOM | 7835 | CB | TYR | 256 | 90.319 | 57.205 | 26.398 | 1.00 | 12.42 | B | C |
| ATOM | 7836 | CG | TYR | 256 | 90.608 | 56.082 | 27.360 | 1.00 | 14.53 | B | C |
| ATOM | 7837 | CD1 | TYR | 256 | 91.021 | 56.355 | 28.662 | 1.00 | 16.44 | B | C |
| ATOM | 7838 | CE1 | TYR | 256 | 91.192 | 55.337 | 29.596 | 1.00 | 17.38 | B | C |
| ATOM | 7839 | CD2 | TYR | 256 | 90.382 | 54.752 | 27.010 | 1.00 | 15.31 | B | C |

FIG. 4-161

| ATOM | 7840 | CE2 | TYR | 256 | 90.548 | 53.724 | 27.941 | 1.00 | 16.91 | B | C |
| ATOM | 7841 | CZ | TYR | 256 | 90.949 | 54.030 | 29.232 | 1.00 | 16.54 | B | C |
| ATOM | 7842 | OH | TYR | 256 | 91.068 | 53.042 | 30.176 | 1.00 | 17.03 | B | O |
| ATOM | 7843 | C | TYR | 256 | 91.040 | 56.094 | 24.263 | 1.00 | 11.63 | B | C |
| ATOM | 7844 | O | TYR | 256 | 89.923 | 55.765 | 23.870 | 1.00 | 13.76 | B | O |
| ATOM | 7845 | N | PRO | 257 | 92.141 | 55.415 | 23.924 | 1.00 | 10.78 | B | N |
| ATOM | 7846 | CD | PRO | 257 | 93.535 | 55.786 | 24.231 | 1.00 | 9.21 | B | C |
| ATOM | 7847 | CA | PRO | 257 | 92.098 | 54.229 | 23.068 | 1.00 | 9.97 | B | C |
| ATOM | 7848 | CB | PRO | 257 | 93.473 | 54.233 | 22.438 | 1.00 | 8.95 | B | C |
| ATOM | 7849 | CG | PRO | 257 | 94.326 | 54.657 | 23.606 | 1.00 | 8.91 | B | C |
| ATOM | 7850 | C | PRO | 257 | 91.859 | 52.949 | 23.869 | 1.00 | 11.12 | B | C |
| ATOM | 7851 | O | PRO | 257 | 92.694 | 52.556 | 24.681 | 1.00 | 9.90 | B | O |
| ATOM | 7852 | N | LYS | 258 | 90.723 | 52.300 | 23.648 | 1.00 | 11.97 | B | N |
| ATOM | 7853 | CA | LYS | 258 | 90.444 | 51.057 | 24.353 | 1.00 | 13.52 | B | C |
| ATOM | 7854 | CB | LYS | 258 | 88.930 | 50.855 | 24.492 | 1.00 | 15.66 | B | C |
| ATOM | 7855 | CG | LYS | 258 | 88.305 | 51.808 | 25.522 | 1.00 | 14.41 | B | C |
| ATOM | 7856 | CD | LYS | 258 | 86.801 | 51.730 | 25.552 | 1.00 | 18.08 | B | C |
| ATOM | 7857 | CE | LYS | 258 | 86.204 | 52.655 | 26.627 | 1.00 | 19.12 | B | C |
| ATOM | 7858 | NZ | LYS | 258 | 86.355 | 52.156 | 28.030 | 1.00 | 14.62 | B | N |
| ATOM | 7859 | C | LYS | 258 | 91.101 | 49.934 | 23.571 | 1.00 | 14.64 | B | C |
| ATOM | 7860 | O | LYS | 258 | 91.522 | 50.139 | 22.437 | 1.00 | 16.07 | B | O |
| ATOM | 7861 | N | ALA | 259 | 91.227 | 48.760 | 24.178 | 1.00 | 16.22 | B | N |
| ATOM | 7862 | CA | ALA | 259 | 91.874 | 47.627 | 23.515 | 1.00 | 14.83 | B | C |
| ATOM | 7863 | CB | ALA | 259 | 91.564 | 46.356 | 24.261 | 1.00 | 14.32 | B | C |
| ATOM | 7864 | C | ALA | 259 | 91.476 | 47.476 | 22.045 | 1.00 | 16.09 | B | C |
| ATOM | 7865 | O | ALA | 259 | 90.293 | 47.415 | 21.710 | 1.00 | 15.64 | B | O |
| ATOM | 7866 | N | GLY | 260 | 92.477 | 47.428 | 21.172 | 1.00 | 15.95 | B | N |
| ATOM | 7867 | CA | GLY | 260 | 92.221 | 47.269 | 19.754 | 1.00 | 15.99 | B | C |
| ATOM | 7868 | C | GLY | 260 | 91.841 | 48.523 | 18.982 | 1.00 | 17.08 | B | C |
| ATOM | 7869 | O | GLY | 260 | 91.781 | 48.488 | 17.752 | 1.00 | 18.87 | B | O |
| ATOM | 7870 | N | ALA | 261 | 91.587 | 49.629 | 19.673 | 1.00 | 14.62 | B | N |
| ATOM | 7871 | CA | ALA | 261 | 91.198 | 50.851 | 18.983 | 1.00 | 14.89 | B | C |
| ATOM | 7872 | CB | ALA | 261 | 90.557 | 51.830 | 19.963 | 1.00 | 13.58 | B | C |
| ATOM | 7873 | C | ALA | 261 | 92.379 | 51.509 | 18.292 | 1.00 | 17.12 | B | C |
| ATOM | 7874 | O | ALA | 261 | 93.489 | 50.986 | 18.298 | 1.00 | 20.05 | B | O |
| ATOM | 7875 | N | VAL | 262 | 92.135 | 52.662 | 17.686 | 1.00 | 17.34 | B | N |
| ATOM | 7876 | CA | VAL | 262 | 93.192 | 53.384 | 17.004 | 1.00 | 16.00 | B | C |
| ATOM | 7877 | CB | VAL | 262 | 92.614 | 54.371 | 15.947 | 1.00 | 14.51 | B | C |
| ATOM | 7878 | CG1 | VAL | 262 | 93.717 | 55.252 | 15.383 | 1.00 | 13.59 | B | C |
| ATOM | 7879 | CG2 | VAL | 262 | 91.970 | 53.596 | 14.820 | 1.00 | 10.82 | B | C |
| ATOM | 7880 | C | VAL | 262 | 93.984 | 54.150 | 18.055 | 1.00 | 17.31 | B | C |
| ATOM | 7881 | O | VAL | 262 | 93.432 | 54.973 | 18.786 | 1.00 | 20.51 | B | O |
| ATOM | 7882 | N | ASN | 263 | 95.275 | 53.856 | 18.128 | 1.00 | 16.87 | B | N |
| ATOM | 7883 | CA | ASN | 263 | 96.190 | 54.493 | 19.068 | 1.00 | 17.45 | B | C |
| ATOM | 7884 | CB | ASN | 263 | 97.406 | 53.595 | 19.292 | 1.00 | 17.58 | B | C |
| ATOM | 7885 | CG | ASN | 263 | 97.230 | 52.629 | 20.437 | 1.00 | 20.08 | B | C |
| ATOM | 7886 | OD1 | ASN | 263 | 97.919 | 51.606 | 20.500 | 1.00 | 19.88 | B | O |
| ATOM | 7887 | ND2 | ASN | 263 | 96.329 | 52.950 | 21.365 | 1.00 | 18.44 | B | N |
| ATOM | 7888 | C | ASN | 263 | 96.706 | 55.827 | 18.533 | 1.00 | 18.01 | B | C |

| | | | | | | | | | | | |
|---|---|---|---|---|---|---|---|---|---|---|---|
| ATOM | 7889 | O | ASN | 263 | 96.578 | 56.134 | 17.345 | 1.00 | 19.39 | B | O |
| ATOM | 7890 | N | PRO | 264 | 97.288 | 56.646 | 19.413 | 1.00 | 17.06 | B | N |
| ATOM | 7891 | CD | PRO | 264 | 97.357 | 56.546 | 20.883 | 1.00 | 15.68 | B | C |
| ATOM | 7892 | CA | PRO | 264 | 97.819 | 57.926 | 18.950 | 1.00 | 15.10 | B | C |
| ATOM | 7893 | CB | PRO | 264 | 98.089 | 58.676 | 20.251 | 1.00 | 14.78 | B | C |
| ATOM | 7894 | CG | PRO | 264 | 98.411 | 57.569 | 21.214 | 1.00 | 14.94 | B | C |
| ATOM | 7895 | C | PRO | 264 | 99.105 | 57.605 | 18.198 | 1.00 | 15.50 | B | C |
| ATOM | 7896 | O | PRO | 264 | 99.669 | 56.527 | 18.369 | 1.00 | 15.27 | B | O |
| ATOM | 7897 | N | THR | 265 | 99.560 | 58.521 | 17.354 | 1.00 | 16.21 | B | N |
| ATOM | 7898 | CA | THR | 265 | 100.796 | 58.305 | 16.617 | 1.00 | 15.30 | B | C |
| ATOM | 7899 | CB | THR | 265 | 100.647 | 58.677 | 15.132 | 1.00 | 15.20 | B | C |
| ATOM | 7900 | OG1 | THR | 265 | 100.081 | 59.983 | 15.029 | 1.00 | 17.05 | B | O |
| ATOM | 7901 | CG2 | THR | 265 | 99.747 | 57.687 | 14.415 | 1.00 | 10.60 | B | C |
| ATOM | 7902 | C | THR | 265 | 101.818 | 59.211 | 17.279 | 1.00 | 16.13 | B | C |
| ATOM | 7903 | O | THR | 265 | 101.454 | 60.126 | 18.007 | 1.00 | 16.83 | B | O |
| ATOM | 7904 | N | VAL | 266 | 103.095 | 58.971 | 17.030 | 1.00 | 17.64 | B | N |
| ATOM | 7905 | CA | VAL | 266 | 104.118 | 59.781 | 17.667 | 1.00 | 17.49 | B | C |
| ATOM | 7906 | CB | VAL | 266 | 104.626 | 59.060 | 18.930 | 1.00 | 15.28 | B | C |
| ATOM | 7907 | CG1 | VAL | 266 | 105.224 | 57.714 | 18.538 | 1.00 | 12.10 | B | C |
| ATOM | 7908 | CG2 | VAL | 266 | 105.642 | 59.921 | 19.666 | 1.00 | 12.62 | B | C |
| ATOM | 7909 | C | VAL | 266 | 105.312 | 60.112 | 16.769 | 1.00 | 19.23 | B | C |
| ATOM | 7910 | O | VAL | 266 | 105.693 | 59.331 | 15.893 | 1.00 | 18.24 | B | O |
| ATOM | 7911 | N | LYS | 267 | 105.889 | 61.287 | 17.003 | 1.00 | 20.19 | B | N |
| ATOM | 7912 | CA | LYS | 267 | 107.058 | 61.756 | 16.272 | 1.00 | 19.42 | B | C |
| ATOM | 7913 | CB | LYS | 267 | 106.678 | 62.855 | 15.291 | 1.00 | 19.76 | B | C |
| ATOM | 7914 | CG | LYS | 267 | 105.786 | 62.413 | 14.168 | 1.00 | 21.59 | B | C |
| ATOM | 7915 | CD | LYS | 267 | 105.452 | 63.605 | 13.291 | 1.00 | 23.15 | B | C |
| ATOM | 7916 | CE | LYS | 267 | 104.593 | 63.205 | 12.119 | 1.00 | 23.47 | B | C |
| ATOM | 7917 | NZ | LYS | 267 | 104.225 | 64.402 | 11.334 | 1.00 | 27.20 | B | N |
| ATOM | 7918 | C | LYS | 267 | 108.032 | 62.334 | 17.288 | 1.00 | 19.59 | B | C |
| ATOM | 7919 | O | LYS | 267 | 107.618 | 62.826 | 18.336 | 1.00 | 20.86 | B | O |
| ATOM | 7920 | N | PHE | 268 | 109.322 | 62.275 | 16.984 | 1.00 | 19.32 | B | N |
| ATOM | 7921 | CA | PHE | 268 | 110.325 | 62.818 | 17.882 | 1.00 | 18.94 | B | C |
| ATOM | 7922 | CB | PHE | 268 | 111.350 | 61.757 | 18.259 | 1.00 | 17.47 | B | C |
| ATOM | 7923 | CG | PHE | 268 | 112.186 | 62.131 | 19.444 | 1.00 | 16.21 | B | C |
| ATOM | 7924 | CD1 | PHE | 268 | 111.601 | 62.290 | 20.692 | 1.00 | 16.98 | B | C |
| ATOM | 7925 | CD2 | PHE | 268 | 113.555 | 62.327 | 19.313 | 1.00 | 16.35 | B | C |
| ATOM | 7926 | CE1 | PHE | 268 | 112.368 | 62.639 | 21.797 | 1.00 | 18.80 | B | C |
| ATOM | 7927 | CE2 | PHE | 268 | 114.332 | 62.674 | 20.405 | 1.00 | 17.68 | B | C |
| ATOM | 7928 | CZ | PHE | 268 | 113.737 | 62.832 | 21.655 | 1.00 | 18.66 | B | C |
| ATOM | 7929 | C | PHE | 268 | 111.016 | 63.979 | 17.192 | 1.00 | 20.34 | B | C |
| ATOM | 7930 | O | PHE | 268 | 111.114 | 64.016 | 15.968 | 1.00 | 21.73 | B | O |
| ATOM | 7931 | N | PHE | 269 | 111.491 | 64.931 | 17.981 | 1.00 | 20.76 | B | N |
| ATOM | 7932 | CA | PHE | 269 | 112.152 | 66.105 | 17.435 | 1.00 | 20.74 | B | C |
| ATOM | 7933 | CB | PHE | 269 | 111.141 | 67.239 | 17.222 | 1.00 | 19.80 | B | C |
| ATOM | 7934 | CG | PHE | 269 | 110.070 | 66.937 | 16.216 | 1.00 | 21.88 | B | C |
| ATOM | 7935 | CD1 | PHE | 269 | 110.332 | 67.019 | 14.853 | 1.00 | 22.75 | B | C |
| ATOM | 7936 | CD2 | PHE | 269 | 108.785 | 66.605 | 16.631 | 1.00 | 23.20 | B | C |
| ATOM | 7937 | CE1 | PHE | 269 | 109.326 | 66.781 | 13.912 | 1.00 | 21.98 | B | C |

FIG. 4-163

| ATOM | 7938 | CE2 | PHE | 269 | 107.771 | 66.364 | 15.700 | 1.00 | 23.06 | B | C |
| --- | --- | --- | --- | --- | --- | --- | --- | --- | --- | --- | --- |
| ATOM | 7939 | CZ  | PHE | 269 | 108.044 | 66.454 | 14.337 | 1.00 | 22.44 | B | C |
| ATOM | 7940 | C   | PHE | 269 | 113.209 | 66.606 | 18.402 | 1.00 | 21.66 | B | C |
| ATOM | 7941 | O   | PHE | 269 | 113.127 | 66.376 | 19.613 | 1.00 | 21.27 | B | O |
| ATOM | 7942 | N   | VAL | 270 | 114.195 | 67.305 | 17.858 | 1.00 | 21.99 | B | N |
| ATOM | 7943 | CA  | VAL | 270 | 115.239 | 67.896 | 18.667 | 1.00 | 23.26 | B | C |
| ATOM | 7944 | CB  | VAL | 270 | 116.527 | 67.062 | 18.635 | 1.00 | 23.10 | B | C |
| ATOM | 7945 | CG1 | VAL | 270 | 117.517 | 67.624 | 19.630 | 1.00 | 23.57 | B | C |
| ATOM | 7946 | CG2 | VAL | 270 | 116.219 | 65.609 | 18.985 | 1.00 | 23.02 | B | C |
| ATOM | 7947 | C   | VAL | 270 | 115.495 | 69.285 | 18.095 | 1.00 | 25.32 | B | C |
| ATOM | 7948 | O   | VAL | 270 | 115.600 | 69.460 | 16.880 | 1.00 | 26.00 | B | O |
| ATOM | 7949 | N   | VAL | 271 | 115.561 | 70.278 | 18.973 | 1.00 | 26.96 | B | N |
| ATOM | 7950 | CA  | VAL | 271 | 115.794 | 71.650 | 18.546 | 1.00 | 27.45 | B | C |
| ATOM | 7951 | CB  | VAL | 271 | 114.516 | 72.514 | 18.714 | 1.00 | 28.95 | B | C |
| ATOM | 7952 | CG1 | VAL | 271 | 114.096 | 72.563 | 20.177 | 1.00 | 28.40 | B | C |
| ATOM | 7953 | CG2 | VAL | 271 | 114.769 | 73.915 | 18.186 | 1.00 | 29.54 | B | C |
| ATOM | 7954 | C   | VAL | 271 | 116.926 | 72.258 | 19.363 | 1.00 | 27.39 | B | C |
| ATOM | 7955 | O   | VAL | 271 | 117.094 | 71.935 | 20.536 | 1.00 | 26.71 | B | O |
| ATOM | 7956 | N   | ASN | 272 | 117.706 | 73.128 | 18.728 | 1.00 | 27.87 | B | N |
| ATOM | 7957 | CA  | ASN | 272 | 118.828 | 73.788 | 19.383 | 1.00 | 27.39 | B | C |
| ATOM | 7958 | CB  | ASN | 272 | 119.951 | 74.056 | 18.378 | 1.00 | 27.64 | B | C |
| ATOM | 7959 | CG  | ASN | 272 | 121.179 | 74.672 | 19.031 | 1.00 | 29.11 | B | C |
| ATOM | 7960 | OD1 | ASN | 272 | 121.094 | 75.706 | 19.696 | 1.00 | 28.35 | B | O |
| ATOM | 7961 | ND2 | ASN | 272 | 122.330 | 74.036 | 18.841 | 1.00 | 30.38 | B | N |
| ATOM | 7962 | C   | ASN | 272 | 118.347 | 75.104 | 19.972 | 1.00 | 27.43 | B | C |
| ATOM | 7963 | O   | ASN | 272 | 117.943 | 76.012 | 19.243 | 1.00 | 27.41 | B | O |
| ATOM | 7964 | N   | THR | 273 | 118.397 | 75.208 | 21.292 | 1.00 | 27.62 | B | N |
| ATOM | 7965 | CA  | THR | 273 | 117.938 | 76.411 | 21.959 | 1.00 | 28.77 | B | C |
| ATOM | 7966 | CB  | THR | 273 | 117.509 | 76.100 | 23.400 | 1.00 | 27.46 | B | C |
| ATOM | 7967 | OG1 | THR | 273 | 118.653 | 75.727 | 24.181 | 1.00 | 28.06 | B | O |
| ATOM | 7968 | CG2 | THR | 273 | 116.510 | 74.960 | 23.403 | 1.00 | 26.33 | B | C |
| ATOM | 7969 | C   | THR | 273 | 118.988 | 77.516 | 21.967 | 1.00 | 31.23 | B | C |
| ATOM | 7970 | O   | THR | 273 | 118.669 | 78.680 | 22.208 | 1.00 | 32.66 | B | O |
| ATOM | 7971 | N   | ASP | 274 | 120.239 | 77.157 | 21.698 | 1.00 | 32.45 | B | N |
| ATOM | 7972 | CA  | ASP | 274 | 121.315 | 78.139 | 21.676 | 1.00 | 33.79 | B | C |
| ATOM | 7973 | CB  | ASP | 274 | 122.671 | 77.446 | 21.775 | 1.00 | 34.63 | B | C |
| ATOM | 7974 | CG  | ASP | 274 | 123.019 | 77.049 | 23.193 | 1.00 | 36.82 | B | C |
| ATOM | 7975 | OD1 | ASP | 274 | 124.047 | 76.363 | 23.385 | 1.00 | 37.48 | B | O |
| ATOM | 7976 | OD2 | ASP | 274 | 122.267 | 77.430 | 24.117 | 1.00 | 37.18 | B | O |
| ATOM | 7977 | C   | ASP | 274 | 121.277 | 78.996 | 20.419 | 1.00 | 35.09 | B | C |
| ATOM | 7978 | O   | ASP | 274 | 121.899 | 80.058 | 20.366 | 1.00 | 34.53 | B | O |
| ATOM | 7979 | N   | SER | 275 | 120.540 | 78.542 | 19.412 | 1.00 | 35.53 | B | N |
| ATOM | 7980 | CA  | SER | 275 | 120.456 | 79.279 | 18.166 | 1.00 | 37.39 | B | C |
| ATOM | 7981 | CB  | SER | 275 | 121.096 | 78.462 | 17.051 | 1.00 | 36.90 | B | C |
| ATOM | 7982 | OG  | SER | 275 | 120.476 | 77.197 | 16.948 | 1.00 | 41.05 | B | O |
| ATOM | 7983 | C   | SER | 275 | 119.030 | 79.652 | 17.781 | 1.00 | 39.58 | B | C |
| ATOM | 7984 | O   | SER | 275 | 118.580 | 79.355 | 16.673 | 1.00 | 40.66 | B | O |
| ATOM | 7985 | N   | LEU | 276 | 118.323 | 80.311 | 18.695 | 1.00 | 40.56 | B | N |
| ATOM | 7986 | CA  | LEU | 276 | 116.949 | 80.732 | 18.443 | 1.00 | 40.53 | B | C |

| | | | | | | | | | | |
|---|---|---|---|---|---|---|---|---|---|---|
| ATOM | 7987 | CB | LEU | 276 | 116.076 | 80.425 | 19.664 | 1.00 | 38.58 | B C |
| ATOM | 7988 | CG | LEU | 276 | 116.002 | 78.958 | 20.097 | 1.00 | 36.34 | B C |
| ATOM | 7989 | CD1 | LEU | 276 | 115.319 | 78.876 | 21.445 | 1.00 | 35.16 | B C |
| ATOM | 7990 | CD2 | LEU | 276 | 115.261 | 78.134 | 19.057 | 1.00 | 32.57 | B C |
| ATOM | 7991 | C | LEU | 276 | 116.914 | 82.229 | 18.140 | 1.00 | 41.99 | B C |
| ATOM | 7992 | O | LEU | 276 | 117.675 | 83.002 | 18.721 | 1.00 | 41.16 | B O |
| ATOM | 7993 | N | SER | 277 | 116.029 | 82.634 | 17.233 | 1.00 | 44.02 | B N |
| ATOM | 7994 | CA | SER | 277 | 115.916 | 84.044 | 16.863 | 1.00 | 46.53 | B C |
| ATOM | 7995 | CB | SER | 277 | 116.489 | 84.277 | 15.462 | 1.00 | 48.49 | B C |
| ATOM | 7996 | OG | SER | 277 | 116.268 | 85.618 | 15.044 | 1.00 | 50.90 | B O |
| ATOM | 7997 | C | SER | 277 | 114.494 | 84.586 | 16.902 | 1.00 | 46.23 | B C |
| ATOM | 7998 | O | SER | 277 | 113.529 | 83.856 | 16.701 | 1.00 | 46.82 | B O |
| ATOM | 7999 | N | SER | 278 | 114.378 | 85.884 | 17.148 | 1.00 | 46.94 | B N |
| ATOM | 8000 | CA | SER | 278 | 113.081 | 86.535 | 17.202 | 1.00 | 47.82 | B C |
| ATOM | 8001 | CB | SER | 278 | 113.204 | 87.899 | 17.884 | 1.00 | 48.09 | B C |
| ATOM | 8002 | OG | SER | 278 | 113.617 | 87.759 | 19.234 | 1.00 | 49.14 | B O |
| ATOM | 8003 | C | SER | 278 | 112.531 | 86.710 | 15.794 | 1.00 | 48.26 | B C |
| ATOM | 8004 | O | SER | 278 | 111.325 | 86.829 | 15.600 | 1.00 | 48.73 | B O |
| ATOM | 8005 | N | VAL | 279 | 113.419 | 86.723 | 14.808 | 1.00 | 48.48 | B N |
| ATOM | 8006 | CA | VAL | 279 | 112.995 | 86.889 | 13.428 | 1.00 | 48.89 | B C |
| ATOM | 8007 | CB | VAL | 279 | 114.189 | 87.229 | 12.514 | 1.00 | 49.95 | B C |
| ATOM | 8008 | CG1 | VAL | 279 | 113.709 | 87.454 | 11.089 | 1.00 | 50.61 | B C |
| ATOM | 8009 | CG2 | VAL | 279 | 114.902 | 88.464 | 13.037 | 1.00 | 50.28 | B C |
| ATOM | 8010 | C | VAL | 279 | 112.340 | 85.606 | 12.941 | 1.00 | 48.52 | B C |
| ATOM | 8011 | O | VAL | 279 | 111.130 | 85.433 | 13.082 | 1.00 | 49.49 | B O |
| ATOM | 8012 | N | THR | 280 | 113.145 | 84.708 | 12.380 | 1.00 | 47.70 | B N |
| ATOM | 8013 | CA | THR | 280 | 112.651 | 83.432 | 11.872 | 1.00 | 46.64 | B C |
| ATOM | 8014 | CB | THR | 280 | 113.719 | 82.709 | 11.032 | 1.00 | 47.86 | B C |
| ATOM | 8015 | OG1 | THR | 280 | 113.179 | 81.479 | 10.531 | 1.00 | 48.07 | B O |
| ATOM | 8016 | CG2 | THR | 280 | 114.946 | 82.399 | 11.883 | 1.00 | 47.49 | B C |
| ATOM | 8017 | C | THR | 280 | 112.238 | 82.484 | 12.992 | 1.00 | 45.40 | B C |
| ATOM | 8018 | O | THR | 280 | 112.586 | 82.677 | 14.155 | 1.00 | 44.24 | B O |
| ATOM | 8019 | N | ASN | 281 | 111.499 | 81.447 | 12.622 | 1.00 | 45.09 | B N |
| ATOM | 8020 | CA | ASN | 281 | 111.040 | 80.454 | 13.581 | 1.00 | 44.81 | B C |
| ATOM | 8021 | CB | ASN | 281 | 109.744 | 79.815 | 13.089 | 1.00 | 46.08 | B C |
| ATOM | 8022 | CG | ASN | 281 | 108.592 | 80.786 | 13.096 | 1.00 | 48.90 | B C |
| ATOM | 8023 | OD1 | ASN | 281 | 108.351 | 81.455 | 14.101 | 1.00 | 49.62 | B O |
| ATOM | 8024 | ND2 | ASN | 281 | 107.873 | 80.868 | 11.984 | 1.00 | 52.14 | B N |
| ATOM | 8025 | C | ASN | 281 | 112.088 | 79.379 | 13.812 | 1.00 | 43.47 | B C |
| ATOM | 8026 | O | ASN | 281 | 112.874 | 79.065 | 12.919 | 1.00 | 44.44 | B O |
| ATOM | 8027 | N | ALA | 282 | 112.100 | 78.823 | 15.019 | 1.00 | 41.76 | B N |
| ATOM | 8028 | CA | ALA | 282 | 113.045 | 77.773 | 15.371 | 1.00 | 38.62 | B C |
| ATOM | 8029 | CB | ALA | 282 | 112.795 | 77.301 | 16.792 | 1.00 | 37.75 | B C |
| ATOM | 8030 | C | ALA | 282 | 112.863 | 76.619 | 14.403 | 1.00 | 37.34 | B C |
| ATOM | 8031 | O | ALA | 282 | 111.797 | 76.463 | 13.815 | 1.00 | 36.86 | B O |
| ATOM | 8032 | N | THR | 283 | 113.905 | 75.816 | 14.231 | 1.00 | 36.50 | B N |
| ATOM | 8033 | CA | THR | 283 | 113.828 | 74.672 | 13.335 | 1.00 | 35.84 | B C |
| ATOM | 8034 | CB | THR | 283 | 114.867 | 74.772 | 12.218 | 1.00 | 37.70 | B C |
| ATOM | 8035 | OG1 | THR | 283 | 114.665 | 75.994 | 11.495 | 1.00 | 41.71 | B O |

FIG. 4-165 (Continued)

| | | | | | | | | | | | |
|---|---|---|---|---|---|---|---|---|---|---|---|
| ATOM | 8036 | CG2 | THR | 283 | 114.736 | 73.595 | 11.265 | 1.00 | 37.32 | B | C |
| ATOM | 8037 | C | THR | 283 | 114.074 | 73.403 | 14.125 | 1.00 | 33.58 | B | C |
| ATOM | 8038 | O | THR | 283 | 115.098 | 73.263 | 14.774 | 1.00 | 34.31 | B | O |
| ATOM | 8039 | N | SER | 284 | 113.123 | 72.482 | 14.073 | 1.00 | 32.05 | B | N |
| ATOM | 8040 | CA | SER | 284 | 113.250 | 71.230 | 14.800 | 1.00 | 30.43 | B | C |
| ATOM | 8041 | CB | SER | 284 | 111.935 | 70.893 | 15.507 | 1.00 | 28.61 | B | C |
| ATOM | 8042 | OG | SER | 284 | 111.722 | 71.761 | 16.605 | 1.00 | 29.31 | B | O |
| ATOM | 8043 | C | SER | 284 | 113.638 | 70.090 | 13.883 | 1.00 | 30.34 | B | C |
| ATOM | 8044 | O | SER | 284 | 113.003 | 69.865 | 12.850 | 1.00 | 31.22 | B | O |
| ATOM | 8045 | N | ILE | 285 | 114.684 | 69.367 | 14.260 | 1.00 | 29.19 | B | N |
| ATOM | 8046 | CA | ILE | 285 | 115.130 | 68.241 | 13.457 | 1.00 | 28.80 | B | C |
| ATOM | 8047 | CB | ILE | 285 | 116.660 | 68.037 | 13.546 | 1.00 | 29.35 | B | C |
| ATOM | 8048 | CG2 | ILE | 285 | 117.103 | 66.979 | 12.548 | 1.00 | 29.12 | B | C |
| ATOM | 8049 | CG1 | ILE | 285 | 117.383 | 69.350 | 13.250 | 1.00 | 30.38 | B | C |
| ATOM | 8050 | CD1 | ILE | 285 | 117.408 | 70.303 | 14.428 | 1.00 | 34.47 | B | C |
| ATOM | 8051 | C | ILE | 285 | 114.429 | 66.996 | 13.976 | 1.00 | 28.14 | B | C |
| ATOM | 8052 | O | ILE | 285 | 114.472 | 66.694 | 15.168 | 1.00 | 30.23 | B | O |
| ATOM | 8053 | N | GLN | 286 | 113.775 | 66.278 | 13.078 | 1.00 | 25.84 | B | N |
| ATOM | 8054 | CA | GLN | 286 | 113.067 | 65.076 | 13.457 | 1.00 | 24.81 | B | C |
| ATOM | 8055 | CB | GLN | 286 | 111.852 | 64.886 | 12.550 | 1.00 | 23.81 | B | C |
| ATOM | 8056 | CG | GLN | 286 | 111.169 | 63.547 | 12.715 | 1.00 | 23.29 | B | C |
| ATOM | 8057 | CD | GLN | 286 | 109.928 | 63.417 | 11.868 | 1.00 | 23.98 | B | C |
| ATOM | 8058 | OE1 | GLN | 286 | 109.253 | 62.388 | 11.894 | 1.00 | 25.22 | B | O |
| ATOM | 8059 | NE2 | GLN | 286 | 109.614 | 64.461 | 11.110 | 1.00 | 23.87 | B | N |
| ATOM | 8060 | C | GLN | 286 | 113.955 | 63.838 | 13.386 | 1.00 | 25.74 | B | C |
| ATOM | 8061 | O | GLN | 286 | 114.832 | 63.732 | 12.526 | 1.00 | 26.39 | B | O |
| ATOM | 8062 | N | ILE | 287 | 113.723 | 62.908 | 14.307 | 1.00 | 24.54 | B | N |
| ATOM | 8063 | CA | ILE | 287 | 114.458 | 61.655 | 14.346 | 1.00 | 23.40 | B | C |
| ATOM | 8064 | CB | ILE | 287 | 115.193 | 61.481 | 15.694 | 1.00 | 21.87 | B | C |
| ATOM | 8065 | CG2 | ILE | 287 | 115.925 | 60.143 | 15.728 | 1.00 | 20.61 | B | C |
| ATOM | 8066 | CG1 | ILE | 287 | 116.180 | 62.632 | 15.887 | 1.00 | 19.27 | B | C |
| ATOM | 8067 | CD1 | ILE | 287 | 117.054 | 62.506 | 17.113 | 1.00 | 20.58 | B | C |
| ATOM | 8068 | C | ILE | 287 | 113.394 | 60.578 | 14.186 | 1.00 | 24.59 | B | C |
| ATOM | 8069 | O | ILE | 287 | 112.729 | 60.204 | 15.142 | 1.00 | 27.03 | B | O |
| ATOM | 8070 | N | THR | 288 | 113.219 | 60.093 | 12.966 | 1.00 | 25.43 | B | N |
| ATOM | 8071 | CA | THR | 288 | 112.205 | 59.088 | 12.708 | 1.00 | 26.10 | B | C |
| ATOM | 8072 | CB | THR | 288 | 111.964 | 58.927 | 11.188 | 1.00 | 26.69 | B | C |
| ATOM | 8073 | OG1 | THR | 288 | 113.172 | 58.516 | 10.539 | 1.00 | 26.37 | B | O |
| ATOM | 8074 | CG2 | THR | 288 | 111.510 | 60.255 | 10.593 | 1.00 | 25.25 | B | C |
| ATOM | 8075 | C | THR | 288 | 112.529 | 57.741 | 13.335 | 1.00 | 26.85 | B | C |
| ATOM | 8076 | O | THR | 288 | 113.687 | 57.379 | 13.503 | 1.00 | 27.04 | B | O |
| ATOM | 8077 | N | ALA | 289 | 111.484 | 57.011 | 13.702 | 1.00 | 28.37 | B | N |
| ATOM | 8078 | CA | ALA | 289 | 111.638 | 55.705 | 14.325 | 1.00 | 27.90 | B | C |
| ATOM | 8079 | CB | ALA | 289 | 110.271 | 55.151 | 14.710 | 1.00 | 26.91 | B | C |
| ATOM | 8080 | C | ALA | 289 | 112.348 | 54.740 | 13.380 | 1.00 | 27.44 | B | C |
| ATOM | 8081 | O | ALA | 289 | 112.550 | 55.038 | 12.205 | 1.00 | 28.30 | B | O |
| ATOM | 8082 | N | PRO | 290 | 112.758 | 53.577 | 13.895 | 1.00 | 26.01 | B | N |
| ATOM | 8083 | CD | PRO | 290 | 112.903 | 53.280 | 15.328 | 1.00 | 24.74 | B | C |
| ATOM | 8084 | CA | PRO | 290 | 113.445 | 52.569 | 13.089 | 1.00 | 25.29 | B | C |

FIG. 4-166

| | | | | | | | | | | |
|---|---|---|---|---|---|---|---|---|---|---|
| ATOM | 8085 | CB | PRO | 290 | 113.949 | 51.587 | 14.138 | 1.00 | 25.76 | B | C |
| ATOM | 8086 | CG | PRO | 290 | 114.151 | 52.467 | 15.342 | 1.00 | 25.10 | B | C |
| ATOM | 8087 | C | PRO | 290 | 112.465 | 51.931 | 12.110 | 1.00 | 25.85 | B | C |
| ATOM | 8088 | O | PRO | 290 | 111.255 | 51.961 | 12.330 | 1.00 | 25.95 | B | O |
| ATOM | 8089 | N | ALA | 291 | 112.988 | 51.345 | 11.038 | 1.00 | 25.39 | B | N |
| ATOM | 8090 | CA | ALA | 291 | 112.143 | 50.730 | 10.024 | 1.00 | 26.17 | B | C |
| ATOM | 8091 | CB | ALA | 291 | 112.987 | 50.271 | 8.846 | 1.00 | 26.28 | B | C |
| ATOM | 8092 | C | ALA | 291 | 111.337 | 49.568 | 10.573 | 1.00 | 27.18 | B | C |
| ATOM | 8093 | O | ALA | 291 | 110.203 | 49.331 | 10.145 | 1.00 | 27.46 | B | O |
| ATOM | 8094 | N | SER | 292 | 111.916 | 48.843 | 11.521 | 1.00 | 27.54 | B | N |
| ATOM | 8095 | CA | SER | 292 | 111.220 | 47.704 | 12.103 | 1.00 | 28.19 | B | C |
| ATOM | 8096 | CB | SER | 292 | 112.161 | 46.892 | 12.993 | 1.00 | 28.00 | B | C |
| ATOM | 8097 | OG | SER | 292 | 112.525 | 47.626 | 14.145 | 1.00 | 32.22 | B | O |
| ATOM | 8098 | C | SER | 292 | 110.027 | 48.182 | 12.922 | 1.00 | 28.13 | B | C |
| ATOM | 8099 | O | SER | 292 | 109.176 | 47.376 | 13.307 | 1.00 | 29.52 | B | O |
| ATOM | 8100 | N | MET | 293 | 109.976 | 49.487 | 13.190 | 1.00 | 25.00 | B | N |
| ATOM | 8101 | CA | MET | 293 | 108.881 | 50.072 | 13.955 | 1.00 | 24.80 | B | C |
| ATOM | 8102 | CB | MET | 293 | 109.387 | 51.173 | 14.892 | 1.00 | 24.61 | B | C |
| ATOM | 8103 | CG | MET | 293 | 110.231 | 50.703 | 16.060 | 1.00 | 26.88 | B | C |
| ATOM | 8104 | SD | MET | 293 | 109.323 | 49.647 | 17.189 | 1.00 | 27.80 | B | S |
| ATOM | 8105 | CE | MET | 293 | 110.457 | 48.319 | 17.438 | 1.00 | 25.74 | B | C |
| ATOM | 8106 | C | MET | 293 | 107.836 | 50.677 | 13.027 | 1.00 | 24.57 | B | C |
| ATOM | 8107 | O | MET | 293 | 106.641 | 50.528 | 13.252 | 1.00 | 25.32 | B | O |
| ATOM | 8108 | N | LEU | 294 | 108.292 | 51.360 | 11.983 | 1.00 | 24.37 | B | N |
| ATOM | 8109 | CA | LEU | 294 | 107.393 | 52.008 | 11.041 | 1.00 | 23.80 | B | C |
| ATOM | 8110 | CB | LEU | 294 | 108.183 | 52.930 | 10.114 | 1.00 | 23.40 | B | C |
| ATOM | 8111 | CG | LEU | 294 | 108.945 | 54.072 | 10.786 | 1.00 | 24.87 | B | C |
| ATOM | 8112 | CD1 | LEU | 294 | 109.806 | 54.787 | 9.758 | 1.00 | 22.08 | B | C |
| ATOM | 8113 | CD2 | LEU | 294 | 107.958 | 55.037 | 11.440 | 1.00 | 23.08 | B | C |
| ATOM | 8114 | C | LEU | 294 | 106.540 | 51.059 | 10.204 | 1.00 | 23.95 | B | C |
| ATOM | 8115 | O | LEU | 294 | 105.714 | 51.510 | 9.422 | 1.00 | 25.36 | B | O |
| ATOM | 8116 | N | ILE | 295 | 106.724 | 49.754 | 10.357 | 1.00 | 23.92 | B | N |
| ATOM | 8117 | CA | ILE | 295 | 105.923 | 48.812 | 9.580 | 1.00 | 25.26 | B | C |
| ATOM | 8118 | CB | ILE | 295 | 106.601 | 47.444 | 9.453 | 1.00 | 26.06 | B | C |
| ATOM | 8119 | CG2 | ILE | 295 | 107.972 | 47.595 | 8.812 | 1.00 | 26.54 | B | C |
| ATOM | 8120 | CG1 | ILE | 295 | 106.698 | 46.796 | 10.831 | 1.00 | 24.44 | B | C |
| ATOM | 8121 | CD1 | ILE | 295 | 107.211 | 45.388 | 10.789 | 1.00 | 28.37 | B | C |
| ATOM | 8122 | C | ILE | 295 | 104.564 | 48.575 | 10.221 | 1.00 | 26.01 | B | C |
| ATOM | 8123 | O | ILE | 295 | 103.805 | 47.712 | 9.775 | 1.00 | 28.75 | B | O |
| ATOM | 8124 | N | GLY | 296 | 104.263 | 49.328 | 11.273 | 1.00 | 24.77 | B | N |
| ATOM | 8125 | CA | GLY | 296 | 102.992 | 49.167 | 11.951 | 1.00 | 22.28 | B | C |
| ATOM | 8126 | C | GLY | 296 | 102.908 | 50.040 | 13.182 | 1.00 | 21.29 | B | C |
| ATOM | 8127 | O | GLY | 296 | 103.820 | 50.818 | 13.447 | 1.00 | 20.80 | B | O |
| ATOM | 8128 | N | ASP | 297 | 101.818 | 49.920 | 13.935 | 1.00 | 20.38 | B | N |
| ATOM | 8129 | CA | ASP | 297 | 101.654 | 50.718 | 15.141 | 1.00 | 20.14 | B | C |
| ATOM | 8130 | CB | ASP | 297 | 100.366 | 50.339 | 15.874 | 1.00 | 21.58 | B | C |
| ATOM | 8131 | CG | ASP | 297 | 99.109 | 50.665 | 15.078 | 1.00 | 22.60 | B | C |
| ATOM | 8132 | OD1 | ASP | 297 | 98.016 | 50.234 | 15.502 | 1.00 | 25.00 | B | O |
| ATOM | 8133 | OD2 | ASP | 297 | 99.200 | 51.350 | 14.041 | 1.00 | 22.18 | B | O |

| ATOM | 8134 | C   | ASP | 297 | 102.845 | 50.481 | 16.065 | 1.00 | 20.31 | B | C |
| --- | --- | --- | --- | --- | --- | --- | --- | --- | --- | --- | --- |
| ATOM | 8135 | O   | ASP | 297 | 103.419 | 49.390 | 16.096 | 1.00 | 20.82 | B | O |
| ATOM | 8136 | N   | HIS | 298 | 103.220 | 51.508 | 16.814 | 1.00 | 16.87 | B | N |
| ATOM | 8137 | CA  | HIS | 298 | 104.335 | 51.384 | 17.734 | 1.00 | 16.48 | B | C |
| ATOM | 8138 | CB  | HIS | 298 | 105.669 | 51.399 | 16.968 | 1.00 | 14.91 | B | C |
| ATOM | 8139 | CG  | HIS | 298 | 105.868 | 52.628 | 16.137 | 1.00 | 12.24 | B | C |
| ATOM | 8140 | CD2 | HIS | 298 | 106.539 | 53.775 | 16.391 | 1.00 | 10.39 | B | C |
| ATOM | 8141 | ND1 | HIS | 298 | 105.264 | 52.802 | 14.909 | 1.00 | 11.35 | B | N |
| ATOM | 8142 | CE1 | HIS | 298 | 105.551 | 54.005 | 14.445 | 1.00 | 11.25 | B | C |
| ATOM | 8143 | NE2 | HIS | 298 | 106.323 | 54.616 | 15.326 | 1.00 | 11.96 | B | N |
| ATOM | 8144 | C   | HIS | 298 | 104.274 | 52.560 | 18.693 | 1.00 | 15.84 | B | C |
| ATOM | 8145 | O   | HIS | 298 | 103.484 | 53.476 | 18.505 | 1.00 | 17.04 | B | O |
| ATOM | 8146 | N   | TYR | 299 | 105.127 | 52.539 | 19.706 | 1.00 | 15.50 | B | N |
| ATOM | 8147 | CA  | TYR | 299 | 105.163 | 53.599 | 20.698 | 1.00 | 15.35 | B | C |
| ATOM | 8148 | CB  | TYR | 299 | 104.640 | 53.095 | 22.047 | 1.00 | 14.51 | B | C |
| ATOM | 8149 | CG  | TYR | 299 | 103.343 | 52.320 | 22.037 | 1.00 | 14.30 | B | C |
| ATOM | 8150 | CD1 | TYR | 299 | 102.120 | 52.973 | 21.942 | 1.00 | 13.49 | B | C |
| ATOM | 8151 | CE1 | TYR | 299 | 100.924 | 52.269 | 22.019 | 1.00 | 15.63 | B | C |
| ATOM | 8152 | CD2 | TYR | 299 | 103.341 | 50.933 | 22.198 | 1.00 | 14.56 | B | C |
| ATOM | 8153 | CE2 | TYR | 299 | 102.150 | 50.216 | 22.273 | 1.00 | 15.40 | B | C |
| ATOM | 8154 | CZ  | TYR | 299 | 100.943 | 50.891 | 22.186 | 1.00 | 15.73 | B | C |
| ATOM | 8155 | OH  | TYR | 299 | 99.756  | 50.197 | 22.286 | 1.00 | 15.37 | B | O |
| ATOM | 8156 | C   | TYR | 299 | 106.583 | 54.084 | 20.952 | 1.00 | 16.54 | B | C |
| ATOM | 8157 | O   | TYR | 299 | 107.559 | 53.364 | 20.732 | 1.00 | 15.53 | B | O |
| ATOM | 8158 | N   | LEU | 300 | 106.688 | 55.316 | 21.428 | 1.00 | 16.67 | B | N |
| ATOM | 8159 | CA  | LEU | 300 | 107.975 | 55.853 | 21.818 | 1.00 | 17.75 | B | C |
| ATOM | 8160 | CB  | LEU | 300 | 107.986 | 57.367 | 21.654 | 1.00 | 18.54 | B | C |
| ATOM | 8161 | CG  | LEU | 300 | 109.238 | 58.059 | 22.183 | 1.00 | 20.06 | B | C |
| ATOM | 8162 | CD1 | LEU | 300 | 110.449 | 57.535 | 21.429 | 1.00 | 20.50 | B | C |
| ATOM | 8163 | CD2 | LEU | 300 | 109.107 | 59.567 | 22.024 | 1.00 | 20.10 | B | C |
| ATOM | 8164 | C   | LEU | 300 | 107.897 | 55.477 | 23.294 | 1.00 | 18.55 | B | C |
| ATOM | 8165 | O   | LEU | 300 | 106.894 | 55.783 | 23.935 | 1.00 | 20.71 | B | O |
| ATOM | 8166 | N   | CYS | 301 | 108.901 | 54.805 | 23.849 | 1.00 | 18.50 | B | N |
| ATOM | 8167 | CA  | CYS | 301 | 108.788 | 54.418 | 25.252 | 1.00 | 20.22 | B | C |
| ATOM | 8168 | CB  | CYS | 301 | 108.582 | 52.907 | 25.375 | 1.00 | 20.55 | B | C |
| ATOM | 8169 | SG  | CYS | 301 | 109.922 | 51.905 | 24.722 | 1.00 | 26.11 | B | S |
| ATOM | 8170 | C   | CYS | 301 | 109.895 | 54.842 | 26.194 | 1.00 | 20.82 | B | C |
| ATOM | 8171 | O   | CYS | 301 | 109.816 | 54.579 | 27.395 | 1.00 | 21.62 | B | O |
| ATOM | 8172 | N   | ASP | 302 | 110.922 | 55.496 | 25.662 | 1.00 | 22.13 | B | N |
| ATOM | 8173 | CA  | ASP | 302 | 112.035 | 55.968 | 26.481 | 1.00 | 20.03 | B | C |
| ATOM | 8174 | CB  | ASP | 302 | 112.875 | 54.810 | 27.014 | 1.00 | 20.49 | B | C |
| ATOM | 8175 | CG  | ASP | 302 | 114.035 | 55.296 | 27.868 | 1.00 | 25.77 | B | C |
| ATOM | 8176 | OD1 | ASP | 302 | 113.880 | 55.344 | 29.109 | 1.00 | 26.02 | B | O |
| ATOM | 8177 | OD2 | ASP | 302 | 115.097 | 55.664 | 27.297 | 1.00 | 27.73 | B | O |
| ATOM | 8178 | C   | ASP | 302 | 112.959 | 56.894 | 25.711 | 1.00 | 20.08 | B | C |
| ATOM | 8179 | O   | ASP | 302 | 113.367 | 56.596 | 24.586 | 1.00 | 19.30 | B | O |
| ATOM | 8180 | N   | VAL | 303 | 113.302 | 58.010 | 26.343 | 1.00 | 20.41 | B | N |
| ATOM | 8181 | CA  | VAL | 303 | 114.188 | 59.000 | 25.756 | 1.00 | 20.36 | B | C |
| ATOM | 8182 | CB  | VAL | 303 | 113.435 | 60.316 | 25.470 | 1.00 | 19.97 | B | C |

FIG. 4-168 (Continued)

| | | | | | | | | | | |
|---|---|---|---|---|---|---|---|---|---|---|
| ATOM | 8183 | CG1 | VAL | 303 | 114.387 | 61.347 | 24.857 | 1.00 | 20.23 | B C |
| ATOM | 8184 | CG2 | VAL | 303 | 112.260 | 60.043 | 24.540 | 1.00 | 17.52 | B C |
| ATOM | 8185 | C | VAL | 303 | 115.267 | 59.251 | 26.788 | 1.00 | 21.02 | B C |
| ATOM | 8186 | O | VAL | 303 | 114.950 | 59.568 | 27.939 | 1.00 | 19.39 | B O |
| ATOM | 8187 | N | THR | 304 | 116.536 | 59.112 | 26.389 | 1.00 | 21.38 | B N |
| ATOM | 8188 | CA | THR | 304 | 117.639 | 59.313 | 27.332 | 1.00 | 21.48 | B C |
| ATOM | 8189 | CB | THR | 304 | 118.008 | 58.002 | 28.046 | 1.00 | 19.77 | B C |
| ATOM | 8190 | OG1 | THR | 304 | 116.869 | 57.496 | 28.751 | 1.00 | 19.55 | B O |
| ATOM | 8191 | CG2 | THR | 304 | 119.136 | 58.242 | 29.026 | 1.00 | 20.57 | B C |
| ATOM | 8192 | C | THR | 304 | 118.925 | 59.851 | 26.729 | 1.00 | 22.96 | B C |
| ATOM | 8193 | O | THR | 304 | 119.579 | 59.159 | 25.952 | 1.00 | 25.30 | B O |
| ATOM | 8194 | N | TRP | 305 | 119.307 | 61.069 | 27.102 | 1.00 | 22.41 | B N |
| ATOM | 8195 | CA | TRP | 305 | 120.545 | 61.643 | 26.583 | 1.00 | 21.86 | B C |
| ATOM | 8196 | CB | TRP | 305 | 120.696 | 63.114 | 26.975 | 1.00 | 20.21 | B C |
| ATOM | 8197 | CG | TRP | 305 | 119.682 | 64.002 | 26.354 | 1.00 | 18.90 | B C |
| ATOM | 8198 | CD2 | TRP | 305 | 119.834 | 64.751 | 25.150 | 1.00 | 18.79 | B C |
| ATOM | 8199 | CE2 | TRP | 305 | 118.614 | 65.413 | 24.917 | 1.00 | 20.14 | B C |
| ATOM | 8200 | CE3 | TRP | 305 | 120.885 | 64.928 | 24.243 | 1.00 | 18.65 | B C |
| ATOM | 8201 | CD1 | TRP | 305 | 118.414 | 64.232 | 26.794 | 1.00 | 17.49 | B C |
| ATOM | 8202 | NE1 | TRP | 305 | 117.764 | 65.077 | 25.938 | 1.00 | 18.37 | B N |
| ATOM | 8203 | CZ2 | TRP | 305 | 118.413 | 66.242 | 23.812 | 1.00 | 19.16 | B C |
| ATOM | 8204 | CZ3 | TRP | 305 | 120.689 | 65.746 | 23.152 | 1.00 | 19.59 | B C |
| ATOM | 8205 | CH2 | TRP | 305 | 119.459 | 66.395 | 22.943 | 1.00 | 21.43 | B C |
| ATOM | 8206 | C | TRP | 305 | 121.722 | 60.875 | 27.148 | 1.00 | 22.21 | B C |
| ATOM | 8207 | O | TRP | 305 | 121.743 | 60.552 | 28.338 | 1.00 | 21.63 | B O |
| ATOM | 8208 | N | ALA | 306 | 122.697 | 60.591 | 26.285 | 1.00 | 22.53 | B N |
| ATOM | 8209 | CA | ALA | 306 | 123.899 | 59.864 | 26.673 | 1.00 | 21.31 | B C |
| ATOM | 8210 | CB | ALA | 306 | 124.350 | 58.969 | 25.533 | 1.00 | 20.65 | B C |
| ATOM | 8211 | C | ALA | 306 | 124.975 | 60.882 | 27.000 | 1.00 | 21.97 | B C |
| ATOM | 8212 | O | ALA | 306 | 125.675 | 60.767 | 28.007 | 1.00 | 20.32 | B O |
| ATOM | 8213 | N | THR | 307 | 125.086 | 61.885 | 26.133 | 1.00 | 23.85 | B N |
| ATOM | 8214 | CA | THR | 307 | 126.057 | 62.964 | 26.284 | 1.00 | 24.42 | B C |
| ATOM | 8215 | CB | THR | 307 | 127.285 | 62.744 | 25.411 | 1.00 | 22.67 | B C |
| ATOM | 8216 | OG1 | THR | 307 | 126.894 | 62.855 | 24.040 | 1.00 | 25.33 | B O |
| ATOM | 8217 | CG2 | THR | 307 | 127.892 | 61.374 | 25.659 | 1.00 | 19.34 | B C |
| ATOM | 8218 | C | THR | 307 | 125.397 | 64.250 | 25.812 | 1.00 | 25.73 | B C |
| ATOM | 8219 | O | THR | 307 | 124.177 | 64.326 | 25.731 | 1.00 | 28.17 | B O |
| ATOM | 8220 | N | GLN | 308 | 126.210 | 65.249 | 25.479 | 1.00 | 26.09 | B N |
| ATOM | 8221 | CA | GLN | 308 | 125.699 | 66.540 | 25.022 | 1.00 | 24.49 | B C |
| ATOM | 8222 | CB | GLN | 308 | 126.762 | 67.634 | 25.175 | 1.00 | 22.95 | B C |
| ATOM | 8223 | CG | GLN | 308 | 127.301 | 67.811 | 26.574 | 1.00 | 21.20 | B C |
| ATOM | 8224 | CD | GLN | 308 | 126.256 | 68.296 | 27.548 | 1.00 | 20.30 | B C |
| ATOM | 8225 | OE1 | GLN | 308 | 126.477 | 68.290 | 28.754 | 1.00 | 23.08 | B O |
| ATOM | 8226 | NE2 | GLN | 308 | 125.116 | 68.727 | 27.032 | 1.00 | 21.02 | B N |
| ATOM | 8227 | C | GLN | 308 | 125.284 | 66.501 | 23.569 | 1.00 | 25.09 | B C |
| ATOM | 8228 | O | GLN | 308 | 124.612 | 67.411 | 23.095 | 1.00 | 26.23 | B O |
| ATOM | 8229 | N | GLU | 309 | 125.687 | 65.459 | 22.855 | 1.00 | 25.59 | B N |
| ATOM | 8230 | CA | GLU | 309 | 125.370 | 65.374 | 21.440 | 1.00 | 26.16 | B C |
| ATOM | 8231 | CB | GLU | 309 | 126.581 | 65.807 | 20.627 | 1.00 | 25.99 | B C |

| | | | | | | | | | | | |
|---|---|---|---|---|---|---|---|---|---|---|---|
| ATOM | 8232 | CG | GLU | 309 | 126.925 | 67.280 | 20.774 | 1.00 | 29.27 | B | C |
| ATOM | 8233 | CD | GLU | 309 | 128.243 | 67.637 | 20.109 | 1.00 | 31.48 | B | C |
| ATOM | 8234 | OE1 | GLU | 309 | 128.614 | 66.968 | 19.115 | 1.00 | 33.35 | B | O |
| ATOM | 8235 | OE2 | GLU | 309 | 128.900 | 68.593 | 20.572 | 1.00 | 32.54 | B | O |
| ATOM | 8236 | C | GLU | 309 | 124.939 | 63.991 | 21.004 | 1.00 | 26.83 | B | C |
| ATOM | 8237 | O | GLU | 309 | 124.850 | 63.712 | 19.806 | 1.00 | 28.64 | B | O |
| ATOM | 8238 | N | ARG | 310 | 124.674 | 63.131 | 21.982 | 1.00 | 25.93 | B | N |
| ATOM | 8239 | CA | ARG | 310 | 124.246 | 61.765 | 21.723 | 1.00 | 24.07 | B | C |
| ATOM | 8240 | CB | ARG | 310 | 125.357 | 60.790 | 22.121 | 1.00 | 24.28 | B | C |
| ATOM | 8241 | CG | ARG | 310 | 125.012 | 59.317 | 21.952 | 1.00 | 25.64 | B | C |
| ATOM | 8242 | CD | ARG | 310 | 126.255 | 58.469 | 22.132 | 1.00 | 24.20 | B | C |
| ATOM | 8243 | NE | ARG | 310 | 127.225 | 58.790 | 21.097 | 1.00 | 25.36 | B | N |
| ATOM | 8244 | CZ | ARG | 310 | 128.533 | 58.590 | 21.195 | 1.00 | 26.41 | B | C |
| ATOM | 8245 | NH1 | ARG | 310 | 129.056 | 58.063 | 22.298 | 1.00 | 26.17 | B | N |
| ATOM | 8246 | NH2 | ARG | 310 | 129.321 | 58.928 | 20.183 | 1.00 | 26.60 | B | N |
| ATOM | 8247 | C | ARG | 310 | 122.984 | 61.488 | 22.528 | 1.00 | 23.55 | B | C |
| ATOM | 8248 | O | ARG | 310 | 122.965 | 61.607 | 23.757 | 1.00 | 23.67 | B | O |
| ATOM | 8249 | N | ILE | 311 | 121.922 | 61.124 | 21.829 | 1.00 | 21.75 | B | N |
| ATOM | 8250 | CA | ILE | 311 | 120.663 | 60.843 | 22.491 | 1.00 | 20.40 | B | C |
| ATOM | 8251 | CB | ILE | 311 | 119.586 | 61.876 | 22.067 | 1.00 | 18.52 | B | C |
| ATOM | 8252 | CG2 | ILE | 311 | 119.293 | 61.742 | 20.593 | 1.00 | 18.77 | B | C |
| ATOM | 8253 | CG1 | ILE | 311 | 118.305 | 61.686 | 22.879 | 1.00 | 18.16 | B | C |
| ATOM | 8254 | CD1 | ILE | 311 | 117.255 | 62.774 | 22.626 | 1.00 | 15.33 | B | C |
| ATOM | 8255 | C | ILE | 311 | 120.233 | 59.440 | 22.107 | 1.00 | 20.81 | B | C |
| ATOM | 8256 | O | ILE | 311 | 120.380 | 59.036 | 20.959 | 1.00 | 21.43 | B | O |
| ATOM | 8257 | N | SER | 312 | 119.734 | 58.686 | 23.080 | 1.00 | 21.54 | B | N |
| ATOM | 8258 | CA | SER | 312 | 119.269 | 57.326 | 22.832 | 1.00 | 21.49 | B | C |
| ATOM | 8259 | CB | SER | 312 | 119.889 | 56.355 | 23.837 | 1.00 | 22.73 | B | C |
| ATOM | 8260 | OG | SER | 312 | 119.365 | 56.575 | 25.132 | 1.00 | 23.02 | B | O |
| ATOM | 8261 | C | SER | 312 | 117.758 | 57.315 | 22.985 | 1.00 | 20.72 | B | C |
| ATOM | 8262 | O | SER | 312 | 117.214 | 57.998 | 23.853 | 1.00 | 22.17 | B | O |
| ATOM | 8263 | N | LEU | 313 | 117.088 | 56.544 | 22.136 | 1.00 | 21.93 | B | N |
| ATOM | 8264 | CA | LEU | 313 | 115.631 | 56.428 | 22.155 | 1.00 | 22.17 | B | C |
| ATOM | 8265 | CB | LEU | 313 | 115.013 | 57.179 | 20.979 | 1.00 | 23.76 | B | C |
| ATOM | 8266 | CG | LEU | 313 | 115.314 | 58.656 | 20.754 | 1.00 | 27.56 | B | C |
| ATOM | 8267 | CD1 | LEU | 313 | 114.707 | 59.068 | 19.410 | 1.00 | 29.23 | B | C |
| ATOM | 8268 | CD2 | LEU | 313 | 114.740 | 59.497 | 21.890 | 1.00 | 28.89 | B | C |
| ATOM | 8269 | C | LEU | 313 | 115.229 | 54.968 | 22.022 | 1.00 | 22.50 | B | C |
| ATOM | 8270 | O | LEU | 313 | 115.868 | 54.209 | 21.293 | 1.00 | 22.55 | B | O |
| ATOM | 8271 | N | GLN | 314 | 114.167 | 54.579 | 22.722 | 1.00 | 22.54 | B | N |
| ATOM | 8272 | CA | GLN | 314 | 113.666 | 53.216 | 22.639 | 1.00 | 23.08 | B | C |
| ATOM | 8273 | CB | GLN | 314 | 113.682 | 52.549 | 24.012 | 1.00 | 22.45 | B | C |
| ATOM | 8274 | CG | GLN | 314 | 115.065 | 52.459 | 24.626 | 1.00 | 25.62 | B | C |
| ATOM | 8275 | CD | GLN | 314 | 115.092 | 51.630 | 25.898 | 1.00 | 26.36 | B | C |
| ATOM | 8276 | OE1 | GLN | 314 | 114.835 | 50.428 | 25.870 | 1.00 | 27.68 | B | O |
| ATOM | 8277 | NE2 | GLN | 314 | 115.403 | 52.273 | 27.023 | 1.00 | 25.65 | B | N |
| ATOM | 8278 | C | GLN | 314 | 112.242 | 53.240 | 22.083 | 1.00 | 23.35 | B | C |
| ATOM | 8279 | O | GLN | 314 | 111.412 | 54.045 | 22.513 | 1.00 | 22.96 | B | O |
| ATOM | 8280 | N | TRP | 315 | 111.984 | 52.372 | 21.108 | 1.00 | 22.35 | B | N |

FIG. 4-170

| | | | | | | | | | | |
|---|---|---|---|---|---|---|---|---|---|---|
| ATOM | 8281 | CA | TRP | 315 | 110.672 | 52.262 | 20.484 | 1.00 | 21.75 | B | C |
| ATOM | 8282 | CB | TRP | 315 | 110.769 | 52.440 | 18.968 | 1.00 | 21.09 | B | C |
| ATOM | 8283 | CG | TRP | 315 | 111.376 | 53.741 | 18.540 | 1.00 | 21.09 | B | C |
| ATOM | 8284 | CD2 | TRP | 315 | 110.678 | 54.940 | 18.176 | 1.00 | 19.81 | B | C |
| ATOM | 8285 | CE2 | TRP | 315 | 111.654 | 55.901 | 17.824 | 1.00 | 20.24 | B | C |
| ATOM | 8286 | CE3 | TRP | 315 | 109.325 | 55.295 | 18.113 | 1.00 | 17.16 | B | C |
| ATOM | 8287 | CD1 | TRP | 315 | 112.705 | 54.018 | 18.405 | 1.00 | 21.12 | B | C |
| ATOM | 8288 | NE1 | TRP | 315 | 112.880 | 55.310 | 17.974 | 1.00 | 21.84 | B | N |
| ATOM | 8289 | CZ2 | TRP | 315 | 111.321 | 57.197 | 17.413 | 1.00 | 18.97 | B | C |
| ATOM | 8290 | CZ3 | TRP | 315 | 108.992 | 56.588 | 17.704 | 1.00 | 20.13 | B | C |
| ATOM | 8291 | CH2 | TRP | 315 | 109.990 | 57.522 | 17.359 | 1.00 | 19.26 | B | C |
| ATOM | 8292 | C | TRP | 315 | 110.118 | 50.880 | 20.790 | 1.00 | 22.37 | B | C |
| ATOM | 8293 | O | TRP | 315 | 110.877 | 49.922 | 20.941 | 1.00 | 24.80 | B | O |
| ATOM | 8294 | N | LEU | 316 | 108.799 | 50.772 | 20.872 | 1.00 | 21.02 | B | N |
| ATOM | 8295 | CA | LEU | 316 | 108.159 | 49.502 | 21.184 | 1.00 | 20.90 | B | C |
| ATOM | 8296 | CB | LEU | 316 | 107.653 | 49.544 | 22.628 | 1.00 | 19.84 | B | C |
| ATOM | 8297 | CG | LEU | 316 | 106.866 | 48.358 | 23.194 | 1.00 | 19.46 | B | C |
| ATOM | 8298 | CD1 | LEU | 316 | 107.786 | 47.157 | 23.408 | 1.00 | 18.22 | B | C |
| ATOM | 8299 | CD2 | LEU | 316 | 106.223 | 48.783 | 24.501 | 1.00 | 16.50 | B | C |
| ATOM | 8300 | C | LEU | 316 | 106.995 | 49.228 | 20.229 | 1.00 | 20.90 | B | C |
| ATOM | 8301 | O | LEU | 316 | 106.161 | 50.098 | 20.000 | 1.00 | 22.41 | B | O |
| ATOM | 8302 | N | ARG | 317 | 106.941 | 48.026 | 19.666 | 1.00 | 19.89 | B | N |
| ATOM | 8303 | CA | ARG | 317 | 105.851 | 47.678 | 18.753 | 1.00 | 20.30 | B | C |
| ATOM | 8304 | CB | ARG | 317 | 106.154 | 46.362 | 18.035 | 1.00 | 20.73 | B | C |
| ATOM | 8305 | CG | ARG | 317 | 107.248 | 46.480 | 16.993 | 1.00 | 23.49 | B | C |
| ATOM | 8306 | CD | ARG | 317 | 107.524 | 45.149 | 16.321 | 1.00 | 24.95 | B | C |
| ATOM | 8307 | NE | ARG | 317 | 108.347 | 45.314 | 15.128 | 1.00 | 25.57 | B | N |
| ATOM | 8308 | CZ | ARG | 317 | 108.925 | 44.313 | 14.476 | 1.00 | 26.73 | B | C |
| ATOM | 8309 | NH1 | ARG | 317 | 108.775 | 43.061 | 14.897 | 1.00 | 23.81 | B | N |
| ATOM | 8310 | NH2 | ARG | 317 | 109.656 | 44.567 | 13.401 | 1.00 | 29.12 | B | N |
| ATOM | 8311 | C | ARG | 317 | 104.537 | 47.545 | 19.512 | 1.00 | 19.31 | B | C |
| ATOM | 8312 | O | ARG | 317 | 104.541 | 47.266 | 20.713 | 1.00 | 17.59 | B | O |
| ATOM | 8313 | N | ARG | 318 | 103.415 | 47.747 | 18.820 | 1.00 | 18.54 | B | N |
| ATOM | 8314 | CA | ARG | 318 | 102.117 | 47.621 | 19.476 | 1.00 | 17.04 | B | C |
| ATOM | 8315 | CB | ARG | 318 | 100.970 | 47.781 | 18.483 | 1.00 | 17.09 | B | C |
| ATOM | 8316 | CG | ARG | 318 | 99.608 | 47.794 | 19.164 | 1.00 | 17.74 | B | C |
| ATOM | 8317 | CD | ARG | 318 | 98.613 | 48.660 | 18.414 | 1.00 | 16.48 | B | C |
| ATOM | 8318 | NE | ARG | 318 | 97.326 | 48.672 | 19.092 | 1.00 | 16.05 | B | N |
| ATOM | 8319 | CZ | ARG | 318 | 96.320 | 49.478 | 18.771 | 1.00 | 17.02 | B | C |
| ATOM | 8320 | NH1 | ARG | 318 | 96.464 | 50.342 | 17.771 | 1.00 | 13.59 | B | N |
| ATOM | 8321 | NH2 | ARG | 318 | 95.180 | 49.428 | 19.460 | 1.00 | 12.42 | B | N |
| ATOM | 8322 | C | ARG | 318 | 102.085 | 46.251 | 20.132 | 1.00 | 15.28 | B | C |
| ATOM | 8323 | O | ARG | 318 | 101.569 | 46.103 | 21.234 | 1.00 | 15.74 | B | O |
| ATOM | 8324 | N | ILE | 319 | 102.627 | 45.251 | 19.440 | 1.00 | 15.27 | B | N |
| ATOM | 8325 | CA | ILE | 319 | 102.757 | 43.912 | 20.007 | 1.00 | 15.37 | B | C |
| ATOM | 8326 | CB | ILE | 319 | 103.006 | 42.848 | 18.949 | 1.00 | 15.60 | B | C |
| ATOM | 8327 | CG2 | ILE | 319 | 103.268 | 41.519 | 19.621 | 1.00 | 17.64 | B | C |
| ATOM | 8328 | CG1 | ILE | 319 | 101.793 | 42.732 | 18.036 | 1.00 | 15.37 | B | C |
| ATOM | 8329 | CD1 | ILE | 319 | 100.524 | 42.425 | 18.781 | 1.00 | 15.54 | B | C |

| ATOM | 8330 | C | ILE | 319 | 104.036 | 44.122 | 20.802 | 1.00 | 16.78 | B | C |
| --- | --- | --- | --- | --- | --- | --- | --- | --- | --- | --- | --- |
| ATOM | 8331 | O | ILE | 319 | 105.145 | 44.086 | 20.257 | 1.00 | 16.37 | B | O |
| ATOM | 8332 | N | GLN | 320 | 103.850 | 44.367 | 22.092 | 1.00 | 17.82 | B | N |
| ATOM | 8333 | CA | GLN | 320 | 104.923 | 44.693 | 23.016 | 1.00 | 18.01 | B | C |
| ATOM | 8334 | CB | GLN | 320 | 104.293 | 45.341 | 24.248 | 1.00 | 16.84 | B | C |
| ATOM | 8335 | CG | GLN | 320 | 103.383 | 46.495 | 23.863 | 1.00 | 16.48 | B | C |
| ATOM | 8336 | CD | GLN | 320 | 102.833 | 47.250 | 25.048 | 1.00 | 17.06 | B | C |
| ATOM | 8337 | OE1 | GLN | 320 | 103.544 | 47.509 | 26.016 | 1.00 | 18.02 | B | O |
| ATOM | 8338 | NE2 | GLN | 320 | 101.566 | 47.633 | 24.966 | 1.00 | 16.46 | B | N |
| ATOM | 8339 | C | GLN | 320 | 105.964 | 43.663 | 23.437 | 1.00 | 18.97 | B | C |
| ATOM | 8340 | O | GLN | 320 | 106.399 | 43.654 | 24.594 | 1.00 | 20.18 | B | O |
| ATOM | 8341 | N | ASN | 321 | 106.382 | 42.800 | 22.520 | 1.00 | 19.64 | B | N |
| ATOM | 8342 | CA | ASN | 321 | 107.420 | 41.846 | 22.875 | 1.00 | 21.44 | B | C |
| ATOM | 8343 | CB | ASN | 321 | 106.950 | 40.399 | 22.719 | 1.00 | 23.79 | B | C |
| ATOM | 8344 | CG | ASN | 321 | 106.409 | 40.085 | 21.332 | 1.00 | 27.68 | B | C |
| ATOM | 8345 | OD1 | ASN | 321 | 106.593 | 40.839 | 20.374 | 1.00 | 28.16 | B | O |
| ATOM | 8346 | ND2 | ASN | 321 | 105.745 | 38.934 | 21.255 | 1.00 | 30.91 | B | N |
| ATOM | 8347 | C | ASN | 321 | 108.658 | 42.087 | 22.036 | 1.00 | 21.63 | B | C |
| ATOM | 8348 | O | ASN | 321 | 109.533 | 41.228 | 21.940 | 1.00 | 23.87 | B | O |
| ATOM | 8349 | N | TYR | 322 | 108.735 | 43.275 | 21.444 | 1.00 | 20.56 | B | N |
| ATOM | 8350 | CA | TYR | 322 | 109.873 | 43.644 | 20.613 | 1.00 | 18.63 | B | C |
| ATOM | 8351 | CB | TYR | 322 | 109.605 | 43.208 | 19.178 | 1.00 | 18.95 | B | C |
| ATOM | 8352 | CG | TYR | 322 | 110.766 | 43.362 | 18.228 | 1.00 | 21.29 | B | C |
| ATOM | 8353 | CD1 | TYR | 322 | 111.086 | 44.604 | 17.677 | 1.00 | 21.18 | B | C |
| ATOM | 8354 | CE1 | TYR | 322 | 112.118 | 44.733 | 16.759 | 1.00 | 22.17 | B | C |
| ATOM | 8355 | CD2 | TYR | 322 | 111.520 | 42.252 | 17.840 | 1.00 | 20.55 | B | C |
| ATOM | 8356 | CE2 | TYR | 322 | 112.557 | 42.372 | 16.925 | 1.00 | 21.33 | B | C |
| ATOM | 8357 | CZ | TYR | 322 | 112.847 | 43.611 | 16.387 | 1.00 | 22.88 | B | C |
| ATOM | 8358 | OH | TYR | 322 | 113.855 | 43.726 | 15.461 | 1.00 | 28.00 | B | O |
| ATOM | 8359 | C | TYR | 322 | 110.115 | 45.149 | 20.678 | 1.00 | 18.95 | B | C |
| ATOM | 8360 | O | TYR | 322 | 109.240 | 45.945 | 20.338 | 1.00 | 20.45 | B | O |
| ATOM | 8361 | N | SER | 323 | 111.299 | 45.537 | 21.139 | 1.00 | 18.50 | B | N |
| ATOM | 8362 | CA | SER | 323 | 111.657 | 46.946 | 21.233 | 1.00 | 17.89 | B | C |
| ATOM | 8363 | CB | SER | 323 | 111.623 | 47.418 | 22.684 | 1.00 | 18.88 | B | C |
| ATOM | 8364 | OG | SER | 323 | 112.602 | 46.740 | 23.444 | 1.00 | 21.21 | B | O |
| ATOM | 8365 | C | SER | 323 | 113.057 | 47.131 | 20.677 | 1.00 | 16.99 | B | C |
| ATOM | 8366 | O | SER | 323 | 113.851 | 46.190 | 20.657 | 1.00 | 15.79 | B | O |
| ATOM | 8367 | N | VAL | 324 | 113.360 | 48.345 | 20.230 | 1.00 | 16.51 | B | N |
| ATOM | 8368 | CA | VAL | 324 | 114.672 | 48.638 | 19.664 | 1.00 | 17.39 | B | C |
| ATOM | 8369 | CB | VAL | 324 | 114.612 | 48.684 | 18.126 | 1.00 | 18.70 | B | C |
| ATOM | 8370 | CG1 | VAL | 324 | 113.454 | 49.550 | 17.692 | 1.00 | 22.04 | B | C |
| ATOM | 8371 | CG2 | VAL | 324 | 115.901 | 49.257 | 17.565 | 1.00 | 20.08 | B | C |
| ATOM | 8372 | C | VAL | 324 | 115.201 | 49.970 | 20.151 | 1.00 | 16.54 | B | C |
| ATOM | 8373 | O | VAL | 324 | 114.460 | 50.946 | 20.243 | 1.00 | 19.05 | B | O |
| ATOM | 8374 | N | MET | 325 | 116.487 | 50.011 | 20.463 | 1.00 | 15.89 | B | N |
| ATOM | 8375 | CA | MET | 325 | 117.104 | 51.243 | 20.914 | 1.00 | 16.61 | B | C |
| ATOM | 8376 | CB | MET | 325 | 118.053 | 50.997 | 22.083 | 1.00 | 17.97 | B | C |
| ATOM | 8377 | CG | MET | 325 | 118.682 | 52.280 | 22.597 | 1.00 | 19.56 | B | C |
| ATOM | 8378 | SD | MET | 325 | 119.851 | 52.014 | 23.915 | 1.00 | 22.61 | B | S |

| | | | | | | | | | | |
|---|---|---|---|---|---|---|---|---|---|---|
| ATOM | 8379 | CE | MET | 325 | 118.765 | 51.442 | 25.211 | 1.00 | 21.39 | B | C |
| ATOM | 8380 | C | MET | 325 | 117.895 | 51.875 | 19.782 | 1.00 | 17.82 | B | C |
| ATOM | 8381 | O | MET | 325 | 118.658 | 51.198 | 19.082 | 1.00 | 15.28 | B | O |
| ATOM | 8382 | N | ASP | 326 | 117.698 | 53.175 | 19.607 | 1.00 | 18.85 | B | N |
| ATOM | 8383 | CA | ASP | 326 | 118.409 | 53.922 | 18.591 | 1.00 | 21.89 | B | C |
| ATOM | 8384 | CB | ASP | 326 | 117.436 | 54.685 | 17.695 | 1.00 | 22.04 | B | C |
| ATOM | 8385 | CG | ASP | 326 | 117.533 | 54.272 | 16.244 | 1.00 | 23.15 | B | C |
| ATOM | 8386 | OD1 | ASP | 326 | 116.800 | 54.855 | 15.418 | 1.00 | 25.35 | B | O |
| ATOM | 8387 | OD2 | ASP | 326 | 118.334 | 53.366 | 15.922 | 1.00 | 23.67 | B | O |
| ATOM | 8388 | C | ASP | 326 | 119.299 | 54.904 | 19.327 | 1.00 | 24.54 | B | C |
| ATOM | 8389 | O | ASP | 326 | 118.896 | 55.494 | 20.335 | 1.00 | 25.63 | B | O |
| ATOM | 8390 | N | ILE | 327 | 120.521 | 55.062 | 18.842 | 1.00 | 25.49 | B | N |
| ATOM | 8391 | CA | ILE | 327 | 121.451 | 55.986 | 19.459 | 1.00 | 27.44 | B | C |
| ATOM | 8392 | CB | ILE | 327 | 122.713 | 55.263 | 19.936 | 1.00 | 27.10 | B | C |
| ATOM | 8393 | CG2 | ILE | 327 | 123.697 | 56.264 | 20.515 | 1.00 | 27.85 | B | C |
| ATOM | 8394 | CG1 | ILE | 327 | 122.321 | 54.221 | 20.984 | 1.00 | 25.49 | B | C |
| ATOM | 8395 | CD1 | ILE | 327 | 123.476 | 53.506 | 21.594 | 1.00 | 27.60 | B | C |
| ATOM | 8396 | C | ILE | 327 | 121.784 | 57.005 | 18.395 | 1.00 | 29.15 | B | C |
| ATOM | 8397 | O | ILE | 327 | 122.357 | 56.673 | 17.357 | 1.00 | 31.19 | B | O |
| ATOM | 8398 | N | CYS | 328 | 121.414 | 58.250 | 18.653 | 1.00 | 30.14 | B | N |
| ATOM | 8399 | CA | CYS | 328 | 121.624 | 59.298 | 17.684 | 1.00 | 31.56 | B | C |
| ATOM | 8400 | C | CYS | 328 | 122.624 | 60.356 | 18.084 | 1.00 | 32.64 | B | C |
| ATOM | 8401 | O | CYS | 328 | 122.525 | 60.972 | 19.153 | 1.00 | 33.03 | B | O |
| ATOM | 8402 | CB | CYS | 328 | 120.286 | 59.938 | 17.366 | 1.00 | 32.73 | B | C |
| ATOM | 8403 | SG | CYS | 328 | 118.979 | 58.689 | 17.154 | 1.00 | 36.31 | B | S |
| ATOM | 8404 | N | ASP | 329 | 123.596 | 60.555 | 17.200 | 1.00 | 32.72 | B | N |
| ATOM | 8405 | CA | ASP | 329 | 124.639 | 61.542 | 17.406 | 1.00 | 32.74 | B | C |
| ATOM | 8406 | CB | ASP | 329 | 125.997 | 60.975 | 16.981 | 1.00 | 34.70 | B | C |
| ATOM | 8407 | CG | ASP | 329 | 126.480 | 59.858 | 17.894 | 1.00 | 36.73 | B | C |
| ATOM | 8408 | OD1 | ASP | 329 | 127.643 | 59.431 | 17.735 | 1.00 | 38.23 | B | O |
| ATOM | 8409 | OD2 | ASP | 329 | 125.706 | 59.405 | 18.767 | 1.00 | 36.00 | B | O |
| ATOM | 8410 | C | ASP | 329 | 124.320 | 62.781 | 16.588 | 1.00 | 31.70 | B | C |
| ATOM | 8411 | O | ASP | 329 | 123.767 | 62.692 | 15.494 | 1.00 | 30.70 | B | O |
| ATOM | 8412 | N | TYR | 330 | 124.662 | 63.940 | 17.129 | 1.00 | 31.69 | B | N |
| ATOM | 8413 | CA | TYR | 330 | 124.420 | 65.191 | 16.428 | 1.00 | 33.40 | B | C |
| ATOM | 8414 | CB | TYR | 330 | 124.376 | 66.354 | 17.411 | 1.00 | 30.81 | B | C |
| ATOM | 8415 | CG | TYR | 330 | 124.322 | 67.693 | 16.728 | 1.00 | 29.75 | B | C |
| ATOM | 8416 | CD1 | TYR | 330 | 123.185 | 68.089 | 16.030 | 1.00 | 30.07 | B | C |
| ATOM | 8417 | CE1 | TYR | 330 | 123.121 | 69.326 | 15.399 | 1.00 | 30.94 | B | C |
| ATOM | 8418 | CD2 | TYR | 330 | 125.407 | 68.568 | 16.777 | 1.00 | 30.62 | B | C |
| ATOM | 8419 | CE2 | TYR | 330 | 125.356 | 69.814 | 16.150 | 1.00 | 30.16 | B | C |
| ATOM | 8420 | CZ | TYR | 330 | 124.206 | 70.186 | 15.465 | 1.00 | 31.10 | B | C |
| ATOM | 8421 | OH | TYR | 330 | 124.122 | 71.422 | 14.867 | 1.00 | 29.92 | B | O |
| ATOM | 8422 | C | TYR | 330 | 125.523 | 65.462 | 15.412 | 1.00 | 35.09 | B | C |
| ATOM | 8423 | O | TYR | 330 | 126.692 | 65.552 | 15.772 | 1.00 | 36.29 | B | O |
| ATOM | 8424 | N | ASP | 331 | 125.149 | 65.600 | 14.146 | 1.00 | 37.07 | B | N |
| ATOM | 8425 | CA | ASP | 331 | 126.123 | 65.886 | 13.106 | 1.00 | 39.50 | B | C |
| ATOM | 8426 | CB | ASP | 331 | 125.611 | 65.391 | 11.756 | 1.00 | 39.77 | B | C |
| ATOM | 8427 | CG | ASP | 331 | 126.665 | 65.464 | 10.677 | 1.00 | 40.31 | B | C |

| ATOM | 8428 | OD1 | ASP | 331 | 126.387 | 65.018 | 9.543 | 1.00 | 41.37 | B | O |
|------|------|-----|-----|-----|---------|--------|-------|------|-------|---|---|
| ATOM | 8429 | OD2 | ASP | 331 | 127.770 | 65.966 | 10.967 | 1.00 | 40.07 | B | O |
| ATOM | 8430 | C | ASP | 331 | 126.355 | 67.395 | 13.062 | 1.00 | 41.15 | B | C |
| ATOM | 8431 | O | ASP | 331 | 125.641 | 68.126 | 12.380 | 1.00 | 40.39 | B | O |
| ATOM | 8432 | N | GLU | 332 | 127.358 | 67.852 | 13.802 | 1.00 | 44.16 | B | N |
| ATOM | 8433 | CA | GLU | 332 | 127.690 | 69.271 | 13.879 | 1.00 | 47.17 | B | C |
| ATOM | 8434 | CB | GLU | 332 | 129.001 | 69.457 | 14.646 | 1.00 | 48.80 | B | C |
| ATOM | 8435 | CG | GLU | 332 | 129.367 | 70.901 | 14.922 | 1.00 | 51.70 | B | C |
| ATOM | 8436 | CD | GLU | 332 | 130.451 | 71.028 | 15.979 | 1.00 | 54.56 | B | C |
| ATOM | 8437 | OE1 | GLU | 332 | 130.203 | 70.623 | 17.136 | 1.00 | 55.51 | B | O |
| ATOM | 8438 | OE2 | GLU | 332 | 131.552 | 71.528 | 15.658 | 1.00 | 56.11 | B | O |
| ATOM | 8439 | C | GLU | 332 | 127.791 | 69.941 | 12.517 | 1.00 | 47.83 | B | C |
| ATOM | 8440 | O | GLU | 332 | 127.518 | 71.130 | 12.383 | 1.00 | 48.20 | B | O |
| ATOM | 8441 | N | SER | 333 | 128.179 | 69.175 | 11.505 | 1.00 | 48.69 | B | N |
| ATOM | 8442 | CA | SER | 333 | 128.312 | 69.715 | 10.161 | 1.00 | 49.93 | B | C |
| ATOM | 8443 | CB | SER | 333 | 129.246 | 68.835 | 9.327 | 1.00 | 50.95 | B | C |
| ATOM | 8444 | OG | SER | 333 | 130.521 | 68.723 | 9.943 | 1.00 | 54.48 | B | O |
| ATOM | 8445 | C | SER | 333 | 126.957 | 69.809 | 9.483 | 1.00 | 49.97 | B | C |
| ATOM | 8446 | O | SER | 333 | 126.514 | 70.893 | 9.108 | 1.00 | 50.95 | B | O |
| ATOM | 8447 | N | SER | 334 | 126.302 | 68.665 | 9.326 | 1.00 | 50.21 | B | N |
| ATOM | 8448 | CA | SER | 334 | 124.993 | 68.609 | 8.687 | 1.00 | 49.04 | B | C |
| ATOM | 8449 | CB | SER | 334 | 124.582 | 67.154 | 8.451 | 1.00 | 50.46 | B | C |
| ATOM | 8450 | OG | SER | 334 | 123.275 | 67.076 | 7.905 | 1.00 | 52.36 | B | O |
| ATOM | 8451 | C | SER | 334 | 123.934 | 69.288 | 9.536 | 1.00 | 47.42 | B | C |
| ATOM | 8452 | O | SER | 334 | 122.917 | 69.742 | 9.021 | 1.00 | 48.45 | B | O |
| ATOM | 8453 | N | GLY | 335 | 124.177 | 69.353 | 10.840 | 1.00 | 45.55 | B | N |
| ATOM | 8454 | CA | GLY | 335 | 123.219 | 69.965 | 11.738 | 1.00 | 42.54 | B | C |
| ATOM | 8455 | C | GLY | 335 | 122.081 | 69.007 | 12.033 | 1.00 | 40.97 | B | C |
| ATOM | 8456 | O | GLY | 335 | 121.179 | 69.318 | 12.807 | 1.00 | 40.87 | B | O |
| ATOM | 8457 | N | ARG | 336 | 122.117 | 67.834 | 11.409 | 1.00 | 38.61 | B | N |
| ATOM | 8458 | CA | ARG | 336 | 121.076 | 66.843 | 11.622 | 1.00 | 37.65 | B | C |
| ATOM | 8459 | CB | ARG | 336 | 120.725 | 66.143 | 10.306 | 1.00 | 39.07 | B | C |
| ATOM | 8460 | CG | ARG | 336 | 120.460 | 67.099 | 9.151 | 1.00 | 41.95 | B | C |
| ATOM | 8461 | CD | ARG | 336 | 119.339 | 66.597 | 8.248 | 1.00 | 45.61 | B | C |
| ATOM | 8462 | NE | ARG | 336 | 118.019 | 67.002 | 8.729 | 1.00 | 48.18 | B | N |
| ATOM | 8463 | CZ | ARG | 336 | 117.522 | 68.233 | 8.613 | 1.00 | 49.86 | B | C |
| ATOM | 8464 | NH1 | ARG | 336 | 118.229 | 69.194 | 8.025 | 1.00 | 50.51 | B | N |
| ATOM | 8465 | NH2 | ARG | 336 | 116.317 | 68.510 | 9.094 | 1.00 | 50.56 | B | N |
| ATOM | 8466 | C | ARG | 336 | 121.524 | 65.817 | 12.654 | 1.00 | 35.64 | B | C |
| ATOM | 8467 | O | ARG | 336 | 122.629 | 65.900 | 13.181 | 1.00 | 35.91 | B | O |
| ATOM | 8468 | N | TRP | 337 | 120.649 | 64.865 | 12.955 | 1.00 | 33.09 | B | N |
| ATOM | 8469 | CA | TRP | 337 | 120.955 | 63.818 | 13.918 | 1.00 | 30.08 | B | C |
| ATOM | 8470 | CB | TRP | 337 | 119.922 | 63.793 | 15.053 | 1.00 | 24.67 | B | C |
| ATOM | 8471 | CG | TRP | 337 | 119.993 | 64.979 | 15.954 | 1.00 | 20.03 | B | C |
| ATOM | 8472 | CD2 | TRP | 337 | 120.670 | 65.059 | 17.214 | 1.00 | 17.75 | B | C |
| ATOM | 8473 | CE2 | TRP | 337 | 120.550 | 66.390 | 17.671 | 1.00 | 17.16 | B | C |
| ATOM | 8474 | CE3 | TRP | 337 | 121.374 | 64.137 | 17.997 | 1.00 | 15.36 | B | C |
| ATOM | 8475 | CD1 | TRP | 337 | 119.498 | 66.224 | 15.709 | 1.00 | 19.73 | B | C |
| ATOM | 8476 | NE1 | TRP | 337 | 119.827 | 67.079 | 16.736 | 1.00 | 18.61 | B | N |

| | | | | | | | | | | |
|---|---|---|---|---|---|---|---|---|---|---|
| ATOM | 8477 | CZ2 | TRP | 337 | 121.110 | 66.825 | 18.875 | 1.00 | 18.08 | B C |
| ATOM | 8478 | CZ3 | TRP | 337 | 121.932 | 64.567 | 19.196 | 1.00 | 15.24 | B C |
| ATOM | 8479 | CH2 | TRP | 337 | 121.798 | 65.900 | 19.622 | 1.00 | 16.71 | B C |
| ATOM | 8480 | C | TRP | 337 | 120.940 | 62.487 | 13.188 | 1.00 | 31.57 | B C |
| ATOM | 8481 | O | TRP | 337 | 119.983 | 62.167 | 12.482 | 1.00 | 33.23 | B O |
| ATOM | 8482 | N | ASN | 338 | 122.003 | 61.712 | 13.347 | 1.00 | 32.12 | B N |
| ATOM | 8483 | CA | ASN | 338 | 122.079 | 60.426 | 12.691 | 1.00 | 33.02 | B C |
| ATOM | 8484 | CB | ASN | 338 | 123.240 | 60.416 | 11.698 | 1.00 | 34.88 | B C |
| ATOM | 8485 | CG | ASN | 338 | 122.957 | 61.271 | 10.471 | 1.00 | 38.68 | B C |
| ATOM | 8486 | OD1 | ASN | 338 | 123.595 | 62.306 | 10.251 | 1.00 | 39.82 | B O |
| ATOM | 8487 | ND2 | ASN | 338 | 121.984 | 60.845 | 9.669 | 1.00 | 38.06 | B N |
| ATOM | 8488 | C | ASN | 338 | 122.216 | 59.294 | 13.693 | 1.00 | 33.48 | B C |
| ATOM | 8489 | O | ASN | 338 | 123.009 | 59.364 | 14.631 | 1.00 | 33.12 | B O |
| ATOM | 8490 | N | CYS | 339 | 121.419 | 58.251 | 13.499 | 1.00 | 33.60 | B N |
| ATOM | 8491 | CA | CYS | 339 | 121.459 | 57.104 | 14.385 | 1.00 | 34.06 | B C |
| ATOM | 8492 | C | CYS | 339 | 121.924 | 55.913 | 13.564 | 1.00 | 33.56 | B C |
| ATOM | 8493 | O | CYS | 339 | 121.135 | 55.296 | 12.848 | 1.00 | 34.05 | B O |
| ATOM | 8494 | CB | CYS | 339 | 120.071 | 56.829 | 14.961 | 1.00 | 34.96 | B C |
| ATOM | 8495 | SG | CYS | 339 | 118.997 | 58.291 | 15.160 | 1.00 | 37.83 | B S |
| ATOM | 8496 | N | LEU | 340 | 123.211 | 55.604 | 13.665 | 1.00 | 32.80 | B N |
| ATOM | 8497 | CA | LEU | 340 | 123.798 | 54.491 | 12.933 | 1.00 | 33.83 | B C |
| ATOM | 8498 | CB | LEU | 340 | 125.303 | 54.413 | 13.218 | 1.00 | 34.61 | B C |
| ATOM | 8499 | CG | LEU | 340 | 126.163 | 55.530 | 12.609 | 1.00 | 34.61 | B C |
| ATOM | 8500 | CD1 | LEU | 340 | 127.500 | 55.633 | 13.322 | 1.00 | 31.70 | B C |
| ATOM | 8501 | CD2 | LEU | 340 | 126.352 | 55.257 | 11.132 | 1.00 | 33.80 | B C |
| ATOM | 8502 | C | LEU | 340 | 123.152 | 53.151 | 13.259 | 1.00 | 34.95 | B C |
| ATOM | 8503 | O | LEU | 340 | 123.061 | 52.752 | 14.418 | 1.00 | 34.65 | B O |
| ATOM | 8504 | N | VAL | 341 | 122.706 | 52.457 | 12.220 | 1.00 | 35.87 | B N |
| ATOM | 8505 | CA | VAL | 341 | 122.093 | 51.152 | 12.387 | 1.00 | 36.37 | B C |
| ATOM | 8506 | CB | VAL | 341 | 121.981 | 50.423 | 11.047 | 1.00 | 36.86 | B C |
| ATOM | 8507 | CG1 | VAL | 341 | 121.012 | 49.256 | 11.175 | 1.00 | 37.20 | B C |
| ATOM | 8508 | CG2 | VAL | 341 | 121.532 | 51.391 | 9.968 | 1.00 | 38.15 | B C |
| ATOM | 8509 | C | VAL | 341 | 122.957 | 50.305 | 13.314 | 1.00 | 36.74 | B C |
| ATOM | 8510 | O | VAL | 341 | 122.511 | 49.872 | 14.366 | 1.00 | 39.77 | B O |
| ATOM | 8511 | N | ALA | 342 | 124.200 | 50.073 | 12.913 | 1.00 | 35.94 | B N |
| ATOM | 8512 | CA | ALA | 342 | 125.134 | 49.283 | 13.704 | 1.00 | 34.75 | B C |
| ATOM | 8513 | CB | ALA | 342 | 126.546 | 49.482 | 13.178 | 1.00 | 34.41 | B C |
| ATOM | 8514 | C | ALA | 342 | 125.095 | 49.609 | 15.194 | 1.00 | 34.74 | B C |
| ATOM | 8515 | O | ALA | 342 | 125.698 | 48.897 | 16.001 | 1.00 | 36.76 | B O |
| ATOM | 8516 | N | ARG | 343 | 124.411 | 50.688 | 15.561 | 1.00 | 32.52 | B N |
| ATOM | 8517 | CA | ARG | 343 | 124.303 | 51.074 | 16.961 | 1.00 | 30.81 | B C |
| ATOM | 8518 | CB | ARG | 343 | 124.611 | 52.562 | 17.120 | 1.00 | 32.62 | B C |
| ATOM | 8519 | CG | ARG | 343 | 126.063 | 52.922 | 16.844 | 1.00 | 34.14 | B C |
| ATOM | 8520 | CD | ARG | 343 | 126.345 | 54.396 | 17.131 | 1.00 | 33.56 | B C |
| ATOM | 8521 | NE | ARG | 343 | 127.775 | 54.692 | 17.108 | 1.00 | 33.70 | B N |
| ATOM | 8522 | CZ | ARG | 343 | 128.301 | 55.885 | 17.374 | 1.00 | 34.14 | B C |
| ATOM | 8523 | NH1 | ARG | 343 | 127.516 | 56.907 | 17.680 | 1.00 | 33.88 | B N |
| ATOM | 8524 | NH2 | ARG | 343 | 129.615 | 56.052 | 17.352 | 1.00 | 33.78 | B N |
| ATOM | 8525 | C | ARG | 343 | 122.919 | 50.751 | 17.535 | 1.00 | 29.28 | B C |

FIG. 4-175 (Continued)

| | | | | | | | | | | | |
|---|---|---|---|---|---|---|---|---|---|---|---|
| ATOM | 8526 | O | ARG | 343 | 122.586 | 51.143 | 18.650 | 1.00 | 28.30 | B | O |
| ATOM | 8527 | N | GLN | 344 | 122.121 | 50.026 | 16.763 | 1.00 | 28.05 | B | N |
| ATOM | 8528 | CA | GLN | 344 | 120.786 | 49.625 | 17.183 | 1.00 | 28.26 | B | C |
| ATOM | 8529 | CB | GLN | 344 | 119.944 | 49.238 | 15.974 | 1.00 | 26.68 | B | C |
| ATOM | 8530 | CG | GLN | 344 | 118.980 | 50.296 | 15.516 | 1.00 | 30.39 | B | C |
| ATOM | 8531 | CD | GLN | 344 | 118.091 | 49.802 | 14.399 | 1.00 | 31.50 | B | C |
| ATOM | 8532 | OE1 | GLN | 344 | 117.567 | 48.685 | 14.457 | 1.00 | 31.52 | B | O |
| ATOM | 8533 | NE2 | GLN | 344 | 117.905 | 50.632 | 13.378 | 1.00 | 32.84 | B | N |
| ATOM | 8534 | C | GLN | 344 | 120.853 | 48.431 | 18.121 | 1.00 | 28.55 | B | C |
| ATOM | 8535 | O | GLN | 344 | 121.655 | 47.515 | 17.919 | 1.00 | 28.32 | B | O |
| ATOM | 8536 | N | HIS | 345 | 120.008 | 48.436 | 19.145 | 1.00 | 28.34 | B | N |
| ATOM | 8537 | CA | HIS | 345 | 119.977 | 47.329 | 20.085 | 1.00 | 28.01 | B | C |
| ATOM | 8538 | CB | HIS | 345 | 120.514 | 47.753 | 21.452 | 1.00 | 28.88 | B | C |
| ATOM | 8539 | CG | HIS | 345 | 121.973 | 48.079 | 21.443 | 1.00 | 27.88 | B | C |
| ATOM | 8540 | CD2 | HIS | 345 | 123.062 | 47.279 | 21.516 | 1.00 | 26.67 | B | C |
| ATOM | 8541 | ND1 | HIS | 345 | 122.449 | 49.361 | 21.270 | 1.00 | 28.37 | B | N |
| ATOM | 8542 | CE1 | HIS | 345 | 123.769 | 49.337 | 21.234 | 1.00 | 28.14 | B | C |
| ATOM | 8543 | NE2 | HIS | 345 | 124.166 | 48.086 | 21.381 | 1.00 | 28.63 | B | N |
| ATOM | 8544 | C | HIS | 345 | 118.568 | 46.799 | 20.215 | 1.00 | 27.76 | B | C |
| ATOM | 8545 | O | HIS | 345 | 117.659 | 47.508 | 20.625 | 1.00 | 30.01 | B | O |
| ATOM | 8546 | N | ILE | 346 | 118.396 | 45.538 | 19.849 | 1.00 | 26.83 | B | N |
| ATOM | 8547 | CA | ILE | 346 | 117.102 | 44.897 | 19.899 | 1.00 | 25.72 | B | C |
| ATOM | 8548 | CB | ILE | 346 | 116.977 | 43.842 | 18.791 | 1.00 | 25.56 | B | C |
| ATOM | 8549 | CG2 | ILE | 346 | 115.655 | 43.114 | 18.919 | 1.00 | 26.17 | B | C |
| ATOM | 8550 | CG1 | ILE | 346 | 117.102 | 44.517 | 17.422 | 1.00 | 26.62 | B | C |
| ATOM | 8551 | CD1 | ILE | 346 | 117.180 | 43.544 | 16.263 | 1.00 | 26.42 | B | C |
| ATOM | 8552 | C | ILE | 346 | 116.854 | 44.218 | 21.228 | 1.00 | 26.11 | B | C |
| ATOM | 8553 | O | ILE | 346 | 117.736 | 43.558 | 21.776 | 1.00 | 25.75 | B | O |
| ATOM | 8554 | N | GLU | 347 | 115.645 | 44.396 | 21.746 | 1.00 | 26.23 | B | N |
| ATOM | 8555 | CA | GLU | 347 | 115.260 | 43.767 | 22.994 | 1.00 | 25.82 | B | C |
| ATOM | 8556 | CB | GLU | 347 | 115.226 | 44.777 | 24.134 | 1.00 | 25.51 | B | C |
| ATOM | 8557 | CG | GLU | 347 | 115.282 | 44.118 | 25.505 | 1.00 | 28.20 | B | C |
| ATOM | 8558 | CD | GLU | 347 | 115.107 | 45.094 | 26.652 | 1.00 | 29.16 | B | C |
| ATOM | 8559 | OE1 | GLU | 347 | 115.667 | 46.208 | 26.592 | 1.00 | 29.18 | B | O |
| ATOM | 8560 | OE2 | GLU | 347 | 114.415 | 44.736 | 27.628 | 1.00 | 32.76 | B | O |
| ATOM | 8561 | C | GLU | 347 | 113.873 | 43.172 | 22.799 | 1.00 | 26.44 | B | C |
| ATOM | 8562 | O | GLU | 347 | 112.919 | 43.889 | 22.495 | 1.00 | 26.00 | B | O |
| ATOM | 8563 | N | MET | 348 | 113.770 | 41.858 | 22.957 | 1.00 | 26.58 | B | N |
| ATOM | 8564 | CA | MET | 348 | 112.492 | 41.181 | 22.807 | 1.00 | 27.90 | B | C |
| ATOM | 8565 | CB | MET | 348 | 112.270 | 40.767 | 21.345 | 1.00 | 30.41 | B | C |
| ATOM | 8566 | CG | MET | 348 | 113.466 | 40.132 | 20.660 | 1.00 | 34.65 | B | C |
| ATOM | 8567 | SD | MET | 348 | 113.695 | 38.420 | 21.117 | 1.00 | 42.21 | B | S |
| ATOM | 8568 | CE | MET | 348 | 112.733 | 37.597 | 19.804 | 1.00 | 38.96 | B | C |
| ATOM | 8569 | C | MET | 348 | 112.371 | 39.980 | 23.732 | 1.00 | 26.60 | B | C |
| ATOM | 8570 | O | MET | 348 | 113.363 | 39.472 | 24.247 | 1.00 | 26.08 | B | O |
| ATOM | 8571 | N | SER | 349 | 111.135 | 39.549 | 23.950 | 1.00 | 23.99 | B | N |
| ATOM | 8572 | CA | SER | 349 | 110.843 | 38.423 | 24.812 | 1.00 | 21.78 | B | C |
| ATOM | 8573 | CB | SER | 349 | 109.989 | 38.894 | 25.997 | 1.00 | 20.79 | B | C |
| ATOM | 8574 | OG | SER | 349 | 109.402 | 37.809 | 26.700 | 1.00 | 21.42 | B | O |

FIG. 4-176 (Continued)

| | | | | | | | | | | |
|---|---|---|---|---|---|---|---|---|---|---|
| ATOM | 8575 | C | SER | 349 | 110.084 | 37.387 | 24.005 | 1.00 | 21.88 | B C |
| ATOM | 8576 | O | SER | 349 | 109.274 | 37.739 | 23.154 | 1.00 | 23.74 | B O |
| ATOM | 8577 | N | THR | 350 | 110.351 | 36.112 | 24.264 | 1.00 | 21.76 | B N |
| ATOM | 8578 | CA | THR | 350 | 109.654 | 35.033 | 23.571 | 1.00 | 23.08 | B C |
| ATOM | 8579 | CB | THR | 350 | 110.603 | 33.882 | 23.214 | 1.00 | 22.77 | B C |
| ATOM | 8580 | OG1 | THR | 350 | 111.310 | 33.483 | 24.391 | 1.00 | 25.37 | B O |
| ATOM | 8581 | CG2 | THR | 350 | 111.583 | 34.299 | 22.152 | 1.00 | 22.93 | B C |
| ATOM | 8582 | C | THR | 350 | 108.561 | 34.453 | 24.475 | 1.00 | 22.93 | B C |
| ATOM | 8583 | O | THR | 350 | 107.732 | 33.650 | 24.035 | 1.00 | 20.70 | B O |
| ATOM | 8584 | N | THR | 351 | 108.564 | 34.871 | 25.737 | 1.00 | 22.30 | B N |
| ATOM | 8585 | CA | THR | 351 | 107.601 | 34.366 | 26.703 | 1.00 | 22.35 | B C |
| ATOM | 8586 | CB | THR | 351 | 108.332 | 33.796 | 27.932 | 1.00 | 23.36 | B C |
| ATOM | 8587 | OG1 | THR | 351 | 108.989 | 34.859 | 28.635 | 1.00 | 25.67 | B O |
| ATOM | 8588 | CG2 | THR | 351 | 109.378 | 32.781 | 27.493 | 1.00 | 22.26 | B C |
| ATOM | 8589 | C | THR | 351 | 106.575 | 35.392 | 27.171 | 1.00 | 21.07 | B C |
| ATOM | 8590 | O | THR | 351 | 105.562 | 35.031 | 27.760 | 1.00 | 20.87 | B O |
| ATOM | 8591 | N | GLY | 352 | 106.839 | 36.668 | 26.918 | 1.00 | 19.83 | B N |
| ATOM | 8592 | CA | GLY | 352 | 105.894 | 37.692 | 27.325 | 1.00 | 19.36 | B C |
| ATOM | 8593 | C | GLY | 352 | 106.182 | 39.027 | 26.672 | 1.00 | 18.63 | B C |
| ATOM | 8594 | O | GLY | 352 | 106.633 | 39.076 | 25.531 | 1.00 | 20.78 | B O |
| ATOM | 8595 | N | TRP | 353 | 105.913 | 40.109 | 27.397 | 1.00 | 17.51 | B N |
| ATOM | 8596 | CA | TRP | 353 | 106.156 | 41.464 | 26.907 | 1.00 | 15.30 | B C |
| ATOM | 8597 | CB | TRP | 353 | 105.195 | 42.451 | 27.587 | 1.00 | 13.08 | B C |
| ATOM | 8598 | CG | TRP | 353 | 105.165 | 42.366 | 29.084 | 1.00 | 9.17 | B C |
| ATOM | 8599 | CD2 | TRP | 353 | 104.479 | 41.387 | 29.877 | 1.00 | 7.79 | B C |
| ATOM | 8600 | CE2 | TRP | 353 | 104.739 | 41.684 | 31.233 | 1.00 | 8.17 | B C |
| ATOM | 8601 | CE3 | TRP | 353 | 103.671 | 40.288 | 29.574 | 1.00 | 10.72 | B C |
| ATOM | 8602 | CD1 | TRP | 353 | 105.798 | 43.195 | 29.966 | 1.00 | 11.19 | B C |
| ATOM | 8603 | NE1 | TRP | 353 | 105.546 | 42.791 | 31.265 | 1.00 | 10.10 | B N |
| ATOM | 8604 | CZ2 | TRP | 353 | 104.217 | 40.921 | 32.281 | 1.00 | 10.66 | B C |
| ATOM | 8605 | CZ3 | TRP | 353 | 103.149 | 39.524 | 30.625 | 1.00 | 10.40 | B C |
| ATOM | 8606 | CH2 | TRP | 353 | 103.426 | 39.848 | 31.958 | 1.00 | 9.81 | B C |
| ATOM | 8607 | C | TRP | 353 | 107.594 | 41.796 | 27.264 | 1.00 | 15.80 | B C |
| ATOM | 8608 | O | TRP | 353 | 108.247 | 40.999 | 27.931 | 1.00 | 16.59 | B O |
| ATOM | 8609 | N | VAL | 354 | 108.092 | 42.946 | 26.819 | 1.00 | 13.84 | B N |
| ATOM | 8610 | CA | VAL | 354 | 109.464 | 43.338 | 27.140 | 1.00 | 13.65 | B C |
| ATOM | 8611 | CB | VAL | 354 | 110.135 | 44.096 | 25.960 | 1.00 | 16.06 | B C |
| ATOM | 8612 | CG1 | VAL | 354 | 111.506 | 44.646 | 26.400 | 1.00 | 12.56 | B C |
| ATOM | 8613 | CG2 | VAL | 354 | 110.284 | 43.163 | 24.751 | 1.00 | 12.49 | B C |
| ATOM | 8614 | C | VAL | 354 | 109.486 | 44.248 | 28.368 | 1.00 | 13.83 | B C |
| ATOM | 8615 | O | VAL | 354 | 108.716 | 45.197 | 28.456 | 1.00 | 13.93 | B O |
| ATOM | 8616 | N | GLY | 355 | 110.373 | 43.957 | 29.313 | 1.00 | 14.87 | B N |
| ATOM | 8617 | CA | GLY | 355 | 110.467 | 44.769 | 30.519 | 1.00 | 16.09 | B C |
| ATOM | 8618 | C | GLY | 355 | 109.333 | 44.554 | 31.513 | 1.00 | 16.34 | B C |
| ATOM | 8619 | O | GLY | 355 | 108.347 | 43.877 | 31.206 | 1.00 | 18.25 | B O |
| ATOM | 8620 | N | ARG | 356 | 109.456 | 45.126 | 32.706 | 1.00 | 15.16 | B N |
| ATOM | 8621 | CA | ARG | 356 | 108.404 | 44.953 | 33.701 | 1.00 | 16.32 | B C |
| ATOM | 8622 | CB | ARG | 356 | 108.856 | 45.494 | 35.066 | 1.00 | 14.18 | B C |
| ATOM | 8623 | CG | ARG | 356 | 110.001 | 44.668 | 35.667 | 1.00 | 13.44 | B C |

| | | | | | | | | | | |
|---|---|---|---|---|---|---|---|---|---|---|
| ATOM | 8624 | CD | ARG | 356 | 110.169 | 44.878 | 37.151 | 1.00 | 14.42 | B | C |
| ATOM | 8625 | NE | ARG | 356 | 111.546 | 45.211 | 37.511 | 1.00 | 18.65 | B | N |
| ATOM | 8626 | CZ | ARG | 356 | 112.457 | 44.341 | 37.935 | 1.00 | 20.17 | B | C |
| ATOM | 8627 | NH1 | ARG | 356 | 112.156 | 43.055 | 38.065 | 1.00 | 22.71 | B | N |
| ATOM | 8628 | NH2 | ARG | 356 | 113.674 | 44.765 | 38.242 | 1.00 | 18.93 | B | N |
| ATOM | 8629 | C | ARG | 356 | 107.111 | 45.607 | 33.209 | 1.00 | 16.01 | B | C |
| ATOM | 8630 | O | ARG | 356 | 106.100 | 44.924 | 33.066 | 1.00 | 16.29 | B | O |
| ATOM | 8631 | N | PHE | 357 | 107.140 | 46.911 | 32.945 | 1.00 | 15.89 | B | N |
| ATOM | 8632 | CA | PHE | 357 | 105.967 | 47.603 | 32.402 | 1.00 | 16.40 | B | C |
| ATOM | 8633 | CB | PHE | 357 | 105.418 | 48.660 | 33.366 | 1.00 | 11.21 | B | C |
| ATOM | 8634 | CG | PHE | 357 | 104.753 | 48.083 | 34.573 | 1.00 | 8.48 | B | C |
| ATOM | 8635 | CD1 | PHE | 357 | 105.467 | 47.878 | 35.748 | 1.00 | 5.58 | B | C |
| ATOM | 8636 | CD2 | PHE | 357 | 103.407 | 47.711 | 34.531 | 1.00 | 8.57 | B | C |
| ATOM | 8637 | CE1 | PHE | 357 | 104.846 | 47.309 | 36.867 | 1.00 | 5.98 | B | C |
| ATOM | 8638 | CE2 | PHE | 357 | 102.777 | 47.136 | 35.648 | 1.00 | 4.59 | B | C |
| ATOM | 8639 | CZ | PHE | 357 | 103.498 | 46.937 | 36.812 | 1.00 | 3.60 | B | C |
| ATOM | 8640 | C | PHE | 357 | 106.344 | 48.259 | 31.076 | 1.00 | 18.69 | B | C |
| ATOM | 8641 | O | PHE | 357 | 105.476 | 48.638 | 30.287 | 1.00 | 21.57 | B | O |
| ATOM | 8642 | N | ARG | 358 | 107.648 | 48.377 | 30.840 | 1.00 | 19.12 | B | N |
| ATOM | 8643 | CA | ARG | 358 | 108.188 | 48.953 | 29.612 | 1.00 | 19.47 | B | C |
| ATOM | 8644 | CB | ARG | 358 | 107.826 | 50.439 | 29.499 | 1.00 | 19.02 | B | C |
| ATOM | 8645 | CG | ARG | 358 | 108.451 | 51.346 | 30.559 | 1.00 | 19.99 | B | C |
| ATOM | 8646 | CD | ARG | 358 | 108.074 | 52.820 | 30.338 | 1.00 | 22.48 | B | C |
| ATOM | 8647 | NE | ARG | 358 | 108.633 | 53.708 | 31.362 | 1.00 | 24.20 | B | N |
| ATOM | 8648 | CZ | ARG | 358 | 109.204 | 54.890 | 31.117 | 1.00 | 24.69 | B | C |
| ATOM | 8649 | NH1 | ARG | 358 | 109.304 | 55.358 | 29.875 | 1.00 | 21.14 | B | N |
| ATOM | 8650 | NH2 | ARG | 358 | 109.696 | 55.603 | 32.121 | 1.00 | 24.33 | B | N |
| ATOM | 8651 | C | ARG | 358 | 109.707 | 48.784 | 29.646 | 1.00 | 20.57 | B | C |
| ATOM | 8652 | O | ARG | 358 | 110.302 | 48.704 | 30.722 | 1.00 | 22.16 | B | O |
| ATOM | 8653 | N | PRO | 359 | 110.355 | 48.723 | 28.473 | 1.00 | 20.23 | B | N |
| ATOM | 8654 | CD | PRO | 359 | 109.783 | 48.894 | 27.124 | 1.00 | 20.61 | B | C |
| ATOM | 8655 | CA | PRO | 359 | 111.816 | 48.564 | 28.411 | 1.00 | 20.48 | B | C |
| ATOM | 8656 | CB | PRO | 359 | 112.137 | 48.916 | 26.959 | 1.00 | 19.85 | B | C |
| ATOM | 8657 | CG | PRO | 359 | 110.919 | 48.431 | 26.229 | 1.00 | 21.21 | B | C |
| ATOM | 8658 | C | PRO | 359 | 112.527 | 49.494 | 29.402 | 1.00 | 20.23 | B | C |
| ATOM | 8659 | O | PRO | 359 | 112.221 | 50.683 | 29.465 | 1.00 | 22.01 | B | O |
| ATOM | 8660 | N | SER | 360 | 113.474 | 48.953 | 30.163 | 1.00 | 19.33 | B | N |
| ATOM | 8661 | CA | SER | 360 | 114.212 | 49.725 | 31.160 | 1.00 | 18.75 | B | C |
| ATOM | 8662 | CB | SER | 360 | 115.122 | 48.806 | 31.968 | 1.00 | 20.74 | B | C |
| ATOM | 8663 | OG | SER | 360 | 116.163 | 48.286 | 31.149 | 1.00 | 26.03 | B | O |
| ATOM | 8664 | C | SER | 360 | 115.060 | 50.841 | 30.560 | 1.00 | 18.77 | B | C |
| ATOM | 8665 | O | SER | 360 | 115.410 | 50.806 | 29.382 | 1.00 | 17.99 | B | O |
| ATOM | 8666 | N | GLU | 361 | 115.394 | 51.824 | 31.393 | 1.00 | 18.96 | B | N |
| ATOM | 8667 | CA | GLU | 361 | 116.199 | 52.970 | 30.978 | 1.00 | 18.11 | B | C |
| ATOM | 8668 | CB | GLU | 361 | 115.982 | 54.159 | 31.919 | 1.00 | 16.34 | B | C |
| ATOM | 8669 | CG | GLU | 361 | 116.654 | 54.007 | 33.269 | 1.00 | 21.67 | B | C |
| ATOM | 8670 | CD | GLU | 361 | 115.743 | 53.431 | 34.342 | 1.00 | 27.42 | B | C |
| ATOM | 8671 | OE1 | GLU | 361 | 115.067 | 52.408 | 34.091 | 1.00 | 28.62 | B | O |
| ATOM | 8672 | OE2 | GLU | 361 | 115.710 | 54.009 | 35.453 | 1.00 | 31.11 | B | O |

FIG. 4-178 (Continued)

| ATOM | 8673 | C   | GLU | 361 | 117.674 | 52.595 | 31.007 | 1.00 | 16.97 | B | C |
| --- | --- | --- | --- | --- | --- | --- | --- | --- | --- | --- | --- |
| ATOM | 8674 | O   | GLU | 361 | 118.118 | 51.870 | 31.888 | 1.00 | 16.23 | B | O |
| ATOM | 8675 | N   | PRO | 362 | 118.449 | 53.079 | 30.030 | 1.00 | 16.09 | B | N |
| ATOM | 8676 | CD  | PRO | 362 | 118.027 | 53.805 | 28.817 | 1.00 | 13.66 | B | C |
| ATOM | 8677 | CA  | PRO | 362 | 119.879 | 52.772 | 29.985 | 1.00 | 15.32 | B | C |
| ATOM | 8678 | CB  | PRO | 362 | 120.207 | 52.916 | 28.505 | 1.00 | 13.19 | B | C |
| ATOM | 8679 | CG  | PRO | 362 | 119.362 | 54.086 | 28.121 | 1.00 | 12.78 | B | C |
| ATOM | 8680 | C   | PRO | 362 | 120.601 | 53.806 | 30.832 | 1.00 | 16.34 | B | C |
| ATOM | 8681 | O   | PRO | 362 | 120.096 | 54.911 | 31.021 | 1.00 | 17.05 | B | O |
| ATOM | 8682 | N   | HIS | 363 | 121.768 | 53.448 | 31.353 | 1.00 | 17.21 | B | N |
| ATOM | 8683 | CA  | HIS | 363 | 122.550 | 54.374 | 32.164 | 1.00 | 18.58 | B | C |
| ATOM | 8684 | CB  | HIS | 363 | 122.626 | 53.875 | 33.603 | 1.00 | 18.05 | B | C |
| ATOM | 8685 | CG  | HIS | 363 | 121.324 | 53.965 | 34.333 | 1.00 | 19.33 | B | C |
| ATOM | 8686 | CD2 | HIS | 363 | 120.156 | 53.301 | 34.158 | 1.00 | 19.36 | B | C |
| ATOM | 8687 | ND1 | HIS | 363 | 121.111 | 54.851 | 35.368 | 1.00 | 18.40 | B | N |
| ATOM | 8688 | CE1 | HIS | 363 | 119.869 | 54.731 | 35.799 | 1.00 | 19.50 | B | C |
| ATOM | 8689 | NE2 | HIS | 363 | 119.267 | 53.798 | 35.081 | 1.00 | 22.85 | B | N |
| ATOM | 8690 | C   | HIS | 363 | 123.942 | 54.499 | 31.551 | 1.00 | 19.40 | B | C |
| ATOM | 8691 | O   | HIS | 363 | 124.833 | 53.691 | 31.806 | 1.00 | 19.73 | B | O |
| ATOM | 8692 | N   | PHE | 364 | 124.110 | 55.520 | 30.723 | 1.00 | 19.14 | B | N |
| ATOM | 8693 | CA  | PHE | 364 | 125.371 | 55.744 | 30.043 | 1.00 | 19.25 | B | C |
| ATOM | 8694 | CB  | PHE | 364 | 125.188 | 56.802 | 28.944 | 1.00 | 17.71 | B | C |
| ATOM | 8695 | CG  | PHE | 364 | 124.368 | 56.319 | 27.777 | 1.00 | 15.99 | B | C |
| ATOM | 8696 | CD1 | PHE | 364 | 122.975 | 56.339 | 27.826 | 1.00 | 12.83 | B | C |
| ATOM | 8697 | CD2 | PHE | 364 | 124.989 | 55.770 | 26.656 | 1.00 | 12.86 | B | C |
| ATOM | 8698 | CE1 | PHE | 364 | 122.216 | 55.816 | 26.781 | 1.00 | 8.09 | B | C |
| ATOM | 8699 | CE2 | PHE | 364 | 124.225 | 55.242 | 25.607 | 1.00 | 10.87 | B | C |
| ATOM | 8700 | CZ  | PHE | 364 | 122.837 | 55.268 | 25.679 | 1.00 | 7.69 | B | C |
| ATOM | 8701 | C   | PHE | 364 | 126.531 | 56.127 | 30.942 | 1.00 | 18.72 | B | C |
| ATOM | 8702 | O   | PHE | 364 | 126.341 | 56.638 | 32.050 | 1.00 | 17.88 | B | O |
| ATOM | 8703 | N   | THR | 365 | 127.735 | 55.854 | 30.448 | 1.00 | 18.23 | B | N |
| ATOM | 8704 | CA  | THR | 365 | 128.967 | 56.178 | 31.159 | 1.00 | 19.73 | B | C |
| ATOM | 8705 | CB  | THR | 365 | 130.132 | 55.288 | 30.697 | 1.00 | 17.73 | B | C |
| ATOM | 8706 | OG1 | THR | 365 | 130.257 | 55.384 | 29.275 | 1.00 | 22.16 | B | O |
| ATOM | 8707 | CG2 | THR | 365 | 129.890 | 53.848 | 31.069 | 1.00 | 13.36 | B | C |
| ATOM | 8708 | C   | THR | 365 | 129.312 | 57.633 | 30.847 | 1.00 | 20.48 | B | C |
| ATOM | 8709 | O   | THR | 365 | 128.662 | 58.260 | 30.015 | 1.00 | 20.68 | B | O |
| ATOM | 8710 | N   | LEU | 366 | 130.329 | 58.163 | 31.515 | 1.00 | 22.60 | B | N |
| ATOM | 8711 | CA  | LEU | 366 | 130.740 | 59.544 | 31.304 | 1.00 | 25.75 | B | C |
| ATOM | 8712 | CB  | LEU | 366 | 132.053 | 59.831 | 32.039 | 1.00 | 29.32 | B | C |
| ATOM | 8713 | CG  | LEU | 366 | 132.172 | 59.429 | 33.516 | 1.00 | 34.01 | B | C |
| ATOM | 8714 | CD1 | LEU | 366 | 132.442 | 57.920 | 33.631 | 1.00 | 33.57 | B | C |
| ATOM | 8715 | CD2 | LEU | 366 | 133.316 | 60.210 | 34.162 | 1.00 | 34.78 | B | C |
| ATOM | 8716 | C   | LEU | 366 | 130.909 | 59.900 | 29.824 | 1.00 | 26.20 | B | C |
| ATOM | 8717 | O   | LEU | 366 | 130.317 | 60.871 | 29.349 | 1.00 | 26.53 | B | O |
| ATOM | 8718 | N   | ASP | 367 | 131.709 | 59.115 | 29.102 | 1.00 | 24.26 | B | N |
| ATOM | 8719 | CA  | ASP | 367 | 131.964 | 59.369 | 27.682 | 1.00 | 23.63 | B | C |
| ATOM | 8720 | CB  | ASP | 367 | 133.232 | 58.636 | 27.214 | 1.00 | 23.47 | B | C |
| ATOM | 8721 | CG  | ASP | 367 | 133.230 | 57.158 | 27.582 | 1.00 | 25.27 | B | C |

FIG. 4-179 (Continued)

| | | | | | | | | | | | |
|---|---|---|---|---|---|---|---|---|---|---|---|
| ATOM | 8722 | OD1 | ASP | 367 | 132.158 | 56.515 | 27.507 | 1.00 | 24.35 | B | O |
| ATOM | 8723 | OD2 | ASP | 367 | 134.311 | 56.634 | 27.935 | 1.00 | 25.99 | B | O |
| ATOM | 8724 | C | ASP | 367 | 130.810 | 58.990 | 26.767 | 1.00 | 22.76 | B | C |
| ATOM | 8725 | O | ASP | 367 | 130.848 | 59.261 | 25.568 | 1.00 | 24.31 | B | O |
| ATOM | 8726 | N | GLY | 368 | 129.795 | 58.348 | 27.330 | 1.00 | 20.91 | B | N |
| ATOM | 8727 | CA | GLY | 368 | 128.646 | 57.950 | 26.547 | 1.00 | 18.80 | B | C |
| ATOM | 8728 | C | GLY | 368 | 128.912 | 56.843 | 25.550 | 1.00 | 19.81 | B | C |
| ATOM | 8729 | O | GLY | 368 | 128.059 | 56.563 | 24.700 | 1.00 | 19.55 | B | O |
| ATOM | 8730 | N | ASN | 369 | 130.073 | 56.198 | 25.643 | 1.00 | 19.20 | B | N |
| ATOM | 8731 | CA | ASN | 369 | 130.398 | 55.117 | 24.706 | 1.00 | 19.60 | B | C |
| ATOM | 8732 | CB | ASN | 369 | 131.907 | 54.986 | 24.526 | 1.00 | 19.65 | B | C |
| ATOM | 8733 | CG | ASN | 369 | 132.519 | 56.217 | 23.921 | 1.00 | 21.94 | B | C |
| ATOM | 8734 | OD1 | ASN | 369 | 132.005 | 56.757 | 22.945 | 1.00 | 25.32 | B | O |
| ATOM | 8735 | ND2 | ASN | 369 | 133.628 | 56.671 | 24.489 | 1.00 | 23.16 | B | N |
| ATOM | 8736 | C | ASN | 369 | 129.828 | 53.760 | 25.090 | 1.00 | 18.53 | B | C |
| ATOM | 8737 | O | ASN | 369 | 129.770 | 52.861 | 24.258 | 1.00 | 18.17 | B | O |
| ATOM | 8738 | N | SER | 370 | 129.420 | 53.608 | 26.346 | 1.00 | 18.61 | B | N |
| ATOM | 8739 | CA | SER | 370 | 128.847 | 52.347 | 26.812 | 1.00 | 19.50 | B | C |
| ATOM | 8740 | CB | SER | 370 | 129.934 | 51.447 | 27.430 | 1.00 | 20.45 | B | C |
| ATOM | 8741 | OG | SER | 370 | 130.577 | 52.057 | 28.538 | 1.00 | 22.81 | B | O |
| ATOM | 8742 | C | SER | 370 | 127.746 | 52.621 | 27.829 | 1.00 | 18.95 | B | C |
| ATOM | 8743 | O | SER | 370 | 127.562 | 53.759 | 28.261 | 1.00 | 19.22 | B | O |
| ATOM | 8744 | N | PHE | 371 | 127.009 | 51.583 | 28.209 | 1.00 | 18.63 | B | N |
| ATOM | 8745 | CA | PHE | 371 | 125.931 | 51.763 | 29.168 | 1.00 | 18.66 | B | C |
| ATOM | 8746 | CB | PHE | 371 | 124.762 | 52.516 | 28.512 | 1.00 | 19.79 | B | C |
| ATOM | 8747 | CG | PHE | 371 | 124.088 | 51.756 | 27.398 | 1.00 | 16.47 | B | C |
| ATOM | 8748 | CD1 | PHE | 371 | 124.532 | 51.874 | 26.093 | 1.00 | 15.63 | B | C |
| ATOM | 8749 | CD2 | PHE | 371 | 122.991 | 50.940 | 27.660 | 1.00 | 17.78 | B | C |
| ATOM | 8750 | CE1 | PHE | 371 | 123.893 | 51.198 | 25.059 | 1.00 | 18.99 | B | C |
| ATOM | 8751 | CE2 | PHE | 371 | 122.340 | 50.255 | 26.631 | 1.00 | 18.61 | B | C |
| ATOM | 8752 | CZ | PHE | 371 | 122.792 | 50.386 | 25.327 | 1.00 | 18.10 | B | C |
| ATOM | 8753 | C | PHE | 371 | 125.402 | 50.473 | 29.784 | 1.00 | 18.78 | B | C |
| ATOM | 8754 | O | PHE | 371 | 125.506 | 49.392 | 29.197 | 1.00 | 17.45 | B | O |
| ATOM | 8755 | N | TYR | 372 | 124.814 | 50.614 | 30.970 | 1.00 | 19.00 | B | N |
| ATOM | 8756 | CA | TYR | 372 | 124.240 | 49.491 | 31.703 | 1.00 | 18.59 | B | C |
| ATOM | 8757 | CB | TYR | 372 | 124.697 | 49.527 | 33.159 | 1.00 | 17.86 | B | C |
| ATOM | 8758 | CG | TYR | 372 | 126.199 | 49.500 | 33.290 | 1.00 | 17.83 | B | C |
| ATOM | 8759 | CD1 | TYR | 372 | 126.951 | 50.676 | 33.201 | 1.00 | 19.52 | B | C |
| ATOM | 8760 | CE1 | TYR | 372 | 128.339 | 50.651 | 33.257 | 1.00 | 18.29 | B | C |
| ATOM | 8761 | CD2 | TYR | 372 | 126.878 | 48.296 | 33.441 | 1.00 | 17.45 | B | C |
| ATOM | 8762 | CE2 | TYR | 372 | 128.266 | 48.257 | 33.498 | 1.00 | 18.99 | B | C |
| ATOM | 8763 | CZ | TYR | 372 | 128.991 | 49.434 | 33.405 | 1.00 | 18.83 | B | C |
| ATOM | 8764 | OH | TYR | 372 | 130.364 | 49.387 | 33.454 | 1.00 | 19.89 | B | O |
| ATOM | 8765 | C | TYR | 372 | 122.727 | 49.558 | 31.620 | 1.00 | 18.38 | B | C |
| ATOM | 8766 | O | TYR | 372 | 122.143 | 50.632 | 31.717 | 1.00 | 20.19 | B | O |
| ATOM | 8767 | N | LYS | 373 | 122.096 | 48.406 | 31.436 | 1.00 | 19.10 | B | N |
| ATOM | 8768 | CA | LYS | 373 | 120.647 | 48.340 | 31.299 | 1.00 | 18.51 | B | C |
| ATOM | 8769 | CB | LYS | 373 | 120.285 | 48.376 | 29.809 | 1.00 | 17.90 | B | C |
| ATOM | 8770 | CG | LYS | 373 | 118.809 | 48.581 | 29.485 | 1.00 | 21.01 | B | C |

FIG. 4-180 (Continued)

| | | | | | | | | | | |
|---|---|---|---|---|---|---|---|---|---|---|
| ATOM | 8771 | CD | LYS | 373 | 118.593 | 48.627 | 27.969 | 1.00 | 21.40 | B C |
| ATOM | 8772 | CE | LYS | 373 | 117.248 | 49.238 | 27.563 | 1.00 | 21.67 | B C |
| ATOM | 8773 | NZ | LYS | 373 | 116.053 | 48.389 | 27.855 | 1.00 | 21.98 | B N |
| ATOM | 8774 | C | LYS | 373 | 120.128 | 47.049 | 31.928 | 1.00 | 18.77 | B C |
| ATOM | 8775 | O | LYS | 373 | 120.695 | 45.980 | 31.712 | 1.00 | 18.48 | B O |
| ATOM | 8776 | N | ILE | 374 | 119.056 | 47.150 | 32.709 | 1.00 | 17.06 | B N |
| ATOM | 8777 | CA | ILE | 374 | 118.474 | 45.972 | 33.332 | 1.00 | 15.88 | B C |
| ATOM | 8778 | CB | ILE | 374 | 117.557 | 46.339 | 34.526 | 1.00 | 14.58 | B C |
| ATOM | 8779 | CG2 | ILE | 374 | 116.955 | 45.076 | 35.130 | 1.00 | 12.18 | B C |
| ATOM | 8780 | CG1 | ILE | 374 | 118.348 | 47.101 | 35.591 | 1.00 | 15.07 | B C |
| ATOM | 8781 | CD1 | ILE | 374 | 117.517 | 47.505 | 36.809 | 1.00 | 13.03 | B C |
| ATOM | 8782 | C | ILE | 374 | 117.618 | 45.244 | 32.303 | 1.00 | 16.94 | B C |
| ATOM | 8783 | O | ILE | 374 | 116.649 | 45.803 | 31.795 | 1.00 | 17.41 | B O |
| ATOM | 8784 | N | ILE | 375 | 117.977 | 44.008 | 31.978 | 1.00 | 18.50 | B N |
| ATOM | 8785 | CA | ILE | 375 | 117.178 | 43.226 | 31.033 | 1.00 | 19.71 | B C |
| ATOM | 8786 | CB | ILE | 375 | 117.842 | 43.117 | 29.625 | 1.00 | 19.62 | B C |
| ATOM | 8787 | CG2 | ILE | 375 | 118.128 | 44.496 | 29.070 | 1.00 | 19.13 | B C |
| ATOM | 8788 | CG1 | ILE | 375 | 119.128 | 42.298 | 29.706 | 1.00 | 21.23 | B C |
| ATOM | 8789 | CD1 | ILE | 375 | 119.824 | 42.129 | 28.373 | 1.00 | 23.06 | B C |
| ATOM | 8790 | C | ILE | 375 | 116.984 | 41.815 | 31.579 | 1.00 | 20.44 | B C |
| ATOM | 8791 | O | ILE | 375 | 117.735 | 41.356 | 32.443 | 1.00 | 20.03 | B O |
| ATOM | 8792 | N | SER | 376 | 115.968 | 41.128 | 31.078 | 1.00 | 21.14 | B N |
| ATOM | 8793 | CA | SER | 376 | 115.705 | 39.771 | 31.516 | 1.00 | 21.95 | B C |
| ATOM | 8794 | CB | SER | 376 | 114.347 | 39.318 | 31.003 | 1.00 | 21.55 | B C |
| ATOM | 8795 | OG | SER | 376 | 114.026 | 38.054 | 31.539 | 1.00 | 25.40 | B O |
| ATOM | 8796 | C | SER | 376 | 116.808 | 38.899 | 30.936 | 1.00 | 23.06 | B C |
| ATOM | 8797 | O | SER | 376 | 117.236 | 39.127 | 29.807 | 1.00 | 24.16 | B O |
| ATOM | 8798 | N | ASN | 377 | 117.281 | 37.914 | 31.698 | 1.00 | 24.67 | B N |
| ATOM | 8799 | CA | ASN | 377 | 118.358 | 37.053 | 31.218 | 1.00 | 25.07 | B C |
| ATOM | 8800 | CB | ASN | 377 | 119.438 | 36.891 | 32.302 | 1.00 | 23.49 | B C |
| ATOM | 8801 | CG | ASN | 377 | 119.010 | 35.971 | 33.444 | 1.00 | 23.86 | B C |
| ATOM | 8802 | OD1 | ASN | 377 | 117.951 | 35.340 | 33.397 | 1.00 | 23.70 | B O |
| ATOM | 8803 | ND2 | ASN | 377 | 119.848 | 35.884 | 34.474 | 1.00 | 20.11 | B N |
| ATOM | 8804 | C | ASN | 377 | 117.897 | 35.681 | 30.736 | 1.00 | 26.79 | B C |
| ATOM | 8805 | O | ASN | 377 | 116.706 | 35.382 | 30.699 | 1.00 | 28.58 | B O |
| ATOM | 8806 | N | GLU | 378 | 118.861 | 34.856 | 30.353 | 1.00 | 29.97 | B N |
| ATOM | 8807 | CA | GLU | 378 | 118.608 | 33.504 | 29.871 | 1.00 | 33.15 | B C |
| ATOM | 8808 | CB | GLU | 378 | 119.914 | 32.716 | 29.870 | 1.00 | 37.08 | B C |
| ATOM | 8809 | CG | GLU | 378 | 120.695 | 32.870 | 31.181 | 1.00 | 43.78 | B C |
| ATOM | 8810 | CD | GLU | 378 | 121.681 | 31.740 | 31.427 | 1.00 | 46.56 | B C |
| ATOM | 8811 | OE1 | GLU | 378 | 121.225 | 30.613 | 31.725 | 1.00 | 47.52 | B O |
| ATOM | 8812 | OE2 | GLU | 378 | 122.906 | 31.981 | 31.321 | 1.00 | 47.91 | B O |
| ATOM | 8813 | C | GLU | 378 | 117.588 | 32.760 | 30.722 | 1.00 | 33.63 | B C |
| ATOM | 8814 | O | GLU | 378 | 116.685 | 32.113 | 30.192 | 1.00 | 35.16 | B O |
| ATOM | 8815 | N | GLU | 379 | 117.740 | 32.842 | 32.041 | 1.00 | 32.70 | B N |
| ATOM | 8816 | CA | GLU | 379 | 116.831 | 32.160 | 32.953 | 1.00 | 30.44 | B C |
| ATOM | 8817 | CB | GLU | 379 | 117.549 | 31.806 | 34.256 | 1.00 | 34.46 | B C |
| ATOM | 8818 | CG | GLU | 379 | 117.845 | 30.323 | 34.412 | 1.00 | 39.45 | B C |
| ATOM | 8819 | CD | GLU | 379 | 116.577 | 29.475 | 34.492 | 1.00 | 43.32 | B C |

FIG. 4-181 (Continued)

| | | | | | | | | | | |
|---|---|---|---|---|---|---|---|---|---|---|
| ATOM | 8820 | OE1 | GLU | 379 | 115.800 | 29.642 | 35.463 | 1.00 42.91 | B | O |
| ATOM | 8821 | OE2 | GLU | 379 | 116.357 | 28.643 | 33.580 | 1.00 45.81 | B | O |
| ATOM | 8822 | C | GLU | 379 | 115.588 | 32.972 | 33.265 | 1.00 28.15 | B | C |
| ATOM | 8823 | O | GLU | 379 | 114.743 | 32.539 | 34.049 | 1.00 28.12 | B | O |
| ATOM | 8824 | N | GLY | 380 | 115.473 | 34.148 | 32.658 | 1.00 24.72 | B | N |
| ATOM | 8825 | CA | GLY | 380 | 114.304 | 34.980 | 32.886 | 1.00 22.38 | B | C |
| ATOM | 8826 | C | GLY | 380 | 114.335 | 35.891 | 34.101 | 1.00 21.23 | B | C |
| ATOM | 8827 | O | GLY | 380 | 113.302 | 36.404 | 34.514 | 1.00 21.76 | B | O |
| ATOM | 8828 | N | TYR | 381 | 115.507 | 36.084 | 34.689 | 1.00 20.24 | B | N |
| ATOM | 8829 | CA | TYR | 381 | 115.642 | 36.963 | 35.842 | 1.00 19.52 | B | C |
| ATOM | 8830 | CB | TYR | 381 | 116.539 | 36.307 | 36.884 | 1.00 20.98 | B | C |
| ATOM | 8831 | CG | TYR | 381 | 115.846 | 35.194 | 37.630 | 1.00 23.80 | B | C |
| ATOM | 8832 | CD1 | TYR | 381 | 115.104 | 35.465 | 38.781 | 1.00 23.87 | B | C |
| ATOM | 8833 | CE1 | TYR | 381 | 114.435 | 34.458 | 39.455 | 1.00 22.94 | B | C |
| ATOM | 8834 | CD2 | TYR | 381 | 115.900 | 33.876 | 37.171 | 1.00 22.81 | B | C |
| ATOM | 8835 | CE2 | TYR | 381 | 115.232 | 32.859 | 37.843 | 1.00 22.55 | B | C |
| ATOM | 8836 | CZ | TYR | 381 | 114.501 | 33.161 | 38.986 | 1.00 24.14 | B | C |
| ATOM | 8837 | OH | TYR | 381 | 113.830 | 32.170 | 39.667 | 1.00 25.04 | B | O |
| ATOM | 8838 | C | TYR | 381 | 116.237 | 38.292 | 35.374 | 1.00 19.14 | B | C |
| ATOM | 8839 | O | TYR | 381 | 117.178 | 38.312 | 34.568 | 1.00 18.95 | B | O |
| ATOM | 8840 | N | ARG | 382 | 115.689 | 39.399 | 35.871 | 1.00 15.40 | B | N |
| ATOM | 8841 | CA | ARG | 382 | 116.160 | 40.715 | 35.458 | 1.00 14.04 | B | C |
| ATOM | 8842 | CB | ARG | 382 | 115.035 | 41.738 | 35.622 | 1.00 13.48 | B | C |
| ATOM | 8843 | CG | ARG | 382 | 113.948 | 41.478 | 34.606 | 1.00 15.55 | B | C |
| ATOM | 8844 | CD | ARG | 382 | 112.581 | 42.001 | 34.993 | 1.00 17.88 | B | C |
| ATOM | 8845 | NE | ARG | 382 | 111.576 | 41.337 | 34.170 | 1.00 19.19 | B | N |
| ATOM | 8846 | CZ | ARG | 382 | 111.438 | 41.515 | 32.859 | 1.00 21.25 | B | C |
| ATOM | 8847 | NH1 | ARG | 382 | 112.230 | 42.357 | 32.203 | 1.00 18.86 | B | N |
| ATOM | 8848 | NH2 | ARG | 382 | 110.534 | 40.810 | 32.190 | 1.00 23.20 | B | N |
| ATOM | 8849 | C | ARG | 382 | 117.438 | 41.172 | 36.140 | 1.00 12.33 | B | C |
| ATOM | 8850 | O | ARG | 382 | 117.497 | 41.376 | 37.349 | 1.00 9.83 | B | O |
| ATOM | 8851 | N | HIS | 383 | 118.474 | 41.303 | 35.323 | 1.00 11.97 | B | N |
| ATOM | 8852 | CA | HIS | 383 | 119.778 | 41.711 | 35.789 | 1.00 12.81 | B | C |
| ATOM | 8853 | CB | HIS | 383 | 120.714 | 40.516 | 35.777 | 1.00 12.29 | B | C |
| ATOM | 8854 | CG | HIS | 383 | 120.377 | 39.496 | 36.813 | 1.00 13.83 | B | C |
| ATOM | 8855 | CD2 | HIS | 383 | 119.726 | 38.313 | 36.721 | 1.00 12.69 | B | C |
| ATOM | 8856 | ND1 | HIS | 383 | 120.670 | 39.675 | 38.148 | 1.00 13.84 | B | N |
| ATOM | 8857 | CE1 | HIS | 383 | 120.212 | 38.643 | 38.834 | 1.00 16.23 | B | C |
| ATOM | 8858 | NE2 | HIS | 383 | 119.635 | 37.803 | 37.993 | 1.00 14.04 | B | N |
| ATOM | 8859 | C | HIS | 383 | 120.351 | 42.830 | 34.949 | 1.00 14.10 | B | C |
| ATOM | 8860 | O | HIS | 383 | 119.788 | 43.207 | 33.913 | 1.00 15.53 | B | O |
| ATOM | 8861 | N | ILE | 384 | 121.476 | 43.354 | 35.412 | 1.00 13.75 | B | N |
| ATOM | 8862 | CA | ILE | 384 | 122.166 | 44.444 | 34.749 | 1.00 15.78 | B | C |
| ATOM | 8863 | CB | ILE | 384 | 122.996 | 45.223 | 35.782 | 1.00 14.50 | B | C |
| ATOM | 8864 | CG2 | ILE | 384 | 123.765 | 46.338 | 35.103 | 1.00 14.15 | B | C |
| ATOM | 8865 | CG1 | ILE | 384 | 122.071 | 45.767 | 36.871 | 1.00 12.97 | B | C |
| ATOM | 8866 | CD1 | ILE | 384 | 122.791 | 46.194 | 38.129 | 1.00 14.46 | B | C |
| ATOM | 8867 | C | ILE | 384 | 123.082 | 43.925 | 33.645 | 1.00 18.38 | B | C |
| ATOM | 8868 | O | ILE | 384 | 123.884 | 43.014 | 33.874 | 1.00 20.02 | B | O |

FIG. 4-182

| ATOM | 8869 | N   | CYS | 385 | 122.956 | 44.485 | 32.446 | 1.00 | 19.06 | B | N |
| ---- | ---- | --- | --- | --- | ------- | ------ | ------ | ---- | ----- | - | - |
| ATOM | 8870 | CA  | CYS | 385 | 123.812 | 44.063 | 31.340 | 1.00 | 20.78 | B | C |
| ATOM | 8871 | C   | CYS | 385 | 124.628 | 45.266 | 30.868 | 1.00 | 19.29 | B | C |
| ATOM | 8872 | O   | CYS | 385 | 124.115 | 46.376 | 30.775 | 1.00 | 19.30 | B | O |
| ATOM | 8873 | CB  | CYS | 385 | 122.980 | 43.476 | 30.178 | 1.00 | 22.83 | B | C |
| ATOM | 8874 | SG  | CYS | 385 | 123.868 | 42.151 | 29.269 | 1.00 | 35.68 | B | S |
| ATOM | 8875 | N   | TYR | 386 | 125.908 | 45.046 | 30.595 | 1.00 | 18.55 | B | N |
| ATOM | 8876 | CA  | TYR | 386 | 126.795 | 46.111 | 30.138 | 1.00 | 17.80 | B | C |
| ATOM | 8877 | CB  | TYR | 386 | 128.222 | 45.849 | 30.615 | 1.00 | 17.85 | B | C |
| ATOM | 8878 | CG  | TYR | 386 | 129.224 | 46.938 | 30.295 | 1.00 | 17.08 | B | C |
| ATOM | 8879 | CD1 | TYR | 386 | 130.557 | 46.620 | 30.049 | 1.00 | 18.50 | B | C |
| ATOM | 8880 | CE1 | TYR | 386 | 131.504 | 47.602 | 29.797 | 1.00 | 20.09 | B | C |
| ATOM | 8881 | CD2 | TYR | 386 | 128.857 | 48.276 | 30.279 | 1.00 | 17.91 | B | C |
| ATOM | 8882 | CE2 | TYR | 386 | 129.798 | 49.274 | 30.032 | 1.00 | 21.21 | B | C |
| ATOM | 8883 | CZ  | TYR | 386 | 131.127 | 48.925 | 29.791 | 1.00 | 21.94 | B | C |
| ATOM | 8884 | OH  | TYR | 386 | 132.082 | 49.894 | 29.561 | 1.00 | 21.36 | B | O |
| ATOM | 8885 | C   | TYR | 386 | 126.765 | 46.116 | 28.625 | 1.00 | 17.85 | B | C |
| ATOM | 8886 | O   | TYR | 386 | 126.911 | 45.069 | 28.004 | 1.00 | 18.61 | B | O |
| ATOM | 8887 | N   | PHE | 387 | 126.573 | 47.291 | 28.035 | 1.00 | 18.83 | B | N |
| ATOM | 8888 | CA  | PHE | 387 | 126.520 | 47.418 | 26.587 | 1.00 | 18.83 | B | C |
| ATOM | 8889 | CB  | PHE | 387 | 125.161 | 47.939 | 26.133 | 1.00 | 17.08 | B | C |
| ATOM | 8890 | CG  | PHE | 387 | 124.014 | 47.000 | 26.347 | 1.00 | 14.86 | B | C |
| ATOM | 8891 | CD1 | PHE | 387 | 123.409 | 46.373 | 25.258 | 1.00 | 14.70 | B | C |
| ATOM | 8892 | CD2 | PHE | 387 | 123.444 | 46.848 | 27.605 | 1.00 | 12.48 | B | C |
| ATOM | 8893 | CE1 | PHE | 387 | 122.246 | 45.624 | 25.419 | 1.00 | 13.25 | B | C |
| ATOM | 8894 | CE2 | PHE | 387 | 122.283 | 46.100 | 27.777 | 1.00 | 11.47 | B | C |
| ATOM | 8895 | CZ  | PHE | 387 | 121.680 | 45.491 | 26.684 | 1.00 | 12.33 | B | C |
| ATOM | 8896 | C   | PHE | 387 | 127.552 | 48.408 | 26.057 | 1.00 | 21.93 | B | C |
| ATOM | 8897 | O   | PHE | 387 | 127.859 | 49.413 | 26.706 | 1.00 | 20.79 | B | O |
| ATOM | 8898 | N   | GLN | 388 | 128.057 | 48.113 | 24.859 | 1.00 | 24.26 | B | N |
| ATOM | 8899 | CA  | GLN | 388 | 128.994 | 48.970 | 24.137 | 1.00 | 26.10 | B | C |
| ATOM | 8900 | CB  | GLN | 388 | 130.122 | 48.140 | 23.534 | 1.00 | 26.78 | B | C |
| ATOM | 8901 | CG  | GLN | 388 | 130.905 | 47.326 | 24.542 | 1.00 | 28.07 | B | C |
| ATOM | 8902 | CD  | GLN | 388 | 131.787 | 48.185 | 25.401 | 1.00 | 27.71 | B | C |
| ATOM | 8903 | OE1 | GLN | 388 | 132.672 | 48.871 | 24.898 | 1.00 | 30.29 | B | O |
| ATOM | 8904 | NE2 | GLN | 388 | 131.553 | 48.160 | 26.705 | 1.00 | 30.63 | B | N |
| ATOM | 8905 | C   | GLN | 388 | 128.074 | 49.474 | 23.024 | 1.00 | 28.20 | B | C |
| ATOM | 8906 | O   | GLN | 388 | 127.300 | 48.690 | 22.478 | 1.00 | 28.61 | B | O |
| ATOM | 8907 | N   | ILE | 389 | 128.130 | 50.755 | 22.681 | 1.00 | 30.33 | B | N |
| ATOM | 8908 | CA  | ILE | 389 | 127.224 | 51.256 | 21.650 | 1.00 | 32.95 | B | C |
| ATOM | 8909 | CB  | ILE | 389 | 127.233 | 52.796 | 21.576 | 1.00 | 29.60 | B | C |
| ATOM | 8910 | CG2 | ILE | 389 | 126.839 | 53.374 | 22.933 | 1.00 | 27.56 | B | C |
| ATOM | 8911 | CG1 | ILE | 389 | 128.606 | 53.296 | 21.129 | 1.00 | 27.72 | B | C |
| ATOM | 8912 | CD1 | ILE | 389 | 128.699 | 54.810 | 21.005 | 1.00 | 26.00 | B | C |
| ATOM | 8913 | C   | ILE | 389 | 127.489 | 50.692 | 20.261 | 1.00 | 37.72 | B | C |
| ATOM | 8914 | O   | ILE | 389 | 126.605 | 50.705 | 19.404 | 1.00 | 40.02 | B | O |
| ATOM | 8915 | N   | ASP | 390 | 128.696 | 50.184 | 20.039 | 1.00 | 41.52 | B | N |
| ATOM | 8916 | CA  | ASP | 390 | 129.044 | 49.621 | 18.741 | 1.00 | 43.97 | B | C |
| ATOM | 8917 | CB  | ASP | 390 | 130.478 | 50.005 | 18.365 | 1.00 | 45.79 | B | C |

| | | | | | | | | | | |
|---|---|---|---|---|---|---|---|---|---|---|
| ATOM | 8918 | CG | ASP | 390 | 130.576 | 51.416 | 17.816 | 1.00 | 49.16 | B | C |
| ATOM | 8919 | OD1 | ASP | 390 | 129.879 | 51.713 | 16.819 | 1.00 | 50.13 | B | O |
| ATOM | 8920 | OD2 | ASP | 390 | 131.349 | 52.227 | 18.372 | 1.00 | 50.30 | B | O |
| ATOM | 8921 | C | ASP | 390 | 128.887 | 48.106 | 18.675 | 1.00 | 44.93 | B | C |
| ATOM | 8922 | O | ASP | 390 | 128.589 | 47.557 | 17.619 | 1.00 | 47.19 | B | O |
| ATOM | 8923 | N | LYS | 391 | 129.081 | 47.427 | 19.798 | 1.00 | 45.32 | B | N |
| ATOM | 8924 | CA | LYS | 391 | 128.967 | 45.977 | 19.826 | 1.00 | 45.91 | B | C |
| ATOM | 8925 | CB | LYS | 391 | 129.981 | 45.409 | 20.818 | 1.00 | 47.86 | B | C |
| ATOM | 8926 | CG | LYS | 391 | 131.416 | 45.724 | 20.407 | 1.00 | 51.34 | B | C |
| ATOM | 8927 | CD | LYS | 391 | 132.428 | 45.397 | 21.494 | 1.00 | 55.03 | B | C |
| ATOM | 8928 | CE | LYS | 391 | 133.816 | 45.911 | 21.112 | 1.00 | 55.62 | B | C |
| ATOM | 8929 | NZ | LYS | 391 | 134.822 | 45.719 | 22.192 | 1.00 | 56.68 | B | N |
| ATOM | 8930 | C | LYS | 391 | 127.550 | 45.535 | 20.163 | 1.00 | 45.76 | B | C |
| ATOM | 8931 | O | LYS | 391 | 126.857 | 46.191 | 20.942 | 1.00 | 46.28 | B | O |
| ATOM | 8932 | N | LYS | 392 | 127.125 | 44.419 | 19.576 | 1.00 | 44.97 | B | N |
| ATOM | 8933 | CA | LYS | 392 | 125.772 | 43.916 | 19.782 | 1.00 | 45.02 | B | C |
| ATOM | 8934 | CB | LYS | 392 | 125.218 | 43.382 | 18.458 | 1.00 | 46.84 | B | C |
| ATOM | 8935 | CG | LYS | 392 | 124.750 | 44.494 | 17.529 | 1.00 | 49.00 | B | C |
| ATOM | 8936 | CD | LYS | 392 | 124.282 | 43.970 | 16.186 | 1.00 | 50.10 | B | C |
| ATOM | 8937 | CE | LYS | 392 | 123.533 | 45.057 | 15.436 | 1.00 | 51.49 | B | C |
| ATOM | 8938 | NZ | LYS | 392 | 124.298 | 46.338 | 15.419 | 1.00 | 52.49 | B | N |
| ATOM | 8939 | C | LYS | 392 | 125.529 | 42.895 | 20.886 | 1.00 | 43.84 | B | C |
| ATOM | 8940 | O | LYS | 392 | 124.386 | 42.512 | 21.134 | 1.00 | 44.15 | B | O |
| ATOM | 8941 | N | ASP | 393 | 126.579 | 42.446 | 21.555 | 1.00 | 41.92 | B | N |
| ATOM | 8942 | CA | ASP | 393 | 126.381 | 41.489 | 22.632 | 1.00 | 40.21 | B | C |
| ATOM | 8943 | CB | ASP | 393 | 127.289 | 40.268 | 22.470 | 1.00 | 41.22 | B | C |
| ATOM | 8944 | CG | ASP | 393 | 127.022 | 39.509 | 21.194 | 1.00 | 41.43 | B | C |
| ATOM | 8945 | OD1 | ASP | 393 | 125.838 | 39.350 | 20.824 | 1.00 | 40.27 | B | O |
| ATOM | 8946 | OD2 | ASP | 393 | 128.005 | 39.062 | 20.569 | 1.00 | 43.49 | B | O |
| ATOM | 8947 | C | ASP | 393 | 126.685 | 42.158 | 23.953 | 1.00 | 38.67 | B | C |
| ATOM | 8948 | O | ASP | 393 | 127.818 | 42.588 | 24.188 | 1.00 | 39.07 | B | O |
| ATOM | 8949 | N | CYS | 394 | 125.678 | 42.252 | 24.816 | 1.00 | 35.47 | B | N |
| ATOM | 8950 | CA | CYS | 394 | 125.882 | 42.870 | 26.117 | 1.00 | 32.02 | B | C |
| ATOM | 8951 | C | CYS | 394 | 126.374 | 41.796 | 27.069 | 1.00 | 29.62 | B | C |
| ATOM | 8952 | O | CYS | 394 | 126.248 | 40.608 | 26.787 | 1.00 | 29.41 | B | O |
| ATOM | 8953 | CB | CYS | 394 | 124.586 | 43.491 | 26.639 | 1.00 | 31.92 | B | C |
| ATOM | 8954 | SG | CYS | 394 | 123.354 | 42.328 | 27.301 | 1.00 | 33.67 | B | S |
| ATOM | 8955 | N | THR | 395 | 126.938 | 42.215 | 28.193 | 1.00 | 26.53 | B | N |
| ATOM | 8956 | CA | THR | 395 | 127.462 | 41.279 | 29.171 | 1.00 | 23.76 | B | C |
| ATOM | 8957 | CB | THR | 395 | 128.964 | 41.493 | 29.358 | 1.00 | 23.30 | B | C |
| ATOM | 8958 | OG1 | THR | 395 | 129.627 | 41.265 | 28.115 | 1.00 | 25.56 | B | O |
| ATOM | 8959 | CG2 | THR | 395 | 129.518 | 40.542 | 30.397 | 1.00 | 22.48 | B | C |
| ATOM | 8960 | C | THR | 395 | 126.784 | 41.448 | 30.519 | 1.00 | 22.20 | B | C |
| ATOM | 8961 | O | THR | 395 | 126.707 | 42.556 | 31.035 | 1.00 | 23.25 | B | O |
| ATOM | 8962 | N | PHE | 396 | 126.300 | 40.354 | 31.095 | 1.00 | 19.02 | B | N |
| ATOM | 8963 | CA | PHE | 396 | 125.658 | 40.444 | 32.396 | 1.00 | 18.94 | B | C |
| ATOM | 8964 | CB | PHE | 396 | 124.794 | 39.206 | 32.652 | 1.00 | 17.62 | B | C |
| ATOM | 8965 | CG | PHE | 396 | 123.486 | 39.225 | 31.918 | 1.00 | 19.32 | B | C |
| ATOM | 8966 | CD1 | PHE | 396 | 122.477 | 40.112 | 32.290 | 1.00 | 20.73 | B | C |

FIG. 4-184

| ATOM | 8967 | CD2 | PHE | 396 | 123.265 | 38.378 | 30.837 | 1.00 | 19.67 | B | C |
| ATOM | 8968 | CE1 | PHE | 396 | 121.267 | 40.157 | 31.593 | 1.00 | 21.82 | B | C |
| ATOM | 8969 | CE2 | PHE | 396 | 122.062 | 38.411 | 30.130 | 1.00 | 20.02 | B | C |
| ATOM | 8970 | CZ | PHE | 396 | 121.057 | 39.303 | 30.507 | 1.00 | 22.36 | B | C |
| ATOM | 8971 | C | PHE | 396 | 126.712 | 40.596 | 33.488 | 1.00 | 19.09 | B | C |
| ATOM | 8972 | O | PHE | 396 | 127.703 | 39.866 | 33.516 | 1.00 | 21.70 | B | O |
| ATOM | 8973 | N | ILE | 397 | 126.511 | 41.559 | 34.380 | 1.00 | 17.18 | B | N |
| ATOM | 8974 | CA | ILE | 397 | 127.454 | 41.774 | 35.460 | 1.00 | 14.91 | B | C |
| ATOM | 8975 | CB | ILE | 397 | 127.819 | 43.240 | 35.566 | 1.00 | 14.47 | B | C |
| ATOM | 8976 | CG2 | ILE | 397 | 128.181 | 43.762 | 34.192 | 1.00 | 14.09 | B | C |
| ATOM | 8977 | CG1 | ILE | 397 | 126.644 | 44.036 | 36.135 | 1.00 | 13.14 | B | C |
| ATOM | 8978 | CD1 | ILE | 397 | 126.993 | 45.472 | 36.449 | 1.00 | 11.32 | B | C |
| ATOM | 8979 | C | ILE | 397 | 126.885 | 41.287 | 36.791 | 1.00 | 16.82 | B | C |
| ATOM | 8980 | O | ILE | 397 | 127.543 | 41.376 | 37.833 | 1.00 | 18.48 | B | O |
| ATOM | 8981 | N | THR | 398 | 125.651 | 40.790 | 36.753 | 1.00 | 15.47 | B | N |
| ATOM | 8982 | CA | THR | 398 | 125.000 | 40.241 | 37.937 | 1.00 | 14.86 | B | C |
| ATOM | 8983 | CB | THR | 398 | 124.049 | 41.255 | 38.652 | 1.00 | 14.72 | B | C |
| ATOM | 8984 | OG1 | THR | 398 | 122.968 | 41.627 | 37.784 | 1.00 | 13.55 | B | O |
| ATOM | 8985 | CG2 | THR | 398 | 124.812 | 42.476 | 39.083 | 1.00 | 13.88 | B | C |
| ATOM | 8986 | C | THR | 398 | 124.185 | 39.040 | 37.490 | 1.00 | 15.72 | B | C |
| ATOM | 8987 | O | THR | 398 | 123.805 | 38.942 | 36.323 | 1.00 | 15.48 | B | O |
| ATOM | 8988 | N | LYS | 399 | 123.915 | 38.127 | 38.416 | 1.00 | 17.12 | B | N |
| ATOM | 8989 | CA | LYS | 399 | 123.147 | 36.935 | 38.094 | 1.00 | 18.19 | B | C |
| ATOM | 8990 | CB | LYS | 399 | 124.026 | 35.960 | 37.314 | 1.00 | 20.96 | B | C |
| ATOM | 8991 | CG | LYS | 399 | 125.322 | 35.630 | 38.023 | 1.00 | 24.93 | B | C |
| ATOM | 8992 | CD | LYS | 399 | 125.970 | 34.380 | 37.458 | 1.00 | 29.93 | B | C |
| ATOM | 8993 | CE | LYS | 399 | 127.055 | 33.860 | 38.402 | 1.00 | 32.81 | B | C |
| ATOM | 8994 | NZ | LYS | 399 | 128.082 | 34.904 | 38.703 | 1.00 | 34.86 | B | N |
| ATOM | 8995 | C | LYS | 399 | 122.616 | 36.259 | 39.354 | 1.00 | 17.75 | B | C |
| ATOM | 8996 | O | LYS | 399 | 123.041 | 36.571 | 40.465 | 1.00 | 18.35 | B | O |
| ATOM | 8997 | N | GLY | 400 | 121.684 | 35.331 | 39.181 | 1.00 | 16.55 | B | N |
| ATOM | 8998 | CA | GLY | 400 | 121.131 | 34.640 | 40.327 | 1.00 | 17.62 | B | C |
| ATOM | 8999 | C | GLY | 400 | 119.616 | 34.629 | 40.320 | 1.00 | 19.66 | B | C |
| ATOM | 9000 | O | GLY | 400 | 118.979 | 35.360 | 39.551 | 1.00 | 22.36 | B | O |
| ATOM | 9001 | N | THR | 401 | 119.028 | 33.797 | 41.172 | 1.00 | 18.45 | B | N |
| ATOM | 9002 | CA | THR | 401 | 117.582 | 33.708 | 41.227 | 1.00 | 17.93 | B | C |
| ATOM | 9003 | CB | THR | 401 | 117.125 | 32.323 | 41.700 | 1.00 | 17.98 | B | C |
| ATOM | 9004 | OG1 | THR | 401 | 117.653 | 32.056 | 43.004 | 1.00 | 20.05 | B | O |
| ATOM | 9005 | CG2 | THR | 401 | 117.607 | 31.267 | 40.730 | 1.00 | 13.15 | B | C |
| ATOM | 9006 | C | THR | 401 | 117.013 | 34.785 | 42.125 | 1.00 | 16.85 | B | C |
| ATOM | 9007 | O | THR | 401 | 116.478 | 34.519 | 43.192 | 1.00 | 18.14 | B | O |
| ATOM | 9008 | N | TRP | 402 | 117.155 | 36.013 | 41.659 | 1.00 | 16.42 | B | N |
| ATOM | 9009 | CA | TRP | 402 | 116.671 | 37.199 | 42.335 | 1.00 | 14.66 | B | C |
| ATOM | 9010 | CB | TRP | 402 | 117.528 | 37.503 | 43.561 | 1.00 | 16.17 | B | C |
| ATOM | 9011 | CG | TRP | 402 | 119.001 | 37.502 | 43.296 | 1.00 | 16.85 | B | C |
| ATOM | 9012 | CD2 | TRP | 402 | 119.793 | 38.614 | 42.861 | 1.00 | 17.78 | B | C |
| ATOM | 9013 | CE2 | TRP | 402 | 121.131 | 38.164 | 42.771 | 1.00 | 18.27 | B | C |
| ATOM | 9014 | CE3 | TRP | 402 | 119.504 | 39.948 | 42.542 | 1.00 | 18.13 | B | C |
| ATOM | 9015 | CD1 | TRP | 402 | 119.859 | 36.453 | 43.440 | 1.00 | 16.20 | B | C |

| ATOM | 9016 | NE1 | TRP | 402 | 121.143 | 36.842 | 43.130 | 1.00 | 18.41 | B | N |
|---|---|---|---|---|---|---|---|---|---|---|---|
| ATOM | 9017 | CZ2 | TRP | 402 | 122.180 | 39.003 | 42.378 | 1.00 | 16.56 | B | C |
| ATOM | 9018 | CZ3 | TRP | 402 | 120.553 | 40.784 | 42.151 | 1.00 | 18.56 | B | C |
| ATOM | 9019 | CH2 | TRP | 402 | 121.874 | 40.303 | 42.075 | 1.00 | 17.33 | B | C |
| ATOM | 9020 | C | TRP | 402 | 116.827 | 38.280 | 41.273 | 1.00 | 14.94 | B | C |
| ATOM | 9021 | O | TRP | 402 | 117.439 | 38.022 | 40.229 | 1.00 | 14.00 | B | O |
| ATOM | 9022 | N | GLU | 403 | 116.309 | 39.480 | 41.534 | 1.00 | 13.41 | B | N |
| ATOM | 9023 | CA | GLU | 403 | 116.368 | 40.554 | 40.548 | 1.00 | 12.05 | B | C |
| ATOM | 9024 | CB | GLU | 403 | 114.990 | 40.703 | 39.899 | 1.00 | 10.24 | B | C |
| ATOM | 9025 | CG | GLU | 403 | 114.408 | 39.396 | 39.398 | 1.00 | 10.20 | B | C |
| ATOM | 9026 | CD | GLU | 403 | 113.288 | 39.607 | 38.391 | 1.00 | 14.00 | B | C |
| ATOM | 9027 | OE1 | GLU | 403 | 112.301 | 40.306 | 38.713 | 1.00 | 15.50 | B | O |
| ATOM | 9028 | OE2 | GLU | 403 | 113.397 | 39.068 | 37.271 | 1.00 | 14.63 | B | O |
| ATOM | 9029 | C | GLU | 403 | 116.852 | 41.938 | 40.999 | 1.00 | 13.29 | B | C |
| ATOM | 9030 | O | GLU | 403 | 116.785 | 42.301 | 42.171 | 1.00 | 14.74 | B | O |
| ATOM | 9031 | N | VAL | 404 | 117.322 | 42.716 | 40.031 | 1.00 | 12.89 | B | N |
| ATOM | 9032 | CA | VAL | 404 | 117.800 | 44.067 | 40.270 | 1.00 | 12.91 | B | C |
| ATOM | 9033 | CB | VAL | 404 | 118.926 | 44.420 | 39.265 | 1.00 | 11.91 | B | C |
| ATOM | 9034 | CG1 | VAL | 404 | 119.374 | 45.859 | 39.453 | 1.00 | 13.92 | B | C |
| ATOM | 9035 | CG2 | VAL | 404 | 120.096 | 43.484 | 39.459 | 1.00 | 8.31 | B | C |
| ATOM | 9036 | C | VAL | 404 | 116.607 | 44.994 | 40.039 | 1.00 | 14.23 | B | C |
| ATOM | 9037 | O | VAL | 404 | 116.129 | 45.105 | 38.918 | 1.00 | 16.13 | B | O |
| ATOM | 9038 | N | ILE | 405 | 116.122 | 45.653 | 41.089 | 1.00 | 13.56 | B | N |
| ATOM | 9039 | CA | ILE | 405 | 114.968 | 46.540 | 40.951 | 1.00 | 12.56 | B | C |
| ATOM | 9040 | CB | ILE | 405 | 114.453 | 47.020 | 42.339 | 1.00 | 12.98 | B | C |
| ATOM | 9041 | CG2 | ILE | 405 | 113.151 | 47.763 | 42.183 | 1.00 | 7.46 | B | C |
| ATOM | 9042 | CG1 | ILE | 405 | 114.256 | 45.824 | 43.282 | 1.00 | 14.03 | B | C |
| ATOM | 9043 | CD1 | ILE | 405 | 113.390 | 44.705 | 42.732 | 1.00 | 10.06 | B | C |
| ATOM | 9044 | C | ILE | 405 | 115.293 | 47.762 | 40.088 | 1.00 | 14.39 | B | C |
| ATOM | 9045 | O | ILE | 405 | 114.504 | 48.156 | 39.226 | 1.00 | 14.58 | B | O |
| ATOM | 9046 | N | GLY | 406 | 116.455 | 48.367 | 40.315 | 1.00 | 14.30 | B | N |
| ATOM | 9047 | CA | GLY | 406 | 116.822 | 49.521 | 39.521 | 1.00 | 12.80 | B | C |
| ATOM | 9048 | C | GLY | 406 | 118.253 | 49.967 | 39.708 | 1.00 | 13.75 | B | C |
| ATOM | 9049 | O | GLY | 406 | 118.858 | 49.708 | 40.737 | 1.00 | 16.89 | B | O |
| ATOM | 9050 | N | ILE | 407 | 118.806 | 50.618 | 38.691 | 1.00 | 14.84 | B | N |
| ATOM | 9051 | CA | ILE | 407 | 120.161 | 51.144 | 38.760 | 1.00 | 13.37 | B | C |
| ATOM | 9052 | CB | ILE | 407 | 120.797 | 51.192 | 37.361 | 1.00 | 11.30 | B | C |
| ATOM | 9053 | CG2 | ILE | 407 | 122.039 | 52.077 | 37.373 | 1.00 | 11.29 | B | C |
| ATOM | 9054 | CG1 | ILE | 407 | 121.163 | 49.768 | 36.936 | 1.00 | 9.82 | B | C |
| ATOM | 9055 | CD1 | ILE | 407 | 121.237 | 49.545 | 35.446 | 1.00 | 9.37 | B | C |
| ATOM | 9056 | C | ILE | 407 | 119.991 | 52.546 | 39.343 | 1.00 | 15.02 | B | C |
| ATOM | 9057 | O | ILE | 407 | 119.236 | 53.361 | 38.819 | 1.00 | 14.39 | B | O |
| ATOM | 9058 | N | GLU | 408 | 120.692 | 52.825 | 40.431 | 1.00 | 16.63 | B | N |
| ATOM | 9059 | CA | GLU | 408 | 120.552 | 54.105 | 41.105 | 1.00 | 18.23 | B | C |
| ATOM | 9060 | CB | GLU | 408 | 120.373 | 53.849 | 42.601 | 1.00 | 21.53 | B | C |
| ATOM | 9061 | CG | GLU | 408 | 119.290 | 52.815 | 42.906 | 1.00 | 23.80 | B | C |
| ATOM | 9062 | CD | GLU | 408 | 117.916 | 53.275 | 42.456 | 1.00 | 27.87 | B | C |
| ATOM | 9063 | OE1 | GLU | 408 | 117.135 | 52.429 | 41.967 | 1.00 | 30.29 | B | O |
| ATOM | 9064 | OE2 | GLU | 408 | 117.612 | 54.483 | 42.598 | 1.00 | 29.06 | B | O |

| | | | | | | | | | | |
|---|---|---|---|---|---|---|---|---|---|---|
| ATOM | 9065 | C | GLU | 408 | 121.687 | 55.094 | 40.888 | 1.00 | 19.22 | B C |
| ATOM | 9066 | O | GLU | 408 | 121.468 | 56.306 | 40.924 | 1.00 | 21.06 | B O |
| ATOM | 9067 | N | ALA | 409 | 122.899 | 54.589 | 40.678 | 1.00 | 18.36 | B N |
| ATOM | 9068 | CA | ALA | 409 | 124.048 | 55.463 | 40.473 | 1.00 | 17.37 | B C |
| ATOM | 9069 | CB | ALA | 409 | 124.533 | 56.012 | 41.816 | 1.00 | 16.78 | B C |
| ATOM | 9070 | C | ALA | 409 | 125.189 | 54.756 | 39.755 | 1.00 | 17.45 | B C |
| ATOM | 9071 | O | ALA | 409 | 125.323 | 53.536 | 39.834 | 1.00 | 15.91 | B O |
| ATOM | 9072 | N | LEU | 410 | 126.009 | 55.545 | 39.062 | 1.00 | 17.35 | B N |
| ATOM | 9073 | CA | LEU | 410 | 127.140 | 55.034 | 38.311 | 1.00 | 17.53 | B C |
| ATOM | 9074 | CB | LEU | 410 | 126.722 | 54.817 | 36.857 | 1.00 | 16.60 | B C |
| ATOM | 9075 | CG | LEU | 410 | 127.767 | 54.292 | 35.862 | 1.00 | 18.12 | B C |
| ATOM | 9076 | CD1 | LEU | 410 | 128.278 | 52.914 | 36.302 | 1.00 | 16.12 | B C |
| ATOM | 9077 | CD2 | LEU | 410 | 127.144 | 54.224 | 34.467 | 1.00 | 14.82 | B C |
| ATOM | 9078 | C | LEU | 410 | 128.356 | 55.969 | 38.356 | 1.00 | 18.72 | B C |
| ATOM | 9079 | O | LEU | 410 | 128.228 | 57.175 | 38.190 | 1.00 | 20.28 | B O |
| ATOM | 9080 | N | THR | 411 | 129.532 | 55.396 | 38.589 | 1.00 | 18.37 | B N |
| ATOM | 9081 | CA | THR | 411 | 130.786 | 56.142 | 38.617 | 1.00 | 19.27 | B C |
| ATOM | 9082 | CB | THR | 411 | 131.360 | 56.286 | 40.060 | 1.00 | 18.85 | B C |
| ATOM | 9083 | OG1 | THR | 411 | 131.869 | 55.024 | 40.514 | 1.00 | 17.72 | B O |
| ATOM | 9084 | CG2 | THR | 411 | 130.284 | 56.764 | 41.012 | 1.00 | 17.11 | B C |
| ATOM | 9085 | C | THR | 411 | 131.744 | 55.293 | 37.784 | 1.00 | 20.67 | B C |
| ATOM | 9086 | O | THR | 411 | 131.374 | 54.200 | 37.357 | 1.00 | 23.60 | B O |
| ATOM | 9087 | N | SER | 412 | 132.961 | 55.772 | 37.543 | 1.00 | 21.07 | B N |
| ATOM | 9088 | CA | SER | 412 | 133.912 | 54.988 | 36.753 | 1.00 | 21.08 | B C |
| ATOM | 9089 | CB | SER | 412 | 135.124 | 55.827 | 36.365 | 1.00 | 18.37 | B C |
| ATOM | 9090 | OG | SER | 412 | 135.926 | 56.086 | 37.496 | 1.00 | 21.11 | B O |
| ATOM | 9091 | C | SER | 412 | 134.387 | 53.778 | 37.548 | 1.00 | 22.07 | B C |
| ATOM | 9092 | O | SER | 412 | 134.961 | 52.843 | 36.995 | 1.00 | 23.13 | B O |
| ATOM | 9093 | N | ASP | 413 | 134.144 | 53.790 | 38.850 | 1.00 | 22.17 | B N |
| ATOM | 9094 | CA | ASP | 413 | 134.581 | 52.677 | 39.673 | 1.00 | 22.98 | B C |
| ATOM | 9095 | CB | ASP | 413 | 135.339 | 53.198 | 40.895 | 1.00 | 25.67 | B C |
| ATOM | 9096 | CG | ASP | 413 | 136.731 | 53.697 | 40.548 | 1.00 | 28.45 | B C |
| ATOM | 9097 | OD1 | ASP | 413 | 137.338 | 54.395 | 41.389 | 1.00 | 31.52 | B O |
| ATOM | 9098 | OD2 | ASP | 413 | 137.228 | 53.385 | 39.444 | 1.00 | 29.95 | B O |
| ATOM | 9099 | C | ASP | 413 | 133.446 | 51.777 | 40.123 | 1.00 | 22.23 | B C |
| ATOM | 9100 | O | ASP | 413 | 133.624 | 50.565 | 40.248 | 1.00 | 22.67 | B O |
| ATOM | 9101 | N | TYR | 414 | 132.274 | 52.362 | 40.351 | 1.00 | 21.41 | B N |
| ATOM | 9102 | CA | TYR | 414 | 131.138 | 51.575 | 40.819 | 1.00 | 18.45 | B C |
| ATOM | 9103 | CB | TYR | 414 | 131.002 | 51.708 | 42.329 | 1.00 | 15.46 | B C |
| ATOM | 9104 | CG | TYR | 414 | 132.101 | 51.071 | 43.131 | 1.00 | 14.79 | B C |
| ATOM | 9105 | CD1 | TYR | 414 | 132.118 | 49.699 | 43.357 | 1.00 | 14.59 | B C |
| ATOM | 9106 | CE1 | TYR | 414 | 133.093 | 49.120 | 44.159 | 1.00 | 16.87 | B C |
| ATOM | 9107 | CD2 | TYR | 414 | 133.093 | 51.850 | 43.718 | 1.00 | 14.91 | B C |
| ATOM | 9108 | CE2 | TYR | 414 | 134.071 | 51.282 | 44.512 | 1.00 | 16.48 | B C |
| ATOM | 9109 | CZ | TYR | 414 | 134.066 | 49.921 | 44.733 | 1.00 | 16.25 | B C |
| ATOM | 9110 | OH | TYR | 414 | 135.030 | 49.369 | 45.541 | 1.00 | 19.68 | B O |
| ATOM | 9111 | C | TYR | 414 | 129.787 | 51.898 | 40.214 | 1.00 | 17.91 | B C |
| ATOM | 9112 | O | TYR | 414 | 129.547 | 52.990 | 39.693 | 1.00 | 17.06 | B O |
| ATOM | 9113 | N | LEU | 415 | 128.901 | 50.917 | 40.323 | 1.00 | 16.46 | B N |

FIG. 4-187

| ATOM | 9114 | CA | LEU | 415 | 127.537 | 51.027 | 39.855 | 1.00 | 14.70 | B | C |
| --- | --- | --- | --- | --- | --- | --- | --- | --- | --- | --- | --- |
| ATOM | 9115 | CB | LEU | 415 | 127.297 | 50.040 | 38.714 | 1.00 | 13.43 | B | C |
| ATOM | 9116 | CG | LEU | 415 | 125.924 | 50.107 | 38.049 | 1.00 | 15.02 | B | C |
| ATOM | 9117 | CD1 | LEU | 415 | 126.044 | 49.620 | 36.619 | 1.00 | 16.33 | B | C |
| ATOM | 9118 | CD2 | LEU | 415 | 124.899 | 49.295 | 38.852 | 1.00 | 15.41 | B | C |
| ATOM | 9119 | C | LEU | 415 | 126.674 | 50.668 | 41.066 | 1.00 | 15.33 | B | C |
| ATOM | 9120 | O | LEU | 415 | 126.777 | 49.566 | 41.601 | 1.00 | 16.82 | B | O |
| ATOM | 9121 | N | TYR | 416 | 125.840 | 51.595 | 41.519 | 1.00 | 15.16 | B | N |
| ATOM | 9122 | CA | TYR | 416 | 124.988 | 51.313 | 42.663 | 1.00 | 14.80 | B | C |
| ATOM | 9123 | CB | TYR | 416 | 124.879 | 52.530 | 43.566 | 1.00 | 13.44 | B | C |
| ATOM | 9124 | CG | TYR | 416 | 126.201 | 52.997 | 44.105 | 1.00 | 15.38 | B | C |
| ATOM | 9125 | CD1 | TYR | 416 | 127.031 | 53.835 | 43.350 | 1.00 | 14.10 | B | C |
| ATOM | 9126 | CE1 | TYR | 416 | 128.240 | 54.306 | 43.866 | 1.00 | 14.05 | B | C |
| ATOM | 9127 | CD2 | TYR | 416 | 126.618 | 52.630 | 45.386 | 1.00 | 14.93 | B | C |
| ATOM | 9128 | CE2 | TYR | 416 | 127.823 | 53.094 | 45.910 | 1.00 | 15.55 | B | C |
| ATOM | 9129 | CZ | TYR | 416 | 128.625 | 53.938 | 45.147 | 1.00 | 15.00 | B | C |
| ATOM | 9130 | OH | TYR | 416 | 129.766 | 54.466 | 45.699 | 1.00 | 14.00 | B | O |
| ATOM | 9131 | C | TYR | 416 | 123.604 | 50.905 | 42.208 | 1.00 | 16.12 | B | C |
| ATOM | 9132 | O | TYR | 416 | 123.041 | 51.511 | 41.296 | 1.00 | 16.07 | B | O |
| ATOM | 9133 | N | TYR | 417 | 123.054 | 49.878 | 42.848 | 1.00 | 16.79 | B | N |
| ATOM | 9134 | CA | TYR | 417 | 121.730 | 49.407 | 42.482 | 1.00 | 18.72 | B | C |
| ATOM | 9135 | CB | TYR | 417 | 121.840 | 48.361 | 41.365 | 1.00 | 20.47 | B | C |
| ATOM | 9136 | CG | TYR | 417 | 122.456 | 47.039 | 41.788 | 1.00 | 21.65 | B | C |
| ATOM | 9137 | CD1 | TYR | 417 | 121.656 | 45.983 | 42.226 | 1.00 | 22.60 | B | C |
| ATOM | 9138 | CE1 | TYR | 417 | 122.217 | 44.760 | 42.612 | 1.00 | 22.32 | B | C |
| ATOM | 9139 | CD2 | TYR | 417 | 123.835 | 46.843 | 41.748 | 1.00 | 21.40 | B | C |
| ATOM | 9140 | CE2 | TYR | 417 | 124.404 | 45.626 | 42.135 | 1.00 | 21.84 | B | C |
| ATOM | 9141 | CZ | TYR | 417 | 123.588 | 44.590 | 42.565 | 1.00 | 22.22 | B | C |
| ATOM | 9142 | OH | TYR | 417 | 124.139 | 43.386 | 42.950 | 1.00 | 22.23 | B | O |
| ATOM | 9143 | C | TYR | 417 | 120.973 | 48.824 | 43.667 | 1.00 | 18.97 | B | C |
| ATOM | 9144 | O | TYR | 417 | 121.523 | 48.640 | 44.746 | 1.00 | 18.94 | B | O |
| ATOM | 9145 | N | ILE | 418 | 119.695 | 48.551 | 43.453 | 1.00 | 19.05 | B | N |
| ATOM | 9146 | CA | ILE | 418 | 118.857 | 47.971 | 44.485 | 1.00 | 20.55 | B | C |
| ATOM | 9147 | CB | ILE | 418 | 117.677 | 48.906 | 44.840 | 1.00 | 19.77 | B | C |
| ATOM | 9148 | CG2 | ILE | 418 | 116.692 | 48.187 | 45.742 | 1.00 | 20.86 | B | C |
| ATOM | 9149 | CG1 | ILE | 418 | 118.210 | 50.148 | 45.551 | 1.00 | 20.46 | B | C |
| ATOM | 9150 | CD1 | ILE | 418 | 117.183 | 51.211 | 45.792 | 1.00 | 23.81 | B | C |
| ATOM | 9151 | C | ILE | 418 | 118.337 | 46.651 | 43.947 | 1.00 | 20.17 | B | C |
| ATOM | 9152 | O | ILE | 418 | 118.011 | 46.546 | 42.767 | 1.00 | 21.74 | B | O |
| ATOM | 9153 | N | SER | 419 | 118.272 | 45.642 | 44.808 | 1.00 | 19.61 | B | N |
| ATOM | 9154 | CA | SER | 419 | 117.798 | 44.327 | 44.396 | 1.00 | 18.91 | B | C |
| ATOM | 9155 | CB | SER | 419 | 118.969 | 43.480 | 43.923 | 1.00 | 17.21 | B | C |
| ATOM | 9156 | OG | SER | 419 | 119.797 | 43.183 | 45.030 | 1.00 | 19.02 | B | O |
| ATOM | 9157 | C | SER | 419 | 117.155 | 43.632 | 45.578 | 1.00 | 18.48 | B | C |
| ATOM | 9158 | O | SER | 419 | 117.216 | 44.131 | 46.699 | 1.00 | 19.32 | B | O |
| ATOM | 9159 | N | ASN | 420 | 116.536 | 42.481 | 45.326 | 1.00 | 17.64 | B | N |
| ATOM | 9160 | CA | ASN | 420 | 115.913 | 41.716 | 46.395 | 1.00 | 16.73 | B | C |
| ATOM | 9161 | CB | ASN | 420 | 114.448 | 41.406 | 46.067 | 1.00 | 13.22 | B | C |
| ATOM | 9162 | CG | ASN | 420 | 114.279 | 40.740 | 44.724 | 1.00 | 13.67 | B | C |

| | | | | | | | | | | |
|---|---|---|---|---|---|---|---|---|---|---|
| ATOM | 9163 | OD1 | ASN | 420 | 115.220 | 40.146 | 44.193 | 1.00 | 14.68 | B | O |
| ATOM | 9164 | ND2 | ASN | 420 | 113.072 | 40.818 | 44.169 | 1.00 | 7.98 | B | N |
| ATOM | 9165 | C | ASN | 420 | 116.700 | 40.426 | 46.638 | 1.00 | 16.85 | B | C |
| ATOM | 9166 | O | ASN | 420 | 116.135 | 39.368 | 46.910 | 1.00 | 18.37 | B | O |
| ATOM | 9167 | N | GLU | 421 | 118.018 | 40.532 | 46.543 | 1.00 | 17.15 | B | N |
| ATOM | 9168 | CA | GLU | 421 | 118.895 | 39.393 | 46.754 | 1.00 | 19.34 | B | C |
| ATOM | 9169 | CB | GLU | 421 | 120.291 | 39.694 | 46.195 | 1.00 | 18.78 | B | C |
| ATOM | 9170 | CG | GLU | 421 | 121.358 | 38.747 | 46.734 | 1.00 | 20.75 | B | C |
| ATOM | 9171 | CD | GLU | 421 | 122.661 | 38.782 | 45.951 | 1.00 | 22.48 | B | C |
| ATOM | 9172 | OE1 | GLU | 421 | 123.169 | 39.890 | 45.661 | 1.00 | 21.18 | B | O |
| ATOM | 9173 | OE2 | GLU | 421 | 123.184 | 37.689 | 45.639 | 1.00 | 22.04 | B | O |
| ATOM | 9174 | C | GLU | 421 | 119.028 | 38.945 | 48.218 | 1.00 | 19.80 | B | C |
| ATOM | 9175 | O | GLU | 421 | 118.960 | 37.756 | 48.519 | 1.00 | 20.89 | B | O |
| ATOM | 9176 | N | TYR | 422 | 119.223 | 39.897 | 49.120 | 1.00 | 19.38 | B | N |
| ATOM | 9177 | CA | TYR | 422 | 119.401 | 39.596 | 50.530 | 1.00 | 19.16 | B | C |
| ATOM | 9178 | CB | TYR | 422 | 119.386 | 40.895 | 51.326 | 1.00 | 19.06 | B | C |
| ATOM | 9179 | CG | TYR | 422 | 119.881 | 40.746 | 52.741 | 1.00 | 21.59 | B | C |
| ATOM | 9180 | CD1 | TYR | 422 | 121.046 | 40.023 | 53.024 | 1.00 | 19.84 | B | C |
| ATOM | 9181 | CE1 | TYR | 422 | 121.510 | 39.893 | 54.314 | 1.00 | 19.73 | B | C |
| ATOM | 9182 | CD2 | TYR | 422 | 119.198 | 41.334 | 53.798 | 1.00 | 21.32 | B | C |
| ATOM | 9183 | CE2 | TYR | 422 | 119.658 | 41.210 | 55.097 | 1.00 | 23.82 | B | C |
| ATOM | 9184 | CZ | TYR | 422 | 120.813 | 40.488 | 55.347 | 1.00 | 23.64 | B | C |
| ATOM | 9185 | OH | TYR | 422 | 121.267 | 40.376 | 56.637 | 1.00 | 28.92 | B | O |
| ATOM | 9186 | C | TYR | 422 | 118.401 | 38.600 | 51.114 | 1.00 | 20.84 | B | C |
| ATOM | 9187 | O | TYR | 422 | 117.187 | 38.779 | 51.012 | 1.00 | 22.40 | B | O |
| ATOM | 9188 | N | LYS | 423 | 118.933 | 37.546 | 51.732 | 1.00 | 21.52 | B | N |
| ATOM | 9189 | CA | LYS | 423 | 118.130 | 36.486 | 52.340 | 1.00 | 21.53 | B | C |
| ATOM | 9190 | CB | LYS | 423 | 117.436 | 36.995 | 53.608 | 1.00 | 22.83 | B | C |
| ATOM | 9191 | CG | LYS | 423 | 118.393 | 37.278 | 54.751 | 1.00 | 25.85 | B | C |
| ATOM | 9192 | CD | LYS | 423 | 117.677 | 37.707 | 56.020 | 1.00 | 27.71 | B | C |
| ATOM | 9193 | CE | LYS | 423 | 118.692 | 38.082 | 57.098 | 1.00 | 31.46 | B | C |
| ATOM | 9194 | NZ | LYS | 423 | 118.052 | 38.548 | 58.367 | 1.00 | 31.96 | B | N |
| ATOM | 9195 | C | LYS | 423 | 117.097 | 35.906 | 51.378 | 1.00 | 21.44 | B | C |
| ATOM | 9196 | O | LYS | 423 | 116.114 | 35.293 | 51.797 | 1.00 | 22.16 | B | O |
| ATOM | 9197 | N | GLY | 424 | 117.331 | 36.106 | 50.086 | 1.00 | 20.50 | B | N |
| ATOM | 9198 | CA | GLY | 424 | 116.430 | 35.595 | 49.070 | 1.00 | 20.06 | B | C |
| ATOM | 9199 | C | GLY | 424 | 114.969 | 35.945 | 49.274 | 1.00 | 20.45 | B | C |
| ATOM | 9200 | O | GLY | 424 | 114.102 | 35.120 | 49.013 | 1.00 | 21.91 | B | O |
| ATOM | 9201 | N | MET | 425 | 114.695 | 37.163 | 49.739 | 1.00 | 20.34 | B | N |
| ATOM | 9202 | CA | MET | 425 | 113.322 | 37.627 | 49.968 | 1.00 | 18.53 | B | C |
| ATOM | 9203 | CB | MET | 425 | 113.234 | 38.329 | 51.317 | 1.00 | 19.68 | B | C |
| ATOM | 9204 | CG | MET | 425 | 113.756 | 37.501 | 52.469 | 1.00 | 22.38 | B | C |
| ATOM | 9205 | SD | MET | 425 | 113.506 | 38.352 | 54.020 | 1.00 | 24.27 | B | S |
| ATOM | 9206 | CE | MET | 425 | 111.741 | 38.663 | 53.907 | 1.00 | 21.26 | B | C |
| ATOM | 9207 | C | MET | 425 | 112.908 | 38.604 | 48.871 | 1.00 | 16.75 | B | C |
| ATOM | 9208 | O | MET | 425 | 113.405 | 39.725 | 48.819 | 1.00 | 17.33 | B | O |
| ATOM | 9209 | N | PRO | 426 | 111.968 | 38.206 | 47.999 | 1.00 | 16.64 | B | N |
| ATOM | 9210 | CD | PRO | 426 | 111.173 | 36.969 | 48.017 | 1.00 | 17.29 | B | C |
| ATOM | 9211 | CA | PRO | 426 | 111.530 | 39.089 | 46.910 | 1.00 | 15.29 | B | C |

FIG. 4-189 (Continued)

| ATOM | 9212 | CB | PRO | 426 | 110.523 | 38.233 | 46.140 | 1.00 | 15.30 | B | C |
| --- | --- | --- | --- | --- | --- | --- | --- | --- | --- | --- | --- |
| ATOM | 9213 | CG | PRO | 426 | 110.816 | 36.823 | 46.561 | 1.00 | 15.73 | B | C |
| ATOM | 9214 | C | PRO | 426 | 110.901 | 40.379 | 47.416 | 1.00 | 15.48 | B | C |
| ATOM | 9215 | O | PRO | 426 | 110.913 | 41.402 | 46.727 | 1.00 | 15.90 | B | O |
| ATOM | 9216 | N | GLY | 427 | 110.362 | 40.321 | 48.630 | 1.00 | 14.46 | B | N |
| ATOM | 9217 | CA | GLY | 427 | 109.718 | 41.480 | 49.217 | 1.00 | 13.34 | B | C |
| ATOM | 9218 | C | GLY | 427 | 110.649 | 42.449 | 49.919 | 1.00 | 13.11 | B | C |
| ATOM | 9219 | O | GLY | 427 | 110.184 | 43.462 | 50.452 | 1.00 | 14.26 | B | O |
| ATOM | 9220 | N | GLY | 428 | 111.947 | 42.144 | 49.942 | 1.00 | 9.68 | B | N |
| ATOM | 9221 | CA | GLY | 428 | 112.902 | 43.036 | 50.577 | 1.00 | 8.65 | B | C |
| ATOM | 9222 | C | GLY | 428 | 113.735 | 43.771 | 49.538 | 1.00 | 10.35 | B | C |
| ATOM | 9223 | O | GLY | 428 | 113.778 | 43.363 | 48.377 | 1.00 | 10.03 | B | O |
| ATOM | 9224 | N | ARG | 429 | 114.406 | 44.844 | 49.946 | 1.00 | 11.09 | B | N |
| ATOM | 9225 | CA | ARG | 429 | 115.224 | 45.630 | 49.023 | 1.00 | 12.98 | B | C |
| ATOM | 9226 | CB | ARG | 429 | 114.349 | 46.667 | 48.314 | 1.00 | 14.68 | B | C |
| ATOM | 9227 | CG | ARG | 429 | 113.580 | 46.084 | 47.144 | 1.00 | 18.95 | B | C |
| ATOM | 9228 | CD | ARG | 429 | 112.423 | 46.947 | 46.701 | 1.00 | 18.69 | B | C |
| ATOM | 9229 | NE | ARG | 429 | 111.590 | 46.279 | 45.699 | 1.00 | 19.88 | B | N |
| ATOM | 9230 | CZ | ARG | 429 | 111.184 | 45.008 | 45.769 | 1.00 | 21.09 | B | C |
| ATOM | 9231 | NH1 | ARG | 429 | 111.535 | 44.227 | 46.791 | 1.00 | 17.36 | B | N |
| ATOM | 9232 | NH2 | ARG | 429 | 110.390 | 44.520 | 44.825 | 1.00 | 20.65 | B | N |
| ATOM | 9233 | C | ARG | 429 | 116.420 | 46.328 | 49.678 | 1.00 | 13.64 | B | C |
| ATOM | 9234 | O | ARG | 429 | 116.291 | 46.983 | 50.707 | 1.00 | 13.96 | B | O |
| ATOM | 9235 | N | ASN | 430 | 117.584 | 46.198 | 49.056 | 1.00 | 12.81 | B | N |
| ATOM | 9236 | CA | ASN | 430 | 118.784 | 46.812 | 49.585 | 1.00 | 13.48 | B | C |
| ATOM | 9237 | CB | ASN | 430 | 119.605 | 45.767 | 50.344 | 1.00 | 11.94 | B | C |
| ATOM | 9238 | CG | ASN | 430 | 118.985 | 45.411 | 51.677 | 1.00 | 12.47 | B | C |
| ATOM | 9239 | OD1 | ASN | 430 | 119.104 | 46.167 | 52.652 | 1.00 | 11.56 | B | O |
| ATOM | 9240 | ND2 | ASN | 430 | 118.293 | 44.277 | 51.727 | 1.00 | 7.39 | B | N |
| ATOM | 9241 | C | ASN | 430 | 119.644 | 47.477 | 48.528 | 1.00 | 14.50 | B | C |
| ATOM | 9242 | O | ASN | 430 | 119.530 | 47.189 | 47.335 | 1.00 | 14.26 | B | O |
| ATOM | 9243 | N | LEU | 431 | 120.504 | 48.377 | 48.992 | 1.00 | 16.18 | B | N |
| ATOM | 9244 | CA | LEU | 431 | 121.425 | 49.107 | 48.135 | 1.00 | 17.01 | B | C |
| ATOM | 9245 | CB | LEU | 431 | 121.709 | 50.496 | 48.713 | 1.00 | 16.67 | B | C |
| ATOM | 9246 | CG | LEU | 431 | 122.825 | 51.279 | 48.012 | 1.00 | 18.10 | B | C |
| ATOM | 9247 | CD1 | LEU | 431 | 122.501 | 51.399 | 46.528 | 1.00 | 17.30 | B | C |
| ATOM | 9248 | CD2 | LEU | 431 | 122.998 | 52.651 | 48.667 | 1.00 | 14.93 | B | C |
| ATOM | 9249 | C | LEU | 431 | 122.729 | 48.338 | 48.022 | 1.00 | 17.39 | B | C |
| ATOM | 9250 | O | LEU | 431 | 123.367 | 48.018 | 49.028 | 1.00 | 19.06 | B | O |
| ATOM | 9251 | N | TYR | 432 | 123.112 | 48.038 | 46.789 | 1.00 | 17.62 | B | N |
| ATOM | 9252 | CA | TYR | 432 | 124.344 | 47.317 | 46.511 | 1.00 | 18.05 | B | C |
| ATOM | 9253 | CB | TYR | 432 | 124.061 | 45.978 | 45.826 | 1.00 | 17.24 | B | C |
| ATOM | 9254 | CG | TYR | 432 | 123.334 | 44.944 | 46.654 | 1.00 | 18.80 | B | C |
| ATOM | 9255 | CD1 | TYR | 432 | 121.962 | 45.034 | 46.883 | 1.00 | 19.62 | B | C |
| ATOM | 9256 | CE1 | TYR | 432 | 121.289 | 44.049 | 47.601 | 1.00 | 19.23 | B | C |
| ATOM | 9257 | CD2 | TYR | 432 | 124.015 | 43.843 | 47.169 | 1.00 | 17.63 | B | C |
| ATOM | 9258 | CE2 | TYR | 432 | 123.360 | 42.862 | 47.882 | 1.00 | 18.49 | B | C |
| ATOM | 9259 | CZ | TYR | 432 | 121.996 | 42.968 | 48.099 | 1.00 | 20.13 | B | C |
| ATOM | 9260 | OH | TYR | 432 | 121.358 | 41.994 | 48.834 | 1.00 | 21.75 | B | O |

| ATOM | 9261 | C | TYR | 432 | 125.193 | 48.142 | 45.557 | 1.00 | 17.78 | B | C |
| --- | --- | --- | --- | --- | --- | --- | --- | --- | --- | --- | --- |
| ATOM | 9262 | O | TYR | 432 | 124.700 | 49.066 | 44.903 | 1.00 | 18.57 | B | O |
| ATOM | 9263 | N | LYS | 433 | 126.474 | 47.805 | 45.486 | 1.00 | 16.13 | B | N |
| ATOM | 9264 | CA | LYS | 433 | 127.386 | 48.460 | 44.563 | 1.00 | 14.57 | B | C |
| ATOM | 9265 | CB | LYS | 433 | 128.237 | 49.536 | 45.251 | 1.00 | 16.46 | B | C |
| ATOM | 9266 | CG | LYS | 433 | 129.297 | 49.022 | 46.215 | 1.00 | 16.27 | B | C |
| ATOM | 9267 | CD | LYS | 433 | 130.239 | 50.146 | 46.606 | 1.00 | 16.51 | B | C |
| ATOM | 9268 | CE | LYS | 433 | 131.190 | 49.723 | 47.712 | 1.00 | 16.69 | B | C |
| ATOM | 9269 | NZ | LYS | 433 | 132.101 | 50.834 | 48.104 | 1.00 | 17.27 | B | N |
| ATOM | 9270 | C | LYS | 433 | 128.269 | 47.343 | 44.058 | 1.00 | 13.68 | B | C |
| ATOM | 9271 | O | LYS | 433 | 128.654 | 46.454 | 44.820 | 1.00 | 11.44 | B | O |
| ATOM | 9272 | N | ILE | 434 | 128.564 | 47.364 | 42.767 | 1.00 | 13.85 | B | N |
| ATOM | 9273 | CA | ILE | 434 | 129.411 | 46.331 | 42.191 | 1.00 | 15.56 | B | C |
| ATOM | 9274 | CB | ILE | 434 | 128.645 | 45.504 | 41.124 | 1.00 | 14.45 | B | C |
| ATOM | 9275 | CG2 | ILE | 434 | 128.054 | 46.429 | 40.061 | 1.00 | 11.95 | B | C |
| ATOM | 9276 | CG1 | ILE | 434 | 129.580 | 44.458 | 40.518 | 1.00 | 14.14 | B | C |
| ATOM | 9277 | CD1 | ILE | 434 | 128.978 | 43.676 | 39.379 | 1.00 | 14.42 | B | C |
| ATOM | 9278 | C | ILE | 434 | 130.646 | 46.973 | 41.573 | 1.00 | 16.13 | B | C |
| ATOM | 9279 | O | ILE | 434 | 130.554 | 48.003 | 40.915 | 1.00 | 17.71 | B | O |
| ATOM | 9280 | N | GLN | 435 | 131.804 | 46.374 | 41.809 | 1.00 | 18.33 | B | N |
| ATOM | 9281 | CA | GLN | 435 | 133.045 | 46.907 | 41.263 | 1.00 | 20.88 | B | C |
| ATOM | 9282 | CB | GLN | 435 | 134.253 | 46.264 | 41.956 | 1.00 | 21.76 | B | C |
| ATOM | 9283 | CG | GLN | 435 | 135.490 | 47.145 | 41.958 | 1.00 | 24.28 | B | C |
| ATOM | 9284 | CD | GLN | 435 | 136.715 | 46.461 | 42.547 | 1.00 | 25.69 | B | C |
| ATOM | 9285 | OE1 | GLN | 435 | 136.763 | 46.154 | 43.741 | 1.00 | 26.08 | B | O |
| ATOM | 9286 | NE2 | GLN | 435 | 137.713 | 46.220 | 41.705 | 1.00 | 24.68 | B | N |
| ATOM | 9287 | C | GLN | 435 | 133.068 | 46.617 | 39.767 | 1.00 | 20.60 | B | C |
| ATOM | 9288 | O | GLN | 435 | 132.969 | 45.465 | 39.348 | 1.00 | 20.57 | B | O |
| ATOM | 9289 | N | LEU | 436 | 133.200 | 47.668 | 38.965 | 1.00 | 21.54 | B | N |
| ATOM | 9290 | CA | LEU | 436 | 133.197 | 47.527 | 37.513 | 1.00 | 23.39 | B | C |
| ATOM | 9291 | CB | LEU | 436 | 133.050 | 48.905 | 36.880 | 1.00 | 21.46 | B | C |
| ATOM | 9292 | CG | LEU | 436 | 131.785 | 49.596 | 37.386 | 1.00 | 19.80 | B | C |
| ATOM | 9293 | CD1 | LEU | 436 | 131.748 | 51.035 | 36.920 | 1.00 | 19.31 | B | C |
| ATOM | 9294 | CD2 | LEU | 436 | 130.572 | 48.831 | 36.895 | 1.00 | 18.85 | B | C |
| ATOM | 9295 | C | LEU | 436 | 134.391 | 46.790 | 36.908 | 1.00 | 25.55 | B | C |
| ATOM | 9296 | O | LEU | 436 | 134.294 | 46.242 | 35.810 | 1.00 | 27.46 | B | O |
| ATOM | 9297 | N | SER | 437 | 135.517 | 46.775 | 37.613 | 1.00 | 26.98 | B | N |
| ATOM | 9298 | CA | SER | 437 | 136.690 | 46.069 | 37.119 | 1.00 | 26.89 | B | C |
| ATOM | 9299 | CB | SER | 437 | 137.967 | 46.683 | 37.689 | 1.00 | 26.26 | B | C |
| ATOM | 9300 | OG | SER | 437 | 137.940 | 46.694 | 39.102 | 1.00 | 31.19 | B | O |
| ATOM | 9301 | C | SER | 437 | 136.593 | 44.597 | 37.507 | 1.00 | 27.29 | B | C |
| ATOM | 9302 | O | SER | 437 | 137.152 | 43.736 | 36.832 | 1.00 | 29.17 | B | O |
| ATOM | 9303 | N | ASP | 438 | 135.882 | 44.310 | 38.595 | 1.00 | 26.66 | B | N |
| ATOM | 9304 | CA | ASP | 438 | 135.704 | 42.930 | 39.049 | 1.00 | 26.32 | B | C |
| ATOM | 9305 | CB | ASP | 438 | 136.702 | 42.588 | 40.151 | 1.00 | 28.65 | B | C |
| ATOM | 9306 | CG | ASP | 438 | 136.622 | 41.135 | 40.571 | 1.00 | 30.81 | B | C |
| ATOM | 9307 | OD1 | ASP | 438 | 135.517 | 40.557 | 40.495 | 1.00 | 32.19 | B | O |
| ATOM | 9308 | OD2 | ASP | 438 | 137.659 | 40.575 | 40.990 | 1.00 | 33.46 | B | O |
| ATOM | 9309 | C | ASP | 438 | 134.286 | 42.691 | 39.572 | 1.00 | 24.90 | B | C |

FIG. 4-191 (Continued)

| | | | | | | | | | | |
|---|---|---|---|---|---|---|---|---|---|---|
| ATOM | 9310 | O | ASP | 438 | 133.959 | 43.060 | 40.700 | 1.00 | 22.15 | B | O |
| ATOM | 9311 | N | TYR | 439 | 133.461 | 42.046 | 38.753 | 1.00 | 23.79 | B | N |
| ATOM | 9312 | CA | TYR | 439 | 132.083 | 41.780 | 39.123 | 1.00 | 23.74 | B | C |
| ATOM | 9313 | CB | TYR | 439 | 131.301 | 41.243 | 37.924 | 1.00 | 22.94 | B | C |
| ATOM | 9314 | CG | TYR | 439 | 131.357 | 42.125 | 36.698 | 1.00 | 22.91 | B | C |
| ATOM | 9315 | CD1 | TYR | 439 | 131.420 | 43.514 | 36.814 | 1.00 | 22.44 | B | C |
| ATOM | 9316 | CE1 | TYR | 439 | 131.442 | 44.329 | 35.687 | 1.00 | 22.19 | B | C |
| ATOM | 9317 | CD2 | TYR | 439 | 131.322 | 41.572 | 35.416 | 1.00 | 22.08 | B | C |
| ATOM | 9318 | CE2 | TYR | 439 | 131.348 | 42.379 | 34.285 | 1.00 | 21.13 | B | C |
| ATOM | 9319 | CZ | TYR | 439 | 131.405 | 43.753 | 34.430 | 1.00 | 21.92 | B | C |
| ATOM | 9320 | OH | TYR | 439 | 131.410 | 44.552 | 33.314 | 1.00 | 24.24 | B | O |
| ATOM | 9321 | C | TYR | 439 | 131.928 | 40.823 | 40.294 | 1.00 | 24.38 | B | C |
| ATOM | 9322 | O | TYR | 439 | 130.882 | 40.801 | 40.933 | 1.00 | 25.27 | B | O |
| ATOM | 9323 | N | THR | 440 | 132.953 | 40.030 | 40.584 | 1.00 | 24.21 | B | N |
| ATOM | 9324 | CA | THR | 440 | 132.858 | 39.094 | 41.699 | 1.00 | 23.35 | B | C |
| ATOM | 9325 | CB | THR | 440 | 134.102 | 38.196 | 41.806 | 1.00 | 23.70 | B | C |
| ATOM | 9326 | OG1 | THR | 440 | 135.221 | 38.975 | 42.250 | 1.00 | 22.70 | B | O |
| ATOM | 9327 | CG2 | THR | 440 | 134.418 | 37.568 | 40.462 | 1.00 | 23.82 | B | C |
| ATOM | 9328 | C | THR | 440 | 132.712 | 39.852 | 43.014 | 1.00 | 22.79 | B | C |
| ATOM | 9329 | O | THR | 440 | 132.169 | 39.328 | 43.987 | 1.00 | 21.81 | B | O |
| ATOM | 9330 | N | LYS | 441 | 133.200 | 41.087 | 43.039 | 1.00 | 22.86 | B | N |
| ATOM | 9331 | CA | LYS | 441 | 133.123 | 41.905 | 44.243 | 1.00 | 22.90 | B | C |
| ATOM | 9332 | CB | LYS | 441 | 134.396 | 42.741 | 44.375 | 1.00 | 25.86 | B | C |
| ATOM | 9333 | CG | LYS | 441 | 135.620 | 41.878 | 44.682 | 1.00 | 30.20 | B | C |
| ATOM | 9334 | CD | LYS | 441 | 136.871 | 42.702 | 44.878 | 1.00 | 34.36 | B | C |
| ATOM | 9335 | CE | LYS | 441 | 138.053 | 41.804 | 45.201 | 1.00 | 37.32 | B | C |
| ATOM | 9336 | NZ | LYS | 441 | 139.319 | 42.577 | 45.346 | 1.00 | 40.04 | B | N |
| ATOM | 9337 | C | LYS | 441 | 131.881 | 42.794 | 44.329 | 1.00 | 21.89 | B | C |
| ATOM | 9338 | O | LYS | 441 | 131.828 | 43.891 | 43.768 | 1.00 | 21.84 | B | O |
| ATOM | 9339 | N | VAL | 442 | 130.880 | 42.289 | 45.039 | 1.00 | 19.62 | B | N |
| ATOM | 9340 | CA | VAL | 442 | 129.624 | 42.984 | 45.242 | 1.00 | 17.69 | B | C |
| ATOM | 9341 | CB | VAL | 442 | 128.458 | 42.093 | 44.799 | 1.00 | 17.33 | B | C |
| ATOM | 9342 | CG1 | VAL | 442 | 127.123 | 42.770 | 45.119 | 1.00 | 15.79 | B | C |
| ATOM | 9343 | CG2 | VAL | 442 | 128.586 | 41.792 | 43.306 | 1.00 | 11.20 | B | C |
| ATOM | 9344 | C | VAL | 442 | 129.502 | 43.299 | 46.733 | 1.00 | 20.40 | B | C |
| ATOM | 9345 | O | VAL | 442 | 129.742 | 42.437 | 47.572 | 1.00 | 22.84 | B | O |
| ATOM | 9346 | N | THR | 443 | 129.129 | 44.528 | 47.066 | 1.00 | 20.64 | B | N |
| ATOM | 9347 | CA | THR | 443 | 129.015 | 44.927 | 48.461 | 1.00 | 22.17 | B | C |
| ATOM | 9348 | CB | THR | 443 | 130.040 | 46.035 | 48.801 | 1.00 | 24.13 | B | C |
| ATOM | 9349 | OG1 | THR | 443 | 131.370 | 45.566 | 48.546 | 1.00 | 28.90 | B | O |
| ATOM | 9350 | CG2 | THR | 443 | 129.923 | 46.442 | 50.255 | 1.00 | 22.91 | B | C |
| ATOM | 9351 | C | THR | 443 | 127.641 | 45.475 | 48.819 | 1.00 | 23.06 | B | C |
| ATOM | 9352 | O | THR | 443 | 127.210 | 46.483 | 48.254 | 1.00 | 26.29 | B | O |
| ATOM | 9353 | N | CYS | 444 | 126.948 | 44.835 | 49.754 | 1.00 | 21.88 | B | N |
| ATOM | 9354 | CA | CYS | 444 | 125.656 | 45.368 | 50.163 | 1.00 | 22.22 | B | C |
| ATOM | 9355 | C | CYS | 444 | 125.963 | 46.516 | 51.115 | 1.00 | 20.79 | B | C |
| ATOM | 9356 | O | CYS | 444 | 126.866 | 46.411 | 51.941 | 1.00 | 19.89 | B | O |
| ATOM | 9357 | CB | CYS | 444 | 124.801 | 44.328 | 50.878 | 1.00 | 24.50 | B | C |
| ATOM | 9358 | SG | CYS | 444 | 123.137 | 44.986 | 51.221 | 1.00 | 27.42 | B | S |

| | | | | | | | | | | |
|---|---|---|---|---|---|---|---|---|---|---|
| ATOM | 9359 | N | LEU | 445 | 125.205 | 47.602 | 51.005 | 1.00 | 20.20 | B | N |
| ATOM | 9360 | CA | LEU | 445 | 125.442 | 48.785 | 51.824 | 1.00 | 17.71 | B | C |
| ATOM | 9361 | CB | LEU | 445 | 125.651 | 49.988 | 50.899 | 1.00 | 15.76 | B | C |
| ATOM | 9362 | CG | LEU | 445 | 126.714 | 49.756 | 49.812 | 1.00 | 15.86 | B | C |
| ATOM | 9363 | CD1 | LEU | 445 | 126.930 | 51.008 | 48.970 | 1.00 | 13.93 | B | C |
| ATOM | 9364 | CD2 | LEU | 445 | 128.007 | 49.333 | 50.480 | 1.00 | 12.34 | B | C |
| ATOM | 9365 | C | LEU | 445 | 124.333 | 49.099 | 52.814 | 1.00 | 19.64 | B | C |
| ATOM | 9366 | O | LEU | 445 | 124.446 | 50.036 | 53.608 | 1.00 | 20.41 | B | O |
| ATOM | 9367 | N | SER | 446 | 123.262 | 48.314 | 52.776 | 1.00 | 21.11 | B | N |
| ATOM | 9368 | CA | SER | 446 | 122.131 | 48.552 | 53.656 | 1.00 | 20.24 | B | C |
| ATOM | 9369 | CB | SER | 446 | 120.947 | 49.077 | 52.834 | 1.00 | 20.38 | B | C |
| ATOM | 9370 | OG | SER | 446 | 120.577 | 48.143 | 51.829 | 1.00 | 18.25 | B | O |
| ATOM | 9371 | C | SER | 446 | 121.708 | 47.307 | 54.411 | 1.00 | 20.86 | B | C |
| ATOM | 9372 | O | SER | 446 | 121.085 | 47.404 | 55.463 | 1.00 | 21.91 | B | O |
| ATOM | 9373 | N | CYS | 447 | 122.043 | 46.141 | 53.874 | 1.00 | 21.42 | B | N |
| ATOM | 9374 | CA | CYS | 447 | 121.667 | 44.875 | 54.495 | 1.00 | 23.05 | B | C |
| ATOM | 9375 | C | CYS | 447 | 121.845 | 44.816 | 56.004 | 1.00 | 23.84 | B | C |
| ATOM | 9376 | O | CYS | 447 | 120.881 | 44.602 | 56.739 | 1.00 | 24.50 | B | O |
| ATOM | 9377 | CB | CYS | 447 | 122.461 | 43.722 | 53.874 | 1.00 | 24.68 | B | C |
| ATOM | 9378 | SG | CYS | 447 | 122.134 | 43.458 | 52.103 | 1.00 | 31.64 | B | S |
| ATOM | 9379 | N | GLU | 448 | 123.080 | 45.011 | 56.463 | 1.00 | 23.42 | B | N |
| ATOM | 9380 | CA | GLU | 448 | 123.394 | 44.913 | 57.881 | 1.00 | 23.49 | B | C |
| ATOM | 9381 | CB | GLU | 448 | 124.805 | 44.358 | 58.061 | 1.00 | 24.37 | B | C |
| ATOM | 9382 | CG | GLU | 448 | 125.060 | 43.017 | 57.395 | 1.00 | 28.24 | B | C |
| ATOM | 9383 | CD | GLU | 448 | 123.996 | 41.985 | 57.713 | 1.00 | 34.11 | B | C |
| ATOM | 9384 | OE1 | GLU | 448 | 123.377 | 42.073 | 58.796 | 1.00 | 36.48 | B | O |
| ATOM | 9385 | OE2 | GLU | 448 | 123.786 | 41.070 | 56.882 | 1.00 | 37.27 | B | O |
| ATOM | 9386 | C | GLU | 448 | 123.249 | 46.162 | 58.738 | 1.00 | 23.12 | B | C |
| ATOM | 9387 | O | GLU | 448 | 123.458 | 46.101 | 59.948 | 1.00 | 24.21 | B | O |
| ATOM | 9388 | N | LEU | 449 | 122.900 | 47.289 | 58.134 | 1.00 | 20.81 | B | N |
| ATOM | 9389 | CA | LEU | 449 | 122.733 | 48.516 | 58.899 | 1.00 | 20.59 | B | C |
| ATOM | 9390 | CB | LEU | 449 | 122.123 | 49.592 | 58.010 | 1.00 | 18.76 | B | C |
| ATOM | 9391 | CG | LEU | 449 | 123.019 | 50.143 | 56.909 | 1.00 | 17.31 | B | C |
| ATOM | 9392 | CD1 | LEU | 449 | 122.221 | 51.089 | 56.045 | 1.00 | 18.95 | B | C |
| ATOM | 9393 | CD2 | LEU | 449 | 124.199 | 50.868 | 57.527 | 1.00 | 16.25 | B | C |
| ATOM | 9394 | C | LEU | 449 | 121.853 | 48.311 | 60.144 | 1.00 | 22.20 | B | C |
| ATOM | 9395 | O | LEU | 449 | 122.232 | 48.674 | 61.261 | 1.00 | 22.97 | B | O |
| ATOM | 9396 | N | ASN | 450 | 120.677 | 47.731 | 59.937 | 1.00 | 22.75 | B | N |
| ATOM | 9397 | CA | ASN | 450 | 119.729 | 47.462 | 61.011 | 1.00 | 21.80 | B | C |
| ATOM | 9398 | CB | ASN | 450 | 118.958 | 48.731 | 61.344 | 1.00 | 23.73 | B | C |
| ATOM | 9399 | CG | ASN | 450 | 118.226 | 48.632 | 62.661 | 1.00 | 26.67 | B | C |
| ATOM | 9400 | OD1 | ASN | 450 | 117.678 | 47.581 | 63.004 | 1.00 | 26.78 | B | O |
| ATOM | 9401 | ND2 | ASN | 450 | 118.199 | 49.733 | 63.406 | 1.00 | 26.73 | B | N |
| ATOM | 9402 | C | ASN | 450 | 118.772 | 46.400 | 60.469 | 1.00 | 22.01 | B | C |
| ATOM | 9403 | O | ASN | 450 | 117.649 | 46.701 | 60.072 | 1.00 | 21.48 | B | O |
| ATOM | 9404 | N | PRO | 451 | 119.215 | 45.134 | 60.442 | 1.00 | 21.65 | B | N |
| ATOM | 9405 | CD | PRO | 451 | 120.506 | 44.673 | 60.969 | 1.00 | 20.73 | B | C |
| ATOM | 9406 | CA | PRO | 451 | 118.430 | 44.004 | 59.941 | 1.00 | 21.39 | B | C |
| ATOM | 9407 | CB | PRO | 451 | 119.362 | 42.817 | 60.162 | 1.00 | 19.94 | B | C |

| | | | | | | | | | | | |
|---|---|---|---|---|---|---|---|---|---|---|---|
| ATOM | 9408 | CG | PRO | 451 | 120.209 | 43.253 | 61.290 | 1.00 | 21.78 | B | C |
| ATOM | 9409 | C | PRO | 451 | 117.035 | 43.774 | 60.509 | 1.00 | 23.49 | B | C |
| ATOM | 9410 | O | PRO | 451 | 116.125 | 43.392 | 59.774 | 1.00 | 25.06 | B | O |
| ATOM | 9411 | N | GLU | 452 | 116.850 | 44.003 | 61.800 | 1.00 | 24.25 | B | N |
| ATOM | 9412 | CA | GLU | 452 | 115.539 | 43.793 | 62.394 | 1.00 | 26.56 | B | C |
| ATOM | 9413 | CB | GLU | 452 | 115.650 | 43.767 | 63.920 | 1.00 | 32.21 | B | C |
| ATOM | 9414 | CG | GLU | 452 | 116.621 | 42.720 | 64.455 | 1.00 | 39.54 | B | C |
| ATOM | 9415 | CD | GLU | 452 | 116.666 | 42.675 | 65.976 | 1.00 | 44.38 | B | C |
| ATOM | 9416 | OE1 | GLU | 452 | 117.355 | 41.782 | 66.521 | 1.00 | 47.19 | B | O |
| ATOM | 9417 | OE2 | GLU | 452 | 116.019 | 43.529 | 66.627 | 1.00 | 46.89 | B | O |
| ATOM | 9418 | C | GLU | 452 | 114.543 | 44.867 | 61.968 | 1.00 | 25.59 | B | C |
| ATOM | 9419 | O | GLU | 452 | 113.374 | 44.582 | 61.733 | 1.00 | 27.44 | B | O |
| ATOM | 9420 | N | ARG | 453 | 115.010 | 46.101 | 61.848 | 1.00 | 23.36 | B | N |
| ATOM | 9421 | CA | ARG | 453 | 114.132 | 47.198 | 61.478 | 1.00 | 21.67 | B | C |
| ATOM | 9422 | CB | ARG | 453 | 114.539 | 48.463 | 62.234 | 1.00 | 21.94 | B | C |
| ATOM | 9423 | CG | ARG | 453 | 113.714 | 49.685 | 61.872 | 1.00 | 20.24 | B | C |
| ATOM | 9424 | CD | ARG | 453 | 114.165 | 50.878 | 62.662 | 1.00 | 17.23 | B | C |
| ATOM | 9425 | NE | ARG | 453 | 113.364 | 52.058 | 62.375 | 1.00 | 16.99 | B | N |
| ATOM | 9426 | CZ | ARG | 453 | 113.582 | 53.245 | 62.927 | 1.00 | 17.21 | B | C |
| ATOM | 9427 | NH1 | ARG | 453 | 114.579 | 53.391 | 63.791 | 1.00 | 17.27 | B | N |
| ATOM | 9428 | NH2 | ARG | 453 | 112.813 | 54.280 | 62.619 | 1.00 | 14.66 | B | N |
| ATOM | 9429 | C | ARG | 453 | 114.077 | 47.527 | 59.994 | 1.00 | 21.78 | B | C |
| ATOM | 9430 | O | ARG | 453 | 113.024 | 47.910 | 59.477 | 1.00 | 20.58 | B | O |
| ATOM | 9431 | N | CYS | 454 | 115.206 | 47.368 | 59.312 | 1.00 | 21.64 | B | N |
| ATOM | 9432 | CA | CYS | 454 | 115.293 | 47.715 | 57.903 | 1.00 | 19.87 | B | C |
| ATOM | 9433 | C | CYS | 454 | 115.598 | 46.616 | 56.896 | 1.00 | 19.70 | B | C |
| ATOM | 9434 | O | CYS | 454 | 116.698 | 46.074 | 56.865 | 1.00 | 21.81 | B | O |
| ATOM | 9435 | CB | CYS | 454 | 116.295 | 48.847 | 57.770 | 1.00 | 19.47 | B | C |
| ATOM | 9436 | SG | CYS | 454 | 115.666 | 50.300 | 58.650 | 1.00 | 18.98 | B | S |
| ATOM | 9437 | N | GLN | 455 | 114.608 | 46.332 | 56.051 | 1.00 | 19.11 | B | N |
| ATOM | 9438 | CA | GLN | 455 | 114.692 | 45.305 | 55.015 | 1.00 | 14.77 | B | C |
| ATOM | 9439 | CB | GLN | 455 | 113.881 | 44.085 | 55.457 | 1.00 | 13.34 | B | C |
| ATOM | 9440 | CG | GLN | 455 | 114.425 | 43.413 | 56.711 | 1.00 | 12.92 | B | C |
| ATOM | 9441 | CD | GLN | 455 | 113.425 | 42.482 | 57.387 | 1.00 | 13.33 | B | C |
| ATOM | 9442 | OE1 | GLN | 455 | 112.514 | 41.958 | 56.749 | 1.00 | 14.25 | B | O |
| ATOM | 9443 | NE2 | GLN | 455 | 113.605 | 42.266 | 58.688 | 1.00 | 13.47 | B | N |
| ATOM | 9444 | C | GLN | 455 | 114.156 | 45.815 | 53.669 | 1.00 | 14.10 | B | C |
| ATOM | 9445 | O | GLN | 455 | 114.058 | 45.059 | 52.704 | 1.00 | 14.35 | B | O |
| ATOM | 9446 | N | TYR | 456 | 113.803 | 47.094 | 53.597 | 1.00 | 13.95 | B | N |
| ATOM | 9447 | CA | TYR | 456 | 113.268 | 47.651 | 52.355 | 1.00 | 13.75 | B | C |
| ATOM | 9448 | CB | TYR | 456 | 111.742 | 47.600 | 52.387 | 1.00 | 13.55 | B | C |
| ATOM | 9449 | CG | TYR | 456 | 111.049 | 47.707 | 51.045 | 1.00 | 10.86 | B | C |
| ATOM | 9450 | CD1 | TYR | 456 | 110.504 | 46.578 | 50.436 | 1.00 | 10.75 | B | C |
| ATOM | 9451 | CE1 | TYR | 456 | 109.815 | 46.674 | 49.236 | 1.00 | 9.29 | B | C |
| ATOM | 9452 | CD2 | TYR | 456 | 110.891 | 48.941 | 50.405 | 1.00 | 9.71 | B | C |
| ATOM | 9453 | CE2 | TYR | 456 | 110.207 | 49.046 | 49.200 | 1.00 | 4.15 | B | C |
| ATOM | 9454 | CZ | TYR | 456 | 109.669 | 47.910 | 48.629 | 1.00 | 8.20 | B | C |
| ATOM | 9455 | OH | TYR | 456 | 108.949 | 47.994 | 47.464 | 1.00 | 11.71 | B | O |
| ATOM | 9456 | C | TYR | 456 | 113.718 | 49.092 | 52.190 | 1.00 | 14.04 | B | C |

| | | | | | | | | | | | |
|---|---|---|---|---|---|---|---|---|---|---|---|
| ATOM | 9457 | O | TYR | 456 | 113.127 | 49.991 | 52.775 | 1.00 | 15.30 | B | O |
| ATOM | 9458 | N | TYR | 457 | 114.752 | 49.309 | 51.382 | 1.00 | 15.11 | B | N |
| ATOM | 9459 | CA | TYR | 457 | 115.286 | 50.646 | 51.152 | 1.00 | 14.85 | B | C |
| ATOM | 9460 | CB | TYR | 457 | 116.792 | 50.674 | 51.390 | 1.00 | 14.57 | B | C |
| ATOM | 9461 | CG | TYR | 457 | 117.271 | 50.394 | 52.786 | 1.00 | 14.62 | B | C |
| ATOM | 9462 | CD1 | TYR | 457 | 117.364 | 49.088 | 53.275 | 1.00 | 14.47 | B | C |
| ATOM | 9463 | CE1 | TYR | 457 | 117.903 | 48.836 | 54.540 | 1.00 | 14.12 | B | C |
| ATOM | 9464 | CD2 | TYR | 457 | 117.714 | 51.434 | 53.595 | 1.00 | 13.34 | B | C |
| ATOM | 9465 | CE2 | TYR | 457 | 118.245 | 51.193 | 54.850 | 1.00 | 13.51 | B | C |
| ATOM | 9466 | CZ | TYR | 457 | 118.341 | 49.902 | 55.318 | 1.00 | 11.72 | B | C |
| ATOM | 9467 | OH | TYR | 457 | 118.877 | 49.701 | 56.559 | 1.00 | 8.57 | B | O |
| ATOM | 9468 | C | TYR | 457 | 115.085 | 51.192 | 49.742 | 1.00 | 15.66 | B | C |
| ATOM | 9469 | O | TYR | 457 | 114.827 | 50.455 | 48.797 | 1.00 | 17.46 | B | O |
| ATOM | 9470 | N | SER | 458 | 115.234 | 52.505 | 49.624 | 1.00 | 14.42 | B | N |
| ATOM | 9471 | CA | SER | 458 | 115.176 | 53.207 | 48.352 | 1.00 | 14.00 | B | C |
| ATOM | 9472 | CB | SER | 458 | 113.853 | 53.950 | 48.163 | 1.00 | 12.81 | B | C |
| ATOM | 9473 | OG | SER | 458 | 113.804 | 55.138 | 48.932 | 1.00 | 15.84 | B | O |
| ATOM | 9474 | C | SER | 458 | 116.318 | 54.175 | 48.620 | 1.00 | 15.10 | B | C |
| ATOM | 9475 | O | SER | 458 | 116.631 | 54.431 | 49.791 | 1.00 | 14.29 | B | O |
| ATOM | 9476 | N | VAL | 459 | 116.946 | 54.709 | 47.574 | 1.00 | 13.45 | B | N |
| ATOM | 9477 | CA | VAL | 459 | 118.086 | 55.593 | 47.779 | 1.00 | 13.00 | B | C |
| ATOM | 9478 | CB | VAL | 459 | 119.392 | 54.853 | 47.433 | 1.00 | 13.28 | B | C |
| ATOM | 9479 | CG1 | VAL | 459 | 119.442 | 54.578 | 45.934 | 1.00 | 10.72 | B | C |
| ATOM | 9480 | CG2 | VAL | 459 | 120.600 | 55.672 | 47.878 | 1.00 | 13.89 | B | C |
| ATOM | 9481 | C | VAL | 459 | 118.051 | 56.882 | 46.969 | 1.00 | 14.23 | B | C |
| ATOM | 9482 | O | VAL | 459 | 117.283 | 57.007 | 46.021 | 1.00 | 14.51 | B | O |
| ATOM | 9483 | N | SER | 460 | 118.901 | 57.834 | 47.347 | 1.00 | 14.01 | B | N |
| ATOM | 9484 | CA | SER | 460 | 118.997 | 59.106 | 46.643 | 1.00 | 14.81 | B | C |
| ATOM | 9485 | CB | SER | 460 | 118.039 | 60.116 | 47.272 | 1.00 | 15.45 | B | C |
| ATOM | 9486 | OG | SER | 460 | 118.038 | 61.333 | 46.553 | 1.00 | 18.07 | B | O |
| ATOM | 9487 | C | SER | 460 | 120.442 | 59.629 | 46.693 | 1.00 | 15.15 | B | C |
| ATOM | 9488 | O | SER | 460 | 120.930 | 60.040 | 47.752 | 1.00 | 14.75 | B | O |
| ATOM | 9489 | N | PHE | 461 | 121.123 | 59.611 | 45.547 | 1.00 | 14.99 | B | N |
| ATOM | 9490 | CA | PHE | 461 | 122.516 | 60.068 | 45.469 | 1.00 | 14.06 | B | C |
| ATOM | 9491 | CB | PHE | 461 | 123.314 | 59.229 | 44.454 | 1.00 | 10.57 | B | C |
| ATOM | 9492 | CG | PHE | 461 | 123.583 | 57.809 | 44.885 | 1.00 | 8.39 | B | C |
| ATOM | 9493 | CD1 | PHE | 461 | 122.594 | 56.832 | 44.792 | 1.00 | 7.71 | B | C |
| ATOM | 9494 | CD2 | PHE | 461 | 124.837 | 57.444 | 45.367 | 1.00 | 6.73 | B | C |
| ATOM | 9495 | CE1 | PHE | 461 | 122.848 | 55.509 | 45.172 | 1.00 | 6.28 | B | C |
| ATOM | 9496 | CE2 | PHE | 461 | 125.105 | 56.118 | 45.752 | 1.00 | 6.24 | B | C |
| ATOM | 9497 | CZ | PHE | 461 | 124.108 | 55.153 | 45.653 | 1.00 | 6.94 | B | C |
| ATOM | 9498 | C | PHE | 461 | 122.665 | 61.533 | 45.066 | 1.00 | 16.79 | B | C |
| ATOM | 9499 | O | PHE | 461 | 121.833 | 62.076 | 44.340 | 1.00 | 17.81 | B | O |
| ATOM | 9500 | N | SER | 462 | 123.740 | 62.170 | 45.528 | 1.00 | 18.84 | B | N |
| ATOM | 9501 | CA | SER | 462 | 124.019 | 63.555 | 45.155 | 1.00 | 20.51 | B | C |
| ATOM | 9502 | CB | SER | 462 | 125.131 | 64.137 | 46.036 | 1.00 | 21.92 | B | C |
| ATOM | 9503 | OG | SER | 462 | 126.346 | 63.421 | 45.878 | 1.00 | 24.40 | B | O |
| ATOM | 9504 | C | SER | 462 | 124.465 | 63.559 | 43.687 | 1.00 | 20.69 | B | C |
| ATOM | 9505 | O | SER | 462 | 124.607 | 62.505 | 43.075 | 1.00 | 21.27 | B | O |

| | | | | | | | | | | | |
|---|---|---|---|---|---|---|---|---|---|---|---|
| ATOM | 9506 | N | LYS | 463 | 124.708 | 64.736 | 43.128 | 1.00 | 22.99 | B | N |
| ATOM | 9507 | CA | LYS | 463 | 125.109 | 64.846 | 41.728 | 1.00 | 25.69 | B | C |
| ATOM | 9508 | CB | LYS | 463 | 125.483 | 66.291 | 41.401 | 1.00 | 27.00 | B | C |
| ATOM | 9509 | CG | LYS | 463 | 124.275 | 67.189 | 41.270 | 1.00 | 30.44 | B | C |
| ATOM | 9510 | CD | LYS | 463 | 124.427 | 68.146 | 40.097 | 1.00 | 35.16 | B | C |
| ATOM | 9511 | CE | LYS | 463 | 123.083 | 68.756 | 39.718 | 1.00 | 37.88 | B | C |
| ATOM | 9512 | NZ | LYS | 463 | 123.169 | 69.566 | 38.471 | 1.00 | 40.00 | B | N |
| ATOM | 9513 | C | LYS | 463 | 126.204 | 63.904 | 41.230 | 1.00 | 26.63 | B | C |
| ATOM | 9514 | O | LYS | 463 | 126.057 | 63.297 | 40.169 | 1.00 | 27.72 | B | O |
| ATOM | 9515 | N | GLU | 464 | 127.305 | 63.777 | 41.959 | 1.00 | 27.45 | B | N |
| ATOM | 9516 | CA | GLU | 464 | 128.355 | 62.868 | 41.502 | 1.00 | 28.40 | B | C |
| ATOM | 9517 | CB | GLU | 464 | 129.710 | 63.576 | 41.429 | 1.00 | 31.19 | B | C |
| ATOM | 9518 | CG | GLU | 464 | 130.079 | 64.030 | 40.027 | 1.00 | 35.17 | B | C |
| ATOM | 9519 | CD | GLU | 464 | 129.150 | 65.100 | 39.495 | 1.00 | 37.56 | B | C |
| ATOM | 9520 | OE1 | GLU | 464 | 129.200 | 66.229 | 40.022 | 1.00 | 41.38 | B | O |
| ATOM | 9521 | OE2 | GLU | 464 | 128.371 | 64.817 | 38.557 | 1.00 | 38.51 | B | O |
| ATOM | 9522 | C | GLU | 464 | 128.476 | 61.627 | 42.367 | 1.00 | 26.36 | B | C |
| ATOM | 9523 | O | GLU | 464 | 129.515 | 60.975 | 42.379 | 1.00 | 25.64 | B | O |
| ATOM | 9524 | N | ALA | 465 | 127.404 | 61.302 | 43.081 | 1.00 | 23.96 | B | N |
| ATOM | 9525 | CA | ALA | 465 | 127.372 | 60.127 | 43.936 | 1.00 | 21.85 | B | C |
| ATOM | 9526 | CB | ALA | 465 | 127.663 | 58.869 | 43.121 | 1.00 | 21.46 | B | C |
| ATOM | 9527 | C | ALA | 465 | 128.362 | 60.245 | 45.074 | 1.00 | 20.68 | B | C |
| ATOM | 9528 | O | ALA | 465 | 128.850 | 59.244 | 45.591 | 1.00 | 16.26 | B | O |
| ATOM | 9529 | N | LYS | 466 | 128.661 | 61.476 | 45.462 | 1.00 | 22.56 | B | N |
| ATOM | 9530 | CA | LYS | 466 | 129.588 | 61.693 | 46.562 | 1.00 | 24.73 | B | C |
| ATOM | 9531 | CB | LYS | 466 | 130.041 | 63.154 | 46.609 | 1.00 | 25.44 | B | C |
| ATOM | 9532 | CG | LYS | 466 | 131.173 | 63.405 | 47.581 | 1.00 | 29.20 | B | C |
| ATOM | 9533 | CD | LYS | 466 | 131.835 | 64.762 | 47.351 | 1.00 | 32.39 | B | C |
| ATOM | 9534 | CE | LYS | 466 | 133.084 | 64.909 | 48.218 | 1.00 | 34.11 | B | C |
| ATOM | 9535 | NZ | LYS | 466 | 133.806 | 66.188 | 47.965 | 1.00 | 36.88 | B | N |
| ATOM | 9536 | C | LYS | 466 | 128.859 | 61.318 | 47.847 | 1.00 | 24.27 | B | C |
| ATOM | 9537 | O | LYS | 466 | 129.469 | 60.850 | 48.809 | 1.00 | 24.32 | B | O |
| ATOM | 9538 | N | TYR | 467 | 127.544 | 61.514 | 47.846 | 1.00 | 22.52 | B | N |
| ATOM | 9539 | CA | TYR | 467 | 126.722 | 61.182 | 49.004 | 1.00 | 23.27 | B | C |
| ATOM | 9540 | CB | TYR | 467 | 126.356 | 62.441 | 49.794 | 1.00 | 23.00 | B | C |
| ATOM | 9541 | CG | TYR | 467 | 127.527 | 63.237 | 50.292 | 1.00 | 24.92 | B | C |
| ATOM | 9542 | CD1 | TYR | 467 | 128.201 | 64.119 | 49.451 | 1.00 | 25.30 | B | C |
| ATOM | 9543 | CE1 | TYR | 467 | 129.301 | 64.841 | 49.902 | 1.00 | 26.01 | B | C |
| ATOM | 9544 | CD2 | TYR | 467 | 127.981 | 63.095 | 51.604 | 1.00 | 26.01 | B | C |
| ATOM | 9545 | CE2 | TYR | 467 | 129.079 | 63.811 | 52.064 | 1.00 | 26.37 | B | C |
| ATOM | 9546 | CZ | TYR | 467 | 129.736 | 64.681 | 51.206 | 1.00 | 26.55 | B | C |
| ATOM | 9547 | OH | TYR | 467 | 130.841 | 65.369 | 51.645 | 1.00 | 26.89 | B | O |
| ATOM | 9548 | C | TYR | 467 | 125.428 | 60.500 | 48.584 | 1.00 | 22.16 | B | C |
| ATOM | 9549 | O | TYR | 467 | 125.034 | 60.557 | 47.420 | 1.00 | 22.32 | B | O |
| ATOM | 9550 | N | TYR | 468 | 124.775 | 59.840 | 49.534 | 1.00 | 21.72 | B | N |
| ATOM | 9551 | CA | TYR | 468 | 123.492 | 59.208 | 49.251 | 1.00 | 21.47 | B | C |
| ATOM | 9552 | CB | TYR | 468 | 123.650 | 57.817 | 48.614 | 1.00 | 19.80 | B | C |
| ATOM | 9553 | CG | TYR | 468 | 124.468 | 56.797 | 49.380 | 1.00 | 19.37 | B | C |
| ATOM | 9554 | CD1 | TYR | 468 | 125.844 | 56.683 | 49.184 | 1.00 | 20.24 | B | C |

FIG. 4-196

| ATOM | 9555 | CE1 | TYR | 468 | 126.588 | 55.695 | 49.833 | 1.00 | 20.33 | B | C |
|---|---|---|---|---|---|---|---|---|---|---|---|
| ATOM | 9556 | CD2 | TYR | 468 | 123.856 | 55.902 | 50.252 | 1.00 | 19.91 | B | C |
| ATOM | 9557 | CE2 | TYR | 468 | 124.588 | 54.915 | 50.909 | 1.00 | 19.25 | B | C |
| ATOM | 9558 | CZ | TYR | 468 | 125.951 | 54.816 | 50.695 | 1.00 | 20.72 | B | C |
| ATOM | 9559 | OH | TYR | 468 | 126.674 | 53.845 | 51.349 | 1.00 | 20.60 | B | O |
| ATOM | 9560 | C | TYR | 468 | 122.602 | 59.103 | 50.474 | 1.00 | 21.65 | B | C |
| ATOM | 9561 | O | TYR | 468 | 123.068 | 58.836 | 51.588 | 1.00 | 21.59 | B | O |
| ATOM | 9562 | N | GLN | 469 | 121.317 | 59.360 | 50.268 | 1.00 | 19.96 | B | N |
| ATOM | 9563 | CA | GLN | 469 | 120.369 | 59.235 | 51.355 | 1.00 | 18.78 | B | C |
| ATOM | 9564 | CB | GLN | 469 | 119.277 | 60.302 | 51.283 | 1.00 | 16.79 | B | C |
| ATOM | 9565 | CG | GLN | 469 | 118.247 | 60.143 | 52.393 | 1.00 | 16.33 | B | C |
| ATOM | 9566 | CD | GLN | 469 | 117.035 | 61.034 | 52.214 | 1.00 | 16.44 | B | C |
| ATOM | 9567 | OE1 | GLN | 469 | 116.438 | 61.076 | 51.147 | 1.00 | 18.52 | B | O |
| ATOM | 9568 | NE2 | GLN | 469 | 116.659 | 61.739 | 53.265 | 1.00 | 16.60 | B | N |
| ATOM | 9569 | C | GLN | 469 | 119.729 | 57.855 | 51.240 | 1.00 | 18.75 | B | C |
| ATOM | 9570 | O | GLN | 469 | 119.353 | 57.413 | 50.156 | 1.00 | 20.25 | B | O |
| ATOM | 9571 | N | LEU | 470 | 119.641 | 57.160 | 52.359 | 1.00 | 18.03 | B | N |
| ATOM | 9572 | CA | LEU | 470 | 119.013 | 55.862 | 52.383 | 1.00 | 16.05 | B | C |
| ATOM | 9573 | CB | LEU | 470 | 119.871 | 54.860 | 53.153 | 1.00 | 12.88 | B | C |
| ATOM | 9574 | CG | LEU | 470 | 120.920 | 54.116 | 52.334 | 1.00 | 7.18 | B | C |
| ATOM | 9575 | CD1 | LEU | 470 | 121.669 | 53.176 | 53.230 | 1.00 | 9.83 | B | C |
| ATOM | 9576 | CD2 | LEU | 470 | 120.248 | 53.344 | 51.241 | 1.00 | 5.95 | B | C |
| ATOM | 9577 | C | LEU | 470 | 117.674 | 56.055 | 53.077 | 1.00 | 18.52 | B | C |
| ATOM | 9578 | O | LEU | 470 | 117.573 | 56.769 | 54.082 | 1.00 | 17.50 | B | O |
| ATOM | 9579 | N | ARG | 471 | 116.644 | 55.437 | 52.517 | 1.00 | 20.97 | B | N |
| ATOM | 9580 | CA | ARG | 471 | 115.306 | 55.521 | 53.070 | 1.00 | 23.15 | B | C |
| ATOM | 9581 | CB | ARG | 471 | 114.354 | 56.203 | 52.085 | 1.00 | 25.88 | B | C |
| ATOM | 9582 | CG | ARG | 471 | 112.907 | 56.240 | 52.553 | 1.00 | 31.75 | B | C |
| ATOM | 9583 | CD | ARG | 471 | 111.997 | 56.927 | 51.541 | 1.00 | 35.75 | B | C |
| ATOM | 9584 | NE | ARG | 471 | 110.677 | 57.213 | 52.102 | 1.00 | 39.62 | B | N |
| ATOM | 9585 | CZ | ARG | 471 | 109.737 | 57.920 | 51.478 | 1.00 | 41.33 | B | C |
| ATOM | 9586 | NH1 | ARG | 471 | 109.972 | 58.412 | 50.269 | 1.00 | 41.52 | B | N |
| ATOM | 9587 | NH2 | ARG | 471 | 108.564 | 58.142 | 52.063 | 1.00 | 40.93 | B | N |
| ATOM | 9588 | C | ARG | 471 | 114.826 | 54.112 | 53.345 | 1.00 | 24.13 | B | C |
| ATOM | 9589 | O | ARG | 471 | 114.604 | 53.323 | 52.425 | 1.00 | 25.84 | B | O |
| ATOM | 9590 | N | CYS | 472 | 114.687 | 53.796 | 54.621 | 1.00 | 23.64 | B | N |
| ATOM | 9591 | CA | CYS | 472 | 114.219 | 52.487 | 55.042 | 1.00 | 23.00 | B | C |
| ATOM | 9592 | C | CYS | 472 | 112.732 | 52.636 | 55.321 | 1.00 | 21.14 | B | C |
| ATOM | 9593 | O | CYS | 472 | 112.323 | 53.547 | 56.036 | 1.00 | 21.12 | B | O |
| ATOM | 9594 | CB | CYS | 472 | 114.981 | 52.073 | 56.299 | 1.00 | 23.91 | B | C |
| ATOM | 9595 | SG | CYS | 472 | 114.149 | 50.907 | 57.416 | 1.00 | 27.85 | B | S |
| ATOM | 9596 | N | SER | 473 | 111.919 | 51.755 | 54.756 | 1.00 | 19.44 | B | N |
| ATOM | 9597 | CA | SER | 473 | 110.482 | 51.846 | 54.967 | 1.00 | 18.92 | B | C |
| ATOM | 9598 | CB | SER | 473 | 109.789 | 52.191 | 53.646 | 1.00 | 18.36 | B | C |
| ATOM | 9599 | OG | SER | 473 | 110.141 | 51.261 | 52.642 | 1.00 | 21.93 | B | O |
| ATOM | 9600 | C | SER | 473 | 109.832 | 50.609 | 55.581 | 1.00 | 17.21 | B | C |
| ATOM | 9601 | O | SER | 473 | 108.615 | 50.465 | 55.530 | 1.00 | 19.59 | B | O |
| ATOM | 9602 | N | GLY | 474 | 110.629 | 49.716 | 56.156 | 1.00 | 16.48 | B | N |
| ATOM | 9603 | CA | GLY | 474 | 110.055 | 48.532 | 56.771 | 1.00 | 16.90 | B | C |

| | | | | | | | | | | |
|---|---|---|---|---|---|---|---|---|---|---|
| ATOM | 9604 | C | GLY | 474 | 111.040 | 47.425 | 57.091 | 1.00 | 16.48 | B C |
| ATOM | 9605 | O | GLY | 474 | 112.149 | 47.403 | 56.563 | 1.00 | 18.05 | B O |
| ATOM | 9606 | N | PRO | 475 | 110.643 | 46.446 | 57.913 | 1.00 | 16.25 | B N |
| ATOM | 9607 | CD | PRO | 475 | 111.562 | 45.333 | 58.219 | 1.00 | 17.27 | B C |
| ATOM | 9608 | CA | PRO | 475 | 109.353 | 46.249 | 58.584 | 1.00 | 14.24 | B C |
| ATOM | 9609 | CB | PRO | 475 | 109.445 | 44.807 | 59.068 | 1.00 | 13.06 | B C |
| ATOM | 9610 | CG | PRO | 475 | 110.896 | 44.680 | 59.411 | 1.00 | 14.77 | B C |
| ATOM | 9611 | C | PRO | 475 | 109.012 | 47.214 | 59.716 | 1.00 | 14.52 | B C |
| ATOM | 9612 | O | PRO | 475 | 107.840 | 47.392 | 60.041 | 1.00 | 16.67 | B O |
| ATOM | 9613 | N | GLY | 476 | 110.023 | 47.818 | 60.331 | 1.00 | 14.14 | B N |
| ATOM | 9614 | CA | GLY | 476 | 109.770 | 48.750 | 61.415 | 1.00 | 11.62 | B C |
| ATOM | 9615 | C | GLY | 476 | 109.524 | 50.140 | 60.868 | 1.00 | 12.63 | B C |
| ATOM | 9616 | O | GLY | 476 | 109.407 | 50.307 | 59.656 | 1.00 | 12.58 | B O |
| ATOM | 9617 | N | LEU | 477 | 109.454 | 51.137 | 61.748 | 1.00 | 11.74 | B N |
| ATOM | 9618 | CA | LEU | 477 | 109.222 | 52.519 | 61.331 | 1.00 | 11.92 | B C |
| ATOM | 9619 | CB | LEU | 477 | 109.072 | 53.412 | 62.563 | 1.00 | 10.87 | B C |
| ATOM | 9620 | CG | LEU | 477 | 107.928 | 53.053 | 63.514 | 1.00 | 13.02 | B C |
| ATOM | 9621 | CD1 | LEU | 477 | 107.940 | 54.009 | 64.698 | 1.00 | 12.46 | B C |
| ATOM | 9622 | CD2 | LEU | 477 | 106.586 | 53.114 | 62.775 | 1.00 | 12.47 | B C |
| ATOM | 9623 | C | LEU | 477 | 110.325 | 53.086 | 60.414 | 1.00 | 13.40 | B C |
| ATOM | 9624 | O | LEU | 477 | 111.516 | 52.819 | 60.604 | 1.00 | 11.34 | B O |
| ATOM | 9625 | N | PRO | 478 | 109.931 | 53.894 | 59.414 | 1.00 | 13.58 | B N |
| ATOM | 9626 | CD | PRO | 478 | 108.541 | 54.283 | 59.121 | 1.00 | 14.52 | B C |
| ATOM | 9627 | CA | PRO | 478 | 110.852 | 54.510 | 58.455 | 1.00 | 14.07 | B C |
| ATOM | 9628 | CB | PRO | 478 | 109.962 | 55.495 | 57.705 | 1.00 | 13.81 | B C |
| ATOM | 9629 | CG | PRO | 478 | 108.638 | 54.795 | 57.702 | 1.00 | 14.19 | B C |
| ATOM | 9630 | C | PRO | 478 | 112.033 | 55.188 | 59.118 | 1.00 | 15.11 | B C |
| ATOM | 9631 | O | PRO | 478 | 111.892 | 55.820 | 60.163 | 1.00 | 16.31 | B O |
| ATOM | 9632 | N | LEU | 479 | 113.197 | 55.048 | 58.490 | 1.00 | 16.04 | B N |
| ATOM | 9633 | CA | LEU | 479 | 114.444 | 55.621 | 58.982 | 1.00 | 15.01 | B C |
| ATOM | 9634 | CB | LEU | 479 | 115.279 | 54.528 | 59.657 | 1.00 | 13.83 | B C |
| ATOM | 9635 | CG | LEU | 479 | 116.675 | 54.866 | 60.179 | 1.00 | 12.46 | B C |
| ATOM | 9636 | CD1 | LEU | 479 | 116.606 | 55.990 | 61.189 | 1.00 | 13.23 | B C |
| ATOM | 9637 | CD2 | LEU | 479 | 117.268 | 53.631 | 60.813 | 1.00 | 12.22 | B C |
| ATOM | 9638 | C | LEU | 479 | 115.204 | 56.217 | 57.801 | 1.00 | 14.97 | B C |
| ATOM | 9639 | O | LEU | 479 | 115.395 | 55.557 | 56.783 | 1.00 | 15.80 | B O |
| ATOM | 9640 | N | TYR | 480 | 115.627 | 57.468 | 57.940 | 1.00 | 15.76 | B N |
| ATOM | 9641 | CA | TYR | 480 | 116.350 | 58.165 | 56.883 | 1.00 | 16.51 | B C |
| ATOM | 9642 | CB | TYR | 480 | 115.631 | 59.471 | 56.517 | 1.00 | 18.80 | B C |
| ATOM | 9643 | CG | TYR | 480 | 114.210 | 59.293 | 56.024 | 1.00 | 20.33 | B C |
| ATOM | 9644 | CD1 | TYR | 480 | 113.910 | 59.364 | 54.664 | 1.00 | 22.57 | B C |
| ATOM | 9645 | CE1 | TYR | 480 | 112.604 | 59.161 | 54.196 | 1.00 | 23.68 | B C |
| ATOM | 9646 | CD2 | TYR | 480 | 113.170 | 59.019 | 56.915 | 1.00 | 20.23 | B C |
| ATOM | 9647 | CE2 | TYR | 480 | 111.870 | 58.815 | 56.464 | 1.00 | 22.45 | B C |
| ATOM | 9648 | CZ | TYR | 480 | 111.591 | 58.885 | 55.102 | 1.00 | 24.15 | B C |
| ATOM | 9649 | OH | TYR | 480 | 110.312 | 58.658 | 54.648 | 1.00 | 24.41 | B O |
| ATOM | 9650 | C | TYR | 480 | 117.744 | 58.483 | 57.379 | 1.00 | 15.96 | B C |
| ATOM | 9651 | O | TYR | 480 | 117.910 | 59.005 | 58.482 | 1.00 | 15.89 | B O |
| ATOM | 9652 | N | THR | 481 | 118.743 | 58.179 | 56.559 | 1.00 | 15.76 | B N |

FIG. 4-198 (Continued)

| ATOM | 9653 | CA | THR | 481 | 120.129 | 58.431 | 56.924 | 1.00 | 15.65 | B | C |
|---|---|---|---|---|---|---|---|---|---|---|---|
| ATOM | 9654 | CB | THR | 481 | 120.774 | 57.163 | 57.480 | 1.00 | 14.54 | B | C |
| ATOM | 9655 | OG1 | THR | 481 | 120.459 | 56.065 | 56.622 | 1.00 | 18.10 | B | O |
| ATOM | 9656 | CG2 | THR | 481 | 120.256 | 56.864 | 58.858 | 1.00 | 15.87 | B | C |
| ATOM | 9657 | C | THR | 481 | 120.964 | 58.919 | 55.752 | 1.00 | 16.24 | B | C |
| ATOM | 9658 | O | THR | 481 | 120.650 | 58.648 | 54.602 | 1.00 | 16.93 | B | O |
| ATOM | 9659 | N | LEU | 482 | 122.035 | 59.646 | 56.058 | 1.00 | 18.90 | B | N |
| ATOM | 9660 | CA | LEU | 482 | 122.937 | 60.166 | 55.038 | 1.00 | 19.21 | B | C |
| ATOM | 9661 | CB | LEU | 482 | 123.203 | 61.653 | 55.279 | 1.00 | 20.10 | B | C |
| ATOM | 9662 | CG | LEU | 482 | 123.765 | 62.439 | 54.092 | 1.00 | 21.90 | B | C |
| ATOM | 9663 | CD1 | LEU | 482 | 122.736 | 62.475 | 52.975 | 1.00 | 21.10 | B | C |
| ATOM | 9664 | CD2 | LEU | 482 | 124.115 | 63.856 | 54.525 | 1.00 | 22.66 | B | C |
| ATOM | 9665 | C | LEU | 482 | 124.243 | 59.373 | 55.121 | 1.00 | 19.39 | B | C |
| ATOM | 9666 | O | LEU | 482 | 124.684 | 59.013 | 56.210 | 1.00 | 20.79 | B | O |
| ATOM | 9667 | N | HIS | 483 | 124.849 | 59.096 | 53.970 | 1.00 | 18.33 | B | N |
| ATOM | 9668 | CA | HIS | 483 | 126.090 | 58.332 | 53.903 | 1.00 | 16.79 | B | C |
| ATOM | 9669 | CB | HIS | 483 | 125.791 | 56.894 | 53.488 | 1.00 | 14.55 | B | C |
| ATOM | 9670 | CG | HIS | 483 | 124.697 | 56.245 | 54.276 | 1.00 | 14.89 | B | C |
| ATOM | 9671 | CD2 | HIS | 483 | 123.358 | 56.434 | 54.264 | 1.00 | 15.13 | B | C |
| ATOM | 9672 | ND1 | HIS | 483 | 124.933 | 55.258 | 55.211 | 1.00 | 16.09 | B | N |
| ATOM | 9673 | CE1 | HIS | 483 | 123.788 | 54.867 | 55.736 | 1.00 | 13.84 | B | C |
| ATOM | 9674 | NE2 | HIS | 483 | 122.816 | 55.565 | 55.178 | 1.00 | 14.31 | B | N |
| ATOM | 9675 | C | HIS | 483 | 127.043 | 58.939 | 52.868 | 1.00 | 18.94 | B | C |
| ATOM | 9676 | O | HIS | 483 | 126.617 | 59.665 | 51.961 | 1.00 | 19.56 | B | O |
| ATOM | 9677 | N | SER | 484 | 128.333 | 58.645 | 53.003 | 1.00 | 19.52 | B | N |
| ATOM | 9678 | CA | SER | 484 | 129.318 | 59.131 | 52.040 | 1.00 | 21.33 | B | C |
| ATOM | 9679 | CB | SER | 484 | 130.520 | 59.779 | 52.738 | 1.00 | 21.77 | B | C |
| ATOM | 9680 | OG | SER | 484 | 131.351 | 58.803 | 53.344 | 1.00 | 24.25 | B | O |
| ATOM | 9681 | C | SER | 484 | 129.774 | 57.907 | 51.259 | 1.00 | 21.22 | B | C |
| ATOM | 9682 | O | SER | 484 | 129.942 | 56.827 | 51.830 | 1.00 | 19.26 | B | O |
| ATOM | 9683 | N | SER | 485 | 129.979 | 58.076 | 49.960 | 1.00 | 22.12 | B | N |
| ATOM | 9684 | CA | SER | 485 | 130.389 | 56.967 | 49.110 | 1.00 | 25.62 | B | C |
| ATOM | 9685 | CB | SER | 485 | 130.095 | 57.301 | 47.645 | 1.00 | 26.28 | B | C |
| ATOM | 9686 | OG | SER | 485 | 128.715 | 57.552 | 47.444 | 1.00 | 30.40 | B | O |
| ATOM | 9687 | C | SER | 485 | 131.840 | 56.495 | 49.221 | 1.00 | 26.33 | B | C |
| ATOM | 9688 | O | SER | 485 | 132.097 | 55.300 | 49.138 | 1.00 | 27.23 | B | O |
| ATOM | 9689 | N | VAL | 486 | 132.781 | 57.416 | 49.407 | 1.00 | 28.07 | B | N |
| ATOM | 9690 | CA | VAL | 486 | 134.194 | 57.056 | 49.468 | 1.00 | 29.41 | B | C |
| ATOM | 9691 | CB | VAL | 486 | 135.084 | 58.284 | 49.798 | 1.00 | 30.37 | B | C |
| ATOM | 9692 | CG1 | VAL | 486 | 134.786 | 58.797 | 51.192 | 1.00 | 31.49 | B | C |
| ATOM | 9693 | CG2 | VAL | 486 | 136.553 | 57.909 | 49.665 | 1.00 | 30.81 | B | C |
| ATOM | 9694 | C | VAL | 486 | 134.507 | 55.929 | 50.442 | 1.00 | 30.57 | B | C |
| ATOM | 9695 | O | VAL | 486 | 135.269 | 55.016 | 50.119 | 1.00 | 31.62 | B | O |
| ATOM | 9696 | N | ASN | 487 | 133.922 | 55.979 | 51.630 | 1.00 | 30.95 | B | N |
| ATOM | 9697 | CA | ASN | 487 | 134.159 | 54.928 | 52.610 | 1.00 | 31.75 | B | C |
| ATOM | 9698 | CB | ASN | 487 | 134.888 | 55.498 | 53.833 | 1.00 | 35.87 | B | C |
| ATOM | 9699 | CG | ASN | 487 | 136.336 | 55.868 | 53.537 | 1.00 | 38.55 | B | C |
| ATOM | 9700 | OD1 | ASN | 487 | 136.838 | 56.895 | 54.014 | 1.00 | 38.47 | B | O |
| ATOM | 9701 | ND2 | ASN | 487 | 137.019 | 55.026 | 52.759 | 1.00 | 37.49 | B | N |

FIG. 4-199 (Continued)

| | | | | | | | | | | | |
|---|---|---|---|---|---|---|---|---|---|---|---|
| ATOM | 9702 | C | ASN | 487 | 132.850 | 54.288 | 53.048 | 1.00 | 30.74 | B | C |
| ATOM | 9703 | O | ASN | 487 | 132.830 | 53.486 | 53.982 | 1.00 | 31.45 | B | O |
| ATOM | 9704 | N | ASP | 488 | 131.762 | 54.633 | 52.364 | 1.00 | 28.68 | B | N |
| ATOM | 9705 | CA | ASP | 488 | 130.449 | 54.108 | 52.707 | 1.00 | 26.66 | B | C |
| ATOM | 9706 | CB | ASP | 488 | 130.331 | 52.636 | 52.313 | 1.00 | 27.90 | B | C |
| ATOM | 9707 | CG | ASP | 488 | 130.253 | 52.440 | 50.816 | 1.00 | 29.72 | B | C |
| ATOM | 9708 | OD1 | ASP | 488 | 129.461 | 53.146 | 50.161 | 1.00 | 31.30 | B | O |
| ATOM | 9709 | OD2 | ASP | 488 | 130.977 | 51.572 | 50.290 | 1.00 | 32.18 | B | O |
| ATOM | 9710 | C | ASP | 488 | 130.219 | 54.259 | 54.204 | 1.00 | 25.72 | B | C |
| ATOM | 9711 | O | ASP | 488 | 129.654 | 53.382 | 54.856 | 1.00 | 24.30 | B | O |
| ATOM | 9712 | N | LYS | 489 | 130.669 | 55.378 | 54.754 | 1.00 | 25.25 | B | N |
| ATOM | 9713 | CA | LYS | 489 | 130.503 | 55.610 | 56.176 | 1.00 | 24.10 | B | C |
| ATOM | 9714 | CB | LYS | 489 | 131.607 | 56.529 | 56.705 | 1.00 | 24.94 | B | C |
| ATOM | 9715 | CG | LYS | 489 | 131.622 | 57.898 | 56.069 | 1.00 | 29.19 | B | C |
| ATOM | 9716 | CD | LYS | 489 | 132.805 | 58.719 | 56.560 | 1.00 | 33.11 | B | C |
| ATOM | 9717 | CE | LYS | 489 | 132.771 | 60.133 | 55.995 | 1.00 | 34.94 | B | C |
| ATOM | 9718 | NZ | LYS | 489 | 133.883 | 60.959 | 56.541 | 1.00 | 39.70 | B | N |
| ATOM | 9719 | C | LYS | 489 | 129.140 | 56.216 | 56.449 | 1.00 | 22.29 | B | C |
| ATOM | 9720 | O | LYS | 489 | 128.556 | 56.872 | 55.585 | 1.00 | 20.15 | B | O |
| ATOM | 9721 | N | GLY | 490 | 128.639 | 55.968 | 57.657 | 1.00 | 22.04 | B | N |
| ATOM | 9722 | CA | GLY | 490 | 127.352 | 56.487 | 58.067 | 1.00 | 20.03 | B | C |
| ATOM | 9723 | C | GLY | 490 | 127.545 | 57.854 | 58.676 | 1.00 | 20.18 | B | C |
| ATOM | 9724 | O | GLY | 490 | 128.091 | 57.989 | 59.769 | 1.00 | 20.54 | B | O |
| ATOM | 9725 | N | LEU | 491 | 127.092 | 58.876 | 57.965 | 1.00 | 19.44 | B | N |
| ATOM | 9726 | CA | LEU | 491 | 127.234 | 60.233 | 58.440 | 1.00 | 19.54 | B | C |
| ATOM | 9727 | CB | LEU | 491 | 127.032 | 61.203 | 57.283 | 1.00 | 20.53 | B | C |
| ATOM | 9728 | CG | LEU | 491 | 128.153 | 61.167 | 56.242 | 1.00 | 18.39 | B | C |
| ATOM | 9729 | CD1 | LEU | 491 | 127.831 | 62.089 | 55.090 | 1.00 | 19.23 | B | C |
| ATOM | 9730 | CD2 | LEU | 491 | 129.441 | 61.577 | 56.898 | 1.00 | 18.31 | B | C |
| ATOM | 9731 | C | LEU | 491 | 126.287 | 60.555 | 59.586 | 1.00 | 20.91 | B | C |
| ATOM | 9732 | O | LEU | 491 | 126.735 | 60.780 | 60.713 | 1.00 | 22.15 | B | O |
| ATOM | 9733 | N | ARG | 492 | 124.984 | 60.566 | 59.316 | 1.00 | 20.73 | B | N |
| ATOM | 9734 | CA | ARG | 492 | 124.020 | 60.881 | 60.364 | 1.00 | 20.06 | B | C |
| ATOM | 9735 | CB | ARG | 492 | 124.036 | 62.382 | 60.644 | 1.00 | 20.71 | B | C |
| ATOM | 9736 | CG | ARG | 492 | 123.393 | 63.244 | 59.568 | 1.00 | 20.08 | B | C |
| ATOM | 9737 | CD | ARG | 492 | 123.759 | 64.698 | 59.798 | 1.00 | 21.15 | B | C |
| ATOM | 9738 | NE | ARG | 492 | 125.193 | 64.888 | 59.625 | 1.00 | 21.60 | B | N |
| ATOM | 9739 | CZ | ARG | 492 | 125.765 | 65.192 | 58.466 | 1.00 | 23.12 | B | C |
| ATOM | 9740 | NH1 | ARG | 492 | 125.022 | 65.360 | 57.380 | 1.00 | 24.47 | B | N |
| ATOM | 9741 | NH2 | ARG | 492 | 127.083 | 65.286 | 58.383 | 1.00 | 23.72 | B | N |
| ATOM | 9742 | C | ARG | 492 | 122.585 | 60.443 | 60.085 | 1.00 | 21.47 | B | C |
| ATOM | 9743 | O | ARG | 492 | 122.247 | 59.998 | 58.983 | 1.00 | 21.32 | B | O |
| ATOM | 9744 | N | VAL | 493 | 121.746 | 60.580 | 61.107 | 1.00 | 20.97 | B | N |
| ATOM | 9745 | CA | VAL | 493 | 120.344 | 60.211 | 61.018 | 1.00 | 21.38 | B | C |
| ATOM | 9746 | CB | VAL | 493 | 119.883 | 59.537 | 62.325 | 1.00 | 22.41 | B | C |
| ATOM | 9747 | CG1 | VAL | 493 | 118.402 | 59.215 | 62.247 | 1.00 | 23.17 | B | C |
| ATOM | 9748 | CG2 | VAL | 493 | 120.698 | 58.266 | 62.574 | 1.00 | 20.83 | B | C |
| ATOM | 9749 | C | VAL | 493 | 119.497 | 61.456 | 60.763 | 1.00 | 21.55 | B | C |
| ATOM | 9750 | O | VAL | 493 | 119.462 | 62.371 | 61.580 | 1.00 | 21.85 | B | O |

FIG. 4-200 (Continued)

| | | | | | | | | | | | |
|---|---|---|---|---|---|---|---|---|---|---|---|
| ATOM | 9751 | N | LEU | 494 | 118.811 | 61.485 | 59.626 | 1.00 | 21.18 | B | N |
| ATOM | 9752 | CA | LEU | 494 | 117.974 | 62.626 | 59.264 | 1.00 | 19.43 | B | C |
| ATOM | 9753 | CB | LEU | 494 | 117.782 | 62.660 | 57.742 | 1.00 | 19.57 | B | C |
| ATOM | 9754 | CG | LEU | 494 | 119.101 | 62.610 | 56.953 | 1.00 | 21.60 | B | C |
| ATOM | 9755 | CD1 | LEU | 494 | 118.832 | 62.502 | 55.456 | 1.00 | 20.38 | B | C |
| ATOM | 9756 | CD2 | LEU | 494 | 119.929 | 63.851 | 57.271 | 1.00 | 19.91 | B | C |
| ATOM | 9757 | C | LEU | 494 | 116.615 | 62.576 | 59.964 | 1.00 | 18.58 | B | C |
| ATOM | 9758 | O | LEU | 494 | 116.111 | 63.595 | 60.443 | 1.00 | 18.81 | B | O |
| ATOM | 9759 | N | GLU | 495 | 116.025 | 61.390 | 60.022 | 1.00 | 16.24 | B | N |
| ATOM | 9760 | CA | GLU | 495 | 114.729 | 61.225 | 60.659 | 1.00 | 16.44 | B | C |
| ATOM | 9761 | CB | GLU | 495 | 113.612 | 61.651 | 59.698 | 1.00 | 17.53 | B | C |
| ATOM | 9762 | CG | GLU | 495 | 112.217 | 61.506 | 60.268 | 1.00 | 19.67 | B | C |
| ATOM | 9763 | CD | GLU | 495 | 111.984 | 62.399 | 61.476 | 1.00 | 22.97 | B | C |
| ATOM | 9764 | OE1 | GLU | 495 | 112.023 | 63.642 | 61.315 | 1.00 | 22.51 | B | O |
| ATOM | 9765 | OE2 | GLU | 495 | 111.767 | 61.858 | 62.585 | 1.00 | 22.70 | B | O |
| ATOM | 9766 | C | GLU | 495 | 114.553 | 59.770 | 61.059 | 1.00 | 14.79 | B | C |
| ATOM | 9767 | O | GLU | 495 | 114.678 | 58.875 | 60.236 | 1.00 | 15.37 | B | O |
| ATOM | 9768 | N | ASP | 496 | 114.264 | 59.534 | 62.329 | 1.00 | 14.29 | B | N |
| ATOM | 9769 | CA | ASP | 496 | 114.100 | 58.175 | 62.811 | 1.00 | 13.80 | B | C |
| ATOM | 9770 | CB | ASP | 496 | 115.128 | 57.867 | 63.909 | 1.00 | 14.57 | B | C |
| ATOM | 9771 | CG | ASP | 496 | 114.938 | 58.715 | 65.154 | 1.00 | 12.87 | B | C |
| ATOM | 9772 | OD1 | ASP | 496 | 113.849 | 59.297 | 65.330 | 1.00 | 12.34 | B | O |
| ATOM | 9773 | OD2 | ASP | 496 | 115.882 | 58.789 | 65.971 | 1.00 | 13.20 | B | O |
| ATOM | 9774 | C | ASP | 496 | 112.711 | 57.895 | 63.341 | 1.00 | 13.42 | B | C |
| ATOM | 9775 | O | ASP | 496 | 112.453 | 56.808 | 63.845 | 1.00 | 14.36 | B | O |
| ATOM | 9776 | N | ASN | 497 | 111.820 | 58.871 | 63.234 | 1.00 | 12.87 | B | N |
| ATOM | 9777 | CA | ASN | 497 | 110.460 | 58.697 | 63.717 | 1.00 | 15.91 | B | C |
| ATOM | 9778 | CB | ASN | 497 | 109.736 | 57.666 | 62.855 | 1.00 | 16.28 | B | C |
| ATOM | 9779 | CG | ASN | 497 | 109.227 | 58.255 | 61.564 | 1.00 | 20.09 | B | C |
| ATOM | 9780 | OD1 | ASN | 497 | 108.308 | 59.077 | 61.570 | 1.00 | 18.95 | B | O |
| ATOM | 9781 | ND2 | ASN | 497 | 109.829 | 57.853 | 60.443 | 1.00 | 19.49 | B | N |
| ATOM | 9782 | C | ASN | 497 | 110.373 | 58.292 | 65.193 | 1.00 | 17.71 | B | C |
| ATOM | 9783 | O | ASN | 497 | 109.591 | 57.420 | 65.564 | 1.00 | 19.20 | B | O |
| ATOM | 9784 | N | SER | 498 | 111.179 | 58.924 | 66.035 | 1.00 | 18.90 | B | N |
| ATOM | 9785 | CA | SER | 498 | 111.147 | 58.627 | 67.458 | 1.00 | 20.75 | B | C |
| ATOM | 9786 | CB | SER | 498 | 112.210 | 59.454 | 68.191 | 1.00 | 20.93 | B | C |
| ATOM | 9787 | OG | SER | 498 | 113.491 | 58.878 | 68.037 | 1.00 | 23.33 | B | O |
| ATOM | 9788 | C | SER | 498 | 109.760 | 58.956 | 68.020 | 1.00 | 20.54 | B | C |
| ATOM | 9789 | O | SER | 498 | 109.183 | 58.184 | 68.777 | 1.00 | 20.68 | B | O |
| ATOM | 9790 | N | ALA | 499 | 109.238 | 60.113 | 67.637 | 1.00 | 20.46 | B | N |
| ATOM | 9791 | CA | ALA | 499 | 107.935 | 60.564 | 68.087 | 1.00 | 21.87 | B | C |
| ATOM | 9792 | CB | ALA | 499 | 107.577 | 61.858 | 67.391 | 1.00 | 21.73 | B | C |
| ATOM | 9793 | C | ALA | 499 | 106.859 | 59.520 | 67.822 | 1.00 | 23.85 | B | C |
| ATOM | 9794 | O | ALA | 499 | 106.279 | 58.961 | 68.758 | 1.00 | 25.77 | B | O |
| ATOM | 9795 | N | LEU | 500 | 106.588 | 59.262 | 66.546 | 1.00 | 23.83 | B | N |
| ATOM | 9796 | CA | LEU | 500 | 105.568 | 58.286 | 66.176 | 1.00 | 24.31 | B | C |
| ATOM | 9797 | CB | LEU | 500 | 105.642 | 57.958 | 64.678 | 1.00 | 22.08 | B | C |
| ATOM | 9798 | CG | LEU | 500 | 104.618 | 56.922 | 64.201 | 1.00 | 20.35 | B | C |
| ATOM | 9799 | CD1 | LEU | 500 | 103.200 | 57.349 | 64.570 | 1.00 | 19.30 | B | C |

| | | | | | | | | | | |
|---|---|---|---|---|---|---|---|---|---|---|
| ATOM | 9800 | CD2 | LEU | 500 | 104.744 | 56.763 | 62.721 | 1.00 19.60 | B | C |
| ATOM | 9801 | C | LEU | 500 | 105.745 | 57.009 | 66.974 | 1.00 24.37 | B | C |
| ATOM | 9802 | O | LEU | 500 | 104.777 | 56.407 | 67.437 | 1.00 24.06 | B | O |
| ATOM | 9803 | N | ASP | 501 | 106.997 | 56.601 | 67.131 | 1.00 26.06 | B | N |
| ATOM | 9804 | CA | ASP | 501 | 107.301 | 55.392 | 67.868 | 1.00 26.81 | B | C |
| ATOM | 9805 | CB | ASP | 501 | 108.793 | 55.120 | 67.844 | 1.00 25.74 | B | C |
| ATOM | 9806 | CG | ASP | 501 | 109.145 | 53.848 | 68.556 | 1.00 26.66 | B | C |
| ATOM | 9807 | OD1 | ASP | 501 | 108.621 | 52.789 | 68.164 | 1.00 29.87 | B | O |
| ATOM | 9808 | OD2 | ASP | 501 | 109.939 | 53.901 | 69.512 | 1.00 30.35 | B | O |
| ATOM | 9809 | C | ASP | 501 | 106.827 | 55.484 | 69.309 | 1.00 27.60 | B | C |
| ATOM | 9810 | O | ASP | 501 | 106.296 | 54.520 | 69.855 | 1.00 27.99 | B | O |
| ATOM | 9811 | N | LYS | 502 | 107.011 | 56.645 | 69.924 | 1.00 28.69 | B | N |
| ATOM | 9812 | CA | LYS | 502 | 106.591 | 56.819 | 71.301 | 1.00 31.12 | B | C |
| ATOM | 9813 | CB | LYS | 502 | 107.034 | 58.184 | 71.834 | 1.00 33.97 | B | C |
| ATOM | 9814 | CG | LYS | 502 | 106.507 | 58.484 | 73.239 | 1.00 35.56 | B | C |
| ATOM | 9815 | CD | LYS | 502 | 106.991 | 59.822 | 73.766 | 1.00 36.56 | B | C |
| ATOM | 9816 | CE | LYS | 502 | 106.308 | 60.162 | 75.083 | 1.00 37.47 | B | C |
| ATOM | 9817 | NZ | LYS | 502 | 106.514 | 59.098 | 76.104 | 1.00 38.22 | B | N |
| ATOM | 9818 | C | LYS | 502 | 105.080 | 56.679 | 71.426 | 1.00 31.95 | B | C |
| ATOM | 9819 | O | LYS | 502 | 104.592 | 55.937 | 72.276 | 1.00 33.49 | B | O |
| ATOM | 9820 | N | MET | 503 | 104.338 | 57.380 | 70.574 | 1.00 32.49 | B | N |
| ATOM | 9821 | CA | MET | 503 | 102.881 | 57.307 | 70.624 | 1.00 33.25 | B | C |
| ATOM | 9822 | CB | MET | 503 | 102.254 | 58.342 | 69.690 | 1.00 35.92 | B | C |
| ATOM | 9823 | CG | MET | 503 | 102.518 | 59.768 | 70.131 | 1.00 42.44 | B | C |
| ATOM | 9824 | SD | MET | 503 | 101.702 | 60.993 | 69.105 | 1.00 52.16 | B | S |
| ATOM | 9825 | CE | MET | 503 | 100.419 | 61.581 | 70.243 | 1.00 50.62 | B | C |
| ATOM | 9826 | C | MET | 503 | 102.361 | 55.927 | 70.279 | 1.00 31.30 | B | C |
| ATOM | 9827 | O | MET | 503 | 101.476 | 55.413 | 70.954 | 1.00 31.92 | B | O |
| ATOM | 9828 | N | LEU | 504 | 102.914 | 55.318 | 69.238 | 1.00 30.00 | B | N |
| ATOM | 9829 | CA | LEU | 504 | 102.471 | 53.993 | 68.836 | 1.00 29.48 | B | C |
| ATOM | 9830 | CB | LEU | 504 | 103.276 | 53.517 | 67.624 | 1.00 28.63 | B | C |
| ATOM | 9831 | CG | LEU | 504 | 102.517 | 53.477 | 66.290 | 1.00 29.55 | B | C |
| ATOM | 9832 | CD1 | LEU | 504 | 101.696 | 54.750 | 66.106 | 1.00 28.10 | B | C |
| ATOM | 9833 | CD2 | LEU | 504 | 103.508 | 53.300 | 65.143 | 1.00 27.73 | B | C |
| ATOM | 9834 | C | LEU | 504 | 102.581 | 52.998 | 69.986 | 1.00 29.56 | B | C |
| ATOM | 9835 | O | LEU | 504 | 101.880 | 51.991 | 70.016 | 1.00 27.71 | B | O |
| ATOM | 9836 | N | GLN | 505 | 103.458 | 53.291 | 70.938 | 1.00 31.52 | B | N |
| ATOM | 9837 | CA | GLN | 505 | 103.641 | 52.425 | 72.096 | 1.00 33.96 | B | C |
| ATOM | 9838 | CB | GLN | 505 | 104.829 | 52.915 | 72.927 | 1.00 36.96 | B | C |
| ATOM | 9839 | CG | GLN | 505 | 106.167 | 52.836 | 72.200 | 1.00 42.44 | B | C |
| ATOM | 9840 | CD | GLN | 505 | 106.652 | 51.408 | 71.996 | 1.00 43.93 | B | C |
| ATOM | 9841 | OE1 | GLN | 505 | 107.079 | 50.746 | 72.943 | 1.00 45.80 | B | O |
| ATOM | 9842 | NE2 | GLN | 505 | 106.581 | 50.925 | 70.758 | 1.00 45.49 | B | N |
| ATOM | 9843 | C | GLN | 505 | 102.375 | 52.393 | 72.960 | 1.00 33.38 | B | C |
| ATOM | 9844 | O | GLN | 505 | 102.104 | 51.400 | 73.634 | 1.00 32.77 | B | O |
| ATOM | 9845 | N | ASN | 506 | 101.607 | 53.482 | 72.928 | 1.00 32.89 | B | N |
| ATOM | 9846 | CA | ASN | 506 | 100.362 | 53.590 | 73.694 | 1.00 32.38 | B | C |
| ATOM | 9847 | CB | ASN | 506 | 99.997 | 55.062 | 73.937 | 1.00 35.05 | B | C |
| ATOM | 9848 | CG | ASN | 506 | 101.108 | 55.848 | 74.629 | 1.00 39.34 | B | C |

| | | | | | | | | | | |
|---|---|---|---|---|---|---|---|---|---|---|
| ATOM | 9849 | OD1 | ASN | 506 | 101.426 | 55.608 | 75.799 | 1.00 | 41.09 | B | O |
| ATOM | 9850 | ND2 | ASN | 506 | 101.703 | 56.796 | 73.903 | 1.00 | 39.00 | B | N |
| ATOM | 9851 | C | ASN | 506 | 99.208 | 52.933 | 72.936 | 1.00 | 30.32 | B | C |
| ATOM | 9852 | O | ASN | 506 | 98.058 | 52.995 | 73.377 | 1.00 | 30.93 | B | O |
| ATOM | 9853 | N | VAL | 507 | 99.516 | 52.305 | 71.803 | 1.00 | 26.94 | B | N |
| ATOM | 9854 | CA | VAL | 507 | 98.497 | 51.664 | 70.974 | 1.00 | 25.15 | B | C |
| ATOM | 9855 | CB | VAL | 507 | 98.456 | 52.293 | 69.545 | 1.00 | 23.88 | B | C |
| ATOM | 9856 | CG1 | VAL | 507 | 97.287 | 51.730 | 68.755 | 1.00 | 21.31 | B | C |
| ATOM | 9857 | CG2 | VAL | 507 | 98.344 | 53.811 | 69.633 | 1.00 | 22.11 | B | C |
| ATOM | 9858 | C | VAL | 507 | 98.717 | 50.164 | 70.825 | 1.00 | 25.62 | B | C |
| ATOM | 9859 | O | VAL | 507 | 99.838 | 49.676 | 70.945 | 1.00 | 26.78 | B | O |
| ATOM | 9860 | N | GLN | 508 | 97.639 | 49.432 | 70.567 | 1.00 | 25.89 | B | N |
| ATOM | 9861 | CA | GLN | 508 | 97.730 | 47.992 | 70.381 | 1.00 | 25.14 | B | C |
| ATOM | 9862 | CB | GLN | 508 | 96.486 | 47.281 | 70.917 | 1.00 | 27.32 | B | C |
| ATOM | 9863 | CG | GLN | 508 | 96.322 | 47.397 | 72.422 | 1.00 | 29.65 | B | C |
| ATOM | 9864 | CD | GLN | 508 | 95.190 | 46.543 | 72.958 | 1.00 | 30.81 | B | C |
| ATOM | 9865 | OE1 | GLN | 508 | 95.208 | 45.312 | 72.836 | 1.00 | 31.32 | B | O |
| ATOM | 9866 | NE2 | GLN | 508 | 94.199 | 47.190 | 73.561 | 1.00 | 29.92 | B | N |
| ATOM | 9867 | C | GLN | 508 | 97.869 | 47.740 | 68.899 | 1.00 | 23.65 | B | C |
| ATOM | 9868 | O | GLN | 508 | 96.944 | 47.277 | 68.241 | 1.00 | 22.60 | B | O |
| ATOM | 9869 | N | MET | 509 | 99.046 | 48.063 | 68.385 | 1.00 | 23.78 | B | N |
| ATOM | 9870 | CA | MET | 509 | 99.347 | 47.895 | 66.980 | 1.00 | 23.48 | B | C |
| ATOM | 9871 | CB | MET | 509 | 100.667 | 48.578 | 66.655 | 1.00 | 23.41 | B | C |
| ATOM | 9872 | CG | MET | 509 | 100.586 | 50.070 | 66.782 | 1.00 | 26.19 | B | C |
| ATOM | 9873 | SD | MET | 509 | 99.279 | 50.681 | 65.719 | 1.00 | 28.03 | B | S |
| ATOM | 9874 | CE | MET | 509 | 100.207 | 50.994 | 64.209 | 1.00 | 25.78 | B | C |
| ATOM | 9875 | C | MET | 509 | 99.425 | 46.440 | 66.579 | 1.00 | 23.44 | B | C |
| ATOM | 9876 | O | MET | 509 | 99.902 | 45.599 | 67.343 | 1.00 | 24.15 | B | O |
| ATOM | 9877 | N | PRO | 510 | 98.951 | 46.121 | 65.365 | 1.00 | 22.69 | B | N |
| ATOM | 9878 | CD | PRO | 510 | 98.308 | 47.027 | 64.395 | 1.00 | 22.87 | B | C |
| ATOM | 9879 | CA | PRO | 510 | 98.974 | 44.751 | 64.854 | 1.00 | 21.97 | B | C |
| ATOM | 9880 | CB | PRO | 510 | 97.987 | 44.807 | 63.701 | 1.00 | 22.62 | B | C |
| ATOM | 9881 | CG | PRO | 510 | 98.248 | 46.171 | 63.141 | 1.00 | 22.72 | B | C |
| ATOM | 9882 | C | PRO | 510 | 100.381 | 44.434 | 64.379 | 1.00 | 21.20 | B | C |
| ATOM | 9883 | O | PRO | 510 | 101.249 | 45.301 | 64.353 | 1.00 | 19.97 | B | O |
| ATOM | 9884 | N | SER | 511 | 100.605 | 43.188 | 63.997 | 1.00 | 22.07 | B | N |
| ATOM | 9885 | CA | SER | 511 | 101.916 | 42.782 | 63.521 | 1.00 | 23.02 | B | C |
| ATOM | 9886 | CB | SER | 511 | 102.481 | 41.654 | 64.392 | 1.00 | 23.03 | B | C |
| ATOM | 9887 | OG | SER | 511 | 101.653 | 40.500 | 64.358 | 1.00 | 26.12 | B | O |
| ATOM | 9888 | C | SER | 511 | 101.773 | 42.299 | 62.094 | 1.00 | 23.35 | B | C |
| ATOM | 9889 | O | SER | 511 | 100.659 | 42.168 | 61.583 | 1.00 | 24.92 | B | O |
| ATOM | 9890 | N | LYS | 512 | 102.906 | 42.035 | 61.458 | 1.00 | 22.83 | B | N |
| ATOM | 9891 | CA | LYS | 512 | 102.916 | 41.556 | 60.094 | 1.00 | 22.46 | B | C |
| ATOM | 9892 | CB | LYS | 512 | 103.490 | 42.615 | 59.168 | 1.00 | 21.81 | B | C |
| ATOM | 9893 | CG | LYS | 512 | 103.494 | 42.209 | 57.705 | 1.00 | 23.24 | B | C |
| ATOM | 9894 | CD | LYS | 512 | 103.820 | 43.411 | 56.851 | 1.00 | 24.28 | B | C |
| ATOM | 9895 | CE | LYS | 512 | 103.824 | 43.080 | 55.393 | 1.00 | 23.13 | B | C |
| ATOM | 9896 | NZ | LYS | 512 | 104.160 | 44.299 | 54.622 | 1.00 | 24.52 | B | N |
| ATOM | 9897 | C | LYS | 512 | 103.742 | 40.289 | 59.993 | 1.00 | 22.87 | B | C |

| ATOM | 9898 | O   | LYS | 512 | 104.803 | 40.180 | 60.585 | 1.00 | 23.26 | B | O |
| --- | --- | --- | --- | --- | --- | --- | --- | --- | --- | --- | --- |
| ATOM | 9899 | N   | LYS | 513 | 103.235 | 39.331 | 59.235 | 1.00 | 24.10 | B | N |
| ATOM | 9900 | CA  | LYS | 513 | 103.910 | 38.069 | 59.039 | 1.00 | 24.49 | B | C |
| ATOM | 9901 | CB  | LYS | 513 | 103.046 | 36.923 | 59.566 | 1.00 | 25.52 | B | C |
| ATOM | 9902 | CG  | LYS | 513 | 103.522 | 35.537 | 59.148 | 1.00 | 26.69 | B | C |
| ATOM | 9903 | CD  | LYS | 513 | 102.493 | 34.471 | 59.522 | 1.00 | 30.85 | B | C |
| ATOM | 9904 | CE  | LYS | 513 | 102.805 | 33.124 | 58.866 | 1.00 | 33.37 | B | C |
| ATOM | 9905 | NZ  | LYS | 513 | 104.131 | 32.573 | 59.287 | 1.00 | 36.04 | B | N |
| ATOM | 9906 | C   | LYS | 513 | 104.143 | 37.888 | 57.552 | 1.00 | 25.44 | B | C |
| ATOM | 9907 | O   | LYS | 513 | 103.196 | 37.871 | 56.763 | 1.00 | 27.00 | B | O |
| ATOM | 9908 | N   | LEU | 514 | 105.409 | 37.771 | 57.171 | 1.00 | 24.62 | B | N |
| ATOM | 9909 | CA  | LEU | 514 | 105.775 | 37.561 | 55.783 | 1.00 | 22.99 | B | C |
| ATOM | 9910 | CB  | LEU | 514 | 106.870 | 38.536 | 55.380 | 1.00 | 22.15 | B | C |
| ATOM | 9911 | CG  | LEU | 514 | 107.307 | 38.465 | 53.925 | 1.00 | 21.19 | B | C |
| ATOM | 9912 | CD1 | LEU | 514 | 106.125 | 38.790 | 53.029 | 1.00 | 19.85 | B | C |
| ATOM | 9913 | CD2 | LEU | 514 | 108.438 | 39.435 | 53.701 | 1.00 | 18.42 | B | C |
| ATOM | 9914 | C   | LEU | 514 | 106.292 | 36.132 | 55.708 | 1.00 | 24.30 | B | C |
| ATOM | 9915 | O   | LEU | 514 | 107.123 | 35.725 | 56.519 | 1.00 | 24.87 | B | O |
| ATOM | 9916 | N   | ASP | 515 | 105.804 | 35.361 | 54.747 | 1.00 | 25.31 | B | N |
| ATOM | 9917 | CA  | ASP | 515 | 106.233 | 33.975 | 54.634 | 1.00 | 26.30 | B | C |
| ATOM | 9918 | CB  | ASP | 515 | 105.599 | 33.156 | 55.757 | 1.00 | 28.58 | B | C |
| ATOM | 9919 | CG  | ASP | 515 | 106.403 | 31.929 | 56.108 | 1.00 | 30.08 | B | C |
| ATOM | 9920 | OD1 | ASP | 515 | 107.209 | 31.474 | 55.272 | 1.00 | 31.89 | B | O |
| ATOM | 9921 | OD2 | ASP | 515 | 106.216 | 31.409 | 57.224 | 1.00 | 33.36 | B | O |
| ATOM | 9922 | C   | ASP | 515 | 105.805 | 33.414 | 53.282 | 1.00 | 26.17 | B | C |
| ATOM | 9923 | O   | ASP | 515 | 105.343 | 34.157 | 52.417 | 1.00 | 26.57 | B | O |
| ATOM | 9924 | N   | PHE | 516 | 105.940 | 32.104 | 53.103 | 1.00 | 25.46 | B | N |
| ATOM | 9925 | CA  | PHE | 516 | 105.571 | 31.496 | 51.838 | 1.00 | 25.82 | B | C |
| ATOM | 9926 | CB  | PHE | 516 | 106.792 | 31.384 | 50.930 | 1.00 | 23.83 | B | C |
| ATOM | 9927 | CG  | PHE | 516 | 107.811 | 30.395 | 51.413 | 1.00 | 22.29 | B | C |
| ATOM | 9928 | CD1 | PHE | 516 | 108.896 | 30.808 | 52.176 | 1.00 | 22.68 | B | C |
| ATOM | 9929 | CD2 | PHE | 516 | 107.678 | 29.042 | 51.119 | 1.00 | 21.58 | B | C |
| ATOM | 9930 | CE1 | PHE | 516 | 109.836 | 29.885 | 52.642 | 1.00 | 21.89 | B | C |
| ATOM | 9931 | CE2 | PHE | 516 | 108.609 | 28.113 | 51.579 | 1.00 | 21.19 | B | C |
| ATOM | 9932 | CZ  | PHE | 516 | 109.689 | 28.536 | 52.342 | 1.00 | 20.70 | B | C |
| ATOM | 9933 | C   | PHE | 516 | 104.955 | 30.117 | 51.954 | 1.00 | 26.95 | B | C |
| ATOM | 9934 | O   | PHE | 516 | 105.063 | 29.452 | 52.980 | 1.00 | 28.94 | B | O |
| ATOM | 9935 | N   | ILE | 517 | 104.307 | 29.707 | 50.872 | 1.00 | 27.35 | B | N |
| ATOM | 9936 | CA  | ILE | 517 | 103.697 | 28.398 | 50.755 | 1.00 | 28.12 | B | C |
| ATOM | 9937 | CB  | ILE | 517 | 102.155 | 28.470 | 50.729 | 1.00 | 26.53 | B | C |
| ATOM | 9938 | CG2 | ILE | 517 | 101.645 | 29.073 | 52.016 | 1.00 | 27.39 | B | C |
| ATOM | 9939 | CG1 | ILE | 517 | 101.682 | 29.296 | 49.537 | 1.00 | 27.43 | B | C |
| ATOM | 9940 | CD1 | ILE | 517 | 100.175 | 29.486 | 49.486 | 1.00 | 26.37 | B | C |
| ATOM | 9941 | C   | ILE | 517 | 104.202 | 27.896 | 49.411 | 1.00 | 30.13 | B | C |
| ATOM | 9942 | O   | ILE | 517 | 104.575 | 28.697 | 48.551 | 1.00 | 29.21 | B | O |
| ATOM | 9943 | N   | ILE | 518 | 104.239 | 26.581 | 49.228 | 1.00 | 33.16 | B | N |
| ATOM | 9944 | CA  | ILE | 518 | 104.709 | 26.029 | 47.969 | 1.00 | 36.01 | B | C |
| ATOM | 9945 | CB  | ILE | 518 | 105.680 | 24.867 | 48.190 | 1.00 | 36.84 | B | C |
| ATOM | 9946 | CG2 | ILE | 518 | 106.133 | 24.311 | 46.845 | 1.00 | 36.94 | B | C |

| ATOM | 9947 | CG1 | ILE | 518 | 106.884 | 25.349 | 49.000 | 1.00 | 38.21 | B | C |
|------|------|-----|-----|-----|---------|--------|--------|------|-------|---|---|
| ATOM | 9948 | CD1 | ILE | 518 | 107.976 | 24.296 | 49.169 | 1.00 | 40.77 | B | C |
| ATOM | 9949 | C | ILE | 518 | 103.558 | 25.534 | 47.114 | 1.00 | 37.38 | B | C |
| ATOM | 9950 | O | ILE | 518 | 102.581 | 25.000 | 47.624 | 1.00 | 38.97 | B | O |
| ATOM | 9951 | N | LEU | 519 | 103.679 | 25.730 | 45.808 | 1.00 | 39.11 | B | N |
| ATOM | 9952 | CA | LEU | 519 | 102.663 | 25.294 | 44.863 | 1.00 | 40.68 | B | C |
| ATOM | 9953 | CB | LEU | 519 | 101.753 | 26.461 | 44.474 | 1.00 | 39.71 | B | C |
| ATOM | 9954 | CG | LEU | 519 | 100.989 | 27.144 | 45.612 | 1.00 | 39.82 | B | C |
| ATOM | 9955 | CD1 | LEU | 519 | 100.051 | 28.205 | 45.045 | 1.00 | 39.14 | B | C |
| ATOM | 9956 | CD2 | LEU | 519 | 100.194 | 26.107 | 46.381 | 1.00 | 40.51 | B | C |
| ATOM | 9957 | C | LEU | 519 | 103.388 | 24.763 | 43.637 | 1.00 | 42.22 | B | C |
| ATOM | 9958 | O | LEU | 519 | 104.028 | 25.524 | 42.910 | 1.00 | 42.60 | B | O |
| ATOM | 9959 | N | ASN | 520 | 103.299 | 23.453 | 43.419 | 1.00 | 43.53 | B | N |
| ATOM | 9960 | CA | ASN | 520 | 103.963 | 22.824 | 42.285 | 1.00 | 44.57 | B | C |
| ATOM | 9961 | CB | ASN | 520 | 103.385 | 23.337 | 40.964 | 1.00 | 46.39 | B | C |
| ATOM | 9962 | CG | ASN | 520 | 102.045 | 22.726 | 40.639 | 1.00 | 48.97 | B | C |
| ATOM | 9963 | OD1 | ASN | 520 | 101.168 | 22.634 | 41.498 | 1.00 | 50.54 | B | O |
| ATOM | 9964 | ND2 | ASN | 520 | 101.871 | 22.312 | 39.386 | 1.00 | 50.46 | B | N |
| ATOM | 9965 | C | ASN | 520 | 105.452 | 23.114 | 42.316 | 1.00 | 44.13 | B | C |
| ATOM | 9966 | O | ASN | 520 | 106.004 | 23.637 | 41.348 | 1.00 | 44.64 | B | O |
| ATOM | 9967 | N | GLU | 521 | 106.097 | 22.791 | 43.431 | 1.00 | 44.10 | B | N |
| ATOM | 9968 | CA | GLU | 521 | 107.536 | 23.012 | 43.562 | 1.00 | 45.15 | B | C |
| ATOM | 9969 | CB | GLU | 521 | 108.272 | 22.387 | 42.368 | 1.00 | 49.07 | B | C |
| ATOM | 9970 | CG | GLU | 521 | 109.775 | 22.642 | 42.339 | 1.00 | 54.49 | B | C |
| ATOM | 9971 | CD | GLU | 521 | 110.401 | 22.274 | 41.004 | 1.00 | 58.04 | B | C |
| ATOM | 9972 | OE1 | GLU | 521 | 110.307 | 21.091 | 40.597 | 1.00 | 59.07 | B | O |
| ATOM | 9973 | OE2 | GLU | 521 | 110.986 | 23.176 | 40.361 | 1.00 | 59.78 | B | O |
| ATOM | 9974 | C | GLU | 521 | 107.922 | 24.486 | 43.661 | 1.00 | 42.18 | B | C |
| ATOM | 9975 | O | GLU | 521 | 109.034 | 24.810 | 44.072 | 1.00 | 42.85 | B | O |
| ATOM | 9976 | N | THR | 522 | 107.014 | 25.378 | 43.283 | 1.00 | 38.59 | B | N |
| ATOM | 9977 | CA | THR | 522 | 107.314 | 26.800 | 43.333 | 1.00 | 34.63 | B | C |
| ATOM | 9978 | CB | THR | 522 | 106.605 | 27.566 | 42.198 | 1.00 | 34.21 | B | C |
| ATOM | 9979 | OG1 | THR | 522 | 107.109 | 27.115 | 40.936 | 1.00 | 34.20 | B | O |
| ATOM | 9980 | CG2 | THR | 522 | 106.866 | 29.057 | 42.318 | 1.00 | 33.69 | B | C |
| ATOM | 9981 | C | THR | 522 | 106.959 | 27.441 | 44.664 | 1.00 | 32.83 | B | C |
| ATOM | 9982 | O | THR | 522 | 106.028 | 27.027 | 45.350 | 1.00 | 32.75 | B | O |
| ATOM | 9983 | N | LYS | 523 | 107.727 | 28.464 | 45.011 | 1.00 | 31.06 | B | N |
| ATOM | 9984 | CA | LYS | 523 | 107.559 | 29.206 | 46.245 | 1.00 | 29.30 | B | C |
| ATOM | 9985 | CB | LYS | 523 | 108.940 | 29.490 | 46.838 | 1.00 | 29.00 | B | C |
| ATOM | 9986 | CG | LYS | 523 | 108.934 | 30.329 | 48.089 | 1.00 | 31.42 | B | C |
| ATOM | 9987 | CD | LYS | 523 | 110.344 | 30.567 | 48.607 | 1.00 | 32.07 | B | C |
| ATOM | 9988 | CE | LYS | 523 | 111.045 | 29.265 | 48.943 | 1.00 | 33.13 | B | C |
| ATOM | 9989 | NZ | LYS | 523 | 112.388 | 29.512 | 49.545 | 1.00 | 35.72 | B | N |
| ATOM | 9990 | C | LYS | 523 | 106.819 | 30.519 | 45.984 | 1.00 | 28.56 | B | C |
| ATOM | 9991 | O | LYS | 523 | 107.256 | 31.335 | 45.173 | 1.00 | 29.36 | B | O |
| ATOM | 9992 | N | PHE | 524 | 105.692 | 30.711 | 46.661 | 1.00 | 25.40 | B | N |
| ATOM | 9993 | CA | PHE | 524 | 104.912 | 31.934 | 46.517 | 1.00 | 22.61 | B | C |
| ATOM | 9994 | CB | PHE | 524 | 103.529 | 31.637 | 45.929 | 1.00 | 22.69 | B | C |
| ATOM | 9995 | CG | PHE | 524 | 103.565 | 31.136 | 44.516 | 1.00 | 21.75 | B | C |

| ATOM | 9996 | CD1 | PHE | 524 | 103.626 | 29.773 | 44.247 | 1.00 | 22.19 | B | C |
|---|---|---|---|---|---|---|---|---|---|---|---|
| ATOM | 9997 | CD2 | PHE | 524 | 103.541 | 32.031 | 43.448 | 1.00 | 22.40 | B | C |
| ATOM | 9998 | CE1 | PHE | 524 | 103.662 | 29.306 | 42.935 | 1.00 | 22.45 | B | C |
| ATOM | 9999 | CE2 | PHE | 524 | 103.576 | 31.579 | 42.131 | 1.00 | 22.01 | B | C |
| ATOM | 10000 | CZ | PHE | 524 | 103.637 | 30.213 | 41.871 | 1.00 | 22.70 | B | C |
| ATOM | 10001 | C | PHE | 524 | 104.765 | 32.593 | 47.890 | 1.00 | 20.73 | B | C |
| ATOM | 10002 | O | PHE | 524 | 104.416 | 31.941 | 48.875 | 1.00 | 19.19 | B | O |
| ATOM | 10003 | N | TRP | 525 | 105.016 | 33.892 | 47.950 | 1.00 | 18.35 | B | N |
| ATOM | 10004 | CA | TRP | 525 | 104.950 | 34.600 | 49.216 | 1.00 | 17.31 | B | C |
| ATOM | 10005 | CB | TRP | 525 | 106.059 | 35.646 | 49.274 | 1.00 | 16.81 | B | C |
| ATOM | 10006 | CG | TRP | 525 | 107.442 | 35.092 | 49.191 | 1.00 | 16.14 | B | C |
| ATOM | 10007 | CD2 | TRP | 525 | 108.393 | 35.031 | 50.253 | 1.00 | 14.70 | B | C |
| ATOM | 10008 | CE2 | TRP | 525 | 109.574 | 34.454 | 49.726 | 1.00 | 16.70 | B | C |
| ATOM | 10009 | CE3 | TRP | 525 | 108.366 | 35.411 | 51.602 | 1.00 | 14.22 | B | C |
| ATOM | 10010 | CD1 | TRP | 525 | 108.062 | 34.560 | 48.086 | 1.00 | 15.59 | B | C |
| ATOM | 10011 | NE1 | TRP | 525 | 109.344 | 34.176 | 48.403 | 1.00 | 14.99 | B | N |
| ATOM | 10012 | CZ2 | TRP | 525 | 110.722 | 34.247 | 50.508 | 1.00 | 17.11 | B | C |
| ATOM | 10013 | CZ3 | TRP | 525 | 109.506 | 35.204 | 52.381 | 1.00 | 14.40 | B | C |
| ATOM | 10014 | CH2 | TRP | 525 | 110.668 | 34.627 | 51.829 | 1.00 | 15.16 | B | C |
| ATOM | 10015 | C | TRP | 525 | 103.630 | 35.280 | 49.554 | 1.00 | 17.78 | B | C |
| ATOM | 10016 | O | TRP | 525 | 102.880 | 35.719 | 48.675 | 1.00 | 17.96 | B | O |
| ATOM | 10017 | N | TYR | 526 | 103.361 | 35.368 | 50.849 | 1.00 | 16.97 | B | N |
| ATOM | 10018 | CA | TYR | 526 | 102.165 | 36.034 | 51.341 | 1.00 | 18.30 | B | C |
| ATOM | 10019 | CB | TYR | 526 | 101.053 | 35.030 | 51.652 | 1.00 | 19.10 | B | C |
| ATOM | 10020 | CG | TYR | 526 | 101.369 | 34.076 | 52.778 | 1.00 | 21.69 | B | C |
| ATOM | 10021 | CD1 | TYR | 526 | 101.132 | 34.422 | 54.110 | 1.00 | 23.52 | B | C |
| ATOM | 10022 | CE1 | TYR | 526 | 101.416 | 33.531 | 55.146 | 1.00 | 25.02 | B | C |
| ATOM | 10023 | CD2 | TYR | 526 | 101.902 | 32.817 | 52.509 | 1.00 | 24.93 | B | C |
| ATOM | 10024 | CE2 | TYR | 526 | 102.189 | 31.922 | 53.527 | 1.00 | 26.65 | B | C |
| ATOM | 10025 | CZ | TYR | 526 | 101.945 | 32.280 | 54.840 | 1.00 | 28.49 | B | C |
| ATOM | 10026 | OH | TYR | 526 | 102.235 | 31.370 | 55.830 | 1.00 | 31.26 | B | O |
| ATOM | 10027 | C | TYR | 526 | 102.540 | 36.770 | 52.609 | 1.00 | 16.76 | B | C |
| ATOM | 10028 | O | TYR | 526 | 103.600 | 36.536 | 53.187 | 1.00 | 15.11 | B | O |
| ATOM | 10029 | N | GLN | 527 | 101.676 | 37.680 | 53.024 | 1.00 | 17.09 | B | N |
| ATOM | 10030 | CA | GLN | 527 | 101.901 | 38.417 | 54.250 | 1.00 | 17.75 | B | C |
| ATOM | 10031 | CB | GLN | 527 | 102.417 | 39.833 | 53.978 | 1.00 | 16.32 | B | C |
| ATOM | 10032 | CG | GLN | 527 | 101.462 | 40.740 | 53.234 | 1.00 | 15.60 | B | C |
| ATOM | 10033 | CD | GLN | 527 | 101.935 | 42.188 | 53.213 | 1.00 | 16.43 | B | C |
| ATOM | 10034 | OE1 | GLN | 527 | 103.016 | 42.502 | 52.707 | 1.00 | 13.50 | B | O |
| ATOM | 10035 | NE2 | GLN | 527 | 101.121 | 43.079 | 53.771 | 1.00 | 15.38 | B | N |
| ATOM | 10036 | C | GLN | 527 | 100.556 | 38.477 | 54.930 | 1.00 | 19.32 | B | C |
| ATOM | 10037 | O | GLN | 527 | 99.519 | 38.439 | 54.269 | 1.00 | 19.02 | B | O |
| ATOM | 10038 | N | MET | 528 | 100.575 | 38.532 | 56.253 | 1.00 | 20.93 | B | N |
| ATOM | 10039 | CA | MET | 528 | 99.346 | 38.608 | 57.018 | 1.00 | 21.02 | B | C |
| ATOM | 10040 | CB | MET | 528 | 99.076 | 37.295 | 57.748 | 1.00 | 21.14 | B | C |
| ATOM | 10041 | CG | MET | 528 | 98.575 | 36.178 | 56.859 | 1.00 | 23.54 | B | C |
| ATOM | 10042 | SD | MET | 528 | 98.325 | 34.650 | 57.776 | 1.00 | 23.43 | B | S |
| ATOM | 10043 | CE | MET | 528 | 96.628 | 34.772 | 58.155 | 1.00 | 26.01 | B | C |
| ATOM | 10044 | C | MET | 528 | 99.458 | 39.720 | 58.033 | 1.00 | 20.94 | B | C |

FIG. 4-206 (Continued)

| | | | | | | | | | | | |
|---|---|---|---|---|---|---|---|---|---|---|---|
| ATOM | 10045 | O | MET | 528 | 100.471 | 39.845 | 58.720 | 1.00 | 21.07 | B | O |
| ATOM | 10046 | N | ILE | 529 | 98.432 | 40.554 | 58.100 | 1.00 | 19.01 | B | N |
| ATOM | 10047 | CA | ILE | 529 | 98.428 | 41.614 | 59.082 | 1.00 | 18.89 | B | C |
| ATOM | 10048 | CB | ILE | 529 | 97.718 | 42.860 | 58.540 | 1.00 | 16.80 | B | C |
| ATOM | 10049 | CG2 | ILE | 529 | 97.656 | 43.937 | 59.615 | 1.00 | 13.98 | B | C |
| ATOM | 10050 | CG1 | ILE | 529 | 98.469 | 43.368 | 57.296 | 1.00 | 15.06 | B | C |
| ATOM | 10051 | CD1 | ILE | 529 | 99.934 | 43.701 | 57.537 | 1.00 | 11.03 | B | C |
| ATOM | 10052 | C | ILE | 529 | 97.656 | 40.969 | 60.225 | 1.00 | 20.15 | B | C |
| ATOM | 10053 | O | ILE | 529 | 96.457 | 40.720 | 60.124 | 1.00 | 20.94 | B | O |
| ATOM | 10054 | N | LEU | 530 | 98.359 | 40.653 | 61.302 | 1.00 | 21.19 | B | N |
| ATOM | 10055 | CA | LEU | 530 | 97.717 | 39.985 | 62.420 | 1.00 | 21.61 | B | C |
| ATOM | 10056 | CB | LEU | 530 | 98.649 | 38.907 | 62.976 | 1.00 | 19.85 | B | C |
| ATOM | 10057 | CG | LEU | 530 | 99.086 | 37.875 | 61.931 | 1.00 | 19.34 | B | C |
| ATOM | 10058 | CD1 | LEU | 530 | 100.238 | 37.027 | 62.461 | 1.00 | 20.33 | B | C |
| ATOM | 10059 | CD2 | LEU | 530 | 97.897 | 37.010 | 61.562 | 1.00 | 19.04 | B | C |
| ATOM | 10060 | C | LEU | 530 | 97.294 | 40.930 | 63.521 | 1.00 | 22.34 | B | C |
| ATOM | 10061 | O | LEU | 530 | 98.006 | 41.878 | 63.854 | 1.00 | 23.45 | B | O |
| ATOM | 10062 | N | PRO | 531 | 96.104 | 40.697 | 64.088 | 1.00 | 23.19 | B | N |
| ATOM | 10063 | CD | PRO | 531 | 95.105 | 39.684 | 63.711 | 1.00 | 22.71 | B | C |
| ATOM | 10064 | CA | PRO | 531 | 95.600 | 41.545 | 65.169 | 1.00 | 24.33 | B | C |
| ATOM | 10065 | CB | PRO | 531 | 94.188 | 41.002 | 65.404 | 1.00 | 22.74 | B | C |
| ATOM | 10066 | CG | PRO | 531 | 94.276 | 39.588 | 64.967 | 1.00 | 23.03 | B | C |
| ATOM | 10067 | C | PRO | 531 | 96.490 | 41.438 | 66.407 | 1.00 | 25.18 | B | C |
| ATOM | 10068 | O | PRO | 531 | 97.244 | 40.478 | 66.562 | 1.00 | 24.64 | B | O |
| ATOM | 10069 | N | PRO | 532 | 96.424 | 42.433 | 67.300 | 1.00 | 26.64 | B | N |
| ATOM | 10070 | CD | PRO | 532 | 95.502 | 43.581 | 67.326 | 1.00 | 25.36 | B | C |
| ATOM | 10071 | CA | PRO | 532 | 97.246 | 42.397 | 68.513 | 1.00 | 27.91 | B | C |
| ATOM | 10072 | CB | PRO | 532 | 96.868 | 43.698 | 69.216 | 1.00 | 27.08 | B | C |
| ATOM | 10073 | CG | PRO | 532 | 95.443 | 43.897 | 68.793 | 1.00 | 26.25 | B | C |
| ATOM | 10074 | C | PRO | 532 | 96.945 | 41.160 | 69.369 | 1.00 | 29.25 | B | C |
| ATOM | 10075 | O | PRO | 532 | 95.865 | 40.579 | 69.279 | 1.00 | 29.62 | B | O |
| ATOM | 10076 | N | HIS | 533 | 97.909 | 40.756 | 70.187 | 1.00 | 30.65 | B | N |
| ATOM | 10077 | CA | HIS | 533 | 97.738 | 39.602 | 71.061 | 1.00 | 31.99 | B | C |
| ATOM | 10078 | CB | HIS | 533 | 96.749 | 39.945 | 72.172 | 1.00 | 32.50 | B | C |
| ATOM | 10079 | CG | HIS | 533 | 96.981 | 41.293 | 72.783 | 1.00 | 35.12 | B | C |
| ATOM | 10080 | CD2 | HIS | 533 | 96.168 | 42.370 | 72.903 | 1.00 | 36.18 | B | C |
| ATOM | 10081 | ND1 | HIS | 533 | 98.181 | 41.653 | 73.358 | 1.00 | 35.49 | B | N |
| ATOM | 10082 | CE1 | HIS | 533 | 98.096 | 42.892 | 73.807 | 1.00 | 36.37 | B | C |
| ATOM | 10083 | NE2 | HIS | 533 | 96.885 | 43.350 | 73.544 | 1.00 | 37.01 | B | N |
| ATOM | 10084 | C | HIS | 533 | 97.249 | 38.382 | 70.286 | 1.00 | 33.21 | B | C |
| ATOM | 10085 | O | HIS | 533 | 96.447 | 37.590 | 70.791 | 1.00 | 32.78 | B | O |
| ATOM | 10086 | N | PHE | 534 | 97.739 | 38.243 | 69.058 | 1.00 | 33.50 | B | N |
| ATOM | 10087 | CA | PHE | 534 | 97.374 | 37.125 | 68.200 | 1.00 | 34.63 | B | C |
| ATOM | 10088 | CB | PHE | 534 | 98.283 | 37.085 | 66.970 | 1.00 | 32.35 | B | C |
| ATOM | 10089 | CG | PHE | 534 | 97.997 | 35.942 | 66.041 | 1.00 | 32.06 | B | C |
| ATOM | 10090 | CD1 | PHE | 534 | 96.790 | 35.871 | 65.354 | 1.00 | 32.10 | B | C |
| ATOM | 10091 | CD2 | PHE | 534 | 98.936 | 34.938 | 65.848 | 1.00 | 32.66 | B | C |
| ATOM | 10092 | CE1 | PHE | 534 | 96.522 | 34.819 | 64.486 | 1.00 | 31.59 | B | C |
| ATOM | 10093 | CE2 | PHE | 534 | 98.679 | 33.879 | 64.982 | 1.00 | 32.91 | B | C |

FIG. 4-207 (Continued)

| | | | | | | | | | | |
|---|---|---|---|---|---|---|---|---|---|---|
| ATOM | 10094 | CZ | PHE | 534 | 97.469 | 33.820 | 64.298 | 1.00 | 32.93 | B | C |
| ATOM | 10095 | C | PHE | 534 | 97.503 | 35.806 | 68.941 | 1.00 | 36.77 | B | C |
| ATOM | 10096 | O | PHE | 534 | 98.532 | 35.534 | 69.565 | 1.00 | 37.84 | B | O |
| ATOM | 10097 | N | ASP | 535 | 96.463 | 34.982 | 68.868 | 1.00 | 39.07 | B | N |
| ATOM | 10098 | CA | ASP | 535 | 96.480 | 33.680 | 69.523 | 1.00 | 40.37 | B | C |
| ATOM | 10099 | CB | ASP | 535 | 95.458 | 33.639 | 70.655 | 1.00 | 42.55 | B | C |
| ATOM | 10100 | CG | ASP | 535 | 95.544 | 32.363 | 71.465 | 1.00 | 45.66 | B | C |
| ATOM | 10101 | OD1 | ASP | 535 | 94.783 | 32.227 | 72.445 | 1.00 | 49.45 | B | O |
| ATOM | 10102 | OD2 | ASP | 535 | 96.372 | 31.494 | 71.125 | 1.00 | 46.59 | B | O |
| ATOM | 10103 | C | ASP | 535 | 96.159 | 32.601 | 68.503 | 1.00 | 39.36 | B | C |
| ATOM | 10104 | O | ASP | 535 | 95.047 | 32.540 | 67.996 | 1.00 | 39.17 | B | O |
| ATOM | 10105 | N | LYS | 536 | 97.135 | 31.746 | 68.216 | 1.00 | 40.23 | B | N |
| ATOM | 10106 | CA | LYS | 536 | 96.964 | 30.680 | 67.233 | 1.00 | 41.20 | B | C |
| ATOM | 10107 | CB | LYS | 536 | 98.302 | 30.001 | 66.947 | 1.00 | 42.62 | B | C |
| ATOM | 10108 | CG | LYS | 536 | 98.266 | 29.089 | 65.731 | 1.00 | 46.75 | B | C |
| ATOM | 10109 | CD | LYS | 536 | 99.657 | 28.577 | 65.355 | 1.00 | 49.06 | B | C |
| ATOM | 10110 | CE | LYS | 536 | 99.624 | 27.800 | 64.040 | 1.00 | 48.68 | B | C |
| ATOM | 10111 | NZ | LYS | 536 | 98.648 | 26.676 | 64.079 | 1.00 | 48.77 | B | N |
| ATOM | 10112 | C | LYS | 536 | 95.937 | 29.620 | 67.607 | 1.00 | 40.95 | B | C |
| ATOM | 10113 | O | LYS | 536 | 95.577 | 28.785 | 66.778 | 1.00 | 41.99 | B | O |
| ATOM | 10114 | N | SER | 537 | 95.464 | 29.649 | 68.848 | 1.00 | 40.73 | B | N |
| ATOM | 10115 | CA | SER | 537 | 94.469 | 28.681 | 69.296 | 1.00 | 40.33 | B | C |
| ATOM | 10116 | CB | SER | 537 | 94.598 | 28.438 | 70.805 | 1.00 | 40.23 | B | C |
| ATOM | 10117 | OG | SER | 537 | 94.434 | 29.636 | 71.541 | 1.00 | 40.12 | B | O |
| ATOM | 10118 | C | SER | 537 | 93.064 | 29.179 | 68.968 | 1.00 | 40.20 | B | C |
| ATOM | 10119 | O | SER | 537 | 92.103 | 28.412 | 68.977 | 1.00 | 40.87 | B | O |
| ATOM | 10120 | N | LYS | 538 | 92.951 | 30.469 | 68.674 | 1.00 | 39.23 | B | N |
| ATOM | 10121 | CA | LYS | 538 | 91.666 | 31.067 | 68.337 | 1.00 | 37.32 | B | C |
| ATOM | 10122 | CB | LYS | 538 | 91.629 | 32.517 | 68.817 | 1.00 | 39.07 | B | C |
| ATOM | 10123 | CG | LYS | 538 | 92.298 | 32.747 | 70.170 | 1.00 | 41.74 | B | C |
| ATOM | 10124 | CD | LYS | 538 | 91.534 | 32.100 | 71.316 | 1.00 | 44.86 | B | C |
| ATOM | 10125 | CE | LYS | 538 | 90.186 | 32.773 | 71.540 | 1.00 | 46.82 | B | C |
| ATOM | 10126 | NZ | LYS | 538 | 89.417 | 32.121 | 72.636 | 1.00 | 47.36 | B | N |
| ATOM | 10127 | C | LYS | 538 | 91.507 | 31.028 | 66.819 | 1.00 | 35.00 | B | C |
| ATOM | 10128 | O | LYS | 538 | 92.464 | 30.754 | 66.101 | 1.00 | 34.33 | B | O |
| ATOM | 10129 | N | LYS | 539 | 90.299 | 31.288 | 66.335 | 1.00 | 33.57 | B | N |
| ATOM | 10130 | CA | LYS | 539 | 90.038 | 31.302 | 64.895 | 1.00 | 32.92 | B | C |
| ATOM | 10131 | CB | LYS | 539 | 89.049 | 30.197 | 64.510 | 1.00 | 32.99 | B | C |
| ATOM | 10132 | CG | LYS | 539 | 89.736 | 28.887 | 64.143 | 1.00 | 36.07 | B | C |
| ATOM | 10133 | CD | LYS | 539 | 88.757 | 27.739 | 63.893 | 1.00 | 39.32 | B | C |
| ATOM | 10134 | CE | LYS | 539 | 87.720 | 28.059 | 62.816 | 1.00 | 39.62 | B | C |
| ATOM | 10135 | NZ | LYS | 539 | 86.644 | 28.969 | 63.310 | 1.00 | 39.49 | B | N |
| ATOM | 10136 | C | LYS | 539 | 89.504 | 32.666 | 64.471 | 1.00 | 31.07 | B | C |
| ATOM | 10137 | O | LYS | 539 | 88.424 | 33.087 | 64.902 | 1.00 | 30.44 | B | O |
| ATOM | 10138 | N | TYR | 540 | 90.274 | 33.356 | 63.633 | 1.00 | 27.48 | B | N |
| ATOM | 10139 | CA | TYR | 540 | 89.893 | 34.682 | 63.165 | 1.00 | 24.82 | B | C |
| ATOM | 10140 | CB | TYR | 540 | 91.096 | 35.624 | 63.178 | 1.00 | 23.82 | B | C |
| ATOM | 10141 | CG | TYR | 540 | 91.849 | 35.702 | 64.482 | 1.00 | 23.61 | B | C |
| ATOM | 10142 | CD1 | TYR | 540 | 92.614 | 34.627 | 64.936 | 1.00 | 21.98 | B | C |

FIG. 4-208 (Continued)

| | | | | | | | | | | |
|---|---|---|---|---|---|---|---|---|---|---|
| ATOM | 10143 | CE1 | TYR | 540 | 93.321 | 34.708 | 66.130 | 1.00 | 21.65 | B C |
| ATOM | 10144 | CD2 | TYR | 540 | 91.810 | 36.863 | 65.257 | 1.00 | 22.89 | B C |
| ATOM | 10145 | CE2 | TYR | 540 | 92.507 | 36.955 | 66.449 | 1.00 | 22.77 | B C |
| ATOM | 10146 | CZ | TYR | 540 | 93.261 | 35.875 | 66.881 | 1.00 | 22.87 | B C |
| ATOM | 10147 | OH | TYR | 540 | 93.950 | 35.965 | 68.062 | 1.00 | 23.97 | B O |
| ATOM | 10148 | C | TYR | 540 | 89.335 | 34.694 | 61.749 | 1.00 | 23.62 | B C |
| ATOM | 10149 | O | TYR | 540 | 89.670 | 33.842 | 60.925 | 1.00 | 23.93 | B O |
| ATOM | 10150 | N | PRO | 541 | 88.457 | 35.660 | 61.452 | 1.00 | 21.89 | B N |
| ATOM | 10151 | CD | PRO | 541 | 87.820 | 36.667 | 62.320 | 1.00 | 21.22 | B C |
| ATOM | 10152 | CA | PRO | 541 | 87.917 | 35.719 | 60.095 | 1.00 | 20.52 | B C |
| ATOM | 10153 | CB | PRO | 541 | 86.770 | 36.717 | 60.228 | 1.00 | 20.30 | B C |
| ATOM | 10154 | CG | PRO | 541 | 87.243 | 37.629 | 61.317 | 1.00 | 20.36 | B C |
| ATOM | 10155 | C | PRO | 541 | 89.077 | 36.266 | 59.276 | 1.00 | 19.86 | B C |
| ATOM | 10156 | O | PRO | 541 | 90.026 | 36.799 | 59.841 | 1.00 | 19.90 | B O |
| ATOM | 10157 | N | LEU | 542 | 89.028 | 36.147 | 57.961 | 1.00 | 19.38 | B N |
| ATOM | 10158 | CA | LEU | 542 | 90.133 | 36.655 | 57.169 | 1.00 | 18.21 | B C |
| ATOM | 10159 | CB | LEU | 542 | 91.027 | 35.483 | 56.741 | 1.00 | 18.98 | B C |
| ATOM | 10160 | CG | LEU | 542 | 92.215 | 35.768 | 55.816 | 1.00 | 19.24 | B C |
| ATOM | 10161 | CD1 | LEU | 542 | 93.296 | 34.721 | 56.025 | 1.00 | 17.89 | B C |
| ATOM | 10162 | CD2 | LEU | 542 | 91.741 | 35.775 | 54.374 | 1.00 | 19.31 | B C |
| ATOM | 10163 | C | LEU | 542 | 89.677 | 37.458 | 55.954 | 1.00 | 17.31 | B C |
| ATOM | 10164 | O | LEU | 542 | 88.720 | 37.087 | 55.282 | 1.00 | 18.08 | B O |
| ATOM | 10165 | N | LEU | 543 | 90.368 | 38.564 | 55.694 | 1.00 | 14.81 | B N |
| ATOM | 10166 | CA | LEU | 543 | 90.075 | 39.430 | 54.559 | 1.00 | 13.79 | B C |
| ATOM | 10167 | CB | LEU | 543 | 89.816 | 40.872 | 55.015 | 1.00 | 12.33 | B C |
| ATOM | 10168 | CG | LEU | 543 | 89.568 | 41.892 | 53.886 | 1.00 | 13.71 | B C |
| ATOM | 10169 | CD1 | LEU | 543 | 88.317 | 41.497 | 53.113 | 1.00 | 9.91 | B C |
| ATOM | 10170 | CD2 | LEU | 543 | 89.409 | 43.294 | 54.454 | 1.00 | 11.87 | B C |
| ATOM | 10171 | C | LEU | 543 | 91.273 | 39.415 | 53.620 | 1.00 | 14.35 | B C |
| ATOM | 10172 | O | LEU | 543 | 92.349 | 39.893 | 53.966 | 1.00 | 14.04 | B O |
| ATOM | 10173 | N | LEU | 544 | 91.091 | 38.866 | 52.428 | 1.00 | 15.02 | B N |
| ATOM | 10174 | CA | LEU | 544 | 92.191 | 38.807 | 51.480 | 1.00 | 16.19 | B C |
| ATOM | 10175 | CB | LEU | 544 | 92.006 | 37.609 | 50.539 | 1.00 | 16.34 | B C |
| ATOM | 10176 | CG | LEU | 544 | 93.163 | 37.231 | 49.608 | 1.00 | 14.93 | B C |
| ATOM | 10177 | CD1 | LEU | 544 | 94.345 | 36.752 | 50.429 | 1.00 | 15.36 | B C |
| ATOM | 10178 | CD2 | LEU | 544 | 92.713 | 36.128 | 48.654 | 1.00 | 15.79 | B C |
| ATOM | 10179 | C | LEU | 544 | 92.276 | 40.109 | 50.679 | 1.00 | 16.49 | B C |
| ATOM | 10180 | O | LEU | 544 | 91.437 | 40.374 | 49.819 | 1.00 | 17.02 | B O |
| ATOM | 10181 | N | ASP | 545 | 93.280 | 40.925 | 50.997 | 1.00 | 15.13 | B N |
| ATOM | 10182 | CA | ASP | 545 | 93.515 | 42.186 | 50.306 | 1.00 | 14.91 | B C |
| ATOM | 10183 | CB | ASP | 545 | 94.479 | 43.069 | 51.117 | 1.00 | 15.71 | B C |
| ATOM | 10184 | CG | ASP | 545 | 94.703 | 44.434 | 50.483 | 1.00 | 15.88 | B C |
| ATOM | 10185 | OD1 | ASP | 545 | 94.285 | 44.641 | 49.324 | 1.00 | 14.36 | B O |
| ATOM | 10186 | OD2 | ASP | 545 | 95.304 | 45.304 | 51.144 | 1.00 | 15.41 | B O |
| ATOM | 10187 | C | ASP | 545 | 94.175 | 41.757 | 49.004 | 1.00 | 14.61 | B C |
| ATOM | 10188 | O | ASP | 545 | 95.235 | 41.135 | 49.014 | 1.00 | 13.17 | B O |
| ATOM | 10189 | N | VAL | 546 | 93.567 | 42.098 | 47.881 | 1.00 | 15.03 | B N |
| ATOM | 10190 | CA | VAL | 546 | 94.116 | 41.667 | 46.614 | 1.00 | 17.39 | B C |
| ATOM | 10191 | CB | VAL | 546 | 93.199 | 40.579 | 46.014 | 1.00 | 19.44 | B C |

| ATOM | 10192 | CG1 | VAL | 546 | 93.717 | 40.124 | 44.647 | 1.00 | 17.87 | B | C |
|------|-------|-----|-----|-----|--------|--------|--------|------|-------|---|---|
| ATOM | 10193 | CG2 | VAL | 546 | 93.109 | 39.410 | 46.983 | 1.00 | 20.93 | B | C |
| ATOM | 10194 | C | VAL | 546 | 94.343 | 42.722 | 45.542 | 1.00 | 17.09 | B | C |
| ATOM | 10195 | O | VAL | 546 | 93.601 | 43.694 | 45.447 | 1.00 | 18.12 | B | O |
| ATOM | 10196 | N | TYR | 547 | 95.391 | 42.519 | 44.745 | 1.00 | 15.70 | B | N |
| ATOM | 10197 | CA | TYR | 547 | 95.670 | 43.378 | 43.595 | 1.00 | 14.90 | B | C |
| ATOM | 10198 | CB | TYR | 547 | 96.838 | 44.335 | 43.821 | 1.00 | 12.56 | B | C |
| ATOM | 10199 | CG | TYR | 547 | 97.008 | 45.241 | 42.622 | 1.00 | 12.84 | B | C |
| ATOM | 10200 | CD1 | TYR | 547 | 98.064 | 45.063 | 41.727 | 1.00 | 12.01 | B | C |
| ATOM | 10201 | CE1 | TYR | 547 | 98.165 | 45.839 | 40.578 | 1.00 | 9.97 | B | C |
| ATOM | 10202 | CD2 | TYR | 547 | 96.057 | 46.226 | 42.331 | 1.00 | 11.82 | B | C |
| ATOM | 10203 | CE2 | TYR | 547 | 96.149 | 47.002 | 41.183 | 1.00 | 8.62 | B | C |
| ATOM | 10204 | CZ | TYR | 547 | 97.204 | 46.804 | 40.314 | 1.00 | 10.60 | B | C |
| ATOM | 10205 | OH | TYR | 547 | 97.304 | 47.573 | 39.179 | 1.00 | 12.10 | B | O |
| ATOM | 10206 | C | TYR | 547 | 96.011 | 42.392 | 42.485 | 1.00 | 13.60 | B | C |
| ATOM | 10207 | O | TYR | 547 | 95.244 | 42.205 | 41.548 | 1.00 | 13.39 | B | O |
| ATOM | 10208 | N | ALA | 548 | 97.170 | 41.763 | 42.608 | 1.00 | 13.66 | B | N |
| ATOM | 10209 | CA | ALA | 548 | 97.594 | 40.730 | 41.672 | 1.00 | 14.14 | B | C |
| ATOM | 10210 | CB | ALA | 548 | 96.658 | 39.518 | 41.807 | 1.00 | 11.57 | B | C |
| ATOM | 10211 | C | ALA | 548 | 97.732 | 41.105 | 40.207 | 1.00 | 13.67 | B | C |
| ATOM | 10212 | O | ALA | 548 | 97.681 | 40.234 | 39.340 | 1.00 | 14.21 | B | O |
| ATOM | 10213 | N | GLY | 549 | 97.905 | 42.386 | 39.913 | 1.00 | 13.87 | B | N |
| ATOM | 10214 | CA | GLY | 549 | 98.078 | 42.765 | 38.524 | 1.00 | 12.26 | B | C |
| ATOM | 10215 | C | GLY | 549 | 99.405 | 42.209 | 38.046 | 1.00 | 12.16 | B | C |
| ATOM | 10216 | O | GLY | 549 | 100.179 | 41.717 | 38.855 | 1.00 | 12.33 | B | O |
| ATOM | 10217 | N | PRO | 550 | 99.700 | 42.256 | 36.739 | 1.00 | 13.98 | B | N |
| ATOM | 10218 | CD | PRO | 550 | 98.853 | 42.760 | 35.644 | 1.00 | 12.99 | B | C |
| ATOM | 10219 | CA | PRO | 550 | 100.969 | 41.736 | 36.217 | 1.00 | 13.32 | B | C |
| ATOM | 10220 | CB | PRO | 550 | 100.863 | 42.007 | 34.721 | 1.00 | 14.56 | B | C |
| ATOM | 10221 | CG | PRO | 550 | 99.391 | 42.015 | 34.473 | 1.00 | 14.10 | B | C |
| ATOM | 10222 | C | PRO | 550 | 102.166 | 42.459 | 36.832 | 1.00 | 13.86 | B | C |
| ATOM | 10223 | O | PRO | 550 | 102.248 | 43.683 | 36.785 | 1.00 | 13.45 | B | O |
| ATOM | 10224 | N | CYS | 551 | 103.088 | 41.694 | 37.405 | 1.00 | 14.79 | B | N |
| ATOM | 10225 | CA | CYS | 551 | 104.283 | 42.244 | 38.027 | 1.00 | 15.51 | B | C |
| ATOM | 10226 | CB | CYS | 551 | 105.035 | 43.139 | 37.036 | 1.00 | 17.05 | B | C |
| ATOM | 10227 | SG | CYS | 551 | 106.732 | 43.567 | 37.543 | 1.00 | 17.09 | B | S |
| ATOM | 10228 | C | CYS | 551 | 103.967 | 43.018 | 39.312 | 1.00 | 16.05 | B | C |
| ATOM | 10229 | O | CYS | 551 | 104.693 | 43.938 | 39.702 | 1.00 | 15.36 | B | O |
| ATOM | 10230 | N | SER | 552 | 102.883 | 42.631 | 39.976 | 1.00 | 15.15 | B | N |
| ATOM | 10231 | CA | SER | 552 | 102.494 | 43.268 | 41.229 | 1.00 | 14.65 | B | C |
| ATOM | 10232 | CB | SER | 552 | 100.990 | 43.149 | 41.425 | 1.00 | 14.47 | B | C |
| ATOM | 10233 | OG | SER | 552 | 100.604 | 41.789 | 41.427 | 1.00 | 14.39 | B | O |
| ATOM | 10234 | C | SER | 552 | 103.201 | 42.608 | 42.418 | 1.00 | 15.21 | B | C |
| ATOM | 10235 | O | SER | 552 | 103.882 | 41.585 | 42.273 | 1.00 | 15.34 | B | O |
| ATOM | 10236 | N | GLN | 553 | 103.048 | 43.201 | 43.594 | 1.00 | 14.73 | B | N |
| ATOM | 10237 | CA | GLN | 553 | 103.654 | 42.647 | 44.794 | 1.00 | 14.31 | B | C |
| ATOM | 10238 | CB | GLN | 553 | 105.138 | 43.017 | 44.892 | 1.00 | 13.21 | B | C |
| ATOM | 10239 | CG | GLN | 553 | 105.852 | 42.332 | 46.056 | 1.00 | 15.05 | B | C |
| ATOM | 10240 | CD | GLN | 553 | 107.359 | 42.585 | 46.090 | 1.00 | 15.66 | B | C |

FIG. 4-210 (Continued)

| | | | | | | | | | | |
|---|---|---|---|---|---|---|---|---|---|---|
| ATOM | 10241 | OE1 | GLN | 553 | 107.812 | 43.686 | 46.400 | 1.00 | 16.56 | B | O |
| ATOM | 10242 | NE2 | GLN | 553 | 108.138 | 41.556 | 45.773 | 1.00 | 15.50 | B | N |
| ATOM | 10243 | C | GLN | 553 | 102.921 | 43.166 | 46.012 | 1.00 | 14.58 | B | C |
| ATOM | 10244 | O | GLN | 553 | 103.148 | 44.295 | 46.434 | 1.00 | 14.77 | B | O |
| ATOM | 10245 | N | LYS | 554 | 102.031 | 42.344 | 46.568 | 1.00 | 14.78 | B | N |
| ATOM | 10246 | CA | LYS | 554 | 101.284 | 42.734 | 47.754 | 1.00 | 16.57 | B | C |
| ATOM | 10247 | CB | LYS | 554 | 99.817 | 42.318 | 47.633 | 1.00 | 17.81 | B | C |
| ATOM | 10248 | CG | LYS | 554 | 99.031 | 43.142 | 46.630 | 1.00 | 18.63 | B | C |
| ATOM | 10249 | CD | LYS | 554 | 99.047 | 44.612 | 47.000 | 1.00 | 18.55 | B | C |
| ATOM | 10250 | CE | LYS | 554 | 98.228 | 44.902 | 48.261 | 1.00 | 18.33 | B | C |
| ATOM | 10251 | NZ | LYS | 554 | 96.769 | 44.771 | 48.035 | 1.00 | 13.33 | B | N |
| ATOM | 10252 | C | LYS | 554 | 101.890 | 42.148 | 49.024 | 1.00 | 16.05 | B | C |
| ATOM | 10253 | O | LYS | 554 | 101.424 | 42.429 | 50.124 | 1.00 | 17.37 | B | O |
| ATOM | 10254 | N | ALA | 555 | 102.939 | 41.350 | 48.866 | 1.00 | 15.91 | B | N |
| ATOM | 10255 | CA | ALA | 555 | 103.622 | 40.730 | 50.004 | 1.00 | 15.84 | B | C |
| ATOM | 10256 | CB | ALA | 555 | 103.656 | 39.210 | 49.833 | 1.00 | 15.51 | B | C |
| ATOM | 10257 | C | ALA | 555 | 105.041 | 41.246 | 50.142 | 1.00 | 14.91 | B | C |
| ATOM | 10258 | O | ALA | 555 | 105.954 | 40.691 | 49.539 | 1.00 | 15.57 | B | O |
| ATOM | 10259 | N | ASP | 556 | 105.233 | 42.304 | 50.924 | 1.00 | 16.20 | B | N |
| ATOM | 10260 | CA | ASP | 556 | 106.571 | 42.854 | 51.134 | 1.00 | 16.65 | B | C |
| ATOM | 10261 | CB | ASP | 556 | 106.801 | 44.085 | 50.243 | 1.00 | 17.94 | B | C |
| ATOM | 10262 | CG | ASP | 556 | 105.750 | 45.159 | 50.430 | 1.00 | 19.95 | B | C |
| ATOM | 10263 | OD1 | ASP | 556 | 105.355 | 45.429 | 51.583 | 1.00 | 22.16 | B | O |
| ATOM | 10264 | OD2 | ASP | 556 | 105.327 | 45.751 | 49.415 | 1.00 | 21.01 | B | O |
| ATOM | 10265 | C | ASP | 556 | 106.862 | 43.202 | 52.597 | 1.00 | 16.87 | B | C |
| ATOM | 10266 | O | ASP | 556 | 106.046 | 42.962 | 53.480 | 1.00 | 15.15 | B | O |
| ATOM | 10267 | N | THR | 557 | 108.039 | 43.762 | 52.847 | 1.00 | 17.93 | B | N |
| ATOM | 10268 | CA | THR | 557 | 108.443 | 44.132 | 54.200 | 1.00 | 18.07 | B | C |
| ATOM | 10269 | CB | THR | 557 | 109.923 | 43.826 | 54.396 | 1.00 | 18.59 | B | C |
| ATOM | 10270 | OG1 | THR | 557 | 110.687 | 44.589 | 53.454 | 1.00 | 20.98 | B | O |
| ATOM | 10271 | CG2 | THR | 557 | 110.188 | 42.358 | 54.157 | 1.00 | 19.55 | B | C |
| ATOM | 10272 | C | THR | 557 | 108.203 | 45.616 | 54.531 | 1.00 | 17.89 | B | C |
| ATOM | 10273 | O | THR | 557 | 108.776 | 46.151 | 55.479 | 1.00 | 16.94 | B | O |
| ATOM | 10274 | N | VAL | 558 | 107.348 | 46.272 | 53.754 | 1.00 | 16.56 | B | N |
| ATOM | 10275 | CA | VAL | 558 | 107.049 | 47.682 | 53.964 | 1.00 | 14.93 | B | C |
| ATOM | 10276 | CB | VAL | 558 | 106.483 | 48.302 | 52.676 | 1.00 | 14.99 | B | C |
| ATOM | 10277 | CG1 | VAL | 558 | 106.033 | 49.733 | 52.940 | 1.00 | 13.18 | B | C |
| ATOM | 10278 | CG2 | VAL | 558 | 107.544 | 48.247 | 51.568 | 1.00 | 13.02 | B | C |
| ATOM | 10279 | C | VAL | 558 | 106.058 | 47.921 | 55.109 | 1.00 | 15.99 | B | C |
| ATOM | 10280 | O | VAL | 558 | 105.060 | 47.211 | 55.238 | 1.00 | 13.36 | B | O |
| ATOM | 10281 | N | PHE | 559 | 106.348 | 48.923 | 55.941 | 1.00 | 15.43 | B | N |
| ATOM | 10282 | CA | PHE | 559 | 105.484 | 49.269 | 57.069 | 1.00 | 14.56 | B | C |
| ATOM | 10283 | CB | PHE | 559 | 106.303 | 49.933 | 58.173 | 1.00 | 12.72 | B | C |
| ATOM | 10284 | CG | PHE | 559 | 105.469 | 50.504 | 59.282 | 1.00 | 11.04 | B | C |
| ATOM | 10285 | CD1 | PHE | 559 | 105.064 | 49.712 | 60.347 | 1.00 | 10.65 | B | C |
| ATOM | 10286 | CD2 | PHE | 559 | 105.056 | 51.833 | 59.244 | 1.00 | 12.10 | B | C |
| ATOM | 10287 | CE1 | PHE | 559 | 104.260 | 50.232 | 61.356 | 1.00 | 8.83 | B | C |
| ATOM | 10288 | CE2 | PHE | 559 | 104.251 | 52.360 | 60.252 | 1.00 | 10.43 | B | C |
| ATOM | 10289 | CZ | PHE | 559 | 103.855 | 51.554 | 61.307 | 1.00 | 8.93 | B | C |

FIG. 4-211 (Continued)

| | | | | | | | | | | |
|---|---|---|---|---|---|---|---|---|---|---|
| ATOM | 10290 | C | PHE | 559 | 104.395 | 50.230 | 56.592 | 1.00 | 14.21 | B C |
| ATOM | 10291 | O | PHE | 559 | 104.696 | 51.255 | 56.000 | 1.00 | 14.64 | B O |
| ATOM | 10292 | N | ARG | 560 | 103.137 | 49.907 | 56.865 | 1.00 | 13.77 | B N |
| ATOM | 10293 | CA | ARG | 560 | 102.029 | 50.744 | 56.421 | 1.00 | 14.06 | B C |
| ATOM | 10294 | CB | ARG | 560 | 101.354 | 50.117 | 55.185 | 1.00 | 12.20 | B C |
| ATOM | 10295 | CG | ARG | 560 | 102.248 | 49.988 | 53.954 | 1.00 | 11.36 | B C |
| ATOM | 10296 | CD | ARG | 560 | 101.491 | 49.421 | 52.755 | 1.00 | 10.73 | B C |
| ATOM | 10297 | NE | ARG | 560 | 102.322 | 48.486 | 51.999 | 1.00 | 13.38 | B N |
| ATOM | 10298 | CZ | ARG | 560 | 103.126 | 48.828 | 51.002 | 1.00 | 14.76 | B C |
| ATOM | 10299 | NH1 | ARG | 560 | 103.203 | 50.090 | 50.614 | 1.00 | 19.68 | B N |
| ATOM | 10300 | NH2 | ARG | 560 | 103.887 | 47.915 | 50.421 | 1.00 | 16.46 | B N |
| ATOM | 10301 | C | ARG | 560 | 100.962 | 50.980 | 57.486 | 1.00 | 14.74 | B C |
| ATOM | 10302 | O | ARG | 560 | 100.661 | 50.100 | 58.291 | 1.00 | 16.54 | B O |
| ATOM | 10303 | N | LEU | 561 | 100.403 | 52.183 | 57.483 | 1.00 | 13.62 | B N |
| ATOM | 10304 | CA | LEU | 561 | 99.325 | 52.551 | 58.392 | 1.00 | 13.55 | B C |
| ATOM | 10305 | CB | LEU | 561 | 99.626 | 53.875 | 59.100 | 1.00 | 11.68 | B C |
| ATOM | 10306 | CG | LEU | 561 | 100.694 | 53.872 | 60.189 | 1.00 | 12.53 | B C |
| ATOM | 10307 | CD1 | LEU | 561 | 100.901 | 55.299 | 60.698 | 1.00 | 8.41 | B C |
| ATOM | 10308 | CD2 | LEU | 561 | 100.275 | 52.934 | 61.319 | 1.00 | 10.22 | B C |
| ATOM | 10309 | C | LEU | 561 | 98.114 | 52.725 | 57.475 | 1.00 | 12.59 | B C |
| ATOM | 10310 | O | LEU | 561 | 97.987 | 53.734 | 56.785 | 1.00 | 10.30 | B O |
| ATOM | 10311 | N | ASN | 562 | 97.222 | 51.748 | 57.465 | 1.00 | 12.69 | B N |
| ATOM | 10312 | CA | ASN | 562 | 96.071 | 51.841 | 56.577 | 1.00 | 15.06 | B C |
| ATOM | 10313 | CB | ASN | 562 | 96.462 | 51.267 | 55.220 | 1.00 | 14.07 | B C |
| ATOM | 10314 | CG | ASN | 562 | 96.924 | 49.823 | 55.318 | 1.00 | 14.26 | B C |
| ATOM | 10315 | OD1 | ASN | 562 | 97.566 | 49.309 | 54.407 | 1.00 | 15.38 | B O |
| ATOM | 10316 | ND2 | ASN | 562 | 96.582 | 49.157 | 56.423 | 1.00 | 11.43 | B N |
| ATOM | 10317 | C | ASN | 562 | 94.818 | 51.139 | 57.086 | 1.00 | 14.89 | B C |
| ATOM | 10318 | O | ASN | 562 | 94.712 | 50.793 | 58.260 | 1.00 | 16.50 | B O |
| ATOM | 10319 | N | TRP | 563 | 93.872 | 50.936 | 56.178 | 1.00 | 15.26 | B N |
| ATOM | 10320 | CA | TRP | 563 | 92.616 | 50.281 | 56.502 | 1.00 | 15.35 | B C |
| ATOM | 10321 | CB | TRP | 563 | 91.770 | 50.132 | 55.244 | 1.00 | 13.87 | B C |
| ATOM | 10322 | CG | TRP | 563 | 90.365 | 49.719 | 55.511 | 1.00 | 15.58 | B C |
| ATOM | 10323 | CD2 | TRP | 563 | 89.623 | 48.721 | 54.804 | 1.00 | 12.95 | B C |
| ATOM | 10324 | CE2 | TRP | 563 | 88.330 | 48.684 | 55.369 | 1.00 | 13.17 | B C |
| ATOM | 10325 | CE3 | TRP | 563 | 89.927 | 47.856 | 53.745 | 1.00 | 10.64 | B C |
| ATOM | 10326 | CD1 | TRP | 563 | 89.512 | 50.237 | 56.456 | 1.00 | 13.99 | B C |
| ATOM | 10327 | NE1 | TRP | 563 | 88.289 | 49.617 | 56.373 | 1.00 | 14.03 | B N |
| ATOM | 10328 | CZ2 | TRP | 563 | 87.346 | 47.816 | 54.911 | 1.00 | 13.35 | B C |
| ATOM | 10329 | CZ3 | TRP | 563 | 88.951 | 46.995 | 53.290 | 1.00 | 9.50 | B C |
| ATOM | 10330 | CH2 | TRP | 563 | 87.673 | 46.980 | 53.872 | 1.00 | 12.48 | B C |
| ATOM | 10331 | C | TRP | 563 | 92.880 | 48.919 | 57.119 | 1.00 | 16.18 | B C |
| ATOM | 10332 | O | TRP | 563 | 92.279 | 48.562 | 58.132 | 1.00 | 15.81 | B O |
| ATOM | 10333 | N | ALA | 564 | 93.790 | 48.161 | 56.515 | 1.00 | 17.44 | B N |
| ATOM | 10334 | CA | ALA | 564 | 94.124 | 46.841 | 57.042 | 1.00 | 17.65 | B C |
| ATOM | 10335 | CB | ALA | 564 | 95.216 | 46.186 | 56.197 | 1.00 | 16.15 | B C |
| ATOM | 10336 | C | ALA | 564 | 94.585 | 46.973 | 58.489 | 1.00 | 18.07 | B C |
| ATOM | 10337 | O | ALA | 564 | 94.256 | 46.127 | 59.320 | 1.00 | 18.92 | B O |
| ATOM | 10338 | N | THR | 565 | 95.332 | 48.037 | 58.793 | 1.00 | 17.73 | B N |

FIG. 4-212 (Continued)

| | | | | | | | | | | |
|---|---|---|---|---|---|---|---|---|---|---|
| ATOM | 10339 | CA | THR | 565 | 95.817 | 48.259 | 60.159 | 1.00 | 17.29 | B | C |
| ATOM | 10340 | CB | THR | 565 | 96.626 | 49.551 | 60.294 | 1.00 | 17.13 | B | C |
| ATOM | 10341 | OG1 | THR | 565 | 97.677 | 49.570 | 59.330 | 1.00 | 20.36 | B | O |
| ATOM | 10342 | CG2 | THR | 565 | 97.238 | 49.636 | 61.676 | 1.00 | 18.23 | B | C |
| ATOM | 10343 | C | THR | 565 | 94.665 | 48.355 | 61.157 | 1.00 | 15.84 | B | C |
| ATOM | 10344 | O | THR | 565 | 94.738 | 47.804 | 62.249 | 1.00 | 14.07 | B | O |
| ATOM | 10345 | N | TYR | 566 | 93.605 | 49.061 | 60.781 | 1.00 | 15.76 | B | N |
| ATOM | 10346 | CA | TYR | 566 | 92.455 | 49.204 | 61.664 | 1.00 | 17.74 | B | C |
| ATOM | 10347 | CB | TYR | 566 | 91.543 | 50.335 | 61.177 | 1.00 | 15.61 | B | C |
| ATOM | 10348 | CG | TYR | 566 | 90.067 | 50.039 | 61.311 | 1.00 | 17.40 | B | C |
| ATOM | 10349 | CD1 | TYR | 566 | 89.303 | 49.688 | 60.195 | 1.00 | 17.77 | B | C |
| ATOM | 10350 | CE1 | TYR | 566 | 87.947 | 49.390 | 60.310 | 1.00 | 15.12 | B | C |
| ATOM | 10351 | CD2 | TYR | 566 | 89.432 | 50.086 | 62.556 | 1.00 | 18.30 | B | C |
| ATOM | 10352 | CE2 | TYR | 566 | 88.073 | 49.789 | 62.682 | 1.00 | 17.35 | B | C |
| ATOM | 10353 | CZ | TYR | 566 | 87.340 | 49.441 | 61.550 | 1.00 | 17.10 | B | C |
| ATOM | 10354 | OH | TYR | 566 | 86.005 | 49.137 | 61.662 | 1.00 | 17.63 | B | O |
| ATOM | 10355 | C | TYR | 566 | 91.667 | 47.899 | 61.777 | 1.00 | 19.12 | B | C |
| ATOM | 10356 | O | TYR | 566 | 91.249 | 47.517 | 62.871 | 1.00 | 20.12 | B | O |
| ATOM | 10357 | N | LEU | 567 | 91.481 | 47.211 | 60.654 | 1.00 | 19.08 | B | N |
| ATOM | 10358 | CA | LEU | 567 | 90.735 | 45.959 | 60.648 | 1.00 | 19.66 | B | C |
| ATOM | 10359 | CB | LEU | 567 | 90.606 | 45.419 | 59.223 | 1.00 | 18.00 | B | C |
| ATOM | 10360 | CG | LEU | 567 | 89.728 | 46.252 | 58.284 | 1.00 | 18.48 | B | C |
| ATOM | 10361 | CD1 | LEU | 567 | 89.735 | 45.628 | 56.889 | 1.00 | 19.22 | B | C |
| ATOM | 10362 | CD2 | LEU | 567 | 88.310 | 46.325 | 58.835 | 1.00 | 15.78 | B | C |
| ATOM | 10363 | C | LEU | 567 | 91.355 | 44.898 | 61.544 | 1.00 | 20.80 | B | C |
| ATOM | 10364 | O | LEU | 567 | 90.645 | 44.102 | 62.157 | 1.00 | 23.88 | B | O |
| ATOM | 10365 | N | ALA | 568 | 92.677 | 44.883 | 61.628 | 1.00 | 19.62 | B | N |
| ATOM | 10366 | CA | ALA | 568 | 93.347 | 43.898 | 62.466 | 1.00 | 20.08 | B | C |
| ATOM | 10367 | CB | ALA | 568 | 94.746 | 43.601 | 61.907 | 1.00 | 18.06 | B | C |
| ATOM | 10368 | C | ALA | 568 | 93.451 | 44.362 | 63.924 | 1.00 | 20.52 | B | C |
| ATOM | 10369 | O | ALA | 568 | 93.319 | 43.569 | 64.849 | 1.00 | 20.37 | B | O |
| ATOM | 10370 | N | SER | 569 | 93.674 | 45.653 | 64.128 | 1.00 | 20.79 | B | N |
| ATOM | 10371 | CA | SER | 569 | 93.827 | 46.182 | 65.474 | 1.00 | 21.75 | B | C |
| ATOM | 10372 | CB | SER | 569 | 94.520 | 47.545 | 65.401 | 1.00 | 21.85 | B | C |
| ATOM | 10373 | OG | SER | 569 | 94.546 | 48.188 | 66.657 | 1.00 | 22.64 | B | O |
| ATOM | 10374 | C | SER | 569 | 92.525 | 46.297 | 66.267 | 1.00 | 22.83 | B | C |
| ATOM | 10375 | O | SER | 569 | 92.505 | 46.029 | 67.470 | 1.00 | 22.38 | B | O |
| ATOM | 10376 | N | THR | 570 | 91.444 | 46.679 | 65.589 | 1.00 | 22.26 | B | N |
| ATOM | 10377 | CA | THR | 570 | 90.153 | 46.862 | 66.232 | 1.00 | 21.45 | B | C |
| ATOM | 10378 | CB | THR | 570 | 89.512 | 48.191 | 65.797 | 1.00 | 19.91 | B | C |
| ATOM | 10379 | OG1 | THR | 570 | 90.349 | 49.285 | 66.188 | 1.00 | 21.12 | B | O |
| ATOM | 10380 | CG2 | THR | 570 | 88.143 | 48.351 | 66.430 | 1.00 | 17.96 | B | C |
| ATOM | 10381 | C | THR | 570 | 89.132 | 45.751 | 65.974 | 1.00 | 24.43 | B | C |
| ATOM | 10382 | O | THR | 570 | 88.453 | 45.301 | 66.894 | 1.00 | 27.79 | B | O |
| ATOM | 10383 | N | GLU | 571 | 89.001 | 45.317 | 64.727 | 1.00 | 23.34 | B | N |
| ATOM | 10384 | CA | GLU | 571 | 88.030 | 44.280 | 64.415 | 1.00 | 21.95 | B | C |
| ATOM | 10385 | CB | GLU | 571 | 87.499 | 44.481 | 62.998 | 1.00 | 22.83 | B | C |
| ATOM | 10386 | CG | GLU | 571 | 87.004 | 45.888 | 62.709 | 1.00 | 24.63 | B | C |
| ATOM | 10387 | CD | GLU | 571 | 85.957 | 46.357 | 63.696 | 1.00 | 25.17 | B | C |

| ATOM | 10388 | OE1 | GLU | 571 | 85.236 | 45.509 | 64.258 | 1.00 | 28.12 | B | O |
| ATOM | 10389 | OE2 | GLU | 571 | 85.834 | 47.580 | 63.897 | 1.00 | 26.28 | B | O |
| ATOM | 10390 | C | GLU | 571 | 88.606 | 42.874 | 64.554 | 1.00 | 21.35 | B | C |
| ATOM | 10391 | O | GLU | 571 | 87.903 | 41.887 | 64.362 | 1.00 | 19.91 | B | O |
| ATOM | 10392 | N | ASN | 572 | 89.887 | 42.784 | 64.894 | 1.00 | 22.55 | B | N |
| ATOM | 10393 | CA | ASN | 572 | 90.539 | 41.491 | 65.043 | 1.00 | 21.58 | B | C |
| ATOM | 10394 | CB | ASN | 572 | 89.998 | 40.744 | 66.255 | 1.00 | 23.76 | B | C |
| ATOM | 10395 | CG | ASN | 572 | 90.523 | 41.303 | 67.552 | 1.00 | 27.80 | B | C |
| ATOM | 10396 | OD1 | ASN | 572 | 90.053 | 42.335 | 68.035 | 1.00 | 30.34 | B | O |
| ATOM | 10397 | ND2 | ASN | 572 | 91.522 | 40.634 | 68.121 | 1.00 | 30.31 | B | N |
| ATOM | 10398 | C | ASN | 572 | 90.347 | 40.639 | 63.806 | 1.00 | 21.12 | B | C |
| ATOM | 10399 | O | ASN | 572 | 90.112 | 39.436 | 63.903 | 1.00 | 20.16 | B | O |
| ATOM | 10400 | N | ILE | 573 | 90.445 | 41.280 | 62.645 | 1.00 | 19.59 | B | N |
| ATOM | 10401 | CA | ILE | 573 | 90.311 | 40.604 | 61.365 | 1.00 | 18.06 | B | C |
| ATOM | 10402 | CB | ILE | 573 | 89.509 | 41.456 | 60.382 | 1.00 | 18.14 | B | C |
| ATOM | 10403 | CG2 | ILE | 573 | 89.371 | 40.735 | 59.057 | 1.00 | 18.53 | B | C |
| ATOM | 10404 | CG1 | ILE | 573 | 88.143 | 41.778 | 60.970 | 1.00 | 19.49 | B | C |
| ATOM | 10405 | CD1 | ILE | 573 | 87.336 | 42.735 | 60.131 | 1.00 | 20.04 | B | C |
| ATOM | 10406 | C | ILE | 573 | 91.706 | 40.425 | 60.777 | 1.00 | 18.47 | B | C |
| ATOM | 10407 | O | ILE | 573 | 92.480 | 41.376 | 60.739 | 1.00 | 19.08 | B | O |
| ATOM | 10408 | N | ILE | 574 | 92.038 | 39.216 | 60.337 | 1.00 | 17.57 | B | N |
| ATOM | 10409 | CA | ILE | 574 | 93.340 | 38.978 | 59.724 | 1.00 | 18.02 | B | C |
| ATOM | 10410 | CB | ILE | 574 | 93.724 | 37.494 | 59.740 | 1.00 | 19.09 | B | C |
| ATOM | 10411 | CG2 | ILE | 574 | 94.950 | 37.280 | 58.870 | 1.00 | 20.13 | B | C |
| ATOM | 10412 | CG1 | ILE | 574 | 94.004 | 37.031 | 61.172 | 1.00 | 21.02 | B | C |
| ATOM | 10413 | CD1 | ILE | 574 | 94.330 | 35.553 | 61.282 | 1.00 | 20.47 | B | C |
| ATOM | 10414 | C | ILE | 574 | 93.298 | 39.423 | 58.265 | 1.00 | 17.84 | B | C |
| ATOM | 10415 | O | ILE | 574 | 92.444 | 38.981 | 57.500 | 1.00 | 19.48 | B | O |
| ATOM | 10416 | N | VAL | 575 | 94.217 | 40.296 | 57.876 | 1.00 | 17.13 | B | N |
| ATOM | 10417 | CA | VAL | 575 | 94.254 | 40.777 | 56.498 | 1.00 | 16.42 | B | C |
| ATOM | 10418 | CB | VAL | 575 | 94.354 | 42.308 | 56.430 | 1.00 | 16.55 | B | C |
| ATOM | 10419 | CG1 | VAL | 575 | 94.271 | 42.753 | 54.985 | 1.00 | 16.06 | B | C |
| ATOM | 10420 | CG2 | VAL | 575 | 93.242 | 42.948 | 57.261 | 1.00 | 15.54 | B | C |
| ATOM | 10421 | C | VAL | 575 | 95.452 | 40.187 | 55.786 | 1.00 | 16.02 | B | C |
| ATOM | 10422 | O | VAL | 575 | 96.592 | 40.488 | 56.124 | 1.00 | 16.68 | B | O |
| ATOM | 10423 | N | ALA | 576 | 95.186 | 39.344 | 54.797 | 1.00 | 16.21 | B | N |
| ATOM | 10424 | CA | ALA | 576 | 96.246 | 38.683 | 54.056 | 1.00 | 15.22 | B | C |
| ATOM | 10425 | CB | ALA | 576 | 96.062 | 37.176 | 54.127 | 1.00 | 12.38 | B | C |
| ATOM | 10426 | C | ALA | 576 | 96.330 | 39.117 | 52.601 | 1.00 | 15.92 | B | C |
| ATOM | 10427 | O | ALA | 576 | 95.397 | 39.710 | 52.046 | 1.00 | 16.20 | B | O |
| ATOM | 10428 | N | SER | 577 | 97.470 | 38.811 | 51.996 | 1.00 | 14.35 | B | N |
| ATOM | 10429 | CA | SER | 577 | 97.722 | 39.123 | 50.606 | 1.00 | 13.57 | B | C |
| ATOM | 10430 | CB | SER | 577 | 98.368 | 40.495 | 50.474 | 1.00 | 13.58 | B | C |
| ATOM | 10431 | OG | SER | 577 | 97.456 | 41.504 | 50.866 | 1.00 | 16.22 | B | O |
| ATOM | 10432 | C | SER | 577 | 98.642 | 38.045 | 50.069 | 1.00 | 13.24 | B | C |
| ATOM | 10433 | O | SER | 577 | 99.497 | 37.522 | 50.788 | 1.00 | 13.05 | B | O |
| ATOM | 10434 | N | PHE | 578 | 98.462 | 37.712 | 48.800 | 1.00 | 11.98 | B | N |
| ATOM | 10435 | CA | PHE | 578 | 99.262 | 36.676 | 48.183 | 1.00 | 11.24 | B | C |
| ATOM | 10436 | CB | PHE | 578 | 98.418 | 35.407 | 48.079 | 1.00 | 11.42 | B | C |

| ATOM | 10437 | CG  | PHE | 578 | 99.136  | 34.232 | 47.481 | 1.00 | 10.60 | B | C |
|------|-------|-----|-----|-----|---------|--------|--------|------|-------|---|---|
| ATOM | 10438 | CD1 | PHE | 578 | 100.196 | 33.628 | 48.152 | 1.00 | 10.29 | B | C |
| ATOM | 10439 | CD2 | PHE | 578 | 98.697  | 33.679 | 46.280 | 1.00 | 10.36 | B | C |
| ATOM | 10440 | CE1 | PHE | 578 | 100.805 | 32.483 | 47.640 | 1.00 | 11.15 | B | C |
| ATOM | 10441 | CE2 | PHE | 578 | 99.297  | 32.537 | 45.762 | 1.00 | 11.72 | B | C |
| ATOM | 10442 | CZ  | PHE | 578 | 100.354 | 31.936 | 46.446 | 1.00 | 10.87 | B | C |
| ATOM | 10443 | C   | PHE | 578 | 99.746  | 37.096 | 46.805 | 1.00 | 10.56 | B | C |
| ATOM | 10444 | O   | PHE | 578 | 99.002  | 37.704 | 46.039 | 1.00 | 10.76 | B | O |
| ATOM | 10445 | N   | ASP | 579 | 101.005 | 36.780 | 46.516 | 1.00 | 11.14 | B | N |
| ATOM | 10446 | CA  | ASP | 579 | 101.617 | 37.069 | 45.227 | 1.00 | 9.94  | B | C |
| ATOM | 10447 | CB  | ASP | 579 | 103.008 | 37.682 | 45.401 | 1.00 | 9.15  | B | C |
| ATOM | 10448 | CG  | ASP | 579 | 102.957 | 39.090 | 45.954 | 1.00 | 13.00 | B | C |
| ATOM | 10449 | OD1 | ASP | 579 | 102.053 | 39.842 | 45.532 | 1.00 | 14.87 | B | O |
| ATOM | 10450 | OD2 | ASP | 579 | 103.816 | 39.451 | 46.796 | 1.00 | 11.19 | B | O |
| ATOM | 10451 | C   | ASP | 579 | 101.734 | 35.741 | 44.488 | 1.00 | 11.60 | B | C |
| ATOM | 10452 | O   | ASP | 579 | 102.633 | 34.927 | 44.753 | 1.00 | 12.07 | B | O |
| ATOM | 10453 | N   | GLY | 580 | 100.809 | 35.510 | 43.570 | 1.00 | 10.77 | B | N |
| ATOM | 10454 | CA  | GLY | 580 | 100.838 | 34.274 | 42.815 | 1.00 | 11.96 | B | C |
| ATOM | 10455 | C   | GLY | 580 | 101.458 | 34.470 | 41.450 | 1.00 | 13.34 | B | C |
| ATOM | 10456 | O   | GLY | 580 | 102.269 | 35.376 | 41.227 | 1.00 | 12.96 | B | O |
| ATOM | 10457 | N   | ARG | 581 | 101.080 | 33.611 | 40.521 | 1.00 | 14.18 | B | N |
| ATOM | 10458 | CA  | ARG | 581 | 101.615 | 33.714 | 39.187 | 1.00 | 15.34 | B | C |
| ATOM | 10459 | CB  | ARG | 581 | 101.085 | 32.570 | 38.338 | 1.00 | 13.67 | B | C |
| ATOM | 10460 | CG  | ARG | 581 | 101.809 | 31.283 | 38.666 | 1.00 | 15.30 | B | C |
| ATOM | 10461 | CD  | ARG | 581 | 101.172 | 30.076 | 38.023 | 1.00 | 14.62 | B | C |
| ATOM | 10462 | NE  | ARG | 581 | 99.980  | 29.652 | 38.740 | 1.00 | 13.01 | B | N |
| ATOM | 10463 | CZ  | ARG | 581 | 99.186  | 28.672 | 38.330 | 1.00 | 13.69 | B | C |
| ATOM | 10464 | NH1 | ARG | 581 | 99.467  | 28.024 | 37.207 | 1.00 | 13.99 | B | N |
| ATOM | 10465 | NH2 | ARG | 581 | 98.112  | 28.348 | 39.036 | 1.00 | 12.41 | B | N |
| ATOM | 10466 | C   | ARG | 581 | 101.237 | 35.069 | 38.624 | 1.00 | 17.21 | B | C |
| ATOM | 10467 | O   | ARG | 581 | 100.175 | 35.615 | 38.934 | 1.00 | 17.96 | B | O |
| ATOM | 10468 | N   | GLY | 582 | 102.128 | 35.628 | 37.817 | 1.00 | 18.14 | B | N |
| ATOM | 10469 | CA  | GLY | 582 | 101.868 | 36.933 | 37.258 | 1.00 | 17.73 | B | C |
| ATOM | 10470 | C   | GLY | 582 | 102.454 | 37.998 | 38.159 | 1.00 | 16.81 | B | C |
| ATOM | 10471 | O   | GLY | 582 | 102.557 | 39.151 | 37.754 | 1.00 | 18.98 | B | O |
| ATOM | 10472 | N   | SER | 583 | 102.835 | 37.625 | 39.378 | 1.00 | 15.90 | B | N |
| ATOM | 10473 | CA  | SER | 583 | 103.423 | 38.588 | 40.309 | 1.00 | 16.60 | B | C |
| ATOM | 10474 | CB  | SER | 583 | 103.437 | 38.024 | 41.730 | 1.00 | 17.47 | B | C |
| ATOM | 10475 | OG  | SER | 583 | 104.229 | 36.856 | 41.811 | 1.00 | 21.54 | B | O |
| ATOM | 10476 | C   | SER | 583 | 104.841 | 38.901 | 39.841 | 1.00 | 15.56 | B | C |
| ATOM | 10477 | O   | SER | 583 | 105.389 | 38.176 | 39.013 | 1.00 | 17.79 | B | O |
| ATOM | 10478 | N   | GLY | 584 | 105.441 | 39.970 | 40.359 | 1.00 | 14.64 | B | N |
| ATOM | 10479 | CA  | GLY | 584 | 106.776 | 40.334 | 39.908 | 1.00 | 13.05 | B | C |
| ATOM | 10480 | C   | GLY | 584 | 107.969 | 40.158 | 40.831 | 1.00 | 12.28 | B | C |
| ATOM | 10481 | O   | GLY | 584 | 107.851 | 39.648 | 41.949 | 1.00 | 11.78 | B | O |
| ATOM | 10482 | N   | TYR | 585 | 109.129 | 40.583 | 40.325 | 1.00 | 12.34 | B | N |
| ATOM | 10483 | CA  | TYR | 585 | 110.412 | 40.536 | 41.034 | 1.00 | 12.19 | B | C |
| ATOM | 10484 | CB  | TYR | 585 | 110.335 | 41.383 | 42.304 | 1.00 | 11.93 | B | C |
| ATOM | 10485 | CG  | TYR | 585 | 109.704 | 42.719 | 42.047 | 1.00 | 12.41 | B | C |

FIG. 4-215

| | | | | | | | | | | |
|---|---|---|---|---|---|---|---|---|---|---|
| ATOM | 10486 | CD1 | TYR | 585 | 110.370 | 43.694 | 41.297 | 1.00 | 12.30 | B C |
| ATOM | 10487 | CE1 | TYR | 585 | 109.756 | 44.891 | 40.979 | 1.00 | 12.43 | B C |
| ATOM | 10488 | CD2 | TYR | 585 | 108.408 | 42.983 | 42.478 | 1.00 | 10.95 | B C |
| ATOM | 10489 | CE2 | TYR | 585 | 107.783 | 44.179 | 42.167 | 1.00 | 12.28 | B C |
| ATOM | 10490 | CZ | TYR | 585 | 108.459 | 45.126 | 41.418 | 1.00 | 13.31 | B C |
| ATOM | 10491 | OH | TYR | 585 | 107.831 | 46.306 | 41.109 | 1.00 | 14.33 | B O |
| ATOM | 10492 | C | TYR | 585 | 110.883 | 39.141 | 41.394 | 1.00 | 12.01 | B C |
| ATOM | 10493 | O | TYR | 585 | 111.673 | 38.979 | 42.319 | 1.00 | 13.01 | B O |
| ATOM | 10494 | N | GLN | 586 | 110.413 | 38.144 | 40.655 | 1.00 | 11.45 | B N |
| ATOM | 10495 | CA | GLN | 586 | 110.787 | 36.763 | 40.906 | 1.00 | 11.62 | B C |
| ATOM | 10496 | CB | GLN | 586 | 109.639 | 36.071 | 41.641 | 1.00 | 10.30 | B C |
| ATOM | 10497 | CG | GLN | 586 | 109.178 | 36.854 | 42.867 | 1.00 | 14.38 | B C |
| ATOM | 10498 | CD | GLN | 586 | 107.749 | 36.533 | 43.295 | 1.00 | 15.38 | B C |
| ATOM | 10499 | OE1 | GLN | 586 | 107.468 | 35.452 | 43.816 | 1.00 | 12.14 | B O |
| ATOM | 10500 | NE2 | GLN | 586 | 106.835 | 37.478 | 43.060 | 1.00 | 15.36 | B N |
| ATOM | 10501 | C | GLN | 586 | 111.118 | 36.023 | 39.602 | 1.00 | 12.85 | B C |
| ATOM | 10502 | O | GLN | 586 | 111.173 | 34.786 | 39.574 | 1.00 | 13.97 | B O |
| ATOM | 10503 | N | GLY | 587 | 111.336 | 36.778 | 38.525 | 1.00 | 11.70 | B N |
| ATOM | 10504 | CA | GLY | 587 | 111.641 | 36.168 | 37.242 | 1.00 | 11.61 | B C |
| ATOM | 10505 | C | GLY | 587 | 110.405 | 35.960 | 36.373 | 1.00 | 14.10 | B C |
| ATOM | 10506 | O | GLY | 587 | 109.302 | 35.786 | 36.884 | 1.00 | 13.91 | B O |
| ATOM | 10507 | N | ASP | 588 | 110.595 | 35.949 | 35.054 | 1.00 | 16.19 | B N |
| ATOM | 10508 | CA | ASP | 588 | 109.500 | 35.776 | 34.105 | 1.00 | 17.70 | B C |
| ATOM | 10509 | CB | ASP | 588 | 110.002 | 35.993 | 32.680 | 1.00 | 18.98 | B C |
| ATOM | 10510 | CG | ASP | 588 | 110.708 | 37.312 | 32.505 | 1.00 | 20.57 | B C |
| ATOM | 10511 | OD1 | ASP | 588 | 110.236 | 38.335 | 33.040 | 1.00 | 23.28 | B O |
| ATOM | 10512 | OD2 | ASP | 588 | 111.738 | 37.327 | 31.809 | 1.00 | 23.25 | B O |
| ATOM | 10513 | C | ASP | 588 | 108.723 | 34.454 | 34.139 | 1.00 | 17.46 | B C |
| ATOM | 10514 | O | ASP | 588 | 107.608 | 34.389 | 33.635 | 1.00 | 16.74 | B O |
| ATOM | 10515 | N | LYS | 589 | 109.294 | 33.397 | 34.697 | 1.00 | 18.02 | B N |
| ATOM | 10516 | CA | LYS | 589 | 108.559 | 32.143 | 34.734 | 1.00 | 20.00 | B C |
| ATOM | 10517 | CB | LYS | 589 | 109.383 | 31.030 | 35.372 | 1.00 | 22.21 | B C |
| ATOM | 10518 | CG | LYS | 589 | 108.633 | 29.710 | 35.443 | 1.00 | 27.16 | B C |
| ATOM | 10519 | CD | LYS | 589 | 109.526 | 28.579 | 35.940 | 1.00 | 32.47 | B C |
| ATOM | 10520 | CE | LYS | 589 | 108.753 | 27.273 | 36.111 | 1.00 | 33.79 | B C |
| ATOM | 10521 | NZ | LYS | 589 | 109.605 | 26.232 | 36.771 | 1.00 | 35.98 | B N |
| ATOM | 10522 | C | LYS | 589 | 107.290 | 32.362 | 35.536 | 1.00 | 20.94 | B C |
| ATOM | 10523 | O | LYS | 589 | 106.244 | 31.781 | 35.242 | 1.00 | 23.79 | B O |
| ATOM | 10524 | N | ILE | 590 | 107.384 | 33.212 | 36.552 | 1.00 | 18.06 | B N |
| ATOM | 10525 | CA | ILE | 590 | 106.237 | 33.523 | 37.379 | 1.00 | 14.07 | B C |
| ATOM | 10526 | CB | ILE | 590 | 106.681 | 33.901 | 38.814 | 1.00 | 11.33 | B C |
| ATOM | 10527 | CG2 | ILE | 590 | 105.585 | 34.654 | 39.538 | 1.00 | 9.61 | B C |
| ATOM | 10528 | CG1 | ILE | 590 | 107.057 | 32.635 | 39.585 | 1.00 | 10.89 | B C |
| ATOM | 10529 | CD1 | ILE | 590 | 107.750 | 32.888 | 40.897 | 1.00 | 7.05 | B C |
| ATOM | 10530 | C | ILE | 590 | 105.461 | 34.682 | 36.753 | 1.00 | 15.70 | B C |
| ATOM | 10531 | O | ILE | 590 | 104.254 | 34.583 | 36.511 | 1.00 | 16.31 | B O |
| ATOM | 10532 | N | MET | 591 | 106.159 | 35.774 | 36.465 | 1.00 | 15.00 | B N |
| ATOM | 10533 | CA | MET | 591 | 105.506 | 36.948 | 35.907 | 1.00 | 14.79 | B C |
| ATOM | 10534 | CB | MET | 591 | 106.512 | 38.088 | 35.759 | 1.00 | 14.22 | B C |

| | | | | | | | | | | |
|---|---|---|---|---|---|---|---|---|---|---|
| ATOM | 10535 | CG | MET | 591 | 105.854 | 39.452 | 35.581 | 1.00 18.55 | B | C |
| ATOM | 10536 | SD | MET | 591 | 107.027 | 40.830 | 35.526 | 1.00 17.84 | B | S |
| ATOM | 10537 | CE | MET | 591 | 107.813 | 40.502 | 33.933 | 1.00 16.39 | B | C |
| ATOM | 10538 | C | MET | 591 | 104.788 | 36.699 | 34.582 | 1.00 14.86 | B | C |
| ATOM | 10539 | O | MET | 591 | 103.643 | 37.113 | 34.418 | 1.00 14.45 | B | O |
| ATOM | 10540 | N | HIS | 592 | 105.451 | 36.022 | 33.647 | 1.00 14.66 | B | N |
| ATOM | 10541 | CA | HIS | 592 | 104.863 | 35.725 | 32.343 | 1.00 14.33 | B | C |
| ATOM | 10542 | CB | HIS | 592 | 105.962 | 35.424 | 31.332 | 1.00 15.14 | B | C |
| ATOM | 10543 | CG | HIS | 592 | 106.753 | 36.626 | 30.922 | 1.00 17.56 | B | C |
| ATOM | 10544 | CD2 | HIS | 592 | 106.626 | 37.933 | 31.252 | 1.00 17.20 | B | C |
| ATOM | 10545 | ND1 | HIS | 592 | 107.810 | 36.555 | 30.041 | 1.00 17.84 | B | N |
| ATOM | 10546 | CE1 | HIS | 592 | 108.300 | 37.765 | 29.845 | 1.00 16.59 | B | C |
| ATOM | 10547 | NE2 | HIS | 592 | 107.598 | 38.620 | 30.567 | 1.00 16.88 | B | N |
| ATOM | 10548 | C | HIS | 592 | 103.859 | 34.569 | 32.355 | 1.00 15.17 | B | C |
| ATOM | 10549 | O | HIS | 592 | 103.224 | 34.274 | 31.344 | 1.00 15.89 | B | O |
| ATOM | 10550 | N | ALA | 593 | 103.708 | 33.917 | 33.500 | 1.00 15.86 | B | N |
| ATOM | 10551 | CA | ALA | 593 | 102.775 | 32.810 | 33.615 | 1.00 14.02 | B | C |
| ATOM | 10552 | CB | ALA | 593 | 102.690 | 32.353 | 35.060 | 1.00 13.60 | B | C |
| ATOM | 10553 | C | ALA | 593 | 101.393 | 33.195 | 33.106 | 1.00 15.66 | B | C |
| ATOM | 10554 | O | ALA | 593 | 100.647 | 32.335 | 32.631 | 1.00 17.83 | B | O |
| ATOM | 10555 | N | ILE | 594 | 101.043 | 34.478 | 33.207 | 1.00 16.63 | B | N |
| ATOM | 10556 | CA | ILE | 594 | 99.731 | 34.945 | 32.745 | 1.00 16.87 | B | C |
| ATOM | 10557 | CB | ILE | 594 | 99.035 | 35.857 | 33.791 | 1.00 15.87 | B | C |
| ATOM | 10558 | CG2 | ILE | 594 | 98.506 | 35.017 | 34.932 | 1.00 16.36 | B | C |
| ATOM | 10559 | CG1 | ILE | 594 | 100.006 | 36.915 | 34.321 | 1.00 16.86 | B | C |
| ATOM | 10560 | CD1 | ILE | 594 | 100.533 | 37.882 | 33.274 | 1.00 16.67 | B | C |
| ATOM | 10561 | C | ILE | 594 | 99.748 | 35.689 | 31.413 | 1.00 17.96 | B | C |
| ATOM | 10562 | O | ILE | 594 | 98.884 | 36.525 | 31.160 | 1.00 19.03 | B | O |
| ATOM | 10563 | N | ASN | 595 | 100.718 | 35.385 | 30.558 | 1.00 17.93 | B | N |
| ATOM | 10564 | CA | ASN | 595 | 100.802 | 36.050 | 29.263 | 1.00 19.09 | B | C |
| ATOM | 10565 | CB | ASN | 595 | 102.140 | 35.737 | 28.592 | 1.00 19.22 | B | C |
| ATOM | 10566 | CG | ASN | 595 | 102.291 | 36.441 | 27.260 | 1.00 19.91 | B | C |
| ATOM | 10567 | OD1 | ASN | 595 | 102.320 | 37.668 | 27.198 | 1.00 19.01 | B | O |
| ATOM | 10568 | ND2 | ASN | 595 | 102.377 | 35.667 | 26.184 | 1.00 19.95 | B | N |
| ATOM | 10569 | C | ASN | 595 | 99.659 | 35.641 | 28.330 | 1.00 19.09 | B | C |
| ATOM | 10570 | O | ASN | 595 | 99.456 | 34.460 | 28.076 | 1.00 19.31 | B | O |
| ATOM | 10571 | N | ARG | 596 | 98.933 | 36.630 | 27.814 | 1.00 19.66 | B | N |
| ATOM | 10572 | CA | ARG | 596 | 97.799 | 36.406 | 26.911 | 1.00 20.07 | B | C |
| ATOM | 10573 | CB | ARG | 596 | 98.212 | 35.588 | 25.677 | 1.00 17.78 | B | C |
| ATOM | 10574 | CG | ARG | 596 | 99.233 | 36.247 | 24.756 | 1.00 17.26 | B | C |
| ATOM | 10575 | CD | ARG | 596 | 99.655 | 35.296 | 23.636 | 1.00 17.14 | B | C |
| ATOM | 10576 | NE | ARG | 596 | 98.553 | 34.982 | 22.728 | 1.00 17.97 | B | N |
| ATOM | 10577 | CZ | ARG | 596 | 98.102 | 35.816 | 21.795 | 1.00 19.85 | B | C |
| ATOM | 10578 | NH1 | ARG | 596 | 98.671 | 37.005 | 21.640 | 1.00 21.47 | B | N |
| ATOM | 10579 | NH2 | ARG | 596 | 97.060 | 35.486 | 21.045 | 1.00 18.12 | B | N |
| ATOM | 10580 | C | ARG | 596 | 96.692 | 35.655 | 27.632 | 1.00 21.03 | B | C |
| ATOM | 10581 | O | ARG | 596 | 95.731 | 35.213 | 27.005 | 1.00 22.67 | B | O |
| ATOM | 10582 | N | ARG | 597 | 96.811 | 35.529 | 28.948 | 1.00 20.90 | B | N |
| ATOM | 10583 | CA | ARG | 597 | 95.831 | 34.770 | 29.714 | 1.00 20.85 | B | C |

| ATOM | 10584 | CB | ARG | 597 | 96.437 | 33.414 | 30.078 | 1.00 | 23.88 | B | C |
| --- | --- | --- | --- | --- | --- | --- | --- | --- | --- | --- | --- |
| ATOM | 10585 | CG | ARG | 597 | 95.850 | 32.257 | 29.300 | 1.00 | 31.40 | B | C |
| ATOM | 10586 | CD | ARG | 597 | 95.913 | 32.520 | 27.810 | 1.00 | 34.67 | B | C |
| ATOM | 10587 | NE | ARG | 597 | 95.006 | 31.660 | 27.059 | 1.00 | 35.49 | B | N |
| ATOM | 10588 | CZ | ARG | 597 | 94.776 | 31.792 | 25.759 | 1.00 | 35.98 | B | C |
| ATOM | 10589 | NH1 | ARG | 597 | 95.386 | 32.748 | 25.075 | 1.00 | 35.20 | B | N |
| ATOM | 10590 | NH2 | ARG | 597 | 93.933 | 30.974 | 25.145 | 1.00 | 39.12 | B | N |
| ATOM | 10591 | C | ARG | 597 | 95.292 | 35.429 | 30.976 | 1.00 | 18.83 | B | C |
| ATOM | 10592 | O | ARG | 597 | 94.981 | 34.739 | 31.945 | 1.00 | 17.54 | B | O |
| ATOM | 10593 | N | LEU | 598 | 95.175 | 36.751 | 30.964 | 1.00 | 16.66 | B | N |
| ATOM | 10594 | CA | LEU | 598 | 94.678 | 37.477 | 32.125 | 1.00 | 15.71 | B | C |
| ATOM | 10595 | CB | LEU | 598 | 94.482 | 38.959 | 31.769 | 1.00 | 12.95 | B | C |
| ATOM | 10596 | CG | LEU | 598 | 95.523 | 39.990 | 32.248 | 1.00 | 12.69 | B | C |
| ATOM | 10597 | CD1 | LEU | 598 | 96.939 | 39.473 | 32.106 | 1.00 | 11.40 | B | C |
| ATOM | 10598 | CD2 | LEU | 598 | 95.361 | 41.267 | 31.466 | 1.00 | 9.68 | B | C |
| ATOM | 10599 | C | LEU | 598 | 93.369 | 36.870 | 32.642 | 1.00 | 17.19 | B | C |
| ATOM | 10600 | O | LEU | 598 | 92.533 | 36.398 | 31.863 | 1.00 | 17.25 | B | O |
| ATOM | 10601 | N | GLY | 599 | 93.207 | 36.864 | 33.961 | 1.00 | 16.06 | B | N |
| ATOM | 10602 | CA | GLY | 599 | 91.997 | 36.328 | 34.547 | 1.00 | 16.44 | B | C |
| ATOM | 10603 | C | GLY | 599 | 91.987 | 34.824 | 34.735 | 1.00 | 17.37 | B | C |
| ATOM | 10604 | O | GLY | 599 | 90.921 | 34.221 | 34.843 | 1.00 | 17.28 | B | O |
| ATOM | 10605 | N | THR | 600 | 93.164 | 34.213 | 34.786 | 1.00 | 17.73 | B | N |
| ATOM | 10606 | CA | THR | 600 | 93.247 | 32.775 | 34.972 | 1.00 | 17.95 | B | C |
| ATOM | 10607 | CB | THR | 600 | 93.823 | 32.091 | 33.722 | 1.00 | 18.93 | B | C |
| ATOM | 10608 | OG1 | THR | 600 | 95.185 | 32.495 | 33.530 | 1.00 | 17.74 | B | O |
| ATOM | 10609 | CG2 | THR | 600 | 93.000 | 32.463 | 32.491 | 1.00 | 17.48 | B | C |
| ATOM | 10610 | C | THR | 600 | 94.087 | 32.384 | 36.183 | 1.00 | 19.93 | B | C |
| ATOM | 10611 | O | THR | 600 | 93.574 | 32.285 | 37.295 | 1.00 | 21.69 | B | O |
| ATOM | 10612 | N | PHE | 601 | 95.382 | 32.177 | 35.971 | 1.00 | 21.11 | B | N |
| ATOM | 10613 | CA | PHE | 601 | 96.279 | 31.768 | 37.048 | 1.00 | 21.56 | B | C |
| ATOM | 10614 | CB | PHE | 601 | 97.686 | 31.542 | 36.494 | 1.00 | 20.77 | B | C |
| ATOM | 10615 | CG | PHE | 601 | 97.757 | 30.452 | 35.475 | 1.00 | 21.75 | B | C |
| ATOM | 10616 | CD1 | PHE | 601 | 98.676 | 30.513 | 34.439 | 1.00 | 23.50 | B | C |
| ATOM | 10617 | CD2 | PHE | 601 | 96.896 | 29.366 | 35.539 | 1.00 | 21.83 | B | C |
| ATOM | 10618 | CE1 | PHE | 601 | 98.731 | 29.502 | 33.474 | 1.00 | 24.75 | B | C |
| ATOM | 10619 | CE2 | PHE | 601 | 96.949 | 28.356 | 34.581 | 1.00 | 22.61 | B | C |
| ATOM | 10620 | CZ | PHE | 601 | 97.868 | 28.427 | 33.547 | 1.00 | 20.03 | B | C |
| ATOM | 10621 | C | PHE | 601 | 96.346 | 32.710 | 38.244 | 1.00 | 21.61 | B | C |
| ATOM | 10622 | O | PHE | 601 | 96.437 | 32.247 | 39.386 | 1.00 | 23.03 | B | O |
| ATOM | 10623 | N | GLU | 602 | 96.312 | 34.018 | 37.997 | 1.00 | 20.14 | B | N |
| ATOM | 10624 | CA | GLU | 602 | 96.374 | 34.976 | 39.097 | 1.00 | 19.30 | B | C |
| ATOM | 10625 | CB | GLU | 602 | 96.505 | 36.422 | 38.581 | 1.00 | 16.90 | B | C |
| ATOM | 10626 | CG | GLU | 602 | 95.193 | 37.072 | 38.135 | 1.00 | 17.16 | B | C |
| ATOM | 10627 | CD | GLU | 602 | 94.857 | 36.847 | 36.661 | 1.00 | 17.31 | B | C |
| ATOM | 10628 | OE1 | GLU | 602 | 94.930 | 35.696 | 36.184 | 1.00 | 18.92 | B | O |
| ATOM | 10629 | OE2 | GLU | 602 | 94.505 | 37.830 | 35.981 | 1.00 | 16.38 | B | O |
| ATOM | 10630 | C | GLU | 602 | 95.111 | 34.838 | 39.952 | 1.00 | 18.97 | B | C |
| ATOM | 10631 | O | GLU | 602 | 95.170 | 34.953 | 41.179 | 1.00 | 18.54 | B | O |
| ATOM | 10632 | N | VAL | 603 | 93.979 | 34.584 | 39.296 | 1.00 | 19.02 | B | N |

```
ATOM  10633  CA   VAL  603   92.696  34.413  39.984  1.00  21.62  B  C
ATOM  10634  CB   VAL  603   91.513  34.471  38.999  1.00  21.51  B  C
ATOM  10635  CG1  VAL  603   90.233  34.055  39.701  1.00  19.24  B  C
ATOM  10636  CG2  VAL  603   91.380  35.876  38.442  1.00  21.00  B  C
ATOM  10637  C    VAL  603   92.643  33.073  40.716  1.00  22.35  B  C
ATOM  10638  O    VAL  603   92.160  32.989  41.848  1.00  21.06  B  O
ATOM  10639  N    GLU  604   93.141  32.031  40.059  1.00  22.98  B  N
ATOM  10640  CA   GLU  604   93.182  30.702  40.656  1.00  26.04  B  C
ATOM  10641  CB   GLU  604   93.721  29.681  39.645  1.00  28.46  B  C
ATOM  10642  CG   GLU  604   92.956  29.671  38.326  1.00  35.94  B  C
ATOM  10643  CD   GLU  604   93.559  28.742  37.273  1.00  40.17  B  C
ATOM  10644  OE1  GLU  604   93.215  28.911  36.076  1.00  40.47  B  O
ATOM  10645  OE2  GLU  604   94.360  27.844  37.637  1.00  41.61  B  O
ATOM  10646  C    GLU  604   94.072  30.705  41.905  1.00  24.63  B  C
ATOM  10647  O    GLU  604   93.657  30.255  42.976  1.00  25.47  B  O
ATOM  10648  N    ASP  605   95.286  31.234  41.775  1.00  22.17  B  N
ATOM  10649  CA   ASP  605   96.213  31.255  42.900  1.00  21.12  B  C
ATOM  10650  CB   ASP  605   97.568  31.827  42.463  1.00  23.09  B  C
ATOM  10651  CG   ASP  605   98.263  30.958  41.414  1.00  24.43  B  C
ATOM  10652  OD1  ASP  605   97.894  29.774  41.266  1.00  26.59  B  O
ATOM  10653  OD2  ASP  605   99.188  31.453  40.742  1.00  25.60  B  O
ATOM  10654  C    ASP  605   95.712  31.967  44.159  1.00  19.42  B  C
ATOM  10655  O    ASP  605   96.099  31.598  45.260  1.00  19.67  B  O
ATOM  10656  N    GLN  606   94.868  32.983  44.014  1.00  17.23  B  N
ATOM  10657  CA   GLN  606   94.337  33.673  45.192  1.00  16.41  B  C
ATOM  10658  CB   GLN  606   93.576  34.951  44.795  1.00  17.09  B  C
ATOM  10659  CG   GLN  606   94.407  36.070  44.165  1.00  15.81  B  C
ATOM  10660  CD   GLN  606   95.332  36.748  45.162  1.00  15.36  B  C
ATOM  10661  OE1  GLN  606   94.879  37.283  46.173  1.00  13.19  B  O
ATOM  10662  NE2  GLN  606   96.637  36.730  44.878  1.00  14.39  B  N
ATOM  10663  C    GLN  606   93.360  32.706  45.878  1.00  15.71  B  C
ATOM  10664  O    GLN  606   93.337  32.583  47.102  1.00  14.30  B  O
ATOM  10665  N    ILE  607   92.549  32.030  45.070  1.00  13.95  B  N
ATOM  10666  CA   ILE  607   91.584  31.076  45.583  1.00  13.95  B  C
ATOM  10667  CB   ILE  607   90.772  30.437  44.448  1.00  12.90  B  C
ATOM  10668  CG2  ILE  607   89.925  29.294  44.996  1.00  11.78  B  C
ATOM  10669  CG1  ILE  607   89.909  31.504  43.773  1.00  12.90  B  C
ATOM  10670  CD1  ILE  607   89.162  31.016  42.560  1.00  11.00  B  C
ATOM  10671  C    ILE  607   92.330  29.985  46.318  1.00  15.04  B  C
ATOM  10672  O    ILE  607   92.008  29.670  47.462  1.00  15.40  B  O
ATOM  10673  N    GLU  608   93.331  29.413  45.652  1.00  16.29  B  N
ATOM  10674  CA   GLU  608   94.144  28.359  46.246  1.00  18.48  B  C
ATOM  10675  CB   GLU  608   95.180  27.864  45.235  1.00  18.74  B  C
ATOM  10676  CG   GLU  608   96.164  26.851  45.792  1.00  22.43  B  C
ATOM  10677  CD   GLU  608   95.498  25.557  46.213  1.00  29.00  B  C
ATOM  10678  OE1  GLU  608   96.096  24.817  47.032  1.00  32.52  B  O
ATOM  10679  OE2  GLU  608   94.382  25.274  45.721  1.00  31.62  B  O
ATOM  10680  C    GLU  608   94.848  28.889  47.501  1.00  20.58  B  C
ATOM  10681  O    GLU  608   95.114  28.138  48.446  1.00  23.01  B  O
```

FIG. 4-219 (Continued)

| | | | | | | | | | | | |
|---|---|---|---|---|---|---|---|---|---|---|---|
| ATOM | 10682 | N | ALA | 609 | 95.150 | 30.183 | 47.506 | 1.00 | 19.99 | B | N |
| ATOM | 10683 | CA | ALA | 609 | 95.811 | 30.789 | 48.646 | 1.00 | 21.28 | B | C |
| ATOM | 10684 | CB | ALA | 609 | 96.269 | 32.196 | 48.310 | 1.00 | 19.81 | B | C |
| ATOM | 10685 | C | ALA | 609 | 94.826 | 30.819 | 49.797 | 1.00 | 21.63 | B | C |
| ATOM | 10686 | O | ALA | 609 | 95.152 | 30.426 | 50.915 | 1.00 | 21.88 | B | O |
| ATOM | 10687 | N | ALA | 610 | 93.618 | 31.286 | 49.516 | 1.00 | 23.07 | B | N |
| ATOM | 10688 | CA | ALA | 610 | 92.580 | 31.358 | 50.535 | 1.00 | 25.56 | B | C |
| ATOM | 10689 | CB | ALA | 610 | 91.317 | 31.963 | 49.957 | 1.00 | 25.38 | B | C |
| ATOM | 10690 | C | ALA | 610 | 92.300 | 29.952 | 51.024 | 1.00 | 26.13 | B | C |
| ATOM | 10691 | O | ALA | 610 | 92.256 | 29.694 | 52.223 | 1.00 | 25.97 | B | O |
| ATOM | 10692 | N | ARG | 611 | 92.119 | 29.044 | 50.073 | 1.00 | 28.12 | B | N |
| ATOM | 10693 | CA | ARG | 611 | 91.838 | 27.647 | 50.374 | 1.00 | 28.88 | B | C |
| ATOM | 10694 | CB | ARG | 611 | 91.886 | 26.826 | 49.087 | 1.00 | 27.27 | B | C |
| ATOM | 10695 | CG | ARG | 611 | 91.518 | 25.372 | 49.260 | 1.00 | 28.40 | B | C |
| ATOM | 10696 | CD | ARG | 611 | 91.547 | 24.668 | 47.925 | 1.00 | 30.54 | B | C |
| ATOM | 10697 | NE | ARG | 611 | 90.501 | 25.152 | 47.028 | 1.00 | 33.73 | B | N |
| ATOM | 10698 | CZ | ARG | 611 | 90.628 | 25.223 | 45.706 | 1.00 | 36.39 | B | C |
| ATOM | 10699 | NH1 | ARG | 611 | 91.764 | 24.848 | 45.129 | 1.00 | 38.00 | B | N |
| ATOM | 10700 | NH2 | ARG | 611 | 89.615 | 25.645 | 44.956 | 1.00 | 37.15 | B | N |
| ATOM | 10701 | C | ARG | 611 | 92.826 | 27.082 | 51.391 | 1.00 | 29.24 | B | C |
| ATOM | 10702 | O | ARG | 611 | 92.446 | 26.330 | 52.287 | 1.00 | 30.51 | B | O |
| ATOM | 10703 | N | GLN | 612 | 94.092 | 27.452 | 51.260 | 1.00 | 30.24 | B | N |
| ATOM | 10704 | CA | GLN | 612 | 95.105 | 26.965 | 52.182 | 1.00 | 30.75 | B | C |
| ATOM | 10705 | CB | GLN | 612 | 96.491 | 27.029 | 51.532 | 1.00 | 29.62 | B | C |
| ATOM | 10706 | CG | GLN | 612 | 96.738 | 25.866 | 50.581 | 1.00 | 31.27 | B | C |
| ATOM | 10707 | CD | GLN | 612 | 98.183 | 25.741 | 50.150 | 1.00 | 32.19 | B | C |
| ATOM | 10708 | OE1 | GLN | 612 | 99.097 | 25.778 | 50.979 | 1.00 | 32.20 | B | O |
| ATOM | 10709 | NE2 | GLN | 612 | 98.400 | 25.578 | 48.848 | 1.00 | 31.86 | B | N |
| ATOM | 10710 | C | GLN | 612 | 95.109 | 27.691 | 53.524 | 1.00 | 31.36 | B | C |
| ATOM | 10711 | O | GLN | 612 | 95.441 | 27.095 | 54.545 | 1.00 | 32.39 | B | O |
| ATOM | 10712 | N | PHE | 613 | 94.740 | 28.969 | 53.533 | 1.00 | 31.39 | B | N |
| ATOM | 10713 | CA | PHE | 613 | 94.705 | 29.717 | 54.784 | 1.00 | 30.50 | B | C |
| ATOM | 10714 | CB | PHE | 613 | 94.527 | 31.217 | 54.538 | 1.00 | 30.43 | B | C |
| ATOM | 10715 | CG | PHE | 613 | 95.651 | 31.853 | 53.775 | 1.00 | 31.06 | B | C |
| ATOM | 10716 | CD1 | PHE | 613 | 96.974 | 31.532 | 54.058 | 1.00 | 32.48 | B | C |
| ATOM | 10717 | CD2 | PHE | 613 | 95.385 | 32.805 | 52.796 | 1.00 | 30.25 | B | C |
| ATOM | 10718 | CE1 | PHE | 613 | 98.024 | 32.156 | 53.371 | 1.00 | 32.97 | B | C |
| ATOM | 10719 | CE2 | PHE | 613 | 96.419 | 33.432 | 52.109 | 1.00 | 31.17 | B | C |
| ATOM | 10720 | CZ | PHE | 613 | 97.742 | 33.109 | 52.394 | 1.00 | 32.13 | B | C |
| ATOM | 10721 | C | PHE | 613 | 93.531 | 29.214 | 55.607 | 1.00 | 30.36 | B | C |
| ATOM | 10722 | O | PHE | 613 | 93.572 | 29.216 | 56.830 | 1.00 | 28.96 | B | O |
| ATOM | 10723 | N | SER | 614 | 92.478 | 28.786 | 54.923 | 1.00 | 31.88 | B | N |
| ATOM | 10724 | CA | SER | 614 | 91.292 | 28.286 | 55.600 | 1.00 | 34.43 | B | C |
| ATOM | 10725 | CB | SER | 614 | 90.141 | 28.104 | 54.607 | 1.00 | 34.30 | B | C |
| ATOM | 10726 | OG | SER | 614 | 90.419 | 27.055 | 53.697 | 1.00 | 34.39 | B | O |
| ATOM | 10727 | C | SER | 614 | 91.609 | 26.953 | 56.264 | 1.00 | 35.74 | B | C |
| ATOM | 10728 | O | SER | 614 | 90.908 | 26.519 | 57.178 | 1.00 | 37.21 | B | O |
| ATOM | 10729 | N | LYS | 615 | 92.670 | 26.307 | 55.797 | 1.00 | 36.52 | B | N |
| ATOM | 10730 | CA | LYS | 615 | 93.079 | 25.030 | 56.350 | 1.00 | 37.25 | B | C |

FIG. 4-220 (Continued)

| | | | | | | | | | | |
|---|---|---|---|---|---|---|---|---|---|---|
| ATOM | 10731 | CB | LYS | 615 | 93.781 | 24.196 | 55.283 | 1.00 | 37.94 | B C |
| ATOM | 10732 | CG | LYS | 615 | 92.839 | 23.516 | 54.293 | 1.00 | 40.25 | B C |
| ATOM | 10733 | CD | LYS | 615 | 93.595 | 23.050 | 53.053 | 1.00 | 42.18 | B C |
| ATOM | 10734 | CE | LYS | 615 | 94.883 | 22.317 | 53.419 | 1.00 | 42.76 | B C |
| ATOM | 10735 | NZ | LYS | 615 | 95.776 | 22.147 | 52.237 | 1.00 | 43.07 | B N |
| ATOM | 10736 | C | LYS | 615 | 94.001 | 25.231 | 57.544 | 1.00 | 37.98 | B C |
| ATOM | 10737 | O | LYS | 615 | 94.379 | 24.275 | 58.217 | 1.00 | 40.67 | B O |
| ATOM | 10738 | N | MET | 616 | 94.373 | 26.474 | 57.809 | 1.00 | 37.04 | B N |
| ATOM | 10739 | CA | MET | 616 | 95.240 | 26.744 | 58.948 | 1.00 | 36.91 | B C |
| ATOM | 10740 | CB | MET | 616 | 96.021 | 28.047 | 58.738 | 1.00 | 36.80 | B C |
| ATOM | 10741 | CG | MET | 616 | 97.042 | 27.961 | 57.613 | 1.00 | 36.28 | B C |
| ATOM | 10742 | SD | MET | 616 | 97.847 | 29.532 | 57.282 | 1.00 | 40.04 | B S |
| ATOM | 10743 | CE | MET | 616 | 99.135 | 29.023 | 56.125 | 1.00 | 35.34 | B C |
| ATOM | 10744 | C | MET | 616 | 94.370 | 26.817 | 60.200 | 1.00 | 35.92 | B C |
| ATOM | 10745 | O | MET | 616 | 93.181 | 27.143 | 60.130 | 1.00 | 35.52 | B O |
| ATOM | 10746 | N | GLY | 617 | 94.973 | 26.514 | 61.343 | 1.00 | 33.40 | B N |
| ATOM | 10747 | CA | GLY | 617 | 94.233 | 26.505 | 62.587 | 1.00 | 31.05 | B C |
| ATOM | 10748 | C | GLY | 617 | 93.584 | 27.783 | 63.072 | 1.00 | 29.42 | B C |
| ATOM | 10749 | O | GLY | 617 | 92.516 | 27.729 | 63.689 | 1.00 | 30.60 | B O |
| ATOM | 10750 | N | PHE | 618 | 94.202 | 28.926 | 62.797 | 1.00 | 26.74 | B N |
| ATOM | 10751 | CA | PHE | 618 | 93.676 | 30.204 | 63.271 | 1.00 | 25.54 | B C |
| ATOM | 10752 | CB | PHE | 618 | 94.852 | 31.118 | 63.636 | 1.00 | 26.06 | B C |
| ATOM | 10753 | CG | PHE | 618 | 95.898 | 31.216 | 62.563 | 1.00 | 25.52 | B C |
| ATOM | 10754 | CD1 | PHE | 618 | 95.763 | 32.127 | 61.523 | 1.00 | 25.78 | B C |
| ATOM | 10755 | CD2 | PHE | 618 | 97.012 | 30.385 | 62.588 | 1.00 | 25.30 | B C |
| ATOM | 10756 | CE1 | PHE | 618 | 96.726 | 32.214 | 60.518 | 1.00 | 26.10 | B C |
| ATOM | 10757 | CE2 | PHE | 618 | 97.981 | 30.459 | 61.590 | 1.00 | 26.94 | B C |
| ATOM | 10758 | CZ | PHE | 618 | 97.836 | 31.380 | 60.549 | 1.00 | 27.08 | B C |
| ATOM | 10759 | C | PHE | 618 | 92.706 | 30.948 | 62.353 | 1.00 | 24.88 | B C |
| ATOM | 10760 | O | PHE | 618 | 92.319 | 32.079 | 62.644 | 1.00 | 24.17 | B O |
| ATOM | 10761 | N | VAL | 619 | 92.297 | 30.313 | 61.259 | 1.00 | 24.78 | B N |
| ATOM | 10762 | CA | VAL | 619 | 91.381 | 30.947 | 60.324 | 1.00 | 25.04 | B C |
| ATOM | 10763 | CB | VAL | 619 | 91.913 | 30.876 | 58.875 | 1.00 | 25.17 | B C |
| ATOM | 10764 | CG1 | VAL | 619 | 91.007 | 31.665 | 57.945 | 1.00 | 23.09 | B C |
| ATOM | 10765 | CG2 | VAL | 619 | 93.326 | 31.415 | 58.817 | 1.00 | 26.33 | B C |
| ATOM | 10766 | C | VAL | 619 | 90.004 | 30.303 | 60.371 | 1.00 | 25.53 | B C |
| ATOM | 10767 | O | VAL | 619 | 89.873 | 29.083 | 60.378 | 1.00 | 25.84 | B O |
| ATOM | 10768 | N | ASP | 620 | 88.981 | 31.146 | 60.405 | 1.00 | 26.00 | B N |
| ATOM | 10769 | CA | ASP | 620 | 87.601 | 30.701 | 60.449 | 1.00 | 26.41 | B C |
| ATOM | 10770 | CB | ASP | 620 | 86.779 | 31.717 | 61.238 | 1.00 | 26.64 | B C |
| ATOM | 10771 | CG | ASP | 620 | 85.324 | 31.334 | 61.355 | 1.00 | 27.36 | B C |
| ATOM | 10772 | OD1 | ASP | 620 | 84.591 | 32.074 | 62.041 | 1.00 | 27.95 | B O |
| ATOM | 10773 | OD2 | ASP | 620 | 84.914 | 30.306 | 60.765 | 1.00 | 26.86 | B O |
| ATOM | 10774 | C | ASP | 620 | 87.104 | 30.610 | 59.011 | 1.00 | 27.59 | B C |
| ATOM | 10775 | O | ASP | 620 | 86.687 | 31.610 | 58.435 | 1.00 | 27.47 | B O |
| ATOM | 10776 | N | ASN | 621 | 87.144 | 29.409 | 58.438 | 1.00 | 29.06 | B N |
| ATOM | 10777 | CA | ASN | 621 | 86.733 | 29.213 | 57.053 | 1.00 | 30.04 | B C |
| ATOM | 10778 | CB | ASN | 621 | 86.925 | 27.752 | 56.622 | 1.00 | 33.33 | B C |
| ATOM | 10779 | CG | ASN | 621 | 86.022 | 26.782 | 57.377 | 1.00 | 36.94 | B C |

FIG. 4-221 (Continued)

| | | | | | | | | | | |
|---|---|---|---|---|---|---|---|---|---|---|
| ATOM | 10780 | OD1 | ASN | 621 | 84.795 | 26.940 | 57.415 | 1.00 | 38.23 | B | O |
| ATOM | 10781 | ND2 | ASN | 621 | 86.630 | 25.763 | 57.972 | 1.00 | 39.37 | B | N |
| ATOM | 10782 | C | ASN | 621 | 85.310 | 29.639 | 56.756 | 1.00 | 29.63 | B | C |
| ATOM | 10783 | O | ASN | 621 | 84.887 | 29.626 | 55.604 | 1.00 | 30.93 | B | O |
| ATOM | 10784 | N | LYS | 622 | 84.563 | 30.007 | 57.787 | 1.00 | 28.32 | B | N |
| ATOM | 10785 | CA | LYS | 622 | 83.195 | 30.441 | 57.573 | 1.00 | 27.00 | B | C |
| ATOM | 10786 | CB | LYS | 622 | 82.303 | 29.986 | 58.740 | 1.00 | 29.24 | B | C |
| ATOM | 10787 | CG | LYS | 622 | 82.062 | 28.471 | 58.738 | 1.00 | 32.47 | B | C |
| ATOM | 10788 | CD | LYS | 622 | 81.029 | 28.002 | 59.761 | 1.00 | 33.84 | B | C |
| ATOM | 10789 | CE | LYS | 622 | 81.527 | 28.099 | 61.197 | 1.00 | 35.48 | B | C |
| ATOM | 10790 | NZ | LYS | 622 | 81.571 | 29.501 | 61.703 | 1.00 | 36.73 | B | N |
| ATOM | 10791 | C | LYS | 622 | 83.168 | 31.957 | 57.404 | 1.00 | 25.42 | B | C |
| ATOM | 10792 | O | LYS | 622 | 82.145 | 32.543 | 57.047 | 1.00 | 26.19 | B | O |
| ATOM | 10793 | N | ARG | 623 | 84.314 | 32.583 | 57.642 | 1.00 | 21.83 | B | N |
| ATOM | 10794 | CA | ARG | 623 | 84.436 | 34.023 | 57.515 | 1.00 | 18.89 | B | C |
| ATOM | 10795 | CB | ARG | 623 | 84.380 | 34.664 | 58.895 | 1.00 | 17.53 | B | C |
| ATOM | 10796 | CG | ARG | 623 | 83.019 | 34.573 | 59.510 | 1.00 | 16.79 | B | C |
| ATOM | 10797 | CD | ARG | 623 | 83.122 | 34.394 | 60.991 | 1.00 | 19.29 | B | C |
| ATOM | 10798 | NE | ARG | 623 | 83.405 | 35.632 | 61.690 | 1.00 | 19.11 | B | N |
| ATOM | 10799 | CZ | ARG | 623 | 84.207 | 35.718 | 62.743 | 1.00 | 18.68 | B | C |
| ATOM | 10800 | NH1 | ARG | 623 | 84.812 | 34.639 | 63.212 | 1.00 | 16.76 | B | N |
| ATOM | 10801 | NH2 | ARG | 623 | 84.388 | 36.884 | 63.336 | 1.00 | 22.60 | B | N |
| ATOM | 10802 | C | ARG | 623 | 85.711 | 34.440 | 56.792 | 1.00 | 18.21 | B | C |
| ATOM | 10803 | O | ARG | 623 | 86.719 | 34.776 | 57.414 | 1.00 | 19.54 | B | O |
| ATOM | 10804 | N | ILE | 624 | 85.651 | 34.412 | 55.468 | 1.00 | 16.09 | B | N |
| ATOM | 10805 | CA | ILE | 624 | 86.769 | 34.798 | 54.629 | 1.00 | 16.59 | B | C |
| ATOM | 10806 | CB | ILE | 624 | 87.439 | 33.572 | 53.991 | 1.00 | 18.45 | B | C |
| ATOM | 10807 | CG2 | ILE | 624 | 88.563 | 34.017 | 53.059 | 1.00 | 18.66 | B | C |
| ATOM | 10808 | CG1 | ILE | 624 | 87.971 | 32.647 | 55.088 | 1.00 | 19.91 | B | C |
| ATOM | 10809 | CD1 | ILE | 624 | 88.623 | 31.385 | 54.564 | 1.00 | 22.12 | B | C |
| ATOM | 10810 | C | ILE | 624 | 86.230 | 35.695 | 53.519 | 1.00 | 16.74 | B | C |
| ATOM | 10811 | O | ILE | 624 | 85.402 | 35.268 | 52.710 | 1.00 | 17.92 | B | O |
| ATOM | 10812 | N | ALA | 625 | 86.688 | 36.939 | 53.494 | 1.00 | 15.06 | B | N |
| ATOM | 10813 | CA | ALA | 625 | 86.250 | 37.886 | 52.488 | 1.00 | 15.59 | B | C |
| ATOM | 10814 | CB | ALA | 625 | 85.816 | 39.174 | 53.155 | 1.00 | 18.31 | B | C |
| ATOM | 10815 | C | ALA | 625 | 87.375 | 38.159 | 51.503 | 1.00 | 16.90 | B | C |
| ATOM | 10816 | O | ALA | 625 | 88.431 | 37.523 | 51.558 | 1.00 | 16.49 | B | O |
| ATOM | 10817 | N | ILE | 626 | 87.149 | 39.107 | 50.598 | 1.00 | 16.75 | B | N |
| ATOM | 10818 | CA | ILE | 626 | 88.158 | 39.454 | 49.608 | 1.00 | 17.73 | B | C |
| ATOM | 10819 | CB | ILE | 626 | 88.207 | 38.397 | 48.478 | 1.00 | 19.21 | B | C |
| ATOM | 10820 | CG2 | ILE | 626 | 86.883 | 38.365 | 47.742 | 1.00 | 19.01 | B | C |
| ATOM | 10821 | CG1 | ILE | 626 | 89.348 | 38.713 | 47.511 | 1.00 | 18.94 | B | C |
| ATOM | 10822 | CD1 | ILE | 626 | 89.576 | 37.642 | 46.471 | 1.00 | 20.78 | B | C |
| ATOM | 10823 | C | ILE | 626 | 87.850 | 40.810 | 49.003 | 1.00 | 17.46 | B | C |
| ATOM | 10824 | O | ILE | 626 | 86.692 | 41.116 | 48.754 | 1.00 | 18.15 | B | O |
| ATOM | 10825 | N | TRP | 627 | 88.878 | 41.628 | 48.781 | 1.00 | 16.65 | B | N |
| ATOM | 10826 | CA | TRP | 627 | 88.663 | 42.938 | 48.177 | 1.00 | 15.95 | B | C |
| ATOM | 10827 | CB | TRP | 627 | 88.215 | 43.945 | 49.231 | 1.00 | 14.07 | B | C |
| ATOM | 10828 | CG | TRP | 627 | 89.318 | 44.713 | 49.875 | 1.00 | 12.00 | B | C |

| | | | | | | | | | | |
|---|---|---|---|---|---|---|---|---|---|---|
| ATOM | 10829 | CD2 | TRP | 627 | 89.641 | 46.084 | 49.646 | 1.00 | 11.41 | B | C |
| ATOM | 10830 | CE2 | TRP | 627 | 90.725 | 46.410 | 50.500 | 1.00 | 10.99 | B | C |
| ATOM | 10831 | CE3 | TRP | 627 | 89.121 | 47.074 | 48.806 | 1.00 | 9.75 | B | C |
| ATOM | 10832 | CD1 | TRP | 627 | 90.198 | 44.267 | 50.826 | 1.00 | 14.55 | B | C |
| ATOM | 10833 | NE1 | TRP | 627 | 91.046 | 45.283 | 51.208 | 1.00 | 10.25 | B | N |
| ATOM | 10834 | CZ2 | TRP | 627 | 91.289 | 47.681 | 50.536 | 1.00 | 9.06 | B | C |
| ATOM | 10835 | CZ3 | TRP | 627 | 89.685 | 48.340 | 48.844 | 1.00 | 9.47 | B | C |
| ATOM | 10836 | CH2 | TRP | 627 | 90.755 | 48.632 | 49.702 | 1.00 | 8.43 | B | C |
| ATOM | 10837 | C | TRP | 627 | 89.881 | 43.489 | 47.433 | 1.00 | 17.27 | B | C |
| ATOM | 10838 | O | TRP | 627 | 91.027 | 43.146 | 47.732 | 1.00 | 16.96 | B | O |
| ATOM | 10839 | N | GLY | 628 | 89.613 | 44.351 | 46.459 | 1.00 | 16.52 | B | N |
| ATOM | 10840 | CA | GLY | 628 | 90.672 | 44.947 | 45.675 | 1.00 | 16.52 | B | C |
| ATOM | 10841 | C | GLY | 628 | 90.186 | 46.198 | 44.975 | 1.00 | 17.44 | B | C |
| ATOM | 10842 | O | GLY | 628 | 88.977 | 46.441 | 44.887 | 1.00 | 17.88 | B | O |
| ATOM | 10843 | N | TRP | 629 | 91.132 | 46.989 | 44.479 | 1.00 | 15.93 | B | N |
| ATOM | 10844 | CA | TRP | 629 | 90.841 | 48.235 | 43.781 | 1.00 | 15.93 | B | C |
| ATOM | 10845 | CB | TRP | 629 | 91.480 | 49.395 | 44.552 | 1.00 | 13.57 | B | C |
| ATOM | 10846 | CG | TRP | 629 | 90.867 | 50.763 | 44.341 | 1.00 | 14.96 | B | C |
| ATOM | 10847 | CD2 | TRP | 629 | 90.389 | 51.656 | 45.360 | 1.00 | 13.15 | B | C |
| ATOM | 10848 | CE2 | TRP | 629 | 89.944 | 52.830 | 44.712 | 1.00 | 13.17 | B | C |
| ATOM | 10849 | CE3 | TRP | 629 | 90.296 | 51.577 | 46.758 | 1.00 | 14.07 | B | C |
| ATOM | 10850 | CD1 | TRP | 629 | 90.694 | 51.419 | 43.149 | 1.00 | 14.45 | B | C |
| ATOM | 10851 | NE1 | TRP | 629 | 90.141 | 52.657 | 43.366 | 1.00 | 12.77 | B | N |
| ATOM | 10852 | CZ2 | TRP | 629 | 89.411 | 53.921 | 45.414 | 1.00 | 13.59 | B | C |
| ATOM | 10853 | CZ3 | TRP | 629 | 89.767 | 52.660 | 47.461 | 1.00 | 14.81 | B | C |
| ATOM | 10854 | CH2 | TRP | 629 | 89.330 | 53.820 | 46.782 | 1.00 | 15.16 | B | C |
| ATOM | 10855 | C | TRP | 629 | 91.481 | 48.074 | 42.399 | 1.00 | 17.34 | B | C |
| ATOM | 10856 | O | TRP | 629 | 92.571 | 47.517 | 42.285 | 1.00 | 18.55 | B | O |
| ATOM | 10857 | N | SER | 630 | 90.802 | 48.538 | 41.354 | 1.00 | 17.70 | B | N |
| ATOM | 10858 | CA | SER | 630 | 91.309 | 48.430 | 39.982 | 1.00 | 17.70 | B | C |
| ATOM | 10859 | CB | SER | 630 | 92.649 | 49.144 | 39.846 | 1.00 | 18.19 | B | C |
| ATOM | 10860 | OG | SER | 630 | 92.574 | 50.437 | 40.404 | 1.00 | 24.67 | B | O |
| ATOM | 10861 | C | SER | 630 | 91.477 | 46.977 | 39.563 | 1.00 | 17.40 | B | C |
| ATOM | 10862 | O | SER | 630 | 90.501 | 46.235 | 39.469 | 1.00 | 18.69 | B | O |
| ATOM | 10863 | N | TYR | 631 | 92.712 | 46.565 | 39.304 | 1.00 | 16.34 | B | N |
| ATOM | 10864 | CA | TYR | 631 | 92.951 | 45.192 | 38.904 | 1.00 | 15.96 | B | C |
| ATOM | 10865 | CB | TYR | 631 | 94.430 | 44.973 | 38.579 | 1.00 | 15.36 | B | C |
| ATOM | 10866 | CG | TYR | 631 | 94.689 | 43.709 | 37.779 | 1.00 | 15.93 | B | C |
| ATOM | 10867 | CD1 | TYR | 631 | 94.626 | 42.450 | 38.380 | 1.00 | 15.38 | B | C |
| ATOM | 10868 | CE1 | TYR | 631 | 94.830 | 41.287 | 37.634 | 1.00 | 16.25 | B | C |
| ATOM | 10869 | CD2 | TYR | 631 | 94.961 | 43.773 | 36.409 | 1.00 | 15.67 | B | C |
| ATOM | 10870 | CE2 | TYR | 631 | 95.160 | 42.620 | 35.655 | 1.00 | 13.59 | B | C |
| ATOM | 10871 | CZ | TYR | 631 | 95.092 | 41.384 | 36.270 | 1.00 | 15.96 | B | C |
| ATOM | 10872 | OH | TYR | 631 | 95.264 | 40.243 | 35.525 | 1.00 | 14.59 | B | O |
| ATOM | 10873 | C | TYR | 631 | 92.499 | 44.286 | 40.049 | 1.00 | 15.68 | B | C |
| ATOM | 10874 | O | TYR | 631 | 91.949 | 43.213 | 39.824 | 1.00 | 16.42 | B | O |
| ATOM | 10875 | N | GLY | 632 | 92.723 | 44.729 | 41.281 | 1.00 | 15.56 | B | N |
| ATOM | 10876 | CA | GLY | 632 | 92.292 | 43.950 | 42.429 | 1.00 | 14.43 | B | C |
| ATOM | 10877 | C | GLY | 632 | 90.777 | 43.807 | 42.398 | 1.00 | 13.07 | B | C |

FIG. 4-223 (Continued)

| ATOM | 10878 | O | GLY | 632 | 90.239 | 42.771 | 42.777 | 1.00 | 12.09 | B | O |
|---|---|---|---|---|---|---|---|---|---|---|---|
| ATOM | 10879 | N | GLY | 633 | 90.087 | 44.855 | 41.946 | 1.00 | 12.57 | B | N |
| ATOM | 10880 | CA | GLY | 633 | 88.637 | 44.800 | 41.846 | 1.00 | 10.88 | B | C |
| ATOM | 10881 | C | GLY | 633 | 88.271 | 43.743 | 40.818 | 1.00 | 10.78 | B | C |
| ATOM | 10882 | O | GLY | 633 | 87.337 | 42.956 | 40.986 | 1.00 | 9.26 | B | O |
| ATOM | 10883 | N | TYR | 634 | 89.031 | 43.729 | 39.734 | 1.00 | 11.33 | B | N |
| ATOM | 10884 | CA | TYR | 634 | 88.822 | 42.755 | 38.682 | 1.00 | 11.09 | B | C |
| ATOM | 10885 | CB | TYR | 634 | 89.860 | 42.951 | 37.595 | 1.00 | 7.35 | B | C |
| ATOM | 10886 | CG | TYR | 634 | 89.815 | 41.899 | 36.526 | 1.00 | 8.04 | B | C |
| ATOM | 10887 | CD1 | TYR | 634 | 90.949 | 41.162 | 36.204 | 1.00 | 7.58 | B | C |
| ATOM | 10888 | CE1 | TYR | 634 | 90.924 | 40.218 | 35.189 | 1.00 | 7.56 | B | C |
| ATOM | 10889 | CD2 | TYR | 634 | 88.649 | 41.660 | 35.805 | 1.00 | 8.82 | B | C |
| ATOM | 10890 | CE2 | TYR | 634 | 88.615 | 40.715 | 34.788 | 1.00 | 7.88 | B | C |
| ATOM | 10891 | CZ | TYR | 634 | 89.756 | 39.996 | 34.488 | 1.00 | 6.90 | B | C |
| ATOM | 10892 | OH | TYR | 634 | 89.722 | 39.039 | 33.504 | 1.00 | 8.03 | B | O |
| ATOM | 10893 | C | TYR | 634 | 88.967 | 41.358 | 39.278 | 1.00 | 13.02 | B | C |
| ATOM | 10894 | O | TYR | 634 | 88.038 | 40.548 | 39.222 | 1.00 | 13.14 | B | O |
| ATOM | 10895 | N | VAL | 635 | 90.140 | 41.091 | 39.858 | 1.00 | 14.38 | B | N |
| ATOM | 10896 | CA | VAL | 635 | 90.426 | 39.796 | 40.467 | 1.00 | 13.39 | B | C |
| ATOM | 10897 | CB | VAL | 635 | 91.839 | 39.747 | 41.093 | 1.00 | 13.28 | B | C |
| ATOM | 10898 | CG1 | VAL | 635 | 91.995 | 38.467 | 41.923 | 1.00 | 13.06 | B | C |
| ATOM | 10899 | CG2 | VAL | 635 | 92.894 | 39.782 | 39.999 | 1.00 | 8.09 | B | C |
| ATOM | 10900 | C | VAL | 635 | 89.412 | 39.443 | 41.533 | 1.00 | 13.35 | B | C |
| ATOM | 10901 | O | VAL | 635 | 88.932 | 38.320 | 41.563 | 1.00 | 15.02 | B | O |
| ATOM | 10902 | N | THR | 636 | 89.091 | 40.394 | 42.405 | 1.00 | 13.48 | B | N |
| ATOM | 10903 | CA | THR | 636 | 88.108 | 40.160 | 43.457 | 1.00 | 13.74 | B | C |
| ATOM | 10904 | CB | THR | 636 | 87.788 | 41.451 | 44.260 | 1.00 | 15.19 | B | C |
| ATOM | 10905 | OG1 | THR | 636 | 88.950 | 41.886 | 44.978 | 1.00 | 15.24 | B | O |
| ATOM | 10906 | CG2 | THR | 636 | 86.655 | 41.188 | 45.259 | 1.00 | 13.51 | B | C |
| ATOM | 10907 | C | THR | 636 | 86.792 | 39.665 | 42.862 | 1.00 | 14.57 | B | C |
| ATOM | 10908 | O | THR | 636 | 86.160 | 38.750 | 43.395 | 1.00 | 15.29 | B | O |
| ATOM | 10909 | N | SER | 637 | 86.373 | 40.281 | 41.762 | 1.00 | 15.59 | B | N |
| ATOM | 10910 | CA | SER | 637 | 85.120 | 39.905 | 41.112 | 1.00 | 15.99 | B | C |
| ATOM | 10911 | CB | SER | 637 | 84.698 | 40.974 | 40.102 | 1.00 | 16.88 | B | C |
| ATOM | 10912 | OG | SER | 637 | 84.303 | 42.158 | 40.766 | 1.00 | 18.07 | B | O |
| ATOM | 10913 | C | SER | 637 | 85.195 | 38.558 | 40.420 | 1.00 | 16.54 | B | C |
| ATOM | 10914 | O | SER | 637 | 84.250 | 37.773 | 40.487 | 1.00 | 17.87 | B | O |
| ATOM | 10915 | N | MET | 638 | 86.309 | 38.300 | 39.740 | 1.00 | 15.64 | B | N |
| ATOM | 10916 | CA | MET | 638 | 86.493 | 37.030 | 39.052 | 1.00 | 15.55 | B | C |
| ATOM | 10917 | CB | MET | 638 | 87.807 | 37.033 | 38.272 | 1.00 | 15.97 | B | C |
| ATOM | 10918 | CG | MET | 638 | 87.822 | 37.959 | 37.067 | 1.00 | 17.38 | B | C |
| ATOM | 10919 | SD | MET | 638 | 86.715 | 37.422 | 35.736 | 1.00 | 19.14 | B | S |
| ATOM | 10920 | CE | MET | 638 | 87.806 | 36.324 | 34.798 | 1.00 | 15.28 | B | C |
| ATOM | 10921 | C | MET | 638 | 86.511 | 35.913 | 40.093 | 1.00 | 17.56 | B | C |
| ATOM | 10922 | O | MET | 638 | 86.018 | 34.807 | 39.843 | 1.00 | 17.45 | B | O |
| ATOM | 10923 | N | VAL | 639 | 87.086 | 36.199 | 41.260 | 1.00 | 16.50 | B | N |
| ATOM | 10924 | CA | VAL | 639 | 87.133 | 35.207 | 42.317 | 1.00 | 17.27 | B | C |
| ATOM | 10925 | CB | VAL | 639 | 88.047 | 35.640 | 43.480 | 1.00 | 16.78 | B | C |
| ATOM | 10926 | CG1 | VAL | 639 | 87.648 | 34.884 | 44.757 | 1.00 | 16.23 | B | C |

FIG. 4-224 (Continued)

| | | | | | | | | | | |
|---|---|---|---|---|---|---|---|---|---|---|
| ATOM | 10927 | CG2 | VAL | 639 | 89.495 | 35.335 | 43.139 | 1.00 | 14.45 | B C |
| ATOM | 10928 | C | VAL | 639 | 85.742 | 34.919 | 42.875 | 1.00 | 17.57 | B C |
| ATOM | 10929 | O | VAL | 639 | 85.387 | 33.760 | 43.081 | 1.00 | 18.52 | B O |
| ATOM | 10930 | N | LEU | 640 | 84.957 | 35.964 | 43.124 | 1.00 | 16.90 | B N |
| ATOM | 10931 | CA | LEU | 640 | 83.618 | 35.766 | 43.661 | 1.00 | 17.42 | B C |
| ATOM | 10932 | CB | LEU | 640 | 82.978 | 37.098 | 44.032 | 1.00 | 17.45 | B C |
| ATOM | 10933 | CG | LEU | 640 | 83.512 | 37.699 | 45.327 | 1.00 | 17.52 | B C |
| ATOM | 10934 | CD1 | LEU | 640 | 82.743 | 38.962 | 45.654 | 1.00 | 14.30 | B C |
| ATOM | 10935 | CD2 | LEU | 640 | 83.378 | 36.677 | 46.447 | 1.00 | 15.97 | B C |
| ATOM | 10936 | C | LEU | 640 | 82.713 | 35.020 | 42.699 | 1.00 | 17.81 | B C |
| ATOM | 10937 | O | LEU | 640 | 81.821 | 34.284 | 43.119 | 1.00 | 20.73 | B O |
| ATOM | 10938 | N | GLY | 641 | 82.952 | 35.198 | 41.409 | 1.00 | 18.14 | B N |
| ATOM | 10939 | CA | GLY | 641 | 82.135 | 34.526 | 40.418 | 1.00 | 17.61 | B C |
| ATOM | 10940 | C | GLY | 641 | 82.758 | 33.235 | 39.936 | 1.00 | 17.52 | B C |
| ATOM | 10941 | O | GLY | 641 | 82.346 | 32.697 | 38.911 | 1.00 | 15.15 | B O |
| ATOM | 10942 | N | SER | 642 | 83.735 | 32.727 | 40.683 | 1.00 | 17.53 | B N |
| ATOM | 10943 | CA | SER | 642 | 84.419 | 31.497 | 40.297 | 1.00 | 19.98 | B C |
| ATOM | 10944 | CB | SER | 642 | 85.841 | 31.479 | 40.864 | 1.00 | 20.78 | B C |
| ATOM | 10945 | OG | SER | 642 | 85.849 | 31.088 | 42.226 | 1.00 | 21.56 | B O |
| ATOM | 10946 | C | SER | 642 | 83.691 | 30.239 | 40.755 | 1.00 | 21.75 | B C |
| ATOM | 10947 | O | SER | 642 | 83.974 | 29.147 | 40.265 | 1.00 | 22.65 | B O |
| ATOM | 10948 | N | GLY | 643 | 82.768 | 30.395 | 41.701 | 1.00 | 22.05 | B N |
| ATOM | 10949 | CA | GLY | 643 | 82.023 | 29.258 | 42.210 | 1.00 | 22.58 | B C |
| ATOM | 10950 | C | GLY | 643 | 82.811 | 28.335 | 43.130 | 1.00 | 24.03 | B C |
| ATOM | 10951 | O | GLY | 643 | 82.460 | 27.162 | 43.271 | 1.00 | 26.05 | B O |
| ATOM | 10952 | N | SER | 644 | 83.859 | 28.849 | 43.772 | 1.00 | 22.41 | B N |
| ATOM | 10953 | CA | SER | 644 | 84.684 | 28.024 | 44.656 | 1.00 | 21.56 | B C |
| ATOM | 10954 | CB | SER | 644 | 86.065 | 28.657 | 44.833 | 1.00 | 21.02 | B C |
| ATOM | 10955 | OG | SER | 644 | 85.992 | 29.798 | 45.666 | 1.00 | 22.35 | B O |
| ATOM | 10956 | C | SER | 644 | 84.084 | 27.773 | 46.037 | 1.00 | 21.06 | B C |
| ATOM | 10957 | O | SER | 644 | 84.451 | 26.807 | 46.707 | 1.00 | 23.51 | B O |
| ATOM | 10958 | N | GLY | 645 | 83.175 | 28.643 | 46.469 | 1.00 | 19.50 | B N |
| ATOM | 10959 | CA | GLY | 645 | 82.561 | 28.485 | 47.774 | 1.00 | 16.85 | B C |
| ATOM | 10960 | C | GLY | 645 | 83.484 | 28.868 | 48.920 | 1.00 | 18.76 | B C |
| ATOM | 10961 | O | GLY | 645 | 83.111 | 28.771 | 50.090 | 1.00 | 18.32 | B O |
| ATOM | 10962 | N | VAL | 646 | 84.691 | 29.320 | 48.591 | 1.00 | 18.97 | B N |
| ATOM | 10963 | CA | VAL | 646 | 85.669 | 29.695 | 49.612 | 1.00 | 18.18 | B C |
| ATOM | 10964 | CB | VAL | 646 | 87.095 | 29.718 | 49.029 | 1.00 | 19.50 | B C |
| ATOM | 10965 | CG1 | VAL | 646 | 88.082 | 30.202 | 50.086 | 1.00 | 17.45 | B C |
| ATOM | 10966 | CG2 | VAL | 646 | 87.471 | 28.341 | 48.516 | 1.00 | 17.29 | B C |
| ATOM | 10967 | C | VAL | 646 | 85.433 | 31.051 | 50.266 | 1.00 | 18.24 | B C |
| ATOM | 10968 | O | VAL | 646 | 85.860 | 31.270 | 51.396 | 1.00 | 20.76 | B O |
| ATOM | 10969 | N | PHE | 647 | 84.763 | 31.957 | 49.561 | 1.00 | 16.76 | B N |
| ATOM | 10970 | CA | PHE | 647 | 84.525 | 33.297 | 50.082 | 1.00 | 16.60 | B C |
| ATOM | 10971 | CB | PHE | 647 | 85.066 | 34.337 | 49.094 | 1.00 | 16.44 | B C |
| ATOM | 10972 | CG | PHE | 647 | 86.528 | 34.204 | 48.820 | 1.00 | 15.63 | B C |
| ATOM | 10973 | CD1 | PHE | 647 | 87.455 | 34.941 | 49.553 | 1.00 | 14.72 | B C |
| ATOM | 10974 | CD2 | PHE | 647 | 86.985 | 33.320 | 47.844 | 1.00 | 14.49 | B C |
| ATOM | 10975 | CE1 | PHE | 647 | 88.826 | 34.800 | 49.317 | 1.00 | 16.66 | B C |

| | | | | | | | | | | |
|---|---|---|---|---|---|---|---|---|---|---|
| ATOM | 10976 | CE2 | PHE | 647 | 88.356 | 33.170 | 47.600 | 1.00 | 16.73 | B C |
| ATOM | 10977 | CZ | PHE | 647 | 89.278 | 33.913 | 48.338 | 1.00 | 13.35 | B C |
| ATOM | 10978 | C | PHE | 647 | 83.068 | 33.604 | 50.365 | 1.00 | 16.77 | B C |
| ATOM | 10979 | O | PHE | 647 | 82.194 | 33.328 | 49.551 | 1.00 | 17.32 | B O |
| ATOM | 10980 | N | LYS | 648 | 82.819 | 34.214 | 51.515 | 1.00 | 16.74 | B N |
| ATOM | 10981 | CA | LYS | 648 | 81.466 | 34.565 | 51.905 | 1.00 | 19.64 | B C |
| ATOM | 10982 | CB | LYS | 648 | 81.369 | 34.634 | 53.429 | 1.00 | 19.84 | B C |
| ATOM | 10983 | CG | LYS | 648 | 80.069 | 35.233 | 53.911 | 1.00 | 21.93 | B C |
| ATOM | 10984 | CD | LYS | 648 | 79.876 | 35.060 | 55.393 | 1.00 | 23.19 | B C |
| ATOM | 10985 | CE | LYS | 648 | 78.548 | 35.645 | 55.814 | 1.00 | 24.97 | B C |
| ATOM | 10986 | NZ | LYS | 648 | 78.180 | 35.150 | 57.165 | 1.00 | 31.55 | B N |
| ATOM | 10987 | C | LYS | 648 | 81.019 | 35.900 | 51.308 | 1.00 | 21.05 | B C |
| ATOM | 10988 | O | LYS | 648 | 79.851 | 36.070 | 50.930 | 1.00 | 20.25 | B O |
| ATOM | 10989 | N | CYS | 649 | 81.954 | 36.842 | 51.237 | 1.00 | 20.69 | B N |
| ATOM | 10990 | CA | CYS | 649 | 81.670 | 38.163 | 50.711 | 1.00 | 21.97 | B C |
| ATOM | 10991 | C | CYS | 649 | 82.928 | 38.811 | 50.134 | 1.00 | 22.72 | B C |
| ATOM | 10992 | O | CYS | 649 | 84.054 | 38.437 | 50.477 | 1.00 | 23.68 | B O |
| ATOM | 10993 | CB | CYS | 649 | 81.124 | 39.045 | 51.822 | 1.00 | 23.52 | B C |
| ATOM | 10994 | SG | CYS | 649 | 82.287 | 39.215 | 53.208 | 1.00 | 26.89 | B S |
| ATOM | 10995 | N | GLY | 650 | 82.728 | 39.796 | 49.267 | 1.00 | 20.11 | B N |
| ATOM | 10996 | CA | GLY | 650 | 83.850 | 40.476 | 48.668 | 1.00 | 18.42 | B C |
| ATOM | 10997 | C | GLY | 650 | 83.484 | 41.895 | 48.308 | 1.00 | 18.08 | B C |
| ATOM | 10998 | O | GLY | 650 | 82.308 | 42.198 | 48.135 | 1.00 | 18.19 | B O |
| ATOM | 10999 | N | ILE | 651 | 84.490 | 42.764 | 48.209 | 1.00 | 17.42 | B N |
| ATOM | 11000 | CA | ILE | 651 | 84.284 | 44.162 | 47.851 | 1.00 | 15.98 | B C |
| ATOM | 11001 | CB | ILE | 651 | 84.632 | 45.117 | 49.014 | 1.00 | 15.40 | B C |
| ATOM | 11002 | CG2 | ILE | 651 | 84.386 | 46.559 | 48.589 | 1.00 | 15.87 | B C |
| ATOM | 11003 | CG1 | ILE | 651 | 83.789 | 44.786 | 50.242 | 1.00 | 15.95 | B C |
| ATOM | 11004 | CD1 | ILE | 651 | 84.017 | 45.721 | 51.411 | 1.00 | 14.84 | B C |
| ATOM | 11005 | C | ILE | 651 | 85.190 | 44.512 | 46.679 | 1.00 | 16.40 | B C |
| ATOM | 11006 | O | ILE | 651 | 86.404 | 44.330 | 46.754 | 1.00 | 16.63 | B O |
| ATOM | 11007 | N | ALA | 652 | 84.594 | 45.025 | 45.608 | 1.00 | 16.04 | B N |
| ATOM | 11008 | CA | ALA | 652 | 85.330 | 45.409 | 44.413 | 1.00 | 15.10 | B C |
| ATOM | 11009 | CB | ALA | 652 | 84.809 | 44.629 | 43.214 | 1.00 | 16.38 | B C |
| ATOM | 11010 | C | ALA | 652 | 85.190 | 46.908 | 44.153 | 1.00 | 15.88 | B C |
| ATOM | 11011 | O | ALA | 652 | 84.089 | 47.399 | 43.895 | 1.00 | 14.37 | B O |
| ATOM | 11012 | N | VAL | 653 | 86.308 | 47.630 | 44.214 | 1.00 | 15.73 | B N |
| ATOM | 11013 | CA | VAL | 653 | 86.298 | 49.070 | 43.978 | 1.00 | 15.50 | B C |
| ATOM | 11014 | CB | VAL | 653 | 87.110 | 49.831 | 45.055 | 1.00 | 17.97 | B C |
| ATOM | 11015 | CG1 | VAL | 653 | 87.050 | 51.327 | 44.787 | 1.00 | 18.06 | B C |
| ATOM | 11016 | CG2 | VAL | 653 | 86.566 | 49.525 | 46.446 | 1.00 | 18.80 | B C |
| ATOM | 11017 | C | VAL | 653 | 86.905 | 49.398 | 42.624 | 1.00 | 15.11 | B C |
| ATOM | 11018 | O | VAL | 653 | 88.071 | 49.087 | 42.373 | 1.00 | 14.41 | B O |
| ATOM | 11019 | N | ALA | 654 | 86.106 | 50.031 | 41.766 | 1.00 | 14.05 | B N |
| ATOM | 11020 | CA | ALA | 654 | 86.532 | 50.438 | 40.427 | 1.00 | 12.10 | B C |
| ATOM | 11021 | CB | ALA | 654 | 87.424 | 51.655 | 40.518 | 1.00 | 12.15 | B C |
| ATOM | 11022 | C | ALA | 654 | 87.258 | 49.318 | 39.700 | 1.00 | 12.48 | B C |
| ATOM | 11023 | O | ALA | 654 | 88.364 | 49.500 | 39.192 | 1.00 | 13.17 | B O |
| ATOM | 11024 | N | PRO | 655 | 86.633 | 48.141 | 39.626 | 1.00 | 11.84 | B N |

FIG. 4-226 (Continued)

| ATOM | 11025 | CD | PRO | 655 | 85.273 | 47.797 | 40.088 | 1.00 | 11.50 | B | C |
|---|---|---|---|---|---|---|---|---|---|---|---|
| ATOM | 11026 | CA | PRO | 655 | 87.247 | 47.003 | 38.954 | 1.00 | 11.05 | B | C |
| ATOM | 11027 | CB | PRO | 655 | 86.399 | 45.841 | 39.436 | 1.00 | 11.09 | B | C |
| ATOM | 11028 | CG | PRO | 655 | 85.030 | 46.451 | 39.428 | 1.00 | 8.50 | B | C |
| ATOM | 11029 | C | PRO | 655 | 87.190 | 47.102 | 37.447 | 1.00 | 10.92 | B | C |
| ATOM | 11030 | O | PRO | 655 | 86.383 | 47.847 | 36.896 | 1.00 | 11.41 | B | O |
| ATOM | 11031 | N | VAL | 656 | 88.066 | 46.352 | 36.791 | 1.00 | 9.60 | B | N |
| ATOM | 11032 | CA | VAL | 656 | 88.052 | 46.250 | 35.345 | 1.00 | 9.08 | B | C |
| ATOM | 11033 | CB | VAL | 656 | 89.452 | 45.888 | 34.790 | 1.00 | 7.45 | B | C |
| ATOM | 11034 | CG1 | VAL | 656 | 89.336 | 45.163 | 33.451 | 1.00 | 5.90 | B | C |
| ATOM | 11035 | CG2 | VAL | 656 | 90.249 | 47.146 | 34.601 | 1.00 | 7.63 | B | C |
| ATOM | 11036 | C | VAL | 656 | 87.107 | 45.056 | 35.224 | 1.00 | 10.20 | B | C |
| ATOM | 11037 | O | VAL | 656 | 87.157 | 44.152 | 36.058 | 1.00 | 10.59 | B | O |
| ATOM | 11038 | N | SER | 657 | 86.231 | 45.038 | 34.230 | 1.00 | 11.76 | B | N |
| ATOM | 11039 | CA | SER | 657 | 85.313 | 43.908 | 34.115 | 1.00 | 14.03 | B | C |
| ATOM | 11040 | CB | SER | 657 | 83.867 | 44.375 | 34.271 | 1.00 | 13.85 | B | C |
| ATOM | 11041 | OG | SER | 657 | 83.495 | 45.242 | 33.218 | 1.00 | 15.07 | B | O |
| ATOM | 11042 | C | SER | 657 | 85.456 | 43.153 | 32.812 | 1.00 | 14.66 | B | C |
| ATOM | 11043 | O | SER | 657 | 85.191 | 41.952 | 32.743 | 1.00 | 17.18 | B | O |
| ATOM | 11044 | N | ARG | 658 | 85.887 | 43.860 | 31.781 | 1.00 | 14.15 | B | N |
| ATOM | 11045 | CA | ARG | 658 | 86.050 | 43.277 | 30.459 | 1.00 | 13.24 | B | C |
| ATOM | 11046 | CB | ARG | 658 | 84.768 | 43.532 | 29.670 | 1.00 | 14.22 | B | C |
| ATOM | 11047 | CG | ARG | 658 | 84.763 | 43.086 | 28.231 | 1.00 | 18.57 | B | C |
| ATOM | 11048 | CD | ARG | 658 | 83.436 | 43.470 | 27.588 | 1.00 | 19.40 | B | C |
| ATOM | 11049 | NE | ARG | 658 | 83.475 | 43.338 | 26.138 | 1.00 | 23.11 | B | N |
| ATOM | 11050 | CZ | ARG | 658 | 82.868 | 42.376 | 25.454 | 1.00 | 22.54 | B | C |
| ATOM | 11051 | NH1 | ARG | 658 | 82.167 | 41.445 | 26.088 | 1.00 | 21.95 | B | N |
| ATOM | 11052 | NH2 | ARG | 658 | 82.955 | 42.361 | 24.131 | 1.00 | 22.77 | B | N |
| ATOM | 11053 | C | ARG | 658 | 87.242 | 44.014 | 29.857 | 1.00 | 12.76 | B | C |
| ATOM | 11054 | O | ARG | 658 | 87.218 | 45.239 | 29.733 | 1.00 | 11.97 | B | O |
| ATOM | 11055 | N | TRP | 659 | 88.282 | 43.283 | 29.476 | 1.00 | 11.05 | B | N |
| ATOM | 11056 | CA | TRP | 659 | 89.468 | 43.942 | 28.955 | 1.00 | 12.23 | B | C |
| ATOM | 11057 | CB | TRP | 659 | 90.578 | 42.918 | 28.777 | 1.00 | 11.99 | B | C |
| ATOM | 11058 | CG | TRP | 659 | 91.026 | 42.392 | 30.112 | 1.00 | 13.26 | B | C |
| ATOM | 11059 | CD2 | TRP | 659 | 91.729 | 43.120 | 31.122 | 1.00 | 12.61 | B | C |
| ATOM | 11060 | CE2 | TRP | 659 | 91.848 | 42.271 | 32.242 | 1.00 | 13.22 | B | C |
| ATOM | 11061 | CE3 | TRP | 659 | 92.268 | 44.412 | 31.193 | 1.00 | 14.19 | B | C |
| ATOM | 11062 | CD1 | TRP | 659 | 90.759 | 41.163 | 30.644 | 1.00 | 13.17 | B | C |
| ATOM | 11063 | NE1 | TRP | 659 | 91.247 | 41.083 | 31.920 | 1.00 | 13.29 | B | N |
| ATOM | 11064 | CZ2 | TRP | 659 | 92.489 | 42.670 | 33.424 | 1.00 | 13.99 | B | C |
| ATOM | 11065 | CZ3 | TRP | 659 | 92.909 | 44.810 | 32.373 | 1.00 | 13.35 | B | C |
| ATOM | 11066 | CH2 | TRP | 659 | 93.011 | 43.940 | 33.468 | 1.00 | 11.92 | B | C |
| ATOM | 11067 | C | TRP | 659 | 89.338 | 44.840 | 27.730 | 1.00 | 13.23 | B | C |
| ATOM | 11068 | O | TRP | 659 | 90.118 | 45.766 | 27.569 | 1.00 | 15.39 | B | O |
| ATOM | 11069 | N | GLU | 660 | 88.361 | 44.595 | 26.871 | 1.00 | 14.59 | B | N |
| ATOM | 11070 | CA | GLU | 660 | 88.181 | 45.453 | 25.708 | 1.00 | 15.33 | B | C |
| ATOM | 11071 | CB | GLU | 660 | 87.147 | 44.854 | 24.743 | 1.00 | 18.10 | B | C |
| ATOM | 11072 | CG | GLU | 660 | 87.572 | 43.527 | 24.130 | 1.00 | 21.82 | B | C |
| ATOM | 11073 | CD | GLU | 660 | 86.452 | 42.829 | 23.386 | 1.00 | 25.49 | B | C |

FIG. 4-227 (Continued)

| | | | | | | | | | | | |
|---|---|---|---|---|---|---|---|---|---|---|---|
| ATOM | 11074 | OE1 | GLU | 660 | 86.087 | 43.278 | 22.279 | 1.00 | 29.78 | B | O |
| ATOM | 11075 | OE2 | GLU | 660 | 85.929 | 41.825 | 23.914 | 1.00 | 26.73 | B | O |
| ATOM | 11076 | C | GLU | 660 | 87.719 | 46.833 | 26.170 | 1.00 | 14.88 | B | C |
| ATOM | 11077 | O | GLU | 660 | 87.661 | 47.769 | 25.375 | 1.00 | 14.50 | B | O |
| ATOM | 11078 | N | TYR | 661 | 87.371 | 46.960 | 27.450 | 1.00 | 14.66 | B | N |
| ATOM | 11079 | CA | TYR | 661 | 86.941 | 48.258 | 27.977 | 1.00 | 15.13 | B | C |
| ATOM | 11080 | CB | TYR | 661 | 85.988 | 48.119 | 29.168 | 1.00 | 15.73 | B | C |
| ATOM | 11081 | CG | TYR | 661 | 84.599 | 47.597 | 28.872 | 1.00 | 19.12 | B | C |
| ATOM | 11082 | CD1 | TYR | 661 | 83.823 | 47.053 | 29.898 | 1.00 | 18.37 | B | C |
| ATOM | 11083 | CE1 | TYR | 661 | 82.553 | 46.548 | 29.653 | 1.00 | 19.84 | B | C |
| ATOM | 11084 | CD2 | TYR | 661 | 84.061 | 47.629 | 27.581 | 1.00 | 19.07 | B | C |
| ATOM | 11085 | CE2 | TYR | 661 | 82.782 | 47.123 | 27.323 | 1.00 | 20.28 | B | C |
| ATOM | 11086 | CZ | TYR | 661 | 82.035 | 46.581 | 28.367 | 1.00 | 20.80 | B | C |
| ATOM | 11087 | OH | TYR | 661 | 80.785 | 46.046 | 28.142 | 1.00 | 20.60 | B | O |
| ATOM | 11088 | C | TYR | 661 | 88.146 | 49.045 | 28.464 | 1.00 | 14.96 | B | C |
| ATOM | 11089 | O | TYR | 661 | 88.083 | 50.266 | 28.555 | 1.00 | 14.55 | B | O |
| ATOM | 11090 | N | TYR | 662 | 89.239 | 48.355 | 28.789 | 1.00 | 14.46 | B | N |
| ATOM | 11091 | CA | TYR | 662 | 90.411 | 49.060 | 29.289 | 1.00 | 15.14 | B | C |
| ATOM | 11092 | CB | TYR | 662 | 91.225 | 48.182 | 30.240 | 1.00 | 13.98 | B | C |
| ATOM | 11093 | CG | TYR | 662 | 92.049 | 49.021 | 31.187 | 1.00 | 14.52 | B | C |
| ATOM | 11094 | CD1 | TYR | 662 | 93.379 | 48.699 | 31.468 | 1.00 | 14.22 | B | C |
| ATOM | 11095 | CE1 | TYR | 662 | 94.168 | 49.531 | 32.255 | 1.00 | 11.31 | B | C |
| ATOM | 11096 | CD2 | TYR | 662 | 91.522 | 50.194 | 31.734 | 1.00 | 13.44 | B | C |
| ATOM | 11097 | CE2 | TYR | 662 | 92.297 | 51.030 | 32.520 | 1.00 | 13.70 | B | C |
| ATOM | 11098 | CZ | TYR | 662 | 93.620 | 50.699 | 32.776 | 1.00 | 13.69 | B | C |
| ATOM | 11099 | OH | TYR | 662 | 94.395 | 51.549 | 33.532 | 1.00 | 12.84 | B | O |
| ATOM | 11100 | C | TYR | 662 | 91.309 | 49.615 | 28.182 | 1.00 | 15.44 | B | C |
| ATOM | 11101 | O | TYR | 662 | 91.095 | 49.337 | 26.996 | 1.00 | 15.06 | B | O |
| ATOM | 11102 | N | ASP | 663 | 92.310 | 50.405 | 28.569 | 1.00 | 13.90 | B | N |
| ATOM | 11103 | CA | ASP | 663 | 93.192 | 51.026 | 27.588 | 1.00 | 13.58 | B | C |
| ATOM | 11104 | CB | ASP | 663 | 93.961 | 52.192 | 28.238 | 1.00 | 13.61 | B | C |
| ATOM | 11105 | CG | ASP | 663 | 95.093 | 51.741 | 29.152 | 1.00 | 14.10 | B | C |
| ATOM | 11106 | OD1 | ASP | 663 | 95.223 | 52.327 | 30.243 | 1.00 | 12.30 | B | O |
| ATOM | 11107 | OD2 | ASP | 663 | 95.869 | 50.836 | 28.780 | 1.00 | 13.70 | B | O |
| ATOM | 11108 | C | ASP | 663 | 94.139 | 50.076 | 26.850 | 1.00 | 13.21 | B | C |
| ATOM | 11109 | O | ASP | 663 | 94.565 | 49.045 | 27.378 | 1.00 | 13.05 | B | O |
| ATOM | 11110 | N | SER | 664 | 94.453 | 50.444 | 25.612 | 1.00 | 13.86 | B | N |
| ATOM | 11111 | CA | SER | 664 | 95.321 | 49.658 | 24.738 | 1.00 | 13.65 | B | C |
| ATOM | 11112 | CB | SER | 664 | 95.464 | 50.364 | 23.394 | 1.00 | 14.44 | B | C |
| ATOM | 11113 | OG | SER | 664 | 96.055 | 51.642 | 23.550 | 1.00 | 16.79 | B | O |
| ATOM | 11114 | C | SER | 664 | 96.714 | 49.340 | 25.278 | 1.00 | 13.42 | B | C |
| ATOM | 11115 | O | SER | 664 | 97.066 | 48.176 | 25.438 | 1.00 | 12.83 | B | O |
| ATOM | 11116 | N | VAL | 665 | 97.503 | 50.371 | 25.559 | 1.00 | 12.98 | B | N |
| ATOM | 11117 | CA | VAL | 665 | 98.865 | 50.158 | 26.041 | 1.00 | 15.86 | B | C |
| ATOM | 11118 | CB | VAL | 665 | 99.547 | 51.496 | 26.427 | 1.00 | 14.66 | B | C |
| ATOM | 11119 | CG1 | VAL | 665 | 101.023 | 51.263 | 26.663 | 1.00 | 14.68 | B | C |
| ATOM | 11120 | CG2 | VAL | 665 | 99.354 | 52.519 | 25.327 | 1.00 | 15.28 | B | C |
| ATOM | 11121 | C | VAL | 665 | 99.020 | 49.169 | 27.206 | 1.00 | 15.25 | B | C |
| ATOM | 11122 | O | VAL | 665 | 99.972 | 48.400 | 27.242 | 1.00 | 15.22 | B | O |

| ATOM | 11123 | N | TYR | 666 | 98.091 | 49.184 | 28.154 | 1.00 | 17.07 | B | N |
|---|---|---|---|---|---|---|---|---|---|---|---|
| ATOM | 11124 | CA | TYR | 666 | 98.175 | 48.276 | 29.299 | 1.00 | 15.32 | B | C |
| ATOM | 11125 | CB | TYR | 666 | 97.504 | 48.896 | 30.531 | 1.00 | 13.28 | B | C |
| ATOM | 11126 | CG | TYR | 666 | 97.483 | 47.997 | 31.751 | 1.00 | 12.79 | B | C |
| ATOM | 11127 | CD1 | TYR | 666 | 96.595 | 46.920 | 31.845 | 1.00 | 12.27 | B | C |
| ATOM | 11128 | CE1 | TYR | 666 | 96.583 | 46.089 | 32.964 | 1.00 | 12.60 | B | C |
| ATOM | 11129 | CD2 | TYR | 666 | 98.360 | 48.215 | 32.809 | 1.00 | 12.83 | B | C |
| ATOM | 11130 | CE2 | TYR | 666 | 98.361 | 47.390 | 33.928 | 1.00 | 11.79 | B | C |
| ATOM | 11131 | CZ | TYR | 666 | 97.472 | 46.332 | 34.005 | 1.00 | 13.90 | B | C |
| ATOM | 11132 | OH | TYR | 666 | 97.471 | 45.531 | 35.131 | 1.00 | 12.51 | B | O |
| ATOM | 11133 | C | TYR | 666 | 97.550 | 46.922 | 29.023 | 1.00 | 15.26 | B | C |
| ATOM | 11134 | O | TYR | 666 | 98.103 | 45.895 | 29.399 | 1.00 | 18.30 | B | O |
| ATOM | 11135 | N | THR | 667 | 96.401 | 46.912 | 28.365 | 1.00 | 14.70 | B | N |
| ATOM | 11136 | CA | THR | 667 | 95.712 | 45.656 | 28.097 | 1.00 | 13.70 | B | C |
| ATOM | 11137 | CB | THR | 667 | 94.264 | 45.925 | 27.656 | 1.00 | 12.07 | B | C |
| ATOM | 11138 | OG1 | THR | 667 | 93.617 | 46.756 | 28.635 | 1.00 | 11.17 | B | O |
| ATOM | 11139 | CG2 | THR | 667 | 93.498 | 44.624 | 27.533 | 1.00 | 10.21 | B | C |
| ATOM | 11140 | C | THR | 667 | 96.423 | 44.792 | 27.067 | 1.00 | 15.29 | B | C |
| ATOM | 11141 | O | THR | 667 | 96.713 | 43.626 | 27.323 | 1.00 | 16.16 | B | O |
| ATOM | 11142 | N | GLU | 668 | 96.707 | 45.372 | 25.906 | 1.00 | 16.99 | B | N |
| ATOM | 11143 | CA | GLU | 668 | 97.389 | 44.672 | 24.823 | 1.00 | 16.90 | B | C |
| ATOM | 11144 | CB | GLU | 668 | 97.537 | 45.612 | 23.625 | 1.00 | 17.50 | B | C |
| ATOM | 11145 | CG | GLU | 668 | 96.231 | 45.808 | 22.867 | 1.00 | 21.31 | B | C |
| ATOM | 11146 | CD | GLU | 668 | 96.275 | 46.928 | 21.850 | 1.00 | 22.06 | B | C |
| ATOM | 11147 | OE1 | GLU | 668 | 97.284 | 47.054 | 21.123 | 1.00 | 25.39 | B | O |
| ATOM | 11148 | OE2 | GLU | 668 | 95.284 | 47.679 | 21.767 | 1.00 | 22.03 | B | O |
| ATOM | 11149 | C | GLU | 668 | 98.751 | 44.127 | 25.247 | 1.00 | 17.77 | B | C |
| ATOM | 11150 | O | GLU | 668 | 99.186 | 43.079 | 24.766 | 1.00 | 19.28 | B | O |
| ATOM | 11151 | N | ARG | 669 | 99.418 | 44.827 | 26.158 | 1.00 | 17.62 | B | N |
| ATOM | 11152 | CA | ARG | 669 | 100.721 | 44.392 | 26.640 | 1.00 | 17.00 | B | C |
| ATOM | 11153 | CB | ARG | 669 | 101.199 | 45.291 | 27.785 | 1.00 | 17.11 | B | C |
| ATOM | 11154 | CG | ARG | 669 | 102.498 | 44.828 | 28.451 | 1.00 | 15.99 | B | C |
| ATOM | 11155 | CD | ARG | 669 | 102.878 | 45.766 | 29.583 | 1.00 | 15.35 | B | C |
| ATOM | 11156 | NE | ARG | 669 | 102.914 | 47.149 | 29.122 | 1.00 | 16.25 | B | N |
| ATOM | 11157 | CZ | ARG | 669 | 102.549 | 48.196 | 29.856 | 1.00 | 16.96 | B | C |
| ATOM | 11158 | NH1 | ARG | 669 | 102.115 | 48.023 | 31.101 | 1.00 | 16.86 | B | N |
| ATOM | 11159 | NH2 | ARG | 669 | 102.602 | 49.417 | 29.340 | 1.00 | 14.86 | B | N |
| ATOM | 11160 | C | ARG | 669 | 100.633 | 42.960 | 27.140 | 1.00 | 17.70 | B | C |
| ATOM | 11161 | O | ARG | 669 | 101.523 | 42.141 | 26.899 | 1.00 | 17.72 | B | O |
| ATOM | 11162 | N | TYR | 670 | 99.539 | 42.655 | 27.825 | 1.00 | 17.60 | B | N |
| ATOM | 11163 | CA | TYR | 670 | 99.357 | 41.333 | 28.385 | 1.00 | 16.56 | B | C |
| ATOM | 11164 | CB | TYR | 670 | 98.823 | 41.465 | 29.810 | 1.00 | 15.82 | B | C |
| ATOM | 11165 | CG | TYR | 670 | 99.571 | 42.491 | 30.631 | 1.00 | 15.47 | B | C |
| ATOM | 11166 | CD1 | TYR | 670 | 98.978 | 43.706 | 30.973 | 1.00 | 14.06 | B | C |
| ATOM | 11167 | CE1 | TYR | 670 | 99.680 | 44.676 | 31.676 | 1.00 | 14.36 | B | C |
| ATOM | 11168 | CD2 | TYR | 670 | 100.894 | 42.268 | 31.024 | 1.00 | 15.93 | B | C |
| ATOM | 11169 | CE2 | TYR | 670 | 101.608 | 43.232 | 31.732 | 1.00 | 15.78 | B | C |
| ATOM | 11170 | CZ | TYR | 670 | 100.998 | 44.433 | 32.051 | 1.00 | 15.30 | B | C |
| ATOM | 11171 | OH | TYR | 670 | 101.713 | 45.403 | 32.714 | 1.00 | 15.22 | B | O |

FIG. 4-229

| | | | | | | | | | | |
|---|---|---|---|---|---|---|---|---|---|---|
| ATOM | 11172 | C | TYR | 670 | 98.435 | 40.441 | 27.578 | 1.00 17.87 | B | C |
| ATOM | 11173 | O | TYR | 670 | 98.637 | 39.231 | 27.508 | 1.00 18.02 | B | O |
| ATOM | 11174 | N | MET | 671 | 97.435 | 41.040 | 26.948 | 1.00 18.57 | B | N |
| ATOM | 11175 | CA | MET | 671 | 96.452 | 40.271 | 26.199 | 1.00 19.04 | B | C |
| ATOM | 11176 | CB | MET | 671 | 95.063 | 40.844 | 26.482 | 1.00 21.47 | B | C |
| ATOM | 11177 | CG | MET | 671 | 94.604 | 40.692 | 27.919 | 1.00 21.74 | B | C |
| ATOM | 11178 | SD | MET | 671 | 94.228 | 38.972 | 28.277 | 1.00 28.61 | B | S |
| ATOM | 11179 | CE | MET | 671 | 92.570 | 38.871 | 27.582 | 1.00 23.84 | B | C |
| ATOM | 11180 | C | MET | 671 | 96.640 | 40.164 | 24.692 | 1.00 19.95 | B | C |
| ATOM | 11181 | O | MET | 671 | 96.121 | 39.240 | 24.075 | 1.00 20.85 | B | O |
| ATOM | 11182 | N | GLY | 672 | 97.380 | 41.092 | 24.094 | 1.00 20.28 | B | N |
| ATOM | 11183 | CA | GLY | 672 | 97.540 | 41.063 | 22.654 | 1.00 19.08 | B | C |
| ATOM | 11184 | C | GLY | 672 | 96.354 | 41.807 | 22.068 | 1.00 21.12 | B | C |
| ATOM | 11185 | O | GLY | 672 | 95.746 | 42.629 | 22.755 | 1.00 21.18 | B | O |
| ATOM | 11186 | N | LEU | 673 | 96.009 | 41.534 | 20.814 | 1.00 21.68 | B | N |
| ATOM | 11187 | CA | LEU | 673 | 94.884 | 42.225 | 20.186 | 1.00 21.44 | B | C |
| ATOM | 11188 | CB | LEU | 673 | 95.204 | 42.569 | 18.732 | 1.00 22.03 | B | C |
| ATOM | 11189 | CG | LEU | 673 | 96.287 | 43.627 | 18.507 | 1.00 24.89 | B | C |
| ATOM | 11190 | CD1 | LEU | 673 | 96.518 | 43.837 | 17.023 | 1.00 23.45 | B | C |
| ATOM | 11191 | CD2 | LEU | 673 | 95.846 | 44.932 | 19.150 | 1.00 27.67 | B | C |
| ATOM | 11192 | C | LEU | 673 | 93.616 | 41.399 | 20.243 | 1.00 21.68 | B | C |
| ATOM | 11193 | O | LEU | 673 | 93.647 | 40.173 | 20.076 | 1.00 21.49 | B | O |
| ATOM | 11194 | N | PRO | 674 | 92.475 | 42.061 | 20.487 | 1.00 21.61 | B | N |
| ATOM | 11195 | CD | PRO | 674 | 92.342 | 43.487 | 20.830 | 1.00 20.79 | B | C |
| ATOM | 11196 | CA | PRO | 674 | 91.180 | 41.388 | 20.571 | 1.00 20.99 | B | C |
| ATOM | 11197 | CB | PRO | 674 | 90.365 | 42.347 | 21.420 | 1.00 19.09 | B | C |
| ATOM | 11198 | CG | PRO | 674 | 90.845 | 43.664 | 20.941 | 1.00 18.24 | B | C |
| ATOM | 11199 | C | PRO | 674 | 90.589 | 41.155 | 19.183 | 1.00 21.53 | B | C |
| ATOM | 11200 | O | PRO | 674 | 89.470 | 41.561 | 18.884 | 1.00 20.30 | B | O |
| ATOM | 11201 | N | THR | 675 | 91.378 | 40.505 | 18.335 | 1.00 23.61 | B | N |
| ATOM | 11202 | CA | THR | 675 | 90.973 | 40.176 | 16.975 | 1.00 23.43 | B | C |
| ATOM | 11203 | CB | THR | 675 | 92.045 | 40.560 | 15.957 | 1.00 22.99 | B | C |
| ATOM | 11204 | OG1 | THR | 675 | 93.221 | 39.783 | 16.200 | 1.00 24.15 | B | O |
| ATOM | 11205 | CG2 | THR | 675 | 92.386 | 42.039 | 16.062 | 1.00 21.26 | B | C |
| ATOM | 11206 | C | THR | 675 | 90.825 | 38.668 | 16.931 | 1.00 25.46 | B | C |
| ATOM | 11207 | O | THR | 675 | 91.424 | 37.952 | 17.736 | 1.00 25.82 | B | O |
| ATOM | 11208 | N | PRO | 676 | 90.023 | 38.160 | 15.991 | 1.00 26.60 | B | N |
| ATOM | 11209 | CD | PRO | 676 | 89.130 | 38.885 | 15.074 | 1.00 25.76 | B | C |
| ATOM | 11210 | CA | PRO | 676 | 89.823 | 36.714 | 15.877 | 1.00 26.64 | B | C |
| ATOM | 11211 | CB | PRO | 676 | 88.860 | 36.599 | 14.702 | 1.00 25.84 | B | C |
| ATOM | 11212 | CG | PRO | 676 | 88.066 | 37.859 | 14.801 | 1.00 24.99 | B | C |
| ATOM | 11213 | C | PRO | 676 | 91.135 | 35.967 | 15.630 | 1.00 28.63 | B | C |
| ATOM | 11214 | O | PRO | 676 | 91.347 | 34.875 | 16.160 | 1.00 28.85 | B | O |
| ATOM | 11215 | N | GLU | 677 | 92.021 | 36.557 | 14.834 | 1.00 30.55 | B | N |
| ATOM | 11216 | CA | GLU | 677 | 93.286 | 35.905 | 14.534 | 1.00 31.94 | B | C |
| ATOM | 11217 | CB | GLU | 677 | 93.772 | 36.290 | 13.135 | 1.00 35.44 | B | C |
| ATOM | 11218 | CG | GLU | 677 | 94.177 | 35.077 | 12.294 | 1.00 41.76 | B | C |
| ATOM | 11219 | CD | GLU | 677 | 92.984 | 34.204 | 11.897 | 1.00 46.15 | B | C |
| ATOM | 11220 | OE1 | GLU | 677 | 92.234 | 34.610 | 10.980 | 1.00 49.52 | B | O |

| | | | | | | | | | | |
|---|---|---|---|---|---|---|---|---|---|---|
| ATOM | 11221 | OE2 | GLU | 677 | 92.789 | 33.121 | 12.503 | 1.00 | 46.47 | B | O |
| ATOM | 11222 | C | GLU | 677 | 94.382 | 36.174 | 15.563 | 1.00 | 31.51 | B | C |
| ATOM | 11223 | O | GLU | 677 | 95.565 | 35.938 | 15.305 | 1.00 | 31.18 | B | O |
| ATOM | 11224 | N | ASP | 678 | 94.003 | 36.680 | 16.730 | 1.00 | 29.04 | B | N |
| ATOM | 11225 | CA | ASP | 678 | 95.005 | 36.896 | 17.756 | 1.00 | 26.71 | B | C |
| ATOM | 11226 | CB | ASP | 678 | 95.359 | 38.374 | 17.917 | 1.00 | 25.30 | B | C |
| ATOM | 11227 | CG | ASP | 678 | 96.500 | 38.586 | 18.902 | 1.00 | 26.53 | B | C |
| ATOM | 11228 | OD1 | ASP | 678 | 97.004 | 39.721 | 19.008 | 1.00 | 29.18 | B | O |
| ATOM | 11229 | OD2 | ASP | 678 | 96.900 | 37.612 | 19.579 | 1.00 | 24.47 | B | O |
| ATOM | 11230 | C | ASP | 678 | 94.586 | 36.325 | 19.098 | 1.00 | 25.24 | B | C |
| ATOM | 11231 | O | ASP | 678 | 94.946 | 35.200 | 19.426 | 1.00 | 26.23 | B | O |
| ATOM | 11232 | N | ASN | 679 | 93.814 | 37.082 | 19.871 | 1.00 | 24.14 | B | N |
| ATOM | 11233 | CA | ASN | 679 | 93.418 | 36.608 | 21.186 | 1.00 | 22.47 | B | C |
| ATOM | 11234 | CB | ASN | 679 | 94.456 | 37.089 | 22.217 | 1.00 | 23.05 | B | C |
| ATOM | 11235 | CG | ASN | 679 | 94.390 | 36.323 | 23.524 | 1.00 | 22.50 | B | C |
| ATOM | 11236 | OD1 | ASN | 679 | 94.644 | 36.880 | 24.592 | 1.00 | 21.44 | B | O |
| ATOM | 11237 | ND2 | ASN | 679 | 94.059 | 35.037 | 23.448 | 1.00 | 22.30 | B | N |
| ATOM | 11238 | C | ASN | 679 | 92.019 | 37.061 | 21.596 | 1.00 | 21.85 | B | C |
| ATOM | 11239 | O | ASN | 679 | 91.727 | 37.174 | 22.785 | 1.00 | 21.56 | B | O |
| ATOM | 11240 | N | LEU | 680 | 91.153 | 37.316 | 20.619 | 1.00 | 22.96 | B | N |
| ATOM | 11241 | CA | LEU | 680 | 89.783 | 37.750 | 20.913 | 1.00 | 22.05 | B | C |
| ATOM | 11242 | CB | LEU | 680 | 88.999 | 37.967 | 19.617 | 1.00 | 20.94 | B | C |
| ATOM | 11243 | CG | LEU | 680 | 87.524 | 38.379 | 19.734 | 1.00 | 20.98 | B | C |
| ATOM | 11244 | CD1 | LEU | 680 | 87.385 | 39.671 | 20.539 | 1.00 | 21.18 | B | C |
| ATOM | 11245 | CD2 | LEU | 680 | 86.946 | 38.567 | 18.348 | 1.00 | 17.15 | B | C |
| ATOM | 11246 | C | LEU | 680 | 89.031 | 36.762 | 21.805 | 1.00 | 22.36 | B | C |
| ATOM | 11247 | O | LEU | 680 | 88.316 | 37.171 | 22.718 | 1.00 | 23.81 | B | O |
| ATOM | 11248 | N | ASP | 681 | 89.193 | 35.466 | 21.555 | 1.00 | 22.95 | B | N |
| ATOM | 11249 | CA | ASP | 681 | 88.502 | 34.469 | 22.371 | 1.00 | 24.27 | B | C |
| ATOM | 11250 | CB | ASP | 681 | 88.910 | 33.048 | 21.980 | 1.00 | 24.73 | B | C |
| ATOM | 11251 | CG | ASP | 681 | 88.270 | 32.587 | 20.695 | 1.00 | 25.98 | B | C |
| ATOM | 11252 | OD1 | ASP | 681 | 87.453 | 33.334 | 20.116 | 1.00 | 28.21 | B | O |
| ATOM | 11253 | OD2 | ASP | 681 | 88.587 | 31.462 | 20.259 | 1.00 | 28.60 | B | O |
| ATOM | 11254 | C | ASP | 681 | 88.754 | 34.655 | 23.862 | 1.00 | 23.99 | B | C |
| ATOM | 11255 | O | ASP | 681 | 87.816 | 34.640 | 24.660 | 1.00 | 24.77 | B | O |
| ATOM | 11256 | N | HIS | 682 | 90.014 | 34.819 | 24.252 | 1.00 | 22.66 | B | N |
| ATOM | 11257 | CA | HIS | 682 | 90.289 | 34.998 | 25.667 | 1.00 | 22.62 | B | C |
| ATOM | 11258 | CB | HIS | 682 | 91.775 | 34.867 | 25.981 | 1.00 | 23.03 | B | C |
| ATOM | 11259 | CG | HIS | 682 | 92.063 | 34.898 | 27.448 | 1.00 | 25.79 | B | C |
| ATOM | 11260 | CD2 | HIS | 682 | 92.844 | 35.718 | 28.190 | 1.00 | 26.73 | B | C |
| ATOM | 11261 | ND1 | HIS | 682 | 91.458 | 34.035 | 28.338 | 1.00 | 25.30 | B | N |
| ATOM | 11262 | CE1 | HIS | 682 | 91.852 | 34.326 | 29.565 | 1.00 | 26.50 | B | C |
| ATOM | 11263 | NE2 | HIS | 682 | 92.693 | 35.344 | 29.504 | 1.00 | 26.09 | B | N |
| ATOM | 11264 | C | HIS | 682 | 89.775 | 36.344 | 26.175 | 1.00 | 21.71 | B | C |
| ATOM | 11265 | O | HIS | 682 | 89.412 | 36.465 | 27.345 | 1.00 | 20.98 | B | O |
| ATOM | 11266 | N | TYR | 683 | 89.753 | 37.355 | 25.307 | 1.00 | 19.91 | B | N |
| ATOM | 11267 | CA | TYR | 683 | 89.232 | 38.657 | 25.707 | 1.00 | 19.50 | B | C |
| ATOM | 11268 | CB | TYR | 683 | 89.226 | 39.646 | 24.542 | 1.00 | 16.55 | B | C |
| ATOM | 11269 | CG | TYR | 683 | 90.419 | 40.574 | 24.472 | 1.00 | 16.85 | B | C |

FIG. 4-231

| ATOM | 11270 | CD1 | TYR | 683 | 91.616 | 40.172 | 23.877 | 1.00 | 16.29 | B | C |
| --- | --- | --- | --- | --- | --- | --- | --- | --- | --- | --- | --- |
| ATOM | 11271 | CE1 | TYR | 683 | 92.700 | 41.040 | 23.786 | 1.00 | 16.38 | B | C |
| ATOM | 11272 | CD2 | TYR | 683 | 90.345 | 41.871 | 24.980 | 1.00 | 16.79 | B | C |
| ATOM | 11273 | CE2 | TYR | 683 | 91.430 | 42.748 | 24.893 | 1.00 | 14.60 | B | C |
| ATOM | 11274 | CZ | TYR | 683 | 92.598 | 42.326 | 24.295 | 1.00 | 15.79 | B | C |
| ATOM | 11275 | OH | TYR | 683 | 93.663 | 43.193 | 24.192 | 1.00 | 16.43 | B | O |
| ATOM | 11276 | C | TYR | 683 | 87.793 | 38.437 | 26.150 | 1.00 | 21.02 | B | C |
| ATOM | 11277 | O | TYR | 683 | 87.355 | 38.955 | 27.174 | 1.00 | 20.95 | B | O |
| ATOM | 11278 | N | ARG | 684 | 87.071 | 37.644 | 25.367 | 1.00 | 22.94 | B | N |
| ATOM | 11279 | CA | ARG | 684 | 85.667 | 37.349 | 25.634 | 1.00 | 24.36 | B | C |
| ATOM | 11280 | CB | ARG | 684 | 84.992 | 36.871 | 24.344 | 1.00 | 24.11 | B | C |
| ATOM | 11281 | CG | ARG | 684 | 84.996 | 37.908 | 23.234 | 1.00 | 25.07 | B | C |
| ATOM | 11282 | CD | ARG | 684 | 84.197 | 39.132 | 23.639 | 1.00 | 25.30 | B | C |
| ATOM | 11283 | NE | ARG | 684 | 84.453 | 40.275 | 22.767 | 1.00 | 27.33 | B | N |
| ATOM | 11284 | CZ | ARG | 684 | 84.126 | 40.344 | 21.480 | 1.00 | 27.26 | B | C |
| ATOM | 11285 | NH1 | ARG | 684 | 83.518 | 39.327 | 20.880 | 1.00 | 27.78 | B | N |
| ATOM | 11286 | NH2 | ARG | 684 | 84.409 | 41.443 | 20.794 | 1.00 | 26.25 | B | N |
| ATOM | 11287 | C | ARG | 684 | 85.401 | 36.340 | 26.745 | 1.00 | 24.46 | B | C |
| ATOM | 11288 | O | ARG | 684 | 84.275 | 36.239 | 27.231 | 1.00 | 26.21 | B | O |
| ATOM | 11289 | N | ASN | 685 | 86.421 | 35.591 | 27.148 | 1.00 | 24.53 | B | N |
| ATOM | 11290 | CA | ASN | 685 | 86.243 | 34.593 | 28.201 | 1.00 | 23.44 | B | C |
| ATOM | 11291 | CB | ASN | 685 | 86.959 | 33.294 | 27.823 | 1.00 | 26.13 | B | C |
| ATOM | 11292 | CG | ASN | 685 | 86.132 | 32.430 | 26.904 | 1.00 | 33.00 | B | C |
| ATOM | 11293 | OD1 | ASN | 685 | 85.076 | 31.924 | 27.296 | 1.00 | 35.72 | B | O |
| ATOM | 11294 | ND2 | ASN | 685 | 86.594 | 32.260 | 25.667 | 1.00 | 36.03 | B | N |
| ATOM | 11295 | C | ASN | 685 | 86.716 | 35.043 | 29.575 | 1.00 | 20.60 | B | C |
| ATOM | 11296 | O | ASN | 685 | 86.472 | 34.361 | 30.566 | 1.00 | 20.98 | B | O |
| ATOM | 11297 | N | SER | 686 | 87.382 | 36.186 | 29.644 | 1.00 | 16.28 | B | N |
| ATOM | 11298 | CA | SER | 686 | 87.887 | 36.666 | 30.918 | 1.00 | 16.33 | B | C |
| ATOM | 11299 | CB | SER | 686 | 89.360 | 37.063 | 30.773 | 1.00 | 17.18 | B | C |
| ATOM | 11300 | OG | SER | 686 | 89.530 | 38.050 | 29.768 | 1.00 | 17.94 | B | O |
| ATOM | 11301 | C | SER | 686 | 87.089 | 37.837 | 31.486 | 1.00 | 15.71 | B | C |
| ATOM | 11302 | O | SER | 686 | 87.625 | 38.667 | 32.221 | 1.00 | 13.91 | B | O |
| ATOM | 11303 | N | THR | 687 | 85.807 | 37.905 | 31.155 | 1.00 | 14.37 | B | N |
| ATOM | 11304 | CA | THR | 687 | 84.989 | 38.992 | 31.655 | 1.00 | 15.19 | B | C |
| ATOM | 11305 | CB | THR | 687 | 83.899 | 39.401 | 30.639 | 1.00 | 16.80 | B | C |
| ATOM | 11306 | OG1 | THR | 687 | 82.915 | 38.362 | 30.537 | 1.00 | 18.14 | B | O |
| ATOM | 11307 | CG2 | THR | 687 | 84.519 | 39.657 | 29.265 | 1.00 | 16.92 | B | C |
| ATOM | 11308 | C | THR | 687 | 84.309 | 38.605 | 32.957 | 1.00 | 14.86 | B | C |
| ATOM | 11309 | O | THR | 687 | 84.153 | 37.425 | 33.264 | 1.00 | 13.79 | B | O |
| ATOM | 11310 | N | VAL | 688 | 83.910 | 39.616 | 33.717 | 1.00 | 14.71 | B | N |
| ATOM | 11311 | CA | VAL | 688 | 83.224 | 39.411 | 34.977 | 1.00 | 14.27 | B | C |
| ATOM | 11312 | CB | VAL | 688 | 83.239 | 40.691 | 35.824 | 1.00 | 15.67 | B | C |
| ATOM | 11313 | CG1 | VAL | 688 | 82.476 | 40.464 | 37.130 | 1.00 | 15.43 | B | C |
| ATOM | 11314 | CG2 | VAL | 688 | 84.687 | 41.115 | 36.100 | 1.00 | 18.49 | B | C |
| ATOM | 11315 | C | VAL | 688 | 81.777 | 39.048 | 34.687 | 1.00 | 14.74 | B | C |
| ATOM | 11316 | O | VAL | 688 | 81.196 | 38.188 | 35.350 | 1.00 | 15.40 | B | O |
| ATOM | 11317 | N | MET | 689 | 81.209 | 39.710 | 33.682 | 1.00 | 13.94 | B | N |
| ATOM | 11318 | CA | MET | 689 | 79.826 | 39.496 | 33.283 | 1.00 | 14.18 | B | C |

| ATOM | 11319 | CB | MET | 689 | 79.519 | 40.287 | 32.010 | 1.00 | 14.10 | B | C |
| ATOM | 11320 | CG | MET | 689 | 79.359 | 41.793 | 32.217 | 1.00 | 18.18 | B | C |
| ATOM | 11321 | SD | MET | 689 | 80.817 | 42.684 | 32.849 | 1.00 | 21.67 | B | S |
| ATOM | 11322 | CE | MET | 689 | 81.693 | 43.067 | 31.308 | 1.00 | 19.11 | B | C |
| ATOM | 11323 | C | MET | 689 | 79.429 | 38.040 | 33.080 | 1.00 | 13.66 | B | C |
| ATOM | 11324 | O | MET | 689 | 78.398 | 37.597 | 33.586 | 1.00 | 14.01 | B | O |
| ATOM | 11325 | N | SER | 690 | 80.246 | 37.290 | 32.356 | 1.00 | 14.32 | B | N |
| ATOM | 11326 | CA | SER | 690 | 79.939 | 35.887 | 32.087 | 1.00 | 16.68 | B | C |
| ATOM | 11327 | CB | SER | 690 | 81.018 | 35.259 | 31.199 | 1.00 | 18.28 | B | C |
| ATOM | 11328 | OG | SER | 690 | 82.225 | 35.062 | 31.923 | 1.00 | 23.11 | B | O |
| ATOM | 11329 | C | SER | 690 | 79.771 | 35.019 | 33.328 | 1.00 | 15.55 | B | C |
| ATOM | 11330 | O | SER | 690 | 79.212 | 33.927 | 33.234 | 1.00 | 16.21 | B | O |
| ATOM | 11331 | N | ARG | 691 | 80.238 | 35.502 | 34.478 | 1.00 | 14.35 | B | N |
| ATOM | 11332 | CA | ARG | 691 | 80.155 | 34.741 | 35.727 | 1.00 | 15.38 | B | C |
| ATOM | 11333 | CB | ARG | 691 | 81.491 | 34.821 | 36.478 | 1.00 | 16.76 | B | C |
| ATOM | 11334 | CG | ARG | 691 | 82.697 | 34.414 | 35.652 | 1.00 | 19.96 | B | C |
| ATOM | 11335 | CD | ARG | 691 | 83.972 | 34.339 | 36.483 | 1.00 | 21.36 | B | C |
| ATOM | 11336 | NE | ARG | 691 | 85.061 | 33.725 | 35.726 | 1.00 | 23.56 | B | N |
| ATOM | 11337 | CZ | ARG | 691 | 86.196 | 33.274 | 36.256 | 1.00 | 26.24 | B | C |
| ATOM | 11338 | NH1 | ARG | 691 | 86.418 | 33.358 | 37.567 | 1.00 | 23.55 | B | N |
| ATOM | 11339 | NH2 | ARG | 691 | 87.114 | 32.728 | 35.468 | 1.00 | 26.33 | B | N |
| ATOM | 11340 | C | ARG | 691 | 79.049 | 35.187 | 36.679 | 1.00 | 15.48 | B | C |
| ATOM | 11341 | O | ARG | 691 | 78.986 | 34.713 | 37.817 | 1.00 | 14.38 | B | O |
| ATOM | 11342 | N | ALA | 692 | 78.178 | 36.081 | 36.220 | 1.00 | 14.78 | B | N |
| ATOM | 11343 | CA | ALA | 692 | 77.111 | 36.618 | 37.064 | 1.00 | 16.42 | B | C |
| ATOM | 11344 | CB | ALA | 692 | 76.105 | 37.383 | 36.198 | 1.00 | 16.75 | B | C |
| ATOM | 11345 | C | ALA | 692 | 76.375 | 35.624 | 37.977 | 1.00 | 17.17 | B | C |
| ATOM | 11346 | O | ALA | 692 | 76.331 | 35.814 | 39.191 | 1.00 | 16.75 | B | O |
| ATOM | 11347 | N | GLU | 693 | 75.803 | 34.571 | 37.404 | 1.00 | 19.44 | B | N |
| ATOM | 11348 | CA | GLU | 693 | 75.062 | 33.589 | 38.191 | 1.00 | 22.16 | B | C |
| ATOM | 11349 | CB | GLU | 693 | 74.570 | 32.443 | 37.299 | 1.00 | 26.71 | B | C |
| ATOM | 11350 | CG | GLU | 693 | 73.251 | 32.745 | 36.598 | 1.00 | 33.79 | B | C |
| ATOM | 11351 | CD | GLU | 693 | 73.017 | 31.873 | 35.379 | 1.00 | 38.47 | B | C |
| ATOM | 11352 | OE1 | GLU | 693 | 72.984 | 30.632 | 35.531 | 1.00 | 40.41 | B | O |
| ATOM | 11353 | OE2 | GLU | 693 | 72.870 | 32.433 | 34.266 | 1.00 | 41.15 | B | O |
| ATOM | 11354 | C | GLU | 693 | 75.827 | 33.022 | 39.369 | 1.00 | 22.08 | B | C |
| ATOM | 11355 | O | GLU | 693 | 75.244 | 32.761 | 40.418 | 1.00 | 24.44 | B | O |
| ATOM | 11356 | N | ASN | 694 | 77.127 | 32.824 | 39.215 | 1.00 | 21.66 | B | N |
| ATOM | 11357 | CA | ASN | 694 | 77.907 | 32.282 | 40.320 | 1.00 | 22.61 | B | C |
| ATOM | 11358 | CB | ASN | 694 | 79.324 | 31.924 | 39.861 | 1.00 | 20.93 | B | C |
| ATOM | 11359 | CG | ASN | 694 | 79.359 | 30.654 | 39.048 | 1.00 | 19.32 | B | C |
| ATOM | 11360 | OD1 | ASN | 694 | 80.284 | 30.420 | 38.278 | 1.00 | 19.68 | B | O |
| ATOM | 11361 | ND2 | ASN | 694 | 78.348 | 29.818 | 39.224 | 1.00 | 18.34 | B | N |
| ATOM | 11362 | C | ASN | 694 | 77.975 | 33.234 | 41.500 | 1.00 | 22.99 | B | C |
| ATOM | 11363 | O | ASN | 694 | 78.650 | 32.946 | 42.479 | 1.00 | 25.59 | B | O |
| ATOM | 11364 | N | PHE | 695 | 77.283 | 34.366 | 41.419 | 1.00 | 22.83 | B | N |
| ATOM | 11365 | CA | PHE | 695 | 77.299 | 35.316 | 42.531 | 1.00 | 23.74 | B | C |
| ATOM | 11366 | CB | PHE | 695 | 77.205 | 36.772 | 42.041 | 1.00 | 20.88 | B | C |
| ATOM | 11367 | CG | PHE | 695 | 78.533 | 37.397 | 41.695 | 1.00 | 19.06 | B | C |

FIG. 4-233 (Continued)

| ATOM | 11368 | CD1 | PHE | 695 | 79.211 | 37.042 | 40.533 | 1.00 | 19.50 | B | C |
|---|---|---|---|---|---|---|---|---|---|---|---|
| ATOM | 11369 | CD2 | PHE | 695 | 79.096 | 38.365 | 42.523 | 1.00 | 19.69 | B | C |
| ATOM | 11370 | CE1 | PHE | 695 | 80.431 | 37.647 | 40.200 | 1.00 | 18.29 | B | C |
| ATOM | 11371 | CE2 | PHE | 695 | 80.316 | 38.977 | 42.199 | 1.00 | 18.53 | B | C |
| ATOM | 11372 | CZ | PHE | 695 | 80.982 | 38.615 | 41.033 | 1.00 | 17.35 | B | C |
| ATOM | 11373 | C | PHE | 695 | 76.146 | 35.052 | 43.483 | 1.00 | 24.37 | B | C |
| ATOM | 11374 | O | PHE | 695 | 76.090 | 35.636 | 44.566 | 1.00 | 25.67 | B | O |
| ATOM | 11375 | N | LYS | 696 | 75.230 | 34.173 | 43.089 | 1.00 | 24.40 | B | N |
| ATOM | 11376 | CA | LYS | 696 | 74.074 | 33.880 | 43.926 | 1.00 | 25.82 | B | C |
| ATOM | 11377 | CB | LYS | 696 | 73.173 | 32.813 | 43.280 | 1.00 | 27.75 | B | C |
| ATOM | 11378 | CG | LYS | 696 | 72.076 | 32.281 | 44.228 | 1.00 | 30.02 | B | C |
| ATOM | 11379 | CD | LYS | 696 | 70.680 | 32.287 | 43.615 | 1.00 | 31.63 | B | C |
| ATOM | 11380 | CE | LYS | 696 | 70.137 | 33.705 | 43.421 | 1.00 | 35.45 | B | C |
| ATOM | 11381 | NZ | LYS | 696 | 69.903 | 34.438 | 44.705 | 1.00 | 35.47 | B | N |
| ATOM | 11382 | C | LYS | 696 | 74.402 | 33.459 | 45.348 | 1.00 | 24.85 | B | C |
| ATOM | 11383 | O | LYS | 696 | 73.583 | 33.641 | 46.242 | 1.00 | 24.94 | B | O |
| ATOM | 11384 | N | GLN | 697 | 75.587 | 32.907 | 45.577 | 1.00 | 25.99 | B | N |
| ATOM | 11385 | CA | GLN | 697 | 75.920 | 32.481 | 46.931 | 1.00 | 27.33 | B | C |
| ATOM | 11386 | CB | GLN | 697 | 76.355 | 31.010 | 46.941 | 1.00 | 29.90 | B | C |
| ATOM | 11387 | CG | GLN | 697 | 75.290 | 30.025 | 46.444 | 1.00 | 30.66 | B | C |
| ATOM | 11388 | CD | GLN | 697 | 75.565 | 28.593 | 46.889 | 1.00 | 30.92 | B | C |
| ATOM | 11389 | OE1 | GLN | 697 | 75.381 | 28.245 | 48.065 | 1.00 | 31.54 | B | O |
| ATOM | 11390 | NE2 | GLN | 697 | 76.019 | 27.761 | 45.958 | 1.00 | 26.21 | B | N |
| ATOM | 11391 | C | GLN | 697 | 76.964 | 33.322 | 47.662 | 1.00 | 26.04 | B | C |
| ATOM | 11392 | O | GLN | 697 | 77.620 | 32.833 | 48.580 | 1.00 | 28.31 | B | O |
| ATOM | 11393 | N | VAL | 698 | 77.125 | 34.580 | 47.270 | 1.00 | 23.16 | B | N |
| ATOM | 11394 | CA | VAL | 698 | 78.085 | 35.445 | 47.947 | 1.00 | 21.23 | B | C |
| ATOM | 11395 | CB | VAL | 698 | 79.411 | 35.596 | 47.156 | 1.00 | 20.63 | B | C |
| ATOM | 11396 | CG1 | VAL | 698 | 80.033 | 34.238 | 46.901 | 1.00 | 17.19 | B | C |
| ATOM | 11397 | CG2 | VAL | 698 | 79.161 | 36.335 | 45.853 | 1.00 | 18.36 | B | C |
| ATOM | 11398 | C | VAL | 698 | 77.496 | 36.829 | 48.118 | 1.00 | 21.50 | B | C |
| ATOM | 11399 | O | VAL | 698 | 76.571 | 37.207 | 47.404 | 1.00 | 23.06 | B | O |
| ATOM | 11400 | N | GLU | 699 | 78.018 | 37.579 | 49.078 | 1.00 | 21.31 | B | N |
| ATOM | 11401 | CA | GLU | 699 | 77.563 | 38.945 | 49.290 | 1.00 | 21.42 | B | C |
| ATOM | 11402 | CB | GLU | 699 | 77.465 | 39.246 | 50.785 | 1.00 | 22.73 | B | C |
| ATOM | 11403 | CG | GLU | 699 | 76.396 | 38.403 | 51.461 | 1.00 | 26.07 | B | C |
| ATOM | 11404 | CD | GLU | 699 | 76.547 | 38.346 | 52.961 | 1.00 | 29.09 | B | C |
| ATOM | 11405 | OE1 | GLU | 699 | 76.343 | 39.387 | 53.624 | 1.00 | 31.29 | B | O |
| ATOM | 11406 | OE2 | GLU | 699 | 76.876 | 37.254 | 53.476 | 1.00 | 31.07 | B | O |
| ATOM | 11407 | C | GLU | 699 | 78.610 | 39.810 | 48.593 | 1.00 | 21.23 | B | C |
| ATOM | 11408 | O | GLU | 699 | 79.802 | 39.751 | 48.905 | 1.00 | 21.45 | B | O |
| ATOM | 11409 | N | TYR | 700 | 78.148 | 40.594 | 47.630 | 1.00 | 19.47 | B | N |
| ATOM | 11410 | CA | TYR | 700 | 79.012 | 41.428 | 46.818 | 1.00 | 18.26 | B | C |
| ATOM | 11411 | CB | TYR | 700 | 78.830 | 41.001 | 45.368 | 1.00 | 18.24 | B | C |
| ATOM | 11412 | CG | TYR | 700 | 79.678 | 41.685 | 44.330 | 1.00 | 18.56 | B | C |
| ATOM | 11413 | CD1 | TYR | 700 | 81.071 | 41.698 | 44.422 | 1.00 | 17.75 | B | C |
| ATOM | 11414 | CE1 | TYR | 700 | 81.856 | 42.206 | 43.378 | 1.00 | 17.99 | B | C |
| ATOM | 11415 | CD2 | TYR | 700 | 79.088 | 42.209 | 43.181 | 1.00 | 19.07 | B | C |
| ATOM | 11416 | CE2 | TYR | 700 | 79.852 | 42.715 | 42.143 | 1.00 | 19.54 | B | C |

| ATOM | 11417 | CZ | TYR | 700 | 81.231 | 42.707 | 42.241 | 1.00 | 19.61 | B | C |
| --- | --- | --- | --- | --- | --- | --- | --- | --- | --- | --- | --- |
| ATOM | 11418 | OH | TYR | 700 | 81.964 | 43.170 | 41.176 | 1.00 | 20.17 | B | O |
| ATOM | 11419 | C | TYR | 700 | 78.697 | 42.902 | 46.972 | 1.00 | 18.20 | B | C |
| ATOM | 11420 | O | TYR | 700 | 77.534 | 43.288 | 47.006 | 1.00 | 19.67 | B | O |
| ATOM | 11421 | N | LEU | 701 | 79.748 | 43.714 | 47.078 | 1.00 | 16.71 | B | N |
| ATOM | 11422 | CA | LEU | 701 | 79.628 | 45.157 | 47.198 | 1.00 | 15.24 | B | C |
| ATOM | 11423 | CB | LEU | 701 | 80.102 | 45.624 | 48.573 | 1.00 | 14.82 | B | C |
| ATOM | 11424 | CG | LEU | 701 | 80.195 | 47.141 | 48.768 | 1.00 | 15.42 | B | C |
| ATOM | 11425 | CD1 | LEU | 701 | 78.926 | 47.810 | 48.280 | 1.00 | 16.37 | B | C |
| ATOM | 11426 | CD2 | LEU | 701 | 80.449 | 47.456 | 50.233 | 1.00 | 13.32 | B | C |
| ATOM | 11427 | C | LEU | 701 | 80.491 | 45.770 | 46.095 | 1.00 | 16.15 | B | C |
| ATOM | 11428 | O | LEU | 701 | 81.714 | 45.617 | 46.082 | 1.00 | 16.12 | B | O |
| ATOM | 11429 | N | LEU | 702 | 79.829 | 46.450 | 45.167 | 1.00 | 14.91 | B | N |
| ATOM | 11430 | CA | LEU | 702 | 80.467 | 47.073 | 44.019 | 1.00 | 13.94 | B | C |
| ATOM | 11431 | CB | LEU | 702 | 79.730 | 46.627 | 42.753 | 1.00 | 15.12 | B | C |
| ATOM | 11432 | CG | LEU | 702 | 80.119 | 47.175 | 41.383 | 1.00 | 15.68 | B | C |
| ATOM | 11433 | CD1 | LEU | 702 | 81.555 | 46.814 | 41.050 | 1.00 | 14.64 | B | C |
| ATOM | 11434 | CD2 | LEU | 702 | 79.173 | 46.593 | 40.354 | 1.00 | 16.45 | B | C |
| ATOM | 11435 | C | LEU | 702 | 80.419 | 48.590 | 44.169 | 1.00 | 14.21 | B | C |
| ATOM | 11436 | O | LEU | 702 | 79.346 | 49.166 | 44.314 | 1.00 | 14.96 | B | O |
| ATOM | 11437 | N | ILE | 703 | 81.591 | 49.220 | 44.132 | 1.00 | 13.90 | B | N |
| ATOM | 11438 | CA | ILE | 703 | 81.737 | 50.662 | 44.294 | 1.00 | 13.91 | B | C |
| ATOM | 11439 | CB | ILE | 703 | 82.543 | 50.967 | 45.578 | 1.00 | 13.87 | B | C |
| ATOM | 11440 | CG2 | ILE | 703 | 82.693 | 52.491 | 45.775 | 1.00 | 15.37 | B | C |
| ATOM | 11441 | CG1 | ILE | 703 | 81.869 | 50.308 | 46.782 | 1.00 | 12.11 | B | C |
| ATOM | 11442 | CD1 | ILE | 703 | 82.714 | 50.328 | 48.047 | 1.00 | 7.95 | B | C |
| ATOM | 11443 | C | ILE | 703 | 82.495 | 51.251 | 43.101 | 1.00 | 15.43 | B | C |
| ATOM | 11444 | O | ILE | 703 | 83.379 | 50.600 | 42.548 | 1.00 | 17.12 | B | O |
| ATOM | 11445 | N | HIS | 704 | 82.175 | 52.484 | 42.714 | 1.00 | 14.44 | B | N |
| ATOM | 11446 | CA | HIS | 704 | 82.866 | 53.098 | 41.579 | 1.00 | 14.11 | B | C |
| ATOM | 11447 | CB | HIS | 704 | 82.483 | 52.356 | 40.288 | 1.00 | 12.85 | B | C |
| ATOM | 11448 | CG | HIS | 704 | 83.539 | 52.386 | 39.224 | 1.00 | 13.44 | B | C |
| ATOM | 11449 | CD2 | HIS | 704 | 84.363 | 53.377 | 38.806 | 1.00 | 12.54 | B | C |
| ATOM | 11450 | ND1 | HIS | 704 | 83.827 | 51.293 | 38.435 | 1.00 | 12.00 | B | N |
| ATOM | 11451 | CE1 | HIS | 704 | 84.782 | 51.607 | 37.578 | 1.00 | 10.09 | B | C |
| ATOM | 11452 | NE2 | HIS | 704 | 85.125 | 52.865 | 37.782 | 1.00 | 12.68 | B | N |
| ATOM | 11453 | C | HIS | 704 | 82.533 | 54.584 | 41.457 | 1.00 | 13.37 | B | C |
| ATOM | 11454 | O | HIS | 704 | 81.420 | 55.007 | 41.770 | 1.00 | 15.67 | B | O |
| ATOM | 11455 | N | GLY | 705 | 83.513 | 55.372 | 41.027 | 1.00 | 10.99 | B | N |
| ATOM | 11456 | CA | GLY | 705 | 83.308 | 56.798 | 40.860 | 1.00 | 10.39 | B | C |
| ATOM | 11457 | C | GLY | 705 | 82.807 | 57.082 | 39.457 | 1.00 | 10.13 | B | C |
| ATOM | 11458 | O | GLY | 705 | 83.326 | 56.536 | 38.483 | 1.00 | 11.85 | B | O |
| ATOM | 11459 | N | THR | 706 | 81.805 | 57.942 | 39.347 | 1.00 | 10.36 | B | N |
| ATOM | 11460 | CA | THR | 706 | 81.215 | 58.272 | 38.054 | 1.00 | 9.96 | B | C |
| ATOM | 11461 | CB | THR | 706 | 79.935 | 59.072 | 38.232 | 1.00 | 6.56 | B | C |
| ATOM | 11462 | OG1 | THR | 706 | 80.251 | 60.367 | 38.739 | 1.00 | 8.64 | B | O |
| ATOM | 11463 | CG2 | THR | 706 | 79.025 | 58.372 | 39.215 | 1.00 | 8.26 | B | C |
| ATOM | 11464 | C | THR | 706 | 82.145 | 59.052 | 37.147 | 1.00 | 11.88 | B | C |
| ATOM | 11465 | O | THR | 706 | 81.994 | 59.018 | 35.927 | 1.00 | 13.83 | B | O |

| | | | | | | | | | | |
|---|---|---|---|---|---|---|---|---|---|---|
| ATOM | 11466 | N | ALA | 707 | 83.114 | 59.741 | 37.739 | 1.00 | 13.21 | B N |
| ATOM | 11467 | CA | ALA | 707 | 84.075 | 60.522 | 36.969 | 1.00 | 14.57 | B C |
| ATOM | 11468 | CB | ALA | 707 | 84.277 | 61.881 | 37.626 | 1.00 | 17.64 | B C |
| ATOM | 11469 | C | ALA | 707 | 85.427 | 59.823 | 36.802 | 1.00 | 13.77 | B C |
| ATOM | 11470 | O | ALA | 707 | 86.445 | 60.484 | 36.639 | 1.00 | 14.15 | B O |
| ATOM | 11471 | N | ASP | 708 | 85.435 | 58.494 | 36.839 | 1.00 | 13.35 | B N |
| ATOM | 11472 | CA | ASP | 708 | 86.667 | 57.721 | 36.685 | 1.00 | 12.65 | B C |
| ATOM | 11473 | CB | ASP | 708 | 86.439 | 56.285 | 37.188 | 1.00 | 12.24 | B C |
| ATOM | 11474 | CG | ASP | 708 | 87.737 | 55.536 | 37.453 | 1.00 | 10.05 | B C |
| ATOM | 11475 | OD1 | ASP | 708 | 88.738 | 55.775 | 36.749 | 1.00 | 11.19 | B O |
| ATOM | 11476 | OD2 | ASP | 708 | 87.751 | 54.686 | 38.362 | 1.00 | 9.31 | B O |
| ATOM | 11477 | C | ASP | 708 | 87.091 | 57.696 | 35.202 | 1.00 | 13.18 | B C |
| ATOM | 11478 | O | ASP | 708 | 86.475 | 57.023 | 34.368 | 1.00 | 13.78 | B O |
| ATOM | 11479 | N | ASP | 709 | 88.156 | 58.423 | 34.891 | 1.00 | 12.80 | B N |
| ATOM | 11480 | CA | ASP | 709 | 88.679 | 58.520 | 33.534 | 1.00 | 12.65 | B C |
| ATOM | 11481 | CB | ASP | 709 | 89.442 | 59.825 | 33.397 | 1.00 | 11.74 | B C |
| ATOM | 11482 | CG | ASP | 709 | 90.612 | 59.912 | 34.366 | 1.00 | 9.63 | B C |
| ATOM | 11483 | OD1 | ASP | 709 | 91.704 | 59.385 | 34.058 | 1.00 | 2.39 | B O |
| ATOM | 11484 | OD2 | ASP | 709 | 90.419 | 60.499 | 35.451 | 1.00 | 11.84 | B O |
| ATOM | 11485 | C | ASP | 709 | 89.605 | 57.366 | 33.167 | 1.00 | 14.57 | B C |
| ATOM | 11486 | O | ASP | 709 | 89.896 | 57.136 | 31.987 | 1.00 | 16.47 | B O |
| ATOM | 11487 | N | ASN | 710 | 90.076 | 56.652 | 34.182 | 1.00 | 13.58 | B N |
| ATOM | 11488 | CA | ASN | 710 | 90.981 | 55.524 | 33.990 | 1.00 | 13.56 | B C |
| ATOM | 11489 | CB | ASN | 710 | 91.841 | 55.385 | 35.243 | 1.00 | 13.26 | B C |
| ATOM | 11490 | CG | ASN | 710 | 92.987 | 54.440 | 35.059 | 1.00 | 12.07 | B C |
| ATOM | 11491 | OD1 | ASN | 710 | 93.951 | 54.478 | 35.821 | 1.00 | 16.69 | B O |
| ATOM | 11492 | ND2 | ASN | 710 | 92.898 | 53.578 | 34.058 | 1.00 | 8.28 | B N |
| ATOM | 11493 | C | ASN | 710 | 90.177 | 54.236 | 33.724 | 1.00 | 14.26 | B C |
| ATOM | 11494 | O | ASN | 710 | 90.142 | 53.737 | 32.598 | 1.00 | 14.29 | B O |
| ATOM | 11495 | N | VAL | 711 | 89.560 | 53.692 | 34.773 | 1.00 | 13.24 | B N |
| ATOM | 11496 | CA | VAL | 711 | 88.715 | 52.511 | 34.652 | 1.00 | 12.56 | B C |
| ATOM | 11497 | CB | VAL | 711 | 88.835 | 51.585 | 35.868 | 1.00 | 11.72 | B C |
| ATOM | 11498 | CG1 | VAL | 711 | 88.048 | 50.311 | 35.624 | 1.00 | 7.36 | B C |
| ATOM | 11499 | CG2 | VAL | 711 | 90.287 | 51.274 | 36.141 | 1.00 | 13.94 | B C |
| ATOM | 11500 | C | VAL | 711 | 87.315 | 53.119 | 34.645 | 1.00 | 14.01 | B C |
| ATOM | 11501 | O | VAL | 711 | 86.768 | 53.471 | 35.694 | 1.00 | 13.52 | B O |
| ATOM | 11502 | N | HIS | 712 | 86.746 | 53.249 | 33.456 | 1.00 | 13.66 | B N |
| ATOM | 11503 | CA | HIS | 712 | 85.440 | 53.869 | 33.290 | 1.00 | 13.44 | B C |
| ATOM | 11504 | CB | HIS | 712 | 85.132 | 53.956 | 31.794 | 1.00 | 12.94 | B C |
| ATOM | 11505 | CG | HIS | 712 | 86.219 | 54.613 | 31.001 | 1.00 | 14.38 | B C |
| ATOM | 11506 | CD2 | HIS | 712 | 87.137 | 55.549 | 31.352 | 1.00 | 15.50 | B C |
| ATOM | 11507 | ND1 | HIS | 712 | 86.477 | 54.299 | 29.684 | 1.00 | 15.76 | B N |
| ATOM | 11508 | CE1 | HIS | 712 | 87.510 | 55.009 | 29.258 | 1.00 | 17.42 | B C |
| ATOM | 11509 | NE2 | HIS | 712 | 87.928 | 55.775 | 30.251 | 1.00 | 16.57 | B N |
| ATOM | 11510 | C | HIS | 712 | 84.293 | 53.205 | 34.048 | 1.00 | 13.09 | B C |
| ATOM | 11511 | O | HIS | 712 | 84.208 | 51.983 | 34.148 | 1.00 | 13.25 | B O |
| ATOM | 11512 | N | PHE | 713 | 83.420 | 54.041 | 34.594 | 1.00 | 13.27 | B N |
| ATOM | 11513 | CA | PHE | 713 | 82.253 | 53.586 | 35.335 | 1.00 | 15.36 | B C |
| ATOM | 11514 | CB | PHE | 713 | 81.288 | 54.759 | 35.530 | 1.00 | 15.17 | B C |

| ATOM | 11515 | CG | PHE | 713 | 80.156 | 54.464 | 36.461 | 1.00 | 16.61 | B | C |
|---|---|---|---|---|---|---|---|---|---|---|---|
| ATOM | 11516 | CD1 | PHE | 713 | 80.346 | 54.508 | 37.841 | 1.00 | 14.51 | B | C |
| ATOM | 11517 | CD2 | PHE | 713 | 78.901 | 54.111 | 35.962 | 1.00 | 15.42 | B | C |
| ATOM | 11518 | CE1 | PHE | 713 | 79.304 | 54.204 | 38.710 | 1.00 | 14.71 | B | C |
| ATOM | 11519 | CE2 | PHE | 713 | 77.848 | 53.803 | 36.829 | 1.00 | 15.24 | B | C |
| ATOM | 11520 | CZ | PHE | 713 | 78.051 | 53.849 | 38.204 | 1.00 | 13.41 | B | C |
| ATOM | 11521 | C | PHE | 713 | 81.586 | 52.486 | 34.499 | 1.00 | 16.62 | B | C |
| ATOM | 11522 | O | PHE | 713 | 81.015 | 51.527 | 35.031 | 1.00 | 16.48 | B | O |
| ATOM | 11523 | N | GLN | 714 | 81.673 | 52.649 | 33.181 | 1.00 | 15.73 | B | N |
| ATOM | 11524 | CA | GLN | 714 | 81.121 | 51.699 | 32.228 | 1.00 | 16.08 | B | C |
| ATOM | 11525 | CB | GLN | 714 | 81.753 | 51.923 | 30.857 | 1.00 | 14.90 | B | C |
| ATOM | 11526 | CG | GLN | 714 | 81.699 | 50.703 | 29.946 | 1.00 | 16.13 | B | C |
| ATOM | 11527 | CD | GLN | 714 | 82.661 | 50.811 | 28.770 | 1.00 | 15.37 | B | C |
| ATOM | 11528 | OE1 | GLN | 714 | 83.821 | 51.167 | 28.943 | 1.00 | 15.11 | B | O |
| ATOM | 11529 | NE2 | GLN | 714 | 82.183 | 50.493 | 27.577 | 1.00 | 15.35 | B | N |
| ATOM | 11530 | C | GLN | 714 | 81.372 | 50.256 | 32.650 | 1.00 | 16.29 | B | C |
| ATOM | 11531 | O | GLN | 714 | 80.512 | 49.389 | 32.487 | 1.00 | 17.82 | B | O |
| ATOM | 11532 | N | GLN | 715 | 82.554 | 49.997 | 33.192 | 1.00 | 14.60 | B | N |
| ATOM | 11533 | CA | GLN | 715 | 82.900 | 48.646 | 33.593 | 1.00 | 14.55 | B | C |
| ATOM | 11534 | CB | GLN | 715 | 84.395 | 48.581 | 33.926 | 1.00 | 16.22 | B | C |
| ATOM | 11535 | CG | GLN | 715 | 85.270 | 49.086 | 32.767 | 1.00 | 16.01 | B | C |
| ATOM | 11536 | CD | GLN | 715 | 86.507 | 48.247 | 32.537 | 1.00 | 14.28 | B | C |
| ATOM | 11537 | OE1 | GLN | 715 | 86.470 | 47.029 | 32.674 | 1.00 | 17.54 | B | O |
| ATOM | 11538 | NE2 | GLN | 715 | 87.601 | 48.889 | 32.155 | 1.00 | 12.78 | B | N |
| ATOM | 11539 | C | GLN | 715 | 82.031 | 48.134 | 34.746 | 1.00 | 14.99 | B | C |
| ATOM | 11540 | O | GLN | 715 | 81.616 | 46.967 | 34.749 | 1.00 | 13.70 | B | O |
| ATOM | 11541 | N | SER | 716 | 81.742 | 49.002 | 35.714 | 1.00 | 12.14 | B | N |
| ATOM | 11542 | CA | SER | 716 | 80.893 | 48.602 | 36.829 | 1.00 | 11.18 | B | C |
| ATOM | 11543 | CB | SER | 716 | 81.057 | 49.544 | 38.028 | 1.00 | 11.19 | B | C |
| ATOM | 11544 | OG | SER | 716 | 82.278 | 49.295 | 38.700 | 1.00 | 13.48 | B | O |
| ATOM | 11545 | C | SER | 716 | 79.432 | 48.570 | 36.394 | 1.00 | 9.18 | B | C |
| ATOM | 11546 | O | SER | 716 | 78.682 | 47.692 | 36.814 | 1.00 | 5.81 | B | O |
| ATOM | 11547 | N | ALA | 717 | 79.026 | 49.517 | 35.552 | 1.00 | 8.69 | B | N |
| ATOM | 11548 | CA | ALA | 717 | 77.639 | 49.537 | 35.083 | 1.00 | 10.91 | B | C |
| ATOM | 11549 | CB | ALA | 717 | 77.400 | 50.708 | 34.143 | 1.00 | 10.07 | B | C |
| ATOM | 11550 | C | ALA | 717 | 77.304 | 48.219 | 34.382 | 1.00 | 10.72 | B | C |
| ATOM | 11551 | O | ALA | 717 | 76.212 | 47.696 | 34.539 | 1.00 | 14.08 | B | O |
| ATOM | 11552 | N | GLN | 718 | 78.252 | 47.682 | 33.623 | 1.00 | 10.89 | B | N |
| ATOM | 11553 | CA | GLN | 718 | 78.052 | 46.417 | 32.928 | 1.00 | 10.32 | B | C |
| ATOM | 11554 | CB | GLN | 718 | 79.137 | 46.224 | 31.858 | 1.00 | 8.83 | B | C |
| ATOM | 11555 | CG | GLN | 718 | 79.074 | 47.232 | 30.722 | 1.00 | 6.53 | B | C |
| ATOM | 11556 | CD | GLN | 718 | 78.002 | 46.900 | 29.691 | 1.00 | 8.70 | B | C |
| ATOM | 11557 | OE1 | GLN | 718 | 76.970 | 46.319 | 30.012 | 1.00 | 13.43 | B | O |
| ATOM | 11558 | NE2 | GLN | 718 | 78.243 | 47.278 | 28.449 | 1.00 | 11.12 | B | N |
| ATOM | 11559 | C | GLN | 718 | 78.056 | 45.235 | 33.908 | 1.00 | 10.68 | B | C |
| ATOM | 11560 | O | GLN | 718 | 77.357 | 44.248 | 33.695 | 1.00 | 13.48 | B | O |
| ATOM | 11561 | N | ILE | 719 | 78.834 | 45.320 | 34.981 | 1.00 | 12.24 | B | N |
| ATOM | 11562 | CA | ILE | 719 | 78.851 | 44.226 | 35.953 | 1.00 | 12.41 | B | C |
| ATOM | 11563 | CB | ILE | 719 | 79.892 | 44.434 | 37.079 | 1.00 | 12.88 | B | C |

| ATOM | 11564 | CG2 | ILE | 719 | 79.550 | 43.532 | 38.266 | 1.00 | 9.78 | B | C |
| --- | --- | --- | --- | --- | --- | --- | --- | --- | --- | --- | --- |
| ATOM | 11565 | CG1 | ILE | 719 | 81.302 | 44.131 | 36.560 | 1.00 | 13.61 | B | C |
| ATOM | 11566 | CD1 | ILE | 719 | 82.383 | 44.146 | 37.643 | 1.00 | 12.97 | B | C |
| ATOM | 11567 | C | ILE | 719 | 77.494 | 44.134 | 36.621 | 1.00 | 12.95 | B | C |
| ATOM | 11568 | O | ILE | 719 | 76.932 | 43.049 | 36.757 | 1.00 | 13.41 | B | O |
| ATOM | 11569 | N | SER | 720 | 76.979 | 45.286 | 37.043 | 1.00 | 12.96 | B | N |
| ATOM | 11570 | CA | SER | 720 | 75.694 | 45.345 | 37.716 | 1.00 | 13.07 | B | C |
| ATOM | 11571 | CB | SER | 720 | 75.418 | 46.771 | 38.211 | 1.00 | 12.56 | B | C |
| ATOM | 11572 | OG | SER | 720 | 75.435 | 47.716 | 37.147 | 1.00 | 15.69 | B | O |
| ATOM | 11573 | C | SER | 720 | 74.558 | 44.865 | 36.814 | 1.00 | 14.11 | B | C |
| ATOM | 11574 | O | SER | 720 | 73.712 | 44.073 | 37.238 | 1.00 | 13.45 | B | O |
| ATOM | 11575 | N | LYS | 721 | 74.536 | 45.329 | 35.569 | 1.00 | 12.91 | B | N |
| ATOM | 11576 | CA | LYS | 721 | 73.474 | 44.919 | 34.664 | 1.00 | 14.31 | B | C |
| ATOM | 11577 | CB | LYS | 721 | 73.647 | 45.596 | 33.303 | 1.00 | 14.17 | B | C |
| ATOM | 11578 | CG | LYS | 721 | 72.613 | 45.188 | 32.264 | 1.00 | 10.06 | B | C |
| ATOM | 11579 | CD | LYS | 721 | 72.241 | 46.368 | 31.378 | 1.00 | 10.77 | B | C |
| ATOM | 11580 | CE | LYS | 721 | 73.427 | 46.932 | 30.611 | 1.00 | 9.97 | B | C |
| ATOM | 11581 | NZ | LYS | 721 | 73.939 | 45.970 | 29.595 | 1.00 | 11.67 | B | N |
| ATOM | 11582 | C | LYS | 721 | 73.431 | 43.396 | 34.504 | 1.00 | 15.75 | B | C |
| ATOM | 11583 | O | LYS | 721 | 72.349 | 42.803 | 34.403 | 1.00 | 14.39 | B | O |
| ATOM | 11584 | N | ALA | 722 | 74.605 | 42.766 | 34.501 | 1.00 | 14.45 | B | N |
| ATOM | 11585 | CA | ALA | 722 | 74.684 | 41.320 | 34.353 | 1.00 | 13.03 | B | C |
| ATOM | 11586 | CB | ALA | 722 | 76.137 | 40.889 | 34.146 | 1.00 | 11.46 | B | C |
| ATOM | 11587 | C | ALA | 722 | 74.083 | 40.607 | 35.564 | 1.00 | 14.14 | B | C |
| ATOM | 11588 | O | ALA | 722 | 73.369 | 39.606 | 35.417 | 1.00 | 14.70 | B | O |
| ATOM | 11589 | N | LEU | 723 | 74.358 | 41.124 | 36.758 | 1.00 | 13.91 | B | N |
| ATOM | 11590 | CA | LEU | 723 | 73.832 | 40.520 | 37.974 | 1.00 | 15.06 | B | C |
| ATOM | 11591 | CB | LEU | 723 | 74.442 | 41.184 | 39.204 | 1.00 | 16.63 | B | C |
| ATOM | 11592 | CG | LEU | 723 | 75.957 | 40.999 | 39.306 | 1.00 | 16.43 | B | C |
| ATOM | 11593 | CD1 | LEU | 723 | 76.504 | 41.863 | 40.415 | 1.00 | 18.97 | B | C |
| ATOM | 11594 | CD2 | LEU | 723 | 76.280 | 39.535 | 39.546 | 1.00 | 15.22 | B | C |
| ATOM | 11595 | C | LEU | 723 | 72.323 | 40.668 | 37.980 | 1.00 | 16.46 | B | C |
| ATOM | 11596 | O | LEU | 723 | 71.586 | 39.731 | 38.310 | 1.00 | 18.39 | B | O |
| ATOM | 11597 | N | VAL | 724 | 71.858 | 41.849 | 37.604 | 1.00 | 16.97 | B | N |
| ATOM | 11598 | CA | VAL | 724 | 70.429 | 42.079 | 37.533 | 1.00 | 17.76 | B | C |
| ATOM | 11599 | CB | VAL | 724 | 70.126 | 43.526 | 37.084 | 1.00 | 17.79 | B | C |
| ATOM | 11600 | CG1 | VAL | 724 | 68.660 | 43.678 | 36.728 | 1.00 | 18.59 | B | C |
| ATOM | 11601 | CG2 | VAL | 724 | 70.479 | 44.487 | 38.213 | 1.00 | 19.61 | B | C |
| ATOM | 11602 | C | VAL | 724 | 69.844 | 41.079 | 36.532 | 1.00 | 18.06 | B | C |
| ATOM | 11603 | O | VAL | 724 | 68.824 | 40.441 | 36.800 | 1.00 | 16.03 | B | O |
| ATOM | 11604 | N | ASP | 725 | 70.509 | 40.920 | 35.391 | 1.00 | 19.41 | B | N |
| ATOM | 11605 | CA | ASP | 725 | 70.015 | 39.999 | 34.379 | 1.00 | 21.58 | B | C |
| ATOM | 11606 | CB | ASP | 725 | 70.965 | 39.930 | 33.191 | 1.00 | 23.71 | B | C |
| ATOM | 11607 | CG | ASP | 725 | 70.957 | 41.197 | 32.372 | 1.00 | 27.35 | B | C |
| ATOM | 11608 | OD1 | ASP | 725 | 69.919 | 41.895 | 32.368 | 1.00 | 27.29 | B | O |
| ATOM | 11609 | OD2 | ASP | 725 | 71.983 | 41.486 | 31.717 | 1.00 | 31.72 | B | O |
| ATOM | 11610 | C | ASP | 725 | 69.748 | 38.591 | 34.893 | 1.00 | 22.63 | B | C |
| ATOM | 11611 | O | ASP | 725 | 68.763 | 37.974 | 34.474 | 1.00 | 24.48 | B | O |
| ATOM | 11612 | N | VAL | 726 | 70.607 | 38.075 | 35.781 | 1.00 | 20.53 | B | N |

| | | | | | | | | | | |
|---|---|---|---|---|---|---|---|---|---|---|
| ATOM | 11613 | CA  | VAL | 726 | 70.409 | 36.726 | 36.329 | 1.00 | 17.93 | B C |
| ATOM | 11614 | CB  | VAL | 726 | 71.727 | 35.920 | 36.392 | 1.00 | 19.28 | B C |
| ATOM | 11615 | CG1 | VAL | 726 | 72.246 | 35.672 | 34.994 | 1.00 | 19.33 | B C |
| ATOM | 11616 | CG2 | VAL | 726 | 72.763 | 36.660 | 37.238 | 1.00 | 19.80 | B C |
| ATOM | 11617 | C   | VAL | 726 | 69.789 | 36.741 | 37.723 | 1.00 | 17.35 | B C |
| ATOM | 11618 | O   | VAL | 726 | 69.858 | 35.756 | 38.463 | 1.00 | 16.63 | B O |
| ATOM | 11619 | N   | GLY | 727 | 69.198 | 37.875 | 38.081 | 1.00 | 17.14 | B N |
| ATOM | 11620 | CA  | GLY | 727 | 68.548 | 38.012 | 39.370 | 1.00 | 15.42 | B C |
| ATOM | 11621 | C   | GLY | 727 | 69.387 | 37.856 | 40.626 | 1.00 | 15.90 | B C |
| ATOM | 11622 | O   | GLY | 727 | 68.961 | 37.182 | 41.559 | 1.00 | 17.97 | B O |
| ATOM | 11623 | N   | VAL | 728 | 70.568 | 38.462 | 40.675 | 1.00 | 15.07 | B N |
| ATOM | 11624 | CA  | VAL | 728 | 71.389 | 38.357 | 41.876 | 1.00 | 14.10 | B C |
| ATOM | 11625 | CB  | VAL | 728 | 72.859 | 37.972 | 41.574 | 1.00 | 14.97 | B C |
| ATOM | 11626 | CG1 | VAL | 728 | 73.693 | 38.145 | 42.829 | 1.00 | 13.51 | B C |
| ATOM | 11627 | CG2 | VAL | 728 | 72.954 | 36.514 | 41.109 | 1.00 | 15.40 | B C |
| ATOM | 11628 | C   | VAL | 728 | 71.396 | 39.687 | 42.603 | 1.00 | 14.73 | B C |
| ATOM | 11629 | O   | VAL | 728 | 71.738 | 40.714 | 42.025 | 1.00 | 14.56 | B O |
| ATOM | 11630 | N   | ASP | 729 | 71.007 | 39.672 | 43.872 | 1.00 | 15.13 | B N |
| ATOM | 11631 | CA  | ASP | 729 | 70.998 | 40.896 | 44.646 | 1.00 | 15.32 | B C |
| ATOM | 11632 | CB  | ASP | 729 | 70.146 | 40.731 | 45.903 | 1.00 | 15.31 | B C |
| ATOM | 11633 | CG  | ASP | 729 | 70.034 | 42.019 | 46.696 | 1.00 | 18.11 | B C |
| ATOM | 11634 | OD1 | ASP | 729 | 69.663 | 43.055 | 46.104 | 1.00 | 20.57 | B O |
| ATOM | 11635 | OD2 | ASP | 729 | 70.317 | 42.011 | 47.907 | 1.00 | 20.06 | B O |
| ATOM | 11636 | C   | ASP | 729 | 72.441 | 41.185 | 45.021 | 1.00 | 16.27 | B C |
| ATOM | 11637 | O   | ASP | 729 | 73.253 | 40.270 | 45.117 | 1.00 | 17.70 | B O |
| ATOM | 11638 | N   | PHE | 730 | 72.772 | 42.454 | 45.211 | 1.00 | 16.74 | B N |
| ATOM | 11639 | CA  | PHE | 730 | 74.136 | 42.824 | 45.579 | 1.00 | 16.43 | B C |
| ATOM | 11640 | CB  | PHE | 730 | 75.061 | 42.734 | 44.361 | 1.00 | 13.47 | B C |
| ATOM | 11641 | CG  | PHE | 730 | 74.744 | 43.728 | 43.304 | 1.00 | 12.81 | B C |
| ATOM | 11642 | CD1 | PHE | 730 | 75.282 | 45.006 | 43.355 | 1.00 | 12.64 | B C |
| ATOM | 11643 | CD2 | PHE | 730 | 73.828 | 43.423 | 42.303 | 1.00 | 12.46 | B C |
| ATOM | 11644 | CE1 | PHE | 730 | 74.907 | 45.966 | 42.432 | 1.00 | 11.61 | B C |
| ATOM | 11645 | CE2 | PHE | 730 | 73.446 | 44.377 | 41.376 | 1.00 | 9.11  | B C |
| ATOM | 11646 | CZ  | PHE | 730 | 73.986 | 45.653 | 41.443 | 1.00 | 10.39 | B C |
| ATOM | 11647 | C   | PHE | 730 | 74.112 | 44.242 | 46.114 | 1.00 | 17.87 | B C |
| ATOM | 11648 | O   | PHE | 730 | 73.094 | 44.928 | 46.014 | 1.00 | 19.72 | B O |
| ATOM | 11649 | N   | GLN | 731 | 75.230 | 44.673 | 46.689 | 1.00 | 18.41 | B N |
| ATOM | 11650 | CA  | GLN | 731 | 75.344 | 46.015 | 47.246 | 1.00 | 17.25 | B C |
| ATOM | 11651 | CB  | GLN | 731 | 76.089 | 45.961 | 48.569 | 1.00 | 18.02 | B C |
| ATOM | 11652 | CG  | GLN | 731 | 75.547 | 44.948 | 49.536 | 1.00 | 25.59 | B C |
| ATOM | 11653 | CD  | GLN | 731 | 74.087 | 45.183 | 49.854 | 1.00 | 29.48 | B C |
| ATOM | 11654 | OE1 | GLN | 731 | 73.699 | 46.275 | 50.281 | 1.00 | 31.32 | B O |
| ATOM | 11655 | NE2 | GLN | 731 | 73.263 | 44.157 | 49.647 | 1.00 | 32.13 | B N |
| ATOM | 11656 | C   | GLN | 731 | 76.124 | 46.889 | 46.272 | 1.00 | 16.69 | B C |
| ATOM | 11657 | O   | GLN | 731 | 77.060 | 46.417 | 45.623 | 1.00 | 13.71 | B O |
| ATOM | 11658 | N   | ALA | 732 | 75.737 | 48.158 | 46.172 | 1.00 | 15.59 | B N |
| ATOM | 11659 | CA  | ALA | 732 | 76.425 | 49.084 | 45.284 | 1.00 | 15.79 | B C |
| ATOM | 11660 | CB  | ALA | 732 | 75.718 | 49.147 | 43.946 | 1.00 | 15.47 | B C |
| ATOM | 11661 | C   | ALA | 732 | 76.540 | 50.486 | 45.867 | 1.00 | 17.21 | B C |

FIG. 4-239

| ATOM | 11662 | O | ALA | 732 | 75.769 | 50.897 | 46.734 | 1.00 | 17.93 | B | O |
|---|---|---|---|---|---|---|---|---|---|---|---|
| ATOM | 11663 | N | MET | 733 | 77.528 | 51.220 | 45.382 | 1.00 | 17.27 | B | N |
| ATOM | 11664 | CA | MET | 733 | 77.737 | 52.587 | 45.812 | 1.00 | 17.39 | B | C |
| ATOM | 11665 | CB | MET | 733 | 78.500 | 52.628 | 47.136 | 1.00 | 18.98 | B | C |
| ATOM | 11666 | CG | MET | 733 | 78.775 | 54.028 | 47.661 | 1.00 | 18.20 | B | C |
| ATOM | 11667 | SD | MET | 733 | 77.278 | 54.979 | 47.988 | 1.00 | 21.42 | B | S |
| ATOM | 11668 | CE | MET | 733 | 76.781 | 54.324 | 49.578 | 1.00 | 19.12 | B | C |
| ATOM | 11669 | C | MET | 733 | 78.539 | 53.268 | 44.719 | 1.00 | 17.47 | B | C |
| ATOM | 11670 | O | MET | 733 | 79.604 | 52.783 | 44.318 | 1.00 | 17.30 | B | O |
| ATOM | 11671 | N | TRP | 734 | 78.007 | 54.378 | 44.220 | 1.00 | 16.37 | B | N |
| ATOM | 11672 | CA | TRP | 734 | 78.673 | 55.147 | 43.175 | 1.00 | 15.48 | B | C |
| ATOM | 11673 | CB | TRP | 734 | 77.685 | 55.428 | 42.033 | 1.00 | 14.82 | B | C |
| ATOM | 11674 | CG | TRP | 734 | 76.691 | 56.523 | 42.353 | 1.00 | 14.06 | B | C |
| ATOM | 11675 | CD2 | TRP | 734 | 75.299 | 56.363 | 42.650 | 1.00 | 12.49 | B | C |
| ATOM | 11676 | CE2 | TRP | 734 | 74.785 | 57.645 | 42.939 | 1.00 | 12.15 | B | C |
| ATOM | 11677 | CE3 | TRP | 734 | 74.437 | 55.259 | 42.701 | 1.00 | 12.01 | B | C |
| ATOM | 11678 | CD1 | TRP | 734 | 76.953 | 57.857 | 42.468 | 1.00 | 12.61 | B | C |
| ATOM | 11679 | NE1 | TRP | 734 | 75.817 | 58.535 | 42.821 | 1.00 | 13.60 | B | N |
| ATOM | 11680 | CZ2 | TRP | 734 | 73.449 | 57.858 | 43.276 | 1.00 | 11.75 | B | C |
| ATOM | 11681 | CZ3 | TRP | 734 | 73.115 | 55.466 | 43.034 | 1.00 | 13.39 | B | C |
| ATOM | 11682 | CH2 | TRP | 734 | 72.629 | 56.762 | 43.319 | 1.00 | 13.13 | B | C |
| ATOM | 11683 | C | TRP | 734 | 79.111 | 56.457 | 43.831 | 1.00 | 13.60 | B | C |
| ATOM | 11684 | O | TRP | 734 | 78.491 | 56.881 | 44.788 | 1.00 | 14.71 | B | O |
| ATOM | 11685 | N | TYR | 735 | 80.174 | 57.090 | 43.346 | 1.00 | 13.31 | B | N |
| ATOM | 11686 | CA | TYR | 735 | 80.598 | 58.366 | 43.926 | 1.00 | 12.17 | B | C |
| ATOM | 11687 | CB | TYR | 735 | 81.990 | 58.260 | 44.575 | 1.00 | 10.49 | B | C |
| ATOM | 11688 | CG | TYR | 735 | 81.964 | 57.577 | 45.920 | 1.00 | 10.18 | B | C |
| ATOM | 11689 | CD1 | TYR | 735 | 81.464 | 58.232 | 47.045 | 1.00 | 11.23 | B | C |
| ATOM | 11690 | CE1 | TYR | 735 | 81.321 | 57.567 | 48.272 | 1.00 | 11.72 | B | C |
| ATOM | 11691 | CD2 | TYR | 735 | 82.336 | 56.241 | 46.052 | 1.00 | 11.30 | B | C |
| ATOM | 11692 | CE2 | TYR | 735 | 82.198 | 55.567 | 47.270 | 1.00 | 11.75 | B | C |
| ATOM | 11693 | CZ | TYR | 735 | 81.687 | 56.235 | 48.372 | 1.00 | 12.02 | B | C |
| ATOM | 11694 | OH | TYR | 735 | 81.511 | 55.564 | 49.563 | 1.00 | 13.79 | B | O |
| ATOM | 11695 | C | TYR | 735 | 80.595 | 59.430 | 42.845 | 1.00 | 14.20 | B | C |
| ATOM | 11696 | O | TYR | 735 | 81.391 | 59.393 | 41.910 | 1.00 | 15.56 | B | O |
| ATOM | 11697 | N | THR | 736 | 79.669 | 60.372 | 42.977 | 1.00 | 15.66 | B | N |
| ATOM | 11698 | CA | THR | 736 | 79.517 | 61.459 | 42.026 | 1.00 | 14.01 | B | C |
| ATOM | 11699 | CB | THR | 736 | 78.395 | 62.401 | 42.469 | 1.00 | 13.01 | B | C |
| ATOM | 11700 | OG1 | THR | 736 | 77.163 | 61.673 | 42.534 | 1.00 | 13.00 | B | O |
| ATOM | 11701 | CG2 | THR | 736 | 78.256 | 63.571 | 41.503 | 1.00 | 11.91 | B | C |
| ATOM | 11702 | C | THR | 736 | 80.789 | 62.278 | 41.882 | 1.00 | 16.80 | B | C |
| ATOM | 11703 | O | THR | 736 | 81.357 | 62.730 | 42.875 | 1.00 | 19.71 | B | O |
| ATOM | 11704 | N | ASP | 737 | 81.230 | 62.457 | 40.640 | 1.00 | 16.82 | B | N |
| ATOM | 11705 | CA | ASP | 737 | 82.407 | 63.257 | 40.322 | 1.00 | 15.22 | B | C |
| ATOM | 11706 | CB | ASP | 737 | 82.151 | 64.728 | 40.684 | 1.00 | 15.24 | B | C |
| ATOM | 11707 | CG | ASP | 737 | 81.101 | 65.380 | 39.785 | 1.00 | 17.61 | B | C |
| ATOM | 11708 | OD1 | ASP | 737 | 80.697 | 64.753 | 38.779 | 1.00 | 16.59 | B | O |
| ATOM | 11709 | OD2 | ASP | 737 | 80.680 | 66.525 | 40.078 | 1.00 | 19.23 | B | O |
| ATOM | 11710 | C | ASP | 737 | 83.737 | 62.811 | 40.912 | 1.00 | 15.17 | B | C |

| | | | | | | | | | | |
|---|---|---|---|---|---|---|---|---|---|---|
| ATOM | 11711 | O | ASP | 737 | 84.716 | 63.560 | 40.882 | 1.00 | 14.33 | B O |
| ATOM | 11712 | N | GLU | 738 | 83.790 | 61.603 | 41.453 | 1.00 | 14.73 | B N |
| ATOM | 11713 | CA | GLU | 738 | 85.054 | 61.112 | 41.986 | 1.00 | 14.51 | B C |
| ATOM | 11714 | CB | GLU | 738 | 84.829 | 60.208 | 43.206 | 1.00 | 15.23 | B C |
| ATOM | 11715 | CG | GLU | 738 | 84.353 | 60.935 | 44.448 | 1.00 | 16.91 | B C |
| ATOM | 11716 | CD | GLU | 738 | 85.355 | 61.958 | 44.956 | 1.00 | 19.02 | B C |
| ATOM | 11717 | OE1 | GLU | 738 | 86.513 | 61.580 | 45.222 | 1.00 | 19.93 | B O |
| ATOM | 11718 | OE2 | GLU | 738 | 84.985 | 63.142 | 45.100 | 1.00 | 19.97 | B O |
| ATOM | 11719 | C | GLU | 738 | 85.718 | 60.319 | 40.867 | 1.00 | 13.36 | B C |
| ATOM | 11720 | O | GLU | 738 | 85.037 | 59.763 | 40.005 | 1.00 | 13.24 | B O |
| ATOM | 11721 | N | ASP | 739 | 87.042 | 60.275 | 40.858 | 1.00 | 12.47 | B N |
| ATOM | 11722 | CA | ASP | 739 | 87.716 | 59.522 | 39.824 | 1.00 | 12.05 | B C |
| ATOM | 11723 | CB | ASP | 739 | 88.809 | 60.369 | 39.166 | 1.00 | 12.46 | B C |
| ATOM | 11724 | CG | ASP | 739 | 89.952 | 60.717 | 40.101 | 1.00 | 16.27 | B C |
| ATOM | 11725 | OD1 | ASP | 739 | 90.706 | 61.653 | 39.751 | 1.00 | 16.93 | B O |
| ATOM | 11726 | OD2 | ASP | 739 | 90.116 | 60.066 | 41.158 | 1.00 | 16.75 | B O |
| ATOM | 11727 | C | ASP | 739 | 88.248 | 58.187 | 40.351 | 1.00 | 13.65 | B C |
| ATOM | 11728 | O | ASP | 739 | 87.781 | 57.686 | 41.372 | 1.00 | 14.63 | B O |
| ATOM | 11729 | N | HIS | 740 | 89.217 | 57.609 | 39.661 | 1.00 | 12.45 | B N |
| ATOM | 11730 | CA | HIS | 740 | 89.735 | 56.311 | 40.041 | 1.00 | 12.91 | B C |
| ATOM | 11731 | CB | HIS | 740 | 90.795 | 55.872 | 39.035 | 1.00 | 12.28 | B C |
| ATOM | 11732 | CG | HIS | 740 | 91.112 | 54.418 | 39.105 | 1.00 | 12.12 | B C |
| ATOM | 11733 | CD2 | HIS | 740 | 92.292 | 53.763 | 39.179 | 1.00 | 12.56 | B C |
| ATOM | 11734 | ND1 | HIS | 740 | 90.133 | 53.449 | 39.081 | 1.00 | 12.00 | B N |
| ATOM | 11735 | CE1 | HIS | 740 | 90.697 | 52.256 | 39.136 | 1.00 | 11.97 | B C |
| ATOM | 11736 | NE2 | HIS | 740 | 92.006 | 52.419 | 39.194 | 1.00 | 12.98 | B N |
| ATOM | 11737 | C | HIS | 740 | 90.298 | 56.209 | 41.447 | 1.00 | 14.77 | B C |
| ATOM | 11738 | O | HIS | 740 | 90.302 | 55.133 | 42.041 | 1.00 | 16.10 | B O |
| ATOM | 11739 | N | GLY | 741 | 90.775 | 57.320 | 41.986 | 1.00 | 14.45 | B N |
| ATOM | 11740 | CA | GLY | 741 | 91.345 | 57.271 | 43.311 | 1.00 | 13.32 | B C |
| ATOM | 11741 | C | GLY | 741 | 90.381 | 57.572 | 44.431 | 1.00 | 14.78 | B C |
| ATOM | 11742 | O | GLY | 741 | 90.763 | 57.445 | 45.590 | 1.00 | 16.71 | B O |
| ATOM | 11743 | N | ILE | 742 | 89.144 | 57.946 | 44.103 | 1.00 | 14.08 | B N |
| ATOM | 11744 | CA | ILE | 742 | 88.146 | 58.298 | 45.111 | 1.00 | 14.39 | B C |
| ATOM | 11745 | CB | ILE | 742 | 87.309 | 57.082 | 45.520 | 1.00 | 14.12 | B C |
| ATOM | 11746 | CG2 | ILE | 742 | 86.121 | 57.539 | 46.345 | 1.00 | 13.12 | B C |
| ATOM | 11747 | CG1 | ILE | 742 | 86.830 | 56.336 | 44.273 | 1.00 | 13.94 | B C |
| ATOM | 11748 | CD1 | ILE | 742 | 85.833 | 55.214 | 44.553 | 1.00 | 10.86 | B C |
| ATOM | 11749 | C | ILE | 742 | 88.892 | 58.827 | 46.335 | 1.00 | 15.89 | B C |
| ATOM | 11750 | O | ILE | 742 | 88.706 | 58.350 | 47.453 | 1.00 | 17.67 | B O |
| ATOM | 11751 | N | ALA | 743 | 89.737 | 59.828 | 46.108 | 1.00 | 16.48 | B N |
| ATOM | 11752 | CA | ALA | 743 | 90.570 | 60.381 | 47.157 | 1.00 | 15.34 | B C |
| ATOM | 11753 | CB | ALA | 743 | 91.985 | 60.508 | 46.651 | 1.00 | 16.86 | B C |
| ATOM | 11754 | C | ALA | 743 | 90.149 | 61.689 | 47.779 | 1.00 | 16.53 | B C |
| ATOM | 11755 | O | ALA | 743 | 90.809 | 62.153 | 48.711 | 1.00 | 18.69 | B O |
| ATOM | 11756 | N | SER | 744 | 89.088 | 62.312 | 47.287 | 1.00 | 14.28 | B N |
| ATOM | 11757 | CA | SER | 744 | 88.681 | 63.556 | 47.908 | 1.00 | 14.62 | B C |
| ATOM | 11758 | CB | SER | 744 | 87.369 | 64.059 | 47.321 | 1.00 | 16.50 | B C |
| ATOM | 11759 | OG | SER | 744 | 86.314 | 63.152 | 47.573 | 1.00 | 22.09 | B O |

| | | | | | | | | | | | |
|---|---|---|---|---|---|---|---|---|---|---|---|
| ATOM | 11760 | C | SER | 744 | 88.515 | 63.251 | 49.390 | 1.00 | 15.05 | B | C |
| ATOM | 11761 | O | SER | 744 | 88.136 | 62.147 | 49.770 | 1.00 | 17.03 | B | O |
| ATOM | 11762 | N | SER | 745 | 88.822 | 64.223 | 50.229 | 1.00 | 16.05 | B | N |
| ATOM | 11763 | CA | SER | 745 | 88.712 | 64.051 | 51.666 | 1.00 | 15.38 | B | C |
| ATOM | 11764 | CB | SER | 745 | 88.811 | 65.410 | 52.361 | 1.00 | 15.23 | B | C |
| ATOM | 11765 | OG | SER | 745 | 88.357 | 65.318 | 53.698 | 1.00 | 20.36 | B | O |
| ATOM | 11766 | C | SER | 745 | 87.427 | 63.360 | 52.103 | 1.00 | 14.58 | B | C |
| ATOM | 11767 | O | SER | 745 | 87.467 | 62.334 | 52.773 | 1.00 | 15.64 | B | O |
| ATOM | 11768 | N | THR | 746 | 86.287 | 63.925 | 51.728 | 1.00 | 13.39 | B | N |
| ATOM | 11769 | CA | THR | 746 | 85.009 | 63.355 | 52.121 | 1.00 | 12.46 | B | C |
| ATOM | 11770 | CB | THR | 746 | 83.836 | 64.299 | 51.755 | 1.00 | 13.02 | B | C |
| ATOM | 11771 | OG1 | THR | 746 | 83.858 | 64.579 | 50.347 | 1.00 | 12.13 | B | O |
| ATOM | 11772 | CG2 | THR | 746 | 83.929 | 65.599 | 52.547 | 1.00 | 6.36 | B | C |
| ATOM | 11773 | C | THR | 746 | 84.748 | 61.982 | 51.513 | 1.00 | 13.71 | B | C |
| ATOM | 11774 | O | THR | 746 | 84.382 | 61.045 | 52.215 | 1.00 | 13.77 | B | O |
| ATOM | 11775 | N | ALA | 747 | 84.948 | 61.852 | 50.211 | 1.00 | 15.70 | B | N |
| ATOM | 11776 | CA | ALA | 747 | 84.698 | 60.575 | 49.556 | 1.00 | 17.75 | B | C |
| ATOM | 11777 | CB | ALA | 747 | 84.918 | 60.698 | 48.047 | 1.00 | 18.85 | B | C |
| ATOM | 11778 | C | ALA | 747 | 85.579 | 59.482 | 50.133 | 1.00 | 16.94 | B | C |
| ATOM | 11779 | O | ALA | 747 | 85.136 | 58.344 | 50.314 | 1.00 | 17.92 | B | O |
| ATOM | 11780 | N | HIS | 748 | 86.828 | 59.829 | 50.418 | 1.00 | 15.98 | B | N |
| ATOM | 11781 | CA | HIS | 748 | 87.772 | 58.873 | 50.987 | 1.00 | 15.53 | B | C |
| ATOM | 11782 | CB | HIS | 748 | 89.130 | 59.547 | 51.194 | 1.00 | 14.50 | B | C |
| ATOM | 11783 | CG | HIS | 748 | 90.106 | 58.721 | 51.974 | 1.00 | 12.65 | B | C |
| ATOM | 11784 | CD2 | HIS | 748 | 90.772 | 58.979 | 53.124 | 1.00 | 12.46 | B | C |
| ATOM | 11785 | ND1 | HIS | 748 | 90.517 | 57.472 | 51.566 | 1.00 | 11.91 | B | N |
| ATOM | 11786 | CE1 | HIS | 748 | 91.397 | 56.998 | 52.430 | 1.00 | 12.20 | B | C |
| ATOM | 11787 | NE2 | HIS | 748 | 91.569 | 57.893 | 53.384 | 1.00 | 9.44 | B | N |
| ATOM | 11788 | C | HIS | 748 | 87.259 | 58.310 | 52.316 | 1.00 | 15.00 | B | C |
| ATOM | 11789 | O | HIS | 748 | 87.272 | 57.097 | 52.533 | 1.00 | 14.52 | B | O |
| ATOM | 11790 | N | GLN | 749 | 86.808 | 59.196 | 53.200 | 1.00 | 14.63 | B | N |
| ATOM | 11791 | CA | GLN | 749 | 86.283 | 58.780 | 54.496 | 1.00 | 15.23 | B | C |
| ATOM | 11792 | CB | GLN | 749 | 86.045 | 59.999 | 55.378 | 1.00 | 15.87 | B | C |
| ATOM | 11793 | CG | GLN | 749 | 87.314 | 60.722 | 55.740 | 1.00 | 22.62 | B | C |
| ATOM | 11794 | CD | GLN | 749 | 87.056 | 61.956 | 56.564 | 1.00 | 25.83 | B | C |
| ATOM | 11795 | OE1 | GLN | 749 | 86.511 | 61.873 | 57.664 | 1.00 | 29.51 | B | O |
| ATOM | 11796 | NE2 | GLN | 749 | 87.443 | 63.116 | 56.039 | 1.00 | 27.64 | B | N |
| ATOM | 11797 | C | GLN | 749 | 84.984 | 57.999 | 54.348 | 1.00 | 14.70 | B | C |
| ATOM | 11798 | O | GLN | 749 | 84.749 | 57.015 | 55.054 | 1.00 | 14.10 | B | O |
| ATOM | 11799 | N | HIS | 750 | 84.147 | 58.440 | 53.415 | 1.00 | 13.44 | B | N |
| ATOM | 11800 | CA | HIS | 750 | 82.865 | 57.808 | 53.174 | 1.00 | 12.63 | B | C |
| ATOM | 11801 | CB | HIS | 750 | 82.021 | 58.685 | 52.247 | 1.00 | 13.59 | B | C |
| ATOM | 11802 | CG | HIS | 750 | 80.587 | 58.272 | 52.176 | 1.00 | 12.41 | B | C |
| ATOM | 11803 | CD2 | HIS | 750 | 79.475 | 58.823 | 52.713 | 1.00 | 13.33 | B | C |
| ATOM | 11804 | ND1 | HIS | 750 | 80.175 | 57.128 | 51.530 | 1.00 | 12.98 | B | N |
| ATOM | 11805 | CE1 | HIS | 750 | 78.869 | 56.992 | 51.673 | 1.00 | 14.44 | B | C |
| ATOM | 11806 | NE2 | HIS | 750 | 78.419 | 58.007 | 52.386 | 1.00 | 13.43 | B | N |
| ATOM | 11807 | C | HIS | 750 | 82.985 | 56.404 | 52.595 | 1.00 | 13.84 | B | C |
| ATOM | 11808 | O | HIS | 750 | 82.265 | 55.499 | 53.011 | 1.00 | 14.53 | B | O |

| | | | | | | | | | | |
|---|---|---|---|---|---|---|---|---|---|---|
| ATOM | 11809 | N | ILE | 751 | 83.885 | 56.203 | 51.638 | 1.00 | 13.03 | B N |
| ATOM | 11810 | CA | ILE | 751 | 84.013 | 54.875 | 51.077 | 1.00 | 12.47 | B C |
| ATOM | 11811 | CB | ILE | 751 | 84.927 | 54.838 | 49.814 | 1.00 | 13.01 | B C |
| ATOM | 11812 | CG2 | ILE | 751 | 86.326 | 55.361 | 50.137 | 1.00 | 12.55 | B C |
| ATOM | 11813 | CG1 | ILE | 751 | 84.999 | 53.395 | 49.287 | 1.00 | 12.09 | B C |
| ATOM | 11814 | CD1 | ILE | 751 | 85.677 | 53.240 | 47.939 | 1.00 | 11.16 | B C |
| ATOM | 11815 | C | ILE | 751 | 84.546 | 53.893 | 52.111 | 1.00 | 12.65 | B C |
| ATOM | 11816 | O | ILE | 751 | 84.025 | 52.790 | 52.241 | 1.00 | 12.49 | B O |
| ATOM | 11817 | N | TYR | 752 | 85.575 | 54.284 | 52.858 | 1.00 | 13.74 | B N |
| ATOM | 11818 | CA | TYR | 752 | 86.137 | 53.364 | 53.850 | 1.00 | 14.04 | B C |
| ATOM | 11819 | CB | TYR | 752 | 87.486 | 53.883 | 54.379 | 1.00 | 11.26 | B C |
| ATOM | 11820 | CG | TYR | 752 | 88.628 | 53.468 | 53.472 | 1.00 | 9.86 | B C |
| ATOM | 11821 | CD1 | TYR | 752 | 89.037 | 52.132 | 53.408 | 1.00 | 10.53 | B C |
| ATOM | 11822 | CE1 | TYR | 752 | 90.015 | 51.712 | 52.502 | 1.00 | 9.48 | B C |
| ATOM | 11823 | CD2 | TYR | 752 | 89.235 | 54.383 | 52.608 | 1.00 | 9.66 | B C |
| ATOM | 11824 | CE2 | TYR | 752 | 90.219 | 53.974 | 51.692 | 1.00 | 8.36 | B C |
| ATOM | 11825 | CZ | TYR | 752 | 90.597 | 52.639 | 51.646 | 1.00 | 9.94 | B C |
| ATOM | 11826 | OH | TYR | 752 | 91.536 | 52.223 | 50.739 | 1.00 | 10.79 | B O |
| ATOM | 11827 | C | TYR | 752 | 85.170 | 53.067 | 54.973 | 1.00 | 13.42 | B C |
| ATOM | 11828 | O | TYR | 752 | 85.176 | 51.972 | 55.524 | 1.00 | 13.56 | B O |
| ATOM | 11829 | N | THR | 753 | 84.323 | 54.040 | 55.295 | 1.00 | 14.48 | B N |
| ATOM | 11830 | CA | THR | 753 | 83.316 | 53.864 | 56.330 | 1.00 | 14.27 | B C |
| ATOM | 11831 | CB | THR | 753 | 82.582 | 55.187 | 56.618 | 1.00 | 13.68 | B C |
| ATOM | 11832 | OG1 | THR | 753 | 83.519 | 56.136 | 57.130 | 1.00 | 17.48 | B O |
| ATOM | 11833 | CG2 | THR | 753 | 81.459 | 54.987 | 57.629 | 1.00 | 7.20 | B C |
| ATOM | 11834 | C | THR | 753 | 82.301 | 52.849 | 55.815 | 1.00 | 16.15 | B C |
| ATOM | 11835 | O | THR | 753 | 81.958 | 51.894 | 56.508 | 1.00 | 18.93 | B O |
| ATOM | 11836 | N | HIS | 754 | 81.830 | 53.056 | 54.589 | 1.00 | 15.38 | B N |
| ATOM | 11837 | CA | HIS | 754 | 80.840 | 52.163 | 53.999 | 1.00 | 16.06 | B C |
| ATOM | 11838 | CB | HIS | 754 | 80.424 | 52.666 | 52.620 | 1.00 | 15.26 | B C |
| ATOM | 11839 | CG | HIS | 754 | 79.109 | 52.128 | 52.162 | 1.00 | 16.39 | B C |
| ATOM | 11840 | CD2 | HIS | 754 | 78.779 | 51.362 | 51.095 | 1.00 | 15.75 | B C |
| ATOM | 11841 | ND1 | HIS | 754 | 77.936 | 52.353 | 52.850 | 1.00 | 17.30 | B N |
| ATOM | 11842 | CE1 | HIS | 754 | 76.940 | 51.750 | 52.228 | 1.00 | 15.86 | B C |
| ATOM | 11843 | NE2 | HIS | 754 | 77.425 | 51.141 | 51.161 | 1.00 | 17.13 | B N |
| ATOM | 11844 | C | HIS | 754 | 81.349 | 50.731 | 53.886 | 1.00 | 16.28 | B C |
| ATOM | 11845 | O | HIS | 754 | 80.639 | 49.788 | 54.238 | 1.00 | 17.31 | B O |
| ATOM | 11846 | N | MET | 755 | 82.571 | 50.564 | 53.383 | 1.00 | 15.98 | B N |
| ATOM | 11847 | CA | MET | 755 | 83.158 | 49.234 | 53.250 | 1.00 | 16.05 | B C |
| ATOM | 11848 | CB | MET | 755 | 84.532 | 49.300 | 52.573 | 1.00 | 15.41 | B C |
| ATOM | 11849 | CG | MET | 755 | 84.491 | 49.542 | 51.081 | 1.00 | 17.11 | B C |
| ATOM | 11850 | SD | MET | 755 | 86.112 | 49.308 | 50.322 | 1.00 | 18.41 | B S |
| ATOM | 11851 | CE | MET | 755 | 86.882 | 50.855 | 50.742 | 1.00 | 20.74 | B C |
| ATOM | 11852 | C | MET | 755 | 83.309 | 48.582 | 54.623 | 1.00 | 15.38 | B C |
| ATOM | 11853 | O | MET | 755 | 83.080 | 47.390 | 54.783 | 1.00 | 13.30 | B O |
| ATOM | 11854 | N | SER | 756 | 83.701 | 49.371 | 55.614 | 1.00 | 15.36 | B N |
| ATOM | 11855 | CA | SER | 756 | 83.854 | 48.833 | 56.946 | 1.00 | 18.52 | B C |
| ATOM | 11856 | CB | SER | 756 | 84.413 | 49.903 | 57.878 | 1.00 | 18.88 | B C |
| ATOM | 11857 | OG | SER | 756 | 85.723 | 50.257 | 57.477 | 1.00 | 18.74 | B O |

| ATOM | 11858 | C | SER | 756 | 82.515 | 48.282 | 57.462 | 1.00 | 19.14 | B | C |
|---|---|---|---|---|---|---|---|---|---|---|---|
| ATOM | 11859 | O | SER | 756 | 82.464 | 47.158 | 57.975 | 1.00 | 19.94 | B | O |
| ATOM | 11860 | N | HIS | 757 | 81.435 | 49.048 | 57.324 | 1.00 | 17.68 | B | N |
| ATOM | 11861 | CA | HIS | 757 | 80.134 | 48.549 | 57.770 | 1.00 | 19.20 | B | C |
| ATOM | 11862 | CB | HIS | 757 | 78.990 | 49.486 | 57.371 | 1.00 | 18.83 | B | C |
| ATOM | 11863 | CG | HIS | 757 | 78.983 | 50.794 | 58.095 | 1.00 | 21.13 | B | C |
| ATOM | 11864 | CD2 | HIS | 757 | 78.697 | 52.046 | 57.666 | 1.00 | 22.10 | B | C |
| ATOM | 11865 | ND1 | HIS | 757 | 79.230 | 50.899 | 59.447 | 1.00 | 22.62 | B | N |
| ATOM | 11866 | CE1 | HIS | 757 | 79.096 | 52.159 | 59.820 | 1.00 | 23.60 | B | C |
| ATOM | 11867 | NE2 | HIS | 757 | 78.772 | 52.876 | 58.758 | 1.00 | 24.81 | B | N |
| ATOM | 11868 | C | HIS | 757 | 79.866 | 47.190 | 57.120 | 1.00 | 17.94 | B | C |
| ATOM | 11869 | O | HIS | 757 | 79.416 | 46.251 | 57.772 | 1.00 | 16.58 | B | O |
| ATOM | 11870 | N | PHE | 758 | 80.158 | 47.103 | 55.828 | 1.00 | 17.93 | B | N |
| ATOM | 11871 | CA | PHE | 758 | 79.926 | 45.888 | 55.052 | 1.00 | 18.80 | B | C |
| ATOM | 11872 | CB | PHE | 758 | 80.286 | 46.138 | 53.586 | 1.00 | 15.70 | B | C |
| ATOM | 11873 | CG | PHE | 758 | 79.952 | 44.997 | 52.677 | 1.00 | 10.77 | B | C |
| ATOM | 11874 | CD1 | PHE | 758 | 78.646 | 44.790 | 52.251 | 1.00 | 8.39 | B | C |
| ATOM | 11875 | CD2 | PHE | 758 | 80.941 | 44.120 | 52.254 | 1.00 | 6.53 | B | C |
| ATOM | 11876 | CE1 | PHE | 758 | 78.334 | 43.716 | 51.409 | 1.00 | 9.32 | B | C |
| ATOM | 11877 | CE2 | PHE | 758 | 80.638 | 43.045 | 51.417 | 1.00 | 6.01 | B | C |
| ATOM | 11878 | CZ | PHE | 758 | 79.340 | 42.836 | 50.991 | 1.00 | 2.78 | B | C |
| ATOM | 11879 | C | PHE | 758 | 80.697 | 44.674 | 55.560 | 1.00 | 20.68 | B | C |
| ATOM | 11880 | O | PHE | 758 | 80.110 | 43.631 | 55.851 | 1.00 | 21.00 | B | O |
| ATOM | 11881 | N | ILE | 759 | 82.014 | 44.811 | 55.654 | 1.00 | 23.57 | B | N |
| ATOM | 11882 | CA | ILE | 759 | 82.858 | 43.722 | 56.117 | 1.00 | 25.05 | B | C |
| ATOM | 11883 | CB | ILE | 759 | 84.364 | 44.129 | 56.069 | 1.00 | 25.44 | B | C |
| ATOM | 11884 | CG2 | ILE | 759 | 84.994 | 44.041 | 57.437 | 1.00 | 28.98 | B | C |
| ATOM | 11885 | CG1 | ILE | 759 | 85.128 | 43.189 | 55.142 | 1.00 | 26.52 | B | C |
| ATOM | 11886 | CD1 | ILE | 759 | 84.706 | 43.263 | 53.704 | 1.00 | 26.84 | B | C |
| ATOM | 11887 | C | ILE | 759 | 82.441 | 43.318 | 57.529 | 1.00 | 25.34 | B | C |
| ATOM | 11888 | O | ILE | 759 | 82.420 | 42.136 | 57.866 | 1.00 | 25.50 | B | O |
| ATOM | 11889 | N | LYS | 760 | 82.081 | 44.299 | 58.346 | 1.00 | 26.11 | B | N |
| ATOM | 11890 | CA | LYS | 760 | 81.671 | 44.012 | 59.713 | 1.00 | 26.62 | B | C |
| ATOM | 11891 | CB | LYS | 760 | 81.444 | 45.300 | 60.487 | 1.00 | 26.43 | B | C |
| ATOM | 11892 | CG | LYS | 760 | 82.178 | 45.298 | 61.792 | 1.00 | 29.00 | B | C |
| ATOM | 11893 | CD | LYS | 760 | 83.666 | 45.271 | 61.537 | 1.00 | 28.96 | B | C |
| ATOM | 11894 | CE | LYS | 760 | 84.139 | 46.665 | 61.250 | 1.00 | 30.01 | B | C |
| ATOM | 11895 | NZ | LYS | 760 | 83.776 | 47.523 | 62.420 | 1.00 | 31.29 | B | N |
| ATOM | 11896 | C | LYS | 760 | 80.406 | 43.179 | 59.740 | 1.00 | 27.08 | B | C |
| ATOM | 11897 | O | LYS | 760 | 80.312 | 42.200 | 60.473 | 1.00 | 28.46 | B | O |
| ATOM | 11898 | N | GLN | 761 | 79.431 | 43.581 | 58.940 | 1.00 | 28.08 | B | N |
| ATOM | 11899 | CA | GLN | 761 | 78.170 | 42.866 | 58.844 | 1.00 | 29.69 | B | C |
| ATOM | 11900 | CB | GLN | 761 | 77.213 | 43.652 | 57.942 | 1.00 | 31.26 | B | C |
| ATOM | 11901 | CG | GLN | 761 | 76.072 | 42.855 | 57.347 | 1.00 | 34.99 | B | C |
| ATOM | 11902 | CD | GLN | 761 | 76.477 | 42.140 | 56.072 | 1.00 | 37.85 | B | C |
| ATOM | 11903 | OE1 | GLN | 761 | 76.800 | 42.775 | 55.062 | 1.00 | 37.29 | B | O |
| ATOM | 11904 | NE2 | GLN | 761 | 76.464 | 40.808 | 56.112 | 1.00 | 39.80 | B | N |
| ATOM | 11905 | C | GLN | 761 | 78.401 | 41.456 | 58.295 | 1.00 | 30.00 | B | C |
| ATOM | 11906 | O | GLN | 761 | 77.791 | 40.494 | 58.753 | 1.00 | 31.14 | B | O |

| | | | | | | | | | | |
|---|---|---|---|---|---|---|---|---|---|---|
| ATOM | 11907 | N | CYS | 762 | 79.291 | 41.333 | 57.320 | 1.00 | 29.71 | B N |
| ATOM | 11908 | CA | CYS | 762 | 79.588 | 40.035 | 56.731 | 1.00 | 30.30 | B C |
| ATOM | 11909 | C | CYS | 762 | 80.275 | 39.077 | 57.712 | 1.00 | 30.21 | B C |
| ATOM | 11910 | O | CYS | 762 | 80.153 | 37.860 | 57.578 | 1.00 | 29.67 | B O |
| ATOM | 11911 | CB | CYS | 762 | 80.458 | 40.212 | 55.474 | 1.00 | 30.01 | B C |
| ATOM | 11912 | SG | CYS | 762 | 81.198 | 38.665 | 54.849 | 1.00 | 33.72 | B S |
| ATOM | 11913 | N | PHE | 763 | 80.986 | 39.618 | 58.698 | 1.00 | 30.53 | B N |
| ATOM | 11914 | CA | PHE | 763 | 81.694 | 38.783 | 59.664 | 1.00 | 31.28 | B C |
| ATOM | 11915 | CB | PHE | 763 | 83.112 | 39.310 | 59.885 | 1.00 | 29.29 | B C |
| ATOM | 11916 | CG | PHE | 763 | 84.052 | 39.057 | 58.736 | 1.00 | 27.21 | B C |
| ATOM | 11917 | CD1 | PHE | 763 | 83.663 | 38.280 | 57.650 | 1.00 | 26.19 | B C |
| ATOM | 11918 | CD2 | PHE | 763 | 85.348 | 39.572 | 58.762 | 1.00 | 26.38 | B C |
| ATOM | 11919 | CE1 | PHE | 763 | 84.552 | 38.015 | 56.605 | 1.00 | 27.91 | B C |
| ATOM | 11920 | CE2 | PHE | 763 | 86.249 | 39.316 | 57.727 | 1.00 | 27.36 | B C |
| ATOM | 11921 | CZ | PHE | 763 | 85.851 | 38.533 | 56.643 | 1.00 | 27.55 | B C |
| ATOM | 11922 | C | PHE | 763 | 80.994 | 38.666 | 61.011 | 1.00 | 34.52 | B C |
| ATOM | 11923 | O | PHE | 763 | 81.473 | 37.970 | 61.908 | 1.00 | 32.78 | B O |
| ATOM | 11924 | N | SER | 764 | 79.862 | 39.346 | 61.151 | 1.00 | 39.49 | B N |
| ATOM | 11925 | CA | SER | 764 | 79.099 | 39.319 | 62.393 | 1.00 | 43.60 | B C |
| ATOM | 11926 | CB | SER | 764 | 77.860 | 40.199 | 62.273 | 1.00 | 44.56 | B C |
| ATOM | 11927 | OG | SER | 764 | 78.218 | 41.528 | 61.948 | 1.00 | 50.05 | B O |
| ATOM | 11928 | C | SER | 764 | 78.668 | 37.909 | 62.746 | 1.00 | 45.96 | B C |
| ATOM | 11929 | O | SER | 764 | 77.885 | 37.289 | 62.028 | 1.00 | 45.86 | B O |
| ATOM | 11930 | N | LEU | 765 | 79.189 | 37.404 | 63.856 | 1.00 | 49.22 | B N |
| ATOM | 11931 | CA | LEU | 765 | 78.845 | 36.070 | 64.317 | 1.00 | 52.03 | B C |
| ATOM | 11932 | CB | LEU | 765 | 79.754 | 35.678 | 65.481 | 1.00 | 52.53 | B C |
| ATOM | 11933 | CG | LEU | 765 | 81.234 | 35.558 | 65.115 | 1.00 | 52.85 | B C |
| ATOM | 11934 | CD1 | LEU | 765 | 82.074 | 35.452 | 66.376 | 1.00 | 53.55 | B C |
| ATOM | 11935 | CD2 | LEU | 765 | 81.435 | 34.344 | 64.214 | 1.00 | 52.54 | B C |
| ATOM | 11936 | C | LEU | 765 | 77.383 | 36.069 | 64.761 | 1.00 | 54.34 | B C |
| ATOM | 11937 | O | LEU | 765 | 77.019 | 36.721 | 65.743 | 1.00 | 53.63 | B O |
| ATOM | 11938 | N | PRO | 766 | 76.523 | 35.340 | 64.031 | 1.00 | 56.38 | B N |
| ATOM | 11939 | CD | PRO | 766 | 76.833 | 34.541 | 62.831 | 1.00 | 56.67 | B C |
| ATOM | 11940 | CA | PRO | 766 | 75.095 | 35.263 | 64.356 | 1.00 | 57.95 | B C |
| ATOM | 11941 | CB | PRO | 766 | 74.509 | 34.544 | 63.141 | 1.00 | 58.24 | B C |
| ATOM | 11942 | CG | PRO | 766 | 75.626 | 33.633 | 62.728 | 1.00 | 57.40 | B C |
| ATOM | 11943 | C | PRO | 766 | 74.805 | 34.523 | 65.664 | 1.00 | 59.30 | B C |
| ATOM | 11944 | O | PRO | 766 | 73.791 | 33.789 | 65.711 | 1.00 | 60.29 | B O |
| ATOM | 11945 | OXT | PRO | 766 | 75.584 | 34.704 | 66.627 | 1.00 | 59.84 | B O |
| TER | 11946 | | PRO | 766 | | | | | | B |
| ATOM | 11947 | C1 | NAG | 901 | 25.105 | 38.477 | 14.927 | 1.00 | 45.03 | E C |
| ATOM | 11948 | C2 | NAG | 901 | 26.266 | 38.501 | 13.922 | 1.00 | 45.16 | E C |
| ATOM | 11949 | N2 | NAG | 901 | 27.447 | 39.002 | 14.595 | 1.00 | 44.20 | E N |
| ATOM | 11950 | C7 | NAG | 901 | 28.662 | 38.702 | 14.153 | 1.00 | 43.63 | E C |
| ATOM | 11951 | O7 | NAG | 901 | 29.050 | 37.546 | 13.997 | 1.00 | 44.60 | E O |
| ATOM | 11952 | C8 | NAG | 901 | 29.588 | 39.864 | 13.838 | 1.00 | 43.83 | E C |
| ATOM | 11953 | C3 | NAG | 901 | 25.942 | 39.385 | 12.713 | 1.00 | 46.38 | E C |
| ATOM | 11954 | O3 | NAG | 901 | 26.953 | 39.235 | 11.728 | 1.00 | 49.49 | E O |
| ATOM | 11955 | C4 | NAG | 901 | 24.591 | 38.987 | 12.124 | 1.00 | 47.76 | E C |

| ATOM | 11956 | O4 | NAG | 901 | 24.256 | 39.836 | 11.036 | 1.00 | 49.01 | E | O |
| ATOM | 11957 | C5 | NAG | 901 | 23.545 | 39.104 | 13.219 | 1.00 | 49.11 | E | C |
| ATOM | 11958 | O5 | NAG | 901 | 23.858 | 38.173 | 14.276 | 1.00 | 47.99 | E | O |
| ATOM | 11959 | C6 | NAG | 901 | 22.143 | 38.804 | 12.731 | 1.00 | 50.99 | E | C |
| ATOM | 11960 | O6 | NAG | 901 | 21.706 | 39.781 | 11.793 | 1.00 | 53.28 | E | O |
| ATOM | 11961 | C1 | NAG | 902 | 34.526 | 67.450 | 4.248 | 1.00 | 29.71 | E | C |
| ATOM | 11962 | C2 | NAG | 902 | 33.682 | 66.990 | 3.051 | 1.00 | 31.02 | E | C |
| ATOM | 11963 | N2 | NAG | 902 | 34.077 | 65.638 | 2.692 | 1.00 | 35.02 | E | N |
| ATOM | 11964 | C7 | NAG | 902 | 33.181 | 64.660 | 2.610 | 1.00 | 35.78 | E | C |
| ATOM | 11965 | O7 | NAG | 902 | 32.213 | 64.701 | 1.852 | 1.00 | 37.59 | E | O |
| ATOM | 11966 | C8 | NAG | 902 | 33.392 | 63.449 | 3.503 | 1.00 | 37.18 | E | C |
| ATOM | 11967 | C3 | NAG | 902 | 33.927 | 67.915 | 1.848 | 1.00 | 31.67 | E | C |
| ATOM | 11968 | O3 | NAG | 902 | 33.032 | 67.583 | 0.794 | 1.00 | 34.76 | E | O |
| ATOM | 11969 | C4 | NAG | 902 | 33.753 | 69.386 | 2.248 | 1.00 | 31.76 | E | C |
| ATOM | 11970 | O4 | NAG | 902 | 34.037 | 70.238 | 1.144 | 1.00 | 30.03 | E | O |
| ATOM | 11971 | C5 | NAG | 902 | 34.701 | 69.674 | 3.412 | 1.00 | 30.64 | E | C |
| ATOM | 11972 | O5 | NAG | 902 | 34.332 | 68.844 | 4.526 | 1.00 | 30.02 | E | O |
| ATOM | 11973 | C6 | NAG | 902 | 34.720 | 71.114 | 3.892 | 1.00 | 30.81 | E | C |
| ATOM | 11974 | O6 | NAG | 902 | 33.457 | 71.512 | 4.409 | 1.00 | 34.26 | E | O |
| ATOM | 11975 | C1 | NAG | 903 | 64.239 | 77.734 | 14.341 | 1.00 | 27.20 | E | C |
| ATOM | 11976 | C2 | NAG | 903 | 63.984 | 78.203 | 12.917 | 1.00 | 26.96 | E | C |
| ATOM | 11977 | N2 | NAG | 903 | 63.551 | 77.080 | 12.116 | 1.00 | 25.19 | E | N |
| ATOM | 11978 | C7 | NAG | 903 | 62.349 | 77.076 | 11.551 | 1.00 | 24.99 | E | C |
| ATOM | 11979 | O7 | NAG | 903 | 62.121 | 76.492 | 10.490 | 1.00 | 25.88 | E | O |
| ATOM | 11980 | C8 | NAG | 903 | 61.222 | 77.800 | 12.272 | 1.00 | 23.55 | E | C |
| ATOM | 11981 | C3 | NAG | 903 | 65.253 | 78.817 | 12.325 | 1.00 | 29.00 | E | C |
| ATOM | 11982 | O3 | NAG | 903 | 64.947 | 79.400 | 11.066 | 1.00 | 29.62 | E | O |
| ATOM | 11983 | C4 | NAG | 903 | 65.814 | 79.900 | 13.248 | 1.00 | 30.83 | E | C |
| ATOM | 11984 | O4 | NAG | 903 | 67.092 | 80.316 | 12.778 | 1.00 | 31.15 | E | O |
| ATOM | 11985 | C5 | NAG | 903 | 65.929 | 79.389 | 14.690 | 1.00 | 30.71 | E | C |
| ATOM | 11986 | O5 | NAG | 903 | 64.669 | 78.842 | 15.133 | 1.00 | 30.11 | E | O |
| ATOM | 11987 | C6 | NAG | 903 | 66.276 | 80.502 | 15.659 | 1.00 | 32.26 | E | C |
| ATOM | 11988 | O6 | NAG | 903 | 65.937 | 80.144 | 16.993 | 1.00 | 35.52 | E | O |
| ATOM | 11989 | C1 | NAG | 904 | 56.857 | 73.229 | -0.933 | 1.00 | 21.65 | E | C |
| ATOM | 11990 | C2 | NAG | 904 | 58.289 | 73.099 | -1.475 | 1.00 | 21.59 | E | C |
| ATOM | 11991 | N2 | NAG | 904 | 58.532 | 71.758 | -1.961 | 1.00 | 21.40 | E | N |
| ATOM | 11992 | C7 | NAG | 904 | 58.567 | 71.523 | -3.267 | 1.00 | 20.76 | E | C |
| ATOM | 11993 | O7 | NAG | 904 | 58.745 | 72.412 | -4.104 | 1.00 | 18.55 | E | O |
| ATOM | 11994 | C8 | NAG | 904 | 58.371 | 70.080 | -3.709 | 1.00 | 20.74 | E | C |
| ATOM | 11995 | C3 | NAG | 904 | 59.325 | 73.441 | -0.417 | 1.00 | 22.32 | E | C |
| ATOM | 11996 | O3 | NAG | 904 | 60.611 | 73.413 | -1.009 | 1.00 | 22.81 | E | O |
| ATOM | 11997 | C4 | NAG | 904 | 59.022 | 74.832 | 0.129 | 1.00 | 22.85 | E | C |
| ATOM | 11998 | O4 | NAG | 904 | 59.986 | 75.217 | 1.101 | 1.00 | 24.62 | E | O |
| ATOM | 11999 | C5 | NAG | 904 | 57.634 | 74.781 | 0.737 | 1.00 | 22.86 | E | C |
| ATOM | 12000 | O5 | NAG | 904 | 56.672 | 74.506 | -0.297 | 1.00 | 21.95 | E | O |
| ATOM | 12001 | C6 | NAG | 904 | 57.232 | 76.083 | 1.385 | 1.00 | 24.39 | E | C |
| ATOM | 12002 | O6 | NAG | 904 | 57.196 | 77.133 | 0.430 | 1.00 | 31.81 | E | O |
| ATOM | 12003 | C1 | NAG | 905 | 49.743 | 85.075 | 37.084 | 1.00 | 31.93 | E | C |
| ATOM | 12004 | C2 | NAG | 905 | 49.010 | 86.230 | 37.756 | 1.00 | 33.35 | E | C |

FIG. 4-246    (Continued)

| | | | | | | | | | | |
|---|---|---|---|---|---|---|---|---|---|---|
| ATOM | 12005 | N2 | NAG | 905 | 47.823 | 86.586 | 37.012 | 1.00 | 34.30 | E N |
| ATOM | 12006 | C7 | NAG | 905 | 46.648 | 86.099 | 37.395 | 1.00 | 35.18 | E C |
| ATOM | 12007 | O7 | NAG | 905 | 46.362 | 85.888 | 38.578 | 1.00 | 36.47 | E O |
| ATOM | 12008 | C8 | NAG | 905 | 45.640 | 85.786 | 36.303 | 1.00 | 37.15 | E C |
| ATOM | 12009 | C3 | NAG | 905 | 49.951 | 87.416 | 37.924 | 1.00 | 33.45 | E C |
| ATOM | 12010 | O3 | NAG | 905 | 49.256 | 88.512 | 38.495 | 1.00 | 33.93 | E O |
| ATOM | 12011 | C4 | NAG | 905 | 51.043 | 86.945 | 38.863 | 1.00 | 35.37 | E C |
| ATOM | 12012 | O4 | NAG | 905 | 51.934 | 88.009 | 39.193 | 1.00 | 35.45 | E O |
| ATOM | 12013 | C5 | NAG | 905 | 51.794 | 85.773 | 38.215 | 1.00 | 34.39 | E C |
| ATOM | 12014 | O5 | NAG | 905 | 50.878 | 84.684 | 37.887 | 1.00 | 32.56 | E O |
| ATOM | 12015 | C6 | NAG | 905 | 52.787 | 85.212 | 39.214 | 1.00 | 36.29 | E C |
| ATOM | 12016 | O6 | NAG | 905 | 52.150 | 84.936 | 40.459 | 1.00 | 35.52 | E O |
| ATOM | 12017 | C1 | NAG | 906 | 128.439 | 74.792 | 56.371 | 1.00 | 36.45 | E C |
| ATOM | 12018 | C2 | NAG | 906 | 127.977 | 75.856 | 55.375 | 1.00 | 37.00 | E C |
| ATOM | 12019 | N2 | NAG | 906 | 126.880 | 75.335 | 54.586 | 1.00 | 37.17 | E N |
| ATOM | 12020 | C7 | NAG | 906 | 125.666 | 75.871 | 54.690 | 1.00 | 38.41 | E C |
| ATOM | 12021 | O7 | NAG | 906 | 125.264 | 76.427 | 55.714 | 1.00 | 38.52 | E O |
| ATOM | 12022 | C8 | NAG | 906 | 124.760 | 75.782 | 53.471 | 1.00 | 36.25 | E C |
| ATOM | 12023 | C3 | NAG | 906 | 129.133 | 76.265 | 54.465 | 1.00 | 38.66 | E C |
| ATOM | 12024 | O3 | NAG | 906 | 128.723 | 77.334 | 53.625 | 1.00 | 39.59 | E O |
| ATOM | 12025 | C4 | NAG | 906 | 130.331 | 76.704 | 55.308 | 1.00 | 39.58 | E C |
| ATOM | 12026 | O4 | NAG | 906 | 131.439 | 76.975 | 54.460 | 1.00 | 41.48 | E O |
| ATOM | 12027 | C5 | NAG | 906 | 130.699 | 75.602 | 56.312 | 1.00 | 40.24 | E C |
| ATOM | 12028 | O5 | NAG | 906 | 129.556 | 75.268 | 57.133 | 1.00 | 38.27 | E O |
| ATOM | 12029 | C6 | NAG | 906 | 131.811 | 76.032 | 57.255 | 1.00 | 41.89 | E C |
| ATOM | 12030 | O6 | NAG | 906 | 131.906 | 75.162 | 58.378 | 1.00 | 46.70 | E O |
| ATOM | 12031 | C1 | NAG | 907 | 126.770 | 72.294 | 25.405 | 1.00 | 33.54 | E C |
| ATOM | 12032 | C2 | NAG | 907 | 127.763 | 73.454 | 25.478 | 1.00 | 35.73 | E C |
| ATOM | 12033 | N2 | NAG | 907 | 127.401 | 74.367 | 26.540 | 1.00 | 37.97 | E N |
| ATOM | 12034 | C7 | NAG | 907 | 128.139 | 74.400 | 27.644 | 1.00 | 41.34 | E C |
| ATOM | 12035 | O7 | NAG | 907 | 128.715 | 73.403 | 28.094 | 1.00 | 42.96 | E O |
| ATOM | 12036 | C8 | NAG | 907 | 128.278 | 75.739 | 28.352 | 1.00 | 42.60 | E C |
| ATOM | 12037 | C3 | NAG | 907 | 127.776 | 74.167 | 24.126 | 1.00 | 36.63 | E C |
| ATOM | 12038 | O3 | NAG | 907 | 128.692 | 75.253 | 24.154 | 1.00 | 38.28 | E O |
| ATOM | 12039 | C4 | NAG | 907 | 128.171 | 73.148 | 23.047 | 1.00 | 35.89 | E C |
| ATOM | 12040 | O4 | NAG | 907 | 128.191 | 73.758 | 21.763 | 1.00 | 35.82 | E O |
| ATOM | 12041 | C5 | NAG | 907 | 127.161 | 71.995 | 23.075 | 1.00 | 35.12 | E C |
| ATOM | 12042 | O5 | NAG | 907 | 127.166 | 71.377 | 24.380 | 1.00 | 32.61 | E O |
| ATOM | 12043 | C6 | NAG | 907 | 127.444 | 70.913 | 22.057 | 1.00 | 36.17 | E C |
| ATOM | 12044 | O6 | NAG | 907 | 128.515 | 70.083 | 22.478 | 1.00 | 38.44 | E O |
| ATOM | 12045 | C1 | NAG | 908 | 97.567 | 64.129 | 12.586 | 1.00 | 33.83 | E C |
| ATOM | 12046 | C2 | NAG | 908 | 98.226 | 65.101 | 11.602 | 1.00 | 36.51 | E C |
| ATOM | 12047 | N2 | NAG | 908 | 98.466 | 66.365 | 12.269 | 1.00 | 40.33 | E N |
| ATOM | 12048 | C7 | NAG | 908 | 99.645 | 66.962 | 12.148 | 1.00 | 43.03 | E C |
| ATOM | 12049 | O7 | NAG | 908 | 100.703 | 66.434 | 12.500 | 1.00 | 45.77 | E O |
| ATOM | 12050 | C8 | NAG | 908 | 99.655 | 68.349 | 11.529 | 1.00 | 43.86 | E C |
| ATOM | 12051 | C3 | NAG | 908 | 97.328 | 65.325 | 10.380 | 1.00 | 37.11 | E C |
| ATOM | 12052 | O3 | NAG | 908 | 98.013 | 66.122 | 9.426 | 1.00 | 37.35 | E O |
| ATOM | 12053 | C4 | NAG | 908 | 96.945 | 63.975 | 9.760 | 1.00 | 36.97 | E C |

FIG. 4-247 (Continued)

| | | | | | | | | | | | |
|---|---|---|---|---|---|---|---|---|---|---|---|
| ATOM | 12054 | O4 | NAG | 908 | 96.049 | 64.165 | 8.668 | 1.00 | 36.08 | E | O |
| ATOM | 12055 | C5 | NAG | 908 | 96.291 | 63.106 | 10.841 | 1.00 | 35.43 | E | C |
| ATOM | 12056 | O5 | NAG | 908 | 97.215 | 62.906 | 11.930 | 1.00 | 33.34 | E | O |
| ATOM | 12057 | C6 | NAG | 908 | 95.890 | 61.735 | 10.341 | 1.00 | 36.72 | E | C |
| ATOM | 12058 | O6 | NAG | 908 | 95.085 | 61.057 | 11.296 | 1.00 | 38.75 | E | O |
| ATOM | 12059 | C1 | NAG | 909 | 106.501 | 80.407 | 11.987 | 1.00 | 55.21 | E | C |
| ATOM | 12060 | C2 | NAG | 909 | 105.627 | 81.255 | 11.048 | 1.00 | 55.75 | E | C |
| ATOM | 12061 | N2 | NAG | 909 | 105.631 | 82.658 | 11.427 | 1.00 | 55.80 | E | N |
| ATOM | 12062 | C7 | NAG | 909 | 106.748 | 83.259 | 11.828 | 1.00 | 56.83 | E | C |
| ATOM | 12063 | O7 | NAG | 909 | 107.685 | 83.526 | 11.066 | 1.00 | 55.16 | E | O |
| ATOM | 12064 | C8 | NAG | 909 | 106.838 | 83.620 | 13.305 | 1.00 | 56.25 | E | C |
| ATOM | 12065 | C3 | NAG | 909 | 104.195 | 80.724 | 11.087 | 1.00 | 56.36 | E | C |
| ATOM | 12066 | O3 | NAG | 909 | 103.396 | 81.452 | 10.166 | 1.00 | 58.58 | E | O |
| ATOM | 12067 | C4 | NAG | 909 | 104.176 | 79.229 | 10.744 | 1.00 | 56.19 | E | C |
| ATOM | 12068 | O4 | NAG | 909 | 102.855 | 78.716 | 10.862 | 1.00 | 55.29 | E | O |
| ATOM | 12069 | C5 | NAG | 909 | 105.117 | 78.478 | 11.692 | 1.00 | 56.24 | E | C |
| ATOM | 12070 | O5 | NAG | 909 | 106.446 | 79.028 | 11.600 | 1.00 | 56.65 | E | O |
| ATOM | 12071 | C6 | NAG | 909 | 105.230 | 76.996 | 11.381 | 1.00 | 57.38 | E | C |
| ATOM | 12072 | O6 | NAG | 909 | 106.370 | 76.423 | 12.010 | 1.00 | 55.01 | E | O |
| ATOM | 12073 | C1 | NAG | 910 | 105.213 | 38.428 | 20.006 | 1.00 | 34.33 | E | C |
| ATOM | 12074 | C2 | NAG | 910 | 106.113 | 37.293 | 19.498 | 1.00 | 37.27 | E | C |
| ATOM | 12075 | N2 | NAG | 910 | 107.447 | 37.789 | 19.211 | 1.00 | 40.05 | E | N |
| ATOM | 12076 | C7 | NAG | 910 | 108.495 | 36.984 | 19.368 | 1.00 | 42.24 | E | C |
| ATOM | 12077 | O7 | NAG | 910 | 109.013 | 36.771 | 20.465 | 1.00 | 42.65 | E | O |
| ATOM | 12078 | C8 | NAG | 910 | 109.047 | 36.295 | 18.126 | 1.00 | 42.65 | E | C |
| ATOM | 12079 | C3 | NAG | 910 | 105.504 | 36.650 | 18.245 | 1.00 | 37.60 | E | C |
| ATOM | 12080 | O3 | NAG | 910 | 106.296 | 35.547 | 17.831 | 1.00 | 38.44 | E | O |
| ATOM | 12081 | C4 | NAG | 910 | 104.084 | 36.182 | 18.551 | 1.00 | 36.63 | E | C |
| ATOM | 12082 | O4 | NAG | 910 | 103.489 | 35.616 | 17.388 | 1.00 | 37.52 | E | O |
| ATOM | 12083 | C5 | NAG | 910 | 103.274 | 37.387 | 19.037 | 1.00 | 35.81 | E | C |
| ATOM | 12084 | O5 | NAG | 910 | 103.883 | 37.930 | 20.229 | 1.00 | 34.96 | E | O |
| ATOM | 12085 | C6 | NAG | 910 | 101.838 | 37.042 | 19.385 | 1.00 | 34.79 | E | C |
| ATOM | 12086 | O6 | NAG | 910 | 101.781 | 36.089 | 20.437 | 1.00 | 34.77 | E | O |
| TER | 12087 | | NAG | 910 | | | | | | E | |
| ATOM | 12088 | O | HOH | 1 | 53.435 | 80.704 | 18.172 | 1.00 | 10.60 | W | O |
| ATOM | 12089 | O | HOH | 2 | 57.473 | 78.703 | 26.320 | 1.00 | 21.03 | W | O |
| ATOM | 12090 | O | HOH | 3 | 65.386 | 56.077 | 37.040 | 1.00 | 7.09 | W | O |
| ATOM | 12091 | O | HOH | 4 | 56.235 | 76.520 | 22.816 | 1.00 | 14.76 | W | O |
| ATOM | 12092 | O | HOH | 5 | 58.127 | 60.758 | 28.066 | 1.00 | 4.57 | W | O |
| ATOM | 12093 | O | HOH | 6 | 40.099 | 59.877 | 48.410 | 1.00 | 16.00 | W | O |
| ATOM | 12094 | O | HOH | 7 | 29.796 | 47.323 | 37.410 | 1.00 | 24.76 | W | O |
| ATOM | 12095 | O | HOH | 8 | 38.634 | 67.195 | 51.371 | 1.00 | 22.65 | W | O |
| ATOM | 12096 | O | HOH | 9 | 41.732 | 52.103 | 37.673 | 1.00 | 13.34 | W | O |
| ATOM | 12097 | O | HOH | 10 | 79.275 | 54.159 | 21.409 | 1.00 | 15.53 | W | O |
| ATOM | 12098 | O | HOH | 11 | 65.287 | 66.160 | 35.128 | 1.00 | 7.29 | W | O |
| ATOM | 12099 | O | HOH | 12 | 79.267 | 49.364 | 26.780 | 1.00 | 14.00 | W | O |
| ATOM | 12100 | O | HOH | 13 | 67.989 | 56.792 | 26.833 | 1.00 | 20.21 | W | O |
| ATOM | 12101 | O | HOH | 14 | 68.995 | 70.138 | 19.815 | 1.00 | 12.98 | W | O |
| ATOM | 12102 | O | HOH | 15 | 59.193 | 63.441 | 21.787 | 1.00 | 5.68 | W | O |

| | | | | | | | | | | | |
|---|---|---|---|---|---|---|---|---|---|---|---|
| ATOM | 12103 | O | HOH | 16 | 49.896 | 66.700 | 47.886 | 1.00 | 13.21 | W | 0 |
| ATOM | 12104 | O | HOH | 17 | 48.544 | 53.043 | 50.567 | 1.00 | 20.65 | W | 0 |
| ATOM | 12105 | O | HOH | 18 | 73.938 | 69.817 | 52.424 | 1.00 | 34.74 | W | 0 |
| ATOM | 12106 | O | HOH | 19 | 36.883 | 69.650 | 29.378 | 1.00 | 25.18 | W | 0 |
| ATOM | 12107 | O | HOH | 20 | 50.912 | 61.115 | 48.431 | 1.00 | 18.77 | W | 0 |
| ATOM | 12108 | O | HOH | 21 | 58.369 | 85.282 | 28.107 | 1.00 | 27.06 | W | 0 |
| ATOM | 12109 | O | HOH | 22 | 62.886 | 63.930 | 21.686 | 1.00 | 29.16 | W | 0 |
| ATOM | 12110 | O | HOH | 23 | 43.777 | 87.394 | 23.730 | 1.00 | 9.96 | W | 0 |
| ATOM | 12111 | O | HOH | 24 | 48.078 | 67.109 | 30.405 | 1.00 | 21.66 | W | 0 |
| ATOM | 12112 | O | HOH | 25 | 36.753 | 80.303 | 31.025 | 1.00 | 34.33 | W | 0 |
| ATOM | 12113 | O | HOH | 26 | 63.225 | 66.634 | 22.568 | 1.00 | 10.18 | W | 0 |
| ATOM | 12114 | O | HOH | 27 | 35.078 | 54.838 | 52.427 | 1.00 | 29.90 | W | 0 |
| ATOM | 12115 | O | HOH | 28 | 57.184 | 80.961 | 23.145 | 1.00 | 17.51 | W | 0 |
| ATOM | 12116 | O | HOH | 29 | 73.677 | 71.484 | 27.824 | 1.00 | 34.92 | W | 0 |
| ATOM | 12117 | O | HOH | 30 | 76.251 | 57.060 | 34.794 | 1.00 | 28.05 | W | 0 |
| ATOM | 12118 | O | HOH | 31 | 72.985 | 72.092 | 24.987 | 1.00 | 14.46 | W | 0 |
| ATOM | 12119 | O | HOH | 32 | 61.839 | 84.543 | 25.502 | 1.00 | 22.75 | W | 0 |
| ATOM | 12120 | O | HOH | 33 | 33.787 | 63.840 | 46.551 | 1.00 | 12.55 | W | 0 |
| ATOM | 12121 | O | HOH | 34 | 47.827 | 47.441 | 47.587 | 1.00 | 25.33 | W | 0 |
| ATOM | 12122 | O | HOH | 35 | 55.562 | 56.510 | 44.904 | 1.00 | 30.51 | W | 0 |
| ATOM | 12123 | O | HOH | 36 | 31.114 | 59.222 | 42.224 | 1.00 | 13.22 | W | 0 |
| ATOM | 12124 | O | HOH | 37 | 82.143 | 64.199 | 47.510 | 1.00 | 21.69 | W | 0 |
| ATOM | 12125 | O | HOH | 38 | 41.587 | 70.385 | 33.904 | 1.00 | 24.19 | W | 0 |
| ATOM | 12126 | O | HOH | 39 | 70.447 | 47.056 | 34.998 | 1.00 | 24.19 | W | 0 |
| ATOM | 12127 | O | HOH | 40 | 23.146 | 49.571 | 32.910 | 1.00 | 22.85 | W | 0 |
| ATOM | 12128 | O | HOH | 41 | 23.427 | 53.516 | 39.573 | 1.00 | 12.47 | W | 0 |
| ATOM | 12129 | O | HOH | 42 | 74.977 | 48.248 | 21.021 | 1.00 | 24.35 | W | 0 |
| ATOM | 12130 | O | HOH | 43 | 81.171 | 53.457 | 19.457 | 1.00 | 32.23 | W | 0 |
| ATOM | 12131 | O | HOH | 44 | 70.982 | 61.003 | 21.232 | 1.00 | 19.07 | W | 0 |
| ATOM | 12132 | O | HOH | 45 | 51.713 | 50.325 | 19.619 | 1.00 | 36.05 | W | 0 |
| ATOM | 12133 | O | HOH | 46 | 75.424 | 58.001 | 59.062 | 1.00 | 20.53 | W | 0 |
| ATOM | 12134 | O | HOH | 47 | 52.251 | 54.978 | 15.598 | 1.00 | 20.74 | W | 0 |
| ATOM | 12135 | O | HOH | 48 | 37.551 | 51.103 | 23.882 | 1.00 | 16.65 | W | 0 |
| ATOM | 12136 | O | HOH | 49 | 31.428 | 66.281 | 21.097 | 1.00 | 18.82 | W | 0 |
| ATOM | 12137 | O | HOH | 50 | 45.546 | 72.589 | -9.525 | 1.00 | 19.51 | W | 0 |
| ATOM | 12138 | O | HOH | 51 | 71.765 | 47.337 | 39.374 | 1.00 | 16.49 | W | 0 |
| ATOM | 12139 | O | HOH | 52 | 57.328 | 68.673 | 61.331 | 1.00 | 26.41 | W | 0 |
| ATOM | 12140 | O | HOH | 53 | 72.778 | 48.947 | 47.621 | 1.00 | 17.49 | W | 0 |
| ATOM | 12141 | O | HOH | 54 | 30.292 | 82.021 | 10.956 | 1.00 | 24.56 | W | 0 |
| ATOM | 12142 | O | HOH | 55 | 47.165 | 45.427 | 40.043 | 1.00 | 35.52 | W | 0 |
| ATOM | 12143 | O | HOH | 56 | 25.673 | 60.491 | 43.209 | 1.00 | 10.79 | W | 0 |
| ATOM | 12144 | O | HOH | 57 | 71.617 | 62.843 | 34.752 | 1.00 | 17.19 | W | 0 |
| ATOM | 12145 | O | HOH | 58 | 46.059 | 55.643 | 2.123 | 1.00 | 19.51 | W | 0 |
| ATOM | 12146 | O | HOH | 59 | 68.766 | 45.985 | 50.017 | 1.00 | 22.18 | W | 0 |
| ATOM | 12147 | O | HOH | 60 | 52.732 | 70.566 | 0.317 | 1.00 | 32.17 | W | 0 |
| ATOM | 12148 | O | HOH | 61 | 61.782 | 69.597 | 25.094 | 1.00 | 13.27 | W | 0 |
| ATOM | 12149 | O | HOH | 62 | 51.352 | 79.521 | 14.538 | 1.00 | 17.25 | W | 0 |
| ATOM | 12150 | O | HOH | 63 | 48.267 | 86.907 | 16.122 | 1.00 | 21.54 | W | 0 |
| ATOM | 12151 | O | HOH | 64 | 49.536 | 54.337 | 14.938 | 1.00 | 22.27 | W | 0 |

| | | | | | | | | | | | |
|---|---|---|---|---|---|---|---|---|---|---|---|
| ATOM | 12152 | O | HOH | 65 | 37.711 | 84.458 | 31.782 | 1.00 | 38.65 | W | 0 |
| ATOM | 12153 | O | HOH | 66 | 41.832 | 62.441 | 48.190 | 1.00 | 23.50 | W | 0 |
| ATOM | 12154 | O | HOH | 67 | 56.514 | 63.214 | 39.402 | 1.00 | 20.39 | W | 0 |
| ATOM | 12155 | O | HOH | 68 | 48.166 | 60.456 | 42.122 | 1.00 | 37.55 | W | 0 |
| ATOM | 12156 | O | HOH | 69 | 52.076 | 51.584 | 45.757 | 1.00 | 22.02 | W | 0 |
| ATOM | 12157 | O | HOH | 70 | 47.607 | 61.634 | 15.612 | 1.00 | 34.50 | W | 0 |
| ATOM | 12158 | O | HOH | 71 | 39.108 | 76.636 | 34.882 | 1.00 | 24.21 | W | 0 |
| ATOM | 12159 | O | HOH | 72 | 62.894 | 85.163 | 44.724 | 1.00 | 38.05 | W | 0 |
| ATOM | 12160 | O | HOH | 73 | 49.937 | 51.963 | 48.658 | 1.00 | 25.50 | W | 0 |
| ATOM | 12161 | O | HOH | 74 | 32.972 | 63.405 | 9.645 | 1.00 | 31.16 | W | 0 |
| ATOM | 12162 | O | HOH | 75 | 76.481 | 50.940 | 55.523 | 1.00 | 8.02 | W | 0 |
| ATOM | 12163 | O | HOH | 76 | 54.751 | 68.666 | -3.038 | 1.00 | 19.33 | W | 0 |
| ATOM | 12164 | O | HOH | 77 | 69.797 | 76.851 | 37.550 | 1.00 | 38.44 | W | 0 |
| ATOM | 12165 | O | HOH | 78 | 60.195 | 69.793 | 56.043 | 1.00 | 27.75 | W | 0 |
| ATOM | 12166 | O | HOH | 79 | 68.721 | 77.775 | 28.423 | 1.00 | 14.61 | W | 0 |
| ATOM | 12167 | O | HOH | 80 | 76.538 | 41.044 | 29.727 | 1.00 | 24.17 | W | 0 |
| ATOM | 12168 | O | HOH | 81 | 27.643 | 63.804 | 39.245 | 1.00 | 20.70 | W | 0 |
| ATOM | 12169 | O | HOH | 82 | 42.573 | 57.621 | 42.066 | 1.00 | 19.56 | W | 0 |
| ATOM | 12170 | O | HOH | 83 | 51.219 | 56.139 | 24.829 | 1.00 | 41.31 | W | 0 |
| ATOM | 12171 | O | HOH | 84 | 64.281 | 54.295 | 25.797 | 1.00 | 15.83 | W | 0 |
| ATOM | 12172 | O | HOH | 85 | 48.093 | 54.052 | 46.307 | 1.00 | 38.41 | W | 0 |
| ATOM | 12173 | O | HOH | 86 | 37.006 | 52.225 | 21.202 | 1.00 | 23.83 | W | 0 |
| ATOM | 12174 | O | HOH | 87 | 44.149 | 74.948 | 5.314 | 1.00 | 17.55 | W | 0 |
| ATOM | 12175 | O | HOH | 88 | 72.912 | 75.091 | 28.633 | 1.00 | 25.98 | W | 0 |
| ATOM | 12176 | O | HOH | 89 | 52.329 | 67.860 | 33.481 | 1.00 | 8.31 | W | 0 |
| ATOM | 12177 | O | HOH | 90 | 66.266 | 74.773 | 42.238 | 1.00 | 16.00 | W | 0 |
| ATOM | 12178 | O | HOH | 91 | 59.283 | 77.076 | 9.072 | 1.00 | 41.29 | W | 0 |
| ATOM | 12179 | O | HOH | 92 | 77.526 | 46.454 | 20.254 | 1.00 | 34.51 | W | 0 |
| ATOM | 12180 | O | HOH | 93 | 59.751 | 56.673 | 29.191 | 1.00 | 24.40 | W | 0 |
| ATOM | 12181 | O | HOH | 94 | 43.531 | 63.248 | 14.122 | 1.00 | 22.64 | W | 0 |
| ATOM | 12182 | O | HOH | 95 | 56.677 | 73.257 | -8.550 | 1.00 | 18.65 | W | 0 |
| ATOM | 12183 | O | HOH | 96 | 64.366 | 82.016 | 33.202 | 1.00 | 24.81 | W | 0 |
| ATOM | 12184 | O | HOH | 97 | 58.839 | 62.776 | 26.537 | 1.00 | 11.00 | W | 0 |
| ATOM | 12185 | O | HOH | 98 | 52.478 | 72.152 | 3.092 | 1.00 | 13.58 | W | 0 |
| ATOM | 12186 | O | HOH | 99 | 59.860 | 59.389 | 29.429 | 1.00 | 20.06 | W | 0 |
| ATOM | 12187 | O | HOH | 100 | 64.047 | 73.184 | 44.557 | 1.00 | 15.66 | W | 0 |
| ATOM | 12188 | O | HOH | 101 | 44.369 | 74.978 | 38.087 | 1.00 | 11.11 | W | 0 |
| ATOM | 12189 | O | HOH | 102 | 61.861 | 50.833 | 14.510 | 1.00 | 31.09 | W | 0 |
| ATOM | 12190 | O | HOH | 103 | 40.708 | 73.940 | 22.137 | 1.00 | 13.81 | W | 0 |
| ATOM | 12191 | O | HOH | 104 | 51.853 | 81.601 | 16.339 | 1.00 | 16.73 | W | 0 |
| ATOM | 12192 | O | HOH | 105 | 59.699 | 55.348 | 63.144 | 1.00 | 20.67 | W | 0 |
| ATOM | 12193 | O | HOH | 106 | 45.186 | 81.560 | 8.416 | 1.00 | 13.89 | W | 0 |
| ATOM | 12194 | O | HOH | 107 | 37.516 | 59.183 | 48.946 | 1.00 | 20.72 | W | 0 |
| ATOM | 12195 | O | HOH | 108 | 22.032 | 56.444 | 27.934 | 1.00 | 30.26 | W | 0 |
| ATOM | 12196 | O | HOH | 109 | 65.773 | 63.945 | 59.504 | 1.00 | 15.82 | W | 0 |
| ATOM | 12197 | O | HOH | 110 | 45.931 | 73.798 | 1.832 | 1.00 | 25.56 | W | 0 |
| ATOM | 12198 | O | HOH | 111 | 29.602 | 40.898 | 24.033 | 1.00 | 25.93 | W | 0 |
| ATOM | 12199 | O | HOH | 112 | 19.080 | 57.313 | 26.663 | 1.00 | 20.07 | W | 0 |
| ATOM | 12200 | O | HOH | 113 | 61.355 | 50.296 | 11.653 | 1.00 | 20.49 | W | 0 |

| | | | | | | | | | | | |
|---|---|---|---|---|---|---|---|---|---|---|---|
| ATOM | 12201 | O | HOH | 114 | 41.491 | 58.601 | 0.047 | 1.00 | 42.91 | W | 0 |
| ATOM | 12202 | O | HOH | 115 | 64.362 | 64.567 | 16.259 | 1.00 | 24.97 | W | 0 |
| ATOM | 12203 | O | HOH | 116 | 43.928 | 76.242 | 2.332 | 1.00 | 21.69 | W | 0 |
| ATOM | 12204 | O | HOH | 117 | 80.703 | 69.349 | 43.827 | 1.00 | 28.64 | W | 0 |
| ATOM | 12205 | O | HOH | 118 | 81.671 | 48.368 | 20.456 | 1.00 | 15.16 | W | 0 |
| ATOM | 12206 | O | HOH | 119 | 59.413 | 71.127 | 54.004 | 1.00 | 22.01 | W | 0 |
| ATOM | 12207 | O | HOH | 120 | 27.474 | 69.426 | 47.288 | 1.00 | 26.74 | W | 0 |
| ATOM | 12208 | O | HOH | 121 | 69.871 | 60.279 | 33.380 | 1.00 | 13.47 | W | 0 |
| ATOM | 12209 | O | HOH | 122 | 67.879 | 38.425 | 47.297 | 1.00 | 25.68 | W | 0 |
| ATOM | 12210 | O | HOH | 123 | 41.866 | 62.152 | 36.306 | 1.00 | 27.91 | W | 0 |
| ATOM | 12211 | O | HOH | 124 | 82.055 | 50.923 | 20.718 | 1.00 | 23.09 | W | 0 |
| ATOM | 12212 | O | HOH | 125 | 38.821 | 82.651 | 33.998 | 1.00 | 14.04 | W | 0 |
| ATOM | 12213 | O | HOH | 126 | 64.420 | 42.195 | 31.710 | 1.00 | 28.88 | W | 0 |
| ATOM | 12214 | O | HOH | 127 | 60.713 | 36.262 | 43.885 | 1.00 | 22.95 | W | 0 |
| ATOM | 12215 | O | HOH | 128 | 63.095 | 38.041 | 44.744 | 1.00 | 26.42 | W | 0 |
| ATOM | 12216 | O | HOH | 129 | 36.718 | 65.633 | 50.633 | 1.00 | 38.12 | W | 0 |
| ATOM | 12217 | O | HOH | 130 | 55.575 | 80.086 | 20.196 | 1.00 | 26.23 | W | 0 |
| ATOM | 12218 | O | HOH | 131 | 41.981 | 65.129 | 15.577 | 1.00 | 23.62 | W | 0 |
| ATOM | 12219 | O | HOH | 132 | 48.067 | 75.632 | 53.563 | 1.00 | 36.38 | W | 0 |
| ATOM | 12220 | O | HOH | 133 | 75.617 | 59.792 | 32.116 | 1.00 | 35.58 | W | 0 |
| ATOM | 12221 | O | HOH | 134 | 73.522 | 67.486 | 30.484 | 1.00 | 21.07 | W | 0 |
| ATOM | 12222 | O | HOH | 135 | 65.965 | 81.671 | 30.091 | 1.00 | 41.74 | W | 0 |
| ATOM | 12223 | O | HOH | 136 | 41.663 | 53.300 | 13.574 | 1.00 | 39.95 | W | 0 |
| ATOM | 12224 | O | HOH | 137 | 42.885 | 39.029 | 29.960 | 1.00 | 29.57 | W | 0 |
| ATOM | 12225 | O | HOH | 138 | 67.606 | 56.683 | 24.253 | 1.00 | 37.19 | W | 0 |
| ATOM | 12226 | O | HOH | 139 | 138.150 | 54.591 | 37.133 | 1.00 | 19.60 | W | 0 |
| ATOM | 12227 | O | HOH | 140 | 76.640 | 48.505 | 51.547 | 1.00 | 22.87 | W | 0 |
| ATOM | 12228 | O | HOH | 141 | 105.346 | 35.319 | 45.478 | 1.00 | 6.28 | W | 0 |
| ATOM | 12229 | O | HOH | 142 | 108.946 | 33.058 | 43.850 | 1.00 | 17.18 | W | 0 |
| ATOM | 12230 | O | HOH | 143 | 101.384 | 50.291 | 32.321 | 1.00 | 12.25 | W | 0 |
| ATOM | 12231 | O | HOH | 144 | 83.691 | 56.732 | 33.886 | 1.00 | 18.52 | W | 0 |
| ATOM | 12232 | O | HOH | 145 | 96.721 | 59.108 | 34.335 | 1.00 | 14.59 | W | 0 |
| ATOM | 12233 | O | HOH | 146 | 122.411 | 66.436 | 57.099 | 1.00 | 19.53 | W | 0 |
| ATOM | 12234 | O | HOH | 147 | 107.303 | 38.674 | 48.678 | 1.00 | 12.12 | W | 0 |
| ATOM | 12235 | O | HOH | 148 | 102.207 | 54.174 | 15.770 | 1.00 | 18.02 | W | 0 |
| ATOM | 12236 | O | HOH | 149 | 104.534 | 49.338 | 27.730 | 1.00 | 13.93 | W | 0 |
| ATOM | 12237 | O | HOH | 150 | 113.995 | 67.497 | 30.740 | 1.00 | 26.00 | W | 0 |
| ATOM | 12238 | O | HOH | 151 | 115.903 | 54.147 | 45.005 | 1.00 | 10.46 | W | 0 |
| ATOM | 12239 | O | HOH | 152 | 114.104 | 55.650 | 9.401 | 1.00 | 27.03 | W | 0 |
| ATOM | 12240 | O | HOH | 153 | 86.360 | 55.414 | 40.305 | 1.00 | 14.32 | W | 0 |
| ATOM | 12241 | O | HOH | 154 | 97.554 | 40.670 | 45.200 | 1.00 | 18.35 | W | 0 |
| ATOM | 12242 | O | HOH | 155 | 119.087 | 37.761 | 27.531 | 1.00 | 31.02 | W | 0 |
| ATOM | 12243 | O | HOH | 156 | 87.809 | 62.914 | 36.962 | 1.00 | 26.29 | W | 0 |
| ATOM | 12244 | O | HOH | 157 | 83.356 | 65.229 | 44.012 | 1.00 | 37.02 | W | 0 |
| ATOM | 12245 | O | HOH | 158 | 98.650 | 46.435 | 54.377 | 1.00 | 26.11 | W | 0 |
| ATOM | 12246 | O | HOH | 159 | 99.982 | 40.104 | 43.504 | 1.00 | 11.71 | W | 0 |
| ATOM | 12247 | O | HOH | 160 | 122.550 | 42.243 | 44.636 | 1.00 | 14.84 | W | 0 |
| ATOM | 12248 | O | HOH | 161 | 101.404 | 56.669 | 35.498 | 1.00 | 35.54 | W | 0 |
| ATOM | 12249 | O | HOH | 162 | 88.481 | 51.896 | 31.163 | 1.00 | 12.64 | W | 0 |

| | | | | | | | | | | |
|---|---|---|---|---|---|---|---|---|---|---|
| ATOM | 12250 | O | HOH | 163 | 95.169 | 58.602 | 25.005 | 1.00 | 10.78 | W | 0 |
| ATOM | 12251 | O | HOH | 164 | 115.235 | 34.630 | 45.444 | 1.00 | 26.24 | W | 0 |
| ATOM | 12252 | O | HOH | 165 | 106.826 | 53.003 | 55.571 | 1.00 | 20.62 | W | 0 |
| ATOM | 12253 | O | HOH | 166 | 84.875 | 59.299 | 19.482 | 1.00 | 36.24 | W | 0 |
| ATOM | 12254 | O | HOH | 167 | 113.139 | 50.670 | 46.942 | 1.00 | 20.56 | W | 0 |
| ATOM | 12255 | O | HOH | 168 | 95.042 | 48.091 | 37.270 | 1.00 | 21.34 | W | 0 |
| ATOM | 12256 | O | HOH | 169 | 76.879 | 72.537 | 31.569 | 1.00 | 23.37 | W | 0 |
| ATOM | 12257 | O | HOH | 170 | 114.148 | 58.106 | 48.086 | 1.00 | 18.43 | W | 0 |
| ATOM | 12258 | O | HOH | 171 | 89.134 | 33.853 | 32.584 | 1.00 | 22.93 | W | 0 |
| ATOM | 12259 | O | HOH | 172 | 104.484 | 32.367 | 28.628 | 1.00 | 23.01 | W | 0 |
| ATOM | 12260 | O | HOH | 173 | 97.990 | 56.523 | 56.950 | 1.00 | 35.07 | W | 0 |
| ATOM | 12261 | O | HOH | 174 | 108.093 | 59.050 | 11.178 | 1.00 | 23.37 | W | 0 |
| ATOM | 12262 | O | HOH | 175 | 95.968 | 47.759 | 51.786 | 1.00 | 19.27 | W | 0 |
| ATOM | 12263 | O | HOH | 176 | 93.653 | 58.234 | 55.683 | 1.00 | 19.54 | W | 0 |
| ATOM | 12264 | O | HOH | 177 | 117.454 | 64.613 | 44.832 | 1.00 | 25.55 | W | 0 |
| ATOM | 12265 | O | HOH | 178 | 96.322 | 67.790 | 27.707 | 1.00 | 29.36 | W | 0 |
| ATOM | 12266 | O | HOH | 179 | 80.831 | 40.760 | 23.388 | 1.00 | 28.01 | W | 0 |
| ATOM | 12267 | O | HOH | 180 | 109.521 | 38.188 | 50.278 | 1.00 | 16.30 | W | 0 |
| ATOM | 12268 | O | HOH | 181 | 88.081 | 40.289 | 29.465 | 1.00 | 7.47 | W | 0 |
| ATOM | 12269 | O | HOH | 182 | 112.135 | 42.102 | 29.409 | 1.00 | 28.14 | W | 0 |
| ATOM | 12270 | O | HOH | 183 | 110.546 | 33.279 | 45.877 | 1.00 | 22.55 | W | 0 |
| ATOM | 12271 | O | HOH | 184 | 101.361 | 45.858 | 44.078 | 1.00 | 28.83 | W | 0 |
| ATOM | 12272 | O | HOH | 185 | 126.633 | 38.023 | 29.778 | 1.00 | 31.97 | W | 0 |
| ATOM | 12273 | O | HOH | 186 | 122.283 | 37.257 | 34.566 | 1.00 | 18.77 | W | 0 |
| ATOM | 12274 | O | HOH | 187 | 99.753 | 38.623 | 40.032 | 1.00 | 18.28 | W | 0 |
| ATOM | 12275 | O | HOH | 188 | 122.547 | 56.954 | 36.341 | 1.00 | 20.05 | W | 0 |
| ATOM | 12276 | O | HOH | 189 | 68.079 | 78.219 | 33.025 | 1.00 | 38.49 | W | 0 |
| ATOM | 12277 | O | HOH | 190 | 134.519 | 46.667 | 45.989 | 1.00 | 34.45 | W | 0 |
| ATOM | 12278 | O | HOH | 191 | 110.945 | 39.354 | 35.865 | 1.00 | 10.27 | W | 0 |
| ATOM | 12279 | O | HOH | 192 | 118.982 | 51.843 | 57.881 | 1.00 | 13.62 | W | 0 |
| ATOM | 12280 | O | HOH | 193 | 123.824 | 35.631 | 32.830 | 1.00 | 19.19 | W | 0 |
| ATOM | 12281 | O | HOH | 194 | 100.524 | 45.123 | 38.393 | 1.00 | 26.68 | W | 0 |
| ATOM | 12282 | O | HOH | 195 | 122.815 | 60.696 | 63.937 | 1.00 | 24.15 | W | 0 |
| ATOM | 12283 | O | HOH | 196 | 96.208 | 59.856 | 31.652 | 1.00 | 12.71 | W | 0 |
| ATOM | 12284 | O | HOH | 197 | 80.023 | 56.246 | 54.587 | 1.00 | 10.61 | W | 0 |
| ATOM | 12285 | O | HOH | 198 | 109.915 | 41.219 | 37.675 | 1.00 | 19.28 | W | 0 |
| ATOM | 12286 | O | HOH | 199 | 96.990 | 75.649 | 27.926 | 1.00 | 9.03 | W | 0 |
| ATOM | 12287 | O | HOH | 200 | 103.494 | 44.373 | 34.046 | 1.00 | 8.20 | W | 0 |
| ATOM | 12288 | O | HOH | 201 | 97.045 | 44.873 | 53.124 | 1.00 | 15.97 | W | 0 |
| ATOM | 12289 | O | HOH | 202 | 109.135 | 58.341 | 13.499 | 1.00 | 22.83 | W | 0 |
| ATOM | 12290 | O | HOH | 203 | 96.465 | 39.089 | 47.689 | 1.00 | 12.68 | W | 0 |
| ATOM | 12291 | O | HOH | 204 | 99.669 | 54.200 | 16.885 | 1.00 | 13.83 | W | 0 |
| ATOM | 12292 | O | HOH | 205 | 85.350 | 34.351 | 33.261 | 1.00 | 15.83 | W | 0 |
| ATOM | 12293 | O | HOH | 206 | 106.252 | 38.178 | 46.273 | 1.00 | 17.78 | W | 0 |
| ATOM | 12294 | O | HOH | 207 | 102.838 | 63.592 | 15.944 | 1.00 | 23.96 | W | 0 |
| ATOM | 12295 | O | HOH | 208 | 114.173 | 52.027 | 44.587 | 1.00 | 12.16 | W | 0 |
| ATOM | 12296 | O | HOH | 209 | 114.209 | 49.450 | 36.803 | 1.00 | 19.70 | W | 0 |
| ATOM | 12297 | O | HOH | 210 | 78.079 | 55.141 | 59.990 | 1.00 | 33.63 | W | 0 |
| ATOM | 12298 | O | HOH | 211 | 95.004 | 41.032 | 14.678 | 1.00 | 29.66 | W | 0 |

| ATOM | 12299 | O | HOH | 212 | 113.170 | 36.816 | 43.347 | 1.00 | 21.90 | W | 0 |
|------|-------|---|-----|-----|---------|--------|--------|------|-------|---|---|
| ATOM | 12300 | O | HOH | 213 | 77.770 | 71.277 | 45.572 | 1.00 | 31.73 | W | 0 |
| ATOM | 12301 | O | HOH | 214 | 128.636 | 66.746 | 61.783 | 1.00 | 37.87 | W | 0 |
| ATOM | 12302 | O | HOH | 215 | 128.566 | 42.261 | 18.644 | 1.00 | 26.65 | W | 0 |
| ATOM | 12303 | O | HOH | 216 | 135.349 | 43.830 | 34.280 | 1.00 | 24.69 | W | 0 |
| ATOM | 12304 | O | HOH | 217 | 85.640 | 67.686 | 27.706 | 1.00 | 32.33 | W | 0 |
| ATOM | 12305 | O | HOH | 218 | 93.669 | 46.427 | 45.506 | 1.00 | 24.39 | W | 0 |
| ATOM | 12306 | O | HOH | 219 | 117.990 | 67.819 | 59.317 | 1.00 | 20.28 | W | 0 |
| ATOM | 12307 | O | HOH | 220 | 79.954 | 55.009 | 62.309 | 1.00 | 19.13 | W | 0 |
| ATOM | 12308 | O | HOH | 221 | 117.228 | 62.083 | 29.483 | 1.00 | 29.50 | W | 0 |
| ATOM | 12309 | O | HOH | 222 | 105.505 | 51.938 | 31.912 | 1.00 | 35.19 | W | 0 |
| ATOM | 12310 | O | HOH | 223 | 106.835 | 57.215 | 14.677 | 1.00 | 21.77 | W | 0 |
| ATOM | 12311 | O | HOH | 224 | 107.489 | 60.380 | 64.395 | 1.00 | 24.53 | W | 0 |
| ATOM | 12312 | O | HOH | 225 | 79.753 | 74.355 | 37.799 | 1.00 | 35.35 | W | 0 |
| ATOM | 12313 | O | HOH | 226 | 116.807 | 64.679 | 29.466 | 1.00 | 24.83 | W | 0 |
| ATOM | 12314 | O | HOH | 227 | 87.239 | 52.355 | 64.706 | 1.00 | 21.19 | W | 0 |
| ATOM | 12315 | O | HOH | 228 | 81.916 | 67.988 | 41.878 | 1.00 | 14.54 | W | 0 |
| ATOM | 12316 | O | HOH | 229 | 106.295 | 62.226 | 36.826 | 1.00 | 26.06 | W | 0 |
| ATOM | 12317 | O | HOH | 230 | 78.057 | 49.553 | 53.991 | 1.00 | 15.40 | W | 0 |
| ATOM | 12318 | O | HOH | 231 | 99.797 | 47.673 | 22.572 | 1.00 | 18.00 | W | 0 |
| ATOM | 12319 | O | HOH | 232 | 80.925 | 62.495 | 37.326 | 1.00 | 9.28 | W | 0 |
| ATOM | 12320 | O | HOH | 233 | 93.378 | 45.857 | 52.934 | 1.00 | 12.13 | W | 0 |
| ATOM | 12321 | O | HOH | 234 | 132.069 | 46.877 | 33.339 | 1.00 | 20.97 | W | 0 |
| ATOM | 12322 | O | HOH | 235 | 93.916 | 62.211 | 25.521 | 1.00 | 13.10 | W | 0 |
| ATOM | 12323 | O | HOH | 236 | 93.249 | 60.882 | 37.895 | 1.00 | 26.19 | W | 0 |
| ATOM | 12324 | O | HOH | 237 | 100.380 | 52.169 | 18.636 | 1.00 | 7.98 | W | 0 |
| ATOM | 12325 | O | HOH | 238 | 82.096 | 55.169 | 32.059 | 1.00 | 10.45 | W | 0 |
| ATOM | 12326 | O | HOH | 239 | 94.471 | 48.635 | 53.699 | 1.00 | 13.21 | W | 0 |
| ATOM | 12327 | O | HOH | 240 | 87.009 | 55.227 | 64.894 | 1.00 | 24.88 | W | 0 |
| ATOM | 12328 | O | HOH | 241 | 95.857 | 52.760 | 15.499 | 1.00 | 29.83 | W | 0 |
| ATOM | 12329 | O | HOH | 242 | 117.688 | 49.829 | 33.274 | 1.00 | 13.15 | W | 0 |
| ATOM | 12330 | O | HOH | 243 | 103.675 | 56.528 | 15.602 | 1.00 | 19.17 | W | 0 |
| ATOM | 12331 | O | HOH | 244 | 99.571 | 37.563 | 42.732 | 1.00 | 22.69 | W | 0 |
| ATOM | 12332 | O | HOH | 245 | 100.413 | 48.087 | 60.147 | 1.00 | 23.84 | W | 0 |
| ATOM | 12333 | O | HOH | 246 | 117.307 | 73.448 | 16.262 | 1.00 | 29.45 | W | 0 |
| ATOM | 12334 | O | HOH | 247 | 124.287 | 57.265 | 34.284 | 1.00 | 15.90 | W | 0 |
| ATOM | 12335 | O | HOH | 248 | 124.770 | 56.884 | 15.714 | 1.00 | 26.61 | W | 0 |
| ATOM | 12336 | O | HOH | 249 | 133.182 | 57.356 | 30.667 | 1.00 | 8.25 | W | 0 |
| ATOM | 12337 | O | HOH | 250 | 106.948 | 46.114 | 47.228 | 1.00 | 18.40 | W | 0 |
| ATOM | 12338 | O | HOH | 251 | 101.409 | 54.086 | 55.370 | 1.00 | 24.76 | W | 0 |
| ATOM | 12339 | O | HOH | 252 | 116.022 | 62.795 | 46.555 | 1.00 | 17.19 | W | 0 |
| ATOM | 12340 | O | HOH | 253 | 95.637 | 65.687 | 28.739 | 1.00 | 22.07 | W | 0 |
| ATOM | 12341 | O | HOH | 254 | 89.440 | 32.347 | 36.665 | 1.00 | 21.89 | W | 0 |
| ATOM | 12342 | O | HOH | 255 | 86.628 | 29.295 | 53.611 | 1.00 | 28.08 | W | 0 |
| ATOM | 12343 | O | HOH | 256 | 102.111 | 48.926 | 69.771 | 1.00 | 28.02 | W | 0 |
| ATOM | 12344 | O | HOH | 257 | 117.835 | 65.790 | 61.089 | 1.00 | 30.23 | W | 0 |
| ATOM | 12345 | O | HOH | 258 | 105.286 | 61.859 | 63.757 | 1.00 | 33.92 | W | 0 |
| ATOM | 12346 | O | HOH | 259 | 86.743 | 64.218 | 34.930 | 1.00 | 28.91 | W | 0 |
| ATOM | 12347 | O | HOH | 260 | 105.249 | 47.160 | 40.635 | 1.00 | 20.28 | W | 0 |

```
ATOM  12348  O  HOH  261  125.748  77.301  50.793  1.00  32.51  W  0
ATOM  12349  O  HOH  262   73.839  74.279  32.315  1.00  30.75  W  0
ATOM  12350  O  HOH  263   92.355  54.248  49.336  1.00  32.87  W  0
ATOM  12351  O  HOH  264  102.237  61.200  14.237  1.00  31.77  W  0
ATOM  12352  O  HOH  265  111.596  65.302  59.180  1.00  14.35  W  0
ATOM  12353  O  HOH  266   76.203  36.588  32.586  1.00  25.41  W  0
ATOM  12354  O  HOH  267   95.406  54.983  52.304  1.00  31.62  W  0
ATOM  12355  O  HOH  268   71.413  36.734  46.233  1.00  28.42  W  0
ATOM  12356  O  HOH  269  127.938  49.749  55.356  1.00  31.01  W  0
ATOM  12357  O  HOH  270  122.216  58.021  31.710  1.00  35.14  W  0
ATOM  12358  O  HOH  271   94.659  59.753  40.284  1.00  27.37  W  0
ATOM  12359  O  HOH  272   77.118  34.975  51.599  1.00  37.45  W  0
ATOM  12360  O  HOH  273  112.752  32.790  41.771  1.00  30.32  W  0
TER   12361     HOH  273                                        W
END
```

THREE-DIMENSIONAL STRUCTURE OF DIPEPTIDYL PEPTIDASE IV

This application is a 35 U.S.C. § 371 filing of International Application No. PCT/JP2003/009523, filed Jul. 28, 2003, which claims priority to U.S. Provisional Application No. 60/398,761, filed Jul. 29, 2002.

TECHNICAL FIELD

The present invention relates to a crystal and a three-dimensional structural coordinate of a dipeptidyl peptidase IV, and an application thereof. More specifically, the present invention relates to a crystal and a three-dimensional structural coordinate, a method for obtaining a three-dimensional structural coordinate of a homolog protein of a dipeptidyl peptidase IV, a method for obtaining a three-dimensional structural coordinate of a crystal of a complex of a dipeptidyl peptidase IV with an effector (e.g. inhibitor) of the dipeptidyl peptidase IV, a method for identifying a pharmacophore of an effector (e.g. inhibitor) of for the dipeptidyl peptidase IV, a method for identifying sites affecting the activity of the dipeptidyl peptidase IV, a method for designing, identifying, evaluating or searching an effector (e.g. inhibitor) of the dipeptidyl peptidase IV, and a program and a medium therefor for use of the three-dimensional structural coordinate, which are useful in the development of an effector (e.g. inhibitor) of the dipeptidyl peptidase IV, useful as a modulatory agent of immune response and as a therapeutic or prophylactic agent for diabetes, inflammation, multiple sclerosis, Graves' disease, chronic rheumatoid arthritis, AIDS, cancer and the like; and an effector (e.g. inhibitor) of the dipeptidyl peptidase IV useful as a modulatory agent of immune response and as a therapeutic or prophylactic agent for diabetes, inflammation, multiple sclerosis, Graves' disease, chronic rheumatoid arthritis, AIDS, cancer and the like.

BACKGROUND ART

Dipeptidyl peptidase IV (hereinafter also referred to as DPPIV) is a cell membrane protein, which has been found in epithelial cell of small intestine, prostate gland, renal tubule, biliary tract and the like, activated T-cell, B-cell, NK-cell and the like. In the DPPIV, deduced active sites of DPPIV in the C-terminal side are located in extracellular portions and those in the N-terminal side are located in cytoplasm in a living body. Also, there has been suggested the relationship of the above-mentioned DPPIV with the activities of various cytokines such as interleukin-1β, interleukin-2, interleukin-3, interleukin-5, interleukin-6, interleukin-13, tumor necrosis factory and the like, and activities of various chemokines such as RANTES and the like in immune system [*Rinsho Menneki (Clinical Immunology)*, 34, Revised and Enlarged Edition 19, 45-53, published by Kagaku Hyoronsha (2000), and the like].

As to the dipeptidyl peptidase IV, it has been shown that some amino acid residues can be involved in exhibition of the activity of the dipeptidyl peptidase IV by experiments such as biochemical experiments using inhibitors, experiments using mutants produced by site-directed mutagenesis [for example, see Misumi et al, *Biochim. Biophys. Acta*, 1131, 333-336 (1992), Ogata et al, *Biochemistry*, 31, 2582-2587 (1992) and the like].

However, it is difficult to know the three-dimensional structures for active sites from the information. Therefore, it is presently difficult to obtain the three-dimensional structural information for identifying, searching, evaluating or designing an interaction of the dipeptidyl peptidase IV and a compound that acts with the dipeptidyl peptidase IV on the level of three-dimensional structure and a novel compound capable of binding with and acting on the dipeptidyl peptidase IV.

DISCLOSURE OF INVENTION

A first object of the present invention is to provide a crystal of a dipeptidyl peptidase IV, which is useful for providing a three-dimensional structural coordinate as the information for designing, identifying, evaluating or searching an effector (e.g. inhibitor) of the dipeptidyl peptidase IV useful as a modulatory agent of immune response and as a therapeutic or prophylactic agent for diabetes, inflammation, multiple sclerosis, Graves' disease, chronic rheumatoid arthritis, AIDS, cancer and the like. A second object of the present invention is to provide a three-dimensional structural coordinate of the crystal, which can provide the information for designing, identifying, evaluating or searching an effector (e.g. inhibitor) of the dipeptidyl peptidase IV useful as a modulatory agent of immune response and as a therapeutic or prophylactic agent for diabetes, inflammation, multiple sclerosis, Graves' disease, chronic rheumatoid arthritis, AIDS, cancer and the like. A third object of the present invention is to provide a method for obtaining a three-dimensional structural coordinate of a homolog protein of the dipeptidyl peptidase IV, whereby refinement of a three-dimensional structural coordinate of a homolog protein of the dipeptidyl peptidase IV can be more readily performed. Furthermore, a fourth object of the present invention is to provide a method for obtaining a three-dimensional structural coordinate of a crystal of a complex of a dipeptidyl peptidase IV and an effector (e.g. inhibitor) of the dipeptidyl peptidase IV, which can provide the information for designing, identifying, evaluating or searching an effector (e.g. inhibitor) of the dipeptidyl peptidase IV which is useful as a modulatory agent of immune response and as a therapeutic or prophylactic agent for diabetes, inflammation, multiple sclerosis, Graves' disease, chronic rheumatoid arthritis, AIDS, cancer and the like, and is excellent in avidity, biological activity, biological stability, absorbency to a living body, and which can favorably act on the dipeptidyl peptidase IV. A fifth object of the present invention is to provide a method for identifying a pharmacophore of the dipeptidyl peptidase IV and the effector (e.g. inhibitor) of the dipeptidyl peptidase IV, which can provide the information for designing, identifying, evaluating or searching an effector (e.g. inhibitor) of the dipeptidyl peptidase IV useful as a modulatory agent of immune response and as a therapeutic or prophylactic agent for diabetes, inflammation, multiple sclerosis, Graves' disease, chronic rheumatoid arthritis, AIDS, cancer and the like, and is excellent in avidity, biological activity, biological stability, absorbency in a living body, and which can be favorably act on the dipeptidyl peptidase IV. A sixth object of the present invention is to provide a method for designing, identifying, evaluating or searching the effector (e.g. inhibitor) of the dipeptidyl peptidase IV, which can logically and conveniently provide the effector (e.g. inhibitor) of the dipeptidyl peptidase IV useful as a modulatory agent of immune response and as a therapeutic or prophylactic agent for diabetes, inflammation, multiple sclerosis, Graves' disease, chronic rheumatoid arthritis, AIDS, cancer and the like, and is excellent in avidity, biological activity, biological stability, absorbency in a living body (in vivo), and which can be favorably act on the dipeptidyl peptidase IV. A seventh object of the present invention is to provide the effector (e.g. inhibitor) of the dipeptidyl peptidase IV useful as a modulatory agent of immune response and as a therapeutic or prophylactic agent for diabetes, inflammation, multiple sclerosis, Graves' disease, chronic rheumatoid arthritis, AIDS, cancer and the like. An eighth object of the present invention is to provide a program and a medium therefor, which can rapidly and conveniently perform design, identification, evaluation or search of the effector (e.g. inhibitor) of the dipeptidyl peptidase IV.

Concretely, the present invention relates to:

[1] a crystal of a dipeptidyl peptidase IV, having characteristics sufficient to ensure a resolution capable of analyzing its three-dimensional structure up to the side chain level by X-ray crystallographic structural analysis;

[2] the crystal according to the above [1], wherein the dipeptidyl peptidase IV is a soluble polypeptide comprising a region located at extramembrane in a full-length human dipeptidyl peptidase IV (SEQ ID NO: 2);

[3] the crystal according to the above [1] or [2], wherein the dipeptidyl peptidase IV is a polypeptide having an amino acid sequence in which a transmembrane region is deleted from the amino acid sequence of SEQ ID NO: 2, and a tag peptide is optionally added to a C-terminal side or N-terminal side thereof;

[4] the crystal according to any one of the above [1] to [3], wherein the crystal has a space group of $P2_12_12_1$, and a lattice constant of the unit cell of $|a|=118.0\pm5.0$ Å, $|b|=125.9\pm5.0$ Å, $|c|=136.8\pm5.0$ Å, and $\alpha=\beta=\gamma=90°$, and is orthorhombic;

[5] the crystal according to any one of the above [1] to [4], wherein the crystal has the structural coordinate shown in FIG. 4;

[6] the crystal according to any one of the above [1] to [4], wherein the crystal has a structural coordinate different from the structural coordinate as shown in FIG. 4 via fluctuation of a protein;

[7] a three-dimensional structural coordinate of a dipeptidyl peptidase IV, comprising the structural coordinate shown in FIG. 4;

[8] a three-dimensional structural coordinate of a dipeptidyl peptidase IV, comprising a structural coordinate different from the structural coordinate as shown in FIG. 4 via fluctuation of a protein;

[9] the three-dimensional structural coordinate according to the above [8], wherein the fluctuation of a protein is a state that is caused by molecular oscillation or temperature, and exhibits an activity for the dipeptidyl peptidase IV in a living body;

[10] the three-dimensional structural coordinate according to any one of the above [7] to [9], wherein the dipeptidyl peptidase IV is a soluble polypeptide comprising a region located at extramembrane in a full-length human dipeptidyl peptidase IV (SEQ ID NO: 2);

[11] the three-dimensional structural coordinate according to any one of the above [7] to [10], wherein the dipeptidyl peptidase IV is a polypeptide having an amino acid sequence in which a transmembrane region is deleted from the amino acid sequence of SEQ ID NO: 2, and a tag peptide is optionally added of to a C-terminal side or N-terminal side thereof;

[12] a three-dimensional structural coordinate of a region in a dipeptidyl peptidase IV, comprising the three-dimensional structural coordinate of the region selected from the group consisting of the following (a) to (d):

(a) a region characterized by Ser 630, Asp 708 and His 740 in the amino acid sequence of SEQ ID NO: 2, and
all or a part of a group of the amino acid residues located in the adjacent area of each of the Ser 630, Asp 708 and His 740 in the structural coordinate shown in FIG. 4 or the three-dimensional structure model defined by the structural coordinate;

(b) a region characterized by Ser 630, Asp 708 and His 740 in the amino acid sequence of SEQ ID NO: 2, and
all or a part of a group of the amino acid residues comprising amino acids capable of maintaining physicochemical characteristics physiologically equivalent to each of amino acids in the group of the amino acid residues located in the adjacent area of each of Ser 630, Asp 708 and His 740, in the structural coordinate shown in FIG. 4 or the three-dimensional structure model defined by the structural coordinate, (c) a region characterized by a group of amino acid residues comprising amino acids capable of maintaining physicochemical characteristics physiologically equivalent to each of Ser 630, Asp 708 and His 740 in the amino acid sequence of SEQ ID NO: 2, and
all or a part of a group of the amino acid residues located in the adjacent area of said group of the amino acid residues in the structural coordinate shown in FIG. 4 or the three-dimensional structure model defined by the structural coordinate; and (d) a region characterized by a group of amino acid residues comprising amino acids capable of maintaining physicochemical characteristics physiologically equivalent to each of Ser 630, Asp 708 and His 740 in the amino acid sequence of SEQ ID NO: 2, and
all or a part of a group of amino acid residues comprising amino acids capable of maintaining physicochemical characteristics physiologically equivalent to each of the amino acids in the group of the amino acid residues located in the adjacent area of said group of the amino acids, in the structural coordinate shown in FIG. 4 or the three-dimensional structure model defined by the structural coordinate, wherein the region in the dipeptidyl peptidase IV is a region involved in binding or interaction between the dipeptidyl peptidase IV and an effector of the dipeptidyl peptidase IV;

[13] the three-dimensional coordinate according to the above [12], wherein the physicochemical characteristic is selected from the group consisting of features in shape of a three-dimensional structure, hydrophobicity, electric charge and pK;

[14] a method for obtaining a three-dimensional coordinate of a homolog protein of a dipeptidyl peptidase IV, characterized in refining an electron density map of the homolog protein of the dipeptidyl peptidase IV comprising the amino acid sequence of SEQ ID NO: 2, based on all and/or a part of the three-dimensional coordinate of any one of the above [7] to [13], to give a three-dimensional structural coordinate;

[15] a method for obtaining a three-dimensional structural coordinate of a crystal of a complex of a dipeptidyl peptidase IV and an effector of the dipeptidyl peptidase IV characterized in using all and/or a part of the three-dimensional structural coordinate of any one of the above [7] to [13], to give a three-dimensional structural coordinate;

[16] a method for identifying pharmacophore of an effector of the dipeptidyl peptidase IV, characterized in identifying the pharmacophore based on all and/or a part of the three-dimensional structural coordinate of any one of the above [7] to [13], and the steric conformation of the effector of the dipeptidyl peptidase IV;

[17] a method for designing, identifying, evaluating or searching an effector of a dipeptidyl peptidase IV, characterized in designing, identifying, evaluating or searching a compound capable of acting on the dipeptidyl peptidase IV, based on all and/or a part of the three-dimensional structural coordinate of any one of the above [7] to [13];

[18] the method according to the above [17], wherein the method for designing, identifying, evaluating or searching an effector comprises the steps of:
(i) identifying a region to be targeted for binding or interaction with the effector in a dipeptidyl peptidase IV, based on all and/or a part of the three-dimensional structural coordinate according to any one of the above [7] to [13] and the steric conformation of the effector of the dipeptidyl peptidase IV;
(ii) identifying atoms or atomic groups capable of generating in the above region at least one intermolecular interaction selected from the group consisting of covalent bond, ionic interaction, ion-dipole interaction, dipole-dipole interaction, hydrogen bonding, van der Waals force, electrostatic interaction and hydrophobic interaction, with the atoms or atomic groups existing in a candidate compound; and
(iii) designing a compound based on the information of the above step (i) and/or (ii);

[19] the method according to the above [18], wherein the method further comprises the steps of:
detecting an interaction between the dipeptidyl peptidase IV and the designed, identified, evaluated or searched candidate compound,
wherein when an interaction is detected, the candidate compound is identified as a compound capable of binding to the dipeptidyl peptidase IV, based on a degree of the interaction as an index;

[20] the method according to the above [18] or [19], wherein the method further comprises the steps of:
contacting the dipeptidyl peptidase IV with the designed, identified, evaluated or searched candidate compound and measuring the activity of the dipeptidyl peptidase IV,
wherein when an activity increases or decreases, the designed, identified, evaluated or searched candidate compound is identified as a compound having enhancing action or inhibitory action on the activity of the dipeptidyl peptidase IV, based on a degree of the increase or decrease as an index;

[21] an effector of the dipeptidyl peptidase IV obtainable by the method of any one of the above [17] to [20];

[22] a program and a medium therefor for use of the three-dimensional structural coordinate of any one of the above [7] to [13], wherein all and/or a part of the three-dimensional structural coordinate of any one of the above [7] to [13] is recorded;

[23] the program and the medium according to the above [22], comprising a means for identifying, searching, evaluating or designing a compound capable of binding to the dipeptidyl peptidase IV or a compound having an enhancing action or inhibitory action on the activity for the dipeptidyl peptidase IV; and

[24] the program and the medium according to the above [23], further comprising a means for displaying a three-dimensional graphic display of a molecule.

BRIEF DESCRIPTION OF THE DRAWINGS

FIG. 3 is a photograph showing a three-dimensional structure of a crystal of a dipeptidyl peptidase IV displayed by the program QUANTA (Accelrys, Inc.).

FIG. 4 is a drawing showing a three-dimensional coordinate of a crystal of a dipeptidyl peptidase IV comprising residues 33-766 of the full-length human dipeptidyl peptidase IV of SEQ ID NO: 2.

BEST MODE FOR CARRYING OUT THE INVENTION

Figure 1:
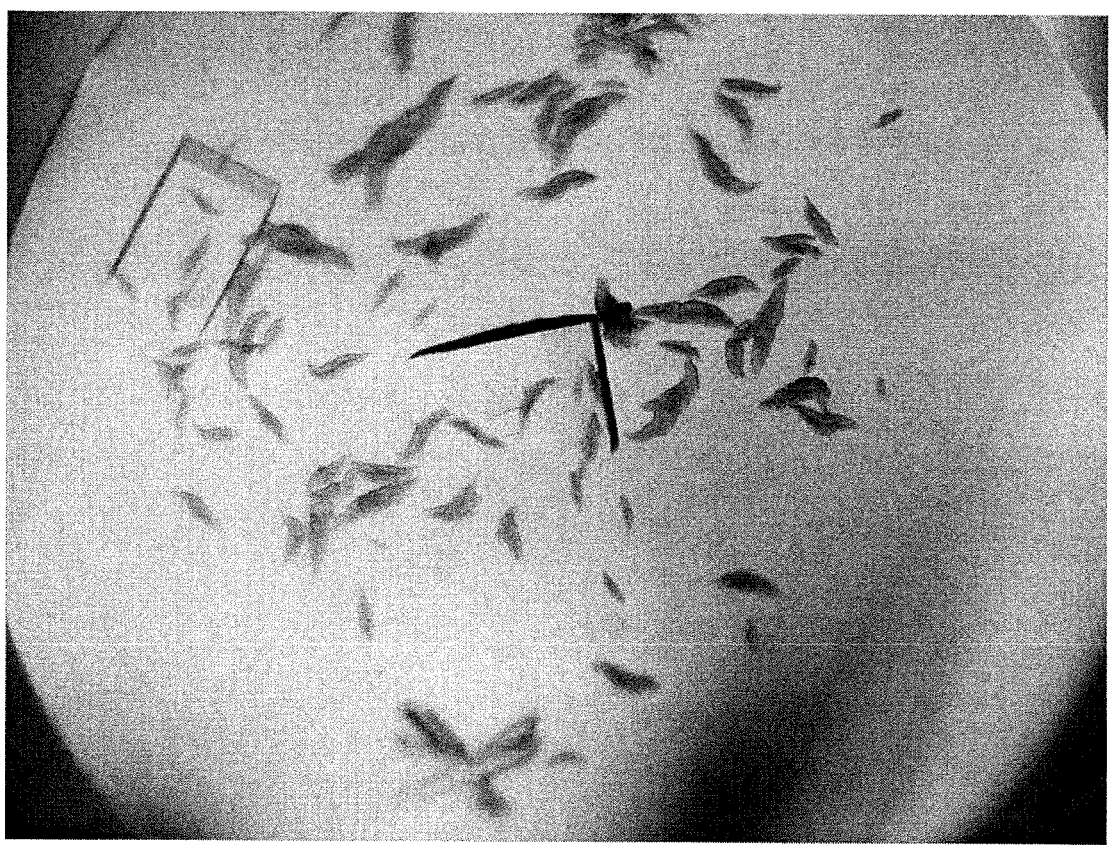
FIG. 1 is a photomicrograph of a crystal of a dipeptidyl peptidase IV, wherein the field of view is 4000 μm×3000 μm.

In the present specification, amino acid residues are expressed by using the following abbreviations, which have been adopted by the IUPAC-IUB Commission on Biochemical Nomenclature (CBN). Also, unless explicitly otherwise indicated, the amino acid sequences of peptides and proteins are identified from N-terminal to C-terminal, left terminal to right terminal, the N-terminal being identified as a first residue. Ala: alanine residue; Asp: aspartate residue; Glu: glutamate residue; Phe: phenylalanine residue; Gly: glycine residue; His: histidine residue; Ile: isoleucine residue; Lys: lysine residue; Leu: leucine residue; Met: methionine residue; Asn: asparagine residue; Pro: proline residue; Gln: glutamine residue; Arg: arginine residue; Ser: serine residue; Thr: threonine residue; Val: valine residue; Trp: tryptophane residue; Tyr: tyrosine residue; Cys: cysteine residue.

The crystal of the present invention is a crystal of a dipeptidyl peptidase IV, having a characteristic sufficient to ensure a resolution capable of analyzing its three-dimensional structure up to the side chain level by X-ray crystallographic structural analysis.

The "characteristic sufficient to ensure a resolution capable of analyzing three-dimensional structure up to the side chain level" is, for example, (1) being in a state that a molecule in a unit cell of a crystal has repeats with high regularity, namely, providing diffraction at high resolution;

(2) having suitable form and size; it is desired that for example, a crystal has at least one side grown to about 0.2 to about 0.5 mm, preferably a cubic crystal having three sides that have similarly grown, or a needle-shaped crystal having a width or thickness of about 0.2 mm or more;

(3) having chemical stability, dynamic stability and physical stability; and the like. In a case of the dipeptidyl peptidase IV, which is a polypeptide having a relatively large molecular weight, the term means characteristics sufficient to ensure a resolution of 3 Å or less, preferably 2.8 Å or less, more preferably 2.6 Å or less.

The dipeptidyl peptidase IV used for the preparation of the crystal of the present invention may have a high purity sufficient for forming the crystal. In the present invention, the dipeptidyl peptidase IV used for the preparation of the crystal includes a soluble polypeptide consisting of a region located at extramembrane in a full-length human dipeptidyl peptidase IV (SEQ ID NO: 2), for example, a polypeptide in which a transmembrane region in the N-terminal side [namely the region including the transmembrane sites (the region containing at least the amino acid nos: 1-28 of SEQ ID NO: 2, preferably the region of the amino acid nos: 1-32)] is deleted from the amino acid sequence of a full-length human dipeptidyl peptidase IV of SEQ ID NO: 2, and a tag peptide is optionally added to a C-terminal side or N-terminal side of the amino acid sequence. Concrete examples include (I) a polypeptide in which a transmembrane region in the N-terminal side is deleted from the amino acid sequence of a full-length human dipeptidyl peptidase IV of SEQ ID NO: 2; and (II) a polypeptide in which a tag peptide is added to a C-terminal side or N-terminal side of the polypeptide of the above (I). In the polypeptide, since the transmembrane site is deleted therefrom, the polypeptide has excellent characteristics that anchoring to the membrane can be prevented, and the polypeptide is a secretory type and soluble. The tag peptide is not particularly limited. For example, a polyhistidine peptide (an oligopeptide consisting of 4 to 20 of histidine residues) or the like can be preferably used as the tag peptide.

SEQ ID NO: 2 shows the amino acid sequence of a full-length dipeptidyl peptidase IV of human colon.

The full-length dipeptidyl peptidase IV means a polypeptide of a dipeptidyl peptidase IV containing a region comprising a transmembrane site in the N-terminal side. The full-length dipeptidyl peptidase IV includes a polypeptide comprising the amino acid sequence of SEQ ID NO: 2, without being limited thereto, and encompasses its naturally occurring variant, artificially modified variant, a homolog and an ortholog derived from heterogeneous organism, and the like.

Concretely, the full-length dipeptidyl peptidase IV, besides the polypeptide comprising the amino acid sequence of SEQ ID NO: 2, includes conservative substitution variants, naturally occurring allelic variants and the like. Also, the full-length dipeptidyl peptidase IV includes a polypeptide having at least one, namely one or more conservative amino acid substitutions, as compared to the polypeptide comprising the amino acid sequence of SEQ ID NO: 2.

The polypeptide as described above may be a polypeptide having biological activities (namely dipeptidyl peptidase IV activity) similar to the polypeptide comprising the amino acid sequence of SEQ ID NO: 2. Concretely, there are included, for instance, a polypeptide having homology of usually about 80% or more, preferably about 90% or more, more preferably about 95% or more on the amino acid level, as compared to the full-length amino acid sequence of SEQ ID NO: 2; a polypeptide encoded by a nucleic acid capable of hybridizing with a nucleic acid consisting of the nucleotide sequence of SEQ ID NO: 1 (nucleotide sequence encoding a full-length dipeptidyl peptidase IV of human colon), under stringent conditions, or a complement thereof; and a polypeptide having deletion, substitution or addition of at least one amino acid, namely one or plural amino acids, preferably one or several amino acids in the amino acid sequence of SEQ ID NO: 2.

The number of deletion, substitution or addition of the amino acids may be to an extent that the biological activities [namely, dipeptidyl peptidase IV activity] are not lost, usually in the number of 1 to about 150, preferably 1 to about 75, more preferably 1 to about 40.

The crystallization is carried out by making a solution containing the desired protein (referred to as a protein solution) supersaturated state, based on the characteristics that the protein in solution state converts to non-soluble state and precipitates as a crystal when specific conditions are satisfied. Concretely, the protein can be precipitated by the following procedures 1. or 2.:

1. Elevating the Effective Concentration of the Protein:
concretely, adding a precipitant such as a salt, polyethylene glycol or an organic solvent to a protein solution; reducing an amount of a solvent in the protein solution by evaporation or the like; or the like.

2. Reducing a Repulsive Force, or Increasing an Attractive Force Between Protein Molecules:
concretely, adding an organic solvent such as an alcohol to a protein solution; changing a hydrogen ion concentration (pH) or temperature of the protein solution; or the like.

As the conditions for the crystallization, physical and chemical factors such as a hydrogen ion concentration (pH), a kind of buffer used and a concentration thereof, a kind of a precipitant added and a concentration thereof, protein concentration, salt concentration, temperature and the like can be involved. A method for controlling and investigating the factors includes batch methods, dialysis methods, vapor diffusion methods (hanging-drop method, sitting-drop method and the like) and the like, described, for instance, in Blundell, T. L. et al., *PROTEIN CRYSTALLOGRAPHY*, 59-82 (1976), published by Academic Press, or the like.

The method for crystallization includes the batch methods, dialysis methods, vapor diffusion methods and the like. By the above method, physical and chemical factors such as a hydrogen ion concentration (pH), a kind and a concentration of the buffer used, and a kind and a concentration of the precipitant used, and physical and chemical factors such as protein concentration, salt concentration and temperature can be also determined.

The hydrogen ion concentration (pH) can be adjusted with a buffer. It is desired that the buffer is a buffer having buffering action in a broad range of pH, and being capable of suppressing precipitation of a non-proteinous crystal between the co-existing ion in the solution used during crystallization and the precipitant or the like. The buffer includes Tris-hydrochloric acid buffer, phosphate buffer, cacodylate buffer, acetate buffer, citrate buffer, glycine buffer and the like.

The precipitant may be a substance capable of elevating an effective concentration of the protein or changing a hydrogen ion concentration (pH) of the protein solution. Generally, the precipitant includes salts such as ammonium sulfate, sodium sulfate, sodium phosphate, potassium phosphate, sodium citrate, ammonium citrate, sodium chloride, potassium chloride and ammonium chloride; polyethylene glycols having various average molecular weights of about 200, about 1000, about 2000, about 4000, about 6000, about 8000, about 20000 or the like; organic solvents such as 2-methyl-2,4-pentadiol, methanol, ethanol, isopropanol, butanol and acetone, and the like.

The protein concentration may be a concentration suitable for crystallization, and it is desired that the protein concentration is, for example, 1 to 50 mg/ml, preferably 5 to 20 mg/ml, more preferably 7 to 15 mg/ml.

It is desired that the temperature conditions are 3° to 25° C., preferably 12° to 22° C.

In the case where the crystallization is carried out by the batch method, the crystallization can be carried out by gradually adding a precipitant solution comprising a precipitant, buffer and the like, so as to form a layer on the top layer of the solution containing the dipeptidyl peptidase IV to give a mixture, or by gradually adding the solution comprising the dipeptidyl peptidase IV, so that the solution is an upper layer of the precipitant solution to give a mixture. Here, the mixture is allowed to stand in a tightly closed vessel.

In the case where the crystallization is carried out by the dialysis method, the crystallization can be carried out by placing a solution comprising dipeptidyl peptidase IV in a size exclusion semi-permeable membrane, and placing a precipitant solution outside of the size exclusion semi-permeable membrane as a reservoir solution, thereby diffusing the reservoir solution to the solution comprising the dipeptidyl peptidase IV via the semi-permeable membrane.

In the case where the crystallization is carried out by the hanging-drop method in the vapor diffusion method, the crystallization can be carried out by placing a mixed solution of a solution comprising the dipeptidyl peptidase IV and a precipitant solution in a closed vessel allowing to be hanged at a position above the upper space of a reservoir in which the precipitant solution is contained as a reservoir solution, wherein the vapor pressure of the reservoir solution in the reservoir is set to be lower than that of the mixed solution.

In the case where the crystallization is carried out by the sitting-drop method in the vapor diffusion method, the crystallization can be carried out by placing a mixed solution comprising a solution comprising the dipeptidyl peptidase IV and a precipitant solution in a closed vessel at a position higher than the liquid surface of a reservoir in which the precipitant solution is contained as a reservoir solution, wherein the vapor pressure of the reservoir solution in the reservoir is set to be lower than that of the mixed solution.

The crystallization can be carried out by the sitting-drop method from the viewpoint of obtaining excellent-quality and large crystal.

When the obtained crystal is a crystal insufficient to ensure the X-ray structural analysis, the crystal may be grown by a seeding method such as macro-seeding method or micro-seeding method, using the obtained crystal as a seed crystal.

When the macro-seeding method is performed, it is desired that the seed crystal is a single crystal that can be isolated by procedures under microscope wherein the seed crystal has excellent external form (having excellent crystallinity). Also, it is desired that the seed crystal is washed with a drop of a solution obtained by diluting the precipitant, for example, by 0.5 to 1.0-fold. It is desired that the solution used for seeding of the seed crystal is a protein solution having a degree of supersaturation that the crystal grows but the crystal nuclei do not grow. On the other hand, when the micro-seeding method is performed, the form and size of the seed crystal are not particularly limited.

The sequence information for the dipeptidyl peptidase IV and cDNA encoding the dipeptidyl peptidase IV can be obtained from a known information source [GenBank/EMBL accession No: X60708; Misumi et al., *Biochim. Biophys. Acta*, 1131, 333-336, (1992); GenBank/EMBL accession No: M80536; Darmoul et al., *J. Biol. Chem.*, 267, 4824-4833, (1992)]. Therefore, the dipeptidyl peptidase IV or a soluble polypeptide thereof can be produced by using conventional means for gene engineering on the basis of the above sequence information.

The nucleic acid used for production of the dipeptidyl peptidase IV or a soluble polypeptide thereof may be any nucleic acid in which the encoded polypeptide exhibits a dipeptidyl peptidase IV activity. For example, a nucleic acid encoding a polypeptide consisting of the amino acid sequence in which a transmembrane region in the N-terminal side (a region containing at least the amino acid nos: 1-28, preferably the region of the amino acid nos: 1-32) is deleted from the full-length human dipeptidyl peptidase IV SEQ ID NO: 2, and a tag peptide is optionally added to a C-terminal side or N-terminal side of the amino acid sequence.

The nucleic acid can be obtained by, for instance, obtaining a fragment comprising a nucleic acid encoding a full-length dipeptidyl peptidase IV or a part thereof by means of conventional DNA recombination technique, and appropriately arranging the obtained fragment.

SEQ ID NO: 1 shows a sequence of a nucleic acid encoding a full-length dipeptidyl peptidase IV of human colon.

The nucleic acid (DNA or RNA) encoding a full-length dipeptidyl peptidase IV includes, for instance, a nucleic acid comprising human nucleic acids comprising the nucleotide sequence of SEQ ID NO: 1 without being limited thereto, and includes its naturally occurring variant, artificially modified variant, a homolog or ortholog derived from heterogeneous organism.

In other words, besides the nucleic acid comprising the nucleotide sequence of SEQ ID NO: 1, the nucleic acid includes a nucleic acid capable of hybridizing with a nucleic acid comprising the nucleotide sequence of SEQ ID NO: 1 under stringent conditions, more preferably under high-stringent conditions), or a complement thereof (nucleic acid having a complementary sequence).

Concrete examples of the nucleic acid described above include, for instance, a nucleic acid having usually about 70% or more, preferably about 80% or more, more preferably about 85% or more, still more preferably about 90% or more, still more preferably about 95% or more, homology to the nucleotide sequence of SEQ ID NO: 1, and it is preferable that the polypeptide encoded by the above nucleic acid has a dipeptidyl peptidase IV activity.

The dipeptidyl peptidase IV activity can be measured by, for example, incubating in a 1.5 ml reaction mixture [composition: 1.5 mM substrate (Gly-Pro-paranitroanilide), 71 mM glycine-NaOH (pH 8.7)] at 37° C. for 10 minutes, and determining the liberated paranitroanilide at the absorbance of 405 nm. One unit (1 U) of a dipeptidyl peptidase IV is defined as an amount of the enzyme required for liberating 1 µmol of paranitroanilide per 1 minute.

In the present invention, the hybridization under stringent conditions can be carried out as normal stringent conditions by performing hybridization in a hybridization solution having a salt concentration of 6×SSC or an equivalent concentration thereto, under the temperature conditions of 50° to 70° C. for about 16 hours, and optionally performing pre-washing with a solution having a salt concentration of 6×SSC or an equivalent concentration thereto, and thereafter performing washing with a solution having a salt concentration of 1×SSC or an equivalent concentration thereof. Furthermore, as the conditions having still higher stringency (high-stringent conditions), the hybridization can be carried out by washing with a solution having a salt concentration of 0.1×SSC or an equivalent concentration thereto in the above method.

The dipeptidyl peptidase IV used for the crystallization has purity that can form a crystal, and the purity can be confirmed by conventional means of confirming purity (for example, a method comprising electrophoresing a fraction by polyacrylamide gel electrophoresis, SDS-polyacrylamide gel electrophoresis or the like, and visualizing the fraction by silver staining, or the like).

The X-ray structural analysis data of the crystal can be obtained by subjecting the crystal of the present invention to an X-ray crystallographic structural analysis known to one of ordinary skill in the art [for example, see Blundell, T. L. et al., *PROTEIN CRYSTALLOGRAPHY*, 59-82 (1976), published by Academic Press, and the like], whereby a three-dimensional structural coordinate (a value showing the relationship of the spatial positions of each atom) and a three-dimensional structure model for the crystal can be obtained. Concretely, the three-dimensional structural coordinate of the dipeptidyl peptidase IV is obtained as an atomic coordinate by procedures comprising the steps of 1) irradiating the crystal of the present invention with a monochromatic X-ray to give an X-ray diffraction pattern, 2) obtaining X-ray diffraction intensity data from the X-ray diffraction pattern, 3) obtaining an electron density map by Fourier transform, and 4) allocating a polypeptide chain and side chain thereof on the electron density map based on the amino acid sequence of the polypeptide used for the crystal. Furthermore, the three-dimensional structure is clarified by molecule-modeling based on the three-dimensional structural coordinate. Therefore, the three-dimensional structural coordinate of the dipeptidyl peptidase IV obtained from the crystal of the present invention is also encompassed within the scope of the present invention.

The crystallographic parameters for the crystal are obtained from the X-ray diffraction intensity data of the crystal of the present invention. The crystal of the present invention is an orthorhombic crystal having a space group of $P2_12_12_1$, and a lattice constant of the unit cell of $|a|=118.0\pm5.0$ Å, $|b|=125.9\pm5.0$ Å, $|c|=136.8\pm5.0$ Å, and $\alpha=\beta=\gamma=90°$. The crystal has a 2.6 Å resolution by X-ray crystallographic structural analysis, that is, the crystal has characteristics sufficient to ensure a resolution capable of analyzing up to the side chain level of the polypeptide.

It is a known fact to one of ordinary skill in the art that the same protein can be crystallized even under different conditions. Therefore, the present invention is not limited to only the conditions for crystallization, and the crystal that shows substantially the same crystallographic constants as those in the present invention are also encompassed within the scope of the present invention.

More concretely, the crystal of the dipeptidyl peptidase IV of the present invention has a structural coordinate as shown in FIG. 4, or a structural coordinate different from the structural coordinate as shown in FIG. 4 via fluctuation of a protein.

The crystal according to the present invention can also be used as a seed crystal for carrying out the crystallization of a polypeptide having a three-dimensional structure similar to that of the dipeptidyl peptidase IV used for, for example, carrying out the crystallization of the dipeptidyl peptidase IV, dipeptidyl peptidase IV-like proteins, homolog proteins and the like, which are derived from other organism species.

When the crystal of the present invention is irradiated with X-ray, a low-temperature measurement may be carried out, as described in Examples set forth below.

The X-ray structural analysis data are converted to a structure factor by evaluating the intensity of X-ray diffraction using MOSFILM Program Package (Version 6.1). Also, in order to obtain the information for the phase, multiple isomorphous replacement method or the like can be performed, for example, as described in Examples.

In the structural analysis, CCP4 (Collaborative Computational Project, Number 4, 1994, "*The CCP4 Suite: Programs for Protein Crystallography,*" *Acta Cryst*. D50, 760-763) program or the like is used.

The three-dimensional structural coordinate of the dipeptidyl peptidase IV of the present invention can be obtained, for example, as follows. Firstly, Fourier transform calculation is carried out using the differences between the diffraction intensity obtained from two kinds of isomorphous replacement crystals of mercury and the diffraction intensity obtained from native crystal, and investigating the large peaks provided by the heavy atoms (mercury) on the Patterson's diagram to determine the locations of each mercury atoms in the unit cell of the real space. The phase of the crystal structure factor for the native crystal is determined using the obtained location coordinate for the mercury atoms. Furthermore, refinement is performed using the crystal structure factor of the native crystal and two kinds of the crystal structure factors of the isomorphous replacement crystals of mercury, and the coordinate for each of the mercury atoms is more accurately determined. An electron density map for the crystal of the dipeptidyl peptidase IV in the real space is obtained using the phase of the crystal structure factor of the native crystal calculated from the refined mercury atoms coordinate. Furthermore, the electron density map is improved by performing smoothing and histogram matching for the electron density map of the solvent region, whereby an electron density map necessary and sufficient for building a molecular model can be obtained. Next, the sites corresponding to the amino acid residues of the dipeptidyl peptidase IV on the electron density map are identified using QUANTA (manufactured by Accelrys, Inc.) to build the molecular model to give a three-dimensional structural coordinate.

The three-dimensional structural coordinate of the dipeptidyl peptidase IV of the present invention is shown in FIG. 4. FIG. 4 shows the obtained three-dimensional structural coordinates, according to the format of the Protein Data Bank, which is a notation generally used by one of ordinary skill in the art.

The three-dimensional structural coordinates shown in FIG. 4 are those represented using the origin of the unit cell of the crystal as the origin of the three-dimensional space. The R factor that is considered as an index for the accuracy of the obtained molecular model is 24.89%, and the free R factor is 30.15%. In addition, the deviation in the interatomic bond distance from the ideal state of the three-dimensional structure (rms-deviation) and the deviation in the bond angle are 0.006 Å and 1.305°, respectively. In the case, for instance, the three-dimensional structural coordinate of the present invention is used for the calculation by a computer, a novel structural coordinate obtained as a result of the operation for mathematical transfer, such as translation, rotation, or symmetry in the three-dimensional space without changing the relative configuration of the atoms, is also encompassed within the scope of the present invention. Furthermore, not only all of the three-dimensional structural coordinate of the present invention but also a part thereof are also encompassed within the scope of the present invention.

The three-dimensional structural coordinate of the dipeptidyl peptidase IV of the present invention can be used, for example, as shown in FIG. 3, for three-dimensional graphic displaying of the stereogram of the three-dimensional structure model, and for evaluation of the structure-activity relationship and the quantitative structure-activity relationship. Also, the structural features of the crystal of the present invention can be more concretely shown using the three-dimensional structural coordinate shown in FIG. 4. The evaluation of the structure-activity relationship or quantitative structure-activity relationship by the three-dimensional structure model is also encompassed within the scope of the present invention.

According to the three-dimensional structural coordinate of the dipeptidyl peptidase IV of the present invention, one of the characteristics of the dipeptidyl peptidase IV can be found in that the dipeptidyl peptidase IV has 273 molecules of bond water in an asymmetric unit and has 5 molecules of N-acetylglucosamine residues per 1 molecule of the dipeptidyl peptidase IV.

According to the three-dimensional structural coordinate of the dipeptidyl peptidase IV of the present invention, the information for atoms or atomic groups of the side chain of the dipeptidyl peptidase IV, interacting with the atoms or atomic groups of a known effector of the dipeptidyl peptidase IV via an intermolecular interaction can be obtained.

Furthermore, according to the three-dimensional structural coordinate of the dipeptidyl peptidase IV of the present invention, the information of regions in the dipeptidyl peptidase IV that are susceptible to binding or intermolecular interaction with the effector can be obtained.

In addition, according to the three-dimensional structural coordinate of the dipeptidyl peptidase IV of the present invention, the information of the structure specific to the dipeptidyl peptidase IV, which is not found in proteins other than the dipeptidyl peptidase IV, can be obtained. Therefore, higher selectivity in the effector targeting a protein other than the dipeptidyl peptidase IV can be designed, when the effector also acts on the dipeptidyl peptidase IV.

The intermolecular interaction includes covalent bond, ionic interaction, ion-dipole interaction, dipole-dipole interaction, hydrogen bonding, van der Waals force, electrostatic interaction, hydrophobic interaction and the like.

In the present specification, the atoms or atomic groups of the effector and atoms or atomic groups of the side chain of the dipeptidyl peptidase IV, which interact with each other via intermolecular interaction, are referred to as "pharmacophore."

Also, according to the three-dimensional structural coordinate of the dipeptidyl peptidase IV of the present invention, the information for the structure specific for the dipeptidyl peptidase IV, which is not found in proteins other than the dipeptidyl peptidase IV, can be provided.

In addition, for example, when the measurement conditions are different in X-ray diffraction, or the three-dimensional structure of the complex in the solution is analyzed using multidimensional NMR, and the like, the three-dimensional structural coordinate may differ from that shown in FIG. 4. The three-dimensional structural coordinate varies depending on the fluctuation of protein and the like, and is encompassed within the scope of the present invention.

In the present specification, the "fluctuation of protein" means a state that is caused by molecular oscillation, temperature and the like, and accompanied with the structural change that can exhibit an activity for the dipeptidyl peptidase IV in a living body.

Also, according to the three-dimensional structural coordinate of the dipeptidyl peptidase IV of the present invention, one of the characteristics of the dipeptidyl peptidase IV resides in that the amino acid residues, Ser 630, Asp 708 and His 740, which are involved in the activity deduced by experiments by using various active inhibitors of the dipeptidyl peptidase IV, exist in the adjacent area, even though the amino acid residues exist in distant locations on the primary sequence. Concretely, the distance between the $O_{\delta 2}$ atom of Asp 708 and the $N_{\delta 1}$ atom of His 740, and the distance between the $N_{\epsilon 2}$ atom of His 740 and the $O_\gamma$ atom of Ser 630 are distances that can form hydrogen bonding.

Therefore, the present invention also includes a three-dimensional structural coordinate of the region in the dipeptidyl peptidase IV, which is involved in binding or interaction of the dipeptidyl peptidase IV with an effector thereof, including a three-dimensional structural coordinate of a region selected from the group consisting of the following (a) to (d):

(a) a region characterized by Ser 630, Asp 708 and His 740 in the amino acid sequence of SEQ ID NO: 2, and
    all or a part of a group of amino acid residues located in the adjacent area of each of the Ser 630, Asp 708 and His 740 in the structural coordinate shown in FIG. 4 or the three-dimensional structure model defined by the structural coordinate;

(b) a region characterized by Ser 630, Asp 708 and His 740 in the amino acid sequence of SEQ ID NO: 2, and
    all or a part of a group of amino acid residues comprising amino acids capable of maintaining physicochemical characteristics physiologically equivalent to each of amino acids of the group of amino acid residues located in the adjacent area of each of Ser 630, Asp 708 and His 740, in the structural coordinate shown in FIG. 4 or the three-dimensional structure model defined by the structural coordinate, (c) a region characterized by a group of amino acid residues comprising amino acids capable of maintaining physicochemical characteristics physiologically equivalent to each of Ser 630, Asp 708 and His 740 in the amino acid sequence of SEQ ID NO: 2, and
    all or a part of a group of amino acid residues located in the adjacent area of said group of the amino acid residue in the structural coordinate shown in FIG. 4 or the three-dimensional structure model defined by the structural coordinate; and (d) a region characterized by a group of amino acid residues comprising amino acids capable of maintaining physicochemical characteristics physiologically equivalent to each of Ser 630, Asp 708 and His 740 in the amino acid sequence of SEQ ID NO: 2, and
    all or a part of a group of amino acid residues of a group of amino acid residues comprising amino acids capable of maintaining physicochemical characteristics physiologically equivalent to the each amino acid of the amino acid residues located in the adjacent area of said groups of the amino acids, in the structural coordinate shown in FIG. 4 or the three-dimensional structure model defined by the structural coordinate.

In the present specification, the "adjacent (area)" refers to an area involved in covalent bond, ionic interaction, ion-dipole interaction, dipole-dipole interaction, hydrogen bonding, van der Waals force, electrostatic interaction, hydrophobic interaction or the like with the amino acid residues, concretely, a region within 10 Å, preferably within 8 Å, more preferably within 5 Å.

The physicochemical characteristic includes features in shape of the three-dimensional structure, hydrophobicity, electric charge, pK and the like.

The "amino acid capable of maintaining physicochemical characteristics physiologically equivalent" may be an amino acid analogue residue obtained by replacing a side chain of amino acid residues in the three-dimensional structural coordinate shown in FIG. 4 with other side chain, for example, showing bioisosterism. Alternatively, the amino acid residue in the three-dimensional structural coordinate shown in FIG. 4, may be replaced with another amino acid residue belonging to the same Group, in any of the following Groups I to VI:

I glycine, alanine;

II valine, isoleucine, leucine;

III aspartic acid, glutamic acid, asparagine, glutamine;

IV serine, threonine;

V lysine, arginine;

VI phenylalanine, tyrosine.

According to the three-dimensional structural coordinate of the dipeptidyl peptidase IV of the present invention, a three-dimensional structural coordinate of a polypeptide can be easily derived if an accurate amino acid sequence is determined, even when the polypeptide is a dipeptidyl peptidase IV or a dipeptidyl peptidase IV-like protein derived from other organism species, as long as the polypeptide is a polypeptide having high homology on the level of amino acid sequence with the dipeptidyl peptidase IV used for the preparation of the crystal of the present invention (for example, at least 20%, preferably 30% or more, more preferably 40% or more).

Furthermore, the three-dimensional structural coordinate of the dipeptidyl peptidase IV of the present invention can be used for X-ray crystallographic structural analysis of the crystal and the like of other proteins having an amino acid sequence with significant homology with the dipeptidyl peptidase IV used for the preparation of the crystal of the present invention. Concretely, according to the molecular replacement method [for example, see Blundell, T. L. et al., *PROTEIN CRYSTALLOGRAPHY*, 446-464 (1976), published by Academic Press and the like], the three-dimensional structural coordinate thereof can be quickly and readily obtained from the structure factors obtained by the X-ray diffraction pattern of the crystal, without using multiple isomorphous replacement method, even for the determination of the structural coordinate of the above-mentioned crystal of which structural coordinate has not yet been known.

In the present specification, the term "significant homology" is a case where there is identity of 20%, or more, preferably by 30% or more, between the amino acid sequences.

When the molecular replacement method is performed, for example, a program such as X-PLOR and CNX (both manufactured by Accelrys Inc.) or AMORE [one of the programs of CCP4 (Collaborative Computational Project, Number 4), *Acta Crystallogr.* D50, 670-673 (1994)] can be run by a computer on which the program can be executed. Here, whether or not the molecular replacement method is applicable can be determined by actually applying the molecular replacement method to the structure factors calculated from the X-ray diffraction pattern of the desired crystal and obtaining a significant solution.

In other words, the three-dimensional structural coordinate obtained by structural analysis by molecular replacement method is encompassed within the scope of the present invention as long as a significant solution is obtained. The present invention also encompasses a three-dimensional structural coordinate of a dipeptidyl peptidase IV, or a dipeptidyl peptidase IV-like protein, namely a homolog protein or the like of other organism species derived by the above method.

Therefore, according to the present invention, a method for obtaining a three-dimensional structural coordinate of a homolog protein of a dipeptidyl peptidase IV comprising the step of performing refinement of an electron density map of the homolog protein of the dipeptidyl peptidase IV comprising the amino acid sequence of SEQ ID NO: 2, based on the three-dimensional structural coordinate of the present invention, to give a three-dimensional structural coordinate is provided. Also, a method for obtaining a three-dimensional structural coordinate of a crystal of a complex of a dipeptidyl peptidase IV and an effector of the dipeptidyl peptidase IV, based on the three-dimensional structural coordinate of the present invention, is likewise provided.

According to the three-dimensional structural coordinate of the dipeptidyl peptidase IV of the present invention, a method for identifying a region or site for a target for binding or interaction between the dipeptidyl peptidase IV and an effector of the dipeptidyl peptidase IV is provided, based on the analysis of the binding regions between the dipeptidyl peptidase IV and a known effector of the dipeptidyl peptidase IV such as an inhibitor, or based on the simulation of the interaction between the dipeptidyl peptidase IV and a known effector of the dipeptidyl peptidase IV.

Also, based on the three-dimensional structural coordinate of the dipeptidyl peptidase IV of the present invention and the steric conformation of the effector of the dipeptidyl peptidase IV, the pharmacophore of the effector of the dipeptidyl peptidase IV can be identified. A method for identifying the pharmacophore is also provided. The method is useful for designing an effector having excellent characteristics such as higher avidity, higher biological activity, higher biological stability, higher thermodynamic stability, higher absorbency to a living body, and lower toxicity.

Concretely, for example, the region or site for a target involved in binding or interaction of the dipeptidyl peptidase IV and an effector of the dipeptidyl peptidase IV, can be identified by:

1) obtaining a crystal of a complex of the dipeptidyl peptidase IV and a known effector of the dipeptidyl peptidase IV such as an inhibitor, and obtaining a three-dimensional structural coordinate of the crystal based on the three-dimensional structural coordinate of the dipeptidyl peptidase IV of the present invention and the steric conformation of the effector of the dipeptidyl peptidase IV, whereby obtaining the three-dimensional structural coordinate of a binding region of the dipeptidyl peptidase IV and the effector;

2) simulating an intermolecular interaction between the dipeptidyl peptidase IV and a known effector of the dipeptidyl peptidase IV based on the three-dimensional structural coordinate of the dipeptidyl peptidase IV of the present invention and the steric conformation of the effector of the dipeptidyl peptidase IV; or the like.

The crystal of the above-mentioned complex can be obtained by, for example, incubating the crystal of the present invention in a solution comprising the effector, forming a complex of the dipeptidyl peptidase IV and the effector, and crystallizing the obtained complex, and the like.

Also, when the three-dimensional structural coordinate of the crystal of the complex is obtained, the steric structure of the effector of the above-mentioned complex can be readily obtained by calculating the differential Fourier diagram utilizing a three-dimensional structure model defined by the three-dimensional structural coordinate of the dipeptidyl peptidase IV of the present invention, whereby specific interaction forms and interaction sites between the dipeptidyl peptidase IV and the effector can be readily clarified.

When the intermolecular interaction is simulated, for example, the space regions, residues and the like in which covalent bond, ionic interaction, ion-dipole interaction, dipole-dipole interaction, hydrogen bonding, van der Waals force, electrostatic interaction, hydrophobic interaction or the like can be simulated, based on the three-dimensional structural coordinate of the dipeptidyl peptidase IV of the present invention and the steric conformation of the effector of the dipeptidyl peptidase IV.

Furthermore, according to the three-dimensional structural coordinate of the dipeptidyl peptidase IV of the present invention, the three-dimensional structural coordinate or the three-dimensional structure model based on the three-dimensional structural coordinate regarded as an active center of the dipeptidyl peptidase IV, sites indirectly acting on the active center and regions or sites involved in binding or interaction with the effector, or the like, is obtained, whereby a compound capable of specifically acting on the dipeptidyl peptidase IV can be designed, identified, evaluated or searched.

For example, in the structural coordinate of FIG. 4 and the three-dimensional structure model defined by the structural coordinate, a compound capable of modifying the activity of the dipeptidyl peptidase IV can be designed, identified, evaluated or searched, based on the regions characterized by Ser 630, Asp 708 and His 740, and all or a part of amino acid residues of the group of the amino acid residues located in the adjacent area of the Ser 630, Asp 708 and His 740.

Therefore, according to the present invention, a method for designing, identifying, evaluating or searching an effector of the dipeptidyl peptidase IV is provided.

One of the significant features of the method of the present invention for designing, identifying, evaluating or searching an effector resides in that the method comprises designing, identifying, evaluating or searching a compound capable of acting on the dipeptidyl peptidase IV, based on the three-dimensional structural coordinate of the present invention.

According to the method of the present invention for designing, identifying, evaluating or searching an effector, since the method is based on the three-dimensional structural coordinate of the dipeptidyl peptidase IV of the present invention, the information for a structure specific to the dipeptidyl peptidase IV, which is not found in proteins other than the dipeptidyl peptidase IV can be obtained. Therefore, according to the method of the present invention for designing, identifying, evaluating or searching an effector, the method has an excellent effect that the selectivity of the effector of the dipeptidyl peptidase IV can be enhanced.

Also, according to the method of the present invention for designing, identifying, evaluating or searching an effector, since the method is based on the three-dimensional structural coordinate of the dipeptidyl peptidase IV of the present invention, visual studies and/or energy calculation can be made according to the method by using a computer and the like. Therefore, there are exhibited some excellent effects that a compound having excellent characteristics such as having higher avidity, higher biological activity, higher biological stability, higher thermodynamic stability, higher absorbency in a living body, and lower toxicity, than those for a known inhibitor can be designed, identified, evaluated or searched, and that logical design can be performed in the three-dimensional space.

In the present specification, the "effector" includes a compound that inhibits or enhances the activity (i.e. inhibitor or activator), which may be natural compounds or synthetic compounds, or may be polymers or low-molecular weight compounds.

A concrete example of the method of the present invention for designing, identifying, evaluating or searching an effector includes a method comprising the steps of:

(i) identifying a region to be targeted for binding or interaction with the effector in a dipeptidyl peptidase IV, based on all and/or a part of the three-dimensional structural coordinate of the present invention and the steric conformation of the effector of the dipeptidyl peptidase IV;

(ii) identifying corresponding atoms or atomic groups capable of generating in the region at least one intermolecular interaction selected from the group consisting of covalent bond, ionic interaction, ion-dipole interaction, dipole-dipole interaction, hydrogen bonding, van der Waals force, electrostatic interaction and hydrophobic interaction, with the atoms or atomic groups existing in a candidate compound; and (iii) designing a compound based on the above information of the above step (i) and/or (ii).

The three-dimensional structural coordinate used for designing, identifying, evaluating or searching a compound capable of binding to the dipeptidyl peptidase IV may be a coordinate fixed in the three-dimensional space, and the intensity of binding with the compound or the like can be calculated by carrying out translation or rotation in the three-dimensional space, and transfer to an extent that the chemical covalent bond would not be cleaved in the amino acid residues of the dipeptidyl peptidase IV.

In the above step (i), the "region to be targeted in the dipeptidyl peptidase IV" preferably includes an active center of the dipeptidyl peptidase IV, sites indirectly acting on the active center and the like. For example, there is included a region characterized by Ser 630, Asp 708 and His 740 and all or a part of a group of the amino acid residues located in the adjacent area of Ser 630, Asp 708 and His 740, and the like in the structural coordinate of FIG. 4 and the three-dimensional structure model defined by the structural coordinate. The atoms or atomic groups that can be matched therewith are identified, based on the three-dimensional structural coordinate of an active center, sites indirectly acting on the active center and the like, whereby the candidate atoms or candidate atomic groups can be obtained.

In the above step (ii), for example, the atoms or atomic groups capable of associating via intermolecular interaction between the atoms or atomic groups in the region, concretely, the corresponding atoms or atomic groups capable of generating covalent bond, ionic interaction, ion-dipole interaction, dipole-dipole interaction, hydrogen bonding, van der Waals force, electrostatic interaction, hydrophobic interaction and the like, are searched and extracted, based on the information identified in the above step (i).

Next, in the above step (iii), the corresponding atoms or atomic groups searched in the above step (i) and/or (ii) are combined to design a compound.

Thereafter, if desired, whether or not the compound designed in the above step (iii) is matched via intermolecular interaction with the side chains and atoms or atomic groups in the dipeptidyl peptidase IV as defined by the three-dimensional structural coordinate of the present invention can be simulated.

The compound designed, identified, evaluated or searched by the above steps (hereinafter also referred to as a candidate compound in the present specification) can be obtained by generally used chemical synthetic methods, depending on the compound.

In addition, in the method of the present invention for designing, identifying, evaluating or searching an effector, there can be carried out a step of detecting the interaction between the dipeptidyl peptidase IV and the candidate compound. When the interaction is detected, the interaction serves as an index showing that the above candidate compound is a compound capable of binding to the dipeptidyl peptidase IV.

The above interaction can be detected by, for example, plasmon resonance analysis apparatus, mass spectrometer, titration isothermal calorimetry, NMR and the like. For example, in the case of plasmon resonance analysis apparatus, when a sensorgram indicates the formation of a complex, by contacting the dipeptidyl peptidase IV-immobilized matrix with the candidate compound and performing analysis by optical detection (for example, photometer, polarization photometer and the like) and the like, it would be an index showing that the interaction between the candidate compound and the dipeptidyl peptidase IV is generated. For example, in the case of a mass spectrometer, when a spectrum indicates the formation of a complex, by contacting the dipeptidyl peptidase IV-immobilized matrix with the candidate compound and performing analysis with a mass spectrometer (matrix-assisted laser desorption/ionization-time of flight mass spectrometry: MALDI-TOF MS, electro spray-ionization mass spectrometer: ESI-MS and the like), it would be an index showing that the interaction between the candidate compound and the dipeptidyl peptidase IV is generated. For example, in the case of titration-thermal calorimetry interaction analysis, when the titration curve indicates the formation of a complex, by contacting a solution of the dipeptidyl peptidase IV with the candidate compound, and measuring the heat coming in and out of a thermal diode and the like, it would be an index showing that the interaction between the candidate compound and dipeptidyl peptidase IV is generated. For example, in the case of NMR, when a spectrum indicates the formation of a complex, by analyzing by NMR a solution prepared mixing the dipeptidyl peptidase IV and a candidate compound, it would be an index showing that the interaction between the candidate compound and the dipeptidyl peptidase IV is generated.

Furthermore, the method of the present invention for designing, identifying, evaluating or searching an effector may further comprise the steps of contacting the dipeptidyl peptidase IV with a candidate compound, and thereafter measuring the activity of the dipeptidyl peptidase IV. When the dipeptidyl peptidase IV activity increases or decreases, it would be an index showing that the candidate compound is a compound having enhancing action or inhibitory action on the activity of the dipeptidyl peptidase IV.

The dipeptidyl peptidase IV activity can be measured by, for example, incubating a 1.5 ml reaction mixture [composition: 1.5 mM substrate (Gly-Pro-paranitroanilide), 71 mM glycine-NaOH (pH 8.7)] at 37° C. for 10 minutes in the presence of a candidate compound, and measuring the liberated paranitroanilide at the absorbance of 405 nm. During the measurement of the activity, the candidate compound may be evaluated by using a reaction system in which a suitable dilution series of the compound is added thereto.

The method of the present invention for designing, identifying, evaluating or searching the effector can be performed by, for example, sequentially selecting the interaction between the dipeptidyl peptidase IV and the compounds in a database in a computer to which the structures of plural of compounds had been inputted, or the interaction between the dipeptidyl peptidase IV and the designed compound, by visual methods (visual selection method) utilizing the database; and/or sequentially calculating the avidity with a computer, and searching a compound capable of stably interacting with the dipeptidyl peptidase IV from the database (computer-assisted avidity evaluation method) and the like, based on the three-dimensional structural coordinate of the present invention.

In the above visual selection method, the database of the structures of compounds may be a database in which the three-dimensional structural coordinates have been determined and inputted. Alternatively, in the case of a compound having a low molecular weight, the database may be a database in which the information for chemical covalent bond of a compound having a low molecular weight had been inputted, because the conformation can be relatively freely changed, and the three-dimensional structural coordinate of each conformation can be derived by calculation in a relatively short time.

Concretely, in the visual selection method, the expected complex between the dipeptidyl peptidase IV and a candidate compound or a part thereof is firstly displayed on a computer screen, based on the three-dimensional structural coordinate of the present invention. Next, the intermolecular interaction binding between a compound in the database and the binding regions of the dipeptidyl peptidase IV is simulated on the computer, taking chemical interaction into consideration. Also, the simulation of the chemical modification of the compound is performed on the computer, and the changes in the interaction caused as a result thereof are observed on the computer screen. During the simulation, the three-dimensional space can be more easily understood by displaying the three-dimensional structure of the protein on the computer screen so that the structure corresponds to Crystal Eye glasses supplied by Silicone Graphics; simultaneously displaying two screens in which each angle is adjusted for displaying the object, according to the visual fields of the right eye and left eye, which is so-called referred to as "stereovision" which is frequently used by one of ordinary skill in the art; or the like. In addition, the three-dimensional structure can be visually studied by methods other than the stereoscopic displaying of the three-dimensional structure.

The candidate compound capable of generating suitable interaction can be obtained by displaying on a computer a group of candidates with appropriate conformation and selecting an appropriate one therefrom; calculating a structure having a low energy state on a computer; or the like. Next, a derivative of a compound capable of generating more preferable binding with the dipeptidyl peptidase IV may be searched among the candidate compound.

More specifically, on the level of the three-dimensional structure, the followings may be taken into consideration:

1 a group likely to be charged negatively, such as carboxyl group, nitro group, or a halogen group in the compound interacts with an amino acid residue having a positive charge, such as lysine, arginine or histidine in the dipeptidyl peptidase IV;

2 a group likely to be charged positively, such as amino group, imino group or guanidyl group in the compound interacts with an amino acid residue having negative charge, such as glutamic acid or aspartic acid in the dipeptidyl peptidase IV;

3 a hydrophobic functional group such as an aliphatic group or an aromatic group in the compound interacts with a hydrophobic amino acid residue such as alanine, leucine, isoleucine, valine, proline, phenylalanine, tryptophane or methionine in the dipeptidyl peptidase IV;

4 a group involved in hydrogen bonding, such as hydroxyl group or amide group is allowed to form hydrogen bonding with a main chain or side chain portion;

5 a group or an atom likely to be charged negatively, such as carboxyl group, nitro group or a halogen group in the compound interacts with a positively charged atom on a main chain or side chain portion;

6 a group or an atom likely to be charged positively, such as amino group, imino group or guanidyl group in the compound interacts with a negative charged atom on a main chain or a side chain portion;

7 the flexibility of the three-dimensional structure of the compound is lowered by, for instance, cyclizing the linear chain portion;

or the like. For example, a derivative may be designed and synthesized so that the atoms having negative charge of the candidate compound are located in the adjacent region of the side chain of an amino acid residue having positive charge such as lysine, arginine or histidine, in the amino acid residue of the dipeptidyl peptidase IV, and that an atom having positive charge of the candidate compound is located in the adjacent region of the side chain of the amino acid residue having negative charge such as glutamic acid or aspartic acid in the amino acid residue of the dipeptidyl peptidase IV. Also, a group suitable for forming a hydrophobic interaction may be introduced into the portion capable of forming a hydrophobic interaction between the compound and the dipeptidyl peptidase IV, to design and synthesize a derivative. In addition, a group suitable for forming hydrogen bonding may be introduced into the portion capable of forming hydrogen bonding between the compound and the dipeptidyl peptidase IV, to design and synthesize a derivative. In the above-mentioned designing, it is desirable that van der Waals interaction is as high as possible, and that steric hindrance does not occur between each of the atoms. Furthermore, it is desirable that new void portions are not produced by modification of the compound and that in regions already containing void portions, the void portions are filled as much as possible.

As described above, the design, identification, evaluation or searching of a final compound can be thus performed with visually comprehensively considering intermolecular interaction and other factors on a computer screen.

In the computer-assisted avidity evaluation method, in order to determine the validity for the designing of a new compound, and to obtain a compound that can stably interact from the compounds in the database, a docking software (DOCK, GOLD, FlexX, Glide or the like) is used for evaluation of binding based on the energy by calculating a molecular force field between the compound and the dipeptidyl peptidase IV, evaluation of binding based on chemical characteristics, evaluation of binding based on the Protein Data Bank (PDB), and the like. Further, in a model system consisting of the compound and the dipeptidyl peptidase IV, or in a model system further comprising solvent molecules and the like, it can be led to a compound that can stably interact by obtaining the index showing avidity, such as free energy of bonding, the ratio obtained from bond state number and non-bond state number, and the like by using molecular kinetic calculation or Monte Carlo calculation. The programs for calculation of molecular force field and molecular kinetic include AMBER, CHARMm, DISCOVER, PRESTO and the like, and the force field used includes AMBER, CHARMm, OPLS, MMCF, CVFF and the like. Furthermore, a program such as Ludi which automatically outputs the candidates for a candidate compound by providing a three-dimensional structural coordinate of the amino acid residues interacting in the dipeptidyl peptidase IV may be used.

The visual selection method and computer-assisted avidity evaluation method can be performed alone or in combination. In the case of performing the methods in combination, the avidity is actually calculated for the compounds that has been expected to be more desirable in visual investigation, and the validity thereof is evaluated. By repeatedly performing the calculation and evaluation, more excellent compounds may be designed, identified, evaluated or searched.

Next, the designed, identified, evaluated or searched compound is optimized to be a more excellent compound, such as a compound having more excellent characteristics as a medicament, such as being excellent in vivo kinetics, having low toxicity and low side-effect; a compound having a still higher biological activity as an effector; a compound having an advantageous structure as a medicament in view of its oral administration; and the like.

The resulting candidate compound can be obtained using generally used techniques for chemical synthesis depending on the kind of the compound.

The present invention also encompasses an effector of the dipeptidyl peptidase IV, which is obtained by the method of the present invention for designing, identifying, evaluating or searching an effector. When the effector is a compound capable of inhibiting or enhancing the activity of the dipeptidyl peptidase IV, the effector (inhibitor or activator) is expected to be an agent for, for example, a modulatory agent of immune response, a therapeutic or prophylactic agent for diabetes, inflammation, multiple sclerosis, Graves' disease, chronic rheumatoid arthritis, AIDS, cancer and the like.

The three-dimensional structural coordinate of the dipeptidyl peptidase IV of the present invention can be provided as a computer program, a medium or the like, which displays the three-dimensional structure of the molecule based on the three-dimensional structural coordinate and can be provided via a telecommunication line or the like. Therefore, using a computer or the like, the three-dimensional coordinate of the dipeptidyl peptidase IV can be displayed in detail, allowing to perform the method of the present invention for designing, identifying, evaluating or searching an effector more rapidly, conveniently and logically.

The present invention also encompasses a program or a medium therefor for use of the three-dimensional structural coordinate, in which all and/or a part of the three-dimensional structural coordinate of the dipeptidyl peptidase IV of the present invention is recorded.

The medium may be any of those in which the three-dimensional structural coordinate of the present invention can be derived on a program that runs on a computer, and includes, for instance, electric memory media referred to as memory; semi-permanent memory media such as a FD, a hard disk, an optical disk, an opto-magnetic disk and a magnetic tape, and the like. In addition, the program and the medium therefor for use of the three-dimensional structural coordinate of the present invention also encompass those having a form which can be communicated via a telecommunication line such as internet.

Also, the program and the medium therefor for use of the three-dimensional structural coordinate of the present invention may further comprise a means for displaying the three-dimensional graphic display of the molecule. The program or the medium therefor which comprises the means for displaying the three-dimensional graphic display has advantages that visual studies and/or calculation of avidity can be made more conveniently, so that there is more facilitated a logical design on the three-dimensional structural level for obtaining a compound having excellent characteristics such as higher avidity, higher biological activity, higher biological stability, higher thermomechanical stability, higher absorbency to a living body, and lower toxicity than those for known effectors of the dipeptidyl peptidase IV.

As the means capable of displaying the three-dimensional graphic display, there may be generally used a program that is made so that a means for inputting the three-dimensional structural coordinate of the molecule, a means for measuring visual representation of the coordinate on a computer screen, the distance between the represented atoms in the molecule, bond angles or the like, a means for addition or modification of the coordinate, and the like can be provided. Furthermore, there may be used a program that has been made so that a means for calculating the structure energy of the molecule based on the coordinate of the molecule, a means for calculating the free energy of bonding, and the ratio of bonding state number to non-bonding state number in consideration of solvent molecules such as water molecule can be provided. Examples of the program suitable for such purposes include Insight II, QUANTA and the like, which are computer programs commercially available from Accelrys Inc., and the present invention is not limited to these programs. Also, the above-mentioned programs can be introduced into a computer referred to as a work station supplied from Silicone Graphics Inc., SunMicro-Systems Ltd., or the like, and used.

According to the crystal of dipeptidyl peptidase IV of the present invention, there can be exhibited excellent effects that the three-dimensional structural coordinate can be obtained as an information for designing, identifying, evaluating or searching an effector of the dipeptidyl peptidase IV useful as a modulatory agent of immune response and as a therapeutic or prophylactic agent for diabetes, inflammation, multiple sclerosis, Graves' disease, chronic rheumatoid arthritis, AIDS, cancer and the like, and that the crystal of a complex of the dipeptidyl peptidase IV and a known effector can be readily prepared. Also, according to the three-dimensional structural coordinate of the present invention, there is exhibited an excellent effect that the effector can be designed, identified, evaluated or searched. In addition, according to the method for obtaining a three-dimensional structural coordinate of the homolog protein of the dipeptidyl peptidase IV of the present invention, there is exhibited an excellent effect that the three-dimensional structural coordinate of the homolog protein of the dipeptidyl peptidase IV of which three-dimensional structure is unknown can be conveniently and rapidly provided. Furthermore, according to the method for obtaining a three-dimensional structure of a crystal of a complex of the dipeptidyl peptidase IV of the present invention and an effector of the dipeptidyl peptidase IV, there is exhibited an excellent effect that the method can provide a target for designing an effector useful as a modulatory agent of immune response and as a therapeutic or prophylactic agent for diabetes, inflammation, multiple sclerosis, Graves' disease, chronic rheumatoid arthritis, AIDS, cancer and the like, and having excellent characteristics such as higher avidity, higher biological activity, higher biological stability, higher thermomechanical stability, and higher absorbency to a living body. Moreover, according to the method of the present invention for identifying a pharmacophore of the dipeptidyl peptidase IV and the effector of the dipeptidyl peptidase IV, there is exhibited an excellent effect that the method can provide a target for designing the effector useful as a modulatory agent of immune response and as a therapeutic or prophylactic agent for diabetes, inflammation, multiple sclerosis, Graves' disease, chronic rheumatoid arthritis, AIDS, cancer and the like, and having excellent characteristics such as higher avidity, higher biological activity, higher biological stability, higher thermomechanical stability, and higher absorbency to a living body. According to the method of the present invention for designing, identifying, evaluating or searching an effector of the dipeptidyl peptidase IV, there is exhibited an excellent effect that the method can logically and conveniently provide an effector useful as a modulatory agent of immune response and as a therapeutic or prophylactic agent for diabetes, inflammation, multiple sclerosis, Graves' disease, chronic rheumatoid arthritis, AIDS, cancer and the like, and having excellent characteristics such as higher avidity, higher biological activity, higher biological stability, higher thermomechanical stability, and higher absorbency to a living body. According to the effector of the dipeptidyl peptidase IV of the present invention, there are exhibited excellent effects that the effector is capable of modifying immune response and capable of treating or preventing diabetes, inflammation, multiple sclerosis, Graves' disease, chronic rheumatoid arthritis, AIDS, cancer and the like. Furthermore, according to the program and medium therefor of the present invention, there is exhibited an excellent effect that the method for designing, identifying, evaluating or searching an effector of the dipeptidyl peptidase IV can be performed more rapidly and conveniently.

The present invention will be hereinafter more specifically explained by the following Examples, but the present invention is not intended to be limited by the Examples in any way. Unless otherwise indicated, the reaction conditions, procedures and the like can be referred to the instruction manual attached to the reagents used, *Molecular Cloning A Laboratory Manual*, third edition, Sambrook et al. [issued by Cold Spring Harbor Laboratory Press (2001)], and the like.

EXAMPLE 1 CONSTRUCTION OF RECOMBINANT BACULOVIRUS FOR EXPRESSION OF SOLUBLE HUMAN DIPEPTIDYL PEPTIDASE IV (1) Cloning of Soluble Human Dipeptidyl Peptidase IV (shDPPIV) (Nucleotide Nos: 97-2298 of SEQ ID NO: 1) cDNA Caco-2 cells [provided by American Type Culture Collection (ATCC)] were cultured at 37° C. using Dulbecco's Modified Eagle Medium (manufactured by Invitrogen) containing 20% by volume of inactivated fetal bovine serum (manufactured by Invitrogen; inactivated by incubation at 56° C. for 30 minutes) and 1% by volume of nonessential amino acid (manufactured by Invitrogen), in the presence of 5% by volume of $CO_2$.

Next, total RNA was extracted from the Caco-2 cells obtained. Extraction of the total RNA was carried out using a product manufactured by Nippon Gene Co. Ltd. under the trade name of ISOGEN in accordance with the attached instruction manual. The obtained total RNA was used as a template for RT-nested PCR method described below.

In order to obtain a nucleic acid corresponding to a soluble human DPPIV from which the signal peptide sequence was removed (amino acid nos: 33-766 of SWISS-PROT Accession No: P27487), first, a cDNA fragment sequence of human DPPIV gene was amplified by RT-nested PCR method with total RNA of the Caco-2 as a template.

The thermal profile in the PCR is 30 cycles of reaction, in which one cycle comprises denaturation at 94° C. for 30 seconds, annealing at 55° C. for 30 seconds and polymerase extension reaction at 72° C. for 1 minute.

The amplified DNA fragment was separated by agarose gel electrophoresis method, and a small fragment of the gel of the corresponding band portions was cut out. Thereafter, the DNA fragment was extracted from the obtained small fragments of the gel using a product manufactured by Bio 101 under the trade name of GENE CLEAN SPIN Kit, and purified. The obtained fragment was inserted into vector pCR2.1-TOPO contained in TOPO TA Cloning (registered trade mark) Kit manufactured by Invitrogen to construct pCR-shDPPIV.

In order to confirm whether or not the obtained cDNA fragment encodes the desired polypeptide, deletion mutants regarding the DNA fragment having various lengths were prepared, and a nucleotide sequence for the DNA fragment was determined as follows.

First, a DNA fragment having a size of 2.2 kbp obtained by double digestion of the pCR-shDPPIV with BamHI and EcoRI was inserted into a corresponding restriction site in pUC19 (manufactured by Takara Bio Inc.), to construct a plasmid pUshDPPIV. Various deletion plasmids were prepared using the plasmid pUshDPPIV by a conventional method.

The nucleotide sequence for the DNA fragment was determined using the obtained deletion plasmid or plasmid pCR-shDPPIV, and a product manufactured by Perkin-Elmer Cetus Inc. under the trade name of TAQ DYEDEOXY Terminator Cycle Sequencing Kit and Model 373S sequencer manufactured by Applied Biosystems.

Also, the amino acid sequence of the polypeptide encoded by the above-mentioned DNA fragment was determined on the basis of the nucleotide sequence.

The determined amino acid sequence was compared with the sequence for a full length DPPIV of human colon shown in SEQ ID NO: 2. As a result, it was confirmed that the corresponding regions (regions excluding the transmembrane region) were identical.

Thus, it was confirmed that the DNA fragment encodes the desired polypeptide shDPPIV, namely a polypeptide in which the transmembrane region (amino acid nos: 1-32 at N-terminal side) in the full-length human DPPIV was deleted and a polyhistidine peptide was added to the C-terminal side.

(2) Preparation of Recombinant Baculovirus

Plasmid pUshDPPIV was digested with a restriction enzyme to give a DNA fragment encoding shDPPIV gene. The obtained fragment was inserted into pAcGP67B (manufactured by BD PharMingen) to construct a baculovirus transfer vector pAcGP67B-shDPPIV.

Fifteen minutes before the transfection, Sf2 cells were washed twice with a TNM-FH medium comprising 10% by volume of fetal bovine serum. The Sf21 cells were then transferred to a well of a 6-well plate by $2.4 \times 10^6$ cells per well.

Furthermore, 2 to 5 µg of the baculovirus transfer vector and a 0.5 µg linear baculovirus DNA (trade name: BACULOGOLD virus DNA, manufactured by BD PharMingen) were mixed, and the mixture was allowed to stand at room temperature for 5 minutes. Next, 1 ml of Transfection Buffer B (manufactured by BD PharMingen) was added to the obtained mixture, and the mixture was thoroughly mixed to give a Transfection Buffer B/DNA mixture.

The medium in the wells of the 6-well plate and the cells that had not been adhered to the wells were removed, and 1 ml of Transfection Buffer A (manufactured by BD PharMingen) was added to each of the wells. The Transfection Buffer B/DNA mixture was gradually added dropwise to the wells of the 6-well plate, with gently stirring the 6-well plate. The cells were incubated at 28° C. for 4 hours in the wells of the 6-well plate. Thereafter, the transfection buffer was removed, and 3 ml of TNM-FH medium containing 10% by volume of fetal bovine serum was added to the wells of the 6-well plate. The cells were cultured at 28° C. in each of the wells of the 6-well plate for 5 days, and the culture supernatant was collected. The culture supernatant was used for amplification of virus using Sf21 cells to give a virus stock solution.

EXAMPLE 2 PREPARATION AND CRYSTALLIZATION OF shDPPIV (1) Expression of shDPPIV in Insect Cells Sf21 cells were cultured using a serum free medium EX-CELL 400 (manufactured by JRH Biosciences) and T flask, and Tn5 cells (provided by Invitrogen) were cultured using a serum free medium EX-CELL 401 (manufactured by JRH Biosciences) and a T flask, at 28° C., respectively. At the time when the proliferation of the cells reached 70% confluent, the old medium was removed, and a fresh medium was added at 40 ml per one 225-cm² flask. Then, 1.5 ml of virus stock solution after amplification for three times (having multiplicity of infection (MOI) of about 2) was added to the cells to infect the cells, and the cells were incubated at 28° C. for 4 days. The culture supernatant four days after the infection was collected and stored at −20° C. The culture supernatant was used for the purification of shDPPIV protein as described below.

(2) Purification of shDPPIV Protein

In each step for the purification of shDPPIV, the activity of DPPIV was measured by incubating a 0.1 ml reaction mixture containing a 1.5 mM substrate [manufactured by Peptide Institute, Gly-Pro-paranitroanilide (pNA)], 71 mM Gly-NaOH (pH 8.7) and the DPPIV, and detecting the liberated pNA. Meanwhile, the reaction mixture was incubated at 37° C. for 10 minutes. During the incubation, the absorbance at 405 nm was monitored.

Also, the protein concentration was quantified by using a product manufactured by Bio-Rad Laboratories, Inc. under the trade name of DC protein Assay Kit II.

The purity of the protein was confirmed by subjecting a protein sample in each step to SDS-PAGE using 7.5% polyacrylamide gel according to the method by Laemmli et al.

The culture supernatant stored at −20° C. in the above-mentioned (1) was melted at 4° C. and filtered with a bottle top filter (manufactured by Becton, Dickinson and Company) or with 0.45 µm filter (KURABO INDUSTRIES LTD.) to remove insoluble materials. The supernatant after the filtration was concentrated to an about tenth volume by using a concentrator VIVAFLOW 50 (manufactured by Sartorius AG) or AMICON stirrer cell model 8400 (manufactured by Millipore Corporation) to give a concentrated solution.

The obtained concentrated solution was dialyzed against buffer A (20 mM HEPES-NaOH, 0.5 M NaCl, pH 8.0) at 4° C. overnight, and applied to a nickel column [one in which nickel was immobilized to HITRAP Chelating column (trade name, manufactured by Amersham-Pharmacia) (5 ml×2)] equilibrated with buffer A. The column was washed with 10 column volumes of buffer A, and then with buffer A containing 50 mM imidazole. The elution of the fraction containing shDPPIV was carried out by a linear gradient of 50 to 500 mM imidazole. The fraction found to have DPPIV activity was collected, and dialyzed overnight at 4° C. against buffer B (20 mM HEPES-NaOH, pH 8.0, 50 mM NaCl). After the dialysis, the sample was purified by using an anion exchange column [manufactured by Amersham-Pharmacia under the trade name: RESOURCE Q (6 ml)] equilibrated with buffer B. The column was washed with buffer B, and thereafter shDPPIV was eluted by a linear gradient of 15 column volumes of 50 to 500 mM NaCl. The fractions found to have DPPIV activity were collected, and used as a purified preparation.

(3) Preparation of Protein Sample for Crystallization

The shDPPIV purification sample (9 ml) obtained in the above (2) was concentrated using a product manufactured by Millipore Corporation under the trade name of CENTRICON 10 until the protein concentration reached 10 mg/ml.

The obtained product was used as a protein sample for crystallization. The protein sample for crystallization was stored at 4° C.

A precipitation agent solution containing 0.18 M glycine-NaOH (pH 9.5), 0.18 M sodium sulfate and 18% by weight of PEG4000, and a 10 mg/ml dipeptidyl peptidase IV solution were mixed, and thereafter, a drop of the obtained mixed solution was placed on a sitting drop plate under the trade name of CRYSCHEM Plate (manufactured by Hampton Research). The above-mentioned precipitation solution was allowed to stand at 20° C. as a reservoir solution to allow crystallization.

(4) Crystallization of shDPPIV

The crystallization of shDPPIV was carried out by a sitting-drop method, which is one of vapor diffusion methods.

The formation of crystal was observed with the passage of time using a stereoscopic microscope. As a result, after about two weeks, a large crystal having a maximum size of 500 μm×300 μm×100 μm was obtained. The crystal is also referred to as a native crystal. The microphotograph of the obtained crystal is shown in FIG. 1. In FIG. 1, the visual field is 4000 μm×3000 μm.

EXAMPLE 3 THREE-DIMENSIONAL STRUCTURAL ANALYSIS OF CRYSTALS (1) X-Ray Diffraction The crystal obtained in Example 2 mentioned above was soaked in a cryoprotecting buffer [composition: 0.18 M glycine-NaOH (pH 9.5), 19% by weight of PEG4000, 0.18 M sodium acetate, 15% glycerol], and immediately thereafter the mixture was placed under nitrogen gas stream (100 K) to rapidly freeze the mixture.

Figure 2:
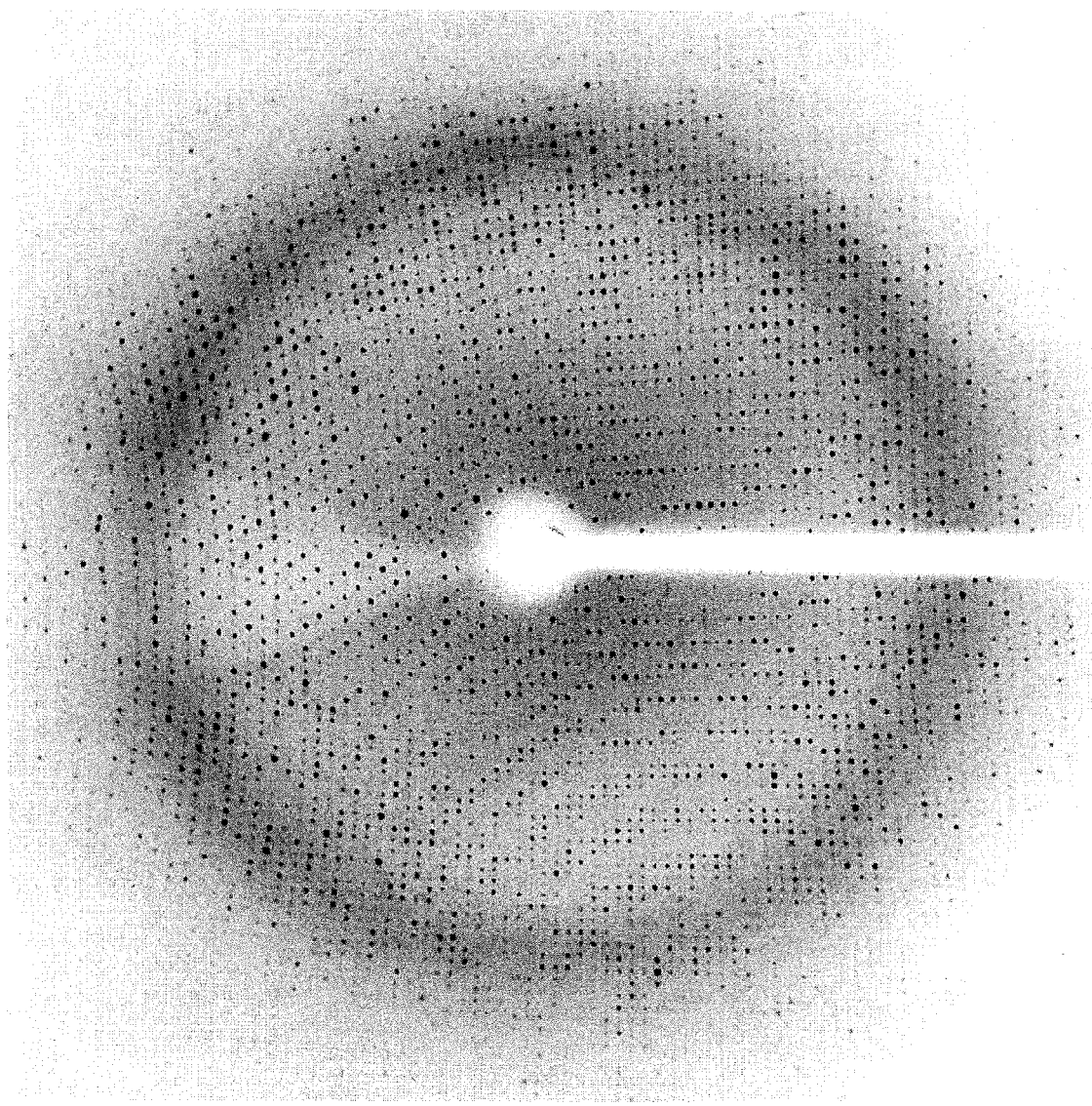
FIG. 2 is a photograph for X-ray diffraction pattern of a crystal of dipeptidyl peptidase IV.

The X-ray diffraction intensity data of the above crystal were collected up to the resolution of 3.0 Å using a product manufactured by Rigaku International Corporation under the trade name of R-AXIS IV in nitrogen gas stream (100 K), and converted to the structure factor using a program MOSFLM (Version 6.11). A photograph of the diffraction pattern is shown in FIG. 2.

From the obtained diffraction intensity data, it was determined that the crystal form to which the crystal belongs was orthorhombic, that the space group was $P2_12_12_1$, and the lattice constants were $\alpha$=118.0±5.0 Å, |b|=125.9±5.0 Å and |c|=136.8±5.0 Å.

(2) Multiple Isomorphous Replacement Method

In order to derive an electron density map, multiple isomorphous replacement method was carried out. The crystal obtained in Example 2 was soaked for 3 days and 4 days in a crystallization solution prepared by dissolving mercury chloride until being saturated, to give two different kinds of isomorphous replacement crystals containing mercury atoms in the crystals. The X-ray diffraction intensity data were collected in the same manner as those for the native crystals.

In the determination of the phase in the structural analysis, CCP4 (Collaborative Computational Project, Number 4, 1994. "The CCP4 Suite: Programs for Protein Crystallography," *Acta Cryst*. D50, 760-763) program was used.

First, Fourier transform calculation utilizing the difference between the diffraction intensity obtained from the two kinds of isomorphous replacement is crystals of mercury and the diffraction intensity obtained from the native crystal was performed using MLPHERE contained in the CCP program package. The position of each mercury atom in the unit cell of the real space was determined by investigating large peaks provided by heavy atoms (mercury) in the obtained Patterson's diagram. The phase of the crystal structure factor of the native crystals was determined by using the obtained position coordinate of mercury atoms. Furthermore, in order to determine the coordinate of each mercury atom more accurately using DM and SOLOMON contained in the CCP program package, refinement was carried out using three crystal structure factors of the native crystals and of the two kinds of mercury isomorphous replacement crystals.

An electron density map of the crystals of the dipeptidyl peptidase IV in real space was obtained using the phase of the crystal structure factor of the native crystals calculated from the refined coordinates of the mercury atoms. Furthermore, the electron density map was improved by carrying out smoothening and histogram matching of the electron density map in a solvent region, to obtain an electron density map critical for molecular modeling.

(3) Molecular Modeling

The sites corresponding to the amino acid residues of the dipeptidyl peptidase IV were identified on the electron density map by using QUANTA (manufactured by Accelrys, Inc.), to build molecular models.

As expected from the lattice constants, there were two molecules of the dipeptidyl peptidase IV in an asymmetry unit, and a model was built for each of the molecules. The refinement of the obtained molecular model was carried out using CNX (manufactured by Accelrys, Inc.), and the molecular model was adjusted again using the QUANTA for the obtained improved electron density map. The procedures were repeated to build a more accurate molecular model. In the refinement of the final coordinate, diffraction intensity data measured again were used after OSMIC confocal mirror (manufactured by Rigaku International Corporation) had been introduced into R-AXIS IV (trade name, manufactured by Rigaku International Corporation).

As a result, the resolution was improved from the previous 3.0 Å to 2.6 Å. Furthermore, 273 molecules of bound water and 5 molecules of N-acetyl glucosamine residues per molecule of the dipeptidyl peptidase IV were identified in an asymmetric unit. R factor, which is an index for accuracy of the obtained molecular model, was 24.89%, and a free R factor, which independently was not taken into account of the calculation of refinement at the step of refinement, was 30.15%. During the procedure, the deviation of the interatomic bond distance (rms-deviation) and the bond angle from the ideal state of the three-dimensional structure were 0.006 Å and 1.305°, respectively. The stereogram of the three-dimensional structure model of the crystals is shown in FIG. 3, and the coordinate is shown in FIG. 4. The present coordinate data were registered in PDB (Brookhaven Protein Data Bank) [PDB Code No: 1J2E, RSCB code No: 005544].

Here, as to those regions which did not take a regular structure in the crystals (in the disordered state), namely, the region from Asp 38 to that closer to the N-terminal side thereof, and the region for the tagged peptide (polyhistidine peptide) of the C-terminal side, the molecular model could not be built. Furthermore, a part of the side chains projected to the surface of the molecules did not take a regular structure. However, these residues were not portions that play an important role for the function of enzymes.

In the three-dimensional structure of the dipeptidyl peptidase IV, which has been clarified by the Examples, it has been revealed that the amino acid residue involved in the activity deduced by various experiments for the dipeptidyl peptidase IV, namely, Ser 630, Asp 708 and His 740, form hydrogen bonds between the $O_{\delta 2}$ atom of Asp 708 and $N_{\delta 1}$ atom of His 740, and with the $N_{\epsilon 2}$ atom of His 740 and $O_\gamma$ atom of Ser 630, even the residues locate in distant locations on the primary sequence. Therefore, for the structural coordinate of FIG. 4 and the three-dimensional structure model defined by the structural coordinate, it is suggested that the regions characterized by Ser 630, Asp 708 and His 740, and the whole or a part of amino acid residues that are located in the vicinity of Ser 630, Asp 708 and His 740 play an important role on the exhibition of the activity for the dipeptidyl peptidase IV and binding or interaction of the dipeptidyl peptidase IV with the effector, and that the compound matching the three-dimensional structure of the regions affect the activity for the dipeptidyl peptidase IV.

The present invention may be embodied in other various forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

INDUSTRIAL APPLICABILITY

According to the crystal of the dipeptidyl peptidase IV of the present invention, the information of a three-dimensional structure coordinate suitable for designing, identifying, evaluating or searching an effector of the dipeptidyl peptidase IV, useful as a modulatory agent of immune response and as a therapeutic or prophylactic agent for diabetes, inflammation, multiple sclerosis, Graves' disease, chronic rheumatoid arthritis, AIDS, cancer and the like can be obtained. Also, according to the three-dimensional structure coordinate, the information of a three-dimensional structure coordinate suitable for designing, identifying, evaluating or searching an effector of the dipeptidyl peptidase IV, useful as a modulatory agent of immune response and as a therapeutic or prophylactic agent for diabetes, inflammation, multiple sclerosis, Graves' disease, chronic rheumatoid arthritis, AIDS, cancer and the like can be obtained. Further, according to the method of the present invention for obtaining a three-dimensional structure coordinate of a homolog protein of a dipeptidyl peptidase IV, the refinement of the three-dimensional structure coordinate of the homolog protein of the dipeptidyl peptidase IV can be more conveniently carried out. Moreover, according to the method of the present invention for obtaining a three-dimensional structure coordinate of a crystal of a complex of a dipeptidyl peptidase IV with an effector of the dipeptidyl peptidase IV, the information of a three-dimensional structure coordinate suitable for designing, identifying, evaluating or searching an effector of the dipeptidyl peptidase IV, which is useful as a modulatory agent of immune response and as a therapeutic or prophylactic agent for diabetes, inflammation, multiple sclerosis, Graves' disease, chronic rheumatoid arthritis, AIDS, cancer and the like, and is excellent in avidity, biological activity, biological stability, absorbency to a living body, and which can favorably act on the dipeptidyl peptidase IV can be obtained. Also, according to the method for identifying a pharmacophore of a dipeptidyl peptidase IV and an effector of the dipeptidyl peptidase, the information of a three-dimensional structure coordinate suitable for designing, identifying, evaluating or searching an effector of the dipeptidyl peptidase IV, which is useful as a modulatory agent of immune response and as a therapeutic or prophylactic agent for diabetes, inflammation, multiple sclerosis, Graves' disease, chronic rheumatoid arthritis, AIDS, cancer and the like, and is excellent in avidity, biological activity, biological stability, absorbency to a living body, and which can favorably act on the dipeptidyl peptidase IV can be obtained. Further, according to the method of the present invention for designing, identifying, evaluating or searching an effector of the dipeptidyl peptidase IV, the information of a three-dimensional structure coordinate suitable for designing, identifying, evaluating or searching an effector of the dipeptidyl peptidase IV, which is useful as a modulatory agent of immune response and as a therapeutic or prophylactic agent for diabetes, inflammation, multiple sclerosis, Graves' disease, chronic rheumatoid arthritis, AIDS, cancer and the like, and is excellent in avidity, biological activity, biological stability, absorbency to a living body, and which can favorably act on the dipeptidyl peptidase IV can be logically and conveniently obtained. In addition, the effector of the dipeptidyl peptidase IV of the present invention is useful as a modulatory agent of immune response and as a therapeutic or prophylactic agent for diabetes, inflammation, multiple sclerosis, Graves' disease, chronic rheumatoid arthritis, AIDS, cancer and the like. Further, according to the program or the medium therefor of the present invention, the design, identification, evaluation and search for an effector of a dipeptidyl peptidase IV can be carried out rapidly and conveniently. Therefore, the present invention can be utilized in modulation of immune response and the treatment or prevention for diabetes, inflammation, multiple sclerosis, Graves' disease, chronic rheumatoid arthritis, AIDS, cancer and the like.

The invention claimed is:

1. A crystal of a polypeptide consisting of the amino acid sequence of residues 33-766 of SEQ ID NO: 2 and a polyhistidine tag added to the C-terminal end thereof wherein the crystal has a space group of $P2_12_12_1$ with unit cell parameters of a=118.0±5.0 Å, b=125.9±5.0 Å, c=136.8±5.0 Å, and $\alpha=\beta=\gamma=90°$, and said crystal diffracts X-rays for the determination of the atomic coordinates of the polypeptide at a resolution of 3 Å or better.

2. The crystal according to claim 1 wherein the crystal has the structural coordinates shown in FIG. 4.

3. The crystal according to claim 1 wherein the crystal diffracts X-rays for the determination of the atomic coordinates of the polypeptide at a resolution of 2.8 Å or better.

4. The crystal according to claim 1 wherein the crystal diffracts X-rays for the determination of the atomic coordinates of the polypeptide at a resolution of 2.6 Å or better.

5. The crystal according to claim 1, wherein amino acid residues Ser 630, Asp 708 and His 740 of SEQ ID NO:2 have the structural coordinates shown in FIG. 4.

* * * * *

SEQUENCE LISTING

```
<160> NUMBER OF SEQ ID NOS: 2

<210> SEQ ID NO 1
<211> LENGTH: 2301
<212> TYPE: DNA
<213> ORGANISM: Homo sapiens
<220> FEATURE:
<221> NAME/KEY: CDS
<222> LOCATION: (1)..(2301)
<223> OTHER INFORMATION:

<400> SEQUENCE: 1 atg aag aca ccg tgg aag gtt ctt ctg gga ctg ctg ggt gct gct gcg      48
Met Lys Thr Pro Trp Lys Val Leu Leu Gly Leu Leu Gly Ala Ala Ala
1               5                   10                  15 ctt gtc acc atc atc acc gtg ccc gtg gtt ctg ctg aac aaa ggc aca      96
Leu Val Thr Ile Ile Thr Val Pro Val Val Leu Leu Asn Lys Gly Thr
            20                  25                  30 gat gat gct aca gct gac agt cgc aaa act tac act cta act gat tac    144
Asp Asp Ala Thr Ala Asp Ser Arg Lys Thr Tyr Thr Leu Thr Asp Tyr
        35                  40                  45
```

| | | | | | | | | | | | | | | | | |
|---|---|---|---|---|---|---|---|---|---|---|---|---|---|---|---|---|
| tta | aaa | aat | act | tat | aga | ctg | aag | tta | tac | tcc | tta | aga | tgg | att | tca | 192 |
| Leu | Lys | Asn | Thr | Tyr | Arg | Leu | Lys | Leu | Tyr | Ser | Leu | Arg | Trp | Ile | Ser | |
| | 50 | | | | 55 | | | | | 60 | | | | | | |
| gat | cat | gaa | tat | ctc | tac | aaa | caa | gaa | aat | aat | atc | ttg | gta | ttc | aat | 240 |
| Asp | His | Glu | Tyr | Leu | Tyr | Lys | Gln | Glu | Asn | Asn | Ile | Leu | Val | Phe | Asn | |
| 65 | | | | | 70 | | | | | 75 | | | | | 80 | |
| gct | gaa | tat | gga | aac | agc | tca | gtt | ttc | ttg | gag | aac | agt | aca | ttt | gat | 288 |
| Ala | Glu | Tyr | Gly | Asn | Ser | Ser | Val | Phe | Leu | Glu | Asn | Ser | Thr | Phe | Asp | |
| | | | | 85 | | | | | 90 | | | | | 95 | | |
| gag | ttt | gga | cat | tct | atc | aat | gat | tat | tca | ata | tct | cct | gat | ggg | cag | 336 |
| Glu | Phe | Gly | His | Ser | Ile | Asn | Asp | Tyr | Ser | Ile | Ser | Pro | Asp | Gly | Gln | |
| | | | 100 | | | | | 105 | | | | | 110 | | | |
| ttt | att | ctc | tta | gaa | tac | aac | tac | gtg | aag | caa | tgg | agg | cat | tcc | tac | 384 |
| Phe | Ile | Leu | Leu | Glu | Tyr | Asn | Tyr | Val | Lys | Gln | Trp | Arg | His | Ser | Tyr | |
| | | 115 | | | | | 120 | | | | | 125 | | | | |
| aca | gct | tca | tat | gac | att | tat | gat | tta | aat | aaa | agg | cag | ctg | att | aca | 432 |
| Thr | Ala | Ser | Tyr | Asp | Ile | Tyr | Asp | Leu | Asn | Lys | Arg | Gln | Leu | Ile | Thr | |
| | 130 | | | | | 135 | | | | | 140 | | | | | |
| gaa | gag | agg | att | cca | aac | aac | aca | cag | tgg | gtc | aca | tgg | tca | cca | gtg | 480 |
| Glu | Glu | Arg | Ile | Pro | Asn | Asn | Thr | Gln | Trp | Val | Thr | Trp | Ser | Pro | Val | |
| 145 | | | | | 150 | | | | | 155 | | | | | 160 | |
| ggt | cat | aaa | ttg | gca | tat | gtt | tgg | aac | aat | gac | att | tat | gtt | aaa | att | 528 |
| Gly | His | Lys | Leu | Ala | Tyr | Val | Trp | Asn | Asn | Asp | Ile | Tyr | Val | Lys | Ile | |
| | | | | 165 | | | | | 170 | | | | | 175 | | |
| gaa | cca | aat | tta | cca | agt | tac | aga | atc | aca | tgg | acg | ggg | aaa | gaa | gat | 576 |
| Glu | Pro | Asn | Leu | Pro | Ser | Tyr | Arg | Ile | Thr | Trp | Thr | Gly | Lys | Glu | Asp | |
| | | | 180 | | | | | 185 | | | | | 190 | | | |
| ata | ata | tat | aat | gga | ata | act | gac | tgg | gtt | tat | gaa | gag | gaa | gtc | ttc | 624 |
| Ile | Ile | Tyr | Asn | Gly | Ile | Thr | Asp | Trp | Val | Tyr | Glu | Glu | Glu | Val | Phe | |
| | | 195 | | | | | 200 | | | | | 205 | | | | |
| agt | gcc | tac | tct | gct | ctg | tgg | tgg | tct | cca | aac | ggc | act | ttt | tta | gca | 672 |
| Ser | Ala | Tyr | Ser | Ala | Leu | Trp | Trp | Ser | Pro | Asn | Gly | Thr | Phe | Leu | Ala | |
| | 210 | | | | | 215 | | | | | 220 | | | | | |
| tat | gcc | caa | ttt | aac | gac | aca | gaa | gtc | cca | ctt | att | gaa | tac | tcc | ttc | 720 |
| Tyr | Ala | Gln | Phe | Asn | Asp | Thr | Glu | Val | Pro | Leu | Ile | Glu | Tyr | Ser | Phe | |
| 225 | | | | | 230 | | | | | 235 | | | | | 240 | |
| tac | tct | gat | gag | tca | ctg | cag | tac | cca | aag | act | gta | cgg | gtt | cca | tat | 768 |
| Tyr | Ser | Asp | Glu | Ser | Leu | Gln | Tyr | Pro | Lys | Thr | Val | Arg | Val | Pro | Tyr | |
| | | | | 245 | | | | | 250 | | | | | 255 | | |
| cca | aag | gca | gga | gct | gtg | aat | cca | act | gta | aag | ttc | ttt | gtt | gta | aat | 816 |
| Pro | Lys | Ala | Gly | Ala | Val | Asn | Pro | Thr | Val | Lys | Phe | Phe | Val | Val | Asn | |
| | | | 260 | | | | | 265 | | | | | 270 | | | |
| aca | gac | tct | ctc | agc | tca | gtc | acc | aat | gca | act | tcc | ata | caa | atc | act | 864 |
| Thr | Asp | Ser | Leu | Ser | Ser | Val | Thr | Asn | Ala | Thr | Ser | Ile | Gln | Ile | Thr | |
| | | 275 | | | | | 280 | | | | | 285 | | | | |
| gct | cct | gct | tct | atg | ttg | ata | ggg | gat | cac | tac | ttg | tgt | gat | gtg | aca | 912 |
| Ala | Pro | Ala | Ser | Met | Leu | Ile | Gly | Asp | His | Tyr | Leu | Cys | Asp | Val | Thr | |
| | 290 | | | | | 295 | | | | | 300 | | | | | |
| tgg | gca | aca | caa | gaa | aga | att | tct | ttg | cag | tgg | ctc | agg | agg | att | cag | 960 |
| Trp | Ala | Thr | Gln | Glu | Arg | Ile | Ser | Leu | Gln | Trp | Leu | Arg | Arg | Ile | Gln | |
| 305 | | | | | 310 | | | | | 315 | | | | | 320 | |
| aac | tat | tcg | gtc | atg | gat | att | tgt | gac | tat | gat | gaa | tcc | agt | gga | aga | 1008 |
| Asn | Tyr | Ser | Val | Met | Asp | Ile | Cys | Asp | Tyr | Asp | Glu | Ser | Ser | Gly | Arg | |
| | | | | 325 | | | | | 330 | | | | | 335 | | |
| tgg | aac | tgc | tta | gtg | gca | cgg | caa | cac | att | gaa | atg | agt | act | act | ggc | 1056 |
| Trp | Asn | Cys | Leu | Val | Ala | Arg | Gln | His | Ile | Glu | Met | Ser | Thr | Thr | Gly | |
| | | | 340 | | | | | 345 | | | | | 350 | | | |
| tgg | gtt | gga | aga | ttt | agg | cct | tca | gaa | cct | cat | ttt | acc | ctt | gat | ggt | 1104 |
| Trp | Val | Gly | Arg | Phe | Arg | Pro | Ser | Glu | Pro | His | Phe | Thr | Leu | Asp | Gly | |

-continued

```
                355                 360                 365
aat agc ttc tac aag atc atc agc aat gaa gaa ggt tac aga cac att       1152
Asn Ser Phe Tyr Lys Ile Ile Ser Asn Glu Glu Gly Tyr Arg His Ile
    370                 375                 380 tgc tat ttc caa ata gat aaa aaa gac tgc aca ttt att aca aaa ggc       1200
Cys Tyr Phe Gln Ile Asp Lys Lys Asp Cys Thr Phe Ile Thr Lys Gly
385                 390                 395                 400 acc tgg gaa gtc atc ggg ata gaa gct cta acc agt gat tat cta tac       1248
Thr Trp Glu Val Ile Gly Ile Glu Ala Leu Thr Ser Asp Tyr Leu Tyr
                405                 410                 415 tac att agt aat gaa tat aaa gga atg cca gga gga agg aat ctt tat       1296
Tyr Ile Ser Asn Glu Tyr Lys Gly Met Pro Gly Gly Arg Asn Leu Tyr
            420                 425                 430 aaa atc caa ctt agt gac tat aca aaa gtg aca tgc ctc agt tgt gag       1344
Lys Ile Gln Leu Ser Asp Tyr Thr Lys Val Thr Cys Leu Ser Cys Glu
        435                 440                 445 ctg aat ccg gaa agg tgt cag tac tat tct gtg tca ttc agt aaa gag       1392
Leu Asn Pro Glu Arg Cys Gln Tyr Tyr Ser Val Ser Phe Ser Lys Glu
    450                 455                 460 gcg aag tat tat cag ctg aga tgt tcc ggt cct ggt ctg ccc ctc tat       1440
Ala Lys Tyr Tyr Gln Leu Arg Cys Ser Gly Pro Gly Leu Pro Leu Tyr
465                 470                 475                 480 act cta cac agc agc gtg aat gat aaa ggg ctg aga gtc ctg gaa gac       1488
Thr Leu His Ser Ser Val Asn Asp Lys Gly Leu Arg Val Leu Glu Asp
                485                 490                 495 aat tca gct ttg gat aaa atg ctg cag aat gtc cag atg ccc tcc aaa       1536
Asn Ser Ala Leu Asp Lys Met Leu Gln Asn Val Gln Met Pro Ser Lys
            500                 505                 510 aaa ctg gac ttc att att ttg aat gaa aca aaa ttt tgg tat cag atg       1584
Lys Leu Asp Phe Ile Ile Leu Asn Glu Thr Lys Phe Trp Tyr Gln Met
        515                 520                 525 atc ttg cct cct cat ttt gat aaa tcc aag aaa tat cct cta cta tta       1632
Ile Leu Pro Pro His Phe Asp Lys Ser Lys Lys Tyr Pro Leu Leu Leu
    530                 535                 540 gat gtg tat gca ggc cca tgt agt caa aaa gca gac act gtc ttc aga       1680
Asp Val Tyr Ala Gly Pro Cys Ser Gln Lys Ala Asp Thr Val Phe Arg
545                 550                 555                 560 ctg aac tgg gcc act tac ctt gca agc aca gaa aac att ata gta gct       1728
Leu Asn Trp Ala Thr Tyr Leu Ala Ser Thr Glu Asn Ile Ile Val Ala
                565                 570                 575 agc ttt gat ggc aga gga agt ggt tac caa gga gat aag atc atg cat       1776
Ser Phe Asp Gly Arg Gly Ser Gly Tyr Gln Gly Asp Lys Ile Met His
            580                 585                 590 gca atc aac aga aga ctg gga aca ttt gaa gtt gaa gat caa att gaa       1824
Ala Ile Asn Arg Arg Leu Gly Thr Phe Glu Val Glu Asp Gln Ile Glu
        595                 600                 605 gca gcc aga caa ttt tca aaa atg gga ttt gtg gac aac aaa cga att       1872
Ala Ala Arg Gln Phe Ser Lys Met Gly Phe Val Asp Asn Lys Arg Ile
    610                 615                 620 gca att tgg ggc tgg tca tat gga ggg tac gta acc tca atg gtc ctg       1920
Ala Ile Trp Gly Trp Ser Tyr Gly Gly Tyr Val Thr Ser Met Val Leu
625                 630                 635                 640 gga tcg gga agt ggc gtg ttc aag tgt gga ata gcc gtg gcg cct gta       1968
Gly Ser Gly Ser Gly Val Phe Lys Cys Gly Ile Ala Val Ala Pro Val
                645                 650                 655 tcc cgg tgg gag tac tat gac tca gtg tac aca gaa cgt tac atg ggt       2016
Ser Arg Trp Glu Tyr Tyr Asp Ser Val Tyr Thr Glu Arg Tyr Met Gly
            660                 665                 670 ctc cca act cca gaa gac aac ctt gac cat tac aga aat tca aca gtc       2064
```

-continued

```
Leu Pro Thr Pro Glu Asp Asn Leu Asp His Tyr Arg Asn Ser Thr Val
            675                 680                 685 atg agc aga gct gaa aat ttt aaa caa gtt gag tac ctc ctt att cat    2112
Met Ser Arg Ala Glu Asn Phe Lys Gln Val Glu Tyr Leu Leu Ile His
    690                 695                 700 gga aca gca gat gat aac gtt cac ttt cag cag tca gct cag atc tcc    2160
Gly Thr Ala Asp Asp Asn Val His Phe Gln Gln Ser Ala Gln Ile Ser
705                 710                 715                 720 aaa gcc ctg gtc gat gtt gga gtg gat ttc cag gca atg tgg tat act    2208
Lys Ala Leu Val Asp Val Gly Val Asp Phe Gln Ala Met Trp Tyr Thr
                725                 730                 735 gat gaa gac cat gga ata gct agc agc aca gca cac caa cat ata tat    2256
Asp Glu Asp His Gly Ile Ala Ser Ser Thr Ala His Gln His Ile Tyr
            740                 745                 750 acc cac atg agc cac ttc ata aaa caa tgt ttc tct tta cct tag        2301
Thr His Met Ser His Phe Ile Lys Gln Cys Phe Ser Leu Pro
                755                 760                 765

<210> SEQ ID NO 2
<211> LENGTH: 766
<212> TYPE: PRT
<213> ORGANISM: Homo sapiens

<400> SEQUENCE: 2

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
            35                  40                  45

Leu Lys Asn Thr Tyr Arg Leu Lys Leu Tyr Ser Leu Arg Trp Ile Ser
        50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255
```

```
Pro Lys Ala Gly Ala Val Asn Pro Thr Val Lys Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
```

-continued

```
              675                 680                 685
Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
    755                 760                 765
```